United States Patent
Brown et al.

(10) Patent No.: US 10,736,883 B2
(45) Date of Patent: Aug. 11, 2020

(54) TRIAZOLE FURAN COMPOUNDS AS AGONISTS OF THE APJ RECEPTOR

(71) Applicant: AMGEN INC., Thousand Oaks, CA (US)

(72) Inventors: Matthew Brown, Santa Clara, CA (US); Ning Chen, Thousand Oaks, CA (US); Xiaoqi Chen, Palo Alto, CA (US); Yinhong Chen, Hayward, CA (US); Alan C. Cheng, San Francisco, CA (US); Richard V. Connors, Mesa, AZ (US); Jeffrey Deignan, San Francisco, CA (US); Paul John Dransfield, Arlington, MA (US); Xiaohui Du, Belmont, CA (US); Zice Fu, Foster City, CA (US); James S. Harvey, Arlington, MA (US); Julie Anne Heath, Chico, CA (US); Lars V. Heumann, Redwood City, CA (US); Jonathan Houze, Cambridge, MA (US); Frank Kayser, San Francisco, CA (US); Aarif Yusuf Khakoo, Woodside, CA (US); David j. Kopecky, Washington D.C., DC (US); Su-Jen Lai, Cambridge, MA (US); Zhihua Ma, Lexington, MA (US); Julio C. Medina, San Carlos, CA (US); Jeffrey T. Mihalic, San Francisco, CA (US); Steven H. Olson, Millbrae, CA (US); Vatee Pattaropong, Bedford, MA (US); Gayathri Swaminath, Brisbane, CA (US); Xiaodong Wang, Johns Creek, GA (US); Malgorzata Wanska, Camarillo, CA (US); Wen-Chen Yeh, Belmont, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 16/347,903

(22) PCT Filed: Nov. 3, 2017

(86) PCT No.: PCT/US2017/059822
§ 371 (c)(1),
(2) Date: May 7, 2019

(87) PCT Pub. No.: WO2018/097944
PCT Pub. Date: May 31, 2018

(65) Prior Publication Data
US 2019/0275008 A1    Sep. 12, 2019

Related U.S. Application Data

(60) Provisional application No. 62/422,688, filed on Nov. 16, 2016.

(51) Int. Cl.
*A61K 31/4196* (2006.01)
*A61K 31/341* (2006.01)
(Continued)

(52) U.S. Cl.
CPC ........ *A61K 31/4196* (2013.01); *A61K 31/421* (2013.01); *A61K 31/437* (2013.01);
(Continued)

(58) Field of Classification Search
CPC .............. A61K 31/4196; A61K 31/341; C07D 405/04; C07D 405/14
(Continued)

(56) References Cited

U.S. PATENT DOCUMENTS

| 4,844,730 | A | 7/1989 | Moriya et al. |
| 4,941,912 | A | 7/1990 | Kirsten et al. |

(Continued)

FOREIGN PATENT DOCUMENTS

| AU | 199886243 B2 | 4/1999 |
| AU | 2012200157 A1 | 9/2012 |

(Continued)

OTHER PUBLICATIONS

Modzelewska-Banachiewicz, B. and D. Matosiuk, "Synthesis and biological action of 3,4-disubsituted 5-arylsulphonylamine-1,2,4-triazoles", Pharmazie (1999), 54, pp. 588-589. (Year: 1999).*

(Continued)

*Primary Examiner* — Matthew P Coughlin
*Assistant Examiner* — Sagar Patel
(74) *Attorney, Agent, or Firm* — Bernard P. Friedrichsen

(57) ABSTRACT

Compounds of Formula (I) and Formula (II), pharmaceutically acceptable salt thereof, stereoisomers of any of the foregoing, or mixtures thereof are agonists of the APJ Receptor and have use in treating cardiovascular and other conditions. Compounds of Formula (I) and Formula (II) have the following structures: (I); (II). Intermediates (V) are also claimed.

I

II (Continued)

-continued

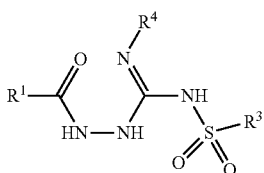

25 Claims, 16 Drawing Sheets

(51) Int. Cl.
| | |
|---|---|
| C07D 405/04 | (2006.01) |
| C07D 405/14 | (2006.01) |
| A61K 31/421 | (2006.01) |
| A61K 31/437 | (2006.01) |
| A61K 31/4439 | (2006.01) |
| A61K 31/501 | (2006.01) |
| A61K 31/506 | (2006.01) |
| C07D 239/26 | (2006.01) |
| C07D 403/12 | (2006.01) |
| C07D 405/12 | (2006.01) |
| C07D 413/12 | (2006.01) |
| C07D 471/04 | (2006.01) |
| C07F 7/08 | (2006.01) |
| A61P 9/00 | (2006.01) |
| A61P 9/02 | (2006.01) |
| C07D 307/54 | (2006.01) |

(52) U.S. Cl.
CPC ........ *A61K 31/4439* (2013.01); *A61K 31/501* (2013.01); *A61K 31/506* (2013.01); *A61P 9/00* (2018.01); *A61P 9/02* (2018.01); *C07D 239/26* (2013.01); *C07D 307/54* (2013.01); *C07D 403/12* (2013.01); *C07D 405/04* (2013.01); *C07D 405/12* (2013.01); *C07D 405/14* (2013.01); *C07D 413/12* (2013.01); *C07D 471/04* (2013.01); *C07F 7/0812* (2013.01)

(58) Field of Classification Search
USPC .......... 514/383, 471, 461; 548/264.8, 266.2; 549/505, 472
See application file for complete search history.

(56) References Cited

U.S. PATENT DOCUMENTS

| | | | |
|---|---|---|---|
| 5,302,718 A | 4/1994 | Agback et al. |
| 5,328,803 A | 7/1994 | Fujikura et al. |
| 5,411,839 A | 5/1995 | Harder et al. |
| 5,451,588 A | 9/1995 | Baker et al. |
| 5,510,362 A | 4/1996 | Matassa et al. |
| 5,563,026 A | 10/1996 | Singer |
| 5,910,504 A | 6/1999 | Hutchinson |
| 6,069,141 A | 5/2000 | Barbachyn et al. |
| 6,194,090 B1 | 2/2001 | Okada |
| 6,555,693 B2 | 4/2003 | Ge et al. |
| 6,586,423 B2 | 7/2003 | Bilodeau et al. |
| 6,727,364 B2 | 4/2004 | Tullis et al. |
| 6,787,555 B2 | 9/2004 | Tullis et al. |
| 6,790,846 B2 | 9/2004 | Clark et al. |
| 7,084,145 B2 | 8/2006 | Armour et al. |
| 7,084,164 B2 | 8/2006 | Tobe et al. |
| 7,169,797 B2 | 1/2007 | Xin et al. |
| 7,297,168 B2 | 11/2007 | Murphy et al. |
| 7,361,669 B2 | 4/2008 | Scarborough et al. |
| 7,371,757 B2 | 5/2008 | Morningstar et al. |
| 7,615,569 B2 | 11/2009 | Fulp et al. |
| 7,635,751 B2 | 12/2009 | Kitada et al. |
| 7,638,541 B2 | 12/2009 | Chen et al. |
| 7,718,683 B2 | 5/2010 | Charvat et al. |
| 7,776,897 B2 | 8/2010 | Murakami et al. |
| 7,820,665 B2 | 10/2010 | Booker et al. |
| 8,034,834 B2 | 10/2011 | Du et al. |
| 8,053,456 B2 | 11/2011 | Sun et al. |
| 8,063,083 B2 | 11/2011 | Foley |
| 8,076,486 B2 | 12/2011 | Goutopoulos et al. |
| 8,101,618 B2 | 1/2012 | Kawamoto et al. |
| 8,252,822 B2 | 8/2012 | An et al. |
| 8,299,107 B2 | 10/2012 | Chimmanamada et al. |
| 8,318,790 B2 | 11/2012 | Ying et al. |
| 8,399,464 B2 | 3/2013 | Kuramochi et al. |
| 8,415,377 B2 | 4/2013 | Sun et al. |
| 8,426,602 B2 | 4/2013 | Meibom et al. |
| 8,431,604 B2 | 4/2013 | Netz et al. |
| 8,445,518 B2 | 5/2013 | Charvat et al. |
| 8,466,170 B2 | 6/2013 | Klein |
| 8,492,427 B2 | 7/2013 | Gancia et al. |
| 8,563,741 B2 | 10/2013 | Qian et al. |
| 8,648,104 B2 | 2/2014 | Du et al. |
| 8,673,848 B2 | 3/2014 | Zecri et al. |
| 8,742,133 B2 | 6/2014 | Ying et al. |
| 8,778,977 B2 | 7/2014 | Lind et al. |
| 8,835,464 B2 | 9/2014 | Sun et al. |
| 8,883,827 B2 | 11/2014 | Holsworth et al. |
| 9,156,796 B2 | 10/2015 | Hachtel et al. |
| 9,573,936 B2 | 2/2017 | Chen et al. |
| 9,656,997 B2 | 5/2017 | Chen et al. |
| 9,656,998 B2 | 5/2017 | Chen et al. |
| 9,745,286 B2 | 8/2017 | Chen et al. |
| 9,751,864 B2 | 9/2017 | Chen et al. |
| 9,845,310 B2 | 12/2017 | Chen et al. |
| 9,868,721 B2 | 1/2018 | Chen et al. |
| 9,988,369 B2 | 6/2018 | Chen et al. |
| 10,058,550 B2 | 8/2018 | Chen et al. |
| 10,100,059 B2 | 10/2018 | Runyon et al. |
| 10,150,760 B2 | 12/2018 | Chen et al. |
| 10,221,162 B2 | 3/2019 | Chen et al. |
| 2002/0107245 A1 | 8/2002 | Wagle et al. |
| 2004/0167188 A1 | 8/2004 | Xin et al. |
| 2005/0075275 A1 | 4/2005 | Albrecht et al. |
| 2005/0165015 A1 | 7/2005 | Ncube |
| 2005/0170431 A1 | 8/2005 | Ibrahim et al. |
| 2005/0288347 A1 | 12/2005 | Hodge et al. |
| 2006/0156480 A1 | 7/2006 | Lim |
| 2006/0281749 A1 | 12/2006 | Wagle et al. |
| 2008/0153869 A1 | 6/2008 | Bressi et al. |
| 2008/0249131 A1 | 10/2008 | Girardet et al. |
| 2009/0318438 A1 | 12/2009 | Chen et al. |
| 2010/0130472 A1 | 5/2010 | Young et al. |
| 2010/0249185 A1 | 9/2010 | Du et al. |
| 2010/0280032 A1 | 11/2010 | Zhou et al. |
| 2011/0046125 A1 | 2/2011 | Ying |
| 2011/0158940 A1 | 6/2011 | Byrd et al. |
| 2011/0190257 A1 | 8/2011 | Heald et al. |
| 2011/0207788 A1 | 8/2011 | Amberg et al. |
| 2011/0265691 A1 | 11/2011 | Orth et al. |
| 2012/0094837 A1 | 4/2012 | Muhlthau et al. |
| 2012/0208828 A1 | 8/2012 | Holsworth et al. |
| 2012/0238576 A1 | 9/2012 | Tao et al. |
| 2013/0034536 A1 | 2/2013 | Gedulin |
| 2013/0040950 A1 | 2/2013 | Short et al. |
| 2013/0059807 A1 | 3/2013 | Gedulin et al. |
| 2013/0059845 A1 | 3/2013 | Song et al. |
| 2013/0108573 A1 | 5/2013 | Gedulin et al. |
| 2013/0109671 A1 | 5/2013 | Gedulin et al. |
| 2013/0150385 A1 | 6/2013 | Blackman et al. |
| 2013/0156755 A1 | 6/2013 | Blackman et al. |
| 2013/0266636 A1 | 10/2013 | Cheresh et al. |
| 2013/0303505 A1 | 11/2013 | Bollu et al. |
| 2014/0005181 A1 | 1/2014 | Smith et al. |
| 2016/0058705 A1 | 3/2016 | Rajadas et al. |
| 2016/0060349 A1 | 3/2016 | Van Schravendijk et al. |
| 2016/0340336 A1 | 11/2016 | Chen et al. |
| 2016/0355507 A1 | 12/2016 | Johnsen et al. |

(56) References Cited

U.S. PATENT DOCUMENTS

| | | |
|---|---|---|
| 2017/0035744 A1 | 2/2017 | Chen et al. |
| 2017/0037026 A1 | 2/2017 | Chen et al. |
| 2017/0042871 A1 | 2/2017 | Chen et al. |
| 2017/0042872 A1 | 2/2017 | Chen et al. |
| 2017/0042897 A1 | 2/2017 | Chen et al. |
| 2017/0044131 A1 | 2/2017 | Chen et al. |
| 2017/0281625 A1 | 10/2017 | Chen et al. |
| 2017/0320860 A1 | 11/2017 | Chen et al. |
| 2017/0355734 A1 | 12/2017 | Llorens-Cortez et al. |
| 2018/0118698 A1 | 5/2018 | Smith et al. |
| 2019/0100510 A1 | 4/2019 | Dransfield et al. |

FOREIGN PATENT DOCUMENTS

| | | | |
|---|---|---|---|
| DE | 3928605 A1 | 3/1991 | |
| DE | 4035141 A1 | 5/1992 | |
| EP | 0121082 B1 | 10/1984 | |
| EP | 0330959 A2 | 2/1989 | |
| EP | 0409332 A2 | 1/1991 | |
| EP | 0484750 A1 | 10/1991 | |
| JP | 2003-5356 A | 8/2003 | |
| JP | 2003-321456 A | 11/2003 | |
| JP | 2005-170939 A | 6/2005 | |
| WO | 91/11909 A1 | 8/1991 | |
| WO | 99/43671 A1 | 9/1999 | |
| WO | 01/87855 A1 | 11/2001 | |
| WO | 2005/039569 A1 | 5/2005 | |
| WO | 2006/026488 A1 | 3/2006 | |
| WO | 2006/055760 A1 | 5/2006 | |
| WO | 2006/080533 A1 | 8/2006 | |
| WO | 2006/095783 A1 | 9/2006 | |
| WO | 2006/100588 A1 | 9/2006 | |
| WO | 2006/109817 A1 | 10/2006 | |
| WO | 2007/007688 A1 | 1/2007 | |
| WO | 2007/139952 A2 | 12/2007 | |
| WO | 2007/139967 A2 | 12/2007 | |
| WO | 2008/008375 A1 | 1/2008 | |
| WO | 2008/021364 A2 | 2/2008 | |
| WO | 2008/103352 A1 | 8/2008 | |
| WO | 2009/075890 A2 | 6/2009 | |
| WO | 2009/115503 A1 | 9/2009 | |
| WO | 2010/017545 A2 | 2/2010 | |
| WO | 2011/146801 A1 | 11/2011 | |
| WO | 2012/076898 A1 | 6/2012 | |
| WO | 2012/116247 A1 | 8/2012 | |
| WO | 2013/067162 A1 | 5/2013 | |
| WO | 2013/067165 A1 | 5/2013 | |
| WO | 2013/074594 A1 | 5/2013 | |
| WO | 2013/106437 A1 | 6/2013 | |
| WO | 2013/106614 A1 | 7/2013 | |
| WO | 2013/111110 A2 | 8/2013 | |
| WO | 2013/148857 A1 | 10/2013 | |
| WO | 2013/184755 A2 | 12/2013 | |
| WO | 2014/044738 A1 | 3/2014 | |
| WO | 2014/099984 A1 | 6/2014 | |
| WO | 2014/150326 A1 | 9/2014 | |
| WO | 2014/194270 A1 | 12/2014 | |
| WO | 2015/140296 A2 | 9/2015 | |
| WO | 2015/163818 A1 | 10/2015 | |
| WO | 2015/184011 A2 | 12/2015 | |
| WO | 2015/188073 A1 | 12/2015 | |
| WO | 2016/151018 A1 | 9/2016 | |
| WO | 2016/196771 A1 | 12/2016 | |
| WO | 2017/066402 A1 | 4/2017 | |
| WO | 2017/091513 A1 | 6/2017 | |
| WO | 2017/096130 A1 | 6/2017 | |
| WO | 2017/100558 A1 | 6/2017 | |
| WO | 2017/106396 A1 | 6/2017 | |
| WO | 2017/165640 A1 | 9/2017 | |
| WO | 2017/174758 A1 | 10/2017 | |
| WO | WO-2017192485 A1 * | 11/2017 | ........... C07D 403/14 |
| WO | 2017/218617 A1 | 12/2017 | |
| WO | 2017/218633 A1 | 12/2017 | |
| WO | 2018/071526 A1 | 4/2018 | |
| WO | 2018/071622 A1 | 4/2018 | |
| WO | 2018/093576 A1 | 5/2018 | |
| WO | 2018/093577 A1 | 5/2018 | |
| WO | 2018/093579 A1 | 5/2018 | |
| WO | 2018/093580 A1 | 5/2018 | |
| WO | 2018/097945 A1 | 5/2018 | |

OTHER PUBLICATIONS

SciFinder Structure Search with Substances Performed May 20, 2016.

SciFinder Structure Search with References Performed May 20, 2016.

SciFinder Structure Search Sulfonamide Tail with Substance Performed May 12, 2016.

Berry, M. F. et al., "Apelin Has In Vivo Inotropic Effects on Normal and Failing Hearts," Circulation 110, pp. II187-II193, (2004).

Cheng, D. et al., "Discovery of Pyridinyl Acetamide Derivatives as Potent, Selective, and Orally Bioavailable Porcupine Inhibitors," ACS Med Chem Letters issn:19485875; doi:10.1021/acsmedchemlett.6b00038; lccn:2009200243; oclcnum:455500725; serissn:1948-5875; itc:84452717; itcp:10547084 (2016).

Chun, H. et al., "Apelin Signaling Antagonizes ANG II Effects in Mouse Models of Atherosclerosis," J. Clin. Invest. 118(10), pp. 3343-3354 (2008).

Japp, A. G. et al., "Acute Cardiovascular Effects of Apelin in Humans," Circulation 121, pp. 1818-1827 (2010).

Modzelewska-Banachiewicz et al., "Synthesis and Biological Action of 3-4-Disubstituted 5-Arylsulphonylamino-1,2,4-triazoles," Pharmazie 54, pp. 588-589 (1999).

Pauli, A. et al., "Toddler: An Embryonic Signal That Promotes Cell Movement via Apelin Receptors," Science 343, pp. 1248636-0-1248636-8 (2014).

Siddiquee, K. et al., "The Apelin receptor Inhibits the Angiotensin II Type 1 Receptor Via Allosteric Trans-Inhibition," Br. J. Pharmacol. 168, pp. 1104-1117 (2013).

Siddiquee, K. et al., "Apelin Protects Against Angiotensin II-Induced Cardiovascular Fibrosis and Decreases Plasminogen Activator Inhibitor Type-1 Production," J. Hypertension 29, pp. 724-731 (2011).

Tatemoto, K. et al., "Isolation and Characterization of a Novel Endogenous Peptide Ligand for the Human APJ Receptor," Bioch. Biophys. Res. Comm., 251, pp. 471-476 (1998).

Hosoya, M. et al., "Molecular and Functional Characteristics of APJ. Tissue Distribution of mRNA and Interaction with the Endogenous Ligand Apelin," J. Biol. Chem. 275(28), pp. 21061-21067 (2000).

Maguire, J. J. et al., "[Pyr$^1$]Apelin-13 Identified as the Predominant Apelin Isoform in the Human Heart: Vasoactive Mechanism and Inotropic Action in Disease," Hypertension 54(3), pp. 598-604, (2009).

Barnes, G. et al., "Translational Promise of the Apelin-APJ System," Heart 96(13), pp. 1011-1016 (2010).

Kawamata, Y. et al., "Molecular Properties of Apelin: Tissue Distribution and Receptor Binding," Biochemica et Biophysica Acta 1538(2-3), pp. 162-171 (2001).

Nishizawa, N. et al., "High Potency Analog of Apelin, A Ligand of Orphan GPCT APJ," T Shiori (ed.) Petptide Science 2000: Proceedings of the 37$^{th}$ Japanese Peptide Symposium, pp. 151-154 (2000).

Medhurst, A. D. et al., "Pharmacological and Immunohistochemical Characteization of the APJ Receptor and its Endogenous Ligand Apelin," J. Neurochem. 84(5), pp. 1162-1172 (2003).

Hamada, J. et al., "Evaluation of Novel Cyclic Analogoues of Apelin," Int. J. Mol. Med. 22, pp. 547-552 (2008).

Murza, A. et al., "Elucidation of the Structure-Activity Relationships of Apelin: Influence of Unnatural Amino Acids on Binding, Signaling, and Plasma Stability," ChemMedChem 7(2), pp. 318-325 (2012).

Thomas, J. B. et al., "Identification of 1-({[1-(4-Fluorophenyl)-5-(2-methoxyphenyl)-1H-pyrazol-3-yl]carbonyl}amino)cyclohexane Carboxylic Acid as a Selective Nonpeptide Neurotensin Receptor Type 2 Compound," J. Med. Chem. 57, pp. 5318-5332 (2014).

(56) References Cited

OTHER PUBLICATIONS

Thomas, J.B. et al., "Identification of N-[5-{[(4-Methylphenyl)sulfonyl]amino}-3- (trifluoroacetyl)-1H-indol-1-yl)acetyl]-L-leucine (NTRC-824), a Neurotensin-like Nonpeptide Compound Selective for the Neurotensin Receptor Type 2," J. Med. Chem. 57, pp. 7472-7477 (2014).

Thomas, J. B. et al., "The Amide Linker in Nonpeptide Neurotensin Receptor Ligands Plays a Key Role in Calcium Signaling at the Neurotensin Receptor Type 2," Bioorg. Med. Chem. Lett 25, pp. 2060-2064 (2015).

Thompson, M. E. "α,N-Alkanesulfonamide Dianions: Formation and Chemoselective C-Alkylation," J. Org. Chem. 49, pp. 1700-1703 (1984).

Wang, Y-G. et al., "Selenium-Based Safety-Catch Linker: Solid-Phase Synthesis of Vinyl-Substituted Oxadiazoles and Triazoles," J. Comb. Chem. 9, pp. 513-519 (2007).

Singh, O. M. et al., "A Facile One-Pot Synthetic Method for 1,2,4-Triazoles and 1,3-Disubstituted Thioureas," J. Chem. Res. pp. 483-485 (2006).

Carlsen, P.J.J. et al., "Synthesis of Unsymmetrically Substituted 4H-1,2,4-Triazoles," J. Heterocyclic Chem. 31, pp. 805-807 (1994).

Navidpour, L. et al., "Synthetic Approaches Towards the Sulfonamide Substituted-4,5-diaryl-4H-1,2,4-triazole-3-thiones," J. Heterocyclic Chem. 44, pp. 1323-1331 (2007).

Hassan, A. A. et al., "Thiosemicarbazides in Heterocyclization," J. Heterocyclic Chem. 48, pp. 495-516 (2011).

Sugane, T. et al., "Synthesis and Biological Evaluation of 3-Biphenyl-4-yl-4-phenyl-4H-1,2,4-triazoles as Novel Glycine Transporter 1 Inhibitors," J. Med. Chem. 54, pp. 387-391 (2011).

Ivanova, N. V. et al., "A Convenient Synthesis of 4,5-Disubstituted 1,2,4-Triazoles Functionalized in Position 3," Synthesis 1, pp. 156-160 (2005).

Modzelewska-Banaschiewicz, B et al., "Antiviral Activity of the Products of Cyclization of Dimethyl 2-[1-arylamino-1-arylmethylideine)hydrazono]succinate," Eur. J. Med. Chem. 36, pp. 93-99 (2001).

SciFinder Structure Search with Substances Performed Sep. 1, 2016.

SciFinder Structure Search with References Performed Sep. 1, 2016.

Sitarz, M. et al., "2. Studies on Pyrazine Derivatives, Part 39. Synthesis, Reactions and Tuberculostatic Activity of 3-Pyrazinyl-1,2,4-triazolo[4.3-a]-1,3-diazacycloalkanes," Chemistry of Heterocyclic Compounds, 41(2), pp. 200-207 (2005).

Johnson, M. G. et al., "Convenient Route to Secondary Sulfinates: Application to the Stereospecific Synthesis of α-C-Chiral Sulfonamides," Organic Letters 16(23), pp. 6248-6251 (2014).

Enders, D. et al., "Asymmetric Synthesis of α-Substituted N-Methylsulfonamides," Helvetica Chimica Acta, 85, pp. 3657-3677 (2002).

Zhou, T. et al., "Enantioselective Synthesis of Chiral Sulfones by Ir-Catalyzed Asymmetric Hydrogenation: A Facile Approach to the Preparation of Chiral Allylic and Homoallylic Compounds," J. Am. Chem Soc., 134, pp. 13592-13595 (2012).

Koch, F. M. et al., "Lewis Acid/Base Catalyzed [2+2]-Cycloaddition of Sulfenes and Aldehydes: A Versatile Entry to Chiral Sulfonyl and Sulfinyl Derivatives," Chem. Eur. J., 17, pp. 3679-03692 (2011).

Choi, J. et al., "Stereoconvergent Arylations and Alkenylations of Unactivated Alkyl Electrophiles: Catalytic Enantioselective Synthesis of Secondary Sulfonamides and Sulfones," J. Am. Chem. Soc., pp. 12161-12165 (2014).

International Search Report and Written Opinion for analogous PCT Application No. PCT/US2017/059822, dated May 3, 2018.

* cited by examiner

TRIAZOLE FURAN COMPOUNDS AS AGONISTS OF THE APJ RECEPTOR

CROSS REFERENCES TO RELATED APPLICATIONS

This application claims the benefit of U.S. Provisional Application No. 62/422,688, filed on Nov. 16, 2016, which is hereby incorporated by reference in its entirety and for all purposes as if fully set forth herein.

FIELD OF THE INVENTION

The present invention relates to compounds capable of acting as agonists of the APJ Receptor, and compositions that include compounds that are agonists of the APJ Receptor. The compounds and compositions may be used to activate the APJ Receptor and to treat various disease conditions. An example of one area where such compounds may be used is in the treatment of cardiovascular conditions. In particular, the compounds may be used to improve contractility and ejection fraction in subjects with chronic heart failure and may be used to treat patients with heart failure with reduced ejection fraction and patients with heart failure with preserved ejection fraction.

BACKGROUND OF THE INVENTION

Apelin is the endogenous ligand for APJ (APLNR, angiotensin receptor like-1). The APJ receptor is a member of the rhodopsin-like G protein-coupled receptor (GPCR) family. The apelin/APJ system has been observed in many tissues such as heart, kidney, pancreas, lung and the central nervous system. This suggests diverse roles of the system in the physiology and pathology of mammals.

Apelin peptides are processed from a 77 residue pre-pro form into smaller bioactive fragments, mainly a 36 residue form (Apelin 42-77—also referred to as Apelin-36) and a smaller 13 residue polypeptide (Apelin 65-77—also referred to as Apelin-13) Hosoya et al., J. Biol. Chem. 275:21061-21067, 2000. Apelin peptides were previously determined to be endogenous ligands for the orphan APJ receptor, a member of the seven transmembrane G-protein-coupled receptor superfamily. Tatemoto et al., Biochem. Biophysi. Res. Commun. 251:471-476, 1998. One of the shorter more active isoforms identified, pyroglutamated apelin-13 ([PE65]Apelin-13 (65-77), has been reported to be the most potent and abundant form of apelin in cardiac tissue. Maguire et al., Hypertension 54:598-604, 2009. In vitro and preclinical models have suggested that the apelin/APJ system has a role in cardiovascular homeostasis as well as metabolism. Barnes et al., Heart 96:1011-1016, 2010. Circulating apelin levels are transient and Apelin-13 has a brief plasma half-life of <5 min leading to short-lived cardiovascular effects.

In vitro, exogenous apelin increases contractility at sub-nanomolar concentrations in atrial strips and whole rat hearts, and increases sarcomere shortening by up to 140% in isolated cardiomyocytes. Barnes et al., Heart 96:1011-1016, 2010. Apelin also has a potent inotropic effect in an ex vivo isolated heart assay. In vivo, acute apelin infusion restores ejection fraction, increases cardiac output and reduces left ventricular end-diastolic pressure in rats with chronic heart failure. Berry et al., Circulation 110:187-193, 2004. Exogenous apelin potently enhances myocardial contractility without inducing left ventricular hypertrophy concomitant with reduction in ventricular preload and afterload. Barnes et al., Heart 96:1011-1016, 2010.

Studies from Kawamata et al and Hosoya et al have shown that that shorter peptide apelin-13 had approximately a 3.5-fold higher in vitro affinity to the APJ receptor than apelin-36. Kawamata et al., BBA 1538: 162-171, 2001, Hosoya et al., JBC 275: 21061-21067. Apelin-13 analogues were reported having a single substitution with either canonical or non-canonical amino acids. The authors also reported double and triple substitutions in apelin 66-77 and apelin 63-77, but not in apelin-13. The emphasis was on peptides reported to have higher in vitro affinity and potency than apelin-13. Nishizawa et al., in: T. Shioiri (ed.), Peptide Science 2000: Proceedings of the 37$^{th}$ Japanese Peptide Symposium, pp. 151-154. Several if not all of these modified peptides are reported in later studies. U.S. Pat. No. 7,635,751.

In a 2003 study (Medhurst et al., J. Neurochemistry 84:1162-1172, 2003) in vitro activity of apelin-36, apelin-17 and apelin-13 was compared. It was concluded that all three peptides were approximately equipotent. C-terminal amidation resulted in about a 14-fold decrease in affinity. A more recent study (Hamada et al., J. Mol. Med. 22:547-552, 2008) reported cyclic analogues of apelin-13. When tested for in vitro activity all three analogues maintained function activity, although with reduced potency relative to apelin-13.

A shortened 12 amino acid-apelin peptide having ligand activity on APJ was reported in a 2009 patent (U.S. Pat. No. 7,635,751). The peptide could have a substitution of one non-canonical amino acid. In another application, WO 2013/111110 A2 and U.S. Pat. No. 8,673,848, cyclic mimetics of apelin have also been reported.

Another study reported synthesizing analogs of apelin-13 with amino acid substitutions with non-canonical amino acids at the C-terminal end of the molecule but no pegylation at the N- or C-terminus or another site specific location. The use of internal PEG spacers (short PEG (n=4 or 6), however, was also reported in lower activity peptide analogs with deletions in the middle of the sequence that contained fewer amino acid residues than apelin-13. Murza et al. Chem Med Chem 7:318-325, 2012. Additionally, PCT/US2013/075773 describes a group of modifications, including substitution of non-canonical amino acids and changes at the N- and C-terminal of the apelin molecule that can affect, inter alfa, the potency of the molecule. The increased potency can be a result of increased half-life or decreased degradation relative to wild-type apelin.

Despite the advancements that have been made with respect to peptides, a need exists for small molecule agonists of the APJ receptor. However, some progress has been made in this area. For example, WO 2014/044738 discloses various benzimidazole-carboxylic acid amide derivatives as modulators of the APJ Receptor. Other small molecule agonists of the APJ receptor are disclosed in U.S. Pat. Appl. Pub. No. US 2016/0340336, WO 2016/187308, WO 2015/184011, and WO 2015/188073.

A need continues to exist for agonists of the APJ receptor that may be used to treat various cardiovascular and other conditions. The present application discloses such agonists of the APJ receptor s that may be suitable for use as therapeutic agents in treating a variety of conditions. These compounds may find particular benefit in treating cardiovascular conditions. For example, such compounds may be beneficial in treating conditions such as chronic systolic heart failure and chronic diastolic heart failure.

SUMMARY OF THE INVENTION

In one aspect, the invention provides a compound of Formula I or Formula II:

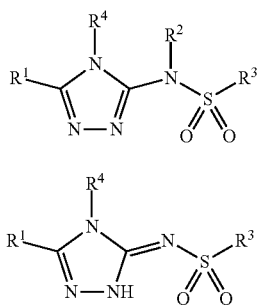

or a pharmaceutically acceptable salt thereof, a tautomer thereof, a pharmaceutically acceptable salt of the tautomer, a stereoisomer of any of the foregoing, or a mixture thereof, wherein:

$R^1$ is an unsubstituted furanyl, or is a furanyl substituted with 1, 2, or 3 $R^{1a}$ substituents;

$R^{1a}$ in each instance is independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), or —C(=O)N($C_1$-$C_6$ alkyl)$_2$;

$R^2$ is selected from —H, or $C_1$-$C_4$ alkyl or is absent in the compounds of Formula II;

$R^3$ is selected from an unsubstituted $C_1$-$C_{10}$ alkyl, a $C_1$-$C_{10}$ alkyl substituted with 1, 2, or 3 $R^{3a}$ substituents, a group of formula —($CR^{3b}R^{3c}$)-Q, a group of formula —($CR^{3b}R^{3c}$)—C(=O)-Q, a group of formula —($C^{3d}R^{3e}$)—($CR^{3f}R^{3g}$)-Q, a group of formula —($CR^{3d}R^{3e}$)—($CR^{3f}R^{3g}$)—C(=O)-Q, a group of formula —($CR^{3d}R^{3e}$)—($CR^{3f}R^{3g}$)—CH(OH)-Q, a group of formula —($CR^{3d}R^{3e}$)—($CR^{3f}R^{3g}$)—($CR^{3f}R^{3g}$)-Q, a group of formula —($CR^{3b}$=$CR^{3c}$)-Q, a group of formula —($C_3$-$C_8$ cycloalkyl)-Q, a group of formula -(heterocyclyl)-Q, or -Q, wherein the heterocyclyl of the -(heterocyclyl)-Q group has 5 to 7 ring members of which 1, 2, or 3 are heteroatoms independently selected from N, O, or S and is unsubstituted or is substituted with 1, 2, or 3 $R^{3h}$ substituents, and further wherein the $C_3$-$C_8$ cycloalkyl of the —($C_3$-$C_8$ cycloalkyl)-Q group is unsubstituted or is substituted with 1 or 2 $R^{3h}$ substituents;

$R^{3a}$ in each instance is independently selected from —F, —Cl, —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$C_2$-$C_6$ alkenyl, —$C_2$-$C_6$ alkynyl, —$NH_2$, —NH($C_1$-$C_6$ alkyl), or —N($C_1$-$C_6$ alkyl)$_2$;

$R^{3b}$ and $R^{3c}$ are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3d}$ and $R^{3e}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3f}$ and $R^{3g}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3h}$ in each instance is independently selected from —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)—($C_3$-$C_6$ cycloalkyl), —C(=O)—O—($C_1$-$C_6$ alkyl), oxo, or —C(=O)-(heterocyclyl), wherein the heterocyclyl group of the $R^h$—C(=O)-(heterocyclyl) has 5 or 6 ring members of which 1 or 2 are heteroatoms independently selected from N, or S or has 3 or 4 ring members of which 1 is a heteroatom selected from N, O, or S;

Q is a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a $C_3$-$C_8$ cycloalkyl group, a 3 to 10 membered heterocyclyl group containing 1, 2, or 3 heteroatoms independently selected from N, O, or S, —C(=O)NH(—$C_1$-$C_6$ alkyl), —C(=O)N(—$C_1$-$C_6$ alkyl)$_2$, or S(=O)$_2$—$C_1$-$C_6$alkyl, wherein the $C_6$-$C_{10}$ aryl, the heteroaryl, the cycloalkyl, and the heterocyclyl Q groups are unsubstituted or are substituted with 1, 2, 3, or 4 $R^Q$ substituent;

$R^Q$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —NHC(=O)($C_1$-$C_6$ alkyl), —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), —($C_1$-$C_6$ alkyl)-OH, —($C_1$-$C_6$ alkyl)-O—($C_1$-$C_6$ alkyl), phenyl, a heterocyclyl group, a —($C_1$-$C_6$ alkyl)heterocyclyl group, or a heteroaryl group with 5 or 6 ring members and 1, 2, or 3, heteroatoms independently selected from N, O, or S, wherein the heterocyclyl groups of the $R^Q$ heterocyclyl and —($C_1$-$C_6$ alkyl)heterocyclyl groups have 3 to 6 ring members of which 1 or 2 are heteroatoms independently selected from N, O, or S, wherein the Q heterocyclyl group may additionally be substituted with 1 or 2 oxo substituents, and the Q heteroaryl group may include an N-oxide if the heteroaryl includes a N heteroatom, and further wherein the heterocyclyl and the heterocyclyl of the ($C_1$-$C_6$ alkyl)heterocyclyl $R^Q$ groups may be further substituted with one or two oxo substituents and a substituent selected from —F, —Cl, —Br, —I, —CN, —OH, —$C_1$-$C_6$ alkyl, or —C(=O)—($C_1$-$C_6$ alkyl);

$R^4$ is selected from a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a monocyclic or bicyclic heterocyclyl group with 5 to 10 ring members containing 1, 2, 3, or 4 heteroatoms independently selected from N, O, or S, a monocyclic 3-6 membered cycloalkyl group, or a straight or branched chain $C_1$-$C_6$ alkyl group, wherein the $C_6$-$C_{10}$ aryl, the heteroaryl, the heterocyclyl, and the cycloalkyl $R^4$ group are unsubstituted or are substituted with 1, 2, 3, or 4 $R^{4a}$ substituents, and further wherein the straight or branched chain $C_1$-$C_6$ alkyl $R^4$ group is unsubstituted or is substituted with 1, 2, or 3 $R^{4b}$ substituents;

$R^{4a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —NH$_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, phenyl, —S(=O)$_2$—($C_1$-$C_6$ alkyl), —($C_1$-$C_6$ alkyl)-heterocyclyl, or heterocyclyl wherein the heterocyclyl of the —($C_1$-$C_6$ alkyl)-heterocyclyl and heterocyclyl $R^{4a}$ groups is a 3-6 membered ring comprising 1 or 2 heteroatoms independently selected from N, O, or S, and is unsaturated or partially unsaturated and is optionally substituted with 1 or 2 oxo substituents and may include an S=O or SO$_2$ moiety, and further wherein the heterocyclyl of the $R^4$ group may be further substituted with 1 oxo substituent; and $R^{4b}$ in each instance is selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —NH$_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, or —S(=O)$_2$—($C_1$-$C_6$ alkyl).

Numerous other embodiments of the compound of Formula I and Formula II are set forth herein.

Also provided are pharmaceutical compositions that include at least one pharmaceutically acceptable excipient, carrier or diluent and the compound or the pharmaceutically acceptable salt thereof, the tautomer thereof, the pharmaceutically acceptable salt of the tautomer, the stereoisomer of any of the foregoing, or the mixture thereof according to any one of the embodiments.

In other embodiments, the invention provides a method of treating a cardiovascular condition. Such methods typically include administering to a subject an effective amount of the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments. In some such embodiments, the cardiovascular condition is heart failure. In some such embodiments, the cardiovascular condition is heart failure with reduced ejection fraction whereas in other embodiments it is heart failure with preserved ejection fraction. Thus, in some embodiments, the cardiovascular condition is chronic systolic heart failure or chronic diastolic heart failure. In other embodiments, the cardiovascular condition is acute heart failure whereas in other embodiments, the cardiovascular condition is hypertension.

In still other embodiments, the invention provides a method of improving cardiac contractility in a subject. Such methods typically include administering to the subject an effective amount of the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments.

In still other embodiments, the invention provides a method of increasing ejection fraction in a subject suffering from a cardiovascular condition. Such methods typically include administering to the subject an effective amount of the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments. In such embodiments, the ejection fraction is increased in the subject after administration.

In still other embodiments, the invention provides a method of treating a condition in a subject where it is desired to activate the APJ Receptor. Such methods typically include administering to the subject an effective amount of the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments. In some such embodiments, the condition is obesity or diabetes whereas in other such embodiments, the condition is diabetic nephropathy.

In other embodiments, the invention provides the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments for use in treating a cardiovascular condition. In some such embodiments, the cardiovascular condition is heart failure. In some such embodiments, the cardiovascular condition is heart failure with reduced ejection fraction whereas in other embodiments it is heart failure with preserved ejection fraction. Thus, in some embodiments, the cardiovascular condition is chronic systolic heart failure or chronic diastolic heart failure. In other embodiments, the cardiovascular condition is acute heart failure whereas in other embodiments, the cardiovascular condition is hypertension.

In still other embodiments, the invention provides the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments for improving the cardiac contractility in a subject suffering from a cardiovascular condition.

In still other embodiments, the invention provides the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments for improving the ejection fraction in a subject suffering from a cardiovascular condition.

In still other embodiments, the invention provides the compound or the pharmaceutically acceptable salt thereof, the tautomer thereof, the pharmaceutically acceptable salt of the tautomer, the stereoisomer of any of the foregoing, or the mixture thereof according to any one of the embodiments or a pharmaceutical composition of any of the embodiments for treating a condition in a subject where it is desired to activate the APJ Receptor. In some such embodiments, the condition is obesity or diabetes whereas in other such embodiments, the condition is diabetic nephropathy.

Other objects, features and advantages of the invention will become apparent to those skilled in the art from the following description and claims.

DETAILED DESCRIPTION OF THE INVENTION

Figure 1A:
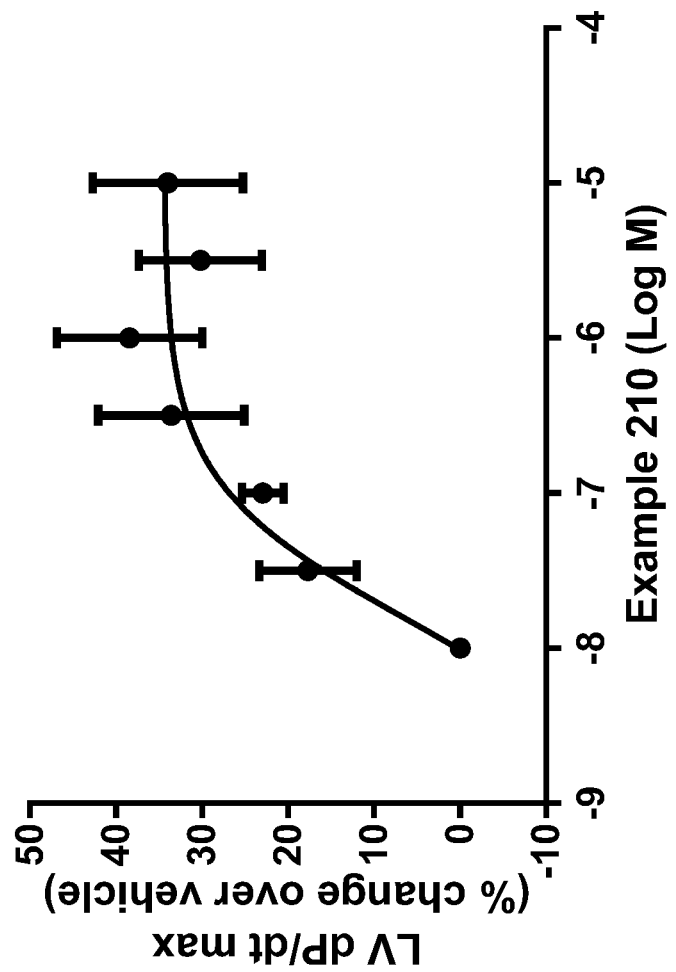
FIG. 1A is a graph of left ventricular $dP/dt_{max}$ as a function of concentration of Example 210.0 compared with vehicle in ex vivo naive Sprague Dawley rat hearts obtained using the Langendorff apparatus. This shows Example 210.0 increases load independent cardiac contractility in isolated perfused rat hearts.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the standard deviation found in their respective testing measurements.

As used herein, if any variable occurs more than one time in a chemical formula, its definition on each occurrence is independent of its definition at every other occurrence. If the chemical structure and chemical name conflict, the chemical structure is determinative of the identity of the compound. The compounds of the present disclosure may contain one or more chiral centers and/or double bonds and therefore, may exist as stereoisomers, such as double-bond isomers (i.e., geometric isomers), enantiomers or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into the component enantiomers or stereoisomers using separation techniques or chiral synthesis techniques well known to the skilled artisan.

The term "comprising" is meant to be open ended, i.e., all encompassing and non-limiting. It may be used herein synonymously with "having" or "including". Comprising is intended to include each and every indicated or recited component or element(s) while not excluding any other components or elements. For example, if a composition is said to comprise A and B. This means that the composition has A and B in it, but may also include C or even C, D, E, and other additional components.

Certain compounds of the invention may possess asymmetric carbon atoms (optical centers) or double bonds; the racemates, enantiomers, diastereomers, geometric isomers and individual isomers are all intended to be encompassed within the scope of the invention. Furthermore, atropisomers and mixtures thereof such as those resulting from restricted rotation about two aromatic or heteroaromatic rings bonded to one another are intended to be encompassed within the scope of the invention. For example, when $R^4$ is a phenyl group and is substituted with two groups bonded to the C atoms adjacent to the point of attachment to the N atom of the triazole, then rotation of the phenyl may be restricted. In some instances, the barrier of rotation is high enough that the different atropisomers may be separated and isolated.

As used herein and unless otherwise indicated, the term "stereoisomer" or "stereomerically pure" means one stereoisomer of a compound that is substantially free of other stereoisomers of that compound. For example, a stereomerically pure compound having one chiral center will be substantially free of the mirror image enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. If the stereochemistry of a structure or a portion of a structure is not indicated with, for example, bold or dashed lines, the structure or portion of the structure is to be interpreted as encompassing all stereoisomers of it. A bond drawn with a wavy line indicates that both stereoisomers are encompassed. This is not to be confused with a wavy line drawn perpendicular to a bond which indicates the point of attachment of a group to the rest of the molecule.

As described above, this invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., Enantiomers, Racemates and Resolutions (Wiley-Interscience, New York, 1981); Wilen, S. H., et al. (1997) Tetrahedron 33:2725; Eliel, E. L., Stereochemistry of Carbon Compounds (McGraw-Hill, NY, 1962); and Wilen, S. H., Tables of Resolving Agents and Optical Resolutions p. 268 (E. L. Eliel, Ed., Univ. of Notre Dame Press, Notre Dame, Ind., 1972).

As known by those skilled in the art, certain compounds of the invention may exist in one or more tautomeric forms. Because one chemical structure may only be used to represent one tautomeric form, it will be understood that for convenience, referral to a compound of a given structural formula includes tautomers of the structure represented by the structural formula.

As noted above, compounds of the invention may exist in multiple tautomeric forms. This is particularly true in compounds of Formula I where $R^2$ is H. These forms are illustrated below as Tautomer A and Tautomer B:

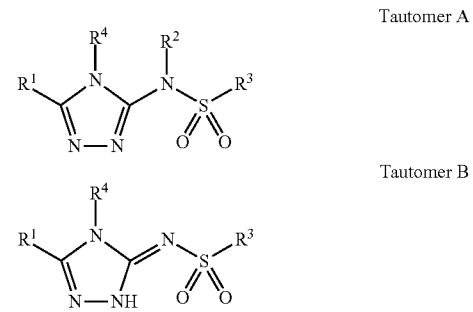

Compounds of the invention are depicted structurally and named as compounds in the "Tautomer A" form. However, it is specifically contemplated and known that the compounds exist in "Tautomer B" form and thus compounds in "Tautomer B" form are expressly considered to be part of the invention. For this reason, the claims refer to compounds of Formula I and Formula II. Depending on the compound, some compounds may exist primarily in one form more than another. Also, depending on the compound and the energy required to convert one tautomer to the other, some compounds may exist as mixtures at room temperature whereas others may be isolated in one tautomeric form or the other. Examples of other tautomers associated with compounds of the invention are those with a pyridone group (a pyridinyl) for which hydroxypyridine is a tautomer and compounds with a ketone group with the enol tautomer. Examples of these are shown below.

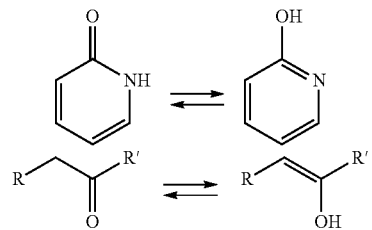

Compounds of the present disclosure include, but are not limited to, compounds of Formula I and Formula II and all pharmaceutically acceptable forms thereof. Pharmaceutically acceptable forms of the compounds recited herein include pharmaceutically acceptable salts, solvates, crystal forms (including polymorphs and clathrates), chelates, non-covalent complexes, prodrugs, and mixtures thereof. In certain embodiments, the compounds described herein are in the form of pharmaceutically acceptable salts. As used herein, the term "compound" encompasses not only the compound itself, but also a pharmaceutically acceptable salt thereof, a solvate thereof, a chelate thereof, a non-covalent complex thereof, a prodrug thereof, and mixtures of any of the foregoing. In some embodiments, the term "compound" encompasses the compound itself, pharmaceutically acceptable salts thereof, tautomers of the compound, pharmaceutically acceptable salts of the tautomers, and ester prodrugs such as ($C_1$-$C_4$)alkyl esters. In other embodiments, the term "compound" encompasses the compound itself, pharmaceutically acceptable salts thereof, tautomers of the compound, pharmaceutically acceptable salts of the tautomers.

The term "solvate" refers to the compound formed by the interaction of a solvent and a compound. Suitable solvates are pharmaceutically acceptable solvates, such as hydrates, including monohydrates and hemi-hydrates.

The compounds of the invention may also contain naturally occurring or unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). Radiolabeled compounds are useful as therapeutic or prophylactic agents, research reagents, e.g., assay reagents, and diagnostic agents, e.g., in vivo imaging agents. All isotopic variations of the compounds of the invention, whether radioactive or not, are intended to be encompassed within the scope of the invention. For example, if a variable is said or shown to be H, this means that variable may also be deuterium (D) or tritium (T).

"Alkyl" refers to a saturated branched or straight-chain monovalent hydrocarbon group derived by the removal of one hydrogen atom from a single carbon atom of a parent alkane. Typical alkyl groups include, but are not limited to, methyl, ethyl, propyls such as propan-1-yl and propan-2-yl, butyls such as butan-1-yl, butan-2-yl, 2-methyl-propan-1-yl, 2-methyl-propan-2-yl, tert-butyl, and the like. In certain embodiments, an alkyl group comprises 1 to 20 carbon atoms. In some embodiments, alkyl groups include 1 to 10 carbon atoms or 1 to 6 carbon atoms whereas in other embodiments, alkyl groups include 1 to 4 carbon atoms. In still other embodiments, an alkyl group includes 1 or 2 carbon atoms. Branched chain alkyl groups include at least 3 carbon atoms and typically include 3 to 7, or in some embodiments, 3 to 6 carbon atoms. An alkyl group having 1 to 6 carbon atoms may be referred to as a ($C_1$-$C_6$)alkyl group and an alkyl group having 1 to 4 carbon atoms may be referred to as a ($C_1$-$C_4$)alkyl. This nomenclature may also be used for alkyl groups with differing numbers of carbon atoms. The term "alkyl may also be used when an alkyl group is a substituent that is further substituted in which case a bond between a second hydrogen atom and a C atom of the alkyl substituent is replaced with a bond to another atom such as, but not limited to, a halogen, or an O, N, or S atom. For example, a group —O—($C_1$-$C_6$ alkyl)-OH will be recognized as a group where an —O atom is bonded to a $C_1$-$C_6$ alkyl group and one of the H atoms bonded to a C atom of the $C_1$-$C_6$ alkyl group is replaced with a bond to the O atom of an —OH group. As another example, a group —O—($C_1$-$C_6$ alkyl)-O—($C_1$-$C_6$ alkyl) will be recognized as a group where an —O atom is bonded to a first $C_1$-$C_6$ alkyl group and one of the H atoms bonded to a C atom of the first $C_1$-$C_6$ alkyl group is replaced with a bond to a second O atom that is bonded to a second $C_1$-$C_6$ alkyl group.

"Alkenyl" refers to an unsaturated branched or straight-chain hydrocarbon group having at least one carbon-carbon double bond derived by the removal of one hydrogen atom from a single carbon atom of a parent alkene. The group may be in either the Z- or E-form (cis or trans) about the double bond(s). Typical alkenyl groups include, but are not limited to, ethenyl; propenyls such as prop-1-en-1-yl, prop-1-en-2-yl, prop-2-en-1-yl (allyl), and prop-2-en-2-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, and buta-1,3-dien-2-yl; and the like. In certain embodiments, an alkenyl group has 2 to 20 carbon atoms and in other embodiments, has 2 to 6 carbon atoms. An alkenyl group having 2 to 6 carbon atoms may be referred to as a ($C_2$-$C_6$)alkenyl group.

"Alkynyl" refers to an unsaturated branched or straight-chain hydrocarbon having at least one carbon-carbon triple bond derived by the removal of one hydrogen atom from a single carbon atom of a parent alkyne. Typical alkynyl groups include, but are not limited to, ethynyl; propynyl; butynyl, 2-pentynyl, 3-pentynyl, 2-hexynyl, 3-hexynyl and the like. In certain embodiments, an alkynyl group has 2 to 20 carbon atoms and in other embodiments, has 2 to 6 carbon atoms. An alkynyl group having 2 to 6 carbon atoms may be referred to as a —($C_2$-$C_6$)alkynyl group.

"Alkoxy" refers to a radical —OR where R represents an alkyl group as defined herein. Representative examples include, but are not limited to, methoxy, ethoxy, propoxy, butoxy, and the like. Typical alkoxy groups include 1 to 10 carbon atoms, 1 to 6 carbon atoms or 1 to 4 carbon atoms in the R group. Alkoxy groups that include 1 to 6 carbon atoms may be designated as —O—($C_1$-$C_6$) alkyl or as —O—($C_1$-$C_6$ alkyl) groups. In some embodiments, an alkoxy group may include 1 to 4 carbon atoms and may be designated as —O—($C_1$-$C_4$) alkyl or as —O—($C_1$-$C_4$ alkyl) groups group.

"Aryl" refers to a monovalent aromatic hydrocarbon group derived by the removal of one hydrogen atom from a single carbon atom of a parent aromatic ring system. Aryl encompasses monocyclic carbocyclic aromatic rings, for example, benzene. Aryl also encompasses bicyclic carbocyclic aromatic ring systems where each of the rings is aromatic, for example, naphthalene. Aryl groups may thus include fused ring systems where each ring is a carbocyclic aromatic ring. In certain embodiments, an aryl group includes 6 to 10 carbon atoms. Such groups may be referred to as $C_6$-$C_{10}$ aryl groups. Aryl, however, does not encompass or overlap in any way with heteroaryl as separately defined below. Hence, if one or more carbocyclic aromatic rings is fused with an aromatic ring that includes at least one heteroatom, the resulting ring system is a heteroaryl group, not an aryl group, as defined herein.

"Carbonyl" refers to the radical —C(O) which may also be referred to as —C(=O) group.

"Carboxy" refers to the radical —C(O)OH which may also be referred to as —C(=O)OH.

"Cyano" refers to the radical —CN.

"Cycloalkyl" refers to a saturated cyclic alkyl group derived by the removal of one hydrogen atom from a single carbon atom of a parent cycloalkane. Typical cycloalkyl groups include, but are not limited to, groups derived from cyclopropane, cyclobutane, cyclopentane, cyclohexane, cycloheptane, cyclooctane, and the like. Cycloalkyl groups may be described by the number of carbon atoms in the ring. For example, a cycloalkyl group having 3 to 8 ring members may be referred to as a ($C_3$-$C_8$)cycloalkyl, a cycloalkyl group having 3 to 7 ring members may be referred to as a ($C_3$-$C_7$)cycloalkyl and a cycloalkyl group having 4 to 7 ring members may be referred to as a ($C_4$-$C_7$)cycloalkyl. In certain embodiments, the cycloalkyl group can be a ($C_3$-$C_{10}$)cycloalkyl, a ($C_3$-$C_8$)cycloalkyl, a ($C_3$-$C_7$)cycloalkyl, a ($C_3$-$C_6$)cycloalkyl, or a ($C_4$-$C_7$)cycloalkyl group and these may be referred to as $C_3$-$C_{10}$ cycloalkyl, $C_3$-$C_8$ cycloalkyl, $C_3$-$C_7$ cycloalkyl, $C_3$-$C_6$ cycloalkyl, or $C_4$-$C_7$ cycloalkyl groups using alternative language.

"Heterocyclyl" refers to a cyclic group that includes at least one saturated, partially unsaturated, but non-aromatic, cyclic ring. Heterocyclyl groups include at least one heteroatom as a ring member. Typical heteroatoms include, O, S and N and are independently chosen. Heterocyclyl groups include monocyclic ring systems and bicyclic ring systems. Bicyclic heterocyclyl groups include at least one non-aromatic ring with at least one heteroatom ring member that may be fused to a cycloalkyl ring or may be fused to an aromatic ring where the aromatic ring may be carbocyclic or may include one or more heteroatoms. The point of attachment of a bicyclic heterocyclyl group may be at the non-aromatic cyclic ring that includes at least one heteroatom or at another ring of the heterocyclyl group. For example, a heterocyclyl group derived by removal of a hydrogen atom from one of the 9 membered heterocyclic compounds shown below may be attached to the rest of the molecule at the 5-membered ring or at the 6-membered ring.

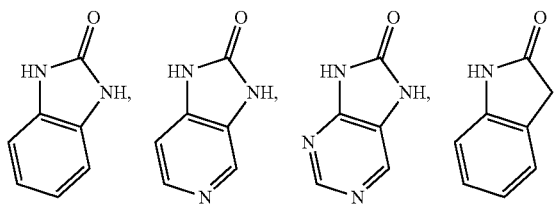 [SMILES: O=c1[nH]c2ccccc2[nH]1 ; O=c1[nH]c2ccncc2[nH]1 ; O=c1[nH]c2cncnc2[nH]1 ; O=C1Cc2ccccc2N1]

In some embodiments, a heterocyclyl group includes 5 to 10 ring members of which 1, 2, 3 or 4 or 1, 2, or 3 are heteroatoms independently selected from O, S, or N. In other embodiments, a heterocyclyl group includes 3 to 7 ring members of which 1, 2, or 3 heteroatom are independently selected from O, S, or N. In such 3-7 membered heterocyclyl groups, only 1 of the ring atoms is a heteroatom when the ring includes only 3 members and includes 1 or 2 heteroatoms when the ring includes 4 members. In some embodiments, a heterocyclyl group includes 3 or 4 ring members of which 1 is a heteroatom selected from O, S, or N. In other embodiments, a heterocyclyl group includes 5 to 7 ring members of which 1, 2, or 3 are heteroatoms independently selected from O, S, or N. Typical heterocyclyl groups include, but are not limited to, groups derived from epoxides, aziridine, azetidine, imidazolidine, morpholine, piperazine, piperidine, hexahydropyrimidine, 1,4,5,6-tetrahydropyrimidine, pyrazolidine, pyrrolidine, quinuclidine, tetrahydrofuran, tetrahydropyran, benzimidazolone, pyridinone, and the like. Heterocyclyl groups may be fully saturated, but may also include one or more double bonds. Examples of such heterocyclyl groups include, but are not limited to, 1,2,3,6-tetrahydropyridinyl, 3,6-dihydro-2H-pyranyl, 3,4-dihydro-2H-pyranyl, 2,5-dihydro-1H-pyrolyl, 2,3-dihydro-1H-pyrolyl, 1H-azirinyl, 1,2-dihydroazetenyl, and the like. Substituted heterocyclyl also includes ring systems substituted with one or more oxo (=O) or oxide (—O⁻) substituents, such as piperidinyl N-oxide, morpholinyl-N-oxide, 1-oxo-1-thiomorpholinyl, pyridinonyl, benzimidazolonyl, benzo[d]oxazol-2(3H)-only, 3,4-dihydroisoquinolin-1(2H)-only, indolin-only, 1H-imidazo[4,5-c]pyridin-2(3H)-only, 7H-purin-8(9H)-only, imidazolidin-2-only, 1H-imidazol-2(3H)-only, 1,1-dioxo-1-thiomorpholinyl, and the like.

"Disease" refers to any disease, disorder, condition, symptom, or indication.

"Halo" or "halogen" refers to a fluoro, chloro, bromo, or iodo group.

"Haloalkyl" refers to an alkyl group in which at least one hydrogen is replaced with a halogen. Thus, the term "haloalkyl" includes monohaloalkyl (alkyl substituted with one halogen atom) and polyhaloalkyl (alkyl substituted with two or more halogen atoms). Representative "haloalkyl" groups include difluoromethyl, 2,2,2-trifluoroethyl, 2,2,2-trichloroethyl, and the like. The term "perhaloalkyl" means, unless otherwise stated, an alkyl group in which each of the hydrogen atoms is replaced with a halogen atom. For example, the term "perhaloalkyl", includes, but is not limited to, trifluoromethyl, pentachloroethyl, 1,1,1-trifluoro-2-bromo-2-chloroethyl, and the like.

"Heteroaryl" refers to a monovalent heteroaromatic group derived by the removal of one hydrogen atom from a single atom of a parent heteroaromatic ring system. Heteroaryl groups typically include 5- to 14-membered, but more typically include 5- to 10-membered aromatic, monocyclic, bicyclic, and tricyclic rings containing one or more, for example, 1, 2, 3, or 4, or in certain embodiments, 1, 2, or 3, heteroatoms chosen from O, S, or N, with the remaining ring atoms being carbon. In monocyclic heteroaryl groups, the single ring is aromatic and includes at least one heteroatom. In some embodiments, a monocyclic heteroaryl group may include 5 or 6 ring members and may include 1, 2, 3, or 4 heteroatoms, 1, 2, or 3 heteroatoms, 1 or 2 heteroatoms, or 1 heteroatom where the heteroatom(s) are independently selected from O, S, or N. In bicyclic aromatic rings, both rings are aromatic. In bicyclic heteroaryl groups, at least one of the rings must include a heteroatom, but it is not necessary that both rings include a heteroatom although it is permitted for them to do so. For example, the term "heteroaryl" includes a 5- to 7-membered heteroaromatic ring fused to a carbocyclic aromatic ring or fused to another heteroaromatic ring. In tricyclic aromatic rings, all three of the rings are aromatic and at least one of the rings includes at least one heteroatom. For fused, bicyclic and tricyclic heteroaryl ring systems where only one of the rings contains one or more heteroatoms, the point of attachment may be at the ring including at least one heteroatom or at a carbocyclic ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Heteroaryl does not encompass or overlap with aryl as defined above. Examples of heteroaryl groups include, but are not limited to, groups derived from acridine, carbazole, cinnoline, furan, imidazole, indazole, indole, indolizine, isobenzofuran, isochromene, isoindole, isoquinoline, isothiazole, 2H-benzo[d][1,2,3]triazole, isoxazole, naphthyridine, oxadiazole, oxazole, perimidine, phenanthridine, phenanthroline, phenazine, phthalazine, pteridine, purine, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, and the like. In certain embodiments, the heteroaryl group can be between 5 to 20 membered heteroaryl, such as, for example, a 5 to 14 membered or 5 to 10 membered heteroaryl. In certain embodiments, heteroaryl groups can be those derived from thiophene, pyrrole, benzothiophene, 2H-benzo[d][1,2,3]triazole benzofuran, indole, pyridine, quinoline, imidazole, benzimidazole, oxazole, tetrazole, and pyrazine.

"Pharmaceutically acceptable" refers to generally recognized for use in animals, and more particularly in humans.

"Pharmaceutically acceptable salt" refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine, dicyclohexylamine, and the like.

"Pharmaceutically acceptable excipient" refers to a broad range of ingredients that may be combined with a compound or salt of the present invention to prepare a pharmaceutical composition or formulation. Typically, excipients include, but are not limited to, diluents, colorants, vehicles, anti-adherants, glidants, disintegrants, flavoring agents, coatings, binders, sweeteners, lubricants, sorbents, preservatives, and the like.

"Stereoisomer" refers to an isomer that differs in the arrangement of the constituent atoms in space. Stereoisomers that are mirror images of each other and optically active are termed "enantiomers," and stereoisomers that are not mirror images of one another and are optically active are termed "diastereomers."

"Subject" includes mammals and humans. The terms "human" and "subject" are used interchangeably herein.

"Therapeutically effective amount" refers to the amount of a compound that, when administered to a subject for treating a disease, or at least one of the clinical symptoms of a disease or disorder, is sufficient to affect such treatment for the disease, disorder, or symptom. As those skilled in the art will recognize this amount is typically not limited to a single dose, but may comprise multiple dosages over a significant period of time as required to bring about a therapeutic or prophylactic response in the subject. Thus, a "therapeutically effective amount" is not limited to the amount in a single capsule or tablet, but may include more than one capsule or tablet, which is the dose prescribed by a qualified physician or medical care provider. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be readily apparent to those skilled in the art or capable of determination by routine experimentation.

"Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, or inhibiting at least one physical parameter which may not be discernible to the subject. Further, "treating" or "treatment" refers to delaying the onset of the disease or disorder or at least symptoms thereof in a subject which may be exposed to or predisposed to a disease or disorder even though that subject does not yet experience or display symptoms of the disease or disorder.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

Embodiments

The embodiments listed below are presented in numbered form for convenience and in ease and clarity of reference in referring back to multiple embodiments.

1. In a first embodiment, the invention provides a compound of Formula I or Formula II:

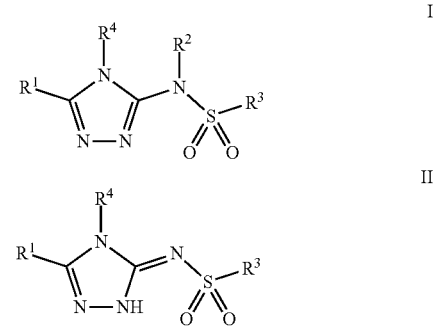

or a pharmaceutically acceptable salt thereof, a tautomer thereof, a pharmaceutically acceptable salt of the tautomer, a stereoisomer of any of the foregoing, or a mixture thereof, wherein:

$R^1$ is an unsubstituted furanyl, or is a furanyl substituted with 1, 2, or 3 $R^{1a}$ substituents;

$R^{1a}$ in each instance is independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), or —C(=O)N($C_1$-$C_6$ alkyl)$_2$;

$R^2$ is selected from —H, or $C_1$-$C_4$ alkyl or is absent in the compounds of Formula II;

$R^3$ is selected from an unsubstituted $C_1$-$C_{10}$ alkyl, a $C_1$-$C_{10}$ alkyl substituted with 1, 2, or 3 $R^{3a}$ substituents, a group of formula —($CR^{3b}R^{3c}$)-Q, a group of formula —($CR^{3b}R^{3c}$)—C(=O)-Q, a group of formula —(CR$^{3d}$R$^{3e}$)—(CR$^{3f}$R$^{3g}$)-Q, a group of formula —(CR$^{3d}$R$^{3e}$)—(CR$^{3f}$R$^{3g}$)—C(=O)-Q, a group of formula —(CR$^{3d}$R$^{3e}$)—(CR$^{3f}$R$^{3g}$)—CH(OH)-Q, a group of formula —(CR$^{3d}$R$^{3e}$)—(CR$^{3f}$R$^{3g}$)-Q, a group of formula —(CR$^{3b}$=CR$^{3c}$)-Q, a group of formula —(C$_3$-C$_8$ cycloalkyl)-Q, a group of formula -(heterocyclyl)-Q, wherein the heterocyclyl of the -(heterocyclyl)-Q group has 5 to 7 ring members of which 1, 2, or 3 are heteroatoms independently selected from N, O, or S and is unsubstituted or is substituted with 1, 2, or 3 R$^{3h}$ substituents, and further wherein the C$_3$-C$_8$ cycloalkyl of the —(C$_3$-C$_8$ cycloalkyl)-Q group is unsubstituted or is substituted with 1 or 2 R$^{3h}$ substituents;

R$^{3a}$ in each instance is independently selected from —F, —Cl, —CN, —OH, —O—(C$_1$-C$_6$ alkyl), —O—(C$_1$-C$_6$ haloalkyl), —O—(C$_1$-C$_6$ perhaloalkyl), —O—(C$_1$-C$_6$ alkyl)-OH, —O—(C$_1$-C$_6$ alkyl)-O—(C$_1$-C$_6$ alkyl), —C$_2$-C$_6$ alkenyl, —C$_2$-C$_6$ alkynyl, —NH$_2$, —NH(C$_1$-C$_6$ alkyl), or —N(C$_1$-C$_6$ alkyl)$_2$;

R$^{3b}$ and R$^{3c}$ are independently selected from —H, —F, —Cl, —CN, —C$_1$-C$_6$ alkyl, —C$_1$-C$_6$ haloalkyl, —C$_1$-C$_6$ perhaloalkyl, —OH, —O—(C$_1$-C$_6$ alkyl), —O—(C$_1$-C$_6$ haloalkyl), —O—(C$_1$-C$_6$ perhaloalkyl), —O—(C$_1$-C$_6$ alkyl)-OH, —O—(C$_1$-C$_6$ alkyl)-O—(C$_1$-C$_6$ alkyl), —NH$_2$, —NH(C$_1$-C$_6$ alkyl), or —N(C$_1$-C$_6$ alkyl)$_2$;

R$^{3d}$ and R$^{3e}$ are independently selected from —H, —F, —Cl, —CN, —C$_1$-C$_6$ alkyl, —C$_1$-C$_6$ haloalkyl, —C$_1$-C$_6$ perhaloalkyl, —OH, —(C$_1$-C$_6$ alkyl)-OH, —(C$_1$-C$_6$ alkyl)-O—(C$_1$-C$_6$ alkyl), —O—(C$_1$-C$_6$ alkyl), —O—(C$_1$-C$_6$ haloalkyl), —O—(C$_1$-C$_6$ perhaloalkyl), —O—(C$_1$-C$_6$ alkyl)-OH, —O—(C$_1$-C$_6$ alkyl)-O—(C$_1$-C$_6$ alkyl), —NH$_2$, —NH(C$_1$-C$_6$ alkyl), or —N(C$_1$-C$_6$ alkyl)$_2$;

R$^{3f}$ and R$^{3g}$ are independently selected from —H, —F, —Cl, —CN, —C$_1$-C$_6$ alkyl, —C$_1$-C$_6$ haloalkyl, —C$_1$-C$_6$ perhaloalkyl, —OH, —(C$_1$-C$_6$ alkyl)-OH, —(C$_1$-C$_6$ alkyl)-O—(C$_1$-C$_6$ alkyl), —O—(C$_1$-C$_6$ alkyl), —O—(C$_1$-C$_6$ haloalkyl), —O—(C$_1$-C$_6$ perhaloalkyl), —O—(C$_1$-C$_6$ alkyl)-OH, —O—(C$_1$-C$_6$ alkyl)-O—(C$_1$-C$_6$ alkyl), —NH$_2$, —NH(C$_1$-C$_6$ alkyl), or —N(C$_1$-C$_6$ alkyl)$_2$;

R$^{3h}$ in each instance is independently selected from —F, —Cl, —CN, —C$_1$-C$_6$ alkyl, —C$_1$-C$_6$ haloalkyl, —C$_1$-C$_6$ perhaloalkyl, —OH, —O—(C$_1$-C$_6$ alkyl), —O—(C$_1$-C$_6$ haloalkyl), —O—(C$_1$-C$_6$ perhaloalkyl), —O—(C$_1$-C$_6$ alkyl)-OH, —O—(C$_1$-C$_6$ alkyl)-O—(C$_1$-C$_6$ alkyl), —NH$_2$, —NH(C$_1$-C$_6$ alkyl), —N(C$_1$-C$_6$ alkyl)$_2$, —C(=O)—(C$_1$-C$_6$ alkyl), —C(=O)—(C$_3$-C$_6$ cycloalkyl), —C(=O)—O—(C$_1$-C$_6$ alkyl), oxo, or —C(=O)-(heterocyclyl), wherein the heterocyclyl group of the R$^h$—C(=O)-(heterocyclyl) has 5 or 6 ring members of which 1 or 2 are heteroatoms independently selected from N, or S or has 3 or 4 ring members of which 1 is a heteroatom selected from N, O, or S;

Q is a monocyclic or bicyclic C$_6$-C$_{10}$ aryl group, a monocyclic or bicyclic heteroaryl group with 5 to 10 ring members containing 1, 2, or 3 heteroatoms independently selected from N, O, or S, a C$_3$-C$_8$ cycloalkyl group, a 3 to 10 membered heterocyclyl group containing 1, 2, or 3 heteroatoms independently selected from N, O, or S, —C(=O)NH(—C$_1$-C$_6$ alkyl), —C(=O)N(—C$_1$-C$_6$ alkyl)$_2$, or —S(=O)$_2$—C$_1$-C$_6$alkyl, wherein the C$_6$-C$_{10}$ aryl, the heteroaryl, the cycloalkyl, and the heterocyclyl Q groups are unsubstituted or are substituted with 1, 2, 3, or 4 R$^Q$ substituent;

R$^Q$ in each instance is independently selected from —F, —Cl, —Br, —I, —CN, —C$_1$-C$_6$ alkyl, —C$_1$-C$_6$ haloalkyl, —C$_1$-C$_6$ perhaloalkyl, —C$_2$-C$_6$ alkenyl, —C$_2$-C$_6$ alkynyl, —OH, —O—(C$_1$-C$_6$ alkyl), —O—(C$_1$-C$_6$ haloalkyl), —O—(C$_1$-C$_6$ perhaloalkyl), —NH$_2$, —NH(C$_1$-C$_6$ alkyl), —N(C$_1$-C$_6$ alkyl)$_2$, —NHC(=O)(C$_1$-C$_6$ alkyl), —C(=O)—(C$_1$-C$_6$ alkyl), —C(=O)OH, —C(=O)—O—(C$_1$-C$_6$ alkyl), —C(=O)NH$_2$, —C(=O)NH(C$_1$-C$_6$ alkyl), —C(=O)N(C$_1$-C$_6$ alkyl)$_2$, —S(=O)$_2$—(C$_1$-C$_6$ alkyl), —(C$_1$-C$_6$ alkyl)-OH, —(C$_1$-C$_6$ alkyl)-O—(C$_1$-C$_6$ alkyl), phenyl, a heterocyclyl group, a —(C$_1$-C$_6$ alkyl)heterocyclyl group, or a heteroaryl group with 5 or 6 ring members and 1, 2, or 3, heteroatoms independently selected from N, O, or S, wherein the heterocyclyl groups of the R$^Q$ heterocyclyl and —(C$_1$-C$_6$ alkyl)heterocyclyl groups have 3 to 6 ring members of which 1 or 2 are heteroatoms independently selected from N, O, or S, wherein the Q heterocyclyl group may additionally be substituted with 1 or 2 oxo substituents, and the Q heteroaryl group may include an N-oxide if the heteroaryl includes a N heteroatom, and further wherein the heterocyclyl and the heterocyclyl of the —(C$_1$-C$_6$ alkyl) heterocyclyl R$^Q$ groups may be further substituted with one or two oxo substituents and a substituent selected from —F, —Cl, —Br, —I, —CN, —OH, —C$_1$-C$_6$ alkyl, or —C(=O)—(C$_1$-C$_6$ alkyl);

R$^4$ is selected from a monocyclic or bicyclic C$_6$-C$_{10}$ aryl group, a monocyclic or bicyclic heteroaryl group with 5 to 10 ring members containing 1, 2, or 3 heteroatoms independently selected from N, O, or S, a monocyclic or bicyclic heterocyclyl group with 5 to 10 ring members containing 1, 2, 3, or 4 heteroatoms independently selected from N, O, or S, a monocyclic 3-6 membered cycloalkyl group, or a straight or branched chain C$_1$-C$_6$ alkyl group, wherein the C$_6$-C$_{10}$ aryl, the heteroaryl, the heterocyclyl, and the cycloalkyl R$^4$ group are unsubstituted or are substituted with 1, 2, 3, or 4 R$^{4a}$ substituents, and further wherein the straight or branched chain C$_1$-C$_6$ alkyl R$^4$ group is unsubstituted or is substituted with 1, 2, or 3 R$^{4b}$ substituents;

R$^{4a}$ in each instance is independently selected from —F, —Cl, —Br, —I, —CN, —C$_1$-C$_6$ alkyl, —C$_1$-C$_6$ haloalkyl, —C$_1$-C$_6$ perhaloalkyl, —(C$_1$-C$_6$ alkyl)-OH, —(C$_1$-C$_6$ alkyl)-O—(C$_1$-C$_6$ alkyl), —OH, —O—(C$_1$-C$_6$ alkyl), —O—(C$_1$-C$_6$ haloalkyl), —O—(C$_1$-C$_6$ perhaloalkyl), —NH$_2$, —NH(C$_1$-C$_6$ alkyl), —N(C$_1$-C$_6$ alkyl)$_2$, NH(C$_1$-C$_6$ alkyl-OH), —N(C$_1$-C$_6$ alkyl-OH)$_2$, —C(=O)—(C$_1$-C$_6$ alkyl), —C(=O)OH, —C(=O)—O—(C$_1$-C$_6$ alkyl), —C(=O)NH$_2$, —C(=O)NH(C$_1$-C$_6$ alkyl), —C(=O)N(C$_1$-C$_6$ alkyl)$_2$, phenyl, —S(=O)$_2$—(C$_1$-C$_6$ alkyl), —(C$_1$-C$_6$ alkyl)-heterocyclyl, or heterocyclyl wherein the heterocyclyl of the —(C$_1$-C$_6$ alkyl)-heterocyclyl and heterocyclyl R$^{4a}$ groups is a 3-6 membered ring comprising 1 or 2 heteroatoms independently selected from N, O, or S, and is unsaturated or partially unsaturated and is optionally substituted with 1 or 2 oxo substituents and may include an S=O or SO$_2$ moiety, and further wherein the heterocyclyl of the R$^4$ group may be further substituted with 1 oxo substituent; and R$^{4b}$ in each instance is selected from —F, —Cl, —Br, —I, —CN, —OH, —O—(C$_1$-C$_6$ alkyl), —O—(C$_1$-C$_6$ haloalkyl), —O—(C$_1$-C$_6$ perhaloalkyl), —NH$_2$, —NH(C$_1$-C$_6$ alkyl), —N(C$_1$-C$_6$ alkyl)$_2$, NH(C$_1$-C$_6$ alkyl-OH), —N(C$_1$-C$_6$ alkyl-OH)$_2$, —C(=O)—(C$_1$-C$_6$ alkyl), —C(=O)OH, —C(=O)—O—(C$_1$-C$_6$ alkyl), —C(=O)NH$_2$, —C(=O)NH(C$_1$-C$_6$ alkyl), —C(=O)N(C$_1$-C$_6$ alkyl)$_2$, or —S(=O)$_2$—(C$_1$-C$_6$ alkyl).

In some embodiments of the compound of embodiment 1 or the pharmaceutically acceptable salt thereof, the tautomer thereof, the pharmaceutically acceptable salt of the tautomer, the stereoisomer of any of the foregoing, or the mixture thereof, R$^1$ is a furan-2yl that is unsubstituted or is substituted with 1 or 2 R$^{1a}$ substituents;

$R^{1a}$ is independently selected from —F, —Cl, —Br, —I, —$C_1$-$C_6$ alkyl, —$C_1$-$C_6$ haloalkyl, —$C_1$-$C_6$ perhaloalkyl, or —($C_1$-$C_6$ alkyl)-O—($C_1$-$C_6$ alkyl);

$R^2$ is —H;

$R^3$ is a group of formula —($CR^{3d}R^{3e}$)—($CR^{3f}R^{3g}$)-Q;

$R^{3d}$ and $R^{3e}$ are independently selected from —H, —$C_1$-$C_6$ alkyl, —($C_1$-$C_6$ alkyl)-OH, or —($C_1$-$C_6$ alkyl)-O—($C_1$-$C_6$ alkyl);

$R^{3f}$ and $R^{3g}$ are independently selected from —H, —F, —$C_1$-$C_6$ alkyl, —OH, —O—($C_1$-$C_6$ alkyl), —O—($C_1$-$C_6$ alkyl)-OH, —O—($C_1$-$C_6$ alkyl)-O—($C_1$-$C_6$ alkyl), or —$NH_2$;

Q is a monocyclic heteroaryl group with 5 or 6 ring members containing 1 or 2 heteroatoms selected from N, O, or S, and Q is unsubstituted or is substituted with 1 or 2 $R^Q$ substituents;

$R^4$ is a phenyl substituted with 1, 2, or 3 $R^{4a}$ substituent; and $R^{4a}$ is independently selected from —F, —Br, —CN, —$C_1$-$C_6$ alkyl, —$C_1$-$C_6$ haloalkyl, —$C_1$-$C_6$ perhaloalkyl, —($C_1$-$C_6$ alkyl)-OH, —O—($C_1$-$C_6$ alkyl), —O—($C_1$-$C_6$ haloalkyl), —O—($C_1$-$C_6$ perhaloalkyl), or —($C_1$-$C_6$ alkyl)-heterocyclyl, wherein the heterocyclyl of the —($C_1$-$C_6$ alkyl)-heterocyclyl $R^{4a}$ group is a 3-6 membered ring comprising 1 or 2 heteroatoms independently selected from N, O, or S.

In some such embodiments, $R^4$ is a phenyl substituted with 2-O—($C_1$-$C_6$ alkyl) $R^{4a}$ substituents such as with 2-O—($C_1$-$C_2$ alkyl) substituents or in some embodiments with 2 —$OCH_3$ groups. In some such embodiments, Q is a pyrimidinyl, pyridinyl, or pyrazinyl group substituted with 1 on 2 $R^Q$ substituent.

2. The compound of embodiment 1 or the pharmaceutically acceptable salt thereof, the tautomer thereof, the pharmaceutically acceptable salt of the tautomer, the stereoisomer of any of the foregoing, or the mixture thereof, wherein $R^1$ is an unsubstituted furan-2-yl or is a furan-2-yl substituted with 1, 2, or 3 $R^{1a}$ substituents.

3. The compound of embodiment 1 or embodiment 2 or the pharmaceutically acceptable salt thereof, the tautomer thereof, the pharmaceutically acceptable salt of the tautomer, the stereoisomer of any of the foregoing, or the mixture thereof, wherein $R^1$ is a an unsubstituted furan-2-yl or a furan-2-yl substituted with 1 or 2 $R^{1a}$ substituents independently selected from —F, —Cl, —Br, —I, —$C_1$-$C_6$ alkyl, —$C_1$-$C_6$ haloalkyl, —$C_1$-$C_6$ perhaloalkyl, or —($C_1$-$C_6$ alkyl)-O—($C_1$-$C_6$ alkyl).

4. The compound of embodiment 3 or the pharmaceutically acceptable salt thereof, the tautomer thereof, the pharmaceutically acceptable salt of the tautomer, the stereoisomer of any of the foregoing, or the mixture thereof, wherein $R^1$ is an unsubstituted or substituted furan-2-yl having the formula

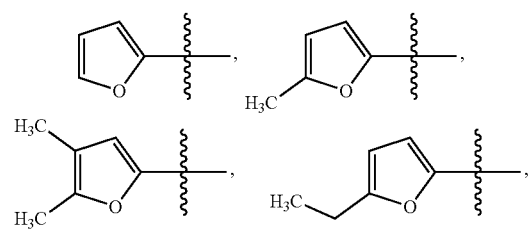

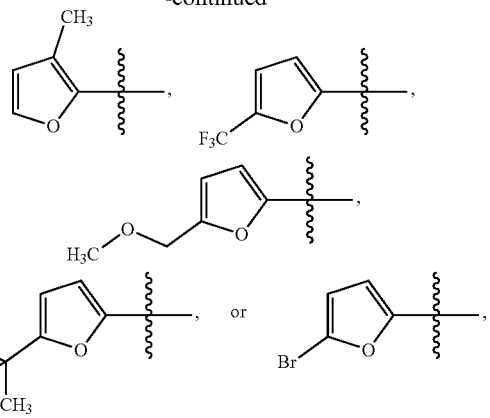

wherein the symbol ∿, when drawn across a bond, indicates the point of attachment to the rest of the molecule.

5. The compound of embodiment 4 or the pharmaceutically acceptable salt thereof, the tautomer thereof, the pharmaceutically acceptable salt of the tautomer, the stereoisomer of any of the foregoing, or the mixture thereof, wherein $R^1$ is a furan-2-yl having the formula

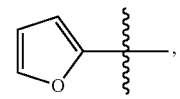

wherein the symbol ∿, when drawn across a bond, indicates the point of attachment to the rest of the molecule.

6. The compound of embodiment 4 or the pharmaceutically acceptable salt thereof, the tautomer thereof, the pharmaceutically acceptable salt of the tautomer, the stereoisomer of any of the foregoing, or the mixture thereof, wherein $R^1$ is a furan-2-yl having the formula

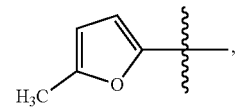

wherein the symbol ∿, when drawn across a bond, indicates the point of attachment to the rest of the molecule.

7. The compound of any one of embodiments 1-3 or the pharmaceutically acceptable salt thereof, the tautomer thereof, the pharmaceutically acceptable salt of the tautomer, the stereoisomer of any of the foregoing, or the mixture thereof, wherein $R^1$ is an unsubstituted furan-2-yl or a substituted furan-2-yl and $R^{1a}$ is independently selected from —$CH_3$, —$CH_2CH_3$, —$C(CH_3)_3$, —$CF_3$, —$CH_2OCH_3$, or —Br.

8. The compound of any one of embodiments 1-7 or the pharmaceutically acceptable salt thereof, the tautomer thereof, the pharmaceutically acceptable salt of the tautomer, the stereoisomer of any of the foregoing, or the mixture thereof, wherein $R^2$ is —H or is absent in the compounds of Formula II.

9. The compound of any one of embodiments 1-8 or the pharmaceutically acceptable salt thereof, the tautomer thereof, the pharmaceutically acceptable salt of the tautomer, the stereoisomer of any of the foregoing, or the mixture thereof, wherein $R^2$ is —H.

10. The compound of any one of embodiments 1-9 or the pharmaceutically acceptable salt thereof, the tautomer thereof, the pharmaceutically acceptable salt of the tautomer, the stereoisomer of any of the foregoing, or the mixture thereof, wherein $R^4$ is a phenyl, pyridinyl, pyrimidinyl, naphthyl, tetrahydropyranyl, cyclohexyl, cyclopentyl, or cyclopropyl, any of which may be unsubstituted or substituted with 1, 2, 3, or 4 $R^{4a}$ substituents.

11. The compound of any one of embodiments 1-10 or the pharmaceutically acceptable salt thereof, the tautomer thereof, the pharmaceutically acceptable salt of the tautomer, the stereoisomer of any of the foregoing, or the mixture thereof, wherein $R^{4a}$ is in each instance independently selected from —F, —Br, —CN, —$C_1$-$C_6$ alkyl, —$C_1$-$C_6$ haloalkyl, —$C_1$-$C_6$ perhaloalkyl, —($C_1$-$C_6$ alkyl)-OH, —O—($C_1$-$C_6$ alkyl), —O—($C_1$-$C_6$ haloalkyl), —O—($C_1$-$C_6$ perhaloalkyl), or —($C_1$-$C_6$ alkyl)-heterocyclyl, wherein the heterocyclyl of the —($C_1$-$C_6$ alkyl)-heterocyclyl $R^{4a}$ group is a 3-6 membered ring comprising 1 or 2 heteroatoms independently selected from N, O, or S.

12. The compound of embodiment 11 or the pharmaceutically acceptable salt thereof, the tautomer thereof, the pharmaceutically acceptable salt of the tautomer, the stereoisomer of any of the foregoing, or the mixture thereof, wherein $R^{4a}$ is in each instance independently selected from —$CH_3$, —F, —Br, —CN, —$CF_3$, —$OCH_3$, —$CH_2OH$, or —$CH_2$-pyrrolidine.

13. The compound of any one of embodiments 1-9 or the pharmaceutically acceptable salt thereof, the tautomer thereof, the pharmaceutically acceptable salt of the tautomer, the stereoisomer of any of the foregoing, or the mixture thereof, wherein $R^4$ is selected from

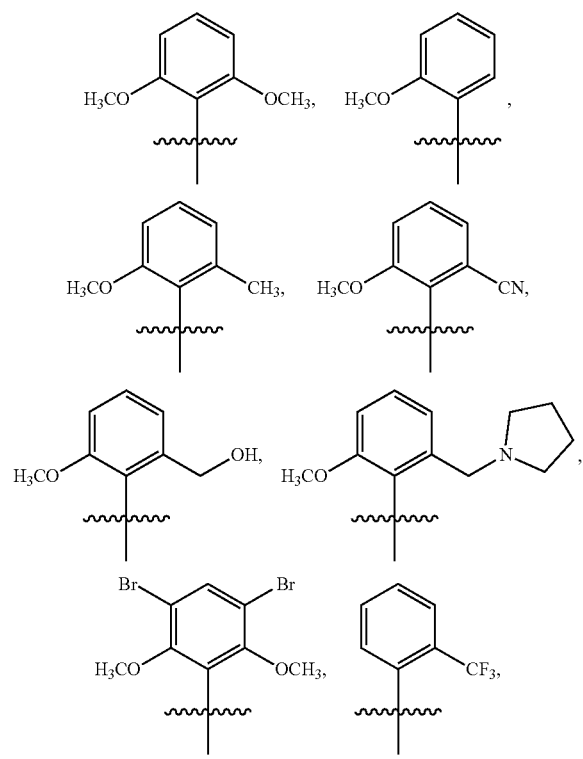

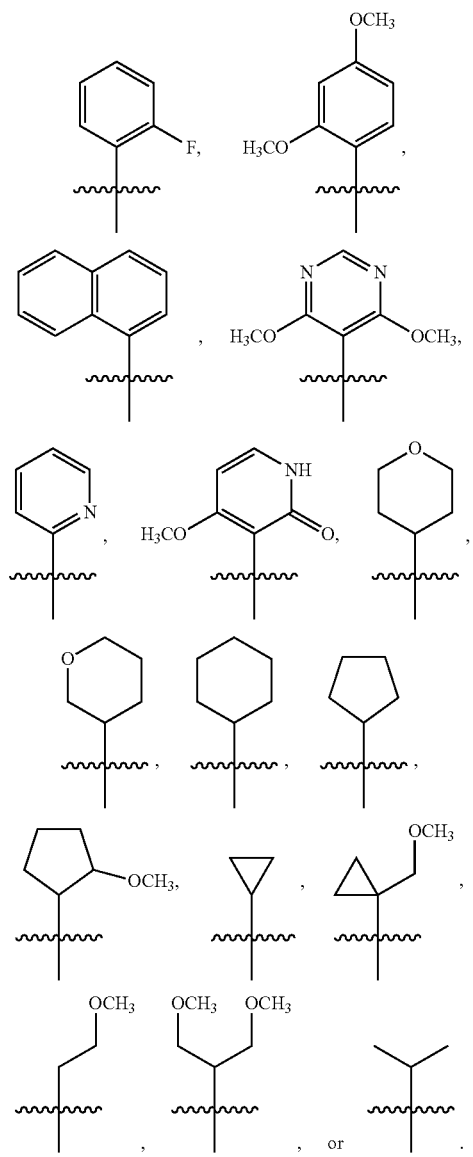

wherein the symbol ⁓, when drawn across a bond, indicates the point of attachment to the rest of the molecule.

14. The compound of any one of embodiments 1-9 or the pharmaceutically acceptable salt thereof, the tautomer thereof, the pharmaceutically acceptable salt of the tautomer, the stereoisomer of any of the foregoing, or the mixture thereof, wherein $R^4$ is a phenyl substituted with 1 or 2 $R^{4a}$ substituents.

15. The compound of embodiment 14 or the pharmaceutically acceptable salt thereof, the tautomer thereof, the pharmaceutically acceptable salt of the tautomer, the stereoisomer of any of the foregoing, or the mixture thereof, wherein the $R^{4a}$ substituents are —O—($C_1$-$C_2$ alkyl) groups.

16. The compound of embodiment 15 or the pharmaceutically acceptable salt thereof, the tautomer thereof, the pharmaceutically acceptable salt of the tautomer, the stereoisomer of any of the foregoing, or the mixture thereof, wherein $R^4$ is

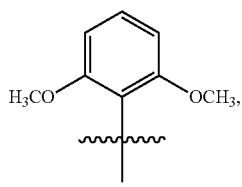

wherein the symbol ⌇, when drawn across a bond, indicates the point of attachment to the rest of the molecule.

17. The compound of any one of embodiments 1-16 or the pharmaceutically acceptable salt thereof, the tautomer thereof, the pharmaceutically acceptable salt of the tautomer, the stereoisomer of any of the foregoing, or the mixture thereof, wherein Q is selected from pyrimidinyl, pyrazinyl, pyradizinyl, pyridinyl, phenyl, oxazolyl, thiazolyl, imidazolyl, pyrazolyl, piperidin-2-onyl, tetrahydropyrimidin-2(1H)-onyl, 1,3-oxazinan-2-onyl, pyrrolidin-2-onyl, pyrrolidinyl, cyclohexyl, benzimidazolyl, isoindolinonyl, 1H-imidazo[4,5-c]pyridinyl, pyrazolo[1,5-a]pyridinyl, imidazo[1,2-a]pyridinyl, imidazo[1,5-a]pyridinyl, 6,7-dihydro-5H-pyrazolo[5,1-b][1,3]oxazinyl, or 3,4-dihydro-2H-pyrano[3,2-b]pyridinyl, any of which may be unsubstituted or substituted with 1 or 2 $R^Q$ substituents.

18. The compound of embodiment 17 or the pharmaceutically acceptable salt thereof, the tautomer thereof, the pharmaceutically acceptable salt of the tautomer, the stereoisomer of any of the foregoing, or the mixture thereof, wherein Q is an unsubstituted phenyl or is a phenyl substituted with 1 or 2 $R^Q$ substituents.

19. The compound of any one of embodiments 1-16 or the pharmaceutically acceptable salt thereof, the tautomer thereof, the pharmaceutically acceptable salt of the tautomer, the stereoisomer of any of the foregoing, or the mixture thereof, wherein Q is a monocyclic heteroaryl group with 5 or 6 ring members containing 1 or 2 heteroatoms selected from N, O, or S and Q is unsubstituted or is substituted with 1 or 2 $R^Q$ substituents.

20. The compound of embodiment 19 or the pharmaceutically acceptable salt thereof, the tautomer thereof, the pharmaceutically acceptable salt of the tautomer, the stereoisomer of any of the foregoing, or the mixture thereof, wherein Q is a pyrimidinyl, pyridinyl, or pyrazinyl group and Q is unsubstituted or is substituted with 1 or 2 $R^Q$ substituents.

21. The compound of any one of embodiments 1-16 or the pharmaceutically acceptable salt thereof, the tautomer thereof, the pharmaceutically acceptable salt of the tautomer, the stereoisomer of any of the foregoing, or the mixture thereof, wherein Q is selected from

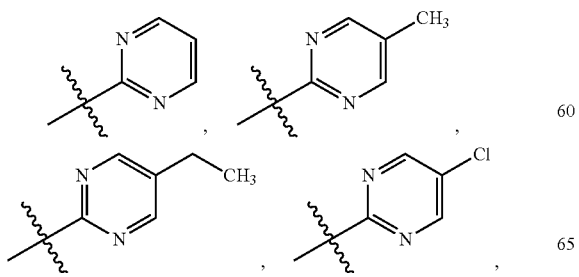

-continued

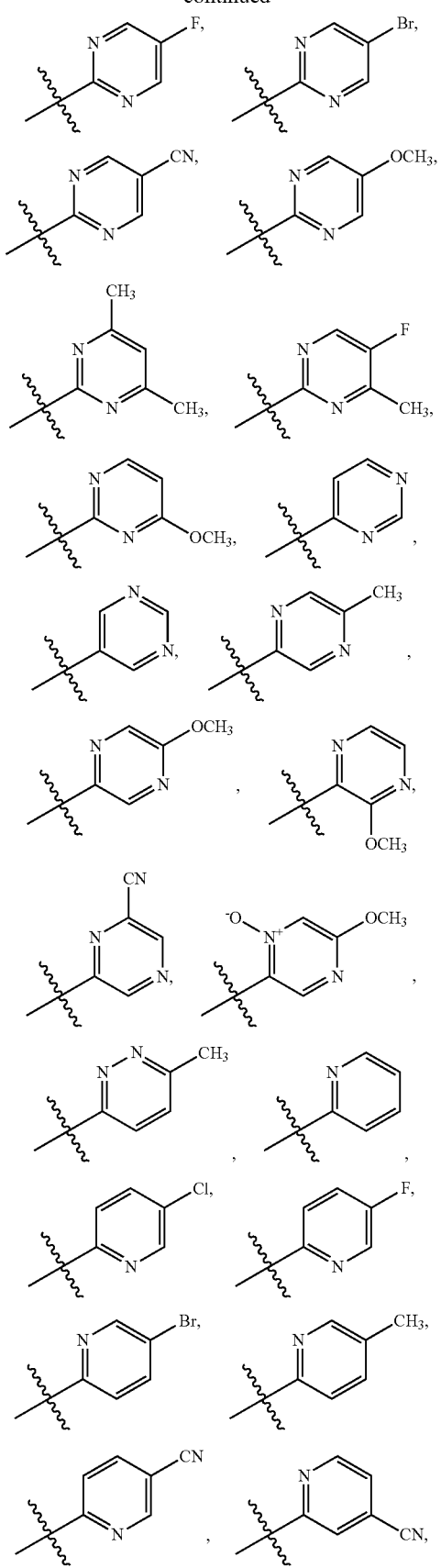

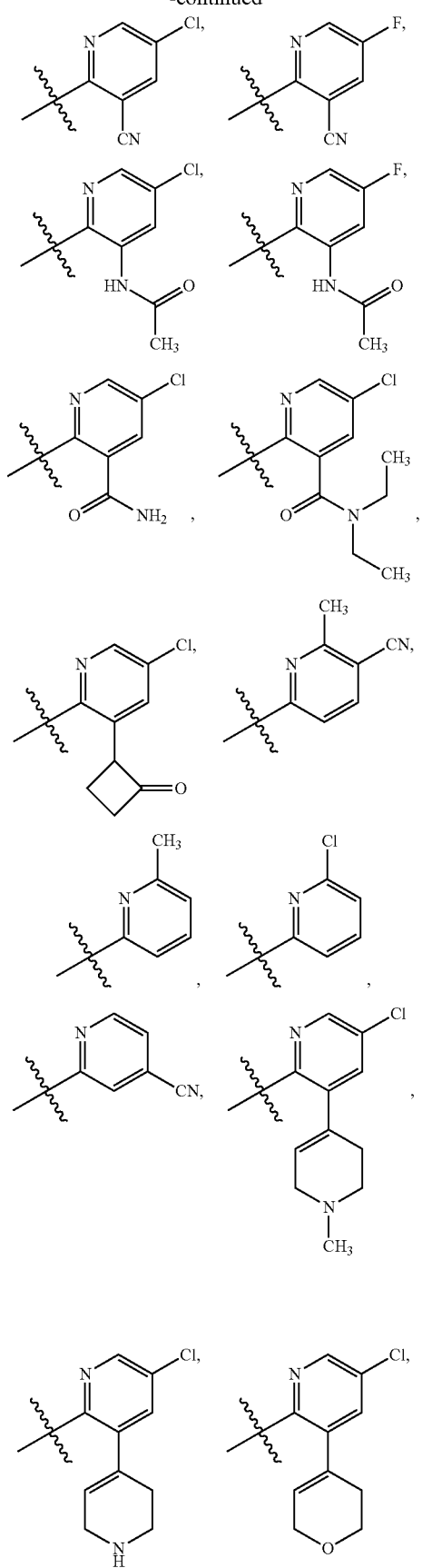
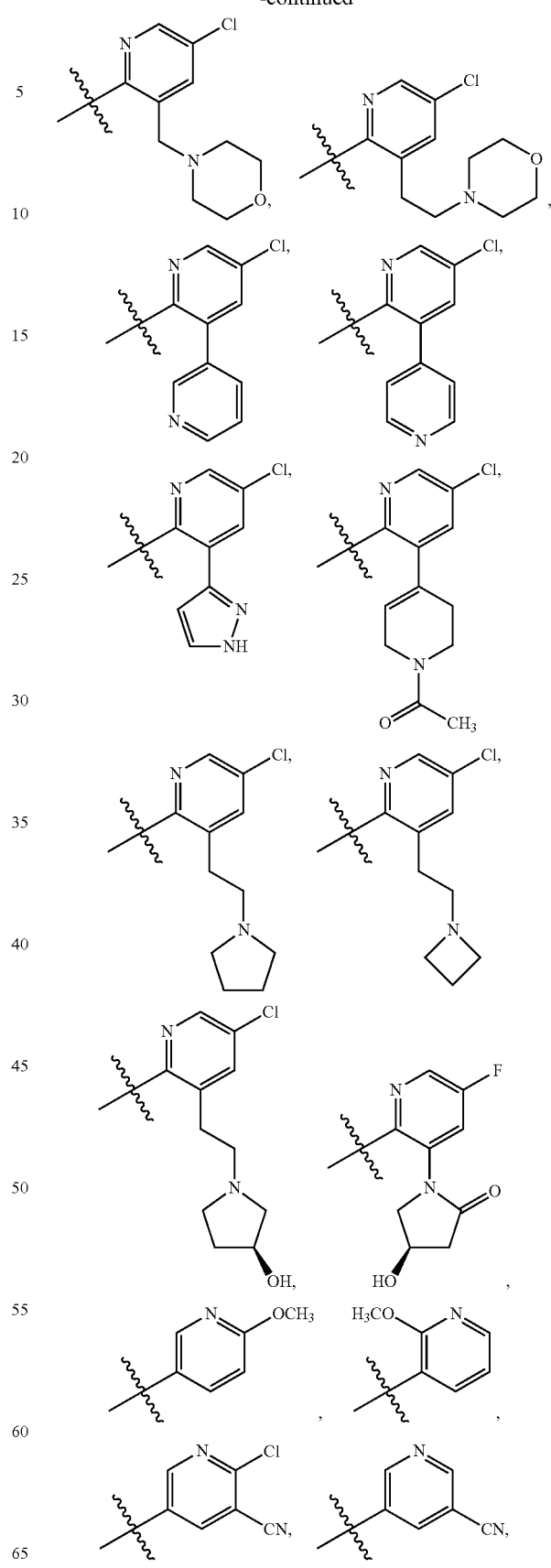

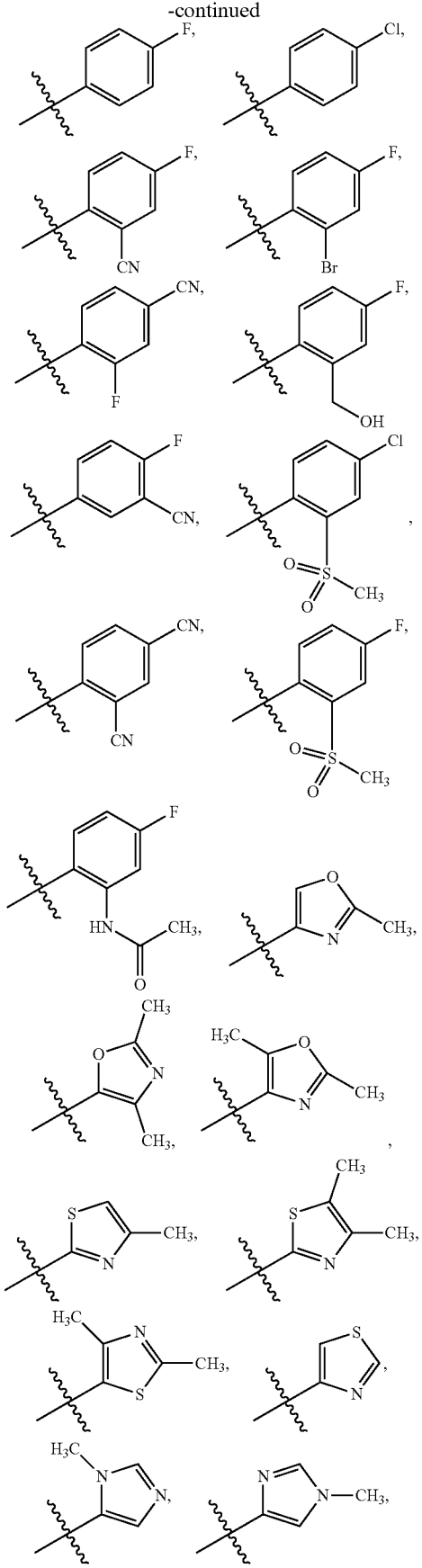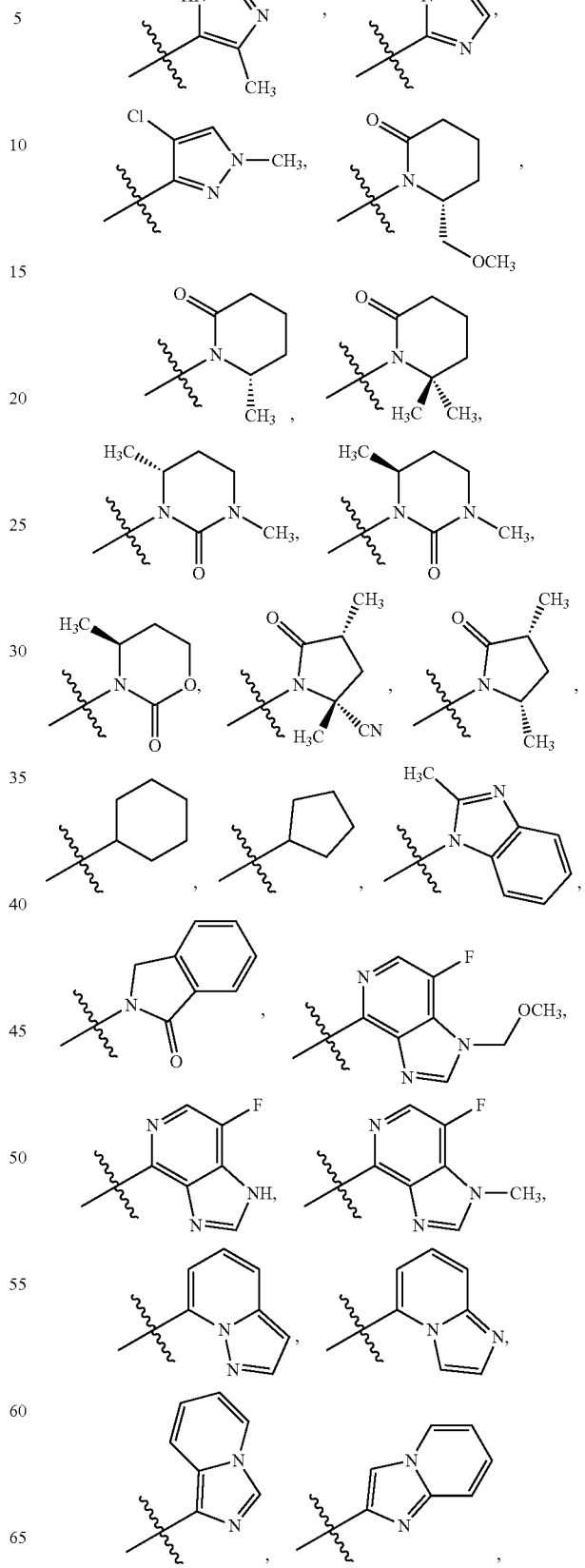

-continued

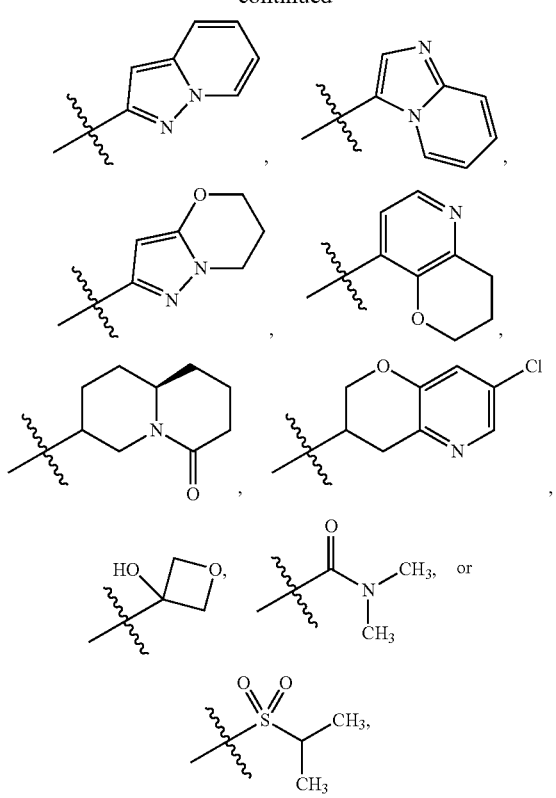

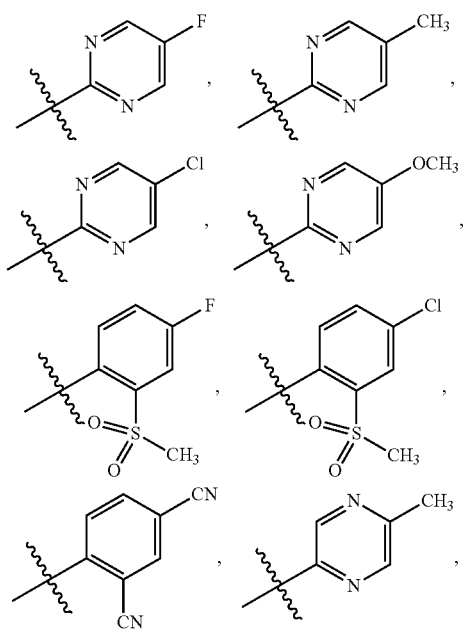

wherein the symbol ⌇, when drawn across a bond, indicates the point of attachment to the rest of the molecule.

22. The compound of embodiment 21 or the pharmaceutically acceptable salt thereof, the tautomer thereof, the pharmaceutically acceptable salt of the tautomer, the stereoisomer of any of the foregoing, or the mixture thereof, wherein Q is selected from

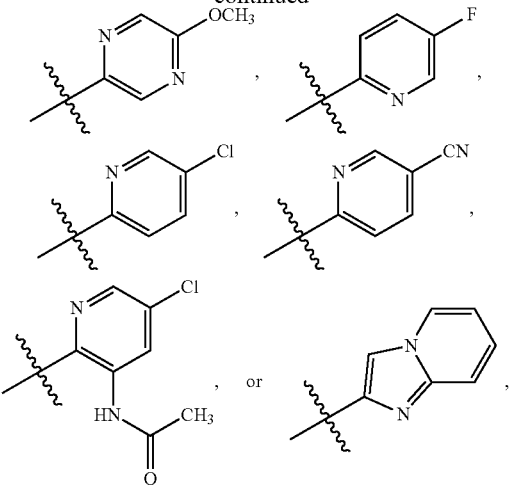

wherein the symbol ⌇, when drawn across a bond, indicates the point of attachment to the rest of the molecule.

23. The compound of embodiment 21 or the pharmaceutically acceptable salt thereof, the tautomer thereof, the pharmaceutically acceptable salt of the tautomer, the stereoisomer of any of the foregoing, or the mixture thereof, wherein Q is

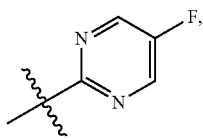 [SMILES: *c1ncc(F)cn1]

wherein the symbol ⌇, when drawn across a bond, indicates the point of attachment to the rest of the molecule.

24. The compound of embodiment 21 or the pharmaceutically acceptable salt thereof, the tautomer thereof, the pharmaceutically acceptable salt of the tautomer, the stereoisomer of any of the foregoing, or the mixture thereof, wherein Q is

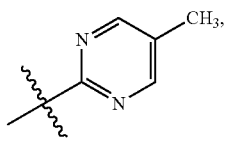 [SMILES: *c1ncc(C)cn1]

wherein the symbol ⌇, when drawn across a bond, indicates the point of attachment to the rest of the molecule.

25. The compound of embodiment 21 or the pharmaceutically acceptable salt thereof, the tautomer thereof, the pharmaceutically acceptable salt of the tautomer, the stereoisomer of any of the foregoing, or the mixture thereof, wherein Q is

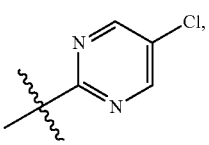 [SMILES: *c1ncc(Cl)cn1]

wherein the symbol ~~, when drawn across a bond, indicates the point of attachment to the rest of the molecule.

26. The compound of embodiment 21 or the pharmaceutically acceptable salt thereof, the tautomer thereof, the pharmaceutically acceptable salt of the tautomer, the stereoisomer of any of the foregoing, or the mixture thereof, wherein Q is

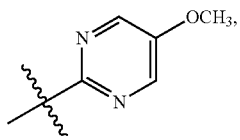 [SMILES: *c1ncc(OC)cn1]

wherein the symbol ~~, when drawn across a bond, indicates the point of attachment to the rest of the molecule.

27. The compound of embodiment 21 or the pharmaceutically acceptable salt thereof, the tautomer thereof, the pharmaceutically acceptable salt of the tautomer, the stereoisomer of any of the foregoing, or the mixture thereof, wherein Q is

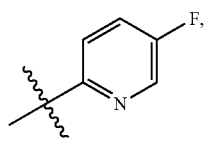 [SMILES: *c1ccc(F)cn1]

wherein the symbol ~~, when drawn across a bond, indicates the point of attachment to the rest of the molecule.

28. The compound of embodiment 21 or the pharmaceutically acceptable salt thereof, the tautomer thereof, the pharmaceutically acceptable salt of the tautomer, the stereoisomer of any of the foregoing, or the mixture thereof, wherein Q is

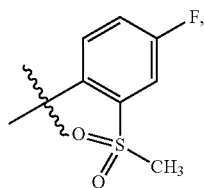 [SMILES: *c1ccc(F)cc1S(C)(=O)=O]

wherein the symbol ~~, when drawn across a bond, indicates the point of attachment to the rest of the molecule.

29. The compound of embodiment 21 or the pharmaceutically acceptable salt thereof, the tautomer thereof, the pharmaceutically acceptable salt of the tautomer, the stereoisomer of any of the foregoing, or the mixture thereof, wherein Q is

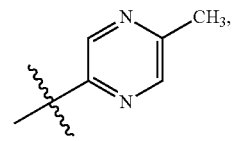 [SMILES: *c1cnc(C)cn1]

wherein the symbol ~~, when drawn across a bond, indicates the point of attachment to the rest of the molecule.

30. The compound of embodiment 21 or the pharmaceutically acceptable salt thereof, the tautomer thereof, the pharmaceutically acceptable salt of the tautomer, the stereoisomer of any of the foregoing, or the mixture thereof, wherein Q is

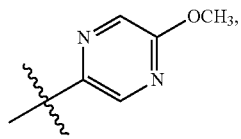 [SMILES: *c1cnc(OC)cn1]

wherein the symbol ~~, when drawn across a bond, indicates the point of attachment to the rest of the molecule.

31. The compound of embodiment 21 or the pharmaceutically acceptable salt thereof, the tautomer thereof, the pharmaceutically acceptable salt of the tautomer, the stereoisomer of any of the foregoing, or the mixture thereof, wherein Q is

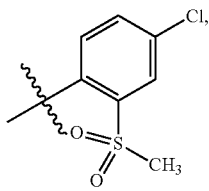 [SMILES: *c1ccc(Cl)cc1S(C)(=O)=O]

wherein the symbol ~~, when drawn across a bond, indicates the point of attachment to the rest of the molecule.

32. The compound of embodiment 21 or the pharmaceutically acceptable salt thereof, the tautomer thereof, the pharmaceutically acceptable salt of the tautomer, the stereoisomer of any of the foregoing, or the mixture thereof, wherein Q is

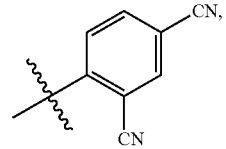 [SMILES: *c1ccc(C#N)cc1C#N]

wherein the symbol ~~, when drawn across a bond, indicates the point of attachment to the rest of the molecule.

33. The compound of embodiment 21 or the pharmaceutically acceptable salt thereof, the tautomer thereof, the pharmaceutically acceptable salt of the tautomer, the stereoisomer of any of the foregoing, or the mixture thereof, wherein Q is

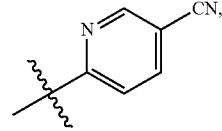 [SMILES: *c1ccc(C#N)cn1]

wherein the symbol ~~, when drawn across a bond, indicates the point of attachment to the rest of the molecule.

34. The compound of embodiment 21 or the pharmaceutically acceptable salt thereof, the tautomer thereof, the pharmaceutically acceptable salt of the tautomer, the stereoisomer of any of the foregoing, or the mixture thereof, wherein Q is

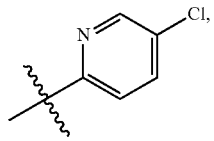 [SMILES: *c1ccc(Cl)cn1]

wherein the symbol ⌇, when drawn across a bond, indicates the point of attachment to the rest of the molecule.

35. The compound of embodiment 21 or the pharmaceutically acceptable salt thereof, the tautomer thereof, the pharmaceutically acceptable salt of the tautomer, the stereoisomer of any of the foregoing, or the mixture thereof, wherein Q is

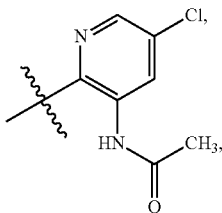 [SMILES: *c1ncc(Cl)cc1NC(C)=O]

wherein the symbol ⌇, when drawn across a bond, indicates the point of attachment to the rest of the molecule.

36. The compound of embodiment 21 or the pharmaceutically acceptable salt thereof, the tautomer thereof, the pharmaceutically acceptable salt of the tautomer, the stereoisomer of any of the foregoing, or the mixture thereof, wherein Q is

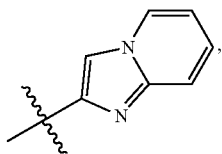 [SMILES: *c1cn2ccccc2n1]

wherein the symbol ⌇, when drawn across a bond, indicates the point of attachment to the rest of the molecule.

37. The compound of any one of embodiments 1-36 or the pharmaceutically acceptable salt thereof, the tautomer thereof, the pharmaceutically acceptable salt of the tautomer, the stereoisomer of any of the foregoing, or the mixture thereof, wherein $R^3$ is selected from a group of formula $-(CR^{3b}R^{3c})$-Q, a group of formula $-(CR^{3d}R^{3e})-(CR^{3f}R^{3g})$-Q, a group of formula $-(CR^{3d}R^{3e})-(CR^{3f}R^{3g})-C(=O)$-Q, a group of formula $-(CR^{3d}R^{3e})-(CR^{3f}R^{3g})-CH(OH)$-Q, a group of formula $-(CR^{3d}R^{3e})-(CR^{3f}R^{3g})-(CR^{3f}R^{3g})$-Q, a group of formula $-(C_3-C_8$ cycloalkyl)-Q, a group of formula -(heterocyclyl)-Q, or Q.

38. The compound of embodiment 37 or the pharmaceutically acceptable salt thereof, the tautomer thereof, the pharmaceutically acceptable salt of the tautomer, the stereoisomer of any of the foregoing, or the mixture thereof, wherein $R^3$ is selected from a group of formula $-(CR^{3d}R^{3e})-(CR^{3f}R^{3g})$-Q, a group of formula $-(C_3-C_8$ cycloalkyl)-Q, or a group of formula -(heterocyclyl)-Q.

39. The compound of embodiment 37 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula $-(CR^{3d}R^{3e})-(CR^{3f}R^{3g})$-Q.

40. The compound of embodiment 39 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula $-(CR^{3d}R^{3e})-(CR^{3f}R^{3g})$-Q and further wherein, $R^{3d}$ and $R^{3e}$ are independently selected from —H, —$C_1$-$C_6$ alkyl, —($C_1$-$C_6$ alkyl)-OH, or —($C_1$-$C_6$ alkyl)-O—($C_1$-$C_6$ alkyl); and $R^{3f}$ and $R^{3g}$ are independently selected from —H, —F, —$C_1$-$C_6$ alkyl, —OH, —O—($C_1$-$C_6$ alkyl), —O—($C_1$-$C_6$ alkyl)-OH, —O—($C_1$-$C_6$ alkyl)-O—($C_1$-$C_6$ alkyl), or —$NH_2$.

41. The compound of embodiment 37 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula —($C_3$-$C_8$ cycloalkyl)-Q.

42. The compound of embodiment 41 or the pharmaceutically acceptable salt thereof, the tautomer thereof, the pharmaceutically acceptable salt of the tautomer, the stereoisomer of any of the foregoing, or the mixture thereof, wherein the $C_3$-$C_8$ cycloalkyl of the —($C_3$-$C_8$ cycloalkyl)-Q $R^3$ group is a cyclopropyl, cyclobutyl, cyclopentyl, or cyclohexyl that is unsubstituted or is substituted with 1 $R^{3h}$ substituent.

43. The compound of embodiment 37 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula -(heterocyclyl)-Q.

44. The compound of embodiment 43 or the pharmaceutically acceptable salt thereof, the tautomer thereof, the pharmaceutically acceptable salt of the tautomer, the stereoisomer of any of the foregoing, or the mixture thereof, wherein the heterocyclyl of the -(heterocyclyl)-Q $R^3$ group is a tetrahydrofuranyl, isoxazolidinyl, tetrahydropyranyl, or piperidinyl that is unsubstituted or is substituted with 1 or 2 $R^{3h}$ substituent.

45. The compound of embodiment 37 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula $-(CR^{3b}R^{3c})$-Q.

46. The compound of embodiment 45 or the pharmaceutically acceptable salt thereof, the tautomer thereof, the pharmaceutically acceptable salt of the tautomer, the stereoisomer of any of the foregoing, or the mixture thereof, wherein.

$R^{3b}$ and $R^{3c}$ are independently selected from H or —$C_1$-$C_6$ alkyl.

47. The compound of embodiment 37 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula $-(CR^{3d}R^{3e})-(CR^{3f}R^{3g})-C(=O)$-Q.

48. The compound of embodiment 37 or the pharmaceutically acceptable salt thereof, the tautomer thereof, the pharmaceutically acceptable salt of the tautomer, the ste-

35 reoisomer of any of the foregoing, or the mixture thereof, wherein R³ is a group of formula —(CR³ᵈR³ᵉ)—(CR³ᶠR³ᵍ)—CH(OH)-Q.

49. The compound of embodiment 37 or the pharmaceutically acceptable salt thereof, the tautomer thereof, the pharmaceutically acceptable salt of the tautomer, the stereoisomer of any of the foregoing, or the mixture thereof, wherein R³ is a group of formula —(CR³ᵈR³ᵉ)—(CR³ᶠR³ᵍ)—(CR³ᶠR³ᵍ)-Q.

50. The compound of embodiment 37 or the pharmaceutically acceptable salt thereof, the tautomer thereof, the pharmaceutically acceptable salt of the tautomer, the stereoisomer of any of the foregoing, or the mixture thereof, wherein R³ is a group of formula -Q.

51. The compound of any one of embodiments 1-36 or the pharmaceutically acceptable salt thereof, the tautomer thereof, the pharmaceutically acceptable salt of the tautomer, the stereoisomer of any of the foregoing, or the mixture thereof, wherein R³ is selected from

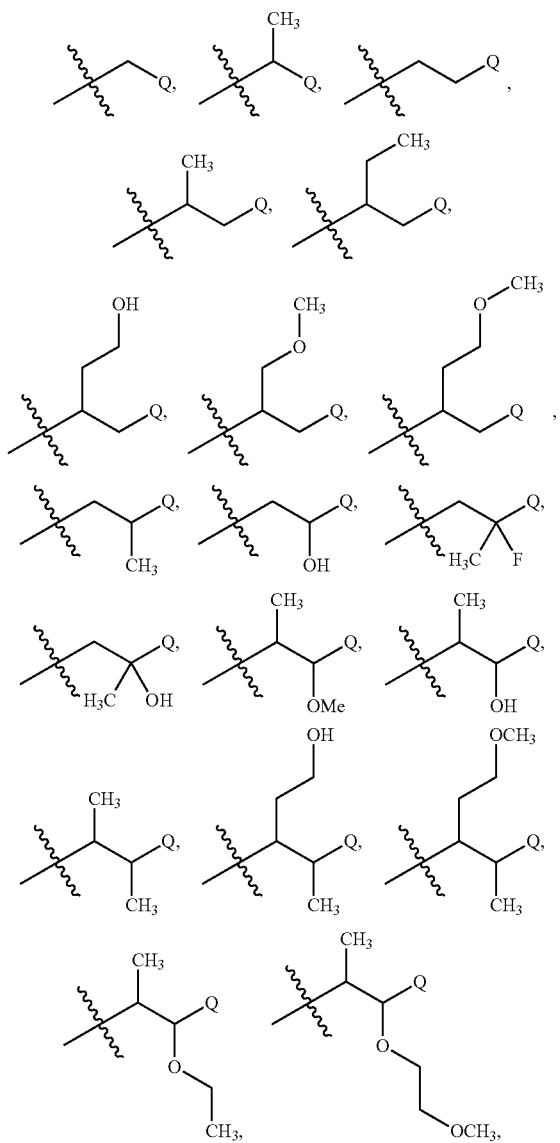

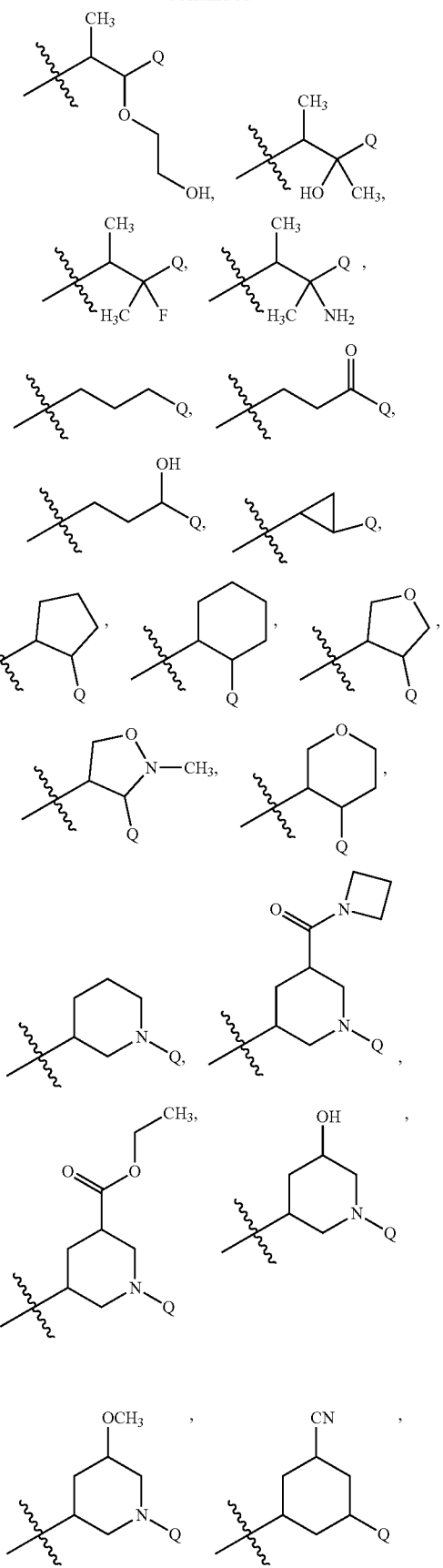

-continued

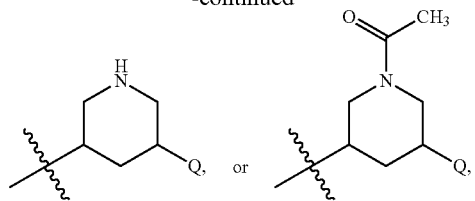

wherein the symbol ~~~, when drawn across a bond, indicates the point of attachment to the rest of the molecule.

52. The compound of any one of embodiments 1-36 or the pharmaceutically acceptable salt thereof, the tautomer thereof, the pharmaceutically acceptable salt of the tautomer, the stereoisomer of any of the foregoing, or the mixture thereof, wherein $R^3$ is selected from

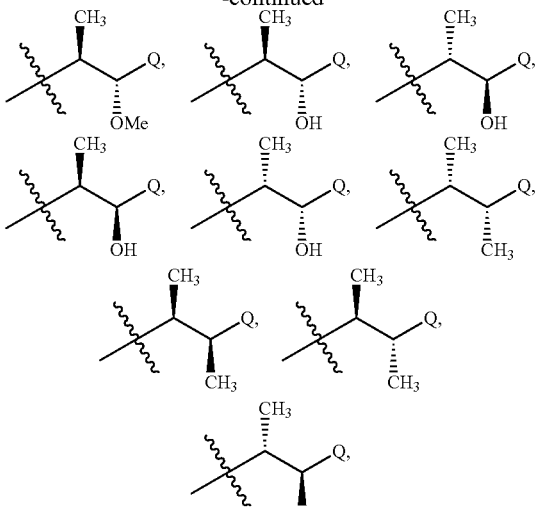

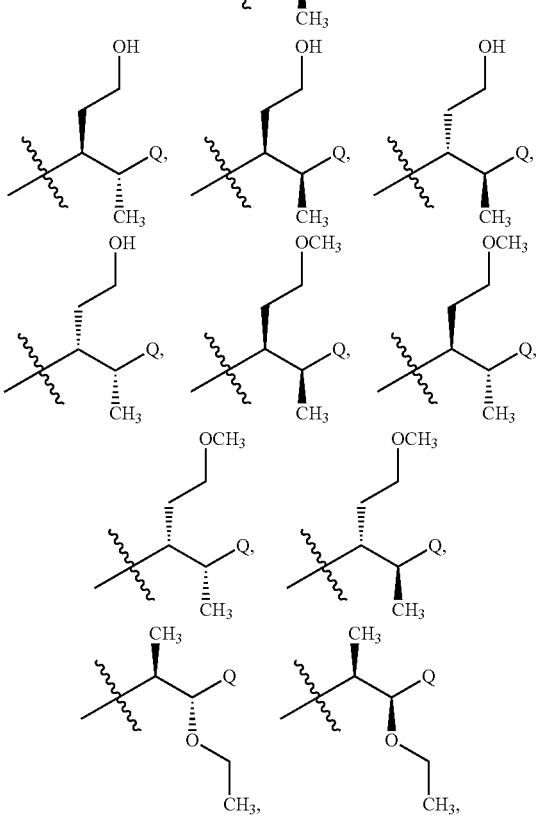

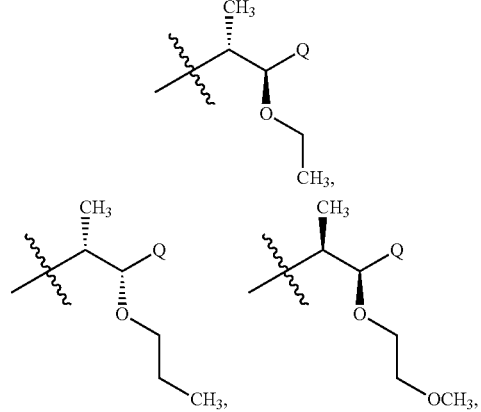

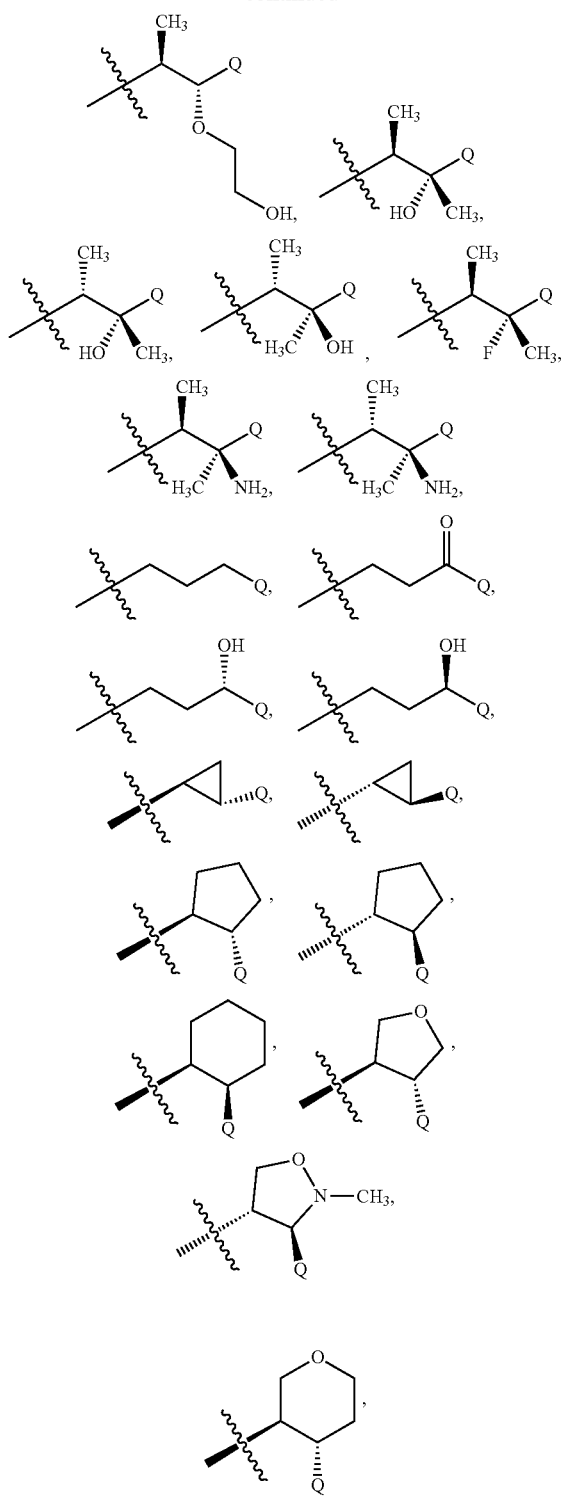
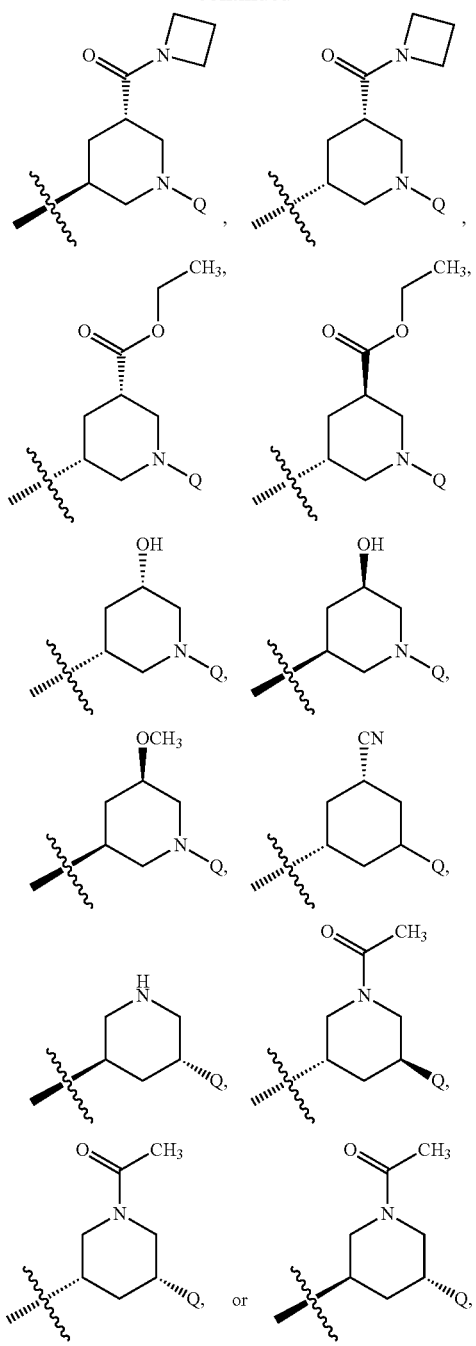
wherein the symbol ∿, when drawn across a bond, indicates the point of attachment to the rest of the molecule.
53. The compound of embodiment 52 or the pharmaceutically acceptable salt thereof, the tautomer thereof, the pharmaceutically acceptable salt of the tautomer, the stereoisomer of any of the foregoing, or the mixture thereof, wherein $R^3$ is selected from
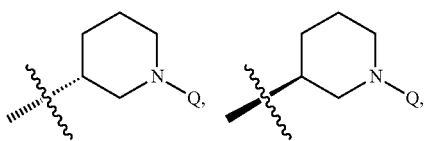
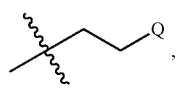

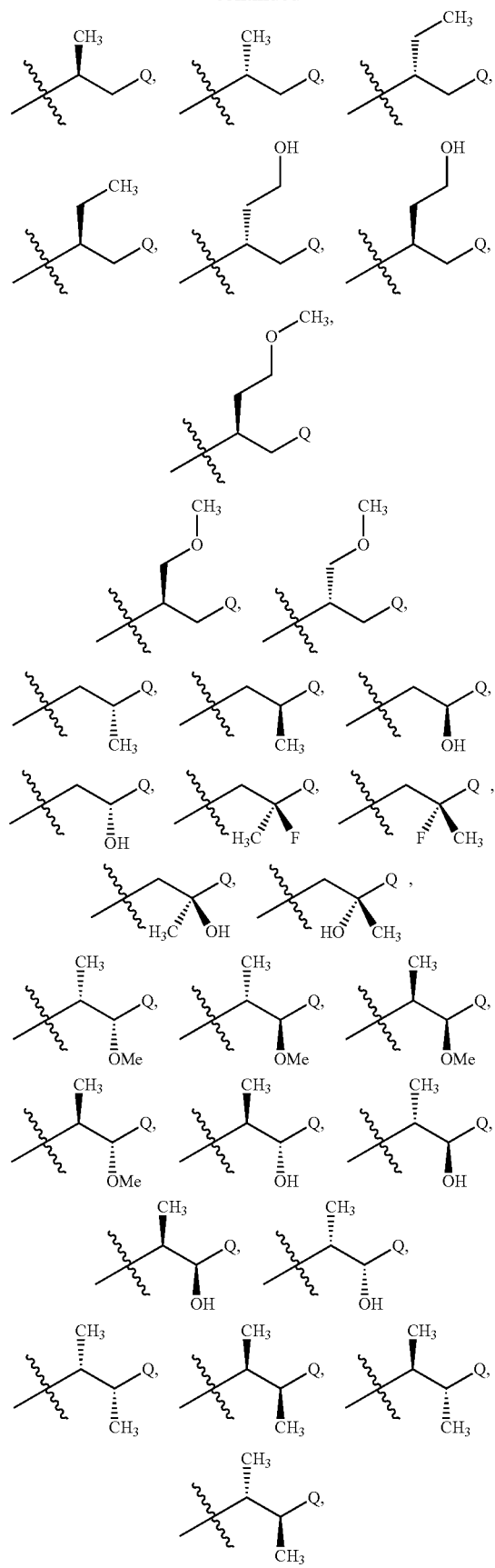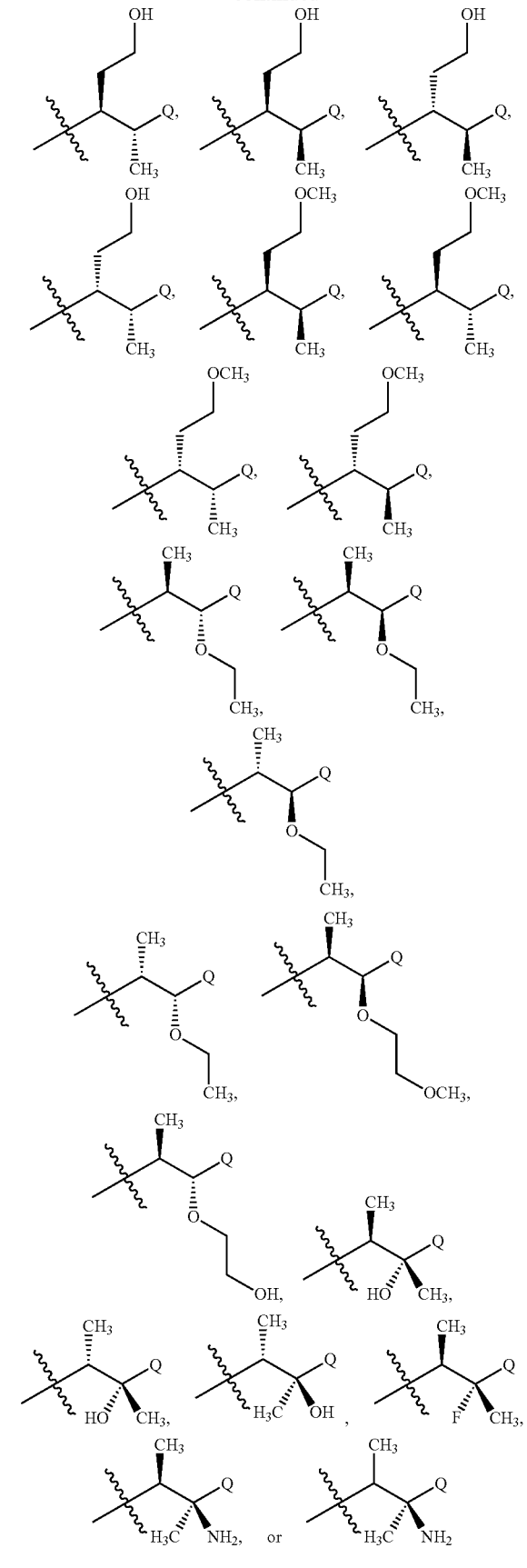

43 wherein the symbol ⁓, when drawn across a bond, indicates the point of attachment to the rest of the molecule.

54. The compound of embodiment 52 or the pharmaceutically acceptable salt thereof, the tautomer thereof, the pharmaceutically acceptable salt of the tautomer, the stereoisomer of any of the foregoing, or the mixture thereof, wherein R³ is selected from

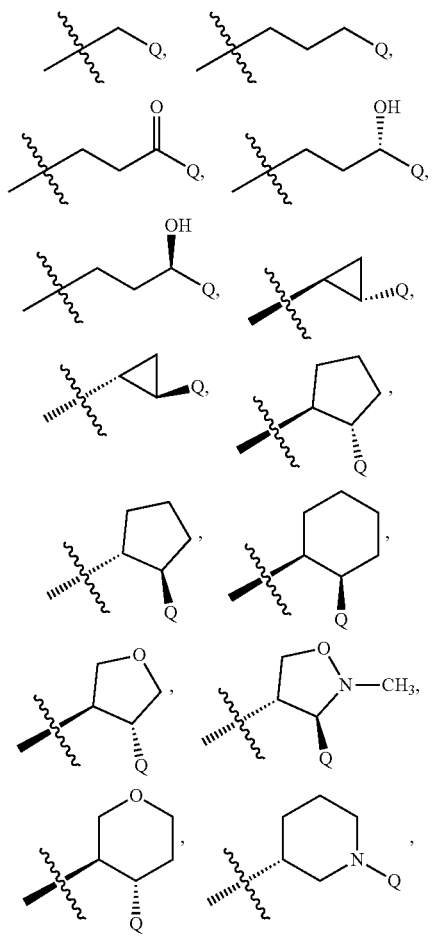

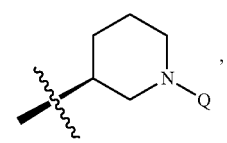

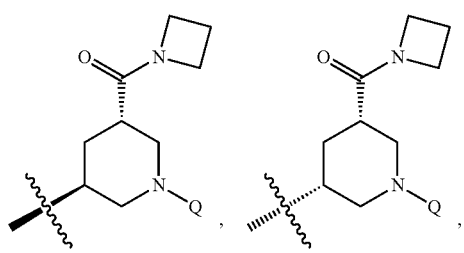

44

-continued

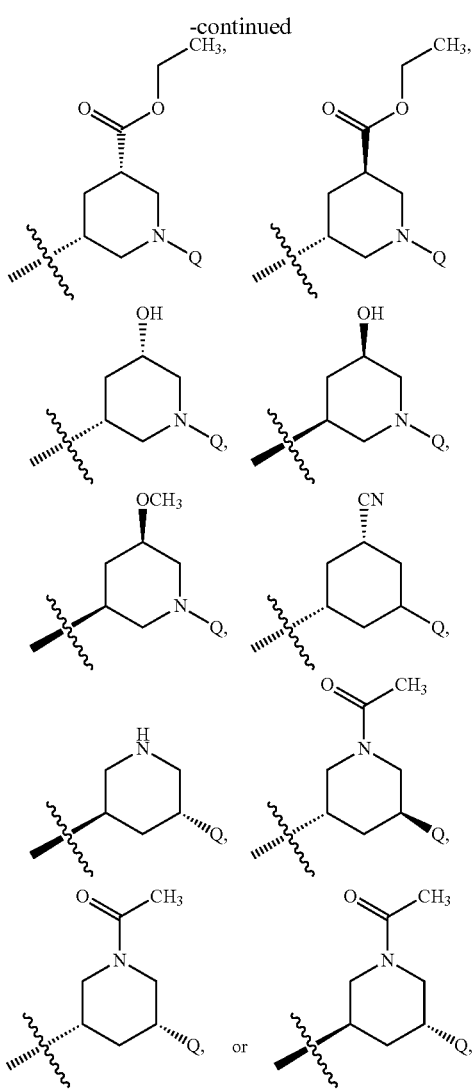

wherein the symbol ⁓, when drawn across a bond, indicates the point of attachment to the rest of the molecule.

55. The compound of embodiment 52 or the pharmaceutically acceptable salt thereof, the tautomer thereof, the pharmaceutically acceptable salt of the tautomer, the stereoisomer of any of the foregoing, or the mixture thereof, wherein R³ is selected from

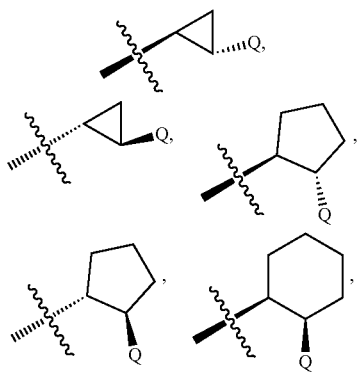

-continued

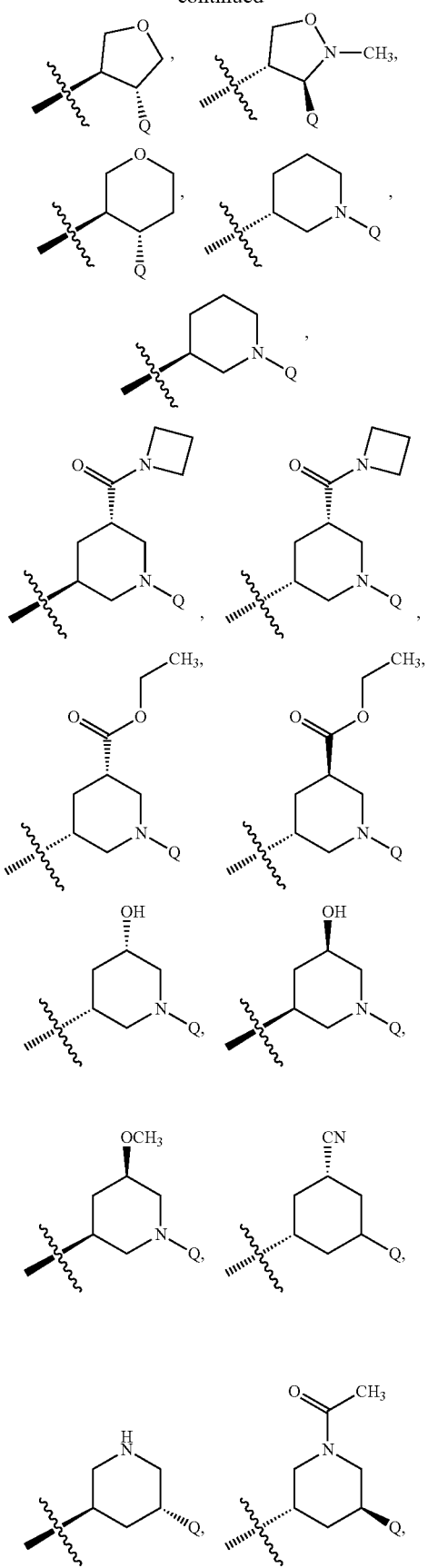

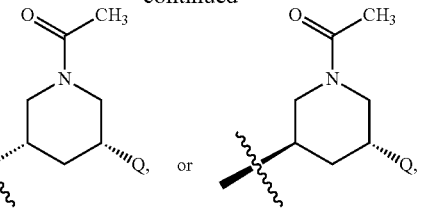

wherein the symbol ∿, when drawn across a bond, indicates the point of attachment to the rest of the molecule.

56. The compound of embodiment 1, wherein the compound is selected from

N-(4-(2,6-dimethoxyphenyl)-5-(2-furanyl)-4H-1,2,4-triazol-3-yl)-2-(2-methyl-1H-benzimidazol-1-yl)ethanesulfonamide;

N-(4-(2,6-dimethoxyphenyl)-5-(2-furanyl)-4H-1,2,4-triazol-3-yl)-2-(1-oxo-1,3-dihydro-2H-isoindol-2-yl)ethanesulfonamide;

(1R,2S)—N-(4-(4,6-dimethoxy-5-pyrimidinyl)-5-(5-methyl-2-furanyl)-4H-1,2,4-triazol-3-yl)-1-methoxy-1-(5-methyl-2-pyrimidinyl)-2-propanesulfonamide;

(2R)—N-(4-(2,6-dimethoxyphenyl)-5-(2-furanyl)-4H-1,2,4-triazol-3-yl)-1-(7-fluoro-1-(methoxymethyl)-1H-imidazo[4,5-c]pyridin-4-yl)-2-propanesulfonamide;

(2S)—N-(4-(2,6-dimethoxyphenyl)-5-(2-furanyl)-4H-1,2,4-triazol-3-yl)-1-(7-fluoro-1-(methoxymethyl)-1H-imidazo[4,5-c]pyridin-4-yl)-2-propanesulfonamide;

(2S)—N-(4-(2,6-dimethoxyphenyl)-5-(2-furanyl)-4H-1,2,4-triazol-3-yl)-1-(7-fluoro-1H-imidazo[4,5-c]pyridin-4-yl)-2-propanesulfonamide;

(2R)—N-(4-(2,6-dimethoxyphenyl)-5-(2-furanyl)-4H-1,2,4-triazol-3-yl)-1-(7-fluoro-1-methyl-1H-imidazo[4,5-c]pyridin-4-yl)-2-propanesulfonamide;

(2R)—N-(4-(4,6-dimethoxy-5-pyrimidinyl)-5-(5-methyl-2-furanyl)-4H-1,2,4-triazol-3-yl)-1-(5-fluoro-2-pyrimidinyl)-2-propanesulfonamide;

(2S)—N-(4-(4,6-dimethoxy-5-pyrimidinyl)-5-(5-methyl-2-furanyl)-4H-1,2,4-triazol-3-yl)-1-(5-fluoro-2-pyrimidinyl)-2-propanesulfonamide;

(2R)—N-(4-(2,6-dimethoxyphenyl)-5-(2-furanyl)-4H-1,2,4-triazol-3-yl)-1-(7-fluoro-1H-imidazo[4,5-c]pyridin-4-yl)-2-propanesulfonamide;

N-(5-chloro-2-((2R)-2-((4-(2,6-dimethoxyphenyl)-5-(2-furanyl)-4H-1,2,4-triazol-3-yl)sulfamoyl)propyl)-3-pyridinyl)acetamide;

(1S,2S)-1-(5-cyano-2-pyridinyl)-N-(4-(2,6-dimethoxyphenyl)-5-(5-methyl-2-furanyl)-4H-1,2,4-triazol-3-yl)-1-hydroxy-2-propanesulfonamide;

(2R)-1-(5-chloro-2-pyridinyl)-N-(4-(2,6-dimethoxyphenyl)-5-(2-furanyl)-4H-1,2,4-triazol-3-yl)-2-propanesulfonamide;

(2R)-1-(5-cyano-2-pyridinyl)-N-(4-(2,6-dimethoxyphenyl)-5-(5-methyl-2-furanyl)-4H-1,2,4-triazol-3-yl)-2-propanesulfonamide;

N-(5-chloro-2-((2S)-2-((4-(2,6-dimethoxyphenyl)-5-(2-furanyl)-4H-1,2,4-triazol-3-yl)sulfamoyl)propyl)-3-pyridinyl)acetamide;

(2S)-1-(5-chloro-2-pyridinyl)-N-(4-(2,6-dimethoxyphenyl)-5-(2-furanyl)-4H-1,2,4-triazol-3-yl)-2-propanesulfonamide;

N-(2-((2R)-2-((4-(2,6-dimethoxyphenyl)-5-(2-furanyl)-4H-1,2,4-triazol-3-yl)sulfamoyl)propyl)-5-fluoro-3-pyridinyl)acetamide;

(2R)—N-(4-(2,6-dimethoxyphenyl)-5-(5-methyl-2-furanyl)-4H-1,2,4-triazol-3-yl)-1-(5-methyl-2-pyrimidinyl)-2-propanesulfonamide;
5-chloro-2-((2R)-2-((4-(2,6-dimethoxyphenyl)-5-(2-furanyl)-4H-1,2,4-triazol-3-yl)sulfamoyl)propyl)-3-pyridinecarboxamide;
(2R)-1-(5-chloro-3-cyano-2-pyridinyl)-N-(4-(2,6-dimethoxyphenyl)-5-(2-furanyl)-4H-1,2,4-triazol-3-yl)-2-propanesulfonamide;
(2S)-1-(5-chloro-3-cyano-2-pyridinyl)-N-(4-(2,6-dimethoxyphenyl)-5-(2-furanyl)-4H-1,2,4-triazol-3-yl)-2-propanesulfonamide;
2-(5-cyano-2-pyridinyl)-N-(4-(2,6-dimethoxyphenyl)-5-(5-methyl-2-furanyl)-4H-1,2,4-triazol-3-yl)ethanesulfonamide;
5-chloro-2-((2S)-2-((4-(2,6-dimethoxyphenyl)-5-(2-furanyl)-4H-1,2,4-triazol-3-yl)sulfamoyl)propyl)-N,N-diethyl-3-pyridinecarboxamide;
(2R)-1-(5-bromo-2-pyrimidinyl)-N-(4-(2,6-dimethoxyphenyl)-5-(2-furanyl)-4H-1,2,4-triazol-3-yl)-2-propanesulfonamide;
(2R)-1-(5-bromo-2-pyridinyl)-N-(4-(2,6-dimethoxyphenyl)-5-(2-furanyl)-4H-1,2,4-triazol-3-yl)-2-propanesulfonamide;
(2R)—N-(4-(2,6-dimethoxyphenyl)-5-(5-methyl-2-furanyl)-4H-1,2,4-triazol-3-yl)-1-(5-methyl-2-pyrazinyl)-2-propanesulfonamide;
(2R)—N-(4-(2,6-dimethoxyphenyl)-5-(2-furanyl)-4H-1,2,4-triazol-3-yl)-1-(5-fluoro-2-pyridinyl)-2-propanesulfonamide;
N-(4-(2,6-dimethoxyphenyl)-5-(5-methyl-2-furanyl)-4H-1,2,4-triazol-3-yl)-2-(5-methyl-2-pyrimidinyl)ethanesulfonamide;
2-(5-chloro-3-(2-oxo-1-azetidinyl)-2-pyridinyl)-N-(4-(2,6-dimethoxyphenyl)-5-(2-furanyl)-4H-1,2,4-triazol-3-yl)ethanesulfonamide;
N-(2-((2S)-2-((4-(2,6-dimethoxyphenyl)-5-(2-furanyl)-4H-1,2,4-triazol-3-yl)sulfamoyl)propyl)-5-fluoro-3-pyridinyl)acetamide;
(2R)-1-(3-cyano-5-fluoro-2-pyridinyl)-N-(4-(2,6-dimethoxyphenyl)-5-(2-furanyl)-4H-1,2,4-triazol-3-yl)-2-propanesulfonamide;
(2R)-1-(5-cyano-2-pyridinyl)-N-(4-(2,6-dimethoxyphenyl)-5-(2-furanyl)-4H-1,2,4-triazol-3-yl)-2-propanesulfonamide;
(2R)—N-(4-(2,6-dimethoxyphenyl)-5-(5-methyl-2-furanyl)-4H-1,2,4-triazol-3-yl)-1-(6-methyl-3-pyridazinyl)-2-propanesulfonamide;
(2R)—N-(4-(2,6-dimethoxyphenyl)-5-(2-furanyl)-4H-1,2,4-triazol-3-yl)-1-(5-methyl-2-pyrazinyl)-2-propanesulfonamide;
(2S)-1-(5-cyano-2-pyridinyl)-N-(4-(2,6-dimethoxyphenyl)-5-(5-methyl-2-furanyl)-4H-1,2,4-triazol-3-yl)-2-propanesulfonamide;
N-(4-(2,6-dimethoxyphenyl)-5-(2-furanyl)-4H-1,2,4-triazol-3-yl)-2-(5-fluoro-2-pyrimidinyl)ethanesulfonamide;
2-(5-cyano-2-pyridinyl)-N-(4-(2,6-dimethoxyphenyl)-5-(2-furanyl)-4H-1,2,4-triazol-3-yl)ethanesulfonamide;
(2S)-1-(5-bromo-2-pyrimidinyl)-N-(4-(2,6-dimethoxyphenyl)-5-(2-furanyl)-4H-1,2,4-triazol-3-yl)-2-propanesulfonamide;
(2S)-1-(5-chloro-2-pyrimidinyl)-N-(4-(2,6-dimethoxyphenyl)-5-(2-furanyl)-4H-1,2,4-triazol-3-yl)-2-propanesulfonamide;
(2S)—N-(4-(2,6-dimethoxyphenyl)-5-(5-methyl-2-furanyl)-4H-1,2,4-triazol-3-yl)-1-(5-methyl-2-pyrazinyl)-2-propanesulfonamide;
N-(4-(2,6-dimethoxyphenyl)-5-(2-furanyl)-4H-1,2,4-triazol-3-yl)-2-(5-methyl-2-pyrimidinyl)ethanesulfonamide;
(1R,2S)-1-(5-cyano-2-pyridinyl)-N-(4-(2,6-dimethoxyphenyl)-5-(5-methyl-2-furanyl)-4H-1,2,4-triazol-3-yl)-1-hydroxy-2-propanesulfonamide;
N-(4-(2,6-dimethoxyphenyl)-5-(2-furanyl)-4H-1,2,4-triazol-3-yl)-2-(5-fluoro-2-pyridinyl)ethanesulfonamide;
(2R)—N-(4-(2,6-dimethoxyphenyl)-5-(2-furanyl)-4H-1,2,4-triazol-3-yl)-1-(6-methyl-3-pyridazinyl)-2-propanesulfonamide;
(2S)—N-(4-(2,6-dimethoxyphenyl)-5-(5-methyl-2-furanyl)-4H-1,2,4-triazol-3-yl)-1-(6-methyl-3-pyridazinyl)-2-propanesulfonamide;
(2R)—N-(4-(2,6-dimethoxyphenyl)-5-(2-furanyl)-4H-1,2,4-triazol-3-yl)-1-(4-pyrimidinyl)-2-propanesulfonamide;
(2R)—N-(4-(2,6-dimethoxyphenyl)-5-(2-furanyl)-4H-1,2,4-triazol-3-yl)-1-(5-pyrimidinyl)-2-propanesulfonamide;
(2S)—N-(4-(2,6-dimethoxyphenyl)-5-(2-furanyl)-4H-1,2,4-triazol-3-yl)-1-(4-pyrimidinyl)-2-propanesulfonamide;
N-(4-(2,6-dimethoxyphenyl)-5-(2-furanyl)-4H-1,2,4-triazol-3-yl)-2-(6-methoxy-3-pyridinyl)ethanesulfonamide;
2-(5-chloro-2-pyridinyl)-N-(4-(2,6-dimethoxyphenyl)-5-(2-furanyl)-4H-1,2,4-triazol-3-yl)ethanesulfonamide;
2-(5-chloro-2-pyrimidinyl)-N-(4-(2,6-dimethoxyphenyl)-5-(2-furanyl)-4H-1,2,4-triazol-3-yl)ethanesulfonamide;
2-(5-chloro-3-cyano-2-pyridinyl)-N-(4-(2,6-dimethoxyphenyl)-5-(2-furanyl)-4H-1,2,4-triazol-3-yl)ethanesulfonamide;
(2S)—N-(4-(2,6-dimethoxyphenyl)-5-(2-furanyl)-4H-1,2,4-triazol-3-yl)-1-(5-fluoro-2-pyrimidinyl)-2-propanesulfonamide;
(2R)—N-(4-(2,6-dimethoxyphenyl)-5-(2-furanyl)-4H-1,2,4-triazol-3-yl)-1-(5-fluoro-2-pyrimidinyl)-2-propanesulfonamide;
(2R,3S)—N-(4-(2,6-dimethoxyphenyl)-5-(5-methyl-2-furanyl)-4H-1,2,4-triazol-3-yl)-3-(5-ethyl-2-pyrimidinyl)-2-butanesulfonamide;
(2S,3R)—N-(4-(2,6-dimethoxyphenyl)-5-(5-methyl-2-furanyl)-4H-1,2,4-triazol-3-yl)-3-(5-fluoro-2-pyrimidinyl)-2-butanesulfonamide;
(1S,2S)—N-(4-(2,6-dimethoxyphenyl)-5-(5-methyl-2-furanyl)-4H-1,2,4-triazol-3-yl)-1-(5-fluoro-2-pyridinyl)-1-hydroxy-2-propanesulfonamide;
(2R)-2-(5-cyano-2-pyridinyl)-N-(4-(2,6-dimethoxyphenyl)-5-(5-methyl-2-furanyl)-4H-1,2,4-triazol-3-yl)-2-hydroxyethanesulfonamide;
(1R,2R)—N-(4-(2,6-dimethoxyphenyl)-5-(5-methyl-2-furanyl)-4H-1,2,4-triazol-3-yl)-1-(5-fluoro-2-pyridinyl)-1-hydroxy-2-propanesulfonamide;
(2R)—N-(4-(2,6-dimethoxyphenyl)-5-(5-methyl-2-furanyl)-4H-1,2,4-triazol-3-yl)-2-(5-fluoro-2-pyridinyl)-2-hydroxyethanesulfonamide;
(2S)—N-(4-(2,6-dimethoxyphenyl)-5-(5-methyl-2-furanyl)-4H-1,2,4-triazol-3-yl)-2-(5-fluoro-2-pyridinyl)-2-hydroxyethanesulfonamide;
(1R,2R)-1-(4-cyano-2-fluorophenyl)-N-(4-(2,6-dimethoxyphenyl)-5-(5-methyl-2-furanyl)-4H-1,2,4-triazol-3-yl)-1-hydroxy-2-propanesulfonamide;
(3S,4S)—N-(4-(2,6-dimethoxyphenyl)-5-(5-methyl-2-furanyl)-4H-1,2,4-triazol-3-yl)-1-hydroxy-4-(5-methyl-2-pyrimidinyl)-3-pentanesulfonamide;
(1R,2R)—N-(4-(2,6-dimethoxyphenyl)-5-(5-methyl-2-furanyl)-4H-1,2,4-triazol-3-yl)-1-hydroxy-1-(5-methyl-2-pyridinyl)-2-propanesulfonamide;

(1S,2S)—N-(4-(2,6-dimethoxyphenyl)-5-(5-methyl-2-furanyl)-4H-1,2,4-triazol-3-yl)-1-hydroxy-1-(5-methyl-2-pyridinyl)-2-propanesulfonamide;

(2S)-2-(5-cyano-2-pyridinyl)-N-(4-(2,6-dimethoxyphenyl)-5-(5-methyl-2-furanyl)-4H-1,2,4-triazol-3-yl)-2-hydroxy ethanesulfonamide;

(3S,4R)—N-(4-(2,6-dimethoxyphenyl)-5-(5-methyl-2-furanyl)-4H-1,2,4-triazol-3-yl)-4-(5-fluoro-2-pyrimidinyl)-1-methoxy-3-pentanesulfonamide;

(1S,2R)-1-(5-cyano-3-fluoro-2-pyridinyl)-N-(4-(2,6-dimethoxy phenyl)-5-(5-methyl-2-furanyl)-4H-1,2,4-triazol-3-yl)-1-hydroxy-2-propanesulfonamide;

(2S)—N-(4-(2,6-dimethoxyphenyl)-5-(5-methyl-2-furanyl)-4H-1,2,4-triazol-3-yl)-4-hydroxy-1-(5-methyl-2-pyrimidinyl)-2-butanesulfonamide;

(2R)—N-(4-(2,6-dimethoxyphenyl)-5-(5-methyl-2-furanyl)-4H-1,2,4-triazol-3-yl)-4-hydroxy-1-(5-methyl-2-pyrimidinyl)-2-butanesulfonamide;

(2R)—N-(4-(2,6-dimethoxyphenyl)-5-(5-methyl-2-furanyl)-4H-1,2,4-triazol-3-yl)-4-methoxy-1-(5-methyl-2-pyrimidinyl)-2-butanesulfonamide;

(2R)—N-(4-(2,6-dimethoxyphenyl)-5-(5-methyl-2-furanyl)-4H-1,2,4-triazol-3-yl)-1-(5-fluoro-2-pyrimidinyl)-3-methoxy-2-propanesulfonamide;

(1R,2R)—N-(4-(2,6-dimethoxyphenyl)-5-(5-methyl-2-furanyl)-4H-1,2,4-triazol-3-yl)-1-(4-fluoro-2-(hydroxymethyl)phenyl)-1-hydroxy-2-propanesulfonamide;

(1S,2S)—N-(4-(2,6-dimethoxyphenyl)-5-(5-methyl-2-furanyl)-4H-1,2,4-triazol-3-yl)-1-(4-fluoro-2-(hydroxymethyl)phenyl)-1-hydroxy-2-propanesulfonamide;

(3R,4R)—N-(4-(2,6-dimethoxyphenyl)-5-(5-methyl-2-furanyl)-4H-1,2,4-triazol-3-yl)-4-(5-fluoro-2-pyrimidinyl)-1-methoxy-3-pentanesulfonamide;

(3R,4S)—N-(4-(2,6-dimethoxyphenyl)-5-(5-methyl-2-furanyl)-4H-1,2,4-triazol-3-yl)-4-(5-fluoro-2-pyrimidinyl)-1-methoxy-3-pentanesulfonamide;

(3S,4S)—N-(4-(2,6-dimethoxyphenyl)-5-(5-methyl-2-furanyl)-4H-1,2,4-triazol-3-yl)-4-(5-fluoro-2-pyrimidinyl)-1-methoxy-3-pentanesulfonamide;

(1R,2S)-1-(4-cyano-2-fluorophenyl)-N-(4-(2,6-dimethoxy phenyl)-5-(5-methyl-2-furanyl)-4H-1,2,4-triazol-3-yl)-1-hydroxy-2-propanesulfonamide;

(1S,2R)-1-(4-cyano-2-fluorophenyl)-N-(4-(2,6-dimethoxy phenyl)-5-(5-methyl-2-furanyl)-4H-1,2,4-triazol-3-yl)-1-hydroxy-2-propanesulfonamide;

(1S,2S)-1-(4-cyano-2-fluorophenyl)-N-(4-(2,6-dimethoxyphenyl)-5-(5-methyl-2-furanyl)-4H-1,2,4-triazol-3-yl)-1-hydroxy-2-propanesulfonamide;

(2S)—N-(4-(2,6-dimethoxyphenyl)-5-(5-methyl-2-furanyl)-4H-1,2,4-triazol-3-yl)-4-methoxy-1-(5-methyl-2-pyrimidinyl)-2-butanesulfonamide;

(3R,4R)—N-(4-(2,6-dimethoxyphenyl)-5-(5-methyl-2-furanyl)-4H-1,2,4-triazol-3-yl)-1-hydroxy-4-(5-methyl-2-pyrimidinyl)-3-pentanesulfonamide;

(3R,4S)—N-(4-(2,6-dimethoxyphenyl)-5-(5-methyl-2-furanyl)-4H-1,2,4-triazol-3-yl)-1-hydroxy-4-(5-methyl-2-pyrimidinyl)-3-pentanesulfonamide;

(3S,4R)—N-(4-(2,6-dimethoxyphenyl)-5-(5-methyl-2-furanyl)-4H-1,2,4-triazol-3-yl)-1-hydroxy-4-(5-methyl-2-pyrimidinyl)-3-pentanesulfonamide;

(2S)—N-(4-(2,6-dimethoxyphenyl)-5-(5-methyl-2-furanyl)-4H-1,2,4-triazol-3-yl)-1-(5-fluoro-2-pyrimidinyl)-3-methoxy-2-propanesulfonamide;

(1R,2S)—N-(4-(2,6-dimethoxyphenyl)-5-(5-methyl-2-furanyl)-4H-1,2,4-triazol-3-yl)-1-(5-fluoro-2-pyridinyl)-1-hydroxy-2-propanesulfonamide;

(1S,2R)—N-(4-(2,6-dimethoxyphenyl)-5-(5-methyl-2-furanyl)-4H-1,2,4-triazol-3-yl)-1-(5-fluoro-2-pyridinyl)-1-hydroxy-2-propanesulfonamide;

(1R,2R)-1-(3-cyano-4-fluorophenyl)-N-(4-(2,6-dimethoxyphenyl)-5-(5-methyl-2-furanyl)-4H-1,2,4-triazol-3-yl)-1-hydroxy-2-propanesulfonamide;

(1S,2S)-1-(3-cyano-4-fluorophenyl)-N-(4-(2,6-dimethoxyphenyl)-5-(5-methyl-2-furanyl)-4H-1,2,4-triazol-3-yl)-1-hydroxy-2-propanesulfonamide;

(1R,2R)—N-(4-(2,6-dimethoxyphenyl)-5-(5-methyl-2-furanyl)-4H-1,2,4-triazol-3-yl)-1-(2,4-dimethyl-1,3-oxazol-5-yl)-1-hydroxy-2-propanesulfonamide;

(1R,2S)—N-(4-(2,6-dimethoxyphenyl)-5-(5-methyl-2-furanyl)-4H-1,2,4-triazol-3-yl)-1-(2,4-dimethyl-1,3-oxazol-5-yl)-1-hydroxy-2-propanesulfonamide;

(1S,2R)—N-(4-(2,6-dimethoxyphenyl)-5-(5-methyl-2-furanyl)-4H-1,2,4-triazol-3-yl)-1-(2,4-dimethyl-1,3-oxazol-5-yl)-1-hydroxy-2-propanesulfonamide;

(1S,2S)—N-(4-(2,6-dimethoxyphenyl)-5-(5-methyl-2-furanyl)-4H-1,2,4-triazol-3-yl)-1-(2,4-dimethyl-1,3-oxazol-5-yl)-1-hydroxy-2-propanesulfonamide;

2-(4-chlorophenyl)-N-(5-(2-furanyl)-4-(1R,2R)-2-methoxy cyclopentyl)-4H-1,2,4-triazol-3-yl)ethanesulfonamide;

2-(4-chlorophenyl)-N-(5-(2-furanyl)-4-(1S,2S)-2-methoxy cyclopentyl)-4H-1,2,4-triazol-3-yl)ethanesulfonamide;

2-(4-chlorophenyl)-N-(5-(2-furanyl)-4-(2-pyridinyl)-4H-1,2,4-triazol-3-yl)ethane sulfonamide;

(1R,2S)-1-(6-chloro-2-pyridinyl)-N-(4-(2,6-dimethoxyphenyl)-5-(5-methyl-2-furanyl)-4H-1,2,4-triazol-3-yl)-1-hydroxy-2-propanesulfonamide;

(1R,2S)-1-(5-cyano-6-methyl-2-pyridinyl)-N-(4-(2,6-dimethoxyphenyl)-5-(5-methyl-2-furanyl)-4H-1,2,4-triazol-3-yl)-1-hydroxy-2-propanesulfonamide;

(1R,2S)—N-(4-(2,6-dimethoxyphenyl)-5-(5-methyl-2-furanyl)-4H-1,2,4-triazol-3-yl)-1-hydroxy-1-(6-methyl-2-pyridinyl)-2-propanesulfonamide;

(1R,2R)-1-(5-cyano-6-methyl-2-pyridinyl)-N-(4-(2,6-dimethoxyphenyl)-5-(5-methyl-2-furanyl)-4H-1,2,4-triazol-3-yl)-1-hydroxy-2-propanesulfonamide;

(1S,2R)-1-(5-cyano-6-methyl-2-pyridinyl)-N-(4-(2,6-dimethoxyphenyl)-5-(5-methyl-2-furanyl)-4H-1,2,4-triazol-3-yl)-1-hydroxy-2-propanesulfonamide;

(1S,2S)-1-(5-cyano-6-methyl-2-pyridinyl)-N-(4-(2,6-dimethoxyphenyl)-5-(5-methyl-2-furanyl)-4H-1,2,4-triazol-3-yl)-1-hydroxy-2-propanesulfonamide;

(2S)—N-(4-(2,6-dimethoxyphenyl)-5-(4,5-dimethyl-2-furanyl)-4H-1,2,4-triazol-3-yl)-1-(5-fluoro-2-pyrimidinyl)-2-propanesulfonamide;

(1R,2R)—N-(4-(2,6-dimethoxyphenyl)-5-(5-methyl-2-furanyl)-4H-1,2,4-triazol-3-yl)-1-hydroxy-1-(2-pyridinyl)-2-propanesulfonamide;

(1S,2S)—N-(4-(2,6-dimethoxyphenyl)-5-(5-methyl-2-furanyl)-4H-1,2,4-triazol-3-yl)-1-hydroxy-1-(2-pyridinyl)-2-propanesulfonamide;

(2R)—N-(4-(2,6-dimethoxyphenyl)-5-(4,5-dimethyl-2-furanyl)-4H-1,2,4-triazol-3-yl)-1-(5-fluoro-2-pyrimidinyl)-2-propanesulfonamide;

(2R)—N-(4-(2,6-dimethoxyphenyl)-5-(5-ethyl-2-furanyl)-4H-1,2,4-triazol-3-yl)-1-(5-fluoro-2-pyrimidinyl)-2-propanesulfonamide;

(2S)—N-(4-(2,6-dimethoxyphenyl)-5-(5-ethyl-2-furanyl)-4H-1,2,4-triazol-3-yl)-1-(5-fluoro-2-pyrimidinyl)-2-propanesulfonamide;

(1S,2R)—N-(4-(2,6-dimethoxyphenyl)-5-(5-methyl-2-furanyl)-4H-1,2,4-triazol-3-yl)-1-(5-fluoro-2-pyrimidinyl)-1-hydroxy-2-propanesulfonamide;

(2R)—N-(4-(2,6-dimethoxyphenyl)-5-(5-methyl-2-furanyl)-4H-1,2,4-triazol-3-yl)-1-(5-fluoro-2-pyrimidinyl)-2-propanesulfonamide;
(2S)—N-(4-(2,6-dimethoxyphenyl)-5-(5-methyl-2-furanyl)-4H-1,2,4-triazol-3-yl)-1-(5-fluoro-2-pyrimidinyl)-2-propanesulfonamide;
(1S,2S)—N-(4-(2,6-dimethoxyphenyl)-5-(5-methyl-2-furanyl)-4H-1,2,4-triazol-3-yl)-1-(5-fluoro-2-pyrimidinyl)-1-hydroxy-2-propanesulfonamide;
(1R,2S)—N-(4-(2,6-dimethoxyphenyl)-5-(5-methyl-2-furanyl)-4H-1,2,4-triazol-3-yl)-1-(5-fluoro-2-pyrimidinyl)-1-hydroxy-2-propanesulfonamide;
N-(4-(2,6-dimethoxyphenyl)-5-(5-ethyl-2-furanyl)-4H-1,2,4-triazol-3-yl)-2-(5-fluoro-2-pyrimidinyl)ethanesulfonamide;
(1R,2S)—N-(4-(2,6-dimethoxyphenyl)-5-(5-methyl-2-furanyl)-4H-1,2,4-triazol-3-yl)-2-(5-fluoro-2-pyrimidinyl)cyclopentanesulfonamide;
(1S,2R)—N-(4-(2,6-dimethoxyphenyl)-5-(5-methyl-2-furanyl)-4H-1,2,4-triazol-3-yl)-2-(5-fluoro-2-pyrimidinyl)cyclopentanesulfonamide;
(1S,2S)—N-(4-(2,6-dimethoxyphenyl)-5-(2-furanyl)-4H-1,2,4-triazol-3-yl)-2-(5-fluoro-2-pyrimidinyl)cyclohexanesulfonamide;
(1R,2S)—N-(4-(2,6-dimethoxyphenyl)-5-(2-furanyl)-4H-1,2,4-triazol-3-yl)-2-(5-fluoro-2-pyrimidinyl)cyclopentanesulfonamide;
(1R,2S)—N-(4-(2,6-dimethoxyphenyl)-5-(2-furanyl)-4H-1,2,4-triazol-3-yl)-2-(5-fluoro-2-pyrimidinyl)cyclohexanesulfonamide;
2-(4-chlorophenyl)-N-(4-(2,6-dimethoxyphenyl)-5-(3-methyl-2-furanyl)-4H-1,2,4-triazol-3-yl)ethanesulfonamide;
N-(4-(2,6-dimethoxyphenyl)-5-(5-(trifluoromethyl)-2-furanyl)-4H-1,2,4-triazol-3-yl)-2-(5-fluoro-2-pyrimidinyl)ethanesulfonamide;
(2R,3S)—N-(4-(2,6-dimethoxyphenyl)-5-(5-methyl-2-furanyl)-4H-1,2,4-triazol-3-yl)-3-(5-fluoro-2-pyrimidinyl)-2-butanesulfonamide;
(2S,3S)—N-(4-(2,6-dimethoxyphenyl)-5-(5-methyl-2-furanyl)-4H-1,2,4-triazol-3-yl)-3-(5-fluoro-2-pyrimidinyl)-2-butanesulfonamide;
2-(4-chlorophenyl)-N-(4-(2,6-dimethoxyphenyl)-5-(2-furanyl)-4H-1,2,4-triazol-3-yl)ethanesulfonamide;
2-(4-chlorophenyl)-N-(5-(2-furanyl)-4-(2-methoxy-6-methylphenyl)-4H-1,2,4-triazol-3-yl)ethanesulfonamide;
3-(4-chlorophenyl)-N-(4-(2,6-dimethoxyphenyl)-5-(2-furanyl)-4H-1,2,4-triazol-3-yl)-1-propanesulfonamide;
(1R,2S)—N-(4-(2,6-dimethoxyphenyl)-5-(5-methyl-2-furanyl)-4H-1,2,4-triazol-3-yl)-1-hydroxy-1-(5-methyl-2-pyrimidinyl)-2-propanesulfonamide;
(1R,2S)—N-(4-(2,6-dimethoxyphenyl)-5-(5-methyl-2-furanyl)-4H-1,2,4-triazol-3-yl)-1-(5-fluoro-2-pyrimidinyl)-1-methoxy-2-propanesulfonamide;
(1S,2S)—N-(4-(2,6-dimethoxyphenyl)-5-(5-methyl-2-furanyl)-4H-1,2,4-triazol-3-yl)-1-ethoxy-1-(5-methyl-2-pyrimidinyl)-2-propanesulfonamide;
(1R,2S)—N-(4-(2,6-dimethoxyphenyl)-5-(5-methyl-2-furanyl)-4H-1,2,4-triazol-3-yl)-1-ethoxy-1-(5-methyl-2-pyrimidinyl)-2-propanesulfonamide;
2-(2-cyano-4-fluorophenyl)-N-(4-(2,6-dimethoxyphenyl)-5-(5-methyl-2-furanyl)-4H-1,2,4-triazol-3-yl)ethanesulfonamide;
(1R,2S)—N-(4-(2,6-dimethoxyphenyl)-5-(5-methyl-2-furanyl)-4H-1,2,4-triazol-3-yl)-1-(2-methoxy ethoxy)-1-(5-methyl-2-pyrimidinyl)-2-propanesulfonamide;
(1S,2S)—N-(4-(2,6-dimethoxyphenyl)-5-(5-methyl-2-furanyl)-4H-1,2,4-triazol-3-yl)-1-(2-hydroxy ethoxy)-1-(5-methyl-2-pyrimidinyl)-2-propanesulfonamide;
(1R,2R)—N-(4-(2,6-dimethoxyphenyl)-5-(5-methyl-2-furanyl)-4H-1,2,4-triazol-3-yl)-1-(5-fluoro-2-pyrimidinyl)-1-methoxy-2-propanesulfonamide;
(2R)—N-(4-(2,6-dimethoxyphenyl)-5-(5-methyl-2-furanyl)-4H-1,2,4-triazol-3-yl)-2-(5-fluoro-2-pyrimidinyl)-1-propanesulfonamide;
(1S,2S)—N-(4-(2,6-dimethoxyphenyl)-5-(5-methyl-2-furanyl)-4H-1,2,4-triazol-3-yl)-1-(5-fluoro-2-pyrimidinyl)-1-methoxy-2-propanesulfonamide;
N-(4-(2,6-dimethoxyphenyl)-5-(5-methyl-2-furanyl)-4H-1,2,4-triazol-3-yl)-2-(5-fluoro-2-pyrimidinyl)ethanesulfonamide;
(2S)—N-(4-(2,6-dimethoxyphenyl)-5-(5-methyl-2-furanyl)-4H-1,2,4-triazol-3-yl)-2-(5-fluoro-2-pyrimidinyl)-1-propanesulfonamide;
(2R)—N-(4-(2,6-dimethoxyphenyl)-5-(5-methyl-2-furanyl)-4H-1,2,4-triazol-3-yl)-1-(5-fluoro-2-pyrimidinyl)-2-butanesulfonamide;
(2S)—N-(4-(2,6-dimethoxyphenyl)-5-(5-methyl-2-furanyl)-4H-1,2,4-triazol-3-yl)-1-(5-fluoro-2-pyrimidinyl)-2-butanesulfonamide;
(2R)—N-(4-(2,6-dimethoxyphenyl)-5-(2-furanyl)-4H-1,2,4-triazol-3-yl)-2-(5-fluoro-2-pyrimidinyl)-1-propanesulfonamide;
(2S)—N-(4-(2,6-dimethoxyphenyl)-5-(2-furanyl)-4H-1,2,4-triazol-3-yl)-2-(5-fluoro-2-pyrimidinyl)-1-propanesulfonamide;
(1R,2R)—N-(4-(2,6-dimethoxyphenyl)-5-(5-methyl-2-furanyl)-4H-1,2,4-triazol-3-yl)-1-ethoxy-1-(5-methyl-2-pyrimidinyl)-2-propanesulfonamide;
2-(2-cyano-4-fluorophenyl)-N-(4-(2,6-dimethoxyphenyl)-5-(5-(trifluoromethyl)-2-furanyl)-4H-1,2,4-triazol-3-yl)ethanesulfonamide;
(2R)—N-(4-(2,6-dimethoxyphenyl)-5-(2-furanyl)-4H-1,2,4-triazol-3-yl)-1-(5-fluoro-2-pyrimidinyl)-2-butanesulfonamide;
(2S)—N-(4-(2,6-dimethoxyphenyl)-5-(2-furanyl)-4H-1,2,4-triazol-3-yl)-1-(5-fluoro-2-pyrimidinyl)-2-butanesulfonamide;
(2R,3R)—N-(4-(2,6-dimethoxyphenyl)-5-(5-methyl-2-furanyl)-4H-1,2,4-triazol-3-yl)-3-(5-fluoro-2-pyrimidinyl)-2-butanesulfonamide;
2-(4-chlorophenyl)-N-(4-(2,6-dimethoxyphenyl)-5-(5-methyl-2-furanyl)-4H-1,2,4-triazol-3-yl)ethanesulfonamide;
2-(4-chlorophenyl)-N-(4-(2,6-dimethoxyphenyl)-5-(5-(methoxymethyl)-2-furanyl)-4H-1,2,4-triazol-3-yl)ethanesulfonamide;
2-(4-chlorophenyl)-N-(4-(2,6-dimethoxyphenyl)-5-(5-(trifluoromethyl)-2-furanyl)-4H-1,2,4-triazol-3-yl)ethanesulfonamide;
N-(5-(5-bromo-2-furanyl)-4-(2,6-dimethoxyphenyl)-4H-1,2,4-triazol-3-yl)-2-(4-chlorophenyl)ethanesulfonamide;
N-(5-(5-tert-butyl-2-furanyl)-4-(2,6-dimethoxyphenyl)-4H-1,2,4-triazol-3-yl)-2-(4-chlorophenyl)ethanesulfonamide;
N-(5-(5-tert-butyl-2-furanyl)-4-(2,6-dimethoxyphenyl)-4H-1,2,4-triazol-3-yl)-2-(2-cyano-4-fluorophenyl)ethanesulfonamide;
(2R)-2-(4-chloro-2-(methylsulfonyl)phenyl)-N-(4-(2,6-dimethoxyphenyl)-5-(5-methyl-2-furanyl)-4H-1,2,4-triazol-3-yl)-2-hydroxyethanesulfonamide;
(2S)-2-(4-chloro-2-(methylsulfonyl)phenyl)-N-(4-(2,6-dimethoxyphenyl)-5-(5-methyl-2-furanyl)-4H-1,2,4-triazol-3-yl)-2-hydroxyethanesulfonamide;

(2R,3S)—N-(4-(2,6-dimethoxyphenyl)-5-(5-methyl-2-furanyl)-4H-1,2,4-triazol-3-yl)-3-(5-methyl-1-oxido-2-pyrazinyl)-2-butanesulfonamide;
(2S,3R)—N-(4-(2,6-dimethoxyphenyl)-5-(5-methyl-2-furanyl)-4H-1,2,4-triazol-3-yl)-3-(5-methyl-1-oxido-2-pyrazinyl)-2-butanesulfonamide;
(2S,3R)—N-(4-(2,6-dimethoxyphenyl)-5-(5-methyl-2-furanyl)-4H-1,2,4-triazol-3-yl)-3-(5-methyl-2-pyrazinyl)-2-butanesulfonamide;
(1R,2S)-1-(2,4-dicyanophenyl)-N-(4-(2,6-dimethoxyphenyl)-5-(5-methyl-2-furanyl)-4H-1,2,4-triazol-3-yl)-1-methoxy-2-propanesulfonamide;
(1S,2R)-1-(2,4-dicyanophenyl)-N-(4-(2,6-dimethoxyphenyl)-5-(5-methyl-2-furanyl)-4H-1,2,4-triazol-3-yl)-1-methoxy-2-propanesulfonamide;
(2R)—N-(4-(2,6-dimethoxyphenyl)-5-(5-methyl-2-furanyl)-4H-1,2,4-triazol-3-yl)-1-((2R)-2-(methoxymethyl)-6-oxo-1-piperidinyl)-2-propanesulfonamide;
(2R)—N-(4-(2,6-dimethoxyphenyl)-5-(5-methyl-2-furanyl)-4H-1,2,4-triazol-3-yl)-1-((2S)-2-(methoxymethyl)-6-oxo-1-piperidinyl)-2-propanesulfonamide;
(1R,2S)—N-(4-(2,6-dimethoxyphenyl)-5-(5-methyl-2-furanyl)-4H-1,2,4-triazol-3-yl)-1-hydroxy-1-(5-methoxy-2-pyrazinyl)-2-propanesulfonamide;
(1R,2R)-1-(4-chloro-2-(methylsulfonyl)phenyl)-N-(4-(2,6-dimethoxyphenyl)-5-(5-methyl-2-furanyl)-4H-1,2,4-triazol-3-yl)-1-hydroxy-2-propanesulfonamide;
(3R,5R)-5-(1-azetidinylcarbonyl)-N-(4-(2,6-dimethoxyphenyl)-5-(5-methyl-2-furanyl)-4H-1,2,4-triazol-3-yl)-1-(5-fluoro-2-pyrimidinyl)-3-piperidinesulfonamide;
(3S,5S)-5-(1-azetidinylcarbonyl)-N-(4-(2,6-dimethoxyphenyl)-5-(5-methyl-2-furanyl)-4H-1,2,4-triazol-3-yl)-1-(5-fluoro-2-pyrimidinyl)-3-piperidinesulfonamide;
(3R,5S)-5-(1-azetidinylcarbonyl)-N-(4-(2,6-dimethoxyphenyl)-5-(5-methyl-2-furanyl)-4H-1,2,4-triazol-3-yl)-1-(5-fluoro-2-pyrimidinyl)-3-piperidinesulfonamide;
(3S,5R)-5-(1-azetidinylcarbonyl)-N-(4-(2,6-dimethoxyphenyl)-5-(5-methyl-2-furanyl)-4H-1,2,4-triazol-3-yl)-1-(5-fluoro-2-pyrimidinyl)-3-piperidinesulfonamide;
ethyl (3S,5R)-5-((4-(2,6-dimethoxyphenyl)-5-(2-furanyl)-4H-1,2,4-triazol-3-yl)sulfamoyl)-1-(5-fluoro-2-pyrimidinyl)-3-piperidinecarboxylate;
(1S,2R)-1-(4-chloro-2-(methylsulfonyl)phenyl)-N-(4-(2,6-dimethoxyphenyl)-5-(5-methyl-2-furanyl)-4H-1,2,4-triazol-3-yl)-1-hydroxy-2-propanesulfonamide;
ethyl (3R,5R)-5-(4-(2,6-dimethoxyphenyl)-5-(2-furanyl)-4H-1,2,4-triazol-3-yl)sulfamoyl)-1-(5-fluoro-2-pyrimidinyl)-3-piperidinecarboxylate;
(3R,5S)-5-(1-azetidinylcarbonyl)-N-(4-(2,6-dimethoxyphenyl)-5-(2-furanyl)-4H-1,2,4-triazol-3-yl)-1-(5-fluoro-2-pyrimidinyl)-3-piperidinesulfonamide;
N-(4-(2,6-dimethoxyphenyl)-5-(2-furanyl)-4H-1,2,4-triazol-3-yl)-2-((6R)-3,6-dimethyl-2-oxotetrahydro-1(2H)-pyrimidinyl)ethanesulfonamide;
N-(4-(2,6-dimethoxyphenyl)-5-(5-methyl-2-furanyl)-4H-1,2,4-triazol-3-yl)-2-((6R)-3,6-dimethyl-2-oxotetrahydro-1(2H)-pyrimidinyl)ethanesulfonamide;
(3S,5R)-1-acetyl-N-(4-(2,6-dimethoxyphenyl)-5-(5-methyl-2-furanyl)-4H-1,2,4-triazol-3-yl)-5-(4-fluorophenyl)-3-piperidinesulfonamide;
(2S,3R)—N-(4-(4-methoxy-2-oxo-1,2-dihydro-3-pyridinyl)-5-(5-methyl-2-furanyl)-4H-1,2,4-triazol-3-yl)-3-(5-methyl-2-pyrimidinyl)-2-butanesulfonamide;
(3R,5S)—N-(4-(2,6-dimethoxyphenyl)-5-(2-furanyl)-4H-1,2,4-triazol-3-yl)-1-(5-fluoro-2-pyrimidinyl)-5-hydroxy-3-piperidinesulfonamide;
2-(2R,4R)-2-cyano-2,4-dimethyl-5-oxo-1-pyrrolidinyl)-N-(4-(2,6-dimethoxyphenyl)-5-(2-furanyl)-4H-1,2,4-triazol-3-yl)ethanesulfonamide;
N-(4-(2,6-dimethoxyphenyl)-5-(2-furanyl)-4H-1,2,4-triazol-3-yl)-2-(2S)-2-methyl-6-oxo-1-piperidinyl)ethanesulfonamide;
(3S,5S)-1-acetyl-N-(4-(2,6-dimethoxyphenyl)-5-(5-methyl-2-furanyl)-4H-1,2,4-triazol-3-yl)-5-(4-fluorophenyl)-3-piperidinesulfonamide;
(3R,5S)-1-acetyl-N-(4-(2,6-dimethoxyphenyl)-5-(5-methyl-2-furanyl)-4H-1,2,4-triazol-3-yl)-5-(4-fluorophenyl)-3-piperidinesulfonamide;
(2S,3R)-3-(5-fluoro-2-pyrimidinyl)-N-(4-(2-methoxyphenyl)-5-(5-methyl-2-furanyl)-4H-1,2,4-triazol-3-yl)-2-butanesulfonamide;
(3S,9aR)—N-(4-(2,6-dimethoxyphenyl)-5-(5-methyl-2-furanyl)-4H-1,2,4-triazol-3-yl)-6-oxooctahydro-2H-quinolizine-3-sulfonamide;
(3R,5S)-5-cyano-N-(4-(2,6-dimethoxyphenyl)-5-(5-methyl-2-furanyl)-4H-1,2,4-triazol-3-yl)-1-(5-fluoro-2-pyrimidinyl)-3-piperidinesulfonamide;
N-(4-(2,6-dimethoxyphenyl)-5-(2-furanyl)-4H-1,2,4-triazol-3-yl)-2-((3R,5S)-3,5-dimethyl-2-oxo-1-pyrrolidinyl)ethanesulfonamide;
N-(4-(2,6-dimethoxyphenyl)-5-(2-furanyl)-4H-1,2,4-triazol-3-yl)-2-((2R)-2-(methoxymethyl)-6-oxo-1-piperidinyl)ethanesulfonamide;
(1S,2R)—N-(4-(2,6-dimethoxyphenyl)-5-(5-methyl-2-furanyl)-4H-1,2,4-triazol-3-yl)-1-hydroxy-1-(5-methoxy-2-pyrazinyl)-2-propanesulfonamide;
(3S,5R)—N-(4-(2,6-dimethoxyphenyl)-5-(2-furanyl)-4H-1,2,4-triazol-3-yl)-1-(5-fluoro-2-pyrimidinyl)-5-methoxy-3-piperidinesulfonamide;
(3R)—N-(4-(2,6-dimethoxyphenyl)-5-(5-methyl-2-furanyl)-4H-1,2,4-triazol-3-yl)-1-(5-fluoro-2-pyrimidinyl)-3-piperidinesulfonamide;
(3R,4S)—N-(4-(2,6-dimethoxyphenyl)-5-(2-furanyl)-4H-1,2,4-triazol-3-yl)-4-(5-fluoro-2-pyrimidinyl)tetrahydro-3-furansulfonamide;
(3S,4R)—N-(4-(2,6-dimethoxyphenyl)-5-(2-furanyl)-4H-1,2,4-triazol-3-yl)-4-(5-fluoro-2-pyrimidinyl)tetrahydro-3-furansulfonamide;
(3R)-7-chloro-N-(4-(2,6-dimethoxyphenyl)-5-(2-furanyl)-4H-1,2,4-triazol-3-yl)-3,4-dihydro-2H-pyrano[3,2-b]pyridine-3-sulfonamide;
(3S)-7-chloro-N-(4-(2,6-dimethoxyphenyl)-5-(2-furanyl)-4H-1,2,4-triazol-3-yl)-3,4-dihydro-2H-pyrano[3,2-b]pyridine-3-sulfonamide;
(2S,3R)-3-(5-fluoro-2-pyrimidiny))-N-(5-(5-methyl-2-furanyl)-4-(tetrahydro-2H-pyran-4-yl)-4H-1,2,4-triazol-3-yl)-2-butanesulfonamide;
(3R,4R)—N-(4-(2,6-dimethoxyphenyl)-5-(2-furanyl)-4H-1,2,4-triazol-3-yl)-4-(5-fluoro-2-pyrimidinyl)tetrahydro-2H-pyran-3-sulfonamide;
(3S,4S)—N-(4-(2,6-dimethoxyphenyl)-5-(2-furanyl)-4H-1,2,4-triazol-3-yl)-4-(5-fluoro-2-pyrimidinyl)tetrahydro-2H-pyran-3-sulfonamide;
(2S)—N-(4-(2,6-dimethoxyphenyl)-5-(5-methyl-2-furanyl)-4H-1,2,4-triazol-3-yl)-1-(2S)-2-(methoxymethyl)-6-oxo-1-piperidinyl)-2-propanesulfonamide;
(2S,3R)-3-(5-fluoro-2-pyrimidiny))-N-(4-(4-methoxy-2-oxo-1,2-dihydro-3-pyridinyl)-5-(5-methyl-2-furanyl)-4H-1,2,4-triazol-3-yl)-2-butanesulfonamide;
(3R,5S)—N-(4-(2,6-dimethoxyphenyl)-5-(2-furanyl)-4H-1,2,4-triazol-3-yl)-5-(4-fluorophenyl)-3-piperidinesulfonamide;

(2S,3R)—N-(4-(3,5-dibromo-2,6-dimethoxyphenyl)-5-(5-methyl-2-furanyl)-4H-1,2,4-triazol-3-yl)-3-(5-fluoro-2-pyrimidiny))-2-butanesulfonamide;

(1R,2S)-2-(4-chlorophenyl)-N-(4-(2,6-dimethoxyphenyl)-5-(2-furanyl)-4H-1,2,4-triazol-3-yl)cyclopropanesulfonamide;

(1S,2R)-2-(4-chlorophenyl)-N-(4-(2,6-dimethoxyphenyl)-5-(2-furanyl)-4H-1,2,4-triazol-3-yl)cyclopropanesulfonamide;

2-(4-chlorophenyl)-N-(4-(2-cyano-6-methoxyphenyl)-5-(2-furanyl)-4H-1,2,4-triazol-3-yl)ethanesulfonamide;

2-(2-bromo-4-fluorophenyl)-N-(4-(2,6-dimethoxy phenyl)-5-(2-furanyl)-4H-1,2,4-triazol-3-yl)ethanesulfonamide;

N-(4-(2,6-dimethoxyphenyl)-5-(2-furanyl)-4H-1,2,4-triazol-3-yl)-2-(4-fluoro-2-(methylsulfonyl)phenyl)ethanesulfonamide;

N-(2-(2-(4-(2,6-dimethoxyphenyl)-5-(2-furanyl)-4H-1,2,4-triazol-3-yl)sulfamoyl)ethyl)-5-fluorophenyl)acetamide;

(2R)—N-(4-(2,6-dimethoxyphenyl)-5-(2-furanyl)-4H-1,2,4-triazol-3-yl)-2-(4-fluorophenyl)-1-propanesulfonamide;

N-(4-(2,6-dimethoxyphenyl)-5-(2-furanyl)-4H-1,2,4-triazol-3-yl)-3-oxo-3-(1-pyrrolidinyl)-1-propanesulfonamide;

(3S)-3-cyclopentyl-N-(4-(2,6-dimethoxyphenyl)-5-(2-furanyl)-4H-1,2,4-triazol-3-yl)-3-hydroxy-1-propanesulfonamide;

(3R)-3-cyclopentyl-N-(4-(2,6-dimethoxyphenyl)-5-(2-furanyl)-4H-1,2,4-triazol-3-yl)-3-hydroxy-1-propanesulfonamide;

N-(4-(2,6-dimethoxyphenyl)-5-(2-furanyl)-4H-1,2,4-triazol-3-yl)-2-((4S)-4-methyl-2-oxo-1,3-oxazinan-3-yl)ethanesulfonamide;

N-(4-(2,6-dimethoxyphenyl)-5-(2-furanyl)-4H-1,2,4-triazol-3-yl)-2-(2-methoxy-3-pyridinyl)ethanesulfonamide;

(2R)—N-(4-(2,6-dimethoxyphenyl)-5-(2-furanyl)-4H-1,2,4-triazol-3-yl)-1-(3-methoxy-2-pyrazinyl)-2-propanesulfonamide;

(2S)—N-(4-(2,6-dimethoxyphenyl)-5-(2-furanyl)-4H-1,2,4-triazol-3-yl)-1-(3-methoxy-2-pyrazinyl)-2-propanesulfonamide;

N-(4-(2,6-dimethoxyphenyl)-5-(5-methyl-2-furanyl)-4H-1,2,4-triazol-3-yl)-2-((6S)-3,6-dimethyl-2-oxotetrahydro-1(2H)-pyrimidinyl)ethanesulfonamide;

(2S)-1-(4-chlorophenyl)-N-(4-(2,6-dimethoxyphenyl)-5-(2-furanyl)-4H-1,2,4-triazol-3-yl)-2-propanesulfonamide;

(3S)—N-(4-(2,6-dimethoxyphenyl)-5-(2-furanyl)-4H-1,2,4-triazol-3-yl)-1-(5-fluoro-2-pyrimidinyl)-3-piperidinesulfonamide;

N-(4-(2,6-dimethoxyphenyl)-5-(2-furanyl)-4H-1,2,4-triazol-3-yl)-2-(4-fluorophenyl)ethanesulfonamide;

(2R)-1-(4-chlorophenyl)-N-(4-(2,6-dimethoxyphenyl)-5-(2-furanyl)-4H-1,2,4-triazol-3-yl)-2-propanesulfonamide;

2-(4-chlorophenyl)-N-(5-(2-furanyl)-4-(2-methoxyphenyl)-4H-1,2,4-triazol-3-yl)ethanesulfonamide;

2-(2-cyano-4-fluorophenyl)-N-(4-(2,6-dimethoxyphenyl)-5-(2-furanyl)-4H-1,2,4-triazol-3-yl)ethanesulfonamide;

(1S,2R)—N-(4-(2,6-dimethoxyphenyl)-5-(5-methyl-2-furanyl)-4H-1,2,4-triazol-3-yl)-1-hydroxy-1-(5-methyl-2-pyrimidinyl)-2-propanesulfonamide;

(1R,2S)-1-(5-chloro-2-pyrimidinyl)-N-(4-(2,6-dimethoxyphenyl)-5-(5-methyl-2-furanyl)-4H-1,2,4-triazol-3-yl)-1-hydroxy-2-propanesulfonamide;

(1S,2S)—N-(4-(2,6-dimethoxyphenyl)-5-(5-methyl-2-furanyl)-4H-1,2,4-triazol-3-yl)-1-hydroxy-1-(5-methyl-2-pyrazinyl)-2-propanesulfonamide;

2-(5-chloro-1'-methyl-1',2',3',6'-tetrahydro-3,4'-bipyridin-2-yl)-N-(4-(2,6-dimethoxyphenyl)-5-(2-furanyl)-4H-1,2,4-triazol-3-yl)ethanesulfonamide;

2-(5-chloro-3-(3,6-dihydro-2H-pyran-4-yl)-2-pyridinyl)-N-(4-(2,6-dimethoxyphenyl)-5-(2-furanyl)-4H-1,2,4-triazol-3-yl)ethanesulfonamide;

(1S,2R)-1-(5-chloro-2-pyrimidinyl)-N-(4-(2,6-dimethoxyphenyl)-5-(5-methyl-2-furanyl)-4H-1,2,4-triazol-3-yl)-1-hydroxy-2-propanesulfonamide;

(2S,3S)—N-(4-(2,6-dimethoxyphenyl)-5-(5-methyl-2-furanyl)-4H-1,2,4-triazol-3-yl)-3-hydroxy-3-(5-methyl-2-pyrimidinyl)-2-butanesulfonamide;

(2R,3R)—N-(4-(2,6-dimethoxyphenyl)-5-(2-furanyl)-4H-1,2,4-triazol-3-yl)-3-(5-fluoro-2-pyrimidinyl)-2-butanesulfonamide;

(2S,3S)—N-(4-(2,6-dimethoxyphenyl)-5-(2-furanyl)-4H-1,2,4-triazol-3-yl)-3-(5-fluoro-2-pyrimidinyl)-2-butanesulfonamide;

2-(5-chloro-3-(4-morpholinylmethyl)-2-pyridinyl)-N-(4-(2,6-dimethoxyphenyl)-5-(2-furanyl)-4H-1,2,4-triazol-3-yl)ethanesulfonamide;

2-(5-chloro-1',2',3',6'-tetrahydro-3,4'-bipyridin-2-yl)-N-(4-(2,6-dimethoxyphenyl)-5-(2-furanyl)-4H-1,2,4-triazol-3-yl)ethanesulfonamide;

2-(5-chloro-3,3'-bipyridin-2-yl)-N-(4-(2,6-dimethoxyphenyl)-5-(2-furanyl)-4H-1,2,4-triazol-3-yl)ethanesulfonamide;

2-(5-chloro-3,4'-bipyridin-2-yl)-N-(4-(2,6-dimethoxyphenyl)-5-(2-furanyl)-4H-1,2,4-triazol-3-yl)ethanesulfonamide;

2-(5-chloro-3-(1H-pyrazol-3-yl)-2-pyridinyl)-N-(4-(2,6-dimethoxyphenyl)-5-(2-furanyl)-4H-1,2,4-triazol-3-yl)ethanesulfonamide;

2-(1'-acetyl-5-chloro-1',2',3',6'-tetrahydro-3,4'-bipyridin-2-yl)-N-(4-(2,6-dimethoxyphenyl)-5-(2-furanyl)-4H-1,2,4-triazol-3-yl)ethanesulfonamide;

(2R,3S)—N-(4-(2,6-dimethoxyphenyl)-5-(5-methyl-2-furanyl)-4H-1,2,4-triazol-3-yl)-3-(5-fluoro-2-pyrimidinyl)-3-hydroxy-2-butanesulfonamide;

(1R,2R)—N-(4-(2,6-dimethoxyphenyl)-5-(5-methyl-2-furanyl)-4H-1,2,4-triazol-3-yl)-1-methoxy-1-(5-methyl-2-pyrimidinyl)-2-propanesulfonamide;

(2S,3S)-3-(5-cyano-2-pyridinyl)-N-(4-(2,6-dimethoxyphenyl)-5-(5-methyl-2-furanyl)-4H-1,2,4-triazol-3-yl)-3-hydroxy-2-butanesulfonamide;

(2S,3R)—N-(4-(2,6-dimethoxyphenyl)-5-(5-methyl-2-furanyl)-4H-1,2,4-triazol-3-yl)-3-(5-fluoro-2-pyrimidinyl)-3-hydroxy-2-butanesulfonamide;

(2R,3R)-3-(5-cyano-2-pyrimidinyl)-N-(4-(2,6-dimethoxyphenyl)-5-(5-methyl-2-furanyl)-4H-1,2,4-triazol-3-yl)-3-fluoro-2-butanesulfonamide;

(2S,3S)-3-(5-cyano-2-pyrimidinyl)-N-(4-(2,6-dimethoxyphenyl)-5-(5-methyl-2-furanyl)-4H-1,2,4-triazol-3-yl)-3-fluoro-2-butanesulfonamide;

(2S)-2-(5-cyano-2-pyrimidinyl)-N-(4-(2,6-dimethoxyphenyl)-5-(5-methyl-2-furanyl)-4H-1,2,4-triazol-3-yl)-2-fluoro-1-propanesulfonamide;

2-(5-chloro-3-(2-(1-pyrrolidinyl)ethyl)-2-pyridinyl)-N-(4-(2,6-dimethoxy phenyl)-5-(2-furanyl)-4H-1,2,4-triazol-3-yl)ethanesulfonamide;

(2R)-2-(5-cyano-2-pyrimidinyl)-N-(4-(2,6-dimethoxyphenyl)-5-(5-methyl-2-furanyl)-4H-1,2,4-triazol-3-yl)-2-hydroxy-1-propanesulfonamide;

(2R)—N-(4-(2,6-dimethoxyphenyl)-5-(2-furanyl)-4H-1,2,4-triazol-3-yl)-1-(5-fluoro-4-methyl-2-pyrimidinyl)-2-propanesulfonamide;

(2S)—N-(4-(2,6-dimethoxyphenyl)-5-(2-furanyl)-4H-1,2,4-triazol-3-yl)-1-(5-fluoro-4-methyl-2-pyrimidinyl)-2-propanesulfonamide;
2-(3-(2-(1-azetidinyl)ethyl)-5-chloro-2-pyridinyl)-N-(4-(2,6-dimethoxyphenyl)-5-(2-furanyl)-4H-1,2,4-triazol-3-yl)ethanesulfonamide;
(2R,3R)—N-(4-(2,6-dimethoxyphenyl)-5-(5-methyl-2-furanyl)-4H-1,2,4-triazol-3-yl)-3-(5-fluoro-2-pyrimidinyl)-3-hydroxy-2-butanesulfonamide;
(2S,3S)—N-(4-(2,6-dimethoxyphenyl)-5-(5-methyl-2-furanyl)-4H-1,2,4-triazol-3-yl)-3-(5-fluoro-2-pyrimidinyl)-3-hydroxy-2-butanesulfonamide;
(2R)—N-(4-(2,6-dimethoxyphenyl)-5-(5-methyl-2-furanyl)-4H-1,2,4-triazol-3-yl)-2-fluoro-2-(5-fluoro-2-pyrimidinyl)-1-propanesulfonamide;
2-(5-chloro-3-(2-((3S)-3-hydroxy-1-pyrrolidinyl)ethyl)-2-pyridinyl)-N-(4-(2,6-dimethoxyphenyl)-5-(2-furanyl)-4H-1,2,4-triazol-3-yl)ethanesulfonamide;
2-(5-chloro-3-(2-(4-morpholinyl)ethyl)-2-pyridinyl)-N-(4-(2,6-dimethoxyphenyl)-5-(2-furanyl)-4H-1,2,4-triazol-3-yl)ethanesulfonamide;
(2R)—N-(4-(2,6-dimethoxyphenyl)-5-(2-furanyl)-4H-1,2,4-triazol-3-yl)-1-(5-fluoro-3-((4R)-4-hydroxy-2-oxo-1-pyrrolidinyl)-2-pyridinyl)-2-propanesulfonamide;
(2S)—N-(4-(2,6-dimethoxyphenyl)-5-(2-furanyl)-4H-1,2,4-triazol-3-yl)-1-(5-fluoro-3-((4R)-4-hydroxy-2-oxo-1-pyrrolidinyl)-2-pyridinyl)-2-propanesulfonamide;
(2S)-2-(5-cyano-2-pyrimidinyl)-N-(4-(2,6-dimethoxyphenyl)-5-(5-methyl-2-furanyl)-4H-1,2,4-triazol-3-yl)-2-hydroxy-1-propanesulfonamide;
(2S,3R)-3-amino-N-(4-(2,6-dimethoxyphenyl)-5-(5-methyl-2-furanyl)-4H-1,2,4-triazol-3-yl)-3-(5-fluoro-2-pyrimidinyl)-2-butanesulfonamide;
(1R,2R)—N-(4-(2,6-dimethoxyphenyl)-5-(5-methyl-2-furanyl)-4H-1,2,4-triazol-3-yl)-1-hydroxy-1-(5-methyl-2-pyrimidinyl)-2-propanesulfonamide;
(2R)-2-(5-cyano-2-pyrimidinyl)-N-(4-(2,6-dimethoxyphenyl)-5-(5-methyl-2-furanyl)-4H-1,2,4-triazol-3-yl)-2-fluoro-1-propanesulfonamide;
(2R,3R)-3-amino-N-(4-(2,6-dimethoxyphenyl)-5-(5-methyl-2-furanyl)-4H-1,2,4-triazol-3-yl)-3-(5-fluoro-2-pyrimidinyl)-2-butanesulfonamide;
(1R,2S)—N-(4-(2,6-dimethoxyphenyl)-5-(5-methyl-2-furanyl)-4H-1,2,4-triazol-3-yl)-1-hydroxy-1-(5-methyl-2-pyrazinyl)-2-propanesulfonamide;
(2S)—N-(4-(2,6-dimethoxyphenyl)-5-(5-methyl-2-furanyl)-4H-1,2,4-triazol-3-yl)-2-(5-fluoro-2-pyrimidinyl)-2-hydroxy-1-propanesulfonamide;
(1S,2S)—N-(4-(2,6-dimethoxyphenyl)-5-(5-methyl-2-furanyl)-4H-1,2,4-triazol-3-yl)-1-methoxy-1-(5-methyl-2-pyrimidinyl)-2-propanesulfonamide;
(2S)—N-(4-(2,6-dimethoxyphenyl)-5-(2-furanyl)-4H-1,2,4-triazol-3-yl)-2-(5-methyl-2-pyrimidinyl)-1-propanesulfonamide;
2-(2-cyano-4-fluorophenyl)-N-(4-(4,6-dimethoxy-5-pyrimidinyl)-5-(2-furanyl)-4H-1,2,4-triazol-3-yl)ethanesulfonamide;
2-(4-chlorophenyl)-N-(4-(4,6-dimethoxy-5-pyrimidinyl)-5-(2-furanyl)-4H-1,2,4-triazol-3-yl)ethanesulfonamide;
2-(4-chlorophenyl)-N-(5-(2-furanyl)-4-(2-(hydroxymethyl)-6-methoxy phenyl)-4H-1,2,4-triazol-3-yl)ethanesulfonamide;
2-(4-chlorophenyl)-N-(5-(2-furanyl)-4-(2-methoxy-6-(methoxy methyl)phenyl)-4H-1,2,4-triazol-3-yl)ethanesulfonamide;
2-(4-chlorophenyl)-N-(5-(2-furanyl)-4-(2-methoxy-6-(1-pyrrolidinylmethyl)phenyl)-4H-1,2,4-triazol-3-yl)ethanesulfonamide;
N-(4-(2,6-dimethoxyphenyl)-5-(2-furanyl)-4H-1,2,4-triazol-3-yl)-2-(2,4-dimethyl-1,3-thiazol-5-yl)ethanesulfonamide;
N-(4-(2,6-dimethoxyphenyl)-5-(2-furanyl)-4H-1,2,4-triazol-3-yl)-2-(1-methyl-1H-imidazol-5-yl)ethanesulfonamide;
N-(4-(2,6-dimethoxyphenyl)-5-(2-furanyl)-4H-1,2,4-triazol-3-yl)-2-(2-ethyl-4-methyl-1H-imidazol-5-yl)ethanesulfonamide;
2-(4-chloro-1-methyl-1H-pyrazol-3-yl)-N-(4-(2,6-dimethoxyphenyl)-5-(2-furanyl)-4H-1,2,4-triazol-3-yl)ethanesulfonamide;
(1R,2S)—N-(4-(2,6-dimethoxyphenyl)-5-(5-methyl-2-furanyl)-4H-1,2,4-triazol-3-yl)-1-methoxy-1-(5-methyl-2-pyrimidinyl)-2-propanesulfonamide;
(2S,3R)—N-(4-(2,6-dimethoxyphenyl)-5-(5-methyl-2-furanyl)-4H-1,2,4-triazol-3-yl)-3-(5-methyl-2-pyrimidinyl)-2-butanesulfonamide;
(1R,2S)—N-(4-(2,6-dimethoxyphenyl)-5-(5-methyl-2-furanyl)-4H-1,2,4-triazol-3-yl)-1-imidazo[1,2-a]pyridin-2-yl-1-methoxy-2-propanesulfonamide;
(1S,2R)—N-(4-(2,6-dimethoxyphenyl)-5-(5-methyl-2-furanyl)-4H-1,2,4-triazol-3-yl)-1-hydroxy-1-imidazo[1,2-a]pyridin-2-yl-2-propanesulfonamide;
(1S,2R)—N-(4-(2,6-dimethoxyphenyl)-5-(5-methyl-2-furanyl)-4H-1,2,4-triazol-3-yl)-1-hydroxy-1-pyrazolo[1,5-a]pyridin-2-yl-2-propanesulfonamide;
(1S,2R)—N-(4-(2,6-dimethoxyphenyl)-5-(5-methyl-2-furanyl)-4H-1,2,4-triazol-3-yl)-1-hydroxy-1-pyrazolo[1,5-a]pyridin-7-yl-2-propanesulfonamide;
(1R,2R)—N-(4-(2,6-dimethoxyphenyl)-5-(5-methyl-2-furanyl)-4H-1,2,4-triazol-3-yl)-1-imidazo[1,2-a]pyridin-2-yl-1-methoxy-2-propanesulfonamide;
(1R,2S)—N-(4-(2,6-dimethoxyphenyl)-5-(5-methyl-2-furanyl)-4H-1,2,4-triazol-3-yl)-1-hydroxy-1-imidazo[1,5-a]pyridin-1-yl-2-propanesulfonamide;
(1S,2S)—N-(4-(2,6-dimethoxyphenyl)-5-(5-methyl-2-furanyl)-4H-1,2,4-triazol-3-yl)-1-hydroxy-1-pyrazolo[1,5-a]pyridin-2-yl-2-propanesulfonamide;
(1R,2R)—N-(4-(2,6-dimethoxyphenyl)-5-(5-methyl-2-furanyl)-4H-1,2,4-triazol-3-yl)-1-hydroxy-1-pyrazolo[1,5-a]pyridin-7-yl-2-propanesulfonamide;
(1S,2S)—N-(4-(2,6-dimethoxyphenyl)-5-(5-methyl-2-furanyl)-4H-1,2,4-triazol-3-yl)-1-hydroxy-1-pyrazolo[1,5-a]pyridin-7-yl-2-propanesulfonamide;
(1R,2R)—N-(4-(2,6-dimethoxyphenyl)-5-(5-methyl-2-furanyl)-4H-1,2,4-triazol-3-yl)-1-hydroxy-1-imidazo[1,2-a]pyridin-3-yl-2-propanesulfonamide;
(1S,2S)—N-(4-(2,6-dimethoxyphenyl)-5-(5-methyl-2-furanyl)-4H-1,2,4-triazol-3-yl)-1-imidazo[1,2-a]pyridin-2-yl-1-methoxy-2-propanesulfonamide;
(1R,2S)—N-(4-(2,6-dimethoxyphenyl)-5-(5-methyl-2-furanyl)-4H-1,2,4-triazol-3-yl)-1-hydroxy-1-(1,3-thiazol-4-yl)-2-propanesulfonamide;
(1R,2R)—N-(4-(2,6-dimethoxyphenyl)-5-(5-methyl-2-furanyl)-4H-1,2,4-triazol-3-yl)-1-hydroxy-1-imidazo[1,5-a]pyridin-1-yl-2-propanesulfonamide;
(1R,2S)—N-(4-(2,6-dimethoxyphenyl)-5-(5-methyl-2-furanyl)-4H-1,2,4-triazol-3-yl)-1-hydroxy-1-(1-methyl-1H-imidazol-4-yl)-2-propanesulfonamide;
(1S,2R)—N-(4-(2,6-dimethoxyphenyl)-5-(5-methyl-2-furanyl)-4H-1,2,4-triazol-3-yl)-1-hydroxy-1-(1-methyl-1H-imidazol-4-yl)-2-propanesulfonamide;

(1R,2S)—N-(4-(2,6-dimethoxyphenyl)-5-(5-methyl-2-furanyl)-4H-1,2,4-triazol-3-yl)-1-hydroxy-1-(2-methyl-1,3-oxazol-4-yl)-2-propanesulfonamide;
(1R,2R)—N-(4-(2,6-dimethoxyphenyl)-5-(5-methyl-2-furanyl)-4H-1,2,4-triazol-3-yl)-1-hydroxy-1-imidazo[1,2-a]pyridin-2-yl-2-propanesulfonamide;
(1R,2S)—N-(4-(2,6-dimethoxyphenyl)-5-(5-methyl-2-furanyl)-4H-1,2,4-triazol-3-yl)-1-hydroxy-1-pyrazolo[1,5-a]pyridin-2-yl-2-propanesulfonamide;
(1S,2R)—N-(4-(2,6-dimethoxyphenyl)-5-(5-methyl-2-furanyl)-4H-1,2,4-triazol-3-yl)-1-imidazo[1,2-a]pyridin-2-yl-1-methoxy-2-propanesulfonamide;
(1S,2R)—N-(4-(2,6-dimethoxyphenyl)-5-(5-methyl-2-furanyl)-4H-1,2,4-triazol-3-yl)-1-hydroxy-1-imidazo[1,5-a]pyridin-1-yl-2-propanesulfonamide;
(1R,2S)—N-(4-(2,6-dimethoxyphenyl)-5-(5-methyl-2-furanyl)-4H-1,2,4-triazol-3-yl)-1-hydroxy-1-imidazo[1,2-a]pyridin-2-yl-2-propanesulfonamide;
(1R,2R)-1-(6,7-dihydro-5H-pyrazolo[5,1-b][1,3]oxazin-2-yl)-N-(4-(2,6-dimethoxyphenyl)-5-(5-methyl-2-furanyl)-4H-1,2,4-triazol-3-yl)-1-hydroxy-2-propane sulfonamide;
(1R,2S)-1-(6,7-dihydro-5H-pyrazolo[5,1-b][1,3]oxazin-2-yl)-N-(4-(2,6-dimethoxyphenyl)-5-(5-methyl-2-furanyl)-4H-1,2,4-triazol-3-yl)-1-hydroxy-2-propane sulfonamide;
(1S,2R)-1-(6,7-dihydro-5H-pyrazolo[5,1-b][1,3]oxazin-2-yl)-N-(4-(2,6-dimethoxyphenyl)-5-(5-methyl-2-furanyl)-4H-1,2,4-triazol-3-yl)-1-hydroxy-2-propane sulfonamide;
(1S,2S)-1-(6,7-dihydro-5H-pyrazolo[5,1-b][1,3]oxazin-2-yl)-N-(4-(2,6-dimethoxyphenyl)-5-(5-methyl-2-furanyl)-4H-1,2,4-triazol-3-yl)-1-hydroxy-2-propane sulfonamide;
(1R,2R)-1-(3,4-dihydro-2H-pyrano[3,2-b]pyridin-8-yl)-N-(4-(2,6-dimethoxyphenyl)-5-(5-methyl-2-furanyl)-4H-1,2,4-triazol-3-yl)-1-hydroxy-2-propanesulfonamide;
(1S,2S)-1-(3,4-dihydro-2H-pyrano[3,2-b]pyridin-8-yl)-N-(4-(2,6-dimethoxyphenyl)-5-(5-methyl-2-furanyl)-4H-1,2,4-triazol-3-yl)-1-hydroxy-2-propanesulfonamide;
(1S,2R)-1-(3,4-dihydro-2H-pyrano[3,2-b]pyridin-8-yl)-N-(4-(2,6-dimethoxyphenyl)-5-(5-methyl-2-furanyl)-4H-1,2,4-triazol-3-yl)-1-hydroxy-2-propanesulfonamide;
(1R,2S)—N-(4-(2,6-dimethoxyphenyl)-5-(5-methyl-2-furanyl)-4H-1,2,4-triazol-3-yl)-1-hydroxy-1-imidazo[1,2-a]pyridin-3-yl-2-propanesulfonamide;
(2R)-1-(5-fluoro-2-pyrimidinyl)-N-(4-(2-methoxyphenyl)-5-(5-methyl-2-furanyl)-4H-1,2,4-triazol-3-yl)-2-propanesulfonamide;
(2S)-1-(5-fluoro-2-pyrimidinyl)-N-(4-(2-methoxyphenyl)-5-(5-methyl-2-furanyl)-4H-1,2,4-triazol-3-yl)-2-propanesulfonamide;
(1R,2S)—N-(4-(2,6-dimethoxyphenyl)-5-(5-methyl-2-furanyl)-4H-1,2,4-triazol-3-yl)-1-hydroxy-1-pyrazolo[1,5-a]pyridin-7-yl-2-propanesulfonamide;
(1S,2R)—N-(4-(2,6-dimethoxyphenyl)-5-(5-methyl-2-furanyl)-4H-1,2,4-triazol-3-yl)-1-hydroxy-1-(1-methyl-1H-imidazol-2-yl)-2-propanesulfonamide;
(1R,2R)—N-(4-(2,6-dimethoxyphenyl)-5-(5-methyl-2-furanyl)-4H-1,2,4-triazol-3-yl-1-hydroxy-1-(1,3-thiazol-4-yl)-2-propanesulfonamide;
(1S,2R)—N-(4-(2,6-dimethoxyphenyl)-5-(5-methyl-2-furanyl)-4H-1,2,4-triazol-3-yl)-1-hydroxy-1-imidazo[1,2-a]pyridin-5-yl-2-propanesulfonamide;
(1R,2R)—N-(4-(2,6-dimethoxyphenyl)-5-(5-methyl-2-furanyl)-4H-1,2,4-triazol-3-yl)-1-hydroxy-1-(2-methyl-1,3-oxazol-4-yl)-2-propanesulfonamide;
(1S,2S)—N-(4-(2,6-dimethoxyphenyl)-5-(5-methyl-2-furanyl)-4H-1,2,4-triazol-3-yl)-1-hydroxy-1-(2-methyl-1,3-oxazol-4-yl)-2-propanesulfonamide;
(1R,2R)—N-(4-(2,6-dimethoxyphenyl)-5-(5-methyl-2-furanyl)-4H-1,2,4-triazol-3-yl)-1-hydroxy-1-(1-methyl-1H-imidazol-4-yl)-2-propanesulfonamide;
(1S,2S)—N-(4-(2,6-dimethoxyphenyl)-5-(5-methyl-2-furanyl)-4H-1,2,4-triazol-3-yl)-1-hydroxy-1-(1-methyl-1H-imidazol-4-yl)-2-propanesulfonamide;
(1R,2S)-1-(3,4-dihydro-2H-pyrano[3,2-b]pyridin-8-yl)-N-(4-(2,6-dimethoxyphenyl)-5-(5-methyl-2-furanyl)-4H-1,2,4-triazol-3-yl)-1-hydroxy-2-propanesulfonamide;
(1S,2R)—N-(4-(2,6-dimethoxyphenyl)-5-(5-methyl-2-furanyl)-4H-1,2,4-triazol-3-yl)-1-hydroxy-1-(2-methyl-1,3-oxazol-4-yl)-2-propanesulfonamide;
(1R,2R)—N-(4-(2,6-dimethoxyphenyl)-5-(5-methyl-2-furanyl)-4H-1,2,4-triazol-3-yl)-1-hydroxy-1-pyrazolo[1,5-a]pyridin-2-yl-2-propanesulfonamide;
(1S,2S)—N-(4-(2,6-dimethoxyphenyl)-5-(5-methyl-2-furanyl)-4H-1,2,4-triazol-3-yl)-1-hydroxy-thiazol-4-yl)-2-propanesulfonamide;
(1R,2R)—N-(4-(2,6-dimethoxyphenyl)-5-(5-methyl-2-furanyl)-4H-1,2,4-triazol-3-yl)-1-hydroxy-1-imidazo[1,2-a]pyridin-5-yl-2-propanesulfonamide;
(1S,2S)—N-(4-(2,6-dimethoxyphenyl)-5-(5-methyl-2-furanyl)-4H-1,2,4-triazol-3-yl)-1-hydroxy-1-imidazo[1,2-a]pyridin-5-yl-2-propanesulfonamide;
(1S,2R)—N-(4-(2,6-dimethoxyphenyl)-5-(5-methyl-2-furanyl)-4H-1,2,4-triazol-3-yl)-1-hydroxy-thiazol-4-yl)-2-propanesulfonamide;
(1S,2S)—N-(4-(2,6-dimethoxyphenyl)-5-(5-methyl-2-furanyl)-4H-1,2,4-triazol-3-yl)-1-hydroxy-1-imidazo[1,2-a]pyridin-2-yl-2-propanesulfonamide;
(2R)-1-(5-fluoro-2-pyrimidinyl)-N-(5-(2-furanyl)-4-(2-methoxyphenyl)-4H-1,2,4-triazol-3-yl)-2-propanesulfonamide;
(2S)-1-(5-fluoro-2-pyrimidinyl)-N-(5-(2-furanyl)-4-(2-methoxyphenyl)-4H-1,2,4-triazol-3-yl)-2-propanesulfonamide;
(1S)—N-(4-(2,6-dimethoxyphenyl)-5-(5-methyl-2-furanyl)-4H-1,2,4-triazol-3-yl)-1-(3-hydroxy-3-oxetanyl)ethanesulfonamide;
(2R)—N-(4-(2-fluorophenyl)-5-(2-furanyl)-4H-1,2,4-triazol-3-yl)-1-(5-fluoro-2-pyrimidinyl)-2-propanesulfonamide;
(2S)—N-(4-(2-fluorophenyl)-5-(2-furanyl)-4H-1,2,4-triazol-3-yl)-1-(5-fluoro-2-pyrimidinyl)-2-propanesulfonamide;
(2R)—N-(4-cyclohexyl-5-(2-furanyl)-4H-1,2,4-triazol-3-yl)-1-(5-fluoro-2-pyrimidinyl)-2-propanesulfonamide;
(2S)—N-(4-cyclohexyl-5-(2-furanyl)-4H-1,2,4-triazol-3-yl)-1-(5-fluoro-2-pyrimidinyl)-2-propanesulfonamide;
(2R)-1-(5-fluoro-2-pyrimidinyl)-N-(5-(2-furanyl)-4-(1-naphthalenyl)-4H-1,2,4-triazol-3-yl)-2-propanesulfonamide;
(2S)-1-(5-fluoro-2-pyrimidinyl)-N-(5-(2-furanyl)-4-(1-naphthalenyl)-4H-1,2,4-triazol-3-yl)-2-propanesulfonamide;
(2R)—N-(4-(2,4-dimethoxyphenyl)-5-(2-furanyl)-4H-1,2,4-triazol-3-yl)-1-(5-fluoro-2-pyrimidinyl)-2-propanesulfonamide;
(2S)—N-(4-(2,4-dimethoxyphenyl)-5-(2-furanyl)-4H-1,2,4-triazol-3-yl)-1-(5-fluoro-2-pyrimidinyl)-2-propanesulfonamide;
(2R)—N-(4-cyclopentyl-5-(5-methyl-2-furanyl)-4H-1,2,4-triazol-3-yl)-1-(5-fluoro-2-pyrimidinyl)-2-propanesulfonamide;

(2S)—N-(4-cyclopentyl-5-(5-methyl-2-furanyl)-4H-1,2,4-triazol-3-yl)-1-(5-fluoro-2-pyrimidinyl)-2-propanesulfonamide;

(2R)-1-(5-fluoro-2-pyrimidinyl)-N-(5-(5-methyl-2-furanyl)-4-(tetrahydro-2H-pyran-4-yl)-4H-1,2,4-triazol-3-yl)-2-propanesulfonamide;

(2S)-1-(5-fluoro-2-pyrimidinyl)-N-(5-(5-methyl-2-furanyl)-4-(tetrahydro-2H-pyran-4-yl)-4H-1,2,4-triazol-3-yl)-2-propanesulfonamide;

(2R)-1-(5-fluoro-2-pyrimidinyl)-N-(5-(2-furanyl)-4-(2-(trifluoromethyl)phenyl)-4H-1,2,4-triazol-3-yl)-2-propanesulfonamide;

(2S)-1-(5-fluoro-2-pyrimidinyl)-N-(5-(2-furanyl)-4-(2-(trifluoromethyl)phenyl)-4H-1,2,4-triazol-3-yl)-2-propanesulfonamide;

(2R)—N-(4-cyclopropyl-5-(5-methyl-2-furanyl)-4H-1,2,4-triazol-3-yl)-1-(5-fluoro-2-pyrimidinyl)-2-propanesulfonamide;

(2S)—N-(4-cyclopropyl-5-(5-methyl-2-furanyl)-4H-1,2,4-triazol-3-yl)-1-(5-fluoro-2-pyrimidinyl)-2-propanesulfonamide;

(3R,5S)-1-(6-cyano-2-pyrazinyl)-N-(4-(2,6-dimethoxyphenyl)-5-(5-methyl-2-furanyl)-4H-1,2,4-triazol-3-yl)-5-hydroxy-3-piperidinesulfonamide;

(3R,5S)-1-(6-chloro-5-cyano-3-pyridinyl)-N-(4-(2,6-dimethoxyphenyl)-5-(5-methyl-2-furanyl)-4H-1,2,4-triazol-3-yl)-5-hydroxy-3-piperidinesulfonamide;

(3S,5R)-1-(6-chloro-5-cyano-3-pyridinyl)-N-(4-(2,6-dimethoxyphenyl)-5-(5-methyl-2-furanyl)-4H-1,2,4-triazol-3-yl)-5-hydroxy-3-piperidinesulfonamide;

(3R,5S)—N-(4-(2,6-dimethoxyphenyl)-5-(5-methyl-2-furanyl)-4H-1,2,4-triazol-3-yl)-1-(5-fluoro-2-pyrimidinyl)-5-hydroxy-3-piperidinesulfonamide;

(3R,5S)—N-(4-(2,6-dimethoxyphenyl)-5-(5-methyl-2-furanyl)-4H-1,2,4-triazol-3-yl)-5-hydroxy-1-(4-methoxy-2-pyrimidinyl)-3-piperidinesulfonamide;

(3S,5R)—N-(4-(2,6-dimethoxyphenyl)-5-(5-methyl-2-furanyl)-4H-1,2,4-triazol-3-yl)-5-hydroxy-1-(4-methoxy-2-pyrimidinyl)-3-piperidinesulfonamide;

(3S,5R)—N-(4-(2,6-dimethoxyphenyl)-5-(5-methyl-2-furanyl)-4H-1,2,4-triazol-3-yl)-1-(4,6-dimethyl-2-pyrimidinyl)-5-hydroxy-3-piperidinesulfonamide;

(3R,5S)-1-(5-chloro-2-pyrimidinyl)-N-(4-(2,6-dimethoxyphenyl)-5-(5-methyl-2-furanyl)-4H-1,2,4-triazol-3-yl)-5-hydroxy-3-piperidinesulfonamide;

(3S,5R)-1-(5-chloro-2-pyrimidinyl)-N-(4-(2,6-dimethoxyphenyl)-5-(5-methyl-2-furanyl)-4H-1,2,4-triazol-3-yl)-5-hydroxy-3-piperidinesulfonamide;

(3R,5S)-1-(3-cyano-4-fluorophenyl)-N-(4-(2,6-dimethoxy phenyl)-5-(5-methyl-2-furanyl)-4H-1,2,4-triazol-3-yl)-5-hydroxy-3-piperidinesulfonamide;

(3S,5R)-1-(3-cyano-4-fluorophenyl)-N-(4-(2,6-dimethoxy phenyl)-5-(5-methyl-2-furanyl)-4H-1,2,4-triazol-3-yl)-5-hydroxy-3-piperidinesulfonamide;

(3R,5S)-1-(3-cyano-5-fluoro-2-pyridinyl)-N-(4-(2,6-dimethoxy phenyl)-5-(5-methyl-2-furanyl)-4H-1,2,4-triazol-3-yl)-5-hydroxy-3-piperidinesulfonamide;

(3S,5R)-1-(3-cyano-5-fluoro-2-pyridinyl)-N-(4-(2,6-dimethoxy phenyl)-5-(5-methyl-2-furanyl)-4H-1,2,4-triazol-3-yl)-5-hydroxy-3-piperidinesulfonamide;

(3R,5R)—N-(4-(2,6-dimethoxyphenyl)-5-(5-methyl-2-furanyl)-4H-1,2,4-triazol-3-yl)-1-(5-fluoro-2-pyrimidinyl)-5-hydroxy-3-piperidinesulfonamide;

(3S,5R)—N-(4-(2,6-dimethoxyphenyl)-5-(5-methyl-2-furanyl)-4H-1,2,4-triazol-3-yl)-1-(5-fluoro-2-pyrimidinyl)-5-hydroxy-3-piperidinesulfonamide;

(3S,5S)—N-(4-(2,6-dimethoxyphenyl)-5-(5-methyl-2-furanyl)-4H-1,2,4-triazol-3-yl)-1-(5-fluoro-2-pyrimidinyl)-5-hydroxy-3-piperidinesulfonamide;

(3R,5S)-1-(4-cyano-2-pyridinyl)-N-(4-(2,6-dimethoxyphenyl)-5-(5-methyl-2-furanyl)-4H-1,2,4-triazol-3-yl)-5-hydroxy-3-piperidinesulfonamide;

(3S,5R)-1-(4-cyano-2-pyridinyl)-N-(4-(2,6-dimethoxyphenyl)-5-(5-methyl-2-furanyl)-4H-1,2,4-triazol-3-yl)-5-hydroxy-3-piperidinesulfonamide;

(3R,5S)-1-(5-cyano-3-pyridinyl)-N-(4-(2,6-dimethoxyphenyl)-5-(5-methyl-2-furanyl)-4H-1,2,4-triazol-3-yl)-5-hydroxy-3-piperidinesulfonamide;

(3S,5R)-1-(5-cyano-3-pyridinyl)-N-(4-(2,6-dimethoxyphenyl)-5-(5-methyl-2-furanyl)-4H-1,2,4-triazol-3-yl)-5-hydroxy-3-piperidinesulfonamide;

(3R,5S)—N-(4-(2,6-dimethoxyphenyl)-5-(5-methyl-2-furanyl)-4H-1,2,4-triazol-3-yl)-5-hydroxy-1-(5-methoxy-2-pyrimidinyl)-3-piperidinesulfonamide;

(3S,5R)—N-(4-(2,6-dimethoxyphenyl)-5-(5-methyl-2-furanyl)-4H-1,2,4-triazol-3-yl)-5-hydroxy-1-(5-methoxy-2-pyrimidinyl)-3-piperidinesulfonamide;

(3R,5S)—N-(4-(2,6-dimethoxyphenyl)-5-(5-methyl-2-furanyl)-4H-1,2,4-triazol-3-yl)-1-(4,6-dimethyl-2-pyrimidinyl)-5-hydroxy-3-piperidinesulfonamide;

(3S,5R)-3-((4-(2,6-dimethoxy phenyl)-5-(5-methyl-2-furanyl)-4H-1,2,4-triazol-3-yl)sulfamoyl)-5-hydroxy-N,N-dimethyl-1-piperidinecarboxamide;

(3R)-3-((4-(2,6-dimethoxyphenyl)-5-(2-furanyl)-4H-1,2,4-triazol-3-yl)sulfamoyl)-N,N-dimethyl-1-piperidinecarboxamide;

(3S)—N-(4-(2,6-dimethoxyphenyl)-5-(2-furanyl)-4H-1,2,4-triazol-3-yl)-1-((1-methylethyl)sulfonyl)-3-piperidinesulfonamide;

(3S)-3-((4-(2,6-dimethoxyphenyl)-5-(2-furanyl)-4H-1,2,4-triazol-3-yl)sulfamoyl)-N,N-dimethyl-1-piperidinecarboxamide;

(2S)-1-((2R)-2-cyano-2-methyl-6-oxo-1-piperidinyl)-N-(4-(2,6-dimethoxyphenyl)-5-(2-furanyl)-4H-1,2,4-triazol-3-yl)-2-propanesulfonamide;

(2S)-1-((2S)-2-cyano-2-methyl-6-oxo-1-piperidinyl)-N-(4-(2,6-dimethoxyphenyl)-5-(2-furanyl)-4H-1,2,4-triazol-3-yl)-2-propanesulfonamide;

(3S,4S)—N-(4-(2,6-dimethoxyphenyl)-5-(2-furanyl)-4H-1,2,4-triazol-3-yl)-3-(5-fluoro-2-pyrimidinyl)-2-methyl-4-isoxazolidinesulfonamide;

N-(4-(2,6-dimethoxyphenyl)-5-(2-furanyl)-4H-1,2,4-triazol-3-yl)-2-(4-methyl-1,3-thiazol-2-yl)ethanesulfonamide;

N-(4-(2,6-dimethoxyphenyl)-5-(2-furanyl)-4H-1,2,4-triazol-3-yl)-2-(4,5-dimethyl-1,3-thiazol-2-yl)ethanesulfonamide;

N-(4-(2,6-dimethoxyphenyl)-5-(2-furanyl)-4H-1,2,4-triazol-3-yl)-2-(2-methyl-1,3-oxazol-4-yl)ethanesulfonamide;

N-(4-(2,6-dimethoxyphenyl)-5-(2-furanyl)-4H-1,2,4-triazol-3-yl)-2-(2,5-dimethyl-1,3-oxazol-4-yl)ethanesulfonamide;

(3S)-3-cyclohexyl-N-(4-(2,6-dimethoxyphenyl)-5-(2-furanyl)-4H-1,2,4-triazol-3-yl)-3-hydroxy-1-propanesulfonamide;

(3R)-3-cyclopentyl-N-(4-(2,6-dimethoxyphenyl)-5-(2-furanyl)-4H-1,2,4-triazol-3-yl)-3-hydroxy-1-butanesulfonamide;

(3S)-3-cyclopentyl-N-(4-(2,6-dimethoxyphenyl)-5-(2-furanyl)-4H-1,2,4-triazol-3-yl)-3-hydroxy-1-butanesulfonamide;

1-(4-chlorophenyl)-N-(5-(2-furanyl)-4-(2-methoxyphenyl)-4H-1,2,4-triazol-3-yl)methane sulfonamide;

(2S,3R)-3-(5-chloro-2-pyrimidinyl)-N-(4-(4,6-dimethoxy-5-pyrimidinyl)-5-(5-methyl-2-furanyl)-4H-1,2,4-triazol-3-yl)-2-butanesulfonamide;

(1R,2S)-1-(5-chloro-2-pyrimidinyl)-N-(4-(4,6-dimethoxy-5-pyrimidinyl)-5-(5-methyl-2-furanyl)-4H-1,2,4-triazol-3-yl)-1-methoxy-2-propanesulfonamide;

(1R,2S)-1-(5-chloro-2-pyrimidinyl)-1-methoxy-N-(4-(1-(methoxymethyl)cyclopropyl)-5-(5-methyl-2-furanyl)-4H-1,2,4-triazol-3-yl)-2-propanesulfonamide;

(1R,2S)-1-(5-chloro-2-pyrimidinyl)-1-methoxy-N-(4-(2-methoxy ethyl)-5-(5-methyl-2-furanyl)-4H-1,2,4-triazol-3-yl)-2-propanesulfonamide;

(1R,2S)-1-(5-chloro-2-pyrimidinyl)-N-(4-(1,3-dimethoxy-2-propanyl)-5-(5-methyl-2-furanyl)-4H-1,2,4-triazol-3-yl)-1-methoxy-2-propanesulfonamide;

(1R,2S)-1-(5-chloro-2-pyrimidinyl)-1-methoxy-N-(5-(5-methyl-2-furanyl)-4-(2-propanyl)-4H-1,2,4-triazol-3-yl)-2-propanesulfonamide;

(1R,2S)-1-(5-chloro-2-pyrimidinyl)-1-methoxy-N-(5-(5-methyl-2-furanyl)-4-((3S)-tetrahydro-2H-pyran-3-yl)-4H-1,2,4-triazol-3-yl)-2-propanesulfonamide; or (1R,2S)-1-(5-chloro-2-pyrimidinyl)-1-methoxy-N-(5-(5-methyl-2-furanyl)-4-((3R)-tetrahydro-2H-pyran-3-yl)-4H-1,2,4-triazol-3-yl)-2-propanesulfonamide; or the pharmaceutically acceptable salt thereof, the tautomer thereof, the pharmaceutically acceptable salt of the tautomer, the stereoisomer of any of the foregoing, or the mixture thereof. In some such embodiments, the embodiment provides any of the compounds shown above or a pharmaceutically acceptable salt thereof. In still other such embodiments, the embodiment provides any of the compounds shown above or a pharmaceutically acceptable salt thereof, or a mixture thereof.

57. The compound of embodiment 1, wherein the compound is selected from

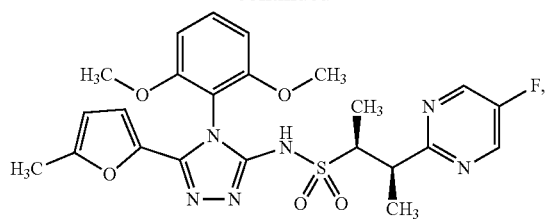

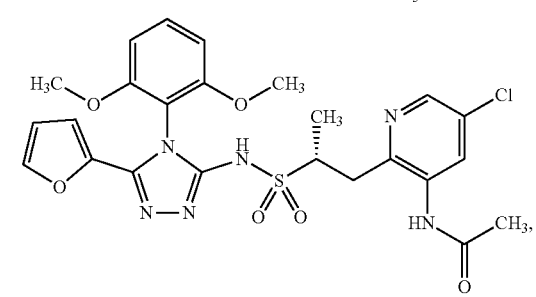

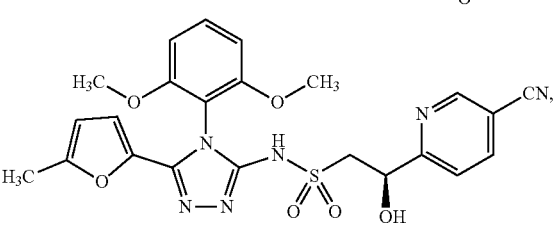

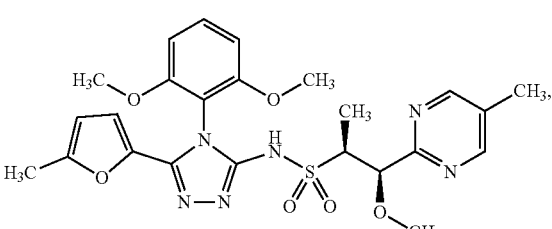

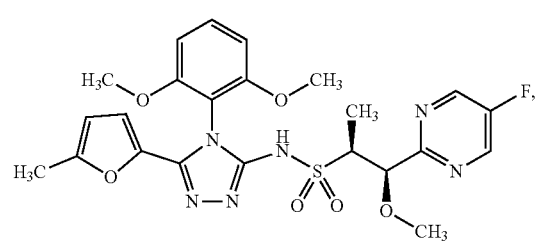

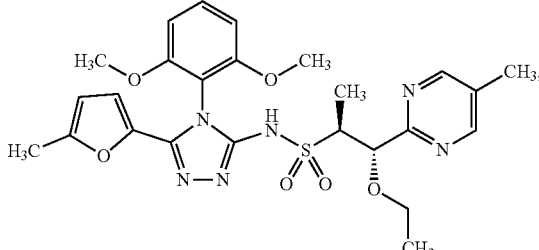

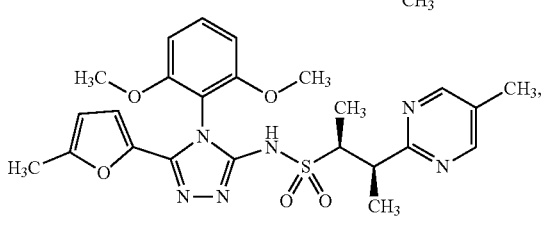

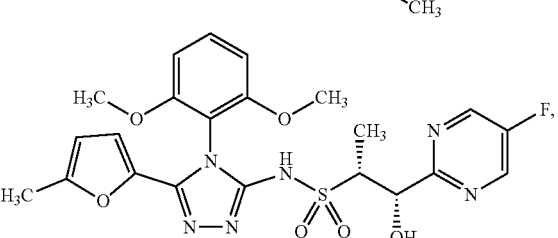

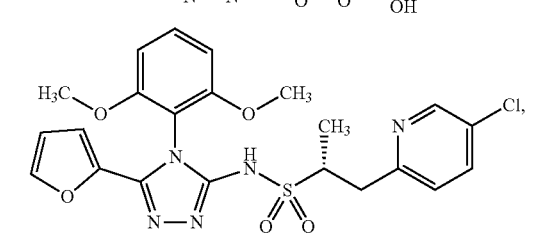

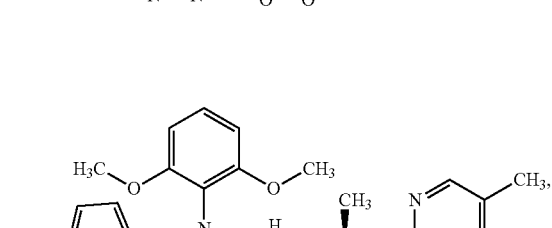

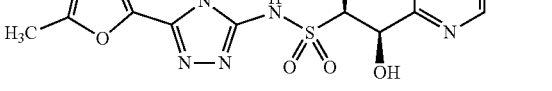

-continued

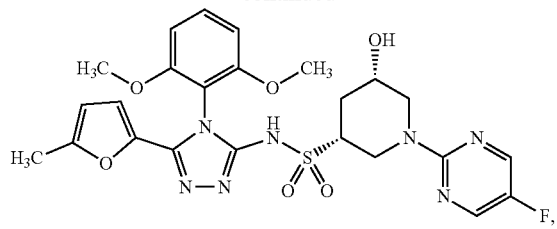
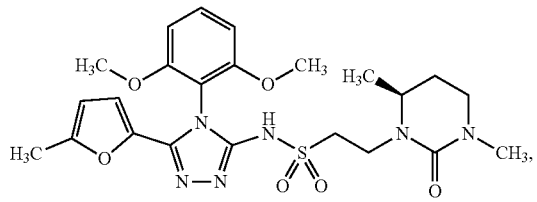 [SMILES: COc1cccc(OC)c1-n1c(NS(=O)(=O)CCN2C(=O)N(C)CC[C@@H]2C)nnc1-c1ccc(C)o1]
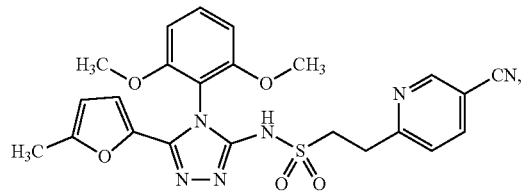
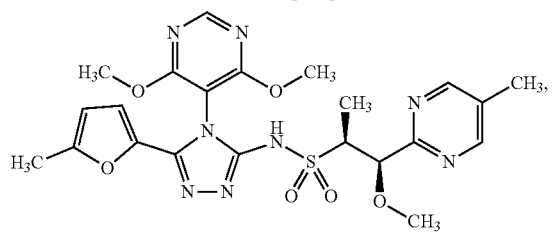
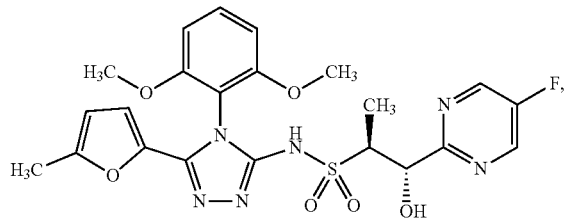
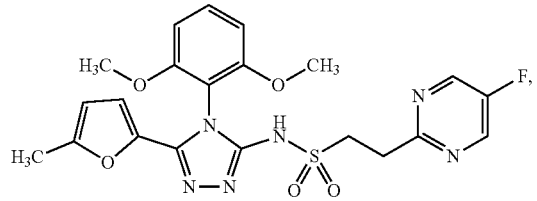
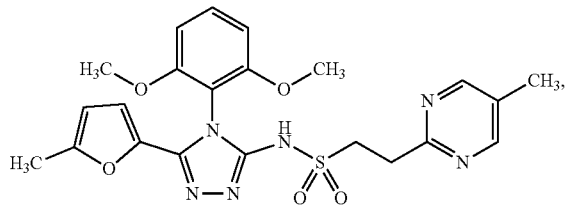
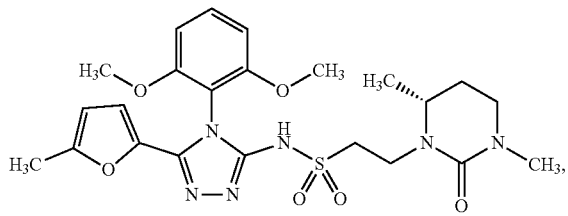

-continued

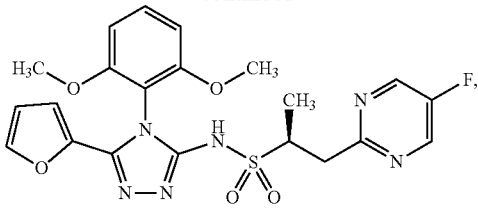
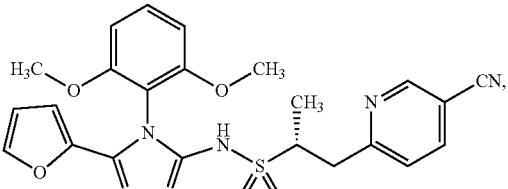
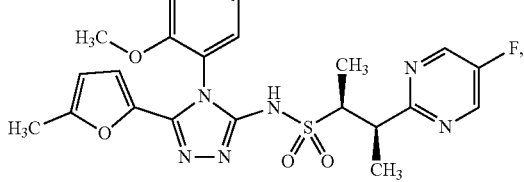
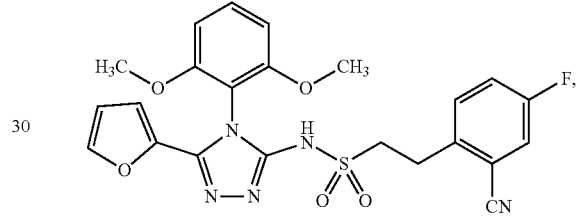
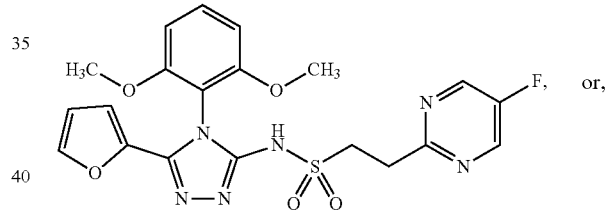
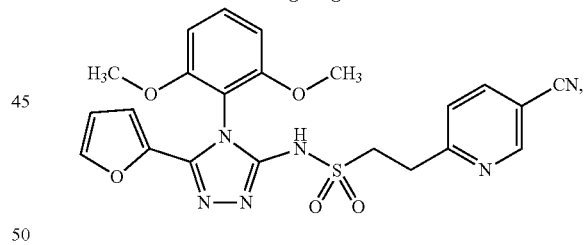

or the pharmaceutically acceptable salt thereof, the tautomer thereof, the pharmaceutically acceptable salt of the tautomer, the stereoisomer of any of the foregoing, or the mixture thereof. In some such embodiments, the embodiment provides any of the compounds shown above or a pharmaceutically acceptable salt thereof. In still other such embodiments, the embodiment provides any of the compounds shown above or a pharmaceutically acceptable salt thereof, or a mixture thereof.

58. The compound of embodiment 1, wherein the compound is selected from (1S,2S)-1-(5-chloro-2-pyrimidinyl)-N-(4-(1,3-dimethoxy-2-propanyl)-5-(5-methyl-2-furanyl)-4H-1,2,4-triazol-3-yl)-1-(2-propanyloxy)-2-propanesulfonamide;

(2S,3R)—N-(4-(4,6-dimethoxy-5-pyrimidinyl)-5-(5-methyl-2-furanyl)-4H-1,2,4-triazol-3-yl)-3-(5-fluoro-2-pyrimidinyl)-2-butanesulfonamide;

(2S,3R)—N-(5-(5-bromo-2-furanyl)-4-(4,6-dimethoxy-5-pyrimidinyl)-4H-1,2,4-triazol-3-yl)-3-(5-fluoro-2-pyrimidinyl)-2-butanesulfonamide;

(2S,3R)—N-(4-(4,6-dimethoxy-5-pyrimidinyl)-5-(5-trideuteromethyl-2-furanyl)-4H-1,2,4-triazol-3-yl)-3-(5-fluoro-2-pyrimidinyl)-2-butanesulfonamide;

(1S,2S)-1-(5-chloro-2-pyrimidinyl)-N-(4-cyclopropyl-5-(5-methyl-2-furanyl)-4H-1,2,4-triazol-3-yl)-1-(2-propanyloxy)-2-propanesulfonamide;

(2S,3R)-3-(5-chloro-2-pyrimidinyl)-N-(4-((2S)-1-methoxy-2-propanyl)-5-(5-methyl-2-furanyl)-4H-1,2,4-triazol-3-yl)-2-butanesulfonamide;

(2S,3R)-3-(5-chloro-2-pyrimidinyl)-N-(4-(4,6-dimethoxy-5-pyrimidinyl)-5-(5-methyl-2-furanyl)-4H-1,2,4-triazol-3-yl)-2-butanesulfonamide;

(1S,2S)—N-(4-(4,6-dimethoxypyrimidin-5-yl)-5-(5-methylfuran-2-yl)-4H-1,2,4-triazol-3-yl)-1-isopropoxy-1-(5-methylpyrimidin-2-yl)propane-2-sulfonamide;

(3R,4S)—N-(4-(2,6-dimethoxyphenyl)-5-(5-methyl-2-furanyl)-4H-1,2,4-triazol-3-yl)-4-hydroxytetrahydro-2H-pyran-3-sulfonamide;

(3S,4R)—N-(4-(2,6-dimethoxyphenyl)-5-(5-methyl-2-furanyl)-4H-1,2,4-triazol-3-yl)-4-hydroxytetrahydro-2H-pyran-3-sulfonamide;

(3R,4R)—N-(4-(2,6-dimethoxyphenyl)-5-(5-methyl-2-furanyl)-4H-1,2,4-triazol-3-yl)-4-hydroxytetrahydro-2H-pyran-3-sulfonamide;

(3S,4S)—N-(4-(2,6-dimethoxyphenyl)-5-(5-methyl-2-furanyl)-4H-1,2,4-triazol-3-yl)-4-hydroxytetrahydro-2H-pyran-3-sulfonamide;

(1R,3R,4R)—N-(4-(2,6-dimethoxyphenyl)-5-(5-methylfuran-2-yl)-4H-1,2,4-triazol-3-yl)-3,4-dihydroxycyclohexane-1-sulfonamide;

(1S,3R,4R)—N-(4-(2,6-dimethoxyphenyl)-5-(5-methylfuran-2-yl)-4H-1,2,4-triazol-3-yl)-3,4-dihydroxycyclohexane-1-sulfonamide;

N-(4-(2,6-dimethoxyphenyl)-5-(5-methyl-2-furanyl)-4H-1,2,4-triazol-3-yl)-3-(hydroxymethyl)benzenesulfonamide;

(R)—N-(4-(2,6-dimethoxyphenyl)-5-(5-methylfuran-2-yl)-4H-1,2,4-triazol-3-yl)-3-(1-hydroxyethyl)benzenesulfonamide; or (S)—N-(4-(2,6-dimethoxyphenyl)-5-(5-methylfuran-2-yl)-4H-1,2,4-triazol-3-yl)-3-(1-hydroxyethyl)benzenesulfonamide; or the pharmaceutically acceptable salt thereof, the tautomer thereof, the pharmaceutically acceptable salt of the tautomer, the stereoisomer of any of the foregoing, or the mixture thereof. In some such embodiments, the embodiment provides any of the compounds shown above or a pharmaceutically acceptable salt thereof. In still other such embodiments, the embodiment provides any of the compounds shown above or a pharmaceutically acceptable salt thereof, or a mixture thereof.

59. The compound of embodiment 1, wherein the compound has the formula IA

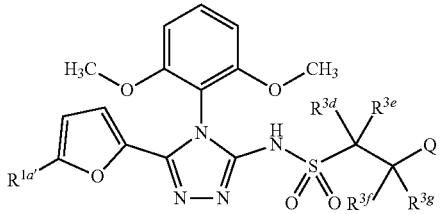

IA or is the pharmaceutically acceptable salt thereof, the tautomer thereof, the pharmaceutically acceptable salt of the tautomer, the stereoisomer of any of the foregoing, or the mixture thereof,
wherein:
$R^{1a'}$ is selected from —H or —$C_1$-$C_4$ alkyl;
$R^{3d}$ and $R^{3e}$ are independently selected from —H, or —$C_1$-$C_3$ alkyl;
$R^{3f}$ and $R^{3g}$ are independently selected from —H, —$C_1$-$C_3$ alkyl, —OH, or —O—($C_1$-$C_3$ alkyl);
Q is a phenyl group, a monocyclic heteroaryl group with 6 ring members containing 1 or 2 N heteroatoms, or a bicyclic heteroaryl group with 9 or 10 ring members containing 1 or 2 N heteroatoms, wherein the phenyl, the monocyclic heteroaryl, and the bicyclic heteroaryl aryl Q groups are unsubstituted or are substituted with 1 or 2 $R^Q$ substituent; and
$R^Q$ is independently selected from —F, —Cl, —CN, —$C_1$-$C_6$ alkyl, —O—($C_1$-$C_6$ alkyl), —NHC(=O)($C_1$-$C_6$ alkyl), or —S(=O)$_2$—($C_1$-$C_6$ alkyl).

60. The compound of embodiment 59 or is the pharmaceutically acceptable salt thereof, the tautomer thereof, the pharmaceutically acceptable salt of the tautomer, the stereoisomer of any of the foregoing, or the mixture thereof,
wherein:
$R^{1a'}$ is selected from —H, —$CH_3$, or —$CH_2CH_3$;
$R^{3d}$ and $R^{3e}$ are independently selected from —H, or —$CH_3$;
$R^{3f}$ and $R^{3g}$ are independently selected from —H, —$CH_3$, —OH, —$OCH_3$, or —$OCH_2CH_3$;
Q is a phenyl, a pyrimidinyl, a pyridinyl, a pyrazinyl, or an imidazo[1,2a]pyridinyl group any of which are unsubstituted or are substituted with 1 or 2 $R^Q$ substituent; and
$R^Q$ is independently selected from —F, —Cl, —CN, —$CH_3$, —$OCH_3$, —NHC(=O)—$CH_3$, or —S(=O)$_2$—$CH_3$.

61. A pharmaceutical composition, comprising the compound of any one of embodiments 1-60 or the pharmaceutically acceptable salt thereof, the tautomer thereof, the pharmaceutically acceptable salt of the tautomer, the stereoisomer of any of the foregoing, or the mixture thereof, and at least one pharmaceutically acceptable excipient.

62. A pharmaceutical composition, comprising the compound of any one of embodiments 1-60 or the pharmaceutically acceptable salt thereof and at least one pharmaceutically acceptable excipient.

63. A pharmaceutical composition, comprising the compound of any one of embodiments 1-60 and at least one pharmaceutically acceptable excipient.

64. A pharmaceutical composition, comprising the pharmaceutically acceptable salt of the compound of any one of embodiments 1-60 and at least one pharmaceutically acceptable excipient.

65. The pharmaceutical composition of embodiment 64, further comprising a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

66. The pharmaceutical composition of embodiment 64, further comprising a therapeutic agent selected from an angiotensin converting enzyme (ACE) inhibitor or an angiotensin-receptor blocker (ARB).

67. A method of treating a cardiovascular condition, the method comprising: administering to a subject an effective amount of the compound of any one of embodiments 1-60 or the pharmaceutically acceptable salt thereof, the stereoisomer of any of the foregoing, or the mixture thereof, or the pharmaceutical composition of any one of embodiments 61-66.

68. The method of embodiment 67, wherein the cardiovascular condition is heart failure.

69. The method of embodiment 67, wherein the cardiovascular condition is heart failure with reduced ejection fraction.

70. The method of embodiment 67, wherein the cardiovascular condition is heart failure with preserved ejection fraction.

71. The method of embodiment 67, wherein the cardiovascular condition is chronic systolic heart failure or chronic diastolic heart failure.

72. The method of embodiment 67, wherein the cardiovascular condition is acute heart failure.

73. The method of embodiment 67, wherein the cardiovascular condition is hypertension.

74. A method of improving cardiac contractility in a subject suffering from a cardiovascular condition, the method comprising: administering to the subject an effective amount of the compound of any one of embodiments 1-60 or the pharmaceutically acceptable salt thereof, the stereoisomer of any of the foregoing, or the mixture thereof, or the pharmaceutical composition of any one of embodiments 61-66, wherein cardiac contractility is improved in the subject after administration.

75. A method of increasing ejection fraction in a subject suffering from a cardiovascular condition, the method comprising: administering to the subject an effective amount of the compound of any one of embodiments 1-60 or the pharmaceutically acceptable salt thereof, the stereoisomer of any of the foregoing, or the mixture thereof, or the pharmaceutical composition of any one of embodiments 61-66, wherein the ejection fraction is increased in the subject after administration.

76. A method of treating a condition in a subject where it is desired to activate the APJ Receptor, the method comprising: administering to the subject an effective amount of the compound of any one of embodiments 1-60 or the pharmaceutically acceptable salt thereof, the stereoisomer of any of the foregoing, or the mixture thereof or the pharmaceutical composition of any one of embodiments 61-66.

77. The method of embodiment 76, wherein the condition is obesity or diabetes.

78. The method of embodiment 76, wherein the condition is diabetic nephropathy or chronic kidney disease.

79. The method of any one of embodiments 67-78, wherein the method includes administering at least one additional therapeutic agent to the subject, wherein the additional therapeutic agent is selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

80. The method of any one of embodiments 67-78, wherein the method includes administering at least one additional therapeutic agent to the subject, wherein the additional therapeutic agent is selected from an angiotensin converting enzyme (ACE) inhibitor or an angiotensin-receptor blocker (ARB).

81. A compound of any one of embodiments 1-60 or the pharmaceutically acceptable salt thereof, the stereoisomer of any of the foregoing, or the mixture thereof, or the pharmaceutical composition of any one of embodiments 61-66 for use in treating a cardiovascular condition.

82. The compound of embodiments 81, wherein the cardiovascular condition is heart failure.

83. The compound of embodiment 801 wherein the cardiovascular condition is heart failure with reduced ejection fraction.

84. The compound of embodiment 81, wherein the cardiovascular condition is heart failure with preserved ejection fraction.

85. The compound of embodiment 81, wherein the cardiovascular condition is chronic systolic heart failure or chronic diastolic heart failure.

86. The compound of embodiment 81, wherein the cardiovascular condition is hypertension.

87. The compound of embodiment 81, wherein the cardiovascular condition is hypertension.

88. A compound of any one of embodiments 1-60 or the pharmaceutically acceptable salt thereof, the stereoisomer of any of the foregoing, or the mixture thereof, or the pharmaceutical composition of any one of embodiments 61-66 for use in activating the APJ Receptor or for treating a condition where it is desirable to activate the APJ Receptor.

89. The compound of embodiment 88, wherein the condition is obesity or diabetes.

90. The compound of embodiment 88, wherein the condition is diabetic nephropathy or chronic kidney disease.

91. A use of the compound of any one of embodiments 1-60 or the pharmaceutically acceptable salt thereof, the stereoisomer of any of the foregoing, or the mixture thereof in the preparation of a medicament for treating a cardiovascular condition.

92. The use of embodiment 91, further comprising a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

93. The use of embodiment 91, further comprising a therapeutic agent selected from an angiotensin converting enzyme (ACE) inhibitor or an angiotensin-receptor blocker (ARB).

94. The use of the compound of embodiment 91, wherein the cardiovascular condition is heart failure.

95. The use of the compound of embodiment 91, wherein the cardiovascular condition is heart failure with reduced ejection fraction.

96. The use of the compound of embodiment 91, wherein the cardiovascular condition is heart failure with preserved ejection fraction.

97. The use of the compound of embodiment 91, wherein the cardiovascular condition is chronic systolic heart failure or chronic diastolic heart failure.

98. The use of the compound of embodiment 91, wherein the cardiovascular condition is acute heart fail.

99. The use of the compound of embodiment 91, wherein the cardiovascular condition is acute heart failure.

100. A use of the compound of any one of embodiments 1-60 or the pharmaceutically acceptable salt thereof, the stereoisomer of any of the foregoing, or the mixture thereof in the preparation of a medicament for activating the APJ Receptor or treating a condition where it is desirable to activate the APJ Receptor.

101. The use of embodiment 100, wherein the condition is obesity or diabetes.

102. The use of embodiment 100, wherein the condition is diabetic nephropathy or chronic kidney disease.

103. A treatment regimen for a cardiovascular disease, the regimen comprising: the compound of any one of embodiments 1-60 or the pharmaceutically acceptable salt thereof, the stereoisomer of any of the foregoing, or the mixture thereof.

104. The treatment regimen of embodiment 103, wherein the regimen further comprises a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

105. The treatment regimen of embodiment 103, wherein the regimen further comprises a therapeutic agent selected from an angiotensin converting enzyme (ACE) inhibitor or an angiotensin-receptor blocker (ARB).

106. A kit, the kit comprising: the compound of any one of embodiments 1-60 or the pharmaceutically acceptable salt thereof, the stereoisomer of any of the foregoing, or the mixture thereof.

107. The kit of embodiment 106, wherein the kit further comprises a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

108. The kit of embodiment 106, wherein the kit further comprises a therapeutic agent selected from an angiotensin converting enzyme (ACE) inhibitor or an angiotensin-receptor blocker (ARB).

109. In one embodiment, the invention provides a compound of Formula V, a salt thereof, a tautomer thereof, or a salt of the tautomer:

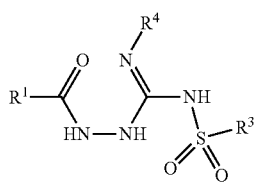

V wherein:

$R^1$ is an unsubstituted furanyl, or is a furanyl substituted with 1, 2, or 3 $R^{1a}$ substituents;

$R^{1a}$ in each instance is independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), or —C(=O)N($C_1$-$C_6$ alkyl)$_2$;

$R^3$ is selected from an unsubstituted $C_1$-$C_{10}$ alkyl, a $C_1$-$C_{10}$ alkyl substituted with 1, 2, or 3 $R^{3a}$ substituents, a group of formula —($CR^{3b}R^{3c}$)-Q, a group of formula —($CR^{3b}R^{3c}$)—C(=O)-Q, a group of formula —($CR^{3d}R^{3e}$)—($CR^{3f}R^{3g}$)-Q, a group of formula —($CR^{3d}R^{3e}$)—($CR^{3f}R^{3g}$)—C(=O)-Q, a group of formula —($CR^{3d}R^{3e}$)—($CR^{3f}R^{3g}$)—CH(OH)-Q, a group of formula —($CR^{3d}R^{3e}$)—($CR^{3f}R^{3g}$)—($CR^{3f}R^{3g}$)-Q, a group of formula —($CR^{3b}$=$CR^{3c}$)-Q, a group of formula —($C_3$-$C_8$ cycloalkyl)-Q, a group of formula -(heterocyclyl)-Q, or -Q, wherein the heterocyclyl of the -(heterocyclyl)-Q group has 5 to 7 ring members of which 1, 2, or 3 are heteroatoms independently selected from N, O, or S and is unsubstituted or is substituted with 1, 2, or 3 $R^{3h}$ substituents, and further wherein the $C_3$-$C_8$ cycloalkyl of the —($C_3$-$C_8$ cycloalkyl)-Q group is unsubstituted or is substituted with 1 or 2 $R^{3h}$ substituents;

$R^{3a}$ in each instance is independently selected from —F, —Cl, —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$C_2$-$C_6$ alkenyl, —$C_2$-$C_6$ alkynyl, —$NH_2$, —NH($C_1$-$C_6$ alkyl), or —N($C_1$-$C_6$ alkyl)$_2$;

$R^{3b}$ and $R^{3c}$ are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3d}$ and $R^{3e}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3f}$ and $R^{3g}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3h}$ in each instance is independently selected from —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)—($C_3$-$C_6$ cycloalkyl), —C(=O)—O—($C_1$-$C_6$ alkyl), oxo, or —C(=O)-(heterocyclyl), wherein the heterocyclyl group of the $R^h$—C(=O)-(heterocyclyl) has 5 or 6 ring members of which 1 or 2 are heteroatoms independently selected from N, or S or has 3 or 4 ring members of which 1 is a heteroatom selected from N, O, or S;

Q is a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a $C_3$-$C_8$ cycloalkyl group, a 3 to 10 membered heterocyclyl group containing 1, 2, or 3 heteroatoms independently selected from N, O, or S, —C(=O)NH(—$C_1$-$C_6$ alkyl), —C(=O)N(—$C_1$-$C_6$ alkyl)$_2$, or —S(=O)$_2$—$C_1$-$C_6$alkyl, wherein the $C_6$-$C_{10}$ aryl, the heteroaryl, the cycloalkyl, and the heterocyclyl Q groups are unsubstituted or are substituted with 1, 2, 3, or 4 $R^Q$ substituent;

$R^Q$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —NHC(=O)($C_1$-$C_6$ alkyl), —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), —($C_1$-$C_6$ alkyl)-OH, —($C_1$-$C_6$ alkyl)-O—($C_1$-$C_6$ alkyl), phenyl, a heterocyclyl group, a —($C_1$-$C_6$ alkyl)heterocyclyl group, or a heteroaryl group with 5 or 6 ring members and 1, 2, or 3, heteroatoms independently selected from N, O, or S, wherein the heterocyclyl groups of the $R^Q$ heterocyclyl and —($C_1$-$C_6$ alkyl)heterocyclyl groups have 3 to 6 ring members of which 1 or 2 are heteroatoms independently selected from N, O, or S, wherein the Q heterocyclyl group may additionally be substituted with 1 or 2 oxo substituents, and the Q heteroaryl group may include an N-oxide if the heteroaryl includes a N heteroatom, and further wherein the heterocyclyl and the heterocyclyl of the —($C_1$-$C_6$ alkyl) heterocyclyl $R^Q$ groups may be further substituted with one or two oxo substituents and a substituent selected from —F, —Cl, —Br, —I, —CN, —OH, $C_1$-$C_6$ alkyl, or —C(=O)—($C_1$-$C_6$ alkyl);

$R^4$ is selected from a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a monocyclic or bicyclic heterocyclyl group with 5 to 10 ring members containing 1, 2, 3, or 4 heteroatoms independently selected from N, O, or S, a monocyclic 3-6 membered cycloalkyl group, or a straight or branched chain $C_1$-$C_6$ alkyl group, wherein the $C_6$-$C_{10}$ aryl, the heteroaryl, the heterocyclyl, and the cycloalkyl $R^4$ group are unsubstituted or are substituted with 1, 2, 3, or 4 $R^{4a}$ substituents, and further wherein the straight or branched chain $C_1$-$C_6$ alkyl $R^4$ group is unsubstituted or is substituted with 1, 2, or 3 $R^{4b}$ substituents;

$R^{4a}$ in each instance is independently selected from —F, —Cl, —Br, —I, —CN, $C_1$-$C_6$ alkyl, $C_1$-$C_6$ haloalkyl, $C_1$-$C_6$ perhaloalkyl, —($C_1$-$C_6$ alkyl)-OH, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —NH$_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)NH$_2$, —C(=O)NH($C_1$-$C_6$ alkyl), —C(=O)N($C_1$-$C_6$ alkyl)$_2$, phenyl, —S(=O)$_2$—($C_1$-$C_6$ alkyl), —($C_1$-$C_6$ alkyl)-heterocyclyl, or heterocyclyl wherein the heterocyclyl of the —($C_1$-$C_6$ alkyl)-heterocyclyl and heterocyclyl $R^{4a}$ groups is a 3-6 membered ring comprising 1 or 2 heteroatoms independently selected from N, O, or S, and is unsaturated or partially unsaturated and is optionally substituted with 1 or 2 oxo substituents and may include an S=O or SO$_2$ moiety, and further wherein the heterocyclyl of the $R^4$ group may be further substituted with 1 oxo substituent; and $R^{4b}$ in each instance is selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —NH$_2$, —NH($C_1$-$C_6$ alkyl), —N($C_1$-$C_6$alkyl)$_2$, NH($C_1$-$C_6$ alkyl-OH), —N($C_1$-$C_6$alkyl-OH)$_2$, —C(=O)—($C_1$-$C_6$ alkyl), —C(=O)OH, —C(=O)—O—($C_1$-$C_6$ alkyl), —C(=O) NH$_2$, —C(=O)NH($C_1$-$C_6$ alkyl), —C(=O)N($C_1$-$C_6$ alkyl)$_2$, or —S(=O)$_2$—($C_1$-$C_6$ alkyl).

110. The compound of embodiment 109, the salt thereof, the tautomer thereof, or the salt of the tautomer, wherein the compound has any of the $R^1$, $R^{1a}$, $R^3$, $R^{3d}$, $R^{3e}$, $R^{3f}$, $R^{3g}$, $R^{3h}$, $R^4$, $R^{4a}$, $R^{4b}$, Q or $R^Q$, values or combinations of values of any one of embodiments 2-55.

111. In another embodiment, the invention provides a method for preparing a compound of Formula VI, a salt thereof, a tautomer thereof, or the salt of the tautomer:

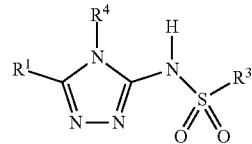

VI the method comprising:
a) cyclizing a compound of Formula V, a salt thereof, a tautomer thereof, or a salt of the tautomer in the presence of an acid or a base to form the compound of Formula VI, the salt thereof, the tautomer thereof, or the salt of the tautomer,

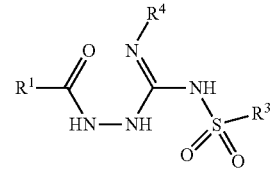

V wherein:
$R^1$ is an unsubstituted furanyl, or is a furanyl substituted with 1, 2, or 3 $R^{1a}$ substituents;

$R^{1a}$ in each instance is independently selected from —F, —Cl, —Br, —I, $C_1$-$C_6$ alkyl, $C_1$-$C_6$ haloalkyl, $C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —NH$_2$, —NH($C_1$-$C_6$ alkyl), —N($C_1$-$C_6$ alkyl)$_2$, —C(=O)—($C_1$-$C_6$ alkyl), —C(=O) OH, —C(=O)—O—($C_1$-$C_6$ alkyl), —C(=O)NH$_2$, —C(=O)NH($C_1$-$C_6$ alkyl), or —C(=O)N($C_1$-$C_6$ alkyl)$_2$;

$R^3$ is selected from an unsubstituted $C_1$-$C_{10}$ alkyl, a $C_1$-$C_{10}$ alkyl substituted with 1, 2, or 3 $R^{3a}$ substituents, a group of formula —(CR$^{3b}$R$^{3c}$)-Q, a group of formula —(CR$^{3b}$R$^{3c}$)—C(=O)-Q, a group of formula —(CR$^{3d}$R$^{3e}$)—(CR$^{3f}$R$^{3g}$)-Q, a group of formula —(CR$^{3d}$R$^{3e}$)—(CR$^{3f}$R$^{3g}$)—C(=O)-Q, a group of formula —(CR$^{3d}$R$^{3e}$)—(CR$^{3f}$R$^{3g}$)—CH(OH)-Q, a group of formula —(CR$^{3d}$R$^{3e}$)—(CR$^{3f}$R$^{3g}$)—(CR$^{3f}$R$^{3g}$)-Q, a group of formula —(CR$^{3b}$=CR$^{3c}$)-Q, a group of formula —($C_3$-$C_8$ cycloalkyl)-Q, a group of formula -(heterocyclyl)-Q, or -Q, wherein the heterocyclyl of the -(heterocyclyl)-Q group has 5 to 7 ring members of which 1, 2, or 3 are heteroatoms independently selected from N, O, or S and is unsubstituted or is substituted with 1, 2, or 3 $R^{3h}$ substituents, and further wherein the $C_3$-$C_8$ cycloalkyl of the —($C_3$-$C_8$ cycloalkyl)-Q group is unsubstituted or is substituted with 1 or 2 $R^{3h}$ substituents;

$R^{3a}$ in each instance is independently selected from —F, —Cl, —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$C_2$-$C_6$ alkenyl, —$C_2$-$C_6$ alkynyl, —NH$_2$, —NH($C_1$-$C_6$ alkyl), or —N($C_1$-$C_6$ alkyl)$_2$;

$R^{3b}$ and $R^{3c}$ are independently selected from —H, —F, —Cl, —CN, $C_1$-$C_6$ alkyl, $C_1$-$C_6$ haloalkyl, $C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3d}$ and $R^{3e}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3f}$ and $R^{3g}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;

$R^{3h}$ in each instance is independently selected from —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)—($C_3$-$C_6$ cycloalkyl), —C(=O)—O—($C_1$-$C_6$ alkyl), oxo, or —C(=O)-(heterocyclyl), wherein the heterocyclyl group of the $R^h$—C(=O)-(heterocyclyl) has 5 or 6 ring members of which 1 or 2 are heteroatoms independently selected from N, or S or has 3 or 4 ring members of which 1 is a heteroatom selected from N, O, or S;

Q is a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a $C_3$-$C_8$ cycloalkyl group, a 3 to 10 membered heterocyclyl group containing 1, 2, or 3 heteroatoms independently selected from N, O, or S, —C(=O)NH(—$C_1$-$C_6$ alkyl), —C(=O)N(—$C_1$-$C_6$ alkyl)$_2$, or —S(=O)$_2$—$C_1$-$C_6$alkyl, wherein the $C_6$-$C_{10}$ aryl, the heteroaryl, the cycloalkyl, and the heterocyclyl Q groups are unsubstituted or are substituted with 1, 2, 3, or 4 $R^Q$ substituent;

$R^Q$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —NHC(=O)($C_1$-$C_6$ alkyl), —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), —($C_1$-$C_6$ alkyl)-OH, —($C_1$-$C_6$ alkyl)-O—($C_1$-$C_6$ alkyl), phenyl, a heterocyclyl group, a —($C_1$-$C_6$ alkyl)heterocyclyl group, or a heteroaryl group with 5 or 6 ring members and 1, 2, or 3, heteroatoms independently selected from N, O, or S, wherein the heterocyclyl groups of the $R^Q$ heterocyclyl and —($C_1$-$C_6$ alkyl)heterocyclyl groups have 3 to 6 ring members of which 1 or 2 are heteroatoms independently selected from N, O, or S, wherein the Q heterocyclyl group may additionally be substituted with 1 or 2 oxo substituents, and the Q heteroaryl group may include an N-oxide if the heteroaryl includes a N heteroatom, and further wherein the heterocyclyl and the heterocyclyl of the —($C_1$-$C_6$ alkyl) heterocyclyl $R^Q$ groups may be further substituted with one or two oxo substituents and a substituent selected from —F, —Cl, —Br, —I, —CN, —OH, —$C_1$-$C_6$ alkyl, or —C(=O)—($C_1$-$C_6$ alkyl);

$R^4$ is selected from a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a monocyclic or bicyclic heterocyclyl group with 5 to 10 ring members containing 1, 2, 3, or 4 heteroatoms independently selected from N, O, or S, a monocyclic 3-6 membered cycloalkyl group, or a straight or branched chain $C_1$-$C_6$ alkyl group, wherein the $C_6$-$C_{10}$ aryl, the heteroaryl, the heterocyclyl, and the cycloalkyl $R^4$ group are unsubstituted or are substituted with 1, 2, 3, or 4 $R^{4a}$ substituents, and further wherein the straight or branched chain $C_1$-$C_6$ alkyl $R^4$ group is unsubstituted or is substituted with 1, 2, or 3 $R^{4b}$ substituents;

$R^{4a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, phenyl, —S(=O)$_2$—($C_1$-$C_6$ alkyl), —($C_1$-$C_6$ alkyl)-heterocyclyl, or heterocyclyl wherein the heterocyclyl of the —($C_1$-$C_6$ alkyl)-heterocyclyl and heterocyclyl $R^{4a}$ groups is a 3-6 membered ring comprising 1 or 2 heteroatoms independently selected from N, O, or S, and is unsaturated or partially unsaturated and is optionally substituted with 1 or 2 oxo substituents and may include an S=O or $SO_2$ moiety, and further wherein the heterocyclyl of the $R^4$ group may be further substituted with 1 oxo substituent; and $R^{4b}$ in each instance is selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, or —S(=O)$_2$—($C_1$-$C_6$ alkyl).

112. The method of embodiment 111, wherein $R^1$, $R^{1a}$, $R^3$, $R^{3d}$, $R^{3e}$, $R^{3f}$, $R^{3g}$, $R^{3h}$, $R^4$, $R^{4a}$, $R^{4b}$, Q or $R^Q$, have any of the values or combination of values of any one of embodiments 2-55.

113. The method of embodiment 111 or embodiment 112, wherein cyclizing further comprises heating the compound of Formula V, the salt thereof, the tautomer thereof, or the salt of the tautomer in the presence of the acid or the base.

114. The method of embodiment 113, wherein heating the compound of Formula V, the salt thereof, the tautomer thereof, or the salt of the tautomer comprises heating the compound to a temperature of from 50° C. to 100° C.

115. The method of embodiment 113, wherein heating the compound of Formula V, the salt thereof, the tautomer thereof, or the salt of the tautomer comprises heating the compound to a temperature of from 60° C. to 85° C.

116. The method of any one of embodiments 111-115, wherein the cyclizing of the compound of Formula V, the salt thereof, the tautomer thereof, or the salt of the tautomer is performed in the presence of the base.

117. The method of any one of embodiments 111-116, wherein the base is a metal hydroxide.

118. The method of embodiment 117, wherein the metal hydroxide is selected from NaOH or LiOH.

119. The method of any one of embodiments 116-118, wherein the cyclizing is carried out in an alcohol solvent.

120. The method of embodiment 119, wherein the alcohol is isopropanol.

121. The method of any one of embodiments 111-115, wherein cyclizing further comprises heating the compound of Formula V, the salt thereof, the tautomer thereof, or the salt of the tautomer in the presence of the acid.

122. The method of embodiment 121, wherein the acid is selected from a sulfonic acid, a carboxylic acid, polyphosphoric acid, phosphoric acid, sulfuric acid, or hydrochloric acid.

123. The method of embodiment 122, wherein the sulfonic acid is methanesulfonic acid.

124. The method of embodiment 122, wherein the acid is trifluoroacetic acid, acetic acid, or trichloroacetic acid.

125. The method of any one of embodiments 121-124, wherein the cyclizing is carried out in a cyclic ether, an acyclic ether, N,N-dimethylformamide, or acetonitrile.

126. The method of embodiment 125, wherein the cyclizing is carried out in a cyclic ether.

127. The method of embodiment 126, wherein the cyclic ether is selected from tetrahydrofuran, tetrahydropyran, or 1,4-dioxane.

128. The method of embodiment 126, wherein the cyclic ether is 1,4-dioxane.

In some embodiments, the compound is a salt. Such salts may be anhydrous or associated with water as a hydrate. In some embodiments, the compound may be in a neutral form as a base or an acid.

Also provided are pharmaceutical compositions that include the compound or the pharmaceutically acceptable salt thereof, the tautomer thereof, the pharmaceutically acceptable salt of the tautomer, the stereoisomer of any of the foregoing, or the mixture thereof according to any one of the embodiments and at least one pharmaceutically acceptable excipient, carrier or diluent. In some such embodiments, the compound or the pharmaceutically acceptable salt thereof, the tautomer thereof, the pharmaceutically acceptable salt of the tautomer, the stereoisomer of any of the foregoing, or the mixture thereof according to any one of the embodiments is present in an amount effective for the treatment of a cardiovascular condition or other condition such as obesity or diabetes, for activating the APJ Receptor. In some embodiments, the pharmaceutical composition is formulated for oral delivery whereas in other embodiments, the pharmaceutical composition is formulated for intravenous delivery. In some embodiments, the pharmaceutical composition is formulated for oral administration once a day or QD, and in some such formulations is a tablet.

In some embodiments, the subject is a mammal. In some such embodiments, the mammal is a rodent. In other such embodiments, the mammal is a canine. In still other embodiments, the subject is a primate and, in some such embodiments, is a human.

The pharmaceutical compositions or formulations for the administration of the compounds of this invention may conveniently be presented in unit dosage form and may be prepared by any of the methods well known in the art. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition, the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Such compositions may contain one or more agents selected from sweetening agents, flavoring agents, coloring agents and preserving agents in order to provide pharmaceutically elegant and palatable preparations. Tablets contain the active ingredient in admixture with other non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,160,452, and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate, or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The pharmaceutical compositions may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include, for example, cocoa butter and polyethylene glycols.

For topical use, creams, ointments, jellies, solutions, or suspensions, etc., containing the compounds of the invention are employed. As used herein, topical application is also meant to include the use of mouthwashes and gargles.

The compounds of the invention can be administered to provide systemic distribution of the compound within the patient. Therefore, in some embodiments, the compounds of the invention are administered to produce a systemic effect in the body.

As indicated above, the compounds of the invention may be administered via oral, mucosal (including sublingual, buccal, rectal, nasal, or vaginal), parenteral (including subcutaneous, intramuscular, bolus injection, intra-arterial, or intravenous), transdermal, or topical administration. In some embodiments, the compounds of the invention are administered via mucosal (including sublingual, buccal, rectal, nasal, or vaginal), parenteral (including subcutaneous, intramuscular, bolus injection, intra-arterial, or intravenous), transdermal, or topical administration. In other embodiments, the compounds of the invention are administered via oral administration. In still other embodiments, the compounds of the invention are not administered via oral administration.

Different therapeutically effective amounts may be applicable for different conditions, as will be readily known by those of ordinary skill in the art. Similarly, amounts sufficient to treat or prevent such conditions, but insufficient to cause, or sufficient to reduce, adverse effects associated with conventional therapies are also encompassed by the above described dosage amounts and dose frequency schedules.

The compound of the invention, the pharmaceutically acceptable salt thereof, the tautomer thereof, the pharmaceutically acceptable salt of the tautomer, the stereoisomer of any of the foregoing, or the mixture thereof may find use in treating a number of conditions. For example, in some embodiments, the invention comprises methods or uses that include the use or administration of the compound, the pharmaceutically acceptable salt thereof, the tautomer thereof, the pharmaceutically acceptable salt of the tautomer, the stereoisomer of any of the foregoing, or the mixture thereof of the invention, in treating a subject suffering from a cardiovascular condition. In some embodiments, the cardiovascular condition includes, but is not limited to, coronary heart disease, stroke, heart failure, systolic heart failure, diastolic heart failure, diabetic heart failure, heart failure with preserved ejection fraction, heart failure with reduced ejection fraction, cardiomyopathy, myocardial infarction, myocardial remodeling after cardiac surgery, valvular heart disease, hypertension including, essential hypertension, pulmonary hypertension, portal hypertension, systolic hypertension, aortic aneurysm such as abdominal aortic aneurysm, or atrial fibrillation including improving arrhythmia. In some embodiments, the cardiovascular condition is heart failure. In some such embodiments, the heart failure is heart failure with reduced ejection fraction whereas in other embodiments it is heart failure with preserved ejection fraction. In other such embodiments the subject may have systolic heart failure or chronic diastolic heart failure and is thus useful in treating heart failure patients with systolic dysfunction and in treating heart failure patients with diastolic dysfunction. In some embodiments, the cardiovascular condition may be acute heart failure whereas in other embodiments, the cardiovascular condition is hypertension.

As noted, the compounds of the invention may be used to treat a number of diseases and disorders. Thus, in some embodiments, the invention provides a method of treating a disease or disorder selected from acute decompensated heart failure, chronic heart failure, pulmonary hypertension, atrial fibrillation, Brugada syndrome, ventricular tachycardia, atherosclerosis, hypertension, restenosis, ischemic cardiovascular diseases, cardiomyopathy, cardiac fibrosis, arrhythmia, water retention, diabetes, gestational diabetes, obesity, peripheral arterial disease, cerebrovascular accidents, transient ischemic attacks, traumatic brain injuries, amyotrophic lateral sclerosis, burn injuries, sunburn, edema, and preeclampsia in a subject. Such methods include administering a compound of the invention, a pharmaceutically acceptable salt thereof, a tautomer thereof, a pharmaceutically acceptable salt of the tautomer, a stereoisomer of any of the foregoing, a mixture thereof, or a pharmaceutical composition that includes any of these to a subject in need thereof.

In some embodiments, the invention provides a method of improving cardiac contractility in a subject suffering from a cardiovascular condition which includes administration of the compound, the pharmaceutically acceptable salt thereof, the tautomer thereof, the pharmaceutically acceptable salt of the tautomer, the stereoisomer of any of the foregoing, or the mixture thereof of the invention to the subject. The improvement in cardiac contraction may lead to significant improvements in methods for treating heart failure patients.

In some embodiments, the invention provides a method of improving cardiac relaxation in a subject suffering from a cardiovascular condition which includes administration of the compound, the pharmaceutically acceptable salt thereof, the tautomer thereof, the pharmaceutically acceptable salt of the tautomer, the stereoisomer of any of the foregoing, or the mixture thereof of the invention to the subject. The improvement in cardiac relaxation may lead to significant improvements in methods for treating heart failure patients.

In some embodiments, the invention provides a method of improving ventricular arterial coupling in a subject suffering from a cardiovascular condition which includes administration of the compound, the pharmaceutically acceptable salt thereof, the tautomer thereof, the pharmaceutically acceptable salt of the tautomer, the stereoisomer of any of the foregoing, or the mixture thereof of the invention to the subject. The improvement in ventricular arterial coupling may lead to significant improvements in methods for treating heart failure patients.

In some embodiments, the invention provides a method of increasing ejection fraction in a subject suffering from a cardiovascular condition which includes administration of the compound, the pharmaceutically acceptable salt thereof, the tautomer thereof, the pharmaceutically acceptable salt of the tautomer, the stereoisomer of any of the foregoing, or the mixture thereof of the invention to the subject.

The compounds of the invention may also find potential benefit in improving cardiac relaxation and thus find utility in treating certain heart failure patients. The compounds of the invention may thus find utility in improving inotropic function in some embodiments and may also find utility in improving lusitropic function.

In some embodiments, the invention provides a method of treating condition in a subject where it is desired to activate the APJ Receptor. Such methods include administration of the compound, the pharmaceutically acceptable salt thereof, the tautomer thereof, the pharmaceutically acceptable salt of the tautomer, the stereoisomer of any of the foregoing, or the mixture thereof of the invention to the subject. In some such embodiments, the condition is obesity or diabetes whereas in other embodiments, the condition is diabetic nephropathy or chronic kidney disease. In some such embodiments, the condition is type II diabetes. In other embodiments, the condition is cardiac wasting.

The compounds of the invention may find utility in treating a number of other conditions. For example, the compounds of the invention may find utility in treating patients with conditions related to renal perfusion, hyperglycemia, aquaresis, and diuresis. In some embodiments, the invention provides a method of treating one of these subjects that includes administration of the compound, the pharmaceutically acceptable salt thereof, the tautomer thereof, the pharmaceutically acceptable salt of the tautomer, the stereoisomer of any of the foregoing, or the mixture thereof of the invention to the subject. The compounds of the invention may further find utility in arginine vasopressin (AVP) regulation and in angiotensin receptor (AT1R) regulation.

The compounds of the invention may find utility in treating a number of other conditions or producing desired outcomes or results. For example, the compounds of the invention may find utility in activating stem cells, more specifically cardiac stem cells, and even more specifically endogenous cardiac stem cells. Thus, the compounds of the invention may find utility in activating heart stem cells in a subject such as in a human patient. The compounds of the invention may yet further find utility in regrowing tissue and in assisting functional recovery after transplanting cells such as cells with bone marrow-derived mesenchymal stem cells. The compounds of the invention may also find utility in increasing cardiac stem cell proliferation and may be used to do such in patients that have suffered a myocardial infarction. As another example, the compounds of the invention may find utility in reducing infarct size, in promoting cardiac repair, and in activating stem cells and progenitors in post-myocardial infarction subjects. As still yet another example, the compounds of the invention may be used during surgery such as heart bypass surgery or heart transplant procedures as a therapeutic to reduce reperfusion injury. In some embodiments, the invention provides a method of treating one of these subjects or improving the condition in a subject that includes administration of the compound, the pharmaceutically acceptable salt thereof, the tautomer thereof, the pharmaceutically acceptable salt of the tautomer, the stereoisomer of any of the foregoing, or the mixture thereof of the invention to the subject.

Some methods of the invention comprise the administration of a compound of the invention and an additional therapeutic agent (i.e., a therapeutic agent other than a compound of the invention). Thus, the compounds of the invention can be used in combination with at least one other therapeutic agent. Examples of additional therapeutic agents include, but are not limited to, antibiotics, anti-emetic agents, antidepressants, antifungal agents, anti-inflammatory agents, antineoplastic agents, antiviral agents, cytotoxic agents, and other anticancer agents, immunomodulatory agents, alpha-interferons, β-interferons, alkylating agents, hormones, and cytokines. In one embodiment, the invention encompasses administration of an additional therapeutic agent that is used to treat subjects with chronic heart failure or hypertension.

As described above some methods of the invention comprise the administration of a compound of the invention and an additional therapeutic agent (i.e., a therapeutic agent other than a compound of the invention). In some embodiments, the invention encompasses administration of an additional therapeutic agent that is used to treat subjects with chronic heart failure or hypertension. In some embodiments, the invention comprises methods or uses that include the use of a compound, the pharmaceutically acceptable salt thereof, the tautomer thereof, the pharmaceutically acceptable salt of the tautomer, the stereoisomer of any of the foregoing, or the mixture thereof of the invention and a therapeutic agent such as, but not limited to, an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, a neutral endopeptidase (NEP) inhibitor, a vasodilator, an aldosterone antagonist, a natriuretic, a saluretic, a centrally acting hypertensive, an aldosterone synthase inhibitor, or an endothelin receptor antagonist. In some embodiments, the invention comprises methods or uses that include the use of a compound, the pharmaceutically acceptable salt thereof, the tautomer thereof, the pharmaceutically acceptable salt of the tautomer, the stereoisomer of any of the foregoing, or the mixture thereof of the invention and a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor. In some such embodiments, the invention includes a method that includes administering a compound of the invention, the pharmaceutically acceptable salt thereof, the tautomer thereof, the pharmaceutically acceptable salt of the tautomer, the stereoisomer of any of the foregoing, or the mixture thereof and an additional therapeutic agent such as an angiotensin converting enzyme (ACE) inhibitor or an angiotensin-receptor blocker (ARB). In some such embodiments, the additional therapeutic agent is thus an angiotensin converting enzyme (ACE) inhibitor whereas in others it is an angiotensin-receptor blocker (ARB). In other such embodiments, the invention includes a method that includes administering a compound of the invention, the pharmaceutically acceptable salt thereof, the tautomer thereof, the pharmaceutically acceptable salt of the tautomer, the stereoisomer of any of the foregoing, or the mixture thereof and an additional therapeutic agent such as a neutral endopeptidase (NEP) inhibitor. In other such embodiments, the invention includes a method that includes administering a compound of the invention, the pharmaceutically acceptable salt thereof, the tautomer thereof, the pharmaceutically acceptable salt of the tautomer, the stereoisomer of any of the foregoing, or the mixture thereof and an additional therapeutic agent such as an inhibitor of the funny current. In some embodiments, the method of use may include two or more additional therapeutic agents. For example, in some embodiments, the invention may include a compound of the invention, the pharmaceutically acceptable salt thereof, the tautomer thereof, the pharmaceutically acceptable salt of the tautomer, the stereoisomer of any of the foregoing, or the mixture thereof and additional therapeutic agents such as an ACE inhibitor and a NEP inhibitor.

Therapeutic agents such as α-blockers may be used in conjunction with the compounds of the invention. Examples of α-blockers include, but are not limited to, doxazosin, prazosin, tamsulosin, and terazosin and their pharmaceutically acceptable salts.

Therapeutic agents such as β-blockers may be used in conjunction with the compounds of the invention. Examples of β-blockers include, but are not limited to, acebutolol, acetutolol, atenolol, bisoprol, bupranolol, carteolol, carvedilol, celiprolol, esmolol, mepindolol, metoprolol, nadolol, oxprenolol, penbutolol, pindolol, propranolol, taliprolol, and their pharmaceutically acceptable salts.

Calcium channel blockers may also be used as therapeutic agents in conjunctions with the compounds of the present invention. Examples of calcium channel blockers, include, but are not limited to, dihydropyridines (DHPs) and non-DHPs. Examples of DHPs include, but are not limited to, amlodipine, felodipine, isradipine, lacidipine, nicardipine, nifedipine, nigulpidine, nilutipine, nimodiphine, nisoldipine, nitrendipine, nivaldipine, ryosidine, and their pharmaceutically acceptable salts. Examples of Non-DHPs include, but are not limited to, anipamil, diltiazem, fendiline, flunarizine, gallpamil, mibefradil, prenylamine, tiapamil, verapamil, and their pharmaceutically acceptable salts.

Diuretics may also be used in conjunction with the compounds of the present invention. Examples include, but are not limited to, thiazide derivatives such as, but not limited to, amiloride, chlorothalidon, chlorothiazide, hydrochlorthiazide, and methylchlorothiazide and pharmaceutically acceptable salts thereof.

Centrally acting hypertensive agents may also be used in conjunction with the compounds of the present invention. Examples, include, but are not limited to, clonidine, guanabenz, guanfacine, methyldopa, and pharmaceutically acceptable salts thereof.

ACE inhibitors may be used in conjunction with the compounds of the present invention. Examples of ACE inhibitors that may be used include, but are not limited to, alaceptril, benazepril, benazaprilat, captopril, ceronapril, cilazapril, delapril, enalapril, analaprilat, fosinopril, Lisinopril, moexipiril, moveltopril, perindopril, quinapril, quinaprilat, ramipril, ramiprilat, spriapril, temocapril, trendolapril, and zofenopril and their pharmaceutically acceptable salts. Examples of some dual ACE/NEP inhibitors include, but are not limited to omapatrilat, fasidotril, and fasidotrilat and their pharmaceutically acceptable salts.

ARBs may also be used as therapeutic agents in conjunction with the compounds of the present invention. Examples of ARBs include, but are not limited to, candesartan, eprosartan, irbesartan, losartan, olmesartan, tasosartan, telmisartan, and valsartan and their pharmaceutically acceptable salts. Examples of some dual ARB/NEP inhibitors include, but are not limited to combinations of valsartan and sacubitril and their pharmaceutically acceptable salts.

NEP inhibitors may also be used as therapeutic agents in conjunction with the compounds of the present invention. An example of a NEP inhibitor includes, but it not limited to, sacubitril and its pharmaceutically acceptable salts.

Aldosterone synthase inhibitors may also be used as therapeutic agents in combination with the compounds of the present invention. Examples of aldosterone synthase inhibitors include, but are not limited to, anastrozole, fadrozole, and exemestane and their pharmaceutically acceptable salts.

Endothelin antagonists are other therapeutic agents that may be used in conjunction with the compounds of the present invention. Examples include, but are not limited to, bosentan, enrasentan, atrasentan, darusentan, macitentan, sitaxentan, and tezosentan, and their pharmaceutically acceptable salts.

Inhibitors of the funny current ($I_f$) may also be used in conjunction with the compounds of the invention. An example of an inhibitor of the funny current is ivabradine and its pharmaceutically acceptable salts.

Myosin activators may also be used in conjunction with the compounds of the invention. Examples of myosin activators include cardiac myosin activators.

It will be recognized that for purposes of this application, a therapeutic agent other than one of the present invention includes compounds such as known prodrugs that are converted into the therapeutic agent after administration. For example, a compound without antineoplastic activity, but that is converted into an antineoplastic agent in the body after administration, may be administered along with a compound of the invention. As another example, sacubitril is considered a NEP inhibitor for the purposes of this application even though it is a prodrug that is converted into sacubitrilat by de-ethylation via esterases.

When administered as a combination, the therapeutic agents can be formulated as separate compositions that are administered at the same time or sequentially at different times, or the therapeutic agents can be given as a single composition. The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent. Specifically, the administration of compounds of the present invention may be in conjunction with additional therapies known to those skilled in the art in the prevention or treatment of cardiovascular conditions.

If formulated as a fixed dose, such combination products employ the compounds of this invention within the accepted dosage ranges. Compounds of any of the embodiments described herein may also be administered sequentially with known agents for use in treating cardiovascular conditions such as heart failure and hypertension when a combination formulation is inappropriate. The invention is not limited in the sequence of administration as compounds of the invention may be administered either prior to, simultaneous with, or after administration of a known therapeutic agent.

The invention is further described by reference to the following examples, which are intended to exemplify the claimed invention but not to limit it in any way.

EXAMPLES

Unless otherwise noted, all materials were obtained from commercial suppliers and were used without further purification. Anhydrous solvents were obtained from Sigma-Aldrich (Milwaukee, Wis.) and used directly. All reactions involving air- or moisture-sensitive reagents were performed under a nitrogen or argon atmosphere. Purity was measured using Agilent 1100 Series high performance liquid chromatography (HPLC) systems with UV detection at 254 nm and 215 nm (System A: Agilent Zorbax Eclipse XDB-C8 4.6× 150 mm, 5 micron, 5 to 100% ACN in $H_2O$ with 0.1% TFA for 15 min at 1.5 mL/min; System B: Zorbax SB-C8, 4.6×75 mm, 10 to 90% ACN in $H_2O$ with 0.1% formic acid for 12 min at 1.0 mL/min). Silica gel chromatography was generally performed with prepacked silica gel cartridges (Biotage or Teledyne-Isco). $^1$H NMR spectra were recorded on a Bruker AV-400 (400 MHz) spectrometer or a Varian 400 MHz spectrometer at ambient temperature, or the NMR spectra were collected with a Bruker Avance III spectrometer operating at a proton frequency of 500.13 MHz using a 10 µL Protasis CapNMR flow probe. NMR samples were delivered to the flow probe using a Protasis One-Minute NMR™ Automation system comprised of a Discovery Tower™ Sample Manager and a Waters Liquid Handler made by CTC, Switzerland (Model 2777). All observed protons are reported as parts per million (ppm) downfield from tetramethylsilane (TMS) or another internal reference in the appropriate solvent indicated. Data are reported as follows: chemical shift, multiplicity (s=singlet, d=doublet, t=triplet, q=quartet, br=broad, m=multiplet), coupling constants, and number of protons. Low-resolution mass spectral (MS) data were determined on an Agilent 1100 Series LC-MS with UV detection at 254 nm and 215 nm and a low resonance electrospray mode (ESI).

A wide variety of sulfonamide tails and $R^4$ groups can be used to synthesize compounds of the invention such as those set forth in WO 2016/187308 and U.S. Pat. Appl. Pub. No. US 2016/0340336 which are hereby incorporated by reference in their entireties and for all purposes as if specifically set forth herein. Thus, compounds of the present invention may be prepared using any of the $R^3$, $R^4$, and Q groups taught in WO 2016/187308 and U.S. Pat. Appl. Pub. No. US 2016/0340336.

The following Abbreviations are used to refer to various reagents and solvents:
ACN Acetonitrile
AcOH Acetic Acid
d day or days
DAST Diethylaminosulfur trifluoride
DCM Dichloromethane
DEA Diethylamine
DIEA N,N-Diisopropylethylamine
DIPA N,N-Diisopropylamine
DMF N,N-Dimethylformamide
DMAc Dimethylacetamide
DMAP 4-Dimethylaminopyridine
DMSO Dimethylsulfoxide
EtOAc Ethyl Acetate
EtOH Ethanol
EtOTf Ethyl trifluoromethanesulfonate
h hour or hours
HATU 1-[Bis(dimethylamino)methylene]-1H-1,2,3-triazolo[4,5-b]pyridinium 3-oxidhexafluorophosphate
HMDS Hexamethyldisilazane
HBTU N,N,N',N'-Tetramethyl-O-(1H-benzotriazol-1-yl)uronium hexafluorophosphate
IPA Isopropanol
KHMDS Potassium bis(trimethylsilyl)amide
LiHMDS Lithium bis(trimethylsilyl)amide
MeOH Methanol
min minute or minutes
MeOTf Methyl trifluoromethanesulfonate
MSA Methanesulfonic acid
RBF RBF
RT Room temperature
SFC Supercritical fluid chromatography
TASF Tris(dimethylamino)sulfonium difluorotrimethylsilicate
TBAF tetrabutylammonium fluoride
TBS t-Butyldimethylsilane
TBDMS t-Butyldimethylsilane
TBSOTf t-Butyldimethylsilyl trifluoromethanesulfonate
TEA Triethylamine
TFA Trifluoroacetic acid
THF Tetrahydrofuran
TLC Thin Layer Chromatography Example 1.0. Preparation of N-(4-(2,6-dimethoxyphenyl)-5-(2-furanyl)-4H-1,2,4-triazol-3-yl)-2-(2-methyl-1H-benzimidazol-1-yl)ethanesulfonamide

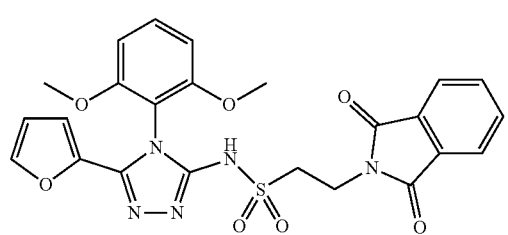

1.1

N-(4-(2,6-Dimethoxyphenyl)-5-(2-furanyl)-4H-1,2,4-triazol-3-yl)-2-(1,3-dioxo-1,3-dihydro-2H-isoindol-2-yl)ethanesulfonamide, Example 1.1. Example 1.1 was prepared from Example 362.03 and 2-phthalimidoethanesulfonyl chloride (commercially available from Oakwood Products, Inc., SC, USA) using the procedure described in Example 111.0 to give the title compound Example 1.1. $^1$H NMR (400 MHz, $CDCl_3$) δ 10.93 (br. s., 1H) 7.79-7.94 (m, 2H) 7.66-7.79 (m, 2H) 7.39-7.58 (m, 2H) 6.70 (d, J=8.61 Hz, 2H) 6.25-6.46 (m, 1H) 6.03 (d, J=3.33 Hz, 1H) 4.11 (t, J=7.04 Hz, 2H) 3.80 (s, 3H) 3.80 (s, 3H) 3.41 (t, J=7.04 Hz, 2H). LCMS-ESI (pos.), m/z: 524.2 (M+H)$^+$.

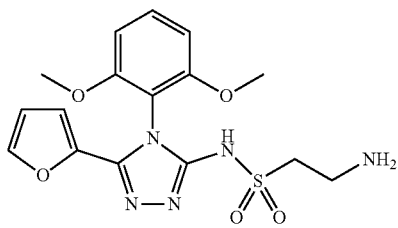

1.2

2-Amino-N-(4-(2,6-dimethoxyphenyl)-5-(2-furanyl)-4H-1,2,4-triazol-3-yl)ethanesulfonamide, Example 1.2. To a stirred solution of 1.1 (4.86 g, 9.28 mmol) in MeOH (37 mL) was added anhydrous hydrazine (1.5 mL, 46.4 mmol). The reaction mixture was stirred at RT for 18 h. LCMS analysis indicated the reaction was complete. The white precipitate was isolated by filtration to afford by-product 2,3-dihydrophthalazine-1,4-dione as a white solid. The mother liquor was concentrated and more by-product 2,3-dihydrophthalazine-1,4-dione was removed by filtration. The secondary mother liquor was concentrated in vacuo and re-crystallized to afford the title compound 1.2 (2.65 g, 6.74 mmol, 72.6% yield) as a white crystalline solid. $^1$H NMR (500 MHz, DMSO-d6) δ 7.62 (dd, J=1.71, 0.73 Hz, 1H) 7.43 (t, J=8.44 Hz, 1H) 6.81 (d, J=8.56 Hz, 2H) 6.38 (dd, J=3.42, 1.71 Hz, 1H) 5.71 (d, J=3.42 Hz, 1H) 3.67 (s, 3H)) 3.67 (s, 3H) 3.30 (t, J=6.48 Hz, 2H) 3.09 (t, J=6.48 Hz, 2H). LCMS-ESI (pos.), m/z: 394.0 (M+H)$^+$.

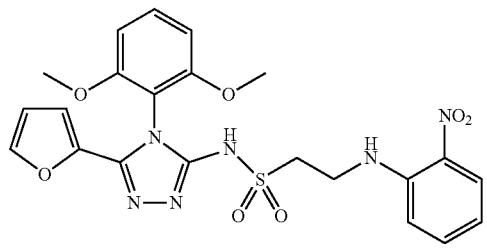

1.3

N-(4-(2,6-Dimethoxyphenyl)-5-(2-furanyl)-4H-1,2,4-triazol-3-yl)-2-((2-nitrophenyl)amino)ethanesulfonamide, Example 1.3. Under an atmosphere of nitrogen, 1.2 (0.550 g, 1.40 mmol) was suspended in DMAc (2.55 mL) and TEA (0.59 mL, 4.19 mmol) was added. The reaction was treated with 1-fluoro-2-nitrobenzene (0.074 mL, 0.70 mmol). After 24 h, the reaction was treated with additional fluoronitrobenzene (0.110 mL) and the reaction was stirred at RT for 72 h. The reaction was diluted with Et$_2$O and filtered. The organics were dried over Na$_2$SO$_4$, filtered and concentrated in vacuo. The initial product was purified on silica gel eluting with 60% to 85% THF in hexanes to afford 1.3 (0.43 g, 0.84 mmol, 60% yield). $^1$H NMR (400 MHz, DMSO-d$_6$) δ 13.52 (s, 1H) 8.29 (t, J=5.58 Hz, 1H) 8.08 (d, J=8.41 Hz, 1H) 7.85 (s, 1H) 7.57 (t, J=8.51 Hz, 1H) 7.49 (t, J=7.43 Hz, 1H) 6.84-6.95 (m, 3H) 6.72 (t, J=7.83 Hz, 1H) 6.50-6.61 (m, 1H) 6.04 (d, J=3.52 Hz, 1H) 3.72 (s, 5H) 3.64 (q, J=6.19 Hz, 2H) 3.27 (t, J=6.55 Hz, 2H). LCMS-ESI (pos.), m/z: 515.0 (M+H)$^+$.

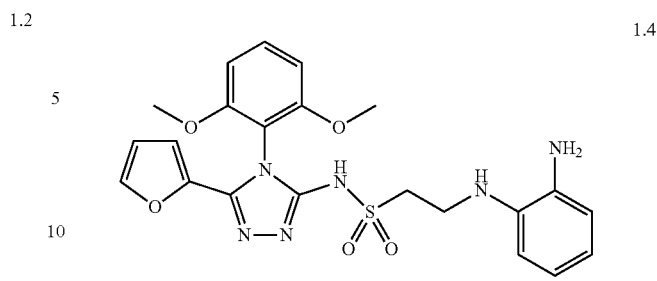

1.4

2-((2-Aminophenyl)amino)-N-(4-(2,6-dimethoxyphenyl)-5-(2-furanyl)-4H-1,2,4-triazol-3-yl)ethanesulfonamide, Example 1.4. Example 1.3 (0.110 g, 0.21 mmol) was suspended in EtOH (2.00 mL). The reaction was treated with 10% palladium on carbon (0.023 g, 0.214 mmol) and placed under an atmosphere of H$_2$. The reaction was stirred ar RT for 2 h. LCMS analysis showed the reaction was incomplete. The reaction was further purged with H$_2$ and placed under an atmosphere of H$_2$ for an additional 4 h. Only a trace of starting material was visible by LCMS. The reaction was purged with N$_2$, and the catalyst was removed by filtration through Celite® brand filter aid. The filtrate was purified on silica gel eluting with 2-5% MeOH in DCM to afford 1.4 (0.075 g, 0.16 mmol, 72% yield). $^1$H NMR (400 MHz, DMSO-d$_6$) δ 7.84 (dd, J=1.76, 0.78 Hz, 1H) 7.57 (t, J=8.51 Hz, 1H) 6.90 (d, J=8.61 Hz, 2H) 6.51-6.58 (m, 2H) 6.43-6.51 (m, 2H) 6.29-6.36 (m, 1H) 6.03 (d, J=3.13 Hz, 1H) 3.69-3.74 (m, 6H) 3.27-3.39 (m, 2H) 3.10-3.26 (m, 2H). LCMS-ESI (pos.), m/z: 485.1 (M+H)$^+$. 1.0 was isolated as a side-product (0.016 g, 0.031 mmol, 14.72% yield).

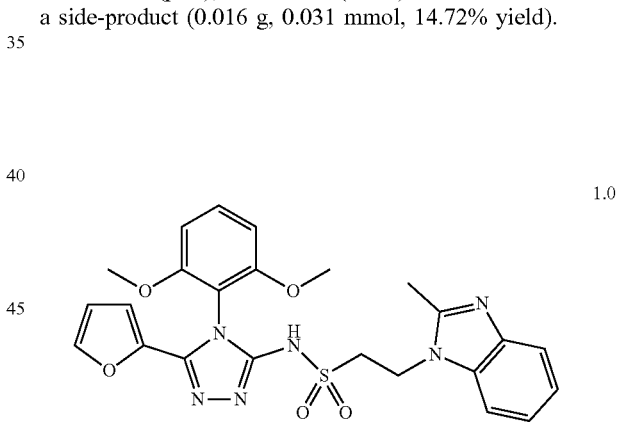

1.0

N-(4-(2,6-Dimethoxyphenyl)-5-(2-furanyl)-4H-1,2,4-triazol-3-yl)-2-(2-methyl-1H-benzimidazol-1-yl)ethanesulfonamide, Example 1.0. The title compound was prepared using the procedure described in Example 1.4. Example 1.0 was isolated as a side-product of the reaction. $^1$H NMR (400 MHz, DMSO-d$_6$) δ 13.60 (br. s., 1H) 7.86 (s, 1H) 7.62 (t, J=8.51 Hz, 1H) 7.48-7.55 (m, 1H) 7.20-7.28 (m, 1H) 7.10-7.20 (m, 2H) 6.95 (d, J=8.61 Hz, 2H) 6.56 (dd, J=3.52, 1.76 Hz, 1H) 6.07 (d, J=3.52 Hz, 1H) 4.43 (t, J=7.04 Hz, 2H) 3.75 (s, 3H) 3.75 (s, 3H) 3.41 (t, J=7.04 Hz, 2H) 2.47 (s, 3H). LCMS-ESI (pos.), m/z: 509.1 (M+H)$^+$.

Example 2.0. Preparation of N-(4-(2,6-dimethoxyphenyl)-5-(2-furanyl)-4H-1,2,4-triazol-3-yl)-2-(2-methyl-1H-benzimidazol-1-yl)ethanesulfonamide

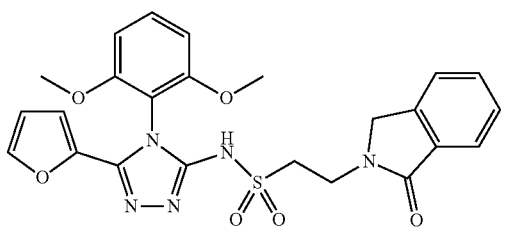

2.0

N-(4-(2,6-Dimethoxyphenyl)-5-(2-furanyl)-4H-1,2,4-triazol-3-yl)-2-(1-oxo-1,3-dihydro-2H-isoindol-2-yl)ethanesulfonamide, Example 2.0. Under an atmosphere of $N_2$, 1.2 (0.17 g, 0.42 mmol) was combined with methyl 2-(bromomethyl)benzoate (0.048 g, 0.210 mmol) and Hunig's base (0.366 mL, 2.095 mmol) in ACN (7.62 mL). The reaction was stirred overnight at RT. The reaction was then diluted with DCM and saturated aqueous $NH_4Cl$. The layers were separated and the organic layer was dried over $Na_2SO_4$, filtered, and concentrated in vacuo. The initial material was purified on silica gel eluting with 5%-15% ACN with 0.1% MeOH in DCM. A second column chromatography on silica gel was performed eluting with 2.5% to 3.0% MeOH in DCM to afford Example 2.0 (0.019 g, 0.037 mmol, 17.80% yield). $^1$H NMR (400 MHz, DMSO-$d_6$) δ 13.44 (br. s., 1H) 7.80-7.89 (m, 1H) 7.67 (d, J=7.63 Hz, 1H) 7.52-7.64 (m, 3H) 7.44-7.52 (m, 1H) 6.90 (d, J=8.61 Hz, 2H) 6.54 (dd, J=3.52, 1.76 Hz, 1H) 6.04 (d, J=3.33 Hz, 1H) 4.51 (s, 2H) 3.79-3.84 (m, 2H) 3.73-3.79 (m, 6H) 3.29 (d, J=7.24 Hz, 2H). LCMS-ESI (pos.), m/z: 510.0 (M+H)+.

Example 3.0. Preparation of (1R,2S)—N-(4-(4,6-dimethoxypyrimidin-5-yl)-5-(5-methylfuran-2-yl)-4H-1,2,4-triazol-3-yl)-1-methoxy-1-(5-methylpyrimidin-2-yl)propane-2-sulfonamide

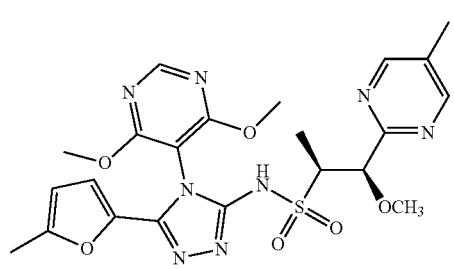

3.0

(1R,2S)—N-(4-(4,6-Dimethoxypyrimidin-5-yl)-5-(5-methylfuran-2-yl)-4H-1,2,4-triazol-3-yl)-1-methoxy-1-(5-methylpyrimidin-2-yl)propane-2-sulfonamide, Example 3.0. The title compound was prepared employing (1R,2S)-1-methoxy-1-(5-methylpyrimidin-2-yl)propane-2-sulfonamide (Example 373.0), 2-5-isothiocyanato-4,6-dimethoxypyrimidine (Example 372.1) and 5-methylfuran-2-carbohydrazide following the general procedure described in Example 314.0 employing MSA instead of TFA. $^1$H NMR (300 MHz, CDCl$_3$) δ 1.40 (d, J=7.02 Hz, 3H) 2.32 (d, J=15.78 Hz, 6H) 3.36 (s, 3H) 3.67-3.85 (m, 1H) 3.98 (d, J=5.85 Hz, 6H) 4.95 (d, J=4.68 Hz, 1H) 5.99-6.07 (m, 1H) 6.27 (d, J=3.51 Hz, 1H) 8.55 (s, 1H) 8.62 (s, 2H) 11.19 (br. s., 1H). LCMS-ESI (pos.) m/z: 531.0 (M+H)+.

Example 4.0. Preparation of (2S)—N-(4-(2,6-dimethoxyphenyl)-5-(2-furanyl)-4H-1,2,4-triazol-3-yl)-1-(7-fluoro-1-(methoxymethyl)-1H-imidazo[4,5-c]pyridin-4-yl)-2-propanesulfonamide and (2R)—N-(4-(2,6-dimethoxyphenyl)-5-(2-furanyl)-4H-1,2,4-triazol-3-yl)-1-(7-fluoro-1-(methoxymethyl)-1H-imidazo[4,5-c]pyridin-4-yl)-2-propanesulfonamide

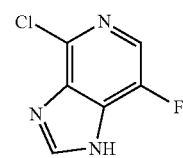

4.1

4-Chloro-7-fluoro-1H-imidazo[4,5-c]pyridine, Example 4.1. Sulfamic acid (187 μL, 4.15 mmol) was added to a solution of 2-chloro-5-fluoropyridine-3,4-diamine (commercially available from Bellen, Beijing, China) (670 mg, 4.15 mmol) and ethyl orthoformate (2.76 mL, 16.6 mmol) in MeOH (10 mL) and the mixture was heated at reflux for 16 h. Thereafter, the mixture was cooled to RT, diluted with saturated aqueous NaHCO$_3$, and extracted with DCM. The DCM extracts were combined, washed with brine, dried over Na$_2$SO$_4$, filtered and concentrated in vacuo. The residue was purified on a silica gel column, employing a gradient of 0-20% MeOH in DCM, to afford 4.1 (560 mg, 3.26 mmol, 79%).

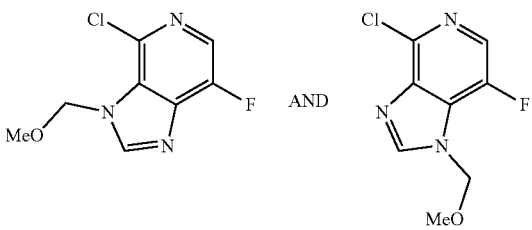

4.2

4-Chloro-7-fluoro-3-(methoxymethyl)-3H-imidazo[4,5-c]pyridine and 4-chloro-7-fluoro-1-(methoxymethyl)-1H-imidazo[4,5-c]pyridine, Example 4.2. Chloromethyl methyl ether (89 μL, 1.17 mmol) was added to a solution of 4.1 (50 mg, 0.29 mmol) and morpholine (152 μL, 1.75 mmol) in DCM (1 mL), and the mixture was stirred for 3 d at RT. Thereafter, the mixture was diluted with saturated aqueous NaHCO$_3$ and extracted with EtOAc. The combined organic layers were washed with brine, dried over Na$_2$SO$_4$, filtered, and concentrated in vacuo. The residue was purified on a silica gel preparative layer plate employing 40% EtOAc in hexanes as eluent to afford 4.2 (30 mg, 0.14 mmol, 48%).

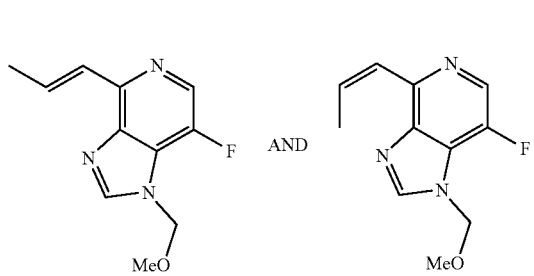

(E)-7-Fluoro-1-(methoxymethyl)-4-(prop-1-en-1-yl)-1H-imidazo[4,5-c]pyridine and (Z)-7-fluoro-1-(methoxymethyl)-4-(prop-1-en-1-yl)-1H-imidazo[4,5-c]pyridine, Example 4.3. A mixture of potassium (E)-trifluoro(prop-1-en-1-yl)borate (commercially available from Frontier Scientific Services Inc.) (782 mg, 5.29 mmol), 4.2 (570 mg, 2.64 mmol), triphenylphosphine (208 mg, 0.79 mmol), and cesium carbonate (861 mg, 2.64 mmol) in dioxane (5 mL) was sparged with argon for 1 min. Palladium (II) chloride (47 mg, 0.26 mmol) was added, the mixture was sparged for 1 min, and then it was stirred at 80° C. for 16 h. Thereafter, the mixture was cooled to RT, diluted with saturated aqueous NaHCO$_3$, and extracted with EtOAc. The combined organic layers were then washed with brine, dried over Na$_2$SO$_4$, filtered, and concentrated in vacuo. The residue was purified on a silica gel column employing a gradient of 0-100% EtOAc in hexanes to afford Example 4.3 (370 mg, 1.67 mmol, 63%). LCMS-ESI (pos.) m/z: 222.2 (M+H)$^+$.

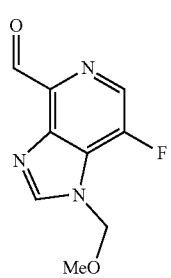

7-Fluoro-1-(methoxymethyl)-1H-imidazo[4,5-c]pyridine-4-carbaldehyde, Example 4.4. Osmium tetroxide (8.5 mg, 0.033 mmol) was added to a stirred solution of 4.3 (370 mg, 1.67 mmol) in ACN:water (4:1, 5 mL) at RT. After 10 min, sodium periodate (1073 mg, 5.02 mmol) was added and the mixture was stirred for 16 h at RT. Thereafter, the mixture was diluted with saturated aqueous NaHCO$_3$ and extracted with EtOAc. The combined organic layers were then washed with brine, dried over Na$_2$SO$_4$, filtered, and concentrated in vacuo. The residue was purified on a silica gel column employing a gradient of 0-100% EtOAc in hexanes to afford Example 4.4 (220 mg, 1.05 mmol, 63%). $^1$H NMR (400 MHz, CDCl$_3$) δ 10.25-10.40 (m, 1H) 8.37-8.51 (m, 1H) 8.21-8.33 (m, 1H) 5.62-5.73 (m, 2H) 3.24-3.37 (m, 3H).

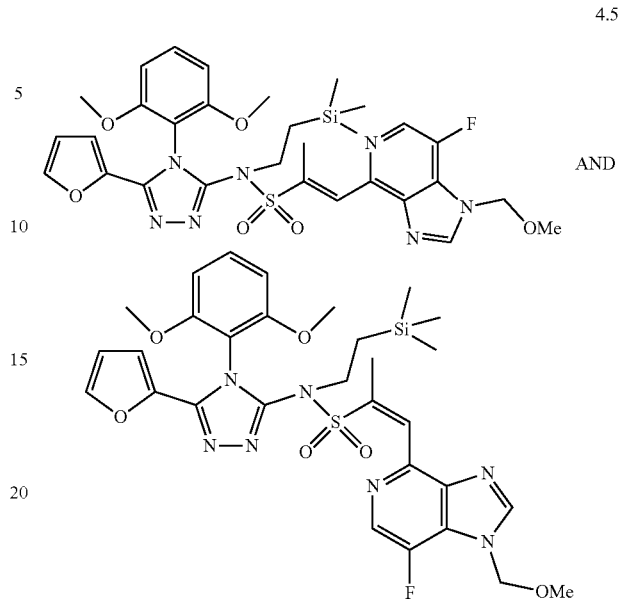

(E)-N-(4-(2,6-Dimethoxyphenyl)-5-(furan-2-yl)-4H-1,2,4-triazol-3-yl)-1-(7-fluoro-1-(methoxymethyl)-1H-imidazo[4,5-c]pyridin-4-yl)-N-(2-(trimethylsilyl)ethyl)prop-1-ene-2-sulfonamide and (Z)—N-(4-(2,6-dimethoxyphenyl)-5-(furan-2-yl)-4H-1,2,4-triazol-3-yl)-1-(7-fluoro-1-(methoxymethyl)-1H-imidazo[4,5-c]pyridin-4-yl)-N-(2-(trimethylsilyl)ethyl)prop-1-ene-2-sulfonamide, Example 4.5. Lithium bis(trimethylsilyl)amide (1.0 M solution in THF, 717 μL, 0.72 mmol) was added to a stirred solution of Example 366.0 (162 mg, 0.26 mmol) in THF at 0° C. After 10 min, a solution of 4.4 (50 mg, 0.24 mmol) in THF was added. The mixture was removed from the cooling bath and stirred for 16 h at RT after which LCMS analysis indicated that the reaction was complete. Thereafter, the mixture was diluted with 1N aqueous HCl and extracted with EtOAc. The combined organic layers were washed with brine, dried over Na$_2$SO$_4$, filtered, and concentrated in vacuo. The residue was purified on a silica gel column employing a gradient of 0-100% EtOAc in hexanes to afford Example 4.5 (75 mg, 0.11 mmol, 47%). LCMS-ESI (pos.) m/z: 670.2 (M+H)$^+$.

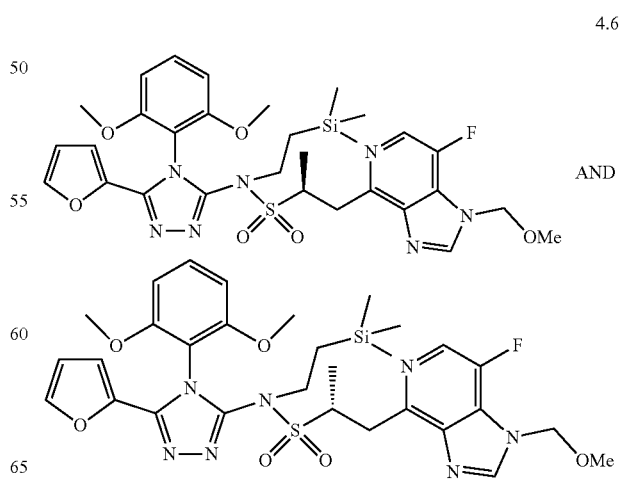

(2R)—N-(4-(2,6-Dimethoxyphenyl)-5-(furan-2-yl)-4H-1,2,4-triazol-3-yl)-1-(7-fluoro-1-(methoxymethyl)-1H-imidazo[4,5-c]pyridin-4-yl)-N-(2-(trimethylsilyl)ethyl)propane-2-sulfonamide and (2S)—N-(4-(2,6-dimethoxyphenyl)-5-(furan-2-yl)-4H-1,2,4-triazol-3-yl)-1-(7-fluoro-1-(methoxymethyl)-1H-imidazo[4,5-c]pyridin-4-yl)-N-(2-(trimethylsilyl)ethyl)propane-2-sulfonamide, Example 4.6. Example 4.5 (75 mg, 0.11 mmol) was dissolved in MeOH and the resulting solution was sparged with N₂ for 2 min before Pd/C (12 mg, 5% Pd dry basis, 50% water, wet paste) (commercially available from Alfa Aesar, Ward Hill, Mass., USA) was carefully added. Hydrogen was introduced at 1 atm (balloon) and the mixture was vigorously stirred until TLC analysis indicated that the reaction was complete (3 h). Thereafter, the mixture was flushed with N₂, filtered over Celite® brand filter aid taking care to keep the pad wet with solvent and concentrated in vacuo. The residue was purified on a silica gel column employing a gradient of 0-100% EtOAc in hexanes to afford Example 4.6 (62 mg, 0.092 mmol, 82%).

4.0

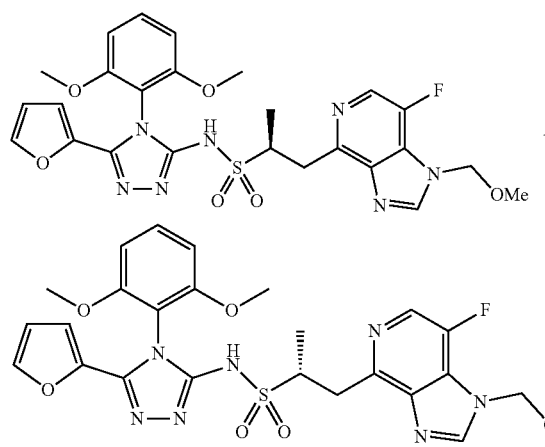

(2S)—N-(4-(2,6-dimethoxyphenyl)-5-(2-furanyl)-4H-1,2,4-triazol-3-yl)-1-(7-fluoro-1-(methoxymethyl)-1H-imidazo[4,5-c]pyridin-4-yl)-2-propanesulfonamide and (2R)—N-(4-(2,6-dimethoxyphenyl)-5-(2-furanyl)-4H-1,2,4-triazol-3-yl)-1-(7-fluoro-1-(methoxymethyl)-1H-imidazo[4,5-c]pyridin-4-yl)-2-propanesulfonamide, Example 4.0. Example 4.6 (62 mg, 0.092 mmol) was dissolved in DMF (0.5 mL). Tris(dimethylamino)sulfonium difluorotrimethylsilicate (commercially available from Sigma-Aldrich Corp., St. Louis, Mo., USA, 25 mg, 0.092 mmol) was added and the resulting mixture was stirred at 80° C. for 3 h. Thereafter, the mixture was cooled to RT and concentrated in vacuo. The residue was purified on a reverse-phase column employing a gradient of 10-80% ACN in water (0.1% TFA in both eluents) to afford Example 4.0 (53 mg, 0.077 mmol, 84%). ¹H NMR (400 MHz, CDCl₃) δ 8.44 (d, J=2.74 Hz, 1H) 8.26 (s, 1H) 7.54 (m, 1H) 7.28 (m, 1H) 7.14 (m, 1H) 6.72 (dd, J=8.61, 1.96 Hz, 1H) 6.36 (m, 1H) 6.05 (d, J=3.52 Hz, 1H) 5.19 (d, J=11.35 Hz, 2H) 3.84-4.03 (m, 2H) 3.79 (s, 3H) 3.78 (s, 3H) 3.57 (dd, J=15.26, 3.91 Hz, 1H) 3.30 (s, 3H) 1.55 (d, J=6.65 Hz, 3H). LCMS-ESI (pos.) m/z: 572.0 (M+H)⁺.

Example 5.0. Preparation of (2S)—N-(4-(2,6-dimethoxyphenyl)-5-(2-furanyl)-4H-1,2,4-triazol-3-yl)-1-(7-fluoro-1H-imidazo[4,5-c]pyridin-4-yl)-2-propanesulfonamide or (2R)—N-(4-(2,6-dimethoxyphenyl)-5-(2-furanyl)-4H-1,2,4-triazol-3-yl)-1-(7-fluoro-1H-imidazo[4,5-c]pyridin-4-yl)-2-propanesulfonamide 5.1

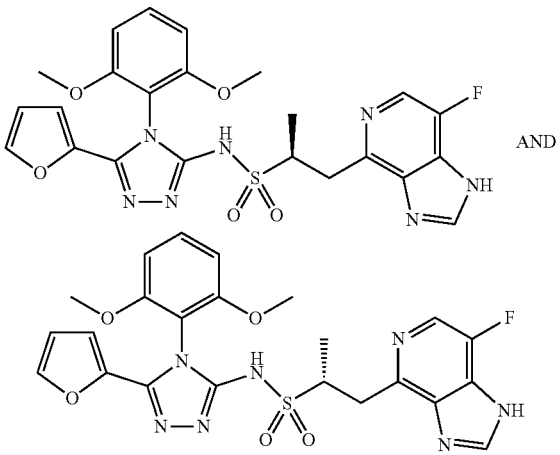

(2S)—N-(4-(2,6-Dimethoxyphenyl)-5-(2-furanyl)-4H-1,2,4-triazol-3-yl)-1-(7-fluoro-1H-imidazo[4,5-c]pyridin-4-yl)-2-propanesulfonamide and (2R)—N-(4-(2,6-dimethoxyphenyl)-5-(2-furanyl)-4H-1,2,4-triazol-3-yl)-1-(7-fluoro-1H-imidazo[4,5-c]pyridin-4-yl)-2-propanesulfonamide, Example 5.1. Example 4.0 (53 mg, 0.077 mmol) was dissolved in hydrochloric acid/dioxane (4M/dioxane, 2.3 mL, 0.077 mmol) and the mixture was stirred for 30 min at RT. Thereafter, the mixture was concentrated in vacuo to afford Example 5.1. LCMS-ESI (pos.) m/z: 528.2 (M+H)⁺.

5.0

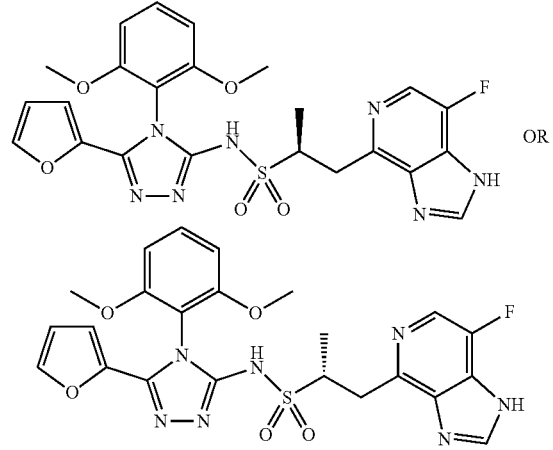

(2S)—N-(4-(2,6-Dimethoxyphenyl)-5-(2-furanyl)-4H-1,2,4-triazol-3-yl)-1-(7-fluoro-1H-imidazo[4,5-c]pyridin-4-yl)-2-propanesulfonamide or (2R)—N-(4-(2,6-dimethoxyphenyl)-5-(2-furanyl)-4H-1,2,4-triazol-3-yl)-1-(7-fluoro-1H-imidazo[4,5-c]pyridin-4-yl)-2-propanesulfonamide, Example 5.0. Purification of Example 5.1 by SFC [30×250 mm AD-H column with 39 g/min MeOH (20 mM NH$_3$) in 31 g/min CO$_2$ at 100 bar] afforded two enantiomers. The title compound Example 5.0 was the first isomer to elute under these conditions. $^1$H NMR (400 MHz, CD$_3$OD) δ 8.37 (s, 1H) 8.17 (d, J=2.15 Hz, 1H) 7.50-7.63 (m, 2H) 6.82 (dd, J=8.51, 2.64 Hz, 2H) 6.43 (dd, J=3.52, 1.76 Hz, 1H) 6.12 (d, J=3.52 Hz, 1H) 3.81 (dd, J=10.56, 6.46 Hz, 1H) 3.73 (d, J=1.96 Hz, 6H) 3.33 (m, 2H) 1.22 (m, 3H). LCMS-ESI (pos.) m/z: 528.1 (M+H)$^+$.

Example 6.0. Preparation of (2S)—N-(4-(2,6-dimethoxyphenyl)-5-(2-furanyl)-4H-1,2,4-triazol-3-yl)-1-(7-fluoro-1-methyl-1H-imidazo[4,5-c]pyridin-4-yl)-2-propanesulfonamide or (2R)—N-(4-(2,6-dimethoxyphenyl)-5-(2-furanyl)-4H-1,2,4-triazol-3-yl)-1-(7-fluoro-1-methyl-1H-imidazo[4,5-c]pyridin-4-yl)-2-propanesulfonamide

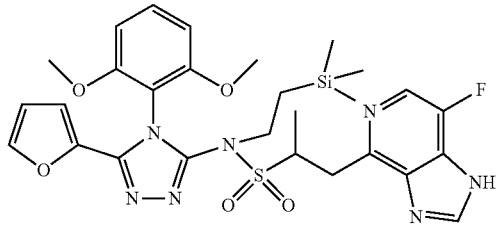

6.1

N-(4-(2,6-Dimethoxyphenyl)-5-(furan-2-yl)-4H-1,2,4-triazol-3-yl)-1-(7-fluoro-1H-imidazo[4,5-c]pyridin-4-yl)-N-(2-(trimethylsilyl)ethyl)propane-2-sulfonamide, Example 6.1. Boron trifluoride diethyl etherate (44 µL, 0.36 mmol) was added to a solution of 4.6 (80 mg, 0.12 mmol) in DCM and the mixture was stirred for 40 min at RT. Thereafter, the mixture was diluted with water and extracted with DCM. The organic extracts were then combined, dried over Na$_2$SO$_4$, filtered, and concentrated in vacuo to afford Example 6.1. LCMS-ESI (pos.) m/z: 628.2 (M+H)$^+$.

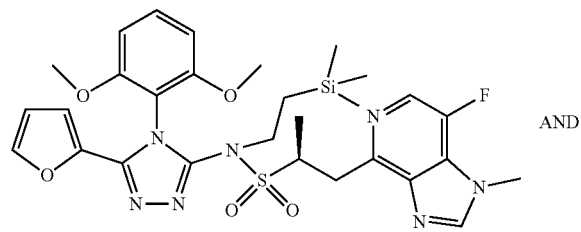

6.2

(2S)—N-(4-(2,6-Dimethoxyphenyl)-5-(furan-2-yl)-4H-1,2,4-triazol-3-yl)-1-(7-fluoro-1-methyl-1H-imidazo[4,5-c]pyridin-4-yl)-N-(2-(trimethylsilyl)ethyl)propane-2-sulfonamide and (2R)—N-(4-(2,6-dimethoxyphenyl)-5-(furan-2-yl)-4H-1,2,4-triazol-3-yl)-1-(7-fluoro-1-methyl-1H-imidazo[4,5-c]pyridin-4-yl)-N-(2-(trimethylsilyl)ethyl)propane-2-sulfonamide, Example 6.2. Potassium tert-butoxide (1.0 M in THF, 526 µL, 0.53 mmol) was added to a stirred solution of 6.1 (110 mg, 0.18 mmol) in THF. Iodomethane (11 µL, 0.18 mmol) was then added and the mixture was stirred for 16 h at RT. Thereafter, the mixture was diluted with 1 N aqueous HCl and extracted with EtOAc. The organic extracts were then combined, washed with brine, dried over Na$_2$SO$_4$, filtered, and concentrated in vacuo to afford 6.2 (101 mg, 0.16 mmol, 90%). LCMS-ESI (pos.) m/z: 642.3 (M+H)$^+$.

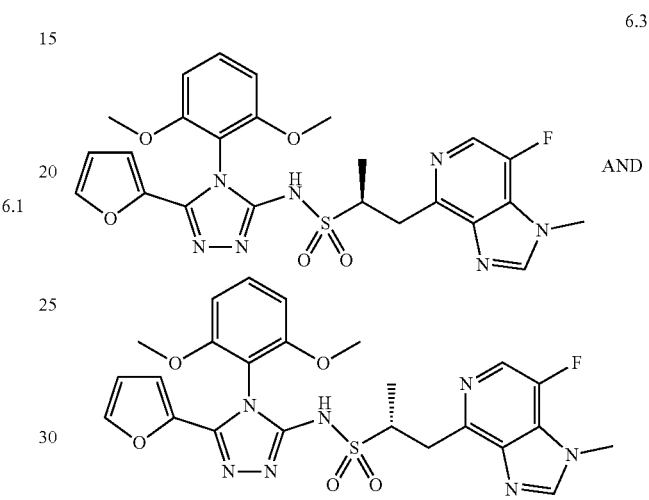

6.3

(2S)—N-(4-(2,6-Dimethoxyphenyl)-5-(2-furanyl)-4H-1,2,4-triazol-3-yl)-1-(7-fluoro-1-methyl-1H-imidazo[4,5-c]pyridin-4-yl)-2-propanesulfonamide and (2R)—N-(4-(2,6-dimethoxyphenyl)-5-(2-furanyl)-4H-1,2,4-triazol-3-yl)-1-(7-fluoro-1-methyl-1H-imidazo[4,5-c]pyridin-4-yl)-2-propanesulfonamide, Example 6.3. Example 6.2 (70 mg, 0.11 mmol) was dissolved in DMF (0.5 mL). Tris(dimethylamino)sulfonium difluorotrimethylsilicate (commercially available from Sigma-Aldrich Corp., St. Louis, Mo., USA) (30 mg, 0.11 mmol) was added and the resulting mixture was stirred at 65° C. for 72 h. Thereafter, the mixture was cooled to RT and concentrated in vacuo. The residue was purified on a reverse-phase column employing a gradient of 10-70% ACN in water (0.1% TFA in both eluents) to afford Example 6.3 (43 mg, 0.067 mmol, 61%). $^1$H NMR (400 MHz, CD$_3$OD) δ 8.52 (s, 1H) 8.46 (d, J=4.11 Hz, 1H) 7.51-7.62 (m, 2H) 6.83 (d, J=8.61 Hz, 2H) 6.42 (dd, J=3.52, 1.76 Hz, 1H) 6.11 (d, J=3.52 Hz, 1H) 4.16 (s, 3H) 3.91 (d, J=7.04 Hz, 1H) 3.77 (m, 1H) 3.76 (app s, 6H) 3.54 (dd, J=14.48, 7.43 Hz, 1H) 1.32 (d, J=6.65 Hz, 3H). LCMS-ESI (pos.) m/z: 542.1 (M+H)$^+$.

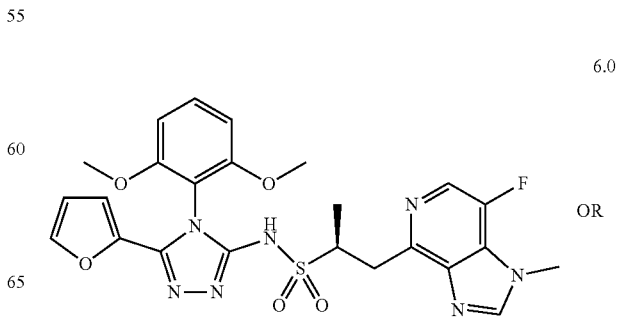

6.0

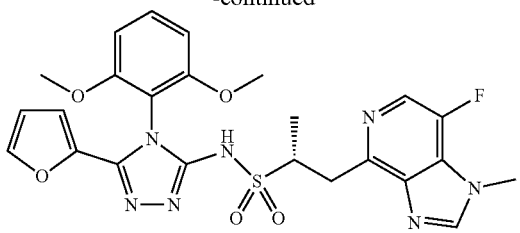

(2S)—N-(4-(2,6-Dimethoxyphenyl)-5-(2-furanyl)-4H-1,2,4-triazol-3-yl)-1-(7-fluoro-1-methyl-1H-imidazo[4,5-c]pyridin-4-yl)-2-propanesulfonamide or (2R)—N-(4-(2,6-dimethoxyphenyl)-5-(2-furanyl)-4H-1,2,4-triazol-3-yl)-1-(7-fluoro-1-methyl-1H-imidazo[4,5-c]pyridin-4-yl)-2-propanesulfonamide, Example 6.0. Purification of 6.3 by SFC [30×400 mm AD column with 35 g/min MeOH (20 mM NH$_3$) in 65 g/min CO$_2$ at 100 bar] afforded two enantiomers. The title compound Example 6.0 was the first isomer to elute under these conditions. $^1$H NMR (400 MHz, CDCl$_3$) δ 8.20 (d, J=2.35 Hz, 1H) 7.87 (s, 1H) 7.40-7.49 (m, 2H) 6.66 (d, J=8.61 Hz, 2H) 6.32 (dd, J=3.62, 1.86 Hz, 1H) 5.96-6.00 (m, 1H) 4.04 (s, 3H) 3.87-3.95 (m, 1H) 3.79-3.87 (m, 1H) 3.77 (s, 3H) 3.72 (s, 3H) 3.28-3.40 (m, 1H) 1.31 (d, J=6.85 Hz, 3H). LCMS-ESI (pos.) m/z: 542.2 (M+H)$^+$.

Example 7.0. Preparation of (2S)—N-(4-(4,6-dimethoxy-5-pyrimidinyl)-5-(5-methyl-2-furanyl)-4H-1,2,4-triazol-3-yl)-1-(5-fluoro-2-pyrimidinyl)-2-propanesulfonamide and (2R)—N-(4-(4,6-dimethoxy-5-pyrimidinyl)-5-(5-methyl-2-furanyl)-4H-1,2,4-triazol-3-yl)-1-(5-fluoro-2-pyrimidinyl)-2-propanesulfonamide 7.0

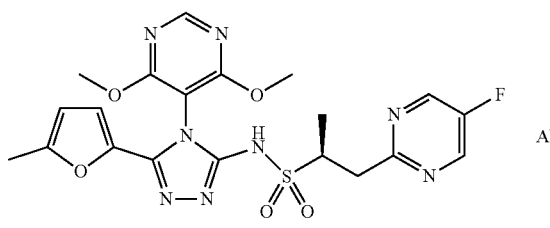

AND

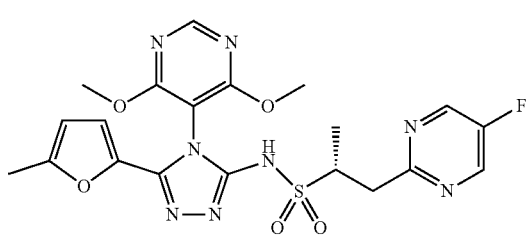

(2S)—N-(4-(4,6-Dimethoxy-5-pyrimidinyl)-5-(5-methyl-2-furanyl)-4H-1,2,4-triazol-3-yl)-1-(5-fluoro-2-pyrimidinyl)-2-propanesulfonamide and (2R)—N-(4-(4,6-dimethoxy-5-pyrimidinyl)-5-(5-methyl-2-furanyl)-4H-1,2,4-triazol-3-yl)-1-(5-fluoro-2-pyrimidinyl)-2-propanesulfonamide, Example 7.0. The title compound was prepared employing 5-methyl-2-furohydrazide (commercially available from Chembridge Corporation, San Diego, Calif., USA), Example 372.1, and Example 353.0 and the procedure described in the synthesis of Example 314.0 employing AcOH instead of TFA. $^1$H NMR (400 MHz, CDCl$_3$) δ 8.52 (d, J=0.98 Hz, 2H) 6.26 (d, J=3.52 Hz, 1H) 6.03 (d, J=3.52 Hz, 1H) 3.98 (s, 3H) 3.96 (s, 3H) 3.81 (ddd, J=9.44, 6.80, 4.69 Hz, 1H) 3.69 (dd, J=14.67, 4.69 Hz, 1H) 3.09 (dd, J=14.87, 9.59 Hz, 1H) 1.33 (d, J=7.62 Hz, 3H). LCMS-ESI (pos.) m/z: 505.0 (M+H)$^+$.

Example 8.0. Preparation of (2S)—N-(4-(2,6-dimethoxyphenyl)-5-(2-furanyl)-4H-1,2,4-triazol-3-yl)-1-(7-fluoro-1H-imidazo[4,5-c]pyridin-4-yl)-2-propanesulfonamide or (2R)—N-(4-(2,6-dimethoxyphenyl)-5-(2-furanyl)-4H-1,2,4-triazol-3-yl)-1-(7-fluoro-1H-imidazo[4,5-c]pyridin-4-yl)-2-propanesulfonamide 8.0

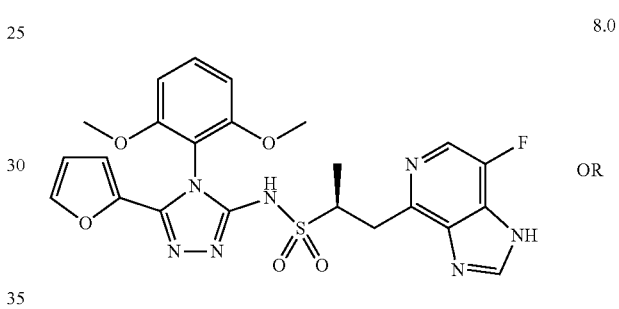

(2S)—N-(4-(2,6-Dimethoxyphenyl)-5-(2-furanyl)-4H-1,2,4-triazol-3-yl)-1-(7-fluoro-1H-imidazo[4,5-c]pyridin-4-yl)-2-propanesulfonamide or (2R)—N-(4-(2,6-dimethoxyphenyl)-5-(2-furanyl)-4H-1,2,4-triazol-3-yl)-1-(7-fluoro-1H-imidazo[4,5-c]pyridin-4-yl)-2-propanesulfonamide, Example 8.0. Further purification of 5.1 by SFC [30×250 mm AD-H column with 39 g/min MeOH (20 mM NH$_3$) in 31 g/min CO$_2$ at 100 bar] afforded the second enantiomer. The title compound, Example 8.0, was the second isomer to elute under these conditions. $^1$H NMR (400 MHz, CD$_3$OD) δ 1.22 (m, 3H) 3.33 (m, 2H) 3.73 (d, J=1.96 Hz, 6H) 3.81 (dd, J=10.56, 6.46 Hz, 1H) 6.12 (d, J=3.52 Hz, 1H) 6.43 (dd, J=3.52, 1.76 Hz, 1H) 6.82 (dd, J=8.51, 2.64 Hz, 2H) 7.50-7.63 (m, 2H) 8.17 (d, J=2.15 Hz, 1H) 8.37 (s, 1H). LCMS ESI (pos.) m/z: 528.1 (M+H)$^+$.

Example 9.0. Preparation of N-(5-chloro-2-((2R)-2-((4-(2,6-dimethoxyphenyl)-5-(2-furanyl)-4H-1,2,4-triazol-3-yl)sulfamoyl)propyl)-3-pyridinyl)acetamide or N-(5-chloro-2-((2S)-2-((4-(2,6-dimethoxyphenyl)-5-(2-furanyl)-4H-1,2,4-triazol-3-yl)sulfamoyl)propyl)-3-pyridinyl)acetamide

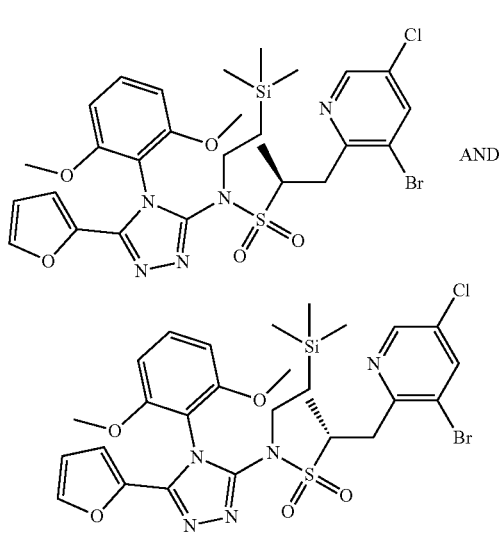

9.1

(S)-1-(3-Bromo-5-chloropyridin-2-yl)-N-(4-(2,6-dimethoxyphenyl)-5-(furan-2-yl)-4H-1,2,4-triazol-3-yl)-N-(2-(trimethylsilyl)ethyl)propane-2-sulfonamide and (R)-1-(3-bromo-5-chloropyridin-2-yl)-N-(4-(2,6-dimethoxyphenyl)-5-(furan-2-yl)-4H-1,2,4-triazol-3-yl)-N-(2-(trimethylsilyl)ethyl)propane-2-sulfonamide, Example 9.1. To a solution of Example 366.0 (1.15 g, 1.871 mmol) in THF (5 mL) was added lithium bis(trimethylsilyl)amide, (1.0 M solution in THF, 2.2 mL, 2.20 mmol). After 15 min, 3-bromo-5-chloropicolinaldehyde (470 mg, 2.132 mmol) was added as a solution in THF (1 mL). The resulting reaction was stirred at RT overnight. The reaction was then quenched with water (0.5 mL), concentrated to dryness and dried under vacuum. The initial material was absorbed onto a plug of silica gel and purified by chromatography through a Redi-Sep pre-packed silica gel column eluting with a gradient of 0% to 100% EtOAc in hexanes. The two isolated isomers were combined and concentrated in vacuo to yield (E/Z)-1-(3-bromo-5-chloropyridin-2-yl)-N-(4-(2,6-dimethoxyphenyl)-5-(furan-2-yl)-4H-1,2,4-triazol-3-yl)-N-(2-(trimethylsilyl)ethyl)prop-1-ene-2-sulfonamide (726 mg). To a solution of the olefin intermediate in EtOH (5 mL) was added Raney 2800 nickel slurry in water (0.2 mL, 1.87 mmol). Hydrogen was then bubbled through the mixture for 1 min and then the mixture was stirred at RT under a hydrogen atmosphere for 8 h. The hydrogen balloon was then removed and the reaction was purged with nitrogen and left to stand overnight. The reaction was redissolved in DCM (2 mL) and the reaction was reinitiated by addition of more Raney 2800 nickel slurry in water (0.2 mL, 1.871 mmol). Hydrogen was then bubbled through the solution for 1 min and then the mixture was stirred at RT under a hydrogen atmosphere for 8 h. More Raney 2800 nickel slurry in water (0.2 mL, 1.871 mmol) was added, and the reaction was placed under an atmosphere of hydrogen and stirred for a further 3 h. The initial reaction mixture was then filtered through a plug of Celite® brand filter aid, the filter was rinsed with MeOH and DCM, and the filtrate was then concentrated to dryness. The initial material was absorbed onto a plug of silica gel and purified by chromatography through a Redi-Sep pre-packed silica gel column eluting with a gradient of 0% to 100% EtOAc in hexanes to provide the title compound (584 mg, 0.86 mmol, 46% yield) as a yellow foam. LCMS-ESI (pos.) m/z: 682.0 (M+H)$^+$.

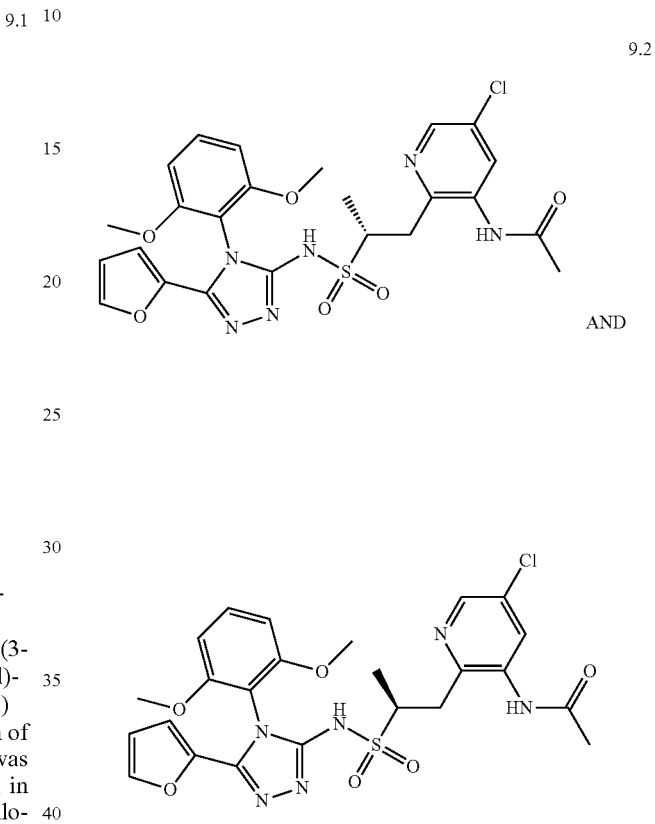

9.2

N-(5-Chloro-2-((2R)-2-((4-(2,6-dimethoxyphenyl)-5-(2-furanyl)-4H-1,2,4-triazol-3-yl)sulfamoyl)propyl)-3-pyridinyl)acetamide and N-(5-chloro-2-((2S)-2-((4-(2,6-dimethoxyphenyl)-5-(2-furanyl)-4H-1,2,4-triazol-3-yl)sulfamoyl)propyl)-3-pyridinyl)acetamide, Example 9.2. 1-(3-Bromo-5-chloropyridin-2-yl)-N-(4-(2,6-dimethoxyphenyl)-5-(furan-2-yl)-4H-1,2,4-triazol-3-yl)propane-2-sulfonamide (91 mg, 0.16 mmol) was combined with XantPhos (26 mg, 0.044 mmol), acetamide (33 mg, 0.56 mmol), cesium carbonate (103 mg, 0.32 mmol), and Pd$_2$(dba)$_3$ (23 mg, 0.025 mmol) in a 10 mL microwave vial. Dioxane (0.5 mL) was then added. The mixture was heated in a microwave for 30 min at 120° C. under argon. The reaction was then filtered through a syringe filter, rinsed with DCM and MeOH, and then concentrated in vacuo. The material was purified by reverse-phase preparative HPLC using an Agilent SB C18 column, 0.1% TFA in ACN/H$_2$O, gradient 10% to 60% over 25 min. The desired fractions were combined to give the title compound (52 mg, 0.092 mmol, 60% yield). $^1$H NMR (500 MHz, CDCl$_3$) δ 1.48 (d, J=6.60 Hz, 3H), 2.14 (s, 3H), 3.18 (dd, J=14.92, 3.67 Hz, 1H), 3.32-3.41 (m, 1H) 3.44 (dt, J=6.85, 3.42 Hz, 1H), 3.72 (d, J=4.16 Hz, 6H), 5.95 (d, J=3.67 Hz, 1H), 6.33 (dd, J=3.55, 1.83 Hz, 1H), 6.67 (t, J=8.07 Hz, 2H), 7.40-7.48 (m, 1H), 7.52 (t, J=8.56 Hz, 1H), 8.34 (d, J=2.20 Hz, 1H), 8.60 (d, J=1.96 Hz, 1H), 9.13 (s, 1H). LCMS ESI (pos.) m/z: 561.1 (M+H)$^+$.

9.0

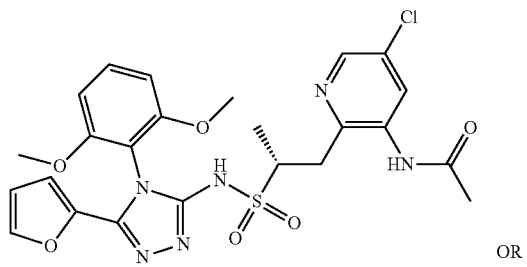

OR

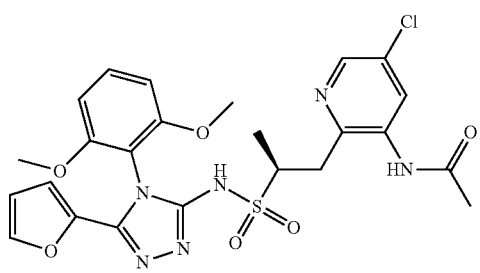

N-(5-Chloro-2-((2R)-2-((4-(2,6-dimethoxyphenyl)-5-(2-furanyl)-4H-1,2,4-triazol-3-yl)sulfamoyl)propyl)-3-pyridinyl)acetamide or N-(5-chloro-2-((2S)-2-((4-(2,6-dimethoxyphenyl)-5-(2-furanyl)-4H-1,2,4-triazol-3-yl)sulfamoyl)propyl)-3-pyridinyl)acetamide, Example 9.0. The enantiomers in Example 9.2 were separated on an AD-H column (2×15 cm) eluting with 35% MeOH/CO$_2$ (with 20 mM NH$_3$), 100 bar, 65 mL/min. The first peak to elute on the AD column was Example 9.0 (13 mg, 0.023 mmol, 15% yield). $^1$H NMR (500 MHz, CDCl$_3$) δ 1.45 (d, J=6.85 Hz, 3H) 2.10 (s, 3H) 2.99 (dd, J=14.67, 4.40 Hz, 1H) 3.24-3.35 (m, 1H) 3.36-3.45 (m, 1H) 3.71 (d, J=7.34 Hz, 6H) 5.93 (d, J=3.42 Hz, 1H) 6.33 (d, J=1.96 Hz, 1H) 6.66 (dd, J=11.86, 8.44 Hz, 2H) 7.46 (d, J=1.22 Hz, 1H) 7.51 (t, J=8.44 Hz, 1H) 8.16 (d, J=2.20 Hz, 1H) 8.24 (d, J=1.71 Hz, 1H) 8.64 (br. s., 1H). LCMS ESI (pos.) m/z: 561.1 (M+H)$^+$.

Example 10.0. Preparation of (1S,2S)-1-(5-cyano-2-pyridinyl)-N-(4-(2,6-dimethoxyphenyl)-5-(5-methyl-2-furanyl)-4H-1,2,4-triazol-3-yl)-1-hydroxy-2-propanesulfonamide or (1R,2R)-1-(5-cyano-2-pyridinyl)-N-(4-(2,6-dimethoxyphenyl)-5-(5-methyl-2-furanyl)-4H-1,2,4-triazol-3-yl)-1-hydroxy-2-propanesulfonamide 10.1

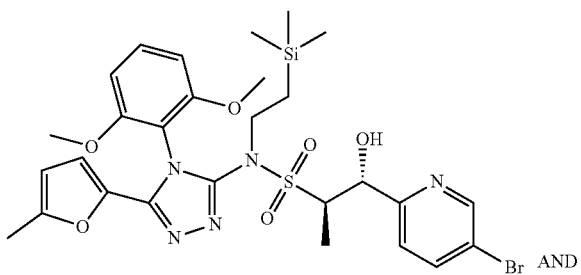

AND

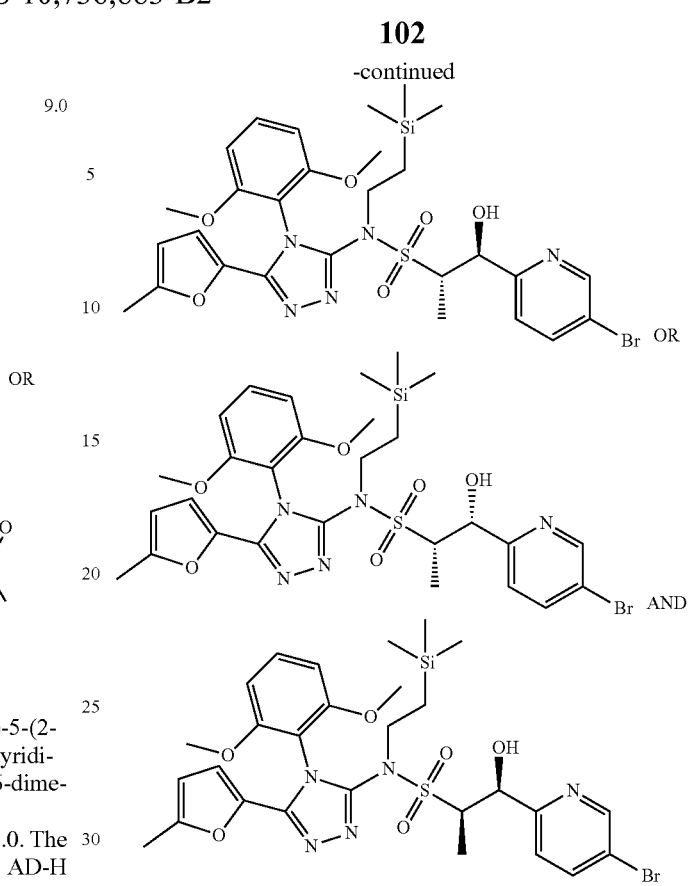

(1R,2S)-1-(5-Bromopyridin-2-yl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide and (1S,2R)-1-(5-bromopyridin-2-yl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide or (1R,2R)-1-(5-bromopyridin-2-yl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide and (1S,2S)-1-(5-bromopyridin-2-yl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide, Example 10.1. To a stirred solution of N-(4-(2,6-dimethoxyphenyl)-5-(5-methylfuran-2-yl)-4H-1,2,4-triazol-3-yl)-N-(2-(trimethylsilyl)ethyl)ethanesulfonamide (Example 369.0, 403 mg, 0.82 mmol) in THF (3 mL) at −78° C. was added n-butyllithium (1.6 M solution in hexanes, 500 µL, 0.80 mmol) dropwise over 10 min. A solution of 5-bromopicolinaldehyde (183 mg, 0.984 mmol, Aldrich) in THF (1 mL) was then added dropwise over 5 min. The cooling bath was removed, and the reaction was warmed to RT overnight. The reaction was then quenched with a saturated aqueous NH$_4$Cl solution and extracted twice with EtOAc. The organic layer was washed with brine and then concentrated in vacuo. The initial material was purified by reverse-phase preparative HPLC using an Agilent SB C8 column, 0.1% TFA in ACN/H$_2$O, gradient 40% to 95% over 25 min. The desired fractions were lyophilized to give two fractions (syn and anti stereochemistry), the initial fraction from the column (81 mg, 0.12 mmol) and the second eluting fraction, the title compound Example 10.1 (130 mg, 0.192 mmol, 23%).

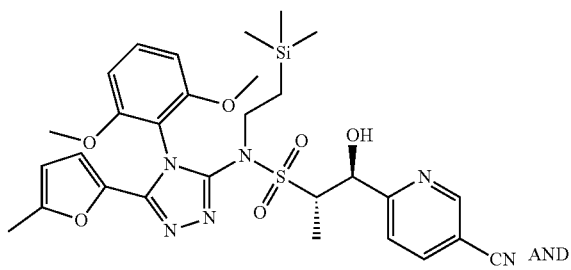

10.2

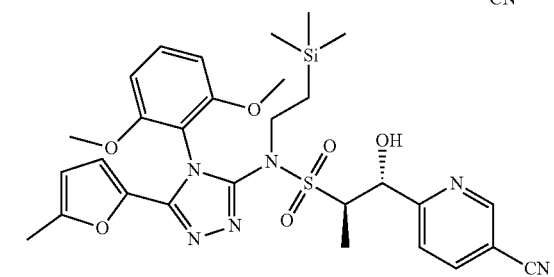

(1R,2R)-1-(5-Cyanopyridin-2-yl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide and (1S,2S)-1-(5-cyanopyridin-2-yl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide, Example 10.2. To a solution of 10.1 (130 mg, 0.16 mmol) in DMF (2 mL) was added tetrakis(triphenylphosphine)palladium(0) (46.3 mg, 0.040 mmol) and zinc cyanide (31.3 mg, 0.27 mmol). The resulting mixture was heated in a microwave for 60 min at 120° C. under argon. The material was then filtered through a syringe filter and then purified by reverse-phase preparative HPLC using an Agilent SB C8 column, 0.1% TFA in ACN/H$_2$O, gradient 30% to 95% over 25 min. The desired fraction was lyophilized overnight to give the title compound Example 10.2 (44.3 mg, 0.071 mmol, 43% yield).

10.3

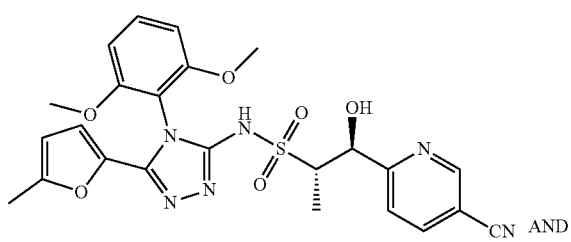

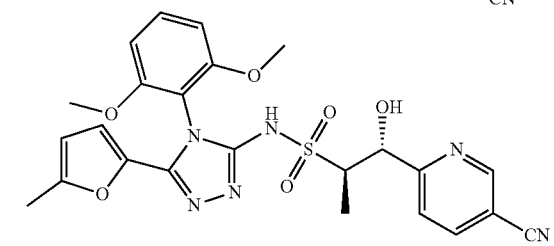

(1S,2S)-1-(5-Cyano-2-pyridinyl)-N-(4-(2,6-dimethoxyphenyl)-5-(5-methyl-2-furanyl)-4H-1,2,4-triazol-3-yl)-1-hydroxy-2-propanesulfonamide and (1R,2R)-1-(5-cyano-2-pyridinyl)-N-(4-(2,6-dimethoxyphenyl)-5-(5-methyl-2-furanyl)-4H-1,2,4-triazol-3-yl)-1-hydroxy-2-propanesulfonamide, Example 10.3. To a solution of 10.2 (44.3 mg, 0.060 mmol) in DMF (1 mL) was added tris(dimethylamino)sulfonium difluorotrimethylsilicate (80 mg, 0.290 mmol). The resulting solution was heated at 60° C. for 2 h under argon. The initial material was purified by reverse-phase preparative HPLC using an Agilent SB C8 column, 0.1% TFA in ACN/H$_2$O, gradient 20% to 60% over 25 min. The desired fraction was lyophilized overnight to give Example 10.3 (9.2 mg, 0.014 mmol, 24.03% yield).

10.0

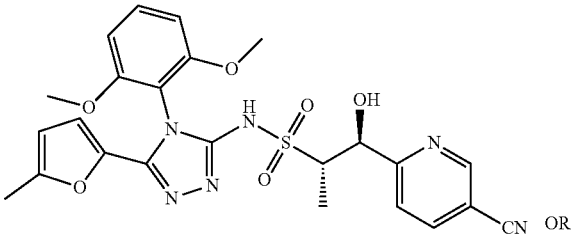

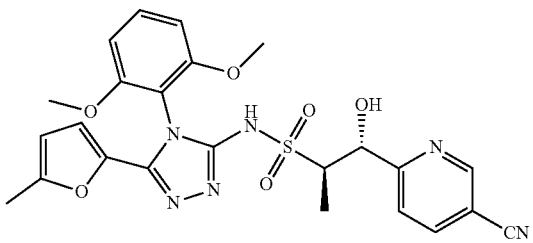

(1S,2S)-1-(5-Cyano-2-pyridinyl)-N-(4-(2,6-dimethoxyphenyl)-5-(5-methyl-2-furanyl)-4H-1,2,4-triazol-3-yl)-1-hydroxy-2-propanesulfonamide and (1R,2R)-1-(5-cyano-2-pyridinyl)-N-(4-(2,6-dimethoxyphenyl)-5-(5-methyl-2-furanyl)-4H-1,2,4-triazol-3-yl)-1-hydroxy-2-propanesulfonamide, Example 10.0. Chiral separation of Example 10.3 was performed using an IA column eluting with 25% MeOH/CO$_2$, 100 bar, 80 mL/min. The first peak to elute on the IA column was the title compound, Example 10.0 (3.76 mg, 7.17 µmol, 12%) $^1$H NMR (400 MHz, CD$_3$OD) δ 1.08 (d, J=7.04 Hz, 3H) 2.26 (s, 3H) 3.63-3.72 (m, 1H) 3.76 (d, J=6.26 Hz, 6H) 5.41 (s, 1H) 5.96 (d, J=3.33 Hz, 1H) 6.02 (d, J=2.35 Hz, 1H) 6.85 (dd, J=8.51, 2.84 Hz, 2H) 7.56 (t, J=8.51 Hz, 1H) 7.73 (d, J=8.22 Hz, 1H) 8.16 (dd, J=8.22, 2.15 Hz, 1H) 8.85 (d, J=1.37 Hz, 1H). LCMS ESI (pos.) m/z: 525.1 (M+H)$^+$.

Example 11.0. Preparation of (2R)-1-(5-chloro-2-pyridinyl)-N-(4-(2,6-dimethoxyphenyl)-5-(2-furanyl)-4H-1,2,4-triazol-3-yl)-2-propanesulfonamide or (2S)-1-(5-chloro-2-pyridinyl)-N-(4-(2,6-dimethoxyphenyl)-5-(2-furanyl)-4H-1,2,4-triazol-3-yl)-2-propanesulfonamide Example 12.0. Preparation of (2R)-1-(5-cyano-2-pyridinyl)-N-(4-(2,6-dimethoxyphenyl)-5-(5-methyl-2-furanyl)-4H-1,2,4-triazol-3-yl)-2-propanesulfonamide or (2S)-1-(5-cyano-2-pyridinyl)-N-(4-(2,6-dimethoxyphenyl)-5-(5-methyl-2-furanyl)-4H-1,2,4-triazol-3-yl)-2-propanesulfonamide

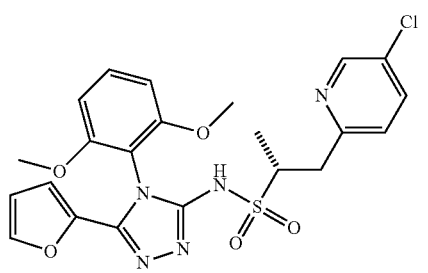

11.0

OR

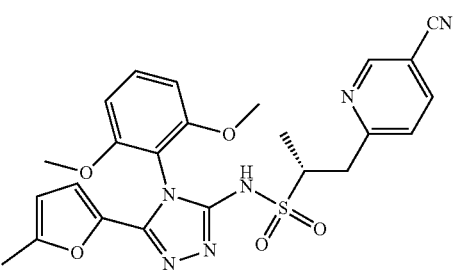

12.1

AND

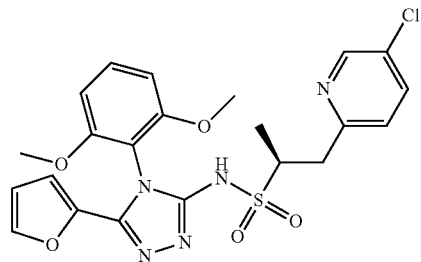

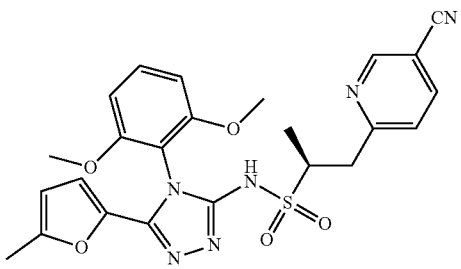

(2R)-1-(5-Chloro-2-pyridinyl)-N-(4-(2,6-dimethoxyphenyl)-5-(2-furanyl)-4H-1,2,4-triazol-3-yl)-2-propanesulfonamide and (2S)-1-(5-chloro-2-pyridinyl)-N-(4-(2,6-dimethoxyphenyl)-5-(2-furanyl)-4H-1,2,4-triazol-3-yl)-2-propanesulfonamide, Example 11.0. Following the procedures described in Examples 4.5, 4.6, and 4.0 employing 5-chloropicolinaldehyde (85 mg, 0.600 mmol) delivered the title compound as a racemic mixture. The first peak to separate on the AD-H column eluted with 20% IPA/80% hexanes isocratic for 45 mins was isolated to give Example 11.0 (19.3 mg, 0.038 mmol, 25.3% yield). $^1$H NMR (500 MHz, CDCl$_3$) δ 1.26 (d, J=6.60 Hz, 3H) 2.85 (dd, J=13.69, 10.03 Hz, 1H) 3.43-3.66 (m, 2H) 3.74 (d, J=5.62 Hz, 6H) 5.99 (d, J=3.18 Hz, 1H) 6.33 (d, J=1.47 Hz, 1H) 6.67 (d, J=8.31 Hz, 2H) 7.12 (d, J=8.31 Hz, 1H) 7.39-7.50 (m, 2H) 7.57 (dd, J=8.07, 1.96 Hz, 1H) 8.48 (br. s., 1H) 11.06 (br. s., 1H). LCMS ESI (pos.) m/z: 504.1 (M+H)$^+$.

(2R)-1-(5-Cyano-2-pyridinyl)-N-(4-(2,6-dimethoxyphenyl)-5-(5-methyl-2-furanyl)-4H-1,2,4-triazol-3-yl)-2-propanesulfonamide and (2S)-1-(5-cyano-2-pyridinyl)-N-(4-(2,6-dimethoxyphenyl)-5-(5-methyl-2-furanyl)-4H-1,2,4-triazol-3-yl)-2-propanesulfonamide, Example 12.1. To a solution of 1-(5-bromopyridin-2-yl)-N-(4-(2,6-dimethoxyphenyl)-5-(5-methylfuran-2-yl)-4H-1,2,4-triazol-3-yl)propane-2-sulfonamide (prepared using Example 367.0 and an analagous sulfonyl chloride prepared in a similar manner to that described in the preparation of 353.2 employing potassium (E)-propenyl-1-trifluoroborate (3.22 g, 21.8 mmol) and 2,5-dibromopyridine (4.75 g, 20.1 mmol) to prepare the requisite alkene) (104 mg, 0.184 mmol) in DMF (1.5 mL), was added tetrakis(triphenylphosphine)palladium(0) (62 mg, 0.054 mmol) and zinc cyanide (36 mg, 0.31 mmol). Argon was then bubbled through the mixture for one min and then the microwave vial was sealed. The resulting mixture was heated in a microwave for 1 h at 120° C. under argon. The reaction was then filtered and rinsed with MeOH and then concentrated in vacuo. The material thus obtained was purified by reverse-phase preparative HPLC using an Agilent SB C8 column, 0.1% TFA in ACN/H$_2$O, gradient 10% to 70% over 25 min. The desired fraction was lyophilized to give Example 12.1 (35.6 mg, 0.070 mmol, 38.0% yield).

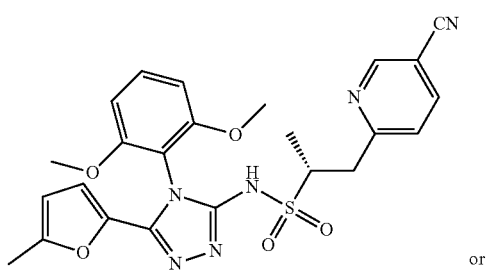

12.0 or

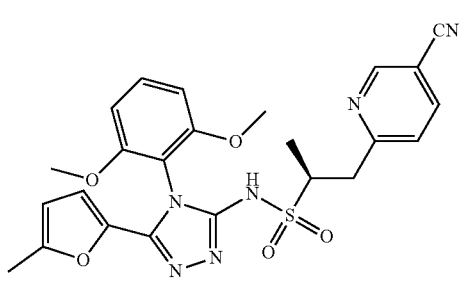

(2R)-1-(5-Cyano-2-pyridinyl)-N-(4-(2,6-dimethoxyphenyl)-5-(5-methyl-2-furanyl)-4H-1,2,4-triazol-3-yl)-2-propanesulfonamide or (2S)-1-(5-cyano-2-pyridinyl)-N-(4-(2,6-dimethoxyphenyl)-5-(5-methyl-2-furanyl)-4H-1,2,4-triazol-3-yl)-2-propanesulfonamide, Example 12.1. Chiral separation was performed using an IA column eluting with 25% MeOH/CO$_2$, 100 bar, 60 mL/min. The first peak to elute on the IA column gave the title compound Example 12.0 (7.6 mg, 0.015 mmol, 8.11% yield). $^1$H NMR (500 MHz, CDCl$_3$) 1.28 (d, J=6.85 Hz, 3H) 2.32 (s, 3H) 2.96 (dd, J=14.06, 9.17 Hz, 1H) 3.54-3.61 (m, 1H) 3.62-3.68 (m, 1H) 3.74 (d, J=3.91 Hz, 6H) 5.80 (d, J=3.42 Hz, 1H) 5.91 (dd, J=3.42, 0.73 Hz, 1H) 6.67 (d, J=8.56 Hz, 2H) 7.30 (d, J=8.07 Hz, 1H) 7.47 (t, J=8.56 Hz, 1H) 7.85 (dd, J=8.07, 1.96 Hz, 1H) 8.79 (d, J=1.71 Hz, 1H) 10.91 (br. s., 1H). LCMS ESI (pos.) m/z: 509.1 (M+H)$^+$.

Example 13.0. Preparation of N-(5-chloro-2-((2S)-2-((4-(2,6-dimethoxyphenyl)-5-(2-furanyl)-4H-1,2,4-triazol-3-yl)sulfamoyl)propyl)-3-pyridinyl)acetamide and N-(5-chloro-2-((2R)-2-((4-(2,6-dimethoxyphenyl)-5-(2-furanyl)-4H-1,2,4-triazol-3-yl)sulfamoyl)propyl)-3-pyridinyl)acetamide

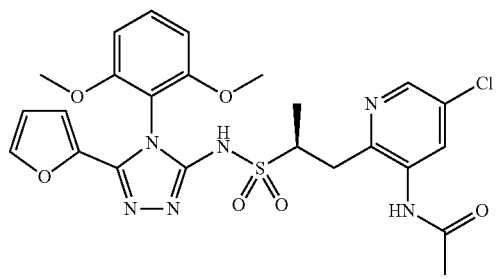

13.0

AND

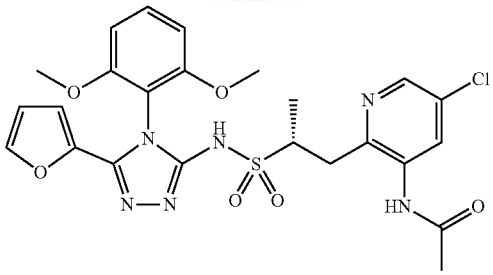

N-(5-Chloro-2-((2S)-2-((4-(2,6-dimethoxyphenyl)-5-(2-furanyl)-4H-1,2,4-triazol-3-yl)sulfamoyl)propyl)-3-pyridinyl)acetamide and N-(5-chloro-2-((2R)-2-((4-(2,6-dimethoxyphenyl)-5-(2-furanyl)-4H-1,2,4-triazol-3-yl)sulfamoyl)propyl)-3-pyridinyl)acetamide, Example 13.0. The title compound is described in Example 9.2 in the preparation of 9.0. $^1$H NMR (500 MHz, CDCl$_3$) δ 9.13 (s, 1H) 8.60 (d, J=1.96 Hz, 1H) 8.34 (d, J=2.20 Hz, 1H) 7.52 (t, J=8.56 Hz, 1H) 7.40-7.48 (m, 1H) 6.67 (t, J=8.07 Hz, 2H) 6.33 (dd, J=3.55, 1.83 Hz, 1H) 5.95 (d, J=3.67 Hz, 1H) 3.72 (d, J=4.16 Hz, 6H) 3.44 (dt, J=6.85, 3.42 Hz, 1H) 3.32-3.41 (m, 1H) 3.18 (dd, J=14.92, 3.67 Hz, 1H) 2.14 (s, 3H) 1.48 (d, J=6.60 Hz, 3H). LCMS-ESI (pos.) m/z: 561.0 (M+H)$^+$.

Example 14.0. Preparation of (2R)-1-(5-chloro-2-pyridinyl)-N-(4-(2,6-dimethoxyphenyl)-5-(2-furanyl)-4H-1,2,4-triazol-3-yl)-2-propanesulfonamide and (2S)-1-(5-chloro-2-pyridinyl)-N-(4-(2,6-dimethoxyphenyl)-5-(2-furanyl)-4H-1,2,4-triazol-3-yl)-2-propanesulfonamide

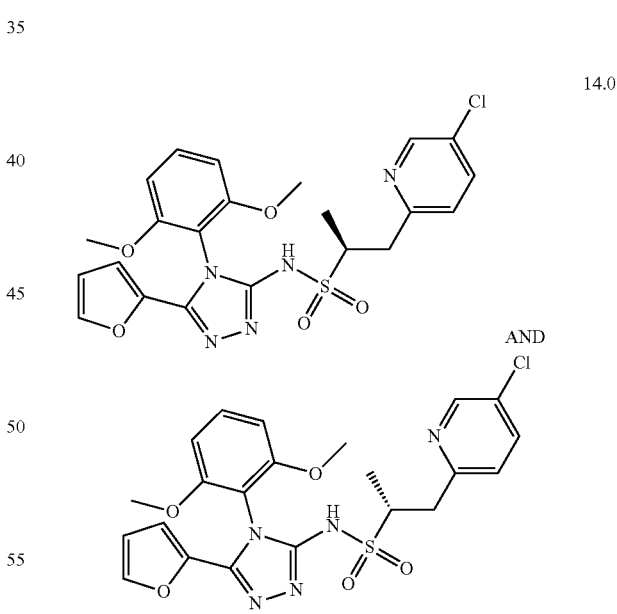

14.0

AND (2R)-1-(5-Chloro-2-pyridinyl)-N-(4-(2,6-dimethoxyphenyl)-5-(2-furanyl)-4H-1,2,4-triazol-3-yl)-2-propanesulfonamide and (2S)-1-(5-chloro-2-pyridinyl)-N-(4-(2,6-dimethoxyphenyl)-5-(2-furanyl)-4H-1,2,4-triazol-3-yl)-2-propanesulfonamide. To a solution of 1-(5-chloropyridin-2-yl)-N-(4-(2,6-dimethoxyphenyl)-5-(furan-2-yl)-4H-1,2,4-triazol-3-yl)-N-(2-(trimethylsilyl)ethyl)propane-2-sulfonamide (prepared in an analogous fashion using reactions described in Examples 4.5 and 4.6 employing Example 365.0 and 5-chloropicolinaldehyde (85 mg, 0.60 mmol) (92 mg, 0.152 mmol)) in DMF (0.5 mL) was added tris(dimethylamino)sulfonium difluorotrimethylsilicate (95 mg, 0.345 mmol). The resulting solution was heated at 60° C. for over 4 h. The reaction mixture was then cooled to RT. The material was purified by reverse-phase preparative HPLC using an Agilent SB C8 column, 0.1% TFA in ACN/H$_2$O, gradient 10% to 70% over 25 min (collected the peaks that were visible at 220 nm). The desired fraction were lyophilized overnight to give the title compound Example 14.0. $^1$H NMR (400 MHz, CDCl$_3$) δ 1.35 (d, J=6.85 Hz, 3H) 3.12 (dd, J=14.28, 6.85 Hz, 1H) 3.41-3.61 (m, 2H) 3.75 (d, J=5.67 Hz, 6H) 6.01 (dd, J=3.52, 0.59 Hz, 1H) 6.34 (dd, J=3.52, 1.76 Hz, 1H) 6.68 (dd, J=8.51, 2.64 Hz, 2H) 7.37-7.54 (m, 3H) 7.79 (dd, J=8.41, 2.35 Hz, 1H) 8.62 (d, J=2.35 Hz, 1H). LCMS ESI (pos.) m/z: 504.1 (M+H)$^+$.

Example 15.0. Preparation of N-(2-((2R)-2-((4-(2,6-dimethoxyphenyl)-5-(2-furanyl)-4H-1,2,4-triazol-3-yl)sulfamoyl)propyl)-5-fluoro-3-pyridinyl)acetamide or N-(2-((2S)-2-((4-(2,6-dimethoxyphenyl)-5-(2-furanyl)-4H-1,2,4-triazol-3-yl)sulfamoyl)propyl)-5-fluoro-3-pyridinyl)acetamide 15.1

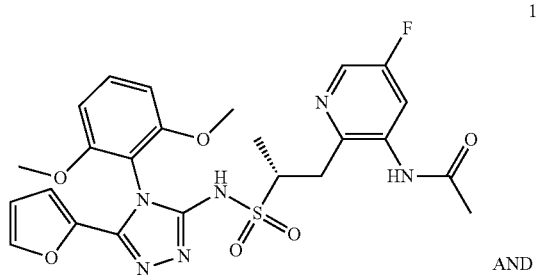

AND

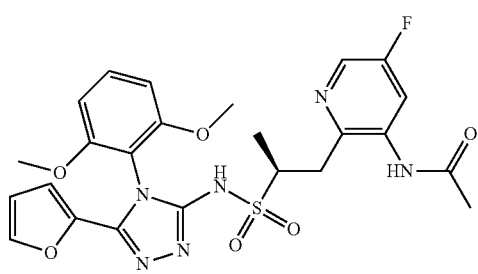

N-(2-((2R)-2-((4-(2,6-Dimethoxyphenyl)-5-(2-furanyl)-4H-1,2,4-triazol-3-yl)sulfamoyl)propyl)-5-fluoro-3-pyridinyl)acetamide and N-(2-((2S)-2-((4-(2,6-dimethoxyphenyl)-5-(2-furanyl)-4H-1,2,4-triazol-3-yl)sulfamoyl)propyl)-5-fluoro-3-pyridinyl)acetamide, Example 15.1. The title compound was prepared in an analagous fashion to that described in Example 9.0 employing 3-bromo-5-fluoropicolinaldehyde. $^1$H NMR (500 MHz, CDCl$_3$) δ 1.49 (d, J=6.85 Hz, 3H) 2.17 (s, 3H) 3.19 (dd, J=15.04, 3.79 Hz, 1H) 3.32-3.40 (m, 1H) 3.42 (dt, J=6.79, 3.33 Hz, 1H) 3.72 (d, J=6.60 Hz, 6H) 5.92 (d, J=3.67 Hz, 1H) 6.33 (dd, J=3.67, 1.71 Hz, 1H) 6.66 (t, J=8.07 Hz, 2H) 7.46 (d, J=1.22 Hz, 1H) 7.51 (t, J=8.56 Hz, 1H) 8.25 (d, J=2.69 Hz, 1H) 8.44 (dd, J=10.27, 2.69 Hz, 1H) 9.22 (s, 1H).

15.0

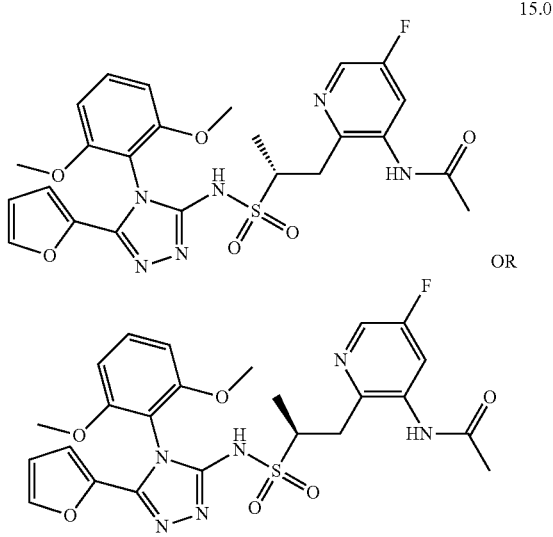

OR

N-(2-((2R)-2-((4-(2,6-Dimethoxyphenyl)-5-(2-furanyl)-4H-1,2,4-triazol-3-yl)sulfamoyl)propyl)-5-fluoro-3-pyridinyl)acetamide or N-(2-((2S)-2-((4-(2,6-dimethoxyphenyl)-5-(2-furanyl)-4H-1,2,4-triazol-3-yl)sulfamoyl)propyl)-5-fluoro-3-pyridinyl)acetamide, Example 15.0. The enantiomers of Example 15.1 were separated on an AD-H column (2×15 cm) eluting with 30% MeOH/CO$_2$ (with 20 mM NH$_3$), 100 bar, 65 mL/min. The first peak to elute on the AD column was the title compound, Example 15.0 (31 mg, 0.056 mmol, 35% yield). $^1$H NMR (500 MHz, CDCl$_3$) δ 1.46 (d, J=6.60 Hz, 3H) 2.12 (s, 3H) 3.00 (dd, J=14.55, 4.52 Hz, 1H) 3.27-3.45 (m, 2H) 3.72 (app s, 6H) 5.93 (d, J=3.42 Hz, 1H) 6.32 (dd, J=3.42, 1.71 Hz, 1H) 6.66 (dd, J=10.64, 8.68 Hz, 2H) 7.39-7.55 (m, 2H) 8.01-8.16 (m, 2H) 8.74 (br. s., 1H) 10.94 (br. s., 1H). LCMS ESI (pos.) m/z: 545.1 (M+H)$^+$.

Example 16.0. Preparation of (2S)—N-(4-(2,6-dimethoxyphenyl)-5-(5-methyl-2-furanyl)-4H-1,2,4-triazol-3-yl)-1-(5-methyl-2-pyrimidinyl)-2-propanesulfonamide or (2R)—N-(4-(2,6-dimethoxyphenyl)-5-(5-methyl-2-furanyl)-4H-1,2,4-triazol-3-yl)-1-(5-methyl-2-pyrimidinyl)-2-propanesulfonamide 16.1

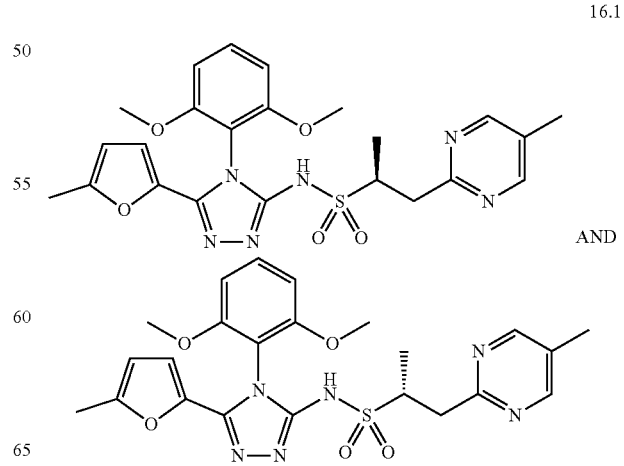

AND (2S)—N-(4-(2,6-Dimethoxyphenyl)-5-(5-methyl-2-furanyl)-4H-1,2,4-triazol-3-yl-1-(5-methyl-2-pyrimidinyl)-2-propanesulfonamide and (2R)—N-(4-(2,6-dimethoxyphenyl)-5-(5-methyl-2-furanyl)-4H-1,2,4-triazol-3-yl)-1-(5-methyl-2-pyrimidinyl)-2-propanesulfonamide, Example 16.1. The title compound was prepared in an analogous to that described in Example 7.0 employing 2-chloro-5-methylpyrimidine.

16.0

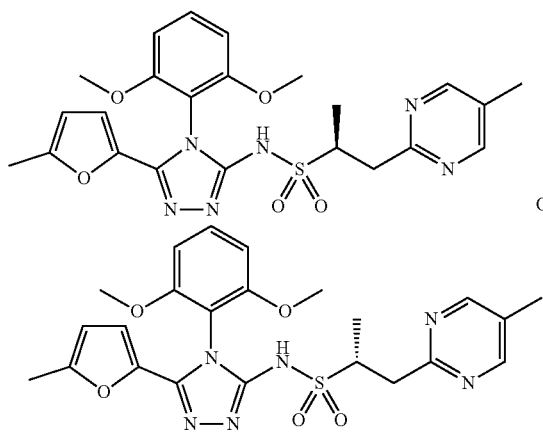

OR (2S)—N-(4-(2,6-Dimethoxyphenyl)-5-(5-methyl-2-furanyl)-4H-1,2,4-triazol-3-yl)-1-(5-methyl-2-pyrimidinyl)-2-propanesulfonamide or (2R)—N-(4-(2,6-dimethoxyphenyl)-5-(5-methyl-2-furanyl)-4H-1,2,4-triazol-3-yl)-1-(5-methyl-2-pyrimidinyl)-2-propanesulfonamide, Example 16.0. Purification of 16.1 by SFC [30×150 mm IA column with 35 g/min MeOH (neat) in 65 g/min CO$_2$ at 100 bar] afforded two enantiomers. The title compound, Example 16.0, was the first isomer to elute under these conditions. $^1$H NMR (500 MHz, CDCl$_3$) δ 11.23 (br. s., 1H) 8.51 (s, 2H) 7.39-7.51 (m, 1H) 6.67 (dd, J=8.44, 3.30 Hz, 2H) 5.91 (d, J=2.69 Hz, 1H) 5.79 (d, J=3.42 Hz, 1H) 3.79-3.88 (m, 1H) 3.75 (d, J=11.00 Hz, 6H) 3.65 (dd, J=14.79, 4.77 Hz, 1H) 3.05 (dd, J=14.67, 9.54 Hz, 1H) 2.29 (s, 3H) 2.32 (s, 3H) 1.31 (d, J=6.85 Hz, 3H). LCMS-ESI (pos.) m/z: 499.0 (M+H)$^+$.

Example 17.0. Preparation of 5-chloro-2-((2S)-2-((4-(2,6-dimethoxyphenyl)-5-(2-furanyl)-4H-1,2,4-triazol-3-yl)sulfamoyl)propyl)-3-pyridinecarboxamide or 5-chloro-2-((2R)-2-((4-(2,6-dimethoxyphenyl)-5-(2-furanyl)-4H-1,2,4-triazol-3-yl)sulfamoyl)propyl)-3-pyridinecarboxamide 17.1

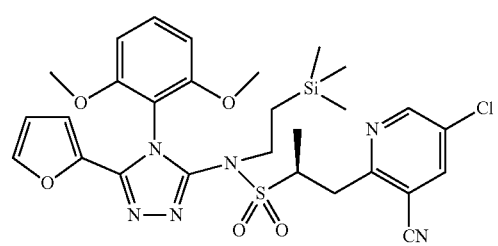

AND

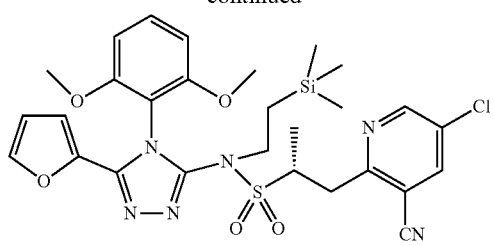

(S)-1-(5-Chloro-3-cyanopyridin-2-yl)-N-(4-(2,6-dimethoxyphenyl)-5-(furan-2-yl)-4H-1,2,4-triazol-3-yl)-N-(2-(trimethylsilyl)ethyl)propane-2-sulfonamide and (R)-1-(5-chloro-3-cyanopyridin-2-yl)-N-(4-(2,6-dimethoxyphenyl)-5-(furan-2-yl)-4H-1,2,4-triazol-3-yl)-N-(2-(trimethylsilyl)ethyl)propane-2-sulfonamide, Example 17.1. The title compound was prepared employing Example 9.1 following the method described in Example 359.1. LCMS-ESI (pos.) m/z: 629.0 (M+H)$^+$.

17.2

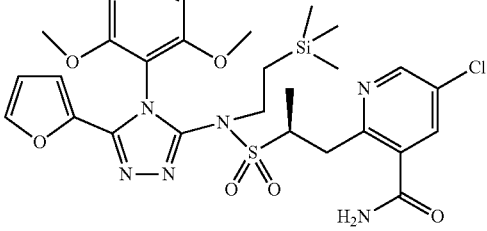

AND

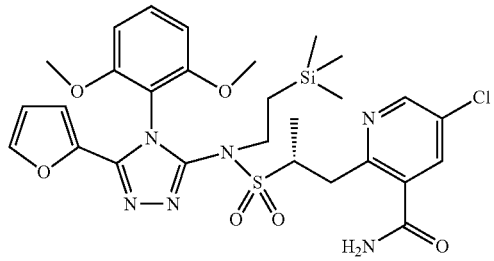

(S)-5-Chloro-2-(2-(N-(4-(2,6-dimethoxyphenyl)-5-(furan-2-yl)-4H-1,2,4-triazol-3-yl)-N-(2-(trimethylsilyl)ethyl)sulfamoyl)propyl)nicotinamide and (R)-5-chloro-2-(2-(N-(4-(2,6-dimethoxyphenyl)-5-(furan-2-yl)-4H-1,2,4-triazol-3-yl)-N-(2-(trimethylsilyl)ethyl)sulfamoyl)propyl)nicotinamide, Example 17.3. Hydrogen peroxide (30%/water, 0.1 mL, 0.98 mmol) was added to a solution of 17.1 (170 mg, 0.23 mmol) and potassium carbonate (46 mg, 0.33 mmol) in DMSO (1 mL) at 0° C. The reaction vessel was then removed from the cooling bath and stirred until LCMS analysis indicated that the transformation was complete (2 h). Thereafter, the mixture was acidified to pH 3 with 1 N aqueous HCl and diluted with MeOH until all solids dissolved. The initial material obtained was purified on a reverse-phase column employing a gradient of 30-60% ACN in water (0.1% TFA in both eluents) to afford Example 17.2. LCMS-ESI (pos.) m/z: 647.0 (M+H)$^+$.

17.3

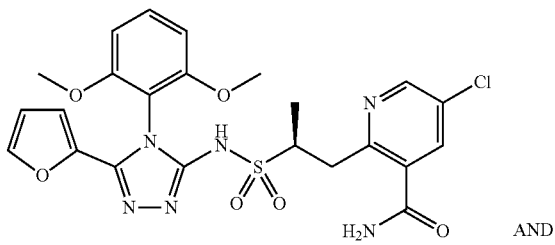

AND

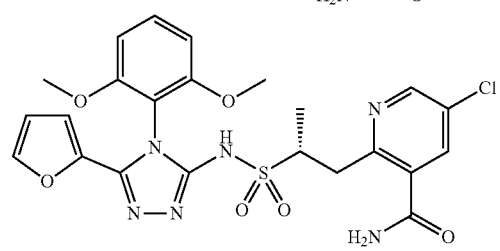

5-Chloro-2-((2S)-2-((4-(2,6-dimethoxyphenyl)-5-(2-furanyl)-4H-1,2,4-triazol-3-yl)sulfamoyl)propyl)-3-pyridinecarboxamide and 5-chloro-2-((2R)-2-((4-(2,6-dimethoxyphenyl)-5-(2-furanyl)-4H-1,2,4-triazol-3-yl)sulfamoyl)propyl)-3-pyridinecarboxamide, Example 17.3. Example 17.2 (128 mg, 0.17 mmol) was azeotroped with benzene (2×) and then dissolved in DMF (1 mL). Tris(dimethylamino)sulfonium difluorotrimethylsilicate (commercially available from Sigma-Aldrich Corp., St. Louis, Mo., USA) (170 mg, 0.62 mmol) was added and the resulting mixture was stirred at 60° C. for 4.5 h. Thereafter, the mixture was cooled to RT and concentrated in vacuo. The residue was purified on a reverse-phase column employing a gradient of 10-70% ACN in water (0.1% TFA in both eluents, to afford Example 17.3 (81 mg, 0.12 mmol, 73%). LCMS-ESI (pos.) m/z: 547.0 (M+H)+.

17.0

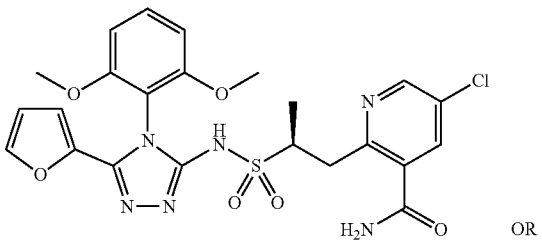

OR

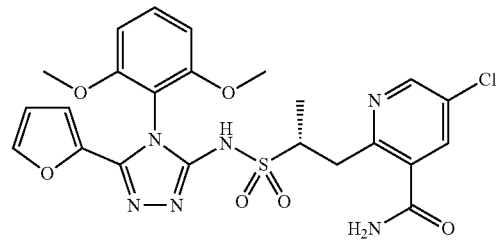

5-Chloro-2-((2S)-2-((4-(2,6-dimethoxyphenyl)-5-(2-furanyl)-4H-1,2,4-triazol-3-yl)sulfamoyl)propyl)-3-pyridinecarboxamide or 5-chloro-2-((2R)-2-((4-(2,6-dimethoxyphenyl)-5-(2-furanyl)-4H-1,2,4-triazol-3-yl)sulfamoyl)propyl)-3-pyridinecarboxamide, Example 17.0. Purification of Example 17.3 by SFC [20×250 mm AD-H column with 35% EtOH (neat) in CO2 at 100 bar] afforded two enantiomers. The title compound was the first isomer to elute under these conditions. 1H NMR (500 MHz, CD3OD) δ 8.58 (d, J=2.44 Hz, 1H) 7.85 (d, J=2.45 Hz, 1H) 7.60 (d, J=1.22 Hz, 1H) 7.56 (t, J=8.56 Hz, 1H) 6.85 (dd, J=8.56, 3.91 Hz, 2H) 6.43 (dd, J=3.67, 1.71 Hz, 1H) 6.13 (d, J=3.42 Hz, 1H) 3.78 (d, J=3.18 Hz, 6H) 3.74 (m, J=4.40 Hz, 1H) 3.59 (dd, J=14.55, 4.28 Hz, 1H) 3.06 (dd, J=14.55, 9.90 Hz, 1H) 1.22 (d, J=6.85 Hz, 3H). LCMS-ESI (pos.) m/z: 547.0 (M+H)+.

Example 18.0. Preparation of (2S)-1-(5-chloro-3-cyano-2-pyridinyl)-N-(4-(2,6-dimethoxyphenyl)-5-(2-furanyl)-4H-1,2,4-triazol-3-yl)-2-propanesulfonamide and (2R)-1-(5-chloro-3-cyano-2-pyridinyl)-N-(4-(2,6-dimethoxyphenyl)-5-(2-furanyl)-4H-1,2,4-triazol-3-yl)-2-propanesulfonamide 18.1

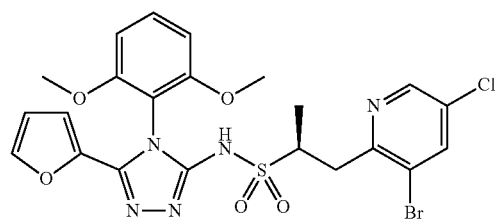

and

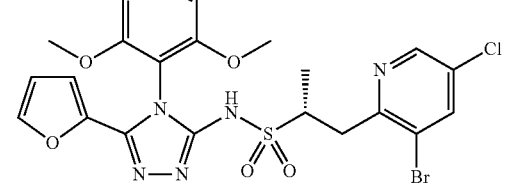

(R)-1-(3-Bromo-5-chloropyridin-2-yl)-N-(4-(2,6-dimethoxyphenyl)-5-(furan-2-yl)-4H-1,2,4-triazol-3-yl)propane-2-sulfonamide and (S)-1-(3-bromo-5-chloropyridin-2-yl)-N-(4-(2,6-dimethoxyphenyl)-5-(furan-2-yl)-4H-1,2,4-triazol-3-yl)propane-2-sulfonamide, Example 18.1. The title compound was prepared employing Example 9.1 and the procedure described in the synthesis of Example 4.0. LCMS-ESI (pos.) m/z: 582.0 (M+H)+.

18.0

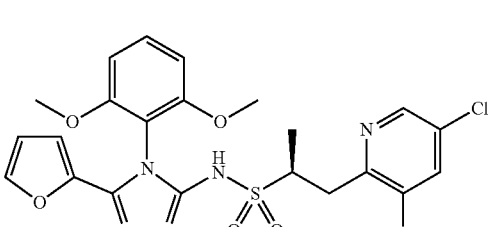

AND

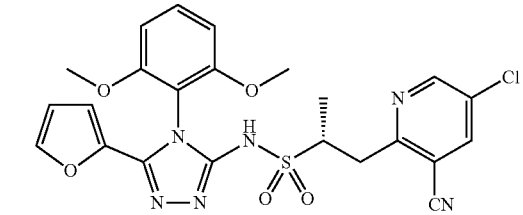

(2S)-1-(5-Chloro-3-cyano-2-pyridinyl)-N-(4-(2,6-dimethoxyphenyl)-5-(2-furanyl)-4H-1,2,4-triazol-3-yl)-2-propanesulfonamide and (2R)-1-(5-chloro-3-cyano-2-pyridinyl)-N-(4-(2,6-dimethoxyphenyl)-5-(2-furanyl)-4H-1,2,4-triazol-3-yl)-2-propanesulfonamide, Example 18.0. The title compound was prepared employing Example 18.1 and the procedure described in the synthesis of Example 50.0. $^1$H NMR (500 MHz, CDCl$_3$) δ 8.68 (d, J=2.20 Hz, 1H) 7.87 (d, J=2.20 Hz, 1H) 7.39-7.52 (m, 2H) 6.69 (t, J=8.44 Hz, 2H) 6.29-6.37 (m, 1H) 6.00 (d, J=3.67 Hz, 1H) 3.78-3.85 (m, 1H) 3.76 (d, J=4.40 Hz, 6H) 3.69 (dd, J=14.92, 4.89 Hz, 1H) 3.14 (dd, J=15.04, 8.93 Hz, 1H) 1.32 (d, J=6.85 Hz, 3H). LCMS-ESI (pos.) m/z: 529.0 (M+H)$^+$.

Example 19.0. Preparation of 2-(5-cyano-2-pyridinyl)-N-(4-(2,6-dimethoxyphenyl)-5-(5-methyl-2-furanyl)-4H-1,2,4-triazol-3-yl)ethanesulfonamide

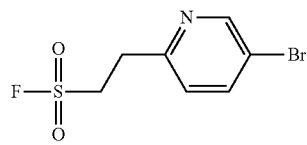

19.1

2-(5-Bromopyridin-2-yl)ethanesulfonyl fluoride, Example 19.1. Example 19.1 was prepared employing 2-(5-bromopyridin-2-yl)ethanesulfonic acid (prepared following conditions described in Example 352.2 employing 2,5-dibromopyridine) and following the conditions described in Example 24.0.

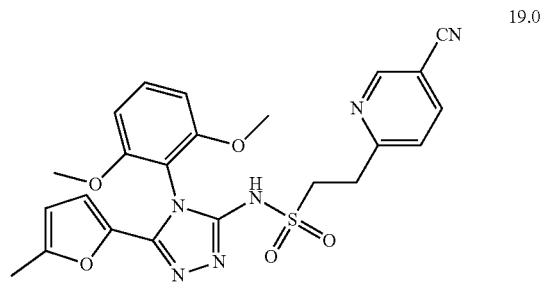 [SMILES: COc1cccc(OC)c1-n1c(NS(=O)(=O)CCc2ccc(C#N)cn2)nnc1-c1ccc(C)o1]

19.0

2-(5-Cyano-2-pyridinyl)-N-(4-(2,6-dimethoxyphenyl)-5-(5-methyl-2-furanyl)-4H-1,2,4-triazol-3-yl)ethanesulfonamide, Example 19.0. To a solution of 2-(5-bromopyridin-2-yl)-N-(4-(2,6-dimethoxyphenyl)-5-(5-methylfuran-2-yl)-4H-1,2,4-triazol-3-yl)ethanesulfonamide 2,2,2-trifluoroacetate (112 mg, 0.169 mmol, prepared in an analogous fashion to that described in Example 24.0) in DMF (2 mL) was added tetrakis(triphenylphosphine)palladium(0) (37.5 mg, 0.032 mmol) and dicyanozinc (32.6 mg, 0.278 mmol). Argon was bubbled through the mixture for one min and then the microwave vial was sealed. The resulting mixture was heated in a microwave for 30 min at 120° C. under argon. Tetrakis(triphenylphosphine)palladium (0) (37.5 mg, 0.032 mmol) and dicyanozinc (32.6 mg, 0.278 mmol) were then added to the reaction mixture and argon was bubbled through the mixture for 1 min. The mixture was then heated at 120° C. for another 30 min. The reaction mixture was then filtered through a syringe filter and purified by reverse-phase preparative HPLC using a Phenomenex Gemini 10u C18, 250×30 mm column, 0.1% TFA in ACN/H$_2$O, gradient 10% to 70% over 21 min. The desired fraction were lyophilized over the weekend. The material was absorbed onto a plug of silica gel and purified by chromatography through a Redi-Sep pre-packed silica gel column (4 g) eluting with a gradient of 0% to 100% EtOAc in DCM to give Example 19.0 (27.3 mg, 0.055 mmol, 33% yield). $^1$H NMR (400 MHz, CDCl$_3$) δ 2.32 (s, 3H) 3.26-3.40 (m, 2H) 3.43-3.54 (m, 2H) 3.74 (app s, 6H) 5.81 (d, J=3.52 Hz, 1H) 5.92 (dd, J=3.42, 0.88 Hz, 1H) 6.68 (d, J=8.61 Hz, 2H) 7.32 (d, J=8.22 Hz, 1H) 7.47 (t, J=8.51 Hz, 1H) 7.85 (dd, J=8.02, 2.15 Hz, 1H) 8.78 (d, J=1.37 Hz, 1H) 10.86 (s, 1H). LCMS ESI (pos.) m/z: 495.1 (M+H)$^+$.

Example 20.0. Preparation of (2R)-1-(5-chloro-3-cyano-2-pyridinyl)-N-(4-(2,6-dimethoxyphenyl)-5-(2-furanyl)-4H-1,2,4-triazol-3-yl)-2-propanesulfonamide or (2S)-1-(5-chloro-3-cyano-2-pyridinyl)-N-(4-(2,6-dimethoxyphenyl)-5-(2-furanyl)-4H-1,2,4-triazol-3-yl)-2-propanesulfonamide

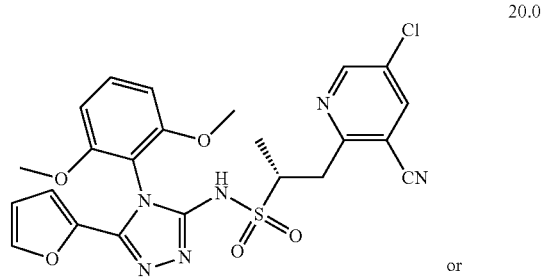

20.0 or

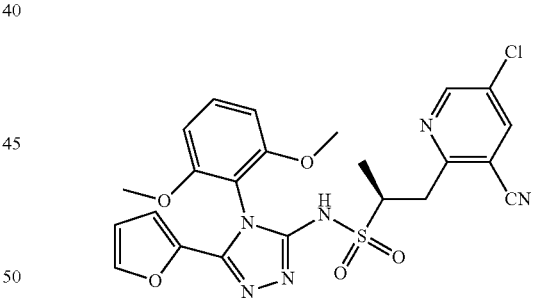

(2R)-1-(5-Chloro-3-cyano-2-pyridinyl)-N-(4-(2,6-dimethoxyphenyl)-5-(2-furanyl)-4H-1,2,4-triazol-3-yl)-2-propanesulfonamide or (2S)-1-(5-chloro-3-cyano-2-pyridinyl)-N-(4-(2,6-dimethoxyphenyl)-5-(2-furanyl)-4H-1,2,4-triazol-3-yl)-2-propanesulfonamide, Example 20.0. Example 18.0 was purified on an AD-H column eluting with 30% MeOH/100 bar CO$_2$ 45 mins to isolate the first peak as the title compound (19 mg, 0.036 mmol, 26% yield). $^1$H NMR (500 MHz, CDCl$_3$) δ 1.32 (d, J=6.85 Hz, 3H) 3.14 (dd, J=15.04, 8.93 Hz, 1H) 3.70 (dd, J=14.92, 4.89 Hz, 1H) 3.76 (d, J=4.40 Hz, 6H) 3.78-3.85 (m, 1H) 6.00 (d, J=3.42 Hz, 1H) 6.33 (dd, J=3.42, 1.71 Hz, 1H) 6.69 (t, J=8.19 Hz, 2H) 7.43-7.51 (m, 2H) 7.87 (d, J=2.45 Hz, 1H) 8.68 (d, J=2.44 Hz, 1H). LCMS ESI (pos.) m/z: 529.1 (M+H)$^+$.

Example 21.0. Preparation of 5-chloro-2-((2R)-2-((4-(2,6-dimethoxyphenyl)-5-(2-furanyl)-4H-1,2,4-triazol-3-yl)sulfamoyl)propyl)-N,N-diethyl-3-pyridinecarboxamide or 5-chloro-2-((2S)-2-((4-(2,6-dimethoxyphenyl)-5-(2-furanyl)-4H-1,2,4-triazol-3-yl)sulfamoyl)propyl)-N,N-diethyl-3-pyridinecarboxamide 21.1

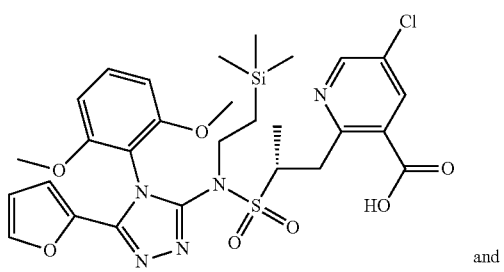

and

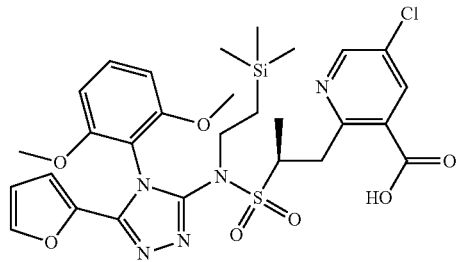

(R)-5-Chloro-2-(2-(N-(4-(2,6-dimethoxyphenyl)-5-(furan-2-yl)-4H-1,2,4-triazol-3-yl)-N-(2-(trimethylsilyl)ethyl)sulfamoyl)propyl)nicotinic acid and (S)-5-chloro-2-(2-(N-(4-(2,6-dimethoxyphenyl)-5-(furan-2-yl)-4H-1,2,4-triazol-3-yl)-N-(2-(trimethylsilyl)ethyl)sulfamoyl)propyl)nicotinic acid, Example 21.1. To a solution of Example 9.1 (101 mg, 0.148 mmol) in THF (1 mL) was added isopropylmagnesium chloride, (2.0 M in THF, 0.2 mL, 0.400 mmol). The reaction mixture was allowed to stir at RT for 1.45 h. The reaction was cooled to 0° C. and then carbon dioxide gas was bubbled into the vial for 35 min. The reaction was concentrated in vacuo. The initial material obtained was purified by reverse-phase preparative HPLC using an Agilent SB C8 column, 0.1% TFA in ACN/H$_2$O, gradient 40% to 70% over 25 min. The desired fraction was lyophilized overnight to give the title compound (47.3 mg, 0.073 mmol, 49% yield). $^1$H NMR 500 MHz, CDCl$_3$) δ 0.03-0.16 (m, 9H) 1.38-1.48 (m, 2H) 2.16-2.23 (m, 3H) 3.70 (apps, 6H) 4.38-4.45 (m, 2H) 5.94 (d, J=3.42 Hz, 1H) 6.32 (dd, J=3.42, 1.71 Hz, 1H) 6.57 (d, J=8.56 Hz, 2H) 7.33 (t, J=8.44 Hz, 1H) 7.48 (d, J=1.22 Hz, 1H) 7.78 (s, 1H) 8.21 (d, J=2.45 Hz, 1H) 8.67 (d, J=2.44 Hz, 1H).

21.2

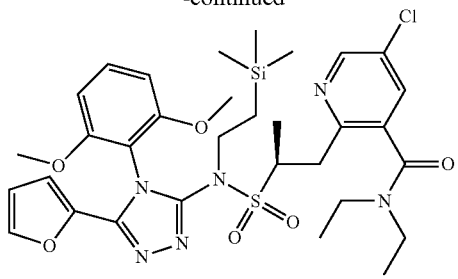

(R)-5-Chloro-2-(2-(N-(4-(2,6-dimethoxyphenyl)-5-(furan-2-yl)-4H-1,2,4-triazol-3-yl)-N-(2-(trimethylsilyl)ethyl)sulfamoyl)propyl)-N,N-diethylnicotinamide compound with (S)-5-chloro-2-(2-(N-(4-(2,6-dimethoxyphenyl)-5-(furan-2-yl)-4H-1,2,4-triazol-3-yl)-N-(2-(trimethylsilyl)ethyl)sulfamoyl)propyl)-N,N-diethylnicotinamide, Example 21.2. To a solution of Example 21.2 (47.3 mg, 0.073 mmol) in DCM (1.0 mL) was added Hunig's base (40 μL, 0.229 mmol) and HTBU (52.8 mg, 0.139 mmol). After 40 min, DEA (40 μL, 0.387 mmol) was added, and the reaction was stirred at RT for 30 mins. The reaction was then concentrated in vacuo. The initial material was purified by reverse-phase preparative HPLC using an Agilent SB C8 column, 0.1% TFA in ACN/H$_2$O, gradient 40% to 70% over 25 min. The desired fractions were lyophilized to give the title compound, Example 21.2 (38 mg, 0.055 mmol, 75% yield).

21.0

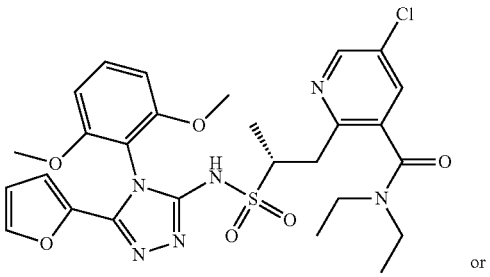

or

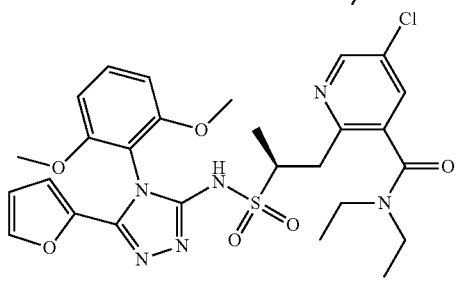

5-Chloro-2-((2R)-2-((4-(2,6-dimethoxyphenyl)-5-(2-furanyl)-4H-1,2,4-triazol-3-yl)sulfamoyl)propyl)-N,N-diethyl-3-pyridinecarboxamide or 5-chloro-2-((2S)-2-((4-(2,6-dimethoxyphenyl)-5-(2-furanyl)-4H-1,2,4-triazol-3-yl)sulfamoyl)propyl)-N,N-diethyl-3-pyridinecarboxamide, Example 21.0. To a solution of Example 21.2 (38.4 mg, 0.055 mmol) in DMF (0.5 mL) was added tris(dimethylamino)sulfonium difluorotrimethylsilicate (65 mg, 0.236 mmol). The resulting solution was heated at 60° C. for 4 h. The reaction was then cooled to RT. The initial material was purified by reverse-phase preparative HPLC using an Agilent SB C8 column, 0.1% TFA in ACN/H$_2$O, gradient 10% to 80% over 25 min. The desired fractions were lyophilized to give the racemic product (28 mg, 0.046 mmol, 84% yield). Chiral separation was performed using an IC column eluting with 40% MeOH/CO$_2$, 100 bar, 60 mL/min. The second peak to elute on the IC column was Example 21.0 (8.0 mg, 0.013 mmol, 24% yield) was isolated. $^1$H NMR (500 MHz, CDCl$_3$) δ 1.08 (br. s., 3H) 1.21 (br. s., 2H) 1.30 (d, J=6.85 Hz, 3H) 1.67 (br. s., 1H) 2.86 (br. s., 1H) 3.14 (br. s., 2H) 3.23-3.53 (m, 2H) 3.62 (br. s., 1H) 3.74 (br. s., 6H) 3.97 (br. s., 1H) 5.97 (d, J=3.42 Hz, 1H) 6.24-6.36 (m, 1H) 6.66 (d, J=8.56 Hz, 2H) 7.38-7.60 (m, 3H) 8.52 (d, J=1.22 Hz, 1H) 11.06 (br. s., 1H). LCMS ESI (pos.) m/z: 603.1 (M+H)$^+$.

Example 22.0. Preparation of (2S)-1-(5-bromo-2-pyrimidinyl)-N-(4-(2,6-dimethoxyphenyl)-5-(2-furanyl)-4H-1,2,4-triazol-3-yl)-2-propanesulfonamide or (2R)-1-(5-bromo-2-pyrimidinyl)-N-(4-(2,6-dimethoxyphenyl)-5-(2-furanyl)-4H-1,2,4-triazol-3-yl)-2-propanesulfonamide

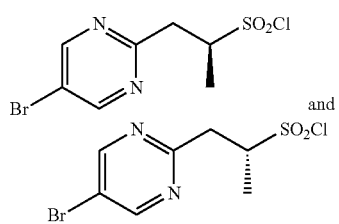

22.1

1-(5-Bromopyrimidin-2-yl)propane-2-sulfonyl chloride, Example 22.1. The title compound was prepared employing 5-bromo-2-iodopyrimidine (commercially available from Oakwood Chemical, West Columbia, S.C., USA) following the general procedure described in Example 72.0. LCMS-ESI (pos.) m/z: 298.9 (M+H)$^+$.

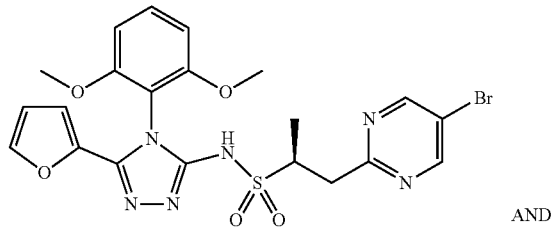

22.2

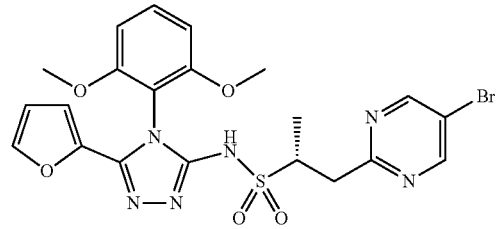

(2S)-1-(5-Bromo-2-pyrimidinyl)-N-(4-(2,6-dimethoxyphenyl)-5-(2-furanyl)-4H-1,2,4-triazol-3-yl)-2-propanesulfonamide and (2R)-1-(5-bromo-2-pyrimidinyl)-N-(4-(2,6-dimethoxyphenyl)-5-(2-furanyl)-4H-1,2,4-triazol-3-yl)-2-propanesulfonamide, Example 22.2. The title compound was prepared employing Example 22.1 and Example 362.03 and the procedure described in Example 111.0. LCMS-ESI (pos.) m/z: 548.9 (M+H)$^+$.

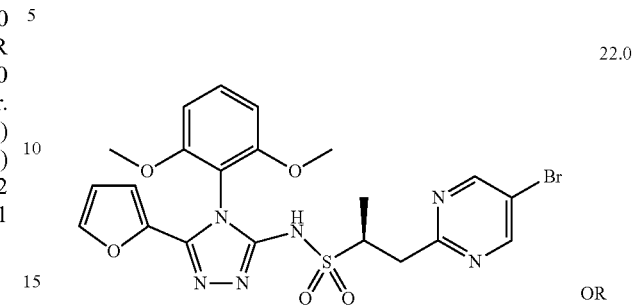

22.0

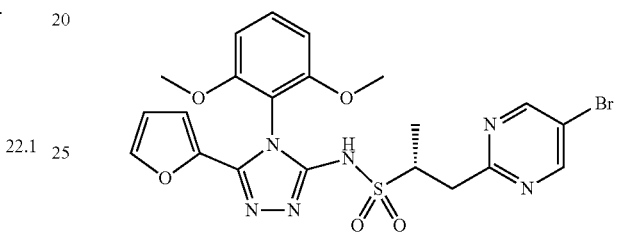

(2S)-1-(5-Bromo-2-pyrimidinyl)-N-(4-(2,6-dimethoxyphenyl)-5-(2-furanyl)-4H-1,2,4-triazol-3-yl)-2-propanesulfonamide or (2R)-1-(5-bromo-2-pyrimidinyl)-N-(4-(2,6-dimethoxyphenyl)-5-(2-furanyl)-4H-1,2,4-triazol-3-yl)-2-propanesulfonamide, Example 22.0. Purification of Example 22.2 by SFC [30×150 mm IA column with 28 g/min MeOH (neat) in 52 g/min CO$_2$ at 100 bar] afforded two enantiomers. The title compound was the first isomer to elute under these conditions. $^1$H NMR (500 MHz, CDCl$_3$) δ 11.07 (br. s., 1H) 8.72 (s, 2H) 7.33-7.63 (m, 2H) 6.68 (d, J=6.36 Hz, 2H) 6.33 (br. s., 1H) 6.00 (d, J=3.18 Hz, 1H) 3.80 (m, J=3.18 Hz, 1H) 3.75 (d, J=9.29 Hz, 6H) 3.65 (dd, J=14.92, 4.16 Hz, 1H) 3.03 (dd, J=14.92, 9.78 Hz, 1H) 1.31 (d, J=6.60 Hz, 3H). LCMS-ESI (pos.) m/z: 548.9 (M+H)$^+$.

Example 23.0. Preparation of (2R)-1-(5-bromo-2-pyridinyl)-N-(4-(2,6-dimethoxyphenyl)-5-(2-furanyl)-4H-1,2,4-triazol-3-yl)-2-propanesulfonamide or (2S)-1-(5-bromo-2-pyridinyl)-N-(4-(2,6-dimethoxyphenyl)-5-(2-furanyl)-4H-1,2,4-triazol-3-yl)-2-propanesulfonamide

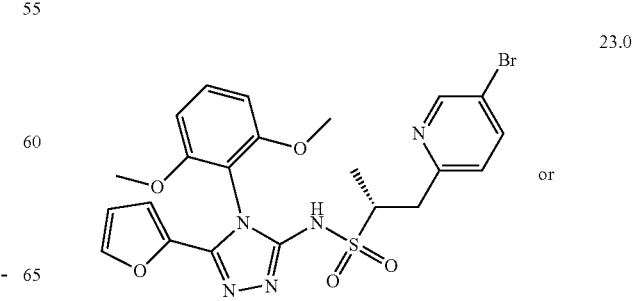

23.0

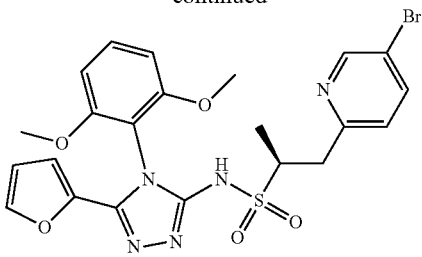

(2R)-1-(5-Bromo-2-pyridinyl)-N-(4-(2,6-dimethoxyphenyl)-5-(2-furanyl)-4H-1,2,4-triazol-3-yl)-2-propanesulfonamide or (2S)-1-(5-bromo-2-pyridinyl)-N-(4-(2,6-dimethoxyphenyl)-5-(2-furanyl)-4H-1,2,4-triazol-3-yl)-2-propanesulfonamide, Example 23.0. Chiral separation was performed with an IA column eluting with 24% MeOH/CO$_2$, 100 bar, 60 mL/min. The second peak to elute on the IA column was the title compound (10.0 mg, 0.018 mmol, 4% yield). $^1$H NMR (500 MHz, CDCl$_3$) δ 1.27 (d, J=6.85 Hz, 3H) 2.85 (dd, J=13.94, 9.78 Hz, 1H) 3.45-3.54 (m, 1H) 3.55-3.64 (m, 1H) 3.74 (d, J=5.38 Hz, 6H) 5.99 (d, J=3.67 Hz, 1H) 6.33 (dd, J=3.55, 1.83 Hz, 1H) 6.67 (d, J=8.31 Hz, 2H) 7.10 (d, J=8.31 Hz, 1H) 7.33-7.54 (m, 2H) 7.74 (dd, J=8.31, 2.20 Hz, 1H) 8.59 (s, 1H) 11.03 (br. s., 1H). LCMS ESI (pos.) m/z: 547.1 (M+H)$^+$.

Example 24.0. Preparation of (2R)—N-(4-(2,6-dimethoxyphenyl)-5-(5-methyl-2-furanyl)-4H-1,2,4-triazol-3-yl)-1-(5-methyl-2-pyrazinyl)-2-propanesulfonamide or (2S)—N-(4-(2,6-dimethoxyphenyl)-5-(5-methyl-2-furanyl)-4H-1,2,4-triazol-3-yl)-1-(5-methyl-2-pyrazinyl)-2-propanesulfonamide

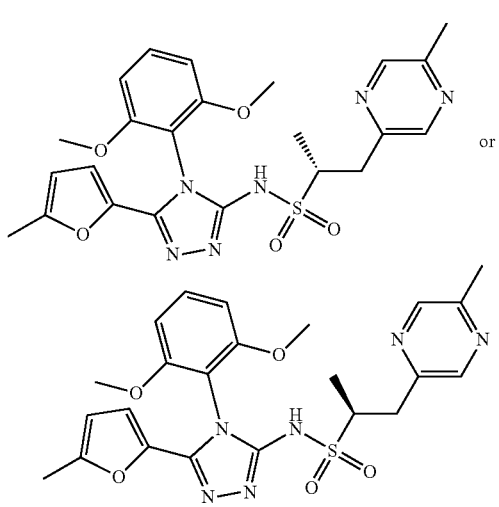

24.0 or (2R)—N-(4-(2,6-Dimethoxyphenyl)-5-(5-methyl-2-furanyl)-4H-1,2,4-triazol-3-yl)-1-(5-methyl-2-pyrazinyl)-2-propanesulfonamide or (2S)—N-(4-(2,6-dimethoxyphenyl)-5-(5-methyl-2-furanyl)-4H-1,2,4-triazol-3-yl)-1-(5-methyl-2-pyrazinyl)-2-propanesulfonamide, Example 24.0. To a suspension of 1-(5-methylpyrazin-2-yl)propane-2-sulfonic acid (284 mg, 1.313 mmol) in DCM (5 mL) was added DAST (0.2 mL, 1.514 mmol, 1.15 eq). The reaction was stirred at RT for 4 h. The reaction was then concentrated to dryness, azeotroped twice with benzene, and then dried under high vacuum. To a suspension of 4-(2,6-dimethoxyphenyl)-5-(5-methylfuran-2-yl)-4H-1,2,4-triazol-3-amine, Example 367.0 (200 mg, 0.666 mmol), in THF (5 mL) was added potassium bis(trimethylsilyl)amide solution in THF (1.0 M, 2 mL, 2.0 mmol). The brown solution was stirred at RT for 2 h. The sulfonyl fluoride in 4 mL THF (4 mL) was then added dropwise to the solution of Example 367.0 over 2 min. The resulting brown solution was stirred at RT overnight. The reaction was quenched with water (0.2 mL) and concentrated to dryness. The initial material was purified by reverse-phase preparative HPLC using a Phenomenex Gemini 10u C18, 250×50 mm column. The mobile phase was 0.1% TFA in ACN/H$_2$O and the gradient was 20-60% for 26 min. The desired fraction were lyophilized overnight to give (2S)—N-(4-(2,6-dimethoxyphenyl)-5-(5-methyl-2-furanyl)-4H-1,2,4-triazol-3-yl)-1-(5-methyl-2-pyrazinyl)-2-propanesulfonamide and (2R)—N-(4-(2,6-dimethoxyphenyl)-5-(5-methyl-2-furanyl)-4H-1,2,4-triazol-3-yl)-1-(5-methyl-2-pyrazinyl)-2-propanesulfonamide (35 mg, 0.071 mmol, 11% yield). Chiral separation was performed with an AD-H column eluting with 35% MeOH/CO$_2$, 100 bar, 60 mL/min. The second peak to elute on the AD-H column was (2S)—N-(4-(2,6-dimethoxyphenyl)-5-(5-methyl-2-furanyl)-4H-1,2,4-triazol-3-yl)-1-(5-methyl-2-pyrazinyl)-2-propanesulfonamide or (2R)—N-(4-(2,6-dimethoxyphenyl)-5-(5-methyl-2-furanyl)-4H-1,2,4-triazol-3-yl)-1-(5-methyl-2-pyrazinyl)-2-propanesulfonamide (12 mg, 0.024 mmol, 4% yield). $^1$H NMR (500 MHz, CDCl$_3$) δ 1.26 (d, J=6.60 Hz, 3H) 2.32 (s, 3H) 2.55 (s, 3H) 2.85 (dd, J=13.82, 9.90 Hz, 1H) 3.46-3.55 (m, 1H) 3.57 (ddd, J=10.21, 6.66, 4.16 Hz, 1H) 3.75 (d, J=3.91 Hz, 6H) 5.80 (d, J=3.42 Hz, 1H) 5.86-5.97 (m, 1H) 6.68 (dd, J=8.56, 1.47 Hz, 2H) 7.47 (t, J=8.56 Hz, 1H) 8.32 (s, 1H) 8.40 (s, 1H) 10.93 (br. s., 1H). LCMS ESI (pos.) m/z: 499.2 (M+H)$^+$.

Example 25.0. Preparation of (2R)—N-(4-(2,6-dimethoxyphenyl)-5-(2-furanyl)-4H-1,2,4-triazol-3-yl)-1-(5-fluoro-2-pyridinyl)-2-propanesulfonamide or (2S)—N-(4-(2,6-dimethoxyphenyl)-5-(2-furanyl)-4H-1,2,4-triazol-3-yl)-1-(5-fluoro-2-pyridinyl)-2-propanesulfonamide

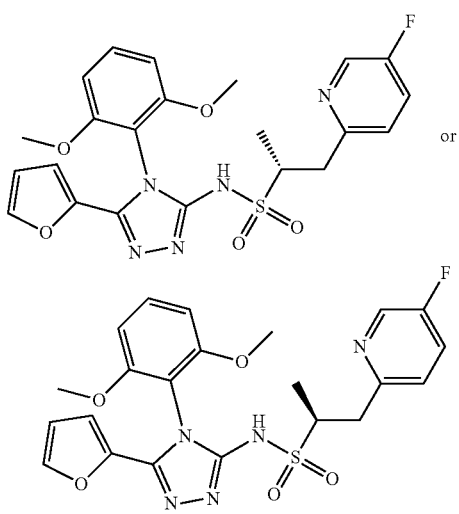

25.0 or (2R)—N-(4-(2,6-Dimethoxyphenyl)-5-(2-furanyl)-4H-1,2,4-triazol-3-yl)-1-(5-fluoro-2-pyridinyl)-2-propanesulfonamide or (2S)—N-(4-(2,6-dimethoxyphenyl)-5-(2-furanyl)-4H-1,2,4-triazol-3-yl)-1-(5-fluoro-2-pyridinyl)-2-propanesulfonamide, Example 25.0. Following the procedure described in Example 34.0 employing Example 365.0 and 5-fluoropicolinaldehyde delivered the racemic title compound. The first peak to elute on an AD-H column eluted with 35% IPA/65% hexanes isocratic for 45 mins was Example 25.0 (15.2 mg, 0.031 mmol, 27.6% yield). $^1$H NMR (500 MHz, CDCl$_3$) δ 1.27 (d, J=6.85 Hz, 3H) 2.87 (dd, J=13.82, 9.66 Hz, 1H) 3.47-3.63 (m, 2H) 3.74 (d, J=5.38 Hz, 6H) 5.99 (d, J=3.67 Hz, 1H) 6.33 (dd, J=3.55, 1.83 Hz, 1H) 6.67 (dd, J=8.44, 1.34 Hz, 2H) 7.17 (dd, J=8.56, 4.16 Hz, 1H) 7.32 (td, J=8.31, 2.93 Hz, 1H) 7.42-7.51 (m, 2H) 8.39 (d, J=2.69 Hz, 1H) 11.03 (br. s., 1H). LCMS ESI (pos.) m/z: 488.1 (M+H)$^+$.

Example 26.0. Preparation of N-(4-(2,6-dimethoxyphenyl)-5-(5-methyl-2-furanyl)-4H-1,2,4-triazol-3-yl)-2-(5-methyl-2-pyrimidinyl)ethanesulfonamide

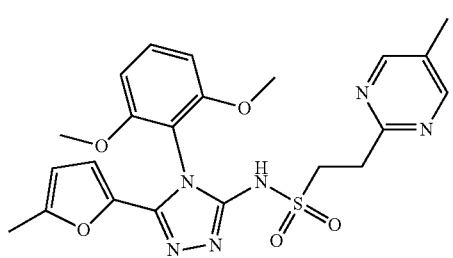

26.0

N-(4-(2,6-Dimethoxyphenyl)-5-(5-methyl-2-furanyl)-4H-1,2,4-triazol-3-yl)-2-(5-methyl-2-pyrimidinyl)ethanesulfonamide, Example 26.0. To a 0° C. suspension of 2-(5-methylpyrimidin-2-yl)ethanesulfonic acid (394 mg, 1.95 mmol, prepared in an analagous manner to that described in Example 352.2 employing 2-chloro-5-methylpyrimidine) in DCM (10 mL) was added oxalyl chloride (215 µL, 2.46 mmol, 1.26 eq), followed by DMF (1 drop). The reaction was stirred over 2 h and then the reaction was concentrated to dryness, azeotroped twice with benzene, and then dried under high vacuum. To a 0° C. suspension of 4-(2,6-dimethoxyphenyl)-5-(5-methylfuran-2-yl)-4H-1,2,4-triazol-3-amine (Example 367.0, 157 mg, 0.52 mmol) in THF (5 mL) was added potassium bis(trimethylsilyl)amide (1 M solution in THF, 1.6 mL, 1.60 mmol). The reaction was stirred at 0° C. for 2 h. The amino triazole solution (still at 0° C.) was added to a 0° C. suspension of the sulfonyl chloride intermediate in THF (5 mL) dropwise over 2 min. Once the addition was complete, the cooling bath was removed and the brown mixture was warmed to RT. The reaction was quenched with water (0.5 mL) and then concentrated down to an oil. The oil was then redissolved using water and MeOH. The material thus obtained was purified by reverse-phase preparative HPLC using an Agilent SB C8 column, 0.1% TFA in ACN/H$_2$O, gradient 10% to 50% over 25 min. The desired fractions were lyophilized over the weekend to give N-(4-(2,6-dimethoxyphenyl)-5-(5-methyl-2-furanyl)-4H-1,2,4-triazol-3-yl)-2-(5-methyl-2-pyrimidinyl)ethanesulfonamide, Example 26.0 (55 mg, 22% yield). $^1$H NMR (500 MHz, CDCl$_3$) δ 2.32 (s, 3H) 2.35 (s, 3H) 3.37-3.51 (m, 2H) 3.56-3.66 (m, 2H) 3.75 (app s, 6H) 5.82 (d, J=3.42 Hz, 1H) 5.92 (dd, J=3.42, 0.98 Hz, 1H) 6.67 (d, J=8.56 Hz, 2H) 7.46 (t, J=8.56 Hz, 1H) 8.62 (s, 2H). LCMS ESI (pos.) m/z: 485.1 (M+H)$^+$.

Example 27.0. Preparation of 2-(5-chloro-3-(2-oxo-1-azetidinyl)-2-pyridinyl)-N-(4-(2,6-dimethoxyphenyl)-5-(2-furanyl)-4H-1,2,4-triazol-3-yl)ethanesulfonamide

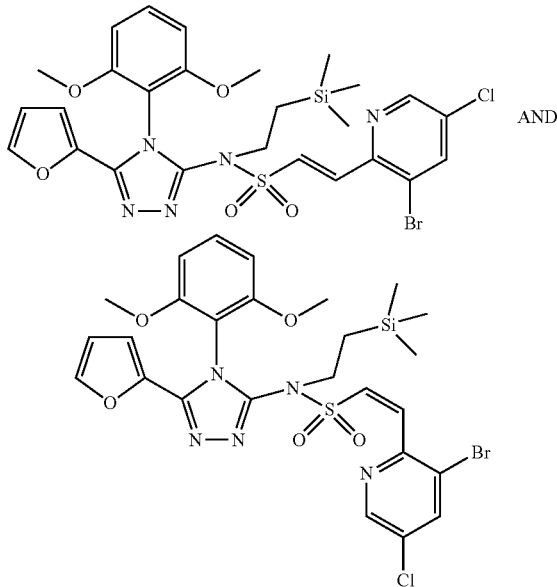

27.1

AND (E)-2-(3-Bromo-5-chloropyridin-2-yl)-N-(4-(2,6-dimethoxyphenyl)-5-(furan-2-yl)-4H-1,2,4-triazol-3-yl)-N-(2-(trimethylsilyl)ethyl)ethenesulfonamide and (Z)-2-(3-bromo-5-chloropyridin-2-yl)-N-(4-(2,6-dimethoxyphenyl)-5-(furan-2-yl)-4H-1,2,4-triazol-3-yl)-N-(2-(trimethylsilyl)ethyl)ethenesulfonamide, Example 27.1. Lithium bis(trimethylsilyl)amide (1.0 M solution in THF, 0.84 mL, 0.84 mmol) was added to a stirred solution of Example 365.0 (449 mg, 0.75 mmol) in THF (4 mL) at RT and the mixture was stirred for 15 min. Subsequently, a solution of 3-bromo-5-chloropicolinaldehyde (commercially available from Bellen, Beijing, China) (195 mg, 0.89 mmol) in THF (1.0 mL) was added and the resulting mixture was stirred at RT until LCMS indicated that the reaction was complete (1.3 h). Thereafter, the reaction was quenched with water (0.5 mL) and concentrated in vacuo. The residue was purified on a silica gel column employing a gradient of 0-100% EtOAc in hexanes to afford Example 27.1. LCMS-ESI (pos.) m/z: 666.0 (M+H)$^+$.

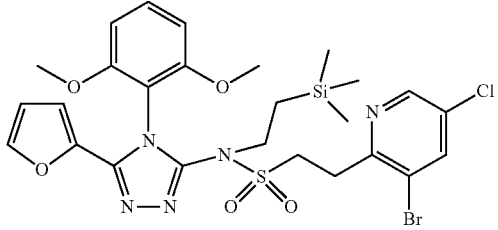

27.2

2-(3-Bromo-5-chloropyridin-2-yl)-N-(4-(2,6-dimethoxyphenyl)-5-(furan-2-yl)-4H-1,2,4-triazol-3-yl)-N-(2-(trimethylsilyl)ethyl)ethanesulfonamide, Example 27.2. Example 27.1 (383 mg, 0.57 mmol) was dissolved in DCM (1 mL). The solution was briefly sparged with N₂ before Crabtree's catalyst ((1,5-cyclooctadiene)(pyridine)(tricyclohexyl-phosphine)-iridium(I) hexafluorophosphate, 465 mg, 0.58 mmol, commercially available from Sigma-Aldrich Corp., St. Louis, Mo., USA) was carefully added. Hydrogen was introduced at 1 atm (balloon) and the mixture was vigorously stirred for 17 h at RT after which LCMS analysis showed that the reaction was complete. Thereafter, the mixture was flushed with N₂ and concentrated in vacuo. The residue was purified on a silica gel column employing a gradient of 0-100% EtOAc in hexanes to afford 27.2 (61 mg, 0.09 mmol, 22%). LCMS-ESI (pos.) m/z: 668.0 (M+H)⁺.

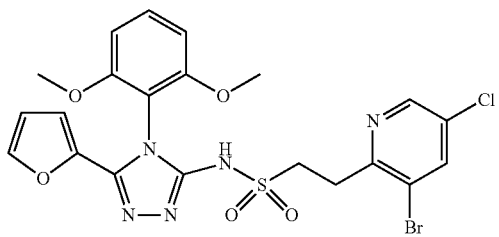

27.3

2-(3-Bromo-5-chloro-2-pyridinyl)-N-(4-(2,6-dimethoxyphenyl)-5-(2-furanyl)-4H-1,2,4-triazol-3-yl)ethanesulfonamide Example 27.3. Example 27.2 (24 mg, 0.035 mmol) was dissolved in DMF (1 mL). Tris(dimethylamino)sulfonium difluorotrimethylsilicate (TAS-F, commercially available from Sigma-Aldrich Corp., St. Louis, Mo., USA) (30 mg, 0.11 mmol) was added, and the resulting mixture was heated at 60° C. for 16 h whereupon LCMS analysis indicated that the reaction was complete. Thereafter, the mixture was cooled to RT and directly purified by reverse-phase HPLC, employing a gradient of 30-60% ACN in water (0.1% TFA in both eluents), to afford Example 27.3 (9 mg, 0.015 mmol, 44%). ¹H NMR (500 MHz, CD₂Cl₂) δ 8.34 (s, 1H) 7.80 (s, 1H) 7.47 (d, J=8.56 Hz, 1H) 7.41 (s, 1H) 6.66 (d, J=8.56 Hz, 2H) 6.27 (s, 1H) 5.97 (dd, J=3.67, 0.73 Hz, 1H) 3.66 (app s, 6H) 3.32-3.39 (m, 2H) 3.18-3.30 (m, 2H). LCMS-ESI (pos.) m/z: 568.0 (M+H)⁺.

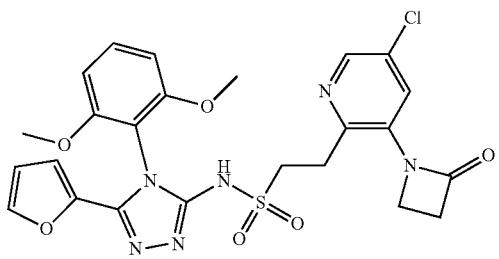

27.0

2-(5-Chloro-3-(2-oxo-1-azetidinyl)-2-pyridinyl)-N-(4-(2,6-dimethoxyphenyl)-5-(2-furanyl)-4H-1,2,4-triazol-3-yl)ethanesulfonamide, Example 27.0. A mixture of Example 27.3 (49.5 mg, 0.087 mmol), 2-azetidinone (11.0 mg, 0.155 mmol), copper(I) iodide (4 mg, 0.021 mmol), trans-N,N'-dimethylcyclohexane-1,2-diamine (0.024 mL, 0.155 mmol), and potassium carbonate (34 mg, 0.246 mmol) in dioxane (0.5 mL) was heated at 110° C. under argon overnight in a sealed 1 dram vial. The reaction was then cooled to RT. The material thus obtained was purified by reverse-phase preparative HPLC using an Agilent SB C8 column, 0.1% TFA in ACN/H₂O, gradient 20% to 55% over 25 min. The desired fractions were lyophilized overnight to give 2-(5-chloro-3-(2-oxo-1-azetidinyl)-2-pyridinyl)-N-(4-(2,6-dimethoxyphenyl)-5-(2-furanyl)-4H-1,2,4-triazol-3-yl)ethanesulfonamide, Example 27.0 (3.44 mg, 6.15 μmol, 7.07% yield). ¹H NMR (500 MHz, CDCl₃) δ 3.13 (t, J=4.52 Hz, 2H) 3.32-3.41 (m, 2H) 3.46-3.53 (m, 2H) 3.74 (app s, 6H) 3.87 (t, J=4.65 Hz, 2H) 6.02 (d, J=3.42 Hz, 1H) 6.34 (dd, J=3.67, 1.71 Hz, 1H) 6.68 (d, J=8.56 Hz, 2H) 7.43-7.53 (m, 2H) 7.99 (d, J=2.20 Hz, 1H) 8.34 (d, J=1.96 Hz, 1H). LCMS ESI (pos.) m/z: 559.1 (M+H)⁺.

Example 28.0. Preparation of N-(2-((2R)-2-((4-(2,6-dimethoxyphenyl)-5-(2-furanyl)-4H-1,2,4-triazol-3-yl)sulfamoyl)propyl)-5-fluoro-3-pyridinyl)acetamide and N-(2-((2S)-2-((4-(2,6-dimethoxyphenyl)-5-(2-furanyl)-4H-1,2,4-triazol-3-yl)sulfamoyl)propyl)-5-fluoro-3-pyridinyl)acetamide

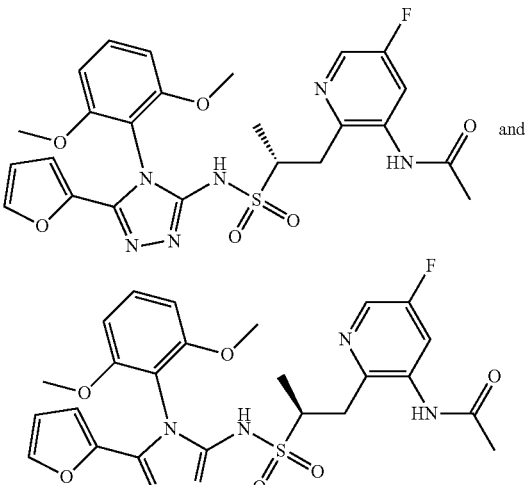

28.0

N-(2-((2R)-2-((4-(2,6-Dimethoxyphenyl)-5-(2-furanyl)-4H-1,2,4-triazol-3-yl)sulfamoyl)propyl)-5-fluoro-3-pyridinyl)acetamide and N-(2-((2S)-2-((4-(2,6-dimethoxyphenyl)-5-(2-furanyl)-4H-1,2,4-triazol-3-yl)sulfamoyl)propyl)-5-fluoro-3-pyridinyl)acetamide, Example 28.0. To a solution of N-(2-(2-(N-(4-(2,6-dimethoxyphenyl)-5-(furan-2-yl)-4H-1,2,4-triazol-3-yl)-N-(2-(trimethylsilyl)ethyl)sulfamoyl)propyl)-5-fluoropyridin-3-yl)acetamide (103.9 mg, 0.161 mmol) in DMF (0.5 mL) was added tris(dimethylamino)sulfonium difluorotrimethylsilicate (89 mg, 0.323 mmol). The resulting solution was heated at 70° C. over 4 h. The reaction mixture was cooled to RT. The material obtained was then purified by reverse-phase preparative HPLC using an Agilent SB C18 column, 0.1% TFA in ACN/H₂O, gradient 10% to 60% over 25 min. The desired fractions were lyophilized overnight to give N-(2-((2R)-2-((4-(2,6-dimethoxyphenyl)-5-(2-furanyl)-4H-1,2,4-triazol-3-yl)sulfamoyl)propyl)-5-fluoro-3-pyridinyl)acetamide and N-(2-((2S)-2-((4-(2,6-dimethoxyphenyl)-5-(2-furanyl)-4H-1,2,4-triazol-3-yl)sulfamoyl)propyl)-5-fluoro-3-pyridinyl)

acetamide, Example 28.0 (65.0 mg, 0.12 mmol, 74% yield). $^1$H NMR (500 MHz, CDCl$_3$) δ 1.49 (d, J=6.85 Hz, 3H) 2.17 (s, 3H) 3.19 (dd, J=15.04, 3.79 Hz, 1H) 3.32-3.40 (m, 1H) 3.42 (dt, J=6.79, 3.33 Hz, 1H) 3.72 (d, J=6.60 Hz, 6H) 5.92 (d, J=3.67 Hz, 1H) 6.33 (dd, J=3.67, 1.71 Hz, 1H) 6.66 (t, J=8.07 Hz, 2H) 7.46 (d, J=1.22 Hz, 1H) 7.51 (t, J=8.56 Hz, 1H) 8.25 (d, J=2.69 Hz, 1H) 8.44 (dd, J=10.27, 2.69 Hz, 1H) 9.22 (s, 1H). LCMS ESI (pos.) m/z: 545.1 (M+H)$^+$.

Example 29.0. Preparation of (2R)-1-(3-cyano-5-fluoro-2-pyridinyl)-N-(4-(2,6-dimethoxyphenyl)-5-(2-furanyl)-4H-1,2,4-triazol-3-yl)-2-propanesulfonamide or (2S)-1-(3-cyano-5-fluoro-2-pyridinyl)-N-(4-(2,6-dimethoxyphenyl)-5-(2-furanyl)-4H-1,2,4-triazol-3-yl)-2-propanesulfonamide

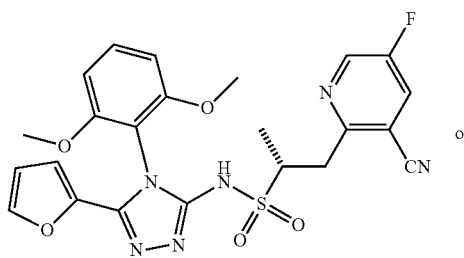

29.0 or

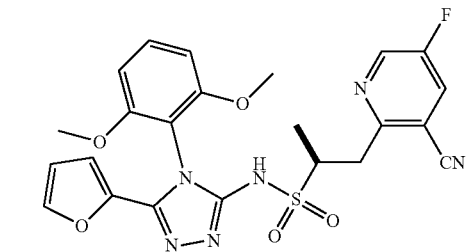

(2R)-1-(3-Cyano-5-fluoro-2-pyridinyl)-N-(4-(2,6-dimethoxyphenyl)-5-(2-furanyl)-4H-1,2,4-triazol-3-yl)-2-propanesulfonamide and (2S)-1-(3-cyano-5-fluoro-2-pyridinyl)-N-(4-(2,6-dimethoxyphenyl)-5-(2-furanyl)-4H-1,2,4-triazol-3-yl)-2-propanesulfonamide, Example 29.0. The enantiomers were separated by DAS; purification method was 30% MeOH/CO$_2$ (with 20 mM NH$_3$), 100 bar, 65 mL/min on AD-H column (2×15 cm). The first peak to elute on the AD column was (2R)-1-(3-cyano-5-fluoro-2-pyridinyl)-N-(4-(2,6-dimethoxyphenyl)-5-(2-furanyl)-4H-1,2,4-triazol-3-yl)-2-propanesulfonamide (31 mg, 0.056 mmol, 35% yield) was isolated. $^1$H NMR 500 MHz, CDCl$_3$) δ 1.46 (d, J=6.60 Hz, 3H) 2.12 (s, 3H) 3.00 (dd, J=14.55, 4.52 Hz, 1H) 3.27-3.45 (m, 2H) 3.72 (app s, 6H) 5.93 (d, J=3.42 Hz, 1H) 6.32 (dd, J=3.42, 1.71 Hz, 1H) 6.66 (dd, J=10.64, 8.68 Hz, 2H) 7.39-7.55 (m, 2H) 8.01-8.16 (m, 2H) 8.74 (br. s., 1H) 10.94 (br. s., 1H). LCMS ESI (pos.) m/z: 545.1 (M+H)$^+$.

Example 30.0. Preparation of (2R)-1-(5-cyano-2-pyridinyl)-N-(4-(2,6-dimethoxyphenyl)-5-(2-furanyl)-4H-1,2,4-triazol-3-yl)-2-propanesulfonamide or (2S)-1-(5-cyano-2-pyridinyl)-N-(4-(2,6-dimethoxyphenyl)-5-(2-furanyl)-4H-1,2,4-triazol-3-yl)-2-propanesulfonamide

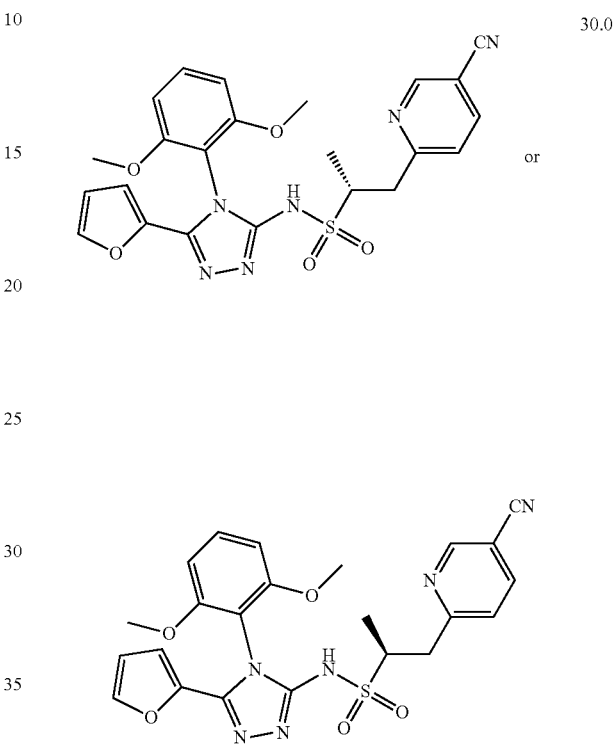

(2R)-1-(5-Cyano-2-pyridinyl)-N-(4-(2,6-dimethoxyphenyl)-5-(2-furanyl)-4H-1,2,4-triazol-3-yl)-2-propanesulfonamide or (2S)-1-(5-cyano-2-pyridinyl)-N-(4-(2,6-dimethoxyphenyl)-5-(2-furanyl)-4H-1,2,4-triazol-3-yl)-2-propanesulfonamide, Example 30.0. To a solution of 1-(5-bromopyridin-2-yl)-N-(4-(2,6-dimethoxyphenyl)-5-(furan-2-yl)-4H-1,2,4-triazol-3-yl)propane-2-sulfonamide 2,2,2-trifluoroacetate (70.4 mg, 0.106 mmol) in DMF (2 mL) was added tetrakis(triphenylphosphine)palladium(0) (11.1 mg, 9.61 μmol) and zinc cyanide (20 mg, 0.170 mmol). The resulting mixture was heated in a microwave for 120 min at 120° C. under argon. The reaction was then filtered through a syringe filter, rinsed with MeOH, and then concentrated in vacuo. The material thus obtained was purified by reverse-phase preparative HPLC using an Agilent Eclipse Plus C18 column, 0.1% TFA in ACN/H$_2$O, gradient 10% to 70% over 25 min. The desired fraction was lyophilized to give the racemate (39 mg, 0.079 mmol, 74% yield). Chiral separation was performed with an IA column eluting with 20% MeOH/CO$_2$, 100 bar, 60 mL/min. The first peak to elute on the IA column was the title compound (10.0 mg, 19% yield). $^1$H NMR (500 MHz, CDCl$_3$) δ 1.29 (d, J=6.60 Hz, 3H) 2.97 (dd, J=13.94, 9.29 Hz, 1H) 3.50-3.70 (m, 2H) 3.74 (d, J=3.42 Hz, 6H) 6.00 (d, J=3.42 Hz, 1H) 6.34 (dd, J=3.67, 1.71 Hz, 1H) 6.68 (d, J=8.56 Hz, 2H) 7.31 (d, J=8.07 Hz, 1H) 7.41-7.59 (m, 2H) 7.85 (dd, J=8.07, 1.96 Hz, 1H) 8.79 (s, 1H) 10.99 (br. s., 1H). LCMS ESI (pos.) m/z: 495.1 (M+H)$^+$.

Example 31.0. Preparation of (2R)—N-(4-(2,6-dimethoxyphenyl)-5-(5-methyl-2-furanyl)-4H-1,2,4-triazol-3-yl)-1-(6-methyl-3-pyridazinyl)-2-propanesulfonamide or (2S)—N-(4-(2,6-dimethoxyphenyl)-5-(5-methyl-2-furanyl)-4H-1,2,4-triazol-3-yl)-1-(6-methyl-3-pyridazinyl)-2-propanesulfonamide

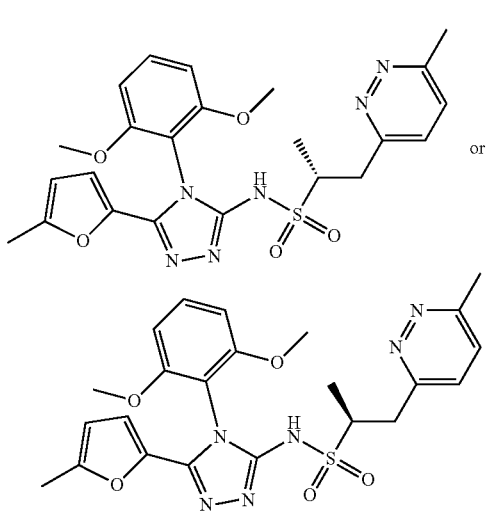

(2R)—N-(4-(2,6-Dimethoxyphenyl)-5-(5-methyl-2-furanyl)-4H-1,2,4-triazol-3-yl)-1-(6-methyl-3-pyridazinyl)-2-propanesulfonamide or (2S)—N-(4-(2,6-dimethoxyphenyl)-5-(5-methyl-2-furanyl)-4H-1,2,4-triazol-3-yl)-1-(6-methyl-3-pyridazinyl)-2-propanesulfonamide, Example 31.0. To a 0° C. suspension of 1-(6-methylpyridazin-3-yl)propane-2-sulfonic acid (310 mg, 1.433 mmol) in DCM (10 mL) was added oxalyl chloride (240 µL, 2.74 mmol) followed by DMF (4.89 mg, 0.067 mmol). The reaction was then stirred for 3 h. The reaction was concentrated to dryness, azeotroped twice with benzene, and then dried under high vacuum. To a slurry of 4-(2,6-dimethoxyphenyl)-5-(5-methylfuran-2-yl)-4H-1,2,4-triazol-3-amine, Example 367.0 (201 mg, 0.67 mmol) in THF (5 mL) was added potassium tert-butoxide (1.0 M solution in THF, 0.8 mL, 0.800 mmol) dropwise over 1 min. After stirring for 10 min, this slurry was added to a slurry of the sulfonyl chloride intermediate in THF (10 mL). The reaction was stirred at RT for 6 h. The reaction was then quenched with water (0.2 mL) and then concentrated to dryness. The initial material obtained was purified by reverse-phase preparative HPLC using an Agilent SB C8 column, 0.1% TFA in ACN/H$_2$O, gradient 10% to 50% over 25 min. The desired fraction was lyophilized overnight to give the racemate (37 mg, 0.074 mmol, 11.09% yield). Chiral separation was performed with an AD-H column eluting with 32% MeOH/CO$_2$, 100 bar, 60 mL/min. The first peak to elute on the AD-H column was the title compound, Example 31.0 (11 mg, 0.022 mmol, 3% yield). $^1$H NMR (500 MHz, CDCl$_3$) δ 1.30 (d, J=6.85 Hz, 3H) 2.32 (s, 3H) 2.69 (s, 3H) 3.05 (dd, J=13.94, 10.03 Hz, 1H) 3.59 (ddd, J=10.21, 6.66, 3.91 Hz, 1H) 3.62-3.67 (m, 1H) 3.77 (app s, 6H) 5.81 (d, J=3.42 Hz, 1H) 5.91 (dd, J=3.55, 0.86 Hz, 1H) 6.66 (d, J=2.93 Hz, 1H) 6.68 (d, J=3.18 Hz, 1H) 7.15-7.31 (m, 2H) 7.45 (t, J=8.44 Hz, 1H) 10.95 (br. s., 1H). LCMS ESI (pos.) m/z: 499.2 (M+H)$^+$.

Example 32.0. Preparation of (2R)—N-(4-(2,6-dimethoxyphenyl)-5-(2-furanyl)-4H-1,2,4-triazol-3-yl)-1-(5-methyl-2-pyrazinyl)-2-propanesulfonamide or (2S)—N-(4-(2,6-dimethoxyphenyl)-5-(2-furanyl)-4H-1,2,4-triazol-3-yl)-1-(5-methyl-2-pyrazinyl)-2-propanesulfonamide

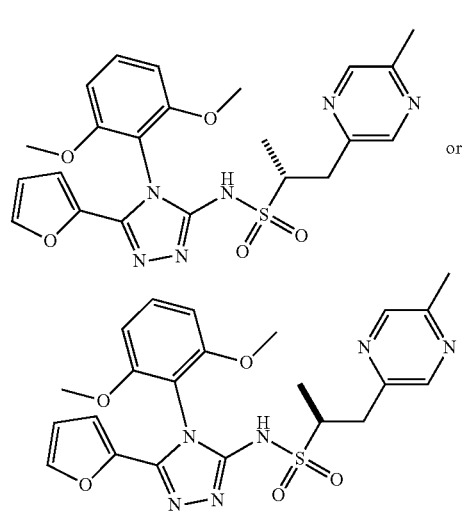

(2R)—N-(4-(2,6-Dimethoxyphenyl)-5-(2-furanyl)-4H-1,2,4-triazol-3-yl)-1-(5-methyl-2-pyrazinyl)-2-propanesulfonamide and (2S)—N-(4-(2,6-dimethoxyphenyl)-5-(2-furanyl)-4H-1,2,4-triazol-3-yl)-1-(5-methyl-2-pyrazinyl)-2-propanesulfonamide. Chiral separation was performed with an AD-H column eluting with 35% MeOH/CO$_2$, 100 bar, 60 mL/min. The first peak to elute on the AD-H column was the title compound (36 mg, 0.075 mmol, 9% yield). $^1$H NMR (500 MHz, CDCl$_3$) δ 1.27 (d, J=6.60 Hz, 3H) 2.55 (s, 3H) 2.85 (dd, J=13.94, 10.03 Hz, 1H) 3.52 (m, J=3.91 Hz, 1H) 3.58 (m, J=6.79, 3.58, 3.58 Hz, 1H) 3.75 (d, J=3.67 Hz, 6H) 6.00 (d, J=3.42 Hz, 1H) 6.33 (dd, J=3.67, 1.71 Hz, 1H) 6.68 (d, J=8.56 Hz, 2H) 7.44-7.49 (m, 2H) 8.31 (s, 1H) 8.39 (s, 1H) 11.02 (br. s., 1H). LCMS ESI (pos.) m/z: 485.1 (M+H)$^+$.

Example 33.0. Preparation of (2R)-1-(5-cyano-2-pyridinyl)-N-(4-(2,6-dimethoxyphenyl)-5-(5-methyl-2-furanyl)-4H-1,2,4-triazol-3-yl)-2-propanesulfonamide or (2S)-1-(5-cyano-2-pyridinyl)-N-(4-(2,6-dimethoxyphenyl)-5-(5-methyl-2-furanyl)-4H-1,2,4-triazol-3-yl)-2-propanesulfonamide

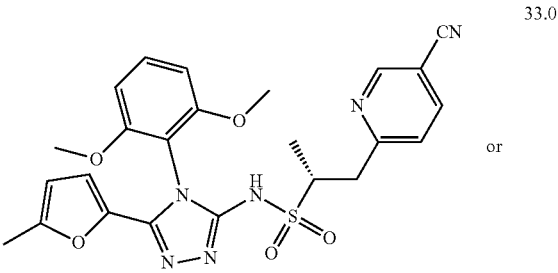

-continued

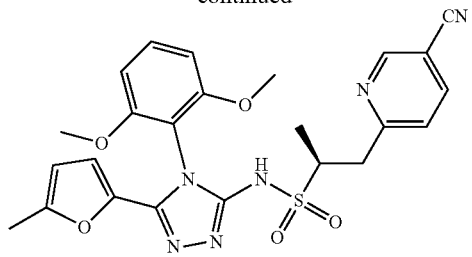

(2R)-1-(5-Cyano-2-pyridinyl)-N-(4-(2,6-dimethoxyphenyl)-5-(5-methyl-2-furanyl)-4H-1,2,4-triazol-3-yl)-2-propanesulfonamide or (2S)-1-(5-cyano-2-pyridinyl)-N-(4-(2,6-dimethoxyphenyl)-5-(5-methyl-2-furanyl)-4H-1,2,4-triazol-3-yl)-2-propanesulfonamide, Example 33.0. To a solution of 1-(5-bromopyridin-2-yl)-N-(4-(2,6-dimethoxyphenyl)-5-(5-methylfuran-2-yl)-4H-1,2,4-triazol-3-yl)propane-2-sulfonamide (103.6 mg, 0.184 mmol) in DMF (1.5 mL) was added tetrakis(triphenylphosphine)palladium(0) (62 mg, 0.054 mmol) and zinc cyanide (36 mg, 0.307 mmol). Argon was bubbled through the mixture for 1 min and then the microwave vial was sealed. The resulting mixture was heated in a microwave for 1 h at 120° C. under argon. The reaction was then filtered through a syringe filter, rinsed with MeOH, and then concentrated in vacuo. The material was purified by reverse-phase preparative HPLC using an Agilent SB C8 column, 0.1% TFA in ACN/H$_2$O, gradient 10% to 70% over 25 min. The desired fraction was lyophilized to give a racemate (35.6 mg, 0.070 mmol, 38.0% yield). Chiral separation was performed with an IA column eluting with 25% MeOH/CO$_2$, 100 bar, 60 mL/min. The second peak to elute on the IA column was the title compound (8.2 mg, 0.016 mmol, 8.75% yield). $^1$H NMR (500 MHz, CDCl$_3$) δ 1.28 (d, J=6.60 Hz, 3H) 2.26-2.35 (m, 3H) 2.96 (dd, J=14.06, 9.17 Hz, 1H) 3.54-3.61 (m, 1H) 3.61-3.69 (m, 1H) 3.74 (d, J=3.91 Hz, 6H) 5.80 (d, J=3.42 Hz, 1H) 5.91 (dd, J=3.42, 0.98 Hz, 1H) 6.67 (d, J=8.56 Hz, 2H) 7.30 (d, J=8.07 Hz, 1H) 7.47 (t, J=8.44 Hz, 1H) 7.84 (dd, J=8.07, 2.20 Hz, 1H) 8.79 (d, J=1.47 Hz, 1H) 10.92 (br. s., 1H). LCMS ESI (pos.) m/z: 509.1 (M+H)$^+$.

Example 34.0. Preparation of N-(4-(2,6-dimethoxyphenyl)-5-(2-furanyl)-4H-1,2,4-triazol-3-yl)-2-(5-fluoro-2-pyrimidinyl)ethanesulfonamide

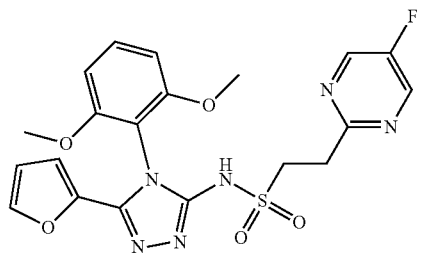

N-(4-(2,6-Dimethoxyphenyl)-5-(2-furanyl)-4H-1,2,4-triazol-3-yl)-2-(5-fluoro-2-pyrimidinyl)ethanesulfonamide, Example 34.0. To a solution of diethyl ((N-(4-(2,6-dimethoxyphenyl)-5-(furan-2-yl)-4H-1,2,4-triazol-3-yl)-N-(2-(trimethylsilyl)ethyl)sulfamoyl)methyl)phosphonate (Example 365.0, 546 mg, 0.909 mmol) in THF (3 mL) was added lithium bis(trimethylsilyl)amide (1 M solution in THF (1.1 mL, 1.100 mmol). After 15 min, 5-fluoropyrimidine-2-carbaldehyde (136.4 mg, 1.082 mmol) was added as a solution in THF (1 mL). The reaction was stirred for 1 h. The initial material was absorbed onto a plug of silica gel and purified by chromatography through a Redi-Sep pre-packed silica gel column (12 g), eluting with a gradient of 0% to 100% EtOAc in hexanes. The two isolated isomers were combined and concentrated in vacuo. To a solution of the olefin (355 mg, 0.62 mmol) in EtOH (20 mL) was added Raney 2800 nickel slurry in water (0.5 mL). The reaction was stirred at RT under a H$_2$ atmosphere over 1.5 h. The reaction mixture was then filtered through a pad of Celite® brand filter aid, the pad was rinsed with MeOH and DCM, and then the filtrate was concentrated to dryness. The filtrate (349 mg, 0.61 mmol) was dissolved in DMF (2 mL) and then tris(dimethylamino)sulfonium difluorotrimethylsilicate (333 mg, 1.209 mmol, 1.98 equiv) was added. The resulting solution was heated at 60° C. overnight. The reaction mixture was cooled to RT. The reaction was then diluted with water (200 mL) and EtOAc. The aqueous layer was extracted with EtOAc (3×). The combined organic layers were washed with brine, dried over Na$_2$SO$_4$, concentrated in vacuo, and then dried under high vacuum. The initial material was absorbed onto a plug of silica gel and purified by chromatography through a Redi-Sep pre-packed silica gel column (12 g), eluting with a gradient of 0% to 5% MeOH in DCM to give the title compound (146.4 mg, 0.31 mmol, 34% yield). $^1$H NMR (500 MHz, CDCl$_3$) δ 3.37-3.50 (m, 2H) 3.53-3.64 (m, 2H) 3.75 (app s, 6H) 6.01 (d, J=3.67 Hz, 1H) 6.34 (dd, J=3.42, 1.71 Hz, 1H) 6.68 (d, J=8.56 Hz, 2H) 7.40-7.52 (m, 2H) 8.52 (s, 2H) 11.03 (br. s., 1H). LCMS ESI (pos.) m/z: 515.1 (M+H)$^+$.

Example 35.0. Preparation of 2-(5-cyano-2-pyridinyl)-N-(4-(2,6-dimethoxyphenyl)-5-(2-furanyl)-4H-1,2,4-triazol-3-yl)ethanesulfonamide

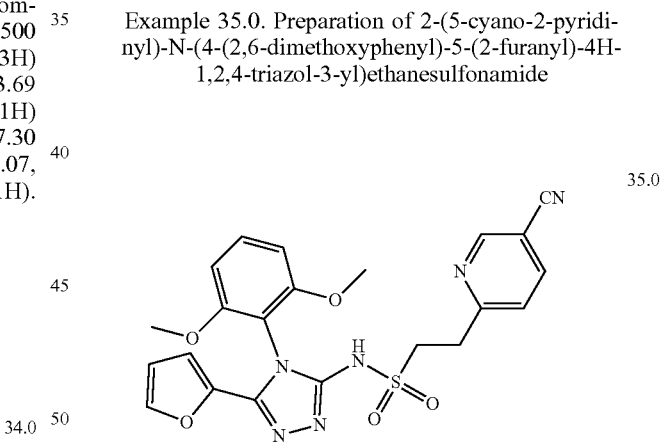

2-(5-Cyano-2-pyridinyl)-N-(4-(2,6-dimethoxyphenyl)-5-(2-furanyl)-4H-1,2,4-triazol-3-yl)ethanesulfonamide, Example 35.0. To a solution of 2-(5-bromopyridin-2-yl)-N-(4-(2,6-dimethoxyphenyl)-5-(furan-2-yl)-4H-1,2,4-triazol-3-yl)ethanesulfonamide (101.8 mg, 0.191 mmol) in DMF (1.5 mL) was added tetrakis(triphenylphosphine)palladium (0) (29.3 mg, 0.025 mmol) and zinc cyanide (33 mg, 0.281 mmol). The resulting mixture was heated in a microwave for 30 min at 120° C. under argon. The reaction was then filtered through a syringe filter, rinsed with MeOH, and then concentrated in vacuo. The material was purified by reverse-phase preparative HPLC using an Agilent Eclipse Plus C18 column, 0.1% TFA in ACN/H$_2$O, gradient 30% to 60% over 25 min. Desired fractions were lyophilized overnight to give the title compound (40.9 mg, 0.085 mmol, 44.7% yield). $^1$H NMR (500 MHz, CDCl$_3$) δ 3.32-3.38 (m, 2H) 3.47-3.54 (m, 2H) 3.74 (app s, 6H) 6.01 (d, J=3.42 Hz, 1H) 6.34 (dd, J=3.42, 1.71 Hz, 1H) 6.68 (d, J=8.31 Hz, 2H) 7.33 (d, J=8.07 Hz, 1H) 7.48 (m, J=17.12 Hz, 2H) 7.86 (dd, J=8.19, 2.08 Hz, 1H) 8.78 (d, J=1.71 Hz, 1H). LCMS ESI (pos.) m/z: 481.1 (M+H)$^+$.

Example 36.0. Preparation of (2R)-1-(5-bromo-2-pyrimidinyl)-N-(4-(2,6-dimethoxyphenyl)-5-(2-furanyl)-4H-1,2,4-triazol-3-yl)-2-propanesulfonamide or (2S)-1-(5-bromo-2-pyrimidinyl)-N-(4-(2,6-dimethoxyphenyl)-5-(2-furanyl)-4H-1,2,4-triazol-3-yl)-2-propanesulfonamide

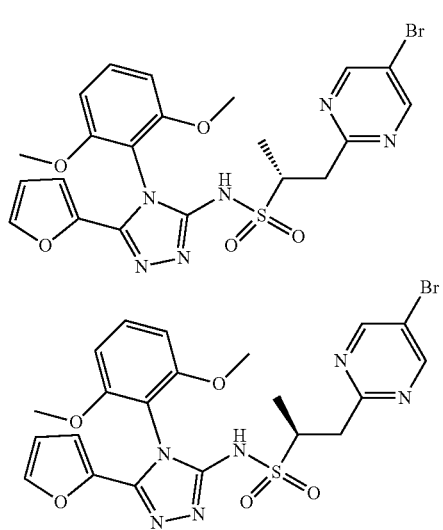

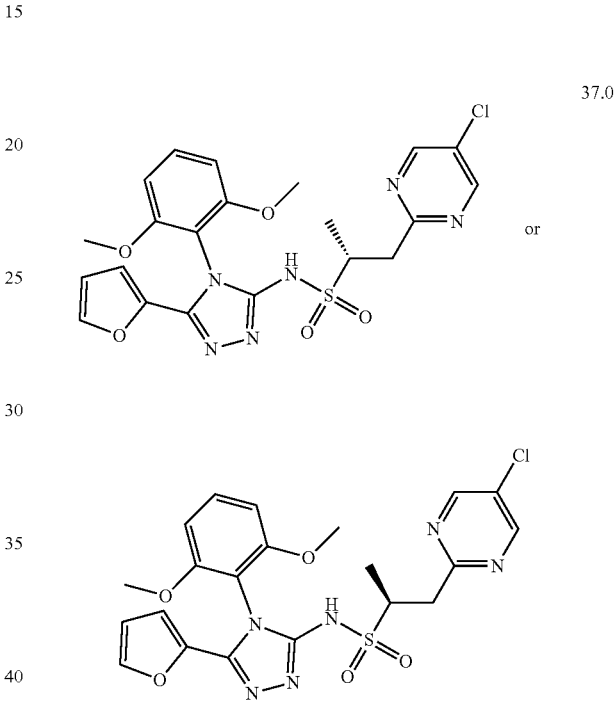

(2R)-1-(5-Bromo-2-pyrimidinyl)-N-(4-(2,6-dimethoxyphenyl)-5-(2-furanyl)-4H-1,2,4-triazol-3-yl)-2-propanesulfonamide or (2S)-1-(5-bromo-2-pyrimidinyl)-N-(4-(2,6-dimethoxyphenyl)-5-(2-furanyl)-4H-1,2,4-triazol-3-yl)-2-propanesulfonamide. To a 0° C. suspension of 1-(5-bromopyrimidin-2-yl)propane-2-sulfonic acid (295 mg, 1.049 mmol) in DCM (5 mL) was added oxalyl chloride (0.12 mL, 1.371 mmol, 1.3 eq) followed by DMF (1 drop). The reaction was stirred for 2 h. The reaction was then concentrated to dryness, azeotroped twice with benzene, and then dried under high vacuum. To a 0° C. suspension of 4-(2,6-dimethoxyphenyl)-5-(furan-2-yl)-4H-1,2,4-triazol-3-amine, Example 362.03, (150 mg, 0.524 mmol) in THF (3 mL) was added potassium bis(trimethylsilyl)amide (1 M solution in THF, 1.6 mL, 1.600 mmol). The amino triazole solution (still at 0° C.) was added to a 0° C. suspension of the sulfonyl chloride in THF (3 mL) dropwise over 5 min. Once the addition was complete, the cooling bath was removed and the brown mixture was warmed to RT overnight. The reaction was then quenched with water (0.5 mL) and then concentrated to dryness. The initial material was purified by reverse-phase preparative HPLC using an Agilent SB C8 column, 0.1% TFA in ACN/H$_2$O, gradient 10% to 70% over 25 min. The desired fractions were lyophilized overnight to give the racemate (53.2 mg, 0.097 mmol, 18.48% yield). Chiral separation was performed with an IA column eluting with 35% MeOH/CO$_2$, 100 bar, 60 mL/min. The second peak to elute on the IA column was the title compound (13.5 mg, 0.025 mmol, 4.69% yield). $^1$H NMR (500 MHz, CDCl$_3$) δ 1.31 (d, J=6.60 Hz, 3H) 3.04 (dd, J=14.67, 9.78 Hz, 1H) 3.65 (dd, J=14.92, 4.16 Hz, 1H) 3.76 (d, J=9.29 Hz, 6H) 3.79-3.87 (m, 1H) 6.00 (d, J=3.18 Hz, 1H) 6.34 (br. s., 1H) 6.68 (d, J=6.60 Hz, 2H) 7.37-7.67 (m, 2H) 8.72 (s, 2H) 11.08 (br. s., 1H). LCMS ESI (pos.) m/z: 549.1 (M+H)$^+$.

Example 37.0. Preparation of (2R)-1-(5-chloro-2-pyrimidinyl)-N-(4-(2,6-dimethoxyphenyl)-5-(2-furanyl)-4H-1,2,4-triazol-3-yl)-2-propanesulfonamide or (2S)-1-(5-chloro-2-pyrimidinyl)-N-(4-(2,6-dimethoxyphenyl)-5-(2-furanyl)-4H-1,2,4-triazol-3-yl)-2-propanesulfonamide (2R)-1-(5-Chloro-2-pyrimidinyl)-N-(4-(2,6-dimethoxyphenyl)-5-(2-furanyl)-4H-1,2,4-triazol-3-yl)-2-propanesulfonamide or (2S)-1-(5-chloro-2-pyrimidinyl)-N-(4-(2,6-dimethoxyphenyl)-5-(2-furanyl)-4H-1,2,4-triazol-3-yl)-2-propanesulfonamide, Example 37.0. To a solution of 1-(5-chloropyrimidin-2-yl)-N-(4-(2,6-dimethoxyphenyl)-5-(furan-2-yl)-4H-1,2,4-triazol-3-yl)-N-(2-(trimethylsilyl)ethyl)propane-2-sulfonamide (20.7 mg, 0.034 mmol) in DMF (0.5 mL) was added tris(dimethylamino)sulfonium difluorotrimethylsilicate (85 mg, 0.309 mmol). The resulting solution was heated at 60° C. over 4 h. The reaction mixture was then cooled to RT. The material obtained was purified by reverse-phase preparative HPLC using an Agilent SB C8 column, 0.1% TFA in ACN/H$_2$O, gradient 10% to 70% over 25 min. The desired fraction was lyophilized overnight. The second peak to separate on the AD-H column eluted with 20% MeOH/100 bar CO$_2$ 45 mins was isolated to give the title compound (4.1 mg, 8.12 µl, 24% yield). $^1$H NMR (500 MHz, CDCl$_3$) δ 1.31 (d, J=6.85 Hz, 3H) 3.06 (dd, J=14.92, 9.78 Hz, 1H) 3.67 (dd, J=14.92, 4.40 Hz, 1H) 3.76 (d, J=9.54 Hz, 6H) 3.78-3.84 (m, 1H) 6.00 (d, J=3.67 Hz, 1H) 6.33 (dd, J=3.42, 1.47 Hz, 1H) 6.68 (dd, J=8.56, 2.93 Hz, 2H) 7.43-7.51 (m, 2H) 8.62 (s, 2H) 11.07 (br. s., 1H). LCMS ESI (pos.) m/z: 505.1 (M+H)$^+$.

Example 38.0. Preparation of (2S)—N-(4-(2,6-dimethoxyphenyl)-5-(5-methyl-2-furanyl)-4H-1,2,4-triazol-3-yl)-1-(5-methyl-2-pyrazinyl)-2-propanesulfonamide or (2R)—N-(4-(2,6-dimethoxyphenyl)-5-(5-methyl-2-furanyl)-4H-1,2,4-triazol-3-yl)-1-(5-methyl-2-pyrazinyl)-2-propanesulfonamide 38.1

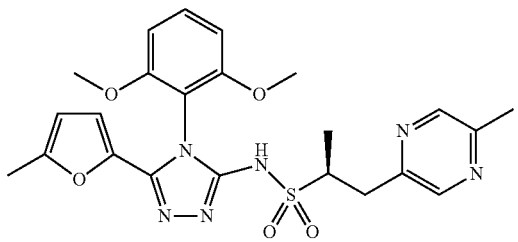

and

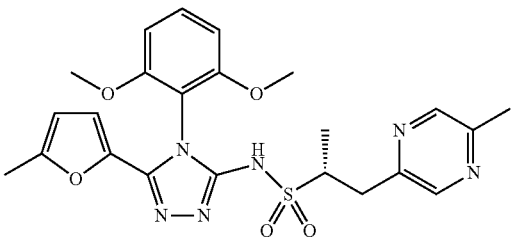

38.0

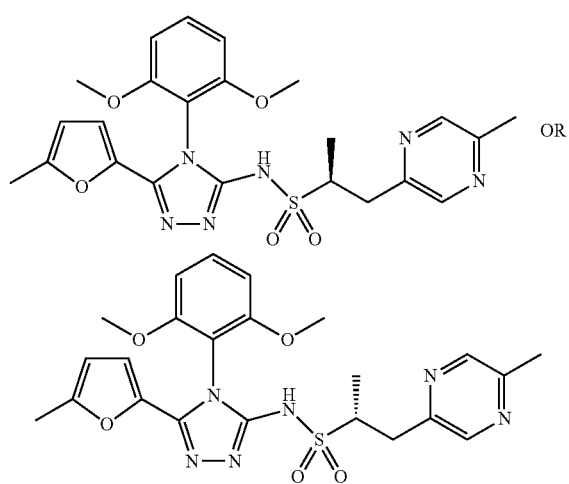

(2S)—N-(4-(2,6-Dimethoxyphenyl)-5-(5-methyl-2-furanyl)-4H-1,2,4-triazol-3-yl)-1-(5-methyl-2-pyrazinyl)-2-propanesulfonamide and (2R)—N-(4-(2,6-dimethoxyphenyl)-5-(5-methyl-2-furanyl)-4H-1,2,4-triazol-3-yl)-1-(5-methyl-2-pyrazinyl)-2-propanesulfonamide, Example 38.0. The title compound was prepared employing Example 367.0 and following the general procedure described in Example 70.0. LCMS-ESI (pos.) m/z: 499.0 (M+H)+.

(2S)—N-(4-(2,6-Dimethoxyphenyl)-5-(5-methyl-2-furanyl)-4H-1,2,4-triazol-3-yl)-1-(5-methyl-2-pyrazinyl)-2-propanesulfonamide or (2R)—N-(4-(2,6-dimethoxyphenyl)-5-(5-methyl-2-furanyl)-4H-1,2,4-triazol-3-yl)-1-(5-methyl-2-pyrazinyl)-2-propanesulfonamide, Example 38.0. Purification of Example 38.1 by SFC [30×250 mm AD-H column with 28 g/min EtOH (neat) in 52 g/min CO₂ at 100 bar] afforded two enantiomers. The title compound was the second isomer to elute on subjecting Example 38.1 to the SFC conditions described above. ¹H NMR (500 MHz, CDCl₃) δ 10.93 (br. s., 1H) 8.40 (s, 1H) 8.32 (s, 1H) 7.47 (t, J=8.56 Hz, 1H) 6.68 (dd, J=8.56, 1.47 Hz, 2H) 5.86-5.97 (m, 1H) 5.80 (d, J=3.42 Hz, 1H) 3.75 (d, J=3.91 Hz, 6H) 3.57 (ddd, J=10.21, 6.66, 4.16 Hz, 1H) 3.46-3.55 (m, 1H) 2.85 (dd, J=13.82, 9.90 Hz, 1H) 2.55 (s, 3H) 2.32 (s, 3H) 1.26 (d, J=6.60 Hz, 3H). LCMS-ESI (pos.) m/z: 499.0 (M+H)+.

Example 39.0. Preparation of N-(4-(2,6-dimethoxyphenyl)-5-(2-furanyl)-4H-1,2,4-triazol-3-yl)-2-(5-methyl-2-pyrimidinyl)ethanesulfonamide

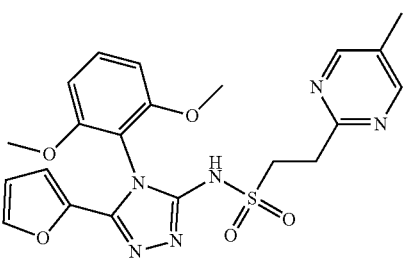 [SMILES: COc1cccc(OC)c1-n1c(NS(=O)(=O)CCc2ncc(C)cn2)nnc1-c1ccco1]

N-(4-(2,6-Dimethoxyphenyl)-5-(2-furanyl)-4H-1,2,4-triazol-3-yl)-2-(5-methyl-2-pyrimidinyl)ethanesulfonamide, Example 39.0. To a 0° C. suspension of 2-(5-methylpyrimidin-2-yl)ethanesulfonic acid (324 mg, 1.60 mmol, prepared in an analogous manner to that described in Example 352.2 employing 2-chloro-5-methylpyrimidine) in DCM (4 mL)) was added oxalyl chloride (175 µL, 2.0 mmol, 1.25 eq.) followed by DMF (1 drop). The reaction was stirred for 2 h. The reaction was then concentrated to dryness, azeotroped twice with benzene, and then dried under high vacuum. To a 0° C. suspension of 4-(2,6-dimethoxyphenyl)-5-(furan-2-yl)-4H-1,2,4-triazol-3-amine (Example 362.03, 152 mg, 0.53 mmol) in THF (4 mL) was added potassium bis(trimethylsilyl)amide (1 M solution in THF, 1.2 mL, 1.2 mmol). The amino triazole solution (still at 0° C.) was then added to a 0° C. suspension of the sulfonyl chloride in THF (4 mL), dropwise over 3 min. Once the addition was complete, the cooling bath was removed and the mixture was warmed to RT for 4 h. The reaction was quenched with water (0.5 mL). The initial material obtained was concentrated down to an oil and then redissolved using water and MeOH. The material was purified by reverse-phase preparative HPLC using an Agilent SB C8 column, 0.1% TFA in ACN/H₂O, gradient 10% to 50% over 25 min. The desired fraction was lyophilized to give N-(4-(2,6-dimethoxyphenyl)-5-(2-furanyl)-4H-1,2,4-triazol-3-yl)-2-(5-methyl-2-pyrimidinyl)ethanesulfonamide, Example 39.0 (39.7 mg, 0.084 mmol, 16% yield). ¹H NMR (500 MHz, CDCl₃) δ 2.35 (s, 3H) 3.37-3.51 (m, 2H) 3.52-3.66 (m, 2H) 3.75 (app s, 6H) 6.01 (dd, J=3.67, 0.49 Hz, 1H) 6.34 (dd, J=3.42, 1.71 Hz, 1H) 6.68 (d, J=8.56 Hz, 2H) 7.36-7.52 (m, 2H) 8.62 (s, 2H). LCMS ESI (pos.) m/z: 471.1 (M+H)+.

Example 40.0. Preparation of (1R,2S)-1-(5-cyano-2-pyridinyl)-N-(4-(2,6-dimethoxyphenyl)-5-(5-methyl-2-furanyl)-4H-1,2,4-triazol-3-yl)-1-hydroxy-2-propanesulfonamide or (1S,2R)-1-(5-cyano-2-pyridinyl)-N-(4-(2,6-dimethoxyphenyl)-5-(5-methyl-2-furanyl)-4H-1,2,4-triazol-3-yl)-1-hydroxy-2-propanesulfonamide Example 41.0. Preparation of N-(4-(2,6-dimethoxyphenyl)-5-(2-furanyl)-4H-1,2,4-triazol-3-yl)-2-(5-fluoro-2-pyridinyl)ethanesulfonamide

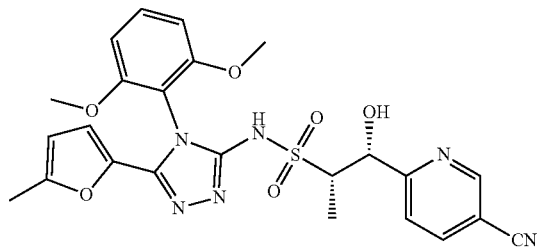

40.0

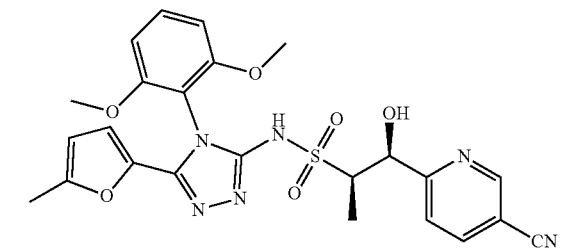

41.0

(1R,2S)-1-(5-Cyano-2-pyridinyl)-N-(4-(2,6-dimethoxyphenyl)-5-(5-methyl-2-furanyl)-4H-1,2,4-triazol-3-yl)-1-hydroxy-2-propanesulfonamide or (1S,2R)-1-(5-cyano-2-pyridinyl)-N-(4-(2,6-dimethoxyphenyl)-5-(5-methyl-2-furanyl)-4H-1,2,4-triazol-3-yl)-1-hydroxy-2-propanesulfonamide, Example 40.0. To a solution of (1R,2S)-1-(5-bromopyridin-2-yl)-N-(4-(2,6-dimethoxyphenyl)-5-(5-methylfuran-2-yl)-4H-1,2,4-triazol-3-yl)-1-hydroxypropane-2-sulfonamide 2,2,2-trifluoroacetate (prepared in Example 10.1, 113 mg, 0.16 mmol) in DMF (2 mL) was added tetrakis(triphenylphosphine)palladium(0) (40 mg, 0.035 mmol) and zinc cyanide (30.5 mg, 0.26 mmol). The resulting mixture was heated in a microwave for 60 min at 120° C. under argon. The material was filtered through a syringe filter and then purified by reverse-phase preparative HPLC using an Agilent SB C8 column, 0.1% TFA in ACN/H$_2$O, gradient 30% to 80% over 25 min. The desired fraction was lyophilized overnight to give a racemic mixture of the title compound (30.4 mg, 0.058 mmol, 36% yield) as a TFA salt. Chiral separation was performed with an OJ-H column eluting with 50% MeOH/CO$_2$, 100 bar, 80 mL/min. The first peak to elute on the OJ-H column was the title compound (10.16 mg, 0.019 mmol, 12% yield). $^1$H NMR (500 MHz, MeOH) δ 1.19 (d, J=6.60 Hz, 3H) 2.26 (s, 3H) 3.46-3.66 (m, 1H) 3.79 (d, J=9.29 Hz, 6H) 4.99 (d, J=5.62 Hz, 1H) 5.95 (d, J=2.93 Hz, 1H) 6.02 (d, J=2.44 Hz, 1H) 6.86 (dd, J=8.19, 5.99 Hz, 2H) 7.57 (t, J=8.56 Hz, 1H) 7.62 (d, J=8.07 Hz, 1H) 8.01-8.14 (m, 1H) 8.81 (s, 1H). LCMS ESI (pos.) m/z: 525.1 (M+H)$^+$.

N-(4-(2,6-Dimethoxyphenyl)-5-(2-furanyl)-4H-1,2,4-triazol-3-yl)-2-(5-fluoro-2-pyridinyl)ethanesulfonamide, Example 41.0. Diethyl ((N-(4-(2,6-dimethoxyphenyl)-5-(furan-2-yl)-4H-1,2,4-triazol-3-yl)-N-(2-(trimethylsilyl)ethyl)sulfamoyl)methyl)phosphonate (Example 365.0, 41 mg, 0.068 mmol) was dissolved in THF (0.5 mL). To this was added lithium bis(trimethylsilyl)amide, (1.0 M solution in THF, 0.085 mL, 0.085 mmol). After 15 min, 5-fluoro-2-formylpyridine (14.1 mg, 0.113 mmol) was added. After 2.75 h, the reaction was quenched with MeOH (0.5 mL), concentrated to dryness, and dried under high vacuum. The olefin was dissolved in EtOH (1.0 mL) and palladium, 10 wt. % on activated carbon (43.0 mg, 0.040 mmol) was added. The resulting mixture was stirred under a hydrogen atmosphere at RT overnight. The reaction was passed through a syringe filter, the filter was rinsed with EtOAc and DCM, and then concentrated to dryness. The filtrate was dissolved in TBAF, (1.0 M solution in THF, 1.0 mL, 1.00 mmol). The resulting solution was heated at 60° C. in a sealed vial for 4 h. The reaction mixture was concentrated to remove the THF. The initial material was purified by reverse-phase preparative HPLC using an Agilent Eclipse Plus C18 column, 0.1% TFA in ACN/H$_2$O, gradient 10% to 50% over 25 min. The desired fractions were then lyophilized overnight. The material thus obtained was absorbed onto a plug of silica gel and purified by chromatography through a Redi-Sep pre-packed silica gel column (4 g), eluting with a gradient of 0% to 6% MeOH in DCM to give the title compound (5.2 mg, 11.0 μmol, 16% yield). $^1$H NMR (400 MHz, CDCl$_3$) δ 3.22-3.31 (m, 2H) 3.44-3.51 (m, 2H) 3.74 (app s, 6H) 6.00 (dd, J=3.52, 0.59 Hz, 1H) 6.34 (dd, J=3.62, 1.86 Hz, 1H) 6.67 (d, J=8.61 Hz, 2H) 7.18 (dd, J=8.61, 4.30 Hz, 1H) 7.32 (td, J=8.41, 2.93 Hz, 1H) 7.41-7.50 (m, 2H) 8.37 (d, J=2.93 Hz, 1H) 11.03 (br. s., 1H). LCMS ESI (pos.) m/z: 214.1 (M+H)$^+$.

Example 42.0. Preparation of (2R)—N-(4-(2,6-dimethoxyphenyl)-5-(2-furanyl)-4H-1,2,4-triazol-3-yl)-1-(6-methyl-3-pyridazinyl)-2-propanesulfonamide or (2S)—N-(4-(2,6-dimethoxyphenyl)-5-(2-furanyl)-4H-1,2,4-triazol-3-yl)-1-(6-methyl-3-pyridazinyl)-2-propanesulfonamide Example 43.0. Preparation of (2R)—N-(4-(2,6-dimethoxyphenyl)-5-(5-methyl-2-furanyl)-4H-1,2,4-triazol-3-yl)-1-(6-methyl-3-pyridazinyl)-2-propanesulfonamide or (2S)—N-(4-(2,6-dimethoxyphenyl)-5-(5-methyl-2-furanyl)-4H-1,2,4-triazol-3-yl)-1-(6-methyl-3-pyridazinyl)-2-propanesulfonamide

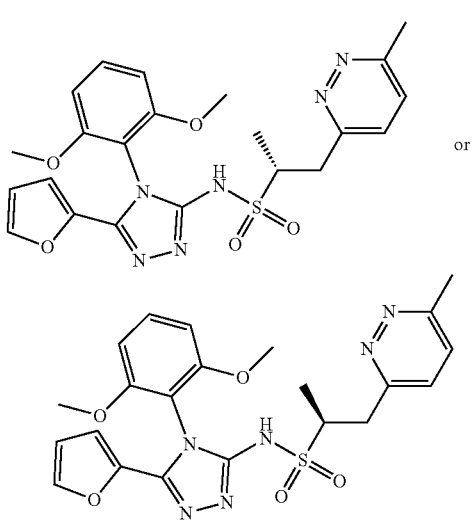

or

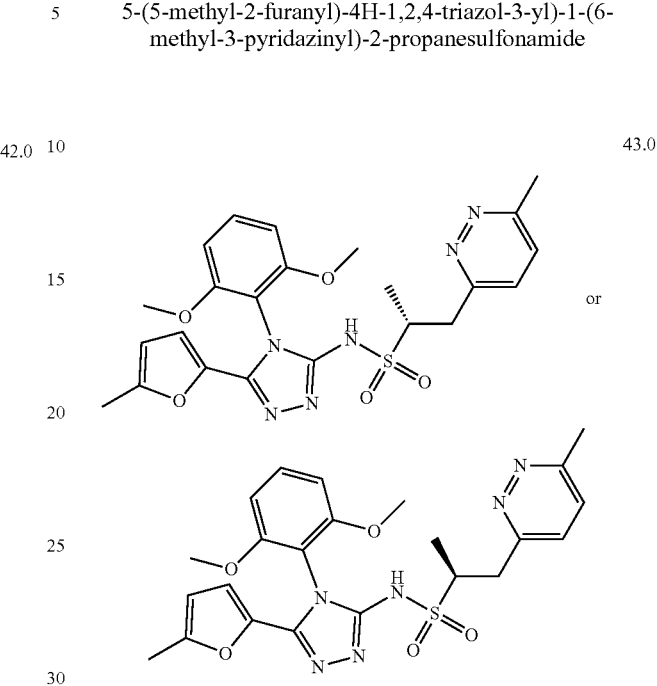

(2R)—N-(4-(2,6-dimethoxyphenyl)-5-(2-furanyl)-4H-1,2,4-triazol-3-yl)-1-(6-methyl-3-pyridazinyl)-2-propanesulfonamide or (2S)—N-(4-(2,6-dimethoxyphenyl)-5-(2-furanyl)-4H-1,2,4-triazol-3-yl)-1-(6-methyl-3-pyridazinyl)-2-propanesulfonamide, Example 42.0. To a 0° C. suspension of 1-(6-methylpyridazin-3-yl)propane-2-sulfonic acid (prepared in an analogous fashion to that described in Example 351.0, 225 mg, 1.04 mmol) in DCM (5 mL) was added oxalyl chloride (120 µL, 1.37 mmol, 1.3 eq) followed by DMF (0.383 mg, 5.24 µmop. The reaction was stirred at RT for 2 h. The reaction was concentrated to dryness, azeotroped twice with benzene and then dried under high vacuum. A very dark blue-green solid was isolated. To an orange slurry of 4-(2,6-dimethoxyphenyl)-5-(furan-2-yl)-4H-1,2,4-triazol-3-amine (Example 362.03, 150 mg, 0.524 mmol) in THF (4 mL) was added potassium tert-butoxide (1.0 M solution in THF, 1.0 mL, 1.00 mmol) dropwise over 1 min. After stirring for 10 min, the solution was added to a slurry of the sulfonyl chloride in THF (4 mL). The reaction was stirred at RT for 3 h. The reaction was quenched with water (0.3 mL) and then concentrated to dryness. The initial material was purified by reverse-phase preparative HPLC using an Agilent SB C8 column, 0.1% TFA in ACN/H$_2$O, gradient 10% to 50% over 25 min. The desired fraction was lyophilized overnight to give the title compound as a racemic mixture (18.2 mg, 0.038 mmol, 7% yield). Chiral separation was performed with an IA column eluting with 27% MeOH/CO$_2$, 100 bar, 60 mL/min. The first peak to elute on the IA column was the title compound (3.0 mg, 6.19 µmol, 1% yield). $^1$H NMR (500 MHz, CDCl$_3$) δ 1.28-1.37 (m, 3H) 2.70 (s, 3H) 3.07 (dd, J=13.69, 9.78 Hz, 1H) 3.52-3.62 (m, 1H) 3.62-3.69 (m, 1H) 3.78 (s, 3H) 3.78 (s, 3H) 6.01 (dd, J=3.67, 0.49 Hz, 1H) 6.33 (dd, J=3.67, 1.71 Hz, 1H) 6.68 (dd, J=8.56, 3.42 Hz, 2H) 7.16-7.32 (m, 2H) 7.38-7.54 (m, 2H) 10.99 (br. s., 1H). LCMS ESI (pos.) m/z: 485.1 (M+H)$^+$.

(2R)—N-(4-(2,6-dimethoxyphenyl)-5-(5-methyl-2-furanyl)-4H-1,2,4-triazol-3-yl)-1-(6-methyl-3-pyridazinyl)-2-propanesulfonamide or (2S)—N-(4-(2,6-dimethoxyphenyl)-5-(5-methyl-2-furanyl)-4H-1,2,4-triazol-3-yl)-1-(6-methyl-3-pyridazinyl)-2-propanesulfonamide, Example 43.0. To a 0° C. suspension of 1-(6-methylpyridazin-3-yl)propane-2-sulfonic acid (prepared in an analogous fashion to that described in Example 351.0, 310 mg, 1.433 mmol) in DCM (10 mL) was added oxalyl chloride (240 µL, 2.74 mmol) followed by DMF (4.89 mg, 0.067 mmol). The reaction was stirred for 3 h. The reaction was then concentrated to dryness, azeotroped twice with benzene, and dried under high vacuum. To a slurry of 4-(2,6-dimethoxyphenyl)-5-(5-methylfuran-2-yl)-4H-1,2,4-triazol-3-amine (Example 367.0, 201 mg, 0.669 mmol) in THF (5 mL) was added potassium tert-butoxide, 1.0 M solution in THF (0.8 mL, 0.800 mmol) dropwise over one min. After stirring for 10 min, this slurry was added to a slurry of the sulfonyl chloride in THF (10 mL). The reaction was stirred at RT for 6 h. The reaction was quenched with water (0.2 mL) and then concentrated to dryness. The initial material was purified by reverse-phase preparative HPLC using an Agilent SB C8 column, 0.1% TFA in ACN/H$_2$O, gradient 10% to 50% over 25 min. The desired fraction was lyophilized overnight to give a racemic mixture of the title compound (37 mg, 0.074 mmol, 11% yield). Chiral separation was performed with an AD-H column eluting with 32% MeOH/CO$_2$, 100 bar, 60 mL/min. The second peak to elute on the AD-H column was the title compound (12 mg, 0.024 mmol, 4% yield). $^1$H NMR (500 MHz, CDCl$_3$) δ 1.30 (d, J=6.85 Hz, 3H) 2.32 (s, 3H) 2.69 (s, 3H) 3.05 (dd, J=13.94, 10.03 Hz, 1H) 3.59 (ddd, J=10.21, 6.66, 3.91 Hz, 1H) 3.62-3.67 (m, 1H) 3.77 (s, 3H) 3.77 (s, 3H) 5.81 (d, J=3.42 Hz, 1H) 5.91 (dd, J=3.42, 0.73 Hz, 1H) 6.66 (d, J=3.18 Hz, 1H) 6.68 (d, J=3.18 Hz, 1H) 7.22-7.28 (m, 2H) 7.45 (t, J=8.44 Hz, 1H) 10.96 (br. s., 1H). LCMS ESI (pos.) m/z: 499.2 (M+H)$^+$.

Example 44.0. Preparation of (2R)—N-(4-(2,6-dimethoxyphenyl)-5-(2-furanyl)-4H-1,2,4-triazol-3-yl)-1-(4-pyrimidinyl)-2-propanesulfonamide or (2S)—N-(4-(2,6-dimethoxyphenyl)-5-(2-furanyl)-4H-1,2,4-triazol-3-yl)-1-(4-pyrimidinyl)-2-propanesulfonamide

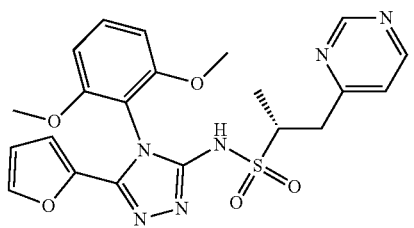

44.0 or

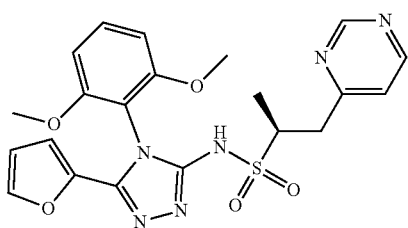

(2R)—N-(4-(2,6-Dimethoxyphenyl)-5-(2-furanyl)-4H-1,2,4-triazol-3-yl)-1-(4-pyrimidinyl)-2-propanesulfonamide and (2S)—N-(4-(2,6-dimethoxyphenyl)-5-(2-furanyl)-4H-1,2,4-triazol-3-yl)-1-(4-pyrimidinyl)-2-propanesulfonamide, Example 44.0. To a solution of N-(4-(2,6-dimethoxyphenyl)-5-(furan-2-yl)-4H-1,2,4-triazol-3-yl)-1-(pyrimidin-5-yl)-N-(2-(trimethylsilyl)ethyl)propane-2-sulfonamide (made in analogous fashion to that described in Example 4.0 using pyrimidine-4-carbaldehyde from Aldrich) in DMF (1 mL) was added tris(dimethylamino)sulfonium difluorotrimethylsilicate. The resulting solution was heated at 60° C. After 4 h of heating, the reaction was cooled to RT and allowed to stand overnight. The material was purified by reverse-phase preparative HPLC using an Agilent SB C18 column, 0.1% TFA in ACN/H$_2$O, gradient 10% to 60% over 25 min. The desired fractions were combined and then lyophilized overnight to give a racemic mixture of the title compound. Chiral separation was then performed with an AD column eluting with 20% MeOH/CO$_2$, 100 bar, 60 mL/min. The first peak to elute on the AD column was the title compound (7.9 mg, 0.017 mmol, 42% yield). $^1$H NMR (500 MHz, CDCl$_3$) δ 1.27-1.38 (m, 3H) 2.84 (dd, J=14.31, 9.90 Hz, 1H) 3.44-3.58 (m, 1H) 3.61-3.71 (m, 1H) 3.75 (d, J=2.45 Hz, 6H) 6.00 (d, J=3.67 Hz, 1H) 6.34 (dd, J=3.42, 1.71 Hz, 1H) 6.68 (dd, J=8.44, 2.81 Hz, 2H) 7.20 (d, J=4.89 Hz, 1H) 7.37-7.52 (m, 2H) 8.61 (d, J=5.13 Hz, 1H) 9.13 (s, 1H) 11.01 (br. s., 1H). LCMS ESI (pos.) m/z: 471.1 (M+H)$^+$.

Example 45.0. Preparation of (2R)—N-(4-(2,6-dimethoxyphenyl)-5-(2-furanyl)-4H-1,2,4-triazol-3-yl)-1-(5-pyrimidinyl)-2-propanesulfonamide or (2S)—N-(4-(2,6-dimethoxyphenyl)-5-(2-furanyl)-4H-1,2,4-triazol-3-yl)-1-(5-pyrimidinyl)-2-propanesulfonamide

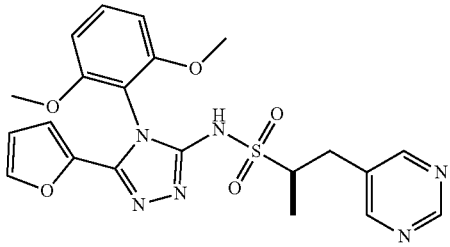

45.0 or

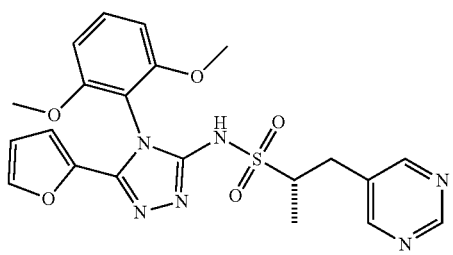

(2R)—N-(4-(2,6-Dimethoxyphenyl)-5-(2-furanyl)-4H-1,2,4-triazol-3-yl)-1-(5-pyrimidinyl)-2-propanesulfonamide or (2S)—N-(4-(2,6-dimethoxyphenyl)-5-(2-furanyl)-4H-1,2,4-triazol-3-yl)-1-(5-pyrimidinyl)-2-propanesulfonamide, Example 45.0. To a solution of N-(4-(2,6-dimethoxyphenyl)-5-(furan-2-yl)-4H-1,2,4-triazol-3-yl)-1-(pyrimidin-5-yl)-N-(2-(trimethylsilyl)ethyl)propane-2-sulfonamide (made in analogous fashion to that described in Example 4.0 using pyrimidine-5-carbaldehyde from Aldrich) in 1 mL of DMF was added tris(dimethylamino)sulfonium difluorotrimethylsilicate. The resulting solution was heated at 60° C. After 4 h of heating, the reaction was cooled to RT and allowed to stand overnight. The material was purified by reverse-phase preparative HPLC using an Agilent SB C18 column, 0.1% TFA in ACN/H$_2$O, gradient 10% to 60% over 25 min. The desired fractions were combined and then lyophilized overnight to give a racemic mixture of the title compound (19 mg, 0.040 mmol, 80% yield). The first peak to elute to elute from the AD column was the title compound (8.5 mg, 0.018 mmol, 45% yield). $^1$H NMR (500 MHz, CDCl$_3$) δ 1.25 (d, J=6.85 Hz, 3H) 2.69 (dd, J=14.18, 10.27 Hz, 1H) 3.21 (ddd, J=10.33, 6.79, 3.91 Hz, 1H) 3.41 (dd, J=14.06, 3.79 Hz, 1H) 3.75 (d, J=7.82 Hz, 6H) 5.99 (d, J=3.42 Hz, 1H) 6.34 (dd, J=3.67, 1.71 Hz, 1H) 6.70 (dd, J=8.56, 1.22 Hz, 2H) 7.38-7.60 (m, 2H) 8.56 (s, 2H) 9.10 (s, 1H) 11.07 (br. s., 1H). LCMS ESI (pos.) m/z: 471.1 (M+H)$^+$.

Example 46.0. Preparation of (2R)—N-(4-(2,6-dimethoxyphenyl)-5-(2-furanyl)-4H-1,2,4-triazol-3-yl)-1-(4-pyrimidinyl)-2-propanesulfonamide or (2S)—N-(4-(2,6-dimethoxyphenyl)-5-(2-furanyl)-4H-1,2,4-triazol-3-yl)-1-(4-pyrimidinyl)-2-propanesulfonamide

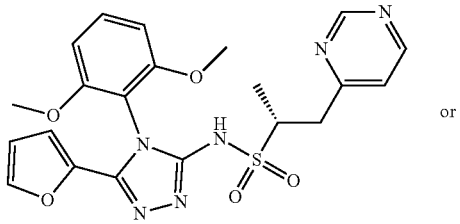

46.0 or

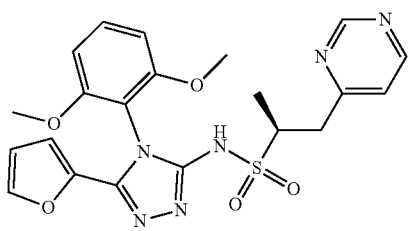

(2R)—N-(4-(2,6-Dimethoxyphenyl)-5-(2-furanyl)-4H-1,2,4-triazol-3-yl)-1-(4-pyrimidinyl)-2-propanesulfonamide or (2S)—N-(4-(2,6-dimethoxyphenyl)-5-(2-furanyl)-4H-1,2,4-triazol-3-yl)-1-(4-pyrimidinyl)-2-propanesulfonamide, Example 46.0. To a solution of N-(4-(2,6-dimethoxyphenyl)-5-(furan-2-yl)-4H-1,2,4-triazol-3-yl)-1-(pyrimidin-5-yl)-N-(2-(trimethylsilyl)ethyl)propane-2-sulfonamide (made in analogous fashion to that described in Example 4.0 using pyrimidine-6-carbaldehyde from Aldrich) in 1 mL of DMF was added tris(dimethylamino)sulfonium difluorotrimethylsilicate. The resulting solution was heated at 60° C. After 4 h of heating, the reaction was cooled to RT and allowed to stand overnight. The material was purified by reverse-phase preparative HPLC using an Agilent SB C18 column, 0.1% TFA in ACN/H$_2$O, gradient 10% to 60% over 25 min. The desired fractions were combined and then lyophilized overnight to give a racemic mixture of the title compound, Chiral separation was performed with an AD column eluting with 20% MeOH/CO$_2$, 100 bar, 60 mL/min. The second peak to elute on the AD column was the title compound (7.0 mg, 0.015 mmol, 36.8% yield). $^1$H NMR (500 MHz, CDCl$_3$) δ 1.30 (d, J=6.85 Hz, 3H) 2.84 (dd, J=14.18, 10.03 Hz, 1H) 3.41-3.57 (m, 1H) 3.61-3.70 (m, 1H) 3.75 (d, J=2.20 Hz, 6H) 6.00 (d, J=3.42 Hz, 1H) 6.34 (d, J=1.71 Hz, 1H) 6.68 (dd, J=8.31, 2.20 Hz, 2H) 7.23 (br. s., 1H) 7.38-7.57 (m, 2H) 8.68 (br. s., 1H) 9.16 (br. s., 1H) 11.02 (br. s., 1H). LCMS ESI (pos.) m/z: 471.1 (M+H)$^+$.

Example 47.0. Preparation of N-(4-(2,6-dimethoxyphenyl)-5-(2-furanyl)-4H-1,2,4-triazol-3-yl)-2-(6-methoxy-3-pyridinyl)ethanesulfonamide

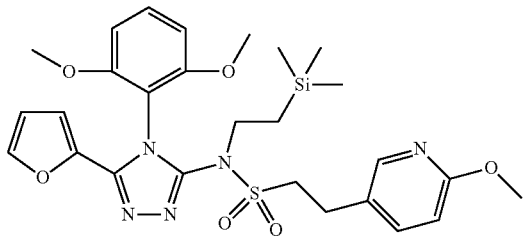

47.1

N-(4-(2,6-Dimethoxyphenyl)-5-(furan-2-yl)-4H-1,2,4-triazol-3-yl)-2-(6-methoxypyridin-3-yl)-N-(2-(trimethylsilyl)ethyl)ethanesulfonamide, Example 47.1. Example 365.0 (41.0 mg, 0.068 mmol) was dissolved in THF (0.5 mL). To this was added lithium bis(trimethylsilyl)amide, (1.0 M solution in THF, 0.085 mL, 0.085 mmol). After 20 min, 6-methoxynicotinaldehyde (15.0 mg, 0.109 mmol) was added. After 30 min, the reaction was quenched with MeOH (0.5 mL) and then concentrated to dryness and dried under high vacuum. The residue was dissolved in EtOAc (0.5 mL), and palladium (10 wt. % on activated carbon, 7.1 mg, 6.67 µmol, 0.5 eq) was added. The resulting mixture was stirred under a hydrogen atmosphere at RT overnight. Next, the mixture was filtered through a syringe filter, the filter was rinsed with EtOAc and DCM, and the filtrated was concentrated in vacuo.

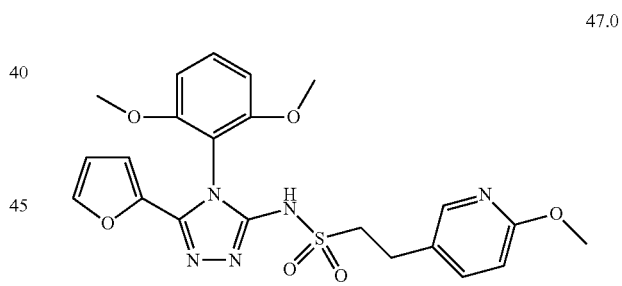

47.0

N-(4-(2,6-Dimethoxyphenyl)-5-(2-furanyl)-4H-1,2,4-triazol-3-yl)-2-(6-methoxy-3-pyridinyl)ethanesulfonamide, Example 47.0. Example 47.1 was dissolved in THF (0.5 mL) and TBAF (1.0 M solution in THF, 0.5 mL, 0.50 mmol) was added. The resulting solution was heated at 60° C. in a sealed vial for 16 h. The reaction mixture was then concentrated in vacuo. The material was purified by reverse-phase preparative HPLC using an Agilent Eclipse Plus C18 column, 0.1% TFA in ACN/H$_2$O, gradient 10% to 50% over 25 min (collected the peaks that were visible at 220 nm). The isolated fractions were lyophilized overnight to give the title compound (6.1 mg, 0.013 mmol, 18% yield). $^1$H NMR (500 MHz, CDCl$_3$) δ 3.02-3.09 (m, 2H) 3.22-3.29 (m, 2H) 3.75 (app s, 6H) 3.96 (s, 3H) 6.00 (dd, J=3.55, 0.61 Hz, 1H) 6.34 (dd, J=3.55, 1.83 Hz, 1H) 6.70 (d, J=8.56 Hz, 2H) 6.76 (d, J=8.56 Hz, 1H) 7.46-7.51 (m, 2H) 7.54 (dd, J=8.56, 2.20 Hz, 1H) 8.04 (br. s., 1H). LCMS ESI (pos.) m/z: 486.1 (M+H)$^+$.

Example 48.0. Preparation of 2-(5-chloro-2-pyridi-nyl)-N-(4-(2,6-dimethoxyphenyl)-5-(2-furanyl)-4H-1,2,4-triazol-3-yl)ethanesulfonamide 48.1

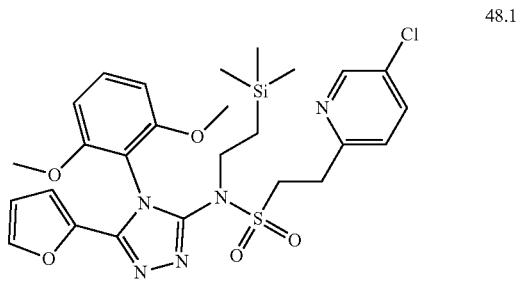 [SMILES: COc1cccc(OC)c1-n1c(-c2ccco2)nnc1N(CC[Si](C)(C)C)S(=O)(=O)CCc1ccc(Cl)cn1]

2-(5-Chloropyridin-2-yl)-N-(4-(2,6-dimethoxyphenyl)-5-(furan-2-yl)-4H-1,2,4-triazol-3-yl)-N-(2-(trimethylsilyl)ethyl)ethanesulfonamide, Example 48.1. To a solution of Example 365.0 (104 mg, 0.173 mmol) in THF (1 mL) was added lithium bis(trimethylsilyl)amide, (1.0 M solution in THF, 200 μL, 0.20 mmol). After 15 min, 5-chloropicolinaldehyde (38 mg, 0.27 mmol) was added. After 2 h, the reaction was quenched with MeOH (0.5 mL) and then concentrated to dryness and dried under high vacuum. The initial material was absorbed onto a plug of silica gel and purified by chromatography through a Redi-Sep pre-packed silica gel column (4 g) eluting with a gradient of 0% to 70% EtOAc in hexanes. The olefin (100 mg, 0.17 mmol) was dissolved in DCM (2 mL) and then hydrogen was bubbled through the solution for 1 min. Then, Crabtree catalyst (467 mg, 0.10 mmol, 0.6 eq) was added. The reaction was stirred overnight. The reaction mixture was absorbed onto a plug of silica gel and purified by chromatography through a Redi-Sep pre-packed silica gel column (4 g) eluting with a gradient of 0% to 100% EtOAc in hexanes. The product eluted at 100% EtOAc to give 2-(5-chloropyridin-2-yl)-N-(4-(2,6-dimethoxyphenyl)-5-(furan-2-yl)-4H-1,2,4-triazol-3-yl)-N-(2-(trimethylsilyl)ethyl)ethanesulfonamide (Example 48.1, 55 mg, 0.093 mmol, 53.8% yield).

48.0

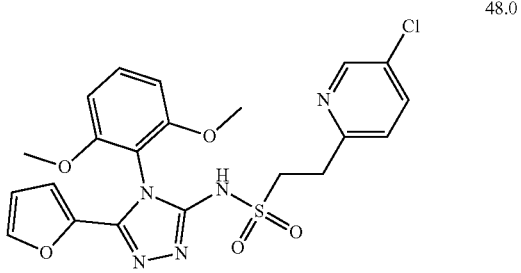 [SMILES: COc1cccc(OC)c1-n1c(NS(=O)(=O)CCc2ccc(Cl)cn2)nnc1-c1ccco1]

2-(5-Chloro-2-pyridinyl)-N-(4-(2,6-dimethoxyphenyl)-5-(2-furanyl)-4H-1,2,4-triazol-3-yl)ethanesulfonamide, Example 48.0. To a solution of Example 48.1 (55 mg, 0.093 mmol) in DMF (1 mL) was added tris(dimethylamino) sulfonium difluorotrimethylsilicate (78.5 mg, 0.29 mmol). The resulting amber solution was heated at 60° C. overnight. The reaction was then cooled to RT. The material was purified by reverse-phase preparative HPLC using an Agilent SB C8 column, 0.1% TFA in ACN/H$_2$O, gradient 10% to 80% over 25 min. The desired fraction was lyophilized overnight to give the title compound (4.22 mg, 9% yield). $^1$H NMR (500 MHz, CD$_2$Cl$_2$) δ 3.20-3.30 (m, 2H) 3.36-3.45 (m, 2H) 3.75 (app s, 6H) 6.06 (d, J=3.67 Hz, 1H) 6.36 (dd, J=3.67, 1.71 Hz, 1H) 6.74 (d, J=8.56 Hz, 2H) 7.25 (d, J=8.56 Hz, 1H) 7.49 (d, J=1.71 Hz, 1H) 7.53 (t, J=8.56 Hz, 1H) 7.71 (dd, J=8.31, 2.45 Hz, 1H) 8.54 (d, J=1.71 Hz, 1H). LCMS ESI (pos.) m/z: 490.1 (M+H)$^+$.

Example 49.0. Preparation of 2-(5-chloro-2-pyrimidinyl)-N-(4-(2,6-dimethoxyphenyl)-5-(2-furanyl)-4H-1,2,4-triazol-3-yl)ethanesulfonamide 49.1

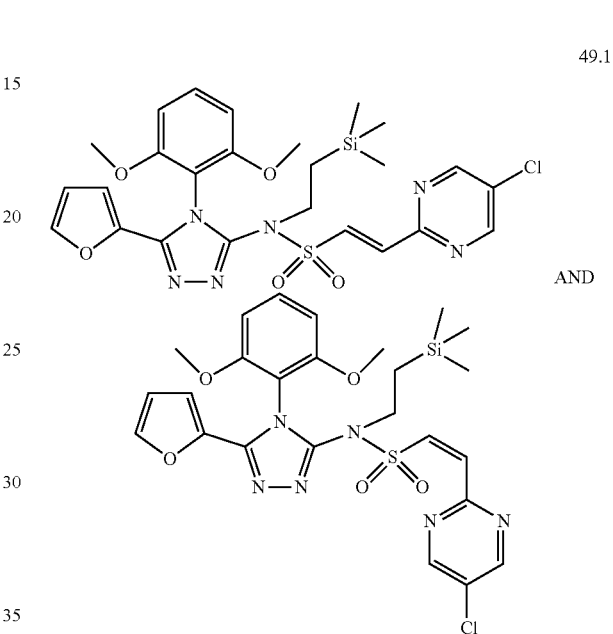

(E)-2-(5-Chloropyrimidin-2-yl)-N-(4-(2,6-dimethoxyphenyl)-5-(furan-2-yl)-4H-1,2,4-triazol-3-yl)-N-(2-(trimethylsilyl)ethyl)ethenesulfonamide and (Z)-2-(5-chloropyrimidin-2-yl)-N-(4-(2,6-dimethoxyphenyl)-5-(furan-2-yl)-4H-1,2,4-triazol-3-yl)-N-(2-(trimethylsilyl)ethyl)ethenesulfonamide, Example 49.1. The title compound was prepared employing 5-chloropyrimidine-2-carbaldehyde (commercially available from Ark Pharm, Inc., Libertyville, Ill., USA) and Example 365.1 following the procedure described in Example 34.0. LCMS-ESI (pos.) m/z: 589.2 (M+H)$^+$.

49.2

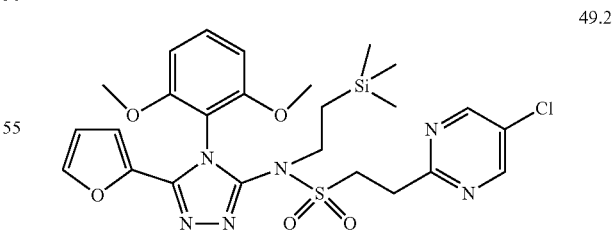

2-(5-Chloropyrimidin-2-yl)-N-(4-(2,6-dimethoxyphenyl)-5-(furan-2-yl)-4H-1,2,4-triazol-3-yl)-N-(2-(trimethylsilyl)ethyl)ethanesulfonamide, Example 49.2. Example 49.1 (322 mg, 0.55 mmol) was dissolved in THF/t-BuOH (1:1 v/v, 10 mL). The solution was briefly sparged with H$_2$ before Wilkinson's catalyst (chlorotris(triphenylphosphine)rhodium (I), (172 mg, 0.19 mmol, commercially available from Strem Chemicals, Inc., Newburyport, Mass., USA)) was added. Hydrogen was introduced at 1 atm (balloon), and the mixture was vigorously stirred for 17 h at RT after which LCMS analysis showed that the reaction was 20% complete. Thus, a second aliquot of Wilkinson's catalyst (203 mg, 0.22 mmol) and THF/t-BuOH (1:1 v/v, 6 mL) was added, and the mixture was stirred for a further 17 h at RT under $H_2$ atmosphere. Thereafter, the mixture was flushed with $N_2$ and concentrated in vacuo. The residue was purified on a silica gel column employing a gradient of 0-100% EtOAc in hexanes to afford 49.2 (147 mg, 0.25 mmol, 45%). LCMS-ESI (pos.) m/z: 591.1 $(M+H)^+$.

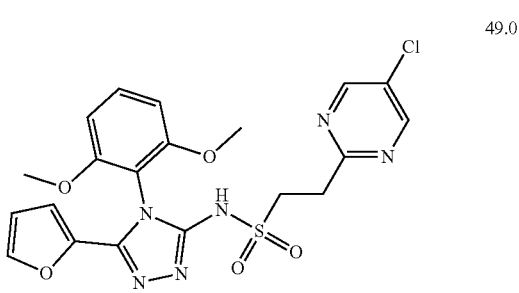 [SMILES: COc1cccc(OC)c1-n1c(NS(=O)(=O)CCc2ncc(Cl)cn2)nnc1-c1ccco1]

49.0

2-(5-Chloro-2-pyrimidinyl)-N-(4-(2,6-dimethoxyphenyl)-5-(2-furanyl)-4H-1,2,4-triazol-3-yl)ethanesulfonamide, Example 49.0. To a solution of 2-(5-chloropyrimidin-2-yl)-N-(4-(2,6-dimethoxyphenyl)-5-(furan-2-yl)-4H-1,2,4-triazol-3-yl)-N-(2-(trimethylsilyl)ethyl)ethane sulfonamide (Example 49.2, 12.1 mg, 0.020 mmol) in DMF (1 mL) was added tris(dimethylamino)sulfur trimethylsilyl difluoride (35 mg, 0.13 mmol, 6.4 equiv). The resulting amber solution was heated at 60° C. overnight. The reaction mixture was then cooled to RT. The material was purified by reverse-phase preparative HPLC using an Agilent SB C8 column, 0.1% TFA in ACN/$H_2O$, gradient 20% to 75% over 25 min. The desired fraction was lyophilized to give Example 49.0 (3.5 mg, 7.13 μmol, 2.88% yield). $^1$H NMR (500 MHz, CDCl$_3$) δ 3.39-3.48 (m, 2H) 3.54-3.63 (m, 2H) 3.76 (app s, 6H) 6.01 (dd, J=3.67, 0.49 Hz, 1H) 6.34 (dd, J=3.55, 1.83 Hz, 1H) 6.68 (d, J=8.56 Hz, 2H) 7.42-7.50 (m, 2H) 8.62 (s, 2H). LCMS ESI (pos.) m/z: 491.1 $(M+H)^+$.

Example 50.0. Preparation of 2-(5-chloro-3-cyano-2-pyridinyl)-N-(4-(2,6-dimethoxyphenyl)-5-(2-furanyl)-4H-1,2,4-triazol-3-yl)ethanesulfonamide

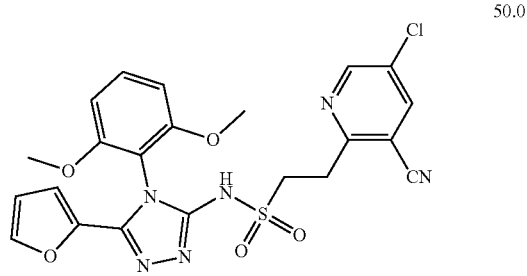 [SMILES: COc1cccc(OC)c1-n1c(NS(=O)(=O)CCc2ncc(Cl)cc2C#N)nnc1-c1ccco1]

50.0

2-(5-Chloro-3-cyano-2-pyridinyl)-N-(4-(2,6-dimethoxyphenyl)-5-(2-furanyl)-4H-1,2,4-triazol-3-yl)ethanesulfonamide, Example 50.0. To a solution of 2-(3-bromo-5-chloropyridin-2-yl)-N-(4-(2,6-dimethoxyphenyl)-5-(furan-2-yl)-4H-1,2,4-triazol-3-yl)ethanesulfonamide (Example 27.3, 151.2 mg, 0.266 mmol) in DMF (2 mL) was added tetrakis(triphenylphosphine)palladium(0) (32 mg, 0.028 mmol) and zinc cyanide (38.1 mg, 0.324 mmol). Argon was bubbled through the mixture for one min and then the microwave vial was sealed. The resulting mixture was heated in a microwave for 8 min 120° C. The reaction was then filtered through a syringe filter, rinsed with MeOH, and concentrated in vacuo. The material thus obtained was purified by reverse-phase preparative HPLC using an Agilent SB C8 column, 0.1% TFA in ACN/$H_2O$, gradient 30% to 60% over 25 min. The desired fractions were lyophilized to give Example 50.0 (107.1 mg, 0.208 mmol, 78% yield). $^1$H NMR (400 MHz, CDCl$_3$) δ 3.42-3.54 (m, 2H) 3.54-3.64 (m, 2H) 3.76 (s, 3H) 3.76 (s, 3H) 6.01 (dd, J=3.62, 0.68 Hz, 1H) 6.33 (dd, J=3.52, 1.76 Hz, 1H) 6.69 (d, J=8.61 Hz, 2H) 7.41-7.51 (m, 2H) 7.87 (d, J=2.35 Hz, 1H) 8.66 (d, J=2.35 Hz, 1H) 10.94 (br. s., 1H). LCMS ESI (pos.) m/z: 515.1 $(M+H)^+$.

Example 52.0. Preparation of (2R)—N-(4-(2,6-dimethoxyphenyl)-5-(2-furanyl)-4H-1,2,4-triazol-3-yl)-1-(5-fluoro-2-pyrimidinyl)-2-propanesulfonamide and (2S)—N-(4-(2,6-dimethoxyphenyl)-5-(2-furanyl)-4H-1,2,4-triazol-3-yl)-1-(5-fluoro-2-pyrimidinyl)-2-propanesulfonamide

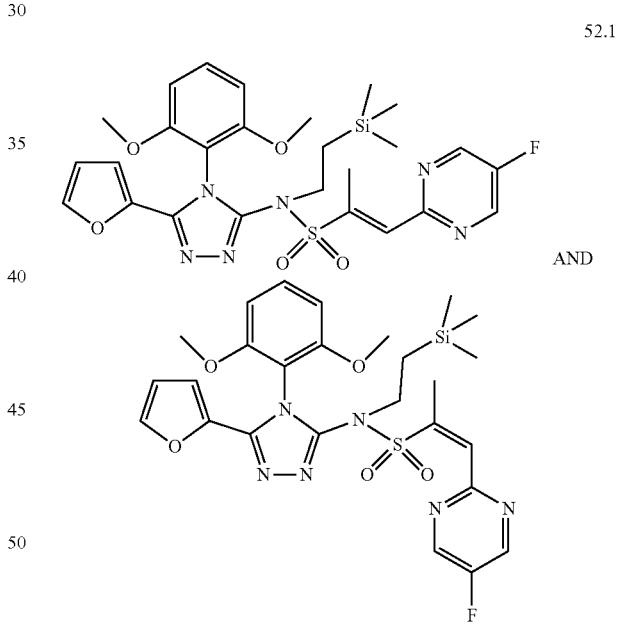

52.1

AND (E)-N-(4-(2,6-Dimethoxyphenyl)-5-(furan-2-yl)-4H-1,2,4-triazol-3-yl)-1-(5-fluoropyrimidin-2-yl)-N-(2-(trimethylsilyl)ethyl)prop-1-ene-2-sulfonamide and (Z)—N-(4-(2,6-dimethoxyphenyl)-5-(furan-2-yl)-4H-1,2,4-triazol-3-yl)-1-(5-fluoropyrimidin-2-yl)-N-(2-(trimethylsilyl)ethyl)prop-1-ene-2-sulfonamide, Example 52.1. The title compound was prepared employing Example 366.0 and 5-fluoropyrimidine-2-carbaldehyde (commercially available from J & W PharmLab, Levittown, Pa., USA) using the procedure described for the synthesis of Example 4.0. LCMS-ESI (pos.) m/z: 587.2 $(M+H)^+$.

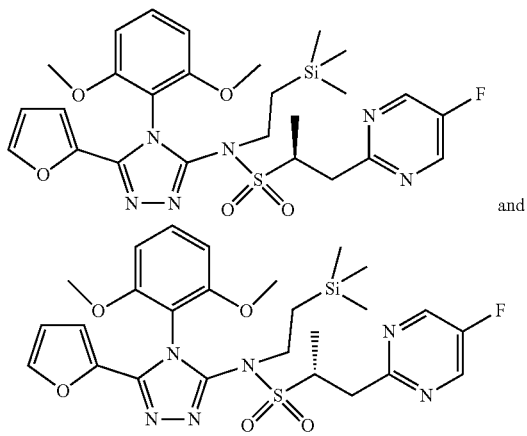

(S)—N-(4-(2,6-Dimethoxyphenyl)-5-(furan-2-yl)-4H-1,2,4-triazol-3-yl)-1-(5-fluoropyrimidin-2-yl)-N-(2-(trimethylsilyl)ethyl)propane-2-sulfonamide and (R)—N-(4-(2,6-dimethoxyphenyl)-5-(furan-2-yl)-4H-1,2,4-triazol-3-yl)-1-(5-fluoropyrimidin-2-yl)-N-(2-(trimethylsilyl)ethyl)propane-2-sulfonamide, Example 52.2. The title compound was prepared employing 52.1, and the procedure described in Example 4.0. LCMS-ESI (pos.) m/z: 589.2 (M+H)+.

52.0

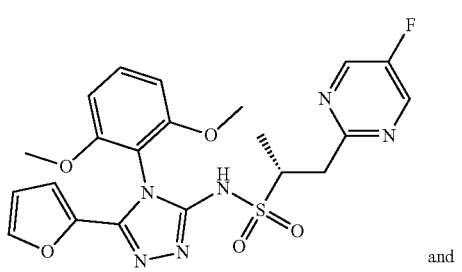

and

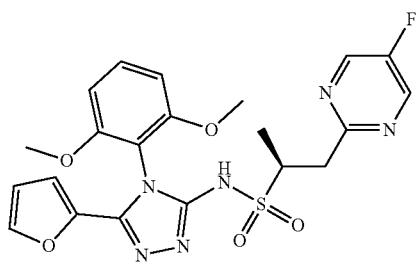

(2R)—N-(4-(2,6-Dimethoxyphenyl)-5-(2-furanyl)-4H-1,2,4-triazol-3-yl)-1-(5-fluoro-2-pyrimidinyl)-2-propanesulfonamide and (2S)—N-(4-(2,6-dimethoxyphenyl)-5-(2-furanyl)-4H-1,2,4-triazol-3-yl)-1-(5-fluoro-2-pyrimidinyl)-2-propanesulfonamide, Example 52.0. To a solution of N-(4-(2,6-dimethoxyphenyl)-5-(furan-2-yl)-4H-1,2,4-triazol-3-yl)-1-(5-fluoropyrimidin-2-yl)-N-(2-(trimethylsilyl)ethyl)propane-2-sulfonamide (Example 52.2, 145.3 mg, 0.247 mmol) in DMF (0.5 mL) was added tris(dimethylamino) sulfur trimethylsilyl difluoride (151 mg, 0.548 mmol). The resulting solution was heated at 60° C. over 4 h. The reaction mixture was then cooled to RT. The material was purified by reverse-phase preparative HPLC using an Agilent SB C8 column, 0.1% TFA in ACN/H$_2$O, gradient 10% to 60% over 25 min. The desired fraction was lyophilized to give a mixture of (2R)—N-(4-(2,6-dimethoxyphenyl)-5-(2-furanyl)-4H-1,2,4-triazol-3-yl)-1-(5-fluoro-2-pyrimidinyl)-2-propanesulfonamide and (2S)—N-(4-(2,6-dimethoxyphenyl)-5-(2-furanyl)-4H-1,2,4-triazol-3-yl)-1-(5-fluoro-2-pyrimidinyl)-2-propanesulfonamide. $^1$H NMR (500 MHz, CDCl$_3$) δ 1.32 (d, J=6.85 Hz, 3H) 3.09 (dd, J=14.67, 9.54 Hz, 1H) 3.68 (dd, J=14.92, 4.65 Hz, 1H) 3.76 (d, J=9.05 Hz, 6H) 3.79-3.85 (m, 1H) 6.01 (d, J=3.42 Hz, 1H) 6.34 (dd, J=3.42, 1.71 Hz, 1H) 6.68 (dd, J=8.56, 2.45 Hz, 2H) 7.43-7.51 (m, 2H) 8.56 (s, 2H). LCMS ESI (pos.) m/z: 489.1 (M+H)+.

Example 53.0. Preparation of (2R,3S)—N-(4-(2,6-dimethoxyphenyl)-5-(5-methyl-2-furanyl)-4H-1,2,4-triazol-3-yl)-3-(5-ethyl-2-pyrimidinyl)-2-butanesulfonamide or (2S,3R)—N-(4-(2,6-dimethoxyphenyl)-5-(5-methyl-2-furanyl)-4H-1,2,4-triazol-3-yl)-3-(5-ethyl-2-pyrimidinyl)-2-butanesulfonamide

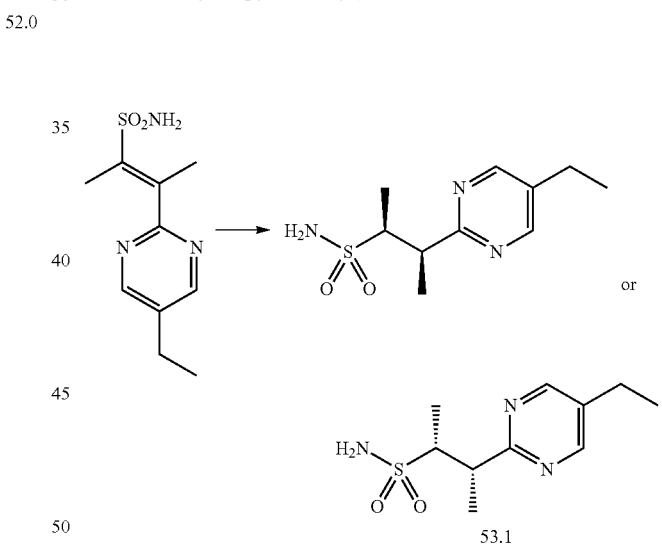

(2S,3R)-3-(5-Ethylpyrimidin-2-yl)butane-2-sulfonamide or (2R,3S)-3-(5-ethylpyrimidin-2-yl)butane-2-sulfonamide, Example 53.1. To a stirred solution of (E)-3-(5-ethylpyrimidin-2-yl)but-2-ene-2-sulfonamide (0.20 g, 0.83 mmol) in IPA (8.3 mL) was added palladium hydroxide (0.012 g, 0.083 mmol). The reaction was then placed under an atmosphere of hydrogen and stirred overnight. To see partial hydrogenation, the products were separated from the starting material using a chiral AD-H column. The racemic mixture was separated on an AD-H column using 20% EtOH (+20 mM NH$_3$); Rf 2.32-peak one and Rf 2.83-peak two. The title compound (0.04 g, 0.164 mmol, 20%) was the second isomer to elute under these conditions. LCMS-ESI (pos.) m/z: 527.3 (M+H)+.

53.0

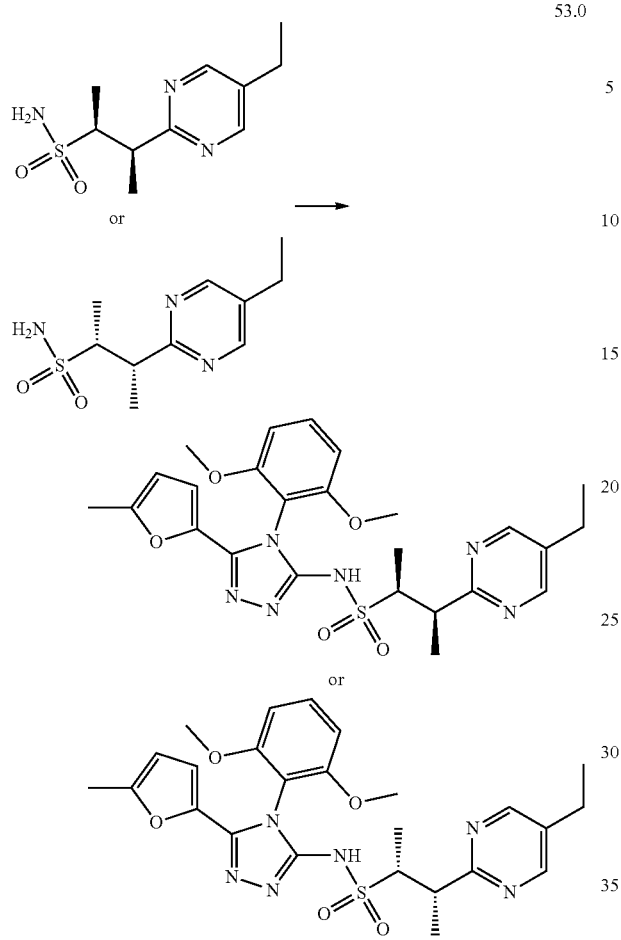

(2R,3S)—N-(4-(2,6-Dimethoxyphenyl)-5-(5-methyl-2-furanyl)-4H-1,2,4-triazol-3-yl)-3-(5-ethyl-2-pyrimidinyl)-2-butanesulfonamide or (2S,3R)—N-(4-(2,6-dimethoxyphenyl)-5-(5-methyl-2-furanyl)-4H-1,2,4-triazol-3-yl)-3-(5-ethyl-2-pyrimidinyl)-2-butanesulfonamide, Example 53.0. The title compound was prepared following the procedure described in Example 149.0 using Example 53.1 (0.020 g, 0.082 mmol), 5-methylfuran-2-carbohydrazide (0.014 g, 0.098 mmol), 2-isothiocyanato-1,3-dimethoxybenzene, Example 372.0 and TFA. The initial product was subjected to SFC purification. Separation conditions for Example 53.0 were a chiral purification using the following parameters: Run on a Thar 80 SFC with 250×21 mm AD-H column with 12.5 g/min MeOH (neat)+37.5 g/min CO₂, 25% co-solvent at 50 g/min. Outlet pressure=100 bar; Temp.=RT; Wavelength=276 nm. Manually injected 0.25 mL of a solution from 3 mg sample dissolved in 0.8 mL of MeOH, c=3.75 mg/mL; 0.94 mg per injection. This separation gave the title compound (0.0009 g, 2%). ¹H NMR (500 MHz, CD₂Cl₂) δ 11.22 (br. s., 1H), 8.53 (s, 2H), 7.54-7.49 (m, 1H), 7.52 (t, J=8.6 Hz, 1H), 6.76-6.69 (m, 2H), 5.93 (dd, J=1.0, 3.4 Hz, 1H), 5.85 (d, J=3.4 Hz, 1H), 3.75 (d, J=8.6 Hz, 7H), 3.68-3.59 (m, 1H), 2.62 (q, J=7.6 Hz, 2H), 2.29 (s, 3H), 1.32 (d, J=7.1 Hz, 3H), 1.29-1.24 (m, 9H). LCMS-ESI (pos.) m/z: 527.3 (M+H)⁺.

Example 54.0. Preparation of (1S,2S)—N-(4-(2,6-dimethoxyphenyl)-5-(5-methyl-2-furanyl)-4H-1,2,4-triazol-3-yl)-1-hydroxy-1-(2-methyl-1,3-oxazol-4-yl)-2-propanesulfonamide or (1R,2R)—N-(4-(2,6-dimethoxyphenyl)-5-(5-methyl-2-furanyl)-4H-1,2,4-triazol-3-yl)-1-hydroxy-1-(2-methyl-1,3-oxazol-4-yl)-2-propanesulfonamide 54.1

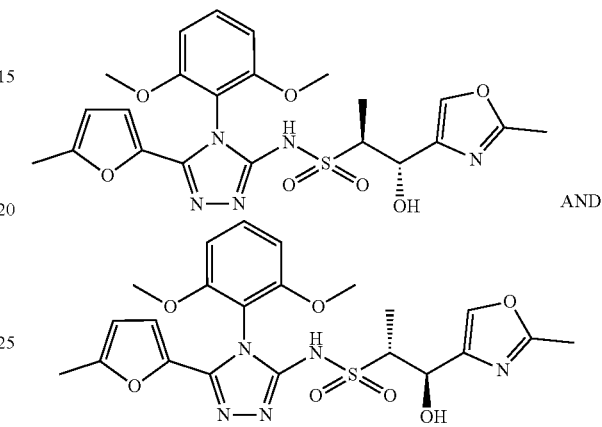

(1R,2R)—N-(4-(2,6-Dimethoxyphenyl)-5-(5-methyl-2-furanyl)-4H-1,2,4-triazol-3-yl)-1-hydroxy-1-(2-methyl-1,3-oxazol-4-yl)-2-propanesulfonamide and (1S,2S)—N-(4-(2,6-dimethoxyphenyl)-5-(5-methyl-2-furanyl)-4H-1,2,4-triazol-3-yl)-1-hydroxy-1-(2-methyl-1,3-oxazol-4-yl)-2-propanesulfonamide, Example 54.1. The title compound was prepared using Example 369.0 and 2-methyloxazole-4-carboxaldehyde following the general procedure described in Example 281.0. ¹H NMR (400 MHz, DMSO-d₆) δ 13.31 (s, 1H), 7.74 (s, 1H), 7.57 (t, J=8.5 Hz, 1H), 6.89 (d, J=8.6 Hz, 2H), 6.13 (d, J=2.5 Hz, 1H), 5.82 (d, J=3.1 Hz, 1H), 4.96-5.08 (m, 1H), 4.68 (dd, J=7.2, 2.9 Hz, 1H), 3.73 (s, 3H), 3.74 (s, 3H), 3.19-3.29 (m, 1H), 2.36 (s, 3H), 2.25 (s, 3H), 1.02 (d, J=7.0 Hz, 3H). LCMS-ESI (pos.) m/z: 504.1 (M+H)⁺.

54.0

(1S,2S)—N-(4-(2,6-Dimethoxyphenyl)-5-(5-methyl-2-furanyl)-4H-1,2,4-triazol-3-yl)-1-hydroxy-1-(2-methyl-1,3- oxazol-4-yl)-2-propanesulfonamide or (1R,2R)—N-(4-(2,6-dimethoxyphenyl)-5-(5-methyl-2-furanyl)-4H-1,2,4-triazol-3-yl)-1-hydroxy-1-(2-methyl-1,3-oxazol-4-yl)-2-propanesulfonamide, Example 54.0. The racemic mixture Example 54.1 was separated by SFC (250×30 mm IC column with 36 g/min MeOH (+20 mM NH₃)+44 g/min CO₂, 45% co-solvent at 80 g/min on Thar 80 SFC. Two enantiomers were obtained. The title compound was the second isomer to elute under these conditions. $^1$H NMR (500 MHz, CD₂Cl₂) δ 7.51 (t, J=8.6 Hz, 1H), 7.47 (s, 1H), 6.73 (d, J=8.6 Hz, 2H), 5.94 (d, J=2.7 Hz, 1H), 5.88 (d, J=2.9 Hz, 1H), 4.74 (d, J=8.8 Hz, 1H), 3.78 (s, 3H), 3.78 (s, 3H), 3.47-3.39 (m, 1H), 2.40 (s, 3H), 2.29 (s, 3H), 1.09 (d, J=7.1 Hz, 3H). LCMS-ESI (pos.) m/z: 504.2 (M+H)⁺.

Example 55.0. Preparation of (1S,2S)—N-(4-(2,6-dimethoxyphenyl)-5-(5-methyl-2-furanyl)-4H-1,2,4-triazol-3-yl)-1-hydroxy-1-(2-methyl-1,3-oxazol-4-yl)-2-propanesulfonamide or (1R,2R)—N-(4-(2,6-dimethoxyphenyl)-5-(5-methyl-2-furanyl)-4H-1,2,4-triazol-3-yl)-1-hydroxy-1-(2-methyl-1,3-oxazol-4-yl)-2-propanesulfonamide

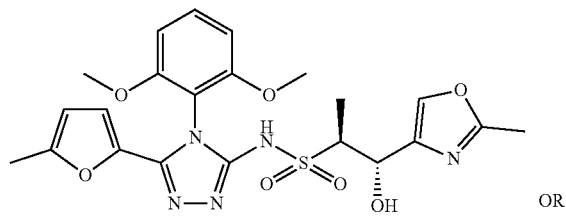

55.0

OR

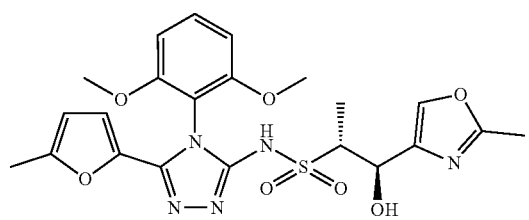

(1S,2S)—N-(4-(2,6-Dimethoxyphenyl)-5-(5-methyl-2-furanyl)-4H-1,2,4-triazol-3-yl)-1-hydroxy-1-(2-methyl-1,3-oxazol-4-yl)-2-propanesulfonamide or (1R,2R)—N-(4-(2,6-dimethoxyphenyl)-5-(5-methyl-2-furanyl)-4H-1,2,4-triazol-3-yl)-1-hydroxy-1-(2-methyl-1,3-oxazol-4-yl)-2-propanesulfonamide, Example 55.0. The racemic mixture (Example 54.1) was separated by SFC (250×30 mm IC column with 36 g/min MeOH (+20 mM NH₃)+44 g/min CO₂, 45% co-solvent at 80 g/min on Thar 80 SFC. Two enantiomers were obtained. The title compound was the first isomer to elute under these conditions. $^1$H NMR (500 MHz, CD₂Cl₂) δ 7.52 (t, J=8.4 Hz, 1H), 7.47 (s, 1H), 6.73 (d, J=8.6 Hz, 2H), 5.97-5.87 (m, 2H), 4.73 (d, J=8.8 Hz, 1H), 3.78 (s, 3H), 3.78 (s, 3H), 3.47-3.38 (m, 1H), 2.40 (s, 3H), 2.29 (s, 3H), 1.09 (d, J=7.1 Hz, 3H). LCMS-ESI (pos.) m/z: 504.2 (M+H)⁺.

Example 56.0. Preparation of (2S,3R)—N-(4-(2,6-dimethoxyphenyl)-5-(5-methyl-2-furanyl)-4H-1,2,4-triazol-3-yl)-3-(5-fluoro-2-pyrimidinyl)-2-butanesulfonamide

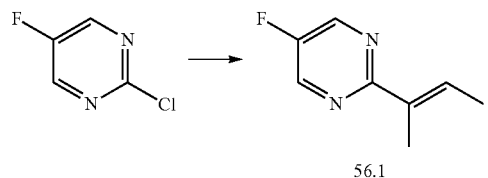

56.1

(E)-2-(But-2-en-2-yl)-5-fluoropyrimidine, Example 56.1. 2-Chloro-5-fluoro-pyrimidine (14.45 mL, 117 mmol), potassium (Z)-but-2-en-2-yltrifluoroborate (24.63 g, 152 mmol), tricyclohexylphosphine (6.56 g, 23.39 mmol), and Pd₂(dba)₃ (10.71 g, 11.70 mmol) were added to a vial which was then degassed and backfilled with nitrogen. 1,4-Dioxane (195 mL) and aqueous potassium phosphate tribasic (29.0 mL, 351 mmol) were then added by syringe. The resulting reaction was heated at 100° C. for 16 h. The reaction was then cooled to RT. The organics were concentrated in vacuo. The residue was filtered through a plug of silica gel and then loaded onto a silica gel column (0-20% EtOAc in hexanes) to afford Example 56.1 (14.24 g, 94 mmol, 80% yield). LCMS-ESI (pos.) m/a: 153.1 (M+H)⁺.

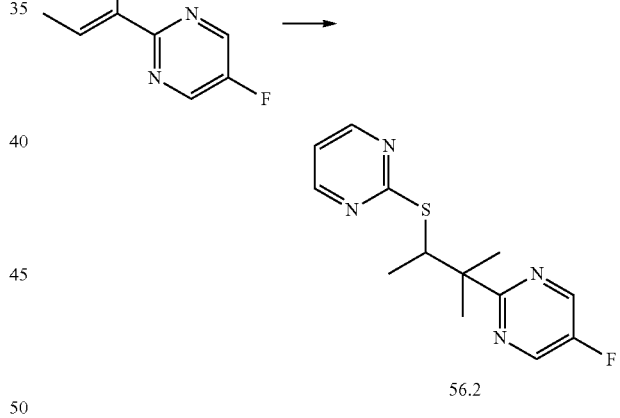

56.2

2-(2-Chloro-3-(pyrimidin-2-ylthio)butan-2-yl)-5-fluoro-pyrimidine, Example 56.2. To a solution of pyrimidine-2-thiol (13.27 g, 118 mmol) in DCM (329 mL) was added sulfuryl dichloride (9.62 mL, 118 mmol). The reaction was stirred at 0° C. for 1 h and for a further 1 h at RT. To the initial cloudy reaction was added Example 56.1 (15 g, 99 mmol) dropwise. The reaction was further stirred for 1 h. Next, the reaction mixture was concentrated in vacuo. A saturated aqueous solution of sodium bicarbonate was added to the mixture to neutralize the reaction mixture. The reaction was then extracted with EtOAc and concentrated in vacuo. The residue was purified on silica gel with 0-25% EtOAc in hexanes to give the desired product (Example 56.2, 21 g, 70.3 mmol, 71.3% yield). LCMS-ESI (pos.) m/z: 291.1 (M+H)⁺.

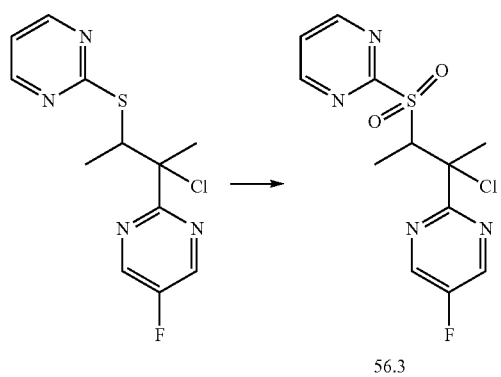 [SMILES: CC(Sc1ncccn1)C(C)(Cl)c1ncc(F)cn1 ; CC(C(C)(Cl)c1ncc(F)cn1)S(=O)(=O)c1ncccn1]

56.3

2-(2-Chloro-3-(pyrimidin-2-ylsulfonyl)butan-2-yl)-5-fluoropyrimidine, Example 56.3. To a solution of Example 56.2 (21 g, 70.3 mmol) in DCM (201 mL) was added 3-chlorobenzoperoxoic acid (24.26 g, 141 mmol) at 0° C. The reaction was then stirred at RT for 1 day. The reaction was concentrated in vacuo and an aqueous solution of sodium bicarbonate and sodium thiosulfate was added. The mixture was extracted with EtOAc and concentrated in vacuo. The material thus was obtained was then purified on silica gel eluting with 0-100% EtOAc in hexanes to give the desired product (18 g, 54.4 mmol, 77% yield). LCMS-ESI (pos.) m/z: 331.1 (M+H)$^+$.

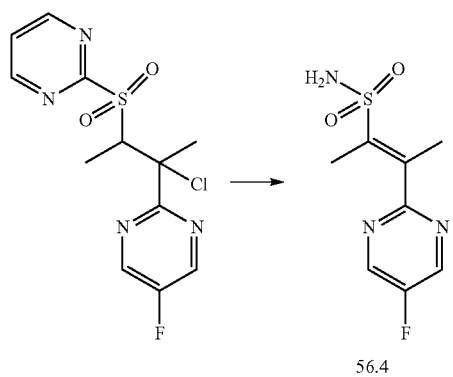 [SMILES: CC(C(C)(Cl)c1ncc(F)cn1)S(=O)(=O)c1ncccn1 ; C/C(=C(/C)S(N)(=O)=O)c1ncc(F)cn1]

56.4

(E)-3-(5-Fluoropyrimidin-2-yl)but-2-ene-2-sulfonamide, Example 56.4. To a stirred solution of Example 56.3 (18 g, 54.4 mmol) in MeOH (136 mL) was added potassium carbonate (15.04 g, 109 mmol). The reaction was stirred at RT for 16 h. Next, the reaction was concentrated in vacuo. The initial sulfinate was dissolved in water (231 mL, 46.3 mmol) and potassium acetate (4.54 g, 46.3 mmol) was added followed by (aminooxy)sulfonic acid (10.47 g, 93 mmol). The reaction was stirred at RT for 3 h. The reaction was then extracted with EtOAc and the combined organic layers were concentrated in vacuo. The product was purified on silica gel eluting with 0-80% EtOAc in hexanes to give the desired product (11.77 g, 46.3 mmol). LCMS-ESI (pos.) m/z: 232.1 (M+H)$^+$.

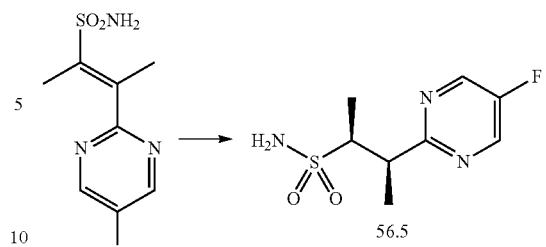

56.5

(2S,3R)-3-(5-Fluoropyrimidin-2-yl)butane-2-sulfonamide, Example 56.5. To a solution of Example 56.4 (0.77 g, 3.33 mmol) in EtOH (8.32 mL) was added zinc(II) trifluoromethanesulfonate (0.121 g, 0.33 mmol), and (R)-(−)-4,12-bis(diphenylphosphino)[2.2]paracyclophane (1,5-cyclooctadiene)rhodium(I) tetrafluoroborate (Strem chemicals, 0.116 g, 0.133 mmol). The reaction mixture was placed under an atmosphere of hydrogen and stirred for 16 h. The reaction was then filtered to give the desired product and the mother liquor was concentrated in vacuo and purified on silica gel eluting with 0-80% EtOAc in hexanes to give the desired product. The combined product was recrystallized from EtOH to give the desired product (0.46 g, 60%, 99% ee). LCMS-ESI (pos.) m/z: 234.2 (M+H)$^+$.

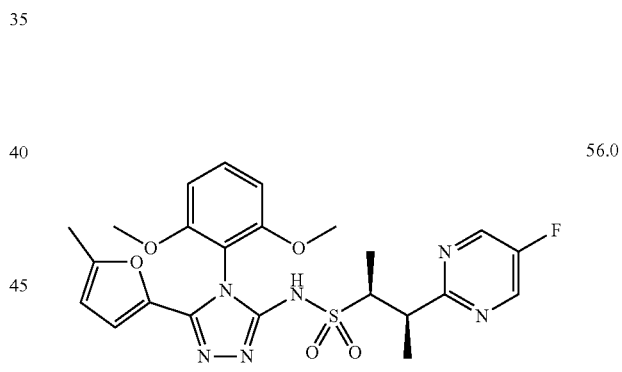

56.0

(2S,3R)—N-(4-(2,6-Dimethoxyphenyl)-5-(5-methyl-2-furanyl)-4H-1,2,4-triazol-3-yl)-3-(5-fluoro-2-pyrimidinyl)-2-butanesulfonamide, Example 56.0. The title compound was prepared following the procedure described in Example 92.0 using Example 56.5 and Example 364.1. $^1$H NMR (500 MHz, CD$_2$Cl$_2$) δ 10.90 (s, 1H), 8.54 (s, 2H), 7.52 (t, J=8.6 Hz, 1H), 6.76-6.70 (m, 2H), 5.95-5.92 (m, 1H), 5.85 (d, J=3.9 Hz, 1H), 3.75 (s, 3H), 3.75 (s, 3H), 3.74-3.67 (m, 2H), 2.29 (s, 3H), 1.32 (d, J=6.8 Hz, 3H), 1.28 (d, J=6.8 Hz, 3H). LCMS-ESI (pos.) m/z: 517.3 (M+H)$^+$.

Example 57.0. Preparation of (1S,2S)—N-(4-(2,6-dimethoxyphenyl)-5-(5-methyl-2-furanyl)-4H-1,2,4-triazol-3-yl)-1-(5-fluoro-2-pyridinyl)-1-hydroxy-2-propanesulfonamide and (1R,2R)—N-(4-(2,6-dimethoxyphenyl)-5-(5-methyl-2-furanyl)-4H-1,2,4-triazol-3-yl)-1-(5-fluoro-2-pyridinyl)-1-hydroxy-2-propanesulfonamide or (1R,2S)—N-(4-(2,6-dimethoxyphenyl)-5-(5-methyl-2-furanyl)-4H-1,2,4-triazol-3-yl)-1-(5-fluoro-2-pyridinyl)-1-hydroxy-2-propanesulfonamide and (1S,2R)—N-(4-(2,6-dimethoxyphenyl)-5-(5-methyl-2-furanyl)-4H-1,2,4-triazol-3-yl)-1-(5-fluoro-2-pyridinyl)-1-hydroxy-2-propanesulfonamide N-(4-(2,6-Dimethoxyphenyl)-5-(5-methylfuran-2-yl)-4H-1,2,4-triazol-3-yl)-N-(2-(trimethylsilyl)ethyl)ethanesulfonamide (Example 369.0, 325 mg, 0.66 mmol) was azeotroped with toluene. THF (2.5 mL) was added, and the mixture was cooled in a dry ice-acetone bath. n-BuLi (0.412 mL, 0.660 mmol) was added and the mixture was stirred for 10 min. A THF (1 mL) solution of 5-fluoropicolinaldehyde (99 mg, 0.79 mmol, Frontier Scientific Services Inc., flushed with nitrogen before adding THF) was added dropwise. The reaction mixture was then stirred in a dry ice-acetone bath for 45 mi. before warming to RT. The reaction was stirred overnight. The reaction was quenched with saturated $NH_4Cl$ and extracted with EtOAc. The EtOAc layer was dried, concentrated, and purified on reverse phase HPLC using an Agilent SB C8 column, 0.1% TFA in $ACN/H_2O$) gradient (30-90%) in 2 batches. The two diastereomers (1.5:1 ratio) were separated. Fractions containing the major diastereomer were lyophilized to give 140 mg of the title compound (Example 57.1) as a TFA salt. LCMS-ESI (pos.) m/z: 618.0 $(M+H)^+$.

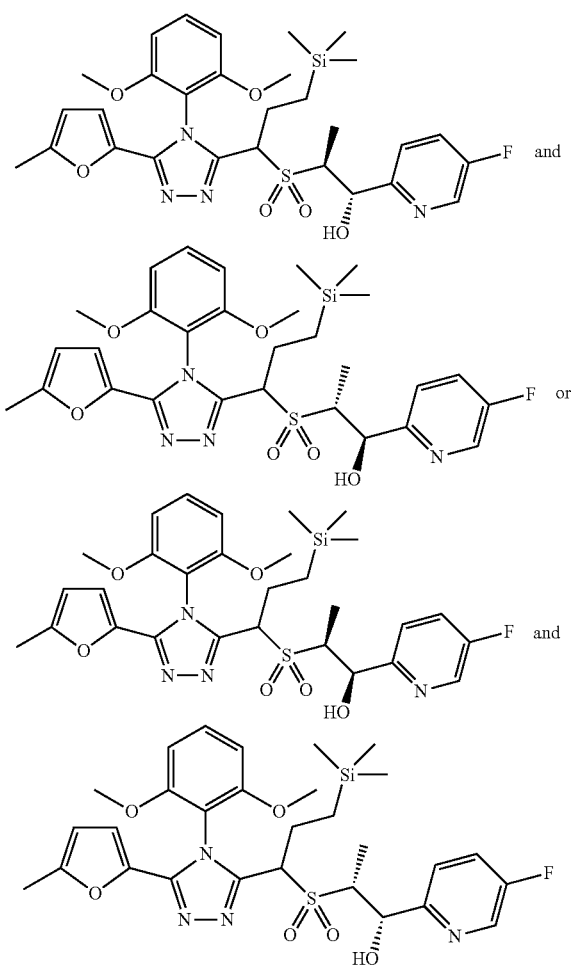

(1S,2S)—N-(4-(2,6-Dimethoxyphenyl)-5-(5-methylfuran-2-yl)-4H-1,2,4-triazol-3-yl)-1-(5-fluoropyridin-2-yl)-1-hydroxy-N-(2-(trimethylsilyl)ethyl)propane-2-sulfonamide and (1R,2R)—N-(4-(2,6-dimethoxyphenyl)-5-(5-methylfuran-2-yl)-4H-1,2,4-triazol-3-yl)-1-(5-fluoropyridin-2-yl)-1-hydroxy-N-(2-(trimethylsilyl)ethyl)propane-2-sulfonamide or (1R, 2S)—N-(4-(2,6-dimethoxyphenyl)-5-(5-methylfuran-2-yl)-4H-1,2,4-triazol-3-yl)-1-(5-fluoropyridin-2-yl)-1-hydroxy-N-(2-(trimethylsilyl)ethyl)propane-2-sulfonamide and (1S,2R)—N-(4-(2,6-dimethoxyphenyl)-5-(5-methylfuran-2-yl)-4H-1,2,4-triazol-3-yl)-1-(5-fluoropyridin-2-yl)-1-hydroxy-N-(2-(trimethylsilyl)ethyl)propane-2-sulfonamide

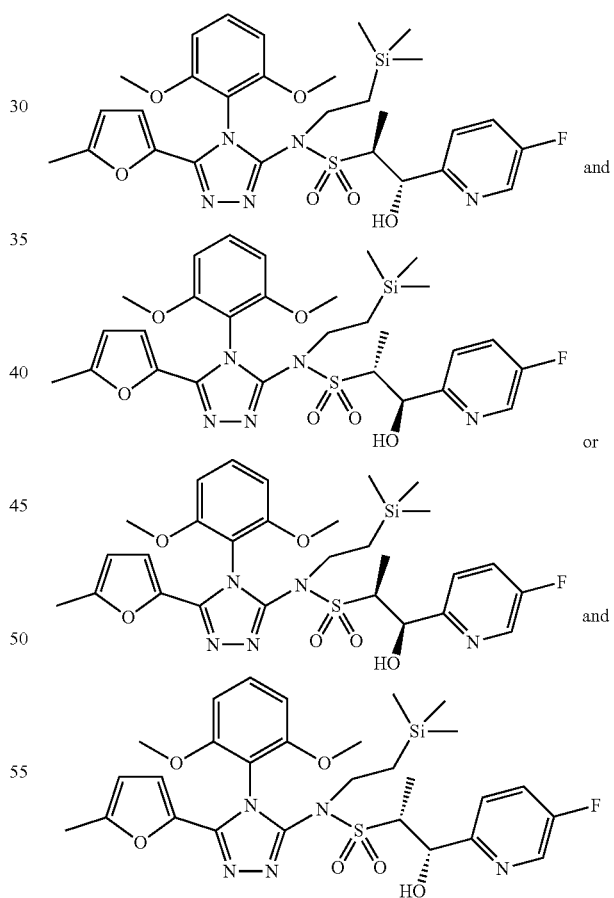

(1S,2S)—N-(4-(2,6-Dimethoxyphenyl)-5-(5-methylfuran-2-yl)-4H-1,2,4-triazol-3-yl)-1-(5-fluoropyridin-2-yl)-1-hydroxy-N-(2-(trimethylsilyl)ethyl)propane-2-sulfonamide and (1R,2R)—N-(4-(2,6-dimethoxyphenyl)-5-(5-methylfuran-2-yl)-4H-1,2,4-triazol-3-yl)-1-(5-fluoropyridin-2-yl)-1-hydroxy-N-(2-(trimethylsilyl)ethyl)

propane-2-sulfonamide or (1R, 2S)—N-(4-(2,6-dimethoxyphenyl)-5-(5-methylfuran-2-yl)-4H-1,2,4-triazol-3-yl)-1-(5-fluoropyridin-2-yl)-1-hydroxy-N-(2-(trimethylsilyl)ethyl)propane-2-sulfonamide and (1S,2R)—N-(4-(2,6-dimethoxyphenyl)-5-(5-methylfuran-2-yl)-4H-1,2,4-triazol-3-yl)-1-(5-fluoropyridin-2-yl)-1-hydroxy-N-(2-(trimethylsilyl)ethyl)propane-2-sulfonamide, Example 57.2. The title compound was the minor diastereomer (100 mg) isolated from the conditions described in Example 57.1.

Example 59.0. Preparation of (1S,2S)—N-(4-(2,6-dimethoxyphenyl)-5-(5-methyl-2-furanyl)-4H-1,2,4-triazol-3-yl)-1-(5-fluoro-2-pyridinyl)-1-hydroxy-2-propanesulfonamide and (1R,2R)—N-(4-(2,6-dimethoxyphenyl)-5-(5-methyl-2-furanyl)-4H-1,2,4-triazol-3-yl)-1-(5-fluoro-2-pyridinyl)-1-hydroxy-2-propanesulfonamide or (1R,2S)—N-(4-(2,6-dimethoxyphenyl)-5-(5-methyl-2-furanyl)-4H-1,2,4-triazol-3-yl)-1-(5-fluoro-2-pyridinyl)-1-hydroxy-2-propanesulfonamide and (1S,2R)—N-(4-(2,6-dimethoxyphenyl)-5-(5-methyl-2-furanyl)-4H-1,2,4-triazol-3-yl)-1-(5-fluoro-2-pyridinyl)-1-hydroxy-2-propanesulfonamide 59.0

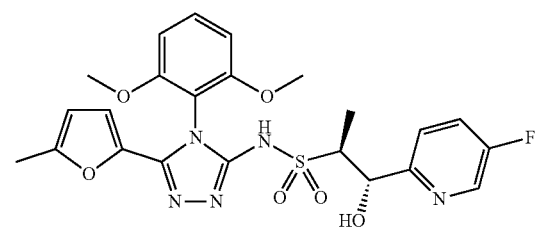

and

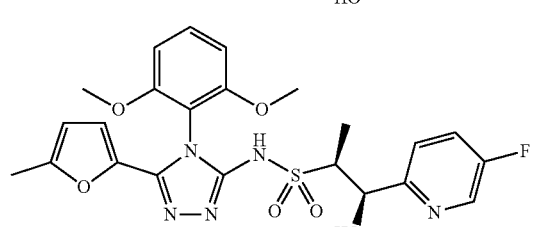

or

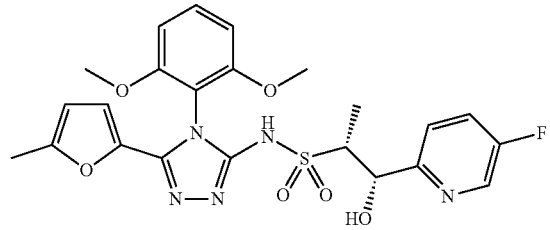

and (1S,2S)—N-(4-(2,6-Dimethoxyphenyl)-5-(5-methyl-2-furanyl)-4H-1,2,4-triazol-3-yl)-1-(5-fluoro-2-pyridinyl)-1-hydroxy-2-propanesulfonamide and (1R,2R)—N-(4-(2,6-dimethoxyphenyl)-5-(5-methyl-2-furanyl)-4H-1,2,4-triazol-3-yl)-1-(5-fluoro-2-pyridinyl)-1-hydroxy-2-propanesulfonamide or (1R,2S)—N-(4-(2,6-dimethoxyphenyl)-5-(5-methyl-2-furanyl)-4H-1,2,4-triazol-3-yl)-1-(5-fluoro-2-pyridinyl)-1-hydroxy-2-propanesulfonamide and (1S,2R)—N-(4-(2,6-dimethoxyphenyl)-5-(5-methyl-2-furanyl)-4H-1,2,4-triazol-3-yl)-1-(5-fluoro-2-pyridinyl)-1-hydroxy-2-propanesulfonamide, Example 59.0. A flask was charged with Example 57.1 (140 mg, 0.191 mmol, TFA salt) and azeotroped with toluene and then dried on a high vacuum pump. Tris(dimethylamino)sulfonium difluorotrimethylsilicate (IV) (158 mg, 0.57 mmol) was added to the flask. DMF (1.8 mL) was then added. The resulting solution was heated at 60° C. for 3 hr. LCMS showed incomplete conversion. More tris(dimethylamino)sulfonium difluorotrimethylsilicate (IV) was added, and the reaction was continued overnight. The reaction was then cooled to RT. The initial material was purified by reverse-phase preparative HPLC using an Agilent SB C8 column, 0.1% TFA in ACN/H$_2$O, gradient 20% to 75% over 25 min (the peaks that were visible at 220 nm were collected). The desired fractions were lyophilized to provide the title compound (Example 59.0, 119 mg) as a TFA salt. $^1$H NMR (400 MHz, CD$_3$OD) δ 8.42 (d, J=2.54 Hz, 1H) 7.59-7.67 (m, 2H) 7.56 (t, J=8.51 Hz, 1H) 6.85 (dd, J=8.51, 2.45 Hz, 2H) 6.01-6.04 (m, 1H) 5.97 (d, J=3.52 Hz, 1H) 5.35-5.39 (m, 1H) 3.78 (s, 3H) 3.76 (s, 3H) 3.60 (qd, J=7.04, 2.15 Hz, 1H) 2.26 (s, 3H) 1.10 (d, J=6.85 Hz, 3H). LCMS-ESI (pos.) m/z: 518.0 (M+H)$^+$.

57.0

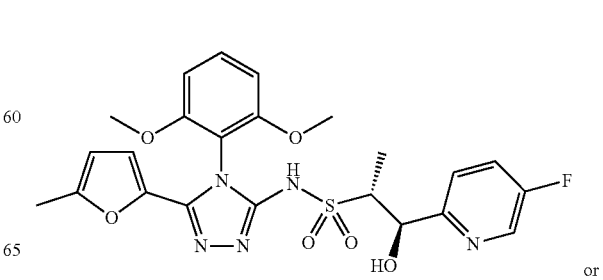

or

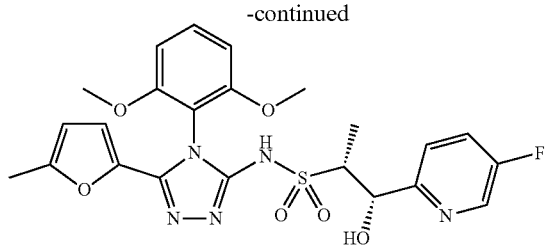

(1S,2S)—N-(4-(2,6-Dimethoxyphenyl)-5-(5-methyl-2-furanyl)-4H-1,2,4-triazol-3-yl)-1-(5-fluoro-2-pyridinyl)-1-hydroxy-2-propanesulfonamide or (1R,2R)—N-(4-(2,6-dimethoxyphenyl)-5-(5-methyl-2-furanyl)-4H-1,2,4-triazol-3-yl)-1-(5-fluoro-2-pyridinyl)-1-hydroxy-2-propanesulfonamide or (1R,2S)—N-(4-(2,6-dimethoxyphenyl)-5-(5-methyl-2-furanyl)-4H-1,2,4-triazol-3-yl)-1-(5-fluoro-2-pyridinyl)-1-hydroxy-2-propanesulfonamide or (1S,2R)—N-(4-(2,6-dimethoxyphenyl)-5-(5-methyl-2-furanyl)-4H-1,2,4-triazol-3-yl)-1-(5-fluoro-2-pyridinyl)-1-hydroxy-2-propanesulfonamide, Example 57.0. Example 59.0 was purified by SFC (Lotus Inc) to give two enantiomers. Chiral separation conditions were as follows: IA (2×15 cm), 25% MeOH/CO₂, 100 bar, 60 mL/min, 220 nm. Inj volume: 0.75 mL, 11 mg/mL 2:1 MeOH:DCM. The title compound (Example 57.0) was the first peak (faster-eluting) off the chiral column ¹H NMR (400 MHz, CD₃OD) δ 8.40 (t, J=1.47 Hz, 1H) 7.53-7.61 (m, 3H) 6.85 (dd, J=8.61, 2.74 Hz, 2H) 6.02 (dd, J=3.52, 0.98 Hz, 1H) 5.97 (d, J=3.52 Hz, 1H) 5.36-5.39 (m, 1H) 3.78 (s, 3H) 3.76 (s, 3H) 3.61 (qd, J=6.98, 1.96 Hz, 1H) 2.22-2.29 (m, 3H) 1.09 (d, J=7.04 Hz, 3H). LCMS-ESI (pos.) m/z: 518.0 (M+H)⁺.

Example 58.0. Preparation of (2R)-2-(5-cyano-2-pyridinyl)-N-(4-(2,6-dimethoxyphenyl)-5-(5-methyl-2-furanyl)-4H-1,2,4-triazol-3-yl)-2-hydroxyethanesulfonamide or (2S)-2-(5-cyano-2-pyridinyl)-N-(4-(2,6-dimethoxyphenyl)-5-(5-methyl-2-furanyl)-4H-1,2,4-triazol-3-yl)-2-hydroxyethanesulfonamide 58.1

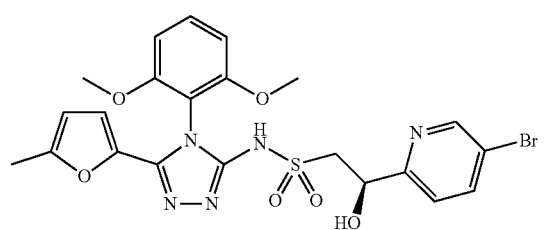

and

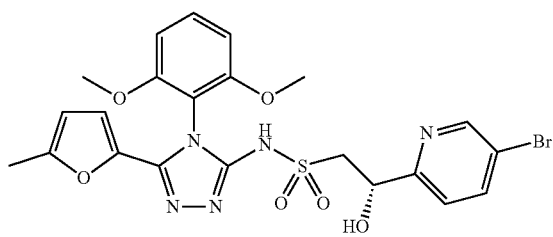

2-(5-Bromopyridin-2-yl)-N-(4-(2,6-dimethoxyphenyl)-5-(5-methylfuran-2-yl)-4H-1,2,4-triazol-3-yl)-2-hydroxy-ethanesulfonamide, Example 58.1. The title compound was prepared as a TFA salt following the procedure described in Example 57.0 employing Example 368.0 and 5-bromopicolinaldehyde. LCMS-ESI (pos.) m/z: 565.9 (M+H)⁺.

58.2

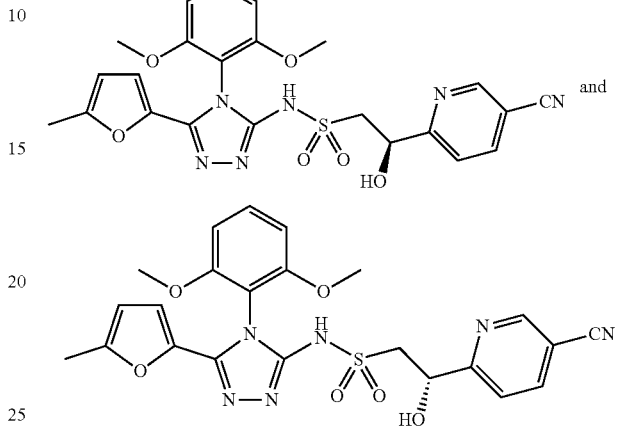

(2R)-2-(5-Cyano-2-pyridinyl)-N-(4-(2,6-dimethoxyphenyl)-5-(5-methyl-2-furanyl)-4H-1,2,4-triazol-3-yl)-2-hydroxyethanesulfonamide and (2S)-2-(5-cyano-2-pyridinyl)-N-(4-(2,6-dimethoxyphenyl)-5-(5-methyl-2-furanyl)-4H-1,2,4-triazol-3-yl)-2-hydroxyethanesulfonamide, Example 58.2. A microwave tube was charged with dicyanozinc (58.2 mg, 0.50 mmol, Alfa Aesar), Pd(PPh₃)₄ (69.8 mg, 0.060 mmol, Strem Chemicals Inc.), and Example 58.1 (205 mg, 0.302 mmol). Argon-degassed DMF (2.5 mL) was added, and the reaction was degassed again with argon. The reaction mixture was then heated to 120° C. for 1 h in a microwave. Water was added, and the reaction was extracted with EtOAc. The EtOAc layer was washed with brine, dried, concentrated in vacuo, and purified on reverse phase HPLC in 2 batches using an Agilent SB C8 column, 0.1% TFA in ACN/H₂O, gradient 30-70% over 25 min and collecting peaks at 220 nM to provide the title compound (Example 58.2, 97 mg) as a white solid. ¹H NMR (400 MHz, CD₃OD) δ 8.83-8.85 (m, 1H) 8.15 (dd, J=8.22, 2.15 Hz, 1H) 7.72 (d, J=8.22 Hz, 1H) 7.56 (t, J=8.51 Hz, 1H) 6.86 (d, J=0.98 Hz, 1H) 6.83 (d, J=0.78 Hz, 1H) 6.02 (dd, J=4.81 Hz, 1H) 5.96 (d, J=3.52 Hz, 1H) 5.21 (dd, J=8.71, 3.23 Hz, 1H) 3.77 (s, 3H) 3.77 (s, 3H) 3.69 (dd, J=14.28, 3.33 Hz, 1H) 3.31 (m, 1H) 2.26 (s, 3H). LCMS-ESI (pos.) m/z: 511.0 (M+H)⁺.

58.0

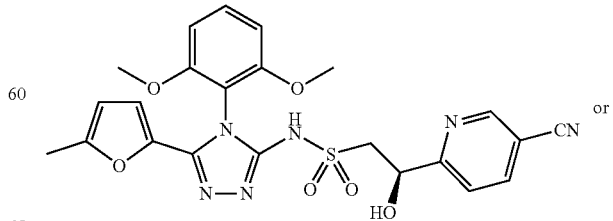

or

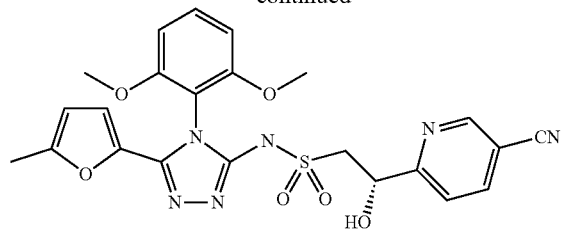

(2R)-2-(5-Cyano-2-pyridinyl)-N-(4-(2,6-dimethoxyphenyl)-5-(5-methyl-2-furanyl)-4H-1,2,4-triazol-3-yl)-2-hydroxyethanesulfonamide or (2S)-2-(5-cyano-2-pyridinyl)-N-(4-(2,6-dimethoxyphenyl)-5-(5-methyl-2-furanyl)-4H-1,2,4-triazol-3-yl)-2-hydroxyethanesulfonamide, Example 58.0. The racemate Example 58.2 was separated by SFC to give two single enantiomers. Chiral separation conditions were as follows: Run on Thar 80 SFC with 250×30 mm IC column with 44 g/min MeOH (neat)+36 g/min $CO_2$, 55% co-solvent at 80 g/min. Outlet pressure=100 bar; Temp.=27° C.; Wavelength=222 nm. injected 0.2 mL of a solution from 29 mg sample dissolved in 3 mL of MeOH/DCM (50% DCM), c=9.6 mg/mL; 1.9 mg per injection. Cycle time 5.2 min, run time 12 min. The title compound was the first peak (faster-eluting) from the chiral separation. $^1$H NMR (400 MHz, $CD_3OD$) δ 8.82-8.85 (m, 1H) 8.15 (dd, J=8.22, 215 Hz, 1H) 7.72 (d, J=8.22 Hz, 1H) 7.56 (t, J=8.30 Hz, 1H) 6.84 (dd, J=8.51, 0.88 Hz, 2H) 6.02 (d, J=3.79 Hz, 1H) 5.96 (d, J=3.52 Hz, 1H) 5.21 (dd, J=8.71, 3.23 Hz, 1H) 3.77 (s, 3H) 3.77 (s, 3H) 3.69 (dd, J=14.08, 3.33 Hz, 1H) 3.27-3.35 (m, 1H) 2.26 (s, 3H). LCMS-ESI (pos.) m/z: 511.0 (M+H)$^+$.

Example 60.0. Preparation of (2R)—N-(4-(2,6-dimethoxyphenyl)-5-(5-methyl-2-furanyl)-4H-1,2,4-triazol-3-yl)-2-(5-fluoro-2-pyridinyl)-2-hydroxyethanesulfonamide and (2S)—N-(4-(2,6-dimethoxyphenyl)-5-(5-methyl-2-furanyl)-4H-1,2,4-triazol-3-yl)-2-(5-fluoro-2-pyridinyl)-2-hydroxyethanesulfonamide

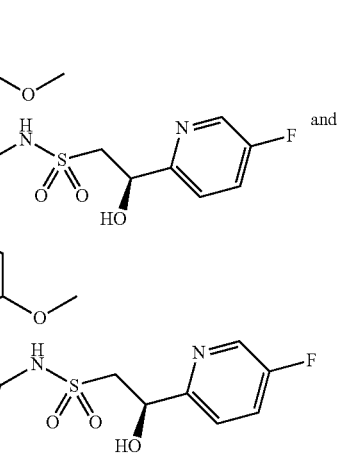

(2R)—N-(4-(2,6-Dimethoxyphenyl)-5-(5-methyl-2-furanyl)-4H-1,2,4-triazol-3-yl)-2-(5-fluoro-2-pyridinyl)-2-hydroxyethanesulfonamide and (2S)—N-(4-(2,6-dimethoxyphenyl)-5-(5-methyl-2-furanyl)-4H-1,2,4-triazol-3-yl)-2-(5-fluoro-2-pyridinyl)-2-hydroxyethanesulfonamide, Example 60.0. The title compound was prepared according to the procedure described in Example 59.0 using Example 368.0 and 5-fluoropicolinaldehyde. $^1$H NMR (400 MHz, $CD_3OD$) δ 8.43 (d, J=2.35 Hz, 1H) 7.59-7.69 (m, 2H) 7.55 (t, J=8.51 Hz, 1H) 6.84 (d, J=8.61 Hz, 2H) 6.02 (d, J=3.93 Hz, 1H) 5.96 (d, J=3.33 Hz, 1H) 5.20 (dd, J=8.51, 3.42 Hz, 1H) 3.77 (s, 3H) 3.76 (s, 3H) 3.63 (dd, J=14.18, 3.42 Hz, 1H) 3.32-3.37 (m, 1H) 2.25 (s, 3H). LCMS-ESI (pos.) m/z: 504.0 (M+H)$^+$.

Example 61.0. Preparation of (1R,2S)-1-(4-cyano-2-fluorophenyl)-N-(4-(2,6-dimethoxyphenyl)-5-(5-methyl-2-furanyl)-4H-1,2,4-triazol-3-yl)-1-hydroxy-2-propanesulfonamide or (1S,2R)-1-(4-cyano-2-fluorophenyl)-N-(4-(2,6-dimethoxyphenyl)-5-(5-methyl-2-furanyl)-4H-1,2,4-triazol-3-yl)-1-hydroxy-2-propanesulfonamide or (1S,2S)-1-(4-cyano-2-fluorophenyl)-N-(4-(2,6-dimethoxyphenyl)-5-(5-methyl-2-furanyl)-4H-1,2,4-triazol-3-yl)-1-hydroxy-2-propanesulfonamide or (1R,2R)-1-(4-cyano-2-fluorophenyl)-N-(4-(2,6-dimethoxyphenyl)-5-(5-methyl-2-furanyl)-4H-1,2,4-triazol-3-yl)-1-hydroxy-2-propanesulfonamide

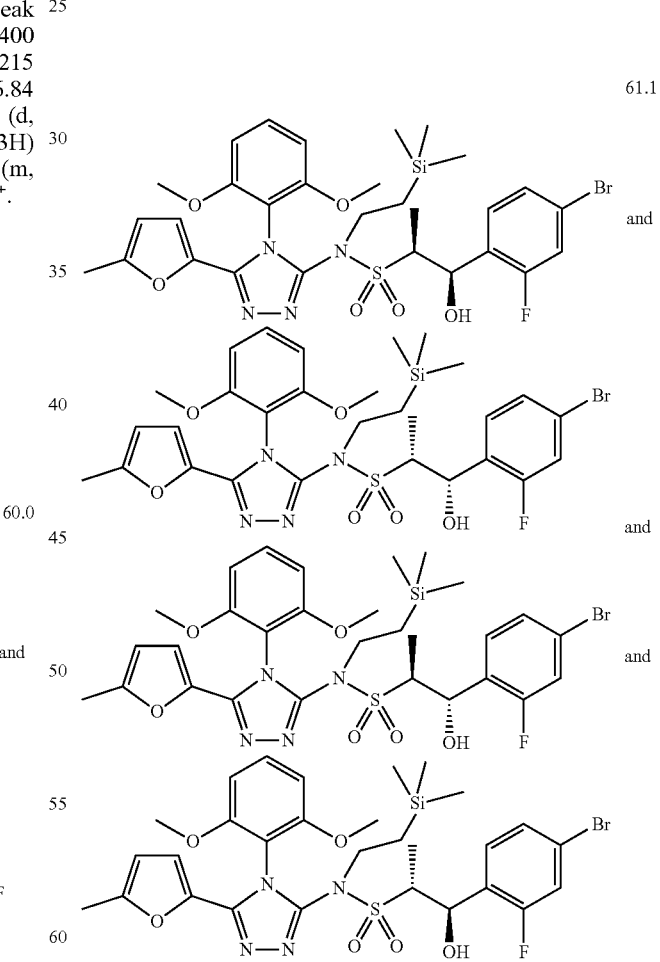

(1S,2S)-1-(4-Bromo-2-fluorophenyl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide and (1R,2R)-1-(4-bromo-2-fluorophenyl)-N-(4-(2,6-dimethoxyphenyl)-5-(5-methylfuran-2-yl)-4H-1,2,4- triazol-3-yl)-1-hydroxy-N-(2-(trimethylsilyl)ethyl)propane-2-sulfonamide and (1S,2R)-1-(4-bromo-2-fluorophenyl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide and (1R,2S)-1-(4-bromo-2-fluorophenyl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide, Example 61.1. The title compound was prepared from Example 369.0 following the procedure described in Example 59.0. The initial product was purified by chromatography on a Redi-Sep pre-packed gold silica gel column with 0-50% gradient EtOAc in hexanes to provide the title compound (Example 61.1) as a 2.3:1 ratio of diastereomers.

NMR (400 MHz, CD$_3$OD) δ 7.61-7.73 (m, 1H) 7.54-7.59 (m, 2H) 7.48-7.54 (m, 1H) 6.87 (d, J=3.52 Hz, 1H) 6.84 (d, J=3.52 Hz, 1H) 6.03 (dd, J=3.52, 0.98 Hz, 1H) 5.96 (d, J=3.52 Hz, 1H) 5.65-5.18 (m, 1H) 3.79-3.81 (m, 3H) 3.76-3.78 (m, 3H) 3.37-3.20 (m, 1H) 2.26 (s, 3H) 1.05-1.19 (m, 3H). LCMS-ESI (pos.) m/z: 542.3 (M+H)$^+$.

75.0

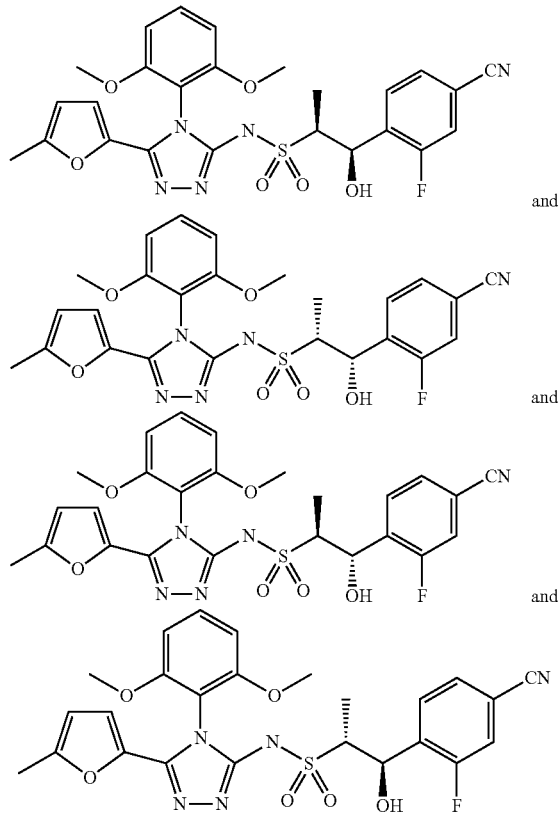

(1R,2S)-1-(4-Bromo-2-fluorophenyl)-N-(4-(2,6-dimethoxyphenyl)-5-(5-methyl-2-furanyl)-4H-1,2,4-triazol-3-yl)-1-hydroxy-2-propanesulfonamide and (1S,2R)-1-(4-bromo-2-fluorophenyl)-N-(4-(2,6-dimethoxyphenyl)-5-(5-methyl-2-furanyl)-4H-1,2,4-triazol-3-yl)-1-hydroxy-2-propanesulfonamide and (1S,2S)-1-(4-bromo-2-fluorophenyl)-N-(4-(2,6-dimethoxyphenyl)-5-(5-methyl-2-furanyl)-4H-1,2,4-triazol-3-yl)-1-hydroxy-2-propanesulfonamide and (1R,2R)-1-(4-bromo-2-fluorophenyl)-N-(4-(2,6-dimethoxyphenyl)-5-(5-methyl-2-furanyl)-4H-1,2,4-triazol-3-yl)-1-hydroxy-2-propanesulfonamide, Example 75.0. The title compound was prepared from Example 61.1 following the procedure described in Example 58.2 to install the cyano group followed by removal of the silyl protecting group following the procedure described in Example 59.0 employing tris(dimethylamino)sulfonium difluorotrimethylsilicate (IV). $^1$H 61.0

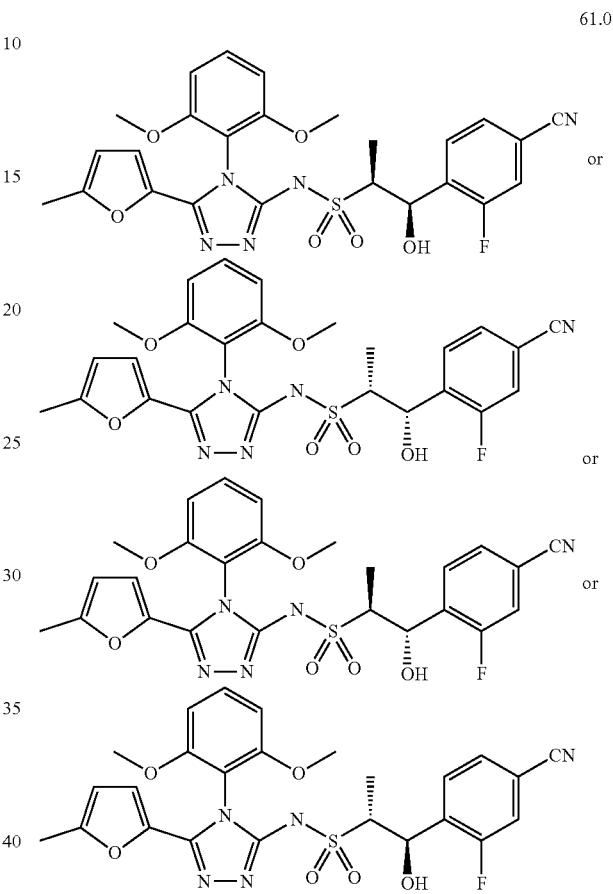

(1R,2S)-1-(4-Cyano-2-fluorophenyl)-N-(4-(2,6-dimethoxyphenyl)-5-(5-methyl-2-furanyl)-4H-1,2,4-triazol-3-yl)-1-hydroxy-2-propanesulfonamide or (1S,2R)-1-(4-cyano-2-fluorophenyl)-N-(4-(2,6-dimethoxyphenyl)-5-(5-methyl-2-furanyl)-4H-1,2,4-triazol-3-yl)-1-hydroxy-2-propanesulfonamide or (1S,2S)-1-(4-cyano-2-fluorophenyl)-N-(4-(2,6-dimethoxyphenyl)-5-(5-methyl-2-furanyl)-4H-1,2,4-triazol-3-yl)-1-hydroxy-2-propanesulfonamide or (1R,2R)-1-(4-cyano-2-fluorophenyl)-N-(4-(2,6-dimethoxyphenyl)-5-(5-methyl-2-furanyl)-4H-1,2,4-triazol-3-yl)-1-hydroxy-2-propanesulfonamide, Example 61.0. Example 75.0 was separated by SFC into four isomers. Separation condition were as follows: Stage 1: Run with 250×30 mm IC column with 30 mL/min EtOH(Neat)+90 g/min CO$_2$ on Thar 200 SFC, 120 g/min at 25% co-solvent. Outlet pressure=100 bar; Temp.=20° C.; Wavelength=225 nm. Used 0.35 mL injections of 30 mg/5 mL (16.6 mg/mL) sample solution MeOH and DCM (1:1), i.e. 5.8 mg/injection. Cycle time 14.5 min. Run time=30 min. Stage 2: Peak 3 from stage 1 was dried down and re-screened for separation. Run with 250×30 mm AS-H column with 24 mL/min MeOH (Neat)+96 g/min CO$_2$ on Thar 200 SFC, 120 g/min at 20% co-solvent. Outlet pressure=100 bar; Temp.=20° C.; Wavelength=225 nm.

Used 1 mL injections sample dissolved in 8 mL MeOH (30% DCM), Cycle time 10.0 min. Run time=12.5 min. The title compound was the second peak of the major diastereomer pair (stage 2, peak 2) to elute on subjecting Example 75.0 to the SFC conditions described above. $^1$H NMR (400 MHz, CDCl$_3$) δ 10.83 (s, 1H) 7.67 (t, J=7.53 Hz, 1H) 7.51 (t, J=8.51 Hz, 1H) 7.45-7.48 (m, 1H) 7.32 (dd, J=9.78, 1.17 Hz, 1H) 6.73 (d, J=8.61 Hz, 1H) 6.70 (d, J=8.61 Hz, 1H) 5.90-6.02 (m, 1H) 5.88 (d, J=3.52 Hz, 1H) 5.76 (s, 1H) 4.13 (s, 1H) 3.86 (s, 3H) 3.77 (s, 3H) 3.45-3.53 (m, 1H) 3.22-3.32 (m, 1H) 2.33 (s, 3H) 1.15 (d, J=7.04 Hz, 3H). LCMS-ESI (pos.) m/z: 542.0 (M+H)$^+$.

Example 62.0. Preparation of (3S,4R)—N-(4-(2,6-dimethoxyphenyl)-5-(5-methyl-2-furanyl)-4H-1,2,4-triazol-3-yl)-1-hydroxy-4-(5-methyl-2-pyrimidinyl)-3-pentanesulfonamide or (3R,4S)—N-(4-(2,6-dimethoxyphenyl)-5-(5-methyl-2-furanyl)-4H-1,2,4-triazol-3-yl)-1-hydroxy-4-(5-methyl-2-pyrimidinyl)-3-pentanesulfonamide or (3S,4S)—N-(4-(2,6-dimethoxyphenyl)-5-(5-methyl-2-furanyl)-4H-1,2,4-triazol-3-yl)-1-hydroxy-4-(5-methyl-2-pyrimidinyl)-3-pentanesulfonamide or (3R,4R)—N-(4-(2,6-dimethoxyphenyl)-5-(5-methyl-2-furanyl)-4H-1,2,4-triazol-3-yl)-1-hydroxy-4-(5-methyl-2-pyrimidinyl)-3-pentanesulfonamide

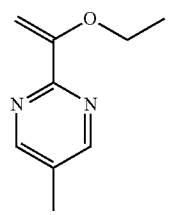

62.1

2-(1-Ethoxyvinyl)-5-methylpyrimidine, Example 62.1. A flask was charged with 2-chloro-5-methylpyrimidine (5.0 g, 38.9 mmol, Indofine Inc.), Pd(PPh$_3$)$_4$ (4.49 g, 3.89 mmol, Strem Chemicals Inc.) and purged with nitrogen. Degassed 1,4-dioxane (90 mL) was added followed by tributyl(1-ethoxyvinyl)stannane (19.71 mL, 58.3 mmol). The reaction was heated to 100° C. for 16 h. The reaction mixture was concentrated and directly purified by chromatography through a Redi-Sep pre-packed gold silica gel column, eluting with a gradient of 0% to 40% EtOAc in hexanes to provide the title compound (Example 62.1, 3.3 g, 52%). LCMS-ESI (pos.) m/z: 165.1 (M+H)$^+$.

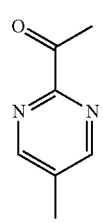

62.2

1-(5-Methylpyrimidin-2-yl)ethanone, Example 62.2. 2-(1-Ethoxyvinyl)-5-methylpyrimidine (Example 62.1, 3.3 g, 20.10 mmol) was dissolved in 1,4-dioxane (20 mL). HCl (8.04 mL, 40.2 mmol, 5 M, Macron Chemicals) was added, and the reaction was heated at 80° C. for 15 min. The reaction was carefully neutralized with 5N NaOH to pH neutral and concentrated to dryness. The mixture was diluted with 30% IPA in CHCl$_3$ and filtered. The filtrate was purified by chromatography through a Redi-Sep pre-packed gold silica gel column eluting with a gradient of 0-80% EtOAc in heptanes and then 2-5% MeOH/DCM to provide the title compound (Example 62.2, 1.69 g) as a white solid. LCMS-ESI (pos.) m/z: 159.1 (M+Na)$^+$.

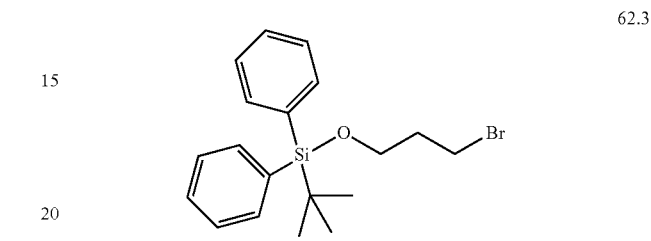

62.3

(3-Bromopropoxy)(tert-butyl)diphenylsilane, Example 62.3. A flask was charged with 1H-imidazole (10.78 g, 158 mmol), and DCM (250 mL) was added followed by 3-bromopropan-1-ol (6.51 mL, 71.9 mmol) and tert-butylchlorodiphenylsilane (18.78 mL, 73.4 mmol). The reaction was stirred overnight under nitrogen. Next, water was added and the reaction was extracted with DCM. The DCM layer was washed with brine, dried, and purified by chromatography through a Redi-Sep pre-packed gold silica gel column eluting with a gradient of 0-5% EtOAc in hexanes to give Example 62.3, (21.72 g, 80%). $^1$H NMR (400 MHz, CDCl$_3$) δ 7.66-7.70 (m, 4H) 7.38-7.47 (m, 6H) 3.80 (t, J=5.77 Hz, 2H) 3.60 (t, J=6.55 Hz, 2H) 2.09 (quin, J=6.16 Hz, 2H) 1.03-1.11 (m, 9H).

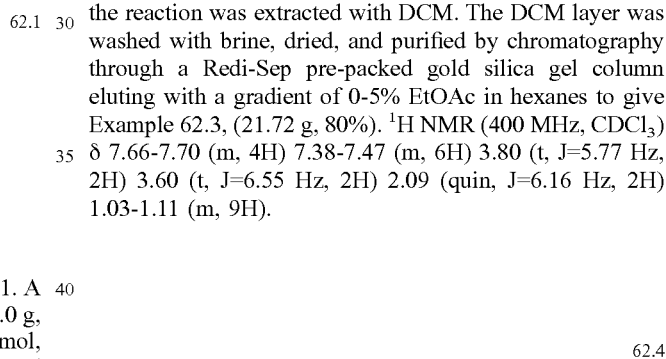

62.4

(3-((tert-Butyldiphenylsilyl)oxy)propyl)triphenylphosphonium bromide, Example 62.4. (3-Bromopropoxy)(tert-butyl)diphenylsilane (Example 62.3, 21.94 g, 58.1 mmol) was azeotroped with toluene. To this was added triphenylphosphine (12.2 g, 46.5 mmol) followed by benzene (31 mL). The resulting mixture was heated overnight at reflux. A white precipitate formed and was removed by filteration. The filtrate was heated to reflux. More precipitate formed which was collected and combined with the previous batch. The solids were dried to yield (3-((tert-butyldiphenylsilyl)oxy)propyl)triphenylphosphonium bromide (Example 62.4, 18.83 g) which was directly used in the next step.

62.5

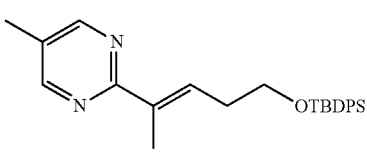

(E)-2-(5-((tert-Butyldiphenylsilyl)oxy)pent-2-en-2-yl)-5-methylpyrimidine, Example 62.5. (3-((tert-Butyldiphenylsilyl)oxy)propyl)triphenylphosphonium bromide (Example 62.4, 15.09 g, 23.58 mmol) was azeotroped with toluene and dried on a high vacuum pump overnight. The material was suspended in THF (100 mL) under nitrogen. The suspension was cooled in an ice-bath and sodium bis(trimethylsilyl) amide (1.0 M, 25.2 mL, 25.2 mmol) was added dropwise. After 30 min., 1-(5-methylpyrimidin-2-yl)ethanone (Example 62.2, 1.97 g, 14.47 mmol) in THF (5 mL) was added. The mixture was stirred overnight. A saturated NH$_4$Cl solution was then added, and the reaction was extracted with EtOAc. The EtOAc layer was dried, concentrated in vacuo, and purified by chromatography through a Redi-Sep pre-packed gold silica gel column eluting with a gradient 0-10% EtOAc in hexanes to obtain the desired product (3.99 g) that contained an impurity but was carried on to the next step without further purification. LCMS-ESI (pos.) m/z: 417.2 (M+H)$^+$.

62.6

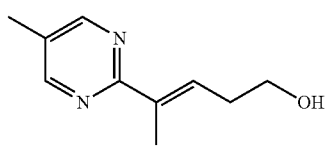

(E)-4-(5-Methylpyrimidin-2-yl)pent-3-en-1-ol, Example 62.6. To a flask containing (E)-2-(5-((tert-butyldiphenylsilyl)oxy)pent-2-en-2-yl)-5-methylpyrimidine (Example 62.5, 3.99 g, 9.58 mmol) was added THF (28 mL) and then TBAF (3.54 mL, 3.54 mmol). The reaction was stirred overnight. Next, the reaction was concentrated and then dry-loaded onto a silica gel column (80 g) and purified with gradient 0-85% EtOAc in hexanes then gradient 0-10% MeOH/DCM to obtain Example 62.6 (1.43 g, 84%) as a white solid. LCMS-ESI (pos.) m/z: 179.2 (M+H)$^+$.

77.0

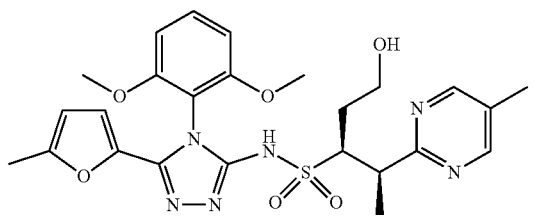

and

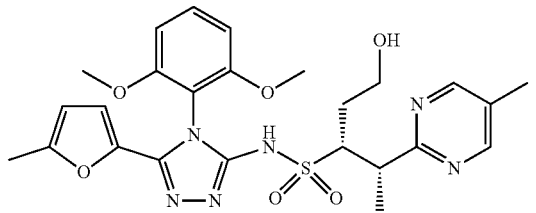

and

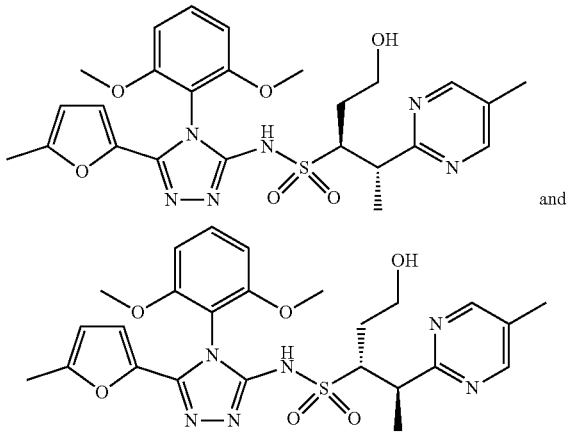

(3S,4R)—N-(4-(2,6-Dimethoxyphenyl)-5-(5-methyl-2-furanyl)-4H-1,2,4-triazol-3-yl)-1-hydroxy-4-(5-methyl-2-pyrimidinyl)-3-pentanesulfonamide and (3R,4S)—N-(4-(2,6-dimethoxyphenyl)-5-(5-methyl-2-furanyl)-4H-1,2,4-triazol-3-yl)-1-hydroxy-4-(5-methyl-2-pyrimidinyl)-3-pentanesulfonamide and (3S,4S)—N-(4-(2,6-dimethoxyphenyl)-5-(5-methyl-2-furanyl)-4H-1,2,4-triazol-3-yl)-1-hydroxy-4-(5-methyl-2-pyrimidinyl)-3-pentanesulfonamide and (3R,4R)—N-(4-(2,6-dimethoxyphenyl)-5-(5-methyl-2-furanyl)-4H-1,2,4-triazol-3-yl)-1-hydroxy-4-(5-methyl-2-pyrimidinyl)-3-pentanesulfonamide, Example 77.0. The title compound was prepared from Example 62.6 following the procedure described in Example 70.0. $^1$H NMR (400 MHz, CD$_3$OD) δ 8.59 (m, 2H) 7.54 (m, 1H) 6.82 (m, 2H) 6.01 (m, 1H) 5.93 (m, 1H) 3.77 (m, 7H) 3.58 (m, 3H) 2.32 (m, 3H) 2.26 (s, 3H) 1.98 (m, 2H) 1.41 (m, 3H). LCMS-ESI (pos.) m/z: 543.0 (M+H)$^+$.

Example 62.0. Preparation of (3S,4R)—N-(4-(2,6-dimethoxyphenyl)-5-(5-methyl-2-furanyl)-4H-1,2,4-triazol-3-yl)-1-hydroxy-4-(5-methyl-2-pyrimidinyl)-3-pentanesulfonamide or (3R,4S)—N-(4-(2,6-dimethoxyphenyl)-5-(5-methyl-2-furanyl)-4H-1,2,4-triazol-3-yl)-1-hydroxy-4-(5-methyl-2-pyrimidinyl)-3-pentanesulfonamide or (3S,4S)—N-(4-(2,6-dimethoxyphenyl)-5-(5-methyl-2-furanyl)-4H-1,2,4-triazol-3-yl)-1-hydroxy-4-(5-methyl-2-pyrimidinyl)-3-pentanesulfonamide or (3R,4R)—N-(4-(2,6-dimethoxyphenyl)-5-(5-methyl-2-furanyl)-4H-1,2,4-triazol-3-yl)-1-hydroxy-4-(5-methyl-2-pyrimidinyl)-3-pentanesulfonamide 62.0

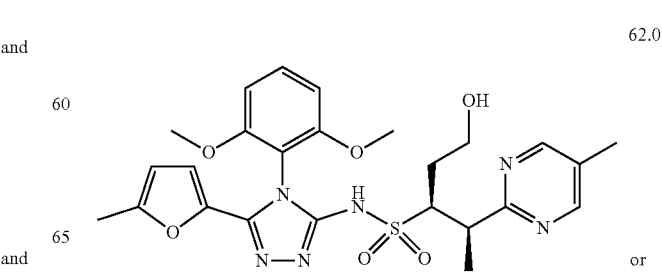

or

-continued

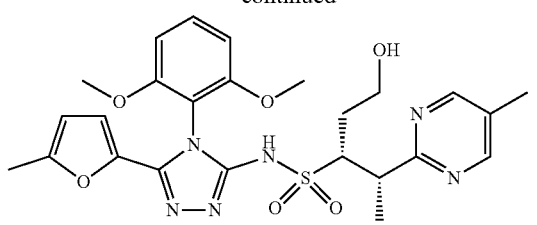

or

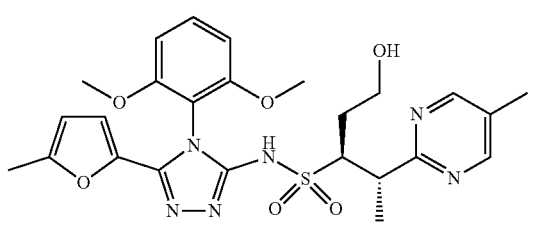

or

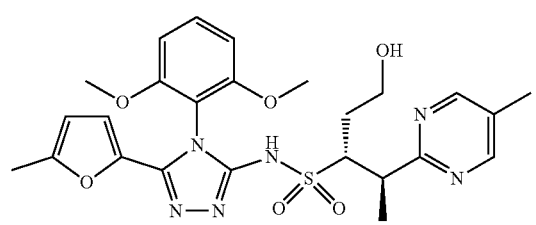

(3S,4R)—N-(4-(2,6-Dimethoxyphenyl)-5-(5-methyl-2-furanyl)-4H-1,2,4-triazol-3-yl)-1-hydroxy-4-(5-methyl-2-pyrimidinyl)-3-pentanesulfonamide or (3R,4S)—N-(4-(2,6-dimethoxyphenyl)-5-(5-methyl-2-furanyl)-4H-1,2,4-triazol-3-yl)-1-hydroxy-4-(5-methyl-2-pyrimidinyl)-3-pentanesulfonamide or (3S,4S)—N-(4-(2,6-dimethoxyphenyl)-5-(5-methyl-2-furanyl)-4H-1,2,4-triazol-3-yl)-1-hydroxy-4-(5-methyl-2-pyrimidinyl)-3-pentanesulfonamide or (3R,4R)—N-(4-(2,6-dimethoxyphenyl)-5-(5-methyl-2-furanyl)-4H-1,2,4-triazol-3-yl)-1-hydroxy-4-(5-methyl-2-pyrimidinyl)-3-pentanesulfonamide, Example 62.0. Example 77.0 was separated by SFC into four peaks. Separation conditions were as follows: 250×30 mm CC₄ column with 54 mL/min MeOH (20 mM Ammonia)+66 g/min $CO_2$ on Thar 350 SFC, 45% co-solvent at 120 g/min. Outlet pressure=100 bar; Temp.=20° C.; Wavelength=276 nm. Used 0.8 mL injections of 140 mg/17 mL (8.2 mg/mL) sample solution in MeOH:DCM (14:3), i.e. 6.6 mg/injection. Cycle time=18 min., Run time=19 min. The title compound was the first peak (faster-eluting) from the chiral separation. ¹H NMR (400 MHz, CD₃OD) δ 8.57 (s, 2H) 7.53 (t, J=8.51 Hz, 1H) 6.82 (dd, J=8.61, 0.98 Hz, 2H) 6.01 (dd, J=3.52, 0.98 Hz, 1H) 5.93 (d, J=3.52 Hz, 1H) 3.90 (m, 1H) 3.78 (m, 1H) 3.75 (s, 3H) 3.74 (s, 3H) 3.49 (m, 1H) 3.40 (m, 1H) 2.30 (s, 3H) 2.26 (s, 3H) 2.08 (m, 1H) 1.82 (m, 1H) 1.37 (d, J=7.04 Hz, 3H). LCMS-ESI (pos.) m/z: 543.0 (M+H)⁺.

Example 63.0. Preparation of (1S,2S)—N-(4-(2,6-dimethoxyphenyl)-5-(5-methyl-2-furanyl)-4H-1,2,4-triazol-3-yl)-1-hydroxy-1-(5-methyl-2-pyridinyl)-2-propanesulfonamide or (1R,2R)—N-(4-(2,6-dimethoxyphenyl)-5-(5-methyl-2-furanyl)-4H-1,2,4-triazol-3-yl)-1-hydroxy-1-(5-methyl-2-pyridinyl)-2-propanesulfonamide or (1R,2S)—N-(4-(2,6-dimethoxyphenyl)-5-(5-methyl-2-furanyl)-4H-1,2,4-triazol-3-yl)-1-hydroxy-1-(5-methyl-2-pyridinyl)-2-propanesulfonamide or (1S,2R)—N-(4-(2,6-dimethoxyphenyl)-5-(5-methyl-2-furanyl)-4H-1,2,4-triazol-3-yl)-1-hydroxy-1-(5-methyl-2-pyridinyl)-2-propanesulfonamide 63.1

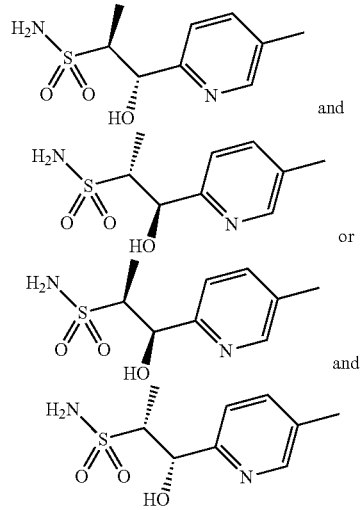

(1S,2S)-1-Hydroxy-1-(5-methylpyridin-2-yl)propane-2-sulfonamide and (1R,2R)-1-hydroxy-1-(5-methylpyridin-2-yl)propane-2-sulfonamide, or (1R,2S)-1-hydroxy-1-(5-methylpyridin-2-yl)propane-2-sulfonamide and (1S,2R)-1-hydroxy-1-(5-methylpyridin-2-yl)propane-2-sulfonamide, Example 63.1. The title compound was prepared according to the procedure described in Example 356.04 using Example 361.0 and 5-methylpicolinaldehyde. Example 63.1 is the major diastereomer pair isolated after purification on silica gel.

63.2

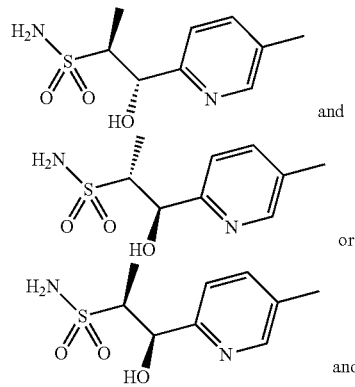

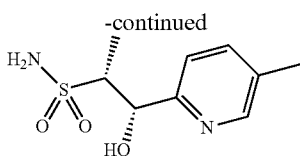

(1S,2S)-1-Hydroxy-1-(5-methylpyridin-2-yl)propane-2-sulfonamide and (1R,2R)-1-hydroxy-1-(5-methylpyridin-2-yl)propane-2-sulfonamide, or (1R,2S)-1-hydroxy-1-(5-methylpyridin-2-yl)propane-2-sulfonamide and (1S,2R)-1-hydroxy-1-(5-methylpyridin-2-yl)propane-2-sulfonamide, Example 63.2. The title compound was prepared according to the procedure described in Example 63.1. Example 63.2 is the minor diastereomer pair isolated after silica gel chromatography.

63.3

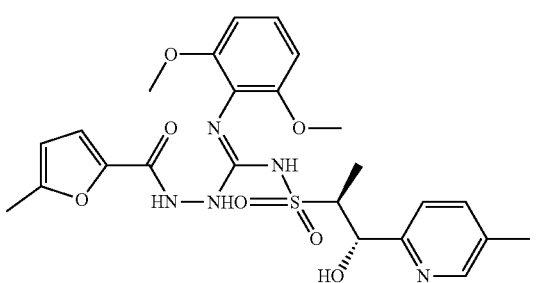

and

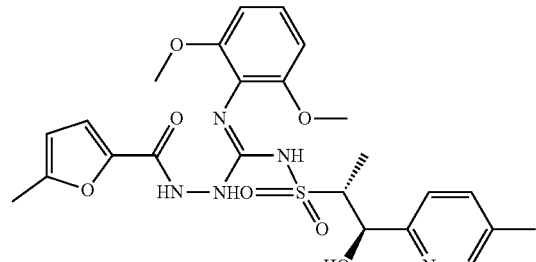

or

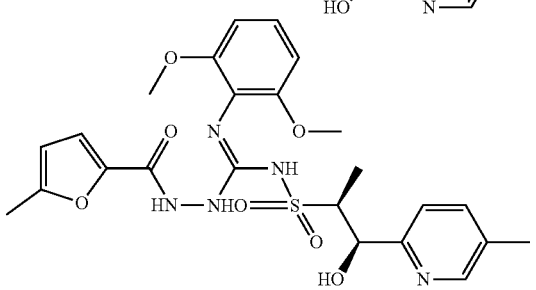

and

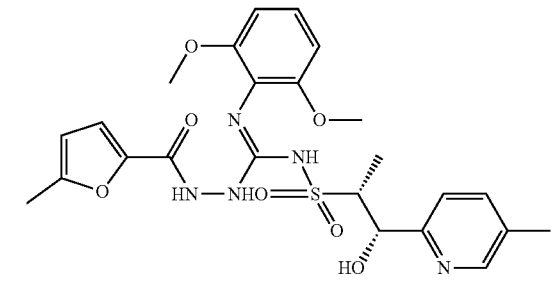

(Z)—N'-(2,6-Dimethoxyphenyl)-N-(((1S,2S)-1-hydroxy-1-(5-methylpyridin-2-yl)propan-2-yl)sulfonyl)-2-(5-methylfuran-2-carbonyl)hydrazinecarboximidamide and (Z)—N'-(2,6-dimethoxyphenyl)-N-(((1R,2R)-1-hydroxy-1-(5-methylpyridin-2-yl)propan-2-yl)sulfonyl)-2-(5-methylfuran-2-carbonyl)hydrazinecarboximidamide or (Z)—N'-(2,6-dimethoxyphenyl)-N-(1R,2S)-1-hydroxy-1-(5-methylpyridin-2-yl)propan-2-yl)sulfonyl)-2-(5-methylfuran-2-carbonyl)hydrazinecarboximidamide and (Z)—N'-(2,6-dimethoxyphenyl)-N-(((1S,2R)-1-hydroxy-1-(5-methylpyridin-2-yl)propan-2-yl)sulfonyl)-2-(5-methylfuran-2-carbonyl)hydrazinecarboximidamide, Example 63.3. The title compound was prepared according to the general procedure described in the synthesis of Example 149.0 using Example 63.1, Example 372.0, and 5-methyl-2-furohydrazide (commercially available from Chembridge Corporation, San Diego, Calif., USA).

Example 65.0. Preparation of (1S,2S)—N-(4-(2,6-dimethoxyphenyl)-5-(5-methyl-2-furanyl)-4H-1,2,4-triazol-3-yl)-1-hydroxy-1-(5-methyl-2-pyridinyl)-2-propanesulfonamide and (1R,2R)—N-(4-(2,6-dimethoxyphenyl)-5-(5-methyl-2-furanyl)-4H-1,2,4-triazol-3-yl)-1-hydroxy-1-(5-methyl-2-pyridinyl)-2-propanesulfonamide or (1R,2S)—N-(4-(2,6-dimethoxyphenyl)-5-(5-methyl-2-furanyl)-4H-1,2,4-triazol-3-yl)-1-hydroxy-1-(5-methyl-2-pyridinyl)-2-propanesulfonamide and (1S,2R)—N-(4-(2,6-dimethoxyphenyl)-5-(5-methyl-2-furanyl)-4H-1,2,4-triazol-3-yl)-1-hydroxy-1-(5-methyl-2-pyridinyl)-2-propanesulfonamide 65.0

-continued

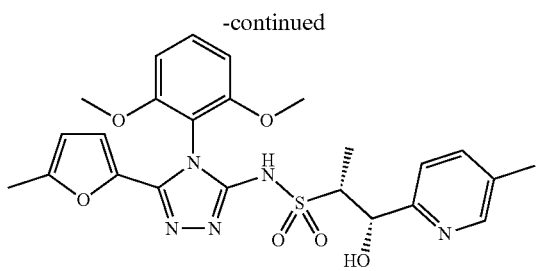

(1S,2S)—N-(4-(2,6-Dimethoxyphenyl)-5-(5-methyl-2-furanyl)-4H-1,2,4-triazol-3-yl)-1-hydroxy-1-(5-methyl-2-pyridinyl)-2-propanesulfonamide and (1R,2R)—N-(4-(2,6-dimethoxyphenyl)-5-(5-methyl-2-furanyl)-4H-1,2,4-triazol-3-yl)-1-hydroxy-1-(5-methyl-2-pyridinyl)-2-propanesulfonamide and (1R,2S)—N-(4-(2,6-dimethoxyphenyl)-5-(5-methyl-2-furanyl)-4H-1,2,4-triazol-3-yl)-1-hydroxy-1-(5-methyl-2-pyridinyl)-2-propanesulfonamide and (1S,2R)—N-(4-(2,6-dimethoxyphenyl)-5-(5-methyl-2-furanyl)-4H-1,2,4-triazol-3-yl)-1-hydroxy-1-(5-methyl-2-pyridinyl)-2-propanesulfonamide, Example 65.0. Example 63.3 (215 mg, 0.404 mmol) was azeotroped with toluene. DMF (0.6 mL) was added followed by TFA (0.156 mL, 2.02 mmol). The resulting mixture was heated at 100° C. under nitrogen for 6 hr. Next, more TFA (0.156 mL, 2.022 mmol) was added and heating was continued overnight. The reaction was then cooled to RT and concentrated in vacuo and directly purified on reverse phase HPLC (Agilent SB C8 column, 0.1% TFA in ACN/water, 10-60% gradient over 25 min) to give title compound. $^1$H NMR (400 MHz, CD$_3$OD) δ 8.48 (s, 1H) 8.12 (d, J=8.22 Hz, 1H) 7.58 (m, 2H) 6.87 (dd, J=8.71, 1.66 Hz, 2H) 6.03 (dd, J=3.52, 0.98 Hz, 1H) 5.98 (d, J=3.52 Hz, 1H) 5.36 (d, J=3.72 Hz, 1H) 3.78 (m, 6H) 3.47 (m, 1H) 2.47 (m, 3H) 2.26 (s, 3H) 1.22 (m, 3H). LCMS-ESI (pos.) m/z: 514.0 (M+H)$^+$.

Example 63.0. Preparation of (1S,2S)—N-(4-(2,6-dimethoxyphenyl)-5-(5-methyl-2-furanyl)-4H-1,2,4-triazol-3-yl)-1-hydroxy-1-(5-methyl-2-pyridinyl)-2-propanesulfonamide or (1R,2R)—N-(4-(2,6-dimethoxyphenyl)-5-(5-methyl-2-furanyl)-4H-1,2,4-triazol-3-yl)-1-hydroxy-1-(5-methyl-2-pyridinyl)-2-propanesulfonamide or (1R,2S)—N-(4-(2,6-dimethoxyphenyl)-5-(5-methyl-2-furanyl)-4H-1,2,4-triazol-3-yl)-1-hydroxy-1-(5-methyl-2-pyridinyl)-2-propanesulfonamide or (1S,2R)—N-(4-(2,6-dimethoxyphenyl)-5-(5-methyl-2-furanyl)-4H-1,2,4-triazol-3-yl)-1-hydroxy-1-(5-methyl-2-pyridinyl)-2-propanesulfonamide 63.0

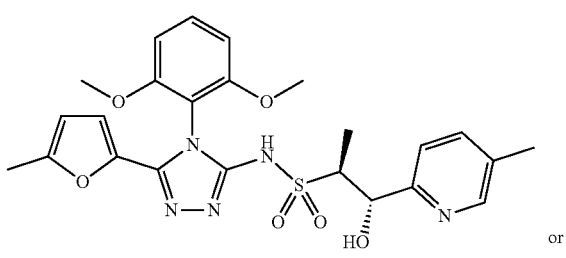

or

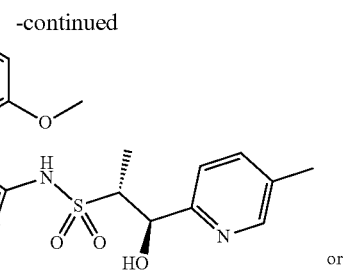

or

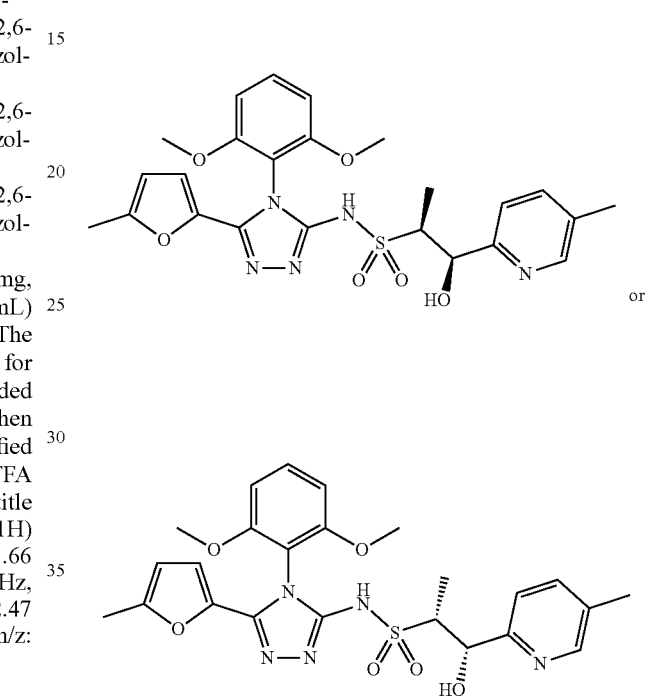

(1S,2S)—N-(4-(2,6-Dimethoxyphenyl)-5-(5-methyl-2-furanyl)-4H-1,2,4-triazol-3-yl)-1-hydroxy-1-(5-methyl-2-pyridinyl)-2-propanesulfonamide or (1R,2R)—N-(4-(2,6-dimethoxyphenyl)-5-(5-methyl-2-furanyl)-4H-1,2,4-triazol-3-yl)-1-hydroxy-1-(5-methyl-2-pyridinyl)-2-propanesulfonamide or (1R,2S)—N-(4-(2,6-dimethoxyphenyl)-5-(5-methyl-2-furanyl)-4H-1,2,4-triazol-3-yl)-1-hydroxy-1-(5-methyl-2-pyridinyl)-2-propanesulfonamide or (1S,2R)—N-(4-(2,6-dimethoxyphenyl)-5-(5-methyl-2-furanyl)-4H-1,2,4-triazol-3-yl)-1-hydroxy-1-(5-methyl-2-pyridinyl)-2-propanesulfonamide, Example 63.0. Example 65.0 was separated by SFC (separation condition: Run on Thar 80 SFC with 250×21 mm IC column with 27 g/min MeOH (neat)+33 g/min CO$_2$, 45% co-solvent at 60 g/min. Outlet pressure=100 bar; Temp.=22° C.; Wavelength=275 nm. Injected 0.5 mL of a solution from 23 mg sample dissolved in 4 mL of MeOH, c=5.8 mg/mL; 2.4 mg per injection.) Two enantiomers were obtained. The title compound was the first peak to elute off the chiral column. $^1$H NMR (400 MHz, CD$_3$OD) δ 8.32 (s, 1H) 7.65 (dd, J=8.02, 1.76 Hz, 1H) 7.56 (t, J=8.51 Hz, 1H) 7.46 (d, J=8.02 Hz, 1H) 6.85 (dd, J=8.61, 2.54 Hz, 2H) 6.02 (dd, J=3.52, 0.78 Hz, 1H) 5.96 (d, J=3.33 Hz, 1H) 5.38 (s, 1H) 3.77 (s, 3H) 3.76 (s, 3H) 3.55 (m, 1H) 2.33 (s, 3H) 2.26 (s, 3H) 1.07 (d, J=7.04 Hz, 3H). LCMS-ESI (pos.) m/z: 514.0 (M+H)$^+$.

Example 64.0. Preparation of (2R)—N-(4-(2,6-dimethoxyphenyl)-5-(5-methyl-2-furanyl)-4H-1,2,4-triazol-3-yl)-2-(5-fluoro-2-pyridinyl)-2-hydroxyethanesulfonamide or (2S)—N-(4-(2,6-dimethoxyphenyl)-5-(5-methyl-2-furanyl)-4H-1,2,4-triazol-3-yl)-2-(5-fluoro-2-pyridinyl)-2-hydroxyethanesulfonamide

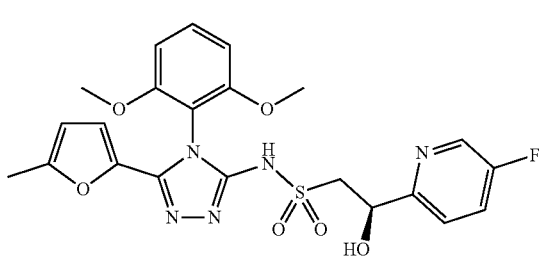

64.0

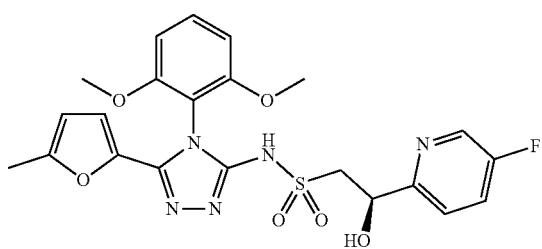

(2R)—N-(4-(2,6-Dimethoxyphenyl)-5-(5-methyl-2-furanyl)-4H-1,2,4-triazol-3-yl)-2-(5-fluoro-2-pyridinyl)-2-hydroxyethanesulfonamide or (2S)—N-(4-(2,6-dimethoxyphenyl)-5-(5-methyl-2-furanyl)-4H-1,2,4-triazol-3-yl)-2-(5-fluoro-2-pyridinyl)-2-hydroxyethanesulfonamide, Example 64.0. Example 60.0 was purified by SFC to give two enantiomers. Chiral separation conditions were as follows: Run on Thar 200 with 250×30 mm AD-H column with 36 g/min EtOH (neat) and 84 g/min CO$_2$, 30% co-solvent at 120 g/min. Wavelength 275 nm. Injected 0.5 mL of 90 mg dissolved in 7.0 mL MeOH (25% DCM); 12.8=x/mL, 6.4 mg/injection. Cycle time 9.0 min, run time 21 min. The title compound was the second peak to elute. $^1$H NMR (400 MHz, CD$_3$OD) δ 8.33-8.44 (m, 1H) 7.52-7.62 (m, 3H) 6.84 (d, J=8.66 Hz, 2H) 6.02 (dd, J=3.87 Hz, 1H) 5.96 (d, J=3.52 Hz, 1H) 5.17 (dd, J=8.71, 3.03 Hz, 1H) 3.78 (s, 3H) 3.77 (s, 3H) 3.63 (dd, J=14.18, 3.23 Hz, 1H) 3.26-3.36 (m, 13H) 2.26 (s, 3H). LCMS-ESI (pos.) m/z: 504.0 (M+H)$^+$.

Example 66.0. Preparation of (2R)-2-(5-cyano-2-pyridinyl)-N-(4-(2,6-dimethoxyphenyl)-5-(5-methyl-2-furanyl)-4H-1,2,4-triazol-3-yl)-2-hydroxyethanesulfonamide or (2S)-2-(5-cyano-2-pyridinyl)-N-(4-(2,6-dimethoxyphenyl)-5-(5-methyl-2-furanyl)-4H-1,2,4-triazol-3-yl)-2-hydroxyethanesulfonamide 66.1

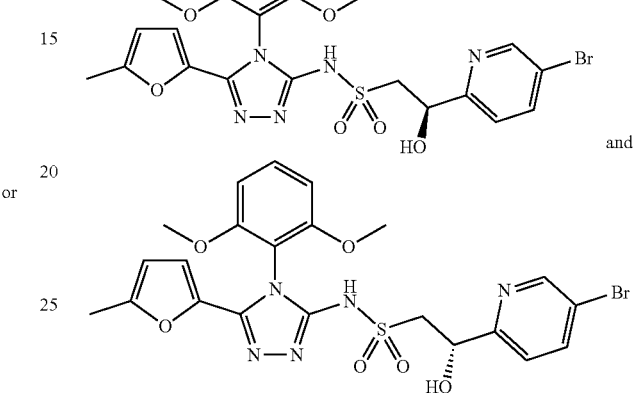

(S)-2-(5-Bromopyridin-2-yl)-N-(4-(2,6-dimethoxyphenyl)-5-(5-methylfuran-2-yl)-4H-1,2,4-triazol-3-yl)-2-hydroxyethanesulfonamide and (R)-2-(5-bromopyridin-2-yl)-N-(4-(2,6-dimethoxyphenyl)-5-(5-methylfuran-2-yl)-4H-1,2,4-triazol-3-yl)-2-hydroxyethanesulfonamide, Example 66.1. The title compound (Example 66.1) was prepared as a TFA salt following procedures described in Example 57.0 and Example 59.0 using 5-bromopicolinaldehyde and Example 365.2. LCMS-ESI (pos.) m/z: 565.9 (M+H)$^+$.

66.2

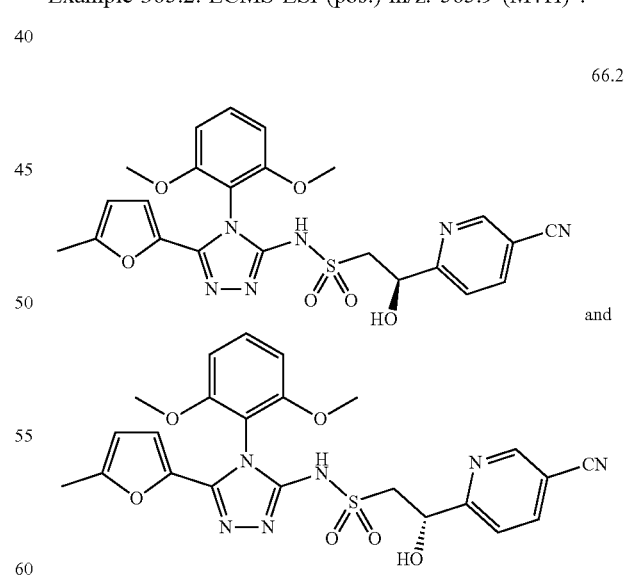

(2R)-2-(5-Cyano-2-pyridinyl)-N-(4-(2,6-dimethoxyphenyl)-5-(5-methyl-2-furanyl)-4H-1,2,4-triazol-3-yl)-2-hydroxyethanesulfonamide and (2S)-2-(5-cyano-2-pyridinyl)-N-(4-(2,6-dimethoxyphenyl)-5-(5-methyl-2-furanyl)-4H-1,2,4-triazol-3-yl)-2-hydroxyethanesulfonamide, Example 66.2. A microwave tube was charged with dicyanozinc (58.2 mg, 0.50 mmol, Alfa Aesar), Pd(PPh$_3$)$_4$ (69.8 mg, 0.060 mmol, Strem Chemicals Inc.), and Example 66.1 (205 mg, 0.302 mmol). Argon-degassed DMF (2.5 mL) was added, and the reaction was degassed again with argon. The reaction was heated to 120° C. for 1 h in a microwave. Water was added and the reaction was extracted with EtOAc. The EtOAc layer was washed with brine, dried, concentrated in vacuo, and purified on reverse phase HPLC in 2 batches using an Agilent SB C8 column, 0.1% TFA in ACN/H$_2$O, gradient 30-70% over 25 min and collecting peaks at 220 nM to provide the title compound (97 mg) as a white solid. $^1$H NMR (400 MHz, CD$_3$OD) δ 8.83-8.85 (m, 1H) 8.15 (dd, J=8.22, 2.15 Hz, 1H) 7.72 (d, J=8.22 Hz, 1H) 7.56 (t, J=8.51 Hz, 1H) 6.86 (d, J=0.98 Hz, 1H) 6.83 (d, J=0.78 Hz, 1H) 6.02 (dd, J=4.81 Hz, 1H) 5.96 (d, J=3.52 Hz, 1H) 5.21 (dd, J=8.71, 3.23 Hz, 1H) 3.77 (s, 3H) 3.77 (s, 3H) 3.69 (dd, J=14.28, 3.33 Hz, 1H) 3.31 (m, 1H) 2.26 (s, 3H). LCMS-ESI (pos.) m/z: 511.0 (M+H)$^+$.

66.0

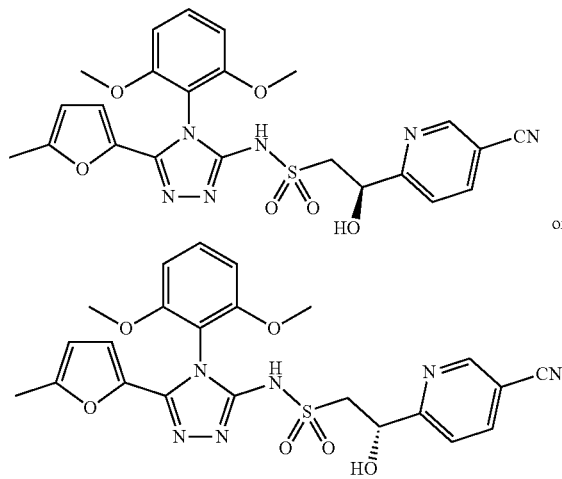

(2R)-2-(5-Cyano-2-pyridinyl)-N-(4-(2,6-dimethoxyphenyl)-5-(5-methyl-2-furanyl)-4H-1,2,4-triazol-3-yl)-2-hydroxyethanesulfonamide or (2S)-2-(5-cyano-2-pyridinyl)-N-(4-(2,6-dimethoxyphenyl)-5-(5-methyl-2-furanyl)-4H-1,2,4-triazol-3-yl)-2-hydroxyethanesulfonamide, Example 66.0. Example 66.2 was separated by SFC into two enantiomers. Chiral separation conditions were as follows: Run on Thar 80 SFC with 250×30 mm IC column with 44 g/min MeOH (neat)+36 g/min CO$_2$, 55% co-solvent at 80 g/min. Outlet pressure=100 bar; Temp.=27° C.; Wavelength=222 nm. injected 0.2 mL of a solution from 29 mg sample dissolved in 3 mL of MeOH/DCM (50% DCM), c=9.6 mg/mL; 1.9 mg per injection. Cycle time 5.2 min, run time 12 min. The title compound was the second peak to elute on subjecting Example 66.2 to the SFC conditions described above. $^1$H NMR (400 MHz, CD$_3$OD) δ 8.82-8.90 (m, 1H) 8.15 (dd, J=8.22, 2.15 Hz, 1H) 7.72 (d, J=8.02 Hz, 1H) 7.56 (t, J=8.34 Hz, 1H) 6.85 (br. s, 1H) 6.83 (br. s, 1H) 6.01-6.04 (m, 1H) 5.96 (d, J=3.33 Hz, 1H) 5.21 (dd, J=8.80, 3.13 Hz, 1H) 3.77 (s, 3H) 3.77 (s, 3H) 3.69 (dd, J=14.18, 3.23 Hz, 1H) 3.26-3.36 (m, 1H) 2.26 (s, 3H). LCMS-ESI (pos.) m/z: 511.0 (M+H)$^+$.

Example 67.0. Preparation of (3S,4R)—N-(4-(2,6-dimethoxyphenyl)-5-(5-methyl-2-furanyl)-4H-1,2,4-triazol-3-yl)-4-(5-fluoro-2-pyrimidinyl)-1-methoxy-3-pentanesulfonamide or (3R,4S)—N-(4-(2,6-dimethoxyphenyl)-5-(5-methyl-2-furanyl)-4H-1,2,4-triazol-3-yl)-4-(5-fluoro-2-pyrimidinyl)-1-methoxy-3-pentanesulfonamide or (3R,4R)—N-(4-(2,6-dimethoxyphenyl)-5-(5-methyl-2-furanyl)-4H-1,2,4-triazol-3-yl)-4-(5-fluoro-2-pyrimidinyl)-1-methoxy-3-pentanesulfonamide or (3S,4S)—N-(4-(2,6-dimethoxyphenyl)-5-(5-methyl-2-furanyl)-4H-1,2,4-triazol-3-yl)-4-(5-fluoro-2-pyrimidinyl)-1-methoxy-3-pentanesulfonamide 67.1

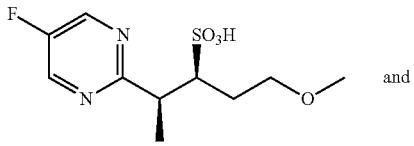
and

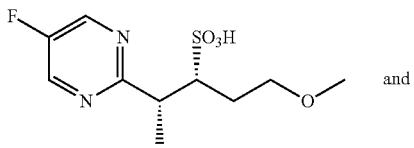
and

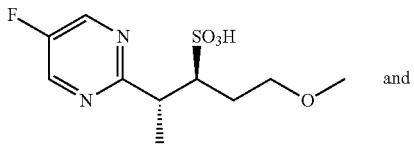
and

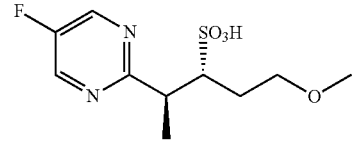

(3R,4S)-4-(5-Fluoropyrimidin-2-yl)-1-methoxypentane-3-sulfonic acid and (3S,4S)-4-(5-fluoropyrimidin-2-yl)-1-methoxypentane-3-sulfonic acid and (3R,4R)-4-(5-fluoropyrimidin-2-yl)-1-methoxypentane-3-sulfonic acid and (3S,4R)-4-(5-fluoropyrimidin-2-yl)-1-methoxypentane-3-sulfonic acid, Example 67.1. The title compound was prepared following the procedures described in Example 72.0 with heating at 60° C. over three days. The initial sulfonic acid was purified further on reverse phase HPLC (Gemini column, the mobile phase was 0.1% TFA in ACN/H$_2$O; the method was 2.5% isocratic for 5 min, then grading to 70% over 10 min, then 95% isocratic for 3 min (collected the peaks that were visible at 220 nm). The desired fractions were lyophilized to obtain the title compound. LCMS-ESI (pos.) m/z: 279.0 (M+H)$^+$.

Example 74.0. Preparation of (3S,4R)—N-(4-(2,6-dimethoxyphenyl)-5-(5-methyl-2-furanyl)-4H-1,2,4-triazol-3-yl)-4-(5-fluoro-2-pyrimidinyl)-1-methoxy-3-pentanesulfonamide and (3R,4S)—N-(4-(2,6-dimethoxyphenyl)-5-(5-methyl-2-furanyl)-4H-1,2,4-triazol-3-yl)-4-(5-fluoro-2-pyrimidinyl)-1-methoxy-3-pentanesulfonamide and (3R,4R)—N-(4-(2,6-dimethoxyphenyl)-5-(5-methyl-2-furanyl)-4H-1,2,4-triazol-3-yl)-4-(5-fluoro-2-pyrimidinyl)-1-methoxy-3-pentanesulfonamide and (3S,4S)—N-(4-(2,6-dimethoxyphenyl)-5-(5-methyl-2-furanyl)-4H-1,2,4-triazol-3-yl)-4-(5-fluoro-2-pyrimidinyl)-1-methoxy-3-pentanesulfonamide

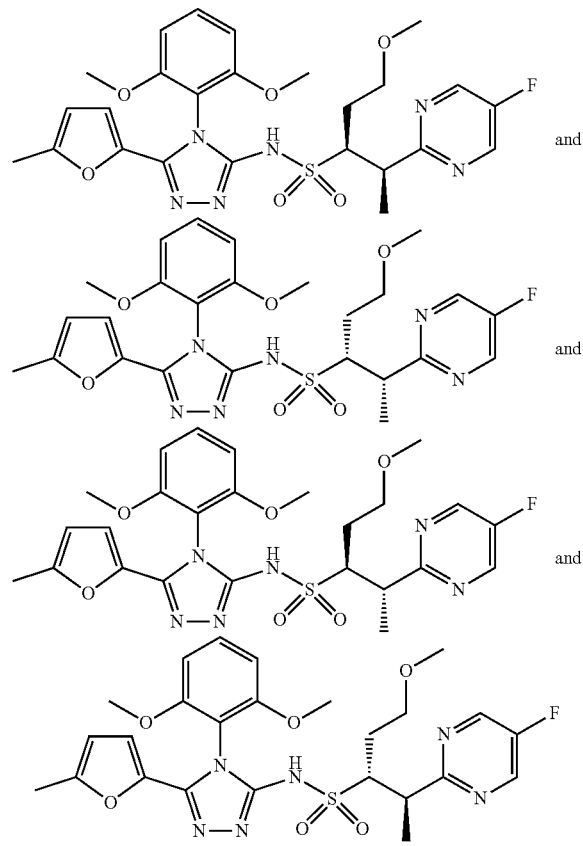

74.0

(3S,4R)—N-(4-(2,6-Dimethoxyphenyl)-5-(5-methyl-2-furanyl)-4H-1,2,4-triazol-3-yl)-4-(5-fluoro-2-pyrimidinyl)-1-methoxy-3-pentanesulfonamide and (3R,4S)—N-(4-(2,6-dimethoxyphenyl)-5-(5-methyl-2-furanyl)-4H-1,2,4-triazol-3-yl)-4-(5-fluoro-2-pyrimidinyl)-1-methoxy-3-pentanesulfonamide and (3R,4R)—N-(4-(2,6-dimethoxyphenyl)-5-(5-methyl-2-furanyl)-4H-1,2,4-triazol-3-yl)-4-(5-fluoro-2-pyrimidinyl)-1-methoxy-3-pentanesulfonamide and (3S,4S)—N-(4-(2,6-dimethoxyphenyl)-5-(5-methyl-2-furanyl)-4H-1,2,4-triazol-3-yl)-4-(5-fluoro-2-pyrimidinyl)-1-methoxy-3-pentanesulfonamide, Example 74.0. The title compound (Example 74.0) was prepared following the same procedure described in Example 72.0 using Example 67.1. $^1$H NMR (400 MHz, CD$_3$OD) δ 8.66 (s, 1H) 8.60 (s, 1H) 7.54 (m, 1H) 6.83 (m, 2H), 6.02 (dd, J=3.42, 0.88 Hz, 1H) 5.93 (m, 1H) 3.93-3.77 (m, 1H) 3.79 (s, 3H) 3.77 (m, 3H) 3.63 (m, 1H) 3.44 (t, J=6.94 Hz, 1H) 3.28 (m, 1H) 3.11 (m, 3H) 2.26 (s, 3H) 1.99 (m, 2H) 1.39 (m, 3H). LCMS-ESI (pos.) m/z: 561.0 (M+H)$^+$.

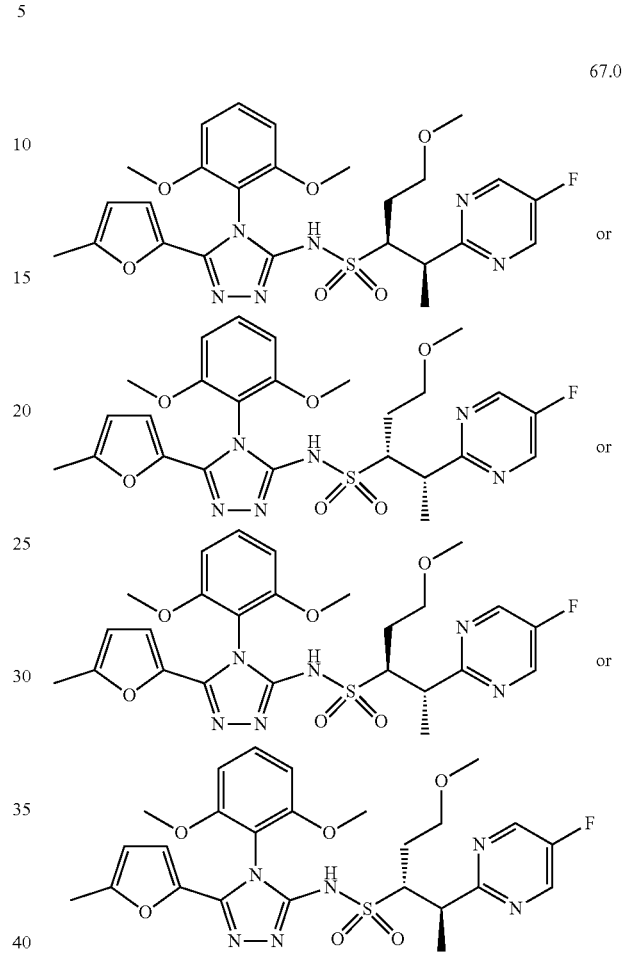

67.0

(3S,4R)—N-(4-(2,6-Dimethoxyphenyl)-5-(5-methyl-2-furanyl)-4H-1,2,4-triazol-3-yl)-4-(5-fluoro-2-pyrimidinyl)-1-methoxy-3-pentanesulfonamide or (3R,4S)—N-(4-(2,6-dimethoxyphenyl)-5-(5-methyl-2-furanyl)-4H-1,2,4-triazol-3-yl)-4-(5-fluoro-2-pyrimidinyl)-1-methoxy-3-pentanesulfonamide or (3R,4R)—N-(4-(2,6-dimethoxyphenyl)-5-(5-methyl-2-furanyl)-4H-1,2,4-triazol-3-yl)-4-(5-fluoro-2-pyrimidinyl)-1-methoxy-3-pentanesulfonamide or (3S,4S)—N-(4-(2,6-dimethoxyphenyl)-5-(5-methyl-2-furanyl)-4H-1,2,4-triazol-3-yl)-4-(5-fluoro-2-pyrimidinyl)-1-methoxy-3-pentanesulfonamide, Example 67.0. The racemate Example 74.0 was separated by SFC into four isomers. Separation conditions were as follows: On Thar 350 SFC with 250×30 mm+150×30 mm CC4 columns in series and 45 mL/min MeOH (neat)+55 g/min CO$_2$, 45% co-solvent. Outlet pressure=100 bar; Temp.=20° C.; Wavelength=277 nm. Used 0.8 mL injections of 104 mg/12 mL (8.7 mg/mL) sample solution in MeOH:DCM (8:4) for 6.9 mg/injection. Cycle time=5.5 min, Run time=15.5 min. Example 67.0 was the first peak (faster-eluting) off the chiral column $^1$H NMR (400 MHz, CD$_3$OD) δ 8.66 (s, 2H), 7.54 (t, J=8.51 Hz, 1H), 6.83 (dd, J=8.61, 2.15 Hz, 2H), 6.01 (d, J=3.52 Hz, 1H), 5.94 (d, J=3.33 Hz, 1H), 3.92 (m, 1H), 3.75 (m, 7H), 3.27 (m, 2H), 3.03 (s, 3H), 2.26 (s, 3H), 2.10 (m, 1H), 1.89 (m, 1H), 1.37 (d, J=7.04 Hz, 3H). LCMS-ESI (pos.) m/z: 561.0 (M+H)+.

Example 68.0. Preparation of (1R,2S)-1-(5-cyano-3-fluoro-2-pyridinyl)-N-(4-(2,6-dimethoxyphenyl)-5-(5-methyl-2-furanyl)-4H-1,2,4-triazol-3-yl)-1-hydroxy-2-propanesulfonamide or (1S,2R)-1-(5-cyano-3-fluoro-2-pyridinyl)-N-(4-(2,6-dimethoxyphenyl)-5-(5-methyl-2-furanyl)-4H-1,2,4-triazol-3-yl)-1-hydroxy-2-propanesulfonamide or (1S,2S)-1-(5-cyano-3-fluoro-2-pyridinyl)-N-(4-(2,6-dimethoxyphenyl)-5-(5-methyl-2-furanyl)-4H-1,2,4-triazol-3-yl)-1-hydroxy-2-propanesulfonamide or (1R,2R)-1-(5-cyano-3-fluoro-2-pyridinyl)-N-(4-(2,6-dimethoxyphenyl)-5-(5-methyl-2-furanyl)-4H-1,2,4-triazol-3-yl)-1-hydroxy-2-propanesulfonamide methylfuran-2-yl)-4H-1,2,4-triazol-3-yl)-1-hydroxy-N-(2-(trimethylsilyl)ethyl)propane-2-sulfonamide and (1R,2R)-1-(5-bromo-3-fluoropyridin-2-yl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide, Example 68.1. The title compound was the less polar diastereomer isolated from the reaction using 5-bromo-3-fluoropicolinaldehyde (Combi-Blocks inc) and Example 369.0 following the procedure described in Example 10.0. LCMS-ESI (pos.) m/z: 698.0 (M+H)+.

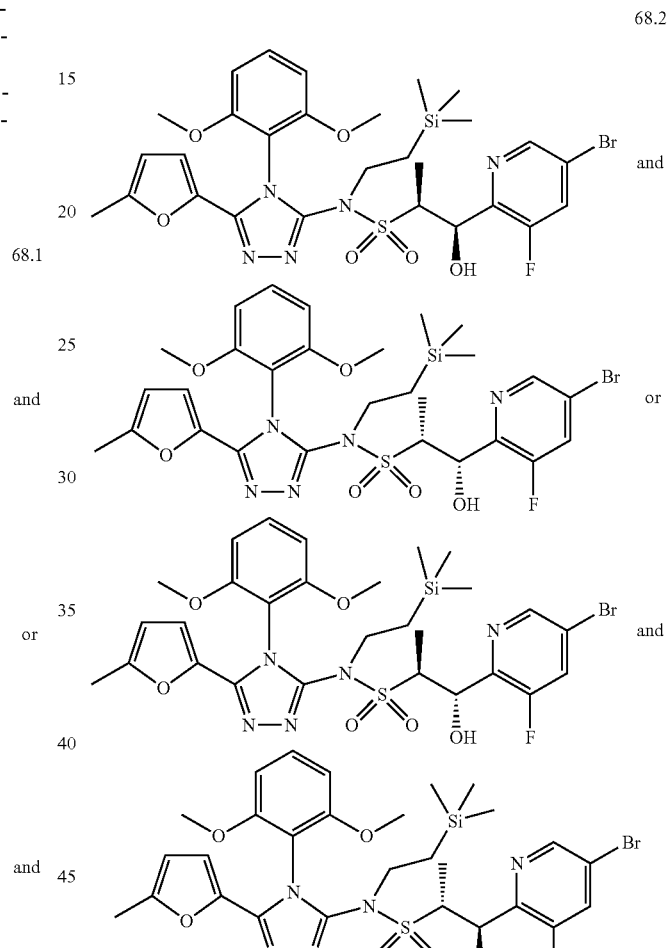

68.2

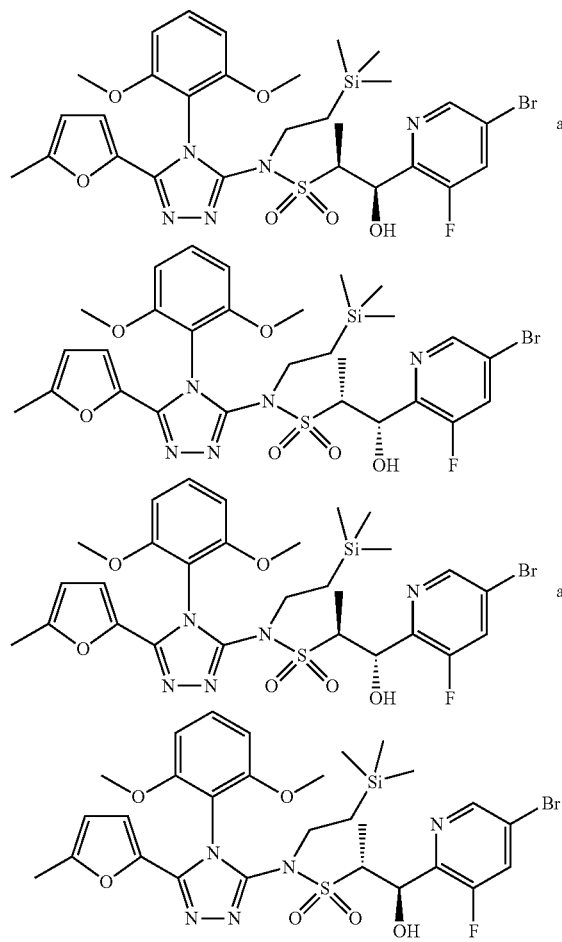

68.1

(1R,2S)-1-(5-Bromo-3-fluoropyridin-2-yl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide and (1S,2R)-1-(5-bromo-3-fluoropyridin-2-yl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide or (1S,2S)-1-(5-bromo-3-fluoropyridin-2-yl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide and (1R,2R)-1-(5-bromo-3-fluoropyridin-2-yl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide, Example 68.2. The title compound is the diastereomer of Example 68.1. It was the more polar diastereomer isolated from the reaction described in Example 68.1.

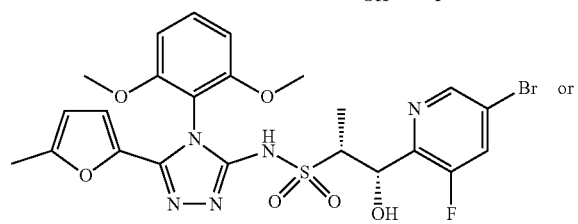 and

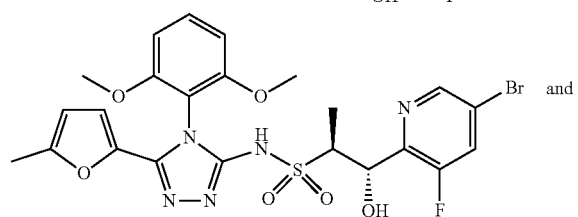 or

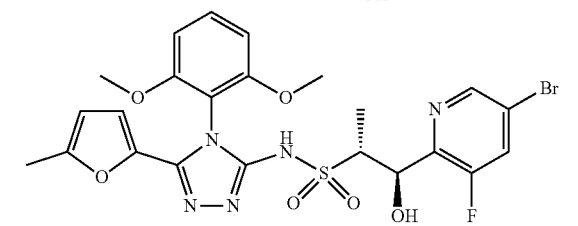 and

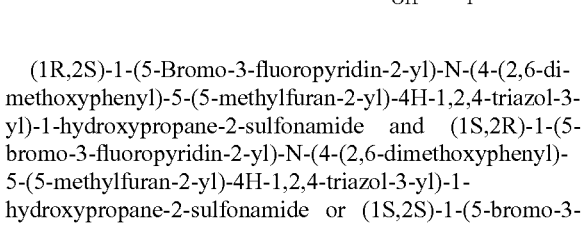

(1R,2S)-1-(5-Bromo-3-fluoropyridin-2-yl)-N-(4-(2,6-dimethoxyphenyl)-5-(5-methylfuran-2-yl)-4H-1,2,4-triazol-3-yl)-1-hydroxypropane-2-sulfonamide and (1S,2R)-1-(5-bromo-3-fluoropyridin-2-yl)-N-(4-(2,6-dimethoxyphenyl)-5-(5-methylfuran-2-yl)-4H-1,2,4-triazol-3-yl)-1-hydroxypropane-2-sulfonamide or (1S,2S)-1-(5-bromo-3-fluoropyridin-2-yl)-N-(4-(2,6-dimethoxyphenyl)-5-(5-methylfuran-2-yl)-4H-1,2,4-triazol-3-yl)-1-hydroxypropane-2-sulfonamide and (1R,2R)-1-(5-bromo-3-fluoropyridin-2-yl)-N-(4-(2,6-dimethoxyphenyl)-5-(5-methylfuran-2-yl)-4H-1,2,4-triazol-3-yl)-1-hydroxypropane-2-sulfonamide, Example 68.3. The title compound was obtained after removal of the trimethylsilyl ethyl group starting from Example 68.1 following the procedure described in Example 57.0. LCMS-ESI (pos.) m/z: 598.0 (M+H)+.

68.4

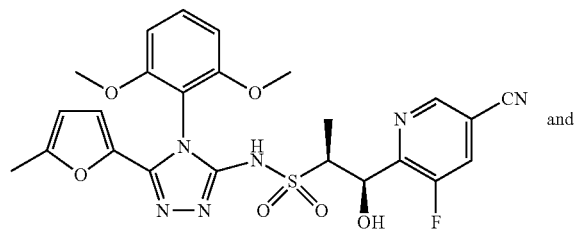 and

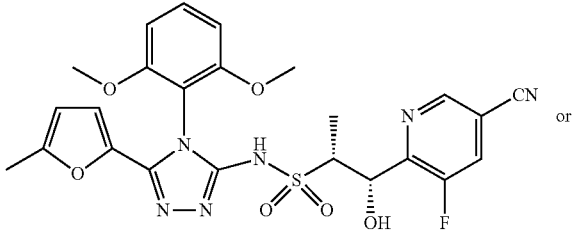

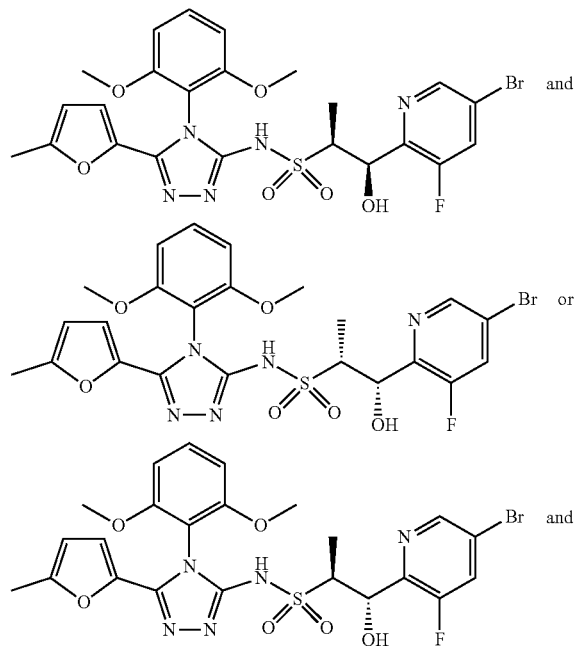 and (1R,2S)-1-(5-Cyano-3-fluoro-2-pyridinyl)-N-(4-(2,6-dimethoxyphenyl)-5-(5-methyl-2-furanyl)-4H-1,2,4-triazol-3-yl)-1-hydroxy-2-propanesulfonamide and (1S,2R)-1-(5-cyano-3-fluoro-2-pyridinyl)-N-(4-(2,6-dimethoxyphenyl)-5-(5-methyl-2-furanyl)-4H-1,2,4-triazol-3-yl)-1-hydroxy-2-propanesulfonamide or (1S,2S)-1-(5-cyano-3-fluoro-2-pyridinyl)-N-(4-(2,6-dimethoxyphenyl)-5-(5-methyl-2-furanyl)-4H-1,2,4-triazol-3-yl)-1-hydroxy-2-propanesulfonamide and (1R,2R)-1-(5-cyano-3-fluoro-2-pyridinyl)-N-(4-(2,6-dimethoxyphenyl)-5-(5-methyl-2-furanyl)-4H-1,2,4-triazol-3-yl)-1-hydroxy-2-propanesulfonamide, Example 68.4. A 10 mL microwave tube was charged with Example 68.4 (36 mg, 0.060 mmol), dicyanozinc (11.62 mg, 0.10 mmol), and Pd(PPh$_3$)$_4$ (13.95 mg, 0.012 mmol). Argon-degassed DMF (1 mL) was added and the microwave tube was degassed again with argon. The mixture was heated at 120° C. for 1 h in a microwave. The reaction mixture was directly purified on reverse phase HPLC using an Agilent SB C8 column, 0.1% TFA in ACN/H$_2$O, gradient 20% to 90% over 25 min (collected the peaks that were visible at 220 nm) to give the title compound (Example 68.4, 13 mg) as a TFA salt. $^1$H NMR (400 MHz, CD$_3$OD) δ 8.74 (s, 1H) 8.04 (dd, J=9.49, 1.66 Hz, 1H) 7.56 (t, J=8.51 Hz, 1H) 6.85 (dd, J=8.61, 0.98 Hz, 2H) 6.02 (dd, J=3.52, 0.98 Hz, 1H) 5.95 (d, J=3.52 Hz, 1H) 5.27 (d, J=7.83 Hz, 1H) 3.80 (s, 3H) 3.78 (s, 3H) 3.56-3.65 (m, 1H) 2.26 (s, 3H) 1.12 (d, J=7.04 Hz, 3H). LCMS-ESI (pos.) m/z: 543.0 (M+H)+.

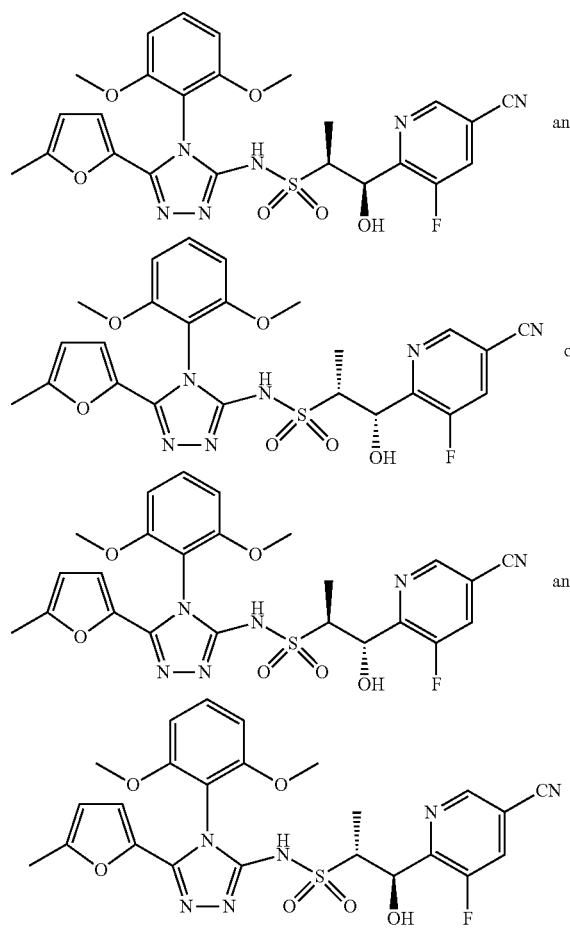

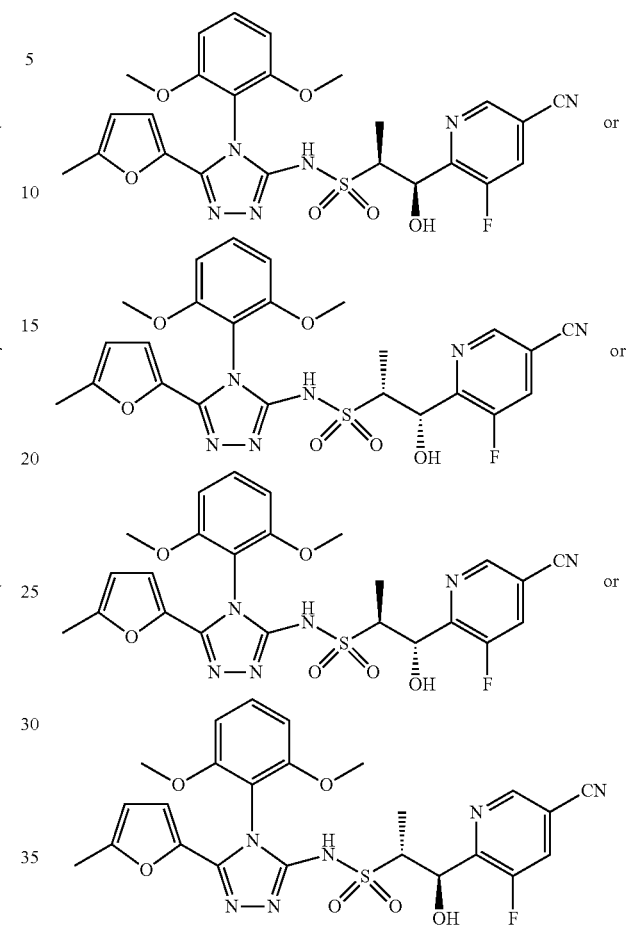

(1R,2S)-1-(5-Cyano-3-fluoro-2-pyridinyl)-N-(4-(2,6-dimethoxyphenyl)-5-(5-methyl-2-furanyl)-4H-1,2,4-triazol-3-yl)-1-hydroxy-2-propanesulfonamide and (1S,2R)-1-(5-cyano-3-fluoro-2-pyridinyl)-N-(4-(2,6-dimethoxyphenyl)-5-(5-methyl-2-furanyl)-4H-1,2,4-triazol-3-yl)-1-hydroxy-2-propanesulfonamide or (1S,2S)-1-(5-cyano-3-fluoro-2-pyridinyl)-N-(4-(2,6-dimethoxyphenyl)-5-(5-methyl-2-furanyl)-4H-1,2,4-triazol-3-yl)-1-hydroxy-2-propanesulfonamide and (1R,2R)-1-(5-cyano-3-fluoro-2-pyridinyl)-N-(4-(2,6-dimethoxyphenyl)-5-(5-methyl-2-furanyl)-4H-1,2,4-triazol-3-yl)-1-hydroxy-2-propanesulfonamide, Example 68.5. Example 68.5 is the diastereomer of Example 68.4. It was prepared from Example 68.2 employing the chemistry described in Example 68.4 and Example 68.3 via installation of the cyanide first and then removal of the trimethylsilyl ethyl protecting group. $^1$H NMR (400 MHz, CD$_3$OD) δ 8.71 (d, J=0.98 Hz, 1H) 7.99 (dd, J=9.49, 1.66 Hz, 1H) 7.56 (t, J=8.61 Hz, 1H) 6.85 (d, J=8.61 Hz, 2H) 6.02 (dd, J=3.42, 1.08 Hz, 1H) 5.95 (d, J=3.13 Hz, 1H) 5.37 (dd, J=6.26, 1.17 Hz, 1H) 3.79 (s, 3H) 3.78 (s, 3H) 3.67 (t, J=6.75 Hz, 1H) 2.26 (s, 3H) 1.41 (d, J=6.85 Hz, 3H). LCMS-ESI (pos.) m/z: 543.0 (M+H)$^+$.

(1R,2S)-1-(5-Cyano-3-fluoro-2-pyridinyl)-N-(4-(2,6-dimethoxyphenyl)-5-(5-methyl-2-furanyl)-4H-1,2,4-triazol-3-yl)-1-hydroxy-2-propanesulfonamide or (1S,2R)-1-(5-cyano-3-fluoro-2-pyridinyl)-N-(4-(2,6-dimethoxyphenyl)-5-(5-methyl-2-furanyl)-4H-1,2,4-triazol-3-yl)-1-hydroxy-2-propanesulfonamide or (1S,2S)-1-(5-cyano-3-fluoro-2-pyridinyl)-N-(4-(2,6-dimethoxyphenyl)-5-(5-methyl-2-furanyl)-4H-1,2,4-triazol-3-yl)-1-hydroxy-2-propanesulfonamide or (1R,2R)-1-(5-cyano-3-fluoro-2-pyridinyl)-N-(4-(2,6-dimethoxyphenyl)-5-(5-methyl-2-furanyl)-4H-1,2,4-triazol-3-yl)-1-hydroxy-2-propanesulfonamide, Example 68.0. The racemic compound Example 68.4 was separated by SFC. The separation conditions were as follows: Run on Thar 80 SFC with 250×21 mm IC column with 24 g/min MeOH (+20 mM NH$_3$)+30 g/min CO$_2$, 45% co-solvent at 55 g/min. Outlet pressure=100 bar; Temp.=22° C.; Wavelength=220 nm. Injected 0.3 mL of a solution from 10.5 mg sample dissolved in 3 mL of MeOH (25% DCM), c=3.5 mg/mL; 1.05 mg per injection. Cycle time 10 min, run time 14 min. The title compound was the second peak to elute on subjecting Example 68.4 to the SFC conditions described herein. $^1$H NMR (400 MHz, CD$_3$OD) δ 8.74 (s, 1H) 8.04 (dd, J=9.39, 1.57 Hz, 1H) 7.56 (t, J=8.61 Hz, 1H) 6.84 (dd, J=8.61, 0.98 Hz, 2H) 6.00-6.04 (m, 1H) 5.94 (d, J=3.33 Hz, 1H) 5.27 (d, J=7.83 Hz, 1H) 3.80 (s, 3H) 3.77 (s, 3H) 3.57-3.66 (m, 1H) 2.26 (s, 3H) 1.12 (d, J=7.04 Hz, 3H). LCMS-ESI (pos.) m/z: 543.0 (M+H)$^+$.

Example 70.0. Preparation of (2R)—N-(4-(2,6-dimethoxyphenyl)-5-(5-methyl-2-furanyl)-4H-1,2,4-triazol-3-yl)-4-hydroxy-1-(5-methyl-2-pyrimidinyl)-2-butanesulfonamide and (2S)—N-(4-(2,6-dimethoxyphenyl)-5-(5-methyl-2-furanyl)-4H-1,2,4-triazol-3-yl)-4-hydroxy-1-(5-methyl-2-pyrimidinyl)-2-butanesulfonamide

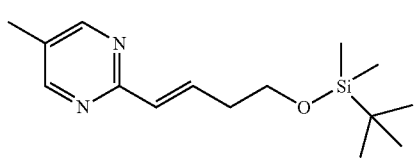

70.1

(E)-2-(4-((tert-Butyldimethylsilyl)oxy)but-1-en-1-yl)-5-methylpyrimidine, Example 70.1. A flask was charged with trans-4-(tert-butyldimethylsiloxy)-1-buten-1-ylboronic acid pinacol ester (3.37 mL, 9.61 mmol), cesium carbonate (6.89 g, 21.13 mmol), triphenylphosphine (1.01 g, 3.84 mmol), 2-bromo-5-methylpyrimidine (1.70 g, 9.80 mmol), ACN (60 mL), and water (15 mL). Argon was bubbled through the reaction mixture. Diacetoxypalladium (0.216 g, 0.96 mmol) was then added and Argon was bubbled through the reaction again. The mixture was then heated at 85° C. for 16 h. Water was added to the mixture which was then extracted with EtOAc. The EtOAc layer was dried, concentrated, and purified by silica gel column chromatography with gradient hexanes/EtOAc solvent system to give (E)-2-(4-((tert-butyldimethylsilyl)oxy)but-1-en-1-yl)-5-methylpyrimidine (Example 70.1, 2.3 g 86%) as a yellow oil. LCMS-ESI (pos.) m/z: 279.2 (M+H)+.

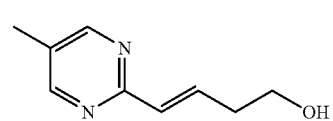

70.2

(E)-4-(5-Methylpyrimidin-2-yl)but-3-en-1-ol, Example 70.2. To a flask with (E)-2-(4-((tert-butyldimethylsilyl)oxy) but-1-en-1-yl)-5-methylpyrimidine (Example 70.1, 2.3 g, 8.26 mmol) was added THF (25 mL) and then TBAF (1.0 M, 3.06 mL, 3.06 mmol). The reaction was stirred overnight and then concentrated. The reaction mixture was directly loaded onto a silica gel column (80 g) and purified with a gradient elution of 0-85% EtOAc in hexanes first, and then a gradient elution of 0-10% MeOH in DCM to give 1.2 g (88%) of the title compound as a white solid. LCMS-ESI (pos.) m/z: 165.1 (M+H)+.

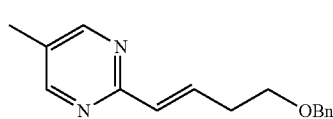

70.3

(E)-2-(4-(Benzyloxy)but-1-en-1-yl)-5-methylpyrimidine, Example 70.3. (E)-4-(5-methylpyrimidin-2-yl)but-3-en-1-ol (Example 70.2, 1.20 g, 7.31 mmol) was azeotroped with toluene and purged with nitrogen. DMF (15 mL) was added and the reaction was cooled in an ice bath. Sodium hydride (0.322 g, 8.04 mmol) was added, and the mixture was stirred for 15 min at 0° C. Benzyl bromide (1.30 mL, 10.96 mmol) was then added and the reaction was stirred overnight. Water was added, and the mixture was extracted with EtOAc. The EtOAc layer was dried, concentrated, and purified by silica gel column chromatography to give (E)-2-(4-(benzyloxy)but-1-en-1-yl)-5-methylpyrimidine (Example 70.3, 1.15 g, 62%). LCMS-ESI (pos.) m/z: 255.1 (M+H)+.

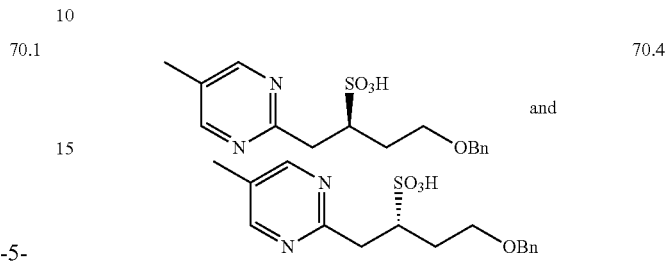

70.4

4-(Benzyloxy)-1-(5-methylpyrimidin-2-yl)butane-2-sulfonic acid, Example 70.4. To a vial containing Example 70.3 (1.35 g, 5.30 mmol) in THF (1 mL) and EtOH (1 mL) was added sodium hydrogensulfite (1.65 g, 15.90 mmol) in water (4 mL). The vial was heated at 85° C. overnight. The mixture was then concentrated in vacuo. The pH of the mixture was then adjusted to pH 5-6 with 1 N HCl. A small amount of DCM was added to extract the nonpolar impurity and was discarded. The aqueous layer was lyophilized and the resulting solid was dissolved in hot EtOH and filtered. The EtOH layer was concentrated and purified on reverse phase HPLC in 2 batches using 2.5%-70% gradient (5 min at 2.5%). The product fractions were lyophilized to give 4-(benzyloxy)-1-(5-methylpyrimidin-2-yl)butane-2-sulfonic acid (1.2 g, 67%) as a white solid. LCMS-ESI (pos.) m/z: 337.1 (M+H)+.

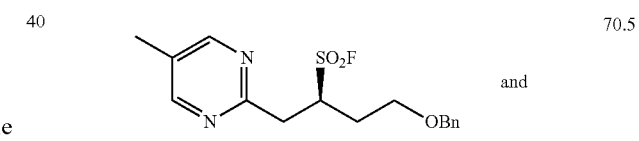

and

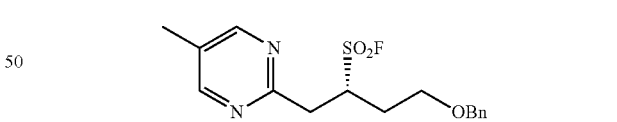

70.5

4-(Benzyloxy)-1-(5-methylpyrimidin-2-yl)butane-2-sulfonyl fluoride, Example 70.5. Example 70.4 (700 mg, 2.08 mmol) was azeotroped with toluene and dried on a vacuum pump. DCM (10 mL) was added followed by slow addition of DAST (0.66 mL, 4.99 mmol). The reaction was stirred for 70 min at RT and LCMS showed the reaction was not complete. Thus, more DAST was added. After 1 h, silica gel was added and the reaction mixture was concentrated in vacuo and dry loaded onto a silica gel column. The material was purified by gradient elution of EtOAc in hexanes to give 4-(benzyloxy)-1-(5-methylpyrimidin-2-yl)butane-2-sulfonyl fluoride (Example 70.5, 375 mg, 53%). LCMS-ESI (pos.) m/z: 337.1 (M+H)+.

70.6

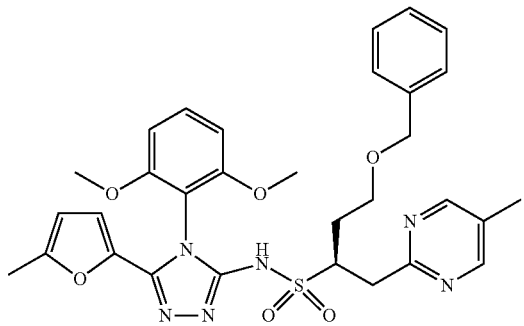

and

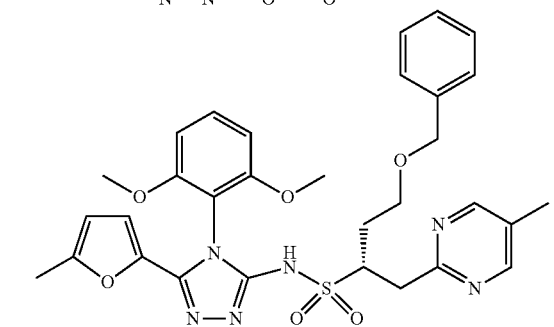

(2R)-4-(Benzyloxy)-N-(4-(2,6-dimethoxyphenyl)-5-(5-methyl-2-furanyl)-4H-1,2,4-triazol-3-yl)-1-(5-methyl-2-pyrimidinyl)-2-butanesulfonamide and (2S)-4-(benzyloxy)-N-(4-(2,6-dimethoxyphenyl)-5-(5-methyl-2-furanyl)-4H-1,2,4-triazol-3-yl)-1-(5-methyl-2-pyrimidinyl)-2-butanesulfonamide, Example 70.6. Example 70.5 (374 mg, 1.11 mmol) was azeotroped with toluene and dried on a pump. THF (2 mL) was then added under nitrogen. In a separate flask, Example 367.0 (431 mg, 1.44 mmol) was flushed with nitrogen on a high vacuum pump. THF (2 mL) was added followed by KHMDS (1.0 M, 2.21 mL, 2.21 mmol). The reaction was stirred at RT for 20 min. The sulfonyl fluoride solution was then added dropwise to the reaction at RT. The reaction was stirred overnight and then quenched with an aqueous solution of NH₄Cl followed by addition of water and extraction with EtOAc. The reaction mixture was purified on reverse phase HPLC using an Agilent SB C8 column, 0.1% TFA in ACN/H₂O, with a 20-85% gradient in 3 batches. The product fractions were lyophilized to give the title compound (157 mg, 23%). $^1$H NMR (400 MHz, CD₃OD) δ 8.52 (s, 2H) 7.52 (t, J=8.26 Hz, 1H) 7.26 (m, 3H) 7.17 (m, 2H) 6.81 (dd, J=8.61, 1.17 Hz, 2H) 6.02 (dd, J=3.52, 0.98 Hz, 1H) 5.94 (d, J=3.33 Hz, 1H) 4.21 (m, 2H) 3.87 (m, 1H) 3.75 (s, 3H) 3.73 (s, 3H) 3.56 (m, 1H) 3.45 (m, 2H) 3.07 (m, 1H) 2.26 (m, J=3.10 Hz, 7H) 1.86 (m, 1H). LCMS-ESI (pos.) m/z: 669.1 (M+H)⁺.

70.0

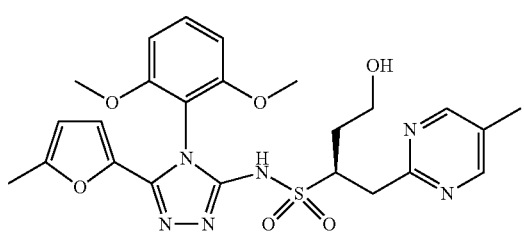

and

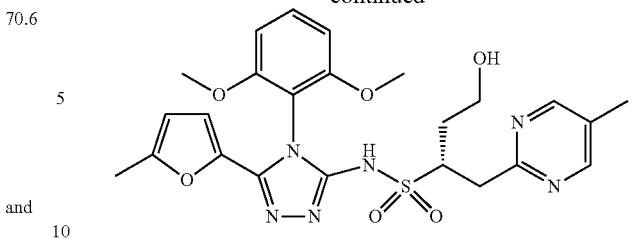

(2R)—N-(4-(2,6-Dimethoxyphenyl)-5-(5-methyl-2-furanyl)-4H-1,2,4-triazol-3-yl)-4-hydroxy-1-(5-methyl-2-pyrimidinyl)-2-butanesulfonamide and (2S)—N-(4-(2,6-dimethoxyphenyl)-5-(5-methyl-2-furanyl)-4H-1,2,4-triazol-3-yl)-4-hydroxy-1-(5-methyl-2-pyrimidinyl)-2-butanesulfonamide, Example 70.0. Example 70.6 (34 mg, 0.055 mmol) was azeotroped with toluene. DCM (1 mL) was added followed by boron trifluoride etherate (0.056 mL, 0.440 mmol) and ethanethiol (0.5 mL, 6.75 mmol, Alfa Aesar). The reaction was stirred for 3 d. LCMS indicated the reaction was complete. Water was added and the mixture was extracted with EtOAc. The EtOAc layer was dried and concentrated in vacuo. The material was then purified by reverse phase HPLC with 10-70% gradient elution. The pure fractions were lyophilized to give the title compound (13 mg, 45%) as a white solid. $^1$H NMR (400 MHz, CD₃OD) δ 8.57 (s, 2H), 7.54 (t, J=8.22 Hz, 1H), 6.83 (dd, J=8.51, 1.27 Hz, 2H), 6.01 (m, 1H), 5.94 (d, J=4.11 Hz, 1H), 3.76 (m, 7H), 3.55 (m, 3H), 3.06 (dd, J=15.26, 9.00 Hz, 1H), 2.31 (s, 3H), 2.25 (s, 3H), 2.13 (m, 1H), 1.74 (m, 1H). LCMS-ESI (pos.) m/z: 529.0 (M+H)⁺.

Example 69.0. Preparation (2R)-4-(benzyloxy)-N-(4-(2,6-dimethoxyphenyl)-5-(5-methyl-2-furanyl)-4H-1,2,4-triazol-3-yl)-1-(5-methyl-2-pyrimidinyl)-2-butanesulfonamide and (2S)-4-(benzyloxy)-N-(4-(2,6-dimethoxyphenyl)-5-(5-methyl-2-furanyl)-4H-1,2,4-triazol-3-yl)-1-(5-methyl-2-pyrimidinyl)-2-butanesulfonamide 69.0

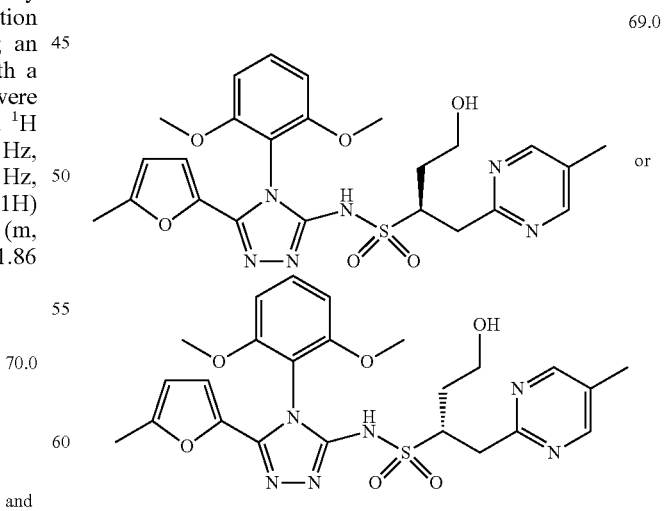

(2R)-4-(Benzyloxy)-N-(4-(2,6-dimethoxyphenyl)-5-(5-methyl-2-furanyl)-4H-1,2,4-triazol-3-yl)-1-(5-methyl-2-pyrimidinyl)-2-butanesulfonamide and (2S)-4-(benzyloxy)-N-(4-(2,6-dimethoxyphenyl)-5-(5-methyl-2-furanyl)-4H-1,2, 4-triazol-3-yl)-1-(5-methyl-2-pyrimidinyl)-2-butanesulfonamide, Example 69.0. Example 70.0 was separated into two enantiomers by SFC. Separation conditions were as follows: Run on Thar 80 SFC with 250×30 mm AS-H column with 15 g/min EtOH (neat)+55 g/min $CO_2$, 22% co-solvent at 70 g/min. Outlet pressure=100 bar; Temp.=21° C.; Wavelength=276 nm. Injected 0.5 mL of a solution from 60 mg sample dissolved in 5 mL of MeOH, c=12.0 mg/mL; 6.0 mg per injection. Cycle time 8 min. runtime 15 min. The title compound was the second peak from chiral separation. $^1$H NMR (400 MHz, $CD_3OD$) δ 8.56 (s, 2H) 7.53 (t, J=8.31 Hz, 1H) 6.83 (dd, J=8.51, 1.27 Hz, 2H) 6.01 (m, 1H) 5.94 (d, J=3.33 Hz, 1H) 3.76 (m, 7H) 3.54 (m, 3H) 3.04 (m, 1H) 2.31 (s, 3H) 2.26 (s, 3H) 2.11 (d, J=6.46 Hz, 1H) 1.74 (m, 1H). LCMS-ESI (pos.) m/z: 529.0 $(M+H)^+$.

Example 71.0. Preparation of (2R)—N-(4-(2,6-dimethoxyphenyl)-5-(5-methyl-2-furanyl)-4H-1,2,4-triazol-3-yl)-4-methoxy-1-(5-methyl-2-pyrimidinyl)-2-butanesulfonamide or (2S)—N-(4-(2,6-dimethoxyphenyl)-5-(5-methyl-2-furanyl)-4H-1,2,4-triazol-3-yl)-4-methoxy-1-(5-methyl-2-pyrimidinyl)-2-butanesulfonamide

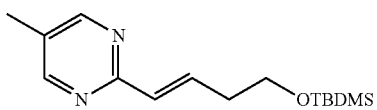

71.1

(E)-2-(4-((tert-Butyldimethylsilyl)oxy)but-1-en-1-yl)-5-methylpyrimidine, Example 71.1. A 30 mL microwave tube was charged with trans-4-(tert-butyldimethylsiloxy)-1-buten-1-ylboronic acid pinacol ester (3.37 mL, 9.61 mmol), cesium carbonate (6.89 g, 21.13 mmol), triphenylphosphine (1.01 g, 3.84 mmol) and 2-bromo-5-methylpyrimidine (1.70 g, 9.80 mmol, Combiphos) in ACN (60 mL) and water (15.00 mL). Argon was bubbled through the mixture and diacetoxypalladium (0.216 g, 0.961 mmol) was added. The mixture was heated at 85° C. for 16 h in a microwave. Water was added, and the reaction was extracted with EtOAc. The EtOAc layer was dried, concentrated in vacuo, and purified by silica gel chromatography eluting with a gradient of EtOAc in hexanes to give title compound (2.3 g, 86%). LCMS-ESI (pos.) m/z: 279.2 $(M+H)^+$.

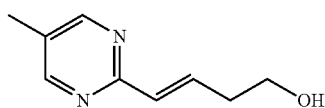

71.2

(E)-4-(5-Methylpyrimidin-2-yl)but-3-en-1-ol, Example 71.2. A flask with Example 71.1 (3.37 g, 12.10 mmol) was azeotroped with toluene. THF (40 mL) was added followed by TBAF (1.0 M, 12.10 mL, 12.10 mmol). The reaction was stirred at RT for 75 min. The reaction mixture was then concentrated in vacuo. Water was added followed by extraction with EtOAc. The EtOAc layer was dried and concentrated in vacuo. The material was purified by reverse phase HPLC to give the title compound (632 mg) as a white solid. LCMS-ESI (pos.) m/z: 165.1 $(M+H)^+$.

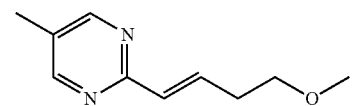

71.3

(E)-2-(4-Methoxybut-1-en-1-yl)-5-methylpyrimidine, Example 71.3. Example 71.2 (320 mg, 1.95 mmol) was azeotroped with toluene. NaH (94 mg, 2.34 mmol) was added and after stirring the mixture for 15 min, methyl iodide (0.244 mL, 3.90 mmol) was added. The reaction was stirred overnight, after which a saturated solution of $NH_4Cl$ was added to quench the reaction followed by EtOAc extraction. The EtOAc layer was dried, concentrated, and purified by silica gel chromatography with a gradient 0-70% EtOAc in hexanes to afford 2-(4-methoxybut-1-en-1-yl)-5-methylpyrimidine (170 mg) as a colorless oil. LCMS-ESI (pos.) m/z: 179.1 $(M+H)^+$.

Example 76.0. Preparation of (2R)—N-(4-(2,6-dimethoxyphenyl)-5-(5-methyl-2-furanyl)-4H-1,2,4-triazol-3-yl)-4-methoxy-1-(5-methyl-2-pyrimidinyl)-2-butanesulfonamide and (2S)—N-(4-(2,6-dimethoxyphenyl)-5-(5-methyl-2-furanyl)-4H-1,2,4-triazol-3-yl)-4-methoxy-1-(5-methyl-2-pyrimidinyl)-2-butanesulfonamide

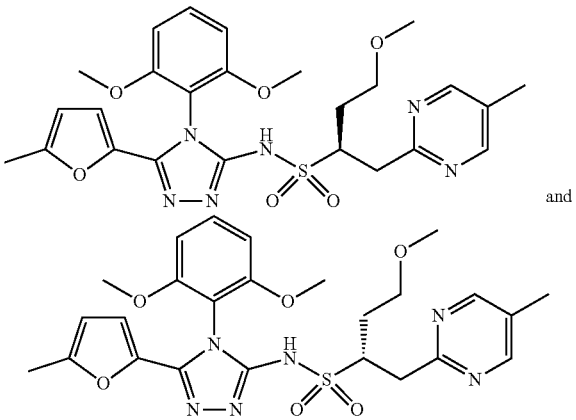

76.0

(2R)—N-(4-(2,6-dimethoxyphenyl)-5-(5-methyl-2-furanyl)-4H-1,2,4-triazol-3-yl-4-methoxy-1-(5-methyl-2-pyrimidinyl)-2-butanesulfonamide and (2S)—N-(4-(2,6-dimethoxyphenyl)-5-(5-methyl-2-furanyl)-4H-1,2,4-triazol-3-yl)-4-methoxy-1-(5-methyl-2-pyrimidinyl)-2-butanesulfonamide, Example 76.0. The title compound was prepared following the procedure as described in Example 72.0 using 2-(4-methoxybut-1-en-1-yl)-5-methylpyrimidine (Example 71.3). $^1$H NMR (400 MHz, $CD_3OD$) δ 8.60 (s, 2H) 7.55 (t, J=8.61 Hz, 1H) 6.84 (d, J=8.61 Hz, 2H) 6.02 (dd, J=3.52, 0.98 Hz, 1H) 5.94 (d, J=3.33 Hz, 1H) 3.82 (m, 1H) 3.77 (s, 3H) 3.76 (s, 3H) 3.55 (dd, J=14.87, 4.89 Hz, 1H) 3.38 (m, 2H) 3.09 (m, 4H) 2.32 (s, 3H) 2.26 (s, 3H), 2.16 (m, 1H) 1.79 (m, 1H). LCMS-ESI (pos.) m/z: 543.1 $(M+H)^+$.

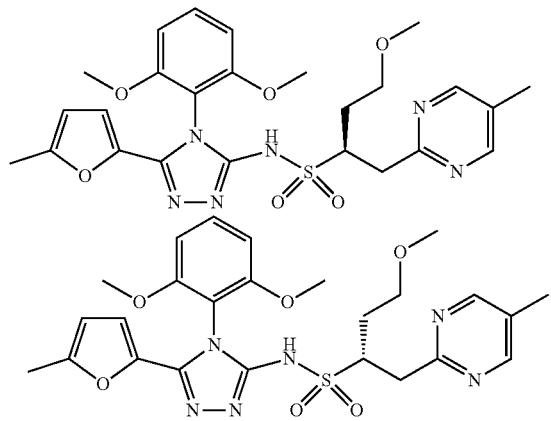

71.0 or (2R)—N-(4-(2,6-Dimethoxyphenyl)-5-(5-methyl-2-furanyl)-4H-1,2,4-triazol-3-yl)-4-methoxy-1-(5-methyl-2-pyrimidinyl)-2-butanesulfonamide or (2S)—N-(4-(2,6-dimethoxyphenyl)-5-(5-methyl-2-furanyl)-4H-1,2,4-triazol-3-yl)-4-methoxy-1-(5-methyl-2-pyrimidinyl)-2-butanesulfonamide, Example 71.0. The racemate Example 76.0 was purified by SFC with the following conditions: Run on Thar 80 SFC with 250×30 mm AD-H column with 28 g/min MeOH (neat)+52 g/min CO$_2$, 35% co-solvent at 80 g/min. Outlet pressure=100 bar; Temp.=24° C.; Wavelength=276 nm. Injected 0.4 mL of a solution in each injection from 43 mg sample dissolved in 4.0 mL of MeOH and 2.0 mL of DCM. Two enantiomers were obtained. Example 71.0 was the first peak off the column. $^1$H NMR (400 MHz, CDCl$_3$) δ 8.51 (s, 2H), 7.45 (t, J=8.51 Hz, 1H), 6.66 (d, J=8.41 Hz, 2H), 5.91 (d, J=2.54 Hz, 1H), 5.79 (d, J=3.33 Hz, 1H), 3.89 (m, 1H), 3.77 (s, 3H), 3.73 (s, 3H), 3.59 (dd, J=15.16, 5.77 Hz, 1H), 3.48 (m, 2H), 3.18 (m, 4H), 2.33 (s, 3H), 2.29 (m, 4H), 1.84 (m, 1H). LCMS-ESI (pos.) m/z: 543.1 (M+H)$^+$.

Example 72.0. Preparation of (2R)—N-(4-(2,6-dimethoxyphenyl)-5-(5-methyl-2-furanyl)-4H-1,2,4-triazol-3-yl)-1-(5-fluoro-2-pyrimidinyl)-3-methoxy-2-propanesulfonamide or (2S)—N-(4-(2,6-dimethoxyphenyl)-5-(5-methyl-2-furanyl)-4H-1,2,4-triazol-3-yl)-1-(5-fluoro-2-pyrimidinyl)-3-methoxy-2-propanesulfonamide

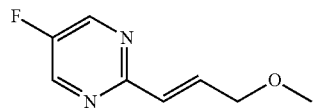

72.1

(E)-5-Fluoro-2-(3-methoxyprop-1-en-1-yl)pyrimidine, Example 72.1. A flask was charged with (E)-2-(3-methoxy-1-propen-1-yl)-4,4,5,5-tetramethyl-(1,3,2)-dioxaborolane (0.193 mL, 0.91 mmol), cesium carbonate (0.651 g, 2.0 mmol), triphenylphosphine (0.095 g, 0.36 mmol), and 2-chloro-5-fluoro-pyrimidine (0.121 mL, 0.98 mmol, Matrix Scientific) in ACN (9 mL) and water (2.25 mL). Argon was bubbled through the mixture and diacetoxypalladium (0.020 g, 0.091 mmol, Strem) was added. The reaction mixture was placed under an atmosphere of Argon and the mixture was heated at 85° C. for 16 h. Water was then added and the reaction was extracted with EtOAc. The EtOAc layer was dried, concentrated in vacuo, and purified by silica gel chromatography with a gradient of EtOAc in hexanes to give the title compound (122 mg) as an yellow oil. LCMS-ESI (pos.) m/z: 169.0 (M+H)$^+$.

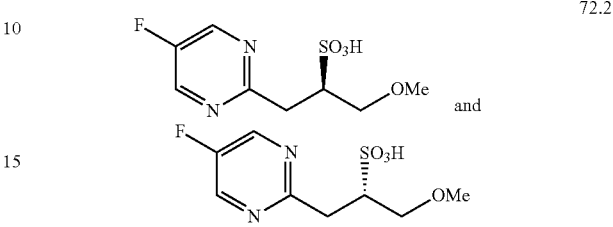

72.2 and (S)-1-(5-Fluoropyrimidin-2-yl)-3-methoxypropane-2-sulfonic acid and (R)-1-(5-fluoropyrimidin-2-yl)-3-methoxypropane-2-sulfonic acid, Example 72.2. A flask was charged with Example 72.1 (988 mg, 5.88 mmol) and THF (0.8 mL), followed by a solution of sodium bisulfite (673 mg, 6.46 mmol) in water (3 mL). The mixture was stirred in a vial at RT overnight. The contents of the vial were then concentrated to remove the THF. Water was added followed by 4 drops of 1 N HCl. The mixture was extracted with DCM to remove any organic impurities. The aqueous layer was concentrated and then azeotroped with toluene and dried on a high vacuum to give a foamy oil. EtOH was added to the mixture, and it was then heated to reflux. The solution was filtered hot to remove any solid impurities. After rinsing the solids with hot EtOH, the combined filtrate was concentrated to give 1-(5-fluoropyrimidin-2-yl)-3-methoxypropane-2-sulfonic acid (1.65 g) as a foamy white solid which was used without further purification. LCMS-ESI (pos.) m/z: 251.0 (M+H)$^+$.

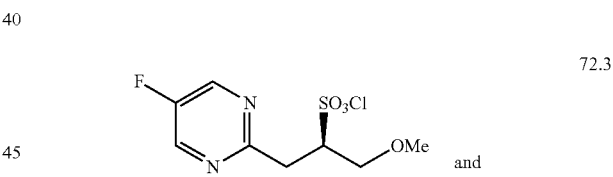

72.3 and

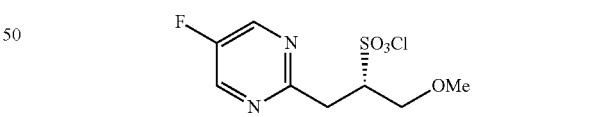

(S)-1-(5-Fluoropyrimidin-2-yl)-3-methoxypropane-2-sulfonyl chloride and (R)-1-(5-fluoropyrimidin-2-yl)-3-methoxypropane-2-sulfonyl chloride, Example 72.3. Example 72.2 (358 mg, 1.43 mmol) was azeotroped with toluene. DCM (4.5 mL) was added and the flask was cooled to 0° C. An oxalyl chloride solution (2.0 M in DCM, 0.98 mL, 1.97 mmol) was added followed by 2 drops of DMF. The reaction was then stirred at 0° C. for 2 h. The reaction mixture was concentrated in vacuo, azeotroped with toluene, and dried on a high vacuum pump. The title compound was directly used in the next step. LCMS-ESI (pos.) m/z: 265.0 (M-Cl+HOMe)$^+$.

72.0

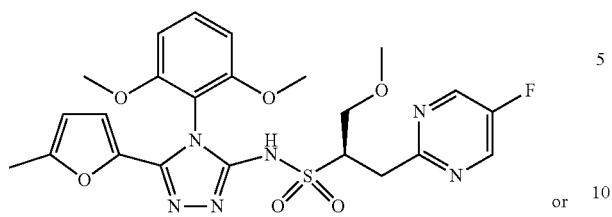

or

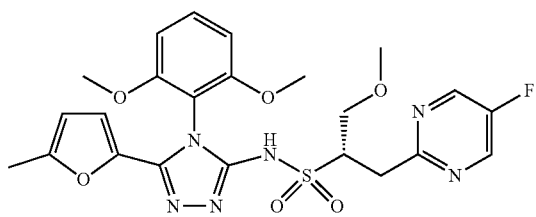

(2R)—N-(4-(2,6-Dimethoxyphenyl)-5-(5-methyl-2-furanyl)-4H-1,2,4-triazol-3-yl)-1-(5-fluoro-2-pyrimidinyl)-3-methoxy-2-propanesulfonamide or (2S)—N-(4-(2,6-dimethoxyphenyl)-5-(5-methyl-2-furanyl)-4H-1,2,4-triazol-3-yl)-1-(5-fluoro-2-pyrimidinyl)-3-methoxy-2-propanesulfonamide, Example 72.0. A flask with 4-(2,6-dimethoxyphenyl)-5-(5-methylfuran-2-yl)-4H-1,2,4-triazol-3-amine (Example 367.0, 210 mg, 0.70 mmol) was purged with nitrogen. THF (4 mL) was added, and the flask was cooled to 0° C. KHMDS (2.10 mL, 2.098 mmol) was added and the reaction was stirred for 18 min at 0° C. A 0° C., a THF (3 mL) solution of 1-(5-fluoropyrimidin-2-yl)-3-methoxypropane-2-sulfonyl chloride (Example 72.3, 376 mg, 1.40 mmol) was added slowly to the reaction. The reaction was then allowed to warm to RT and stirred overnight. The reaction was quenched with a minimal amount of water and purified on reverse phase HPLC in two batches, using an Agilent SB C8 column, 0.1% TFA in ACN/H$_2$O, 20-70% gradient elution over 25 min. Two mixed fractions were obtained. Both fractions were re-purified using the following SFC chiral separation conditions: IA column (2×15 cm), 20% MeOH/CO$_2$, 100 bar, 60 mL/min, 220 nm, injection volume: 0.7 mL, 3 mg/mL MeOH. The title compound (Example 72.0) was the first peak (faster-eluting) to elute under these conditions. $^1$H NMR (400 MHz, CDCl$_3$) δ 11.10 (br. s, 1H), 8.53 (s, 2H), 7.46 (t, J=8.51 Hz, 1H), 6.68 (d, J=8.61 Hz, 2H), 5.92 (dd, J=3.42, 0.88 Hz, 1H), 5.80 (d, J=3.33 Hz, 1H), 4.08 (dq, J=7.60, 4.30 Hz, 1H), 3.85 (dd, J=10.27, 4.21 Hz, 1H), 3.78 (s, 3H), 3.75 (s, 3H), 3.64 (dd, J=10.17, 7.82 Hz, 1H), 3.55 (dd, J=15.45, 6.06 Hz, 1H), 3.41 (m, 1H), 3.23 (s, 3H), 2.33 (s, 3H). LCMS-ESI (pos.) m/z: 533.0 (M+H)$^+$.

Example 78.0. Preparation of (2R)—N-(4-(2,6-dimethoxyphenyl)-5-(5-methyl-2-furanyl)-4H-1,2,4-triazol-3-yl)-1-(5-fluoro-2-pyrimidinyl)-3-methoxy-2-propanesulfonamide or (2S)—N-(4-(2,6-dimethoxyphenyl)-5-(5-methyl-2-furanyl)-4H-1,2,4-triazol-3-yl)-1-(5-fluoro-2-pyrimidinyl)-3-methoxy-2-propanesulfonamide 78.0

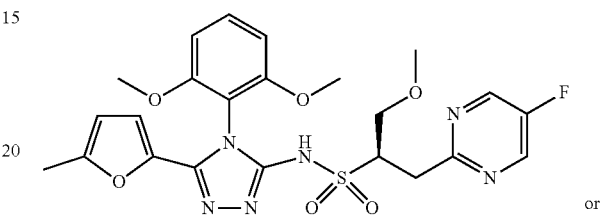

or

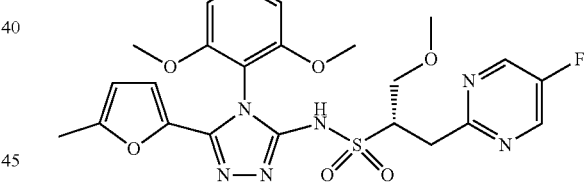

(2R)—N-(4-(2,6-Dimethoxyphenyl)-5-(5-methyl-2-furanyl)-4H-1,2,4-triazol-3-yl)-1-(5-fluoro-2-pyrimidinyl)-3-methoxy-2-propanesulfonamide or (2S)—N-(4-(2,6-dimethoxyphenyl)-5-(5-methyl-2-furanyl)-4H-1,2,4-triazol-3-yl)-1-(5-fluoro-2-pyrimidinyl)-3-methoxy-2-propanesulfonamide, Example 78.0. Example 78.0 is the enantiomer of Example 72.0. It was the second peak isolated from the chiral purification described in Example 72.0. $^1$H NMR (400 MHz, CDCl$_3$) δ 11.12 (br. s, 1H), 8.52 (s, 2H), 7.46 (t, J=8.51 Hz, 1H), 6.68 (d, J=8.41 Hz, 2H), 5.91 (dd, J=3.52, 0.98 Hz, 1H), 5.80 (d, J=3.33 Hz, 1H), 4.10 (m., 1H), 4.08 (dq, J=7.70, 4.20 Hz, 1H), 3.84 (m, J=10.27, 4.21 Hz, 1H), 3.78 (s, 3H), 3.76 (m, 3H), 3.64 (dd, J=10.17, 7.83 Hz, 1H), 3.54 (dd, J=15.26, 7.04 Hz, 1H), 3.41 (dd, J=15.30, 7.40 Hz, 1H), 3.22 (s, 3H). LCMS-ESI (pos.) m/z: 533.0 (M+H)$^+$.

Example 73.0. Preparation of (1R,2S)—N-(4-(2,6-dimethoxyphenyl)-5-(5-methyl-2-furanyl)-4H-1,2,4-triazol-3-yl)-1-(4-fluoro-2-(hydroxymethyl)phenyl)-1-hydroxy-2-propanesulfonamide and (1S,2R)—N-(4-(2,6-dimethoxyphenyl)-5-(5-methyl-2-furanyl)-4H-1,2,4-triazol-3-yl)-1-(4-fluoro-2-(hydroxymethyl)phenyl)-1-hydroxy-2-propanesulfonamide or (1S,2S)—N-(4-(2,6-dimethoxyphenyl)-5-(5-methyl-2-furanyl)-4H-1,2,4-triazol-3-yl)-1-(4-fluoro-2-(hydroxymethyl)phenyl)-1-hydroxy-2-propanesulfonamide and (1R,2R)—N-(4-(2,6-dimethoxyphenyl)-5-(5-methyl-2-furanyl)-4H-1,2,4-triazol-3-yl)-1-(4-fluoro-2-(hydroxymethyl)phenyl)-1-hydroxy-2-propanesulfonamide

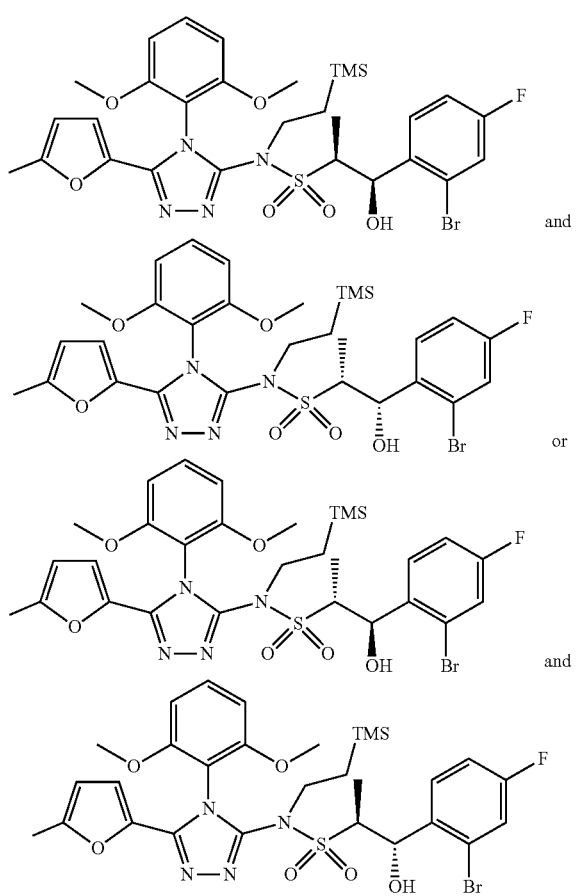

(1R,2R)-1-(2-Bromo-4-fluorophenyl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide and (1S,2S)-1-(2-bromo-4-fluorophenyl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide or (1S,2R)-1-(2-bromo-4-fluorophenyl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide and (1R,2S)-1-(2-bromo-4-fluorophenyl)-N-(4-(2,6-dimethoxyphenyl)-5-(5-methylfuran-2-yl)-4H-1,2,4-triazol-3-yl)-1-hydroxy-N-(2-(trimethylsilyl)ethyl) propane-2-sulfonamide, Example 73.1. The title compound was prepared using Example 369.0 and 2-bromo-4-fluorobenzaldehyde following the procedure described in Example 57.1. LCMS-ESI (pos.) m/z: 697.0 (M+H)$^+$.

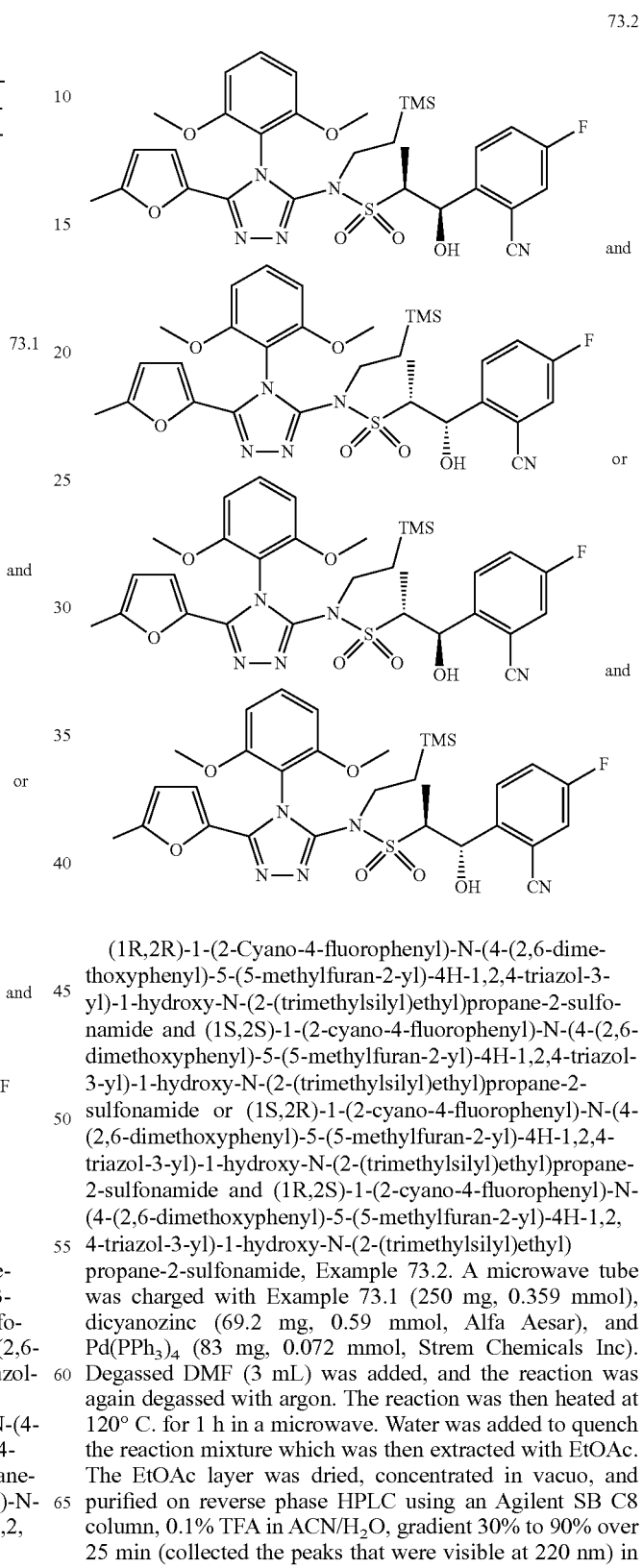

(1R,2R)-1-(2-Cyano-4-fluorophenyl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide and (1S,2S)-1-(2-cyano-4-fluorophenyl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide or (1S,2R)-1-(2-cyano-4-fluorophenyl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide and (1R,2S)-1-(2-cyano-4-fluorophenyl)-N-(4-(2,6-dimethoxyphenyl)-5-(5-methylfuran-2-yl)-4H-1,2,4-triazol-3-yl)-1-hydroxy-N-(2-(trimethylsilyl)ethyl) propane-2-sulfonamide, Example 73.2. A microwave tube was charged with Example 73.1 (250 mg, 0.359 mmol), dicyanozinc (69.2 mg, 0.59 mmol, Alfa Aesar), and Pd(PPh$_3$)$_4$ (83 mg, 0.072 mmol, Strem Chemicals Inc). Degassed DMF (3 mL) was added, and the reaction was again degassed with argon. The reaction was then heated at 120° C. for 1 h in a microwave. Water was added to quench the reaction mixture which was then extracted with EtOAc. The EtOAc layer was dried, concentrated in vacuo, and purified on reverse phase HPLC using an Agilent SB C8 column, 0.1% TFA in ACN/H$_2$O, gradient 30% to 90% over 25 min (collected the peaks that were visible at 220 nm) in 2 batches. The product fractions were lyophilized and the material was repurified on a Redi-Sep pre-packed gold silica gel column, eluting with a gradient EtOAc/hexanes 0-70% and then 2-8% MeOH/DCM to give the title compound (56 mg). LCMS-ESI (pos.) m/z: 642.0 (M+H)+.

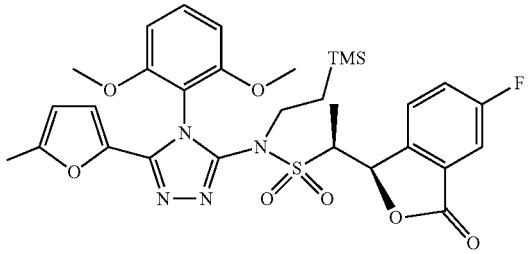

and

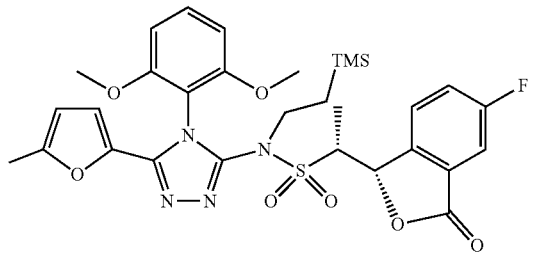

or

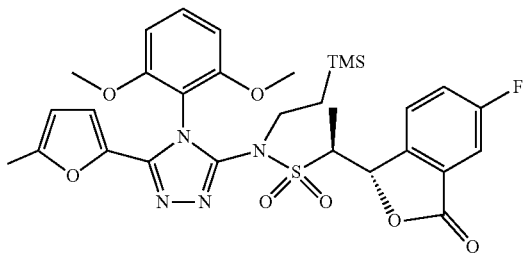

and

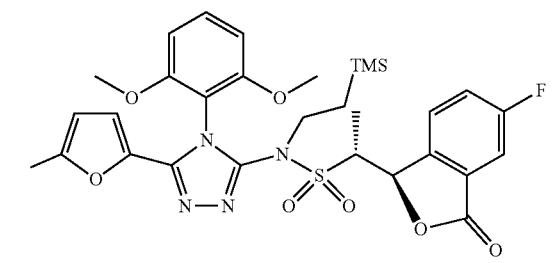

(1R,2S)—N-(4-(2,6-Dimethoxyphenyl)-5-(5-methyl-furan-2-yl)-4H-1,2,4-triazol-3-yl)-1-(5-fluoro-3-oxo-1,3-dihydroisobenzofuran-1-yl)-N-(2-(trimethylsilyl)ethyl)ethanesulfonamide and (1S,2R)—N-(4-(2,6-dimethoxyphenyl)-5-(5-methylfuran-2-yl)-4H-1,2,4-triazol-3-yl)-1-(5-fluoro-3-oxo-1,3-dihydroisobenzofuran-1-yl)-N-(2-(trimethylsilyl)ethyl)ethanesulfonamide, or (1R,2R)—N-(4-(2,6-dimethoxyphenyl)-5-(5-methylfuran-2-yl)-4H-1,2,4-triazol-3-yl)-1-(5-fluoro-3-oxo-1,3-dihydroisobenzofuran-1-yl)-N-(2-(trimethylsilyl)ethyl)ethanesulfonamide and (1S,2S)—N-(4-(2,6-dimethoxyphenyl)-5-(5-methylfuran-2-yl)-4H-1,2,4-triazol-3-yl)-1-(5-fluoro-3-oxo-1,3-dihydroisobenzofuran-1-yl)-N-(2-(trimethylsilyl)ethyl)ethanesulfonamide, Example 73.3. A by-product formed from Example 73.2 was isolated after HPLC reverse phase purification to yield the title compound (43 mg). LCMS-ESI (pos.) m/z: 643.0 (M+H)+.

73.4

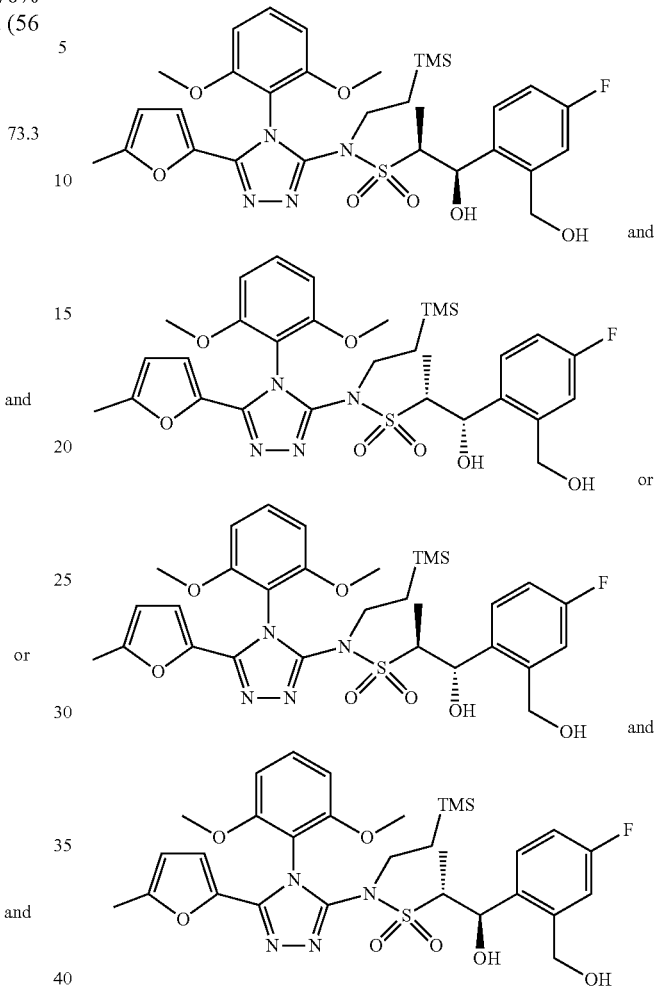

(1R,2S)—N-(4-(2,6-Dimethoxyphenyl)-5-(5-methyl-furan-2-yl)-4H-1,2,4-triazol-3-yl)-1-(4-fluoro-2-(hydroxymethyl)phenyl)-1-hydroxy-N-(2-(trimethylsilyl)ethyl) propane-2-sulfonamide and (1S,2R)—N-(4-(2,6-dimethoxyphenyl)-5-(5-methylfuran-2-yl)-4H-1,2,4-triazol-3-yl)-1-(4-fluoro-2-(hydroxymethyl)phenyl)-1-hydroxy-N-(2-(trimethylsilyl)ethyl)propane-2-sulfonamide, or (1S, 2S)—N-(4-(2,6-dimethoxyphenyl)-5-(5-methylfuran-2-yl)-4H-1,2,4-triazol-3-yl)-1-(4-fluoro-2-(hydroxymethyl) phenyl)-1-hydroxy-N-(2-(trimethylsilyl)ethyl)propane-2-sulfonamide and (1R,2R)—N-(4-(2,6-dimethoxyphenyl)-5-(5-methylfuran-2-yl)-4H-1,2,4-triazol-3-yl)-1-(4-fluoro-2-(hydroxymethyl)phenyl)-1-hydroxy-N-(2-(trimethylsilyl) ethyl)propane-2-sulfonamide, Example 73.4. Example 73.3 (43 mg, 0.067 mmol) was azeotroped with toluene. THF (2 mL) was added under nitrogen followed by lithium borohydride (2.0 M solution in THF, 0.100 mL, 0.201 mmol). The reaction was heated at reflux for 2.5 h. 1 N HCl was added to quench the reaction and both EtOAc and water were added to the mixture. The mixture was washed with brine and the EtOAc layer was dried and concentrated in vacuo to give the title compound (43 mg) which was carried to the next step without further purification. LCMS-ESI (pos.) m/z: 647.0 (M+H)+.

73.0

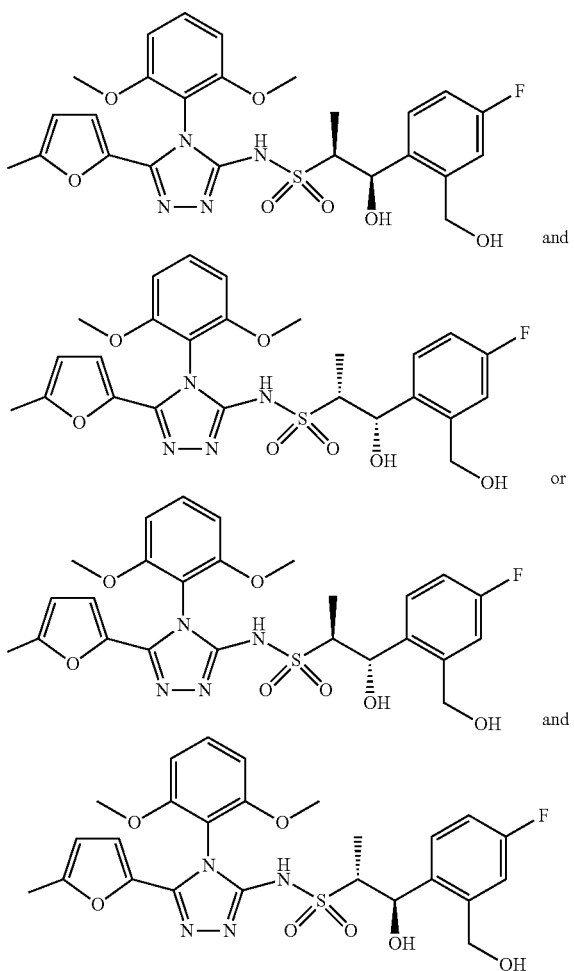

(1R,2S)—N-(4-(2,6-Dimethoxyphenyl)-5-(5-methyl-2-furanyl)-4H-1,2,4-triazol-3-yl)-1-(4-fluoro-2-(hydroxymethyl)phenyl)-1-hydroxy-2-propanesulfonamide and (1S,2R)—N-(4-(2,6-dimethoxyphenyl)-5-(5-methyl-2-furanyl)-4H-1,2,4-triazol-3-yl)-1-(4-fluoro-2-(hydroxymethyl)phenyl)-1-hydroxy-2-propanesulfonamide or (1S,2S)—N-(4-(2,6-dimethoxyphenyl)-5-(5-methyl-2-furanyl)-4H-1,2,4-triazol-3-yl)-1-(4-fluoro-2-(hydroxymethyl)phenyl)-1-hydroxy-2-propanesulfonamide and (1R,2R)—N-(4-(2,6-dimethoxyphenyl)-5-(5-methyl-2-furanyl)-4H-1,2,4-triazol-3-yl)-1-(4-fluoro-2-(hydroxymethyl)phenyl)-1-hydroxy-2-propanesulfonamide, Example 73.0. To a solution of Example 73.4 (43 mg, 0.066 mmol) was added tris(dimethylamino)sulfonium difluorotrimethylsilicate (IV) (54.9 mg, 0.20 mmol). DMF (1 mL) was added, and the resulting solution was heated at 70° C. for 3 h. The reaction was cooled to RT. Water was added to the mixture and it was extracted with EtOAc. The EtOAc layer was dried, concentrated in vacuo, and purified by silica gel chromatography to give the title compound (26 mg). $^1$H NMR (400 MHz, DMSO-$d_6$) δ 13.24 (s, 1H) 7.56 (t, J=8.51 Hz, 1H) 7.43 (dd, J=8.61, 6.06 Hz, 1H) 7.18 (dd, J=10.37, 2.93 Hz, 1H) 7.05 (td, J=8.51, 2.74 Hz, 1H) 6.90 (d, J=3.13 Hz, 1H) 6.88 (d, J=3.13 Hz, 1H) 6.02-6.23 (m, 1H) 5.82 (d, J=3.33 Hz, 1H) 5.75 (br. s, 1H) 5.37 (br. s., 1H) 5.27 (t, J=5.38 Hz, 1H) 4.68 (br. s., 1H) 4.44 (qd, J=14.02, 5.09 Hz, 2H) 3.72 (s, 3H) 3.73 (d, J=7.24 Hz, 6H) 2.97 (q, J=7.04 Hz, 1H) 2.25 (s, 3H) 0.92-1.16 (m, 3H). LCMS-ESI (pos.) m/z: 547.0 (M+H)$^+$.

Example 79.0. Preparation of (1S,2S)—N-(4-(2,6-dimethoxyphenyl)-5-(5-methyl-2-furanyl)-4H-1,2,4-triazol-3-yl)-1-(5-fluoro-2-pyridinyl)-1-hydroxy-2-propanesulfonamide and (1R,2R)—N-(4-(2,6-dimethoxyphenyl)-5-(5-methyl-2-furanyl)-4H-1,2,4-triazol-3-yl)-1-(5-fluoro-2-pyridinyl)-1-hydroxy-2-propanesulfonamide or (1R,2S)—N-(4-(2,6-dimethoxyphenyl)-5-(5-methyl-2-furanyl)-4H-1,2,4-triazol-3-yl)-1-(5-fluoro-2-pyridinyl)-1-hydroxy-2-propanesulfonamide and (1S,2R)—N-(4-(2,6-dimethoxyphenyl)-5-(5-methyl-2-furanyl)-4H-1,2,4-triazol-3-yl)-1-(5-fluoro-2-pyridinyl)-1-hydroxy-2-propanesulfonamide 79.0

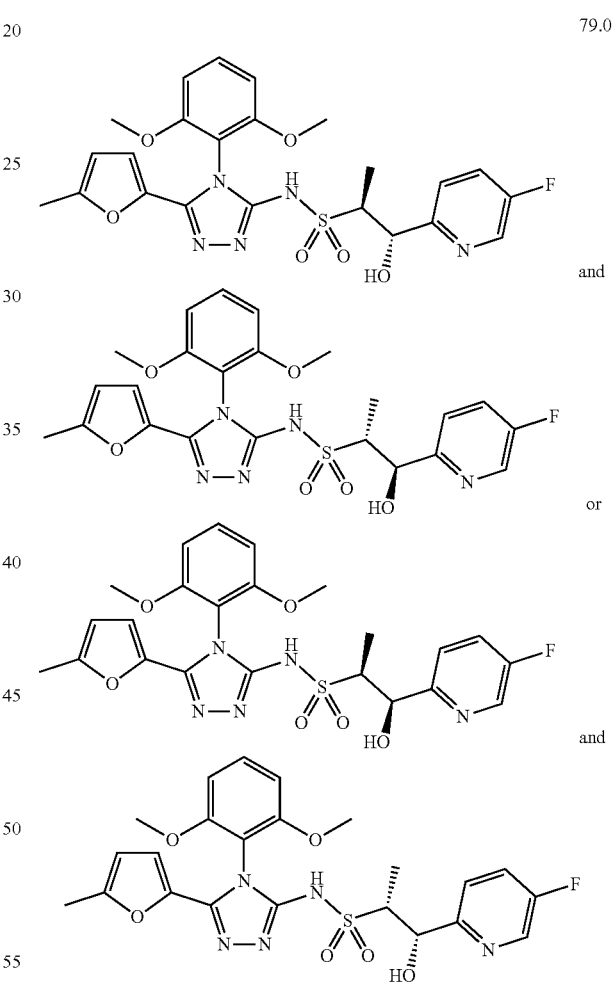

(1S,2S)—N-(4-(2,6-Dimethoxyphenyl)-5-(5-methyl-2-furanyl)-4H-1,2,4-triazol-3-yl)-1-(5-fluoro-2-pyridinyl)-1-hydroxy-2-propanesulfonamide and (1R,2R)—N-(4-(2,6-dimethoxyphenyl)-5-(5-methyl-2-furanyl)-4H-1,2,4-triazol-3-yl)-1-(5-fluoro-2-pyridinyl)-1-hydroxy-2-propanesulfonamide or (1R,2S)—N-(4-(2,6-dimethoxyphenyl)-5-(5-methyl-2-furanyl)-4H-1,2,4-triazol-3-yl)-1-(5-fluoro-2-pyridinyl)-1-hydroxy-2-propanesulfonamide and (1S,2R)—N-(4-(2,6-dimethoxyphenyl)-5-(5-methyl-2-furanyl)-4H-1,2,4-triazol- 3-yl)-1-(5-fluoro-2-pyridinyl)-1-hydroxy-2-propanesulfonamide, Example 79.0. Example 79.0 was prepared using Example 57.2 following the procedure described in Example 59.0. ¹H NMR (400 MHz, CD₃OD) δ 8.43 (d, J=2.74 Hz, 1H) 7.64 (td, J=9.00, 3.13 Hz, 1H) 7.53-7.59 (m, 2H) 6.78-6.94 (m, 2H) 6.02 (dd, J=4.64 Hz, 1H) 5.96 (d, J=3.52 Hz, 1H) 4.99 (d, J=6.85 Hz, 1H) 3.80 (s, 3H) 3.78 (s, 3H) 3.49 (quin, J=6.99 Hz, 1H) 2.26 (s, 3H) 1.09 (d, J=7.04 Hz, 3H). LCMS-ESI (pos.) m/z: 518.0 (M+H)⁺.

Example 80.0. Preparation of (2R)-4-(benzyloxy)-N-(4-(2,6-dimethoxyphenyl)-5-(5-methyl-2-furanyl)-4H-1,2,4-triazol-3-yl)-1-(5-methyl-2-pyrimidinyl)-2-butanesulfonamide and (2S)-4-(benzyloxy)-N-(4-(2,6-dimethoxyphenyl)-5-(5-methyl-2-furanyl)-4H-1,2,4-triazol-3-yl)-1-(5-methyl-2-pyrimidinyl)-2-butanesulfonamide 80.0

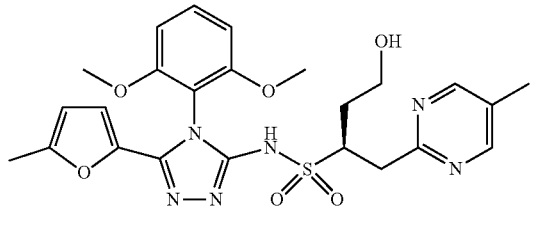

or

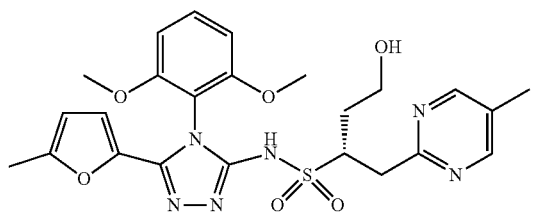

(2R)-4-(Benzyloxy)-N-(4-(2,6-dimethoxyphenyl)-5-(5-methyl-2-furanyl)-4H-1,2,4-triazol-3-yl)-1-(5-methyl-2-pyrimidinyl)-2-butanesulfonamide and (2S)-4-(benzyloxy)-N-(4-(2,6-dimethoxyphenyl)-5-(5-methyl-2-furanyl)-4H-1,2,4-triazol-3-yl)-1-(5-methyl-2-pyrimidinyl)-2-butanesulfonamide, Example 80.0. Example 70.0 was chirally separated into two enantiomers by SFC. The separation conditions were as follows: Run on Thar 80 SFC with 250×30 mm AS-H column with 15 g/min EtOH (neat)+55 g/min CO₂, 22% co-solvent at 70 g/min. Outlet pressure=100 bar; Temp.=21° C.; Wavelength=276 nm. Injected 0.5 mL of a solution from 60 mg sample dissolved in 5 mL of MeOH, c=12.0 mg/mL; 6.0 mg per injection. Cycle time 8 min. runtime 15 min. The title compound was the first peak (faster-eluting) from chiral separation. ¹H NMR (400 MHz, CD₃OD) δ 8.56 (s, 2H) 7.53 (t, J=8.31 Hz, 1H) 6.83 (dd, J=8.51, 1.27 Hz, 2H) 6.01 (m, 1H) 5.94 (d, J=3.33 Hz, 1H) 3.76 (m, 7H) 3.54 (m, 3H) 3.04 (m, 1H) 2.31 (s, 3H) 2.26 (s, 3H) 2.11 (d, J=6.46 Hz, 1H) 1.74 (m, 1H). LCMS-ESI (pos.) m/z: 529.0 (M+H)⁺.

Example 81.0. Preparation of (1R,2S)-1-(3-cyano-4-fluorophenyl)-N-(4-(2,6-dimethoxyphenyl)-5-(5-methyl-2-furanyl)-4H-1,2,4-triazol-3-yl)-1-hydroxy-2-propanesulfonamide and (1S,2R)-1-(3-cyano-4-fluorophenyl)-N-(4-(2,6-dimethoxyphenyl)-5-(5-methyl-2-furanyl)-4H-1,2,4-triazol-3-yl)-1-hydroxy-2-propanesulfonamide or (1S,2S)-1-(3-cyano-4-fluorophenyl)-N-(4-(2,6-dimethoxyphenyl)-5-(5-methyl-2-furanyl)-4H-1,2,4-triazol-3-yl)-1-hydroxy-2-propanesulfonamide and (1R,2R)-1-(3-cyano-4-fluorophenyl)-N-(4-(2,6-dimethoxyphenyl)-5-(5-methyl-2-furanyl)-4H-1,2,4-triazol-3-yl)-1-hydroxy-2-propanesulfonamide 81.1

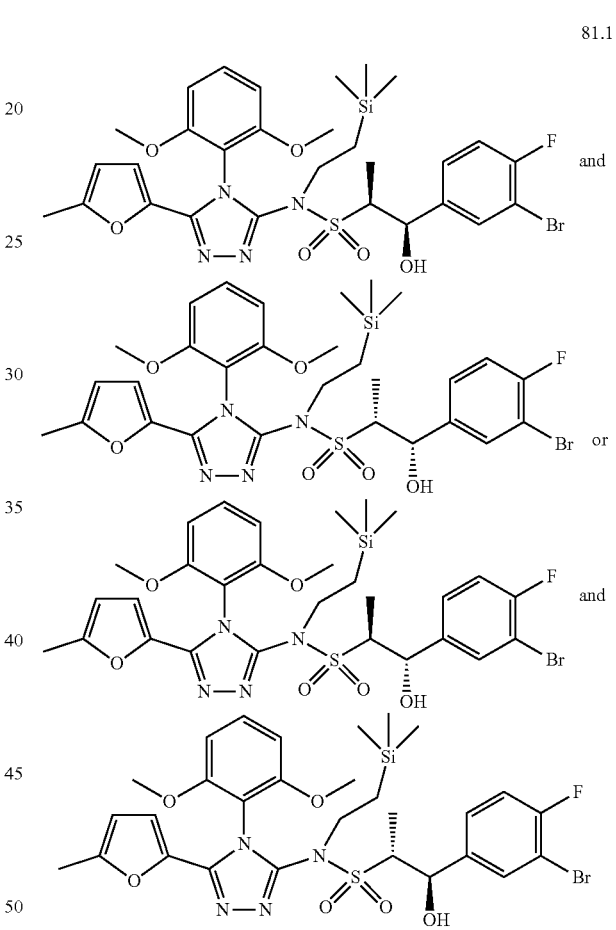

(1R,2S)-1-(3-Bromo-4-fluorophenyl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide and (1S,2R)-1-(3-bromo-4-fluorophenyl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide or (1S,2S)-1-(3-bromo-4-fluorophenyl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide and (1R,2R)-1-(3-bromo-4-fluorophenyl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide, Example 81.1. Example 81.1 was prepared using Example 369.0 and 3-bromo-4-fluorobenzaldehyde following the procedure described in Example 57.1. The reaction mixture was purified by silica gel chromatography eluting with a gradient of 0-40% EtOAc in hexanes to give two diastereomers in a 3:1 ratio. The title compound (Example 81.1) was the major diastereomer (less polar) from this reaction.

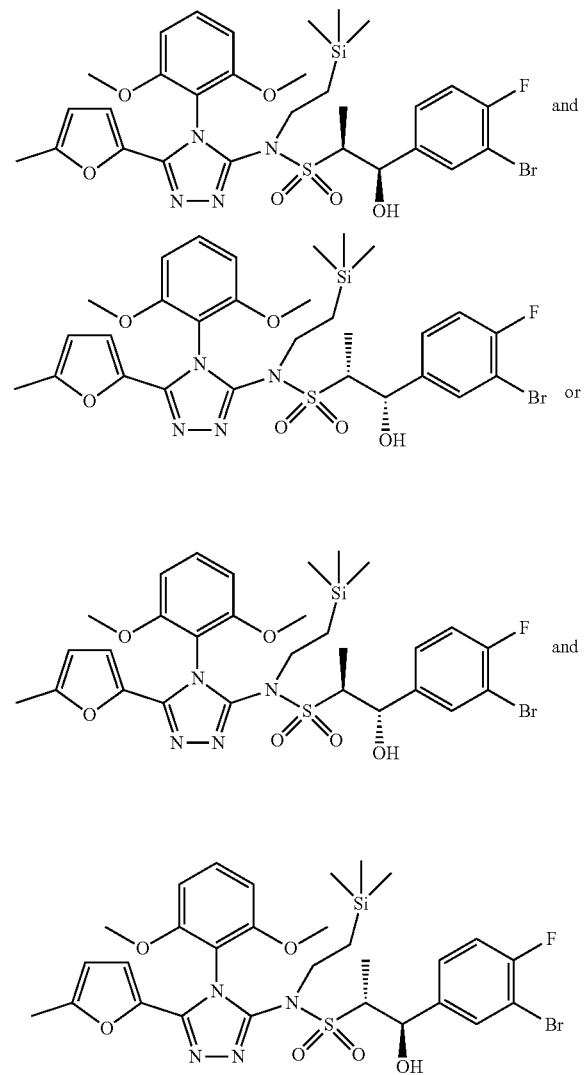

(1R,2S)-1-(3-Bromo-4-fluorophenyl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide and (1S,2R)-1-(3-bromo-4-fluorophenyl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide or (1S,2S)-1-(3-bromo-4-fluorophenyl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide and (1R,2R)-1-(3-bromo-4-fluorophenyl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide, Example 81.2. The title compound (Example 81.2) was the minor diastereomer (more polar) isolated from the same reaction described in Example 81.1.

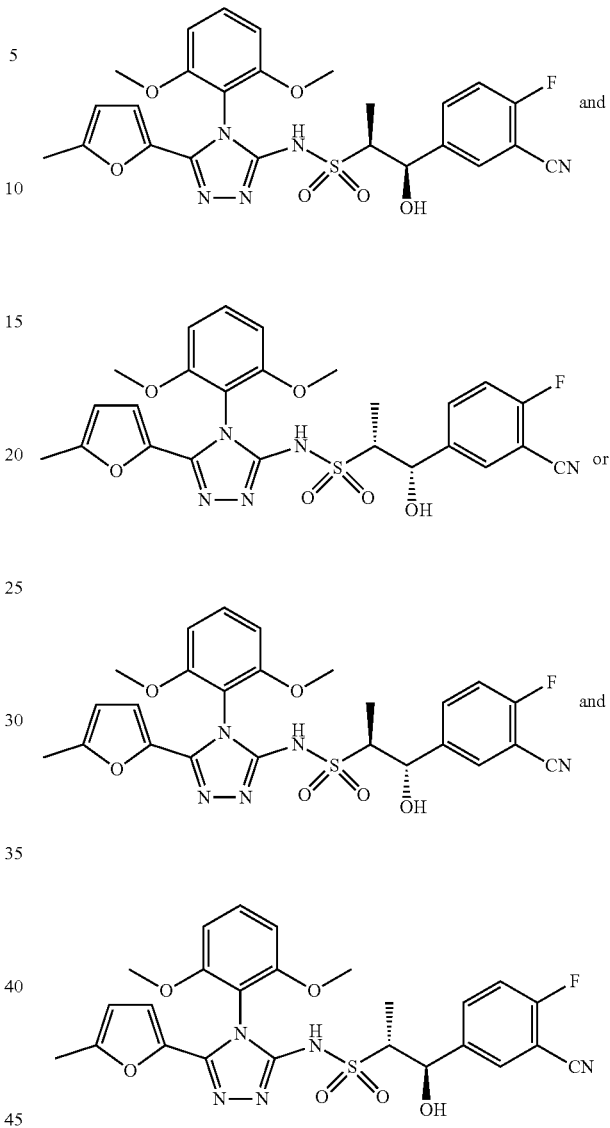

(1R,2S)-1-(3-Cyano-4-fluorophenyl)-N-(4-(2,6-dimethoxyphenyl)-5-(5-methyl-2-furanyl)-4H-1,2,4-triazol-3-yl)-1-hydroxy-2-propanesulfonamide and (1S,2R)-1-(3-cyano-4-fluorophenyl)-N-(4-(2,6-dimethoxyphenyl)-5-(5-methyl-2-furanyl)-4H-1,2,4-triazol-3-yl)-1-hydroxy-2-propanesulfonamide or (1S,2S)-1-(3-cyano-4-fluorophenyl)-N-(4-(2,6-dimethoxyphenyl)-5-(5-methyl-2-furanyl)-4H-1,2,4-triazol-3-yl)-1-hydroxy-2-propanesulfonamide and (1R,2R)-1-(3-cyano-4-fluorophenyl)-N-(4-(2,6-dimethoxyphenyl)-5-(5-methyl-2-furanyl)-4H-1,2,4-triazol-3-yl)-1-hydroxy-2-propanesulfonamide, Example 81.0. The title compound was prepared from Example 81.1 following the procedure described in Example 68.0. $^1$H NMR (400 MHz, CDCl$_3$) δ 10.86 (br. s, 1H) 7.64 (dd, J=5.97, 2.05 Hz, 1H) 7.45-7.59 (m, 2H) 7.18 (t, J=8.61 Hz, 1H) 6.74-6.79 (m, 1H) 6.69-6.74 (m, 1H) 5.95 (dd, J=3.52, 0.98 Hz, 1H) 5.89 (d, J=3.52 Hz, 1H) 5.49 (s, 1H) 3.87 (s, 3H) 3.78 (s, 3H) 3.10 (m, J=6.94, 1.27 Hz, 1H) 2.33 (s, 3H) 1.14 (d, J=6.85 Hz, 3H). LCMS-ESI (pos.) m/z: 542.0 (M+H)$^+$.

Example 82.0. Preparation of (1R,2R)—N-(4-(2,6-dimethoxyphenyl)-5-(5-methyl-2-furanyl)-4H-1,2,4-triazol-3-yl)-1-(2,4-dimethyl-1,3-oxazol-5-yl)-1-hydroxy-2-propanesulfonamide, and (1S,2S)—N-(4-(2,6-dimethoxyphenyl)-5-(5-methyl-2-furanyl)-4H-1,2,4-triazol-3-yl)-1-(2,4-dimethyl-1,3-oxazol-5-yl)-1-hydroxy-2-propanesulfonamide, and (1R,2S)—N-(4-(2,6-dimethoxyphenyl)-5-(5-methyl-2-furanyl)-4H-1,2,4-triazol-3-yl)-1-(2,4-dimethyl-1,3-oxazol-5-yl)-1-hydroxy-2-propanesulfonamide, and (1S,2R)—N-(4-(2,6-dimethoxyphenyl)-5-(5-methyl-2-furanyl)-4H-1,2,4-triazol-3-yl)-1-(2,4-dimethyl-1,3-oxazol-5-yl)-1-hydroxy-2-propanesulfonamide 3-yl)-1-(2,4-dimethyl-1,3-oxazol-5-yl)-1-hydroxy-2-propanesulfonamide and (1S,2R)—N-(4-(2,6-dimethoxyphenyl)-5-(5-methyl-2-furanyl)-4H-1,2,4-triazol-3-yl)-1-(2,4-dimethyl-1,3-oxazol-5-yl)-1-hydroxy-2-propanesulfonamide, Example 82.0. The title compound was prepared using Example 369.0 and 2,4-dimethyl-oxazole-5-carbaldehyde following the procedures described in Example 86.0 and Example 59.0 to deliver the title compound as a mixtures of diastereomers in a 3:1 diastereomeric ratio. $^1$H NMR (400 MHz, CD$_3$OD) δ 7.53-7.60 (m, 1H) 6.83-6.89 (m, 2H) 6.02 (dd, J=5.49 Hz, 1H) 5.96 (d, J=3.52 Hz, 1H) 4.95-5.08 (m, 1H) 3.76-3.83 (m, 6H) 3.26-3.47 (m, 1H) 2.43-2.48 (m, 3H) 2.25 (s, 3H) 1.87-2.05 (m, 3H) 1.15-1.50 (m, 3H). LCMS-ESI (pos.) m/z: 518.0 (M+H)$^+$.

Example 83.0. Preparation of 2-(4-chlorophenyl)-N-(5-(furan-2-yl)-4-(pyridin-2-yl)-4H-1,2,4-triazol-3-yl)ethanesulfonamide


82.0

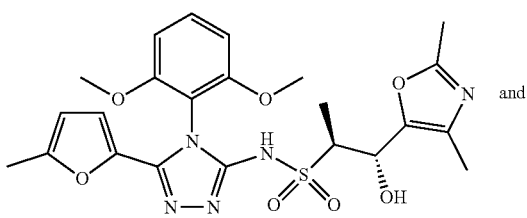

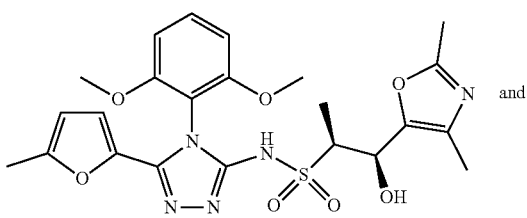

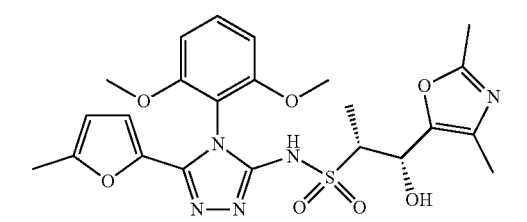

(1R,2R)—N-(4-(2,6-Dimethoxyphenyl)-5-(5-methyl-2-furanyl)-4H-1,2,4-triazol-3-yl)-1-(2,4-dimethyl-1,3-oxazol-5-yl)-1-hydroxy-2-propanesulfonamide and (1S,2S)—N-(4-(2,6-dimethoxyphenyl)-5-(5-methyl-2-furanyl)-4H-1,2,4-triazol-3-yl)-1-(2,4-dimethyl-1,3-oxazol-5-yl)-1-hydroxy-2-propanesulfonamide and (1R,2S)—N-(4-(2,6-dimethoxyphenyl)-5-(5-methyl-2-furanyl)-4H-1,2,4-triazol-

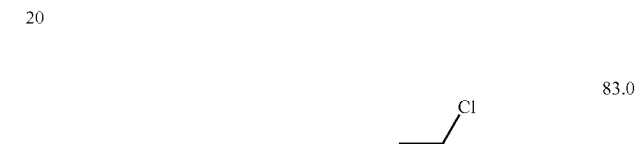

83.0

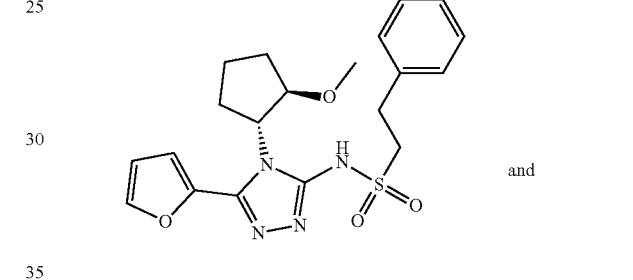

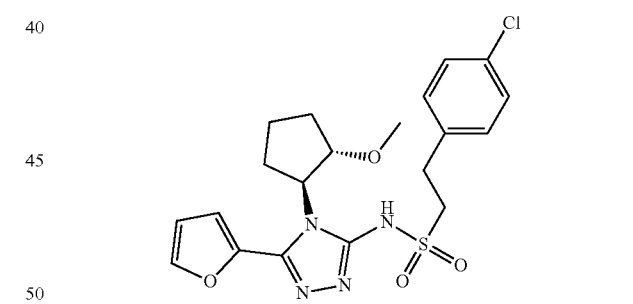

2-(4-Chlorophenyl)-N-(5-(furan-2-yl)-4-((1R,2R)-2-methoxycyclopentyl)-4H-1,2,4-triazol-3-yl)ethanesulfonamide and 2-(4-chlorophenyl)-N-(5-(furan-2-yl)-4-((1S,2S)-2-methoxycyclopentyl)-4H-1,2,4-triazol-3-yl)ethanesulfonamide, Example 84.0. Following the procedure described in Example 112.0 employing (1R,2R)-2-methoxycyclopentanamine and (1S,2S)-2-methoxycyclopentanamine (commercially available from Aurum Pharmatech) yielded the title compound as a white solid. $^1$H NMR (400 MHz, DMSO-d$_6$) δ 1.33 (s, 1H), 1.54-1.67 (m, 2H), 1.79-1.80 (m, 1H), 2.01-2.06 (m, 2H), 2.07-2.15 (m, 1H), 2.97-3.01 (m, 2H), 3.10 (s, 3H), 3.33-3.39 (m, 1H), 4.28-4.32 (m, 1H), 4.48-4.54 (m, 1H), 6.74 (s, 1H), 7.06-7.09 (m, 1H), 7.28 (d, 2H, J=8.4), 7.33 (d, 2H, J=8), 7.99 (s, 1H), 13.02 (s, 1H); LCMS-ESI (pos.), m/z, 450.94 (M+H)$^+$.

Example 84.0. Preparation of 2-(4-chlorophenyl)-N-(5-(furan-2-yl)-4-(pyridin-2-yl)-4H-1,2,4-triazol-3-yl)ethanesulfonamide

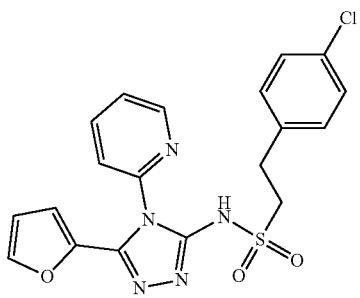

84.0

2-(4-Chlorophenyl)-N-(5-(furan-2-yl)-4-(pyridin-2-yl)-4H-1,2,4-triazol-3-yl)ethanesulfonamide, Example 84.0. Following the procedure described in Example 112.0 employing pyridin-2-amine yielded the title compound as a white solid. $^1$H NMR (400 MHz, DMSO-$d_6$) δ 2.92 (t, 2H, J=8.4), 3.26 (t, 2H, J=7.6), 6.23 (d, 1H, J=3.2), 6.55 (s, 1H), 7.26 (d, 2H, J=8), 7.32 (d, 2H, J=8.4), 7.65-7.68 (m, 1H), 7.73 (d, 1H, J=8), 7.78 (s, 1H), 8.14 (t, 1H, J=7.2), 8.64 (d, 1H, J=4), 13.45 (s, 1H). LCMS-ESI (pos.) m/z: 429.88 (M+H)$^+$.

Example 86.0. Preparation of (1R,2S)-1-(5-cyano-6-methylpyridin-2-yl)-N-(4-(2,6-dimethoxyphenyl)-5-(5-methylfuran-2-yl)-4H-1,2,4-triazol-3-yl)-1-hydroxypropane-2-sulfonamide

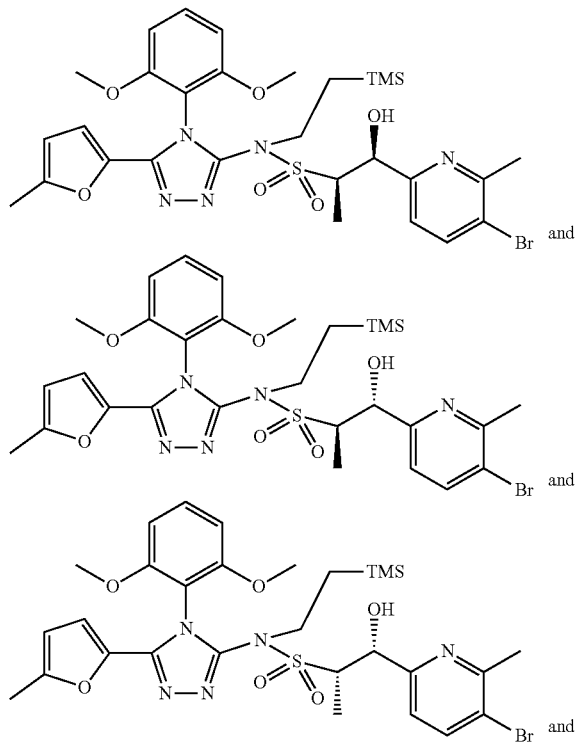

86.1

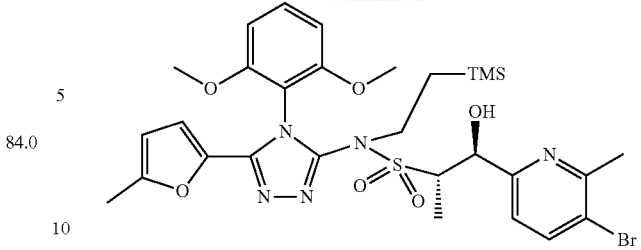

(1R,2R)-1-(5-Bromo-6-methylpyridin-2-yl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide compound and (1R,2S)-1-(5-bromo-6-methylpyridin-2-yl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide and (1S,2R)-1-(5-bromo-6-methylpyridin-2-yl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide and (1S,2S)-1-(5-bromo-6-methylpyridin-2-yl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide, Example 86.1. To a solution of Example 369.0 (0.524 g, 1.06 mmol) in THF (5.32 mL) was added n-butyllithium (1.6 M solution in hexanes, 1.33 mL, 2.13 mmol) at −78° C. dropwise. The resulting mixture was stirred at the same temperature for 20 min and then a solution of 3-bromo-2-methyl-pyridine-6-carbaldehyde (AOBChem USA, 0.426 g, 2.13 mmol) in THF (2 mL) was added. The resulting mixture was allowed to stir overnight while gradually warming to RT. The mixture was quenched with a saturated aqueous solution of NH$_4$Cl and extracted with EtOAc. The EtOAc layer was dried and concentrated in vacuo. The residue was then purified by an Isco CombiFlash on a Redi Gold 40 g silica gel column using a 0-100% EtOAc gradient in hexanes to give Example 86.1 (335 mg, 45%). LCMS-ESI (pos.) m/z: 693.6 (M+H)$^+$.

86.2

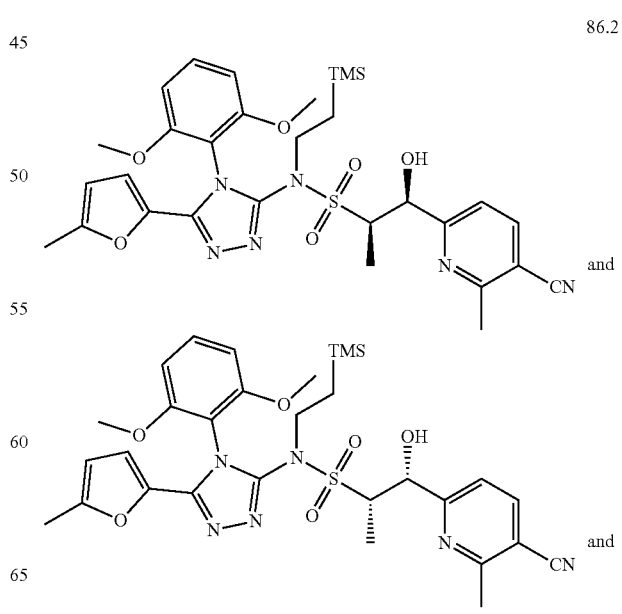

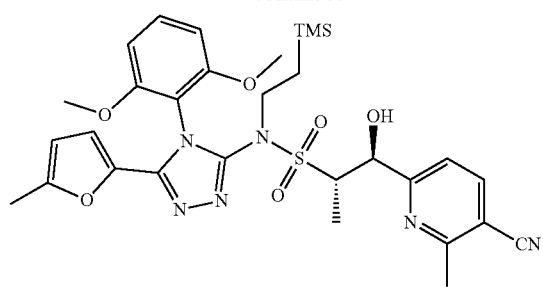

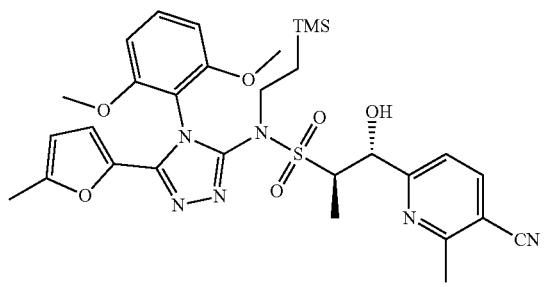

(1R,2R)-1-(5-Cyano-6-methylpyridin-2-yl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide and (1R,2S)-1-(5-cyano-6-methylpyridin-2-yl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide and (1S,2R)-1-(5-cyano-6-methylpyridin-2-yl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide and (1S,2S)-1-(5-cyano-6-methylpyridin-2-yl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide, Example 86.2. Argon was bubbled through a mixture of zinc cyanide (0.092 mL, 1.45 mmol) and Example 86.1 (0.335 g, 0.484 mmol) in DMF (2.5 mL) for 5 min. Tetrakis(triphenylphosphine)palladium (0.056 g, 0.048 mmol) was then added and argon was further bubbled through the mixture for an additional 1 min. The mixture was then placed under an atmosphere of argon and stirred at 115° C. overnight. The mixture was cooled to RT and then directly loaded onto a silica gel cartridge and purified by Isco CombiFlash on a Redi 40 g gold column using a 0-100% EtOAc gradient in hexanes as the eluent to give Example 86.2 (220 mg, 71%). LCMS-ESI (pso.) m/z: 639.2 (M+H)⁺.

88.0

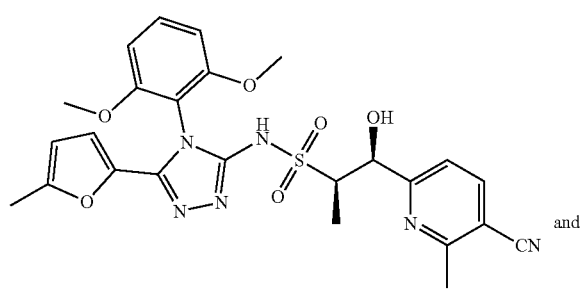

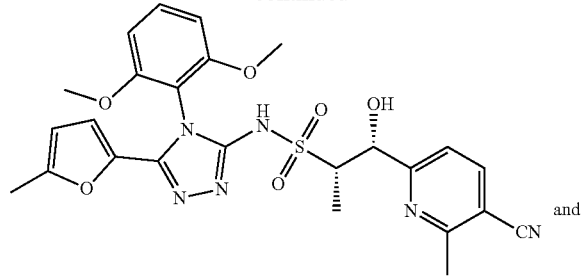

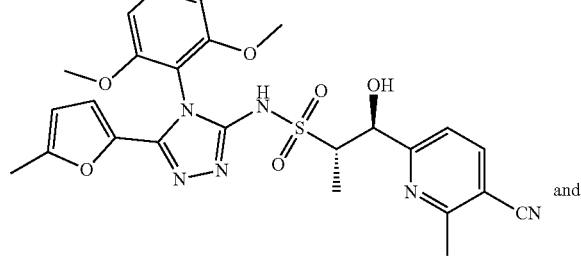

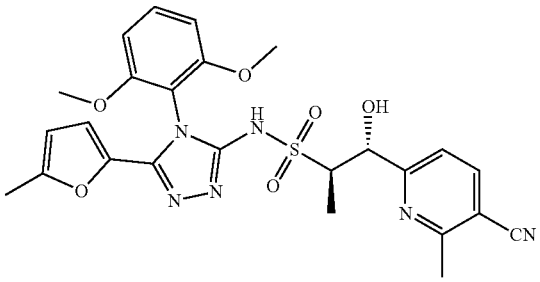

(1R,2R)-1-(5-Cyano-6-methylpyridin-2-yl)-N-(4-(2,6-dimethoxyphenyl)-5-(5-methylfuran-2-yl)-4H-1,2,4-triazol-3-yl)-1-hydroxypropane-2-sulfonamide and (1R,2S)-1-(5-cyano-6-methylpyridin-2-yl)-N-(4-(2,6-dimethoxyphenyl)-5-(5-methylfuran-2-yl)-4H-1,2,4-triazol-3-yl)-1-hydroxypropane-2-sulfonamide and (1S,2R)-1-(5-cyano-6-methylpyridin-2-yl)-N-(4-(2,6-dimethoxyphenyl)-5-(5-methylfuran-2-yl)-4H-1,2,4-triazol-3-yl)-1-hydroxypropane-2-sulfonamide and (1S,2S)-1-(5-cyano-6-methylpyridin-2-yl)-N-(4-(2,6-dimethoxyphenyl)-5-(5-methylfuran-2-yl)-4H-1,2,4-triazol-3-yl)-1-hydroxypropane-2-sulfonamide, Example 88.0. To a solution of Example 86.2 (0.220 g, 0.344 mmol) in DMF (2.5 mL) was added tris(dimethylamino)sulfonium difluorotrimethylsilicate (0.285 g, 1.03 mmol) in portions at RT. The resulting mixture was stirred at 60° C. overnight. The mixture was cooled to RT and then was directly loaded onto a silica gel cartridge and purified by Isco CombiFlash on a Redi 40 g gold silica gel column using a 0-100% EtOAc gradient in hexanes as the eluent to give Example 88.0 (118 mg, 63%). LCMS-ESI (pos.): 539.2 (M+H)⁺.

86.0

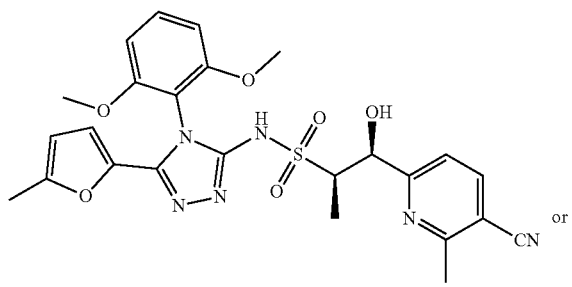

or


or

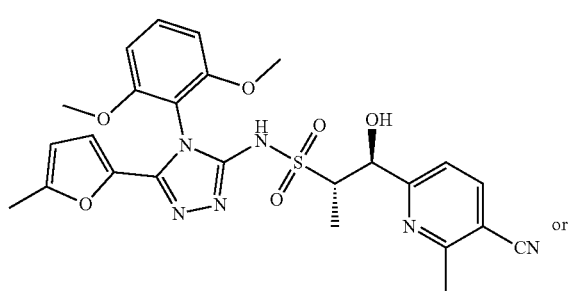

or

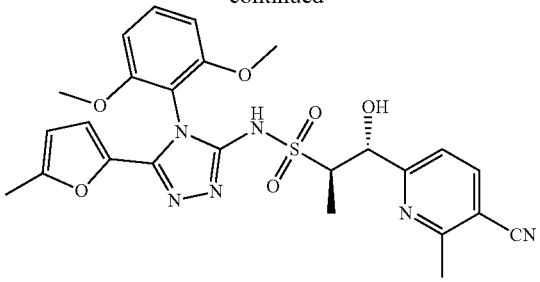

(1R,2R)-1-(5-Cyano-6-methylpyridin-2-yl)-N-(4-(2,6-dimethoxyphenyl)-5-(5-methylfuran-2-yl)-4H-1,2,4-triazol-3-yl)-1-hydroxypropane-2-sulfonamide or (1R,2S)-1-(5-cyano-6-methylpyridin-2-yl)-N-(4-(2,6-dimethoxyphenyl)-5-(5-methylfuran-2-yl)-4H-1,2,4-triazol-3-yl)-1-hydroxypropane-2-sulfonamide or (1S,2R)-1-(5-cyano-6-methylpyridin-2-yl)-N-(4-(2,6-dimethoxyphenyl)-5-(5-methylfuran-2-yl)-4H-1,2,4-triazol-3-yl)-1-hydroxypropane-2-sulfonamide or (1S,2S)-1-(5-cyano-6-methylpyridin-2-yl)-N-(4-(2,6-dimethoxyphenyl)-5-(5-methylfuran-2-yl)-4H-1,2,4-triazol-3-yl)-1-hydroxypropane-2-sulfonamide, Example 86.0. Example 88.0 was separated by SFC (250×30 AD-H column with 31.5 g/min EtOH (20 mM $NH_3$)+59 g/min $CO_2$, 35% co-solvent at 90 g/min. Temp.=20° C., Outlet pressure=100 bar, Wavelength=275 nm. Injected 1.2 mL of 115 mg sample dissolved in 10 mL MeOH, c=11.5 mg/mL and 13.8 mg per injection. Cycle time=14 min, run time=16 min.). Four enantiomers were obtained. The title compound (Example 86.0) was the third isomer to elute under these conditions. $^1$H NMR (400 MHz, $CDCl_3$) δ 10.97 (br s, 1H), 7.87 (d, J=8.0 Hz, 1H), 7.48-7.52 (m, 2H), 6.71 (t, J=10 Hz, 2H), 5.93 (br s, 1H), 5.88 (br s, 1H), 5.45 (br s, 1H), 4.08 (br s, 1H), 3.82-3.86 (obscured m, 1H), 3.81 (s, 3H), 3.76 (s, 3H), 2.72 (s, 3H), 2.32 (s, 3H), 1.08 (d, J=6.7 Hz, 3H). LCMS-ESI (pos.): 539.2 $(M+H)^+$.

The compounds set forth in the following table were synthesized following the procedure in Example 10.0 using the starting materials as described.

TABLE 1

| Example | Reagents | Structure, Name and Data |
|---|---|---|
| 85.1 | N-(4-(2,6-dimethoxyphenyl)-5-(5-methylfuran-2-yl)-4H-1,2,4-triazol-3-yl)-N-(2-(trimethylsilyl)ethyl)ethanesulfonamide (Example 369.0) and 6-chloropicolinaldehyde (Bionet Research). | and |

TABLE 1-continued

| Example | Reagents | Structure, Name and Data |
|---|---|---|

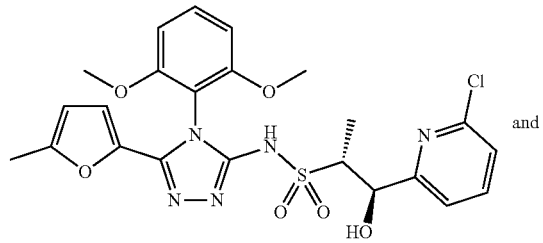

(1R,2R)-1-(6-chloropyridin-2-yl)-N-(4-(2,6-
dimethoxyphenyl)-5-(5-methylfuran-2-yl)-4H-1,2,4-
triazol-3-yl)-1-hydroxypropane-2-sulfonamide
compound and (1R,2S)-1-(6-chloropyridin-2-yl)-N-(4-
(2,6-dimethoxyphenyl)-5-(5-methylfuran-2-yl)-4H-
1,2,4-triazol-3-yl)-1-hydroxypropane-2-sulfonamide and
(1S,2R)-1-(6-chloropyridin-2-yl)-N-(4-(2,6-
dimethoxyphenyl)-5-(5-methylfuran-2-yl)-4H-1,2,4-
triazol-3-yl)-1-hydroxypropane-2-sulfonamide and
(1S,2S)-1-(6-chloropyridin-2-yl)-N-(4-(2,6-
dimethoxyphenyl)-5-(5-methylfuran-2-yl)-4H-1,2,4-
triazol-3-yl)-1-hydroxypropane-2-sulfonamide.
LCMS (pos.) m/z: 534.1 (M + H)+.

| 85.0 | The mixture (Example 85.1) was separated by SFC using the following methodology: (2 × 15 cm AD-H column with 65 mL/min 30% EtOH (0.2% NH$_4$OH)/CO$_2$. Outlet pressure = 100 bar; wavelength = 280 nm; injection volumn = 0.8 mL, 7 mg/mL 1:2 DCM:EtOH). Four isomers were obtained. This was the third isomer to elute under these conditions. | 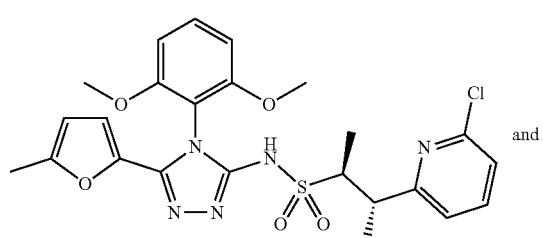<br>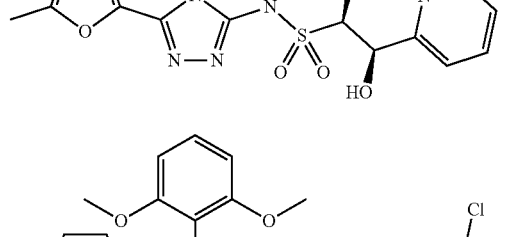<br>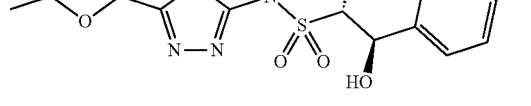 |

TABLE 1-continued

| Example | Reagents | Structure, Name and Data |
|---|---|---|
| | | 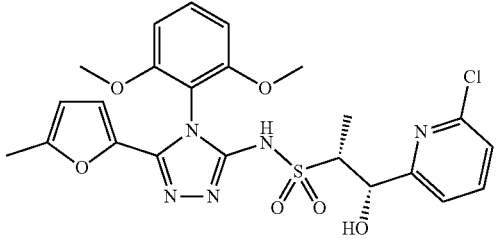 [SMILES: COc1cccc(OC)c1-n1c(NS(=O)(=O)[C@H](C)[C@@H](O)c2cccc(Cl)n2)nnc1-c1ccc(C)o1] |

(1R,2R)-1-(6-chloropyridin-2-yl)-N-(4-(2,6-dimethoxyphenyl)-5-(5-methylfuran-2-yl)-4H-1,2,4-triazol-3-yl)-1-hydroxypropane-2-sulfonamide compound or (1R,2S)-1-(6-chloropyridin-2-yl)-N-(4-(2,6-dimethoxyphenyl)-5-(5-methylfuran-2-yl)-4H-1,2,4-triazol-3-yl)-1-hydroxypropane-2-sulfonamide or (1S,2R)-1-(6-chloropyridin-2-yl)-N-(4-(2,6-dimethoxyphenyl)-5-(5-methylfuran-2-yl)-4H-1,2,4-triazol-3-yl)-1-hydroxypropane-2-sulfonamide or (1S,2S)-1-(6-chloropyridin-2-yl)-N-(4-(2,6-dimethoxyphenyl)-5-(5-methylfuran-2-yl)-4H-1,2,4-triazol-3-yl)-1-hydroxypropane-2-sulfonamide.

$^1$H NMR (400 MHz, CDCl$_3$) δ 7.64 (dd, J = 7.7, 7.7 Hz, 1 H), 7.46-7.51 (m, 2 H), 7.18 (d, J = 7.6 Hz, 1 H), 6.70 (ddd, J = 11.3, 8.6, 0.78 Hz, 2 H), 5.93 (dd, J = 3.33, 0.98 Hz, 1 H), 5.86 (d, J = 3.52 Hz, 1 H), 5.43 (s, 1 H), 4.03 (br. s., 1 H), 3.80 (s, 3 H), 3.75-3.80 (m, 1 H), 3.77 (s, 3 H), 2.32 (s, 3 H), 1.11 (d, J = 7.04 Hz, 3 H). LCMS-ESI (pos.): 534.0 (M + H)$^+$.

| 87.1 | N-(4-(2,6-dimethoxyphenyl)-5-(5-methylfuran-2-yl)-4H-1,2,4-triazol-3-yl)-N-(2-(trimethylsilyl)ethyl)ethane-sulfonamide (Example 369.0) and 6-methylpicolinaldehyde. | 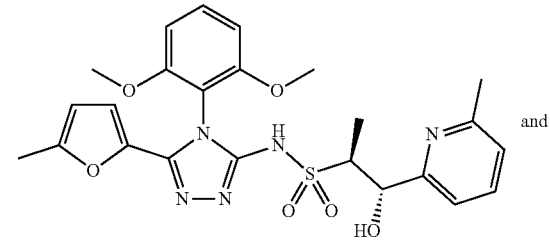 and 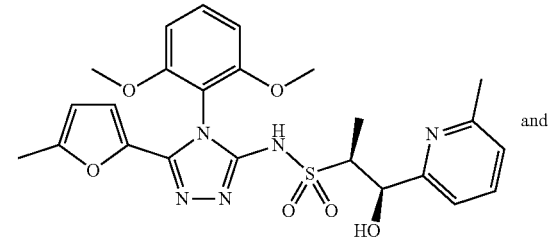 [SMILES: COc1cccc(OC)c1-n1c(NS(=O)(=O)[C@@H](C)[C@H](O)c2cccc(C)n2)nnc1-c1ccc(C)o1] and 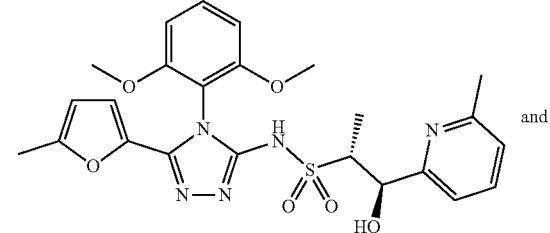 [SMILES: COc1cccc(OC)c1-n1c(NS(=O)(=O)[C@H](C)[C@H](O)c2cccc(C)n2)nnc1-c1ccc(C)o1] and |

| Example | Reagents | Structure, Name and Data |
|---|---|---|
| | | 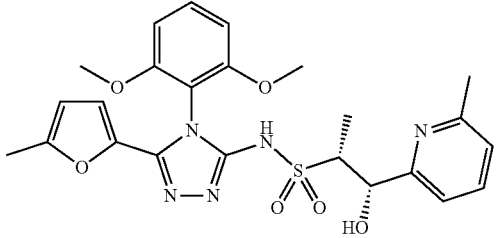 [SMILES: COc1cccc(OC)c1-n1c(NS(=O)(=O)[C@H](C)[C@@H](O)c2cccc(C)n2)nnc1-c1ccc(C)o1]<br>(1R,2R)-N-(4-(2,6-dimethoxyphenyl)-5-(5-methylfuran-2-yl)-4H-1,2,4-triazol-3-yl)-1-hydroxy-1-(6-methylpyridin-2-yl)propane-2-sulfonamide compound and (1R,2S)-N-(4-(2,6-dimethoxyphenyl)-5-(5-methylfuran-2-yl)-4H-1,2,4-triazol-3-yl)-1-hydroxy-1-(6-methylpyridin-2-yl)propane-2-sulfonamide and (1S,2R)-N-(4-(2,6-dimethoxyphenyl)-5-(5-methylfuran-2-yl)-4H-1,2,4-triazol-3-yl)-1-hydroxy-1-(6-methylpyridin-2-yl)propane-2-sulfonamide and (1S,2S)-N-(4-(2,6-dimethoxyphenyl)-5-(5-methylfuran-2-yl)-4H-1,2,4-triazol-3-yl)-1-hydroxy-1-(6-methylpyridin-2-yl)propane-2-sulfonamide.<br>LCMS (pos.) m/z: 514.1 (M + H)$^+$. |
| 87.0 | The mixture (Example 87.1) was separated by SFC using the following methodology: (2 × 15 cm AD-H column with 65 mL/min 35% EtOH (0.2% NH$_4$OH)/CO$_2$. Outlet pressure = 100 bar; wavelength = 220 nm; injection volumn = 0.7 mL, 7 mg/mL 1:3 DCM:MeOH). Four isomers were obtained. This compound (Example 87.0) was the third isomer to elute under these conditions. | 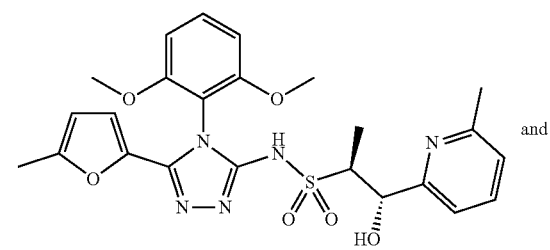 [SMILES: COc1cccc(OC)c1-n1c(NS(=O)(=O)[C@@H](C)[C@@H](O)c2cccc(C)n2)nnc1-c1ccc(C)o1] and<br>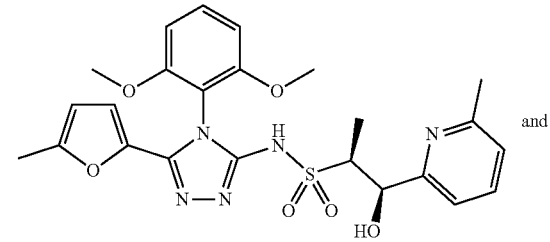 and<br>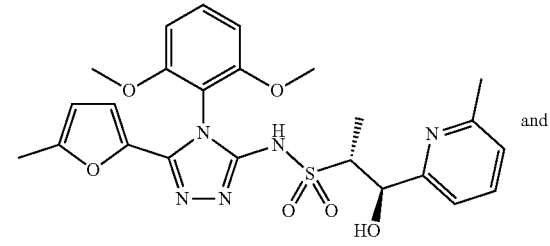 [SMILES: COc1cccc(OC)c1-n1c(NS(=O)(=O)[C@H](C)[C@H](O)c2cccc(C)n2)nnc1-c1ccc(C)o1] and<br>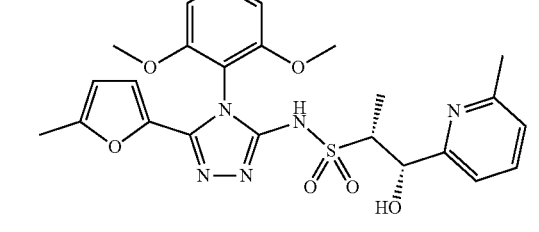<br>(1R,2R)-N-(4-(2,6-dimethoxyphenyl)-5-(5-methylfuran-2-yl)-4H-1,2,4-triazol-3-yl)-1-hydroxy-1-(6- |

TABLE 1-continued

| Example | Reagents | Structure, Name and Data |
|---|---|---|
| | | methylpyridin-2-yl)propane-2-sulfonamide compound or (1R,2S)-N-(4-(2,6-dimethoxyphenyl)-5-(5-methylfuran-2-yl)-4H-1,2,4-triazol-3-yl)-1-hydroxy-1-(6-methylpyridin-2-yl)propane-2-sulfonamide or (1S,2R)-N-(4-(2,6-dimethoxyphenyl)-5-(5-methylfuran-2-yl)-4H-1,2,4-triazol-3-yl)-1-hydroxy-1-(6-methylpyridin-2-yl)propane-2-sulfonamide or (1S,2S)-N-(4-(2,6-dimethoxyphenyl)-5-(5-methylfuran-2-yl)-4H-1,2,4-triazol-3-yl)-1-hydroxy-1-(6-methylpyridin-2-yl)propane-2-sulfonamide.<br>$^1$H NMR (400 MHz, CDCl$_3$) δ 7.54 (t, J = 7.6 Hz, 1 H), 7.47 (t, J = 8.2 Hz, 1 H), 7.27 (d, J = 6.8 Hz, 1 H), 7.00 (d, J = 7.6 Hz, 1 H), 6.70 (dd, J = 11.44, 8.51 Hz, 2 H), 5.92 (dd, J = 3.4, 0.9 Hz, 1 H), 5.85 (d, J = 3.3 Hz, 1 H), 5.44 (s, 1 H), 3.79 (s, 3 H), 3.77-3.80 (obscured m, 1 H), 3.74 (s, 3 H), 3.70-3.75 (obscured m, 1 H), 2.49 (s, 3 H), 2.12 (s, 3 H), 1.09 (d, J = 7.0 Hz, 3 H). LCMS-ESI (pos.): 514.1 (M + H)$^+$. |
| 90.1 | N-(4-(2,6-dimethoxyphenyl)-5-(5-methylfuran-2-yl)-4H-1,2,4-triazol-3-yl)-N-(2-(trimethylsilyl)ethyl)ethane-sulfonamide (Example 369.0) and 2-pyridinecarboxaldehyde (Frontier Scientific Services Inc.).<br>The mixture of the diastereomers was purified by ISCO CombiFlash on a Redi 24 g silica gel column using 0-100% EtOAc gradient in hexane as the eluent.<br>Two peaks were collected. This was the second peak to elute under these conditions. | 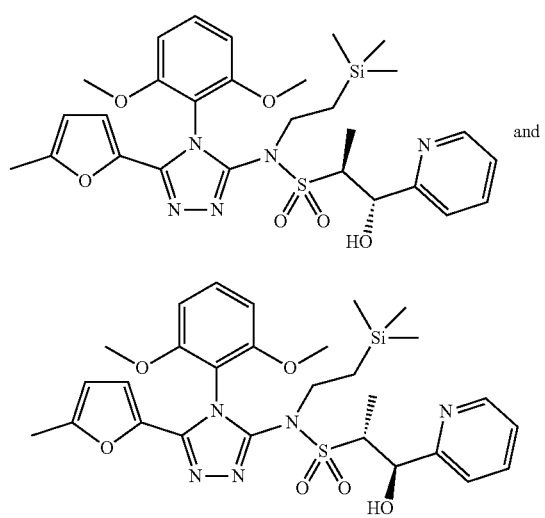<br>((1R,2R)-N-(4-(2,6-dimethoxyphenyl)-5-(5-methylfuran-2-yl)-4H-1,2,4-triazol-3-yl)-1-hydroxy-1-(pyridin-2-yl)-N-(2-(trimethylsilyl)ethyl)propane-2-sulfonamide compound and (1S,2S)-N-(4-(2,6-dimethoxyphenyl)-5-(5-methylfuran-2-yl)-4H-1,2,4-triazol-3-yl)-1-hydroxy-1-(pyridin-2-yl)-N-(2-(trimethylsilyl)ethyl)propane-2-sulfonamide.<br>LCMS (pos.) m/z: 600.2 (M + H)$^+$. |
| 90.0 | Example 90.1. | 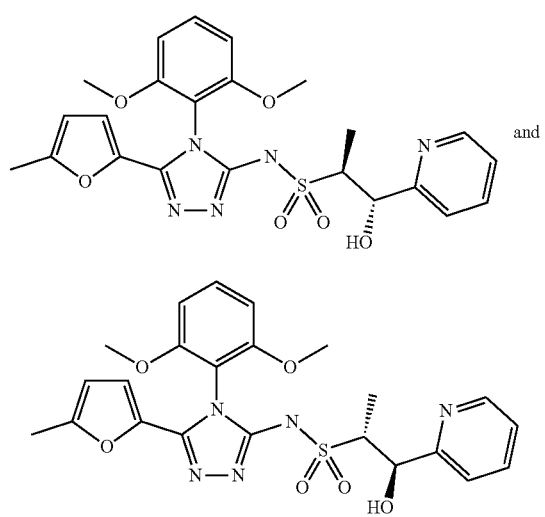 |

| Example | Reagents | Structure, Name and Data |
|---|---|---|
| | | (1R,2R)-N-(4-(2,6-dimethoxyphenyl)-5-(5-methylfuran-2-yl)-4H-1,2,4-triazol-3-yl)-1-hydroxy-1-(pyridin-2-yl)propane-2-sulfonamide compound and (1S,2S)-N-(4-(2,6-dimethoxyphenyl)-5-(5-methylfuran-2-yl)-4H-1,2,4-triazol-3-yl)-1-hydroxy-1-(pyridin-2-yl)propane-2-sulfonamide.<br>¹H NMR (400 MHz, CDCl₃) δ 8.54 (dt, J = 4.11, 0.78 Hz, 1 H), 7.65 (td, J = 7.63, 1.76 Hz, 1 H), 7.46 (t, J = 8.51 Hz, 1 H), 7.39 (d, J = 7.83 Hz, 1 H), 7.18 (ddd, J = 7.48, 4.84, 1.17 Hz, 1 H), 6.67-6.70 (m, 2 H), 5.89-5.92 (m, 1 H), 5.84 (d, J = 3.3 Hz, 1 H), 4.98 (d, J = 7.4 Hz, 2 H), 3.75-3.80 (obscured m, 1H), 3.78 (app s, 6 H), 3.54-3.61 (m, 1 H), 2.32 (s, 3 H), 1.11 (d, J = 7.0 Hz, 3 H). LCMS (pos.) m/z: 500.1 (M + H)⁺. |

Example 89.0. Preparation of (R)—N-(4-(2,6-dimethoxyphenyl)-5-(4,5-dimethylfuran-2-yl)-4H-1,2,4-triazol-3-yl)-1-(5-fluoropyrimidin-2-yl)propane-2-sulfonamide compound or (S)—N-(4-(2,6-dimethoxyphenyl)-5-(4,5-dimethylfuran-2-yl)-4H-1,2,4-triazol-3-yl)-1-(5-fluoropyrimidin-2-yl)propane-2-sulfonamide

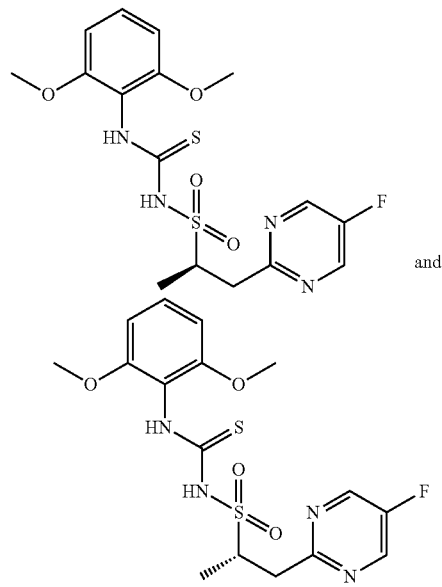

(R)—N-((2,6-Dimethoxyphenyl)carbamothioyl)-1-(5-fluoropyrimidin-2-yl)propane-2-sulfonamide and (S)—N-((2,6-dimethoxyphenyl)carbamothioyl)-1-(5-fluoropyrimidin-2-yl)propane-2-sulfonamide, Example 89.1. To a solution of (S)-1-(5-fluoropyrimidin-2-yl)propane-2-sulfonamide and (R)-1-(5-fluoropyrimidin-2-yl)propane-2-sulfonamide (Example 353.0, 1.8 g, 8.21 mmol) in DMF (10 mL) was added cesium carbonate (4.01 g, 12.32 mmol) in portions. The mixture was stirred at RT for 5 min before 2-isothiocyanato-1,3-dimethoxybenzene (Example 372.0, 1.683 g, 8.62 mmol) was added in portions. The resulting mixture was stirred at RT and monitored by LCMS. Upon completion of reaction, 20 mL of water was added, and the mixture was acidified by addition of aqueous HCl solution, 2.0 N (6.16 mL, 12.32 mmol) to a pH of about 5. The precipitate was collected and washed with water three times and dried under vacuum to give Example 89.1 (3.37 g, 8.13 mmol, 99% yield). LCMS-ESI (pos.) m/z: 415.1 (M+H)⁺.

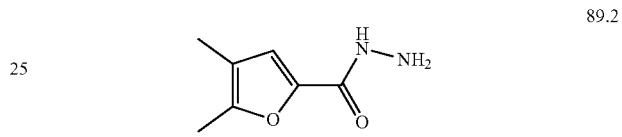

4,5-Dimethylfuran-2-carbohydrazide, Example 89.2. To a mixture of 4,5-dimethyl-2-furoic acid (2.0 g, 14.27 mmol) and cesium carbonate (5.58 g, 17.13 mmol) in ACN (28.5 mL) was added iodomethane (1.773 mL, 28.5 mmol) at 0° C. The resulting mixture was stirred at RT for 24 h. The mixture was concentrated in vacuo to give methyl 4,5-dimethylfuran-2-carboxylate (1.33 g, 60%). The residue (1.33 g, 8.63 mmol) was dissolved in MeOH (8.5 mL) and hydrazine (1.38 g, 43.1 mmol) was added. The resulting mixture was stirred at RT. Upon completion of reaction as determined by LCMS, the mixture was concentrated. The residue was dissolved in 100 mL of water. The aqueous solution was then lyophilized to give Example 89.2 (1.25 g, 94%). LCMS-ESI (pos.) m/z: 155.1 (M+H)⁺.


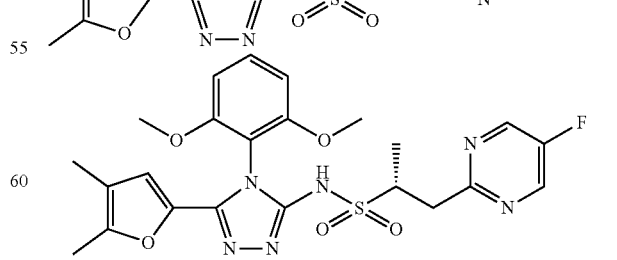

(R)—N-(4-(2,6-Dimethoxyphenyl)-5-(4,5-dimethylfuran-2-yl)-4H-1,2,4-triazol-3-yl)-1-(5-fluoropyrimidin-2-yl)propane-2-sulfonamide and (S)—N-(4-(2,6-dimethoxyphenyl)-5-(4,5-dimethylfuran-2-yl)-4H-1,2,4-triazol-3-yl)-1-(5-fluoropyrimidin-2-yl)propane-2-sulfonamide, Example 89.3. To a mixture of Example 89.1 (0.300 g, 0.72 mmol) and Example 89.2 (0.335 g, 2.17 mmol) in DMF (3.5 mL) was added mercuric acetate (0.074 mL, 0.760 mmol) in portions. The mixture was stirred at RT for 1 h. TFA (0.335 mL, 4.34 mmol) and AcOH (0.418 mL, 7.24 mmol) were then added. The resulting mixture was then stirred at 100° C. for two days. Additional AcOH (0.418 mL, 7.24 mmol) was added, and the resulting mixture was stirred at 100° C. for an additional 24 h. The mixture was cooled to RT and was then directly purified by Isco CombiFlash on a Redi 24 g silica gel column using 0-100% EtOAc gradient in hexanes as eluent to give the product which was further purified by reverse phase HPLC to give Example 89.3 (121 mg). LCMS-ESI (pos.) m/z: 517.1 (M+H)+.

89.0

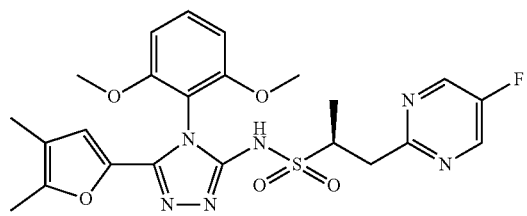

or

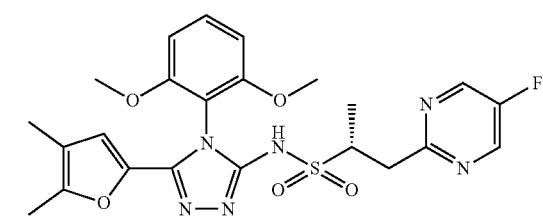

(R)—N-(4-(2,6-Dimethoxyphenyl)-5-(4,5-dimethyl-furan-2-yl)-4H-1,2,4-triazol-3-yl)-1-(5-fluoropyrimidin-2-yl)propane-2-sulfonamide or (S)—N-(4-(2,6-dimethoxyphenyl)-5-(4,5-dimethylfuran-2-yl)-4H-1,2,4-triazol-3-yl)-1-(5-fluoropyrimidin-2-yl)propane-2-sulfonamide, Example 89.0. Example 89.3 was separated by SFC (2×15 cm IA column with 80 mL/min 15% MeOH/CO₂. Outlet pressure=100 bar; wavelength=220 nm; injection volumn=1 mL, 6 mg/mL MeOH). Two enantiomers were obtained. The title compound was the first isomer to elute under these conditions. ¹H NMR (400 MHz, CDCl₃) δ 8.52 (s, 2H), 7.46 (t, J=8.5 Hz, 1H), 6.68 (dd, J=8.6, 2.2 Hz, 2H), 5.68 (s, 1H), 3.78-3.82 (m, 1H), 3.77 (s, 3H), 3.75 (s, 3H), 3.65-3.70 (m, 1H), 3.07 (dd, J=14.7, 9.8 Hz, 1H), 2.22 (s, 3H), 1.82 (s, 3H), 1.29 (d, J=6.8 Hz, 3H). LCMS-ESI (pos.): 517.1 (M+H)+.

Example 91.0. Preparation of (R)—N-(4-(2,6-dimethoxyphenyl)-5-(4,5-dimethylfuran-2-yl)-4H-1,2,4-triazol-3-yl)-1-(5-fluoropyrimidin-2-yl)propane-2-sulfonamide or (S)—N-(4-(2,6-dimethoxyphenyl)-5-(4,5-dimethylfuran-2-yl)-4H-1,2,4-triazol-3-yl)-1-(5-fluoropyrimidin-2-yl)propane-2-sulfonamide 91.0

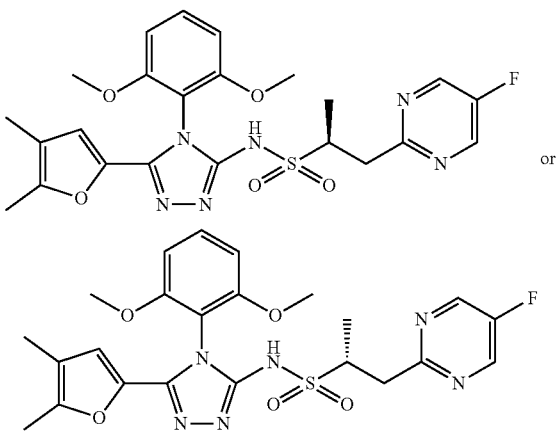

(R)—N-(4-(2,6-Dimethoxyphenyl)-5-(4,5-dimethyl-furan-2-yl)-4H-1,2,4-triazol-3-yl)-1-(5-fluoropyrimidin-2-yl)propane-2-sulfonamide or (S)—N-(4-(2,6-dimethoxyphenyl)-5-(4,5-dimethylfuran-2-yl)-4H-1,2,4-triazol-3-yl)-1-(5-fluoropyrimidin-2-yl)propane-2-sulfonamide, Example 91.0. Example 91.0 is the enantiomer of Example 89.0. The title compound was the second isomer to elute on subjecting Example 89.3 to the SFC conditions described in Example 89.0. ¹H NMR (400 MHz, CDCl₃) δ 8.52 (s, 2H), 7.46 (t, J=8.5 Hz, 1H), 6.68 (dd, J=8.6, 2.2 Hz, 2H), 5.68 (s, 1H), 3.78-3.84 (m, 1H), 3.77 (s, 3H), 3.75 (s, 3H), 3.65-3.70 (m, 1H), 3.07 (dd, J=14.7, 9.8 Hz, 1H), 2.22 (s, 3H), 1.83 (s, 3H), 1.29 (d, J=6.7 Hz, 3H). LCMS-ESI (pos.): 517.1 (M+H)+.

Example 51.0. Preparation of (2S)—N-(4-(2,6-dimethoxyphenyl)-5-(2-furanyl)-4H-1,2,4-triazol-3-yl)-1-(5-fluoro-2-pyrimidinyl)-2-propanesulfonamide or (2R)—N-(4-(2,6-dimethoxyphenyl)-5-(2-furanyl)-4H-1,2,4-triazol-3-yl)-1-(5-fluoro-2-pyrimidinyl)-2-propanesulfonamide 51.1

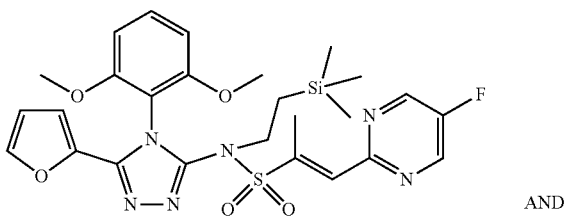

AND

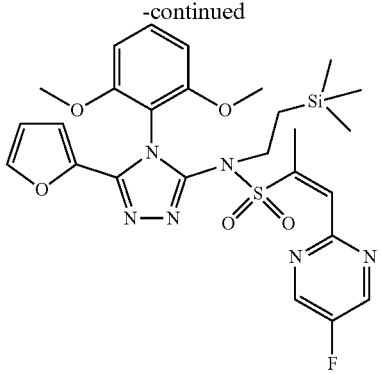

(E)-N-(4-(2,6-Dimethoxyphenyl)-5-(furan-2-yl)-4H-1,2,4-triazol-3-yl)-1-(5-fluoropyrimidin-2-yl)-N-(2-(trimethylsilyl)ethyl)prop-1-ene-2-sulfonamide and (Z)—N-(4-(2,6-dimethoxyphenyl)-5-(furan-2-yl)-4H-1,2,4-triazol-3-yl)-1-(5-fluoropyrimidin-2-yl)-N-(2-(trimethylsilyl)ethyl)prop-1-ene-2-sulfonamide, Example 51.0. The title compound was prepared employing Example 366.0 and 5-fluoropyrimidine-2-carbaldehyde (commercially available from J & W PharmLab, Levittown, Pa., USA) following the procedure described in Example 4.0. LCMS-ESI (pos.) m/z: 587.2 (M+H)⁺.

51.2

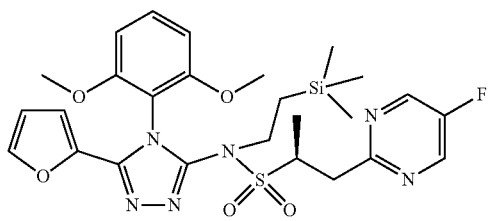

and

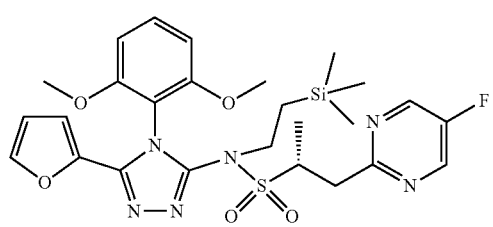

(S)—N-(4-(2,6-Dimethoxyphenyl)-5-(furan-2-yl)-4H-1,2,4-triazol-3-yl)-1-(5-fluoropyrimidin-2-yl)-N-(2-(trimethylsilyl)ethyl)propane-2-sulfonamide and (R)—N-(4-(2,6-dimethoxyphenyl)-5-(furan-2-yl)-4H-1,2,4-triazol-3-yl)-1-(5-fluoropyrimidin-2-yl)-N-(2-(trimethylsilyl)ethyl)propane-2-sulfonamide, Example 51.2. The title compound was prepared employing Example 51.2 following the procedure described in Example 4.0. LCMS-ESI (pos.) m/z: 589.2 (M+H)⁺.

51.3

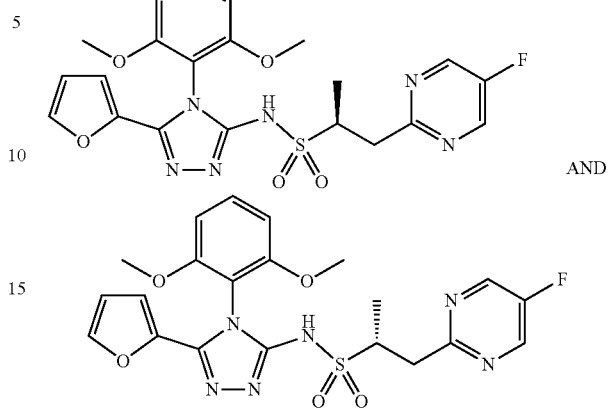

AND (2S)—N-(4-(2,6-Dimethoxyphenyl)-5-(2-furanyl)-4H-1,2,4-triazol-3-yl)-1-(5-fluoro-2-pyrimidinyl)-2-propanesulfonamide and (2R)—N-(4-(2,6-dimethoxyphenyl)-5-(2-furanyl)-4H-1,2,4-triazol-3-yl)-1-(5-fluoro-2-pyrimidinyl)-2-propanesulfonamide, Example 51.3. The title compound was prepared employing Example 51.2 following the procedure described in Example 4.0. ¹H NMR (500 MHz, CDCl₃) δ 8.56 (s, 2H) 7.43-7.51 (m, 2H) 6.68 (dd, J=8.56, 2.45 Hz, 2H) 6.34 (dd, J=3.42, 1.71 Hz, 1H) 6.01 (d, J=3.42 Hz, 1H) 3.79-3.85 (m, 1H) 3.76 (d, J=9.05 Hz, 6H) 3.68 (dd, J=14.92, 4.65 Hz, 1H) 3.09 (dd, J=14.67, 9.54 Hz, 1H) 1.32 (d, J=6.85 Hz, 3H). LCMS-ESI (pos.) m/z: 489.2 (M+H)⁺.

51.0

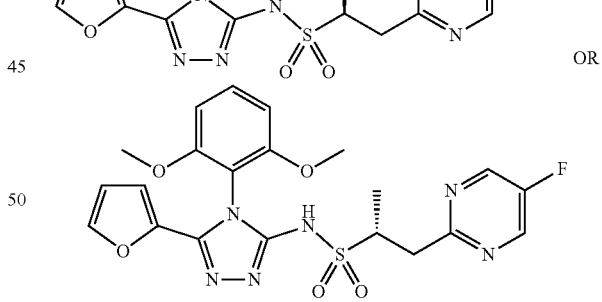

OR (2S)—N-(4-(2,6-Dimethoxyphenyl)-5-(2-furanyl)-4H-1,2,4-triazol-3-yl)-1-(5-fluoro-2-pyrimidinyl)-2-propanesulfonamide or (2R)—N-(4-(2,6-dimethoxyphenyl)-5-(2-furanyl)-4H-1,2,4-triazol-3-yl)-1-(5-fluoro-2-pyrimidinyl)-2-propanesulfonamide, Example 51.0. Purification of Example 51.3 by SFC [4.6×250 mm AD-H column with 22% MeOH (neat) in CO₂ at 100 bar] afforded two enantiomers. The title compound was the first isomer to elute under these conditions. ¹H NMR (500 MHz, CDCl₃) δ 11.07 (br. s., 1H) 8.53 (s, 2H) 7.40-7.51 (m, 2H) 6.68 (dd, J=8.56, 2.93 Hz, 2H) 6.33 (dd, J=3.42, 1.71 Hz, 1H) 6.00 (d, J=3.42 Hz, 1H) 3.78-3.84 (m, 1H) 3.76 (d, J=9.78 Hz, 6H)

3.69 (dd, J=14.79, 4.28 Hz, 1H) 3.08 (dd, J=14.67, 9.78 Hz, 1H) 1.31 (d, J=6.60 Hz, 3H). LCMS-ESI (pos.) m/z: 489.2 (M+H)+.

Example 92.0. Preparation of (2S)—N-(4-(2,6-dimethoxyphenyl)-5-(5-ethyl-2-furanyl)-4H-1,2,4-triazol-3-yl)-1-(5-fluoro-2-pyrimidinyl)-2-propanesulfonamide and (2R)—N-(4-(2,6-dimethoxyphenyl)-5-(5-ethyl-2-furanyl)-4H-1,2,4-triazol-3-yl)-1-(5-fluoro-2-pyrimidinyl)-2-propanesulfonamide

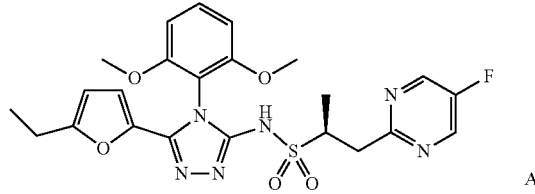

92.0

AND

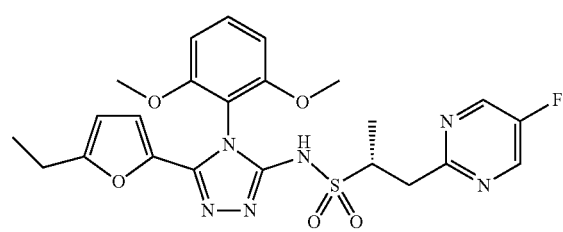

(2S)—N-(4-(2,6-Dimethoxyphenyl)-5-(5-ethyl-2-furanyl)-4H-1,2,4-triazol-3-yl)-1-(5-fluoro-2-pyrimidinyl)-2-propanesulfonamide and (2R)—N-(4-(2,6-dimethoxyphenyl)-5-(5-ethyl-2-furanyl)-4H-1,2,4-triazol-3-yl)-1-(5-fluoro-2-pyrimidinyl)-2-propanesulfonamide, Example 92.0. A suspension of Example 364.2 (60 mg, 0.16 mmol), Example 353.0 (70 mg, 0.32 mmol), rac-trans-N,N'-dimethylcyclohexane-1,2-diamine (49 μL, 0.32 mmol), cesium carbonate (129 mg, 0.40 mmol) and 4 Å dried and crushed molecular sieves (60 mg) in dioxane (0.3 mL) was sparged with argon for 3 min. Copper(I) iodide (15 mg, 0.079 mmol) was added and the mixture was briefly degassed. The reaction vessel was then heated in a microwave at 90° C. until LCMS analysis indicated that the reaction was complete (12 h). Thereafter, the mixture was cooled to RT, diluted with water, filtered, and extracted with EtOAc (3x). The combined organic layers were dried over MgSO4, filtered, and concentrated in vacuo. The residue was purified on a silica gel column employing a gradient of 0-5% IPA in DCM to afford Example 92.0 (13 mg, 16%). 1H NMR (400 MHz, CDCl3) δ 11.00 (br. s., 1H) 8.56 (br. s., 2H) 7.45 (t, J=8.5 Hz, 1H) 6.67 (dd, J=8.5, 2.1 Hz, 2H) 5.81-5.99 (m, 2H) 3.75 (d, J=7.8 Hz, 7H) 3.68 (d, J=13.1 Hz, 1H) 2.97-3.17 (m, 1H) 2.65 (q, J=7.6 Hz, 2H) 1.30 (d, J=6.7 Hz, 3H) 1.18 (t, J=7.6 Hz, 3H). LCMS-ESI (pos.) m/z: 517.2 (M+H)+.

Example 97.0. Preparation of (2S)—N-(4-(2,6-dimethoxyphenyl)-5-(5-ethyl-2-furanyl)-4H-1,2,4-triazol-3-yl)-1-(5-fluoro-2-pyrimidinyl)-2-propanesulfonamide or (2R)—N-(4-(2,6-dimethoxyphenyl)-5-(5-ethyl-2-furanyl)-4H-1,2,4-triazol-3-yl)-1-(5-fluoro-2-pyrimidinyl)-2-propanesulfonamide

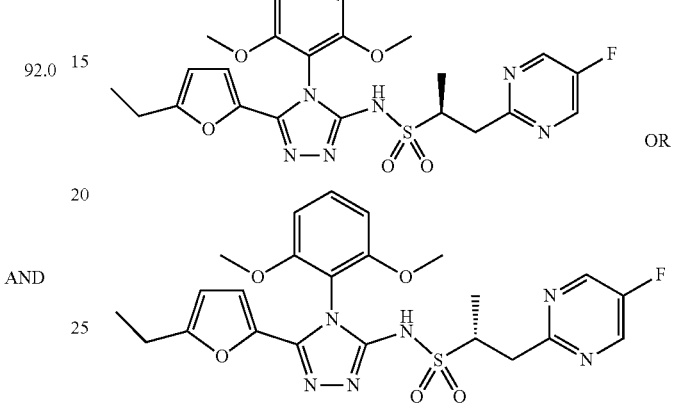

97.0

OR (2S)—N-(4-(2,6-Dimethoxyphenyl)-5-(5-ethyl-2-furanyl)-4H-1,2,4-triazol-3-yl)-1-(5-fluoro-2-pyrimidinyl)-2-propanesulfonamide or (2R)—N-(4-(2,6-dimethoxyphenyl)-5-(5-ethyl-2-furanyl)-4H-1,2,4-triazol-3-yl)-1-(5-fluoro-2-pyrimidinyl)-2-propanesulfonamide, Example 97.0. Purification of Example 92.0 by SFC [20×250 mm IA column with 30 g/min MeOH (20 mM NH3) in 90 g/min CO2 at 100 bar] afforded two enantiomers. The title compound was the first isomer to elute under these conditions. 1H NMR (400 MHz, CDCl3) δ 8.54 (s, 2H), 7.39-7.54 (m, 1H), 6.69 (dd, J=8.5, 1.3 Hz, 2H), 5.86-6.01 (m, 2H), 3.63-3.91 (m, 8H), 3.09 (dd, J=14.7, 9.8 Hz, 1H), 2.66 (q, J=7.4 Hz, 2H), 1.31 (d, J=6.8 Hz, 3H), 1.19 (t, J=7.6 Hz, 3H). LCMS-ESI (pos.) m/z: 517.1 (M+H)+.

Example 99.0. Preparation of (2S)—N-(4-(2,6-dimethoxyphenyl)-5-(5-ethyl-2-furanyl)-4H-1,2,4-triazol-3-yl)-1-(5-fluoro-2-pyrimidinyl)-2-propanesulfonamide or (2R)—N-(4-(2,6-dimethoxyphenyl)-5-(5-ethyl-2-furanyl)-4H-1,2,4-triazol-3-yl)-1-(5-fluoro-2-pyrimidinyl)-2-propanesulfonamide 99.0

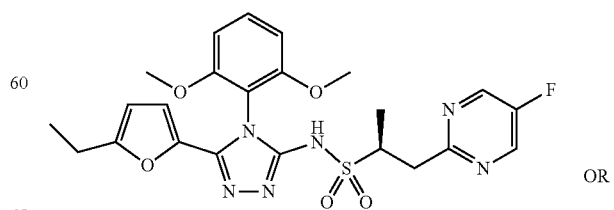

OR

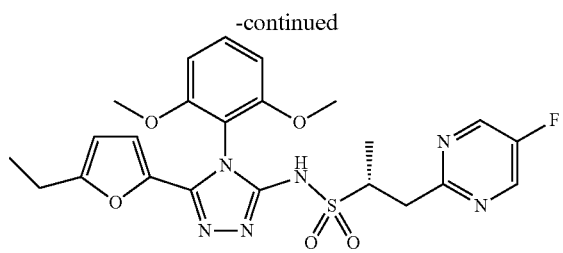

(2S)—N-(4-(2,6-Dimethoxyphenyl)-5-(5-ethyl-2-furanyl)-4H-1,2,4-triazol-3-yl)-1-(5-fluoro-2-pyrimidinyl)-2-propanesulfonamide or (2R)—N-(4-(2,6-dimethoxyphenyl)-5-(5-ethyl-2-furanyl)-4H-1,2,4-triazol-3-yl)-1-(5-fluoro-2-pyrimidinyl)-2-propanesulfonamide, Example 99.0. Example 99.0 is the enantiomer of Example 97.0. The title compound was the second isomer to elute on subjecting racemic Example 92.0 to the SFC conditions described in Example 97.0. $^1$H NMR (400 MHz, CDCl$_3$) δ 11.03 (br. s., 1H), 8.55 (s, 2H), 7.47 (t, J=8.5 Hz, 1H), 6.69 (dd, J=8.5, 2.1 Hz, 2H), 5.91-5.96 (m, 2H), 3.76-3.85 (m, 7H), 3.70 (dd, J=14.4, 4.2 Hz, 1H), 3.10 (dd, J=14.7, 9.8 Hz, 1H), 2.67 (q, J=7.5 Hz, 2H), 1.32 (d, J=6.7 Hz, 3H), 1.20 (t, J=7.5 Hz, 3H). LCMS-ESI (pos.) m/z: 517.1 (M+H)$^+$.

Example 96.0. Preparation of (1R,2S)—N-(4-(2,6-dimethoxyphenyl)-5-(5-methyl-2-furanyl)-4H-1,2,4-triazol-3-yl)-1-(5-fluoro-2-pyrimidinyl)-1-hydroxy-2-propanesulfonamide and (1S,2R)—N-(4-(2,6-dimethoxyphenyl)-5-(5-methyl-2-furanyl)-4H-1,2,4-triazol-3-yl)-1-(5-fluoro-2-pyrimidinyl)-1-hydroxy-2-propanesulfonamide

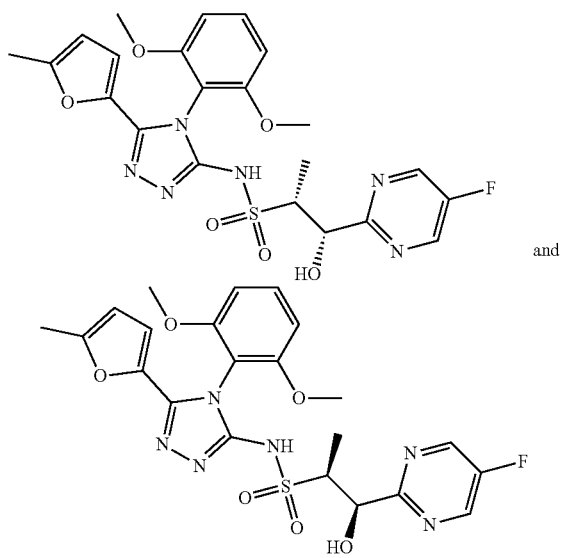

(1R,2S)—N-(4-(2,6-Dimethoxyphenyl)-5-(5-methyl-2-furanyl)-4H-1,2,4-triazol-3-yl)-1-(5-fluoro-2-pyrimidinyl)-1-hydroxy-2-propanesulfonamide and (1S,2R)—N-(4-(2,6-dimethoxyphenyl)-5-(5-methyl-2-furanyl)-4H-1,2,4-triazol-3-yl)-1-(5-fluoro-2-pyrimidinyl)-1-hydroxy-2-propanesulfonamide, Example 93.1. The title compound was prepared employing Example 364.1 and Example 355.1 using the procedure described in Example 94.0. The reaction was diluted with a small volume of water and stirred vigorously. EtOAc was added followed by dropwise addition of concentrated HCl. Any precipitants were removed by filtration through Celite® brand filter aid. The organics were dried on MgSO$_4$, filtered, and evaporated. The filtrate was purified by silica gel using an eluent of 0-5% IPA/DCM. The material was repurified by preparatory RP-HPLC (25 to 65% ACN, water, 0.1% TFA, gradient elution) over 20 min using Eclipse Plus Prep C18 column, 5 μm, 30×150 mm (Agilent Technologies, Inc., Santa Clara, Calif.) at 50 mLs/min and provided Example 96.0 (34 mg, 12%) as a white amorphous solid. $^1$H NMR (500 MHz, CDCl$_3$) δ 8.64 (s, 2H) 7.49 (t, J=8.4 Hz, 1H) 6.71 (dd, J=14.9, 8.6 Hz, 2H) 5.92-5.99 (m, 1H) 5.85 (d, J=3.4 Hz, 1H) 5.63 (s, 1H) 3.71-3.91 (m, 7H) 2.34 (s, 3H) 1.24 (d, J=6.8 Hz, 3H). LCMS-ESI (pos.), m/z: 519.0 (M+H)$^+$.

Example 93.0. Preparation of (1R,2S)—N-(4-(2,6-dimethoxyphenyl)-5-(5-methyl-2-furanyl)-4H-1,2,4-triazol-3-yl)-1-(5-fluoro-2-pyrimidinyl)-1-hydroxy-2-propanesulfonamide or (1S,2R)—N-(4-(2,6-dimethoxyphenyl)-5-(5-methyl-2-furanyl)-4H-1,2,4-triazol-3-yl)-1-(5-fluoro-2-pyrimidinyl)-1-hydroxy-2-propanesulfonamide

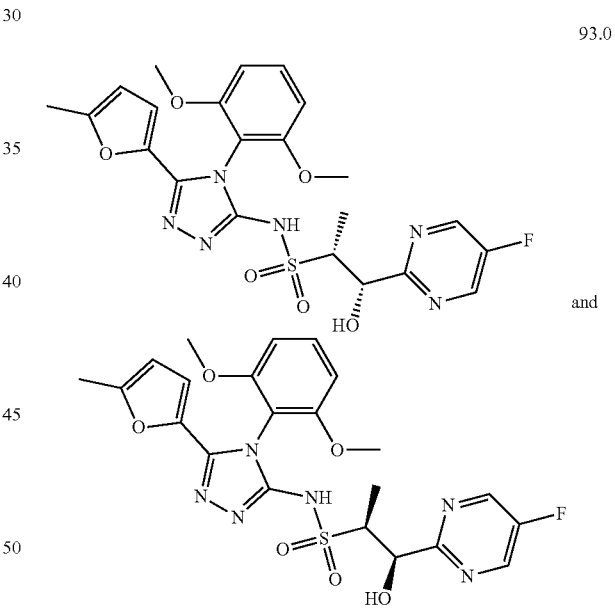

(1R,2S)—N-(4-(2,6-Dimethoxyphenyl)-5-(5-methyl-2-furanyl)-4H-1,2,4-triazol-3-yl)-1-(5-fluoro-2-pyrimidinyl)-1-hydroxy-2-propanesulfonamide or (1S,2R)—N-(4-(2,6-dimethoxyphenyl)-5-(5-methyl-2-furanyl)-4H-1,2,4-triazol-3-yl)-1-(5-fluoro-2-pyrimidinyl)-1-hydroxy-2-propanesulfonamide, Example 93.0. Example 96.0 was separated via chiral purification techniques to deliver the title compound. $^1$H NMR (500 MHz, CDCl$_3$) δ 10.85 (br. s., 1H) 8.53 (s, 2H) 7.39 (t, J=8.4 Hz, 1H) 6.62 (d, J=8.3 Hz, 1H) 6.60 (d, J=8.6 Hz, 1H) 5.80-5.90 (m, 1H) 5.75 (d, J=3.4 Hz, 1H) 5.53 (br. s., 1H) 3.70 (s, 4H) 3.68 (s, 3H) 2.24 (s, 3H) 1.15 (d, J=6.8 Hz, 3H). LCMS-ESI (pos.) m/z: 519.0 (M+H)$^+$.

Example 94.0. Preparation of (2S)—N-(4-(2,6-dimethoxyphenyl)-5-(5-methyl-2-furanyl)-4H-1,2,4-triazol-3-yl)-1-(5-fluoro-2-pyrimidinyl)-2-propanesulfonamide and (2R)—N-(4-(2,6-dimethoxyphenyl)-5-(5-methyl-2-furanyl)-4H-1,2,4-triazol-3-yl)-1-(5-fluoro-2-pyrimidinyl)-2-propanesulfonamide

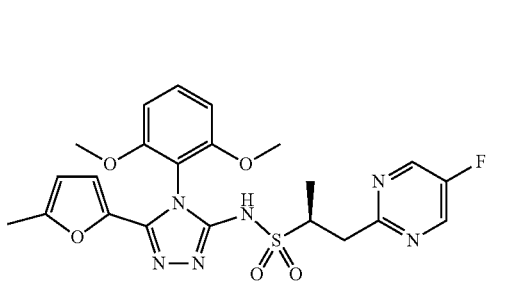

94.0

AND

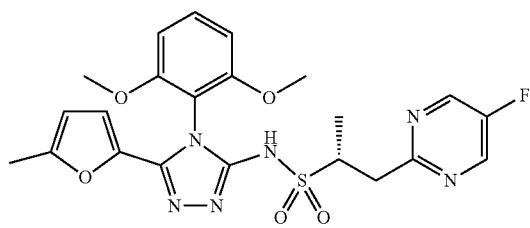

(2S)—N-(4-(2,6-Dimethoxyphenyl)-5-(5-methyl-2-furanyl)-4H-1,2,4-triazol-3-yl)-1-(5-fluoro-2-pyrimidinyl)-2-propanesulfonamide and (2R)—N-(4-(2,6-dimethoxyphenyl)-5-(5-methyl-2-furanyl)-4H-1,2,4-triazol-3-yl)-1-(5-fluoro-2-pyrimidinyl)-2-propanesulfonamide, Example 94.0. A suspension of Example 364.1 (64 mg, 0.18 mmol), Example 353.0 (77 mg, 0.35 mmol), rac-trans-N,N'-dimethylcyclohexane-1,2-diamine (54 μL, 0.35 mmol), cesium carbonate (143 mg, 0.44 mmol) and 5 Å dried and crushed molecular sieves (100 mg) in dioxane (0.4 mL) was sparged with argon for 3 min. Copper(I) iodide (17 mg, 0.089 mmol) was then added and the mixture was briefly degassed. The reaction vessel was then heated in a microwave at 90° C. until LCMS analysis indicated that the reaction was complete (12 h). Thereafter, the mixture was cooled to RT, filtered, diluted with 10% aqueous NH$_4$OH, and stirred vigorously for 20 min. The mixture was then acidified with concentrated HCl, filtered, and extracted with EtOAc (3×). The organic layers were then combined, dried over MgSO$_4$, filtered, and concentrated in vacuo. The residue was purified on a reverse-phase column employing a gradient of 20-70% ACN in water (0.1% TFA in both eluents) to afford Example 94.0 (62 mg, 70%). $^1$H NMR (400 MHz, CDCl$_3$) δ 8.57 (br. s., 2H) 7.46 (t, J=8.4 Hz, 1H) 6.68 (d, J=8.4 Hz, 2H) 5.87-5.98 (m, 1H) 5.82 (d, J=3.3 Hz, 1H) 3.71-3.88 (m, 7H) 3.67 (d, J=14.1 Hz, 1H) 2.96-3.19 (m, 1H) 2.32 (s, 3H) 1.32 (d, J=5.9 Hz, 3H). LCMS-ESI (pos.) m/z: 503.0 (M+H)$^+$.

Example 108.0. Preparation of (2S)—N-(4-(2,6-dimethoxyphenyl)-5-(5-methyl-2-furanyl)-4H-1,2,4-triazol-3-yl)-1-(5-fluoro-2-pyrimidinyl)-2-propanesulfonamide or (2R)—N-(4-(2,6-dimethoxyphenyl)-5-(5-methyl-2-furanyl)-4H-1,2,4-triazol-3-yl)-1-(5-fluoro-2-pyrimidinyl)-2-propanesulfonamide

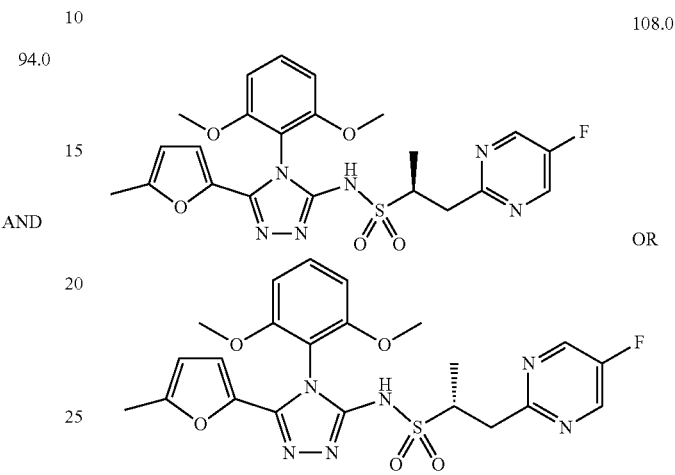

108.0

OR (2S)—N-(4-(2,6-Dimethoxyphenyl)-5-(5-methyl-2-furanyl)-4H-1,2,4-triazol-3-yl)-1-(5-fluoro-2-pyrimidinyl)-2-propanesulfonamide or (2R)—N-(4-(2,6-dimethoxyphenyl)-5-(5-methyl-2-furanyl)-4H-1,2,4-triazol-3-yl)-1-(5-fluoro-2-pyrimidinyl)-2-propanesulfonamide, Example 108.0. Purification of Example 94.0 was accomplished using SFC [21×250 mm IA column with 24 g/min MeOH (20 mM NH$_3$) in 56 g/min CO$_2$ at 100 bar] and afforded two enantiomers. The title compound (Example 108.0) was the first isomer to elute under these conditions. $^1$H NMR (400 MHz, CDCl$_3$) δ 8.57 (br. s., 2H) 7.48 (t, J=8.5 Hz, 1H) 6.70 (dd, J=8.5, 2.2 Hz, 2H) 5.93 (dd, J=3.4, 0.9 Hz, 1H) 5.83 (d, J=3.3 Hz, 1H) 3.76-3.83 (m, 7H) 3.71 (d, J=14.7 Hz, 1H) 3.10 (dd, J=14.3, 10.0 Hz, 1H) 2.34 (s, 3H) 1.33 (d, J=6.7 Hz, 3H). LCMS-ESI (pos.) m/z: 503.1 (M+H)$^+$.

Example 95.0. Preparation of (1R,2R)—N-(4-(2,6-dimethoxyphenyl)-5-(5-methyl-2-furanyl)-4H-1,2,4-triazol-3-yl)-1-(5-fluoro-2-pyrimidinyl)-1-hydroxy-2-propanesulfonamide or (1S,2S)—N-(4-(2,6-dimethoxyphenyl)-5-(5-methyl-2-furanyl)-4H-1,2,4-triazol-3-yl)-1-(5-fluoro-2-pyrimidinyl)-1-hydroxy-2-propanesulfonamide

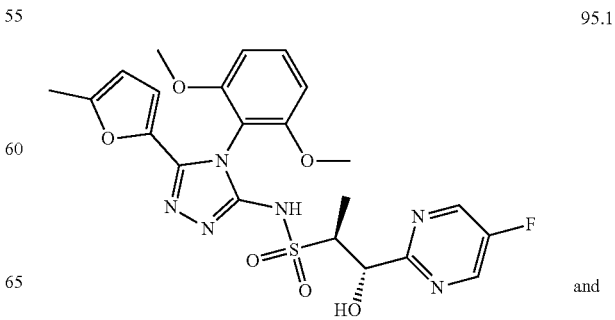

95.1 and

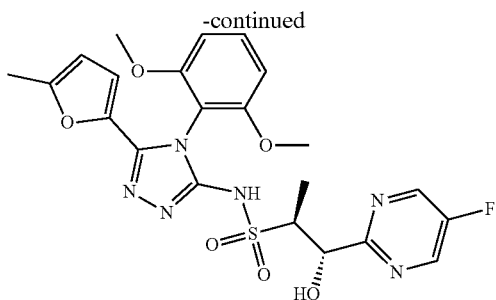

(1R,2R)—N-(4-(2,6-Dimethoxyphenyl)-5-(5-methyl-2-furanyl)-4H-1,2,4-triazol-3-yl)-1-(5-fluoro-2-pyrimidinyl)-1-hydroxy-2-propanesulfonamide and (1S,2S)—N-(4-(2,6-dimethoxyphenyl)-5-(5-methyl-2-furanyl)-4H-1,2,4-triazol-3-yl)-1-(5-fluoro-2-pyrimidinyl)-1-hydroxy-2-propanesulfonamide, Example 95.1. The title compound was prepared employing Example 364.1 and Example 355.0 using the procedure described in Example 94.0 (using 1.5 eq of Example 364.1 and 1 eq Example 355.0, and the reaction was heated to 90° C. for 12 h in a microwave reactor). The reaction was then diluted with a small volume of water and stirred vigorously. EtOAc was added followed by dropwise addition of concentrated HCl. Any precipitants were removed by filtration through a a pad of Celite® brand filter aid. The organics were dried on MgSO₄, filtered, and evaporated. Purification by flash chromatography on 40 g Redisep Gold pre-packed spherical silica gel column (Teledyne Isco Inc., Lincoln, Nebr.) (eluent: 3-5% IPA/DCM, gradient elution) provided the title compound (26 mg, 28%) as a light-yellow powder. ¹H NMR (500 MHz, CDCl₃) δ 10.84 (br. s., 1H) 8.60 (s, 2H) 7.50 (t, J=8.6 Hz, 1H) 6.71 (dd, J=8.6, 3.4 Hz, 2H) 5.94 (dd, J=3.4, 1.0 Hz, 1H) 5.86 (d, J=3.4 Hz, 1H) 5.07 (d, J=6.4 Hz, 1H) 3.81 (d, J=1.5 Hz, 6H) 2.34 (s, 3H) 1.29 (d, J=7.1 Hz, 3H). LCMS-ESI (pos.), m/z: 519.2 (M+H)⁺.

95.0

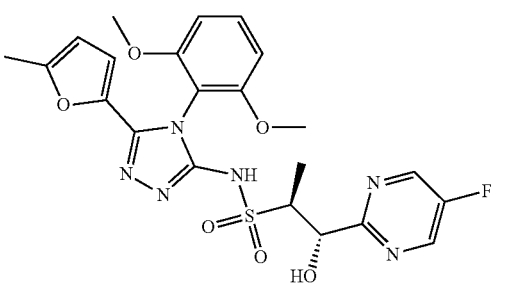

or

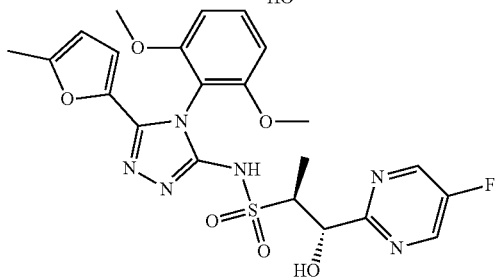

(1R,2R)—N-(4-(2,6-Dimethoxyphenyl)-5-(5-methyl-2-furanyl)-4H-1,2,4-triazol-3-yl)-1-(5-fluoro-2-pyrimidinyl)-1-hydroxy-2-propanesulfonamide or (1S,2S)—N-(4-(2,6-di-methoxyphenyl)-5-(5-methyl-2-furanyl)-4H-1,2,4-triazol-3-yl)-1-(5-fluoro-2-pyrimidinyl)-1-hydroxy-2-propanesulfonamide, Example 95.1. Example 95.0 was separated via chiral purification techniques to deliver the title compound as peak 2. ¹H NMR (500 MHz, CDCl₃) δ 10.84 (br. s., 1H) 8.58 (s, 2H) 7.48 (t, J=8.4 Hz, 1H) 6.69 (dd, J=8.4, 3.5 Hz, 2H) 5.90-5.94 (m, 1H) 5.84 (d, J=3.4 Hz, 1H) 5.05 (d, J=6.4 Hz, 1H) 3.74-3.81 (m, 7H) 3.72 (s, 1H) 2.32 (s, 3H) 1.27 (d, J=7.1 Hz, 3H). LCMS-ESI (pos.) m/z: 519.0 (M+H)⁺.

Example 98.0. Preparation of N-(4-(2,6-dimethoxyphenyl)-5-(5-ethyl-2-furanyl)-4H-1,2,4-triazol-3-yl)-2-(5-fluoro-2-pyrimidinyl)ethanesulfonamide 98.0

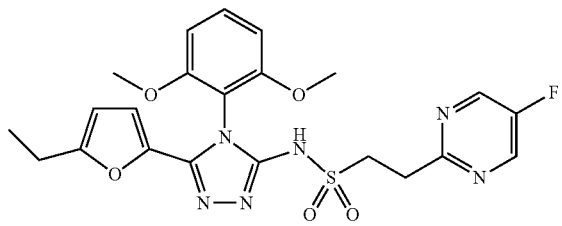

N-(4-(2,6-dimethoxyphenyl)-5-(5-ethyl-2-furanyl)-4H-1,2,4-triazol-3-yl)-2-(5-fluoro-2-pyrimidinyl)ethanesulfonamide, Example 98.0. A suspension of Example 364.2 (35 mg, 0.093 mmol), Example 351.0 (76 mg, 0.37 mmol), rac-trans-N,N'-dimethylcyclohexane-1,2-diamine (26 μL, 0.19 mmol), cesium carbonate (151 mg, 0.46 mmol), and 5 Å dried and crushed molecular sieves (75 mg) in dioxane (0.9 mL) was sparged with argon for 3 min. Copper(I) iodide (18 mg, 0.093 mmol) was then added, the mixture was briefly degassed, and the reaction vessel was heated in a microwave at 100° C. until LCMS analysis indicated that the reaction was complete (4 h). Thereafter, the mixture was cooled to RT, filtered, and concentrated in vacuo. The residue was purified on a reverse-phase column, employing a gradient of 25-75% ACN in water (0.1% TFA in both eluents) to afford Example 98.0 (10 mg, 22%). ¹H NMR (400 MHz, CDCl₃) δ 8.54 (s, 2H), 7.46 (t, J=8.5 Hz, 1H), 6.67 (d, J=8.4 Hz, 2H), 5.90-5.95 (m, 2H), 3.75 (s, 3H), 3.75 (s, 3H), 3.53-3.66 (m, 2H), 3.38-3.53 (m, 2H), 2.64 (q, J=7.6 Hz, 2H), 1.18 (t, J=7.6 Hz, 3H). LCMS-ESI (pos.) m/z: 503.1 (M+H)⁺.

Example 100.0. Preparation of (1R,2S)—N-(4-(2,6-dimethoxyphenyl)-5-(5-methyl-2-furanyl)-4H-1,2,4-triazol-3-yl)-2-(5-fluoro-2-pyrimidinyl)cyclopentanesulfonamide and (1S,2R)—N-(4-(2,6-dimethoxyphenyl)-5-(5-methyl-2-furanyl)-4H-1,2,4-triazol-3-yl)-2-(5-fluoro-2-pyrimidinyl)cyclopentanesulfonamide 100.1

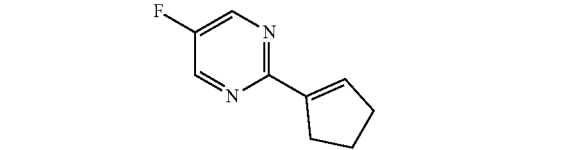

2-(Cyclopent-1-en-1-yl)-5-fluoropyrimidine, Example 100.1. A slurry of cyclopentene-1-boronic acid (Combi-Blocks, 2.05 g, 18.3 mmol), sodium carbonate (3.88 g, 36.6 mmol), and 2-chloro-5-fluoro-pyrimidine (2.26 mL, 18.3 mmol) in a mixture of THF (24 mL) and water (12 mL) was deoxygenated with an Ar stream. Tetrakis(triphenylphosphine)palladium (2.12 g, 1.8 mmol) was added and the slurry was again deoxygenated with an Ar stream. The reaction was heated under Ar at 100° C. for 3 d. The reaction mixture was extracted with DCM (3×). The combined organic layers were dried over anhydrous magnesium sulfate and concentrated. The residue was purified by silica gel chromatography (eluent: DCM) to provide 100.1 (2.6 g, 86% yield) as a colorless oil. LCMS-ESI (pos.) m/z: 165.2 (M+H)$^+$.

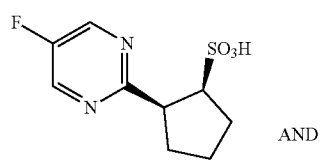

AND

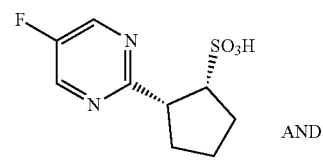

AND

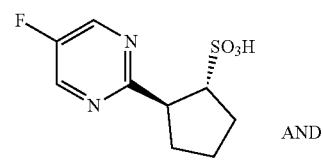

AND

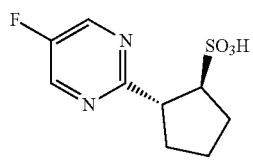

(1S,2S)-2-(5-Fluoropyrimidin-2-yl)cyclopentane-1-sulfonic acid and (1R,2R)-2-(5-fluoropyrimidin-2-yl)cyclopentane-1-sulfonic acid and (1R,2S)-2-(5-fluoropyrimidin-2-yl) cyclopentane-1-sulfonic acid and (1S,2R)-2-(5-fluoropyrimidin-2-yl)cyclopentane-1-sulfonic acid, Example 100.2. To a microwave vial containing a suspension of 100.1 (2.6 g, 15.8 mmol) in 4 M aqueous sodium bisulfite solution (3.76 mL, 15.0 mmol) was added EtOH (4 mL). The vial was sealed and the resulting slurry was heated at 90° C. in the microwave for 12 h. The reaction was filtered and the filtrate was directly purified by reverse phase preparatory HPLC (Sunfire 5 µM C18 column, eluent: 0-40% ACN in water over a 15 min period where both solvents contain 0.1% TFA) to provide 100.2 (3.09 g, 79% yield). LCMS-ESI (pos.) m/z: 247.2 (M+H)$^+$.

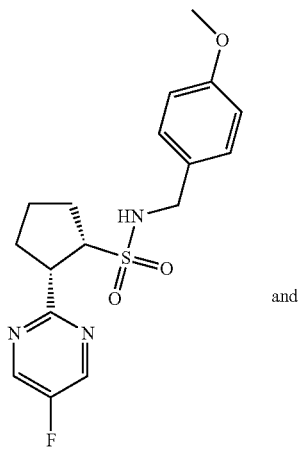

and

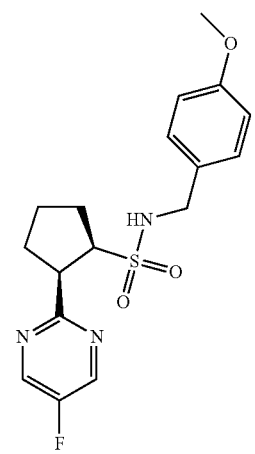

(1R,2R)-2-(5-Fluoropyrimidin-2-yl)-N-(4-methoxybenzyl)cyclopentane-1-sulfonamide and (1S,2S)-2-(5-fluoropyrimidin-2-yl)-N-(4-methoxybenzyl)cyclopentane-1-sulfonamide, Example 100.3. To a suspension of 100.2 (1.24 g, 5.0 mmol) in DCM (50 mL) was added oxalyl chloride (1.34 mL, 15.1 mmol) via syringe followed by a catalytic amount of DMF via syringe. Vigorous bubbling was observed. The resulting white slurry was stirred at RT for 2 h and then was concentrated. The residue was azeotroped to dryness with cyclopentylmethyl ether and then was suspended in DCM (50 mL). 2,4-Dimethoxybenzylamine (2.53 mL, 15.1 mmol) and TEA (3.51 mL, 25.2 mmol) were added sequentially via syringe. The resulting slurry was then stirred at RT overnight. The reaction mixture was partitioned between water and DCM (3×). The combined organic layers were dried over anhydrous magnesium sulfate and concentrated. The residue was purified by silica gel chromatography (eluent: 10-40% EtOAc in hexanes over a 30 min period) to provide Example 100.3 (21%) as a clear colorless oil. LCMS-ESI (pos.), m/z: 366.0 (M+H)$^+$.

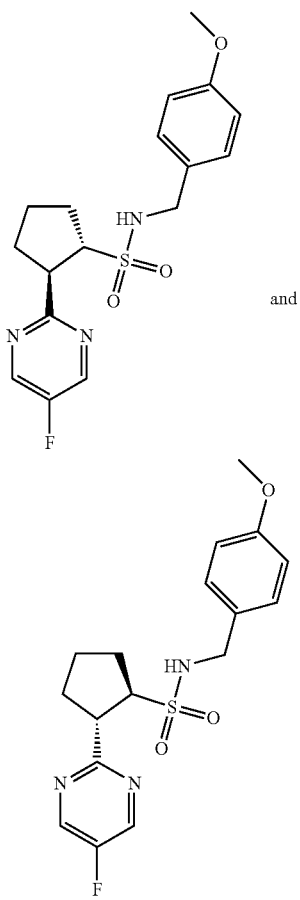

and

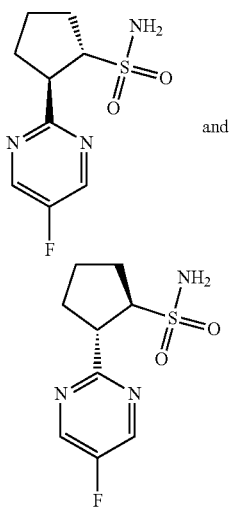

(1R,2S)-2-(5-Fluoropyrimidin-2-yl)-N-(4-methoxybenzyl)cyclopentane-1-sulfonamide and (1S,2R)-2-(5-fluoropyrimidin-2-yl)-N-(4-methoxybenzyl)cyclopentane-1-sulfonamide, Example 100.4. Further elution under the conditions described in Example 100.3 delivered the title compound (1.07 g, 54%) as a colorless oil.

(1R,2S)-2-(5-Fluoropyrimidin-2-yl)cyclopentane-1-sulfonamide and (1S,2R)-2-(5-fluoropyrimidin-2-yl)cyclopentane-1-sulfonamide, Example 100.5. An ice-cooled solution of Example 100.4 (1.09 g, 2.7 mmol) in DCM (14 mL) was treated sequentially with anisole (899 μL, 8.3 mmol) via syringe and TFA (2.05 mL, 27.6 mmol) via syringe. The resulting solution was stirred at 0° C. for 30 min and then was warmed to RT and stirred for an additional 3 h. The reaction was directly concentrated and the residue was purified by silica gel chromatography (eluent: 30-100% EtOAc in hexanes over a 30 min period) to provide Example 100.5 (540 mg, 80% yield) as a white solid. LCMS-ESI (pos.) m/z: 246.1 (M+H)⁺.

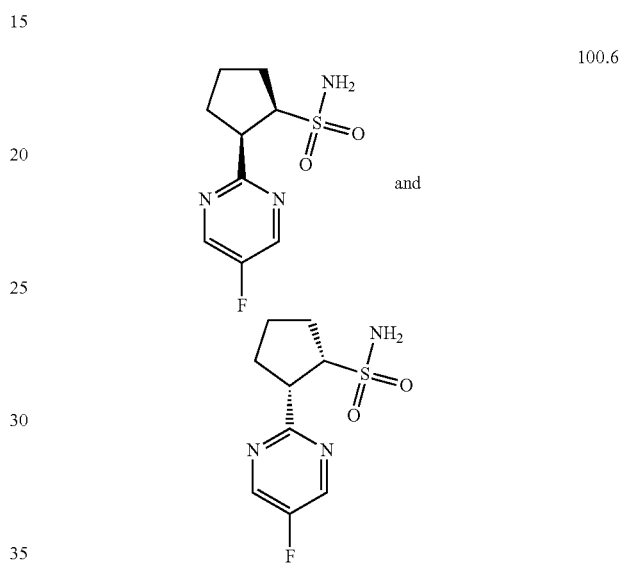

(1S,2S)-2-(5-Fluoropyrimidin-2-yl)cyclopentane-1-sulfonamide and (1R,2R)-2-(5-fluoropyrimidin-2-yl)cyclopentane-1-sulfonamide, Example 100.6. An ice-cooled solution of Example 100.3 (408 mg, 1.0 mmol) in DCM (5 mL) was treated sequentially with anisole (336 μL, 3.1 mmol) via syringe and TFA (767 μL, 10.3 mmol) via syringe. The resulting solution was stirred at 0° C. for 30 min and then was warmed to RT and stirred for an additional 3 h. The reaction was directly concentrated and the residue was purified by silica gel chromatography (eluent: 30-100% EtOAc in hexanes over a 30 min period) to provide Example 100.6 (60 mg, 24% yield) as a white solid. LCMS-ESI (pos.) m/z: 246.2 (M+H)⁺.

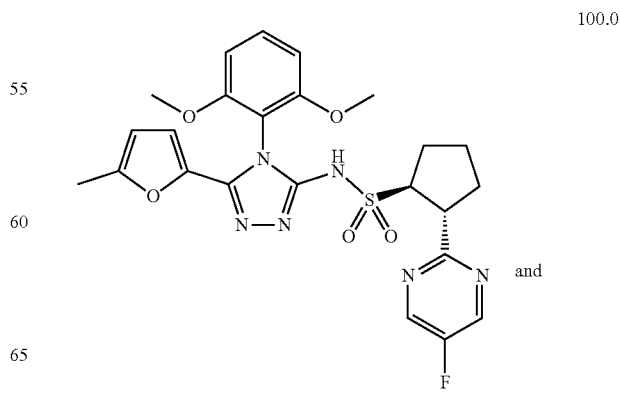

and

243
-continued

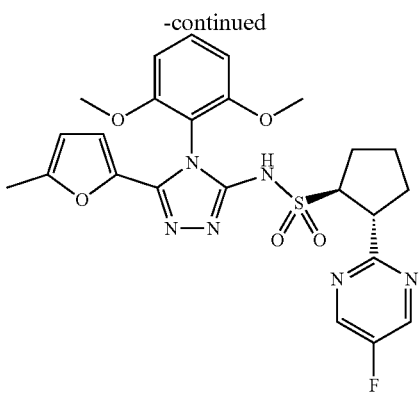

(1R,2S)—N-(4-(2,6-Dimethoxyphenyl)-5-(5-methyl-2-furanyl)-4H-1,2,4-triazol-3-yl)-2-(5-fluoro-2-pyrimidinyl)cyclopentanesulfonamide and (1S,2R)—N-(4-(2,6-dimethoxyphenyl)-5-(5-methyl-2-furanyl)-4H-1,2,4-triazol-3-yl)-2-(5-fluoro-2-pyrimidinyl)cyclopentanesulfonamide, Example 100.0. The title compound was prepared employing Example 364.1 and Example 100.5 as the sulfonamide coupling partner using the Cut coupling procedure described in Example 94.0 (the reaction was heated to 90° C. for 16 h). The reaction was then diluted with a small volume of water and stirred vigorously. EtOAc was added followed by dropwise addition of concentrated HCl. Any precipitants were removed by filtration through a pad of Celite® brand filter aid. The organics were dried over MgSO₄, filtered, evaporated, and then triturated in MeOH. Purification by preparatory reverse phase HPLC (20 to 55% ACN, water, 0.1% TFA, gradient elution) over 20 min using Sunfire™ Prep C18 OBD column, 10 μm, 30×150 mm (Waters, Milford, Mass.) at 50 mLs/min provided Example 100.0 (90 mg, 42%). ¹H NMR (500 MHz, CDCl₃) δ 8.52 (s, 2H) 7.46 (t, J=8.3 Hz, 1H) 6.66 (d, J=7.9 Hz, 2H) 5.90 (dd, J=3.3, 0.9 Hz, 1H) 5.77 (d, J=3.4 Hz, 1H) 4.20 (q, J=7.8 Hz, 1H) 3.86 (q, J=8.0 Hz, 1H) 3.75 (s, 3H) 3.75 (s, 3H) 2.32 (s, 3H) 2.14-2.30 (m, 3H) 1.75-1.88 (m, 3H). LCMS-ESI (pos.), m/z: 529.1 (M+H)⁺.

Example 101.0. Preparation of (1R,2S)—N-(4-(2,6-dimethoxyphenyl)-5-(5-methyl-2-furanyl)-4H-1,2,4-triazol-3-yl)-2-(5-fluoro-2-pyrimidinyl)cyclopentanesulfonamide or (1S,2R)—N-(4-(2,6-dimethoxyphenyl)-5-(5-methyl-2-furanyl)-4H-1,2,4-triazol-3-yl)-2-(5-fluoro-2-pyrimidinyl)cyclopentanesulfonamide 244
-continued

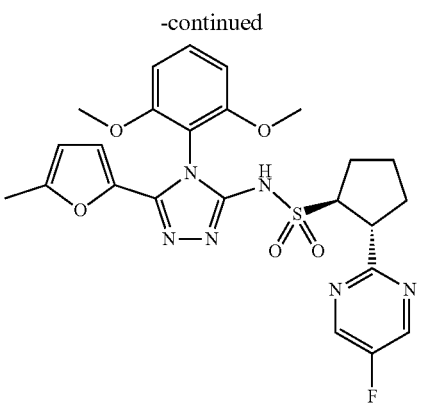

(1R,2S)—N-(4-(2,6-Dimethoxyphenyl)-5-(5-methyl-2-furanyl)-4H-1,2,4-triazol-3-yl)-2-(5-fluoro-2-pyrimidinyl)cyclopentanesulfonamide or (1S,2R)—N-(4-(2,6-dimethoxyphenyl)-5-(5-methyl-2-furanyl)-4H-1,2,4-triazol-3-yl)-2-(5-fluoro-2-pyrimidinyl)cyclopentanesulfonamide, Example 101.0. Chiral purification of Example 100.0 was performed using the following preparative SFC method: Column: 250×30 mm Phenomenex Lux-2 Cell, 60 mL/min MeOH+60 g/min CO₂, 100 bar, 215 nm, Inj volume: 4.0 mL of a 5.0 mg/mL solution of sample in MeOH provided the initial peak as the title compound. ¹H NMR (500 MHz, CDCl₃) δ 10.98 (br. s., 1H) 8.51 (s, 2H) 7.45 (t, J=8.6 Hz, 1H) 6.66 (d, J=8.6 Hz, 2H) 5.90 (dd, J=3.4, 1.0 Hz, 1H) 5.76 (d, J=3.4 Hz, 1H) 4.19 (q, J=7.8 Hz, 1H) 3.86 (q, J=8.1 Hz, 1H) 3.76 (s, 3H) 3.75 (s, 3H) 2.32 (s, 3H) 2.14-2.29 (m, 3H) 1.73-1.89 (m, 3H). LCMS-ESI (pos.) m/z: 529.1 (M+H)⁺.

Example 102.0. Preparation of (1R,2S)—N-(4-(2,6-dimethoxyphenyl)-5-(5-methyl-2-furanyl)-4H-1,2,4-triazol-3-yl)-2-(5-fluoro-2-pyrimidinyl)cyclopentanesulfonamide or (1S,2R)—N-(4-(2,6-dimethoxyphenyl)-5-(5-methyl-2-furanyl)-4H-1,2,4-triazol-3-yl)-2-(5-fluoro-2-pyrimidinyl)cyclopentanesulfonamide 101.0

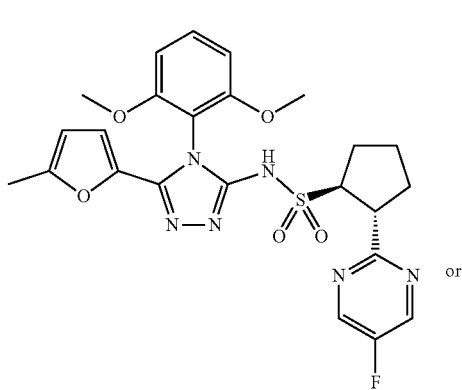

or 102.0

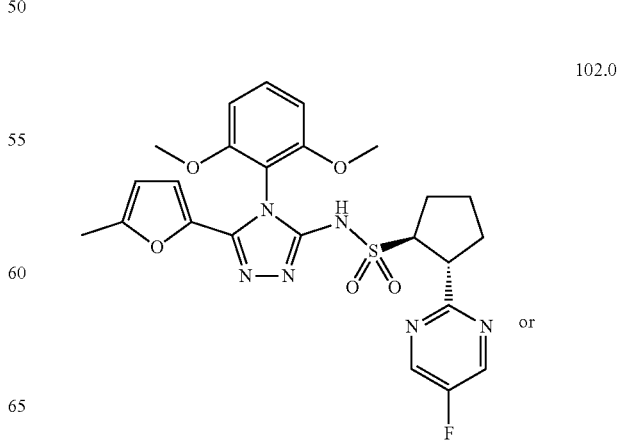

or

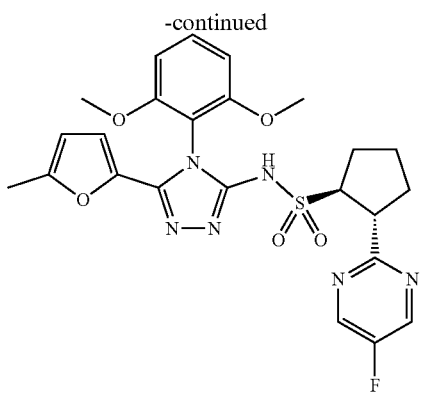

(1R,2S)—N-(4-(2,6-Dimethoxyphenyl)-5-(5-methyl-2-furanyl)-4H-1,2,4-triazol-3-yl)-2-(5-fluoro-2-pyrimidinyl)cyclopentanesulfonamide or (1S,2R)—N-(4-(2,6-dimethoxyphenyl)-5-(5-methyl-2-furanyl)-4H-1,2,4-triazol-3-yl)-2-(5-fluoro-2-pyrimidinyl)cyclopentanesulfonamide, Example 102.0. Chiral purification of Example 100.0 was conducted using the following preparative SFC method: Column: 250×30 mm Phenomenex Lux-2 Cell, 60 mL/min MeOH+60 g/min $CO_2$, 100 bar, 215 nm, Inj volume: 4.0 mL of a 5.0 mg/mL solution of sample in MeOH provided the second peak as the title compound. $^1$H NMR (500 MHz, CDCl$_3$) δ 10.97 (s, 1H) 8.51 (s, 2H) 7.45 (t, J=8.6 Hz, 1H) 6.66 (d, J=8.6 Hz, 2H) 5.90 (dd, J=3.4, 1.0 Hz, 1H) 5.76 (d, J=3.4 Hz, 1H) 4.19 (q, J=7.8 Hz, 1H) 3.86 (q, J=8.2 Hz, 1H) 3.76 (s, 3H) 3.75 (s, 3H) 2.32 (s, 3H) 2.12-2.29 (m, 3H) 1.75-1.91 (m, 3H). LCMS-ESI (pos.) m/z: 529.1 (M+H)$^+$.

Example 103.0. Preparation of (1S,2S)—N-(4-(2,6-dimethoxyphenyl)-5-(2-furanyl)-4H-1,2,4-triazol-3-yl)-2-(5-fluoro-2-pyrimidinyl)cyclohexanesulfonamide or (1R,2R)—N-(4-(2,6-dimethoxyphenyl)-5-(2-furanyl)-4H-1,2,4-triazol-3-yl)-2-(5-fluoro-2-pyrimidinyl)cyclohexanesulfonamide

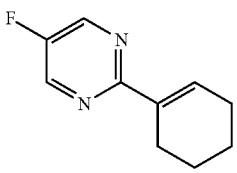

2-(Cyclohex-1-en-1-yl)-5-fluoropyrimidine, Example 103.1. A slurry of cyclohexene-1-boronic acid (CombiPhos Catalysts, 4.00 g, 31.8 mmol), sodium carbonate (6.73 g, 63.5 mmol) and 2-chloro-5-fluoro-pyrimidine (3.92 mL, 31.8 mmol) in a mixture of ACN (53 mL) and water (26.5 mL) was deoxygenated with an Ar stream. Tetrakis(triphenylphosphine)palladium (1.84 g, 1.6 mmol) was added and the slurry was again deoxygenated with an Ar stream. The reaction was heated under Ar at 95° C. for 3 d. The reaction mixture was then extracted with DCM (3×). The combined organic layers were dried over anhydrous magnesium sulfate and concentrated. The residue was purified by silica gel chromatography (eluent: 0-50% DCM in hexanes over a 30 min period) to provide Example 103.1 (2.8 g, 50% yield) as a colorless oil. LCMS-ESI (pos.) m/z: 179.1 (M+H)$^+$.

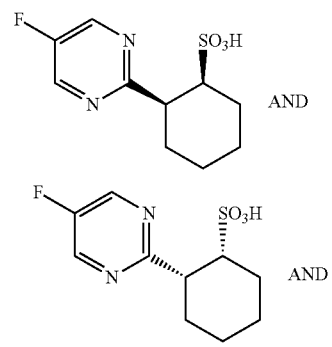

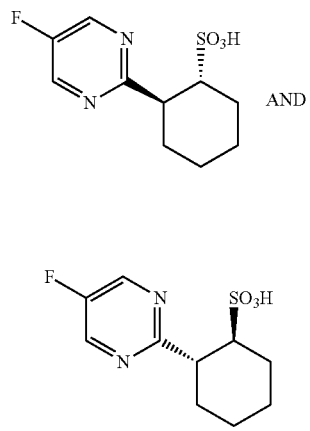

(1R,2S)-2-(5-Fluoropyrimidin-2-yl)cyclohexane-1-sulfonic acid and (1R,2R)-2-(5-fluoropyrimidin-2-yl)cyclohexane-1-sulfonic acid and (1S,2S)-2-(5-fluoropyrimidin-2-yl)cyclohexane-1-sulfonic acid and (1S,2R)-2-(5-fluoropyrimidin-2-yl)cyclohexane-1-sulfonic acid, Example 103.2. To a microwave vial containing a suspension of Example 103.1 (2.8 g, 15.7 mmol) in 4 M aqueous sodium bisulfite solution (9.82 mL, 39.3 mmol) was added EtOH (3.9 mL). The vial was sealed and the resulting slurry was heated at 90° C. in the microwave for 3 h. The reaction was concentrated and then the residue was suspended in EtOH (30 mL). The mixture was heated, filtered, and the filtered solids were rinsed with more EtOH. The filtrate was concentrated to provide Example 103.2 (2.03 g, 50% yield). LCMS-ESI (pos.) m/z: 261.2 (M+H)$^+$.

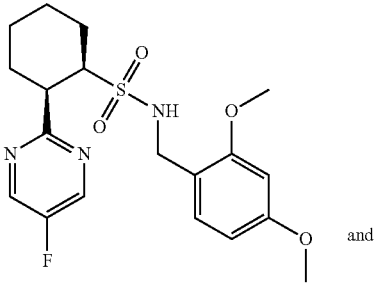

and

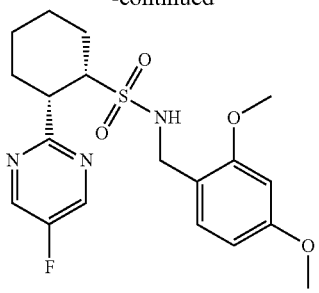

(1R,2R)—N-(2,4-Dimethoxybenzyl)-2-(5-fluoropyrimidin-2-yl)cyclohexane-1-sulfonamide and (1S,2S)—N-(2,4-dimethoxybenzyl)-2-(5-fluoropyrimidin-2-yl)cyclohexane-1-sulfonamide, Example 103.3. To a suspension of Example 03.2 (565 mg, 2.2 mmol) in DCM (11 mL) was added oxalyl chloride (578 μL, 6.5 mmol) via syringe followed by a catalytic amount of DMF via syringe. Vigorous bubbling was observed. The resulting white slurry was stirred at RT for 2 h and then was concentrated. The residue was azeotroped to dryness with cyclopentylmethyl ether and then was suspended in DCM (11 mL). 2,4-Dimethoxybenzylamine (423 μL, 6.5 mmol) and TEA (1.51 mL, 10.9 mmol) were added sequentially via syringe. The resulting slurry was stirred at RT overnight. The reaction mixture was then partitioned between water and DCM (3×). The combined organic layers were dried over anhydrous magnesium sulfate and concentrated. The residue was purified by silica gel chromatography (eluent: 30-50% EtOAc in hexanes over a 30 min period) to provide the title compound (84 mg, 10%). LCMS-ESI (pos.) m/z: 432.0 (M+Na)$^+$.

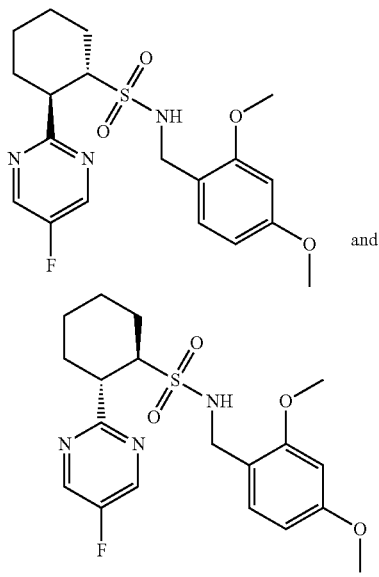

(1R,2S)—N-(2,4-Dimethoxybenzyl)-2-(5-fluoropyrimidin-2-yl)cyclohexane-1-sulfonamide and (1S,2R)—N-(2,4-dimethoxybenzyl)-2-(5-fluoropyrimidin-2-yl)cyclohexane-1-sulfonamide, Example 103.4. Further elution under the conditions described in Example 103.3 delivered the title compound (52 mg, 5.8%). LCMS-ESI (pos.) m/z: 432.0 (M+Na)$^+$.

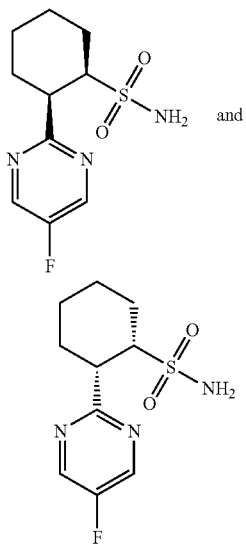

(1R,2R)-2-(5-Fluoropyrimidin-2-yl)cyclohexane-1-sulfonamide and (1S,2S)-2-(5-fluoropyrimidin-2-yl)cyclohexane-1-sulfonamide, Example 103.5. An ice-cooled solution of Example 103.3 (84 mg, 0.21 mmol) in DCM (2 mL) was treated sequentially with anisole (67 μL, 0.62 mmol) via syringe and TFA (227 μL, 3.0 mmol) via syringe. The resulting solution was warmed to RT and stirred for 2 h. The reaction was directly concentrated and the residue was purified by reverse phase preparatory HPLC (Sunfire 5 μM C18 column, eluent: 0-65% ACN in water over a 20 min period where both solvents contain 0.1% TFA) to provide Example 103.5 (15 mg, 28% yield) as a white solid. LCMS-ESI (pos.) m/z: 260.1 (M+H)$^+$.

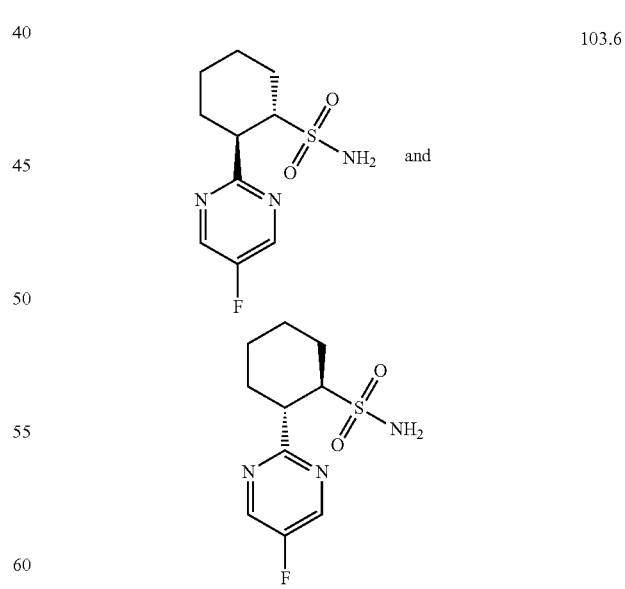

(1R,2S)-2-(5-Fluoropyrimidin-2-yl)cyclohexane-1-sulfonamide and (1S,2R)-2-(5-fluoropyrimidin-2-yl)cyclohexane-1-sulfonamide, Example 103.5. An ice-cooled solution of Example 103.4 (52 mg, 0.13 mmol) in DCM (2 mL) was treated sequentially with anisole (67 μL, 0.62 mmol) via syringe and TFA (227 μL, 3.0 mmol) via syringe. The resulting solution was warmed to RT and stirred for 2 h. The reaction was directly concentrated and the residue was purified by reverse phase preparatory HPLC (Sunfire 5 μM C18 column, eluent: 0-65% ACN in water over a 20 min period where both solvents contain 0.1% TFA) to provide Example 103.6 (33 mg, 100% yield) as a white solid. LCMS-ESI (pos.) m/z: 260.1 (M+H)⁺.

reverse phase HPLC (20 to 90% ACN, water, 0.1% TFA, gradient elution) over 20 min using an Eclipse Plus Prep C18 column, 5 μm, 30×150 mm (Agilent Technologies, Inc., Santa Clara, Calif.) at 50 mLs/min. This provided Example 103.7 (17 mg, 56%) as a yellow solid. $^1$H NMR (500 MHz, $C_6D_6$) δ 8.03 (s, 2H) 7.05 (t, J=8.4 Hz, 1H) 6.75 (d, J=1.2 Hz, 1H) 6.20 (dd, J=8.3, 4.9 Hz, 2H) 6.14 (d, J=3.7 Hz, 1H) 5.69 (dd, J=3.4, 1.7 Hz, 1H) 3.89 (d, J=4.6 Hz, 1H) 3.54-3.62 (m, 1H) 3.16 (d, J=13.2 Hz, 6H) 2.73-2.85 (m, 1H) 1.90-2.18 (m, 4H) 1.56-1.68 (m, 1H) 1.07-1.25 (m, 2H). LCMS-ESI (pos.), m/z: 529.1 (M+H)⁺.

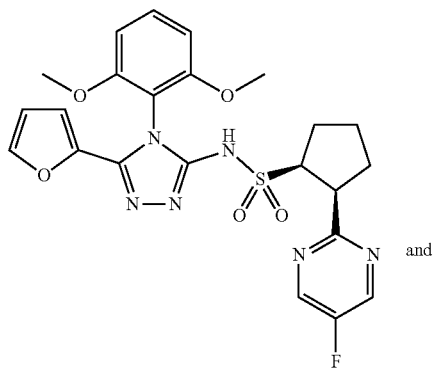

103.7 and

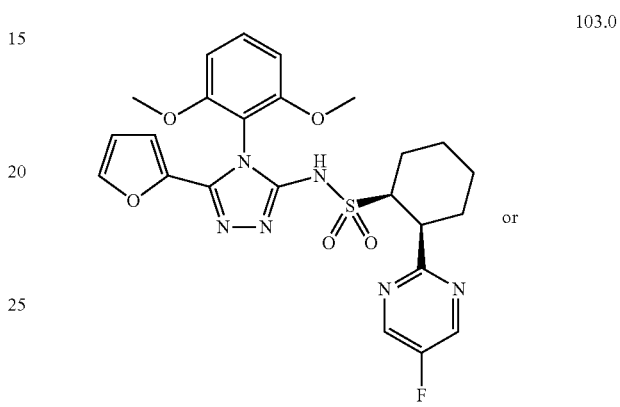

103.0 or

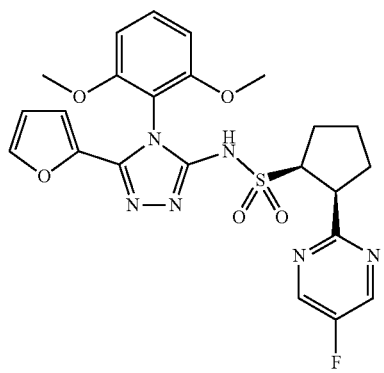

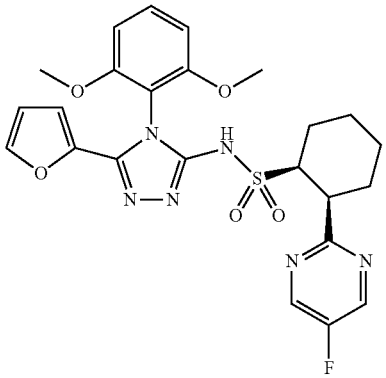

(1S,2S)—N-(4-(2,6-Dimethoxyphenyl)-5-(2-furanyl)-4H-1,2,4-triazol-3-yl)-2-(5-fluoro-2-pyrimidinyl)cyclohexanesulfonamide and (1R,2R)—N-(4-(2,6-dimethoxyphenyl)-5-(furan-2-yl)-4H-1,2,4-triazol-3-yl)-2-(5-fluoropyrimidin-2-yl)cyclohexane-1-sulfonamide, Example 103.7. The title compound was prepared employing 3-bromo-4-(2,6-dimethoxyphenyl)-5-(furan-2-yl)-4H-1,2,4-triazole, Example 364.3 and Example 103.5 using the general procedure described in Example 94.0 (employing 2 eq Example 364.3, 1 eq of Example 103.5, 0.35M in dioxane, no molecular sieves, and the reaction was heated to 90° C. for 4 h in a microwave reactor). The reaction was then diluted with a small volume of water and stirred vigorously. EtOAc was added followed by dropwise addition of concentrated HCl. Any precipitants were removed by filtration through a pad of Celite® brand filter aid. The organics were dried over MgSO₄, filtered, and concentrated in vacuo. The residue was dissolved in DMF and purified by preparatory (1S,2S)—N-(4-(2,6-Dimethoxyphenyl)-5-(2-furanyl)-4H-1,2,4-triazol-3-yl)-2-(5-fluoro-2-pyrimidinyl)cyclohexanesulfonamide or (1R,2R)—N-(4-(2,6-dimethoxyphenyl)-5-(furan-2-yl)-4H-1,2,4-triazol-3-yl)-2-(5-fluoropyrimidin-2-yl)cyclohexane-1-sulfonamide, Example 103.0. The title compound was isolated from the racemic material by chiral HPLC purification on a 250×30 mm IC column with 50 g/min MeOH+(20 mM NH₃)+60 g/min CO₂ on Thar 200 SFC. Outlet pressure=100 bar; Temp.=29° C.; Wavelength=266 nm. Used 5.0 mL injections of 28 mg/15 mL (1.87 mg/mL) sample solution in MeOH, i.e. 9.3 mg/injection. Run time=14 min. This delivered the title compound. $^1$H NMR (500 MHz, $C_6D_6$) δ 8.05 (br. s., 2H) 6.98-7.07 (m, 1H) 6.68-6.86 (m, 1H) 6.04-6.31 (m, 3H) 5.70 (br. s., 1H) 3.95 (br. s., 1H) 3.64 (br. s., 1H) 3.15 (d, J=19.1 Hz, 6H) 2.87 (d, J=7.8 Hz, 1H) 1.91-2.26 (m, 4H) 1.66 (br. s., 1H) 1.22 (br. s., 2H). LCMS-ESI (pos.) m/z: 529.1 (M+H)⁺.

Example 104.0. Preparation of (1R,2S)—N-(4-(2,6-dimethoxyphenyl)-5-(2-furanyl)-4H-1,2,4-triazol-3-yl)-2-(5-fluoro-2-pyrimidinyl)cyclopentanesulfonamide and (1S,2R)—N-(4-(2,6-dimethoxyphenyl)-5-(2-furanyl)-4H-1,2,4-triazol-3-yl)-2-(5-fluoro-2-pyrimidinyl)cyclopentanesulfonamide Trituration in ether removed the majority of the impurities. Further trituration in MeOH yielded a tan solid (107 mg, 43%), which was carried forward as such to the chiral separation. $^1$H NMR (500 MHz, CDCl$_3$) δ 8.56 (s, 2H) 7.43-7.51 (m, 2H) 6.67 (d, J=8.6 Hz, 2H) 6.33 (dd, J=3.5, 1.8 Hz, 1H) 5.99 (d, J=3.7 Hz, 1H) 4.21 (q, J=7.9 Hz, 1H) 3.85 (q, J=8.2 Hz, 1H) 3.76 (d, J=1.0 Hz, 7H) 2.15-2.31 (m, 3H) 1.76-1.88 (m, 3H). LCMS-ESI (pos.), m/z: 515.0 (M+H)$^+$.

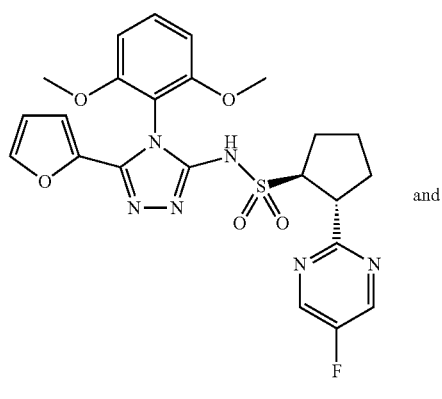

and

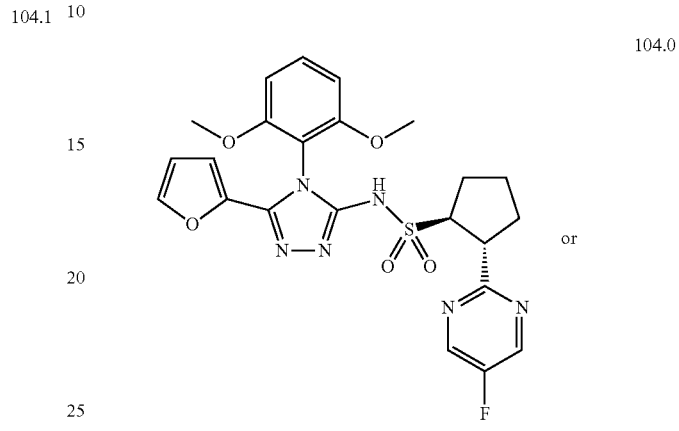

or (1R,2S)—N-(4-(2,6-Dimethoxyphenyl)-5-(2-furanyl)-4H-1,2,4-triazol-3-yl)-2-(5-fluoro-2-pyrimidinyl)cyclopentanesulfonamide and (1S,2R)—N-(4-(2,6-dimethoxyphenyl)-5-(2-furanyl)-4H-1,2,4-triazol-3-yl)-2-(5-fluoro-2-pyrimidinyl)cyclopentanesulfonamide, Example 104.1. The title compound was prepared employing 3-bromo-4-(2,6-dimethoxyphenyl)-5-(furan-2-yl)-4H-1,2,4-triazole, Example 364.3 and 100.5 as the sulfonamide coupling partner using the CuI coupling procedure described in Example 94.0 (employing 1 eq of Example 364.3, 1 eq of Example 100.5, no molecular sieves, and the reaction was heated to 90° C. for 15 h in a microwave reactor). The reaction was diluted with a small volume of water and stirred vigorously. EtOAc was added followed by dropwise addition of concentrated HCl. Any precipitants were removed by filtration through a pad of Celite® brand filter aid. The organics were dried on MgSO$_4$, filtered, and evaporated.

(1R,2S)—N-(4-(2,6-Dimethoxyphenyl)-5-(2-furanyl)-4H-1,2,4-triazol-3-yl)-2-(5-fluoro-2-pyrimidinyl)cyclopentanesulfonamide or (1S,2R)—N-(4-(2,6-dimethoxyphenyl)-5-(2-furanyl)-4H-1,2,4-triazol-3-yl)-2-(5-fluoro-2-pyrimidinyl)cyclopentanesulfonamide, Example 104.0. The title compound was isolated from the racemic material by chromatography using a 250 mm×21 mm Lux2 column with 36 g/min MeOH (20 mM NH$_3$)+44 g/min CO$_2$ on Thar 80 SFC. Outlet pressure=100 bar; Temperature=25° C.; Wavelength=267 nm. Used 2.0 mL injections of 108 mg/40 mL (2.7 mg/mL) sample solution in MeOH:DCM (1:1) i.e. 5.4 mg/injection. Run time=9 min, Cycle time=6 min. This delivered the title compound as the second eluting compound. $^1$H NMR (400 MHz, CDCl$_3$) δ 11.04 (s, 1H) 8.51 (s, 2H) 7.39-7.55 (m, 2H) 6.67 (d, J=8.6 Hz, 2H) 6.33 (dd, J=3.5, 1.8 Hz, 1H) 5.97 (dd, J=3.5, 0.6 Hz, 1H) 4.20 (q, J=7.8 Hz, 1H) 3.82-4.03 (m, 1H) 3.76 (s, 3H) 3.75 (s, 3H) 2.08-2.34 (m, 3H) 1.75-1.90 (m, 3H). LCMS-ESI (pos.) m/z: 515.2 (M+H)$^+$.

Example 105.0. Preparation of (1R,2S)—N-(4-(2,6-dimethoxyphenyl)-5-(2-furanyl)-4H-1,2,4-triazol-3-yl)-2-(5-fluoro-2-pyrimidinyl)cyclohexanesulfonamide or (1S,2R)—N-(4-(2,6-dimethoxyphenyl)-5-(2-furanyl)-4H-1,2,4-triazol-3-yl)-2-(5-fluoro-2-pyrimidinyl)cyclohexanesulfonamide

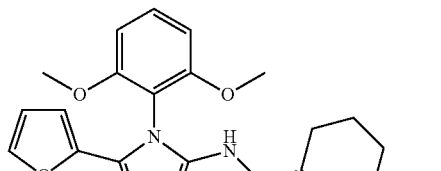

and

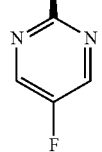

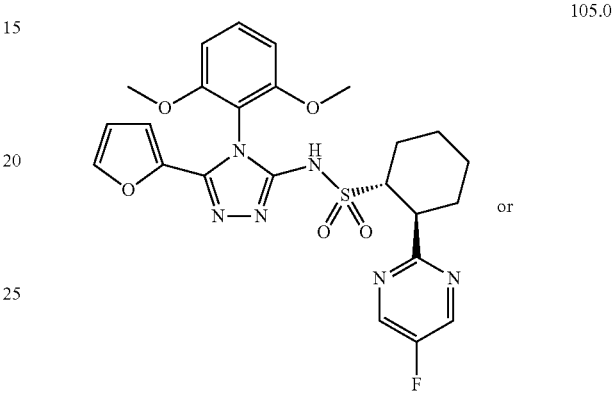

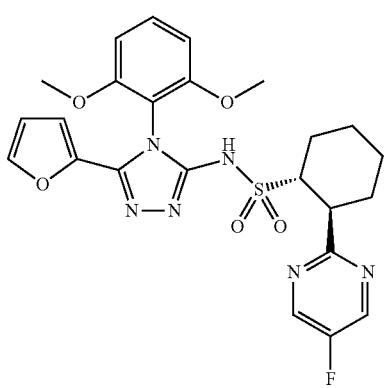

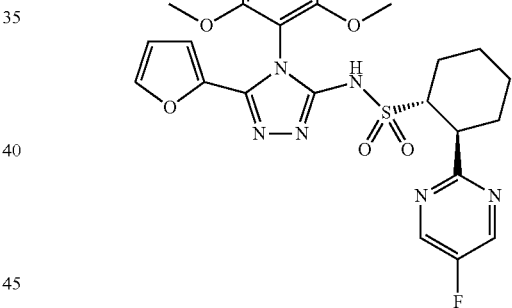

(1R,2S)—N-(4-(2,6-Dimethoxyphenyl)-5-(2-furanyl)-4H-1,2,4-triazol-3-yl)-2-(5-fluoro-2-pyrimidinyl)cyclohexanesulfonamide and (1S,2R)—N-(4-(2,6-dimethoxyphenyl)-5-(2-furanyl)-4H-1,2,4-triazol-3-yl)-2-(5-fluoro-2-pyrimidinyl)cyclohexanesulfonamide, Example 105.1. The title compound was prepared employing 3-bromo-4-(2,6-dimethoxyphenyl)-5-(furan-2-yl)-4H-1,2,4-triazole, Example 364.3 and Example 103.6 as the sulfonamide coupling partner using the CuI coupling procedure described in Example 94.0 (employing 2 eq Example 364.3, 1 eq Example 103.6, 0.35M in dioxane, no molecular sieves, and the reaction was heated to 90° C. for 4 h in a microwave reactor). The reaction was diluted with a small volume of water and stirred vigorously. EtOAc was added followed by dropwise addition of concentrated HCl. Any precipitants were removed by filtration through a pad of Celite® brand filter aid. The organics were dried on MgSO₄, filtered, and evaporated. Purification by preparatory reverse phase HPLC (12 to 85% ACN, water, 0.1% TFA, gradient elution) over 20 min using Eclipse Plus Prep C18 column, 5 μm, 30×150 mm (Agilent Technologies, Inc., Santa Clara, Calif.) at 50 mLs/min. This provided Example 105.1 (34 mg, 51%) as a yellow solid. $^1$H NMR (500 MHz, CD$_3$CN) δ 8.56 (s, 2H) 7.54-7.61 (m, 2H) 6.84 (t, J=8.5 Hz, 2H) 6.42 (dd, J=3.5, 1.8 Hz, 1H) 6.06 (d, J=3.4 Hz, 1H) 3.79 (s, 3H) 3.75 (s, 3H) 3.49 (td, J=11.6, 3.9 Hz, 1H) 3.14 (td, J=11.6, 4.3 Hz, 1H) 2.17-2.23 (m, 1H) 1.91 (d, J=2.9 Hz, 1H) 1.81-1.88 (m, 1H) 1.75 (d, J=13.0 Hz, 1H) 1.49-1.63 (m, 2H) 1.40 (dt, J=12.9, 3.2 Hz, 1H) 1.26-1.36 (m, 1H). LCMS-ESI (pos.), m/z: 529.1 (M+H)$^+$.

(1R,2S)—N-(4-(2,6-Dimethoxyphenyl)-5-(2-furanyl)-4H-1,2,4-triazol-3-yl)-2-(5-fluoro-2-pyrimidinyl)cyclohexanesulfonamide or (1S,2R)—N-(4-(2,6-dimethoxyphenyl)-5-(2-furanyl)-4H-1,2,4-triazol-3-yl)-2-(5-fluoro-2-pyrimidinyl)cyclohexanesulfonamide, Example 105.0. The title compound was isolated from the racemic material on a 250×30 mm Lux2 column with 40 g/min MeOH+(20 mM NH$_3$)+60 g/min CO$_2$ on Thar 200 SFC. Outlet pressure=100 bar; Temp.=20° C.; Wavelength=267 nm. Used 4.0 mL injections of 28 mg/18 mL (1.56 mg/mL) sample solution in MeOH, i.e. 6.2 mg/injection. Run time=16 min.; Cycle time=7 min. This delivered the title compound as the first compound from the column. $^1$H NMR (500 MHz, CD$_3$CN) δ 8.60 (s, 2H) 7.57-7.62 (m, 2H) 6.87 (t, J=8.4 Hz, 2H) 6.44 (dd, J=3.4, 1.7 Hz, 1H) 6.07 (d, J=3.7 Hz, 1H) 3.82 (s, 3H) 3.78 (s, 3H) 3.53 (td, J=11.6, 3.8 Hz, 1H) 3.19 (td, J=11.5, 4.2 Hz, 1H) 2.24 (dd, J=13.3, 3.1 Hz, 1H) 1.91-1.95 (m, 1H) 1.84-1.91 (m, 1H) 1.78 (d, J=12.7 Hz, 1H) 1.59 (m, 2H) 1.28-1.49 (m, 2H). LCMS-ESI (pos.) m/z: 529.1 (M+H)$^+$.

Example 106.0 Preparation of 2-(4-chlorophenyl)-N-(4-(2,6-dimethoxyphenyl)-5-(3-methyl-2-furanyl)-4H-1,2,4-triazol-3-yl)ethanesulfonamide

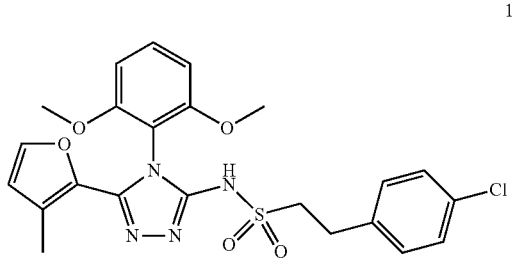

106.0

2-(4-Chlorophenyl)-N-(4-(2,6-dimethoxyphenyl)-5-(3-methyl-2-furanyl)-4H-1,2,4-triazol-3-yl)ethanesulfonamide, Example 106.0. The title compound was prepared employing Example 363.4 and 2-(4-chloro-phenyl)-ethanesulfonyl chloride (commercially available from Synchem Inc., IL, USA) and following the procedure described in Example 111.0 except for the addition of a catalytic quantity of DMAP to the reaction mixture. This yielded the title compound (Example 106.0, 31 mg, 29%) as an off-white solid. $^1$H NMR (400 MHz, CD$_3$OD) δ 7.38 (t, J=8.5 Hz, 1H), 7.22-7.26 (m, 1H), 7.05-7.14 (m, 3H), 6.61 (d, J=8.4 Hz, 2H), 6.28 (d, J=1.8 Hz, 1H), 3.71 (app s, 6H), 3.23-3.33 (m, 2H), 3.04-3.11 (m, 2H), 2.25 (s, 3H). LCMS-ESI (pos.) m/z: 503.0 (M+H)$^+$.

Example 107.0. Preparation of N-(4-(2,6-dimethoxyphenyl)-5-(5-(trifluoromethyl)-2-furanyl)-4H-1,2,4-triazol-3-yl)-2-(5-fluoro-2-pyrimidinyl)ethanesulfonamide

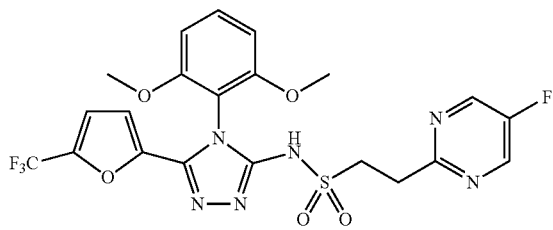

107.0

N-(4-(2,6-Dimethoxyphenyl)-5-(5-(trifluoromethyl)-2-furanyl)-4H-1,2,4-triazol-3-yl)-2-(5-fluoro-2-pyrimidinyl)ethanesulfonamide, Example 107.0. A suspension of Example 364.0 (55 mg, 0.13 mmol), Example 351.0 (108 mg, 0.53 mmol), rac-trans-N,N'-dimethylcyclohexane-1,2-diamine (37 μL, 0.26 mmol), cesium carbonate (171 mg, 0.53 mmol) and 5 Å dried and crushed molecular sieves (75 mg) in dioxane (1.3 mL) was sparged with argon for 3 min. Copper(I) iodide (20 mg, 0.11 mmol) was then added. The mixture was briefly degassed and the reaction vessel was then heated in a microwave at 100° C. until LCMS analysis indicated that the reaction was complete (3 h). Thereafter, the mixture was cooled to RT, diluted with saturated aqueous Na$_2$CO$_3$, and extracted with EtOAc (3×). The EtOAc layers were combined, dried over MgSO$_4$, filtered, and concentrated in vacuo. The residue was purified on a reverse-phase column, employing a gradient of 30-60% ACN in water (0.1% TFA in both eluents) to afford the title compound. $^1$H NMR (400 MHz, CDCl$_3$) δ 8.52 (s, 2H), 7.47 (t, J=8.5 Hz, 1H), 6.73-6.75 (m, 1H), 6.67 (d, J=8.6 Hz, 2H), 6.29 (d, J=3.8 Hz, 1H), 3.76 (s, 3H), 3.76 (3H), 3.56-3.62 (m, 2H), 3.43-3.48 (m, 2H). LCMS-ESI (pos.) m/z: 543.0 (M+H)$^+$.

Example 111.0. Preparation of 2-(4-chlorophenyl)-N-(4-(2,6-dimethoxyphenyl)-5-(furan-2-yl)-4H-1,2,4-triazol-3-yl)ethanesulfonamide

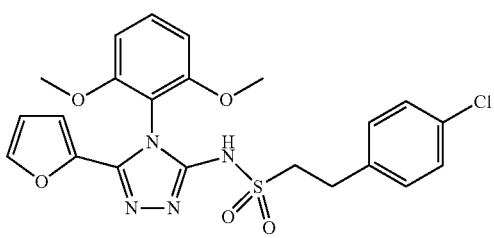

111.0

2-(4-Chlorophenyl)-N-(4-(2,6-dimethoxyphenyl)-5-(furan-2-yl)-4H-1,2,4-triazol-3-yl)ethanesulfonamide, Example 111.0. To a 50 mL RBF was added Example 362.03 (1.3 g, 4.0 mmol) and TEA (2.8 mL, 20.2 mmol) in DCM (20 mL). At RT, 2-(4-chloro-phenyl)-ethanesulfonyl chloride (commercially available from Synchem Inc., IL, USA), 1.3 g, 5.3 mmol) was added. The reaction mixture was stirred at RT for 6 h. LCMS analysis showed a small amount of starting material remained 2-(4-Chloro-phenyl)-ethanesulfonyl chloride (200 mg) was then added. The reaction mixture was stirred at RT for 6 h. LCMS analysis showed the reaction was complete. The reaction mixture was diluted with water and extracted with DCM. The combined organic layers were washed with brine and dried over Na$_2$SO$_4$. The solution was filtered and concentrated in vacuo to give as a light-yellow glass. The initial material was absorbed onto a plug of silica gel and purified by chromatography through a Redi-Sep pre-packed silica gel column (40 g) eluting with a gradient of 20% to 100% EtOAc in hexanes to provide the title compound (1.2 g, 2.5 mmol, 61% yield) as an off-white solid. $^1$H NMR (400 MHz, CD$_3$OD) δ 7.82 (d, J=1.2 Hz, 1H), 7.56 (t, J=8.6 Hz, 1H), 7.29-7.35 (m, 2H), 7.17-7.24 (m, 2H), 6.89 (d, J=8.4 Hz, 2H), 6.51 (dd, J=3.5, 1.8 Hz, 1H), 6.02 (d, J=3.5 Hz, 1H), 3.70 (s, 3H), 3.70 (s, 3H), 3.13-3.21 (m, 2H), 2.84-2.91 (m, 2H). LCMS-ESI (pos.) m/z: 489.1 (M+H)$^+$.

The compounds set forth in the following table were synthesized following the procedure in Example 127.0 using the starting materials as described.

TABLE 2

| Example | Reagents | Structure, Name and Data |
|---|---|---|
| 109.0 110.0 | 3-bromo-4-(2,6-dimethoxyphenyl)-5-(5-methylfuran-2-yl)-4H-1,2,4-triazole (Example 364.1) and (2S,3R)-3-(5-fluoropyrimidin-2-yl)butane-2-sulfonamide, (2R,3S)-3-(5-fluoropyrimidin-2-yl)butane-2-sulfonamide and (2R,3R)-3-(5-fluoropyrimidin-2-yl)butane-2-sulfonamide and (2S,3S)-3-(5-fluoropyrimidin-2-yl)butane-2-sulfonamide (Example 354.0). Preparative SFC method, stage one (separates Peak 1 from Peaks 2-4): Column: 250 × 21 mm Chiralpak AS-H, 30 g/min IPA containing 20 mM ammonia + 30 g/min CO₂, 100 bar, 276 nm, Inj volume: 0.2 mL of a 4.5 mg/mL solution of sample in 33:7 MeOH/DCM. Preparative SFC method, stage two (separates Peaks 2-4): Column: 150 × 30 mm CC4, 39 g/min EtOH containing 20 mM ammonia + 91 g/min CO₂, 100 bar, 276 nm, Inj volume: 0.4 mL of a 1.9 mg/mL solution of sample in 5:2 MeOH/DCM. | Second eluting peak:<br>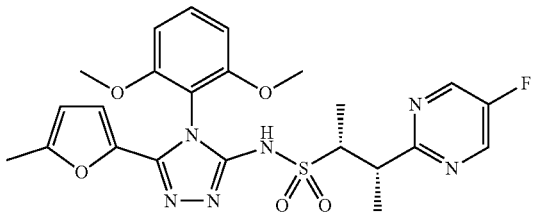<br>(2R,3S)-N-(4-(2,6-dimethoxyphenyl)-5-(5-methylfuran-2-yl)-4H-1,2,4-triazol-3-yl)-3-(5-fluoropyrimidin-2-yl)butane-2-sulfonamide.<br>$^1$H NMR (400 M,Hz, CDCl$_3$) δ: 10.96 (br. s., 1H), 8.54 (s, 2H), 7.46 (t, J = 8.5 Hz, 1H), 6.67 (dd, J = 8.5, 4.6 Hz, 2H), 5.89-5.93 (m, 1H), 5.79 (d, J = 3.3 Hz, 1H), 3.78-3.89 (m, 2H), 3.75 (s, 3H), 3.74 (s, 3H), 2.32 (s, 3H), 1.37 (d, J = 6.6 Hz, 3H), 1.34 (d, J = 6.9 Hz, 3H). LCMS-ESI (pos.) m/z: 517.1 (M + H)$^+$.<br><br>Third eluting peak:<br>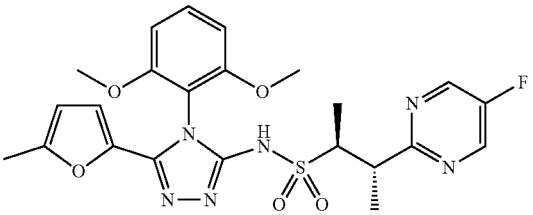<br>(2S,3S)-N-(4-(2,6-dimethoxyphenyl)-5-(5-methylfuran-2-yl)-4H-1,2,4-triazol-3-yl)-3-(5-fluoropyrimidin-2-yl)butane-2-sulfonamide.<br>$^1$H NMR (500 MHz, CDCl$_3$) δ: 11.14 (br. s., 1H), 8.53 (s, 2H), 7.46 (t, J = 8.6 Hz, 1H), 6.67 (d, J = 8.6 Hz, 2H), 5.91 (dd, J = 3.4, 1.0 Hz, 1H), 5.78 (d, J = 3.4 Hz, 1H), 3.76 (s, 3H), 3.76 (s, 3H), 3.60-3.67 (m, 1H), 3.53-3.59 (m, 1H), 2.32 (s, 3H), 1.49 (d, J = 7.1 Hz, 3H), 1.25 (d, J = 6.9 Hz, 3H). LCMS-ESI (pos.) m/z: 517.1 (M + H)$^+$. |

Example 112.0. Preparation of (P)-2-(4-chlorophenyl)-N-(5-(furan-2-yl)-4-(2-methoxy-6-methylphenyl)-4H-1,2,4-triazol-3-yl)ethanesulfonamide or (M)-2-(4-chlorophenyl)-N-(5-(furan-2-yl)-4-(2-methoxy-6-methylphenyl)-4H-1,2,4-triazol-3-yl)ethanesulfonamide 5-(Furan-2-yl)-4-(2-methoxy-6-methylphenyl)-4H-1,2,4-triazol-3-amine, Example 112.1. Employing 2-methoxy-6-methylaniline (commercially available from CombiBlocks, San Diego, Calif., USA) and the procedures described in Example 363.0 yielded Example 112.1 (0.31 g, 1.16 mmol, 9% over 4 steps). LCMS-ESI (pos.), m/z: 271.2 (M+H)$^+$.

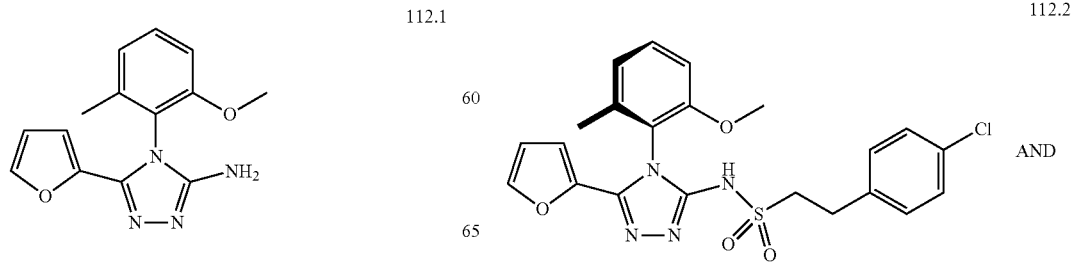

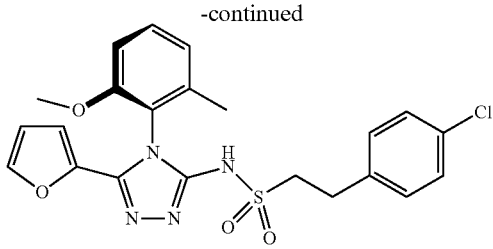

(P)-2-(4-Chlorophenyl)-N-(5-(furan-2-yl)-4-(2-methoxy-6-methylphenyl)-4H-1,2,4-triazol-3-yl)ethanesulfonamide and (M)-2-(4-chlorophenyl)-N-(5-(furan-2-yl)-4-(2-methoxy-6-methylphenyl)-4H-1,2,4-triazol-3-yl)ethanesulfonamide Example 112.2. To a 5 mL RBF was added Example 112.1 (0.10 g, 0.38 mmol) and TEA (0.21 mL, 1.48 mmol) in DCM (7.4 mL). Subsequently, 2-(4-chlorophenyl) ethanesulfonyl chloride (commercially available from Oakwood Products, Inc., SC, USA, 0.10 g, 0.41 mmol) was added at 0° C. After 30 min, the reaction was removed from the ice bath and maintained at RT for 90 min. The mixture was then cooled to 0° C. and a second aliquot of TEA (0.21 mL, 1.48 mmol) and 2-(4-chlorophenyl)ethanesulfonyl chloride (0.10 g, 0.41 mmol) was added. The reaction was then warmed to RT and stirred overnight. The mixture was then diluted with water and extracted with EtOAc. The combined organic layers were then washed with brine, dried over Na$_2$SO$_4$, filtered, and concentrated in vacuo to give a residue. The residue was then purified on a 12 g silica gel column employing a gradient of 1-3% MeOH in DCM affording Example 112.2 (94 mg, 0.20 mmol, 53% yield) as an off-white solid. $^1$H NMR (400 MHz, CDCl$_3$) δ 10.95 (s, 1H) 7.51 (d, J=1.76 Hz, 1H) 7.47 (t, J=8.02 Hz, 1H) 7.24-7.31 (m, 2H) 7.10 (d, J=8.22 Hz, 2H) 7.02 (d, J=7.83 Hz, 1H) 6.91 (d, J=8.22 Hz, 1H) 6.35 (dd, J=3.52, 1.76 Hz, 1H) 5.89 (d, J=3.52 Hz, 1H) 3.66-3.74 (m, 3H) 3.22-3.33 (m, 2H) 3.03-3.13 (m, 2H) 2.14-2.23 (m, 3H). LCMS-ESI (pos.), m/z: 473.0 (M+H)$^+$.

112.0

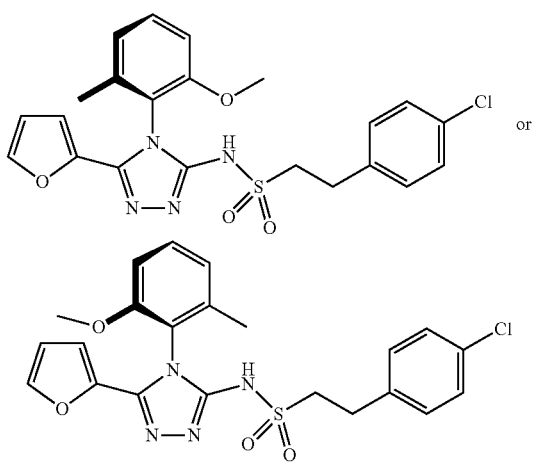

(P)-2-(4-Chlorophenyl)-N-(5-(furan-2-yl)-4-(2-methoxy-6-methylphenyl)-4H-1,2,4-triazol-3-yl)ethanesulfonamide or (M)-2-(4-chlorophenyl)-N-(5-(furan-2-yl)-4-(2-methoxy-6-methylphenyl)-4H-1,2,4-triazol-3-yl)ethanesulfonamide, Example 112.0. Purification of Example 112.2 was performed by SFC [250×30 mm OJ column with 20 g/min IPA (+20 mM NH$_3$)+60 g/min CO$_2$ on Thar 80 SFC. Outlet pressure=100 bar; Temp.=22° C.; Wavelength=270 nm. Used 0.5 mL injections of 90 mg/15 mL (6 mg/mL) sample solution in MeOH, i.e. 3 mg/injection. Run time=10 min, Cycle time 6 min]. This afforded two atropisomers. The title compound was the first isomer to elute under these conditions. $^1$H NMR (400 MHz, CDCl$_3$) δ 11.11 (br. s., 1H) 7.50 (d, J=1.37 Hz, 1H) 7.46 (t, J=8.02 Hz, 1H) 7.23-7.31 (m, 2H) 7.07-7.14 (m, 2H) 7.01 (d, J=7.83 Hz, 1H) 6.91 (d, J=8.22 Hz, 1H) 6.35 (dd, J=3.52, 1.76 Hz, 1H) 5.90 (d, J=3.52 Hz, 1H) 3.70 (s, 3H) 3.24-3.32 (m, 2H) 3.03-3.12 (m, 2H) 2.18 (s, 3H). LCMS-ESI (pos.), m/z: 473.0 (M+H)$^+$. Specific Optical Rotation: [α]=−22.5 (c=1.395 g/100 mL, CHCl$_3$, ee=99%).

Example 113.0. Preparation of (P)-2-(4-chlorophenyl)-N-(5-(furan-2-yl)-4-(2-methoxy-6-methylphenyl)-4H-1,2,4-triazol-3-yl)ethanesulfonamide or (M)-2-(4-chlorophenyl)-N-(5-(furan-2-yl)-4-(2-methoxy-6-methylphenyl)-4H-1,2,4-triazol-3-yl)ethanesulfonamide 113.0

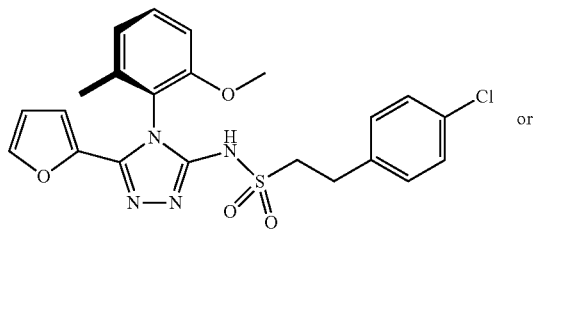

or

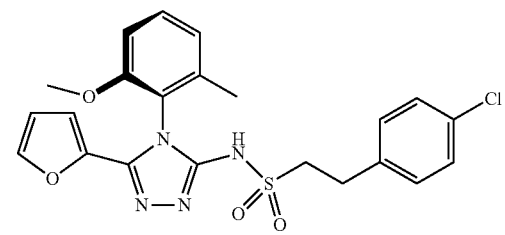

(P)-2-(4-Chlorophenyl)-N-(5-(furan-2-yl)-4-(2-methoxy-6-methylphenyl)-4H-1,2,4-triazol-3-yl)ethanesulfonamide or (M)-2-(4-chlorophenyl)-N-(5-(furan-2-yl)-4-(2-methoxy-6-methylphenyl)-4H-1,2,4-triazol-3-yl)ethanesulfonamide, Example 113.0. Example 113.0 is the atropisomer of Example 112.0. The title compound was the second isomer to elute on subjecting Example 112.2 to the SFC conditions described in Example 112.0. $^1$H NMR (400 MHz, CDCl$_3$) δ 11.11 (br. s., 1H) 7.50 (d, J=1.76 Hz, 1H) 7.42-7.49 (m, 1H) 7.23-7.31 (m, 2H) 7.07-7.14 (m, 2H) 7.01 (d, J=7.63 Hz, 1H) 6.91 (d, J=8.41 Hz, 1H) 6.32-6.37 (m, 1H) 5.90 (d, J=3.52 Hz, 1H) 3.66-3.71 (m, 3H) 3.24-3.31 (m, 2H) 3.03-3.12 (m, 2H) 2.18 (s, 3H). LCMS-ESI (pos.), m/z: 473.0 (M+H)$^+$. Specific Optical Rotation: [α]=+24.7 (c=1.450 g/100 mL, CHCl$_3$, ee=96%).

Example 114.0. Preparation of (3-(4-chlorophenyl)-N-(4-(2,6-dimethoxyphenyl)-5-(2-furanyl)-4H-1,2,4-triazol-3-yl)-1-propanesulfonamide

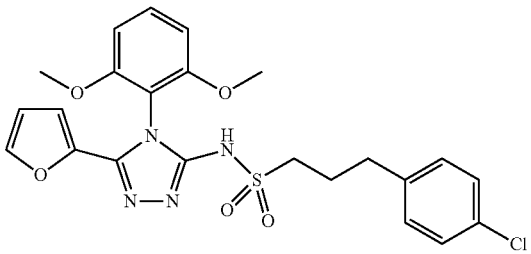

114.0

3-(4-Chlorophenyl)-N-(4-(2,6-dimethoxyphenyl)-5-(2-furanyl)-4H-1,2,4-triazol-3-yl)-1-propanesulfonamide, Example 114.0. The title compound was prepared employing 3-(4-chlorophenyl)propane-1-sulfonyl chloride (commercially available from Sigma-Aldrich Corp., St. Louis, Mo., USA) using the procedure described for the synthesis of Example 210.0 (employing the use of 2 eq of sulfonyl chloride and 8 eq of TEA). $^1$H NMR (400 MHz, CDCl$_3$) δ 10.92 (br. s., 1H) 7.41-7.50 (m, 2H) 7.19-7.26 (m, 2H) 7.06 (d, J=8.41 Hz, 2H) 6.62-6.69 (m, 2H) 6.33 (dd, J=3.52, 1.76 Hz, 1H) 5.98 (d, J=3.52 Hz, 1H) 3.68 (s, 3H) 3.68 (s, 3H) 2.96-3.07 (m, 2H) 2.70 (t, J=7.63 Hz, 2H) 2.03-2.14 (m, 2H). LCMS-ESI (pos.) m/z: 503.0 (M+H)$^+$.

The compounds set forth in the following table were synthesized following the procedure in Example 127.0 using the starting materials as described.

TABLE 3

| Example | Reagents | Structure, Name and Data |
|---------|----------|--------------------------|
| 116.0 | 3-bromo-4-(2,6-dimethoxyphenyl)-5-(5-methylfuran-2-yl)-4H-1,2,4-triazole (Example 364.1), (1R,2S)-1-(5-fluoropyrimidin-2-yl)-1-methoxypropane-2-sulfonamide and (1S,2R)-1-(5-fluoropyrimidin-2-yl)-1-methoxypropane-2-sulfonamide (Example 359.0). Preparative SFC method: Column: 250 × 30 mm Chiralpak AS-H, 10.5 g/min MeOH + 59.5 g/min CO$_2$, 100 bar, 277 nm, Inj volume: 0.5 mL of a 7.5 mg/mL solution of sample in 2:1 MeOH/DCM. | Second eluting peak:<br><br>(1R,2S)-N-(4-(2,6-dimethoxyphenyl)-5-(5-methylfuran-2-yl)-4H-1,2,4-triazol-3-yl)-1-(5-fluoropyrimidin-2-yl)-1-methoxypropane-2-sulfonamide or (1S,2R)-N-(4-(2,6-dimethoxyphenyl)-5-(5-methylfuran-2-yl)-4H-1,2,4-triazol-3-yl)-1-(5-fluoropyrimidin-2-yl)-1-methoxypropane-2-sulfonamide.<br><br>1H NMR (400 MHz, CDCl$_3$) δ 10.95 (br. s., 1H), 8.61 (s, 2H), 7.45 (t, J = 8.4 Hz, 1H), 6.67 (d, J = 8.6 Hz, 2H), 5.90 (dd, J = 3.5, 0.8 Hz, 1H), 5.79 (d, J = 3.3 Hz, 1H), 4.96 (d, J = 4.9 Hz, 1H), 3.67-3.79 (m, 7H), 3.33 (s, 3H), 2.31 (s, 3H), 1.38 (d, J = 7.0 Hz, 3H). LCMS-ESI (pos.) m/z: 533.2 (M + H). |

TABLE 3-continued

| Example | Reagents | Structure, Name and Data |
|---|---|---|
| 117.0 | 3-bromo-4-(2,6-dimethoxyphenyl)-5-(5-methylfuran-2-yl)-4H-1,2,4-triazole (Example 364.1), (1S,2S)-1-ethoxy-1-(5-methylpyrimidin-2-yl)propane-2-sulfonamide and (1R,2R)-1-ethoxy-1-(5-methylpyrimidin-2-yl)propane-2-sulfonamide (Example 356.1). Preparative SFC method: Column: 2 × 15 cm Phenomenex Lux-2 Cell, 40% EtOH/CO$_2$, 100 bar, 65 mL/min, 220 nm, Inj volume: 2.0 mL of a 5.0 mg/mL solution of sample in 5:1 MeOH/DCM. | First eluting peak:<br><br>(1S,2S)-N-(4-(2,6-dimethoxyphenyl)-5-(5-methylfuran-2-yl)-4H-1,2,4-triazol-3-yl)-1-ethoxy-1-(5-methylpyrimidin-2-yl)propane-2-sulfonamide or (1R,2R)-N-(4-(2,6-dimethoxyphenyl)-5-(5-methylfuran-2-yl)-4H-1,2,4-triazol-3-yl)-1-ethoxy-1-(5-methylpyrimidin-2-yl)propane-2-sulfonamide<br>$^1$H NMR (500 MHz, CDCl$_3$) δ 8.62 (s, 2H), 7.42 (t, J = 8.5 Hz, 1H), 6.66 (t, J = 8.1 Hz, 2H), 5.89 (dd, J = 3.4, 0.9 Hz, 1H), 5.73 (d, J = 3.5 Hz, 1H), 4.78 (d, J = 4.9 Hz, 1H), 3.80 (s, 3H), 3.70-3.79 (m, 4H), 3.49-3.62 (m, 1H), 3.31-3.41 (m, 1H), 2.33 (s, 3H), 2.33 (s, 3H), 1.39 (d, J = 7.0 Hz, 3H), 1.08 (t, J = 6.9 Hz, 3H). LCMS-ESI (pos.) m/z: 543.2 (M + H)$^+$. |
| 118.0 | 3-bromo-4-(2,6-dimethoxyphenyl)-5-(5-methylfuran-2-yl)-4H-1,2,4-triazole (Example 364.1), (1S,2R)-1-ethoxy-1-(5-methylpyrimidin-2-yl)propane-2-sulfonamide and (1R,2S)-1-ethoxy-1-(5-methylpyrimidin-2-yl)propane-2-sulfonamide (Example 356.0). Preparative SFC method: Column: 2 × 15 cm Chiralpak AD-H, 30% EtOH/CO$_2$, 100 bar, 220 um, Inj volume: 0.5 mL of a 5.0 mg/mL solution of sample in MeOH. | Second eluting peak:<br><br>(1R,2S)-N-(4-(2,6-dimethoxyphenyl)-5-(5-methylfuran-2-yl)-4H-1,2,4-triazol-3-yl)-1-ethoxy-1-(5-methylpyrimidin-2-yl)propane-2-sulfonamide.<br>1H NMR (500 MHz, CDCl$_3$) δ 11.23 (br. s., 1H), 8.58 (s, |

2H), 7.44 (t, J = 8.6 Hz, 1H), 6.66 (d, J = 8.6 Hz, 2H), 5.90 (br. s., 1H), 5.75-5.80 (m, 1H), 4.96 (d, J = 5.6 Hz, 1H), 3.70-3.82 (m, 7H), 3.42-3.56 (m, 2H), 2.32 (s, 3H), 2.31 (s, 3H), 1.43 (d, J = 7.0 Hz, 3H), 1.14 (t, J = 7.0 Hz, 3H). LCMS-ESI (pos.) m/z: 543.2 (M + H)+.

Example 119.0. Preparation of 2-(2-cyano-4-fluorophenyl)-N-(4-(2,6-dimethoxyphenyl)-5-(5-methylfuran-2-yl)-4H-1,2,4-triazol-3-yl)ethanesulfonamide

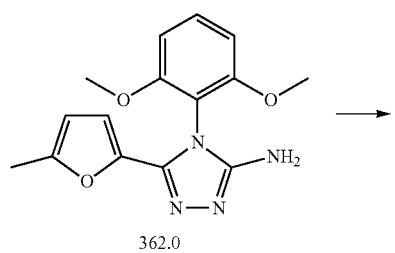

362.0

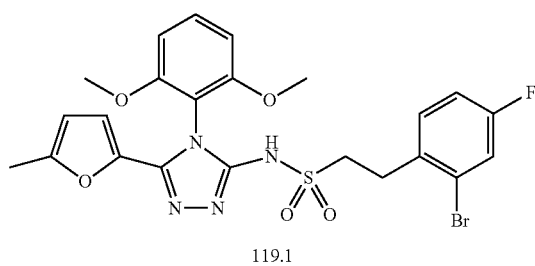

119.1

2-(2-Bromo-4-fluorophenyl)-N-(4-(2,6-dimethoxyphenyl)-5-(5-methylfuran-2-yl)-4H-1,2,4-triazol-3-yl)ethanesulfonamide, Example 119.1. To a solution of 362.0 (45 mg, 0.15 mmol) and TEA (83 μL, 0.60 mmol) in DCM (2.3 mL) was added 2-(2-bromo-4-fluorophenyl)ethanesulfonyl chloride (Synchem, 68 mg, 0.22 mmol). The resulting orange solution was stirred at RT for 1.5 h and then was quenched with water (5 mL) and extracted with DCM (3×). The combined organic layers were dried over anhydrous sodium sulfate and concentrated. The residue was purified by reverse phase preparatory HPLC (Sunfire 5 μM C18 column, eluent: 45-70% ACN in water where both solvents contain 0.1% TFA) to provide Example 119.1 (17.4 mg, 21% yield) as a white solid. LCMS-ESI (pos.) m/z: 565.0 (M+H)+.

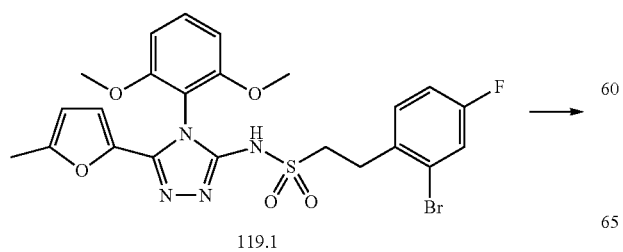

119.1

-continued

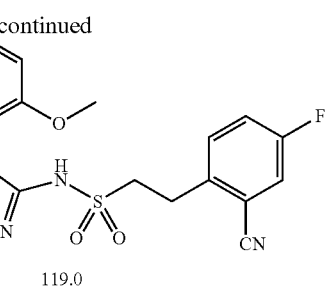

119.0

2-(2-Cyano-4-fluorophenyl)-N-(4-(2,6-dimethoxyphenyl)-5-(5-methylfuran-2-yl)-4H-1,2,4-triazol-3-yl)ethanesulfonamide, Example 20.0. To a vial containing a solution of Example 119.1 (8.5 mg, 0.02 mmol) in DMF (1.4 mL) was added copper cyanide (35 mg, 0.39 mmol). The resulting yellow slurry was capped and heated at 130° C. for 23 h. After this period, more copper cyanide (35 mg, 0.39 mmol) was added. After an additional 23 h at 130° C., the reaction mixture was diluted with MeOH/DMSO and filtered. A small amount of ACN containing 0.1% TFA was added, and the solution was directly purified by reverse phase preparatory HPLC (Sunfire 5 μM C18 column, eluent: 45-65% ACN in water where both solvents contain 0.1% TFA) to provide Example 119.0 (0.6 mg, 8% yield) as a white solid. $^1$H NMR (400 MHz, CD$_3$OD) δ 7.44-7.60 (m, 3H), 7.35-7.43 (m, 1H), 6.86 (d, J=8.6 Hz, 2H), 6.03 (d, J=3.3 Hz, 1H), 5.93 (d, J=3.3 Hz, 1H), 3.79 (s, 3H), 3.36-3.42 (m, 2H), 3.24-3.31 (m, 2H), 2.28 (s, 3H). LCMS-ESI (pos.) m/z: 512.2 (M+H)$^+$.

Example 120.0. Preparation of (1R,2S)—N-(4-(2,6-dimethoxyphenyl)-5-(5-methylfuran-2-yl)-4H-1,2,4-triazol-3-yl)-1-(2-methoxyethoxy)-1-(5-methylpyrimidin-2-yl)propane-2-sulfonamide

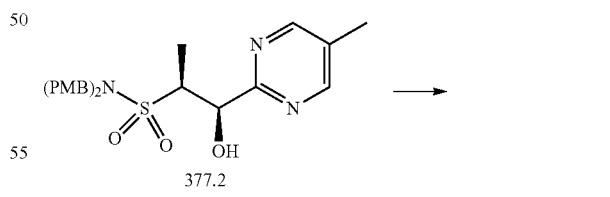

377.2

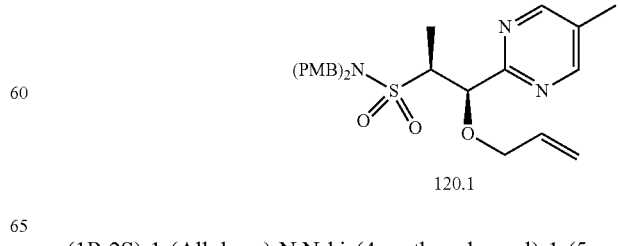

120.1

(1R,2S)-1-(Allyloxy)-N,N-bis(4-methoxybenzyl)-1-(5-methylpyrimidin-2-yl)propane-2-sulfonamide, Example 120.1. To a −78° C. solution of Example 377.2 (1.76 g, 3.7 mmol) in THF (40 mL) was added potassium bis(trimethylsilyl)amide (1.0 M solution in THF, 5.0 mL, 5.0 mmol) slowly via syringe. After 7 min, allyl bromide (1.3 mL, 15.0 mmol) was added slowly via syringe. The resulting bright yellow solution was stirred at −78° C. for 6 min and then was warmed to 0° C. and stirred for an additional 40 min. The reaction mixture was quenched with a 5.5:1 mixture of saturated aqueous ammonium chloride and water (65 mL) and then was extracted with EtOAc (4×). The combined organic layers were dried over anhydrous sodium sulfate and concentrated. The residue was purified by silica gel chromatography (eluent: 5-75% EtOAc in hexanes) to provide Example 120.1 (1.33 g, 70% yield) as a light yellow oil. LCMS-ESI (pos.) m/z: 512.2 (M+H)⁺.

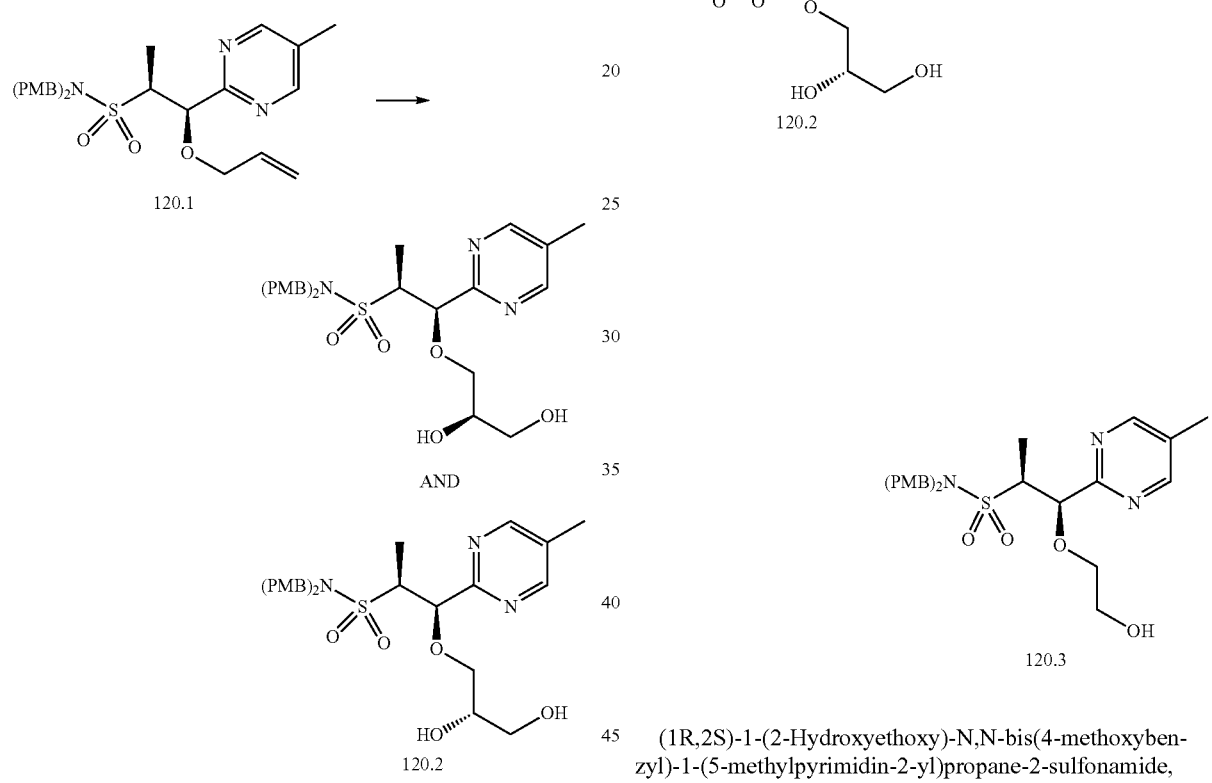

(1R,2S)-1-((S)-2,3-Dihydroxypropoxy)-N,N-bis(4-methoxybenzyl)-1-(5-methylpyrimidin-2-yl)propane-2-sulfonamide and (1R,2S)-1-((R)-2,3-dihydroxypropoxy)-N,N-bis(4-methoxybenzyl)-1-(5-methylpyrimidin-2-yl)propane-2-sulfonamide, Example 120.2. To a solution of Example 120.1 (1.33 g, 2.6 mmol) in a mixture of acetone (45 mL) and water (15 mL) was added a catalytic amount of osmium tetroxide and then 4-methylmorpholine-N-oxide (1.07 g, 9.1 mmol). The resulting brown solution was stirred at RT for 24 h and then was partially concentrated to remove the acetone. The aqueous residue was diluted with water and extracted with DCM (7×). The combined organic layers were dried over anhydrous sodium sulfate and concentrated. The residue was purified by silica gel chromatography (eluent: 0-10% MeOH in DCM) to provide Example 120.2 (1.32 g, 93% yield) as a tan solid. LCMS-ESI (pos.) m/z: 546.2 (M+H)⁺.

(1R,2S)-1-(2-Hydroxyethoxy)-N,N-bis(4-methoxybenzyl)-1-(5-methylpyrimidin-2-yl)propane-2-sulfonamide, Example 120.3. To a solution of Example 120.2 (1.32 g, 2.4 mmol) in a mixture of THF (30 mL) and water (10 mL) was added sodium periodate (1.44 g, 6.8 mmol). The resulting yellow slurry was stirred at RT for 3.75 h and then was filtered and the filtrate rinsed with DCM. The mixture was partially concentrated to remove the organic solvents and then was diluted with water and extracted with DCM (4×). The combined organic layers were dried over anhydrous sodium sulfate and concentrated to afford the initial aldehyde as a pink solid. To an ice-cooled solution of the initial aldehyde in MeOH (60 mL) was added sodium borohydride (728 mg, 19.2 mmol). The resulting yellow solution was stirred at 0° C. for 2 h and then was quenched with 1 N HCl solution (35 mL). The mixture was partially concentrated to remove the MeOH and then was extracted with DCM (4×). The combined organic layers were dried over anhydrous sodium sulfate and concentrated. The residue was purified by silica gel chromatography (eluent: 0-15% MeOH in DCM) to provide Example 120.3 (965 mg, 78% yield) as a tan solid. LCMS-ESI (pos.) m/z: 516.0 (M+H)⁺.

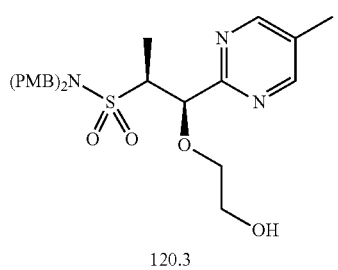

120.3

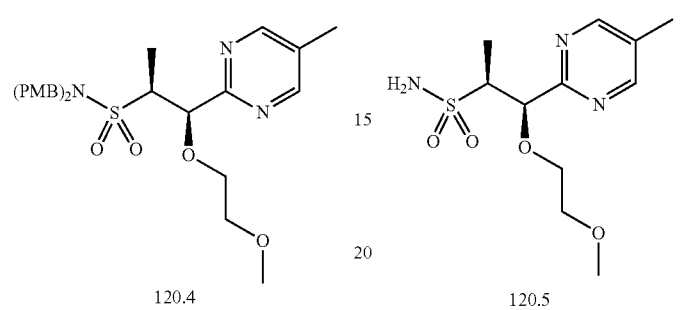

120.4

(1R,2S)—N,N-Bis(4-methoxybenzyl)-1-(2-methoxy-ethoxy)-1-(5-methylpyrimidin-2-yl)propane-2-sulfonamide, Example 120.4. To a −78° C. solution of Example 120.3 (964 mg, 1.9 mmol) in THF (50 mL) was added potassium bis(trimethylsilyl)amide, (1.0 M solution in THF, 3.93 mL, 3.9 mmol) slowly via syringe. After stirring for 10 min at −78° C., the reaction was warmed to −40° C. and stirred for an additional 8 min. The reaction was then recooled to −78° C. and MeOTf (307 µL, 2.0 mmol) was added slowly via syringe. The resulting red solution was stirred at −78° C. for 25 min and then was quenched with a 2:1 mixture of saturated aqueous ammonium chloride and water (30 mL). The resulting mixture was extracted with DCM (4×). The combined organic layers were dried over anhydrous sodium sulfate and concentrated. The residue was purified by silica gel chromatography (eluent: 0-12% MeOH in DCM) to provide Example 120.4 (376 mg, 38% yield) as an orange oil. LCMS-ESI (pos.) m/z: 530.2 (M+H)+.

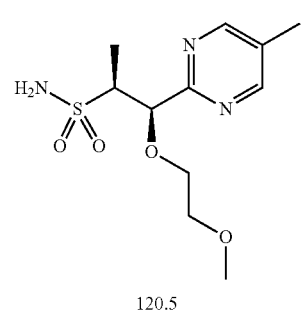

120.4

120.5

(1R,2S)-1-(2-Methoxyethoxy)-1-(5-methylpyrimidin-2-yl)propane-2-sulfonamide, Example 120.05. Example 120.4 (376 mg, 0.71 mmol) was dissolved in TFA (5 mL). Anisole (170 µL, 1.5 mmol) was then added via syringe. The resulting orange solution was stirred at RT for 7 h and then concentrated. The residue was purified by silica gel chromatography (eluent: 0-7% MeOH in DCM) to provide Example 120.5 (143 mg, 70% yield) as a light yellow solid. LCMS-ESI (pos.) m/z: 290.1 (M+H)+.

+

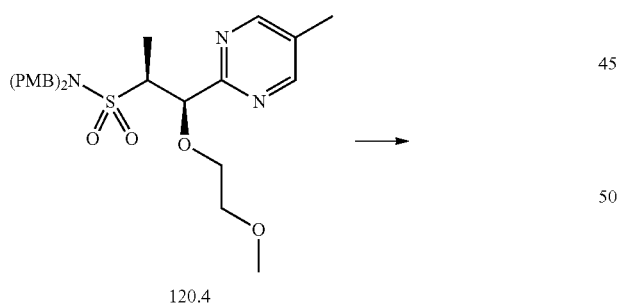

120.5

364.1

120.0

(1R,2S)—N-(4-(2,6-Dimethoxyphenyl)-5-(5-methyl-furan-2-yl)-4H-1,2,4-triazol-3-yl)-1-(2-methoxyethoxy)-1-(5-methylpyrimidin-2-yl)propane-2-sulfonamide, Example 120.0. Following the procedure described in Example 94.0, Example 364.1 (70 mg, 0.19 mmol) and Example 120.5 (40 mg, 0.14 mmol) were coupled to provide Example 120.0 (65 mg, 82% yield) as a light yellow solid. $^1$H NMR (400 MHz, CDCl$_3$) δ 11.37 (br. s., 1H), 8.60 (s, 2H), 7.44 (t, J=8.5 Hz, 1H), 6.66 (dd, J=3.4, 0.9 Hz, 2H), 5.90 (dd, J=3.4, 0.9 Hz, 1H), 5.79 (d, J=5.3 Hz, 1H), 5.07 (d, J=3.5 Hz, 1H), 3.79-3.89 (m, 1H), 3.76 (s, 3H), 3.76 (s. 3H), 3.67-3.74 (m, 1H), 3.54-3.62 (m, 2H), 3.46-3.53 (m, 1H), 3.34 (s, 3H), 2.32 (s, 3H), 1.42 (d, J=7.0 Hz, 3H). LCMS-ESI (pos.) m/z: 573.0 (M+H)+.

Example 121.0. Preparation of (1S,2S)—N-(4-(2,6-dimethoxyphenyl)-5-(5-methylfuran-2-yl)-4H-1,2,4-triazol-3-yl)-1-(2-hydroxyethoxy)-1-(5-methylpyrimidin-2-yl)propane-2-sulfonamide

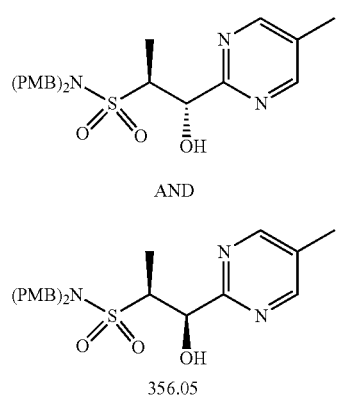

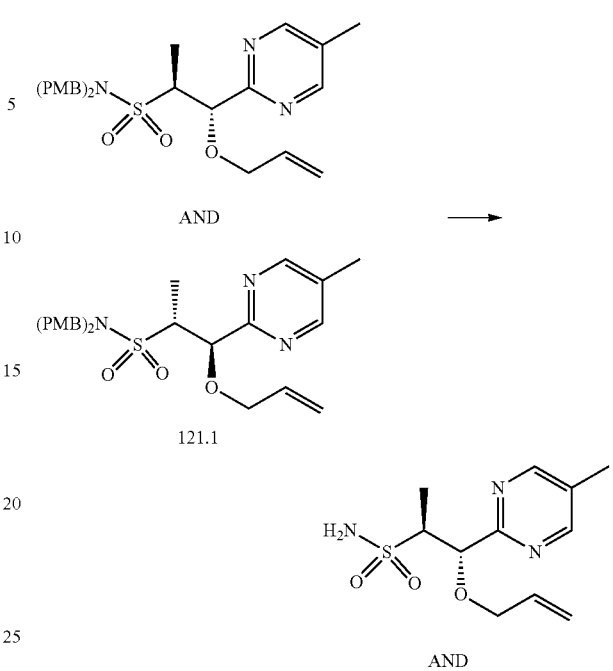

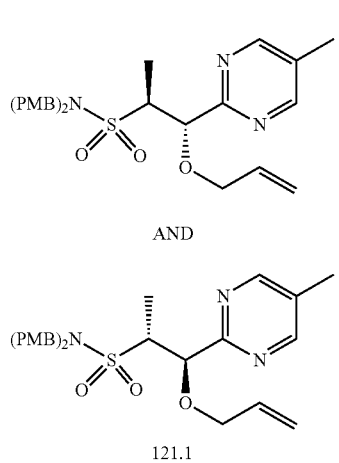

(1S,2S)-1-(Allyloxy)-N,N-bis(4-methoxybenzyl)-1-(5-methylpyrimidin-2-yl)propane-2-sulfonamide and (1R,2R)-1-(allyloxy)-N,N-bis(4-methoxybenzyl)-1-(5-methylpyrimidin-2-yl)propane-2-sulfonamide, Example 121.1. To a −78° C. solution of Example 356.05 (401 mg, 0.85 mmol) in THF (10 mL) was added potassium bis(trimethylsilyl)amide (1.0 M solution in THF, 1.15 mL, 1.15 mmol) slowly via syringe. After 6 min, allyl iodide (313 μL, 3.40 mmol) was added slowly via syringe. The resulting bright yellow solution was stirred at −78° C. for 5 min and then was warmed to 0° C. and stirred for an additional 2.5 h. The reaction mixture was quenched with saturated aqueous ammonium chloride (35 mL) and then was extracted with EtOAc (4×). The combined organic layers were dried over anhydrous sodium sulfate and concentrated. The residue was purified by silica gel chromatography (eluent: 5-65% EtOAc in hexanes) to provide Example 121.1 (197 mg, 45% yield) as a colorless oil. LCMS-ESI (pos.) m/z: 512.2 (M+H)$^+$.

(1S,2S)-1-(Allyloxy)-1-(5-methylpyrimidin-2-yl)propane-2-sulfonamide and (1R,2R)-1-(allyloxy)-1-(5-methylpyrimidin-2-yl)propane-2-sulfonamide, Example 121.2. Example 121.1 (197 mg, 0.39 mmol) was dissolved in TFA (5 mL) and anisole (209 μL, 1.93 mmol) was added via syringe. The resulting yellow solution was stirred at RT for 22.5 h and then was concentrated in vacuo. The residue was purified by silica gel chromatography (eluent: 0-4.5% MeOH in DCM) to provide Example 121.2 (92 mg, 88% yield) as a white solid. LCMS-ESI (pos.) m/z: 277.1 (M+H)$^+$.

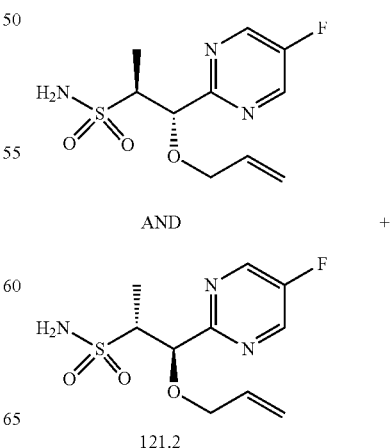

273

-continued

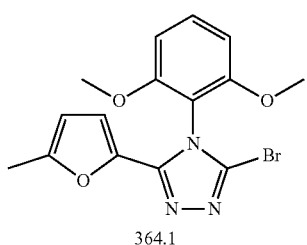

364.1

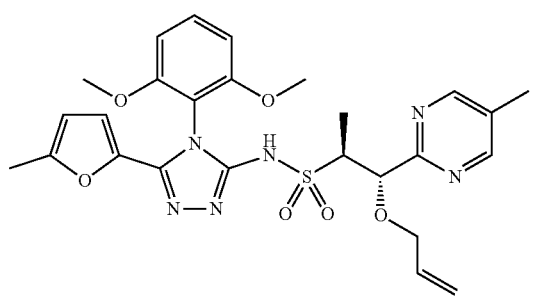

121.3

(1S,2S)-1-(Allyloxy)-N-(4-(2,6-dimethoxyphenyl)-5-(5-methylfuran-2-yl)-4H-1,2,4-triazol-3-yl)-1-(5-methylpyrimidin-2-yl)propane-2-sulfonamide and (1R,2R)-1-(allyloxy)-N-(4-(2,6-dimethoxyphenyl)-5-(5-methylfuran-2-yl)-4H-1,2,4-triazol-3-yl)-1-(5-methylpyrimidin-2-yl)propane-2-sulfonamide, Example 121.3. Following the procedure described in Example 94.0, Example 364.1 (173 mg, 0.48 mmol) and Example 121.2 (92 mg, 0.34 mmol) were coupled to provide Example 121.3 (43 mg, 23% yield) as a light yellow solid. LCMS-ESI (pos.) m/z: 555.2 (M+H)⁺.

121.4

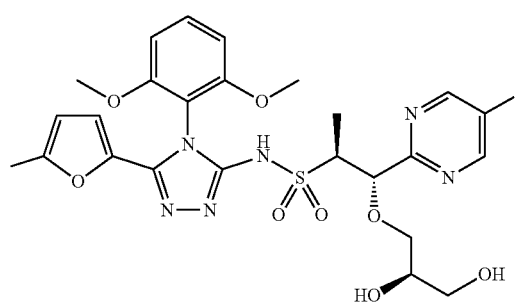

274

-continued

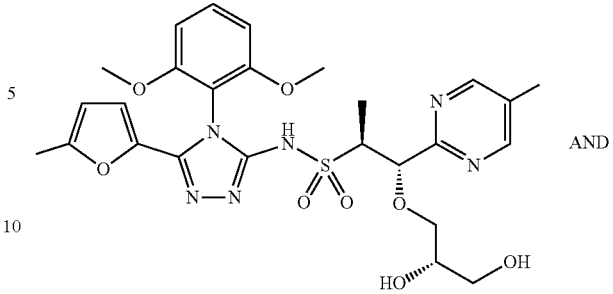

AND

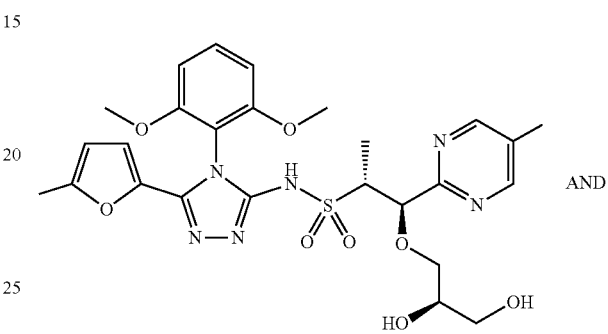

AND

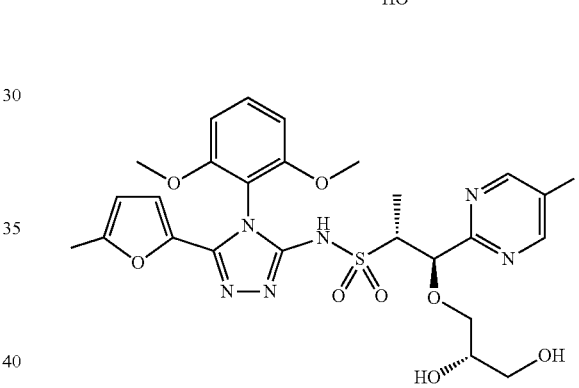

(1S,2S)-1-((R)-2,3-Dihydroxypropoxy)-N-(4-(2,6-dimethoxyphenyl)-5-(5-methylfuran-2-yl)-4H-1,2,4-triazol-3-yl)-1-(5-methylpyrimidin-2-yl)propane-2-sulfonamide and (1S,2S)-1-((S)-2,3-dihydroxypropoxy)-N-(4-(2,6-dimethoxyphenyl)-5-(5-methylfuran-2-yl)-4H-1,2,4-triazol-3-yl)-1-(5-methylpyrimidin-2-yl)propane-2-sulfonamide and (1R,2R)-1-((R)-2,3-dihydroxypropoxy)-N-(4-(2,6-dimethoxyphenyl)-5-(5-methylfuran-2-yl)-4H-1,2,4-triazol-3-yl)-1-(5-methylpyrimidin-2-yl)propane-2-sulfonamide and (1R,2R)-1-((S)-2,3-dihydroxypropoxy)-N-(4-(2,6-dimethoxyphenyl)-5-(5-methylfuran-2-yl)-4H-1,2,4-triazol-3-yl)-1-(5-methylpyrimidin-2-yl)propane-2-sulfonamide, Example 121.4. To a solution of Example 121.3 (43 mg, 0.08 mmol) in a mixture of acetone (2.85 mL) and water (1 mL) was added a catalytic amount of osmium tetroxide followed by 4-methylmorpholine-N-oxide (32 mg, 0.27 mmol). The resulting dark yellow solution was stirred at RT for 5 h and then was partially concentrated to remove the acetone. The aqueous residue was diluted with water and extracted with DCM (3×). The combined organic layers were dried over anhydrous sodium sulfate and concentrated. The residue was purified by silica gel chromatography (eluent: 0-8% MeOH in DCM) to provide Example 121.4 (32 mg, 70% yield) as a light yellow solid. LCMS-ESI (pos.) m/z: 589.1 (M+H)⁺.

AND

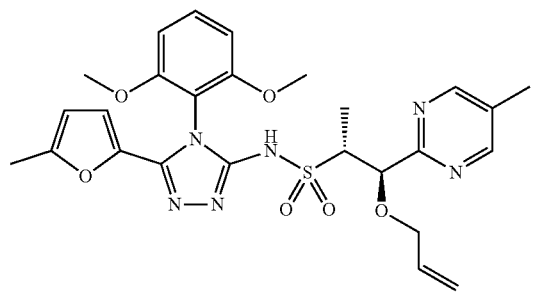

AND 121.5

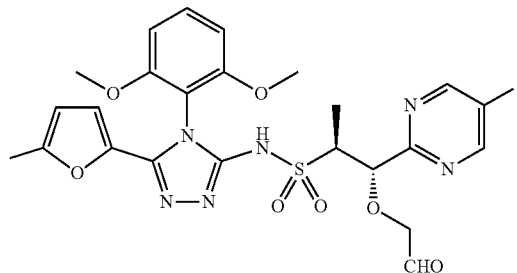

AND

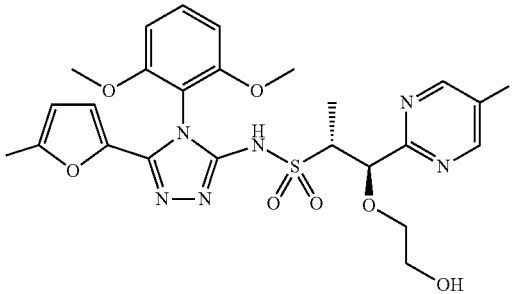

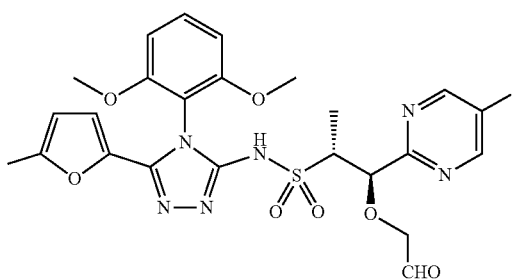

(1S,2S)—N-(4-(2,6-Dimethoxyphenyl)-5-(5-methyl-furan-2-yl)-4H-1,2,4-triazol-3-yl)-1-(5-methylpyrimidin-2-yl)-1-(2-oxoethoxy)propane-2-sulfonamide and (1R,2R)—N-(4-(2,6-dimethoxyphenyl)-5-(5-methylfuran-2-yl)-4H-1,2,4-triazol-3-yl)-1-(5-methylpyrimidin-2-yl)-1-(2-oxoethoxy)propane-2-sulfonamide, Example 121.5. To a solution of Example 121.4 (32 mg, 0.05 mmol) in a mixture of THF (2.9 mL) and water (1 mL) was added sodium periodate (32.5 mg, 0.15 mmol). The resulting yellow slurry was stirred at RT for 4 h and then was filtered rinsing the filtered solids with DCM. The filtrate was partially concentrated to remove the organic solvents and then was diluted with water and extracted with DCM (3×). The combined organic layers were dried over anhydrous sodium sulfate and concentrated to afford Example 121.5 (26 mg, 86% yield) as a white solid. LCMS-ESI (pos.) m/z: 557.2 (M+H)⁺.

121.6

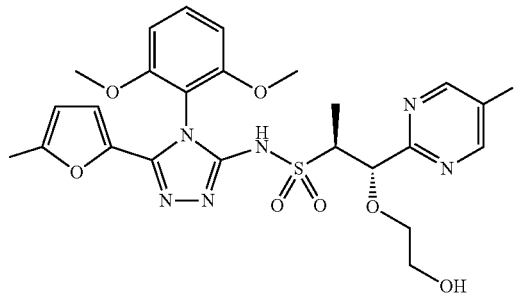

AND

-continued (1S,2S)—N-(4-(2,6-Dimethoxyphenyl)-5-(5-methyl-furan-2-yl)-4H-1,2,4-triazol-3-yl)-1-(2-hydroxyethoxy)-1-(5-methylpyrimidin-2-yl)propane-2-sulfonamide and (1R,2R)—N-(4-(2,6-dimethoxyphenyl)-5-(5-methylfuran-2-yl)-4H-1,2,4-triazol-3-yl)-1-(2-hydroxyethoxy)-1-(5-methylpyrimidin-2-yl)propane-2-sulfonamide, Example 121.6. To an ice-cooled solution of Example 121.5 (26 mg, 0.05 mmol) in MeOH (6 mL) was added sodium borohydride (5 mg, 0.13 mmol). The resulting light yellow solution was stirred at 0° C. for 1 h and then more sodium borohydride (5 mg, 0.13 mmol) was added. After an additional 4 h, another portion of sodium borohydride (5 mg, 0.13 mmol) was added. The reaction mixture was stirred for an additional 20 min and then quenched with 1 N HCl (5 mL). The reaction was partially concentrated to remove MeOH and was extracted with DCM (3×). The combined organic layers were dried over anhydrous sodium sulfate and concentrated to afford Example 121.6 (27 mg, 93% yield) as an off-white solid. LCMS-ESI (pos.) m/z: 559.1 (M+H)⁺.

121.0

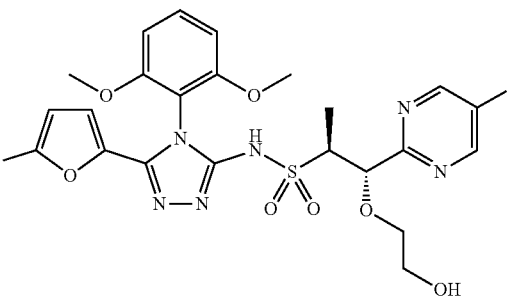

or

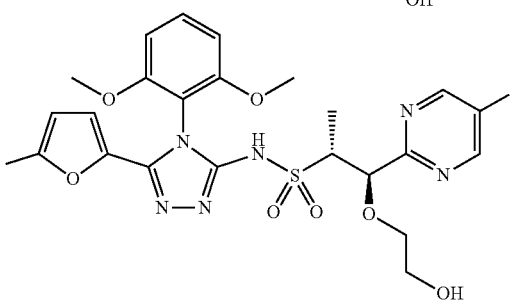

(1S,2S)—N-(4-(2,6-Dimethoxyphenyl)-5-(5-methyl-furan-2-yl)-4H-1,2,4-triazol-3-yl)-1-(2-hydroxyethoxy)-1-(5-methylpyrimidin-2-yl)propane-2-sulfonamide or (1R,2R)—N-(4-(2,6-dimethoxyphenyl)-5-(5-methylfuran-2-yl)-4H-1,2,4-triazol-3-yl)-1-(2-hydroxyethoxy)-1-(5-methylpyrimidin-2-yl)propane-2-sulfonamide, Example 121.0. Example 121.6 was separated by preparative SFC (column: 250×21 mm Chiralpak AD, 19 g/min MeOH+41 g/min CO$_2$, 100 bar, 275 nm, Inj volume: 0.4 mL of a 9.0 mg/mL solution of sample in 2:1 MeOH/DCM). The title compound Example 121.0 was the first eluting peak (9.7 mg). $^1$H NMR (500 MHz, CDCl$_3$) δ 11.68 (br. s., 1H), 8.61 (s, 2H), 7.45 (t, J=8.4 Hz, 1H), 6.68 (d, J=8.6 Hz, 2H), 5.88-5.94 (m, 1H), 5.80 (d, J=3.2 Hz, 1H), 4.74 (d, J=7.1 Hz, 1H), 3.73-3.88 (m, 7H), 3.45-3.60 (m, 4H), 2.34 (s, 3H), 2.32 (s, 3H), 1.22 (d, J=7.1 Hz, 3H). LCMS-ESI (pos.) m/z: 559.1 (M+H)$^+$.

The compounds set forth in the following table were synthesized following the procedure in Example 127.0 using the starting materials as described.

5-Fluoro-2-(prop-1-en-2-yl)pyrimidine, Example 123.1. To a solution of potassium isopropenyltrifluoroborate (4.19 g, 28.3 mmol) in THF (56 mL) were added oven-dried cesium carbonate (27.4 g, 84 mmol), triphenylphosphine (1.49 g, 5.7 mmol), 2-chloro-5-fluoropyrimidine (3.5 mL, 28.3 mmol) and water (14 mL). The slurry was degassed with an argon stream, and then palladium(II) chloride (603 mg, 3.4 mmol) was added. The slurry was again degassed with an argon stream, and the resulting mixture was heated at reflux under argon for 24 h. The reaction mixture was then filtered through a Whatman GF/F disposable plastic cup and

TABLE 4

| Example | Reagents | Structure, Name and Data |
|---|---|---|
| 122.0 | 3-bromo-4-(2,6-dimethoxyphenyl)-5-(5-methylfuran-2-yl)-4H-1,2,4-triazole (Example 364.1), (1R,2R)-1-(5-fluoropyrimidin-2-yl)-1-methoxypropane-2-sulfonamide and (1S,2S)-1-(5-fluoropyrimidin-2-yl)-1-methoxypropane-2-sulfonamide (Example 359.1). Preparative SFC method: Column: 150 × 30 mm ChromegaChiral CC4, 28 g/min MeOH + 42 g/min CO$_2$, 100 bar, 277 nm, Inj volume: 1.0 mL of a 4.0 mg/mL solution of sample in 3:1 MeOH/DCM. | First eluting peak: 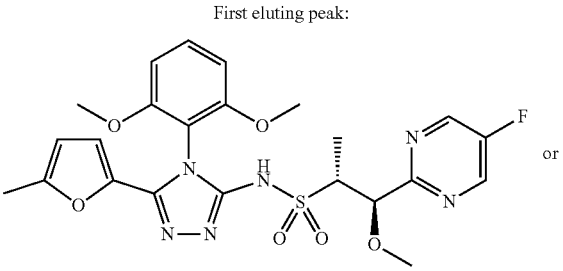 [SMILES: COc1cccc(OC)c1-n1c(NS(=O)(=O)[C@H](C)[C@H](OC)c2ncc(F)cn2)nnc1-c1ccc(C)o1] (1R,2R)-N-(4-(2,6-dimethoxyphenyl)-5-(5-methylfuran-2-yl)-4H-1,2,4-triazol-3-yl)-1-(5-fluoropyrimidin-2-yl)-1-methoxypropane-2-sulfonamide or (1S,2S)-N-(4-(2,6-dimethoxyphenyl)-5-(5-methylfuran-2-yl)-4H-1,2,4-triazol-3-yl)-1-(5-fluoropyrimidin-2-yl)-1-methoxypropane-2-sulfonamide. $^1$H NMR (500 MHz, CDCl$_3$) δ 11.25 (br. s., 1H), 8.62 (s, 2H), 7.46 (t, J = 8.5 Hz, 1H), 6.67 (dd, J = 8.2, 5.0 Hz, 2H), 5.91 (d, J = 2.7 Hz, 1H), 5.76 (d, J = 2.4 Hz, 1H), 4.80 (d, J = 6.1 Hz, 1H), 3.81 (s, 3H), 3.71-3.80 (m, 4H), 3.24 (s, 3H), 2.32 (s, 3H), 1.24 (d, J = 6.6 Hz, 3H). LCMS-ESI (pos.) m/z: 533.2 (M + H)$^+$. |

Example 123.0. Preparation of (S)—N-(4-(2,6-dimethoxyphenyl)-5-(5-methylfuran-2-yl)-4H-1,2,4-triazol-3-yl)-2-(5-fluoropyrimidin-2-yl)propane-1-sulfonamide or (R)—N-(4-(2,6-dimethoxyphenyl)-5-(5-methylfuran-2-yl)-4H-1,2,4-triazol-3-yl)-2-(5-fluoropyrimidin-2-yl)propane-1-sulfonamide was washed with water (1×) and brine (1×). The organic layer was dried over anhydrous sodium sulfate and partially concentrated on rotary evaporator at a pressure of 150 torr. The residue was purified by silica gel chromatography (eluent: pure DCM) to provide Example 123.1 (2.88 g, 74% yield) as a yellow oil. LCMS-ESI (pos.): 139.1 (M+H).

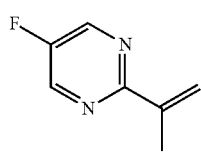

123.1

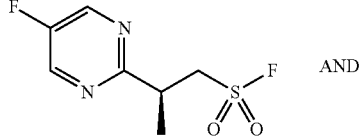

123.2

AND

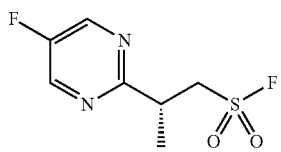

(S)-2-(5-Fluoropyrimidin-2-yl)propane-1-sulfonyl fluoride and (R)-2-(5-fluoropyrimidin-2-yl)propane-1-sulfonyl fluoride, Example 123.2. To a solution of 5-fluoro-2-(prop-1-en-2-yl)pyrimidine Example 123.1 (2.88 g, 20.9 mmol) in THF (30 mL) was added a solution of sodium bisulfite (6.51 g, 62.5 mmol) in water (11 mL) slowly via pipette. The resulting cloudy biphasic mixture was heated at 65° C. for 3 d and then partially concentrated to remove the THF. To the sulfonic acid slurry was added DCM (55 mL) followed by DAST (4.13 mL, 31.3 mmol) slowly via syringe. A mild exotherm was observed. The resulting yellow slurry was stirred for 18 h and then was directly purified by silica gel chromatography (eluent: pure DCM) to provide Example 123.2 (230 mg, 5% yield) as a white solid. LCMS-ESI (pos.): 223.1 (M+H).

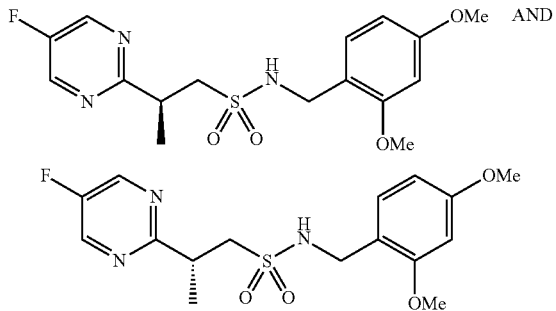

(S)—N-(2,4-Dimethoxybenzyl)-2-(5-fluoropyrimidin-2-yl)propane-1-sulfonamide and (R)—N-(2,4-dimethoxybenzyl)-2-(5-fluoropyrimidin-2-yl)propane-1-sulfonamide, Example 123.3. To a solution of 2-(5-fluoropyrimidin-2-yl)propane-1-sulfonyl fluoride Example 123.2 (230 mg, 1.04 mmol) in ACN (10 mL) was added 2,4-dimethoxybenzylamine (544 µL, 3.62 mmol) via syringe followed by TEA (1.01 mL, 7.25 mmol) dropwise via syringe. The resulting white slurry was stirred at 50° C. for 17.5 h and then was partitioned between water and DCM (3×). The combined organic layers were dried over anhydrous sodium sulfate and concentrated. The residue was purified directly by silica gel chromatography (eluent: 10-50% EtOAc in hexanes) to provide Example 123.3 (327 mg, 86% yield) as a colorless oil. LCMS-ESI (pos.): 392.0 (M+Na).

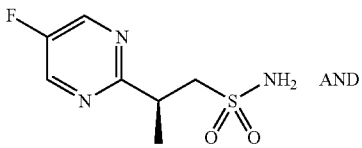

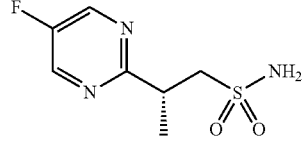

(S)-2-(5-Fluoropyrimidin-2-yl)propane-1-sulfonamide and (R)-2-(5-fluoropyrimidin-2-yl)propane-1-sulfonamide, Example 123.4. To an ice-cooled flask containing N-(2,4-dimethoxybenzyl)-2-(5-fluoropyrimidin-2-yl)propane-1-sulfonamide (Example 123.3, 326 mg, 0.88 mmol) was added TFA (3.0 mL, 40.4 mmol) slowly via syringe. The resulting pink solution was stirred at 0° C. for 40 min and then was concentrated in vacuo. The residue was purified by silica gel chromatography (eluent: 0.8-5% MeOH in DCM) to provide Example 123.4 (176 mg, 90% yield) as a white solid. LCMS-ESI (pos.): 220.1 (M+H).

Example 127.0. Preparation of (S)—N-(4-(2,6-dimethoxyphenyl)-5-(5-methylfuran-2-yl)-4H-1,2,4-triazol-3-yl)-2-(5-fluoropyrimidin-2-yl)propane-1-sulfonamide and (R)—N-(4-(2,6-dimethoxyphenyl)-5-(5-methylfuran-2-yl)-4H-1,2,4-triazol-3-yl)-2-(5-fluoropyrimidin-2-yl)propane-1-sulfonamide

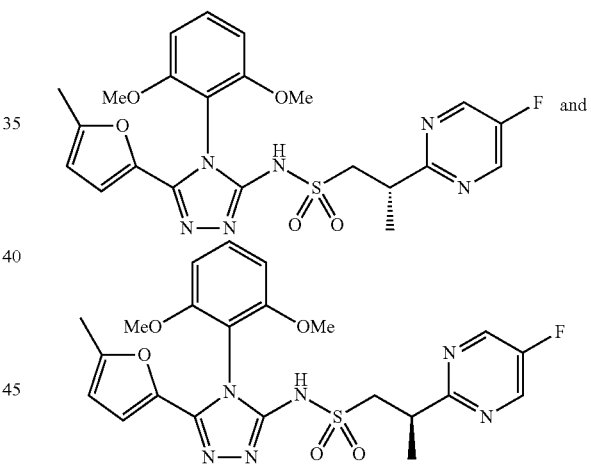

(S)—N-(4-(2,6-Dimethoxyphenyl)-5-(5-methylfuran-2-yl)-4H-1,2,4-triazol-3-yl)-2-(5-fluoropyrimidin-2-yl)propane-1-sulfonamide and (R)—N-(4-(2,6-dimethoxyphenyl)-5-(5-methylfuran-2-yl)-4H-1,2,4-triazol-3-yl)-2-(5-fluoropyrimidin-2-yl)propane-1-sulfonamide, Example 127.0. A microwave vial was charged with 3-bromo-4-(2,6-dimethoxyphenyl)-5-(5-methylfuran-2-yl)-4H-1,2,4-triazole (Example 364.1, 381 mg, 1.05 mmol), 2-(5-fluoropyrimidin-2-yl)propane-1-sulfonamide (Example 123.4, 164 mg, 0.75 mmol), cesium carbonate (609 mg, 1.87 mmol) and rac-trans-N,N'-dimethylcyclohexane-1,2-diamine (236 µL, 1.50 mmol). Dioxane (1.87 mL) was added, and the slurry was degassed with an argon strem. Copper(I) iodide (71 mg, 0.37 mmol) was added and then the slurry was again degassed with an argon strem. The resulting blue slurry was heated in a microwave at 90° C. for 15 h and then was filtered through a plug of Celite® brand filter aid rinsing with EtOAc. The filtrate was transferred to a RBF and concentrated HCl was added dropwise until the color changed to light brown. The mixture was then partitioned between water and EtOAc (2×). The combined organic layers were dried over anhydrous sodium sulfate and concentrated in vacuo. The residue was purified by silica gel chromatography (eluent: 20% EtOAc in hexanes grading to 100% EtOAc) to provide Example 127.0 (97 mg, 26% yield) as an off-white. LCMS-ESI (pos.): 503.1 (M+H).

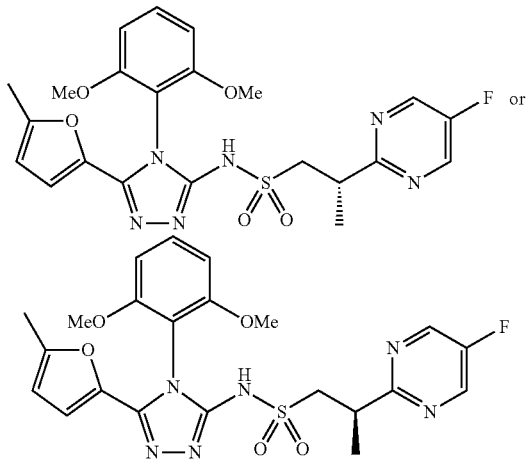

123.0

(S)—N-(4-(2,6-Dimethoxyphenyl)-5-(5-methylfuran-2-yl)-4H-1,2,4-triazol-3-yl)-2-(5-fluoropyrimidin-2-yl)propane-1-sulfonamide or (R)—N-(4-(2,6-dimethoxyphenyl)-5-(5-methylfuran-2-yl)-4H-1,2,4-triazol-3-yl)-2-(5-fluoropyrimidin-2-yl)propane-1-sulfonamide, Example 123.0. Example 127.0 (91 mg, 0.18 mmol) was separated by chiral SFC; Preparative SFC method: Column: 2×25 cm Chiralpak AS-H, 35% i-PrOH/CO$_2$, 100 bar, 65 mL/min, 220 nm, Inj volume: 0.75-1 mL of a 9.0 mg/mL solution of sample in 1:1 MeOH/DCM. This provided the title compound as peak two (36.2 mg, 40% yield, >99% ee) as a white solid. $^1$H NMR (500 MHz, CDCl$_3$) δ: 10.89 (br. s., 1H), 8.53 (s, 2H), 7.46 (t, J=8.5 Hz, 1H), 6.68 (dd, J=8.5, 1.7 Hz, 2H), 5.91 (dd, J=3.5, 1.0 Hz, 1H), 5.75 (d, J=3.5 Hz, 1H), 3.70-3.86 (m, 8H), 3.29 (dd, J=13.8, 5.0 Hz, 1H), 2.32 (s, 3H), 1.42 (d, J=6.9 Hz, 3H). LCMS-ESI (pos.) m/z: 503.1 (M+H)$^+$.

Example 126.0. Preparation of (S)—N-(4-(2,6-dimethoxyphenyl)-5-(5-methylfuran-2-yl)-4H-1,2,4-triazol-3-yl)-2-(5-fluoropyrimidin-2-yl)propane-1-sulfonamide or (R)—N-(4-(2,6-dimethoxyphenyl)-5-(5-methylfuran-2-yl)-4H-1,2,4-triazol-3-yl)-2-(5-fluoropyrimidin-2-yl)propane-1-sulfonamide

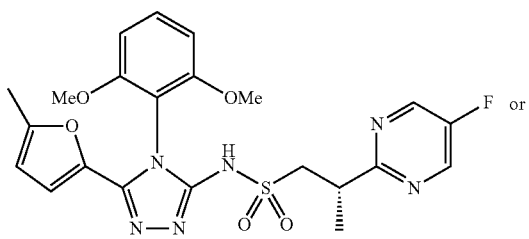

126.0

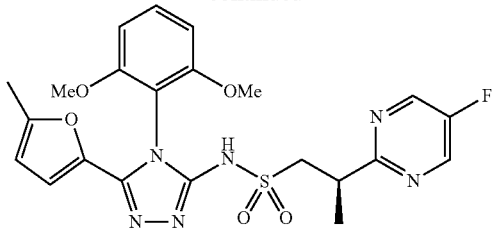

(S)—N-(4-(2,6-Dimethoxyphenyl)-5-(5-methylfuran-2-yl)-4H-1,2,4-triazol-3-yl)-2-(5-fluoropyrimidin-2-yl)propane-1-sulfonamide or (R)—N-(4-(2,6-dimethoxyphenyl)-5-(5-methylfuran-2-yl)-4H-1,2,4-triazol-3-yl)-2-(5-fluoropyrimidin-2-yl)propane-1-sulfonamide, Example 126.0. Example 127.0 (91 mg, 0.18 mmol) was separated by chiral SFC; Preparative SFC method: Column: 2×25 cm Chiralpak AS-H, 35% i-PrOH/CO$_2$, 100 bar, 65 mL/min, 220 nm, Inj volume: 0.75-1 mL of a 9.0 mg/mL solution of sample in 1:1 MeOH/DCM. This provided the title compound as peak one (37.5 mg, 41% yield, >99% ee) as a white solid. $^1$H NMR (500 MHz, CDCl$_3$) δ: 10.90 (br. s., 1H), 8.53 (s, 2H), 7.46 (t, J=8.5 Hz, 1H), 6.68 (dd, J=8.6, 1.7 Hz, 2H), 5.91 (dd, J=3.4, 0.9 Hz, 1H), 5.75 (d, J=3.5 Hz, 1H), 3.70-3.85 (m, 8H), 3.29 (dd, J=13.8, 5.0 Hz, 1H), 2.32 (s, 3H), 1.42 (d, J=7.0 Hz, 3H). LCMS-ESI (pos.) m/z: 503.1 (M+H)$^+$.

Example 125.0. Preparation of N-(4-(2,6-dimethoxyphenyl)-5-(5-methylfuran-2-yl)-4H-1,2,4-triazol-3-yl)-2-(5-fluoropyrimidin-2-yl)ethanesulfonamide 125.0

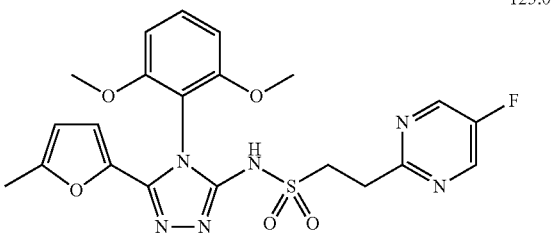

N-(4-(2,6-Dimethoxyphenyl)-5-(5-methylfuran-2-yl)-4H-1,2,4-triazol-3-yl)-2-(5-fluoropyrimidin-2-yl)ethanesulfonamide, Example 125.0. A microwave vial containing Example 364.1 (49 mg, 0.14 mmol), Example 351.0 (110 mg, 0.54 mmol), copper(I) iodide (25.5 mg, 0.14 mmol), trans-N,N'-dimethyl-1,2-cyclohexanediamine (42 μL, 0.27 mmol), and cesium carbonate (219 mg, 0.67 mmol) was degassed and then backfilled with argon. Evacuation and backfilling were repeated three times. 1,4-Dioxane (1.4 mL) was then added and the dark blue-green slurry was heated in a microwave at 100° C. for 4 h. The reaction was concentrated in vacuo and the residue was dissolved in DCM (10 mL) and treated with 1 N citric acid solution (5 mL). The layers were separated and the aqueous layer was extracted with more DCM (4×). The combined organic layers were dried over anhydrous sodium sulfate and concentrated. The residue was purified by reverse phase preparatory HPLC (Sunfire 5 μM C18 column, eluent: 35-75% ACN in water where both solvents contain 0.1% TFA) to provide Example 25.0 (22 mg, 33% yield) as a light yellow solid. $^1$H NMR (500 MHz, CD$_3$OD) δ8.64 (s, 2H), 7.54 (t, J=8.3 Hz, 1H), 6.83 (d, J=8.3 Hz, 2H), 6.01-6.04 (m, 1H), 5.95 (d, J=3.4 Hz, 1H), 3.77 (s, 3H), 3.50-3.55 (m, 2H), 3.34-3.39 (m, 2H), 2.26 (s, 3H). LCMS-ESI (pos.) m/z: 489.0 (M+H)+.

The compounds set forth in the following table were synthesized following the procedure in Example 127.0 using the starting materials as described.

TABLE 5

| Example | Reagents | Structure, Name and Data |
|---|---|---|
| 128.0 | 3-bromo-4-(2,6-dimethoxyphenyl)-5-(5-methylfuran-2-yl)-4H-1,2,4-triazole (Example 364.1), and (S)-1-(5-fluoropyrimidin-2-yl)butane-2-sulfonamide and (R)-1-(5-fluoropyrimidin-2-yl)butane-2-sulfonamide (Example 358.0) | 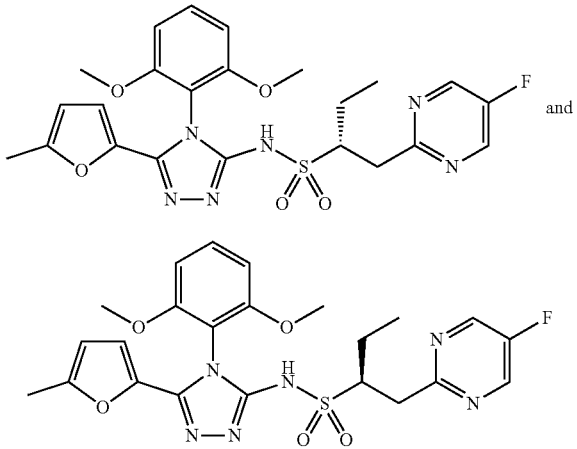(R)-N-(4-(2,6-dimethoxyphenyl)-5-(5-methylfuran-2-yl)-4H-1,2,4-triazol-3-yl)-1-(5-fluoropyrimidin-2-yl)butane-2-sulfonamide and (R)-N-(4-(2,6-dimethoxyphenyl)-5-(5-methylfuran-2-yl)-4H-1,2,4-triazol-3-yl)-1-(5-fluoropyrimidin-2-yl)butane-2-sulfonamide.<br>1H NMR (500 MHz, CDCl3) δ: 8.53 (s, 2H), 7.46 (t, J = 8.5 Hz, 1H), 6.67 (d, J = 8.4 Hz, 2H), 5.89-5.93 (m, 1H), 5.79 (d, J = 3.3 Hz, 1H), 3.76 (s, 3H), 3.58-3.75 (m, 4H), 3.58 (dd, J = 15.1, 6.1 Hz, 1H), 3.21 (dd, J = 15.3, 7.4 Hz, 1H), 2.32 (s, 3H), 1.96-2.07 (m, 1H), 1.65-1.75 (m, 1H), 0.95 (t, J = 7.5 Hz, 3H). LCMS-ESI (pos.) m/z: 517.1 (M + H)+. |
| 129.0 | 3-bromo-4-(2,6-3-bromo-4-(2,6-dimethoxyphenyl)-5-(furan-2-yl)-4H-1,2,4-triazole (Example 364.3), and (R)-2-(5-fluoropyrimidin-2-yl)propane-1-sulfonamide and (S)-2-(5-fluoropyrimidin-2-yl)propane-1-sulfonamide (Example 123.4). | First eluting peak:<br>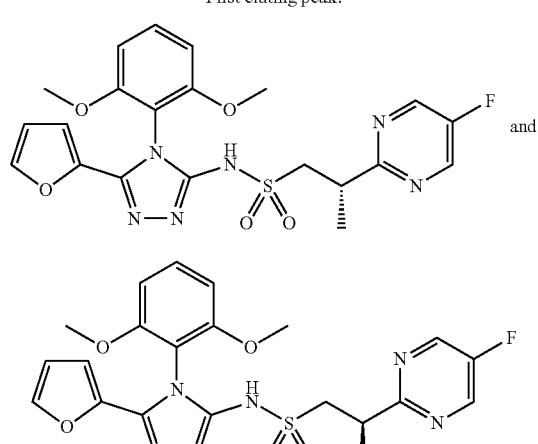(S)-N-(4-(2,6-dimethoxyphenyl)-5-(furan-2-yl)-4H-1,2,4-triazol-3-yl)-2-(5-fluoropyrimidin-2-yl)propane-1-sulfonamide and (R)-N-(4-(2,6-dimethoxyphenyl)-5-(furan-2-yl)-4H-1,2,4-triazol-3-yl)-2-(5-fluoropyrimidin-2-yl)propane-1-sulfonamide.<br>1H NMR (500 MHz, CDCl3) δ: 10.99 (br. s., 1H), 8.53 (s, 2H), 7.44-7.50 (m, 2H), 6.68 (dd, J = 8.4, 3.1 Hz, 2H), 6.34 (dd, J = 3.4, 1.7 Hz, 1H), 5.99 (d, J = 3.7 Hz, 1H), 3.70-3.86 (m, 8H), 3.30 (dd, J = 14.0, 5.1 Hz, 1H), 1.42 (d, J = 7.1 Hz, 3H). LCMS-ESI (pos.) m/z: 489.0 (M + H)+. |

TABLE 5-continued

| Example | Reagents | Structure, Name and Data |
|---|---|---|
| 130.0 | 3-bromo-4-(2,6-dimethoxyphenyl)-5-(5-methylfuran-2-yl)-4H-1,2,4-triazole (Example 364.1), and (1S,2S)-1-ethoxy-1-(5-methylpyrimidin-2-yl)propane-2-sulfonamide and (1R,2R)-1-ethoxy-1-(5-methylpyrimidin-2-yl)propane-2-sulfonamide (Example 356.1). Preparative SFC method: Column: 2 × 15 cm Phenomenex Lux-2 Cell, 40% EtOH/CO$_2$, 100 bar, 65 mL/min, 220 nm, Inj volume: 2.0 mL of a 5.0 mg/mL solution of sample in 5:1 MeOH/DCM. | Second eluting peak:<br>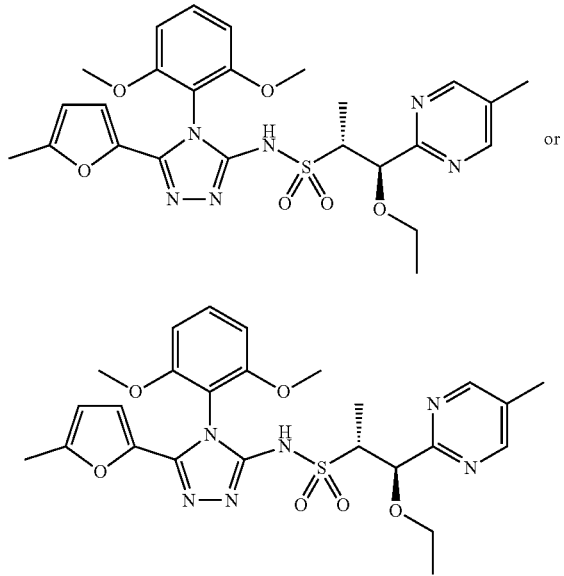<br>(1R,2R)-N-(4-(2,6-dimethoxyphenyl)-5-(5-methylfuran-2-yl)-4H-1,2,4-triazol-3-yl)-1-ethoxy-1-(5-methylpyrimidin-2-yl)propane-2-sulfonamide or (1S,2S)-N-(4-(2,6-dimethoxyphenyl)-5-(5-methylfuran-2-yl)-4H-1,2,4-triazol-3-yl)-1-ethoxy-1-(5-methylpyrimidin-2-yl)propane-2-sulfonamide.<br>$^1$H NMR (500 MHz, CDCl$_3$) δ 12.40 (br. s., 1H), 8.62 (s, 2H), 7.43 (t, J = 8.5 Hz, 1H), 6.61-6.73 (m, 2H), 5.90 (dd, J = 3.3, 1.0 Hz, 1H), 5.73 (d, J = 3.3 Hz, 1H), 4.78 (d, J = 4.9 Hz, 1H), 3.80 (s, 3H), 3.69-3.78 (m, 4H), 3.55 (dq, J = 8.8, 7.0 Hz, 1H), 3.36 (dq, J = 8.9, 7.0 Hz, 1H), 2.33 (s, 3H), 2.33 (s, 3H), 1.39 (d, J = 7.0 Hz, 3H), 1.08 (t, J = 7.0 Hz, 3H). LCMS-ESI (pos.) m/z: 543.2 (M + H)$^+$. |

Example 131.0. Preparation of 2-(2-cyano-4-fluorophenyl)-N-(4-(2,6-dimethoxyphenyl)-5-(5-(trifluoromethyl)furan-2-yl)-4H-1,2,4-triazol-3-yl)ethanesulfonamide

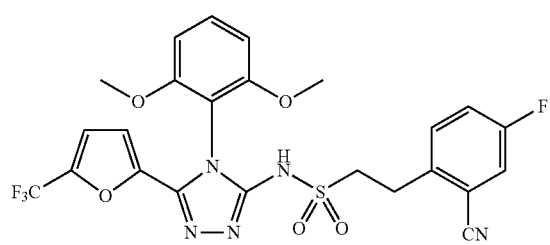

131.0

2-(2-Cyano-4-fluorophenyl)-N-(4-(2,6-dimethoxyphenyl)-5-(5-(trifluoromethyl)furan-2-yl)-4H-1,2,4-triazol-3-yl)ethanesulfonamide, Example 131.0. To a solution of 363.0 (52 mg, 0.15 mmol) and TEA (82 μL, 0.59 mmol) in DCM (2.0 mL) was added 352.6 (51 mg, 0.21 mmol). The resulting orange solution was stirred at RT for 1.5 h and then was quenched with water (5 mL) and extracted with DCM (3×). The combined organic layers were dried over anhydrous sodium sulfate and concentrated. The residue was purified by reverse phase preparatory HPLC (Sunfire 5 μM C18 column, eluent: 45-70% ACN in water where both solvents contain 0.1% TFA) to provide Example 131.0 (36 mg, 41% yield) as a light yellow solid. $^1$H NMR (500 MHz, CD$_3$OD) δ 7.56 (t, J=8.5 Hz, 1H), 7.42-7.52 (m, 2H), 7.32-7.40 (m, 1H), 6.98-7.03 (m, 1H), 6.84 (d, J=8.6 Hz, 2H), 6.40 (d, J=3.9 Hz, 1H), 3.78 (s, 3H), 3.32-3.38 (m, 2H), 3.23-3.30 (m, 2H). LCMS-ESI (pos.) m/z: 566.0 (M+H)$^+$.

The compounds set forth in the following table were synthesized following the procedure in Example 127.0 using the starting materials as described.

TABLE 6

| Example | Reagents | Structure, Name and Data |
|---------|----------|--------------------------|
| 132.0 | 3-bromo-4-(2,6-dimethoxyphenyl)-5-(5-methylfuran-2-yl)-4H-1,2,4-triazole (Example 364.1), and (1R,2R)-1-(5-fluoropyrimidin-2-yl)-1-methoxypropane-2-sulfonamide and (1S,2S)-1-(5-fluoropyrimidin-2-yl)-1-methoxypropane-2-sulfonamide (Example 359.1). Preparative SFC method: Column: 150 × 30 mm ChromegaChiral CC4, 28 g/min MeOH + 42 g/min $CO_2$, 100 bar, 277 nm, Inj volume: 1.0 mL, of a 4.0 mg/mL solution of sample in 3:1 MeOH/DCM. | Second eluting peak:<br />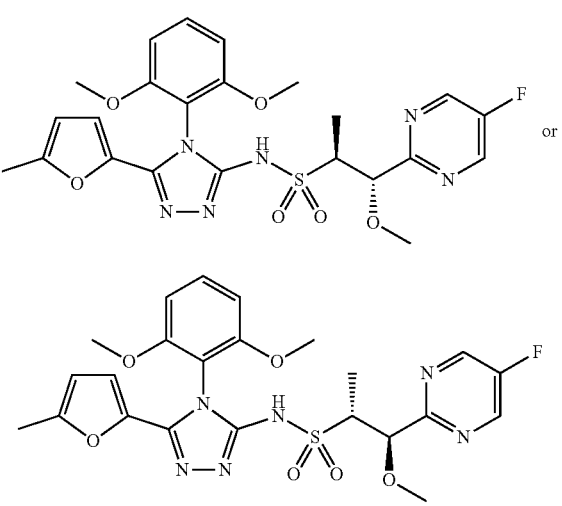<br />(1S,2S)-N-(4-(2,6-dimethoxyphenyl)-5-(5-methylfuran-2-yl)-4H-1,2,4-triazol-3-yl)-1-(5-fluoropyrimidin-2-yl)-1-methoxypropane-2-sulfonamide or (1R,2R)-N-(4-(2,6-dimethoxyphenyl)-5-(5-methylfuran-2-yl)-4H-1,2,4-triazol-3-yl)-1-(5-fluoropyrimidin-2-yl)-1-methoxypropane-2-sulfonamide.<br />$^1$H NMR (400 MHz, $CDCl_3$) δ 11.24 (br. s., 1H), 8.62 (s, 2H), 7.46 (t, J = 8.4 Hz, 1H), 6.67 (dd, J = 8.5, 3.4 Hz, 2H), 5.91 (dd, J = 3.4, 0.9 Hz, 1H), 5.76 (d, J = 3.5 Hz, 1H), 4.80 (d, J = 6.5 Hz, 1H), 3.81 (s, 3H), 3.71-3.80 (m, 4H), 3.24 (s, 3H), 2.32 (s, 3H), 1.24 (d, J = 7.0 Hz, 3H). LCMS-ESI (pos.) m/z: 533.2 (M + H)$^+$. |

Example 134.0. Preparation of (R)—N-(4-(2,6-dimethoxyphenyl)-5-(5-methylfuran-2-yl)-4H-1,2,4-triazol-3-yl)-1-(5-fluoropyrimidin-2-yl)butane-2-sulfonamide or (S)—N-(4-(2,6-dimethoxyphenyl)-5-(5-methylfuran-2-yl)-4H-1,2,4-triazol-3-yl)-1-(5-fluoropyrimidin-2-yl)butane-2-sulfonamide 134.1

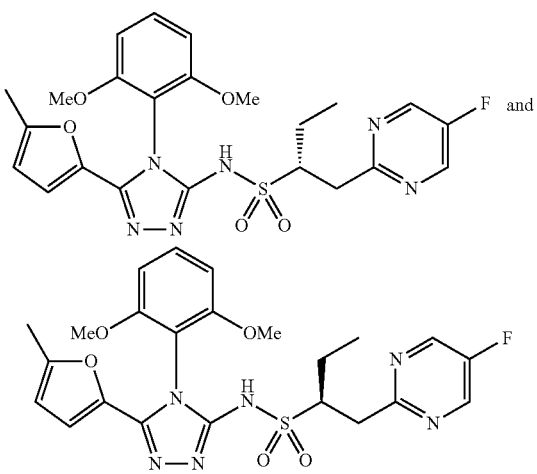

(R)—N-(4-(2,6-Dimethoxyphenyl)-5-(5-methylfuran-2-yl)-4H-1,2,4-triazol-3-yl)-1-(5-fluoropyrimidin-2-yl)butane-2-sulfonamide and (S)—N-(4-(2,6-dimethoxyphenyl)-5-(5-methylfuran-2-yl)-4H-1,2,4-triazol-3-yl)-1-(5-fluoropyrimidin-2-yl)butane-2-sulfonamide, Example 134.1. A microwave vial was charged with 3-bromo-4-(2,6-dimethoxyphenyl)-5-(5-methylfuran-2-yl)-4H-1,2,4-triazole (Example 364.1, 120 mg, 0.33 mmol), 1-(5-fluoropyrimidin-2-yl)butane-2-sulfonamide (Example 358.0, 96 mg, 0.412 mmol), cesium carbonate (268 mg, 0.82 mmol), rac-trans-N,N'-dimethylcyclohexane-1,2-diamine (104 µL, 0.66 mmol) and crushed, powdered 4 Å molecular sieves (125 mg). Dioxane (720 µL) was added and the slurry was degassed with an argon stream. Copper(I) iodide (31.5 mg, 0.17 mmol) was added and then the slurry was again degassed with an argon strem. The resulting blue slurry was heated in a microwave at 90° C. for 15 h and then was filtered through a pad of Celite® brand filter aid rinsing with EtOAc. The filtrate was partitioned between water and EtOAc (4×). The combined organic layers were dried over anhydrous sodium sulfate and concentrated. The residue was purified twice by reverse phase preparatory HPLC (eluent: 30% ACN in water grading to 60% ACN in water where both solvents contain 0.1% TFA) to provide Example 134.1 (56 mg, 33% yield) as a tan solid. LCMS-ESI (pos.): 517.1 (M+H).

134.0

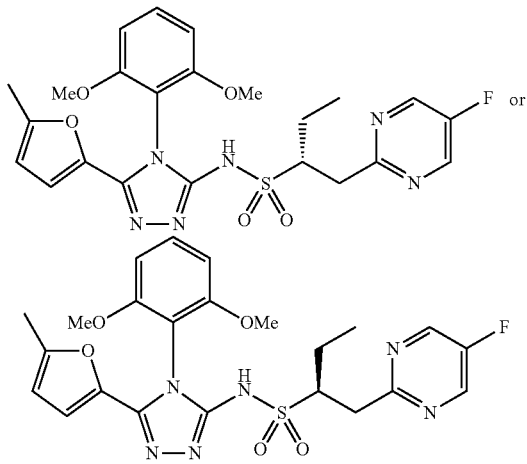

(R)—N-(4-(2,6-Dimethoxyphenyl)-5-(5-methylfuran-2-yl)-4H-1,2,4-triazol-3-yl)-1-(5-fluoropyrimidin-2-yl)butane-2-sulfonamide or (S)—N-(4-(2,6-dimethoxyphenyl)-5-(5-methylfuran-2-yl)-4H-1,2,4-triazol-3-yl)-1-(5-fluoropyrimidin-2-yl)butane-2-sulfonamide, Example 133.0. Example 131.1 (51 mg, 0.10 mmol) was separated by chiral SFC using the following preparative SFC method: Column: 2×15 cm Chiralpak AD-H, 35% i-PrOH/CO$_2$, 100 bar, 60 mL/min, 220 nm, Inj volume: 1.0 mL of a 4.6 mg/mL solution of sample in 4:1 EtOH/DCM. This delivered the title compound as peak two (16.4 mg, 32% yield, >99% ee) as an off-white solid. $^1$H NMR (500 MHz, CDCl$_3$) δ: 8.54 (s, 2H), 7.46 (t, J=8.4 Hz, 1H), 6.67 (d, J=8.4 Hz, 2H), 5.91 (d, J=3.1 Hz, 1H), 5.79 (d, J=3.5 Hz, 1H), 3.76 (s, 3H), 3.58-3.75 (m, 4H), 3.58 (dd, J=15.1, 6.3 Hz, 1H), 3.21 (dd, J=14.9, 7.2 Hz, 1H), 2.32 (s, 3H), 1.95-2.06 (m, 1H), 1.65-1.75 (m, 1H), 0.95 (t, J=7.5 Hz, 3H). LCMS-ESI (pos.) m/z: 517.1 (M+H)$^+$.

Example 135.0. Preparation of (2S,3R)—N-(4-(2,6-dimethoxyphenyl)-5-(5-methylfuran-2-yl)-4H-1,2,4-triazol-3-yl)-3-(5-fluoropyrimidin-2-yl)butane-2-sulfonamide and (2R,3S)—N-(4-(2,6-dimethoxyphenyl)-5-(5-methylfuran-2-yl)-4H-1,2,4-triazol-3-yl)-3-(5-fluoropyrimidin-2-yl)butane-2-sulfonamide and (2S,3S)—N-(4-(2,6-dimethoxyphenyl)-5-(5-methylfuran-2-yl)-4H-1,2,4-triazol-3-yl)-3-(5-fluoropyrimidin-2-yl)butane-2-sulfonamide and (2R,3R)—N-(4-(2,6-dimethoxyphenyl)-5-(5-methylfuran-2-yl)-4H-1,2,4-triazol-3-yl)-3-(5-fluoropyrimidin-2-yl)butane-2-sulfonamide 135.0

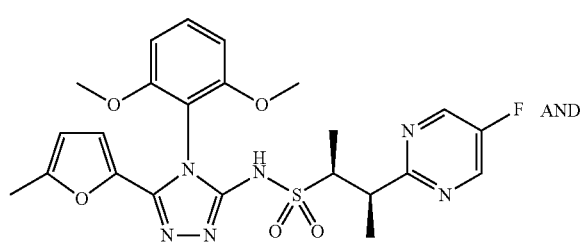

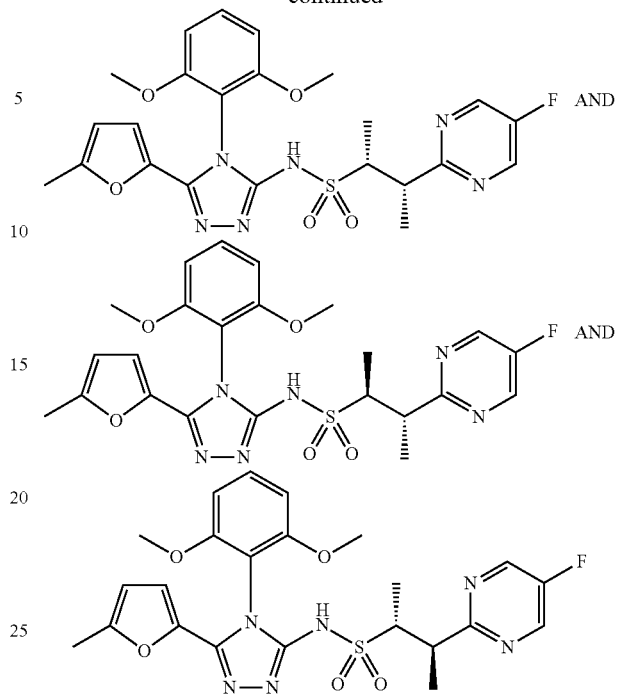

(2S,3R)—N-(4-(2,6-Dimethoxyphenyl)-5-(5-methylfuran-2-yl)-4H-1,2,4-triazol-3-yl)-3-(5-fluoropyrimidin-2-yl)butane-2-sulfonamide and (2R,3S)—N-(4-(2,6-dimethoxyphenyl)-5-(5-methylfuran-2-yl)-4H-1,2,4-triazol-3-yl)-3-(5-fluoropyrimidin-2-yl)butane-2-sulfonamide and (2S,3S)—N-(4-(2,6-dimethoxyphenyl)-5-(5-methylfuran-2-yl)-4H-1,2,4-triazol-3-yl)-3-(5-fluoropyrimidin-2-yl)butane-2-sulfonamide and (2R,3R)—N-(4-(2,6-dimethoxyphenyl)-5-(5-methylfuran-2-yl)-4H-1,2,4-triazol-3-yl)-3-(5-fluoropyrimidin-2-yl)butane-2-sulfonamide, Example 135.0. A microwave vial containing Example 364.1 (70 mg, 0.19 mmol), Example 354.0 (50 mg, 0.21 mmol), copper(I) iodide (18.3 mg, 0.10 mmol), trans-N,N-dimethyl-1,2-cyclohexanediamine (60 µL, 0.38 mmol), and cesium carbonate (157 mg, 0.48 mmol) was degassed and then backfilled with argon. Evacuation and backfilling were repeated three times. 1,4-Dioxane (0.48 mL) was then added and the dark blue-green slurry was heated in a microwave at 90° C. for 15 h. The reaction was then filtered through a plug of Celite® brand filter aid rinsing with EtOAc and water. The filtrate was extracted with EtOAc (3×). The combined organic layers were dried over anhydrous sodium sulfate and concentrated. The residue was purified by reverse phase preparatory HPLC (Sunfire 5 µM C18 column, eluent: 35-55% ACN in water over a 35 min period where both solvents contain 0.1% TFA) to provide Example 135.0 (19.4 mg, 20% yield) as a white solid. $^1$H NMR (500 MHz, CDCl$_3$) δ 8.55 (br. s, 2H), 7.46 (t, J=8.3 Hz, 1H), 6.67 (d, J=7.7 Hz, 2H), 5.83-5.91 (m, 1H), 5.77-5.81 (m, 1H), 3.76 (s, 3H, major diastereomer), 3.76 (s, 3H, major diastereomer), 3.75 (s, 3H, minor diastereomer), 3.74 (s, 3H, minor diastereomer), 3.62-3.70 (m, 1H), 3.53-3.60 (m, 1H), 2.32 (s, 3H), 1.49 (d, J=6.4 Hz, 3H, major diastereomer), 1.37 (d, J=6.2 Hz, 3H, minor diastereomer), 1.35 (d, J=6.2 Hz, 3H, minor diastereomer), 1.26 (d, J=6.2 Hz, 3H, major diastereomer). $^1$H NMR analysis indicated that a 2.2:1 d.r. was obtained. LCMS-ESI (pos.) m/z: 517.1 (M+H)$^+$.

Example 136.0. Preparation of (R)—N-(4-(2,6-dimethoxyphenyl)-5-(furan-2-yl)-4H-1,2,4-triazol-3-yl)-1-(5-fluoropyrimidin-2-yl)butane-2-sulfonamide or (S)—N-(4-(2,6-dimethoxyphenyl)-5-(furan-2-yl)-4H-1,2,4-triazol-3-yl)-1-(5-fluoropyrimidin-2-yl)butane-2-sulfonamide 136.1

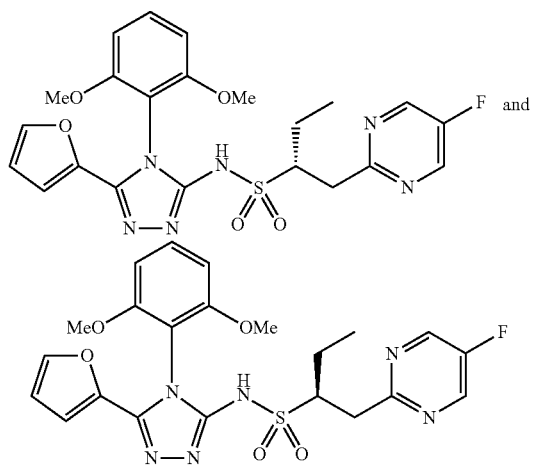

(R)—N-(4-(2,6-Dimethoxyphenyl)-5-(furan-2-yl)-4H-1,2,4-triazol-3-yl)-1-(5-fluoropyrimidin-2-yl)butane-2-sulfonamide and (S)—N-(4-(2,6-dimethoxyphenyl)-5-(furan-2-yl)-4H-1,2,4-triazol-3-yl)-1-(5-fluoropyrimidin-2-yl)butane-2-sulfonamide, Example 136.1. A microwave vial was charged with 3-bromo-4-(2,6-dimethoxyphenyl)-5-(furan-2-yl)-4H-1,2,4-triazole (Example 364.3, 105 mg, 0.30 mmol), 1-(5-fluoropyrimidin-2-yl)butane-2-sulfonamide (Example 358.0, 80 mg, 0.35 mmol), cesium carbonate (244 mg, 0.75 mmol), rac-trans-N,N'-dimethylcyclohexane-1,2-diamine (95 µL, 0.60 mmol) and powdered 4 A molecular sieves (110 mg). Dioxane (650 µL) was added and the slurry was degassed with an argon stream. Copper(I) iodide (29 mg, 0.15 mmol) was then added and the slurry was again degassed with an argon stream. The resulting blue slurry was heated in a microwave at 90° C. for 12 h and then was filtered through a plug of Celite® brand filter aid rinsing with EtOAc. The filtrate was partitioned between water and EtOAc (4×). The combined organic layers were dried over anhydrous sodium sulfate and concentrated. The residue was purified twice by reverse phase preparatory HPLC (eluent: 30% ACN in water grading to 65% ACN in water where both solvents contain 0.1% TFA) to provide the title compound (38 mg, 25% yield) as a light pink solid. LCMS-ESI (pos.): 503.1 (M+H).

136.0

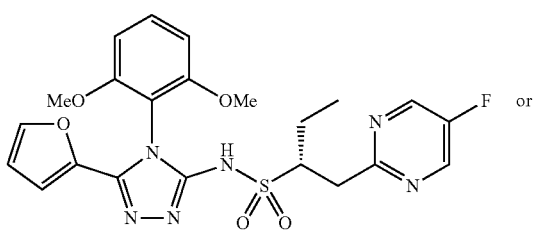

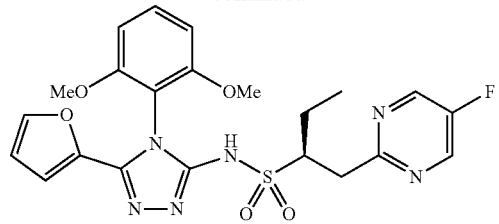

(R)—N-(4-(2,6-Dimethoxyphenyl)-5-(furan-2-yl)-4H-1,2,4-triazol-3-yl)-1-(5-fluoropyrimidin-2-yl)butane-2-sulfonamide or (S)—N-(4-(2,6-dimethoxyphenyl)-5-(furan-2-yl)-4H-1,2,4-triazol-3-yl)-1-(5-fluoropyrimidin-2-yl)butane-2-sulfonamide, Example 136.0. Example 136.1 (52 mg, 0.10 mmol) was separated by chiral SFC using the following preparative SFC method: Column: 250×21 mm Chirlpak IA 16.5 g/min MeOH containing 20 mM ammonia+38.5 g/min $CO_2$, 100 bar, 215 nm, Inj volume: 0.2 mL of a 5.0 mg/mL solution of sample in 1:1 MeOH/DCM. This provided peak two as the title compound (10.7 mg, 53% yield, % ee not determined) as an off-white solid. $^1$H NMR (500 MHz, $CDCl_3$) δ: 11.15 (br. s., 1H), 8.53 (s, 2H), 7.43-7.50 (m, 2H), 6.67 (d, J=8.4 Hz, 2H), 6.33 (dd, J=3.5, 1.8 Hz, 1H), 5.99 (d, J=3.5 Hz, 1H), 3.76 (s, 3H), 3.68-3.75 (m, 4H), 3.58 (dd, J=15.2, 6.0 Hz, 1H), 3.21 (dd, J=15.3, 7.6 Hz, 1H), 1.94-2.07 (m, 1H), 1.62-1.75 (m, 1H), 0.94 (t, J=7.5 Hz, 3H). LCMS-ESI (pos.) m/z: 503.1 $(M+H)^+$.

Example 137.0. Preparation of 2-(4-chlorophenyl)-N-(4-(2,6-dimethoxyphenyl)-5-(5-methylfuran-2-yl)-4H-1,2,4-triazol-3-yl)ethanesulfonamide

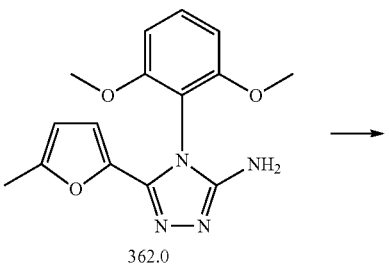

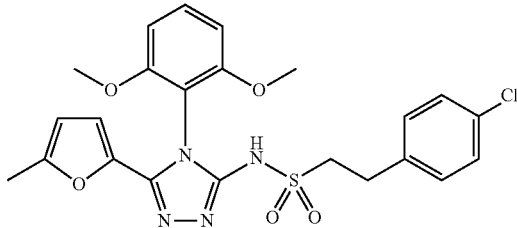

137.0

2-(4-Chlorophenyl)-N-(4-(2,6-dimethoxyphenyl)-5-(5-methylfuran-2-yl)-4H-1,2,4-triazol-3-yl)ethanesulfonamide, Example 137.0. To a solution of Example 362.0 (14.5 mg, 0.05 mmol) and TEA (54 µL, 0.39 mmol) in DCM (1.8 mL) was added 2-(4-chlorophenyl)ethanesulfonyl chloride (35 mg, 0.15 mmol). The resulting yellow solution was stirred at RT for 5.25 h and then was quenched with water (5 mL) and extracted with DCM (3×). The combined organic layers were dried over anhydrous sodium sulfate and concentrated. The residue was purified by reverse phase preparatory HPLC (Sunfire 5 μM C18 column, eluent: 55-75% ACN in water where both solvents contain 0.1% TFA) and provided Example 137.0 (3.2 mg, 13% yield) as a light yellow solid. ¹H NMR (500 MHz, CD₃OD) δ 7.55 (t, J=8.6 Hz, 1H), 7.27 (d, J=8.1 Hz, 2H), 7.18 (d, J=8.3 Hz, 2H), 6.85 (d, J=8.6 Hz, 2H), 6.01 (d, J=2.9 Hz, 1H), 5.93 (d, J=2.7 Hz, 1H), 3.75 (s, 3H), 3.21-3.28 (m, 2H), 2.96-3.06 (m, 2H), 2.25 (s, 3H). LCMS-ESI (pos.) m/z: 503.0 (M+H)⁺.

The compounds set forth in the following table were synthesized following the procedure in Example 137.0 using the starting material as described.

TABLE 7

| Example | Reagents | Structure, Name and Data |
|---|---|---|
| 138.0 | 4-(2,6-dimethoxyphenyl)-5-(5-(methoxymethyl)furan-2-yl)-4H-1,2,4-triazol-3-amine (Example 16.3). | 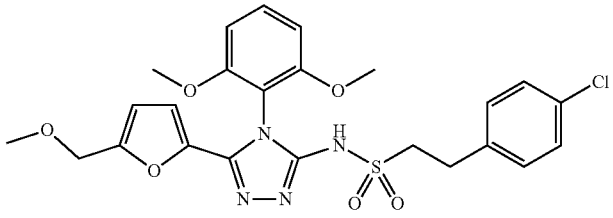 [SMILES: COCc1ccc(-c2nnc(NS(=O)(=O)CCc3ccc(Cl)cc3)n2-c2c(OC)cccc2OC)o1]<br>2-(4-chlorophenyl)-N-(4-(2,6-dimethoxyphenyl)-5-(5-(methoxymethyl)furan-2-yl)-4H-1,2,4-triazol-3-yl)ethanesulfonamide.<br>¹H NMR (400 MHz, DMSO-d₆) δ 13.38 (s, 1H), 7.57 (t, J = 8.5 Hz, 1H), 7.30-7.36 (m, 2H), 7.22 (d, J = 8.6 Hz, 2H), 6.90 (d, J = 8.6 Hz, 2H), 6.47 (d, J = 3.5 Hz, 1H), 5.98 (d, J = 3.5 Hz, 1H), 4.31 (s, 2H), 3.72 (s, 3H), 3.72 (s, 3H), 3.18 (s, 3H), 3.14-3.22 (m, 2H), 2.85-2.92 (m, 2H). LCMS-ESI (pos.) m/z: 533.0 (M + H)⁺. |
| 139.0 | 4-(2,6-dimethoxyphenyl)-5-(5-(trifluoromethyl)furan-2-yl)-4H-1,2,4-triazol-3-amine (Example 363.0). | 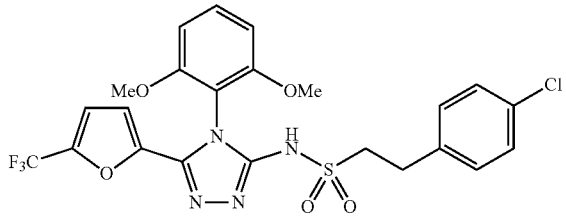 [SMILES: COc1cccc(OC)c1-n1c(NS(=O)(=O)CCc2ccc(Cl)cc2)nnc1-c1ccc(C(F)(F)F)o1]<br>2-(4-chlorophenyl)-N-(4-(2,6-dimethoxyphenyl)-5-(5-(trifluoromethyl)furan-2-yl)-4H-1,2,4-triazol-3-yl)ethanesulfonamide.<br>¹H NMR (400 MHz, CD₃OD) δ 7.57 (t, J = 8.41 Hz, 1H), 7.26-7.33 (m, 2H), 7.14-7.21 (m, 2H), 6.99-7.05 (m, 1H), 6.82-6.89 (d, J = 8.41 Hz, 2H), 6.38-6.44 (m, 1H), 3.78 (s, 3H), 3.78 (s, 3H), 3.22-3.28 (m, 2H), 2.97-3.05 (m, 2H). Mass spectrum (ESI) m/z = 557.0 (M + H). |
| 140.0 | 5-(5-bromofuran-2-yl)-4-(2,6-dimethoxyphenyl)-4H-1,2,4-triazol-3-amine (Example 362.04). | 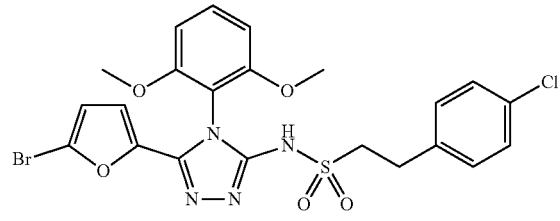 [SMILES: COc1cccc(OC)c1-n1c(NS(=O)(=O)CCc2ccc(Cl)cc2)nnc1-c1ccc(Br)o1]<br>N-(5-(5-bromofuran-2-yl)-4-(2,6-dimethoxyphenyl)-4H-1,2,4-triazol-3-yl)-2-(4-chlorophenyl)ethanesulfonamide.<br>¹H NMR (400 MHz, DMSO-d₆) δ 13.46 (s, 1H), 7.57 (t, J = 8.5 Hz, 1H), 7.31-7.36 (m, 2H), 7.18-7.24 (m, 2H), 6.90 (d, J = 8.6 Hz, 2H), 6.66 (d, J = 3.7 Hz, 1H), 6.06 (d, J = 3.7 Hz, 1H), 3.73 (s, 3H), 3.73 (s, 3H), 3.16-3.23 (m, 2H), 2.85-2.92 (m, 2H). LCMS-ESI (pos.) m/z: 567.0 (M + H)⁺. |

TABLE 7-continued

| Example | Reagents | Structure, Name and Data |
|---------|----------|--------------------------|
| 141.0 | 5-(5-(tert-butyl)furan-2-yl)-4-(2,6-dimethoxyphenyl)-4H-1,2,4-triazol-3-amine (Example 16.2). | 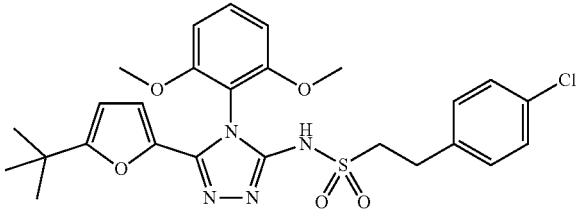 [SMILES: COc1cccc(OC)c1-n1c(NS(=O)(=O)CCc2ccc(Cl)cc2)nnc1-c1ccc(C(C)(C)C)o1]<br>N-(5-(5-(tert-butyl)furan-2-yl)-4-(2,6-dimethoxyphenyl)-4H-1,2,4-triazol-3-yl)-2-(4-chlorophenyl)ethanesulfonamide.<br>$^1$H NMR (400 MHz, CD$_3$OD) δ 7.53 (t, J = 8.5 Hz, 1H), 7.24-7.32 (m, 2H), 7.13-7.21 (m, 2H), 6.85 (d, J = 8.6 Hz, 2H), 6.41 (d, J = 3.5 Hz, 1H), 6.06 (d, J = 3.5 Hz, 1H), 3.73 (s, 3H), 3.73 (s, 3H), 3.20-3.26 (m, 2H), 2.97-3.05 (m, 2H), 1.11 (s, 9H).<br>LCMS-ESI (pos.) m/z: 545.2 (M + H)$^+$. |

Example 142.0. Preparation of N-(5-(5-(tert-butyl)furan-2-yl)-4-(2,6-dimethoxyphenyl)-4H-1,2,4-triazol-3-yl)-2-(2-cyano-4-fluorophenyl)ethanesulfonamide

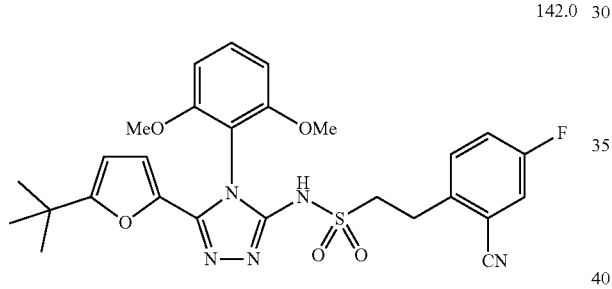

142.0

N-(5-(5-(tert-Butyl)furan-2-yl)-4-(2,6-dimethoxyphenyl)-4H-1,2,4-triazol-3-yl)-2-(2-cyano-4-fluorophenyl)ethanesulfonamide, Example 142.0. To a solution of 5-(5-(tert-butyl)furan-2-yl)-4-(2,6-dimethoxyphenyl)-4H-1,2,4-triazol-3-amine, Example 363.2 (48 mg, 0.14 mmol) in DCM (2 mL), was added TEA (78 µL, 0.56 mmol) via syringe followed by 2-(2-cyano-4-fluorophenyl)ethanesulfonyl chloride Example 352.6 (49 mg, 0.20 mmol) directly. The resulting orange solution was stirred at RT for 3 h and then was partitioned between water and DCM (3×). The combined organic layers were dried over anhydrous sodium sulfate and concentrated. The residue was purified by reverse phase preparatory HPLC (eluent: 50% ACN in water grading to 75% ACN in water where both solvents contain 0.1% TFA) to provide Example 142.0 (18 mg, 23% yield) as an off-white solid. $^1$H NMR (500 MHz, DMSO-d$_6$) δ 13.34 (s, 1H), 7.80 (dd, J=2.69, 8.56 Hz, 1H), 7.46-7.59 (m, 3H), 6.89 (d, J=8.56 Hz, 2H), 6.40 (d, J=3.67 Hz, 1H), 6.16 (d, J=3.42 Hz, 1H), 3.71 (s, 3H), 3.71 (s, 3H), 3.24-3.30 (m, 2H), 3.07-3.14 (m, 2H), 1.06 (m, 9H). LCMS-ESI (pos.): 554.2 (M+H).

Example 143.0. Preparation of (1S,2R)-1-(2,4-dicyanophenyl)-N-(4-(2,6-dimethoxyphenyl)-5-(5-methyl-2-furanyl)-4H-1,2,4-triazol-3-yl)-1-methoxy-2-propanesulfonamide or (1R,2S)-1-(2,4-dicyanophenyl)-N-(4-(2,6-dimethoxyphenyl)-5-(5-methyl-2-furanyl)-4H-1,2,4-triazol-3-yl)-1-methoxy-2-propanesulfonamide 143.1

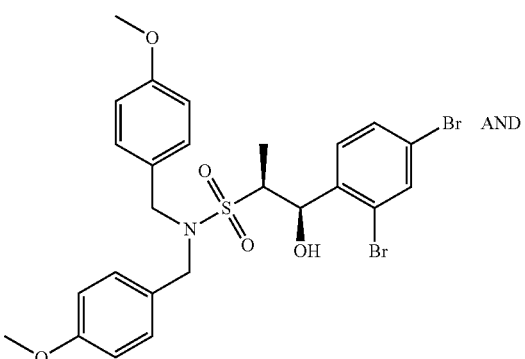

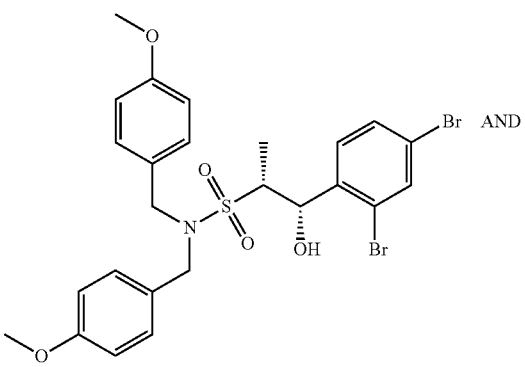

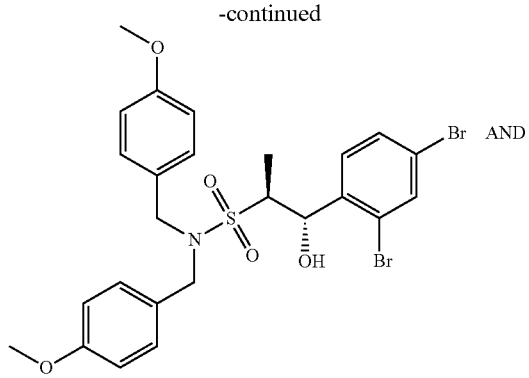

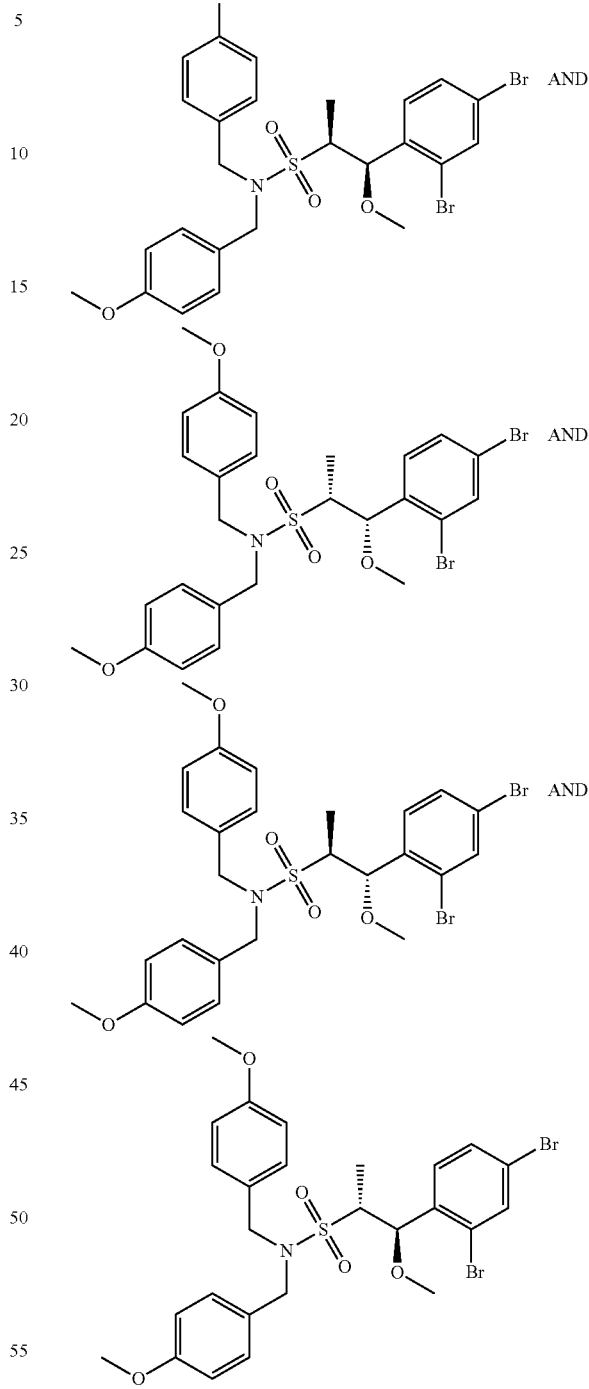

143.2

(1R,2R)-1-(2,4-Dibromophenyl)-1-hydroxy-N,N-bis(4-methoxybenzyl)propane-2-sulfonamide and (1R,2S)-1-(2,4-dibromophenyl)-1-hydroxy-N,N-bis(4-methoxybenzyl)propane-2-sulfonamide and (1S,2R)-1-(2,4-dibromophenyl)-1-hydroxy-N,N-bis(4-methoxybenzyl)propane-2-sulfonamide and (1S,2S)-1-(2,4-dibromophenyl)-1-hydroxy-N,N-bis(4-methoxybenzyl)propane-2-sulfonamide, Example 143.1. To a 250 mL RBF was added Example 361.0 (3.06 g, 8.76 mmol) in 2-methyltetrahydrofuran (22 mL). n-Butyllithium, (2.5M solution in hexanes, 4.20 mL, 10.51 mmol) was then added under $N_2$ at −78° C. The reaction mixture was stirred at −78° C. for 10 min and then left at RT for 20 min. 2,4-Dibromobenzaldehyde (2.54 g, 9.63 mmol) in 2-methyltetrahydrofuran (22 mL) was then added dropwise under $N_2$ at −78° C. The reaction mixture was stirred at −78° C. for 1 h. LCMS analysis indicated formation of the desired product. The reaction was quenched with a saturated aqueous solution of $NH_4Cl$. The reaction mixture was diluted with a saturated solution of $NH_4Cl$ and extracted with EtOAc. The organic layer was washed with brine and dried over $Na_2SO_4$. The solution was filtered and concentrated in vacuo to give a light-yellow solid which was purified by silica gel chromatography (a gradient of 0% to 100% EtOAc in DCM). This provided the title compound Example 143.1 (4.9 g, 7.99 mmol, 91% yield) as a white solid which was a mixture of diastereomers. LCMS-ESI (pos.), m/z: 634.0 $(M+Na)^+$.

(1R,2R)-1-(2,4-Dibromophenyl)-1-methoxy-N,N-bis(4-methoxybenzyl)propane-2-sulfonamide and (1R,2S)-1-(2,4-dibromophenyl)-1-methoxy-N,N-bis(4-methoxybenzyl)propane-2-sulfonamide and (1S,2R)-1-(2,4-dibromophenyl)-1-methoxy-N,N-bis(4-methoxybenzyl)propane-2-sulfonamide and (1S,2S)-1-(2,4-dibromophenyl)-1-methoxy-N,N-bis(4-methoxybenzyl)propane-2-sulfonamide, Example 143.2. To a 250 mL RBF was added Example 143.1 (4.9 g, 7.99 mmol) in 2-methyltetrahydrofuran (53.3 mL). Potassium bis(trimethylsilyl)amide, (1.0 M in THF, 8.79 mL, 8.79 mmol) was added under N₂ at −78° C. The reaction mixture was stirred at −78° C. for 10 min and then left at RT for 5 min. Iodomethane (0.546 mL, 8.79 mmol) was then added dropwise under N₂ at −78° C. The reaction mixture was stirred at −78° C. for 30 min and then the dry ice-acetone bath was removed. The mixture was then left at RT for 10 min. LCMS analysis indicated formation of the desired product but the reaction was not complete. The reaction mixture was stirred at RT for 16 h. The reaction mixture was cooled to −78° C. again and quenched with saturated aqueous NaHCO₃. The reaction mixture was diluted with water and extracted with EtOAc. The combined organic layers were washed with brine and dried over Na₂SO₄. The solution was then filtered and concentrated in vacuo to give a light-yellow oil which was purified by silica gel chromatography (0% to 100% EtOAc in hexanes), to provide Example 143.2 (5.0 g, 7.97 mmol, 100% yield) as a white solid which was a mixture of diastereomers. LCMS-ESI (pos.), m/z: 626.0 (M+H)⁺.

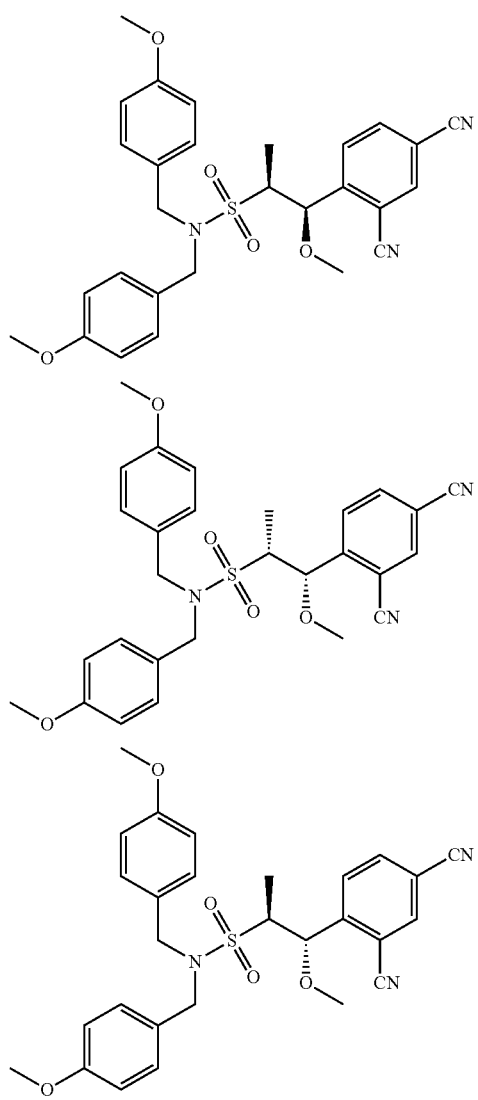

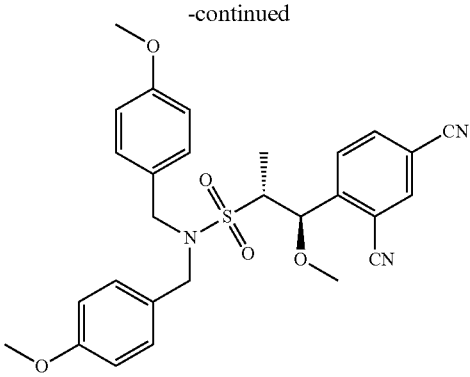

(1R,2R)-1-(2,4-Dicyanophenyl)-1-methoxy-N,N-bis(4-methoxybenzyl)propane-2-sulfonamide and (1R,2S)-1-(2,4-dicyanophenyl)-1-methoxy-N,N-bis(4-methoxybenzyl)propane-2-sulfonamide and (1S,2R)-1-(2,4-dicyanophenyl)-1-methoxy-N,N-bis(4-methoxybenzyl)propane-2-sulfonamide and (1S,2S)-1-(2,4-dicyanophenyl)-1-methoxy-N,N-bis(4-methoxybenzyl)propane-2-sulfonamide, Example 143.3. To a 250 mL RBF was added Example 143.2 (5.0 g, 7.97 mmol) in DMAc (53.1 mL). Under N₂, zinc cyanide (2.059 g, 17.53 mmol) and bis(tri-tert-butylphosphine)palladium (0) (0.815 g, 1.594 mmol) were added. The reaction mixture was stirred at 100° C. for 15 h. The reaction mixture was then cooled and filtered. The solution was concentrated in vacuo at 75° C. The material thus obtained was purified by silica gel chromatography (gradient of 0% to 100% EtOAc in DCM) to provide Example 143.3 (4 g, 7.70 mmol, 97% yield) as a white solid which was a mixture of diastereomers. LCMS-ESI (pos.), m/z: 542.2 (M+Na)⁺.

(1R,2R)-1-(2,4-Dicyanophenyl)-1-methoxypropane-2-sulfonamide and (1R,2S)-1-(2,4-dicyanophenyl)-1-methoxypropane-2-sulfonamide and (1S,2R)-1-(2,4-dicyanophenyl)-1-methoxypropane-2-sulfonamide and (1S,2S)-1-(2,4-dicyanophenyl)-1-methoxypropane-2-sulfonamide, Example 143.4. To a 250 mL RBF was added Example 143.3 (4 g, 7.70 mmol) and anisole (4.18 mL, 38.5 mmol) in TFA (42.8 mL, 7.70 mmol). The reaction mixture was stirred at RT for 15 h. The reaction mixture was concentrated in vacuo. The material thus obtained was purified by silica gel chromatography (gradient of 0% to 100% EtOAc in DCM). This provided Example 143.4 (1.6 g, 5.73 mmol, 74% yield) as a white solid which was a mixture of diastereomers. LCMS-ESI (pos.), m/z: 302.1 (M+Na)+.

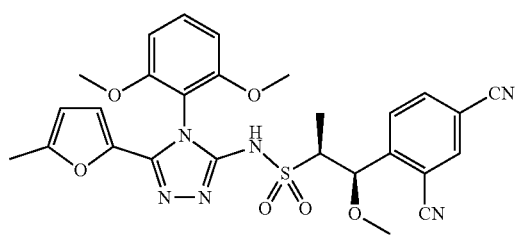

143.0

OR

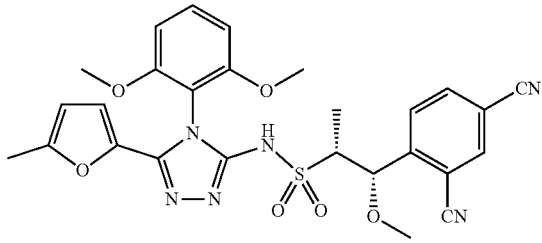

(1S,2R)-1-(2,4-Dicyanophenyl)-N-(4-(2,6-dimethoxyphenyl)-5-(5-methyl-2-furanyl)-4H-1,2,4-triazol-3-yl)-1-methoxy-2-propanesulfonamide or (1R,2S)-1-(2,4-dicyanophenyl)-N-(4-(2,6-dimethoxyphenyl)-5-(5-methyl-2-furanyl)-4H-1,2,4-triazol-3-yl)-1-methoxy-2-propanesulfonamide, Example 143.0. Example 143.0 was the second isomer to elute from a CC4 column on subjecting Example 149.0 to the following SFC conditions: Thar 80 SFC with 250×30 mm CC4 column with 44 g/min MeOH (neat)+36 g/min CO$_2$, 55% co-solvent at 80 g/min. Temp.=27° C., Outlet pressure=100 bar, Wavelength=276 nm. Injected 0.7 mL of 164 mg sample dissolved in 12 mL (8:4) MeOH:DCM; c=13.6 mg/mL, i.e. 10.9 mg per injection. Cycle time 10.8 min, run time=17 min. $^1$H NMR (500 MHz, CD$_3$OD) 8.20 (d, J=1.71 Hz, 1H) 8.43 (d, J=1.37 Hz, 1H) 8.02 (dd, J=8.31, 1.71 Hz, 1H) 7.67 (d, J=7.94 Hz, 1H) 7.58 (t, J=8.40 Hz, 1H) 6.88 (d, J=8.38 Hz, 2H) 6.00-6.08 (m, 1H) 5.96 (d, J=3.42 Hz, 1H) 5.16 (d, J=3.91 Hz, 1H) 4.84-4.92 (m, 17H) 3.79-3.84 (m, 6H) 3.39 (dd, J=6.85, 4.16 Hz, 1H) 3.19 (s, 3H) 2.26-2.29 (m, 3H) 1.20-1.31 (m, 3H) 1.13 (d, J=7.09 Hz, 1H). LCMS-ESI (pos.), m/z: 563.2 (M+H)+.

Example 144.0. Preparation of (2R)-2-(4-chloro-2-(methylsulfonyl)phenyl)-N-(4-(2,6-dimethoxyphenyl)-5-(5-methyl-2-furanyl)-4H-1,2,4-triazol-3-yl)-2-hydroxyethanesulfonamide or (2S)-2-(4-chloro-2-(methylsulfonyl)phenyl)-N-(4-(2,6-dimethoxyphenyl)-5-(5-methyl-2-furanyl)-4H-1,2,4-triazol-3-yl)-2-hydroxyethanesulfonamide

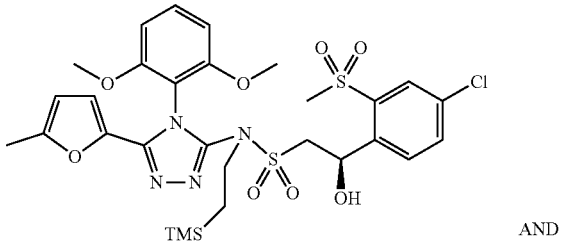

144.1

AND

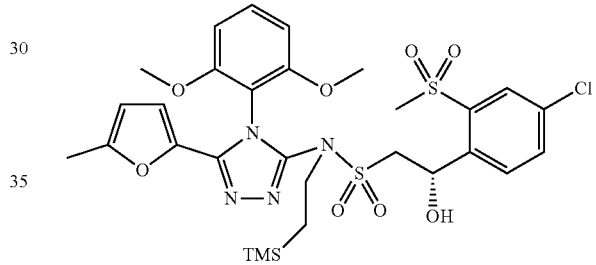

(R)-2-(4-Chloro-2-(methylsulfonyl)phenyl)-N-(4-(2,6-dimethoxyphenyl)-5-(5-methylfuran-2-yl)-4H-1,2,4-triazol-3-yl)-2-hydroxy-N-(2-(trimethylsilyl)ethyl)ethanesulfonamide and (S)-2-(4-chloro-2-(methylsulfonyl)phenyl)-N-(4-(2,6-dimethoxyphenyl)-5-(5-methylfuran-2-yl)-4H-1,2,4-triazol-3-yl)-2-hydroxy-N-(2-(trimethylsilyl)ethyl) ethanesulfonamide, Example 144.1. To a 50 mL RBF was added Example 368.0 (375 mg, 0.783 mmol) in 2-methyltetrahydrofuran (5 mL). n-Butyllithium solution, (2.5M in hexanes, 0.376 mL, 0.940 mmol) was added dropwise via syringe under N$_2$ at −78° C. The solution was stirred at −78° C. for 10 min and then 4-chloro-2-(methylsulfonyl)benzaldehyde (188 mg, 0.862 mmol) in 2-methyltetrahydrofuran (5 mL) was added dropwise via syringe under N$_2$ at −78° C. The reaction mixture was stirred at −78° C. for 10 min before the dry-ice bath was removed and the mixture warmed to RT. The reaction mixture was stirred at −78° C. to RT for 60 min in total before being quenched with saturated NH$_4$Cl. The reaction mixture was then diluted with water and extracted with EtOAc. The combined organic layers were washed with brine and dried over Na$_2$SO$_4$. The solution was filtered and concentrated in vacuo to give a light-yellow oil which was purified by silica gel chromatography (a gradient of 0% to 100% EtOAc in DCM), to provide Example 144.1 (290 mg, 0.416 mmol, 53% yield) and provided the title compound as a light-yellow oil. LCMS-ESI (pos.), m/z: 697.1 (M+H)+.

144.2

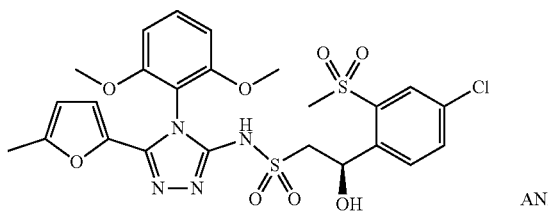

AND

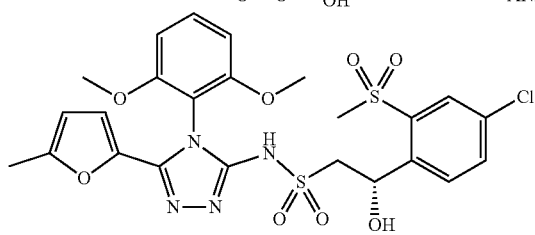

(2R)-2-(4-Chloro-2-(methylsulfonyl)phenyl)-N-(4-(2,6-dimethoxyphenyl)-5-(5-methyl-2-furanyl)-4H-1,2,4-triazol-3-yl)-2-hydroxyethanesulfonamide and (2S)-2-(4-chloro-2-(methylsulfonyl)phenyl)-N-(4-(2,6-dimethoxyphenyl)-5-(5-methyl-2-furanyl)-4H-1,2,4-triazol-3-yl)-2-hydroxyethanesulfonamide, Example 144.2. Example 144.2 was prepared from Example 144.1 by deprotection as described in Example 88.0. $^1$H NMR (500 MHz, CD$_3$OD) δ 7.96 (d, J=2.45 Hz, 1H) 7.84 (d, J=8.31 Hz, 1H) 7.73 (dd, J=8.56, 2.20 Hz, 1H) 7.58 (t, J=8.56 Hz, 1H) 6.89 (d, J=8.56 Hz, 1H) 6.86 (d, J=8.56 Hz, 1H) 6.04 (d, J=2.69 Hz, 1H) 5.94-6.02 (m, 2H) 3.83 (s, 3H) 3.79 (s, 3H) 3.55 (dd, J=14.18, 4.65 Hz, 1H) 3.48 (dd, J=14.31, 7.70 Hz, 1H) 3.12 (s, 3H) 2.28 (s, 3H). LCMS-ESI (pos.), m/z: 597.0 (M+H)$^+$.

144.0

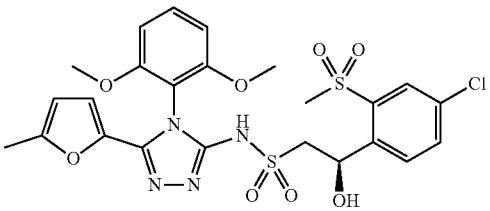

OR

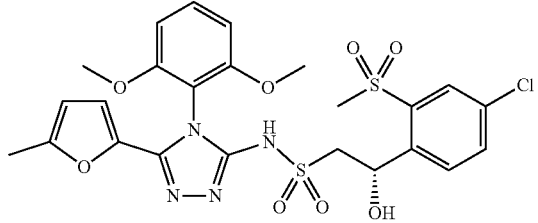

(2R)-2-(4-Chloro-2-(methylsulfonyl)phenyl)-N-(4-(2,6-dimethoxyphenyl)-5-(5-methyl-2-furanyl)-4H-1,2,4-triazol-3-yl)-2-hydroxyethanesulfonamide or (2S)-2-(4-chloro-2-(methylsulfonyl)phenyl)-N-(4-(2,6-dimethoxyphenyl)-5-(5-methyl-2-furanyl)-4H-1,2,4-triazol-3-yl)-2-hydroxyethanesulfonamide, Example 144.0. Example 144.0 was the second isomer to elute from an OD-H column on subjecting Example 144.2 to the following SFC conditions: OD-H (3×15 cm), 25% MeOH (0.1% NH$_4$OH)/CO$_2$, 100 bar, 70 mL/min, 220 nm. injection volume: 0.75 mL, 6 mg/mL 1:1 DCM:MeOH solution. $^1$H NMR (500 MHz, CD$_3$OD) 7.96 (d, J=2.45 Hz, 1H) 7.84 (d, J=8.31 Hz, 1H) 7.73 (dd, J=8.56, 2.20 Hz, 1H) 7.58 (t, J=8.56 Hz, 1H) 6.86 (d, J=8.56 Hz, 1H) 6.89 (d, J=8.56 Hz, 1H) 6.04 (d, J=2.69 Hz, 1H) 5.94-6.02 (m, 2H) 3.83 (s, 3H) 3.79 (s, 3H) 3.55 (dd, J=14.18, 4.65 Hz, 1H) 3.48 (dd, J=14.31, 7.70 Hz, 1H) 3.12 (s, 3H) 2.28 (s, 3H). LCMS-ESI (pos.), m/z: 597.0 (M+H)$^+$.

Example 145.0. Preparation of (2R)-2-(4-chloro-2-(methylsulfonyl)phenyl)-N-(4-(2,6-dimethoxyphenyl)-5-(5-methyl-2-furanyl)-4H-1,2,4-triazol-3-yl)-2-hydroxyethanesulfonamide or (2S)-2-(4-chloro-2-(methylsulfonyl)phenyl)-N-(4-(2,6-dimethoxyphenyl)-5-(5-methyl-2-furanyl)-4H-1,2,4-triazol-3-yl)-2-hydroxyethanesulfonamide 145.0

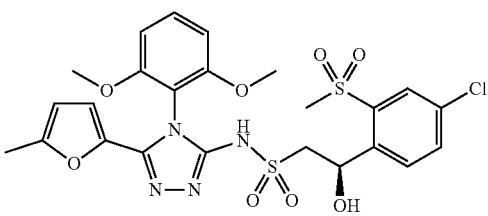

OR

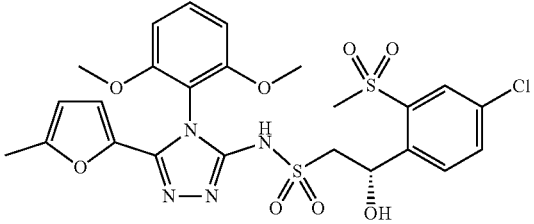

(2R)-2-(4-Chloro-2-(methylsulfonyl)phenyl)-N-(4-(2,6-dimethoxyphenyl)-5-(5-methyl-2-furanyl)-4H-1,2,4-triazol-3-yl)-2-hydroxyethanesulfonamide or (2S)-2-(4-chloro-2-(methylsulfonyl)phenyl)-N-(4-(2,6-dimethoxyphenyl)-5-(5-methyl-2-furanyl)-4H-1,2,4-triazol-3-yl)-2-hydroxyethanesulfonamide, Example 145.0. Example 145.0 is the enantiomer of Example 144.0. Example 145.0 was the first isomer to elute from an OD-H column on subjecting Example 145.2 to the SFC conditions described in Example 144.0. LCMS-ESI (pos.), m/z: 597.0 (M+H)$^+$.

Example 146.0. Preparation of (1R, 2S)—N-(4-(2,6-dimethoxyphenyl)-5-(5-methyl-2-furanyl)-4H-1,2,4-triazol-3-yl)-1-hydroxy-1-(5-methoxy-2-pyrazinyl)-2-propanesulfonamide or (1S, 2R)—N-(4-(2,6-dimethoxyphenyl)-5-(5-methyl-2-furanyl)-4H-1,2,4-triazol-3-yl)-1-hydroxy-1-(5-methoxy-2-pyrazinyl)-2-propanesulfonamide 146.0

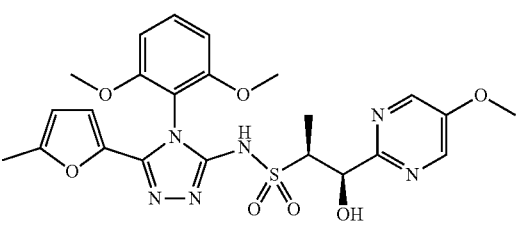

OR

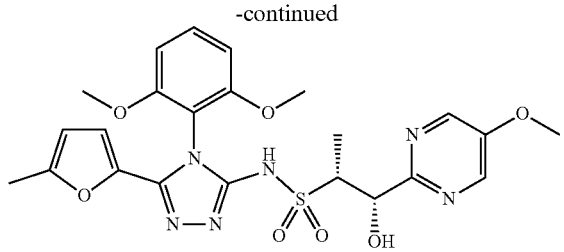

(1R, 2S)—N-(4-(2,6-Dimethoxyphenyl)-5-(5-methyl-2-furanyl)-4H-1,2,4-triazol-3-yl)-1-hydroxy-1-(5-methoxy-2-pyrazinyl)-2-propanesulfonamide or (1S, 2R)—N-(4-(2,6-dimethoxyphenyl)-5-(5-methyl-2-furanyl)-4H-1,2,4-triazol-3-yl)-1-hydroxy-1-(5-methoxy-2-pyrazinyl)-2-propanesulfonamide, Example 146.0. Example 146.0 was obtained as the second peak (later peak vs. its opposite enantiomer) on an IA column upon injection of Example 152.0 on the IA column under the following SFC conditions: Thar 80 SFC with 150×30 mm IA columns with 48.0 mL/min EtOH (+20 mM NH$_3$)+32.0 g/min CO$_2$, 60% co-solvent at 80.0 g/min. Temp.=29° C., Outlet pressure=100 bar, Wavelength=280 nm. Injected 0.9 mL of 122 mg sample dissolved in 12.0 mL of MeOH:DCM 7:5; c=10.2 mg/mL and 9.2 mg per injection. Cycle time 7.0 min, run time 10.0 min. $^1$H NMR (500 MHz, CDCl$_3$) δ 10.95 (br s, 1H) 8.27 (s, 1H) 8.15 (d, J=1.22 Hz, 1H) 7.52 (t, J=8.56 Hz, 1H) 6.72 (dd, J=14.67, 8.56 Hz, 2H) 5.95 (dd, J=3.42, 0.98 Hz, 1H) 5.87 (d, J=3.42 Hz, 1H) 5.52 (d, J=0.73 Hz, 1H) 4.01 (d, J=0.98 Hz, 1H) 3.98 (s, 3H) 3.84 (s, 3H) 3.77 (s, 3H) 3.69 (qd, J=7.01, 1.22 Hz, 1H) 2.34 (s, 3H) 1.15 (d, J=7.09 Hz, 3H). LCMS-ESI (pos.), m/z: 531.0 (M+H)$^+$.

Example 147.0. Preparation of (2R,3S)—N-(4-(2,6-dimethoxyphenyl)-5-(5-methyl-2-furanyl)-4H-1,2,4-triazol-3-yl)-3-(5-methyl-1-oxido-2-pyrazinyl)-2-butanesulfonamide and (2S,3R)—N-(4-(2,6-dimethoxyphenyl)-5-(5-methyl-2-furanyl)-4H-1,2,4-triazol-3-yl)-3-(5-methyl-1-oxido-2-pyrazinyl)-2-butanesulfonamide 147.1

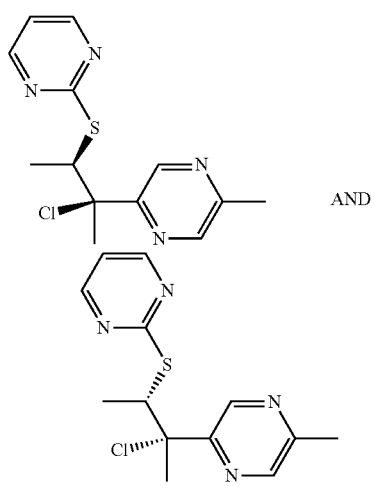

2-(((2R,3R)-3-Chloro-3-(5-methylpyrazin-2-yl)butan-2-yl)thio)pyrimidine and 2-(((2S,3S)-3-chloro-3-(5-methyl-pyrazin-2-yl)butan-2-yl)thio)pyrimidine, Example 147.1. To a stirred suspension of 2-mercaptopyrimidine (5.57 g, 49.7 mmol) in DCM (72 mL) was quickly added sulfuryl chloride (4.03 mL, 49.7 mmol) at −20° C. The reaction was then stirred for 2 h allowing the bath to warm to RT. A solution of (E)-2-(but-2-en-2-yl)-5-methylpyrazine (3.68 g, 24.8 mmol) in DCM (11 mL) was then added dropwise at 0° C. The mixture was stirred at 0° C. and gradually warmed to RT for 2 h. The reaction mixture was then cooled to 0° C. again, and saturated NaHCO$_3$ (100 mL) was added dropwise to the mixture while stirring. The reaction mixture was extracted with DCM (3×100 mL). The combined organic layers were washed with brine and dried over Na$_2$SO$_4$. The solution was filtered and concentrated in vacuo to give an orange oil which was absorbed onto a plug of silica gel and purified by chromatography through a Redi-Sep pre-packed silica gel column (80 g) eluting with a gradient of 0% to 100% EtOAc in hexanes (with 26% EtOH in EtOAc) to afford the desired product (5.24 g, 17.8 mmol, 72% yield) as a yellow oil. LCMS-ESI (pos.) m/z: 295.0 (M+H)$^+$.

147.2

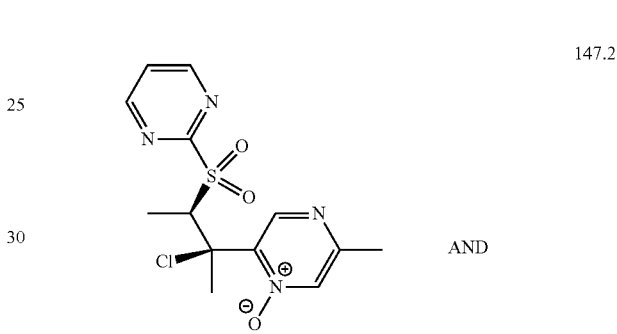

2-((2R,3R)-2-Chloro-3-(pyrimidin-2-ylsulfonyl)butan-2-yl)-5-methylpyrazine 1-oxide and 2-((2S,3S)-2-chloro-3-(pyrimidin-2-ylsulfonyl)butan-2-yl)-5-methylpyrazine 1-oxide, Example 147.2. To a solution of 2-((3-chloro-3-(5-methylpyrazin-2-yl)butan-2-yl)thio)pyrimidine (2.03 g, 6.89 mmol) in DCM (25 mL) at 0° C., was added 3-chloroperoxybenzoic acid, 77% max. (2.97 g, 17.21 mmol) portionwise. The reaction was warmed to RT slowly and stirred overnight. The initial reaction mixture was washed with a 1.0 M solution of sodium thiosulfate (25 mL), saturated sodium bicarbonate (25 mL), and brine (25 mL). The organic layers were concentrated in vacuo and purified on silica gel (0-100% EtOAc in hexanes) to give the desired product (0.531 g, 1.63 mmol, 24% yield).

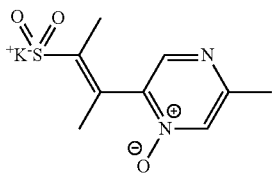

Potassium (E)-3-(5-Methyl-1-oxidopyrazin-2-yl)but-2-ene-2-sulfinate, Example 147.3. To a slurry of 2-((3-chloro-3-(5-methylpyrazin-2-yl)butan-2-yl)sulfonyl)pyrimidine (520 mg, 1.59 mmol) in MeOH (5 mL) was added anhydrous potassium carbonate (462 mg, 3.34 mmol). The resulting light yellow slurry was stirred at room temperature for 6 h. The reaction turned into a white slurry. The reaction mixture was then concentrated in vacuo and azeotroped with toluene two times to afford the initial product as an off-white solid which was used without further purification.

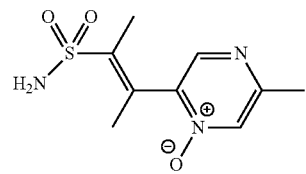

(E)-5-Methyl-2-(3-sulfamoylbut-2-en-2-yl)pyrazine 1-oxide, Example 147.4. To a cloudy solution of Example 147.3 (398 mg, 1.59 mmol) in water (8 mL), was added potassium acetate (156 mg, 1.59 mmol) in one portion. To the mixture was slowly added (aminooxy)sulfonic acid (378 mg, 3.34 mmol). The resulting colorless solution was stirred at RT for 4 h. The reaction mixture was then extracted with EtOAc (3×10 mL). The organic layers were combined and dried $Na_2SO_4$ and concentrated in vacuo. The initial material was absorbed onto a plug of silica gel and purified by chromatography through a Redi-Sep pre-packed silica gel column (12 g) eluting with a gradient of 0% to 100% EtOAc in hexanes to provide the desired product (290 mg, 1.28 mmol, 80% yield for two steps) as a white crystalline solid.

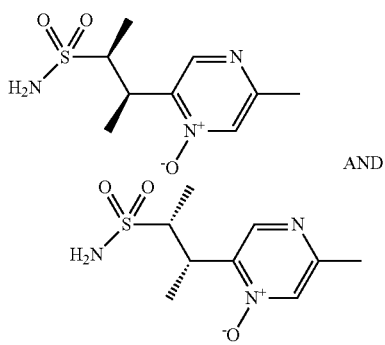

5-Methyl-2-((2R,3S)-3-sulfamoylbutan-2-yl)pyrazine 1-oxide and 5-methyl-2-((2S,3R)-3-sulfamoylbutan-2-yl)pyrazine 1-oxide, Example 147.5. To Example 147.4 (2.22 g, 9.13 mmol) in EtOH (45.6 mL) was added zinc(II) trifluoromethanesulfonate (1.659 g, 4.56 mmol) and (R)-(–)-4,12-bis(diphenylphosphino)[2.2]paracyclophane(1,5-cyclooctadiene)rhodium tetrafluroborate (strem chemicals, 1.596 g, 1.825 mmol). The mixture was then stirred under $H_2$ (50 psi). The reaction was stirred at RT for 15 h with the pressure of hydrogen gas replenished to maintain 50 psi. The reaction was concentrated and the mixture was absorbed onto a plug of silica gel and purified by chromatography through a Redi-Sep pre-packed silica gel column (80 g) eluting with a gradient of 0% to 100% EtOAc in DCM to provide 5-methyl-2-((2R,3S)-3-sulfamoylbutan-2-yl)pyrazine 1-oxide (2.01 g, 8.19 mmol, 90% yield) as a brown solid. LCMS-ESI (pos.), m/z: 246.2 (M+H)+.

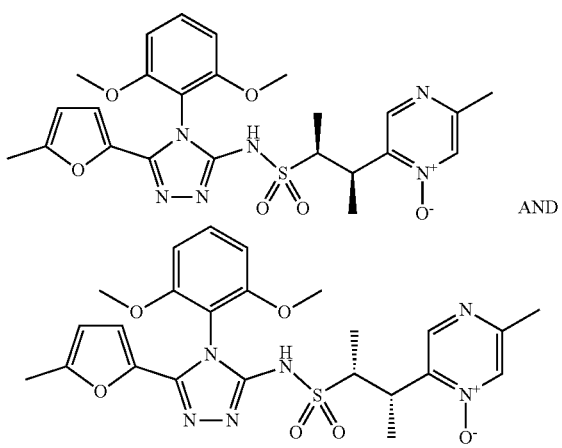

(2R,3S)—N-(4-(2,6-Dimethoxyphenyl)-5-(5-methyl-2-furanyl)-4H-1,2,4-triazol-3-yl)-3-(5-methyl-1-oxido-2-pyrazinyl)-2-butanesulfonamide and (2S,3R)—N-(4-(2,6-dimethoxyphenyl)-5-(5-methyl-2-furanyl)-4H-1,2,4-triazol-3-yl)-3-(5-methyl-1-oxido-2-pyrazinyl)-2-butanesulfonamide, Example 147.0. Example 147.0 was prepared using Example 147.5 and 3-bromo-4-(2,6-dimethoxyphenyl)-5-(5-methylfuran-2-yl)-4H-1,2,4-triazole (Example 364.1) following the procedure described in Example 94.0. $^1$H NMR (500 MHz, $CD_2Cl_2$) δ 8.46 (s, 1H) 8.06 (s, 1H) 7.57 (t, J=8.56 Hz, 1H) 6.76-6.81 (m, 2H) 5.98 (dd, J=3.42, 0.98 Hz, 1H) 5.89 (d, J=3.42 Hz, 1H) 3.80 (s, 3H) 3.80 (s, 3H) 3.50-3.61 (m, 2H) 2.45 (s, 3H) 2.33 (d, J=0.98 Hz, 3H) 1.34 (d, J=7.09 Hz, 3H) 1.31 (d, J=6.85 Hz, 3H). LCMS-ESI (pos.), m/z: 529.1 (M+H)+.

Example 148.0. Preparation of (2S,3R)—N-(4-(2,6-dimethoxyphenyl)-5-(5-methyl-2-furanyl)-4H-1,2,4-triazol-3-yl)-3-(5-methyl-2-pyrazinyl)-2-butanesulfonamide

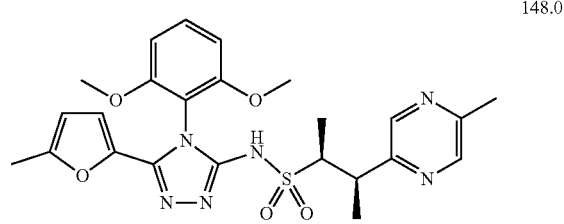

(2S,3R)—N-(4-(2,6-Dimethoxyphenyl)-5-(5-methyl-2-furanyl)-4H-1,2,4-triazol-3-yl)-3-(5-methyl-2-pyrazinyl)-2-butanesulfonamide, Example 148.0. Example 148.0 was prepared using (2S,3R)-3-(5-methylpyrazin-2-yl)butane-2-sulfonamide, Example 371.2 and 3-bromo-4-(2,6-dimethoxyphenyl)-5-(5-methylfuran-2-yl)-4H-1,2,4-triazole (Example 364.1) following the procedure described in Example 94.0. The title compound was obtained as a TFA salt after reverse phase preparatory HPLC purification. $^1$H NMR (500 MHz, CD$_3$OD) δ 8.47 (br s, 1H) 8.26 (br s, 1H) 7.59 (t, J=8.56 Hz, 1H) 6.88 (dd, J=8.56, 3.67 Hz, 2H) 6.04 (dd, J=3.42, 0.73 Hz, 1H) 5.96 (d, J=3.42 Hz, 1H) 3.79 (d, J=1.47 Hz, 6H) 3.55-3.66 (m, 1H) 3.43-3.55 (m, 1H) 2.53 (s, 3H) 2.28 (s, 3H) 1.35 (d, J=7.09 Hz, 3H) 1.32 (d, J=6.85 Hz, 3H). LCMS-ESI (pos.), m/z: 513.2 (M+H)$^+$.

Example 149.0. Preparation of (1S,2R)-1-(2,4-dicyanophenyl)-N-(4-(2,6-dimethoxyphenyl)-5-(5-methyl-2-furanyl)-4H-1,2,4-triazol-3-yl)-1-methoxy-2-propanesulfonamide and (1R,2S)-1-(2,4-dicyanophenyl)-N-(4-(2,6-dimethoxyphenyl)-5-(5-methyl-2-furanyl)-4H-1,2,4-triazol-3-yl)-1-methoxy-2-propanesulfonamide

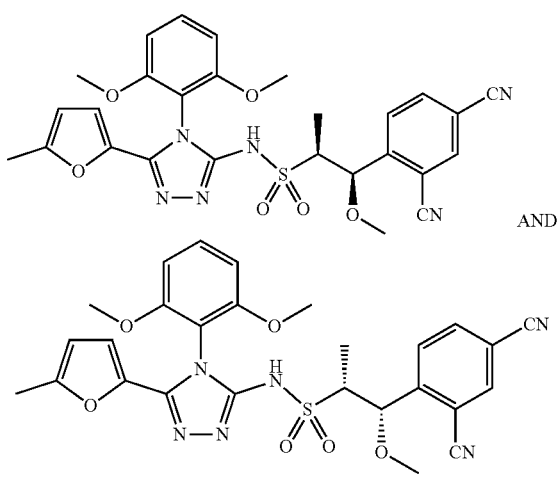

149.0

AND (1S,2R)-1-(2,4-Dicyanophenyl)-N-(4-(2,6-dimethoxyphenyl)-5-(5-methyl-2-furanyl)-4H-1,2,4-triazol-3-yl)-1-methoxy-2-propanesulfonamide and (1R,2S)-1-(2,4-dicyanophenyl)-N-(4-(2,6-dimethoxyphenyl)-5-(5-methyl-2-furanyl)-4H-1,2,4-triazol-3-yl)-1-methoxy-2-propanesulfonamide, Example 149.0. To a solution of Example 143.4 (208 mg, 0.745 mmol) and 2-isothiocyanato-1,3-dimethoxybenzene (Example 372.0, 145 mg, 0.745 mmol) in ACN (4.9 mL) was added cesium carbonate (485 mg, 1.49 mmol). The reaction was stirred at RT over the weekend. To the reaction mixture was then added 5-methyl-2-furohydrazide (104 mg, 0.75 mmol) and silver(I) nitrate (253 mg, 1.49 mmol). The reaction was then stirred for 30 mins at 23° C. Saturated NaCl (5 mL) and 5 g of Celite® brand filter aid were added to the reaction mixture. The reaction mixture was then stirred at RT for 30 min. The reaction was filtered and the cake was rinsed with DCM. The organic solution was washed with brine. The DCM solution was concentrated in vacuo to give the intermediate as a light yellow foam. To a 250 mL RBF was added the above intermediate and TFA (0.553 mL, 7.44 mmol) in 1,4-dioxane (10 mL). The reaction mixture was stirred at 100° C. under N$_2$ for 38 h. LCMS analysis indicated formation of the desired products. The reaction mixture was then concentrated in vacuo. The initial product was further purified by chromatography through Redi-Sep pre-packed silica gel column (40 g) eluting with a gradient of 0% to 100% EtOAc in DCM (26% EtOH in EtOAc). The enriched product was triturated with EtOAc to provide the major product, syn isomer Example 149.0 (170 mg, 0.302 mmol, 40.6% yield), as an off-white solid. The fraction of mixture of syn and anti isomers was processed separately. $^1$H NMR (500 MHz, CD$_3$OD) δ 8.20 (d, J=1.71 Hz, 1H) 8.43 (d, J=1.37 Hz, 1H) 8.02 (dd, J=8.31, 1.71 Hz, 1H) 7.67 (d, J=7.94 Hz, 1H) 7.58 (t, J=8.40 Hz, 1H) 6.88 (d, J=8.38 Hz, 2H) 6.00-6.08 (m, 1H) 5.96 (d, J=3.42 Hz, 1H) 5.16 (d, J=3.91 Hz, 1H) 4.84-4.92 (m, 17H) 3.79-3.84 (m, 6H) 3.39 (dd, J=6.85, 4.16 Hz, 1H) 3.19 (s, 3H) 2.26-2.29 (m, 3H) 1.20-1.31 (m, 3H) 1.13 (d, J=7.09 Hz, 1H). LCMS-ESI (pos.), m/z: 563.2 (M+H)$^+$.

Example 150.0. Preparation of (2R)—N-(4-(2,6-dimethoxyphenyl)-5-(5-methyl-2-furanyl)-4H-1,2,4-triazol-3-yl)-1-((2R)-2-(methoxymethyl)-6-oxo-1-piperidinyl)-2-propanesulfonamide or (2R)—N-(4-(2,6-dimethoxyphenyl)-5-(5-methyl-2-furanyl)-4H-1,2,4-triazol-3-yl)-1-((2S)-2-(methoxymethyl)-6-oxo-1-piperidinyl)-2-propanesulfonamide or (2S)—N-(4-(2,6-dimethoxyphenyl)-5-(5-methyl-2-furanyl)-4H-1,2,4-triazol-3-yl)-1-((2R)-2-(methoxymethyl)-6-oxo-1-piperidinyl)-2-propanesulfonamide or (2S)—N-(4-(2,6-dimethoxyphenyl)-5-(5-methyl-2-furanyl)-4H-1,2,4-triazol-3-yl)-1-((2S)-2-(methoxymethyl)-6-oxo-1-piperidinyl)-2-propanesulfonamide

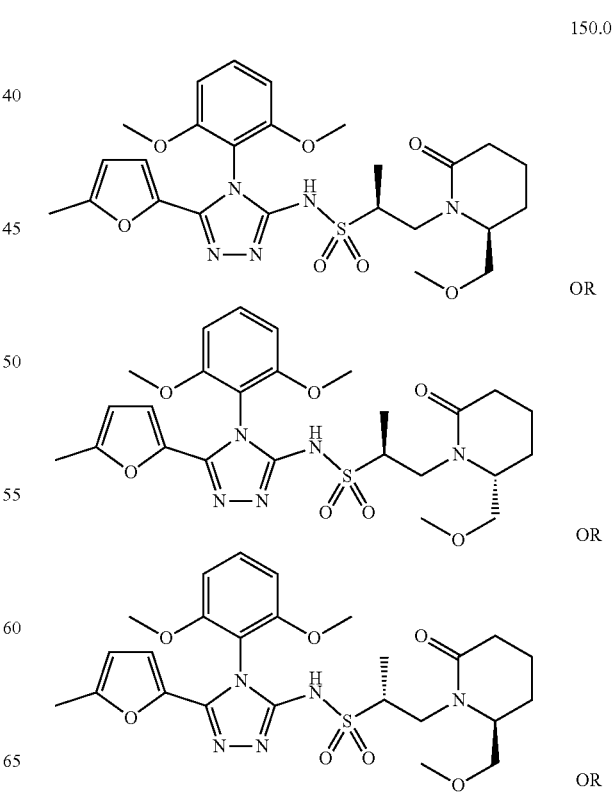

150.0

OR

OR

OR

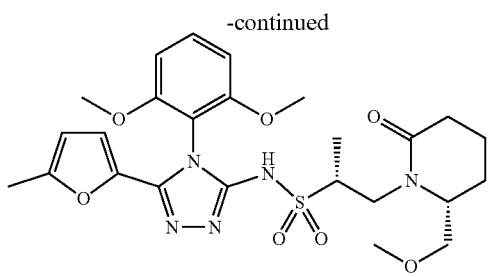

(2R)—N-(4-(2,6-Dimethoxyphenyl)-5-(5-methyl-2-furanyl)-4H-1,2,4-triazol-3-yl)-1-((2R)-2-(methoxymethyl)-6-oxo-1-piperidinyl)-2-propanesulfonamide or (2R)—N-(4-(2,6-dimethoxyphenyl)-5-(5-methyl-2-furanyl)-4H-1,2,4-triazol-3-yl)-1-((2S)-2-(methoxymethyl)-6-oxo-1-piperidinyl)-2-propanesulfonamide or (2S)—N-(4-(2,6-dimethoxyphenyl)-5-(5-methyl-2-furanyl)-4H-1,2,4-triazol-3-yl)-1-((2R)-2-(methoxymethyl)-6-oxo-1-piperidinyl)-2-propanesulfonamide or (2S)—N-(4-(2,6-dimethoxyphenyl)-5-(5-methyl-2-furanyl)-4H-1,2,4-triazol-3-yl)-1-((2S)-2-(methoxymethyl)-6-oxo-1-piperidinyl)-2-propanesulfonamide, Example 150.0. Example 150.0 was the second peak (later peak vs. its C-2 MeOCH$_2$ epimer) to elute a on Regis Whelk-O column (45% IPA). It was obtained by SFC separation of Example 151.0 on the Regis Whelk-O column. $^1$H NMR (400 MHz, CD$_3$OD) δ 7.56 (t, J=8.50 Hz, 1H) 6.82-6.89 (m, 2H) 6.03 (dd, J=3.32, 1.04 Hz, 1H) 5.91-5.98 (m, 1H) 4.17 (dd, J=13.58, 4.66 Hz, 1H) 3.79 (s, 3H) 3.79 (s, 3H) 3.54-3.66 (m, 2H) 3.46-3.53 (m, 1H) 3.38-3.43 (m, 1H) 3.19 (dd, J=13.68, 9.74 Hz, 1H) 2.30-2.38 (m, 2H) 2.24-2.29 (m, 3H) 1.83-1.98 (m, 3H) 1.67-1.77 (m, 1H) 1.29-1.37 (m, 3H) 1.27 (d, J=7.05 Hz, 3H). LCMS-ESI (pos.), m/z: 548.0 (M+H)$^+$.

Example 151.0. Preparation of (2R)—N-(4-(2,6-dimethoxyphenyl)-5-(5-methyl-2-furanyl)-4H-1,2,4-triazol-3-yl)-1-((2R)-2-(methoxymethyl)-6-oxo-1-piperidinyl)-2-propanesulfonamide and (2R)—N-(4-(2,6-dimethoxyphenyl)-5-(5-methyl-2-furanyl)-4H-1,2,4-triazol-3-yl)-1-((2S)-2-(methoxymethyl)-6-oxo-1-piperidinyl)-2-propanesulfonamide or (2S)—N-(4-(2,6-dimethoxyphenyl)-5-(5-methyl-2-furanyl)-4H-1,2,4-triazol-3-yl)-1-((2R)-2-(methoxymethyl)-6-oxo-1-piperidinyl)-2-propanesulfonamide and (2S)—N-(4-(2,6-dimethoxyphenyl)-5-(5-methyl-2-furanyl)-4H-1,2,4-triazol-3-yl)-1-((2S)-2-(methoxymethyl)-6-oxo-1-piperidinyl)-2-propanesulfonamide

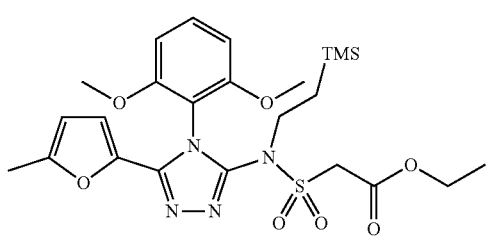

151.1

Ethyl 2-(N-(4-(2,6-dimethoxyphenyl)-5-(5-methylfuran-2-yl)-4H-1,2,4-triazol-3-yl)-N-(2-(trimethylsilyl)ethyl)sulfamoyl)acetate, Example 151.1. Diethyl carbonate (0.693 mL, 5.72 mmol) was injected into a solution of Example 368.0 (2.28 g, 4.76 mmol) in THF (20 mL) in a 250 mL RBF under N$_2$. The mixture was cooled to −78° C., and a solution of lithium bis(trimethylsilyl)amide in THF (1.0 M, 11.91 mL, 11.91 mmol) was injected dropwise. The resulting mixture was stirred at −78° C. for 30 min and then warmed to RT for 2.5 h. LCMS analysis indicated there was still a small amount of starting material remaining. The reaction mixture was cooled to −78° C., and diethyl carbonate (0.14 mL, 0.25 eq) and lithium bis(trimethylsilyl)amide in THF (1.0 M, 2.38 mL, 0.5 eq) were added to the reaction. The reaction mixture was then warmed to RT for 1.5 h. The reaction mixture was diluted with EtOAc (50 mL) and saturated NH$_4$Cl(aq). The layers were separated and the aqueous layer was extracted with EtOAc. The combined organic layers were dried over Na$_2$SO$_4$. The solution was filtered and concentrated in vacuo to give a brown oil. The imaterial thus obtained was absorbed onto a plug of silica gel and purified by chromatography through a Redi-Sep pre-packed silica gel column (120 g) eluting with a gradient of 0% to 100% EtOAc in hexanes to provide Example 151.1 (1.98 g, 3.60 mmol, 75% yield) as a brown gum. LCMS-ESI (pos.), m/z: 551.2 (M+H)$^+$.

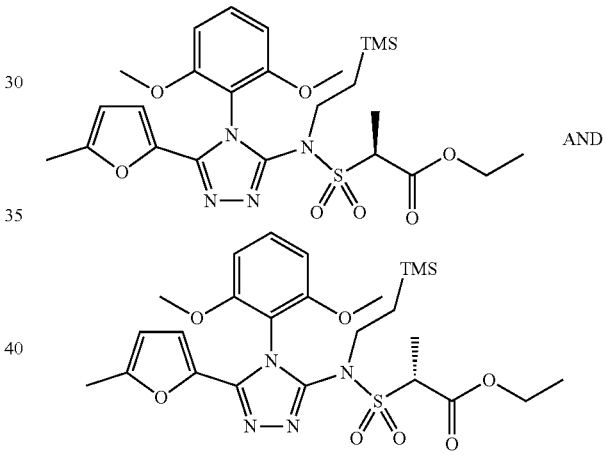

151.2

(R)-Ethyl 2-(N-(4-(2,6-dimethoxyphenyl)-5-(5-methylfuran-2-yl)-4H-1,2,4-triazol-3-yl)-N-(2-(trimethylsilyl)ethyl)sulfamoyl)propanoate and (S)-ethyl 2-(N-(4-(2,6-dimethoxyphenyl)-5-(5-methylfuran-2-yl)-4H-1,2,4-triazol-3-yl)-N-(2-(trimethylsilyl)ethyl)sulfamoyl)propanoate, Example 151.2. Iodomethane (0.444 mL, 7.15 mmol) was injected dropwise into a mixture of Example 151.1 (1.97 g, 3.58 mmol) and cesium carbonate (2.331 g, 7.15 mmol) in DMF (18 mL) in a 250 mL RBF at RT and stirred for 2.5 h. Additional MeI (0.11 mL, 0.50 eq) was added, and the mixture was stirred for 2 h. The reaction mixture was diluted with 80 mL EtOAc. The solid was removed by filtration and rinsed with EtOAc. The solution was extracted with a saturated aqueous solution of NH$_4$Cl (1×80 mL) and then brine. The organic layer was separated and dried over Na$_2$SO$_4$, filtered, and concentrated in vacuo. The initial material was absorbed onto a plug of silica gel and purified by chromatography through a Redi-Sep pre-packed silica gel column (120 g) eluting with a gradient of 0% to 100% EtOAc/hexanes to provide Example 151.2 (1.91 g, 3.38 mmol, 95% yield) as an off-white glass. LCMS-ESI (pos.), m/z: 565.3 (M+H)$^+$.

151.3

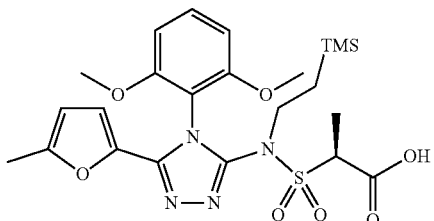

AND (R)—N-(4-(2,6-Dimethoxyphenyl)-5-(5-methylfuran-2-yl)-4H-1,2,4-triazol-3-yl)-1-hydroxy-N-(2-(trimethylsilyl)ethyl)propane-2-sulfonamide and (S)—N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide, Example 151.3. To a 250 mL RBF was added Example 151.2 (1.90 g, 3.36 mmol) in THF (15 mL). Lithium borohydride (2.0 M solution in THF, 4.21 mL, 8.41 mmol) was then injected dropwise under nitrogen at RT. The reaction was then stirred at RT for 1 h. The reaction was quenched with 1.0 N HCl(aq) at 0° C. and extracted with DCM. The organic layers were combined, dried over Na$_2$SO$_4$, filtered, and concentrated. The material thus obtained was purified on a 125 g silica gel column (0-100% EtOAc/DCM) to provide Example 151.3 (1.52 g, 2.91 mmol, 86% yield) as white needles. LCMS-ESI (pos.), m/z: 523.3 (M+H)$^+$.

151.4

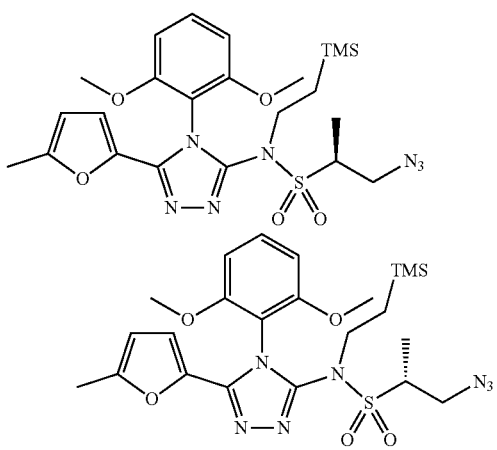

AND (R)-1-Azido-N-(4-(2,6-dimethoxyphenyl)-5-(5-methylfuran-2-yl)-4H-1,2,4-triazol-3-yl)-N-(2-(trimethylsilyl)ethyl)propane-2-sulfonamide and (S)-1-azido-N-(4-(2,6-dimethoxyphenyl)-5-(5-methylfuran-2-yl)-4H-1,2,4-triazol-3-yl)-N-(2-(trimethylsilyl)ethyl)propane-2-sulfonamide, Example 151.4. Example 151.3 (1.50 g, 2.87 mmol), triphenylphosphine (0.903 g, 3.44 mmol) and diisopropyl azodicarboxylate (0.677 mL, 3.44 mmol) were mixed in THF (28.7 mL) in a 250 mL RBF at RT. The mixture was purged with nitrogen gas for 2 min. Diphenyl phosphoryl azide (0.742 mL, 3.44 mmol) was injected dropwise into the mixture, and the mixture was stirred for 3 h. The solvent was then evaporated on a rotary evaporator. The residue was dissolved in a minimum amount of DCM and absorbed onto a plug of silica gel and purified by chromatography through a Redi-Sep pre-packed silica gel column (80 g) eluting with a gradient of 0% to 50% EtOAc in hexanes to provide enriched Example 151.4 (2.05 g, 3.74 mmol, 130% yield) as a pale yellow oil. The material was used directly in the next step without further purification. LCMS-ESI (pos.), m/z: 548.2 (M+H)$^+$.

151.5

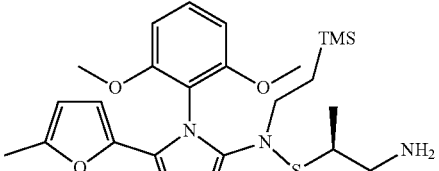

AND

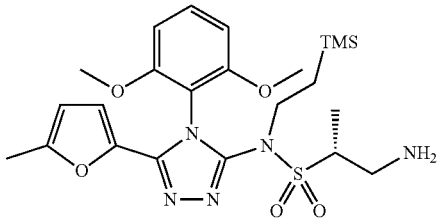

(R)-1-Amino-N-(4-(2,6-dimethoxyphenyl)-5-(5-methylfuran-2-yl)-4H-1,2,4-triazol-3-yl)-N-(2-(trimethylsilyl)ethyl)propane-2-sulfonamide and (S)-1-amino-N-(4-(2,6-dimethoxyphenyl)-5-(5-methylfuran-2-yl)-4H-1,2,4-triazol-3-yl)-N-(2-(trimethylsilyl)ethyl)propane-2-sulfonamide, Example 151.5. To a solution of Example 151.4 (2.04 g, 3.72 mmol) in EtOAc (35 mL) in a 250 mL RBF under nitogen gas was added palladium (10% wt. on activated carbon, 1.19 g, 1.12 mmol) in one portion. A hydrogen balloon was placed over the solution and the flask was purged and back-filled three times. The resulting mixture was then stirred at RT under a hydrogen atmosphere for 5 h and the reaction was determined to be complete by LCMS analysis. The initial reaction mixture was absorbed onto a plug of silica gel and purified by chromatography through a Redi-Sep pre-packed silica gel column (40 g) eluting with a gradient of 0% to 100% EtOAc/DCM and then 0-100% B/A (A=DCM, B=10% MeOH/DCM with 1% NH$_4$OH). This provided Example 151.5 (1.05 g, 2.01 mmol, 54.0% yield) as a white glass. LCMS-ESI (pos.), m/z: 522.2 (M+H)$^+$.

151.6

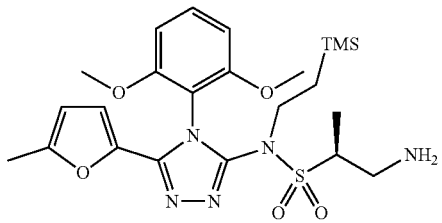

OR

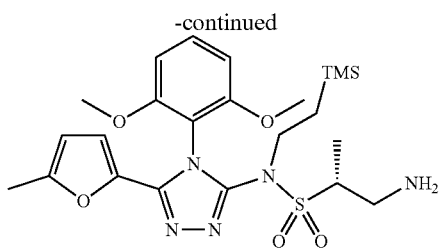

(R)-1-Amino-N-(4-(2,6-dimethoxyphenyl)-5-(5-methyl-furan-2-yl)-4H-1,2,4-triazol-3-yl)-N-(2-(trimethylsilyl)ethyl)propane-2-sulfonamide or (S)-1-amino-N-(4-(2,6-dimethoxyphenyl)-5-(5-methylfuran-2-yl)-4H-1,2,4-triazol-3-yl)-N-(2-(trimethylsilyl)ethyl)propane-2-sulfonamide, Example 151.6. Example 151.6 was the second peak to elute (later peak vs. its enantiomer) on an IC column (45% IPA). It was obtained by SFC separation of Example 151.5 under the following conditions: IC (2×15 cm), 25% IPA (0.2% NH$_4$OH)/CO$_2$, 100 bar, 60 mL/min, 220 nm, injection volume: 0.50 mL, 25 mg/mL MeOH solution of the sample. LCMS-ESI (pos.), m/z: 522.1 (M+H)$^+$.

lyl)ethyl)sulfamoyl)propyl)-6-oxopiperidine-2-carboxylate and (R)-ethyl 1-((S)-2-(N-(4-(2,6-dimethoxyphenyl)-5-(5-methylfuran-2-yl)-4H-1,2,4-triazol-3-yl)-N-(2-(trimethylsilyl)ethyl)sulfamoyl)propyl)-6-oxopiperidine-2-carboxylate or (S)-ethyl 1-((R)-2-(N-(4-(2,6-dimethoxyphenyl)-5-(5-methylfuran-2-yl)-4H-1,2,4-triazol-3-yl)-N-(2-(trimethylsilyl)ethyl)sulfamoyl)propyl)-6-oxopiperidine-2-carboxylate and (R)-ethyl 1-((R)-2-(N-(4-(2,6-dimethoxyphenyl)-5-(5-methylfuran-2-yl)-4H-1,2,4-triazol-3-yl)-N-(2-(trimethylsilyl)ethyl)sulfamoyl)propyl)-6-oxopiperidine-2-carboxylate, Example 151.7. To a 40 mL vial was added Example 151.6 (333 mg, 0.638 mmol) and diethyl 2-oxohexane-1,6-dicarboxylate (276 mg, 1.28 mmol) in CHCl$_3$ (6383 µL). AcOH (73.7 µl, 1.28 mmol) was added followed by sodium triacetoxyborohydride (271 mg, 1.28 mmol). The reaction mixture was then stirred at 60° C. for 60 h. The reaction mixture was then allowed to cool to RT. The reaction mixture was diluted with water and extracted with DCM. The combined organic layers were washed with brine and dried over Na$_2$SO$_4$. The solution was filtered and concentrated in vacuo to give Example 151.7 as a light-yellow solid. The product was directly used in the next step. LCMS-ESI (pos.), m/z: 676.4 (M+H)$^+$.

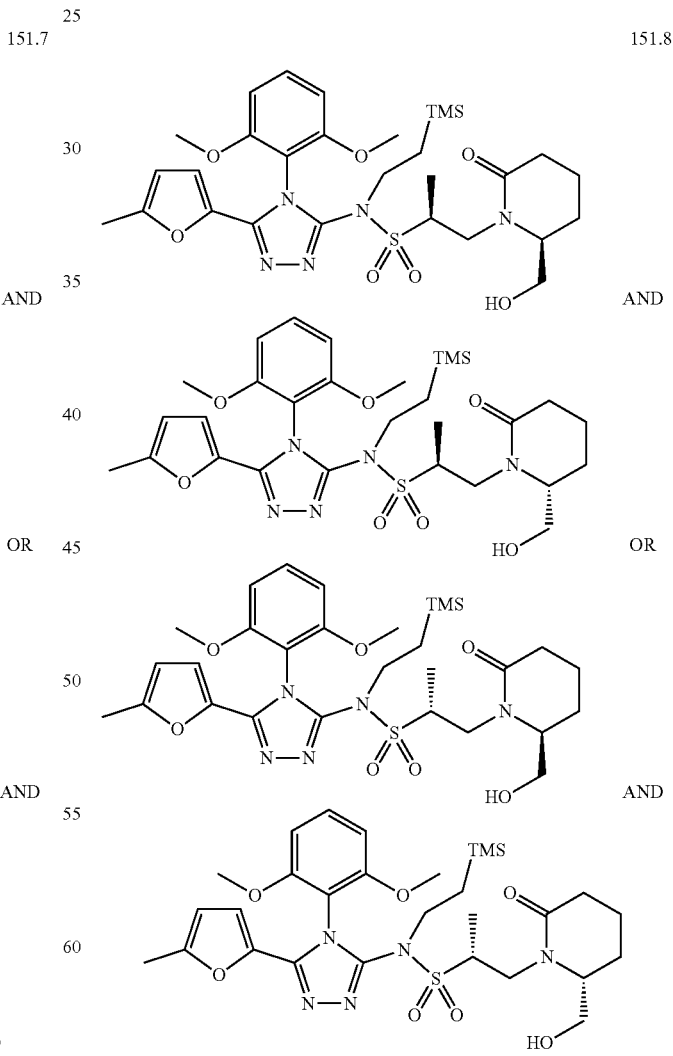

(S)-ethyl 1-((S)-2-(N-(4-(2,6-Dimethoxyphenyl)-5-(5-methylfuran-2-yl)-4H-1,2,4-triazol-3-yl)-N-(2-(trimethylsi- (S)—N-(4-(2,6-Dimethoxyphenyl)-5-(5-methylfuran-2-yl)-4H-1,2,4-triazol-3-yl)-1-((R)-2-(hydroxymethyl)-6-oxopiperidin-1-yl)-N-(2-(trimethylsilyl)ethyl)propane-2-sulfonamide and (S)—N-(4-(2,6-dimethoxyphenyl)-5-(5-methylfuran-2-yl)-4H-1,2,4-triazol-3-yl)-1-((S)-2-(hydroxymethyl)-6-oxopiperidin-1-yl)-N-(2-(trimethylsilyl)ethyl)propane-2-sulfonamide or (R)—N-(4-(2,6-dimethoxyphenyl)-5-(5-methylfuran-2-yl)-4H-1,2,4-triazol-3-yl)-1-((R)-2-(hydroxymethyl)-6-oxopiperidin-1-yl)-N-(2-(trimethylsilyl)ethyl)propane-2-sulfonamide and (R)—N-(4-(2,6-dimethoxyphenyl)-5-(5-methylfuran-2-yl)-4H-1,2,4-triazol-3-yl)-1-((S)-2-(hydroxymethyl)-6-oxopiperidin-1-yl)-N-(2-(trimethylsilyl)ethyl)propane-2-sulfonamide, Example 151.8. To a vial was added Example 151.7 (480 mg, 0.710 mmol) in MeOH (7.1 mL). Sodium borohydride (32.2 mg, 0.852 mmol) was added at 0° C. The reaction mixture was stirred at 0° C. for 1 h. LCMS indicated the reaction was not complete. Thus, a further batch of sodium borohydride (32.2 mg, 0.852 mmol) was added and the reaction was stirred for 1 h. Another batch of sodium borohydride (32.2 mg, 0.852 mmol) was added and the reaction was stirred overnight. The reaction was still not complete. The reaction mixture was then diluted with water and extracted with DCM. The combined organic layers were washed with brine and dried over Na$_2$SO$_4$. The solution was filtered and concentrated in vacuo to give a light-yellow oil. The material thus obtained was absorbed onto a plug of silica gel and purified by chromatography through a Redi-Sep pre-packed silica gel column (40 g) eluting with a gradient of 0% to 100% EtOAc in DCM to provide Example 151.8 (150 mg, 0.237 mmol, 33% yield) as a light-yellow solid. LCMS-ESI (pos.), m/z: 634.3 (M+H)$^+$.

151.9

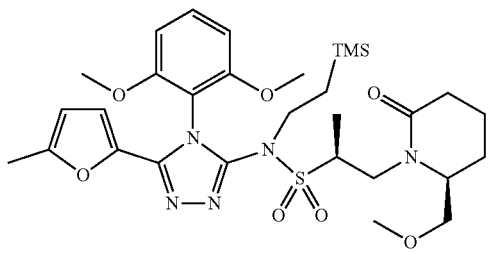

AND

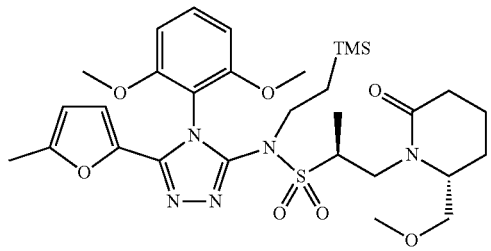

OR

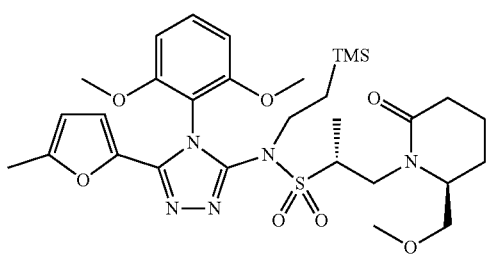

AND

-continued

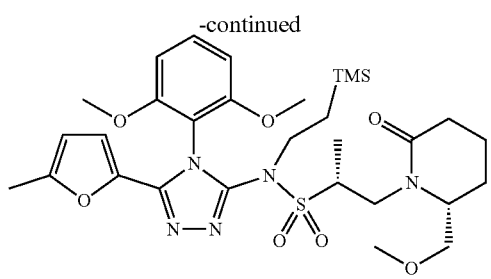

(S)—N-(4-(2,6-Dimethoxyphenyl)-5-(5-methylfuran-2-yl)-4H-1,2,4-triazol-3-yl)-1-((R)-2-(methoxymethyl)-6-oxopiperidin-1-yl)-N-(2-(trimethylsilyl)ethyl)propane-2-sulfonamide and (S)—N-(4-(2,6-dimethoxyphenyl)-5-(5-methylfuran-2-yl)-4H-1,2,4-triazol-3-yl)-1-((S)-2-(methoxymethyl)-6-oxopiperidin-1-yl)-N-(2-(trimethylsilyl)ethyl)propane-2-sulfonamide or (R)—N-(4-(2,6-dimethoxyphenyl)-5-(5-methylfuran-2-yl)-4H-1,2,4-triazol-3-yl)-1-((R)-2-(methoxymethyl)-6-oxopiperidin-1-yl)-N-(2-(trimethylsilyl)ethyl)propane-2-sulfonamide and (R)—N-(4-(2,6-dimethoxyphenyl)-5-(5-methylfuran-2-yl)-4H-1,2,4-triazol-3-yl)-1-((S)-2-(methoxymethyl)-6-oxopiperidin-1-yl)-N-(2-(trimethylsilyl)ethyl)propane-2-sulfonamide, Example 151.9. To a 30 mL vial was added Example 151.8 (116 mg, 0.183 mmol) in THF (1830 µL). Potassium bis(trimethylsilyl)amide, (1.0 M in THF, 275 µL, 0.275 mmol) was added at −78° C. under an atmosphere of nitrogen. The reaction mixture was stirred at −78° C. for 1 h. Iodomethane (34.2 µL, 0.549 mmol) was added at this temperature. The reaction mixture was then stirred at −78° C. for 3 h. LCMS indicated formation of the desired product. The reaction mixture was diluted with saturated NH$_4$Cl and extracted with EtOAc. The combined organic layers were washed with brine and dried over Na$_2$SO$_4$. The solution was filtered and concentrated in vacuo to give a light-yellow oil. The material thus obtained was absorbed onto a plug of silica gel and purified by chromatography through a Redi-Sep pre-packed silica gel column (12 g) eluting with a gradient of 0% to 100% EtOAc in hexanes to provide Example 151.9 (96 mg, 0.148 mmol, 81% yield) as a light-yellow glass. LCMS-ESI (pos.), m/z: 648.3 (M+H)$^+$.

151.0

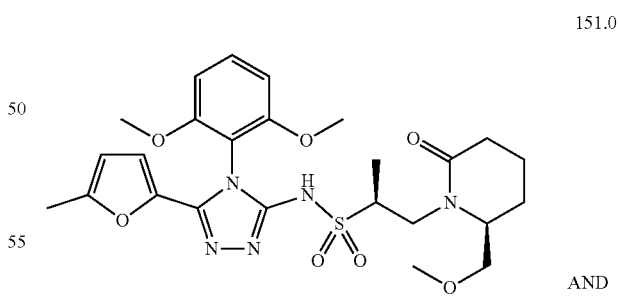

AND

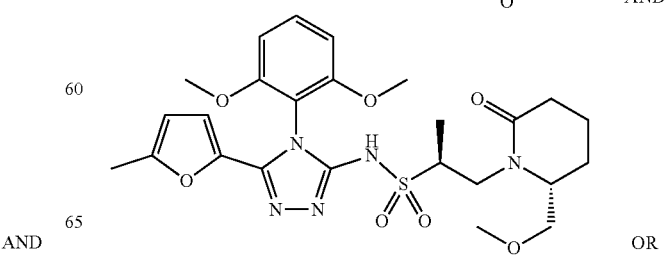

OR

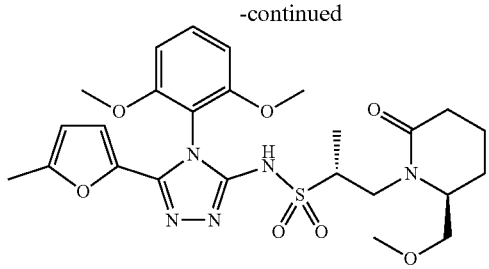

AND

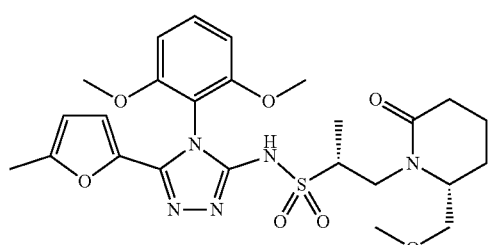

(2R)—N-(4-(2,6-Dimethoxyphenyl)-5-(5-methyl-2-furanyl)-4H-1,2,4-triazol-3-yl)-1-((2R)-2-(methoxymethyl)-6-oxo-1-piperidinyl)-2-propanesulfonamide and (2R)—N-(4-(2,6-dimethoxyphenyl)-5-(5-methyl-2-furanyl)-4H-1,2,4-triazol-3-yl)-1-((2S)-2-(methoxymethyl)-6-oxo-1-piperidinyl)-2-propanesulfonamide or a mixture of (2S)—N-(4-(2,6-dimethoxyphenyl)-5-(5-methyl-2-furanyl)-4H-1,2,4-triazol-3-yl)-1-((2R)-2-(methoxymethyl)-6-oxo-1-piperidinyl)-2-propanesulfonamide and (2S)—N-(4-(2,6-dimethoxyphenyl)-5-(5-methyl-2-furanyl)-4H-1,2,4-triazol-3-yl)-1-((2S)-2-(methoxymethyl)-6-oxo-1-piperidinyl)-2-propanesulfonamide, Example 151.0. To a 30 mL vial was added Example 151.9 (96 mg, 0.148 mmol) in DMF (1.4 mL). To the mixture was added tris(dimethylamino)sulfonium difluorotrimethylsilicate (122 mg, 0.45 mmol), and the reaction mixture was stirred at 90° C. for 2 h. The reaction mixture was then diluted with water (20 mL) and extracted with EtOAc (2×20 mL). The combined organic layers were washed with brine and dried over Na$_2$SO$_4$. The solution was filtered and concentrated in vacuo to give a light-yellow oil. The initial material was absorbed onto a plug of silica gel and purified by chromatography through a Redi-Sep prepacked silica gel column (12 g) eluting with a gradient of 0% to 100% EtOAc in hexanes (with 26% EtOH in EtOAc) to provide the desired product-enriched material as a light-yellow film. The enriched material was further purified by reverse-phase preparative HPLC using a Phenomenex Gemini column, 10 micron, C18, 100 Å, 150×30 mm, 0.1% TFA in ACN/H$_2$O, to provide the product, Example 151.0 (25 mg, 0.046 mmol, 30.8% yield), as a mixture of two diastereomers and as a white solid. $^1$H NMR (400 MHz, CD$_3$OD) δ 7.58 (td, J=8.50, 4.52 Hz, 1H) 6.83-6.91 (m, 2H) 6.04 (td, J=2.38, 1.34 Hz, 1H) 5.96 (dd, J=7.83, 3.42 Hz, 1H) 4.19 (dd, J=13.57, 4.77 Hz, app. ~0.5H) 3.94 (dd, J=14.18, 5.38 Hz, app. ~0.5H) 3.79-3.85 (m, 6H) 3.73-3.79 (m, 1H) 3.55-3.65 (m, 1H) 3.44-3.54 (m, 1H) 3.37-3.44 (m, 1H) 3.16-3.26 (m, 1H) 2.29-2.40 (m, 2H) 2.28 (s, 3H) 1.78-1.99 (m, 3H) 1.64-1.77 (m, 1H) 1.28 (d, J=6.85 Hz, app. ~1.5H) 1.23 (d, J=6.85 Hz, app. ~1.5H). LCMS-ESI (pos.), m/z: 548.3 (M+H)$^+$.

Example 152.0. Preparation of (1R,2S)—N-(4-(2,6-dimethoxyphenyl)-5-(5-methyl-2-furanyl)-4H-1,2,4-triazol-3-yl)-1-hydroxy-1-(5-methoxy-2-pyrazinyl)-2-propanesulfonamide and (1S,2R)—N-(4-(2,6-dimethoxyphenyl)-5-(5-methyl-2-furanyl)-4H-1,2,4-triazol-3-yl)-1-hydroxy-1-(5-methoxy-2-pyrazinyl)-2-propanesulfonamide

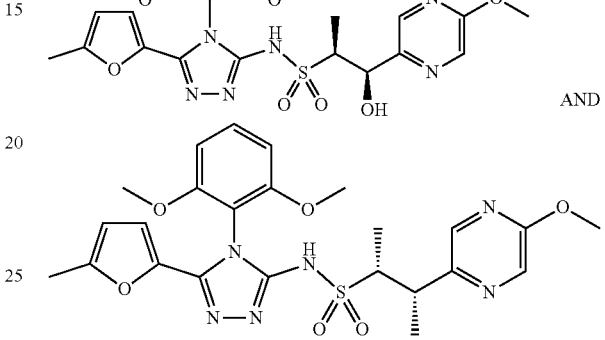

AND (1R,2S)—N-(4-(2,6-Dimethoxyphenyl)-5-(5-methyl-2-furanyl)-4H-1,2,4-triazol-3-yl)-1-hydroxy-1-(5-methoxy-2-pyrazinyl)-2-propanesulfonamide and (1S,2R)—N-(4-(2,6-dimethoxyphenyl)-5-(5-methyl-2-furanyl)-4H-1,2,4-triazol-3-yl)-1-hydroxy-1-(5-methoxy-2-pyrazinyl)-2-propanesulfonamide, Example 152.0. Example 152.0 was prepared from Example 369.0 and 5-methoxypyrazine-2-carbaldehyde following the procedure described in Example 153.0. The product was the major isomer obtained under the reaction condition. $^1$H NMR (500 MHz, CDCl$_3$) δ 10.95 (br s, 1H) 8.27 (s, 1H) 8.15 (d, J=1.22 Hz, 1H) 7.52 (t, J=8.56 Hz, 1H) 6.72 (dd, J=14.67, 8.56 Hz, 2H) 5.95 (dd, J=3.42, 0.98 Hz, 1H) 5.87 (d, J=3.42 Hz, 1H) 5.52 (d, J=0.73 Hz, 1H) 4.01 (d, J=0.98 Hz, 1H) 3.98 (s, 3H) 3.84 (s, 3H) 3.77 (s, 3H) 3.69 (qd, J=7.01, 1.22 Hz, 1H) 2.34 (s, 3H) 1.15 (d, J=7.09 Hz, 3H). LCMS-ESI (pos.), m/z: 531.0 (M+H)$^+$.

Example 153.0. Preparation of 1R,2R)-1-(4-chloro-2-(methylsulfonyl)phenyl)-N-(4-(2,6-dimethoxyphenyl)-5-(5-methyl-2-furanyl)-4H-1,2,4-triazol-3-yl)-1-hydroxy-2-propanesulfonamide or (1S,2S)-1-(4-chloro-2-(methylsulfonyl)phenyl)-N-(4-(2,6-dimethoxyphenyl)-5-(5-methyl-2-furanyl)-4H-1,2,4-triazol-3-yl)-1-hydroxy-2-propanesulfonamide

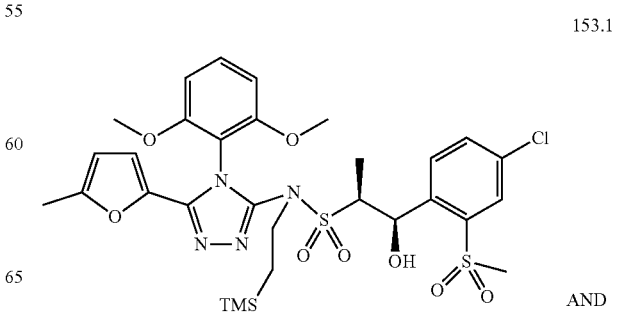

AND

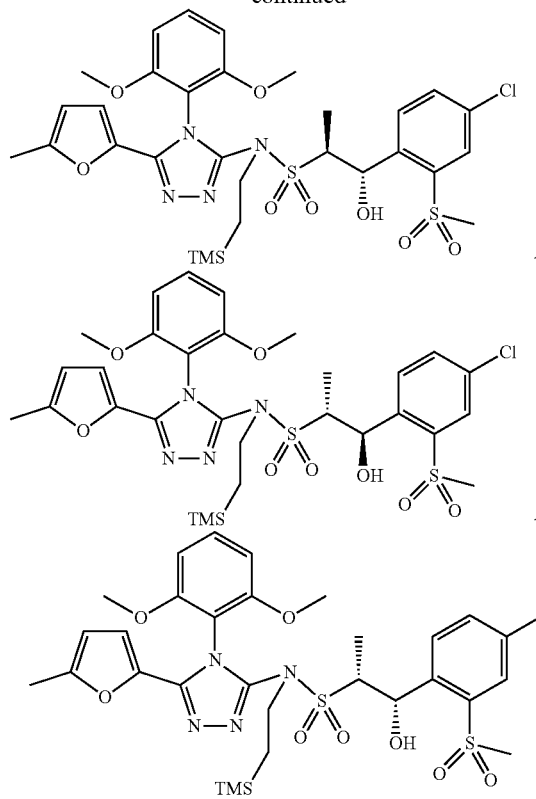

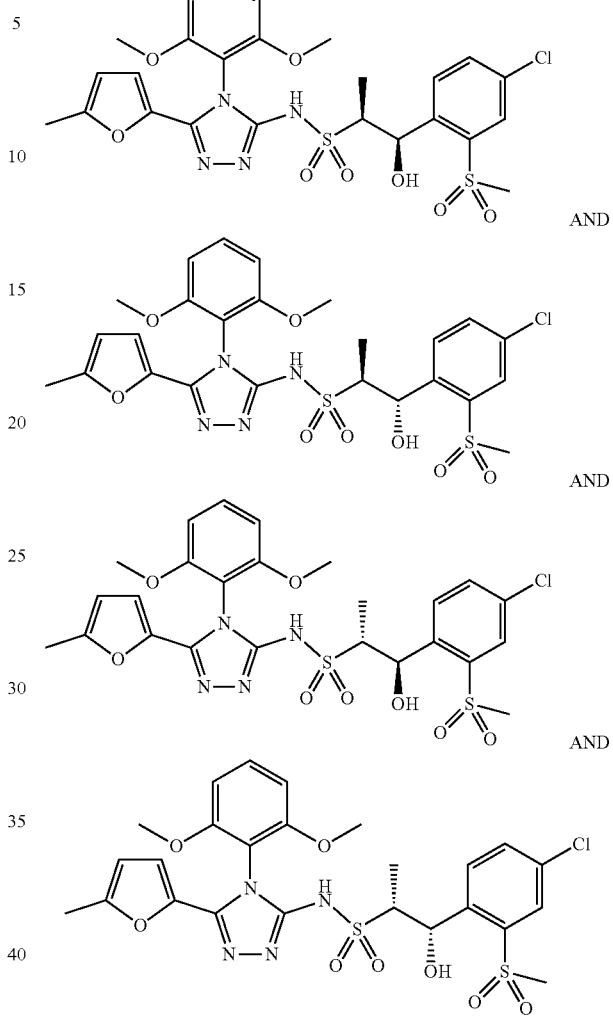

(1R,2R)-1-(4-Chloro-2-(methylsulfonyl)phenyl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide and (1R,2S)-1-(4-chloro-2-(methylsulfonyl)phenyl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide and (1S,2R)-1-(4-chloro-2-(methylsulfonyl)phenyl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide and (1S,2S)-1-(4-chloro-2-(methylsulfonyl)phenyl)-N-(4-(2,6-dimethoxyphenyl)-5-(5-methylfuran-2-yl)-4H-1,2,4-triazol-3-yl)-1-hydroxy-N-(2-(trimethylsilyl)ethyl)propane-2-sulfonamide, Example 153.1. To a 250 mL RBF was added Example 369.0 (542 mg, 1.10 mmol) in 2-methyltetrahydrofuran (8.0 mL). n-Butyllithium solution (2.5 M in hexanes, 0.53 mL, 1.32 mmol) was then added dropwise via syringe under $N_2$ at −78° C. The mixture was stirred at −78° C. for 10 min and then 4-chloro-2-(methylsulfonyl)benzaldehyde (265 mg, 1.21 mmol) in 2-methyltetrahydrofuran (8 mL) was added dropwise via syringe under $N_2$ at −78° C. The reaction mixture was then stirred at −78° C. for 10 min before the dry-ice bath was removed. The reaction mixture was stirred at −78° C. and allowed to warm to RT for 60 min in total before being quenched with a saturated aqueous solution of $NH_4Cl$ at lower temperature. The reaction mixture was diluted with a saturated aqueous solution of $NH_4Cl$ and extracted with EtOAc. The combined organic layers were washed with brine and dried over $Na_2SO_4$. The solution was filtered and concentrated in vacuo to give a light-yellow oil which was purified by chromatography (gradient of 0% to 100% EtOAc in DCM) to provide the product as a mixture of diastereomers, Example 153.1 (150 mg, 0.211 mmol, 19% yield), and as a light-yellow oil. LCMS-ESI (pos.), m/z: 711.1 (M+H)$^+$.

(1R,2R)-1-(4-Chloro-2-(methylsulfonyl)phenyl)-N-(4-(2,6-dimethoxyphenyl)-5-(5-methylfuran-2-yl)-4H-1,2,4-triazol-3-yl)-1-hydroxypropane-2-sulfonamide and (1R,2S)-1-(4-chloro-2-(methylsulfonyl)phenyl)-N-(4-(2,6-dimethoxyphenyl)-5-(5-methylfuran-2-yl)-4H-1,2,4-triazol-3-yl)-1-hydroxypropane-2-sulfonamide and (1S,2R)-1-(4-chloro-2-(methylsulfonyl)phenyl)-N-(4-(2,6-dimethoxyphenyl)-5-(5-methylfuran-2-yl)-4H-1,2,4-triazol-3-yl)-1-hydroxypropane-2-sulfonamide and (1S,2S)-1-(4-chloro-2-(methylsulfonyl)phenyl)-N-(4-(2,6-dimethoxyphenyl)-5-(5-methylfuran-2-yl)-4H-1,2,4-triazol-3-yl)-1-hydroxypropane-2-sulfonamide, Example 153.2. To a 50 mL RBF was added Example 153.1 (150 mg, 0.211 mmol) in DMF (3 mL). To the mixture was added tris(dimethylamino)sulfonium difluorotrimethylsilicatetris(dimethylamino)sulfonium difluorotrimethylsilicate (174 mg, 0.633 mmol) under $N_2$ flow. The solution was stirred at 90° C. for 120 min. LCMS analysis indicated the reaction was complete. The reaction mixture was diluted with water and extracted with DCM. The combined organic layers were washed with brine and dried over $Na_2SO_4$. The solution was filtered and concentrated in vacuo to give a light-yellow oil. The material thus obtained was absorbed onto a plug of silica gel and purified by chromatography through a Redi-Sep pre-packed silica gel column (12 g) eluting with a gradient of 0% to 100% EtOAc in DCM to provide Example 153.1 (110 mg, 0.180 mmol, 85% yield) as a mixture of diastereomers and as la ight-yellow solid. LCMS-ESI (pos.), m/z: 611.2 (M+H)⁺.

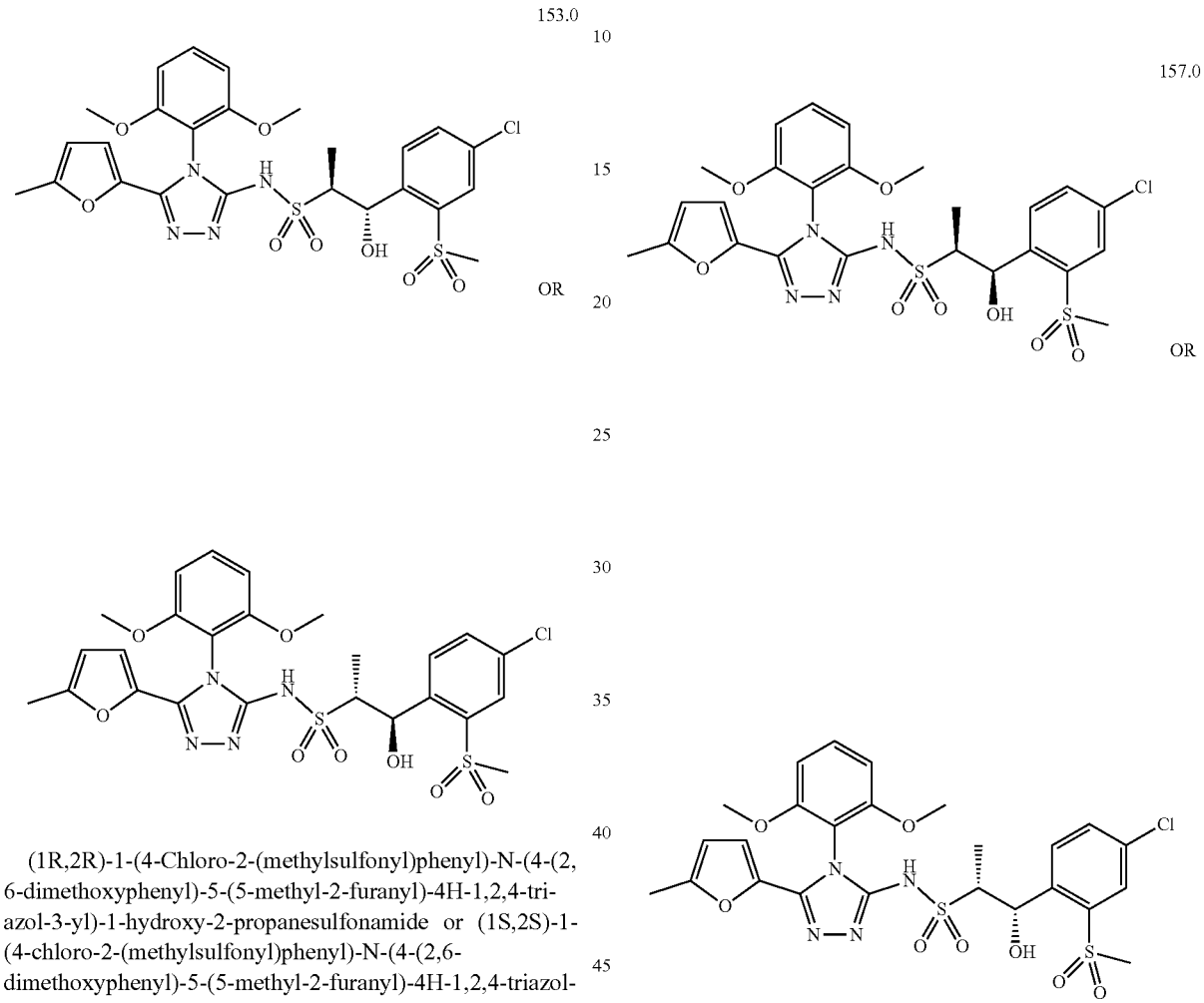

(1R,2R)-1-(4-Chloro-2-(methylsulfonyl)phenyl)-N-(4-(2,6-dimethoxyphenyl)-5-(5-methyl-2-furanyl)-4H-1,2,4-triazol-3-yl)-1-hydroxy-2-propanesulfonamide or (1S,2S)-1-(4-chloro-2-(methylsulfonyl)phenyl)-N-(4-(2,6-dimethoxyphenyl)-5-(5-methyl-2-furanyl)-4H-1,2,4-triazol-3-yl)-1-hydroxy-2-propanesulfonamide, Example 153.0. Example 153.0 was obtained from the separation of Example 153.2 in two stages of SFC chiral separation under the following conditions. Step 1: Separation of peak 1 (the first isomer to elute from the IA column) from peaks 2, 3 and 4; IA (2×15 cm), 20% MeOH (0.1% NH₄OH)/CO₂, 100 bar, 60 mL/min, 220 nm. injection volume: 0.5 mL, 11 mg/mL 1:1 DCM:MeOH. Step 2: Separation of peak 2, Peak 3 and Peak 4; IC (2×15 cm), 32% EtOH/CO₂, 100 bar, 60 mL/min, 220 nm. injection volume: 1 mL. The title compound, Example 153.0, was the later isomer to elute from the IA column compared to its opposite enantiomer which was the first among the four isomers to elute from the IA column as described above. ¹H NMR (500 MHz, CD₃OD) δ 8.02 (s, 1H) 7.75 (s, 2H) 7.55 (t, J=8.32 Hz, 1H) 6.85 (d, J=8.56 Hz, 2H) 6.03 (d, J=2.69 Hz, 1H) 5.92-5.98 (m, 1H) 5.81 (d, J=8.31 Hz, 1H) 3.80 (s, 3H) 3.78 (s, 3H) 3.59-3.70 (m, 1H) 3.20 (s, 3H) 2.28 (s, 3H) 1.05 (d, J=6.60 Hz, 3H). LCMS-ESI (pos.), m/z: 611.2 (M+H)⁺.

Example 157.0. Preparation of (1R,2S)-1-(4-chloro-2-(methylsulfonyl)phenyl)-N-(4-(2,6-dimethoxyphenyl)-5-(5-methyl-2-furanyl)-4H-1,2,4-triazol-3-yl)-1-hydroxy-2-propanesulfonamide or (1S,2R)-1-(4-chloro-2-(methylsulfonyl)phenyl)-N-(4-(2,6-dimethoxyphenyl)-5-(5-methyl-2-furanyl)-4H-1,2,4-triazol-3-yl)-1-hydroxy-2-propanesulfonamide (1R,2S)-1-(4-Chloro-2-(methylsulfonyl)phenyl)-N-(4-(2,6-dimethoxyphenyl)-5-(5-methyl-2-furanyl)-4H-1,2,4-triazol-3-yl)-1-hydroxy-2-propanesulfonamide or (1S,2R)-1-(4-chloro-2-(methylsulfonyl)phenyl)-N-(4-(2,6-dimethoxyphenyl)-5-(5-methyl-2-furanyl)-4H-1,2,4-triazol-3-yl)-1-hydroxy-2-propanesulfonamide, Example 157.0. Example 157.0 is not the enanatiomer of, but is the diastereomer of, Example 153.0 and was the second among three isomers to elute in the second stage separation of Example 153.2 from the IC column as described in Example 153.0. ¹H NMR (500 MHz, CD₃OD) δ 7.97 (d, J=2.45 Hz, 1H) 7.84 (d, J=8.56 Hz, 1H) 7.73 (dd, J=8.56, 2.20 Hz, 1H) 7.59 (t, J=8.56 Hz, 1H) 6.91 (d, J=8.31 Hz, 1H) 6.87 (d, J=8.56 Hz, 1H) 6.04 (d, J=2.93 Hz, 1H) 5.96-6.01 (m, 2H) 3.86 (s, 3H) 3.79 (s, 3H) 3.59-3.67 (m, 2H) 3.10 (s, 3H) 2.28 (s, 3H) 1.36 (d, J=6.85 Hz, 3H). LCMS-ESI (pos.), m/z: 611.2 (M+H)⁺.

Example 154.0. Preparation of (3S,5S)-5-(1-azetidi-nylcarbonyl)-N-(4-(2,6-dimethoxyphenyl)-5-(5-methyl-2-furanyl)-4H-1,2,4-triazol-3-yl)-1-(5-fluoro-2-pyrimidinyl)-3-piperidinesulfonamide and (3R,5R)-5-(1-azetidinylcarbonyl)-N-(4-(2,6-dimethoxyphenyl)-5-(5-methyl-2-furanyl)-4H-1,2,4-triazol-3-yl)-1-(5-fluoro-2-pyrimidinyl)-3-piperidinesulfonamide

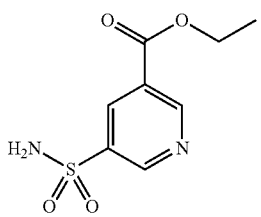

154.1

Ethyl 5-sulfamoylnicotinate, Example 154.1. To a 250 mL RBF was added 5-bromopyridine-3-sulfonamide (commercially available from Combi-Blocks Inc., CA, USA, 2.29 g, 9.66 mmol) and 1,1'-bis(diphenylphosphino)ferrocene)dichloropalladium(II) (commercially available from Frontier Scientific Services Inc., 0.707 g, 0.97 mmol). The flask was placed under vacuum and back-filled with EtOH (25 mL), DMAc, (anhydrous, 25 mL, 269 mmol) and TEA (4.03 mL, 29.0 mmol). The flask was vacuumed and back-filled with $N_2$ two times, and then vacuumed and back-filled with carbon monoxide gas (CO balloon). The reaction mixture was then stirred at 90° C. for 40 h under carbon monoxide gas. LCMS analysis indicated the reaction was complete. The reaction mixture was allowed to cool to RT. The solution was concentrated in vacuo to remove most of the EtOH and DMAc. The residual solution was diluted with water. The precipitate was removed by filtration through a pad of Celite® brand filter aid. The pad was rinsed with water multiple times and then with 1 N HCl and then water. All aqueous phases were combined and treated with a saturated solution of $NaHCO_3$ (pH>9) and extracted with DCM. The DCM solution was then washed with water. The DCM solution was concentrated in vacuo and the residue was purified by silica gel chromatography (gradient of 0% to 100% EtOAc in DCM, with 30% EtOH in EtOAc) to provide Example 154.1 (1.85 g, 83% yield) as a light yellow solid. $^1$H NMR (500 MHz, $CD_3OD$) δ 9.31 (d, J=1.96 Hz, 1H) 9.22 (d, J=2.20 Hz, 1H) 8.79 (t, J=2.08 Hz, 1H) 4.48 (q, J=7.09 Hz, 2H) 1.45 (t, J=7.21 Hz, 3H). LCMS-ESI (pos.), m/z: 231.1 (M+H)$^+$.

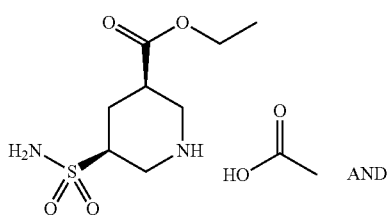

154.2

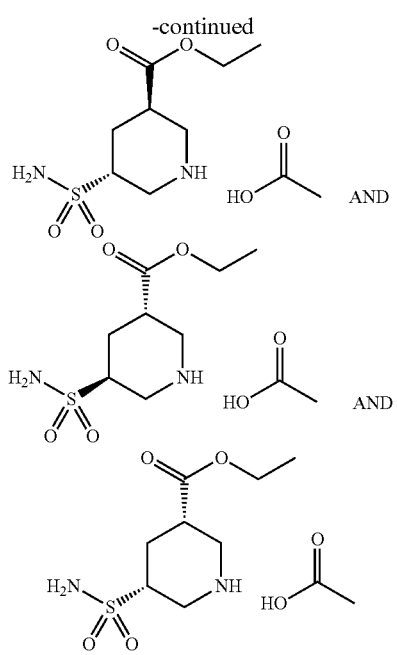

(3R,5R)-Ethyl 5-sulfamoylpiperidine-3-carboxylate acetate and (3R,5S)-ethyl 5-sulfamoylpiperidine-3-carboxylate acetate and (3S,5R)-ethyl 5-sulfamoylpiperidine-3-carboxylate acetate and (3S,5S)-ethyl 5-sulfamoylpiperidine-3-carboxylate acetate, Example 154.2. Under a stream of $N_2$, Example 154.1 (1.85 g, 8.04 mmol) and platinum (IV) oxide (1.825 g, 8.04 mmol) were added to a 250 mL RBF. The flask was vacuumed and back-filled with AcOH (40 mL). The flask was placed under vacuum and back-filled with $N_2$ two times, and then placed under vacuum and back-filled with hydrogen gas (balloon). The reaction mixture was then stirred at RT under hydrogen gas for 3 days. LCMS analysis indicated the reaction was complete. Celite® brand filter aid (10 g) was added to the stirred mixture. The solid was then removed by filtration after 10 min. The filter cake was rinsed with MeOH. The combined organics were concentrated in vacuo to afford Example 154.2 as a light yellow oil which was directly used in the next step without purification. LCMS-ESI (pos.), m/z: 237.2 (M+H)$^+$.

154.3

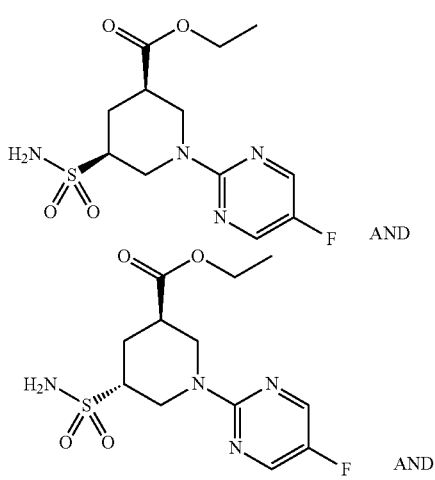

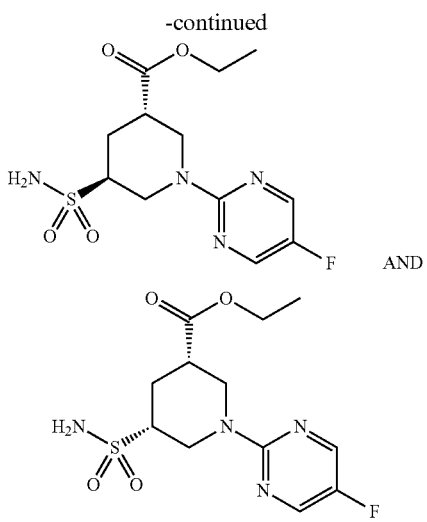

AND

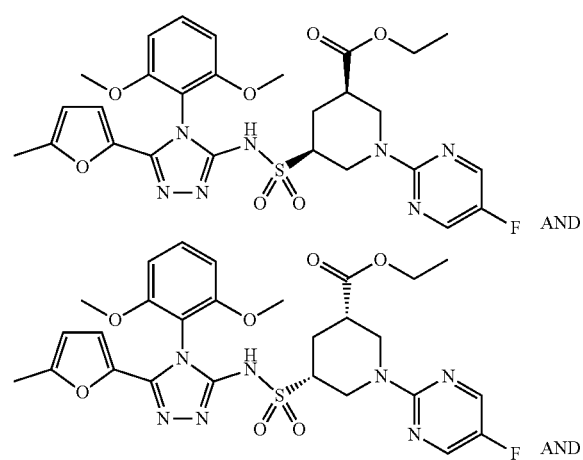

(3R,5R)-Ethyl 1-(5-fluoropyrimidin-2-yl)-5-sulfamoylpiperidine-3-carboxylate and (3R,5S)-ethyl 1-(5-fluoropyrimidin-2-yl)-5-sulfamoylpiperidine-3-carboxylate and (3S,5R)-ethyl 1-(5-fluoropyrimidin-2-yl)-5-sulfamoylpiperidine-3-carboxylate and (3S,5S)-ethyl 1-(5-fluoropyrimidin-2-yl)-5-sulfamoylpiperidine-3-carboxylate, Example 154.3. To a 250 mL RBF was added the initial product of Example 154.2 (2.38 g, 8.03 mmol). The flask was vacuumed and back-filled with DMSO (12 mL), 2-chloro-5-fluoro-pyrimidine (4.96 mL, 40.2 mmol) and Hunig's base (9.78 mL, 56.2 mmol). The flask was vacuumed and back-filled with $N_2$ two times. The reaction mixture was then stirred at 80° C. for 8.5 h under $N_2$. LCMS analysis indicated the reaction was complete. The reaction mixture was allowed to cool to RT and then diluted with water and extracted with DCM. The combined organic layers were washed with brine and dried over $Na_2SO_4$. The solution was filtered and concentrated in vacuo to give a light-yellow oil which was purified by silica gel chromatography (a gradient of 0% to 100% EtOAc in DCM) to provide the title compound Example 154.3 (902 mg, 2.71 mmol, 34% yield) as a light-yellow solid. LCMS-ESI (pos.), m/z: 333.2 $(M+H)^+$ 355.1 $(M+Na)^+$.

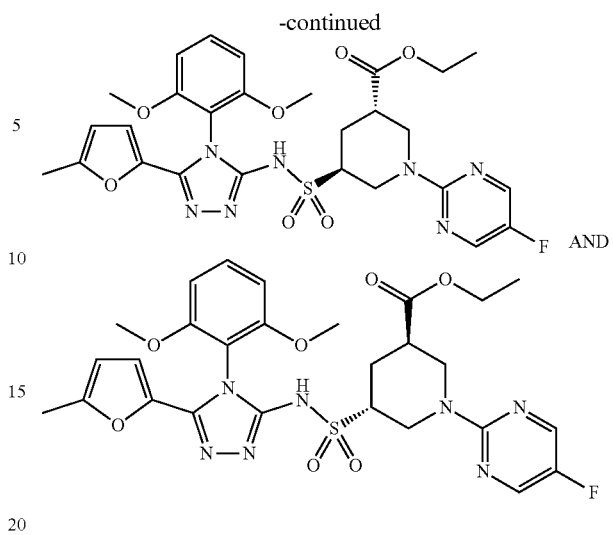

(3R,5R)-ethyl 5-(N-(4-(2,6-Dimethoxyphenyl)-5-(5-methylfuran-2-yl)-4H-1,2,4-triazol-3-yl)sulfamoyl)-1-(5-fluoropyrimidin-2-yl)piperidine-3-carboxylate and (3S,5S)-ethyl 5-(N-(4-(2,6-dimethoxyphenyl)-5-(5-methylfuran-2-yl)-4H-1,2,4-triazol-3-yl)sulfamoyl)-1-(5-fluoropyrimidin-2-yl)piperidine-3-carboxylate and (3R,5S)-ethyl 5-(N-(4-(2,6-dimethoxyphenyl)-5-(5-methylfuran-2-yl)-4H-1,2,4-triazol-3-yl)sulfamoyl)-1-(5-fluoropyrimidin-2-yl) piperidine-3-carboxylate and (3S,5R)-ethyl 5-(N-(4-(2,6-dimethoxyphenyl)-5-(5-methylfuran-2-yl)-4H-1,2,4-triazol-3-yl)sulfamoyl)-1-(5-fluoropyrimidin-2-yl)piperidine-3-carboxylate, Example 154.4. Example 154.4 was prepared from Example 364.1 and Example 154.3 using the procedure described in Example 94.0. LCMS-ESI (pos.), m/z: 616.3 $(M+H)^+$.

154.0

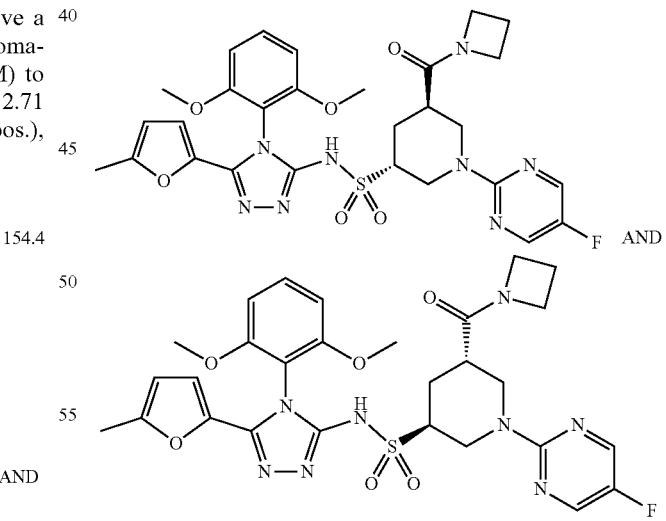

(3S,5S)-5-(1-Azetidinylcarbonyl)-N-(4-(2,6-dimethoxyphenyl)-5-(5-methyl-2-furanyl)-4H-1,2,4-triazol-3-yl)-1-(5-fluoro-2-pyrimidinyl)-3-piperidinesulfonamide and (3R,5R)-5-(1-azetidinylcarbonyl)-N-(4-(2,6-dimethoxyphenyl)-5-(5-methyl-2-furanyl)-4H-1,2,4-triazol-3-yl)-1-(5-fluoro-2-pyrimidinyl)-3-piperidinesulfonamide, Example 154.0. To a 5 mL vial was added Example 154.4 (148 mg, 0.24 mmol)

and azetidine (0.32 mL, 4.75 mmol) in DMSO (1.5 mL). The reaction mixture was then stirred at RT for 63 h. LCMS analysis indicated formation of the desired product along with unreacted starting material. The initial material obtained was purified by reverse-phase preparative HPLC (0.1% TFA in ACN/H$_2$O, gradient 5% to 95%) to provide Example 154.0 (10 mg, 0.016 mmol, 7% yield) as a white solid and Example 155.0 (19 mg, 0.030 mmol, 12.61% yield) as a white solid. The title compound, Example 154.0, was the earlier peak to elute using the reverse-phase preparative HPLC. $^1$H NMR (500 MHz, CDCl$_3$) δ 8.21 (s, 2H) 7.50 (t, J=8.56 Hz, 1H) 6.71 (dd, J=8.56, 1.96 Hz, 2H) 5.95 (dd, J=3.42, 0.98 Hz, 1H) 5.84 (d, J=3.42 Hz, 1H) 5.02 (d, J=14.67 Hz, 1H) 4.49 (dd, J=13.45, 3.18 Hz, 1H) 4.34 (d, J=7.34 Hz, 1H) 4.24 (d, J=7.34 Hz, 1H) 4.07 (t, J=7.09 Hz, 2H) 3.75-3.82 (m, 7H) 3.68 (dd, J=14.67, 4.40 Hz, 1H) 3.35-3.46 (m, 2H) 3.10 (br. s., 1H) 2.49 (d, J=14.43 Hz, 1H) 2.28-2.37 (m, 6H) 2.18-2.27 (m, 1H). LCMS-ESI (pos.), m/z: 627.2 (M+H)$^+$.

Example 155.0. Preparation of (3S,5R)-5-(1-azetidinylcarbonyl)-N-(4-(2,6-dimethoxyphenyl)-5-(5-methyl-2-furanyl)-4H-1,2,4-triazol-3-yl)-1-(5-fluoro-2-pyrimidinyl)-3-piperidinesulfonamide and (3R,5S)-5-(1-azetidinylcarbonyl)-N-(4-(2,6-dimethoxyphenyl)-5-(5-methyl-2-furanyl)-4H-1,2,4-triazol-3-yl)-1-(5-fluoro-2-pyrimidinyl)-3-piperidinesulfonamide

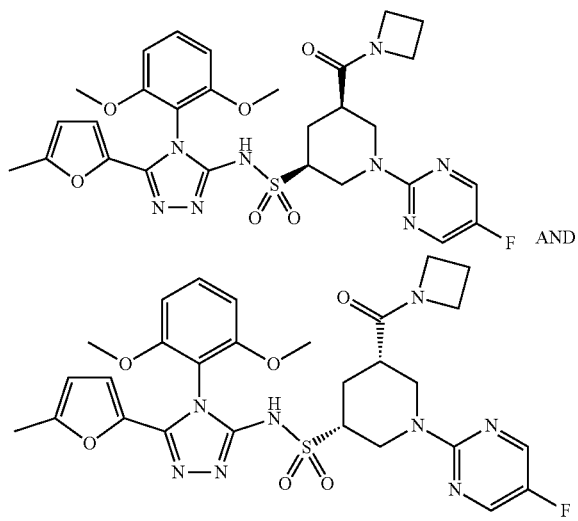

155.0

(3S,5R)-5-(1-Azetidinylcarbonyl)-N-(4-(2,6-dimethoxyphenyl)-5-(5-methyl-2-furanyl)-4H-1,2,4-triazol-3-yl)-1-(5-fluoro-2-pyrimidinyl)-3-piperidinesulfonamide and (3R, 5S)-5-(1-azetidinylcarbonyl)-N-(4-(2,6-dimethoxyphenyl)-5-(5-methyl-2-furanyl)-4H-1,2,4-triazol-3-yl)-1-(5-fluoro-2-pyrimidinyl)-3-piperidinesulfonamide, Example 155.0. Example 155.0 was the later peak to elute on the reverse-phase preparative HPLC and a mixture of two syn enantiomers as described in Example 154.0. $^1$H NMR (500 MHz, CDCl$_3$) δ 8.21-8.24 (m, 2H) 7.48 (t, J=8.56 Hz, 1H) 6.71 (t, J=7.70 Hz, 2H) 5.91-5.95 (m, 1H) 5.82 (d, J=3.42 Hz, 1H) 5.17-5.27 (m, 1H) 4.66-4.77 (m, 1H) 4.31 (d, J=7.34 Hz, 1H) 4.20 (d, J=7.34 Hz, 1H) 4.09 (t, J=7.83 Hz, 2H) 3.78-3.86 (m, 6H) 3.02-3.13 (m, 1H) 2.88-3.00 (m, 2H) 2.27-2.43 (m, 7H) 2.04 (d, J=12.72 Hz, 1H). LCMS-ESI (pos.), m/z: 627.2 (M+H)$^+$.

Example 156.0. Preparation of Ethyl (3R,5S)-5-((4-(2,6-dimethoxyphenyl)-5-(2-furanyl)-4H-1,2,4-triazol-3-yl)sulfamoyl)-1-(5-fluoro-2-pyrimidinyl)-3-piperidinecarboxylate or Ethyl (3S,5R)-5-((4-(2,6-dimethoxyphenyl)-5-(2-furanyl)-4H-1,2,4-triazol-3-yl)sulfamoyl)-1-(5-fluoro-2-pyrimidinyl)-3-piperidinecarboxylate

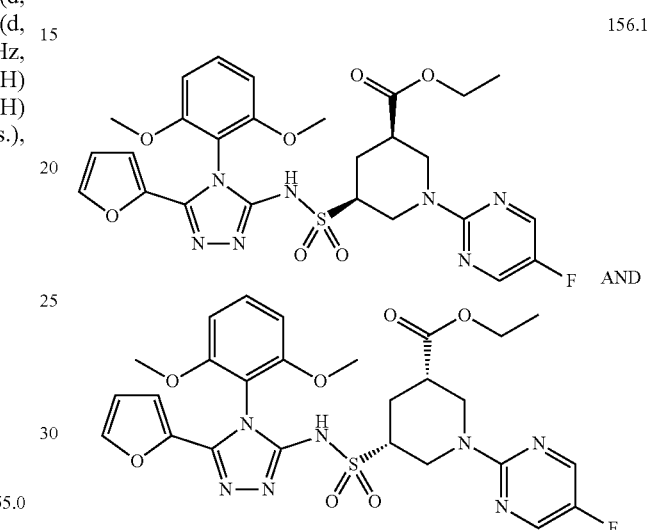

156.1

Ethyl (3R,5S)-5-((4-(2,6-Dimethoxyphenyl)-5-(2-furanyl)-4H-1,2,4-triazol-3-yl)sulfamoyl)-1-(5-fluoro-2-pyrimidinyl)-3-piperidinecarboxylate and Ethyl (3S,5R)-5-((4-(2,6-dimethoxyphenyl)-5-(2-furanyl)-4H-1,2,4-triazol-3-yl)sulfamoyl)-1-(5-fluoro-2-pyrimidinyl)-3-piperidinecarboxylate, Example 156.1. Example 156.1 was prepared from 3-bromo-4-(2,6-dimethoxyphenyl)-5-(furan-2-yl)-4H-1,2,4-triazole, Example 364.3 and Example 154.3 using the procedure described in Example 94.0. The title compound, Example 156.1, was isolated as a white solid and was a mixture of two syn enantiomers. $^1$H NMR (500 MHz, CDCl$_3$) δ 8.21 (s, 2H) 7.44-7.52 (m, 2H) 6.69 (d, J=8.56 Hz, 2H) 6.34 (dd, J=3.42, 1.71 Hz, 1H) 6.00 (d, J=3.67 Hz, 1H) 5.22 (dd, J=12.96, 1.96 Hz, 1H) 4.87-4.97 (m, 1H) 4.17 (q, J=7.17 Hz, 2H) 3.73-3.81 (m, 6H) 3.03-3.14 (m, 1H) 2.91-3.00 (m, 1H) 2.87 (dd, J=13.20, 11.74 Hz, 1H) 2.60 (d, J=12.47 Hz, 1H) 2.44-2.56 (m, 1H) 1.24-1.31 (m, 3H). LCMS-ESI (pos.), m/z: 602.2 (M+H)$^+$.

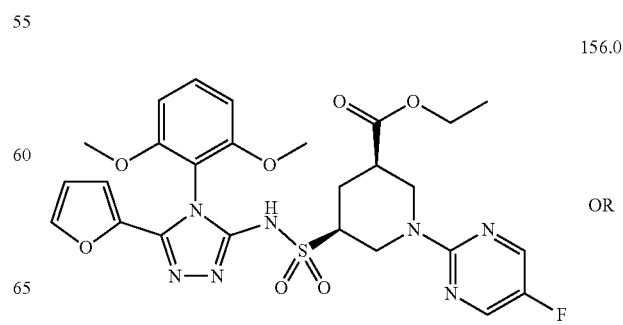

156.0

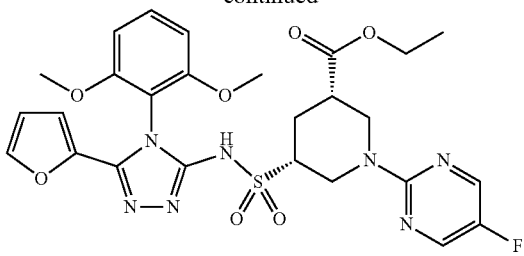

Ethyl (3R,5S)-5-((4-(2,6-Dimethoxyphenyl)-5-(2-furanyl)-4H-1,2,4-triazol-3-yl)sulfamoyl)-1-(5-fluoro-2-pyrimidinyl)-3-piperidinecarboxylate or Ethyl (3S,5R)-5-((4-(2,6-dimethoxyphenyl-5-(2-furanyl)-4H-1,2,4-triazol-3-yl)sulfamoyl)-1-(5-fluoro-2-pyrimidinyl)-3-piperidinecarboxylate, Example 156.0. Example 156.0 was prepared from SFC chiral separation of Example 156.1. Example 156.0 was the second enantiomer to elute from an AS-H column under the following conditions: Thar 80 SFC with 250×30 mm AS-H column with 36 g/min MeOH (neat))+44 g/min CO$_2$, 45% co-solvent at 80 g/min. Outlet pressure=99 bar; Temp.=25° C.; Wavelength=243 nm. Injected 1.0 mL of a solution from 216 mg sample dissolved in 18 mL of MeOH:DCM 16:2, c=12.0 mg/mL; 12.0 mg per injection. $^1$H NMR (500 MHz, CDCl$_3$) δ 8.22 (s, 2H) 7.44-7.54 (m, 2H) 6.70 (d, J=8.31 Hz, 2H) 6.35 (dd, J=3.55, 1.59 Hz, 1H) 6.01 (d, J=3.42 Hz, 1H) 5.24 (d, J=12.47 Hz, 1H) 4.94 (d, J=12.23 Hz, 1H) 4.18 (q, J=7.09 Hz, 2H) 3.80 (s, 3H) 3.78 (s, 3H) 3.04-3.18 (m, 1H) 2.92-3.03 (m, 1H) 2.88 (t, J=12.23 Hz, 1H) 2.62 (d, J=12.23 Hz, 1H) 2.52 (br. s., 1H) 1.96 (q, J=12.23 Hz, 1H) 1.29 (t, J=6.97 Hz, 3H). LCMS-ESI (pos.), m/z: 602.2 (M+H)$^+$.

Example 157.0. Preparation of (1R,2R)-1-(4-chloro-2-(methylsulfonyl)phenyl)-N-(4-(2,6-dimethoxyphenyl)-5-(5-methyl-2-furanyl)-4H-1,2,4-triazol-3-yl)-1-hydroxy-2-propanesulfonamide or (1S,2S)-1-(4-chloro-2-(methylsulfonyl)phenyl)-N-(4-(2,6-dimethoxyphenyl)-5-(5-methyl-2-furanyl)-4H-1,2,4-triazol-3-yl)-1-hydroxy-2-propanesulfonamide 157.0

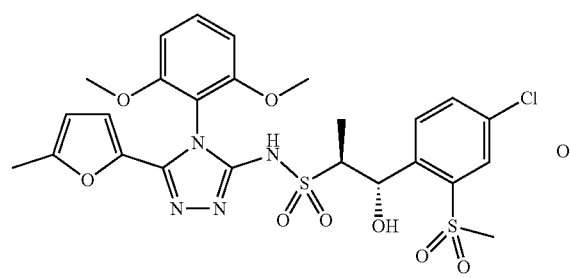

OR

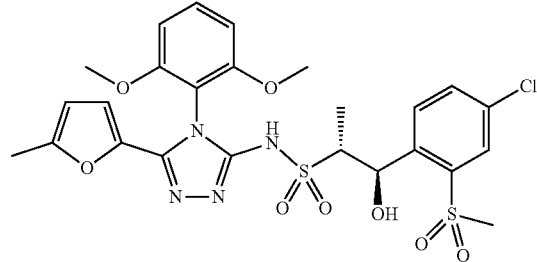

(1R,2R)-1-(4-Chloro-2-(methylsulfonyl)phenyl)-N-(4-(2,6-dimethoxyphenyl)-5-(5-methyl-2-furanyl)-4H-1,2,4-triazol-3-yl-1-hydroxy-2-propanesulfonamide or (1S,2S)-1-(4-chloro-2-(methylsulfonyl)phenyl)-N-(4-(2,6-dimethoxyphenyl)-5-(5-methyl-2-furanyl)-4H-1,2,4-triazol-3-yl-1-hydroxy-2-propanesulfonamide, Example 157.0. Example 157.0 is not the enantiomer of, but is a diastereomer of, Example 153.0 and was the second among three isomers to elute in the second stage separation of Example 153.2 from the IC column as described in Example 153.0. $^1$H NMR (500 MHz, CD$_3$OD) δ 7.97 (d, J=2.45 Hz, 1H) 7.84 (d, J=8.56 Hz, 1H) 7.73 (dd, J=8.56, 2.20 Hz, 1H) 7.59 (t, J=8.56 Hz, 1H) 6.91 (d, J=8.31 Hz, 1H) 6.87 (d, J=8.56 Hz, 1H) 6.04 (d, J=2.93 Hz, 1H) 5.96-6.01 (m, 2H) 3.86 (s, 3H) 3.79 (s, 3H) 3.59-3.67 (m, 2H) 3.10 (s, 3H) 2.28 (s, 3H) 1.36 (d, J=6.85 Hz, 3H). LCMS-ESI (pos.), m/z: 611.2 (M+H)$^+$.

Example 158.0. Preparation of Ethyl (3R,5R)-5-((4-(2,6-dimethoxyphenyl)-5-(2-furanyl)-4H-1,2,4-triazol-3-yl)sulfamoyl)-1-(5-fluoro-2-pyrimidinyl)-3-piperidinecarboxylate or ethyl (3S,5S)-5-((4-(2,6-dimethoxyphenyl)-5-(2-furanyl)-4H-1,2,4-triazol-3-yl)sulfamoyl)-1-(5-fluoro-2-pyrimidinyl)-3-piperidinecarboxylate 158.1

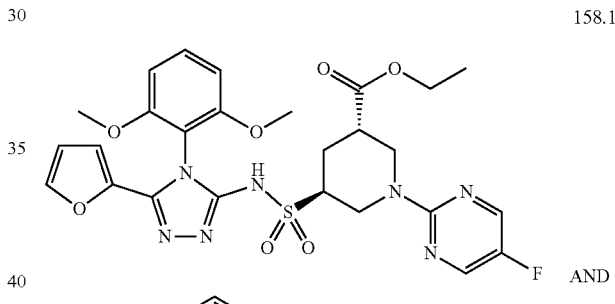

AND

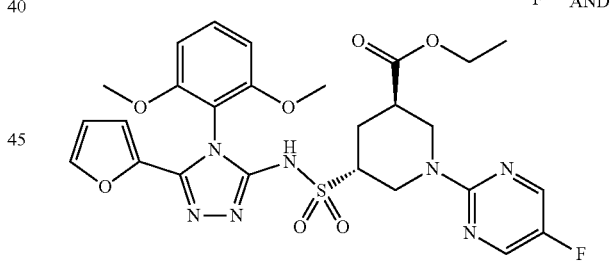

Ethyl (3R,5R)-5-((4-(2,6-Dimethoxyphenyl)-5-(2-furanyl)-4H-1,2,4-triazol-3-yl)sulfamoyl)-1-(5-fluoro-2-pyrimidinyl)-3-piperidinecarboxylate and ethyl (3S,5S)-5-((4-(2,6-dimethoxyphenyl)-5-(2-furanyl)-4H-1,2,4-triazol-3-yl)sulfamoyl)-1-(5-fluoro-2-pyrimidinyl)-3-piperidinecarboxylate, Example 158.1. Example 158.1 was prepared from 3-bromo-4-(2,6-dimethoxyphenyl)-5-(furan-2-yl)-4H-1,2,4-triazole, Example 364.3, and Example 154.3 using the procedure described in Example 94.0. The title compound, Example 158.1, was isolated as a white solid. $^1$H NMR (500 MHz, CDCl$_3$) δ 8.16 (s, 2H) 7.43-7.51 (m, 2H) 6.68 (dd, J=8.56, 1.71 Hz, 2H) 6.34 (dd, J=3.55, 1.83 Hz, 1H) 5.96-6.03 (m, 1H) 4.59 (dd, J=13.57, 4.28 Hz, 1H) 4.47 (dd, J=13.45, 4.89 Hz, 1H) 4.04 (q, J=7.09 Hz, 2H) 3.69-3.81 (m, 7H) 3.61 (dd, J=13.45, 3.91 Hz, 1H) 3.49 (dt, J=8.80, 4.40 Hz, 1H) 2.97 (t, J=4.77 Hz, 1H) 2.45 (dt, J=13.75, 5.10 Hz, 1H) 2.23 (ddd, J=13.82, 9.17, 4.89 Hz, 1H) 1.16 (t, J=7.21 Hz, 3H). LCMS-ESI (pos.), m/z: 602.2 (M+H)⁺.

158.0

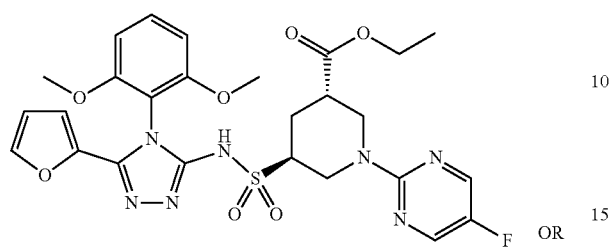

OR

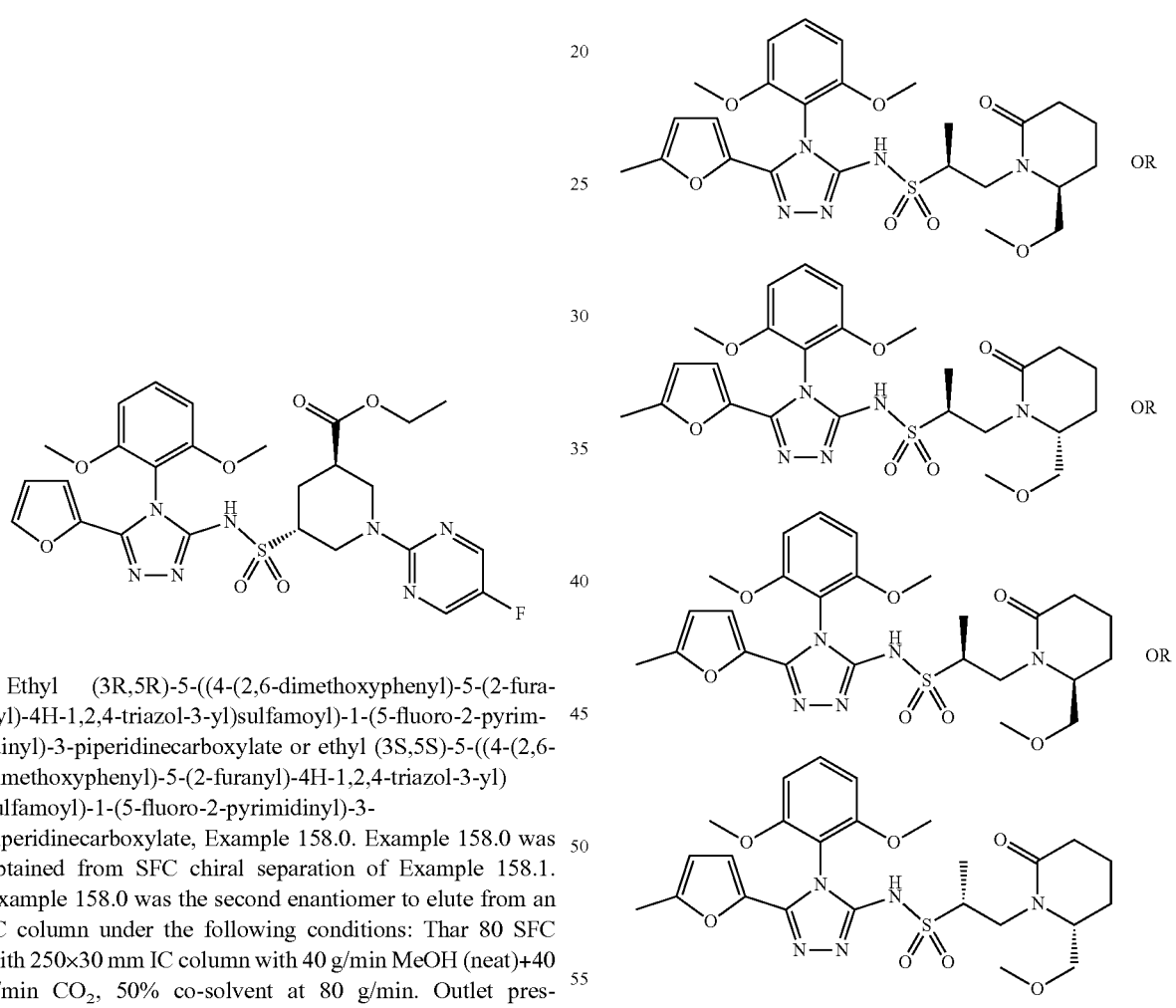

Ethyl (3R,5R)-5-((4-(2,6-dimethoxyphenyl)-5-(2-furanyl)-4H-1,2,4-triazol-3-yl)sulfamoyl)-1-(5-fluoro-2-pyrimidinyl)-3-piperidinecarboxylate or ethyl (3S,5S)-5-((4-(2,6-dimethoxyphenyl)-5-(2-furanyl)-4H-1,2,4-triazol-3-yl)sulfamoyl)-1-(5-fluoro-2-pyrimidinyl)-3-piperidinecarboxylate, Example 158.0. Example 158.0 was obtained from SFC chiral separation of Example 158.1. Example 158.0 was the second enantiomer to elute from an IC column under the following conditions: Thar 80 SFC with 250×30 mm IC column with 40 g/min MeOH (neat)+40 g/min CO₂, 50% co-solvent at 80 g/min. Outlet pressure=100 bar; Temp.=26° C.; Wavelength=244 nm. Manually injected 1.0 mL of a solution from 40 mg sample dissolved in 5.0 mL of MeOH:DCM 4:1, c=8.0 mg/mL; 8.0 mg per injection. ¹H NMR (500 MHz, CD₃OD) δ 8.25 (s, 2H) 7.51-7.64 (m, 2H) 6.86 (dd, J=8.44, 4.28 Hz, 2H) 6.44 (dd, J=3.42, 1.71 Hz, 1H) 6.11 (d, J=2.69 Hz, 1H) 4.68-4.79 (m, 2H) 4.03 (q, J=7.09 Hz, 2H) 3.80 (s, 3H) 3.79 (s, 3H) 3.40-3.55 (m, 3H) 2.99 (t, J=4.03 Hz, 1H) 2.47 (d, J=13.69 Hz, 1H) 2.03-2.14 (m, 1H) 1.16 (t, J=7.09 Hz, 3H). LCMS-ESI (pos.), m/z: 602.2 (M+H)⁺.

Example 159.0. Preparation of (2R)—N-(4-(2,6-dimethoxyphenyl)-5-(5-methyl-2-furanyl)-4H-1,2,4-triazol-3-yl)-1-((2R)-2-(methoxymethyl)-6-oxo-1-piperidinyl)-2-propanesulfonamide or (2R)—N-(4-(2,6-dimethoxyphenyl)-5-(5-methyl-2-furanyl)-4H-1,2,4-triazol-3-yl)-1-((2R)-2-(methoxymethyl)-6-oxo-1-piperidinyl)-2-propanesulfonamide or (2S)—N-(4-(2,6-dimethoxyphenyl)-5-(5-methyl-2-furanyl)-4H-1,2,4-triazol-3-yl)-1-((2R)-2-(methoxymethyl)-6-oxo-1-piperidinyl)-2-propanesulfonamide or (2S)—N-(4-(2,6-dimethoxyphenyl)-5-(5-methyl-2-furanyl)-4H-1,2,4-triazol-3-yl)-1-1(2S)-2-(methoxymethyl)-6-oxo-1-piperidinyl)-2-propanesulfonamide 159.0

(2R)—N-(4-(2,6-Dimethoxyphenyl)-5-(5-methyl-2-furanyl)-4H-1,2,4-triazol-3-yl)-1-((2R)-2-(methoxymethyl)-6-oxo-1-piperidinyl)-2-propanesulfonamide or (2R)—N-(4-(2,6-dimethoxyphenyl)-5-(5-methyl-2-furanyl)-4H-1,2,4-triazol-3-yl)-1-((2S)-2-(methoxymethyl)-6-oxo-1-piperidinyl)-2-propanesulfonamide or (2S)—N-(4-(2,6-dimethoxyphenyl)-5-(5-methyl-2-furanyl)-4H-1,2,4-triazol-3-yl)-1-((2R)-2-(methoxymethyl)-6-oxo-1-piperidinyl)-2-propanesulfonamide or (2S)—N-(4-(2,6-dimethoxyphenyl)-5-(5-methyl-2-furanyl)-4H-1,2,4-triazol-3-yl)-1-((2S)-2-

(methoxymethyl)-6-oxo-1-piperidinyl)-2-propanesulfonamide, Example 159.0. Example 159.0 is the 6-oxo-1-piperidinyl C-2 epimer of Example 150.0. Example 159.0 was the first peak (earlier peak vs. its C-2 MeOCH$_2$ epimer) to elute from a Regis Whelk-O column (45% IPA). It was obtained by SFC separation of Example 151.0 on the Regis Whelk-O column. $^1$H NMR (400 MHz, CD$_3$OD) δ 7.57 (t, J=8.50 Hz, 1H) 6.83-6.90 (m, 2H) 6.03 (dd, J=3.42, 0.93 Hz, 1H) 5.93-5.98 (m, 1H) 3.93 (dd, J=14.20, 5.49 Hz, 1H) 3.81 (s, 3H) 3.80 (s, 3H) 3.71-3.78 (m, 1H) 3.34-3.53 (m, 3H) 3.17-3.27 (m, 1H) 2.28-2.36 (m, 2H) 2.27 (s, 3H) 1.75-1.95 (m, 3H) 1.60-1.74 (m, 1H) 1.22 (d, J=6.84 Hz, 3H). LCMS-ESI (pos.), m/z: 548.2 (M+H)$^+$.

Example 160.0. Preparation of N-(4-(2,6-dimethoxyphenyl)-5-(5-methyl-2-furanyl)-4H-1,2,4-triazol-3-yl)-2-((6S)-3,6-dimethyl-2-oxotetrahydro-1(2H)-pyrimidinyl)ethanesulfonamide and N-(4-(2,6-dimethoxyphenyl)-5-(5-methyl-2-furanyl)-4H-1,2,4-triazol-3-yl)-2-((6R)-3,6-dimethyl-2-oxotetrahydro-1(2H)-pyrimidinyl)ethanesulfonamide

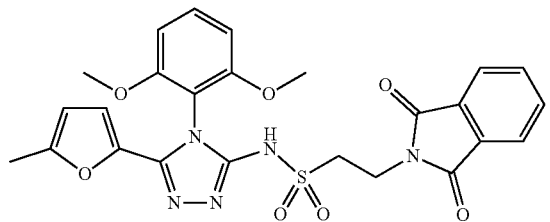

160.1

N-(4-(2,6-Dimethoxyphenyl)-5-(5-methylfuran-2-yl)-4H-1,2,4-triazol-3-yl)-2-(1,3-dioxoisoindolin-2-yl)ethanesulfonamide, Example 160.1. Example 160.1 was prepared from Example 362.03 and 2-phthalimidoethanesulfonyl chloride (commercially available from Oakwood Products, Inc., SC, USA) using the procedure described in Example 1.1. $^1$H NMR (500 MHz, CD$_2$Cl$_2$) δ 7.86-7.91 (m, 2H) 7.76-7.80 (m, 2H) 7.57 (t, J=8.56 Hz, 1H) 6.80 (d, J=8.56 Hz, 2H) 5.99 (dd, J=3.67, 0.98 Hz, 1H) 5.93 (d, J=3.42 Hz, 1H) 4.04-4.10 (m, 2H) 3.82-3.86 (m, 6H) 3.37 (dd, J=7.58, 6.60 Hz, 2H) 2.34 (s, 3H). LCMS-ESI (pos.), m/z: 538.1 (M+H)$^+$.

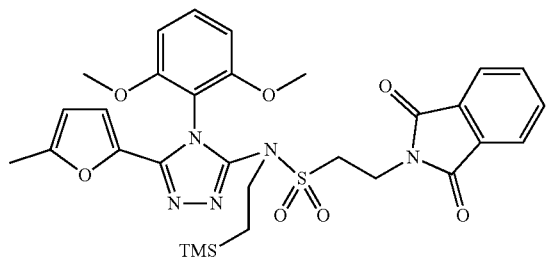

160.2

N-(4-(2,6-Dimethoxyphenyl)-5-(5-methylfuran-2-yl)-4H-1,2,4-triazol-3-yl)-2-(1,3-dioxoisoindolin-2-yl)-N-(2-(trimethylsilyl)ethyl)ethanesulfonamide, Example 160.2. To a 1 L RBF was added Example 160.1 (28.8 g, 53.6 mmol) and 2-(trimethylsilyl)ethanol (Sigma-Aldrich, 15.36 mL, 107 mmol) in toluene (268 mL). Cyanomethylenetributylphosphorane (TCI—Tokyo Chemical Industry Co., Ltd., 23.28 mL, 96 mmol) was then added under N$_2$ flow and the reaction mixture was then stirred at 90° C. under N$_2$ for 30 mins. LCMS analysis indicated the reaction was complete. The reaction mixture was then allowed to cool to RT. The reaction mixture was diluted with 1 N HCl at 0° C. for 5 min and then extracted with EtOAc. The combined organic layers were washed with brine and dried over Na$_2$SO$_4$. The solution was filtered and concentrated in vacuo to give a brown oil. The material was absorbed onto a plug of silica gel and purified by chromatography through a Redi-Sep pre-packed silica gel column (330 g) eluting with a gradient of 0% to 100% EtOAc in hexanes to provide Example 160.2 (28.8 g, 45.2 mmol, 84% yield) as an orange solid. LCMS-ESI (pos.), m/z: 638.2 (M+H)$^+$.

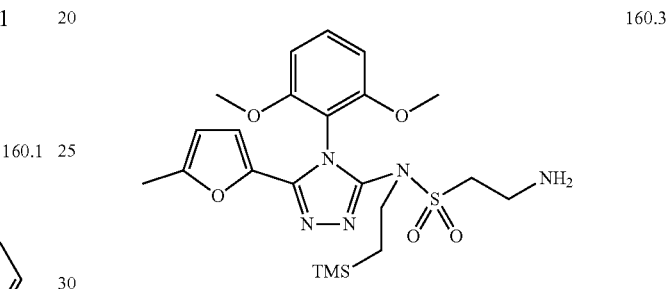

160.3

2-Amino-N-(4-(2,6-dimethoxyphenyl)-5-(5-methylfuran-2-yl)-4H-1,2,4-triazol-3-yl)-N-(2-(trimethylsilyl)ethyl)ethanesulfonamide Example 160.3. To a 1 L RBF was added Example 160.2 (28.0 g, 43.9 mmol) and hydrazine (anhydrous, 10.05 mL, 439 mmol) in MeOH (210 mL). The reaction mixture was stirred at RT under N$_2$ for 15 h. The white solid (by-product, 2,3-dihydrophthalazine-1,4-dione) was isolated by filtration and the cake was rinsed with DCM. More white solid precipitated out from the solution and was isolated by filtration. The filter cake was rinsed with DCM and diethyl ether. The above procedure was repeated until no more white solid formed in the solution. All phases were monitored by LCMS analysis. The organic solution was concentrated in vacuo and the residue was re-dissolved in DCM and washed with water. The organic solution was concentrated in vacuo to give Example 160.3 (22.4 g, 44.1 mmol, 100% yield) as a light-yellow oil. The product was directly used in the next step without further purification. LCMS-ESI (pos.), m/z: 508.3 (M+H)$^+$.

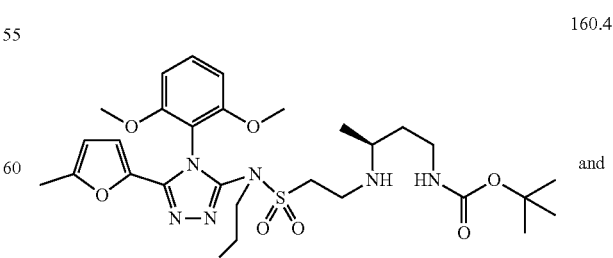

160.4 and

-continued

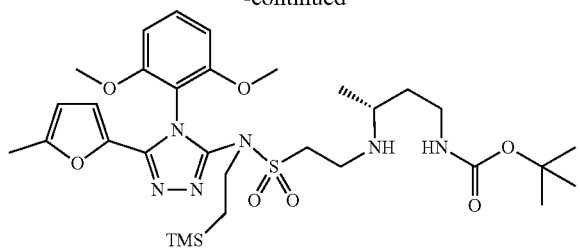

(S)-tert-Butyl (3-((2-(N-(4-(2,6-dimethoxyphenyl)-5-(5-methylfuran-2-yl)-4H-1,2,4-triazol-3-yl)-N-(2-(trimethylsilyl)ethylsulfamoyl)ethyl)amino)butyl)carbamate and (R)-tert-butyl (3-((2-(N-(4-(2,6-dimethoxyphenyl)-5-(5-methylfuran-2-yl)-4H-1,2,4-triazol-3-yl)-N-(2-(trimethylsilyl)ethylsulfamoyl)ethyl)amino)butyl) carbamate, Example 160.4. To a 500 mL RBF was added Example 160.3 (7.12 g, 14.02 mmol) and N-Boc-4-amino-2-butanone (commercially available from AstaTech, Inc., PA, USA, 2.89 mL, 15.43 mmol) in toluene (120 mL). The reaction mixture was stirred at 120° C. with Dean-Stark distillation under $N_2$ for 14 h. The reaction mixture was then allowed to cool to RT. Toluene was removed on a rotary evaporator and MeOH (100 mL) was added to the residue. The solution was then cooled to 0° C. Sodium borohydride (0.584 g, 15.43 mmol) was then added slowly at 0° C. The reaction mixture was stirred at 0° C. for 1.5 h at which time LCMS analysis indicated the reaction was complete. The reaction mixture was quenched with cold water. Most of the MeOH was removed in vacuo, and the residue was diluted with saturated $NaHCO_3$ and extracted with DCM. The combined organic layers were washed with brine and dried over $Na_2SO_4$. The solution was filtered and concentrated in vacuo to give Example 160.4 (9.52 g, 100% yield) as a light-yellow oil which was directly used in the next step without purification. LCMS-ESI (pos.), m/z: 679.3 $(M+H)^+$.

160.5

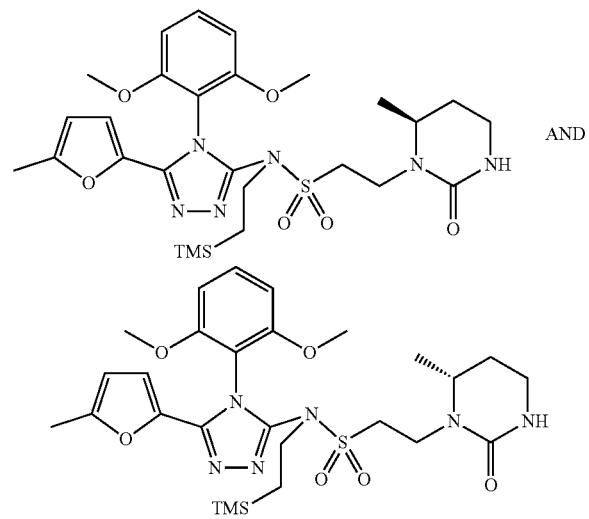

(S)-2-((4-Aminobutan-2-yl)amino)-N-(4-(2,6-dimethoxyphenyl)-5-(5-methylfuran-2-yl)-4H-1,2,4-triazol-3-yl)-N-(2-(trimethylsilyl)ethyl)ethanesulfonamide and (R)-2-((4-aminobutan-2-yl)amino)-N-(4-(2,6-dimethoxyphenyl)-5-(5-methylfuran-2-yl)-4H-1,2,4-triazol-3-yl)-N-(2-(trimethylsilyl)ethyl)ethanesulfonamide HCl salt, Example 160.5. To a 250 mL RBF was added Example 160.4 (8.4 g, 12.37 mmol) and HCl (4.0 M solution in 1,4-dioxane, 30.9 mL, 124 mmol) in DCM (60 mL). The reaction mixture was stirred at RT for 30 min. At that time, LCMS analysis indicated that the reaction was complete. The solution was then concentrated in vacuo to give Example 160.5 as a light-yellow thick oil which was directly used in the next step without purification. LCMS-ESI (pos.), m/z: 579.3 $(M+H)^+$.

160.6

(S)—N-(4-(2,6-Dimethoxyphenyl)-5-(5-methylfuran-2-yl)-4H-1,2,4-triazol-3-yl)-2-(6-methyl-2-oxotetrahydropyrimidin-1(2H)-yl)-N-(2-(trimethylsilyl)ethyl)ethanesulfonamide and (R)—N-(4-(2,6-dimethoxyphenyl)-5-(5-methylfuran-2-yl)-4H-1,2,4-triazol-3-yl)-2-(6-methyl-2-oxotetrahydropyrimidin-1(2H)-yl)-N-(2-(trimethylsilyl)ethyl)ethanesulfonamide, Example 160.6. To a 1 L RBF was added Example 160.5 (7.61 g, 12.37 mmol) and TEA (5.16 mL, 37.1 mmol) in DCM (100 mL). 1,1'-Carbonyldiimidazole solution (0.4 M in DCM, 34.0 mL, 13.61 mmol) was added dropwise. Upon completion of addition (5 min), the reaction mixture was stirred at RT for 15 h. The reaction mixture was then diluted with water and extracted with DCM. The combined organic layers were washed with brine and dried over $Na_2SO_4$. The solution was filtered and concentrated in vacuo to give Example 160.6 (7.48 g, 100% yield) as a light-yellow oil which was directly used in the next step without purification. LCMS-ESI (pos.), m/z: 605.3 $(M+H)^+$.

160.7

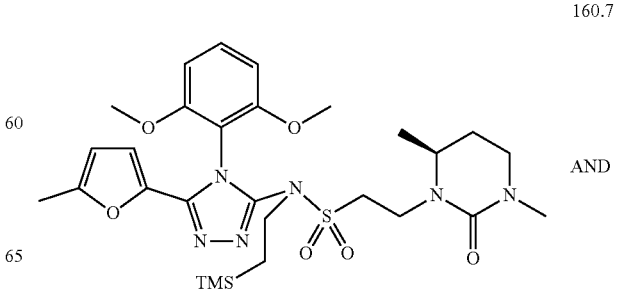

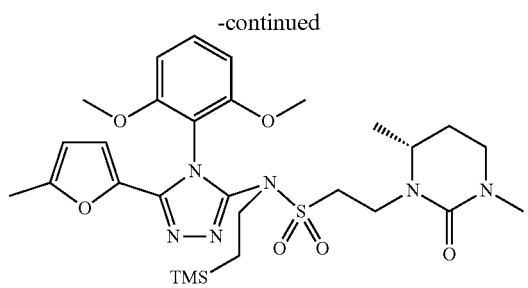

(S)—N-(4-(2,6-Dimethoxyphenyl)-5-(5-methylfuran-2-yl)-4H-1,2,4-triazol-3-yl)-2-(3,6-dimethyl-2-oxotetrahydropyrimidin-1 (2H)-yl)-N-(2-(trimethylsilyl)ethyl)ethanesulfonamide and (R)—N-(4-(2,6-dimethoxyphenyl)-5-(5-methylfuran-2-yl)-4H-1,2,4-triazol-3-yl)-2-(3,6-dimethyl-2-oxotetrahydropyrimidin-1(2H)-yl)-N-(2-(trimethylsilyl)ethyl)ethanesulfonamide, Example 160.7. To a 1 L RBF was added Example 160.6 (7.48 g, 12.37 mmol) in DMF (100 mL). Sodium hydride (60% dispersion in mineral oil, 0.742 g, 18.55 mmol) was added slowly under N₂ flow. Upon completion of addition (1 min), the reaction mixture was stirred at 0° C. for 10 min before iodomethane (1.15 mL, 18.6 mmol) was added. The reaction mixture was then stirred at RT for 1 h. LCMS analysis indicated the reaction was not complete. Another batch of sodium hydride (60% dispersion in mineral oil, 0.68 g) was added at 0° C. The reaction mixture was then stirred at 0° C. for 5 min before another batch of iodomethane (1.0 mL) was added. The reaction mixture was stirred at RT for another 1.5 h. LCMS analysis indicated the reaction was complete. The reaction mixture was diluted with ice-water at 0° C. and extracted with DCM. The combined organic layers were washed with brine and dried over Na₂SO₄. The solution was filtered and concentrated in vacuo to give Example 160.7 (7.65 g, 100% yield) as an orange oil which was directly used in the next step without purification. LCMS-ESI (pos.), m/z: 619.3 (M+H)⁺.

160.0

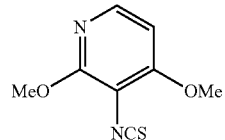

AND

N-(4-(2,6-Dimethoxyphenyl)-5-(5-methyl-2-furanyl)-4H-1,2,4-triazol-3-yl)-2-((6R)-3,6-dimethyl-2-oxotetrahydro-1 (2H)-pyrimidinyl)ethanesulfonamide and N-(4-(2,6-dimethoxyphenyl)-5-(5-methyl-2-furanyl)-4H-1,2,4-triazol-3-yl)-2-((6S)-3,6-dimethyl-2-oxotetrahydro-1(2H)-pyrimidinyl)ethanesulfonamide, Example 160.0. To a 1 L RBF was added Example 160.7 (7.65 g, 12.36 mmol) in DMF (100 mL). To the reaction was added tris(dimethylamino)sulfonium difluorotrimethylsilicate (6.81 g, 24.7 mmol) under N₂ flow. Upon completion of the addition, the reaction mixture was stirred at 95° C. for 19 h. LCMS analysis indicated the reaction was complete. The reaction mixture was then allowed to cool to RT and diluted with water (20 mL). Most of DMF was removed in vacuo at 66° C. The residual mixture was diluted with water and extracted with DCM. The combined organic layers were washed with brine and dried over Na₂SO₄. The solution was filtered and concentrated in vacuo to give an orange solid which was triturated with EtOAc to afford the title compound, Example 160.0 (5.66 g, 10.91 mmol, 88% yield), as an off-white solid. ¹H NMR (500 MHz, CD₃OD) δ 7.57 (t, J=8.56 Hz, 1H) 6.87 (d, J=8.56 Hz, 2H) 6.04 (dd, J=3.42, 0.98 Hz, 1H) 5.96 (d, J=3.42 Hz, 1H) 3.84-3.93 (m, 1H) 3.78-3.84 (m, 6H) 3.61 (dd, J=8.93, 5.50 Hz, 1H) 3.44 (td, J=11.92, 4.28 Hz, 1H) 3.29-3.40 (m, 2H) 3.09-3.25 (m, 2H) 2.90 (s, 3H) 2.28 (s, 3H) 2.00-2.12 (m, 1H) 1.61-1.75 (m, 1H) 1.16 (d, J=6.60 Hz, 3H). LCMS-ESI (pos.), m/z: 519.1 (M+H)⁺.

Example 161.0. Preparation of (2S,3R,P)-3-(5-fluoro-2-pyrimidinyl)-N-(4-(4-methoxy-2-oxo-1,2-dihydro-3-pyridinyl)-5-(5-methyl-2-furanyl)-4H-1,2,4-triazol-3-yl)-2-butanesulfonamide or (2S,3R,M)-3-(5-fluoro-2-pyrimidinyl)-N-(4-(4-methoxy-2-oxo-1,2-dihydro-3-pyridinyl)-5-(5-methyl-2-furanyl)-4H-1,2,4-triazol-3-yl)-2-butanesulfonamide 161.1

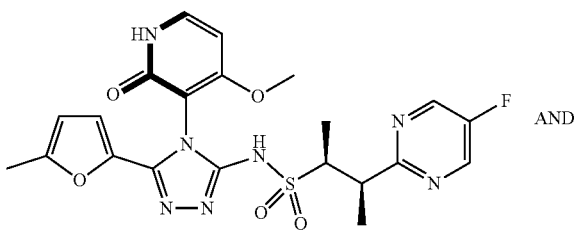

3-Isothiocyanato-2,4-dimethoxypyridine, Example 161.1. A 2 L RBF was charged with 1,1"-thiocarbonyldi-2(1H)-pyridone (47.0 g, 202 mmol) and then dry DCM (405 mL) was added. To that solution was added 2,6-dimethoxyaniline (31 g, 202 mmol) dissolved in DCM (405 mL) via an addition funnel at RT over 40 min. After 16 h, the reaction was concentrated in vacuo and purified on silica gel (0-20% EtOAc in heptanes) to give Example 161.1 (32 g, 164 mmol, 81% yield). LCMS-ESI (pos.), m/z: 197.1 (M+H)⁺.

161.2

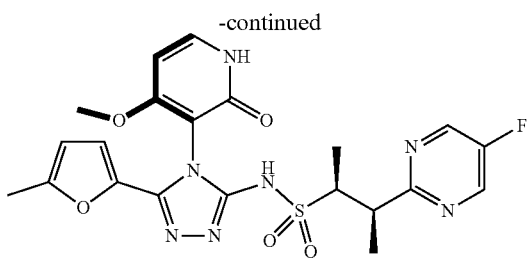

(2S,3R,P)-3-(5-Fluoro-2-pyrimidinyl)-N-(4-(4-methoxy-2-oxo-1,2-dihydro-3-pyridinyl)-5-(5-methyl-2-furanyl)-4H-1,2,4-triazol-3-yl)-2-butanesulfonamide and (2S,3R,M)-3-(5-fluoro-2-pyrimidinyl)-N-(4-(4-methoxy-2-oxo-1,2-dihydro-3-pyridinyl)-5-(5-methyl-2-furanyl)-4H-1,2,4-triazol-3-yl)-2-butanesulfonamidem, Example 161.2. Example 161.2 was prepared using Example 161.1, (2S,3R)-3-(5-fluoropyrimidin-2-yl)butane-2-sulfonamide (Example 56.5) and 5-methylfuran-2-carbohydrazide (commercially available from Chembridge, CA, USA) following the procedure described in Example 367.0. LCMS-ESI (pos.), m/z: 504.1 (M+H)⁺.

161.0

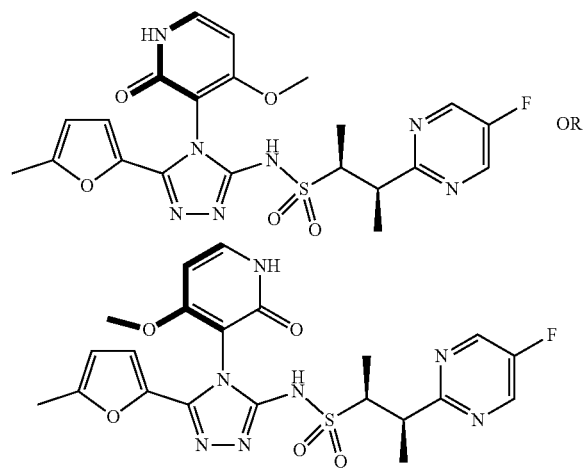

(2S,3R,P)-3-(5-Fluoro-2-pyrimidinyl)-N-(4-(4-methoxy-2-oxo-1,2-dihydro-3-pyridinyl)-5-(5-methyl-2-furanyl)-4H-1,2,4-triazol-3-yl)-2-butanesulfonamide or (2S,3R,M)-3-(5-fluoro-2-pyrimidinyl)-N-(4-(4-methoxy-2-oxo-1,2-dihydro-3-pyridinyl)-5-(5-methyl-2-furanyl)-4H-1,2,4-triazol-3-yl)-2-butanesulfonamide, Example 161.0. Example 161.0 was the 2nd peak to elute (later peak vs. its opposite atropisomers) on a Lux column by SFC chiral separation of Example 161.1 under the following conditions: Thar 80 SFC with 250×30 mm Lux column with 42.0 mL/min MeOH (+20 mM NH₃)+38.0 g/min CO₂, 52% co-solvent at 80 g/min. Temp.=36° C., Outlet pressure=100 bar, Wavelength=279 nm. Injected 1.0 mL of 26 mg sample dissolved in 4.0 mL of MeOH:DCM 3:1; c=6.5 mg/mL. Cycle time 9.0 min, run time 13 min. ¹H NMR (500 MHz, CD₃OD) δ 8.66 (d, J=0.73 Hz, 2H) 7.71 (d, J=7.58 Hz, 1H) 6.56 (d, J=7.58 Hz, 1H) 6.49 (d, J=3.18 Hz, 1H) 6.13 (dd, J=3.42, 0.98 Hz, 1H) 4.64 (s, 1H) 3.92 (s, 3H) 3.79-3.90 (m, 2H) 2.29 (s, 3H) 1.38-1.42 (m, 3H) 1.34 (d, J=6.85 Hz, 3H). LCMS-ESI (pos.), m/z: 504.1 (M+H)⁺.

Example 162.0. Preparation of (3R,5S)-5-(1-azetidinylcarbonyl)-N-(4-(2,6-dimethoxyphenyl)-5-(2-furanyl)-4H-1,2,4-triazol-3-yl)-1-(5-fluoro-2-pyrimidinyl)-3-piperidinesulfonamide or (3S,5R)-5-(1-azetidinylcarbonyl)-N-(4-(2,6-dimethoxyphenyl)-5-(2-furanyl)-4H-1,2,4-triazol-3-yl)-1-(5-fluoro-2-pyrimidinyl)-3-piperidinesulfonamide 162.1

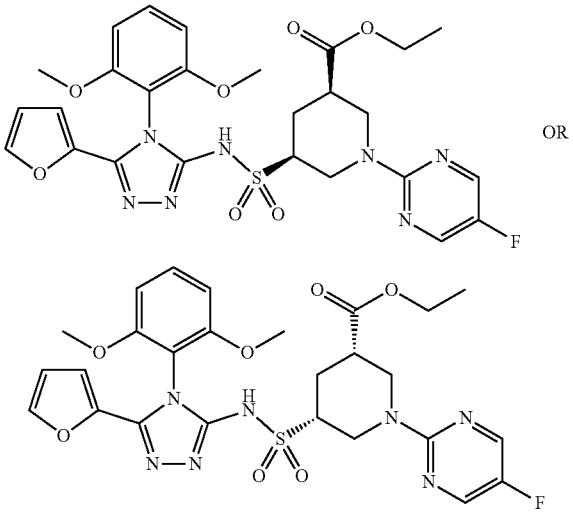

Ethyl (3R,5S)-5-((4-(2,6-Dimethoxyphenyl)-5-(2-furanyl)-4H-1,2,4-triazol-3-yl)sulfamoyl)-1-(5-fluoro-2-pyrimidinyl)-3-piperidinecarboxylate or Ethyl (3S,5R)-5-((4-(2,6-dimethoxyphenyl)-5-(2-furanyl)-4H-1,2,4-triazol-3-yl)sulfamoyl)-1-(5-fluoro-2-pyrimidinyl)-3-piperidinecarboxylate, Example 162.1. Example 162.1 was obtained from SFC chiral separation of Example 156.1. Example 162.1 was the first isomer to elute from the AS-H column under the conditions described in Example 156.0. ¹H NMR (500 MHz, CDCl₃) δ 8.22 (s, 2H) 7.44-7.54 (m, 2H) 6.70 (d, J=8.31 Hz, 2H) 6.35 (dd, J=3.55, 1.59 Hz, 1H) 6.01 (d, J=3.42 Hz, 1H) 5.24 (d, J=12.47 Hz, 1H) 4.94 (d, J=12.23 Hz, 1H) 4.18 (q, J=7.09 Hz, 2H) 3.80 (s, 3H) 3.78 (s, 3H) 3.04-3.18 (m, 1H) 2.92-3.03 (m, 1H) 2.88 (t, J=12.23 Hz, 1H) 2.62 (d, J=12.23 Hz, 1H) 2.52 (br. s., 1H) 1.96 (q, J=12.23 Hz, 1H) 1.29 (t, J=6.97 Hz, 3H). LCMS-ESI (pos.), m/z: 602.2 (M+H)⁺.

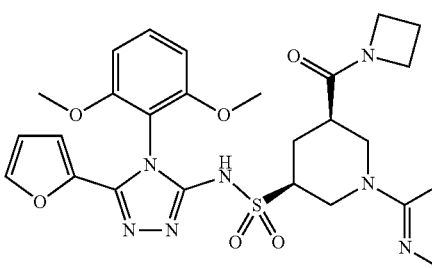

OR

-continued

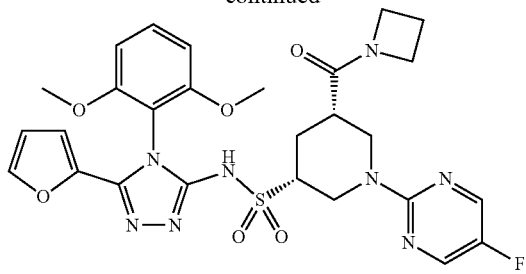

Example 162.0

(3R,5S)-5-(1-Azetidinylcarbonyl)-N-(4-(2,6-dimethoxyphenyl)-5-(2-furanyl)-4H-1,2,4-triazol-3-yl)-1-(5-fluoro-2-pyrimidinyl)-3-piperidinesulfonamide or (3S,5R)-5-(1-azetidinylcarbonyl)-N-(4-(2,6-dimethoxyphenyl)-5-(2-furanyl)-4H-1,2,4-triazol-3-yl)-1-(5-fluoro-2-pyrimidinyl)-3-piperidinesulfonamide, Example 162.0. To a 5 mL vial was added Example 162.1 (80 mg, 0.133 mmol, 99% ee) and azetidine (0.2 mL, 2.97 mmol) in MeOH (0.5 mL). The reaction mixture was stirred at RT for 22 h. LCMS analysis indicated the reaction was complete and clean. The reaction mixture was then concentrated in vacuo to afford Example 162.0 (81 mg) as a white solid. $^1$H NMR (400 MHz, CDCl$_3$) δ 8.11 (s, 2H) 7.31-7.47 (m, 2H) 6.53-6.69 (m, 2H) 6.25 (br. s., 1H) 5.92 (d, J=3.13 Hz, 1H) 5.13 (d, J=11.93 Hz, 1H) 4.63 (d, J=12.91 Hz, 1H) 4.02-4.24 (m, 2H) 3.94 (t, J=7.63 Hz, 2H) 3.76 (s, 3H) 3.71 (s, 3H) 2.99 (t, J=11.84 Hz, 1H) 2.84 (t, J=12.32 Hz, 2H) 2.13-2.37 (m, 4H) 1.86-2.05 (m, 1H). LCMS-ESI (pos.), m/z: 613.3 (M+H)$^+$.

Example 163.0. Preparation of N-(4-(2,6-dimethoxyphenyl)-5-(2-furanyl)-4H-1,2,4-triazol-3-yl)-2-((6R)-3,6-dimethyl-2-oxotetrahydro-1(2H)-pyrimidinyl)ethanesulfonamide or N-(4-(2,6-dimethoxyphenyl)-5-(2-furanyl)-4H-1,2,4-triazol-3-yl)-2-((6S)-3,6-dimethyl-2-oxotetrahydro-1(2H)-pyrimidinyl)ethanesulfonamide

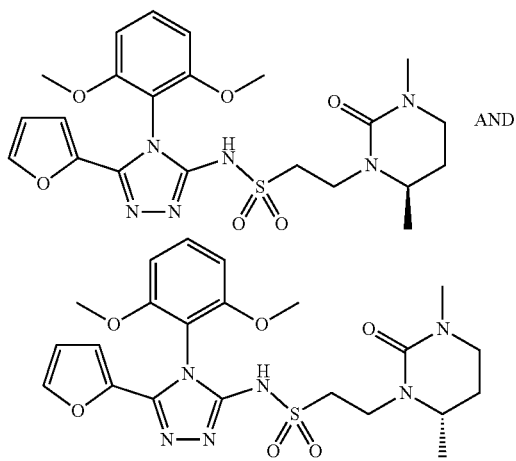

N-(4-(2,6-Dimethoxyphenyl)-5-(2-furanyl)-4H-1,2,4-triazol-3-yl)-2-((6R)-3,6-dimethyl-2-oxotetrahydro-1(2H)-pyrimidinyl)ethanesulfonamide and N-(4-(2,6-dimethoxyphenyl)-5-(2-furanyl)-4H-1,2,4-triazol-3-yl)-2-((6S)-3,6-dimethyl-2-oxotetrahydro-1(2H)-pyrimidinyl)ethanesulfonamide, Example 163.1. Example 163.1 was prepared from 4-(2,6-dimethoxyphenyl)-5-(furan-2-yl)-4H-1,2,4-triazol-3-amine, Example 362.03, using the procedures described in Example 160.0. $^1$H NMR (500 MHz, CD$_3$OD) δ 7.57 (t, J=8.56 Hz, 1H) 6.87 (d, J=8.56 Hz, 2H) 6.04 (dd, J=3.42, 0.98 Hz, 1H) 5.96 (d, J=3.42 Hz, 1H) 3.84-3.93 (m, 1H) 3.78-3.84 (m, 6H) 3.61 (dd, J=8.93, 5.50 Hz, 1H) 3.44 (td, J=11.92, 4.28 Hz, 1H) 3.29-3.40 (m, 2H) 3.09-3.25 (m, 2H) 2.90 (s, 3H) 2.28 (s, 3H) 2.00-2.12 (m, 1H) 1.61-1.75 (m, 1H) 1.16 (d, J=6.60 Hz, 3H). LCMS-ESI (pos.), m/z: 505.1 (M+H)$^+$.

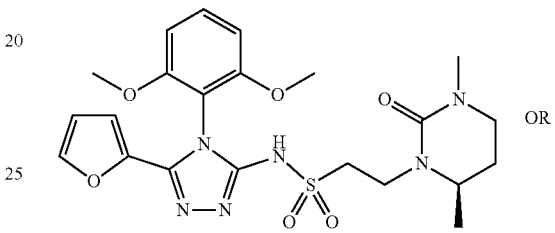

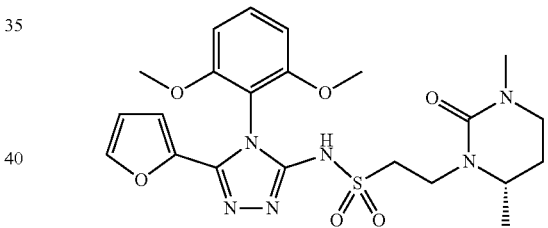

N-(4-(2,6-Dimethoxyphenyl)-5-(2-furanyl)-4H-1,2,4-triazol-3-yl)-2-((6R)-3,6-dimethyl-2-oxotetrahydro-1(2H)-pyrimidinyl)ethanesulfonamide or N-(4-(2,6-dimethoxyphenyl)-5-(2-furanyl)-4H-1,2,4-triazol-3-yl)-2-((6S)-3,6-dimethyl-2-oxotetrahydro-1(2H)-pyrimidinyl)ethanesulfonamide, Example 163.0. Example 163.0 was the second peak to elute from a Lux2 column column by SFC chiral separation of Example 163.1 under the following conditions: 250×30 mm Lux2 column with 44 g/min MeOH (Neat)+36 g/min CO$_2$ on Thar 80 SFC. Outlet pressure=100 bar; Temp.=28° C.; Wavelength=270 nm. Used 0.7 mL injections of 40 mg/4 mL (10 mg/mL) sample solution in MeOH/DCM (3 mL MeOH/1 mL DCM) i.e. 7 mg/injection. Run time=15 min.; Cycle time 11.2 min. $^1$H NMR (400 MHz, CDCl$_3$) δ 7.40-7.50 (m, 2H) 6.67 (d, J=8.41 Hz, 2H) 6.33 (dd, J=3.62, 1.86 Hz, 1H) 6.01 (dd, J=3.62, 0.68 Hz, 1H) 3.93-4.08 (m, 1H) 3.76 (d, J=2.54 Hz, 6H) 3.61-3.74 (m, 1H) 3.31-3.48 (m, 3H) 3.18-3.29 (m, 1H) 3.05-3.16 (m, 1H) 2.93 (s, 3H) 2.02-2.19 (m, 1H) 1.57-1.69 (m, 1H) 1.15 (d, J=6.65 Hz, 3H). LCMS-ESI (pos.), m/z: 505.1 (M+H)$^+$.

Example 164.0. Preparation of N-(4-(2,6-dimethoxyphenyl)-5-(5-methyl-2-furanyl)-4H-1,2,4-triazol-3-yl)-2-((6R)-3,6-dimethyl-2-oxotetrahydro-1(2H)-pyrimidinyl)ethanesulfonamide or N-(4-(2,6-dimethoxyphenyl)-5-(5-methyl-2-furanyl)-4H-1,2,4-triazol-3-yl)-2-((6S)-3,6-dimethyl-2-oxotetrahydro-1(2H)-pyrimidinyl)ethanesulfonamide

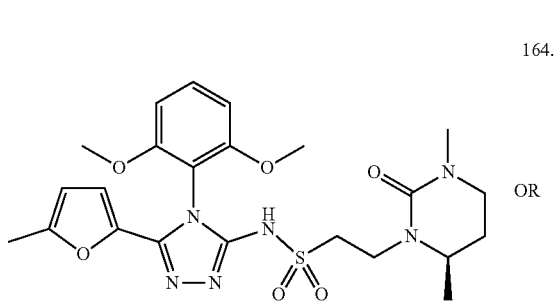

164.0

OR

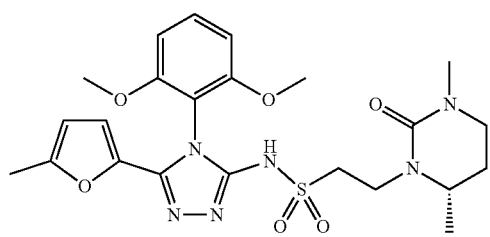

N-(4-(2,6-Dimethoxyphenyl)-5-(5-methyl-2-furanyl)-4H-1,2,4-triazol-3-yl)-2-((6S)-3,6-dimethyl-2-oxotetrahydro-1(2H)-pyrimidinyl)ethanesulfonamide or N-(4-(2,6-dimethoxyphenyl)-5-(5-methyl-2-furanyl)-4H-1,2,4-triazol-3-yl)-2-((6R)-3,6-dimethyl-2-oxotetrahydro-1(2H)-pyrimidinyl)ethanesulfonamide, Example 164.0. Example 164.0 was the first peak to elute from a CC4 column (or AD-H or Lux2 column) by SFC chiral separation of Example 160.0 under the following conditions: 250×30 mm CC4 column with 60 mL/min MeOH (20 mM NH$_3$)+60 g/min; CO$_2$ on Thar 350 SFC, 50% co-solvent at 120 g/min. Outlet pressure=100 bar; Temp.=20° C.; Wavelength=276 nm. Used 1.5 mL injections of 5.66 g sample dissolved in 125 mL (3:2) MeOH:DCM (45.3 mg/mL), i.e. 67.9 mg/injection. Run time=15.8 min; Cycle time=8.0 min. $^1$H NMR (500 MHz, CD$_3$OD) δ 7.57 (t, J=8.56 Hz, 1H) 6.87 (d, J=8.56 Hz, 2H) 6.04 (dd, J=3.42, 0.98 Hz, 1H) 5.96 (d, J=3.42 Hz, 1H) 3.84-3.93 (m, 1H) 3.78-3.84 (m, 6H) 3.61 (dd, J=8.93, 5.50 Hz, 1H) 3.44 (td, J=11.92, 4.28 Hz, 1H) 3.29-3.40 (m, 2H) 3.09-3.25 (m, 2H) 2.90 (s, 3H) 2.28 (s, 3H) 2.00-2.12 (m, 1H) 1.61-1.75 (m, 1H) 1.16 (d, J=6.60 Hz, 3H). LCMS-ESI (pos.), m/z: 519.1 (M+H)$^+$.

Example 165.0, Preparation (3R,5S)-1-acetyl-N-(4-(2,6-dimethoxyphenyl)-5-(5-methyl-2-furanyl)-4H-1,2,4-triazol-3-yl)-5-(4-fluorophenyl)-3-piperidinesulfonamide or (3S,5R)-1-acetyl-N-(4-(2,6-dimethoxyphenyl)-5-(5-methyl-2-furanyl)-4H-1,2,4-triazol-3-yl)-5-(4-fluorophenyl)-3-piperidinesulfonamide

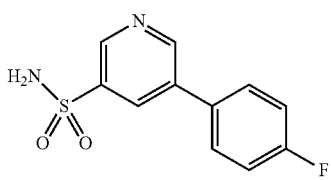

165.1

5-(4-Fluorophenyl)pyridine-3-sulfonamide, Example 165.1. To a 100 mL RBF was added 4-fluorobenzeneboronic acid (1.138 g, 8.13 mmol), potassium phosphate (1.726 g, 8.13 mmol), xantphos (0.235 g, 0.41 mmol), palladium (II) acetate (0.046 g, 0.20 mmol), and 5-bromopyridine-3-sulfonamide (commercially available from Enamine, KIEV, Ukraine, 0.964 g, 4.07 mmol). The flask was placed under vacuum and back-filled with dioxane (10 mL) and water (0.2 mL). The reaction mixture was stirred at 100° C. for 8 h under N$_2$. LCMS analysis indicated the reaction was complete. The reaction mixture was then allowed to cool to RT. The reaction mixture was diluted with water and extracted with DCM. The combined organic layers were washed with brine and dried over Na$_2$SO$_4$. The solution was filtered and concentrated in vacuo to give a light-yellow solid. The product was triturated with EtOAc to afford Example 165.1 (0.7 g, 2.77 mmol, 68.2% yield) as an off-white solid. LCMS-ESI (pos.), m/z: 253.1 (M+H)$^+$.

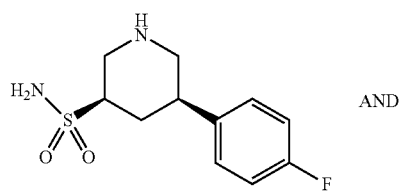

165.2

AND


AND

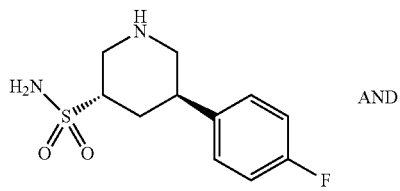

AND

-continued

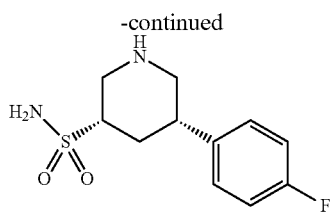

(3R,5R)-5-(4-Fluorophenyl)piperidine-3-sulfonamide and (3R,5S)-5-(4-fluorophenyl)piperidine-3-sulfonamide and (3S,5R)-5-(4-fluorophenyl)piperidine-3-sulfonamide and (3S,5S)-5-(4-fluorophenyl)piperidine-3-sulfonamide, Example 165.2. To a 250 mL RBF was added Example 165.1 (0.688 g, 2.73 mmol) in AcOH (20 mL). $N_2$ was bubbled through the mixture for 5 min and then platinum (IV) oxide (commercially available from Sigma-Aldrich, Mo., USA, 0.619 g, 2.73 mmol) was added under $N_2$ flow. The flask was then sealed with a septum and placed under vacuum. A hydrogen gas balloon was then connected via a needle. The reaction mixture was stirred at RT under hydrogen gas for 16 h. LCMS analysis indicated the reaction was not complete. Thus, another batch of platinum (IV) oxide (0.619 g, 2.73 mmol) was added under $N_2$ flow and then the above procedure was repeated. The reaction mixture was stirred at RT under hydrogen gas for three days. LCMS analysis indicated the reaction was complete. Celite® brand filter aid (20 g) was added to the reaction stirred mixture. The solution was filtered and concentrated in vacuo to give Example 165.2 (0.71 g, 2.75 mmol, 100% yield) as a light-yellow glass. LCMS-ESI (pos.), m/z: 259.1 (M+H)$^+$.

165.3

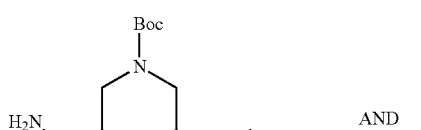

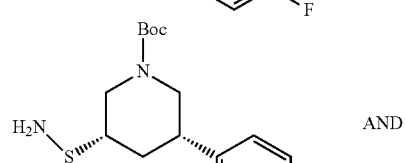

(3R,5R)-tert-Butyl 3-(4-fluorophenyl)-5-sulfamoylpiperidine-1-carboxylate and (3R,5S)-tert-butyl 3-(4-fluorophenyl)-5-sulfamoylpiperidine-1-carboxylate and (3S,5R)-tert-butyl 3-(4-fluorophenyl)-5-sulfamoylpiperidine-1-carboxylate and (3S,5S)-tert-butyl 3-(4-fluorophenyl)-5-sulfamoylpiperidine-1-carboxylate, Example 165.3. To a 250 mL RBF was added Example 165.2 (0.71 g, 2.75 mmol) and anhydrous TEA (0.765 mL, 5.50 mmol) in DCM (30 mL). Di-tert-butyl dicarbonate (0.900 g, 4.12 mmol) was added, and the reaction mixture was stirred at RT for 1.5 h. The reaction mixture was diluted with water and extracted with DCM. The combined organic layers were washed with brine and dried over $Na_2SO_4$. The solution was filtered and concentrated in vacuo to give a light-yellow oil. The material was purified by silica gel chromatography (0% to 100% EtOAc in hexanes) to provide the title compound, Example 165.3 (0.41 g, 0.1.14 mmol, 42% yield), as a white powder. LCMS-ESI (pos.), m/z: 381.2 (M+Na)$^+$.

165.4

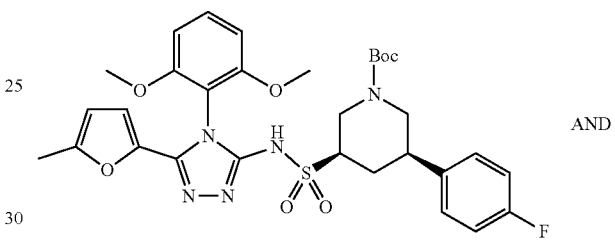

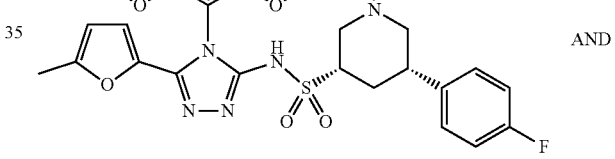

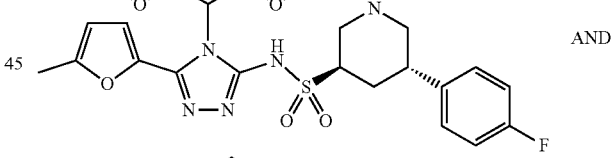

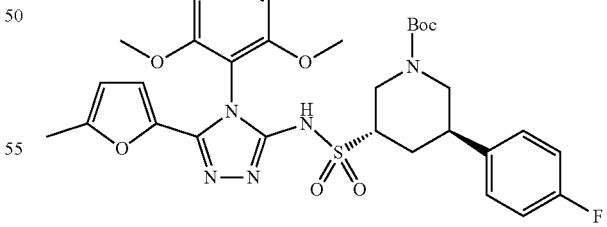

(3R,5R)-tert-Butyl 3-(N-(4-(2,6-dimethoxyphenyl)-5-(5-methylfuran-2-yl)-4H-1,2,4-triazol-3-yl)sulfamoyl)-5-(4-fluorophenyl)piperidine-1-carboxylate and (3R,5S)-tert-butyl 3-(N-(4-(2,6-dimethoxyphenyl)-5-(5-methylfuran-2-yl)-4H-1,2,4-triazol-3-yl)sulfamoyl)-5-(4-fluorophenyl) piperidine-1-carboxylate and (3S,5R)-tert-butyl 3-(N-(4-(2,6-dimethoxyphenyl)-5-(5-methylfuran-2-yl)-4H-1,2,4-triazol-3-yl)sulfamoyl)-5-(4-fluorophenyl)piperidine-1- carboxylate and (3S,5S)-tert-butyl 3-(N-(4-(2,6-dimethoxyphenyl)-5-(5-methylfuran-2-yl)-4H-1,2,4-triazol-3-yl)sulfamoyl)-5-(4-fluorophenyl)piperidine-1-carboxylate, Example 165.4. Example 165.4 was prepared from Example 364.1 and Example 165.3 using the procedure described in Example 94.0. LCMS-ESI (pos.), m/z: 642.2 (M+Na)⁺.

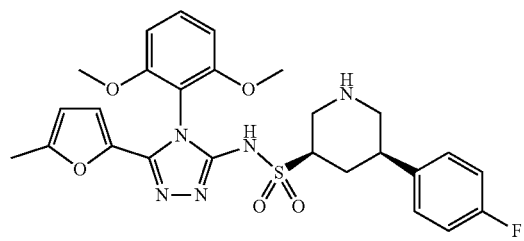

AND

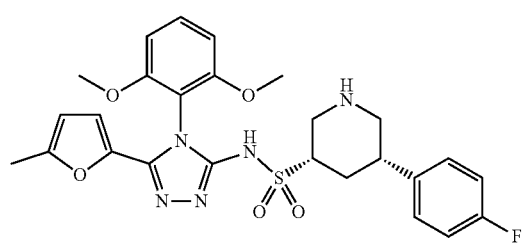

AND

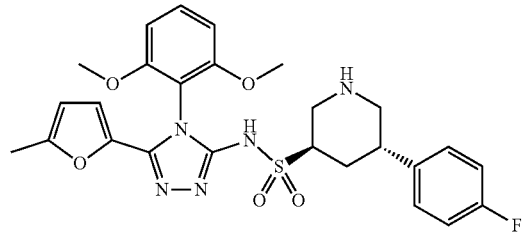

AND

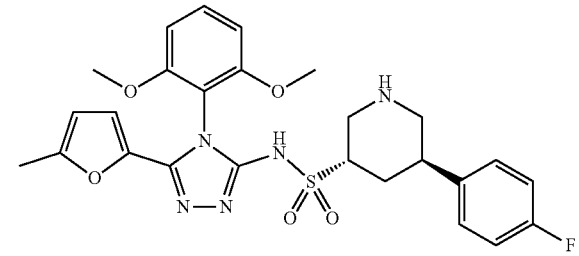

(3R,5R)—N-(4-(2,6-Dimethoxyphenyl)-5-(5-methylfuran-2-yl)-4H-1,2,4-triazol-3-yl)-5-(4-fluorophenyl)piperidine-3-sulfonamide and (3R,5S)—N-(4-(2,6-dimethoxyphenyl)-5-(5-methylfuran-2-yl)-4H-1,2,4-triazol-3-yl)-5-(4-fluorophenyl)piperidine-3-sulfonamide and (3S,5R)—N-(4-(2,6-dimethoxyphenyl)-5-(5-methylfuran-2-yl)-4H-1,2,4-triazol-3-yl)-5-(4-fluorophenyl)piperidine-3-sulfonamide and (3S,5S)—N-(4-(2,6-dimethoxyphenyl)-5-(5-methylfuran-2-yl)-4H-1,2,4-triazol-3-yl)-5-(4-fluorophenyl)piperidine-3-sulfonamide, Example 165.5. To a solution of Example 165.4 (0.38 g, 0.592 mmol) in DCM (5 mL) was added TFA (3 mL, 40.4 mmol). The reaction mixture was stirred at RT for 30 min. The solution was concentrated in vacuo to give the TFA salt of the Example 165.5 as a white foam. The product was directly used in the next step assuming 100% yield. LCMS-ESI (pos.), m/z: 542.2 (M+H)⁺.

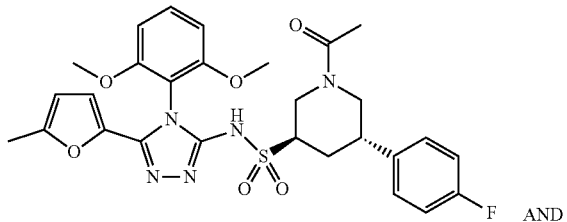

AND

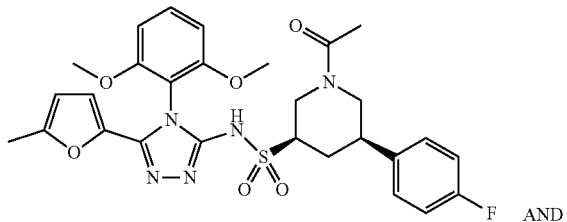

(3R,5S)-1-Acetyl-N-(4-(2,6-dimethoxyphenyl)-5-(5-methyl-2-furanyl)-4H-1,2,4-triazol-3-yl)-5-(4-fluorophenyl)-3-piperidinesulfonamide and (3S,5R)-1-acetyl-N-(4-(2,6-dimethoxyphenyl)-5-(5-methyl-2-furanyl)-4H-1,2,4-triazol-3-yl)-5-(4-fluorophenyl)-3-piperidinesulfonamide Example 165.6. To a 25 mL vial was added Example 165.5 (190 mg, 0.298 mmol) and pyridine (0.485 mL, 5.95 mmol) in DCM (10 mL). Acetic anhydride (0.281 mL, 2.98 mmol) was then added. The reaction mixture was stirred at RT for 1.5 h. LCMS analysis showed the reaction was complete. The reaction mixture was diluted with 1 N HCl and extracted with DCM. The combined organic layers were washed with brine and dried over Na₂SO₄. The solution was filtered and concentrated in vacuo to give a light-yellow solid. The material thus obtained was absorbed onto a plug of silica gel and purified by chromatography through a Redi-Sep prepacked silica gel column (12 g) eluting with a gradient of 50% to 100% EtOAc in DCM to provide the product as a light-yellow solid (the isomers were not separated) which was further purified by reverse-phase preparative HPLC using a Phenomenex Gemini column, 10 micron, C18, 100 Å, 150×30 mm, 0.1% TFA in ACN/H2O, gradient 5% to 95% over 30 min to provide Example 165.6 (39 mg, 22.46% yield) as a white solid.

AND

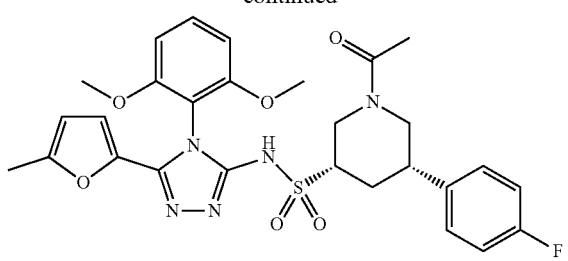

(3R,5R)-1-Acetyl-N-(4-(2,6-dimethoxyphenyl)-5-(5-methyl-2-furanyl)-4H-1,2,4-triazol-3-yl)-5-(4-fluorophenyl)-3-piperidinesulfonamide and (3S,5S)-1-acetyl-N-(4-(2,6-dimethoxyphenyl)-5-(5-methyl-2-furanyl)-4H-1,2,4-triazol-3-yl)-5-(4-fluorophenyl)-3-piperidinesulfonamide, Example 165.7. Further elution under the conditions described in Example 165.6 delivered the mixture of cis isomers (47 mg, 27.1% yield) as a white solid. LCMS-ESI (pos.), m/z: 584.2 (M+H)$^+$.

165.0

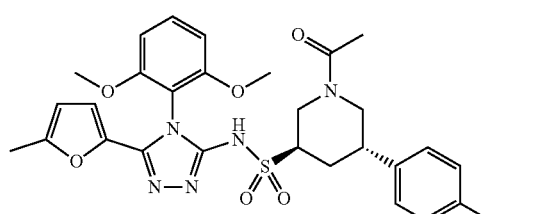

(3R,5S)-1-Acetyl-N-(4-(2,6-dimethoxyphenyl)-5-(5-methyl-2-furanyl)-4H-1,2,4-triazol-3-yl)-5-(4-fluorophenyl)-3-piperidinesulfonamide or (3S,5R)-1-acetyl-N-(4-(2,6-dimethoxyphenyl)-5-(5-methyl-2-furanyl)-4H-1,2,4-triazol-3-yl)-5-(4-fluorophenyl)-3-piperidinesulfonamide, Example 165.0. Example 165.0 was obtained from SFC chiral separation of Example 165.6. Example 165.0 was the second isomer to elute from an OD column under the following conditions: 250×30 mm OD column with 36 g/min MeOH+(20 mM NH$_3$)+84 g/min CO$_2$ on Thar 350 SFC. Outlet pressure=100 bar; Temp.=20° C.; Wavelength=276 nm. Used 1.0 mL injections of 36 mg/6 mL (6.0 mg/mL) sample solution in MeOH, i.e. 6.0 mg/injection. Cycle time=9 min, Runtime=11 min. $^1$H NMR (500 MHz, CD$_3$OD) δ 7.50-7.61 (m, 1H) 7.21-7.32 (m, 2H) 7.01-7.12 (m, 2H) 6.80-6.89 (m, 2H) 6.01-6.07 (m, 1H) 5.92-5.99 (m, 1H) 4.44 (d, J=13.94 Hz, 2H) 3.60-3.77 (m, 7H) 3.45-3.54 (m, 1H) 3.34-3.43 (m, 2H) 3.20-3.27 (m, 1H) 2.87 (t, J=11.98 Hz, 1H) 2.53 (d, J=14.92 Hz, 1H) 2.28 (s, 3H) 2.15 (ddd, J=14.67, 12.23, 5.87 Hz, 1H) 2.04-2.09 (m, 2H) 2.02 (s, 1H). LCMS-ESI (pos.), m/z: 584.2 (M+H)$^+$.

Example 166.0. Preparation of (2S,3R,P)—N-(4-(4-methoxy-2-oxo-1,2-dihydro-3-pyridinyl)-5-(5-methyl-2-furanyl)-4H-1,2,4-triazol-3-yl)-3-(5-methyl-2-pyrimidinyl)-2-butanesulfonamide or (2S,3R,M)-N-(4-(4-methoxy-2-oxo-1,2-dihydro-3-pyridinyl)-5-(5-methyl-2-furanyl)-4H-1,2,4-triazol-3-yl)-3-(5-methyl-2-pyrimidinyl)-2-butanesulfonamide 166.1

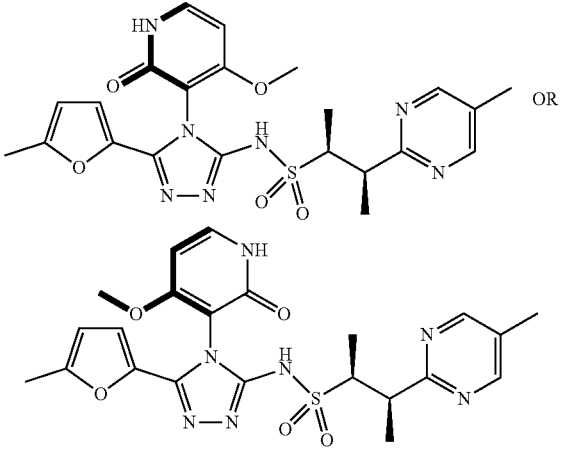

(2S,3R,P)—N-(4-(4-Methoxy-2-oxo-1,2-dihydro-3-pyridinyl)-5-(5-methyl-2-furanyl)-4H-1,2,4-triazol-3-yl)-3-(5-methyl-2-pyrimidinyl)-2-butanesulfonamide and (2S,3R,M)-N-(4-(4-methoxy-2-oxo-1,2-dihydro-3-pyridinyl)-5-(5-methyl-2-furanyl)-4H-1,2,4-triazol-3-yl)-3-(5-methyl-2-pyrimidinyl)-2-butanesulfonamide, Example 166.1. Example 166.1 was prepared using Example 161.1, Example 371.0, and 5-methylfuran-2-carbohydrazide (commercially available from Chembridge, CA, USA) following the procedure described in Example 229.0. LCMS-ESI (pos.), m/z: 500.1 (M+H)$^+$.

166.0

(2S,3R,P)—N-(4-(4-Methoxy-2-oxo-1,2-dihydro-3-pyridinyl)-5-(5-methyl-2-furanyl)-4H-1,2,4-triazol-3-yl)-3-(5-methyl-2-pyrimidinyl)-2-butanesulfonamide or (2S,3R, M)-N-(4-(4-methoxy-2-oxo-1,2-dihydro-3-pyridinyl)-5-(5-methyl-2-furanyl)-4H-1,2,4-triazol-3-yl)-3-(5-methyl-2-pyrimidinyl)-2-butanesulfonamide, Example 166.0. Example 166.0 was the second peak to elute (later peak vs. its opposite atropisomers) on a CC4 column by SFC chiral separation of Example 166.1 under the following conditions: Run on Thar 80 SFC with 150×30 mm CC4 column with 37.2 mL/min MeOH (neat)+32.8 g/min CO$_2$, 53% co-solvent at 70 g/min. Temp.=28° C., Outlet pressure=100 bar, Wavelength=278 nm. Injected 0.8 mL of 85 mg sample dissolved in 10.0 mL of MeOH; c=8.5 mg/mL and 6.8 mg per injection. Cycle time 7 min, runtime 12 min. $^1$H NMR (500 MHz, CD$_3$OD) δ 8.58 (s, 2H) 7.72 (d, J=7.58 Hz, 1H) 6.57 (d, J=7.58 Hz, 1H) 6.52 (d, J=3.18 Hz, 1H) 6.11-6.17 (m, 1H) 3.93 (s, 3H) 3.74-3.84 (m, 2H) 2.32 (s, 3H) 2.29 (s, 3H) 1.39 (d, J=6.85 Hz, 3H) 1.32 (d, J=6.60 Hz, 3H). LCMS-ESI (pos.), m/z: 500.1 (M+H)$^+$.

Example 167.0. Preparation of (3S,5R)—N-(4-(2,6-dimethoxyphenyl)-5-(2-furanyl)-4H-1,2,4-triazol-3-yl)-1-(5-fluoro-2-pyrimidinyl)-5-hydroxy-3-piperidinesulfonamide or (3R,5S)—N-(4-(2,6-dimethoxyphenyl)-5-(2-furanyl)-4H-1,2,4-triazol-3-yl)-1-(5-fluoro-2-pyrimidinyl)-5-hydroxy-3-piperidinesulfonamide

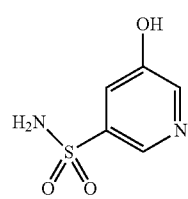

167.1

5-Hydroxypyridine-3-sulfonamide, Example 167.1. To a 100 mL RBF was added 5-bromopyridine-3-sulfonamide (commercially available from Enamine, KIEV, Ukraine, 0.486 g, 2.05 mmol), 2-di-t-butylphosphino-3,4,5,6-tetramethyl-2',4',6'-tri-i-isopropylbiphenyl (commercially available from Strem Chemicals, Inc., MA, USA, 0.079 g, 0.164 mmol), and Pd$_2$(dba)$_3$ (Sigma-Aldrich Chemical Company, Inc., 0.038 g, 0.041 mmol). The flask was placed under vacuum and back-filled with a potassium hydroxide (0.345 g, 6.15 mmol) solution in dioxane (5 mL) and water (5 mL). The reaction mixture was then stirred at 100° C. under N$_2$ for 17 h. LCMS analysis indicated the reaction was complete. The reaction mixture was allowed to cool to RT. The reaction mixture was diluted with 1 N HCl and extracted with Et$_2$O. The insoluble white solid was removed by filtration. The aqueous layer was concentrated in vacuo to afford the title compound, Example 167.1, as a white solid which was directly used in the next step. LCMS-ESI (pos.), m/z: 175.1 (M+H)$^+$.

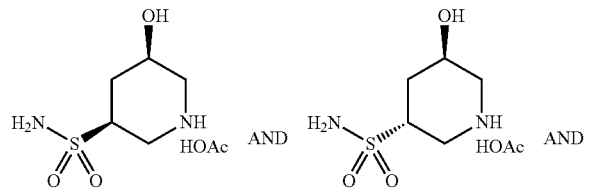

167.2

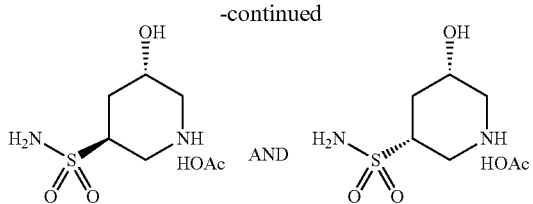

(3R,5R)-5-Hydroxypiperidine-3-sulfonamide acetate and (3S,5R)-5-hydroxypiperidine-3-sulfonamide acetate and (3R,5S)-5-hydroxypiperidine-3-sulfonamide acetate and (3S,5S)-5-hydroxypiperidine-3-sulfonamide acetate, Example 167.2. To a 1 L hydrogenation flask was added Example 167.1 (6.46 g, 37.1 mmol), AcOH (250 mL) and water (20 mL). The mixture was bubbled with N$_2$ for 2 min before platinum (IV) oxide hydrate (8.42 g, 37.1 mmol) was added under N$_2$ flow. The flask was set up on a Parr shaker, placed under vacuum, back-filled with N$_2$ two times, and placed under vacuum and back-filled with hydrogen gas. The reaction mixture was stirred at RT under 50 psi of hydrogen gas for 24 h. LCMS analysis indicated the reaction was complete. Celite® brand filter aid (20 g) was added to the stirred mixture. The solid was removed by filtration after 10 min of stirring. The filter cake was rinsed with MeOH. The combined organics were concentrated in vacuo to afford Example 167.2 (8.91 g, 100% yield) as a light-yellow oil which was directly used in the next step without purification. LCMS-ESI (pos.), m/z: 181.1 (M+H)$^+$.

167.3

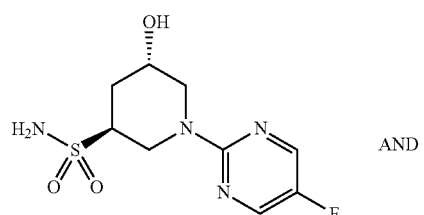

AND

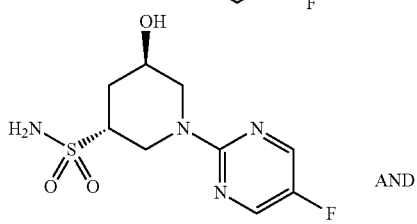

AND

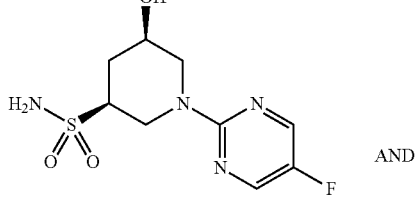

AND

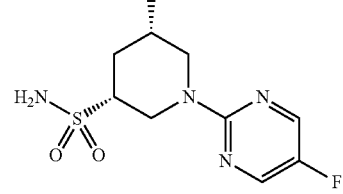

(3S,5S)-1-(5-Fluoropyrimidin-2-yl)-5-hydroxypiperidine-3-sulfonamide and (3S,5R)-1-(5-fluoropyrimidin-2- yl)-5-hydroxypiperidine-3-sulfonamide and (3R,5S)-1-(5-fluoropyrimidin-2-yl)-5-hydroxypiperidine-3-sulfonamide and (3R,5R)-1-(5-fluoropyrimidin-2-yl)-5-hydroxypiperidine-3-sulfonamide, Example 167.3. To a 500 mL RBF was added Example 167.2 (8.91 g, 37.1 mmol) and Hunig's base (32.3 mL, 185 mmol) in DMF (80 mL). 2-Chloro-5-fluoropyrimidine (18.32 mL, 148 mmol) was added. The reaction mixture was then stirred at 120° C. for 18 h. LCMS analysis indicated the reaction was complete. The reaction mixture was allowed to cool to RT, diluted with water, and extracted with DCM. The combined organic layers were washed with brine and dried over $Na_2SO_4$. The solution was filtered and concentrated in vacuo to give an orange oil. The material was purified by silica gel chromatography (gradient of 0% to 100% EtOAc in DCM) to provide Example 167.3 (3.7 g, 10.93 mmol, 36% yield) as a light-yellow solid. LCMS-ESI (pos.), m/z: 277.0 (M+H)⁺.

Example 167.0

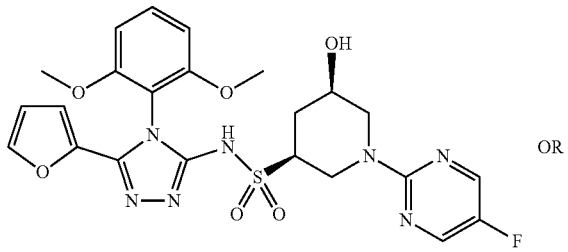

OR 167.4

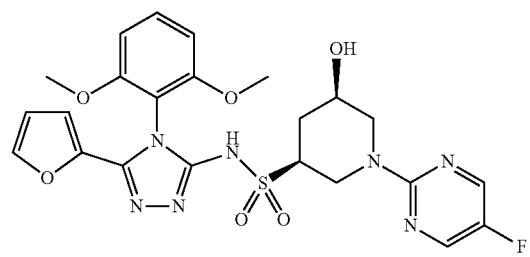

AND

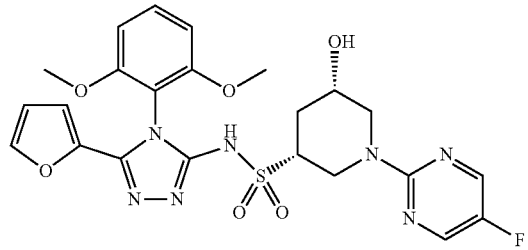

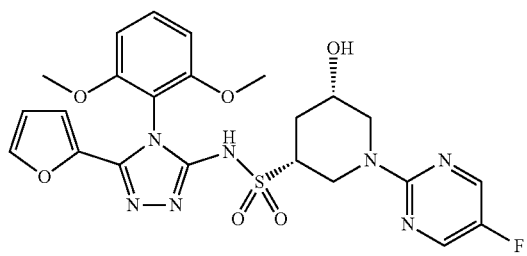

(3S,5R)—N-(4-(2,6-Dimethoxyphenyl)-5-(2-furanyl)-4H-1,2,4-triazol-3-yl)-1-(5-fluoro-2-pyrimidinyl)-5-hydroxy-3-piperidinesulfonamide and (3R,5S)—N-(4-(2,6-dimethoxyphenyl)-5-(2-furanyl)-4H-1,2,4-triazol-3-yl)-1-(5-fluoro-2-pyrimidinyl)-5-hydroxy-3-piperidinesulfonamide, Example 167.4. Example 167.4 was prepared from Example 364.3 and Example 167.3 using the procedure described in Example 94.0. Example 167.4 was isolated as an off-white solid and was the major product. ¹H NMR (500 MHz, CD₃OD) δ 8.30 (s, 2H) 7.54-7.64 (m, 2H) 6.84-6.92 (m, 2H) 6.45 (dd, J=3.55, 1.83 Hz, 1H) 6.12-6.18 (m, 1H) 5.09 (dt, J=12.84, 1.90 Hz, 1H) 4.80-4.87 (m, 1H) 3.77-3.86 (m, 7H) 3.54-3.64 (m, 1H) 3.04-3.14 (m, 1H) 2.81-2.91 (m, 1H) 2.45-2.59 (m, 2H) 1.66 (q, J=12.06 Hz, 1H). LCMS-ESI (pos.), m/z: 546.0 (M+H)⁺.

(3S,5R)—N-(4-(2,6-Dimethoxyphenyl)-5-(2-furanyl)-4H-1,2,4-triazol-3-yl)-1-(5-fluoro-2-pyrimidinyl)-5-hydroxy-3-piperidinesulfonamide or (3R,5S)—N-(4-(2,6-dimethoxyphenyl)-5-(2-furanyl)-4H-1,2,4-triazol-3-yl)-1-(5-fluoro-2-pyrimidinyl)-5-hydroxy-3-piperidinesulfonamide, Example 167.0. Example 167.0 was obtained by chiral separation of Example 167.4. Example 167.0 was the second enantiomer to elute from an AS column under the following conditions: 250×30 mm AS column with 42 mL/min MeOH+(20 mM Ammonia)+78 g/min CO₂ on Thar 200 SFC. Outlet pressure=100 bar; Temp.=RT; Wavelength=242 nm. Using 5.0 mL injections of 41 mg/15 mL (2.7 mg/mL) sample solution in MeOH, i.e. 13.6 mg/injection. Runtime=12 min. ¹H NMR (500 MHz, CDCl₃) δ 8.19 (s, 2H) 7.43-7.53 (m, 2H) 6.70 (dd, J=8.44, 3.55 Hz, 2H) 6.35 (dd, J=3.67, 1.71 Hz, 1H) 6.02 (d, J=3.42 Hz, 1H) 4.94 (dd, J=13.08, 3.79 Hz, 1H) 4.63 (dd, J=12.72, 4.16 Hz, 1H) 3.80 (s, 3H) 3.78 (s, 3H) 3.73 (tt, J=9.54, 4.65 Hz, 1H) 3.25 (dd, J=13.08, 10.15 Hz, 1H) 3.10-3.19 (m, 1H) 2.87 (dd, J=12.72, 9.54 Hz, 1H) 2.54 (d, J=12.47 Hz, 1H) 1.81-1.95 (m, 1H). LCMS-ESI (pos.), m/z: 546.2 (M+H)⁺.

Example 168.0. Preparation of 2-((2R,4S)-2-cyano-2,4-dimethyl-5-oxo-1-pyrrolidinyl)-N-(4-(2,6-dimethoxyphenyl)-5-(2-furanyl)-4H-1,2,4-triazol-3-yl)ethanesulfonamide or 2-((2S,4S)-2-cyano-2,4-dimethyl-5-oxo-1-pyrrolidinyl)-N-(4-(2,6-dimethoxyphenyl)-5-(2-furanyl)-4H-1,2,4-triazol-3-yl)ethanesulfonamide or 2-((2S,4R)-2-cyano-2,4-dimethyl-5-oxo-1-pyrrolidinyl)-N-(4-(2,6-dimethoxyphenyl)-5-(2-furanyl)-4H-1,2,4-triazol-3-yl)ethanesulfonamide or 2-((2R,4R)-2-cyano-2,4-dimethyl-5-oxo-1-pyrrolidinyl)-N-(4-(2,6-dimethoxyphenyl)-5-(2-furanyl)-4H-1,2,4-triazol-3-yl)ethanesulfonamide 168.1

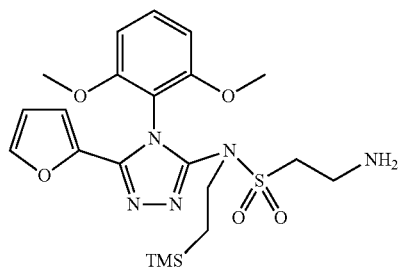

2-Amino-N-(4-(2,6-dimethoxyphenyl)-5-(furan-2-yl)-4H-1,2,4-triazol-3-yl)-N-(2-(trimethylsilyl)ethyl)ethanesulfonamide, Example 168.1. Example 168.1 was prepared using Example 362.03 following the procedures described in Example 160.0. LCMS-ESI (pos.), m/z: 494.1 (M+H)$^+$.

168.2

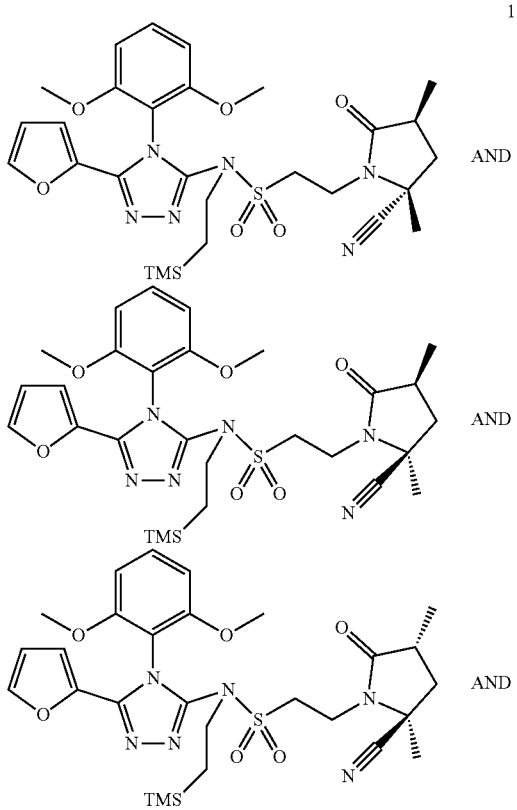

AND

AND

AND 168.2

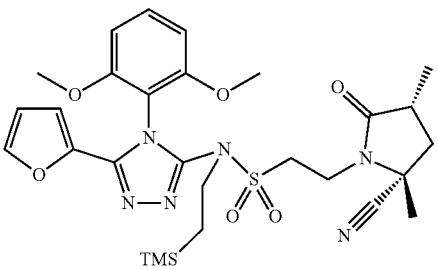

2-((2R,4R)-2-Cyano-2,4-dimethyl-5-oxopyrrolidin-1-yl)-N-(4-(2,6-dimethoxyphenyl)-5-(furan-2-yl)-4H-1,2,4-triazol-3-yl)-N-(2-(trimethylsilyl)ethyl)ethanesulfonamide and 2-((2R,4S)-2-cyano-2,4-dimethyl-5-oxopyrrolidin-1-yl)-N-(4-(2,6-dimethoxyphenyl)-5-(furan-2-yl)-4H-1,2,4-triazol-3-yl)-N-(2-(trimethylsilyl)ethyl)ethanesulfonamide and 2-((2S,4R)-2-cyano-2,4-dimethyl-5-oxopyrrolidin-1-yl)-N-(4-(2,6-dimethoxyphenyl)-5-(furan-2-yl)-4H-1,2,4-triazol-3-yl)-N-(2-(trimethylsilyl)ethyl)ethanesulfonamide and 2-((2S,4S)-2-cyano-2,4-dimethyl-5-oxopyrrolidin-1-yl)-N-(4-(2,6-dimethoxyphenyl)-5-(furan-2-yl)-4H-1,2,4-triazol-3-yl)-N-(2-(trimethylsilyl)ethyl)ethanesulfonamide, Example 168.2. To a 5 dram vial was added Example 168.1 (360 mg, 0.73 mmol) and alpha-methyllevulinic acid (TCI-America, 0.174 mL, 1.46 mmol) in MeOH (8 mL) followed by addition of trimethylsilyl cyanide (Sigma-Aldrich, 0.214 mL, 1.60 mmol). The reaction mixture was stirred at 70° C. for 6 h. The reaction mixture was concentrated in vacuo, diluted with water and extracted with DCM. The combined organic layers were washed with brine and dried over Na$_2$SO$_4$. The solution was filtered and concentrated in vacuo to give a light-yellow solid. The material thus obtained was absorbed onto a plug of silica gel and purified by chromatography through a Redi-Sep pre-packed silica gel column (40 g) eluting with a gradient of 0% to 100% EtOAc in hexanes to provide Example 168.2 (450 mg, 0.732 mmol, 100% yield) as a white solid. LCMS-ESI (pos.), m/z: 615.2 (M+H)$^+$.

168.3

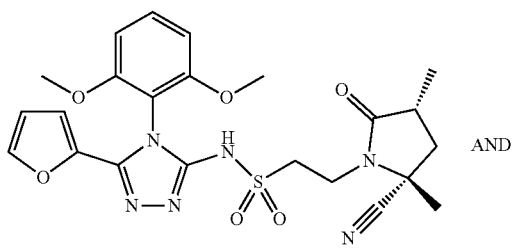

AND

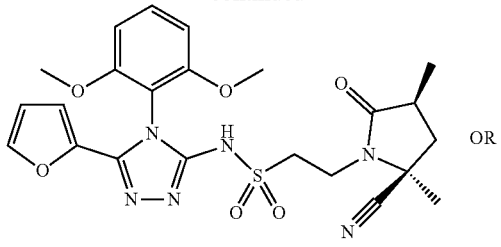

OR

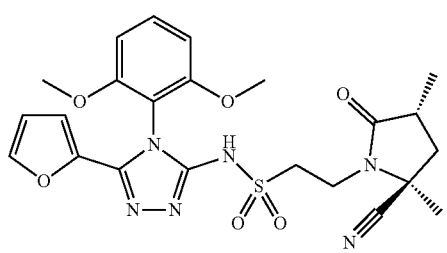

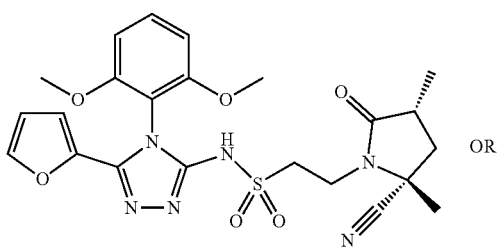

OR 2-((2R,4S)-2-Cyano-2,4-dimethyl-5-oxo-1-pyrrolidinyl)-N-(4-(2,6-dimethoxyphenyl)-5-(2-furanyl)-4H-1,2,4-triazol-3-yl)ethanesulfonamide and 2-((2S,4S)-2-cyano-2,4-dimethyl-5-oxo-1-pyrrolidinyl)-N-(4-(2,6-dimethoxyphenyl)-5-(2-furanyl)-4H-1,2,4-triazol-3-yl)ethanesulfonamide and 2-((2S,4R)-2-cyano-2,4-dimethyl-5-oxo-1-pyrrolidinyl)-N-(4-(2,6-dimethoxyphenyl)-5-(2-furanyl)-4H-1,2,4-triazol-3-yl)ethanesulfonamide and 2-((2R,4R)-2-cyano-2,4-dimethyl-5-oxo-1-pyrrolidinyl)-N-(4-(2,6-dimethoxyphenyl)-5-(2-furanyl)-4H-1,2,4-triazol-3-yl)ethanesulfonamide, Example 168.3. To a 5 dram vial was added Example 168.2 (290 mg, 0.47 mmol) in DMF (8 mL). At RT and under $N_2$, tris(dimethylamino)sulfonium difluorotrimethylsilicate (390 mg, 1.42 mmol) was added. The reaction mixture was then stirred at 70° C. for 16 h. The reaction mixture was cooled, diluted with water, and extracted with DCM. The combined organic layers were washed with brine and dried over $Na_2SO_4$. The solution was filtered and concentrated in vacuo to give a tan oil. The material thus obtained was absorbed onto a plug of silica gel and purified by chromatography through a Redi-Sep pre-packed silica gel column (12 g) eluting with a gradient of 0% to 100% EtOAc in DCM to provide Example 168.3 (200 mg, 0.389 mmol, 82% yield) as a white solid. LCMS-ESI (pos.), m/z: 515.2 (M+H)$^+$.

168.0

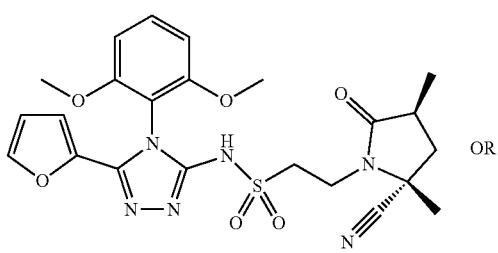

OR 2-((2R,4S)-2-Cyano-2,4-dimethyl-5-oxo-1-pyrrolidinyl)-N-(4-(2,6-dimethoxyphenyl)-5-(2-furanyl)-4H-1,2,4-triazol-3-yl)ethanesulfonamide or 2-((2S,4S)-2-cyano-2,4-dimethyl-5-oxo-1-pyrrolidinyl)-N-(4-(2,6-dimethoxyphenyl)-5-(2-furanyl)-4H-1,2,4-triazol-3-yl)ethanesulfonamide or 2-((2S,4R)-2-cyano-2,4-dimethyl-5-oxo-1-pyrrolidinyl)-N-(4-(2,6-dimethoxyphenyl)-5-(2-furanyl)-4H-1,2,4-triazol-3-yl)ethanesulfonamide or 2-((2R,4R)-2-cyano-2,4-dimethyl-5-oxo-1-pyrrolidinyl)-N-(4-(2,6-dimethoxyphenyl)-5-(2-furanyl)-4H-1,2,4-triazol-3-yl)ethanesulfonamide, Example 168.0. Example 168.0 was obtained from SFC chiral separation of Example 168.3 under the following condition: 35% MeOH containing 20 mM Ammonia, IC-H column, 70 mL/min, 272 nm, p=186, 200 mg of the racemic sample in 20 mL (MeOH/DCM), 0.5 mL per injection. Example 168.0 was the second isomer on the IC-H column to elute under the above condition. $^1$H NMR (500 MHz, $CD_3OD$) δ 7.61 (s, 1H) 7.57 (t, J=8.40 Hz, 1H) 6.87 (dd, J=8.68, 2.81 Hz, 2H) 6.45 (dd, J=3.55, 1.83 Hz, 1H) 6.14 (d, J=3.42 Hz, 1H) 3.82 (s, 3H) 3.81 (s, 3H) 3.64-3.75 (m, 2H) 3.45 (ddd, J=13.69, 9.90, 5.75 Hz, 1H) 3.30-3.36 (m, 1H) 2.60-2.67 (m, 1H) 2.45 (dd, J=13.33, 8.93 Hz, 1H) 2.28 (dd, J=13.45, 6.11 Hz, 1H) 1.63 (s, 3H) 1.31 (s, 1H). LCMS-ESI (pos.), m/z: 515.2 (M+H)$^+$.

Example 169.0. Preparation of N-(4-(2,6-dimethoxyphenyl)-5-(2-furanyl)-4H-1,2,4-triazol-3-yl)-2-((2S)-2-methyl-6-oxo-1-piperidinyl)ethanesulfonamide or N-(4-(2,6-dimethoxyphenyl)-5-(2-furanyl)-4H-1,2,4-triazol-3-yl)-2-((2R)-2-methyl-6-oxo-1-piperidinyl)ethanesulfonamide

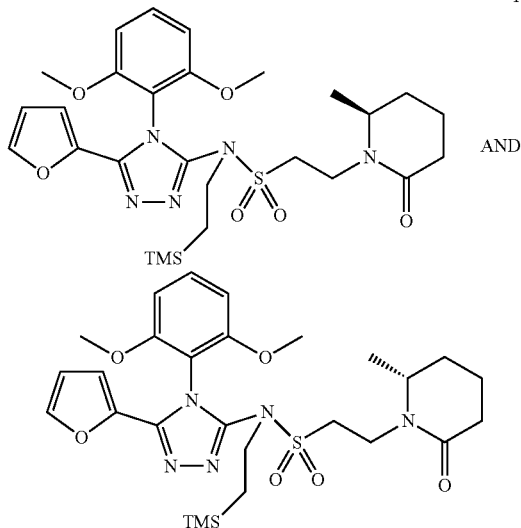

(S)—N-(4-(2,6-Dimethoxyphenyl)-5-(furan-2-yl)-4H-1,2,4-triazol-3-yl)-2-(2-methyl-6-oxopiperidin-1-yl)-N-(2-(trimethylsilyl)ethyl)ethanesulfonamide and (R)—N-(4-(2,6-dimethoxyphenyl)-5-(furan-2-yl)-4H-1,2,4-triazol-3-yl)-2-(2-methyl-6-oxopiperidin-1-yl)-N-(2-(trimethylsilyl)ethyl)ethanesulfonamide, Example 169.1. To a 50 mL RBF was added Example 168.1 (0.546 g, 1.11 mmol) and 4-acetylbutyric acid (0.288 mL, 2.21 mmol) in 1,2-dichloroethane (11 mL). At RT, sodium triacetoxyborohydride (0.469 g, 2.21 mmol) was added. The reaction mixture was then stirred at RT for 1.5 h. LCMS analysis showed that the desired reductive amination product formed. Activated 4 Å molecular sieves (4 g) were then added to the reaction mixture. The reaction mixture was stirred at RT for 1 h. LCMS analysis indicated no formation of the desired cyclization product. MeOH (2 mL) was then added, and the reaction mixture was stirred at 60° C. for 15 h. LCMS analysis indicated formation of the desired product. The reaction mixture was filtered through a short pad of silica gel and the pad was rinsed with MeOH. The initial material obtained was concentrated in vacuo and absorbed onto a plug of silica gel and purified by chromatography through a Redi-Sep pre-packed silica gel column (12 g) eluting with a gradient of 20% to 100% EtOAc in DCM to provide the title compound, Example 169.1 (0.530 g, 0.899 mmol, 81% yield), as a white solid. $^1$H NMR (400 MHz, MeOH) δ 7.64 (dd, J=1.76, 0.59 Hz, 1H) 7.59 (t, J=8.51 Hz, 1H) 6.88 (d, J=8.41 Hz, 2H) 6.47 (dd, J=3.52, 1.76 Hz, 1H) 6.18 (dd, J=3.62, 0.68 Hz, 1H) 4.37-4.49 (m, 2H) 3.81 (d, J=1.17 Hz, 6H) 3.67 (ddd, J=13.25, 8.56, 4.60 Hz, 1H) 3.49-3.59 (m, 1H) 3.14-3.32 (m, 2H) 2.95 (ddd, J=13.16, 8.36, 4.70 Hz, 1H) 2.21-2.37 (m, 2H) 1.81-1.97 (m, 2H) 1.54-1.77 (m, 2H) 1.31-1.42 (m, 2H) 1.13 (d, J=6.46 Hz, 3H) 0.09-0.18 (m, 9H). LCMS-ESI (pos.), m/z: 590.2 (M+H)$^+$.

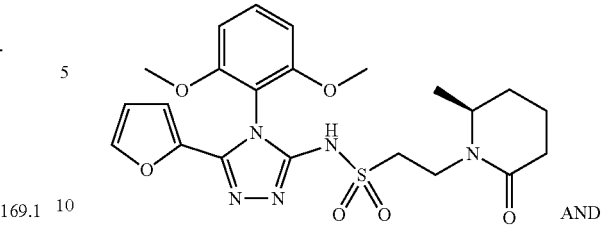

(R)—N-(4-(2,6-Dimethoxyphenyl)-5-(furan-2-yl)-4H-1,2,4-triazol-3-yl)-2-(2-methyl-6-oxopiperidin-1-yl)ethanesulfonamide and (S)—N-(4-(2,6-dimethoxyphenyl)-5-(furan-2-yl)-4H-1,2,4-triazol-3-yl)-2-(2-methyl-6-oxopiperidin-1-yl)ethanesulfonamide, Example 169.2. Example 169.2 was prepared from Example 169.1 using the procedure described in Example 168.3. $^1$H NMR (500 MHz, MeOH) δ 7.61 (dd, J=1.71, 0.73 Hz, 1H) 7.57 (t, J=8.56 Hz, 1H) 6.87 (d, J=8.56 Hz, 2H) 6.45 (dd, J=3.55, 1.83 Hz, 1H) 6.14 (dd, J=3.55, 0.61 Hz, 1H) 3.83-3.91 (m, 1H) 3.81 (d, J=1.96 Hz, 6H) 3.65-3.72 (m, 1H) 3.38-3.50 (m, 2H) 3.16-3.24 (m, 1H) 2.24-2.37 (m, 2H) 1.83-1.97 (m, 2H) 1.66-1.76 (m, 1H) 1.56-1.66 (m, 1H) 1.21 (d, J=6.60 Hz, 3H). LCMS-ESI (pos.), m/z: 490.1 (M+H)$^+$.

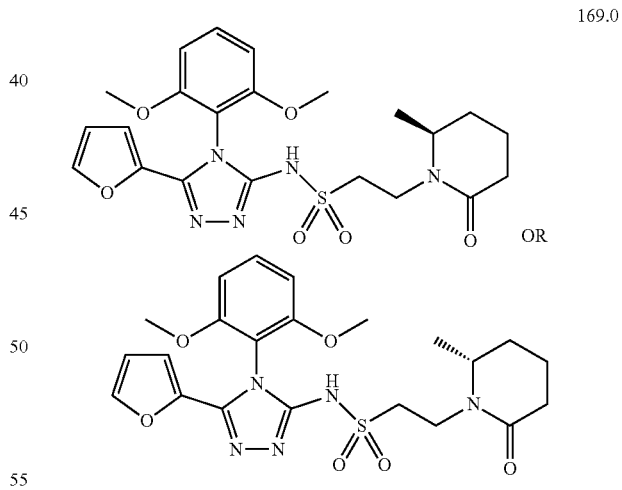

(R)—N-(4-(2,6-Dimethoxyphenyl)-5-(furan-2-yl)-4H-1,2,4-triazol-3-yl)-2-(2-methyl-6-oxopiperidin-1-yl)ethanesulfonamide or (S)—N-(4-(2,6-dimethoxyphenyl)-5-(furan-2-yl)-4H-1,2,4-triazol-3-yl)-2-(2-methyl-6-oxopiperidin-1-yl)ethanesulfonamide, Example 169.0. Example 169.0 was obtained by SFC chiral separation of Example 169.2. The title compound, Example 169.0, was the second isomer to elute under the following conditions: 150×20 mm Lux-2 column with 35% MeOH (0.1% NH$_4$OH)/CO$_2$, 70 mL/min, 254 nm. Injection volume: 1.5 mL, 13 mg/mL MeOH solution of the racemic compound. $^1$H NMR (500 MHz, CD₃OD) δ 1.21 (d, J=6.60 Hz, 3H) 1.56-1.66 (m, 1H) 1.66-1.76 (m, 1H) 1.83-1.97 (m, 2H) 2.24-2.37 (m, 2H) 3.16-3.24 (m, 1H) 3.38-3.50 (m, 2H) 3.65-3.72 (m, 1H) 3.81 (d, J=1.96 Hz, 6H) 3.83-3.91 (m, 1H) 6.14 (dd, J=3.55, 0.61 Hz, 1H) 6.45 (dd, J=3.55, 1.83 Hz, 1H) 6.87 (d, J=8.56 Hz, 2H) 7.57 (t, J=8.56 Hz, 1H) 7.61 (dd, J=1.71, 0.73 Hz, 1H). LCMS-ESI (pos.), m/z: 490.1 (M+H)⁺.

Example 170.0. Preparation of (3R,5R)-1-acetyl-N-(4-(2,6-dimethoxyphenyl)-5-(5-methyl-2-furanyl)-4H-1,2,4-triazol-3-yl)-5-(4-fluorophenyl)-3-piperidinesulfonamide or (3S,5S)-1-acetyl-N-(4-(2,6-dimethoxyphenyl)-5-(5-methyl-2-furanyl)-4H-1,2,4-triazol-3-yl)-5-(4-fluorophenyl)-3-piperidinesulfonamide

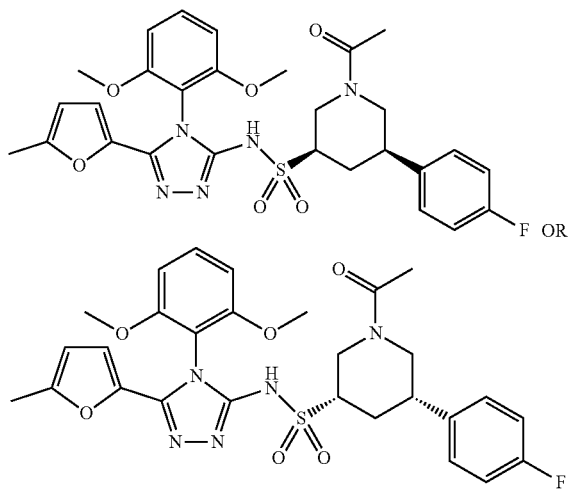

170.0

(3R,5R)-1-Acetyl-N-(4-(2,6-dimethoxyphenyl)-5-(5-methyl-2-furanyl)-4H-1,2,4-triazol-3-yl)-5-(4-fluorophenyl)-3-piperidinesulfonamide or (3S,5S)-1-acetyl-N-(4-(2,6-dimethoxyphenyl)-5-(5-methyl-2-furanyl)-4H-1,2,4-triazol-3-yl)-5-(4-fluorophenyl)-3-piperidinesulfonamide, Example 170.0. Example 170.0 was obtained from SFC chiral separation of Example 165.7. Example 170.0 was the second isomer to elute from an IA column under the following conditions: 300×30 mm IA columns with 36 g/min MeOH+(20 mM NH₃)+84 g/min CO₂ on Thar 350 SFC. Outlet pressure=100 bar; Temp.=20° C.; Wavelength=276 nm. Used 0.5 mL injections of 44 mg/6 mL (7.3 mg/mL) sample solution in MeOH, i.e. 3.7 mg/injection, Runtime=30 min. ¹H NMR (500 MHz, CD₃OD) δ 7.57 (td, J=8.56, 4.16 Hz, 1H) 7.23-7.38 (m, 2H) 7.10 (td, J=8.74, 6.48 Hz, 2H) 6.81-6.90 (m, 2H) 6.00-6.08 (m, 1H) 5.96 (t, J=3.18 Hz, 1H) 5.03-5.10 (m, 1H) 4.52-4.63 (m, 1H) 4.31 (d, J=9.54 Hz, 1H) 3.93 (d, J=13.20 Hz, 1H) 3.67-3.79 (m, 7H) 3.26-3.31 (m, 1H) 3.12-3.21 (m, 1H) 3.03-3.12 (m, 1H) 2.82-2.93 (m, 1H) 2.69-2.80 (m, 1H) 2.53 (t, J=12.47 Hz, 1H) 2.39 (d, J=12.23 Hz, 1H) 2.27 (s, 3H) 2.11-2.18 (m, 3H) 1.86-2.01 (m, 1H). LCMS-ESI (pos.), m/z: 584.2 (M+H)⁺.

Example 171.0. Preparation of (3R,5S)-1-acetyl-N-(4-(2,6-dimethoxyphenyl)-5-(5-methyl-2-furanyl)-4H-1,2,4-triazol-3-yl)-5-(4-fluorophenyl)-3-piperidinesulfonamide or (3S,5R)-1-acetyl-N-(4-(2,6-dimethoxyphenyl)-5-(5-methyl-2-furanyl)-4H-1,2,4-triazol-3-yl)-5-(4-fluorophenyl)-3-piperidinesulfonamide

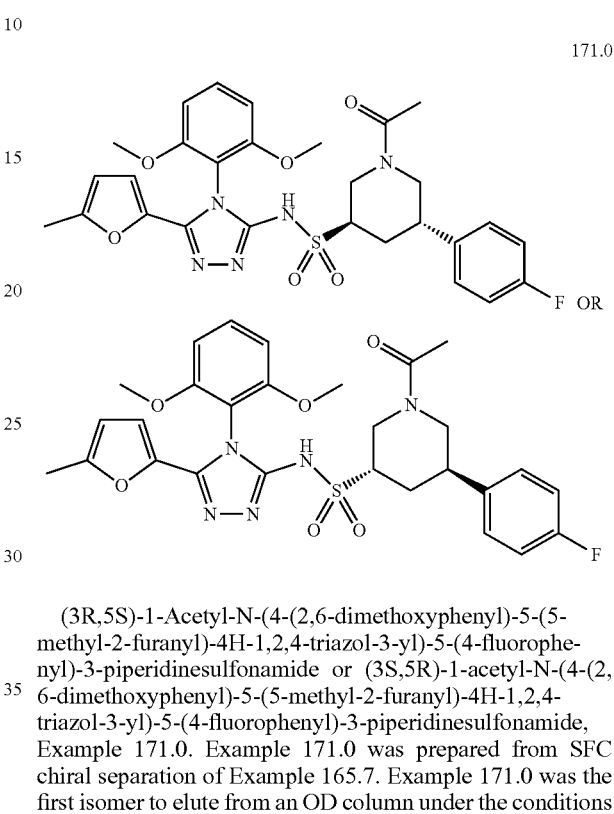

171.0

(3R,5S)-1-Acetyl-N-(4-(2,6-dimethoxyphenyl)-5-(5-methyl-2-furanyl)-4H-1,2,4-triazol-3-yl)-5-(4-fluorophenyl)-3-piperidinesulfonamide or (3S,5R)-1-acetyl-N-(4-(2,6-dimethoxyphenyl)-5-(5-methyl-2-furanyl)-4H-1,2,4-triazol-3-yl)-5-(4-fluorophenyl)-3-piperidinesulfonamide, Example 171.0. Example 171.0 was prepared from SFC chiral separation of Example 165.7. Example 171.0 was the first isomer to elute from an OD column under the conditions described in Example 165.0. ¹H NMR (500 MHz, CD₃OD) δ 7.50-7.61 (m, 1H) 7.21-7.32 (m, 2H) 7.01-7.12 (m, 2H) 6.80-6.89 (m, 2H) 6.01-6.07 (m, 1H) 5.92-5.99 (m, 1H) 4.44 (d, J=13.94 Hz, 2H) 3.60-3.77 (m, 7H) 3.45-3.54 (m, 1H) 3.34-3.43 (m, 2H) 3.20-3.27 (m, 1H) 2.87 (t, J=11.98 Hz, 1H) 2.53 (d, J=14.92 Hz, 1H) 2.28 (s, 3H) 2.15 (ddd, J=14.67, 12.23, 5.87 Hz, 1H) 2.04-2.09 (m, 2H) 2.02 (s, 1H). LCMS-ESI (pos.), m/z: 584.2 (M+H)⁺.

Example 172.0. Preparation of (2S,3R)-3-(5-fluoro-2-pyrimidinyl)-N-(4-(2-methoxyphenyl)-5-(5-methyl-2-furanyl)-4H-1,2,4-triazol-3-yl)-2-butanesulfonamide 172.0

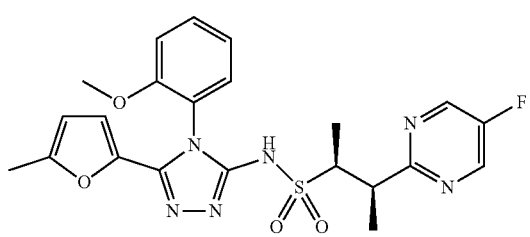

(2S,3R)-3-(5-Fluoro-2-pyrimidinyl)-N-(4-(2-methoxyphenyl)-5-(5-methyl-2-furanyl)-4H-1,2,4-triazol-3-yl)-2-butanesulfonamide, Example 172.0. Example 172.0 was prepared using Example 56.5, 5-methyl-2-furohydrazide (ChemBridge Corporation), and 1-isothiocyanato-2-methoxybenzene Example 372.2 following the procedure described in the Example 229.0. $^1$H NMR (500 MHz, CDCl$_3$) δ 1.32-1.43 (m, 6H) 2.33 (s, 3H) 3.75 (s, 1.5H) 3.77 (s, 1.5H) 3.79-3.89 (m, 2H) 3.79-3.89 (m, 1H) 5.76 (dd, J=7.50, 3.52 Hz, 1H) 5.93 (ddd, J=2.91, 1.99, 1.22 Hz, 1H) 7.07 (ddd, J=8.34, 4.21, 0.92 Hz, 1H) 7.12 (tdd, J=7.69, 7.69, 4.82, 1.22 Hz, 1H) 7.31 (dd, J=7.80, 1.68 Hz, 0.5H) 7.37 (dd, J=7.80, 1.68 Hz, 0.5H) 7.55 (ddd, J=8.34, 7.57, 1.84 Hz, 1H) 8.56 (d, J=1.22 Hz, 2H). LCMS-ESI (pos.), m/z: 487.1 (M+H)$^+$.

Example 173.0. Preparation of (3R,9aR)—N-(4-(2,6-dimethoxyphenyl)-5-(5-methyl-2-furanyl)-4H-1,2,4-triazol-3-yl)-6-oxooctahydro-2H-quinolizine-3-sulfonamide or (3S,9aS)—N-(4-(2,6-dimethoxyphenyl)-5-(5-methyl-2-furanyl)-4H-1,2,4-triazol-3-yl)-6-oxooctahydro-2H-quinolizine-3-sulfonamide or (3R,9aS)—N-(4-(2,6-dimethoxyphenyl)-5-(5-methyl-2-furanyl)-4H-1,2,4-triazol-3-yl)-6-oxooctahydro-2H-quinolizine-3-sulfonamide or (3S,9aR)—N-(4-(2,6-dimethoxyphenyl)-5-(5-methyl-2-furanyl)-4H-1,2,4-triazol-3-yl)-6-oxooctahydro-2H-quinolizine-3-sulfonamide

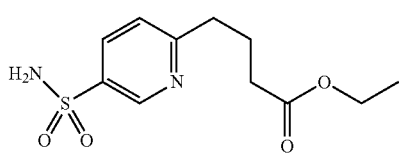

173.1

Ethyl 4-(5-sulfamoylpyridin-2-yl)butanoate, Example 173.1. Under N$_2$ and to a 250 mL RBF, was added 6-chloropyridine-3-sulfonamide (commercially available from Enamine, Kiev, Ukraine, 0.826 g, 4.29 mmol) and bis(tricyclohexylphosphine)palladium(0) (commercially available from Strem Chemicals, Inc., MA, USA, 0.572 g, 0.858 mmol) in THF (20 mL). 4-Ethoxy-4-oxobutylzinc bromide (0.5M solution in THF, commercially available from Sigma-Aldrich, USA, 12.0 mL, 6.0 mmol) was added to the stirred mixture via syringe under N$_2$. The reaction mixture was then stirred at RT for 4 h. The reaction was further stirred at 60° C. overnight. The reaction mixture was then allowed to cool to RT. (1,1'-Bis(diphenylphosphino)ferrocene)dichloropalladium (II) (commercially available from Strem Chemicals, Inc., MA, USA, 0.628 g, 0.858 mmol) was added under N$_2$ followed with another batch of 4-ethoxy-4-oxobutylzinc bromide (0.5M solution in THF, 12.0 L 6.0 mmol). The reaction mixture was stirred at 60° C. for 40 h. The reaction mixture was then allowed to cool to RT, diluted with a saturated solution of NH$_4$Cl, extracted with EtOAc, and concentrated in vacuo. The material was purified by silica gel chromatography (gradient of 0% to 100% EtOAc in DCM, with 30% EtOH in EtOAc). This provided Example 173.1 (0.70 g, 2.57 mmol, 60% yield) as an off-white solid. $^1$H NMR (400 MHz, CDCl$_3$) δ 8.94-9.02 (m, 1H) 8.13 (dd, J=8.22, 2.35 Hz, 1H) 7.33 (d, J=8.22 Hz, 1H) 5.99 (br. s., 2H) 4.09 (q, J=7.24 Hz, 2H) 2.91 (t, J=7.63 Hz, 2H) 2.35 (t, J=7.24 Hz, 2H) 2.01 (quin, J=7.53 Hz, 2H) 1.22 (t, J=7.14 Hz, 4H). LCMS-ESI (pos.), m/z: 273.2 (M+H)$^+$.

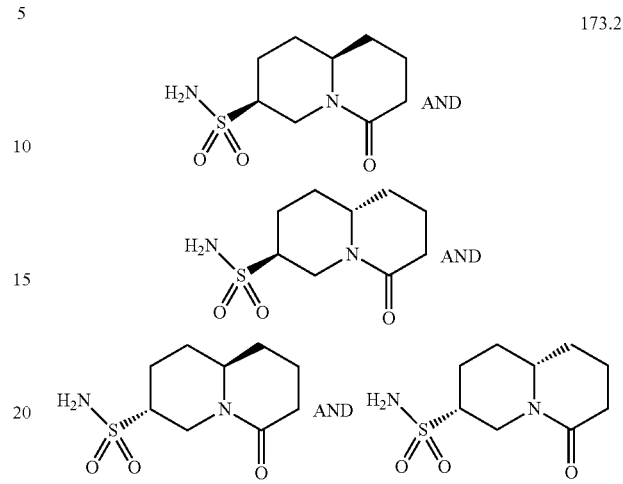

173.2

(3R,9aR)-6-Oxooctahydro-1H-quinolizine-3-sulfonamide and (3R,9aS)-6-oxooctahydro-1H-quinolizine-3-sulfonamide and (3S,9aR)-6-oxooctahydro-1H-quinolizine-3-sulfonamide and (3S,9aS)-6-oxooctahydro-1H-quinolizine-3-sulfonamide, Example 173.2. To a 250 mL hydrogenation flask was added Example 173.1 (380 mg, 1.395 mmol) and AcOH (10 mL). The mixture was bubbled with N$_2$ for 3 min before platinum (IV) oxide (317 mg, 1.395 mmol) was added under N$_2$. The flask was placed under vacuum and back-filled with N$_2$ two times. It was then placed under vacuum and back-filled with hydrogen gas. The reaction mixture was then stirred at RT under hydrogen gas for three days. LCMS analysis indicated the reaction was complete. Celite® brand filter aid (10 g) was added to the stirred mixture. The solid was removed by filtration after 10 min. The filter cake was rinsed with MeOH. The combined organics were concentrated in vacuo to afford Example 173.2 as a light yellow oil which was directly used in the next step without purification. LCMS-ESI (pos.), m/z: 233.1 (M+H)$^+$.

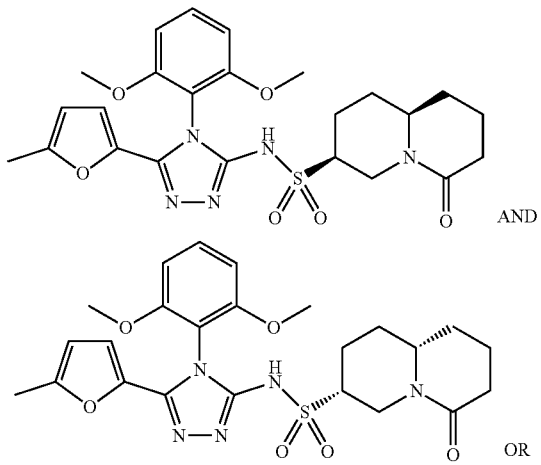

173.3

-continued

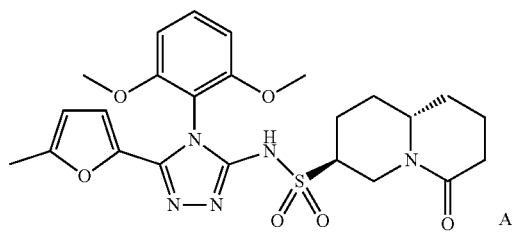

AND

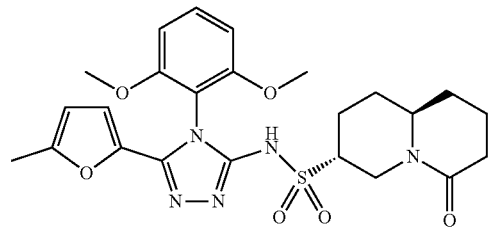

(3R,9aR)—N-(4-(2,6-Dimethoxyphenyl)-5-(5-methyl-2-furanyl)-4H-1,2,4-triazol-3-yl)-6-oxooctahydro-2H-quinolizine-3-sulfonamide and (3S,9aS)—N-(4-(2,6-dimethoxyphenyl)-5-(5-methyl-2-furanyl)-4H-1,2,4-triazol-3-yl)-6-oxooctahydro-2H-quinolizine-3-sulfonamide or A mixture of (3R,9aS)—N-(4-(2,6-dimethoxyphenyl)-5-(5-methyl-2-furanyl)-4H-1,2,4-triazol-3-yl)-6-oxooctahydro-2H-quinolizine-3-sulfonamide and (3S,9aR)—N-(4-(2,6-dimethoxyphenyl)-5-(5-methyl-2-furanyl)-4H-1,2,4-triazol-3-yl)-6-oxooctahydro-2H-quinolizine-3-sulfonamide, Example 173.3. Example 173.3 was prepared from Example 364.1 and Example 173.2 using the procedure described in Example 94.0. A mixture of diastereomers was obtained and was purified by reverse-phase preparative HPLC (0.1% TFA in ACN/H$_2$O, gradient 5% to 95%). Example 173.3 was the earlier peak to elute from a C18 column. $^1$H NMR (500 MHz, CD$_2$Cl$_2$) δ 7.55 (t, J=8.56 Hz, 1H) 6.77 (dd, J=8.56, 3.91 Hz, 2H) 5.98 (s, 2H) 5.26 (d, J=14.43 Hz, 1H) 3.81 (s, 3H) 3.80 (s, 3H) 3.36-3.48 (m, 1H) 3.17 (br. s., 1H) 2.95 (dd, J=14.67, 3.18 Hz, 1H) 2.54 (d, J=14.67 Hz, 1H) 2.48 (br. s., 2H) 2.31 (s, 3H) 1.98-2.20 (m, 2H) 1.78-1.98 (m, 2H) 1.70 (br. s., 1H) 1.54-1.67 (m, 2H). LCMS-ESI (pos.), m/z: 516.2 (M+H)$^+$.

-continued

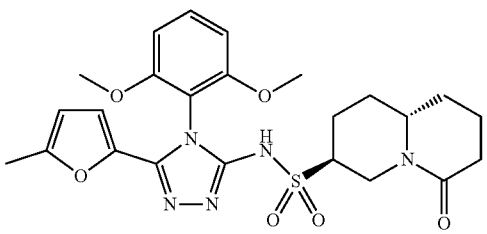

AND

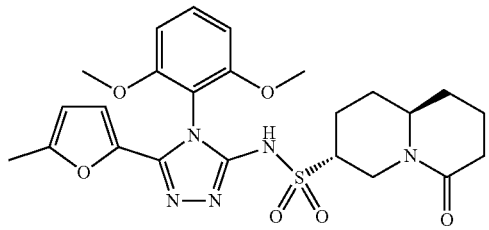

(3R,9aR)—N-(4-(2,6-Dimethoxyphenyl)-5-(5-methyl-2-furanyl)-4H-1,2,4-triazol-3-yl)-6-oxooctahydro-2H-quinolizine-3-sulfonamide and (3S,9aS)—N-(4-(2,6-dimethoxyphenyl)-5-(5-methyl-2-furanyl)-4H-1,2,4-triazol-3-yl)-6-oxooctahydro-2H-quinolizine-3-sulfonamide or A mixture of (3R,9aS)—N-(4-(2,6-dimethoxyphenyl)-5-(5-methyl-2-furanyl)-4H-1,2,4-triazol-3-yl)-6-oxooctahydro-2H-quinolizine-3-sulfonamide and (3S,9aR)—N-(4-(2,6-dimethoxyphenyl)-5-(5-methyl-2-furanyl)-4H-1,2,4-triazol-3-yl)-6-oxooctahydro-2H-quinolizine-3-sulfonamide, Example 173.4. Example 173.4 was the later peak to elute from the C18 column described in Example 173.3. $^1$H NMR (500 MHz, CD$_2$Cl$_2$) δ 7.56 (t, J=8.56 Hz, 1H) 6.78 (dd, J=8.56, 3.18 Hz, 2H) 5.94-6.02 (m, 1H) 5.90 (d, J=3.42 Hz, 1H) 5.09 (d, J=12.23 Hz, 1H) 3.79-3.85 (m, 6H) 3.18-3.30 (m, 1H) 2.96 (t, J=11.98 Hz, 1H) 2.60 (t, J=12.35 Hz, 1H) 2.41-2.51 (m, 1H) 2.23-2.41 (m, 5H) 1.99-2.11 (m, 1H) 1.90 (dd, J=13.20, 2.93 Hz, 1H) 1.79-1.87 (m, 1H) 1.76 (dd, J=12.72, 3.91 Hz, 1H) 1.64-1.74 (m, 1H) 1.49-1.60 (m, 1H) 1.41 (dd, J=12.10, 3.55 Hz, 1H). LCMS-ESI (pos.), m/z: 516.2 (M+H)$^+$.

173.4

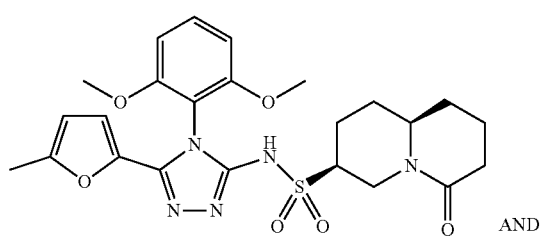

AND

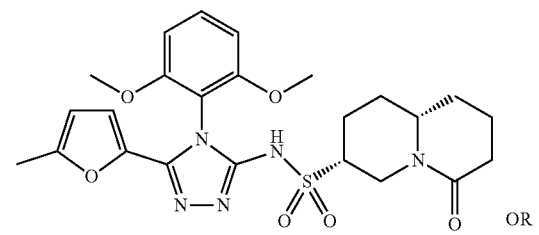

OR 173.0

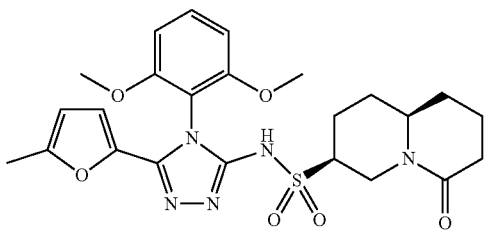

OR

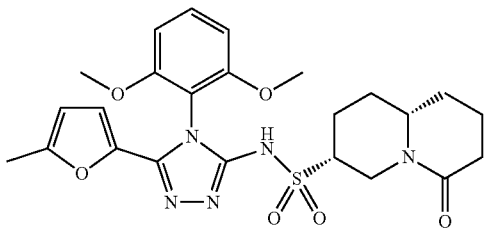

OR

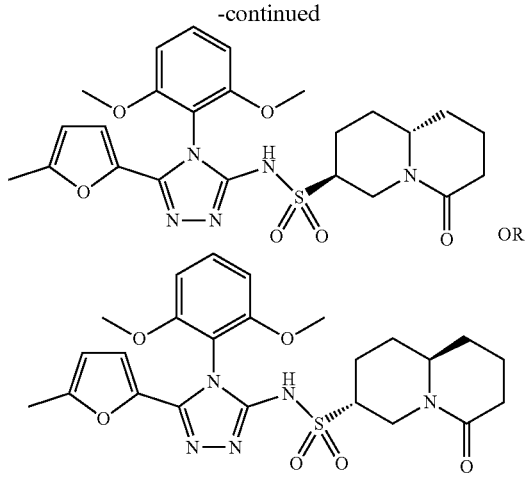

(3R,9aR)—N-(4-(2,6-Dimethoxyphenyl)-5-(5-methyl-2-furanyl)-4H-1,2,4-triazol-3-yl)-6-oxooctahydro-2H-quinolizine-3-sulfonamide or (3S,9aS)—N-(4-(2,6-dimethoxyphenyl)-5-(5-methyl-2-furanyl)-4H-1,2,4-triazol-3-yl)-6-oxooctahydro-2H-quinolizine-3-sulfonamide or (3R,9aS)—N-(4-(2,6-dimethoxyphenyl)-5-(5-methyl-2-furanyl)-4H-1,2,4-triazol-3-yl)-6-oxooctahydro-2H-quinolizine-3-sulfonamide or (3S,9aR)—N-(4-(2,6-dimethoxyphenyl)-5-(5-methyl-2-furanyl)-4H-1,2,4-triazol-3-yl)-6-oxooctahydro-2H-quinolizine-3-sulfonamide, Example 173.0. Example 173.0 was obtained from SFC chiral separation of Example 173.4. Example 173.0 was the first isomer to elute from an AD-H column under the following conditions: Run on Thar 80 SFC with 21 g/min MeOH (20 mM NH$_3$)+49 g/min CO$_2$ on 150×30 mm AD-H column, 30% co-solvent at 70 g/min. Outlet pressure=100 bar; Temp.=RT; Wavelength=277 nm. Manually injected 1.0 mL of a solution from 25 mg sample dissolved in 3.0 mL of MeOH, c=8.1 mg/mL; 8.1 mg per injection. $^1$H NMR (500 MHz, CD$_3$OD) δ 7.57 (t, J=8.56 Hz, 1H) 6.87 (d, J=8.56 Hz, 2H) 6.01-6.07 (m, 1H) 5.96 (d, J=3.67 Hz, 1H) 5.05-5.14 (m, 1H) 3.82 (d, J=1.47 Hz, 6H) 3.24-3.31 (m, 1H) 2.97 (tt, J=11.98, 3.67 Hz, 1H) 2.58 (t, J=12.35 Hz, 1H) 2.30-2.41 (m, 2H) 2.21-2.30 (m, 4H) 2.07 (dd, J=7.95, 5.50 Hz, 1H) 1.91 (dq, J=13.42, 3.11 Hz, 1H) 1.84 (ddd, J=12.96, 7.09, 2.93 Hz, 1H) 1.64-1.80 (m, 2H) 1.51-1.62 (m, 1H) 1.38-1.51 (m, 1H). LCMS-ESI (pos.), m/z: 516.2 (M+H)$^+$.

Example 174.0. Preparation of (3R,5S)-5-cyano-N-(4-(2,6-dimethoxyphenyl)-5-(5-methyl-2-furanyl)-4H-1,2,4-triazol-3-yl)-1-(5-fluoro-2-pyrimidinyl)-3-piperidinesulfonamide or (3S,5R)-5-cyano-N-(4-(2,6-dimethoxyphenyl)-5-(5-methyl-2-furanyl)-4H-1,2,4-triazol-3-yl)-1-(5-fluoro-2-pyrimidinyl)-3-piperidinesulfonamide 174.1

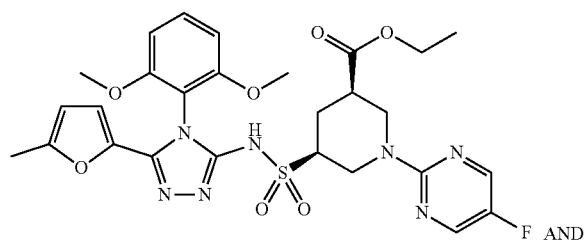

AND

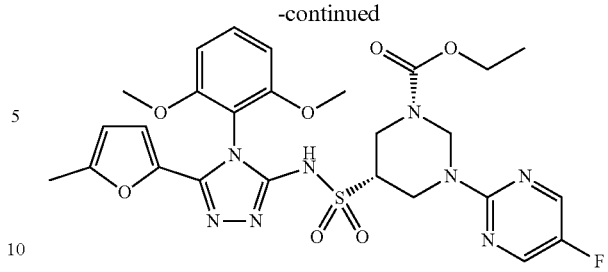

(3R,5S)-ethyl 5-(N-(4-(2,6-Dimethoxyphenyl)-5-(5-methylfuran-2-yl)-4H-1,2,4-triazol-3-yl)sulfamoyl)-1-(5-fluoropyrimidin-2-yl)piperidine-3-carboxylate and (3S,5R)-ethyl 5-(N-(4-(2,6-dimethoxyphenyl)-5-(5-methylfuran-2-yl)-4H-1,2,4-triazol-3-yl)sulfamoyl)-1-(5-fluoropyrimidin-2-yl)piperidine-3-carboxylate, Example 174.1. Example 174.1 was obtained by purification of Example 154.4 on a silica gel column. LCMS-ESI (pos.), m/z: 616.3 (M+H)$^+$.

174.2

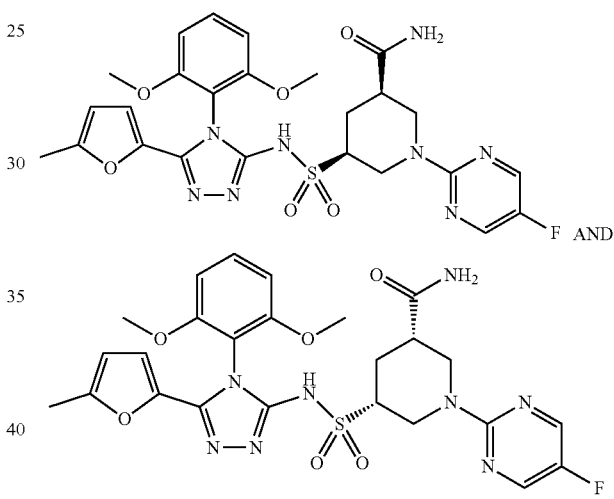

(3R,5S)-5-((4-(2,6-Dimethoxyphenyl)-5-(5-methyl-2-furanyl)-4H-1,2,4-triazol-3-yl)sulfamoyl)-1-(5-fluoro-2-pyrimidinyl)-3-piperidinecarboxamide and (3S,5R)-5-((4-(2,6-dimethoxyphenyl)-5-(5-methyl-2-furanyl)-4H-1,2,4-triazol-3-yl)sulfamoyl)-1-(5-fluoro-2-pyrimidinyl)-3-piperidinecarboxamide, Example 174.2. A glass microwave reaction vessel was charged with Example 174.1 (166 mg, 0.27 mmol) and ammonia (7.0 M solution in MeOH, 3 mL, 21.0 mmol). The reaction mixture was stirred and heated in a Discover model microwave reactor (CEM, Matthews, N.C.) at 100° C. 3 h until the desired products formed as determined by LCMS analysis. The reaction mixture was then concentrated in vacuo and the material was purified by reverse-phase preparative HPLC (0.1% TFA in ACN/H$_2$O, gradient 5% to 95%) to provide Example 174.2 (28 mg, 18% yield) as a white solid which was the later peak to elute on reverse phase preparative HPLC and a mixture of two cis enantiomers. $^1$H NMR (500 MHz, DMSO-d$_6$) δ 13.29 (s, 1H) 8.49 (s, 2H) 7.58 (t, J=8.56 Hz, 1H) 7.46 (s, 1H) 6.96 (s, 1H) 6.90 (t, J=7.83 Hz, 2H) 6.14 (dd, J=3.30, 0.86 Hz, 1H) 5.82 (d, J=3.42 Hz, 1H) 5.82 (d, J=3.42 Hz, 1H) 4.98 (d, J=11.00 Hz, 1H) 4.65 (d, J=9.54 Hz, 1H) 3.69-3.79 (m, 7H) 2.92 (d, J=11.98 Hz, 1H) 2.75 (td, J=12.29, 8.68 Hz, 2H)

2.30-2.41 (m, 1H) 2.26 (s, 3H) 2.20 (d, J=12.47 Hz, 1H) 1.73 (d, J=12.72 Hz, 1H). LCMS-ESI (pos.), m/z: 587.2 (M+H)⁺.

174.3

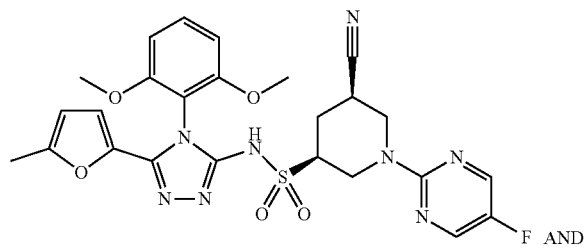

AND

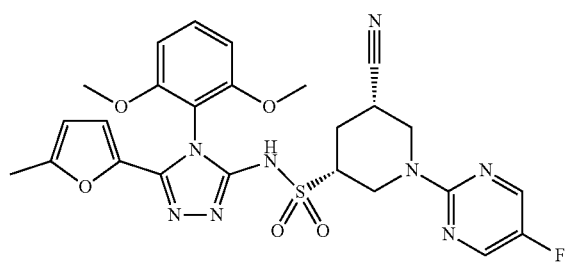

(3R,5S)-5-Cyano-N-(4-(2,6-dimethoxyphenyl)-5-(5-methyl-2-furanyl)-4H-1,2,4-triazol-3-yl)-1-(5-fluoro-2-pyrimidinyl)-3-piperidinesulfonamide and (3S,5R)-5-cyano-N-(4-(2,6-dimethoxyphenyl)-5-(5-methyl-2-furanyl)-4H-1,2,4-triazol-3-yl)-1-(5-fluoro-2-pyrimidinyl)-3-piperidinesulfonamide, Example 174.3. A glass reaction vessel was charged with Example 174.2 (22 mg, 0.038 mmol) and trifluoromethanesulfonic anhydride (0.013 mL, 0.075 mmol) in DCM (1.5 mL). The reaction mixture was stirred at RT for 60 min. LCMS analysis indicated the reaction was complete. The reaction mixture was purified by silica gel chromatography (0% to 100% EtOAc in DCM) and reverse-phase preparative HPLC (0.1% TFA in ACN/H₂O, gradient 20% to 80%) provided the title compound, Example 174.3 (12 mg, 0.021 mmol, 56% yield), as a white solid. ¹H NMR (500 MHz, CD₂Cl₂) δ 8.30 (s, 2H) 7.59 (t, J=8.56 Hz, 1H) 6.80 (dd, J=8.56, 1.96 Hz, 2H) 5.99 (dd, J=3.42, 0.98 Hz, 1H) 5.90 (d, J=3.42 Hz, 1H) 5.15 (d, J=9.54 Hz, 1H) 5.08 (dt, J=13.14, 1.99 Hz, 1H) 3.83 (s, 3H) 3.85 (s, 3H) 2.90-3.07 (m, 3H) 2.60-2.76 (m, 2H) 2.33 (s, 3H) 2.06 (d, J=12.23 Hz, 1H). LCMS-ESI (pos.), m/z: 569.2 (M+H)⁺.

174.0

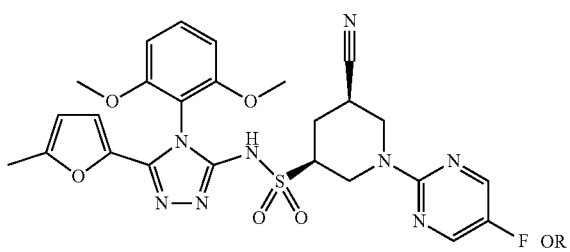

OR

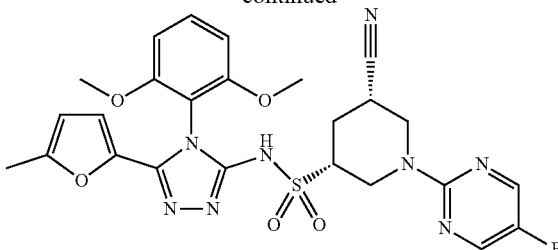

(3R,5S)-5-Cyano-N-(4-(2,6-dimethoxyphenyl)-5-(5-methyl-2-furanyl)-4H-1,2,4-triazol-3-yl)-1-(5-fluoro-2-pyrimidinyl)-3-piperidinesulfonamide or (3S,5R)-5-cyano-N-(4-(2,6-dimethoxyphenyl)-5-(5-methyl-2-furanyl)-4H-1,2,4-triazol-3-yl)-1-(5-fluoro-2-pyrimidinyl)-3-piperidinesulfonamide, Example 174.0. Example 174.0 was obtained from SFC chiral separation of Example 174.3. Example 174.0 was the second isomer to elute from an AS-H column under the following conditions: Thar 200 with 250×30 mm AS-H column with 54 g/min MeOH (neat) and 66 g/min CO₂, 45% co-solvent at 120 g/min. Wavelength 276 nm. Injected 1.0 mL of 80 mg dissolved in 10.0 mL MeOH; c=8.0 mg/mL, 8.0 mg/injection. Cycle time 7.0 min, run time 11 min. ¹H NMR (400 MHz, CDCl₃) δ 10.92 (br. s., 1H) 8.14-8.35 (m, 2H) 7.51 (t, J=8.51 Hz, 1H) 6.73 (dd, J=8.51, 1.86 Hz, 2H) 5.94 (dd, J=3.42, 0.88 Hz, 1H) 5.83 (d, J=3.52 Hz, 1H) 5.24 (d, J=9.19 Hz, 1H) 5.07 (dt, J=13.16, 1.93 Hz, 1H) 3.82 (s, 3H) 3.80 (s, 3H) 2.97-3.10 (m, 2H) 2.92 (dd, J=13.11, 11.54 Hz, 1H) 2.57-2.77 (m, 2H) 2.34 (s, 3H) 1.94-2.20 (m, 1H) 1.67 (br. s., 1H). LCMS-ESI (pos.), m/z: 569.2 (M+H)⁺.

Example 175.0. Preparation of N-(4-(2,6-dimethoxyphenyl)-5-(2-furanyl)-4H-1,2,4-triazol-3-yl)-2-((3S,5S)-3,5-dimethyl-2-oxo-1-pyrrolidinyl)ethanesulfonamide or N-(4-(2,6-dimethoxyphenyl-5-(2-furanyl)-4H-1,2,4-triazol-3-yl)-2-((3S,5R)-3,5-dimethyl-2-oxo-1-pyrrolidinyl)ethanesulfonamide or N-(4-(2,6-dimethoxyphenyl)-5-(2-furanyl)-4H-1,2,4-triazol-3-yl)-2-((3R,5R)-3,5-dimethyl-2-oxo-1-pyrrolidinyl)ethanesulfonamide or N-(4-(2,6-dimethoxyphenyl)-5-(2-furanyl)-4H-1,2,4-triazol-3-yl)-2-((3R,5S)-3,5-dimethyl-2-oxo-1-pyrrolidinyl)ethanesulfonamide 175.1

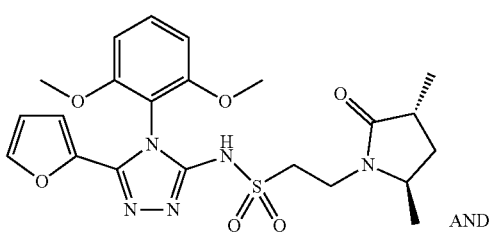

AND

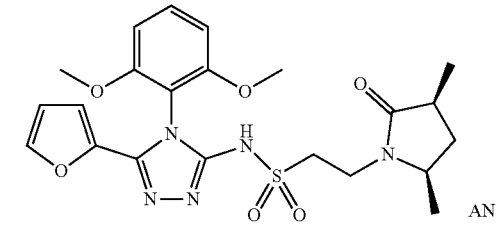

AND

-continued

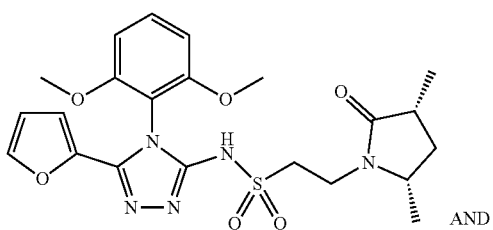

AND

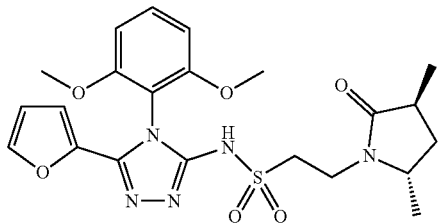

N-(4-(2,6-Dimethoxyphenyl)-5-(2-furanyl)-4H-1,2,4-triazol-3-yl)-2-((3S,5S)-3,5-dimethyl-2-oxo-1-pyrrolidinyl)ethanesulfonamide and N-(4-(2,6-dimethoxyphenyl)-5-(2-furanyl)-4H-1,2,4-triazol-3-yl)-2-((3S,5R)-3,5-dimethyl-2-oxo-1-pyrrolidinyl)ethanesulfonamide and N-(4-(2,6-dimethoxyphenyl)-5-(2-furanyl)-4H-1,2,4-triazol-3-yl)-2-((3R,5R)-3,5-dimethyl-2-oxo-1-pyrrolidinyl) ethanesulfonamide and N-(4-(2,6-dimethoxyphenyl)-5-(2-furanyl)-4H-1,2,4-triazol-3-yl)-2-((3R,5S)-3,5-dimethyl-2-oxo-1-pyrrolidinyl)ethanesulfonamide, Example 175.1. Example 175.1 was prepared from Example 168.1 and alpha-methyllevulinic acid (commercially available from TCI America) according to methods analogous to those described in Example 169.0. LCMS-ESI (pos.), m/z: 490.1 (M+H)$^+$.

175.0

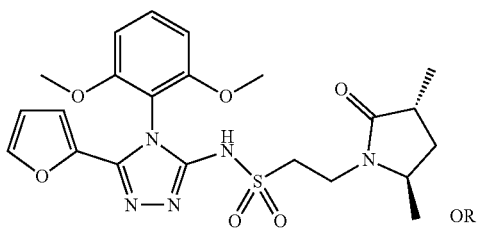

OR

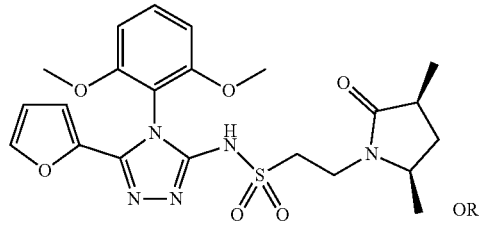

OR

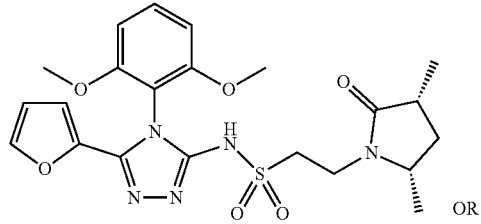

OR

-continued

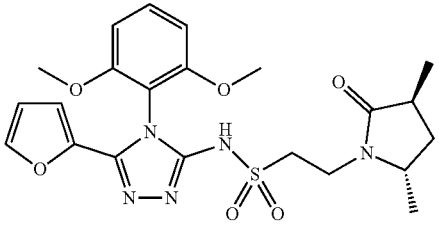

N-(4-(2,6-Dimethoxyphenyl)-5-(2-furanyl)-4H-1,2,4-triazol-3-yl)-2-((3S,5S)-3,5-dimethyl-2-oxo-1-pyrrolidinyl)ethanesulfonamide or N-(4-(2,6-dimethoxyphenyl)-5-(2-furanyl)-4H-1,2,4-triazol-3-yl)-2-((3S,5R)-3,5-dimethyl-2-oxo-1-pyrrolidinyl)ethanesulfonamide or N-(4-(2,6-dimethoxyphenyl)-5-(2-furanyl)-4H-1,2,4-triazol-3-yl)-2-((3R,5R)-3,5-dimethyl-2-oxo-1-pyrrolidinyl)ethanesulfonamide or N-(4-(2,6-dimethoxyphenyl)-5-(2-furanyl)-4H-1,2,4-triazol-3-yl)-2-((3R,5S)-3,5-dimethyl-2-oxo-1-pyrrolidinyl)ethanesulfonamide, Example 175.0. Example 175.0 was the fourth of the four diastereomers eluted from the AD column (30% MeOH/CO$_2$) with the SFC separation of Example 175.1. $^1$H NMR (500 MHz, Solvent) δ 7.54 (s, 1H) 7.51 (t, J=8.37 Hz, 1H) 6.82 (d, J=8.56 Hz, 2H) 6.39 (s, 1H) 5.99 (d, J=3.42 Hz, 1H) 3.82-3.89 (m, 2H) 3.78 (s, 3H) 3.77 (s, 3H) 3.44-3.51 (m, 1H) 3.37-3.44 (m, 1H) 2.51-2.59 (m, 1H) 2.34-2.39 (m, 1H) 1.83-1.92 (m, 1H) 1.63-1.70 (m, 1H) 1.16-1.21 (m, 3H) 1.15 (d, J=7.09 Hz, 3H). LCMS-ESI (pos.), m/z: 490.2 (M+H)$^+$.

Example 176.0. Preparation of N-(4-(2,6-dimethoxyphenyl)-5-(2-furanyl)-4H-1,2,4-triazol-3-yl)-2-((2R)-2-(methoxymethyl)-6-oxo-1-piperidinyl)ethanesulfonamide or N-(4-(2,6-dimethoxyphenyl)-5-(2-furanyl)-4H-1,2,4-triazol-3-yl)-2-((2S)-2-(methoxymethyl)-6-oxo-1-piperidinyl)ethanesulfonamide 176.1

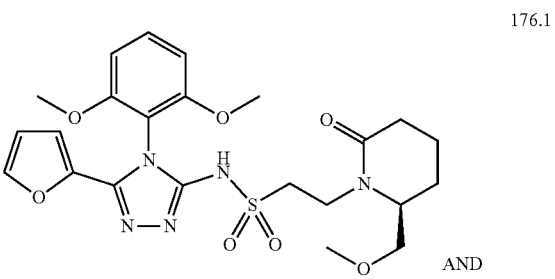

AND

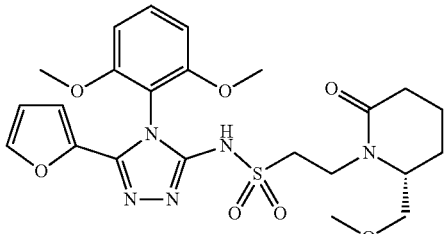

N-(4-(2,6-Dimethoxyphenyl)-5-(2-furanyl)-4H-1,2,4-triazol-3-yl)-2-((2R)-2-(methoxymethyl)-6-oxo-1-piperidinyl)ethanesulfonamide and N-(4-(2,6-dimethoxyphenyl)-5-(2-furanyl)-4H-1,2,4-triazol-3-yl)-2-((2S)-2-(methoxymethyl)-6-oxo-1-piperidinyl)ethanesulfonamide, Example 176.1.

Example 176.1 was prepared from Example 168.1 and diethyl 2-oxohexane-1,6-dicarboxylate (commercially available from Rieke Metals, Inc., NE, USA) using the procedure described in Example 169.0. $^1$H NMR (500 MHz, CD$_3$OD) δ 7.61 (d, J=1.71 Hz, 1H) 7.57 (t, J=8.56 Hz, 1H) 6.87 (dd, J=8.68, 0.86 Hz, 2H) 6.45 (dd, J=3.55, 1.83 Hz, 1H) 6.14 (d, J=3.42 Hz, 1H) 3.80-3.84 (m, 6H) 3.75-3.80 (m, 1H) 3.58-3.73 (m, 2H) 3.43-3.53 (m, 2H) 3.37-3.43 (m, 1H) 3.32 (s, 3H) 3.19 (ddd, J=13.51, 8.62, 4.52 Hz, 1H) 2.24-2.37 (m, 2H) 1.80-1.96 (m, 3H) 1.62-1.76 (m, 1H). LCMS-ESI (pos.), m/z: 520.1 (M+H)$^+$.

176.0

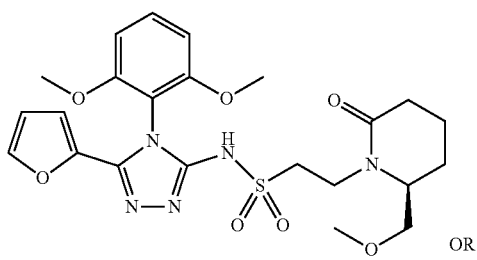

OR

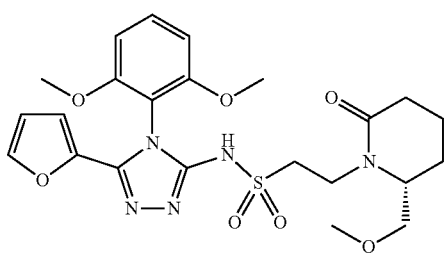

N-(4-(2,6-Dimethoxyphenyl)-5-(2-furanyl)-4H-1,2,4-triazol-3-yl)-2-((2R)-2-(methoxymethyl)-6-oxo-1-piperidinyl)ethanesulfonamide or N-(4-(2,6-dimethoxyphenyl)-5-(2-furanyl)-4H-1,2,4-triazol-3-yl)-2-((2S)-2-(methoxymethyl)-6-oxo-1-piperidinyl)ethanesulfonamide, Example 176.0. Example 176.0 was the second isomer to elute on an AD-H column subjecting Example 176.1 to the following SFC conditions: AD-H (2×15 cm), 25% MeOH (0.1% NH$_4$OH)/CO$_2$, 100 bar, 65 mL/min, 220 nm. injection volume: 0.5 mL, 7 mg/mL MeOH solution of Example 176.1. $^1$H NMR (500 MHz, CD$_3$OD) δ 7.51-7.65 (m, 2H) 6.86 (d, J=8.56 Hz, 2H) 6.44 (dd, J=3.42, 1.71 Hz, 1H) 6.13 (d, J=3.42 Hz, 1H) 3.74-3.85 (m, 7H) 3.58-3.72 (m, 2H) 3.44-3.54 (m, 2H) 3.40 (dd, J=10.03, 4.65 Hz, 1H) 3.32 (s, 3H) 3.22 (td, J=8.93, 4.16 Hz, 1H) 2.27-2.35 (m, 2H) 1.82-1.94 (m, 3H) 1.62-1.75 (m, 1H). LCMS-ESI (pos.), m/z: 520.2 (M+H)$^+$.

Example 177.0. Preparation of (1S,2R)—N-(4-(2,6-dimethoxyphenyl)-5-(5-methyl-2-furanyl)-4H-1,2,4-triazol-3-yl)-1-hydroxy-1-(5-methoxy-2-pyrazinyl)-2-propanesulfonamide or (1R,2S)—N-(4-(2,6-dimethoxyphenyl)-5-(5-methyl-2-furanyl)-4H-1,2,4-triazol-3-yl)-1-hydroxy-1-(5-methoxy-2-pyrazinyl)-2-propanesulfonamide 177.1

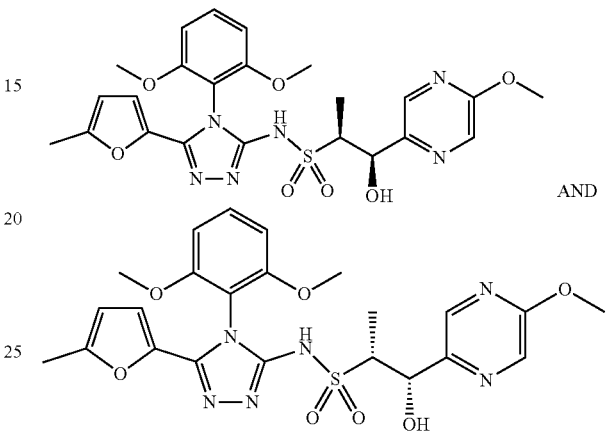

AND (1S,2R)—N-(4-(2,6-Dimethoxyphenyl)-5-(5-methyl-2-furanyl)-4H-1,2,4-triazol-3-yl)-1-hydroxy-1-(5-methoxy-2-pyrazinyl)-2-propanesulfonamide and (1R,2S)—N-(4-(2,6-dimethoxyphenyl)-5-(5-methyl-2-furanyl)-4H-1,2,4-triazol-3-yl)-1-hydroxy-1-(5-methoxy-2-pyrazinyl)-2-propanesulfonamide, Example 177.1. Example 177.1 was prepared using Example 369.0 and 5-methoxypyrazine-2-carboxaldehyde (commercially available from Frontier Scientific Services Inc.) following the general procedure described in Example 10.0. LCMS-ESI (pos.), m/z: 531.1 (M+H)$^+$.

177.0

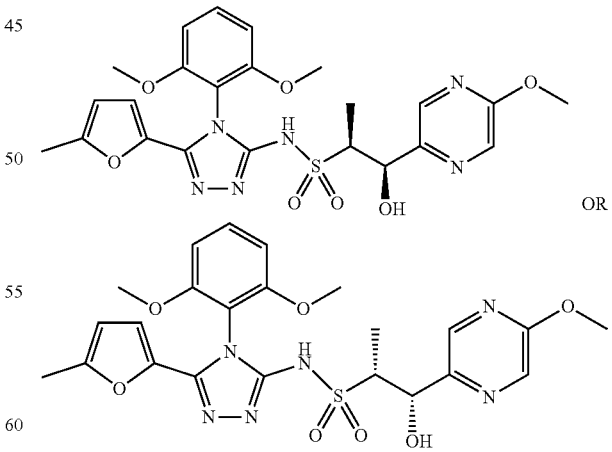

OR (1S,2R)—N-(4-(2,6-Dimethoxyphenyl)-5-(5-methyl-2-furanyl)-4H-1,2,4-triazol-3-yl)-1-hydroxy-1-(5-methoxy-2-pyrazinyl)-2-propanesulfonamide or (1R,2S)—N-(4-(2,6-dimethoxyphenyl)-5-(5-methyl-2-furanyl)-4H-1,2,4-triazol-3-yl)-1-hydroxy-1-(5-methoxy-2-pyrazinyl)-2- propanesulfonamide, Example 177.0. Example 177.0 was the first (earlier peak vs. its opposite enantiomer) peak to elute from an IA column by injecting Example 177.1 for the chiral separation under the following conditions: Run on Thar 80 SFC with 150×30 mm IA columns with 48.0 mL/min EtOH (+20 mM NH$_3$)+32.0 g/min CO$_2$, 60% co-solvent at 80.0 g/min. Temp.=29° C., Outlet pressure=100 bar, Wavelength=280 nm. Injected 0.9 mL of 122 mg sample dissolved in 12.0 mL of MeOH:DCM 7:5; c=10.2 mg/mL and 9.2 mg per injection. Cycle time 7.0 min, run time 10.0 min. $^1$H NMR (500 MHz, CDCl$_3$) δ 10.94 (s, 1H), 8.25 (t, J=1.1 Hz, 1H), 8.13 (d, J=1.2 Hz, 1H), 7.50 (t, J=8.6 Hz, 1H), 6.66-6.75 (m, 2H), 5.93 (dd, J=3.4, 1.0 Hz, 1H), 5.86 (d, J=3.4 Hz, 1H), 3.99 (s, 1H), 3.96 (s, 3H), 3.82 (s, 3H), 3.76 (s, 3H), 3.67 (qd, J=7.0, 1.2 Hz, 1H), 2.33 (s, 3H), 1.13 (d, J=7.1 Hz, 3H). LCMS-ESI (pos.), m/z: 531.1 (M+H)$^+$.

Example 178.0. Preparation of (3S,5S)—N-(4-(2,6-dimethoxyphenyl)-5-(2-furanyl)-4H-1,2,4-triazol-3-yl)-1-(5-fluoro-2-pyrimidinyl)-5-methoxy-3-piperidinesulfonamide or (3R,5R)—N-(4-(2,6-dimethoxyphenyl)-5-(2-furanyl)-4H-1,2,4-triazol-3-yl)-1-(5-fluoro-2-pyrimidinyl)-5-methoxy-3-piperidinesulfonamide or (3S,5R)—N-(4-(2,6-dimethoxyphenyl)-5-(2-furanyl)-4H-1,2,4-triazol-3-yl)-1-(5-fluoro-2-pyrimidinyl)-5-methoxy-3-piperidinesulfonamide or (3R,5S)—N-(4-(2,6-dimethoxyphenyl)-5-(2-furanyl)-4H-1,2,4-triazol-3-yl)-1-(5-fluoro-2-pyrimidinyl)-5-methoxy-3-piperidinesulfonamide

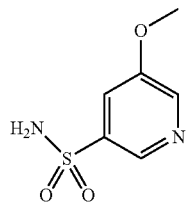

178.1

5-Methoxypyridine-3-sulfonamide, Example 178.1. To a 50 mL RBF was added 5-bromopyridine-3-sulfonamide (commercially available from Combi-Blocks Inc., CA, USA, 1.20 g, 5.06 mmol), copper(I) iodide (0.096 g, 0.51 mmol), 8-hydroxyquinoline (0.147 g, 1.01 mmol), and potassium phosphate (2.149 g, 10.12 mmol). The flask was placed under vacuum and back-filled with N$_2$ two times before MeOH (20 mL) was added. The reaction mixture was then stirred at 80° C. for 44 h. The reaction mixture was allowed to cool to RT. The reaction mixture was then diluted with water and extracted with DCM. The desired product was found to be in the aqueous phase and was concentrated in vacuo. The residual solid was then extracted with MeOH. The MeOH solution was concentrated in vacuo and the material was purified by silica gel chromatography (a gradient of 0% to 20% MeOH in DCM). This provided Example 178.1 (0.11 g, 0.584 mmol, 12% yield) as a white solid. LCMS-ESI (pos.), m/z 188.8 (M+H)$^+$.

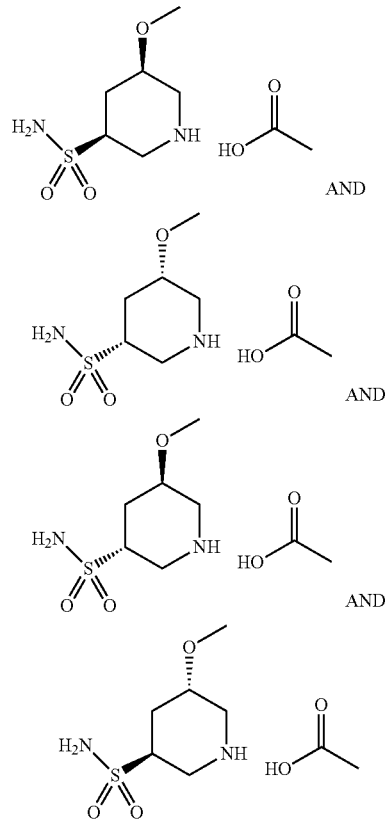

178.2

(3R,5R)-5-Methoxypiperidine-3-sulfonamide acetate and (3R,5S)-5-methoxypiperidine-3-sulfonamide acetate and (3S,5R)-5-methoxypiperidine-3-sulfonamide acetate and (3S,5S)-5-methoxypiperidine-3-sulfonamide acetate, Example 178.2. Under a N$_2$ stream and to a 250 mL RBF, was added Example 178.1 (0.18 g, 0.956 mmol) and platinum (IV) oxide (0.217 g, 0.956 mmol). The flask was placed under vacuum and back-filled with AcOH (20 mL). The flask was then placed under vacuum and back-filled with N$_2$ two times. The reaction was then placed under vacuum and back-filled with hydrogen gas. The reaction mixture was stirred at RT under hydrogen gas for 20 h. LCMS analysis indicated that the reaction was complete. Celite® brand filter aid (10 g) was added to the stirred mixture. The solid was removed by filtration after 10 min. The filter cake was rinsed with MeOH. The combined organics were then concentrated in vacuo to afford Example 178.2 as a light yellow oil which was directly used in the next step without purification. LCMS-ESI (pos.), m/z: 195.2 (M+H)$^+$.

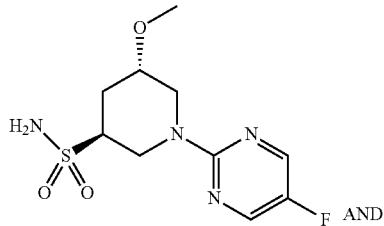

178.3

AND

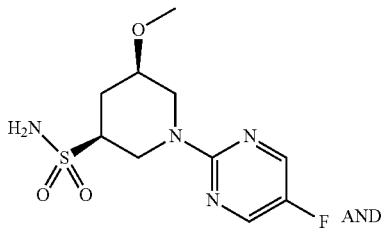
AND

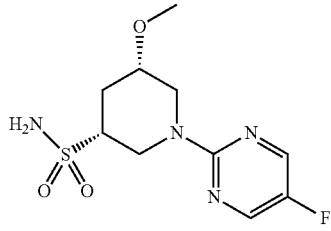

(3R,5R)-1-(5-Fluoropyrimidin-2-yl)-5-methoxypiperidine-3-sulfonamide and (3R,5S)-1-(5-fluoropyrimidin-2-yl)-5-methoxypiperidine-3-sulfonamide and (3S,5R)-1-(5-fluoropyrimidin-2-yl)-5-methoxypiperidine-3-sulfonamide and (3S,5S)-1-(5-fluoropyrimidin-2-yl)-5-methoxypiperidine-3-sulfonamide, Example 178.3. Example 178.3 was prepared from Example 178.2 using the procedure described in Example 154.0. The title compound, Example 178.3, was a mixture of cis and trans isomers. LCMS-ESI (pos.), m/z: 291.2 (M+H)⁺, 313.1 (M+Na)⁺.

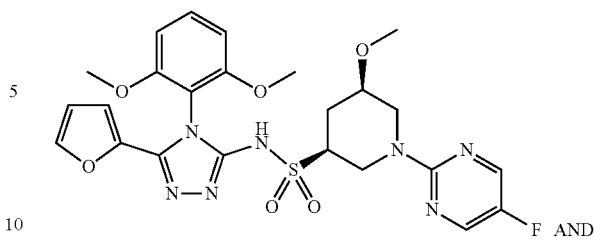
AND

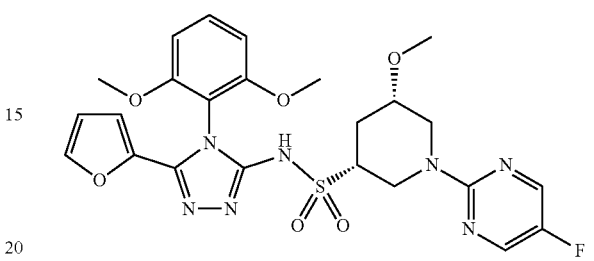

(3S,5S)—N-(4-(2,6-Dimethoxyphenyl)-5-(2-furanyl)-4H-1,2,4-triazol-3-yl)-1-(5-fluoro-2-pyrimidinyl)-5-methoxy-3-piperidinesulfonamide and (3R,5R)—N-(4-(2,6-dimethoxyphenyl)-5-(2-furanyl)-4H-1,2,4-triazol-3-yl)-1-(5-fluoro-2-pyrimidinyl)-5-methoxy-3-piperidinesulfonamide and (3S,5R)—N-(4-(2,6-dimethoxyphenyl)-5-(2-furanyl)-4H-1,2,4-triazol-3-yl)-1-(5-fluoro-2-pyrimidinyl)-5-methoxy-3-piperidinesulfonamide and (3R,5S)—N-(4-(2,6-dimethoxyphenyl)-5-(2-furanyl)-4H-1,2,4-triazol-3-yl)-1-(5-fluoro-2-pyrimidinyl)-5-methoxy-3-piperidinesulfonamide, Example 178.4. Example 178.4 was prepared from Example 364.1 and Example 178.3 using the procedure described in Example 94.0. The title compound, Example 178.4, was isolated as a white solid. LCMS-ESI (pos.), m/z: 560.2 (M+H)⁺.

178.4

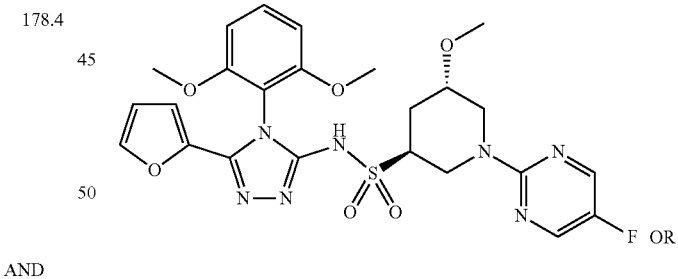

178.0

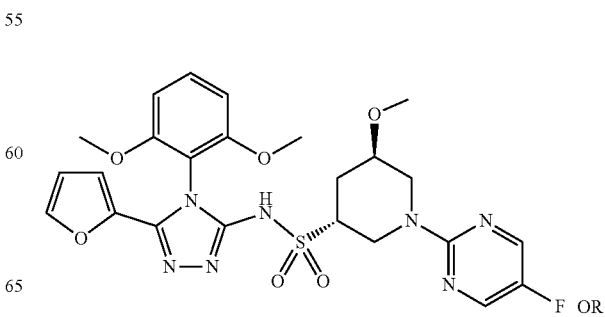

-continued

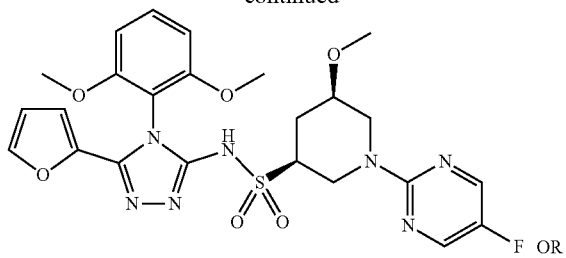

F OR

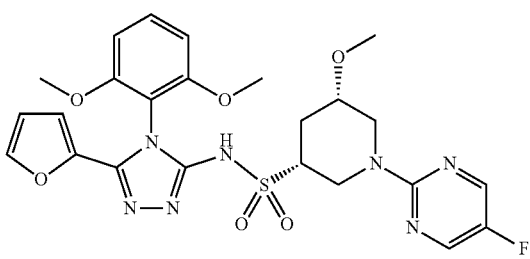

F (3S,5S)—N-(4-(2,6-Dimethoxyphenyl)-5-(2-furanyl)-4H-1,2,4-triazol-3-yl)-1-(5-fluoro-2-pyrimidinyl)-5-methoxy-3-piperidinesulfonamide or (3R,5R)—N-(4-(2,6-dimethoxyphenyl)-5-(2-furanyl)-4H-1,2,4-triazol-3-yl)-1-(5-fluoro-2-pyrimidinyl)-5-methoxy-3-piperidinesulfonamide or (3S,5R)—N-(4-(2,6-dimethoxyphenyl)-5-(2-furanyl)-4H-1,2,4-triazol-3-yl)-1-(5-fluoro-2-pyrimidinyl)-5-methoxy-3-piperidinesulfonamide or (3R,5S)—N-(4-(2,6-dimethoxyphenyl)-5-(2-furanyl)-4H-1,2,4-triazol-3-yl)-1-(5-fluoro-2-pyrimidinyl)-5-methoxy-3-piperidinesulfonamide, Example 178.0. Example 178.0 was obtained from SFC chiral separation of Example 178.4 under the following conditions: First step: Run on Thar 80 SFC with 400×30 mm OJ-H column with 12 g/min MeOH (20 mM NH$_3$)+68 g/min CO$_2$, 15% co-solvent at 80 g/min. Outlet pressure=100 bar; Temp.=21° C.; Wavelength=245 nm. Injected 0.5 mL of a solution from 30 mg sample dissolved in 5.0 mL of MeOH:DCM 4:1, c=6.0 mg/mL; 3.0 mg per injection. Second step: Thar 80 SFC with 500×30 mm AS-H column with 32 g/min MeOH (20 mM NH$_3$)+48 g/min CO$_2$, 40% co-solvent at 80 g/min. Outlet pressure=100 bar; Temp.=25° C.; Wavelength=242 nm. Manually injected 1.0 mL of a solution from 22 mg sample dissolved in 4.0 mL of MeOH/DCM 3/1, c=5.5 mg/mL; 5.5 mg per injection. Third step: Thar 80 SFC with 250×30 mm AD-H column with 32 g/min MeOH (20 mM NH$_3$)+48 g/min CO$_2$, 40% co-solvent at 80 g/min. Outlet pressure=100 bar; Temp.=RT; Wavelength=242 nm. Manually injected 2×1.0 mL of a solution from ~6 mg sample dissolved in 2.0 mL of MeOH:DCM 3:1, c=3.0 mg/mL; 3.0 mg per injection. Example 178.0 was the second among four isomers to elute from the AD column $^1$H NMR (500 MHz, CD$_3$OD) δ 8.31 (s, 2H) 7.53-7.64 (m, 2H) 6.88 (dd, J=8.56, 3.18 Hz, 2H) 6.45 (dd, J=3.55, 1.83 Hz, 1H) 6.14 (d, J=3.18 Hz, 1H) 5.02-5.13 (m, 1H) 4.94-5.01 (m, 1H) 4.61 (br. s., 1H) 3.82 (s, 3H) 3.80 (s, 3H) 3.43 (s, 3H) 3.21-3.32 (m, 2H) 3.00-3.15 (m, 1H) 2.78-2.90 (m, 1H) 2.59 (d, J=11.49 Hz, 1H) 2.48 (dd, J=12.72, 10.51 Hz, 1H) 1.51-1.64 (m, 1H). LCMS-ESI (pos.), m/z: 560.2 (M+H)$^+$.

Example 179.0. Preparation of (3R)—N-(4-(2,6-dimethoxyphenyl)-5-(5-methyl-2-furanyl)-4H-1,2,4-triazol-3-yl)-1-(5-fluoro-2-pyrimidinyl)-3-piperidinesulfonamide or (3S)—N-(4-(2,6-dimethoxyphenyl)-5-(5-methyl-2-furanyl)-4H-1,2,4-triazol-3-yl)-1-(5-fluoro-2-pyrimidinyl)-3-piperidinesulfonamide 179.1

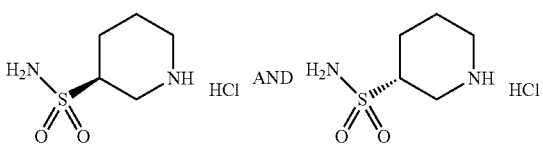

(R)-Piperidine-3-sulfonamide hydrochloride and (S)-piperidine-3-sulfonamide hydrochloride, Example 179.1. To a 100 mL RBF was added 4-chloro-3-pyridinesulfonamide (commercially available from Alfa Aesar, 0.56 g, 2.91 mmol) in AcOH (25 mL). N$_2$ was bubbled through the suspension for 5 min before platinum (IV) oxide (commercially available from Sigma-Aldrich, USA, 0.330 g, 1.45 mmol) was added under N$_2$ flow. The flask was then sealed with a septum and placed under vacuum. Hydrogen gas was back-filled from a balloon. The reaction mixture was stirred at RT under hydrogen gas for 3 days. Celite® brand filter aid (20 g) was added to the stirred mixture. The solution was then filtered through a short pad of Celite® brand filter aid. The pad was rinsed with MeOH. The combined organic layers were concentrated in vacuo to give a light-yellow glass. The residue was triturated with DCM to afford Example 179.1 (0.6 g, 2.99 mmol, 103% yield) as a light yellow solid. LCMS-ESI (pos.), m/z: 165.2 (M+H)$^+$.

179.2

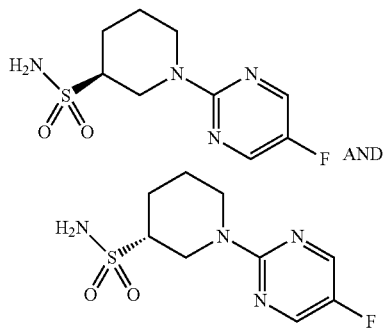

(R)-1-(5-Fluoropyrimidin-2-yl)piperidine-3-sulfonamide and (S)-1-(5-fluoropyrimidin-2-yl)piperidine-3-sulfonamide, Example 179.2. To a 50 mL vial was added Example 179.1 (200 mg, 1.0 mmol) and 2-chloro-5-fluoro-pyrimidine (Matrix Scientific, SC, USA, 0.66 mL, 4.98 mmol) in DMSO (5 mL). Hunig's base (0.87 mL, 4.98 mmol) was then added. Next, the reaction mixture was stirred at 100° C. for 2 h. LCMS analysis indicated the reaction was complete. The reaction mixture was allowed to cool to RT. The reaction mixture was then diluted with water and extracted with DCM. The combined organic layers were washed with brine and dried over Na$_2$SO$_4$. The solution was filtered and concentrated in vacuo to give a light-yellow glass which was triturated with IPA to afford Example 179.2 (240 mg, 93% yield) as an off-white solid. ¹H NMR (500 MHz, CDCl₃) δ 8.21 (s, 2H) 4.98-5.07 (m, 1H) 4.76 (s, 2H) 4.49-4.59 (m, 1H) 3.31 (dd, J=12.96, 10.27 Hz, 1H) 3.15 (tt, J=10.51, 3.91 Hz, 1H) 3.04 (ddd, J=13.69, 11.49, 2.69 Hz, 1H) 2.32-2.43 (m, 1H) 1.87-2.02 (m, 2H) 1.51-1.63 (m, 1H). LCMS-ESI (pos.), m/z: 261.2 (M+H)⁺.

179.3

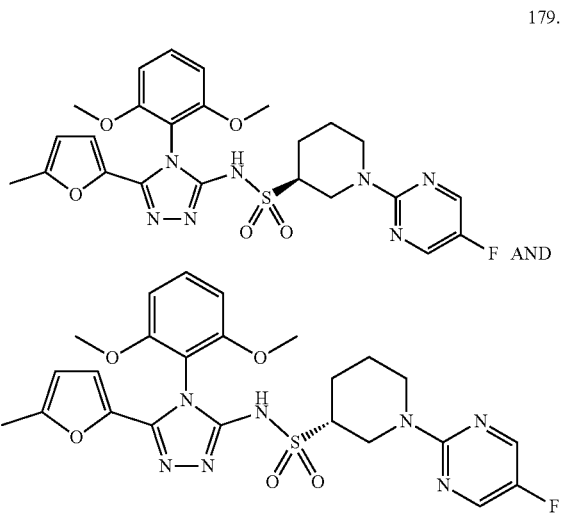

(3R)—N-(4-(2,6-Dimethoxyphenyl)-5-(5-methyl-2-furanyl)-4H-1,2,4-triazol-3-yl)-1-(5-fluoro-2-pyrimidinyl)-3-piperidinesulfonamide and (3S)—N-(4-(2,6-dimethoxyphenyl)-5-(5-methyl-2-furanyl)-4H-1,2,4-triazol-3-yl)-1-(5-fluoro-2-pyrimidinyl)-3-piperidinesulfonamide, Example 179.3. Example 179.3 was prepared from Example 364.1 and Example 179.2 using the procedure described in Example 94.0. ¹H NMR (500 MHz, CD₂Cl₂) δ 8.24 (s, 2H) 7.57 (t, J=8.56 Hz, 1H) 6.78 (d, J=8.56 Hz, 2H) 5.98 (dd, J=3.42, 0.98 Hz, 1H) 5.89 (d, J=3.42 Hz, 1H) 4.99-5.07 (m, 1H) 4.59-4.68 (m, 1H) 3.82 (s, 3H) 3.80 (s, 3H) 2.98-3.09 (m, 2H) 2.84 (td, J=12.84, 2.93 Hz, 1H) 2.33 (s, 3H) 2.27 (d, J=12.23 Hz, 1H) 1.81-1.89 (m, 1H) 1.79 (dd, J=11.37, 4.28 Hz, 1H) 1.52 (dt, J=12.78, 4.13 Hz, 1H). LCMS-ESI (pos.), m/z: 544.1 (M+H)⁺.

179.0

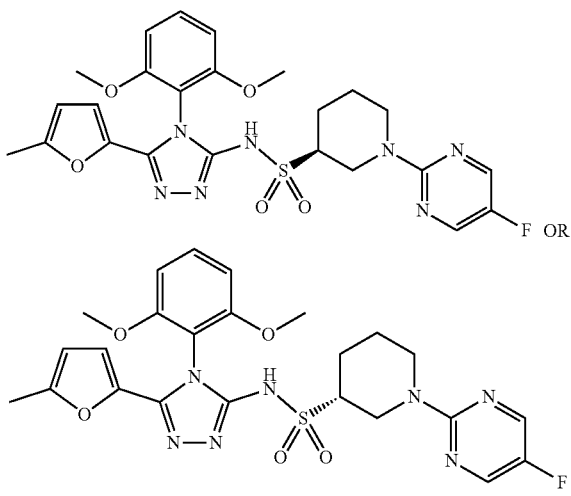

(3R)—N-(4-(2,6-Dimethoxyphenyl)-5-(5-methyl-2-furanyl)-4H-1,2,4-triazol-3-yl)-1-(5-fluoro-2-pyrimidinyl)-3-piperidinesulfonamide or (3S)—N-(4-(2,6-dimethoxyphenyl)-5-(5-methyl-2-furanyl)-4H-1,2,4-triazol-3-yl)-1-(5-fluoro-2-pyrimidinyl)-3-piperidinesulfonamide, Example 179.0. Example 179.0 was obtained from SFC chiral separation of Example 179.3. Example 179.0 was the second enantiomer to elute from an AS column under the following conditions: AS-H (2×15 cm), 30% MeOH (0.1% NH₄OH)/CO₂, 100 bar, 60 mL/min, 220 nm. Injection volume: 2.0 mL, 7 mg/mL MeOH. ¹H NMR (500 MHz, CD₂Cl₂) δ 8.24 (s, 2H) 7.57 (t, J=8.44 Hz, 1H) 6.78 (d, J=8.56 Hz, 2H) 5.98 (dd, J=3.42, 0.98 Hz, 1H) 5.89 (d, J=3.42 Hz, 1H) 5.00-5.09 (m, 1H) 4.65 (dd, J=13.45, 1.47 Hz, 1H) 3.78-3.84 (m, 6H) 2.95-3.08 (m, 2H) 2.83 (td, J=12.78, 2.81 Hz, 1H) 2.33 (s, 3H) 2.22-2.31 (m, 1H) 1.73-1.90 (m, 2H) 1.44-1.57 (m, 1H). LCMS-ESI (pos.), m/z: 544.1 (M+H)⁺.

Example 180.0. Preparation of (3R,4S)—N-(4-(2,6-dimethoxyphenyl)-5-(2-furanyl)-4H-1,2,4-triazol-3-yl)-4-(5-fluoro-2-pyrimidinyl)tetrahydro-3-furansulfonamide and (3S,4R)—N-(4-(2,6-dimethoxyphenyl)-5-(2-furanyl)-4H-1,2,4-triazol-3-yl)-4-(5-fluoro-2-pyrimidinyl)tetrahydro-3-furansulfonamide Example 180.1

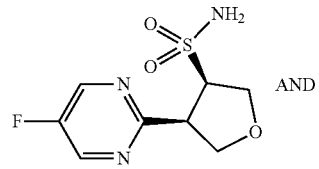

AND

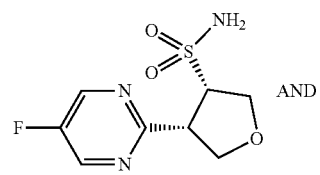

AND (3R,4R)-4-(5-Fluoropyrimidin-2-yl)tetrahydrofuran-3-sulfonamide and (3R,4S)-4-(5-fluoropyrimidin-2-yl)tetrahydrofuran-3-sulfonamide and (3S,4R)-4-(5-fluoropyrimidin-2-yl)tetrahydrofuran-3-sulfonamide and (3S,4S)-4-(5-fluoropyrimidin-2-yl)tetrahydrofuran-3-sulfonamide, Example 180.1. Example 180.1 was prepared from 2-(2,5-dihydrofuran-3-yl)-4,4,5,5-tetramethyl-1,3,2-dioxaborolane (commercially available from Frontier Scientific Services Inc.) using the procedure described in Example 184.0. LCMS-ESI (pos.), m/z: 248.1 (M+H)⁺.

Example 180.0

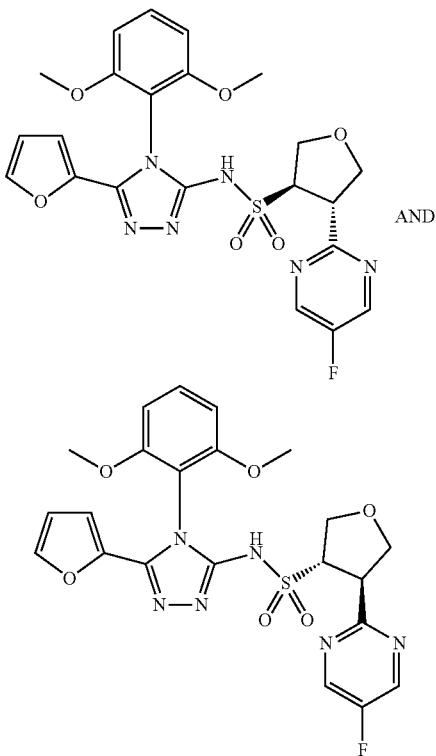

AND (3R,4S)—N-(4-(2,6-Dimethoxyphenyl)-5-(2-furanyl)-4H-1,2,4-triazol-3-yl)-4-(5-fluoro-2-pyrimidinyl)tetrahydro-3-furansulfonamide and (3S,4R)—N-(4-(2,6-dimethoxyphenyl)-5-(2-furanyl)-4H-1,2,4-triazol-3-yl)-4-(5-fluoro-2-pyrimidinyl)tetrahydro-3-furansulfonamide, Example 180.0. Example 180.0 was prepared from Example 364.3 and Example 180.1 using the procedure described in Example 94.0. The title compound was isolated as the major product. $^1$H NMR (500 MHz, CD$_2$Cl$_2$) δ 8.60 (s, 2H) 7.49-7.62 (m, 2H) 6.77 (dd, J=8.56, 2.20 Hz, 2H) 6.40 (dd, J=3.55, 1.83 Hz, 1H) 6.09 (dd, J=3.55, 0.61 Hz, 1H) 4.51 (dt, J=8.25, 5.78 Hz, 1H) 4.19-4.32 (m, 2H) 4.07-4.19 (m, 2H) 3.97 (dd, J=8.31, 5.87 Hz, 1H) 3.80 (s, 3H) 3.79 (s, 3H). LCMS-ESI (pos.), m/z: 517.1 (M+H)$^+$.

Example 181.0. Preparation of (3R)-7-chloro-N-(4-(2,6-dimethoxyphenyl)-5-(2-furanyl)-4H-1,2,4-triazol-3-yl)-3,4-dihydro-2H-pyrano[3,2-b]pyridine-3-sulfonamide and (3S)-7-chloro-N-(4-(2,6-dimethoxyphenyl)-5-(2-furanyl)-4H-1,2,4-triazol-3-yl)-3,4-dihydro-2H-pyrano[3,2-b]pyridine-3-sulfonamide 181.1

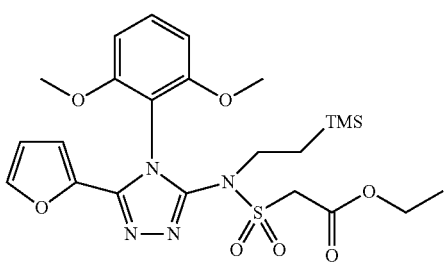

Ethyl 2-(N-(4-(2,6-Dimethoxyphenyl)-5-(furan-2-yl)-4H-1,2,4-triazol-3-yl)-N-(2-(trimethylsilyl)ethyl)sulfamoyl)acetate, Example 181.1. To a 500 mL RBF was added Example 365.2 (8.80 g, 18.94 mmol) and anhydrous diethyl carbonate (2.41 mL, 19.9 mmol) in THF (95 mL). The mixture was cooled to −78° C. and lithium bis(trimethylsilyl)amide, (1.0 M solution in THF, 18.94 mL, 18.94 mmol) was added via a syringe slowly under N$_2$. The reaction mixture was then stirred at −78 to 23° C. for 16 h (the dry ice bath gradually warmed to RT). The mixture was then cooled to −78° C. and another batch of anhydrous diethyl carbonate (1.5 mL) was added followed by lithium bis(trimethylsilyl)amide (1.0M solution in THF, 15 mL). Upon completion of addition, the dry ice bath was removed. The reaction mixture was then stirred at RT for another 2 h. The reaction mixture was diluted with a saturated solution of NH$_4$Cl and extracted with EtOAc. The combined organic layers were washed with 1 N HCl and dried over Na$_2$SO$_4$. The solution was filtered and concentrated in vacuo to give a tan oil. The material was purified by silica gel chromatography (gradient of 0% to 60% EtOAc in DCM). This provided Example 181.1 (8.2 g, 15.28 mmol, 81% yield) as a light-yellow oil. $^1$H NMR (500 MHz, CDCl$_3$) δ 7.33-7.41 (m, 2H) 6.58 (d, J=8.56 Hz, 2H) 6.21 (dd, J=3.42, 1.71 Hz, 1H) 5.83 (d, J=3.42 Hz, 1H) 4.15-4.23 (m, 2H) 4.02 (q, J=7.17 Hz, 2H) 3.71 (s, 2H) 3.64-3.70 (m, 6H) 1.20-1.29 (m, 2H) 1.08-1.15 (m, 3H) −0.03-0.02 (m, 9H). LCMS-ESI (pos.), m/z: 537.2 (M+H)$^+$.

181.2

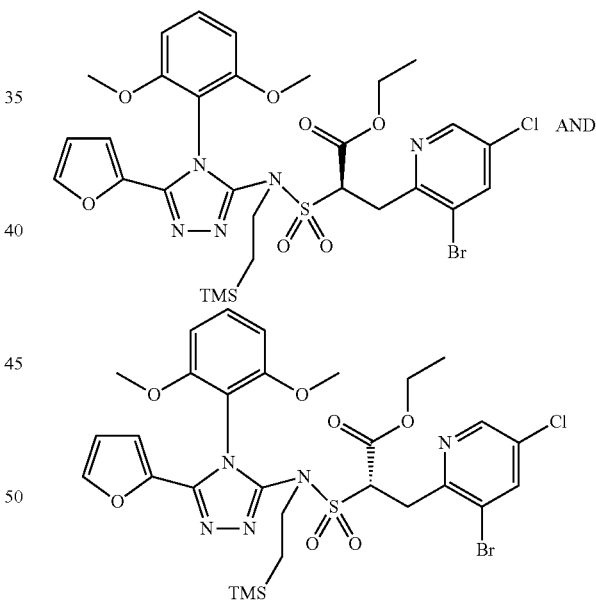

AND (R)-Ethyl 3-(3-bromo-5-chloropyridin-2-yl)-2-(N-(4-(2,6-dimethoxyphenyl)-5-(furan-2-yl)-4H-1,2,4-triazol-3-yl)-N-(2-(trimethylsilyl)ethyl)sulfamoyl)propanoate and (S)-Ethyl 3-(3-bromo-5-chloropyridin-2-yl)-2-(N-(4-(2,6-dimethoxyphenyl)-5-(furan-2-yl)-4H-1,2,4-triazol-3-yl)-N-(2-(trimethylsilyl)ethyl)sulfamoyl)propanoate, Example 181.2. To a 250 mL RBF was added Example 181.1 (3.12 g, 5.81 mmol) and 3-bromo-5-chloro-2-(chloromethyl)pyridine (Bellen Chemical Company, Inc., Beijing, China, 1.82 g, 7.56 mmol) in THF (50 mL). Potassium bis(trimethylsilyl)amide (1.0 M in THF, 7.56 mL, 7.56 mmol) was added at −78° C. The reaction mixture was stirred at −78° C. to RT for 3 h. The reaction mixture was then diluted with a saturated solution of NH₄Cl and extracted with EtOAc. The combined organic layers were washed with brine and dried over Na₂SO₄. The solution was filtered and concentrated in vacuo to give an orange oil which was absorbed onto a plug of silica gel and purified by silica gel chromatography (0% to 100% EtOAc in DCM). This provided Example 181.2 (1.61 g, 2.172 mmol, 37.4% yield) as an orange solid. LCMS-ESI (pos.), m/z: 740.0 (M+H)⁺.

181.3

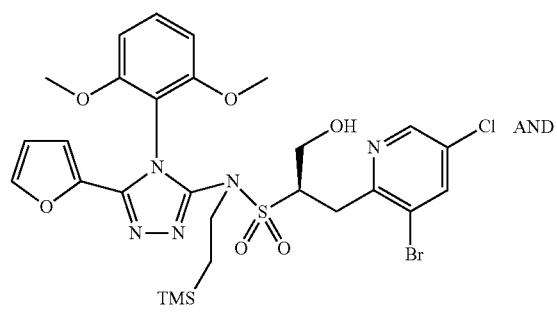

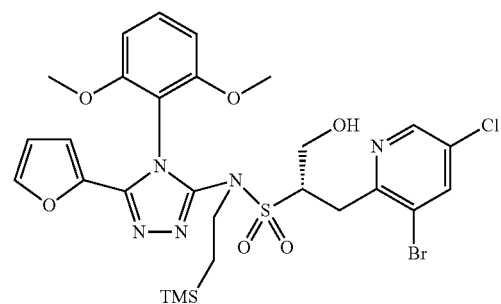

(R)-1-(3-Bromo-5-chloropyridin-2-yl)-N-(4-(2,6-dimethoxyphenyl)-5-(furan-2-yl)-4H-1,2,4-triazol-3-yl)-3-hydroxy-N-(2-(trimethylsilyl)ethyl)propane-2-sulfonamide and (S)-1-(3-bromo-5-chloropyridin-2-yl)-N-(4-(2,6-dimethoxyphenyl)-5-(furan-2-yl)-4H-1,2,4-triazol-3-yl)-3-hydroxy-N-(2-(trimethylsilyl)ethyl)propane-2-sulfonamide, Example 181.3. To a stirred 250 mL RBF was added Example 181.3 (578 mg, 0.780 mmol) in THF (15 mL). Lithium borohydride, (2.0 M solution in THF, 3.90 mL, 7.80 mmol) was added at −78° C. Upon completion of the addition, the dry-ice bath was removed. The reaction mixture was stirred at −78° C. to RT for 50 min. The reaction was quenched at −78° C. with a saturated aqueous solution of NH₄Cl. The reaction mixture was diluted with water and extracted with EtOAc. The combined organic layers were washed with brine and dried over Na₂SO₄. The solution was filtered and concentrated in vacuo to give an orange oil which was purified by silica gel chromatography (a gradient of 0% to 100% EtOAc in DCM) to provide Example 181.3 (100 mg, 0.143 mmol, 18.34% yield) as an orange glass. LCMS-ESI (pos.), m/z: 698.0 (M+H)⁺.

181.4

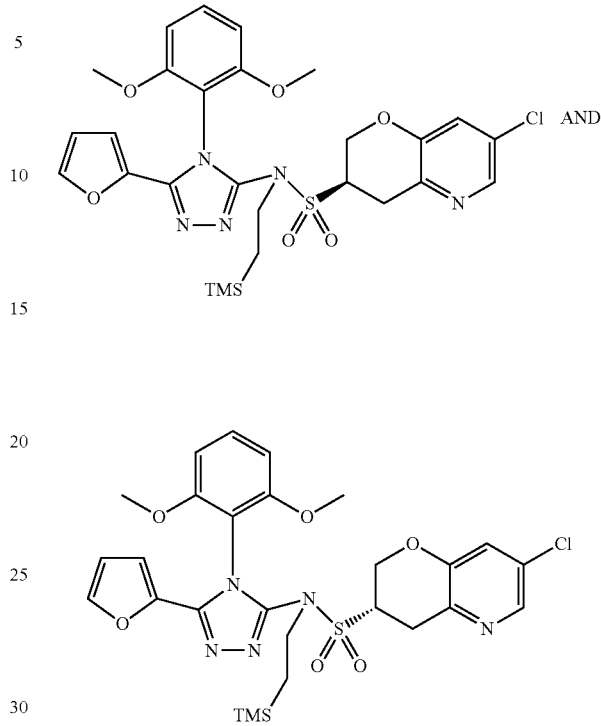

(R)-7-Chloro-N-(4-(2,6-dimethoxyphenyl)-5-(furan-2-yl)-4H-1,2,4-triazol-3-yl)-N-(2-(trimethylsilyl)ethyl)-3,4-dihydro-2H-pyrano[3,2-b]pyridine-3-sulfonamide and (S)-7-chloro-N-(4-(2,6-dimethoxyphenyl)-5-(furan-2-yl)-4H-1,2,4-triazol-3-yl)-N-(2-(trimethylsilyl)ethyl)-3,4-dihydro-2H-pyrano[3,2-b]pyridine-3-sulfonamide, Example 181.4. To a 25 mL RBF was added Example 181.3 (100 mg, 0.143 mmol), 5-[di(1-adamantyl)phosphino]-1',3',5'-triphenyl-1'H-[1,4]'bipyrazole (Sigma-Aldrich Chemical Company, Inc, 9.48 mg, 0.014 mmol), cesium carbonate (69.9 mg, 0.22 mmol), and palladium acetate (1.6 mg, 7.15 μmol). The flask was sealed, and placed under vacuum and back-filled with argon three times, before toluene (3 mL) was added via syringe. The reaction mixture was then stirred at 80° C. for 18 h. The reaction mixture was then cooled to RT. The reaction material was purified by silica gel chromatography (gradient of 0% to 100% EtOAc in DCM) to provide Example 181.4 (60 mg, 0.097 mmol, 68% yield) as an orange film. LCMS-ESI (pos.), m/z: 618.2 (M+H)⁺.

181.0

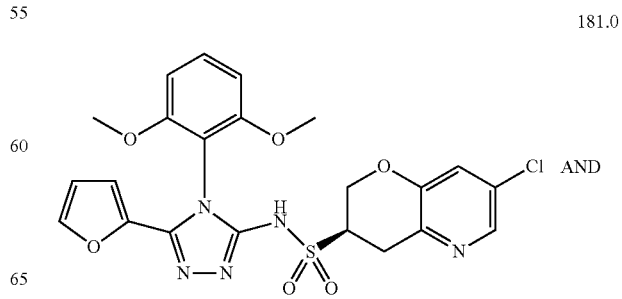

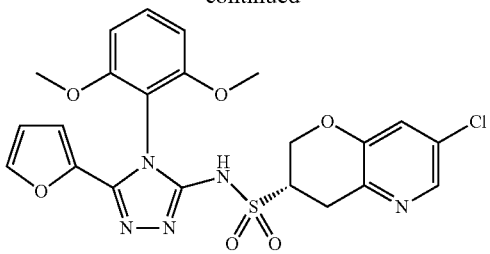

(3R)-7-Chloro-N-(4-(2,6-dimethoxyphenyl)-5-(2-furanyl)-4H-1,2,4-triazol-3-yl)-3,4-dihydro-2H-pyrano[3,2-b]pyridine-3-sulfonamide and (3S)-7-chloro-N-(4-(2,6-dimethoxyphenyl)-5-(2-furanyl)-4H-1,2,4-triazol-3-yl)-3,4-dihydro-2H-pyrano[3,2-b]pyridine-3-sulfonamide, Example 181.0. To a stirred 25 mL RBF was added Example 181.4 (60 mg, 0.097 mmol) and tris(dimethylamino)sulfonium difluorotrimethylsilicate (80 mg, 0.291 mmol). The flask was sealed, and placed under vacuum and back-filled with argon three times, before DMF (3 mL) was added via syringe. The reaction mixture was then stirred at 80° C. for 1.5 h. The reaction mixture was then cooled to RT. The reaction mixture was diluted with water and extracted with DCM. The combined organic layers were washed with brine and dried over $Na_2SO_4$. The solution was filtered and concentrated in vacuo to give an orange oil which was purified by reverse-phase preparative HPLC (0.1% TFA in ACN/$H_2O$, gradient 20% to 80%) to provide Example 181.0 (13 mg, 0.025 mmol, 25.9% yield) as a white solid. $^1$H NMR (500 MHz, $CDCl_3$) δ 8.10 (d, J=1.96 Hz, 1H) 7.31-7.40 (m, 2H) 7.19 (d, J=2.20 Hz, 1H) 6.56 (dd, J=8.56, 3.18 Hz, 2H) 6.23 (dd, J=3.67, 1.71 Hz, 1H) 5.86-5.97 (m, 1H) 4.52 (dt, J=11.25, 1.71 Hz, 1H) 4.07 (dd, J=11.13, 9.41 Hz, 1H) 3.57 (s, 3H) 3.61 (s, 3H) 3.52 (tdd, J=9.45, 5.93, 3.55 Hz, 1H) 3.17-3.32 (m, 2H). LCMS-ESI (pos.), m/z: 518.2 (M+H)$^+$.

Example 182.0. Preparation of (2S,3R)-3-(5-fluoro-2-pyrimidinyl)-N-(5-(5-methyl-2-furanyl)-4-(tetrahydro-2H-pyran-4-yl)-4H-1,2,4-triazol-3-yl)-2-butanesulfonamide 182.0

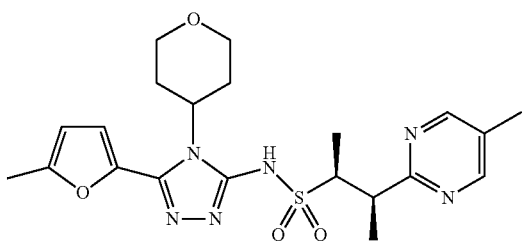

(2S,3R)-3-(5-Fluoro-2-pyrimidinyl)-N-(5-(5-methyl-2-furanyl)-4-(tetrahydro-2H-pyran-4-yl)-4H-1,2,4-triazol-3-yl)-2-butanesulfonamide, Example 182.0. Example 182.0 was prepared from Example 371.0, 4-isothiocyanatotetrahydro-2H-pyran (Enamine net) and 5-methyl-2-furohydrazide (ChemBridge Corporation) using the procedure described in Example 229.0. $^1$H NMR (500 MHz, $CDCl_3$) δ 1.45 (dd, J=6.72, 4.77 Hz, 6H) 1.66-1.76 (m, 2H) 2.42 (s, 3H) 2.51-2.67 (m, 2H) 3.36-3.47 (m, 2H) 3.80-3.92 (m, 2H) 4.08 (dd, J=11.74, 4.16 Hz, 2H) 4.56 (tt, J=12.23, 4.16 Hz, 1H) 6.16-6.23 (m, 1H) 6.83 (d, J=3.42 Hz, 1H) 8.54 (s, 2H). LCMS-ESI (pos.), m/z: 465.1 (M+H)$^+$.

Example 183.0. Preparation of (3R,4S)—N-(4-(2,6-dimethoxyphenyl)-5-(2-furanyl)-4H-1,2,4-triazol-3-yl)-4-(5-fluoro-2-pyrimidinyl)tetrahydro-3-furansulfonamide or (3S,4R)—N-(4-(2,6-dimethoxyphenyl)-5-(2-furanyl)-4H-1,2,4-triazol-3-yl)-4-(5-fluoro-2-pyrimidinyl)tetrahydro-3-furansulfonamide 183.0

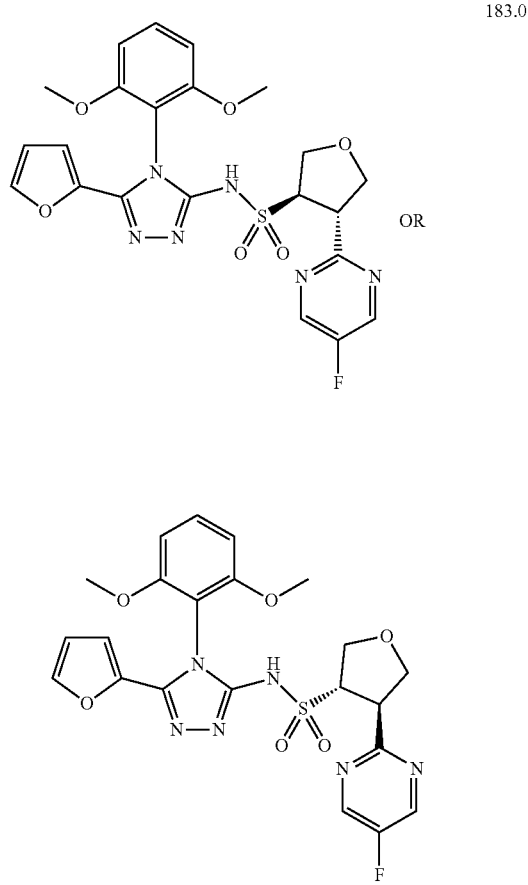

(3R,4S)—N-(4-(2,6-Dimethoxyphenyl)-5-(2-furanyl)-4H-1,2,4-triazol-3-yl)-4-(5-fluoro-2-pyrimidinyl)tetrahydro-3-furansulfonamide or (3S,4R)—N-(4-(2,6-dimethoxyphenyl)-5-(2-furanyl)-4H-1,2,4-triazol-3-yl)-4-(5-fluoro-2-pyrimidinyl)tetrahydro-3-furansulfonamide, Example 183.0. Example 183.0 was obtained from SFC chiral separation of Example 180.0 under the following conditions: 250 mm×30 mm AS column with 28 g/min MeOH+(20 mM Ammonia)+52 g/min $CO_2$ on Thar 80 SFC. Outlet pressure=100 bar; Temp.=RT; Wavelength=265 nm. Used 1.5 mL injections of 27 mg/5 mL (5.4 mg/mL) sample solution in MeOH i.e. 8.1 mg/injection. Run time=8 min, cycle time 5.5 min. Example 183.0 was the first isomer to elute from the AS column. $^1$H NMR (500 MHz, $CDCl_3$) δ 8.56 (s, 2H) 7.44-7.53 (m, 2H) 6.65-6.74 (m, 2H) 6.36 (dd, J=3.42, 1.71 Hz, 1H) 6.03 (d, J=3.67 Hz, 1H) 4.53-4.62 (m, 1H) 4.22-4.33 (m, 2H) 4.14-4.22 (m, 2H) 4.02 (dd, J=8.07, 5.14 Hz, 1H) 3.78 (s, 3H) 3.77 (s, 3H). LCMS-ESI (pos.), m/z: 517.1 (M+H)$^+$.

Example 184.0. Preparation of (3R,4R)—N-(4-(2,6-dimethoxyphenyl)-5-(2-furanyl)-4H-1,2,4-triazol-3-yl)-4-(5-fluoro-2-pyrimidinyl)tetrahydro-2H-pyran-3-sulfonamide and (3S,4S)—N-(4-(2,6-dimethoxyphenyl)-5-(2-furanyl)-4H-1,2,4-triazol-3-yl)-4-(5-fluoro-2-pyrimidinyl)tetrahydro-2H-pyran-3-sulfonamide or (3R,4S)—N-(4-(2,6-dimethoxyphenyl)-5-(2-furanyl)-4H-1,2,4-triazol-3-yl)-4-(5-fluoro-2-pyrimidinyl)tetrahydro-2H-pyran-3-sulfonamide and (3S,4R)—N-(4-(2,6-dimethoxyphenyl)-5-(2-furanyl)-4H-1,2,4-triazol-3-yl)-4-(5-fluoro-2-pyrimidinyl)tetrahydro-2H-pyran-3-sulfonamide

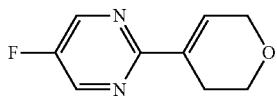

184.1

2-(3,6-Dihydro-2H-pyran-4-yl)-5-fluoropyrimidine, Example 184.1. To a 500 mL RBF was added 3,6-dihydro-2h-pyran-4-boronic acid pinacol ester (commercially available from Sigma-Aldrich, Mo., USA, 2.5 g, 11.90 mmol) and 2-chloro-5-fluoro-pyrimidine (commercially available from Matrix Scientific, S.C., USA, 1.74 mL, 13.09 mmol) in 1,4-dioxane (54 mL), and water (5.4 mL). Under $N_2$ flow, 2-dicyclohexylphosphino-2',6'-dimethoxy-1'1'-biphenyl (0.489 g, 1.19 mmol), potassium phosphate (5.05 g, 23.80 mmol), and palladium (II) acetate (0.134 g, 0.595 mmol) were added to the reaction mixture. The reaction mixture was then stirred at 70° C. in a pre-heated oil bath for 21 h. The reaction mixture was then allowed to cool to RT. The reaction mixture was diluted with water and extracted with $Et_2O$ and then DCM. The combined organic layers were washed with brine and dried over $Na_2SO_4$. The solution was filtered and concentrated in vacuo to give a light-yellow oil. The initial material was purified by silica gel chromatography (0% to 100% EtOAc in hexanes) to provide Example 184.1 (2.2 g, 100% yield) as a colorless oil. LCMS-ESI (pos.), m/z: 181.1 (M+H)$^+$.

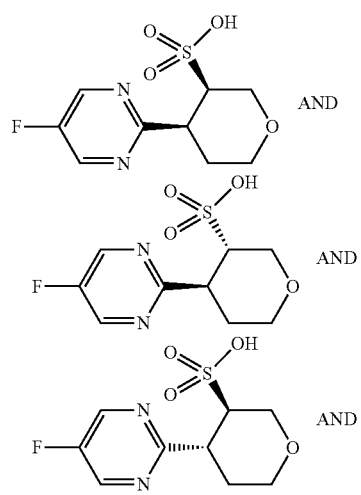

184.2

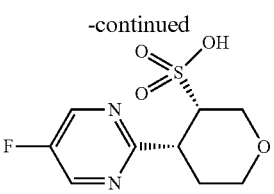

(3R,4R)-4-(5-Fluoropyrimidin-2-yl)tetrahydro-2H-pyran-3-sulfonic acid and (3R,4S)-4-(5-fluoropyrimidin-2-yl)tetrahydro-2H-pyran-3-sulfonic acid and (3S,4R)-4-(5-fluoropyrimidin-2-yl)tetrahydro-2H-pyran-3-sulfonic acid and (3S,4S)-4-(5-fluoropyrimidin-2-yl)tetrahydro-2H-pyran-3-sulfonic acid, Example 184.2. To a 250 mL RBF was added Example 184.1 (2.2 g, 12.3 mmol) and sodium bisulfite (2.58 g, 24.75 mmol) in 1,4-dioxane (40 mL) and water (20 mL). The reaction mixture was stirred at 100° C. for 6 days. The reaction mixture was then allowed to cool to RT. The reaction mixture was diluted with 1 N HCl and extracted with DCM. It was found that most of the desired product was in the aqueous phase which was then concentrated in vacuo. The residual solid was extracted with MeOH. The MeOH solution was concentrated in vacuo to afford Example 184.2 as an off-white solid. LCMS-ESI (pos.), m/z: 263.1 (M+H)$^+$.

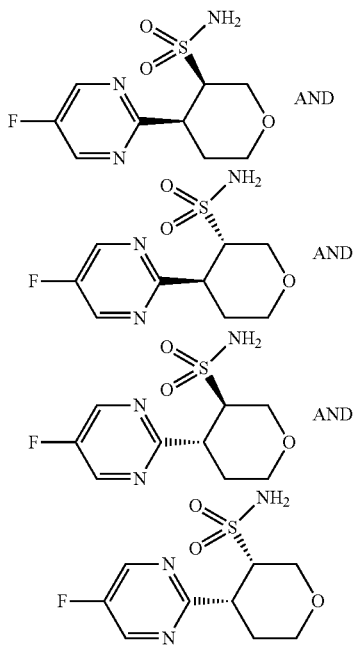

184.3

(3R,4R)-4-(5-Fluoropyrimidin-2-yl)tetrahydro-2H-pyran-3-sulfonamide and (3R,4S)-4-(5-fluoropyrimidin-2-yl)tetrahydro-2H-pyran-3-sulfonamide and (3S,4R)-4-(5-fluoropyrimidin-2-yl)tetrahydro-2H-pyran-3-sulfonamide and (3S,4S)-4-(5-fluoropyrimidin-2-yl)tetrahydro-2H-pyran-3-sulfonamide, Example 184.3. To a stirred 250 mL RBF was added Example 184.2 (0.333 g, 1.27 mmol) in DCM (10 mL). Under $N_2$ and at 0° C., oxalyl chloride (0.676 mL, 7.62 mmol) was slowly added to the suspension. DMF (0.05 mL) in DCM (1.0 mL) was added dropwise. The reaction mixture was then stirred at RT for 3 h. The mixture turned cloudy. The solution was concentrated in vacuo to give a light-yellow glass. Toluene (10 mL) was added to the residue, and the mixture was concentrated in vacuo to give a light-yellow glass. DCM (20 mL) was added to the above residue, and ammonia gas was bubbled into the mixture for 5 min at RT. The reaction mixture was then stirred at RT for 19 h. The reaction mixture was diluted with water and extracted with DCM. The desired product was found to be enriched in the aqueous phase which was dried in vacuo to afford Example 184.3 (0.21 g, 0.804 mmol, 63% yield) as an off-white solid. LCMS-ESI (pos.), m/z: 284.1 (M+Na)$^+$.

184.0

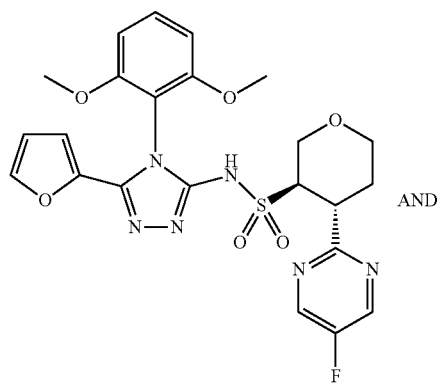

AND

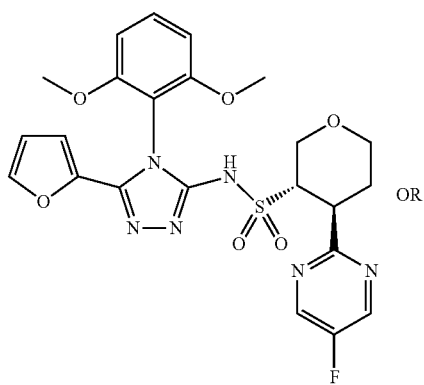

OR

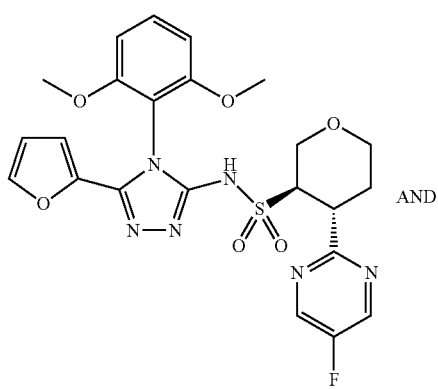

AND

-continued

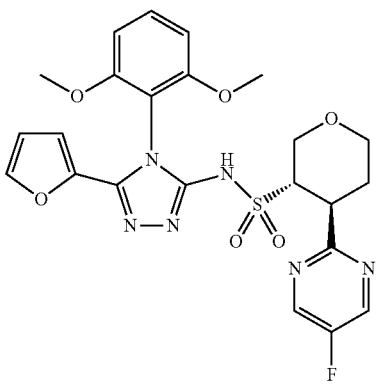

(3R,4R)—N-(4-(2,6-Dimethoxyphenyl)-5-(2-furanyl)-4H-1,2,4-triazol-3-yl)-4-(5-fluoro-2-pyrimidinyl)tetrahydro-2H-pyran-3-sulfonamide and (3S,4S)—N-(4-(2,6-dimethoxyphenyl)-5-(2-furanyl)-4H-1,2,4-triazol-3-yl)-4-(5-fluoro-2-pyrimidinyl)tetrahydro-2H-pyran-3-sulfonamide or (3R,4S)—N-(4-(2,6-dimethoxyphenyl)-5-(2-furanyl)-4H-1,2,4-triazol-3-yl)-4-(5-fluoro-2-pyrimidinyl)tetrahydro-2H-pyran-3-sulfonamide and (3S,4R)—N-(4-(2,6-dimethoxyphenyl)-5-(2-furanyl)-4H-1,2,4-triazol-3-yl)-4-(5-fluoro-2-pyrimidinyl)tetrahydro-2H-pyran-3-sulfonamide, Example 184.0. Example 184.0 was prepared from Example 364.3 and Example 184.3 using the procedure described in Example 94.0. $^1$H NMR (500 MHz, CDCl$_3$) δ 8.59 (s, 2H) 7.47-7.54 (m, 2H) 6.66-6.76 (m, 2H) 6.36 (dd, J=3.67, 1.71 Hz, 1H) 6.02 (d, J=3.42 Hz, 1H) 4.40 (dd, J=11.49, 4.40 Hz, 1H) 4.03 (dd, J=11.37, 3.30 Hz, 1H) 3.95 (td, J=11.00, 4.40 Hz, 1H) 3.82 (s, 3H) 3.78 (s, 3H) 3.58-3.71 (m, 2H) 3.48 (td, J=11.92, 2.32 Hz, 1H) 1.99-2.11 (m, 1H) 1.90-1.99 (m, 1H). LCMS-ESI (pos.), m/z: 53L1 (M+H)$^+$.

Example 185.0. Preparation of (2R)—N-(4-(2,6-dimethoxyphenyl)-5-(5-methyl-2-furanyl)-4H-1,2,4-triazol-3-yl)-1-((2R)-2-(methoxymethyl)-6-oxo-1-piperidinyl)-2-propanesulfonamide or (2R)—N-(4-(2,6-dimethoxyphenyl)-5-(5-methyl-2-furanyl)-4H-1,2,4-triazol-3-yl)-1-((2S)-2-(methoxymethyl)-6-oxo-1-piperidinyl)-2-propanesulfonamide or (2S)—N-(4-(2,6-dimethoxyphenyl)-5-(5-methyl-2-furanyl)-4H-1,2,4-triazol-3-yl)-1-((2R)-2-(methoxymethyl)-6-oxo-1-piperidinyl)-2-propanesulfonamide or (2S)—N-(4-(2,6-dimethoxyphenyl)-5-(5-methyl-2-furanyl)-4H-1,2,4-triazol-3-yl)-1-((2S)-2-(methoxymethyl)-6-oxo-1-piperidinyl)-2-propanesulfonamide 185.1

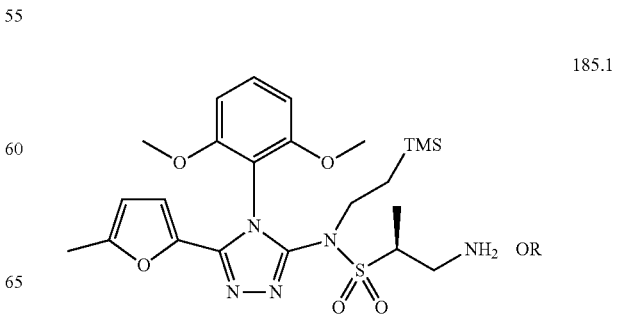

OR

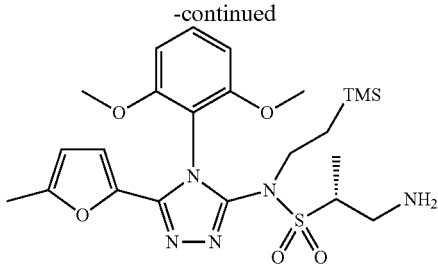

(R)-1-Amino-N-(4-(2,6-dimethoxyphenyl)-5-(5-methyl-furan-2-yl)-4H-1,2,4-triazol-3-yl)-N-(2-(trimethylsilyl)ethyl)propane-2-sulfonamide or (S)-1-amino-N-(4-(2,6-dimethoxyphenyl)-5-(5-methylfuran-2-yl)-4H-1,2,4-triazol-3-yl)-N-(2-(trimethylsilyl)ethyl)propane-2-sulfonamide, Example 185.1. Example 185.1 is the enantiomer of Example 151.6 and was the first peak to elute (earlier peak vs. its enantiomer) on the IC column (45% IPA). It was obtained by SFC separation of Example 151.5 under the conditions described in Example 151.6. LCMS-ESI (pos.), m/z: 522.1 (M+H)$^+$.

(2R)—N-(4-(2,6-Dimethoxyphenyl)-5-(5-methyl-2-furanyl)-4H-1,2,4-triazol-3-yl)-1-((2R)-2-(methoxymethyl)-6-oxo-1-piperidinyl)-2-propanesulfonamide and (2R)—N-(4-(2,6-dimethoxyphenyl)-5-(5-methyl-2-furanyl)-4H-1,2,4-triazol-3-yl)-1-((2S)-2-(methoxymethyl)-6-oxo-1-piperidinyl)-2-propanesulfonamide or a mixture of (2S)—N-(4-(2,6-dimethoxyphenyl)-5-(5-methyl-2-furanyl)-4H-1,2,4-triazol-3-yl)-1-((2R)-2-(methoxymethyl)-6-oxo-1-piperidinyl)-2-propanesulfonamide and (2S)—N-(4-(2,6-dimethoxyphenyl)-5-(5-methyl-2-furanyl)-4H-1,2,4-triazol-3-yl)-1-((2S)-2-(methoxymethyl)-6-oxo-1-piperidinyl)-2-propanesulfonamide, Example 185.2. Example 185.2 was prepared from Example 185.1 following the procedures described in Example 151.0. LCMS-ESI (pos.), m/z: 548.3 (M+H)$^+$.

185.2

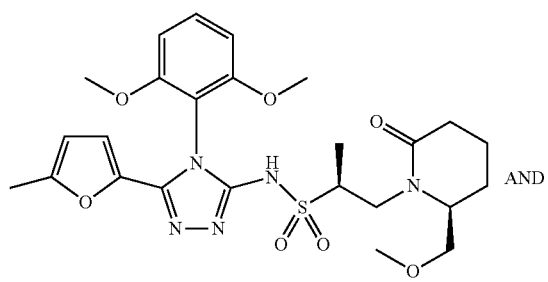 AND

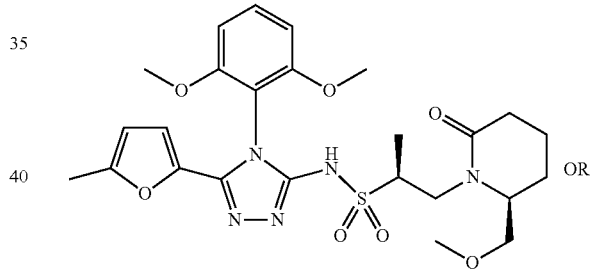 OR

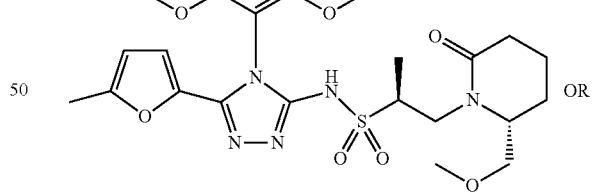 AND 185.0

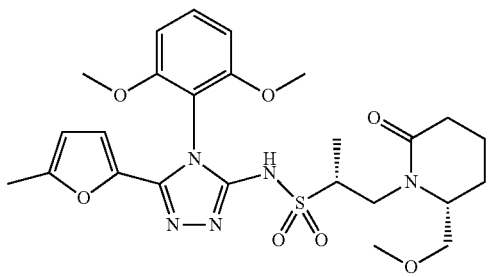

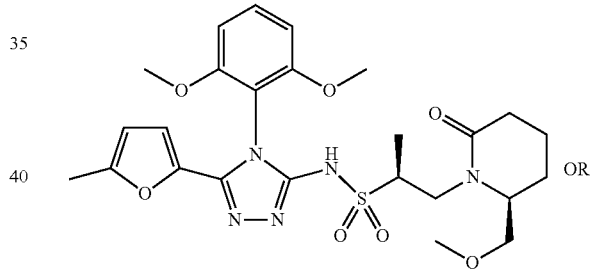 OR

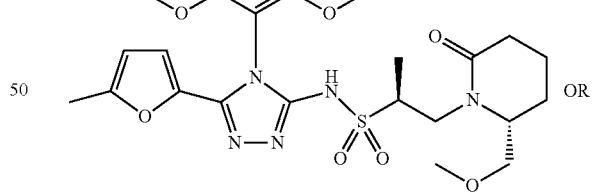 OR

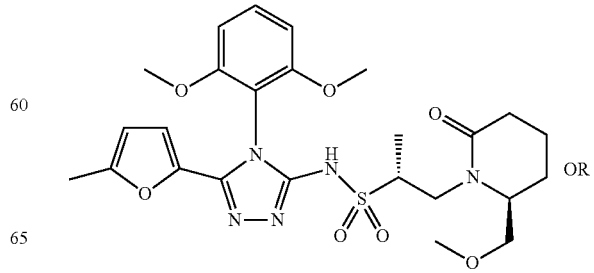 OR

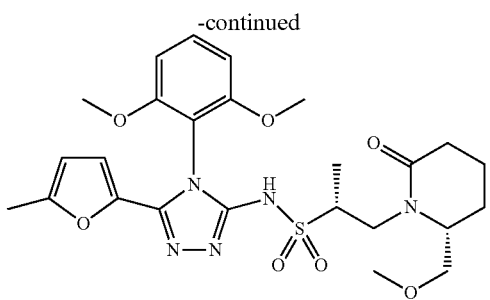

(2R)—N-(4-(2,6-Dimethoxyphenyl)-5-(5-methyl-2-furanyl)-4H-1,2,4-triazol-3-yl)-1-((2R)-2-(methoxymethyl)-6-oxo-1-piperidinyl)-2-propanesulfonamide or (2R)—N-(4-(2,6-dimethoxyphenyl)-5-(5-methyl-2-furanyl)-4H-1,2,4-triazol-3-yl)-1-(2S)-2-(methoxymethyl)-6-oxo-1-piperidinyl)-2-propanesulfonamide or (2S)—N-(4-(2,6-dimethoxyphenyl)-5-(5-methyl-2-furanyl)-4H-1,2,4-triazol-3-yl)-1-((2R)-2-(methoxymethyl)-6-oxo-1-piperidinyl)-2-propanesulfonamide or (2S)—N-(4-(2,6-dimethoxyphenyl)-5-(5-methyl-2-furanyl)-4H-1,2,4-triazol-3-yl)-1-((2S)-2-(methoxymethyl)-6-oxo-1-piperidinyl)-2-propanesulfonamide, Example 185.0. Example 185.0 was the second peak to elute (later peak vs. its C-2 MeOCH$_2$ epimer) on a Regis Whelk-O column (45% IPA). It was obtained by SFC separation of Example 185.2 on the Regis Whelk-O column. $^1$H NMR (400 MHz, CD$_3$OD) δ 7.56 (t, J=8.60 Hz, 1H) 6.83-6.90 (m, 2H) 6.03 (dd, J=3.52, 1.04 Hz, 1H) 5.94 (d, J=3.52 Hz, 1H) 4.17 (dd, J=13.68, 4.77 Hz, 1H) 4.02 (d, J=5.80 Hz, 4H) 3.79 (s, 3H) 3.79 (s, 3H) 3.54-3.66 (m, 2H) 3.46-3.53 (m, 1H) 3.38-3.43 (m, 1H) 3.12-3.29 (m, 1H) 2.30-2.38 (m, 2H) 2.24-2.29 (m, 3H) 1.83-1.98 (m, 3H) 1.67-1.77 (m, 1H) 1.29-1.36 (m, 3H) 1.27 (d, J=7.05 Hz, 3H). LCMS-ESI (pos.), m/z: 548.0 (M+H)$^+$.

Example 186.0. Preparation of (2S,3R,P)—N-(4-(4-methoxy-2-oxo-1,2-dihydro-3-pyridinyl)-5-(5-methyl-2-furanyl)-4H-1,2,4-triazol-3-yl)-3-(5-methyl-2-pyrimidinyl)-2-butanesulfonamide or (2S,3R,M)-N-(4-(4-methoxy-2-oxo-1,2-dihydro-3-pyridinyl)-5-(5-methyl-2-furanyl)-4H-1,2,4-triazol-3-yl)-3-(5-methyl-2-pyrimidinyl)-2-butanesulfonamide 186.0

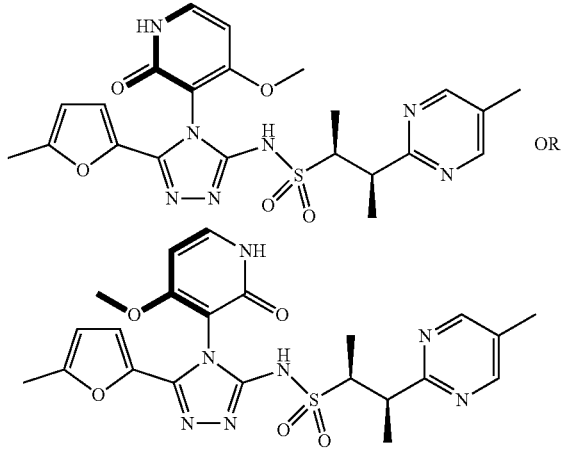

(2S,3R,P)—N-(4-(4-Methoxy-2-oxo-1,2-dihydro-3-pyridinyl)-5-(5-methyl-2-furanyl)-4H-1,2,4-triazol-3-yl)-3-(5-methyl-2-pyrimidinyl)-2-butanesulfonamide or (2S,3R,M)-N-(4-(4-methoxy-2-oxo-1,2-dihydro-3-pyridinyl)-5-(5-methyl-2-furanyl)-4H-1,2,4-triazol-3-yl)-3-(5-methyl-2-pyrimidinyl)-2-butanesulfonamide, Example 186.0. Example 186.0 was the first peak to elute (earlier peak vs. its opposite atropisomers, Example 166.0) on a CC4 column by SFC chiral separation of Example 166.1 under the conditions described in Example 166.0. $^1$H NMR (500 MHz, CD$_3$OD) δ 8.58 (d, J=0.73 Hz, 2H) 7.73 (d, J=7.58 Hz, 1H) 6.56 (d, J=7.58 Hz, 1H) 6.52 (d, J=3.42 Hz, 1H) 6.12-6.17 (m, 1H) 3.92 (s, 3H) 3.73-3.83 (m, 2H) 2.32 (s, 3H) 2.29 (s, 3H) 1.39 (d, J=6.85 Hz, 3H) 1.34 (d, J=6.85 Hz, 3H). LCMS-ESI (pos.), m/z: 500.1 (M+H)$^+$.

Example 187.0. Preparation of (2S,3R,P)-3-(5-fluoro-2-pyrimidinyl)-N-(4-(4-methoxy-2-oxo-1,2-dihydro-3-pyridinyl)-5-(5-methyl-2-furanyl)-4H-1,2,4-triazol-3-yl)-2-butanesulfonamide or (2S,3R,M)-3-(5-fluoro-2-pyrimidinyl)-N-(4-(4-methoxy-2-oxo-1,2-dihydro-3-pyridinyl)-5-(5-methyl-2-furanyl)-4H-1,2,4-triazol-3-yl)-2-butanesulfonamide 187.0

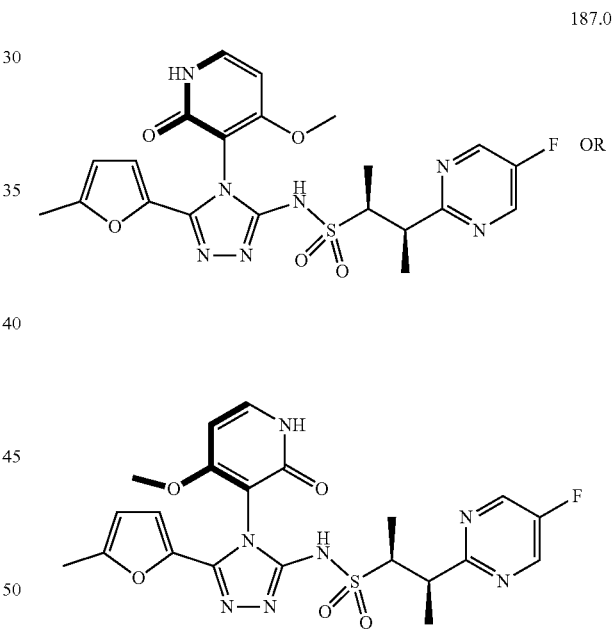

(2S,3R,P)-3-(5-Fluoro-2-pyrimidinyl)-N-(4-(4-methoxy-2-oxo-1,2-dihydro-3-pyridinyl)-5-(5-methyl-2-furanyl)-4H-1,2,4-triazol-3-yl)-2-butanesulfonamide or (2S,3R,M)-3-(5-fluoro-2-pyrimidinyl)-N-(4-(4-methoxy-2-oxo-1,2-dihydro-3-pyridinyl)-5-(5-methyl-2-furanyl)-4H-1,2,4-triazol-3-yl)-2-butanesulfonamide, Example 187.0. Example 187.0 was the first peak to elute (earlier peak vs. its opposite atropisomers) on a Lux column by SFC chiral separation of Example 161.1 under conditions described in Example 161.0. $^1$H NMR (500 MHz, CD$_3$OD) δ 8.66 (s, 2H) 7.71 (d, J=7.34 Hz, 1H) 6.56 (d, J=7.58 Hz, 1H) 6.49 (d, J=3.42 Hz, 1H) 6.13 (dd, J=3.42, 0.98 Hz, 1H) 3.92 (s, 3H) 3.79-3.90 (m, 2H) 2.29 (s, 3H) 1.40 (d, J=6.85 Hz, 3H) 1.35 (d, J=6.85 Hz, 3H). LCMS-ESI (pos.), m/z: 504.1 (M+H)$^+$.

Example 188.0. Preparation of (3R,5S)—N-(4-(2,6-dimethoxyphenyl)-5-(2-furanyl)-4H-1,2,4-triazol-3-yl)-5-(4-fluorophenyl)-3-piperidinesulfonamide or (3S,5R)—N-(4-(2,6-dimethoxyphenyl)-5-(2-furanyl)-4H-1,2,4-triazol-3-yl)-5-(4-fluorophenyl)-3-piperidinesulfonamide 188.1

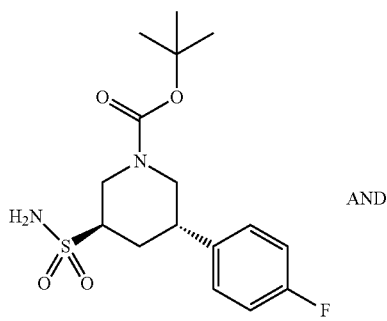

(3R,5S)-tert-Butyl 3-(4-fluorophenyl)-5-sulfamoylpiperidine-1-carboxylate and (3S,5R)-tert-butyl 3-(4-fluorophenyl)-5-sulfamoylpiperidine-1-carboxylate, Example 188.1. Example 188.1 was isolated by silica gel column chromatography of Example 165.3. LCMS-ESI (pos.), m/z: 381.2 (M+Na)+.

188.2

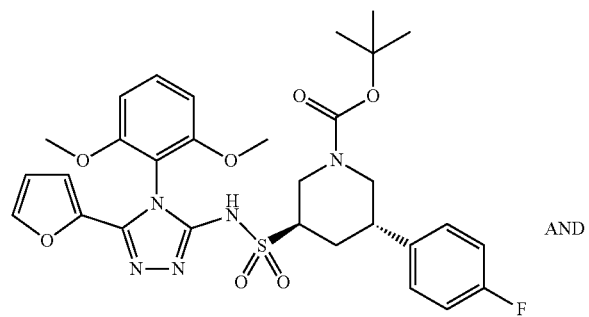

AND

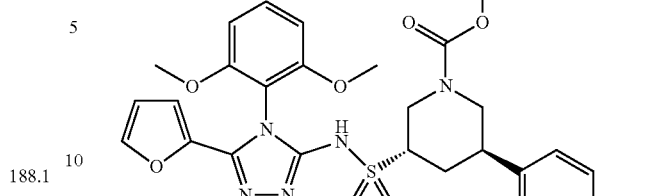

tert-butyl (3R,5S)-3-((4-(2,6-Dimethoxyphenyl)-5-(2-furanyl)-4H-1,2,4-triazol-3-yl)sulfamoyl)-5-(4-fluorophenyl)-1-piperidinecarboxylate and tert-butyl (3S,5R)-3-((4-(2,6-dimethoxyphenyl)-5-(2-furanyl)-4H-1,2,4-triazol-3-yl)sulfamoyl)-5-(4-fluorophenyl)-1-piperidinecarboxylate, Example 188.2. Example 188.2 was prepared from Example 364.3 and Example 188.1 using the procedure described in Example 94.0. $^1$H NMR (500 MHz, CDCl$_3$) δ 7.44-7.51 (m, 2H) 7.21 (br. s., 2H) 6.94-7.05 (m, 2H) 6.68 (d, J=8.31 Hz, 2H) 6.35 (dd, J=3.55, 1.83 Hz, 1H) 6.01 (d, J=3.42 Hz, 1H) 4.17 (br. s., 1H) 3.75 (s, 3H) 3.71 (s, 3H) 3.28-3.38 (m, 2H) 3.10-3.28 (m, 2H) 2.61 (br. s., 1H) 2.43 (br. s., 1H) 2.15 (br. s., 1H) 1.48 (br. s., 9H). LCMS-ESI (pos.), m/z: 628.3 (M+H)+.

188.3

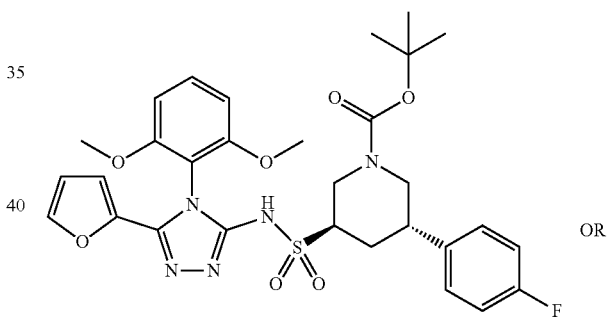

OR tert-butyl (3R,5S)-3-((4-(2,6-Dimethoxyphenyl)-5-(2-furanyl)-4H-1,2,4-triazol-3-yl)sulfamoyl)-5-(4-fluorophenyl)-1-piperidinecarboxylate or tert-butyl (3S,5R)-3-((4-(2,6-dimethoxyphenyl)-5-(2-furanyl)-4H-1,2,4-triazol-3-yl)sulfamoyl)-5-(4-fluorophenyl)-1-piperidinecarboxylate, Example 188.3. Example 188.3 was prepared from SFC chiral separation of Example 188.2 under the following conditions: AD-H (2×25 cm) column, 35% MeOH/CO$_2$, 100 bar, 60 mL/min, 220 nm. Injection volume: 2.0 mL, 8 mg/mL 1:1 DCM:MeOH. Example 188.3 was the first isomer to elute from AD-H column ¹H NMR (500 MHz, CDCl₃) δ 7.44-7.51 (m, 2H) 7.21 (br. s., 2H) 6.94-7.05 (m, 2H) 6.68 (d, J=8.31 Hz, 2H) 6.35 (dd, J=3.55, 1.83 Hz, 1H) 6.01 (d, J=3.42 Hz, 1H) 4.17 (br. s., 1H) 3.75 (s, 3H) 3.71 (s, 3H) 3.28-3.38 (m, 2H) 3.10-3.28 (m, 2H) 2.61 (br. s., 1H) 2.43 (br. s., 1H) 2.15 (br. s., 1H) 1.48 (br. s., 9H). LCMS-ESI (pos.), m/z: 628.3 (M+H)⁺.

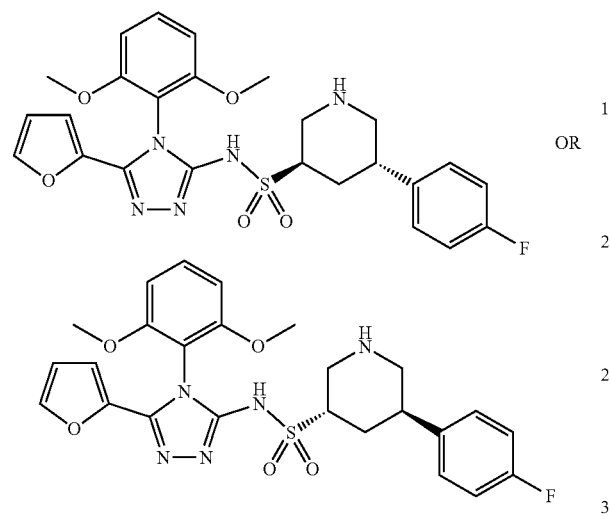

188.0

OR (3R,5S)—N-(4-(2,6-Dimethoxyphenyl)-5-(2-furanyl)-4H-1,2,4-triazol-3-yl)-5-(4-fluorophenyl)-3-piperidinesulfonamide or (3S,5R)—N-(4-(2,6-dimethoxyphenyl)-5-(2-furanyl)-4H-1,2,4-triazol-3-yl)-5-(4-fluorophenyl)-3-piperidinesulfonamide, Example 188.0. Example 188.0 was prepared from Example 188.3 using the procedure described in Example 165.5. ¹H NMR (500 MHz, CD₃OD) δ 7.63 (dd, J=1.83, 0.61 Hz, 1H) 7.58 (t, J=8.56 Hz, 1H) 7.24-7.30 (m, 2H) 7.09-7.16 (m, 2H) 6.88 (d, J=8.56 Hz, 1H) 6.82 (d, J=8.56 Hz, 1H) 6.46 (dd, J=3.55, 1.83 Hz, 1H) 6.17 (dd, J=3.67, 0.73 Hz, 1H) 3.91 (d, J=13.94 Hz, 1H) 3.74-3.79 (m, 1H) 3.66-3.73 (m, 8H) 3.58-3.63 (m, 2H) 3.50-3.58 (m, 2H) 3.39 (dd, J=12.35, 3.79 Hz, 1H) 3.20 (t, J=12.35 Hz, 1H) 2.60 (dd, J=14.67, 1.71 Hz, 1H) 2.19 (ddd, J=14.73, 13.02, 5.50 Hz, 1H). LCMS-ESI (pos.), m/z: 528.2 (M+H)⁺.

Example 189.0. Preparation of (2S,3R)—N-(4-(3,5-dibromo-2,6-dimethoxyphenyl)-5-(5-methyl-2-furanyl)-4H-1,2,4-triazol-3-yl)-3-(5-fluoro-2-pyrimidinyl)-2-butanesulfonamide

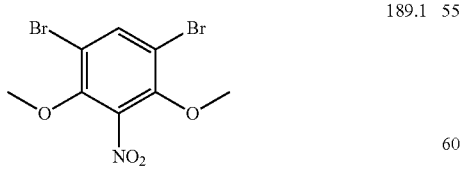

189.1

1,5-Dibromo-2,4-dimethoxy-3-nitrobenzene, Example 189.1. To a solution of 4,6-dibromo-2-nitrobenzene-1,3-diol amine (commercially available from Aces Pharma, NJ, USA, 603 mg, 1.927 mmol) in MeOH (6 mL) was added (trimethylsilyl)diazomethane in Et₂O (2.0 M, 10 mL, 20 mmol). The reaction was stirred at RT for 20 h. Another batch of (trimethylsilyl)diazomethane in Et₂O (2.0 M) (10 mL, 20 mmol) was added. The reaction mixture was then stirred at RT for 4 h. LCMS analysis indicated the reaction was complete. The reaction mixture was concentrated in vacuo. The material was absorbed onto a plug of silica gel and purified by chromatography through a Redi-Sep prepacked silica gel column (12 g) eluting with a gradient of 0% to 50% EtOAc in hexanes to provide Example 189.1 (650 mg, 99% yield) as a yellow solid. ¹H NMR (500 MHz, CDCl₃) δ 7.87 (s, 1H) 3.97 (s, 6H).

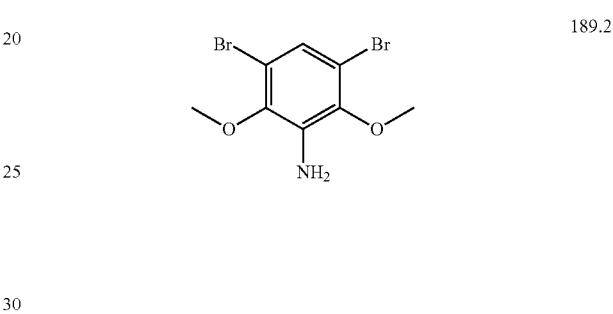

189.2

3,5-Dibromo-2,6-dimethoxyaniline, Example 189.2. To a solution of Example 189.1 (650 mg, 1.91 mmol) in MeOH (19 mL) was added stannous chloride (1.8 g, 9.53 mmol) and HCl (2.0 M, 5 mL, 10 mmol). The reaction was stirred at 23° C. for 20 h. LCMS analysis showed formation of the desired product, but the reaction did not go to completion. Thus, additional stannous chloride (0.6 g) and HCl (2.0 M, 2 mL) were added followed by MeOH (10 mL). The reaction mixture was stirred at RT for another 6 h. The solvent was removed in vacuo to give an oil. This oil was dissolved in EtOAc and treated with 5 N NaOH. The resulting suspension was stirred vigorously for 1 h. The resulting layers were then separated, and the aqueous layer was extracted with EtOAc. The combined organic layers were dried (MgSO₄), filtered, and concentrated to give Example 189.2 (600 mg, 101% yield) as a white solid which was used in the next step without purification. LCMS-ESI (pos.), m/z: 310.0 (M+H)⁺.

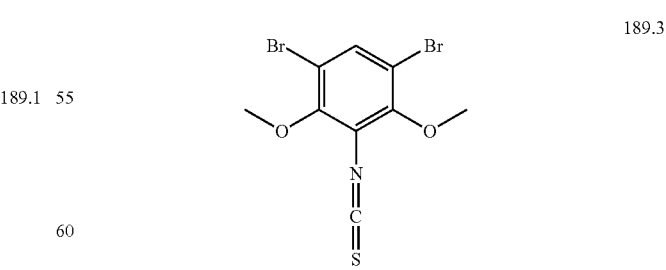

189.3

1,5-Dibromo-3-isothiocyanato-2,4-dimethoxybenzene, Example 189.3. Example 189.3 was prepared from Example 189.2 using the procedure described in Example 372.0. LCMS-ESI (pos.), m/z: 352.4 (M+H)⁺.

189.0

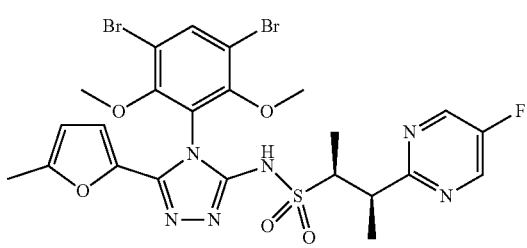

(2S,3R)—N-(4-(3,5-Dibromo-2,6-dimethoxyphenyl)-5-(5-methyl-2-furanyl)-4H-1,2,4-triazol-3-yl)-3-(5-fluoro-2-pyrimidinyl)-2-butanesulfonamide, Example 189.0. Example 189.0 was prepared from Example 189.3 (2S,3R)-3-(5-fluoropyrimidin-2-yl)butane-2-sulfonamide (Example 56.5) and 5-methylfuran-2-carbohydrazide (commercially available from Chembridge, CA, USA) following the procedure described in Example 229.0. ¹H NMR (500 MHz, CDCl₃) δ 8.58 (s, 2H) 7.98 (s, 1H) 6.10 (d, J=3.42 Hz, 1H) 6.00 (dd, J=3.42, 0.98 Hz, 1H) 3.82-3.89 (m, 1H) 3.80 (s, 3H) 3.78 (s, 3H) 3.70-3.77 (m, 1H) 2.28 (s, 3H) 1.40 (d, J=5.87 Hz, 3H) 1.38 (d, J=5.87 Hz, 3H). LCMS-ESI (pos.), m/z: 537.2 (M+H)⁺.

Example 190.0. Preparation of (1R,2S)-2-(4-chlorophenyl)-N-(4-(2,6-dimethoxyphenyl)-5-(2-furanyl)-4H-1,2,4-triazol-3-yl)cyclopropanesulfonamide and (1S,2R)-2-(4-chlorophenyl)-N-(4-(2,6-dimethoxyphenyl)-5-(2-furanyl)-4H-1,2,4-triazol-3-yl)cyclopropanesulfonamide 190.0

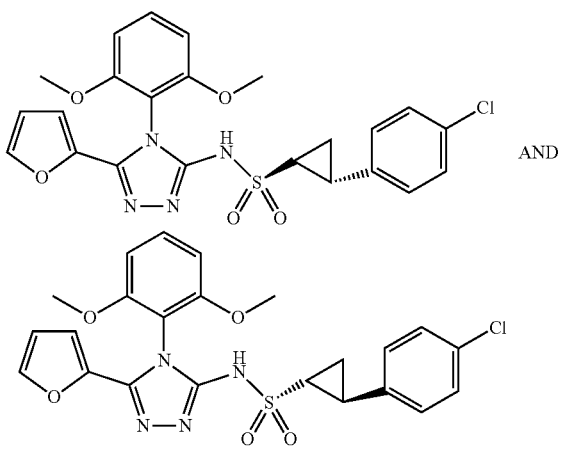

(1R,2S)-2-(4-Chlorophenyl)-N-(4-(2,6-dimethoxyphenyl)-5-(2-furanyl)-4H-1,2,4-triazol-3-yl)cyclopropanesulfonamide and (1S,2R)-2-(4-chlorophenyl)-N-(4-(2,6-dimethoxyphenyl)-5-(2-furanyl)-4H-1,2,4-triazol-3-yl) cyclopropanesulfonamide, Example 190.0. Example 190.0 was prepared from Example 362.03 and trans-2-(4-chlorophenyl)cyclopropane-1-sulfonyl chloride (commercially available from Chemizon, a division of OptoMagic Co., Ltd, Seongnam Si, South Korea) using the procedure described in Example 1.1. ¹H NMR (400 MHz, CDCl₃) δ 7.51 (d, J=1.17 Hz, 1H) 7.46 (t, J=8.51 Hz, 1H) 7.22-7.27 (m, 2H) 7.07-7.16 (m, 2H) 6.64-6.73 (m, 2H) 6.36 (dd, J=3.52, 1.76 Hz, 1H) 6.03 (d, J=3.52 Hz, 1H) 3.72 (s, 3H) 3.67 (s, 3H) 2.95-3.16 (m, 2H) 2.03-2.14 (m, 1H) 1.47-1.70 (m, 1H). LCMS-ESI (pos.) m/z: 501.0 (M+H)⁺.

Example 191.0. Preparation of (1R,2S)-2-(4-chlorophenyl)-N-(4-(2,6-dimethoxyphenyl)-5-(2-furanyl)-4H-1,2,4-triazol-3-yl)cyclopropanesulfonamide or (1S,2R)-2-(4-chlorophenyl)-N-(4-(2,6-dimethoxyphenyl)-5-(2-furanyl)-4H-1,2,4-triazol-3-yl)cyclopropanesulfonamide 191.0

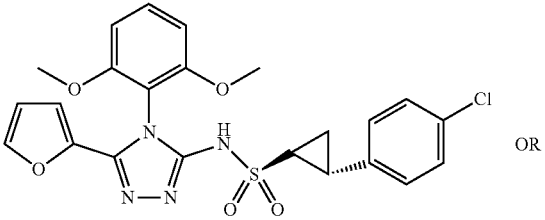

OR

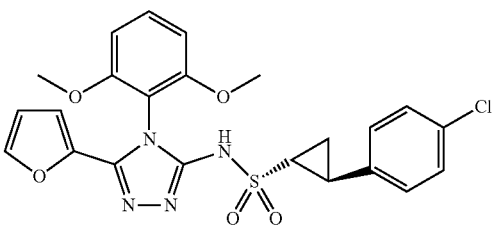

(1R,2S)-2-(4-Chlorophenyl)-N-(4-(2,6-dimethoxyphenyl)-5-(2-furanyl)-4H-1,2,4-triazol-3-yl)cyclopropanesulfonamide or (1S,2R)-2-(4-chlorophenyl)-N-(4-(2,6-dimethoxyphenyl)-5-(2-furanyl)-4H-1,2,4-triazol-3-yl) cyclopropanesulfonamide, Example 191.0. Example 191.0 was the first isomer to elute under the following conditions to separate the racemic compound Example 190.0: 250×30 mm AD column with 30 g/min MeOH+(20 mM NH₃)+90 g/min CO₂ on Thar 350 SFC. Outlet pressure=100 bar; Temp.=22° C.; Wavelength=222 nm. Used 0.5 mL injections of 180 mg/8 mL (22.5 mg/mL) sample solution in MeOH, i.e. 11.3 mg/injection. Run time=7 min.; Cycle time=4 min. ¹H NMR (400 MHz, CDCl₃) δ 7.50 (d, J=1.76 Hz, 1H) 7.46 (t, J=8.34 Hz, 1H) 7.18-7.26 (m, 2H) 7.07-7.17 (m, 2H) 6.69 (t, J=7.42 Hz, 2H) 6.35 (dd, J=3.52, 1.76 Hz, 1H) 6.03 (d, J=3.76 Hz, 1H) 3.70-3.76 (s, 3H) 3.66 (s, 3H) 2.98-3.14 (m, 2H) 2.07 (dt, J=9.63, 5.84 Hz, 1H) 1.62 (dt, J=8.41, 6.55 Hz, 1H). LCMS-ESI (pos.), m/z: 501.0 (M+H)⁺.

Example 192.0. Preparation of (1R,2S)-2-(4-chlorophenyl)-N-(4-(2,6-dimethoxyphenyl)-5-(2-furanyl)-4H-1,2,4-triazol-3-yl)cyclopropanesulfonamide or (1S,2R)-2-(4-chlorophenyl)-N-(4-(2,6-dimethoxyphenyl)-5-(2-furanyl)-4H-1,2,4-triazol-3-yl)cyclopropanesulfonamide

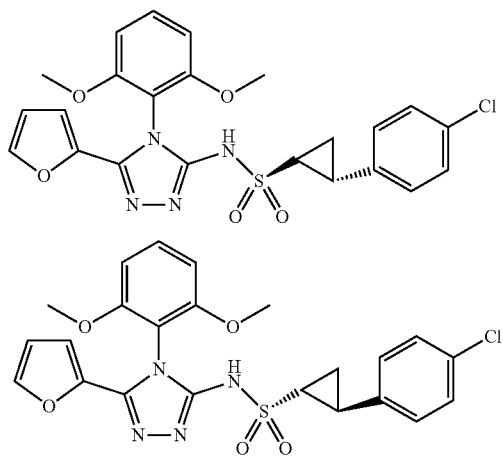

(1R,2S)-2-(4-Chlorophenyl)-N-(4-(2,6-dimethoxyphenyl)-5-(2-furanyl)-4H-1,2,4-triazol-3-yl)cyclopropanesulfonamide or (1S,2R)-2-(4-chlorophenyl)-N-(4-(2,6-dimethoxyphenyl)-5-(2-furanyl)-4H-1,2,4-triazol-3-yl)cyclopropanesulfonamide, Example 192.0. Example 192.0 is the enantiomer of Example 191.0. Example 192.0 was the second isomer to elute on subjecting Example 190.0 to the SFC conditions described in Example 191.0. LCMS-ESI (pos.), m/z: 501.0 (M+H)+.

Example 193.0. Preparation of (P)-2-(4-chlorophenyl)-N-(4-(2-cyano-6-methoxyphenyl)-5-(2-furanyl)-4H-1,2,4-triazol-3-yl)ethanesulfonamide and (M)-2-(4-chlorophenyl)-N-(4-(2-cyano-6-methoxyphenyl)-5-(2-furanyl)-4H-1,2,4-triazol-3-yl)ethanesulfonamide

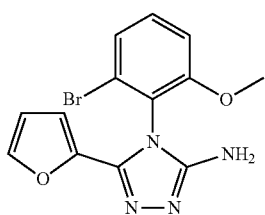

4-(2-Bromo-6-methoxyphenyl)-5-(furan-2-yl)-4H-1,2,4-triazol-3-amine, Example 193.1. Example 193.1 was prepared from 2-bromo-6-methoxyaniline (commercially available from Apollo Scientific Ltd., Manchester, UK) using procedures described in the preparation of Example 362.03. LCMS-ESI (pos.), m/z: 337.0 (M+H)+.

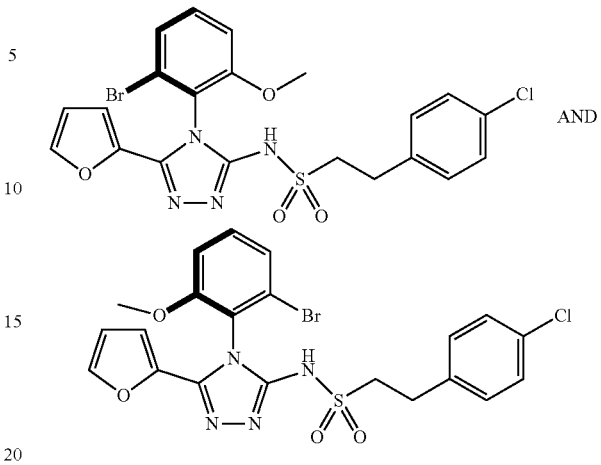

(P)—N-(4-(2-Bromo-6-methoxyphenyl)-5-(2-furanyl)-4H-1,2,4-triazol-3-yl)-2-(4-chlorophenyl)ethanesulfonamide and (M)-N-(4-(2-bromo-6-methoxyphenyl)-5-(2-furanyl)-4H-1,2,4-triazol-3-yl)-2-(4-chlorophenyl)ethanesulfonamide, Example 193.2. Example 193.2 was prepared employing Example 193.1 and 2-(4-chloro-phenyl)-ethanesulfonyl chloride using the procedure described in Example 1.1. $^1$H NMR (400 MHz, CDCl$_3$) δ 10.94 (s, 1H) 7.42-7.53 (m, 2H) 7.36-7.42 (m, 1H) 7.27-7.28 (m, 1H) 7.14 (d, J=7.70 Hz, 2H) 7.06 (dd, J=8.41, 1.17 Hz, 1H) 6.39 (dd, J=3.72, 1.76 Hz, 1H) 6.11 (d, J=3.72 Hz, 1H) 3.79 (s, 3H) 3.25-3.34 (m, 2H) 3.08-3.17 (m, 2H). LCMS-ESI (pos.), m/z: 536.9 (M+H)+.

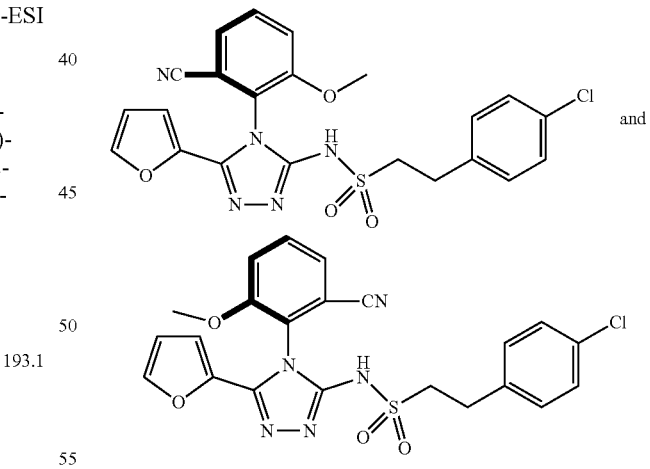

(P)-2-(4-Chlorophenyl)-N-(4-(2-cyano-6-methoxyphenyl)-5-(2-furanyl)-4H-1,2,4-triazol-3-yl)ethanesulfonamide and (M)-2-(4-chlorophenyl)-N-(4-(2-cyano-6-methoxyphenyl)-5-(2-furanyl)-4H-1,2,4-triazol-3-yl)ethanesulfonamide, Example 193.0. A glass microwave reaction vessel was charged with Example 193.2 (58 mg, 0.108 mmol) and copper (I) cyanide (88 mg, 1.1 mmol) in DMF (2 mL). The reaction mixture was stirred and heated in a Discover model microwave reactor (CEM, Matthews, N.C.) at 180° C. for 45 min. LCMS analysis showed the desired product. The mixture was partitioned between DCM and water resulting in an emulsion. The emulsion layer was removed and filtered through a coarse fritted funnel and worked up separately. The organics were washed with brine and evaporated to give a black solid. The material thus obtained was absorbed onto a plug of silica gel and purified by chromatography through a Redi-Sep pre-packed silica gel column (4 g) eluting with a gradient of 0% to 100% EtOAc in DCM to provide a white solid. The material was purified by reverse-phase preparative HPLC using a Phenomenex Luna column, 5 micron, C18(2), 100 Å, 150×30 mm, 0.1% TFA in ACN/H$_2$O, gradient 30% to 95% over 30 min to provide the title compound, Example 193.0 (9 mg, 0.019 mmol, 17% yield) as a white powder. $^1$H NMR (400 MHz, CD$_2$Cl$_2$) δ 11.08 (br. s., 1H) 7.69-7.79 (m, 1H) 7.39-7.57 (m, 3H) 7.28-7.34 (m, 2H) 7.19-7.27 (m, 2H) 6.41-6.53 (m, 2H) 3.82 (s, 3H) 3.28-3.39 (m, 2H) 3.09-3.21 (m, 2H). LCMS-ESI (pos.), m/z: 484.1 (M+H)$^+$.

Example 194.0. Preparation of 2-(2-bromo-4-fluorophenyl)-N-(4-(2,6-dimethoxyphenyl)-5-(2-furanyl)-4H-1,2,4-triazol-3-yl)ethanesulfonamide

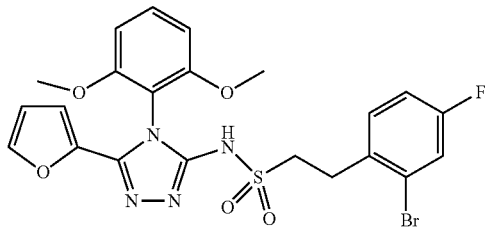

194.0

2-(2-Bromo-4-fluorophenyl)-N-(4-(2,6-dimethoxyphenyl)-5-(2-furanyl)-4H-1,2,4-triazol-3-yl)ethanesulfonamide, Example 194.0. Example 194.0 was prepared from Example 362.03 and 2-(2-bromo-4-fluorophenyl)ethanesulfonyl chloride (Synchem, IL, US) using the procedure described in Example 1.1. $^1$H NMR (400 MHz, DMSO-d$_6$) δ 13.42 (s, 1H) 7.83 (dd, J=1.76, 0.59 Hz, 1H) 7.48-7.63 (m, 2H) 7.35 (dd, J=8.61, 6.06 Hz, 1H) 7.13-7.28 (m, 1H) 6.90 (d, J=8.61 Hz, 2H) 6.53 (dd, J=3.52, 1.76 Hz, 1H) 6.02 (dd, J=3.52, 0.59 Hz, 1H) 3.71 (s, 3H) 3.71 (s, 3H) 3.07-3.21 (m, 2H) 2.88-3.05 (m, 2H). LCMS-ESI (pos.) m/z: 551.0 (M+H)$^+$.

Example 195.0. Preparation of N-(4-(2,6-dimethoxyphenyl)-5-(2-furanyl)-4H-1,2,4-triazol-3-yl)-2-(4-fluoro-2-(methylsulfonyl)phenyl)ethanesulfonamide

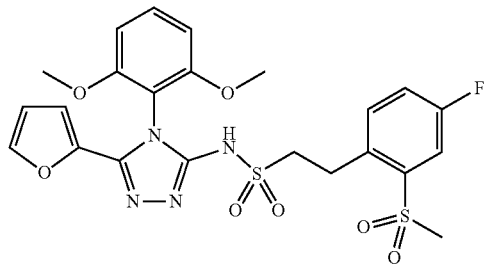

195.0

N-(4-(2,6-Dimethoxyphenyl)-5-(2-furanyl)-4H-1,2,4-triazol-3-yl)-2-(4-fluoro-2-(methylsulfonyl)phenyl)ethanesulfonamide, Example 195.0. A mixture of Example 194.0 (85.5 mg, 0.160 mmol), copper(I) iodide (6 mg, 0.032 mmol), sodium methanesulfinate (29 mg, 0.240 mmol) and N,N'-dimethylethylenediamine (7 µL, 0.064 mmol) in DMSO (1.6 mL) was combined in a 5 mL vial. The mixture was heated at 110° C. for 18 h. The mixture was then filtered through a short pad of silica gel and the filter cake was rinsed with EtOAc. The solution was concentrated in vacuo to afford a white solid. The material was purified by silica gel chromatography (0% to 30% MeOH in DCM) to provide Example 195.0 as a white solid. $^1$H NMR (400 MHz, CDCl$_3$) δ 7.66 (dd, J=8.41, 2.74 Hz, 1H) 7.31-7.44 (m, 3H) 7.14-7.19 (m, 1H) 6.62 (d, J=8.61 Hz, 2H) 6.26 (dd, J=3.52, 1.76 Hz, 1H) 5.94 (dd, J=3.52, 0.78 Hz, 1H) 3.68 (s, 3H) 3.68 (s, 3H) 3.28-3.46 (m, 4H) 2.95 (s, 3H). LCMS-ESI (pos.), m/z: 551.0 (M+H)$^+$.

Example 196.0. Preparation of N-(2-(2-((4-(2,6-dimethoxyphenyl)-5-(2-furanyl)-4H-1,2,4-triazol-3-yl)sulfamoyl)ethyl)-5-fluorophenyl)acetamide

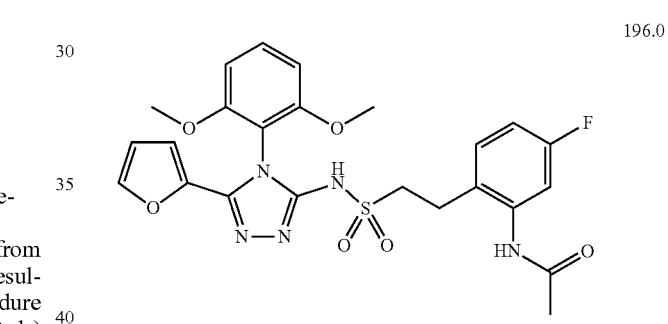

196.0

N-(2-(2-((4-(2,6-Dimethoxyphenyl)-5-(2-furanyl)-4H-1,2,4-triazol-3-yl)sulfamoyl)ethyl)-5-fluorophenyl)acetamide, Example 196.0. Under N$_2$ and to a dry 50 mL RBF was added Example 194.0 (260 mg, 0.472 mmol), acetamide (56 mg, 0.943 mmol), cesium carbonate (307 mg, 0.943 mmol), pd$_2$(dba)$_3$ (0.022 g, 0.024 mmol) and xantphos (27 mg, 0.047 mmol). The flask was sealed with a septum and placed under vacuum and dry dioxane (9 mL) was added. The system was placed under vacuum and back filled with N$_2$ three times. The reaction mixture was stirred at 110° C. for 20 h. LCMS analysis indicated the reaction was complete. The reaction mixture was then diluted with EtOAc and filtered through a pad of silica gel. The filter cake was rinsed with EtOAc. The solution was concentrated in vacuo and purified by silica gel chromatography (0% to 100% EtOAc in hexanes) to afford Example 196.0 (156 mg, 0.295 mmol, 63% yield) as a white solid. $^1$H NMR (400 MHz, DMSO-d$_6$) δ 13.36 (s, 1H) 9.45 (s, 1H) 7.84 (d, J=0.98 Hz, 1H) 7.58 (t, J=8.51 Hz, 1H) 7.13-7.28 (m, 2H) 6.99 (td, J=8.46, 2.64 Hz, 1H) 6.90 (d, J=8.61 Hz, 2H) 6.54 (dd, J=3.52, 1.76 Hz, 1H) 6.04 (d, J=3.13 Hz, 1H) 3.71 (s, 3H) 3.71 (s, 3H) 3.07-3.18 (m, 2H) 2.81-2.93 (m, 2H) 2.03 (s, 3H). LCMS-ESI (pos.), m/z: 530.2 (M+H)$^+$.

Example 197.0. Preparation of (2R)—N-(4-(2,6-dimethoxyphenyl)-5-(2-furanyl)-4H-1,2,4-triazol-3-yl)-2-(4-fluorophenyl)-1-propanesulfonamide or (2S)—N-(4-(2,6-dimethoxyphenyl)-5-(2-furanyl)-4H-1,2,4-triazol-3-yl)-2-(4-fluorophenyl)-1-propanesulfonamide

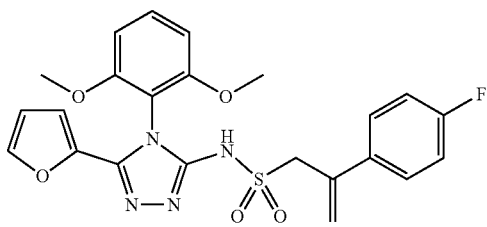

197.1

N-(4-(2,6-Dimethoxyphenyl)-5-(2-furanyl)-4H-1,2,4-triazol-3-yl)-2-(4-fluorophenyl)-2-propene-1-sulfonamide Example 197.1. Sulfuryl chloride (20.9 mL, 258 mmol) was added dropwise to DMF (20.0 mL) at 0° C. with stirring. After completion of the addition, the reaction mixture was stirred at RT for 0.5 h. 4-Fluoro-alpha-methylstyrene (17.6 mL, 129 mmol) was added in three portions to the reaction mixture with stirring. The reaction mixture was then heated gradually on a water bath to 90° C. over 3 h. The reaction mixture was allowed to cool to RT and was diluted with water and extracted with Et$_2$O. The combined organic layers were washed with brine and dried over Na$_2$SO$_4$. The solution was filtered and concentrated in vacuo to give a dark-red oil which was purified by silica gel chromatography (0% to 30% EtOAc in hexanes) to give a tan oil (1.8 g). $^1$H NMR (400 MHz, CDCl$_3$) δ 7.47-7.55 (m, 2H) 7.12-7.20 (m, 2H) 6.96 (q, J=1.17 Hz, 1H) 2.67 (d, J=1.17 Hz, 3H). Example 197.1 was prepared using the product described above and Example 362.03 using the procedure described in Example 1.1. $^1$H NMR (400 MHz, DMSO-d$_6$) δ 13.22 (br. s., 1H) 7.83 (d, J=1.56 Hz, 1H) 7.49-7.67 (m, 3H) 7.13 (t, J=8.90 Hz, 3H) 6.89 (d, J=8.61 Hz, 2H) 6.53 (dd, J=3.42, 1.66 Hz, 1H) 5.99 (d, J=3.52 Hz, 1H) 5.60 (s, 1H) 5.30 (s, 1H) 4.12 (s, 2H) 3.74 (s, 3H) 3.74 (s, 3H). LCMS-ESI (pos.) m/z: 485.0 (M+H)$^+$.

197.2

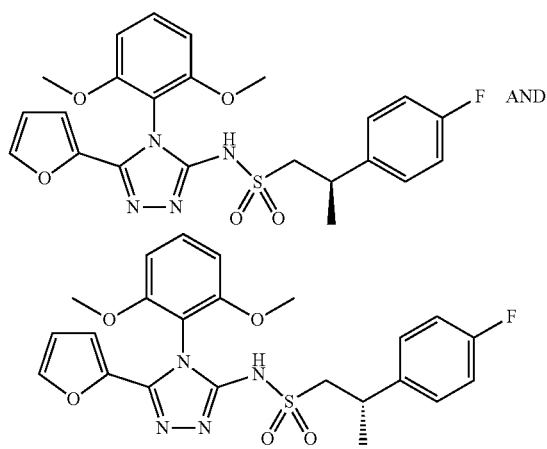

(2R)—N-(4-(2,6-Dimethoxyphenyl)-5-(2-furanyl)-4H-1,2,4-triazol-3-yl)-2-(4-fluorophenyl)-1-propanesulfonamide and (2S)—N-(4-(2,6-dimethoxyphenyl)-5-(2-furanyl)-4H-1,2,4-triazol-3-yl)-2-(4-fluorophenyl)-1-propanesulfonamide, Example 197.2. To a 100 mL RBF was added Example 197.1 (0.138 g, 0.285 mmol) in EtOAc (14 mL). Under N$_2$ flow, 10% palladium on carbon (30 mg, 0.028 mmol) was added. The reaction mixture was stirred under an atmosphere of H$_2$ at RT for 18 h. The solution was then filtered and concentrated in vacuo to give a light-yellow solid. The initial material was purified by silica gel chromatography (0% to 100% EtOAc in hexanes) to provide the title compound, Example 197.2 (0.080 g, 0.164 mmol, 58% yield), as an off-white solid. $^1$H NMR (400 MHz, CDCl$_3$) δ 10.82 (br. s., 1H) 7.44-7.51 (m, 2H) 7.12 (t, J=6.11 Hz, 2H) 6.92-7.01 (m, 2H) 6.68 (d, J=8.41 Hz, 2H) 6.33 (dd, J=3.52, 1.76 Hz, 1H) 5.97-6.01 (m, 1H) 3.73 (s, 3H) 3.73 (s, 3H) 3.38 (td, J=7.58, 4.99 Hz, 1H) 3.18-3.32 (m, 2H) 1.40 (d, J=7.04 Hz, 3H). LCMS-ESI (pos.) m/z: 487.2 (M+H)$^+$.

197.0

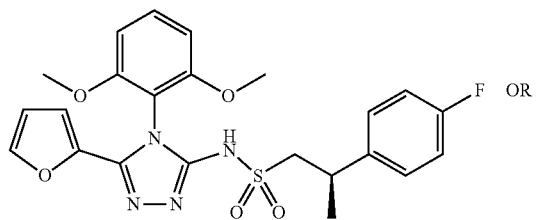

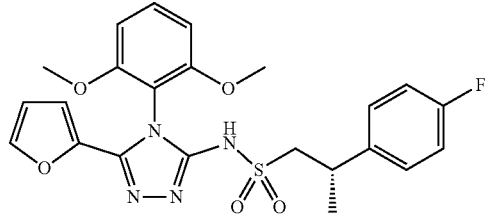

(2R)—N-(4-(2,6-Dimethoxyphenyl)-5-(2-furanyl)-4H-1,2,4-triazol-3-yl)-2-(4-fluorophenyl)-1-propanesulfonamide or (2S)—N-(4-(2,6-dimethoxyphenyl)-5-(2-furanyl)-4H-1,2,4-triazol-3-yl)-2-(4-fluorophenyl)-1-propanesulfonamide, Example 197.0. Example 197.0 was the first isomer to elute under the following SFC conditions: AD-H (2×15 cm), 30% MeOH (0.1% NH$_4$OH)/CO$_2$, 100 bar. 65 mL/min, 220 nm. injection volume: 0.6 mL, 4 mg/mL MeOH solution of the racemic compound Example 197.2. $^1$H NMR (400 MHz, CDCl$_3$) δ 7.44-7.52 (m, 2H) 7.09-7.16 (m, 2H) 6.92-7.01 (m, 2H) 6.68 (d, J=8.61 Hz, 2H) 6.33 (dd, J=3.62, 1.86 Hz, 1H) 5.99 (dd, J=3.52, 0.59 Hz, 1H) 3.73 (s, 3H) 3.73 (s, 3H) 3.37 (dd, J=6.94, 4.99 Hz, 1H) 3.16-3.32 (m, 2H) 1.40 (d, J=6.85 Hz, 3H). LCMS-ESI (pos.), m/z: 487.2 (M+H)$^+$.

Example 198.0. Preparation of N-(4-(2,6-dimethoxyphenyl)-5-(2-furanyl)-4H-1,2,4-triazol-3-yl)-3-oxo-3-(1-pyrrolidinyl)-1-propanesulfonamide

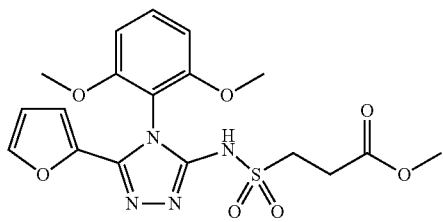

198.1

Methyl 3-((4-(2,6-methoxyphenyl)-5-(2-furanyl)-4H-1,2,4-triazol-3-yl)sulfamoyl)propanoate, Example 198.1. Example 198.1 was prepared from Example 362.03 and 3-chlorosulfonyl-propionic acid methyl ester (commercially available from Enamine, Kiev, Ukraine) using the procedure described in Example 1.1. $^1$H NMR (400 MHz, CDCl$_3$) δ 10.89 (br. s., 1H) 7.45-7.56 (m, 2H) 6.71 (d, J=8.56 Hz, 2H) 6.36 (dd, J=3.52, 1.76 Hz, 1H) 6.04 (d, J=3.73 Hz, 1H) 3.77-3.81 (m, 6H) 3.72 (s, 3H) 3.27-3.45 (m, 2H) 2.75-2.92 (m, 2H). LCMS-ESI (pos.) m/z: 437.0 (M+H)$^+$.

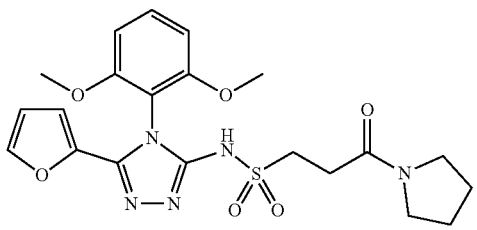

198.0

N-(4-(2,6-Dimethoxyphenyl)-5-(2-furanyl)-4H-1,2,4-triazol-3-yl)-3-oxo-3-(1-pyrrolidinyl)-1-propanesulfonamide, Example 198.0. To a 1 dram vial was added Example 198.1 (88 mg, 0.141 mmol) in MeOH (0.7 mL). Pyrrolidine (118 μL, 1.41 mmol) was then added at RT. The vial was sealed and the reaction mixture was stirred at 100° C. for 16 h. The solution was concentrated in vacuo to give a light-yellow solid which was diluted with 1 N HCl and extracted with DCM. The combined organic layers were washed with brine and dried over Na$_2$SO$_4$. The solution was then filtered and concentrated in vacuo to give a light-yellow solid. The material was purified by reverse-phase preparative HPLC (0.1% TFA in ACN/H$_2$O, gradient 30% to 95%) to provide Example 198.0 (22 mg, 0.046 mmol, 33% yield) as a light-yellow solid. $^1$H NMR (400 MHz, CDCl$_3$) δ 7.41-7.52 (m, 2H) 6.69 (d, J=8.61 Hz, 2H) 6.35 (dd, J=3.52, 1.76 Hz, 1H) 6.05 (dd, J=3.52, 0.59 Hz, 1H) 3.78 (s, 3H) 3.78 (s, 3H) 3.37-3.54 (m, 6H) 2.74-2.85 (m, 2H) 1.98 (t, J=6.55 Hz, 2H) 1.88 (t, J=6.94 Hz, 2H). LCMS-ESI (pos.), m/z: 476.0 (M+H)$^+$.

Example 199.0. Preparation of (3R)-3-cyclopentyl-N-(4-(2,6-dimethoxyphenyl)-5-(2-furanyl)-4H-1,2,4-triazol-3-yl)-3-hydroxy-1-propanesulfonamide or (3S)-3-cyclopentyl-N-(4-(2,6-dimethoxyphenyl)-5-(2-furanyl)-4H-1,2,4-triazol-3-yl)-3-hydroxy-1-propanesulfonamide

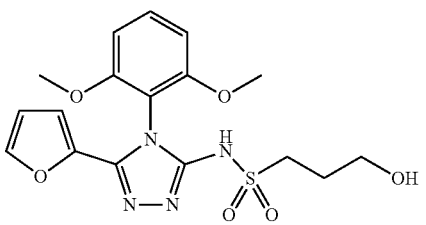

199.1

(N-(4-(2,6-Dimethoxyphenyl)-5-(2-furanyl)-4H-1,2,4-triazol-3-yl)-3-hydroxy-1-propanesulfonamide, Example 199.1. To a 100 mL RBF was added Example 198.1 (446 mg, 1.02 mmol) in THF (2 mL). Lithium borohydride (2.0 M solution in THF, 2.55 mL, 5.11 mmol) was added to the stirred solution at 0° C. under N$_2$. The reaction mixture was then stirred for 14 h at 0° C. allowing the reaction to warm to RT. LCMS analysis indicated the reaction was complete. The reaction mixture was diluted with a saturated aqueous solution of NH$_4$Cl and 2 N HCl and then extracted with DCM. The combined organic layers were washed with brine and dried over Na$_2$SO$_4$. The solution was filtered and concentrated in vacuo to give a solid. The solid was triturated with ether to provide Example 199.1 as a white solid. $^1$H NMR (500 MHz, DMSO-d$_6$) δ 13.25 (s, 1H) 7.80-7.86 (m, 1H) 7.56 (t, J=8.56 Hz, 1H) 6.90 (d, J=8.56 Hz, 2H) 6.53 (dd, J=3.55, 1.83 Hz, 1H) 6.03 (d, J=3.67 Hz, 1H) 4.57 (t, J=5.14 Hz, 1H) 3.74 (s, 3H) 3.74 (s, 3H) 3.44 (q, J=6.11 Hz, 2H) 2.87-2.97 (m, 2H) 1.67-1.79 (m, 2H). LCMS-ESI (pos.), m/z: 409.0 (M+H)$^+$.

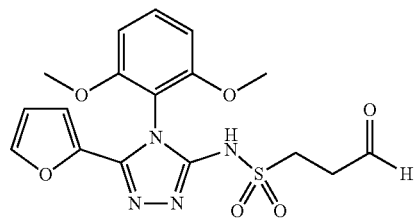

199.2

N-(4-(2,6-Dimethoxyphenyl)-5-(furan-2-yl)-4H-1,2,4-triazol-3-yl)-3-oxopropane-1-sulfonamide, Example 199.2. To a stirred 250 mL RBF was added Example 199.1 (516 mg, 1.01 mmol) in DCM (67.4 mL) and water (0.073 mL, 4.04 mmol). At 0° C., Dess-Martin periodinane (514 mg, 1.21 mmol) was added, and the reaction mixture was then stirred at 0° C. for 30 min and then at RT for 2 h. Another batch of Dess-Martin periodinane (514 mg, 1.21 mmol) was added. After, 2 h, a further batch of Dess-Martin periodinane (514 mg, 1.213 mmol) was added and the reaction mixture was stirred at RT for another 15 h. The white solid was removed by filtration. The solution was diluted with water and extracted with DCM. The combined organic layers were washed with brine and dried over Na$_2$SO$_4$. The solution was filtered and concentrated in vacuo to give Example 199.2 as a light-yellow solid. The material was used in the next step without further purification.

199.3

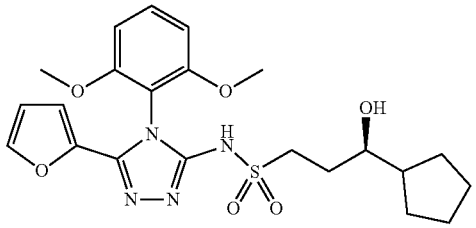

AND

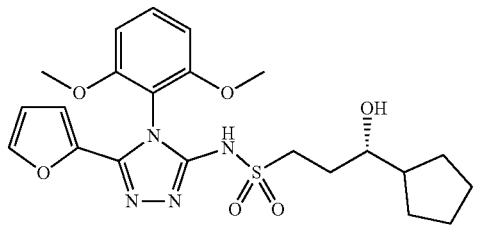

(3R)-3-Cyclopentyl-N-(4-(2,6-dimethoxyphenyl)-5-(2-furanyl)-4H-1,2,4-triazol-3-yl)-3-hydroxy-1-propanesulfonamide and (3S)-3-cyclopentyl-N-(4-(2,6-dimethoxyphenyl)-5-(2-furanyl)-4H-1,2,4-triazol-3-yl)-3-hydroxy-1-propanesulfonamide, Example 199.3. To a stirred 250 mL RBF was added Example 199.2 (680 mg, 0.67 mmol) in THF (7 mL). At −78° C., cyclopentyl magnesium bromide (2.0 M solution in diethyl ether, 3.35 mL, 6.69 mmol) was added, and the reaction mixture was stirred at −78 to 0° C. for 30 min. The reaction mixture was then diluted with 1 N HCl at −78° C. and extracted with EtOAc. The combined organic layers were washed with brine and dried over Na$_2$SO$_4$. The solution was filtered and concentrated in vacuo to give a light-yellow glass. The material thus obtained was purified by silica gel chromatography (0% to 100% EtOAc in DCM) to provide Example 199.3 (156 mg, 0.33 mmol, 49% yield) as an off-white solid. $^1$H NMR (400 MHz, CDCl$_3$) δ 7.44-7.53 (m, 2H) 6.65-6.75 (m, 2H) 6.36 (dd, J=3.62, 1.86 Hz, 1H) 5.98-6.09 (m, 1H) 3.74-3.84 (m, 6H) 3.49-3.59 (m, 1H) 3.25 (t, J=7.24 Hz, 2H) 2.01-2.17 (m, 1H) 1.72-1.91 (m, 3H) 1.46-1.72 (m, 5H) 1.32 (dt, J=7.14, 3.67 Hz, 1H) 1.09-1.24 (m, 1H). LCMS-ESI (pos.), m/z: 477.0 (M+H)$^+$.

199.0

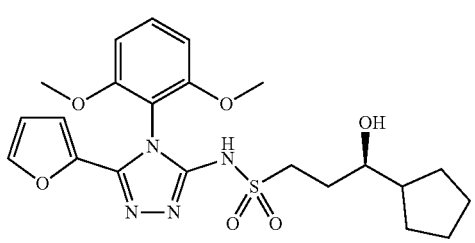

OR

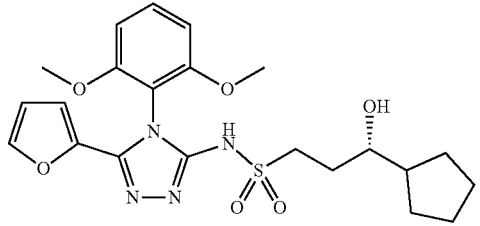

(3R)-3-Cyclopentyl-N-(4-(2,6-dimethoxyphenyl)-5-(2-furanyl)-4H-1,2,4-triazol-3-yl)-3-hydroxy-1-propanesulfonamide or (3S)-3-cyclopentyl-N-(4-(2,6-dimethoxyphenyl)-5-(2-furanyl)-4H-1,2,4-triazol-3-yl)-3-hydroxy-1-propanesulfonamide, Example 199.0. Example 199.0 was the first isomer to elute under the following SFC conditions: AD-H (2×15 cm) column, 20% EtOH (0.1% NH$_4$OH)/CO$_2$, 100 bar, 70 mL/min, 220 nm. Injection volume: 0.5-1 mL, 7.5 mg/mL EtOH solution of Example 199.3. $^1$H NMR (400 MHz, CDCl$_3$) δ 7.44-7.53 (m, 2H) 6.65-6.75 (m, 2H) 6.36 (dd, J=3.62, 1.86 Hz, 1H) 5.98-6.09 (m, 1H) 3.74-3.84 (m, 6H) 3.49-3.59 (m, 1H) 3.25 (t, J=7.24 Hz, 2H) 2.01-2.17 (m, 1H) 1.72-1.91 (m, 3H) 1.46-1.72 (m, 5H) 1.32 (dt, J=7.14, 3.67 Hz, 1H) 1.09-1.24 (m, 1H). LCMS-ESI (pos.), m/z: 477.0 (M+H)$^+$.

Example 200.0. Preparation of (3R)-3-cyclopentyl-N-(4-(2,6-dimethoxyphenyl)-5-(2-furanyl)-4H-1,2,4-triazol-3-yl)-3-hydroxy-1-propanesulfonamide or (3S)-3-cyclopentyl-N-(4-(2,6-dimethoxyphenyl)-5-(2-furanyl)-4H-1,2,4-triazol-3-yl)-3-hydroxy-1-propanesulfonamide 200.0

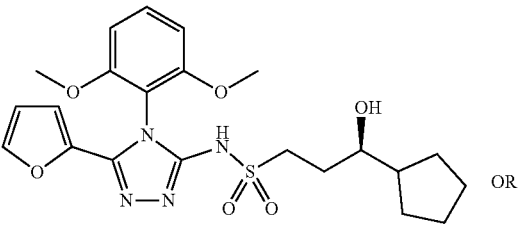

OR

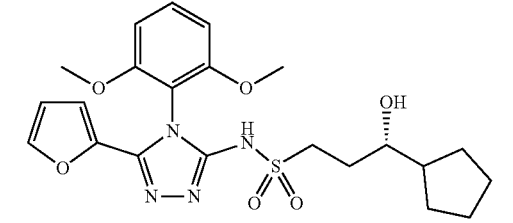

(3R)-3-Cyclopentyl-N-(4-(2,6-dimethoxyphenyl-5-(2-furanyl)-4H-1,2,4-triazol-3-yl)-3-hydroxy-1-propanesulfonamide or (3S)-3-cyclopentyl-N-(4-(2,6-dimethoxyphenyl)-5-(2-furanyl)-4H-1,2,4-triazol-3-yl)-3-hydroxy-1-propanesulfonamide, Example 200.0. Example 200.0 was the second isomer to elute by SFC chiral separation of Example 199.3 under the conditions described in Example 199.0. $^1$H NMR (400 MHz, CDCl$_3$) δ 7.44-7.53 (m, 2H) 6.65-6.75 (m, 2H) 6.36 (dd, J=3.62, 1.86 Hz, 1H) 5.98-6.09 (m, 1H) 3.74-3.84 (m, 6H) 3.49-3.59 (m, 1H) 3.25 (t, J=7.24 Hz, 2H) 2.01-2.17 (m, 1H) 1.72-1.91 (m, 3H) 1.46-1.72 (m, 5H) 1.32 (dt, J=7.14, 3.67 Hz, 1H) 1.09-1.24 (m, 1H). LCMS-ESI (pos.), m/z: 477.0 (M+H)⁺.

Example 201.0. N-(4-(2,6-dimethoxyphenyl)-5-(furan-2-yl)-4H-1,2,4-triazol-3-yl)-2-((4R)-4-methyl-2-oxo-1,3-oxazinan-3-yl)-N-(2-(trimethylsilyl)ethyl)ethanesulfonamide and N-(4-(2,6-dimethoxyphenyl)-5-(furan-2-yl)-4H-1,2,4-triazol-3-yl)-2-((4S)-4-methyl-2-oxo-1,3-oxazinan-3-yl)-N-(2-(trimethylsilyl)ethyl)ethanesulfonamide 201.1

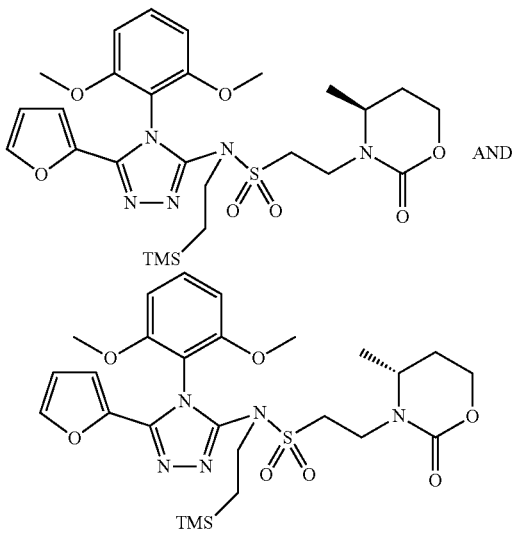

N-(4-(2,6-Dimethoxyphenyl)-5-(furan-2-yl)-4H-1,2,4-triazol-3-yl)-2-((4R)-4-methyl-2-oxo-1,3-oxazinan-3-yl)-N-(2-(trimethylsilyl)ethyl)ethanesulfonamide and N-(4-(2,6-dimethoxyphenyl)-5-(furan-2-yl)-4H-1,2,4-triazol-3-yl)-2-((4S)-4-methyl-2-oxo-1,3-oxazinan-3-yl)-N-(2-(trimethylsilyl)ethyl)ethanesulfonamide, Example 201.1. To a stirred 50 mL RBF was added Example 168.1 (0.280 g, 0.567 mmol) and 4-hydroxy-2-butanone (0.067 mL, 0.681 mmol) in 1,2-dichloroethane (6 mL). The reaction mixture was stirred at RT for 30 min before sodium triacetoxyborohydride (0.24 g, 1.134 mmol) was added. The reaction mixture was then stirred at RT for 1.5 h. The reaction mixture was diluted with water and extracted with DCM. The combined organic layers were washed with brine and dried over Na₂SO₄. The solution was filtered and concentrated in vacuo to give a light-yellow oil. The above product was dissolved in DCM (50 mL) and treated with 1,1'-carbonyldiimidazole (0.138 g, 0.851 mmol) at RT. The reaction mixture was stirred at RT for 2 h. The reaction mixture was then diluted with 1 N HCl and extracted with DCM. The combined organic layers were washed with brine and dried over Na₂SO₄. The solution was filtered and concentrated in vacuo to give a light-yellow oil. The material thus obtained was absorbed onto a plug of silica gel and purified by chromatography through a Redi-Sep pre-packed silica gel column (12 g) eluting with a gradient of 0% to 100% EtOAc in DCM to provide Example 201.1 (0.16 g, 0.270 mmol, 47.7% yield) as a light-yellow glass. LCMS-ESI (pos.), m/z: 592.3 (M+H)⁺.

201.2

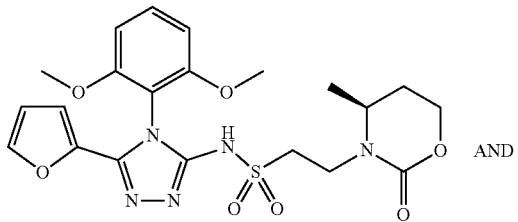

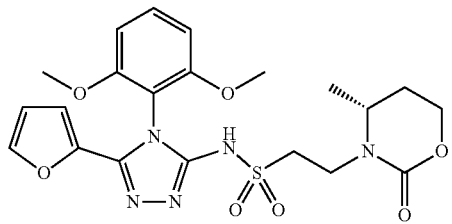

N-(4-(2,6-Dimethoxyphenyl)-5-(2-furanyl)-4H-1,2,4-triazol-3-yl)-2-((4R)-4-methyl-2-oxo-1,3-oxazinan-3-yl)ethanesulfonamide and N-(4-(2,6-dimethoxyphenyl)-5-(2-furanyl)-4H-1,2,4-triazol-3-yl)-2-((4S)-4-methyl-2-oxo-1,3-oxazinan-3-yl)ethanesulfonamide, Example 201.2. Example 201.2 was prepared from Example 201.1 using the procedure described in Example 168.0. ¹H NMR (500 MHz, CDCl₃) δ 7.43-7.50 (m, 2H) 6.68 (dd, J=8.44, 5.50 Hz, 2H) 6.34 (dd, J=3.42, 1.71 Hz, 1H) 5.96-6.03 (m, 1H) 4.28 (td, J=11.00, 2.93 Hz, 1H) 4.17 (dt, J=11.13, 4.22 Hz, 1H) 3.79-3.89 (m, 2H) 3.74-3.79 (m, 6H) 3.45-3.61 (m, 2H) 3.19-3.26 (m, 1H) 2.01-2.12 (m, 1H) 1.56-1.68 (m, 1H) 1.24 (d, J=6.36 Hz, 3H). LCMS-ESI (pos.), m/z: 492.0 (M+H)⁺.

201.0

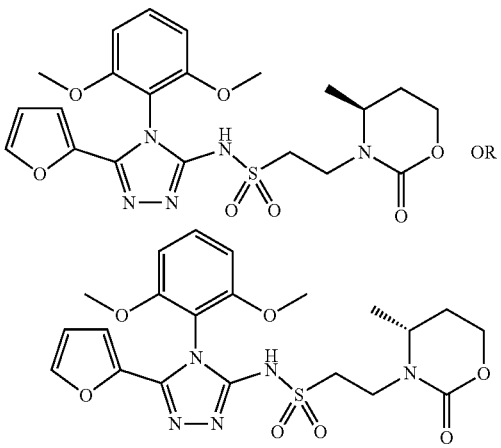

N-(4-(2,6-Dimethoxyphenyl)-5-(2-furanyl)-4H-1,2,4-triazol-3-yl)-2-((4R)-4-methyl-2-oxo-1,3-oxazinan-3-yl)ethanesulfonamide or N-(4-(2,6-dimethoxyphenyl)-5-(2-furanyl)-4H-1,2,4-triazol-3-yl)-2-((4S)-4-methyl-2-oxo-1,3-oxazinan-3-yl)ethanesulfonamide, Example 201.0. Example 201.0 was the first isomer to elute on subjecting Example 201.2 under the following SFC conditions: AD-H (2×25 cm) 25% MeOH (0.1% NH₄OH)/CO₂, 100 bar 70 mL/min, 220 nm. injection volume: 0.5 mL, 18 mg/mL MeOH. LCMS-ESI (pos.), m/z: 492.0 (M+H)⁺.

Example 202.0. Preparation of N-(4-(2,6-dimethoxyphenyl)-5-(2-furanyl)-4H-1,2,4-triazol-3-yl)-2-(2-methoxy-3-pyridinyl)ethanesulfonamide

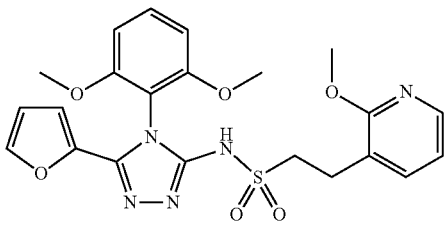

202.0

N-(4-(2,6-Dimethoxyphenyl)-5-(2-furanyl)-4H-1,2,4-triazol-3-yl)-2-(2-methoxy-3-pyridinyl)ethanesulfonamide, Example 202.0. The title compound was prepared using Example 365.0 and 2-methoxynicotinaldehyde following the procedure described in Example 47.0. $^1$H NMR (500 MHz, DMSO-$d_6$) δ 13.37 (s, 1H) 8.04 (dd, J=5.14, 1.71 Hz, 1H) 7.84 (d, J=1.22 Hz, 1H) 7.58 (t, J=8.56 Hz, 1H) 7.51 (dd, J=7.21, 1.59 Hz, 1H) 6.87-6.95 (m, 3H) 6.54 (dd, J=3.67, 1.71 Hz, 1H) 6.04 (d, J=3.42 Hz, 1H) 3.84 (s, 3H) 3.71 (s, 3H) 3.71 (s, 3H) 3.10-3.20 (m, 2H) 2.80-2.90 (m, 2H) LCMS-ESI (pos.) m/z: 486.2 (M+H)$^+$.

Example 203.0. Preparation of (2R)—N-(4-(2,6-dimethoxyphenyl)-5-(2-furanyl)-4H-1,2,4-triazol-3-yl)-1-(3-methoxy-2-pyrazinyl)-2-propanesulfonamide and (2S)—N-(4-(2,6-dimethoxyphenyl)-5-(2-furanyl)-4H-1,2,4-triazol-3-yl)-1-(3-methoxy-2-pyrazinyl)-2-propanesulfonamide

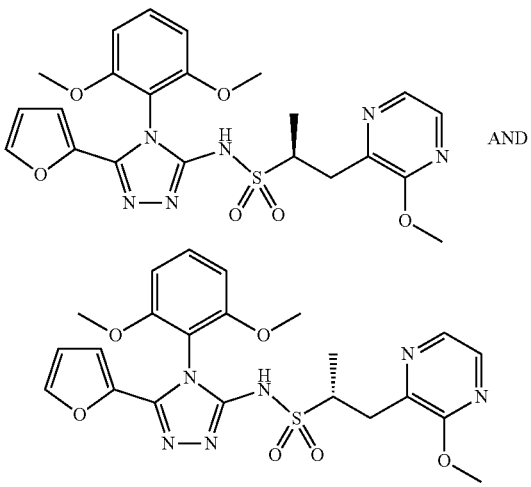

203.0

AND (2R)—N-(4-(2,6-Dimethoxyphenyl)-5-(2-furanyl)-4H-1,2,4-triazol-3-yl)-1-(3-methoxy-2-pyrazinyl)-2-propanesulfonamide and (2S)—N-(4-(2,6-dimethoxyphenyl)-5-(2-furanyl)-4H-1,2,4-triazol-3-yl)-1-(3-methoxy-2-pyrazinyl)-2-propanesulfonamide, Example 203.0. The title compound was prepared using Example 365.0 and 3-methoxypyrazine-2-carbaldehyde following the procedure described in Example 47.0. $^1$H NMR (500 MHz, CD$_3$OD) δ 8.02-8.07 (m, 2H) 7.60-7.63 (m, 1H) 7.57 (t, J=8.44 Hz, 1H) 6.86 (dd, J=8.56, 4.65 Hz, 2H) 6.45 (dd, J=3.55, 1.83 Hz, 1H) 6.15 (d, J=3.67 Hz, 1H) 3.97 (s, 3H) 3.78 (s, 3H) 3.76 (s, 3H) 3.69 (ddd, J=10.45, 6.79, 3.79 Hz, 1H) 3.48 (dd, J=14.67, 3.67 Hz, 1H) 2.85-2.91 (m, 1H) 1.23 (d, J=6.85 Hz, 3H). LCMS-ESI (pos.), m/z: 501.2 (M+H)$^+$.

Example 204.0. Preparation of N-(4-(2,6-dimethoxyphenyl)-5-(5-methyl-2-furanyl)-4H-1,2,4-triazol-3-yl)-2-((6S)-3,6-dimethyl-2-oxotetrahydro-1(2H)-pyrimidinyl)ethanesulfonamide Ethanesulfonamide or N-(4-(2,6-dimethoxyphenyl)-5-(5-methyl-2-furanyl)-4H-1,2,4-triazol-3-yl)-2-((6R)-3,6-dimethyl-2-oxotetrahydro-1(2H)-pyrimidinyl)ethanesulfonamide

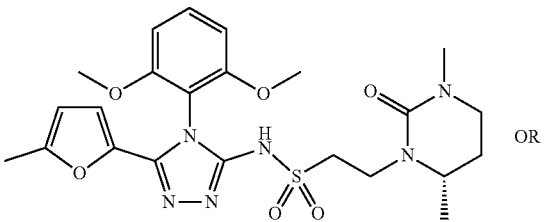

204.0

OR

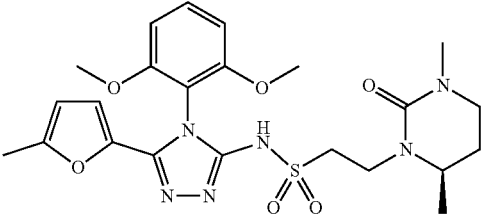

N-(4-(2,6-Dimethoxyphenyl)-5-(5-methyl-2-furanyl)-4H-1,2,4-triazol-3-yl)-2-((6S)-3,6-dimethyl-2-oxotetrahydro-1 (2H)-pyrimidinyl)ethanesulfonamide ethanesulfonamide or N-(4-(2,6-dimethoxyphenyl)-5-(5-methyl-2-furanyl)-4H-1,2,4-triazol-3-yl)-2-((6R)-3,6-dimethyl-2-oxotetrahydro-1(2H)-pyrimidinyl)ethanesulfonamide, Example 204.0. Example 204.0 was the second peak to elute from an AD-H column (or CC$_4$ or Lux2 column) by SFC chiral separation of Example 160.0 under the conditions described in Example 164.0. $^1$H NMR (500 MHz, CD$_3$OD) δ 7.57 (t, J=8.56 Hz, 1H) 6.87 (d, J=8.56 Hz, 2H) 6.02-6.06 (m, 1H) 5.96 (d, J=3.42 Hz, 1H) 3.83-3.91 (m, 1H) 3.82 (s, 3H) 3.81 (s, 3H) 3.57-3.65 (m, 1H) 3.39-3.49 (m, 1H) 3.30-3.39 (m, 2H) 3.13-3.26 (m, 2H) 2.90 (s, 3H) 2.28 (s, 3H) 2.07 (ddt, J=13.36, 11.71, 5.32, 5.32 Hz, 1H) 1.62-1.72 (m, 1H) 1.16 (d, J=6.60 Hz, 3H). LCMS-ESI (pos.), m/z: 519.1 (M+H)$^+$.

Example 205.0. Preparation of (2R)-1-(4-chlorophenyl)-N-(4-(2,6-dimethoxyphenyl)-5-(2-furanyl)-4H-1,2,4-triazol-3-yl)-2-propanesulfonamide or (2S)-1-(4-chlorophenyl)-N-(4-(2,6-dimethoxyphenyl)-5-(2-furanyl)-4H-1,2,4-triazol-3-yl)-2-propanesulfonamide

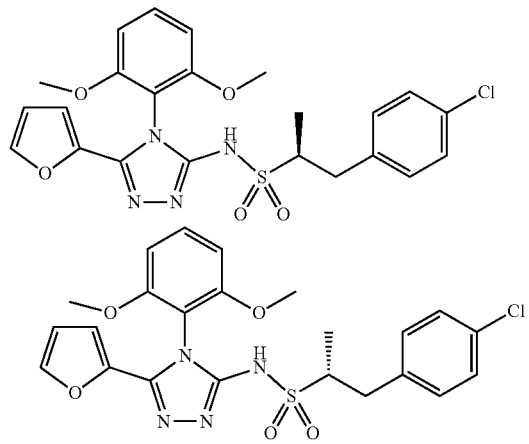

205.0

(2R)-1-(4-Chlorophenyl)-N-(4-(2,6-dimethoxyphenyl)-5-(2-furanyl)-4H-1,2,4-triazol-3-yl)-2-propanesulfonamide or (2S)-1-(4-chlorophenyl)-N-(4-(2,6-dimethoxyphenyl)-5-(2-furanyl)-4H-1,2,4-triazol-3-yl)-2-propanesulfonamide, Example 205.0. Example 205.0 was the first isomer to elute by subjecting Example 208.0 to an AD column under the following SFC separation conditions: 250×30 mm AD column with 50 g/min IPA+50 g/min $CO_2$ on Thar 350 SFC. Outlet pressure=100 bar; Temp.=22° C.; Wavelength=272 nM. Used 0.7 mL injections of 80 mg/6 mL (13.3 mg/mL) sample solution in MeOH, i.e. 9.3 mg/injection. Run time=10 min.; Cycle time=6 min. $^1$H NMR (500 MHz, $CDCl_3$) δ 10.69-11.18 (br s, 1H) 7.39-7.59 (m, 2H) 7.27-7.29 (m, 2H) 7.05-7.13 (m, 2H) 6.70 (d, J=8.56 Hz, 2H) 6.35 (dd, J=3.42, 1.71 Hz, 1H) 6.00 (d, J=3.67 Hz, 1H) 3.77 (s, 3H) 3.74 (s, 3H) 3.47 (dd, J=13.45, 3.18 Hz, 1H) 3.15-3.24 (m, 1H) 2.58 (dd, J=13.57, 11.37 Hz, 1H) 1.21 (d, J=6.85 Hz, 3H). LCMS-ESI (pos.) m/z: 503.0 (M+H)$^+$.

Example 206.0. Preparation of (3S)—N-(4-(2,6-dimethoxyphenyl)-5-(2-furanyl)-4H-1,2,4-triazol-3-yl)-1-(5-fluoro-2-pyrimidinyl)-3-piperidinesulfonamide

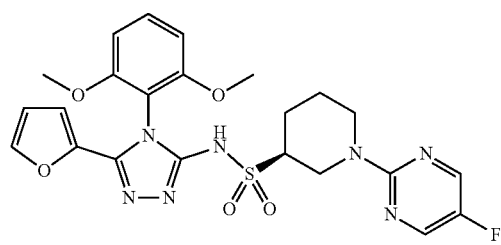

206.1

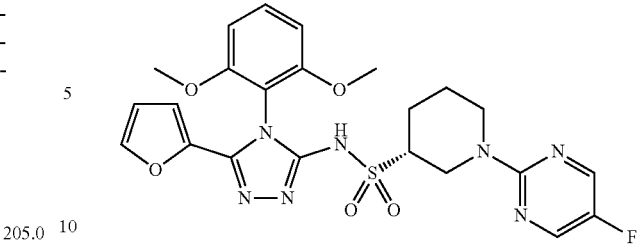

206.0

(3R)—N-(4-(2,6-Dimethoxyphenyl)-5-(2-furanyl)-4H-1,2,4-triazol-3-yl)-1-(5-fluoro-2-pyrimidinyl)-3-piperidinesulfonamide and (3S)—N-(4-(2,6-dimethoxyphenyl)-5-(2-furanyl)-4H-1,2,4-triazol-3-yl)-1-(5-fluoro-2-pyrimidinyl)-3-piperidinesulfonamide, Example 206.1. Example 206.1 was prepared from Example 364.1 and Example 179.2 using the procedure described in Example 94.0. This provided the title compound, Example 206.1 (164 mg, 42.4% yield), as an off-white solid. $^1$H NMR (500 MHz, $CD_2Cl_2$) δ 1.53 (dt, J=12.76, 4.18 Hz, 1H) 1.72-1.91 (m, 2H) 2.23-2.32 (m, 1H) 2.84 (td, J=12.76, 2.64 Hz, 1H) 2.96-3.10 (m, 2H) 3.81 (d, J=7.04 Hz, 7H) 4.59-4.71 (m, 1H) 4.99-5.10 (m, 1H) 6.08 (dd, J=3.52, 0.59 Hz, 1H) 6.40 (dd, J=3.52, 1.76 Hz, 1H) 6.79 (d, J=8.61 Hz, 2H) 7.53 (dd, J=1.76, 0.78 Hz, 1H) 7.58 (t, J=8.51 Hz, 1H) 8.24 (d, J=0.59 Hz, 2H). LCMS-ESI (pos.), m/z: 530.2 (M+H)$^+$.

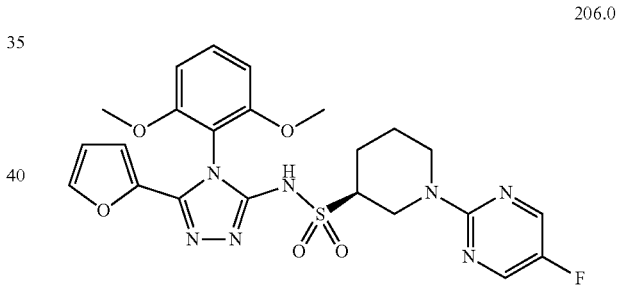

(3S)—N-(4-(2,6-Dimethoxyphenyl)-5-(2-furanyl)-4H-1,2,4-triazol-3-yl)-1-(5-fluoro-2-pyrimidinyl)-3-piperidinesulfonamide, Example 206.0. Example 206.0 was obtained by the SFC chiral separation of Example 206.1 and was the second enantiomer to elute from an AS-H column under the following conditions: 250 mm×30 mm AS-H column with 36 g/min MeOH (20 mM Ammonia)+44 g/min $CO_2$ on Thar 80 SFC. Outlet pressure=100 bar; Temp.=26° C.; Wavelength=215 nm. Used 1 mL injections of 3.75 mg/mL Example 206.1 solution in MeOH/DCM (50% DCM), i.e. 37.5 mg/injection. Run time=9 min, cycle time 8 min. $^1$H NMR (500 MHz, $CD_2Cl_2$) δ 8.23 (s, 2H) 7.57 (t, J=8.56 Hz, 1H) 7.53 (s, 1H) 6.79 (d, J=8.56 Hz, 2H) 6.39 (br. s., 1H) 6.08 (d, J=2.93 Hz, 1H) 4.97-5.11 (m, 1H) 4.64 (d, J=12.72 Hz, 1H) 3.81 (s, 3H) 3.80 (s, 3H) 2.97-3.09 (m, 2H) 2.83 (t, J=11.74 Hz, 1H) 2.28 (d, J=13.45 Hz, 1H) 1.71-1.90 (m, 2H) 1.43-1.59 (m, 1H). LCMS-ESI (pos.), m/z: 530.2 (M+H)$^+$.

Example 207.0. Preparation of N-(4-(2,6-dimethoxyphenyl)-5-(2-furanyl)-4H-1,2,4-triazol-3-yl)-2-(4-fluorophenyl)ethanesulfonamide

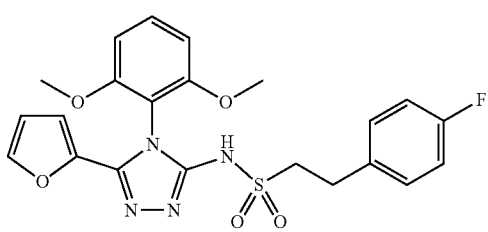

207.0

N-(4-(2,6-Dimethoxyphenyl)-5-(2-furanyl)-4H-1,2,4-triazol-3-yl)-2-(4-fluorophenyl)ethanesulfonamide, Example 207.0. Example 207.0 was prepared from Example 362.03 and 2-(4-fluorophenyl)ethanesulfonyl chloride using the procedure described in Example 1.1. $^1$H NMR (500 MHz, CD$_2$Cl$_2$) δ 10.94 (br. s., 1H) 7.58 (t, J=8.56 Hz, 1H) 7.53 (dd, J=1.71, 0.73 Hz, 1H) 7.18 (t, J=6.39 Hz, 2H) 6.99-7.06 (m, 2H) 6.79 (d, J=8.56 Hz, 2H) 6.40 (s, 1H) 6.08 (d, J=3.60 Hz, 1H) 3.78-3.80 (m, 6H) 3.23-3.28 (m, 2H) 3.03-3.10 (m, 2H). LCMS-ESI (pos.) m/z: 473.1 (M+H)$^+$.

Example 208.0. Preparation of (2R)-1-(4-chlorophenyl)-N-(4-(2,6-dimethoxyphenyl)-5-(2-furanyl)-4H-1,2,4-triazol-3-yl)-2-propanesulfonamide and (2S)-1-(4-chlorophenyl)-N-(4-(2,6-dimethoxyphenyl)-5-(2-furanyl)-4H-1,2,4-triazol-3-yl)-2-propanesulfonamide

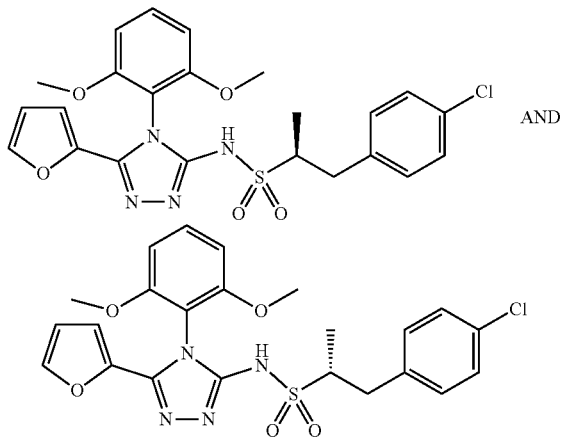

208.0

AND (2R)-1-(4-Chlorophenyl)-N-(4-(2,6-dimethoxyphenyl)-5-(2-furanyl)-4H-1,2,4-triazol-3-yl)-2-propanesulfonamide and (2S)-1-(4-chlorophenyl)-N-(4-(2,6-dimethoxyphenyl)-5-(2-furanyl)-4H-1,2,4-triazol-3-yl)-2-propanesulfonamide, Example 208.0. To a stirred suspension of Example 362.03 (2.77 g, 9.68 mmol) in THF (40.0 mL) at −78° C. was added dropwise potassium bis(trimethylsilyl)amide in THF (1.0M, 33.9 mL). The reaction mixture was warmed up to −20° C. for 30 min. A solution of 1-(4-chlorophenyl)propane-2-sulfonyl chloride (commercially available from Synchem, Inc., IL USA, 7.35 g, 29.0 mmol) in THF (10.0 mL) was added dropwise into the reaction mixture at −20° C., and the mixture was stirred for 30 min. More 1-(4-chlorophenyl)propane-2-sulfonyl chloride (7.35 g, 29.0 mmol) in THF (10 mL) was injected dropwise, and the reaction was stirred at −20° C. for another 30 min. The reaction was then quenched with a saturated aqueous solution of NH$_4$Cl (100 mL) and then it was extracted with DCM (3×100 mL). The combined organic layers were dried over Na$_2$SO$_4$, filtered and concentrated. The product was triturated with 5% EtOAc in hexanes three times. The residue was redissolved in DCM and purified by a 125 g silica gel column (0-20% EtOAc in DCM) to provide the title compound (2.22 g, 4.41 mmol, 46% yield) as a white powder. $^1$H NMR (400 MHz, DMSO-d$_6$) δ 13.30 (s, 1H) 7.83 (dd, J=1.76, 0.59 Hz, 1H) 7.57 (t, J=8.51 Hz, 1H) 7.32-7.38 (m, 2H) 7.19 (m, J=8.41 Hz, 2H) 6.90 (d, J=8.61 Hz, 2H) 6.52 (dd, J=3.62, 1.86 Hz, 1H) 6.03 (dd, J=3.62, 0.49 Hz, 1H) 3.72 (s, 3H) 3.71 (s, 3H) 3.23 (dd, J=13.30, 3.13 Hz, 1H) 3.14 (ddd, J=10.66, 6.94, 3.33 Hz, 1H) 2.44 (dd, J=13.30, 11.15 Hz, 1H) 1.00 (d, J=6.65 Hz, 3H). LCMS-ESI (pos.) m/z: 503.0 (M+H)$^+$.

Example 209.0. Preparation of 2-(4-chlorophenyl)-N-(5-(2-furanyl)-4-(2-methoxyphenyl)-4H-1,2,4-triazol-3-yl)ethanesulfonamide

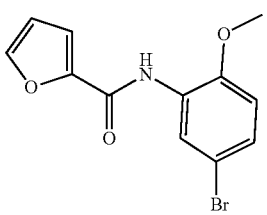

209.1

N-(5-Bromo-2-methoxyphenyl)furan-2-carboxamide, Example 209.1. To a stirred 100 mL RBF was added 5-bromo-2-methoxyaniline (7 g, 34.6 mmol) and DIEA (12.05 mL, 69.3 mmol) in DCM (100 mL). At 0° C., furan-2-carbonyl chloride (3.41 mL, 34.6 mmol) was added dropwise. The reaction mixture was stirred at 0° C. and allowed to warm to RT overnight. The reaction mixture was diluted with water and extracted with DCM. The combined organic layers were washed with brine and dried over MgSO$_4$. The solution was filtered and concentrated in vacuo. The sample was preloaded on silica and purified with flash chromatography on a CombiFlash silica gel column (80 g, Teledyne Isco, gradient 20% EtOAc in hexanes) to give Example 209.1. LCMS (ESI) m/z=297 [M+H]$^+$.

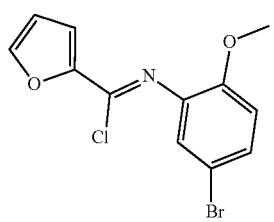

209.2

(Z)—N-(5-Bromo-2-methoxyphenyl)furan-2-carbimidoyl, Example 209.2. To a stirred 500 mL RBF containing Example 209.1 (9.4 g, 31.7 mmol) was added sulfurous dichloride (23.16 mL, 317 mmol) dropwise. The reaction mixture was then stirred at 80° C. for 20 h. The reaction mixture was then concentrated in vacuo to give of Example 209.2 as a tan oil. LCMS (ESI) m/z=315 [M+H]⁺.

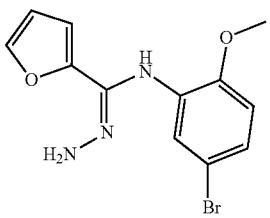

209.3

(Z)—N'-(5-Bromo-2-methoxyphenyl)furan-2-carboximidhydrazide, Example 209.3. To a stirred 500 mL RBF was added hydrazine (19.96 mL, 636 mmol) in toluene (79 mL) at 0° C. followed by dropwise addition of Example 209.2 (10 g, 31.8 mmol) in toluene (79 mL). The reaction mixture was then stirred at RT for 20 h. The reaction mixture was diluted with water and extracted with Et₂O. The combined organic layers were washed with a saturated solution of NaHCO₃ and brine and dried over MgSO₄. The solution was filtered and concentrated in vacuo to give of Example 209.3 as a yellow powder. LCMS (ESI) m/z=311 [M+H]⁺.

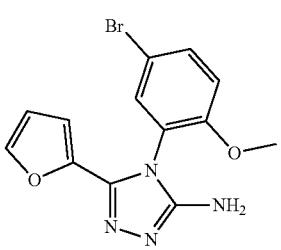

209.4

4-(5-Bromo-2-methoxyphenyl)-5-(furan-2-yl)-4H-1,2,4-triazol-3-amine, Example 209.4. To a stirred 500 mL RBF was added Example 209.3 (4.4 g, 14.19 mmol) followed by dropwise addition of cyanogen bromide (2.84 mL, 14.19 mmol) in MeOH (80 mL). The reaction mixture was stirred at 86° C. for 20 h. The material was then absorbed onto a plug of silica gel and purified by chromatography through a Redi-Sep pre-packed silica gel column (120 g, gold) eluting with a gradient of 60% to 100% EtOAc in DCM to provide the title compound, Example 209.4. LCMS (ESI) m/z=366 [M+H]⁺.

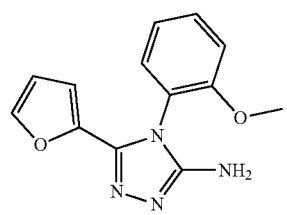

209.5

5-(Furan-2-yl)-4-(2-methoxyphenyl)-4H-1,2,4-triazol-3-amine, Example 209.5. Example 209.4 (1.0 g, 2.98 mmol) was placed in 250 mL flask and dissolved in EtOH. Pd on carbon (10% wt.) was added, and the reaction was stirred under an atmosphere of H₂ for 3 h. The sample was filtered through a pad of Celite® brand filter aid (Celpure P300, USP-NF, Pharmaceutical Grade) and concentrated in vacuo yielding the title compound, Example 209.5. LCMS (ESI) m/z=257 [M+H]⁺.

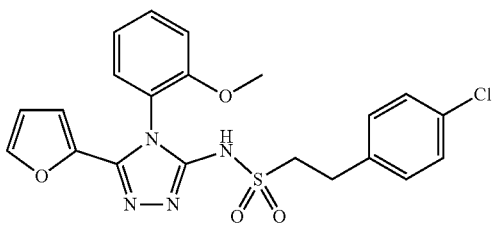

209.0

2-(4-Chlorophenyl)-N-(5-(2-furanyl)-4-(2-methoxyphenyl)-4H-1,2,4-triazol-3-yl)ethanesulfonamide, Example 209.0. Example 209.0 was prepared from Example 209.5 and 2-(4-chlorophenyl)ethanesulfonyl chloride using the procedure described in Example 1.1. ¹H NMR (400 MHz, DMSO-d₆) δ 7.83 (1H, d, J=1.6 Hz), 7.57-7.64 (1H, m), 7.50 (1H, dd, J=7.7, 1.5 Hz), 7.21-7.39 (5H, m), 7.16 (1H, t, J=7.6 Hz), 6.52 (1H, dd, J=3.4, 1.7 Hz), 5.98 (1H, d, J=3.5 Hz), 3.70 (3H, s), 3.17-3.27 (2H, m), 2.91 (2H, t, J=8.1 Hz). LCMS (ESI) m/z=459 [M+H]⁺.

Example 210.0. Preparation of 2-(2-cyano-4-fluorophenyl)-N-(4-(2,6-dimethoxyphenyl)-5-(2-furanyl)-4H-1,2,4-triazol-3-yl)ethanesulfonamide

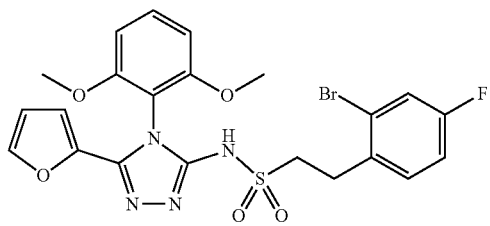

210.1

2-(2-Bromo-4-fluorophenyl)-N-(4-(2,6-dimethoxyphenyl)-5-(2-furanyl)-4H-1,2,4-triazol-3-yl)ethanesulfonamide, Example 210.1. Example 210.1 was prepared from Example 362.03 and 2-(2-bromo-4-fluorophenyl)ethanesulfonyl chloride (commercially available from SynChem, IL, US) using the procedure described in Example 1.1. LCMS-ESI (pos.) m/z: 551.0 (M+H)⁺. ¹H NMR (400 MHz, DMSO-d₆) δ 13.42 (s, 1H) 7.83 (dd, J=1.76, 0.59 Hz, 1H) 7.48-7.63 (m, 2H) 7.35 (dd, J=8.61, 6.06 Hz, 1H) 7.13-7.28 (m, 1H) 6.90 (d, J=8.61 Hz, 2H) 6.53 (dd, J=3.52, 1.76 Hz, 1H) 6.02 (dd, J=3.52, 0.59 Hz, 1H) 3.71 (s, 3H) 3.71 (s, 3H) 3.07-3.21 (m, 2H) 2.88-3.05 (m, 2H).

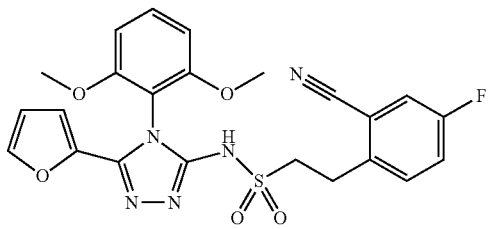

2-(2-Cyano-4-fluorophenyl)-N-(4-(2,6-dimethoxyphenyl)-5-(2-furanyl)-4H-1,2,4-triazol-3-yl)ethanesulfonamide, Example 210.0. To a 500 mL RBF was added Example 210.1 (14.61 g, 26.5 mmol), zinc cyanide (3.73 g, 31.8 mmol) and bis(tri-tert-butylphosphine)palladium (0) (1.625 g, 3.18 mmol) in dry DMAc (200 mL) under $N_2$. The flask was then sealed with a septum. The flask was placed under vacuum and back-filled with $N_2$ three times. The reaction mixture was then stirred at 110° C. in a pre-heated oil bath for 20 h. LCMS analysis indicated the reaction was complete. The reaction mixture was allowed to cool to RT. The solution was filtered through a Celite® brand filter aid pad and concentrated under high vacuum to give a light-yellow oil. The reaction mixture was diluted with water and extracted with DCM. The combined organic layers were washed with brine and dried over $Na_2SO_4$. The solution was filtered and concentrated in vacuo to give the title compound (12.85 g, 25.8 mmol, 97% yield) as an off-white solid. This was triturated with EtOAc to afford Example 210.0 as a white solid. $^1$H NMR (400 MHz, CDCl$_3$) δ 10.97 (br. s., 1H) 7.45-7.65 (m, 2H) 7.41 (dd, J=8.61, 5.09 Hz, 1H) 7.19-7.36 (m, 2H) 6.71 (d, J=8.61 Hz, 2H) 6.35 (dd, J=3.42, 1.66 Hz, 1H) 6.03 (d, J=3.33 Hz, 1H) 3.70-3.85 (m, 6H) 3.21-3.42 (m, 4H). LCMS-ESI (pos.), m/z: 498.2 (M+H)$^+$.

The compounds set forth in the following table were synthesized following the procedure in Example 127.0 using the starting materials as described.

TABLE 8

| Example | Reagents | Structure, Name and Data |
|---|---|---|
| 211.0 | 3-bromo-4-(2,6-dimethoxyphenyl)-5-(5-methylfuran-2-yl)-4H-1,2,4-triazole (Example 364.1), (1R,2R)-1-(5-fluoropyrimidin-2-yl)-1-hydroxypropane-2-sulfonamide and (1S,2S)-1-(5-fluoropyrimidin-2-yl)-1-hydroxypropane-2-sulfonamide (Example 355.0) and (1S,2R)-1-(5-fluoropyrimidin-2-yl)-1-hydroxypropane-2-sulfonamide and (1S,2R)-1-(5-fluoropyrimidin-2-yl)-1-hydroxypropane-2-sulfonamide (Example 355.1). Chiral Purification by SFC, first stage: Run on Thar 80 SFC with 250 x 30 mm OJ-H column with 11 g/min MeOH(neat)) + 59 g/min CO$_2$, 16% co-solvent at 70 g/min. Outlet pressure = 100 bar; Temp. = 21° C.; Wavelength = 275 nm. Manually injected 0.7 mL of a solution from 47 mg sample dissolved in 4.0 mL of MeOH, c = 11.8 mg/mL; 8.2 mg per injection to deliver Peak 1, of purification of major set of diastereomers. | (1S,2R)-N-(4-(2,6-dimethoxyphenyl)-5-(5-methylfuran-2-yl)-4H-1,2,4-triazol-3-yl)-1-(5-fluoropyrimidin-2-yl)-1-hydroxypropane-2-sulfonamide. $^1$H NMR (400 MHz, CD$_3$OD) δ 8.65 (s, 2 H) 7.55 (t, J = 8.61 Hz, 1 H) 6.84 (d, J = 8.61 Hz, 2 H) 6.03 (d, J = 2.54 Hz, 1 H) 5.94 (d, J = 3.13 Hz, 1 H) 5.41 (s, 1 H) 4.59 (s, 1 H) 3.77 (app s, 6 H) 2.34 (s, 3 H) 2.28 (s, 3 H). LCMS ESI (pos.) m/z: 515.1 (M + H)$^+$. |
| 115.0 | 3-bromo-4-(2,6-dimethoxyphenyl)-5-(5-methylfuran-2-yl)-4H-1,2,4-triazole (Example 364.1), (1R,2R)-1-(5-fluoropyrimidin-2-yl)-1-hydroxypropane-2-sulfonamide and (1S,2S)-1-(5-fluoropyrimidin-2-yl)-1-hydroxypropane-2-sulfonamide (Example 355.0) and (1S,2R)-1-(5-fluoropyrimidin-2-yl)-1-hydroxypropane-2-sulfonamide and (1S,2R)-1-(5-fluoropyrimidin-2-yl)-1-hydroxypropane-2-sulfonamide (Example 355.1). Chiral Purification by SFC, first stage: Run on Thar 80 SFC with 250 x 30 mm OJ-H column with 11 g/min MeOH(neat)) + 59 g/min CO$_2$, 16% co-solvent at 70 g/min. Outlet pressure = 100 bar; Temp. = 21° C.; Wavelength = 275 nm. Manually injected 0.7 mL of a solution from 47 mg sample dissolved in 4.0 mL of MeOH, c = 11.8 mg/mL; 8.2 mg per injection to deliver Peak 2, only the major set of diastereomers were purified. | (1R,2S)-N-(4-(2,6-dimethoxyphenyl)-5-(5-methylfuran-2-yl)-4H-1,2,4-triazol-3-yl)-1-(5-fluoropyrimidin-2-yl)-1-hydroxypropane-2-sulfonamide. $^1$H NMR (400 MHz, CD$_3$OD) δ 8.64 (s, 2 H) 7.55 (t, J = 8.61 Hz, 1 H) 6.84 (d, J = 8.61 Hz, 1 H) 6.02 (d, J = 2.74 Hz, 1 H) 5.93 (d, J = 2.93 Hz, 1 H) 5.40 (s, 1 H) 4.59 (s, 1 H) 3.77 (app s, 6 H) 2.34 (s, 1 H) 2.27 (s, 1 H). LCMS ESI (pos.) m/z: 515.1 (M + H)$^+$. |

TABLE 8-continued

| Example | Reagents | Structure, Name and Data |
|---|---|---|
| 212.0 | 3-bromo-4-(2,6-dimethoxyphenyl)-5-(5-methylfuran-2-yl)-4H-1,2,4-triazole (Example 364.1), (1R,2R)-1-(5-chloropyrimidin-2-yl)-1-hydroxypropane-2-sulfonamide and (1S,2S)-1-(5-chloropyrimidin-2-yl)-1-hydroxypropane-2-sulfonamide and (1S,2R)-1-(5-chloropyrimidin-2-yl)-1-hydroxypropane-2-sulfonamide and (1R,2S)-1-(5-chloropyrimidin-2-yl)-1-hydroxypropane-2-sulfonamide. This material was prepared in analogous fashion to that described in Example 355.0 employing 5-chloropyrimidine-2-carbaldehyde.<br>Preparative SFC method: Column: Chiralpak AD-H (250 x 21 mm, 5 µm) Mobile Phase: 50:50 (A:B), A: Liquid CO2, B: EtOH, Flow Rate: 50 mL/min, 220 nm, 3 mg/injection to deliver Peak 2, only the major set of diastereomers were purified. . | 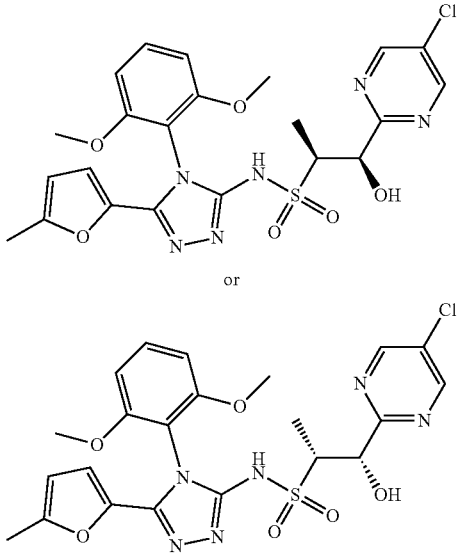 [SMILES: COc1cccc(OC)c1-n1c(NS(=O)(=O)[C@@H](C)[C@H](O)c2ncc(Cl)cn2)nnc1-c1ccc(C)o1 ; COc1cccc(OC)c1-n1c(NS(=O)(=O)[C@H](C)[C@@H](O)c2ncc(Cl)cn2)nnc1-c1ccc(C)o1]<br>(1R,2S)-1-(5-chloro-2-pyrimidinyl)-N-(4-(2,6-dimethoxyphenyl)-5-(5-methyl-2-furanyl)-4H-1,2,4-triazol-3-yl)-1-hydroxy-2-propanesulfonamide or (1S,2R)-1-(5-chloro-2-pyrimidinyl)-N-(4-(2,6-dimethoxyphenyl)-5-(5-methyl-2-furanyl)-4H-1,2,4-triazol-3-yl)-1-hydroxy-2-propanesulfonamide.<br>$^1$H NMR (400 MHz, CD$_3$OD) δ 8.84 (s, 2H), 7.58 (dd, J = 8.5, 8.5 Hz, 1H), 6.87 (d, J = 8.6 Hz, 2H), 6.60 (d, J = 3.5 Hz, 1H), 5.99 (d, J = 3.3 Hz, 1H), 5.39 (d, J = 3.5 Hz, 1H), 3.81 (s, 3H), 3.80 (s, 3H), 2.75-2.78 (m, 1H), 2.29 (s, 3H), 1.26 (d, J = 6.8 Hz, 3H). LCMS ESI (pos.) m/z: 535.1 (M + H)$^+$. |
| 213.0 | 3-bromo-4-(2,6-dimethoxyphenyl)-5-(5-methylfuran-2-yl)-4H-1,2,4-triazole (Example 364.1), (1R,2S)-1-hydroxy-1-(5-methylpyrazin-2-yl)propane-2-sulfonamide and (1S,2S)-1-hydroxy-1-(5-methylpyrazin-2-yl)propane-2-sulfonamide and (1R,2R)-1-hydroxy-1-(5-methylpyrazin-2-yl)propane-2-sulfonamide and (1S,2S)-1-hydroxy-1-(5-methylpyrazin-2-yl)propane-2-sulfonamide. This material was prepared in analogous fashion to that described in Example 355.0 employing 5-methylpyrazine-2-carbaldehyde.<br>Preparative SFC method: Column: Chiralpak AS-H (250 x 21 mm, 5 µm), Mobile Phase: 80:20 (A:B), A: Liquid CO2, B: MeOH, Flow Rate: 70 mL/min, 220 nm, 22.4 mg/injection to deliver Peak 1, only the major set of diastereomers were purified. | 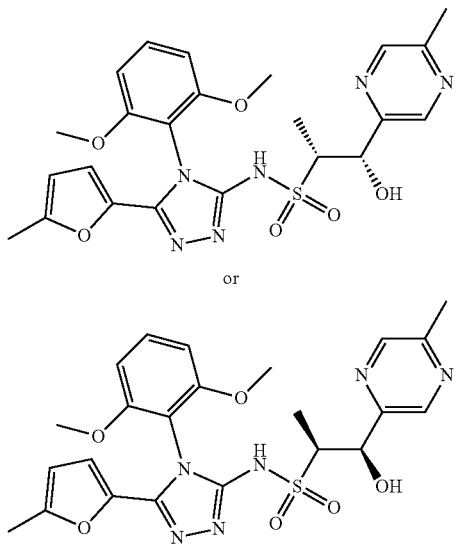<br>(1S,2R)-N-(4-(2,6-dimethoxyphenyl)-5-(5-methyl-2-furanyl)-4H-1,2,4-triazol-3-yl)-1-hydroxy-1-(5-methyl-2-pyrazinyl)-2-propanesulfonamide or (1R,2S)-N-(4-(2,6-dimethoxyphenyl)-5-(5-methyl-2-furanyl)-4H-1,2,4-triazol-3-yl)-1-hydroxy-1-(5-methyl-2-pyrazinyl)-2-propanesulfonamide.<br>$^1$H NMR (500 MHz, CD$_3$OD) δ 8.59 (s, 1H), |

TABLE 8-continued

| Example | Reagents | Structure, Name and Data |
|---|---|---|
| | | 8.51 (s, 1H), 7.6 (dd, J = 8.6, 8.6 Hz, 1H), 6.89 (dd, J = 8.6, 4.3 Hz, 2H), 6.6 (d, J = 4.0 Hz, 1H), 6.01 (d, J = 4.0 Hz, 1H), 5.42 (br s, 1H), 3.82 (s, 3H), 3.80 (s, 3H), 3.64-3.70 (m, 1H), 2.58 (s, 3H), 2.30 (s, 3H), 1.19 (d, J = 6.8 Hz, 3H). LCMS ESI (pos.) m/z: 515.2 (M + H)+. |
| 216.0 | 3-bromo-4-(2,6-dimethoxyphenyl)-5-(5-methylfuran-2-yl)-4H-1,2,4-triazole (Example 364.1), (1R,2R)-1-(5-chloropyrimidin-2-yl)-1-hydroxypropane-2-sulfonamide and (1S,2S)-1-(5-chloropyrimidin-2-yl)-1-hydroxypropane-2-sulfonamide and (1S,2R)-1-(5-chloropyrimidin-2-yl)-1-hydroxypropane-2-sulfonamide and (1R,2S)-1-(5-chloropyrimidin-2-yl)-1-hydroxypropane-2-sulfonamide. This material was prepared in analogous fashion to that described in Example 355.0 employing 5-chloropyrimidine-2-carbaldehyde. Preparative SFC method: Column: Chiralpak AD-H (250 x 21 mm, 5 μm) Mobile Phase: 50:50 (A:B), A: Liquid CO2, B: EtOH, Flow Rate: 50 mL/min, 220 nm, 3 mg/injection to deliver Peak 1, only the major set of diastereomers were purified. | or<br><br>(1R,2S)-1-(5-chloro-2-pyrimidinyl)-N-(4-(2,6-dimethoxyphenyl)-5-(5-methyl-2-furanyl)-4H-1,2,4-triazol-3-yl)-1-hydroxy-2-propanesulfonamide or (1S,2R)-1-(5-chloro-2-pyrimidinyl)-N-(4-(2,6-dimethoxyphenyl)-5-(5-methyl-2-furanyl)-4H-1,2,4-triazol-3-yl)-1-hydroxy-2-propanesulfonamide.<br>1H NMR (400 MHz, CD3OD ) δ 8.84 (s, 2H), 7.58 (dd, J = 8.5, 8.5 Hz, 1H), 6.87 (d, J = 8.6 Hz, 2H), 6.05-7.06 (m, 1H), 5.98 (d, J = 3.3 Hz, 1H), 5.4 (d, J = 3.3 Hz, 1H), 3.80 (s, 3H), 3.80 (s, 3H), 3.75-3.78 (m, 1H), 2.29 (s, 3H), 1.26 (d, J = 6.8 Hz, 3H). LCMS ESI (pos.) m/z: 535.1 (M + H)+. |
| 217.0 | 3-bromo-4-(2,6-dimethoxyphenyl)-5-(5-methylfuran-2-yl)-4H-1,2,4-triazole (Example 364.1), (2S,3R)-3-hydroxy-3-(5-methylpyrimidin-2-yl)butane-2-sulfonamide and (2R,3R)-3-hydroxy-3-(5-methylpyrimidin-2-yl)butane-2-sulfonamide and (2S,3S)-3-hydroxy-3-(5-methylpyrimidin-2-yl)butane-2-sulfonamide and (2R,3S)-3-hydroxy-3-(5-methylpyrimidin-2-yl)butane-2-sulfonamide prepared employing 1-(5-methylpyrimidin-2-yl)ethanone and Example 361.0 following procedures described in Example 10.0. Preparative SFC method: 35 g/min EtOH(neat) + 65 g/min CO2 on 250 x 30 mm AS-H column. Outlet pressure = 100 bar, Temp. = 20° C., Wavelength = 275 nm. Used 0.6 mL injections of 16 mg sample in 4 mL MeOH/DCM 1:1 (c = 4 mg/mL), resulting in 2.4 mg/injection. Run time 7.0 min., cycle time = 5.0 min to deliver Peak 1, only the major set of diastereomers were purified. | or<br><br>or |

TABLE 8-continued

| Example | Reagents | Structure, Name and Data |
|---|---|---|
| | | 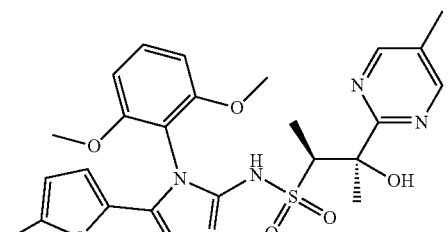<br>or<br>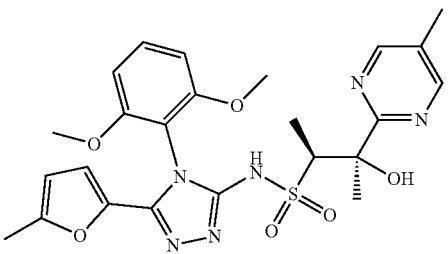<br>(2S,3S)-N-(4-(2,6-dimethoxyphenyl)-5-(5-methyl-2-furanyl)-4H-1,2,4-triazol-3-yl)-3-hydroxy-3-(5-methyl-2-pyrimidinyl)-2-butanesulfonamide or (2R,3S)-N-(4-(2,6-dimethoxyphenyl)-5-(5-methyl-2-furanyl)-4H-1,2,4-triazol-3-yl)-3-hydroxy-3-(5-methyl-2-pyrimidinyl)-2-butanesulfonamide or (2S,3R)-N-(4-(2,6-dimethoxyphenyl)-5-(5-methyl-2-furanyl)-4H-1,2,4-triazol-3-yl)-3-hydroxy-3-(5-methyl-2-pyrimidinyl)-2-butanesulfonamide or (2R,3R)-N-(4-(2,6-dimethoxyphenyl)-5-(5-methyl-2-furanyl)-4H-1,2,4-triazol-3-yl)-3-hydroxy-3-(5-methyl-2-pyrimidinyl)-2-butanesulfonamide.<br>$^1$H NMR (400 MHz, CD$_3$OD) δ 8.65 (s, 2 H) 7.58 (t, J = 8.61 Hz, 1 H) 6.87 (dd, J = 8.61, 0.98 Hz, 2 H) 6.04 (dd, J = 3.68 Hz, 1 H) 5.97 (d, J = 3.52 Hz, 1 H) 4.87 (s, 15 H) 3.92 (q, J = 7.04 Hz, 1 H) 3.82 (d, J = 2.74 Hz, 6 H) 2.37 (s, 3 H) 2.28 (s, 3 H) 1.55 (s, 3 H) 1.46 (d, J = 7.04 Hz, 3 H). LCMS ESI (pos.) m/z: 529.1 (M + H)$^+$. |
| 225.0 | 3-bromo-4-(2,6-dimethoxyphenyl)-5-(5-methylfuran-2-yl)-4H-1,2,4-triazole (Example 364.1), (2R,3S)-3-(5-fluoropyrimidin-2-yl)-3-hydroxybutane-2-sulfonamide and (2R,3R)-3-(5-fluoropyrimidin-2-yl)-3-hydroxybutane-2-sulfonamide and (2S,3S)-3-(5-fluoropyrimidin-2-yl)-3-hydroxybutane-2-sulfonamide and (2S,3R)-3-(5-fluoropyrimidin-2-yl)-3-hydroxybutane-2-sulfonamide prepared employing 1-(5-fluoropyrimidin-2-yl)ethanone and Example 361.0 following procedures described in Example 10.0.<br>Preparative SFC method: 250 x 30 mm IC column with 55 mL/min EtOH(neat) + 55 g/min CO$_2$ on Thar 350 SFC. Outlet pressure = 100 bar; Temp. = 21 C.; Wavelength = 276 nm. Used 1.0 mL injections of 292 mg/35 mL (8.3 mg/mL) sample solution in MeOH:DCM (33:2), i.e. 8.3 mg/injection. Cycle time = 10.4 min, Runtime =18 min to deliver Peak 4. | 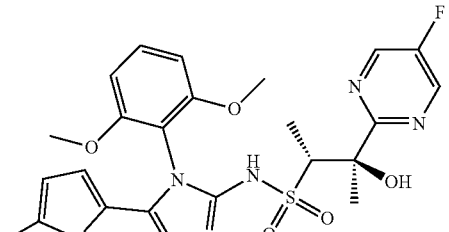<br>or<br>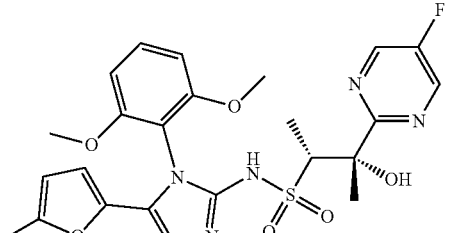<br>or |

TABLE 8-continued

| Example | Reagents | Structure, Name and Data |
|---|---|---|

(2R,3S)-N-(4-(2,6-dimethoxyphenyl)-5-(5-methyl-2-furanyl)-4H-1,2,4-triazol-3-yl)-3-(5-fluoro-2-pyrimidinyl)-3-hydroxy-2-butanesulfonamide and (2R,3R)-N-(4-(2,6-dimethoxyphenyl)-5-(5-methyl-2-furanyl)-4H-1,2,4-triazol-3-yl)-3-(5-fluoro-2-pyrimidinyl)-3-hydroxy-2-butanesulfonamide and (2S,3S)-N-(4-(2,6-dimethoxyphenyl)-5-(5-methyl-2-furanyl)-4H-1,2,4-triazol-3-yl)-3-(5-fluoro-2-pyrimidinyl)-3-hydroxy-2-butanesulfonamide and (2S,3R)-N-(4-(2,6-dimethoxyphenyl)-5-(5-methyl-2-furanyl)-4H-1,2,4-triazol-3-yl)-3-(5-fluoro-2-pyrimidinyl)-3-hydroxy-2-butanesulfonamide.
$^1$H NMR (400 MHz, CD$_3$OD) δ 8.66 (s, 2 H) 7.51 (t, J = 8.33 Hz, 1 H) 6.82 (dd, J = 8.61, 3.52 Hz, 2 H) 5.97 (d, J = 3.13 Hz, 1 H) 5.82 (d, J = 3.33 Hz, 1 H) 4.03 (m, 1 H) 3.77 (app s, 6 H) 2.27 (s, 3 H) 1.75 (s, 3 H) 1.32 (d, J = 7.04 Hz, 4 H). LCMS ESI (pos.) m/z: 533.0 (M + H)$^+$.

226.0 | 3-bromo-4-(2,6-dimethoxyphenyl)-5-(5-methylfuran-2-yl)-4H-1,2,4-triazole (Example 364.1), (1S,2S)-1-methoxy-1-(5-methylpyrimidin-2-yl)propane-2-sulfonamide and (1R,2S)-1-methoxy-1-(5-methylpyrimidin-2-yl)propane-2-sulfonamide and (1S,2R)-1-methoxy-1-(5-methylpyrimidin-2-yl)propane-2-sulfonamide and (1R,2R)-1-methoxy-1-(5-methylpyrimidin-2-yl)propane-2-sulfonamide was prepared following procedures described in Example 356.0 employing 2,4-dimethoxybenzylamine, 5-methylpyrimidine-2-carbaldehyde and MeI.
Preparative SFC method: Chiral separation of the racemic mixture was conducted through a 2 step purification process. First purification step: Run on Thar 350 with 400×30 mm AD-H columns using 32 mL/min neat IPA and 58 g/min CO$_2$ on SFC, 35% co-solvent at 90 g/min. Outlet pressure = 100 bar; Temp. = 20° C.; Wavelength = 276 nm. Used 0.5 mL injections of 432 mg sample dissolved in 70 mL of solvent (55 mL IPA, 10 mL MeOH, 5 mL DCM); c = 6.5 mg/mL, 3.25 mg/injection. Cycle time =

(1R,2R)-N-(4-(2,6-dimethoxyphenyl)-5-(5-methyl-2-furanyl)-4H-1,2,4-triazol-3-yl)-1-methoxy-1-(5-methyl-2-pyrimidinyl)-2-propanesulfonamide or (1S,2S)-N-(4-(2,6-

TABLE 8-continued

| Example | Reagents | Structure, Name and Data |
|---|---|---|
| | 11 min; Run time = 20 min. Separation conditions for step2: Run on Thar 80 SFC with 250 x 30 mm AS-H column with 28 g/min IPA(neat) + 52 g/min CO$_2$, 35% co-solvent at 80 g/min. Outlet pressure = 100 bar; Temp. = 21° C.; Wavelength = 276 nm. Injected 0.8 mL of a solution from 150 mg sample dissolved in 40 mL of IPA:MeOH 25:15 mL. c = 3.8 mg/mL; 3.0 mg per injection. Cycle time = 7.6 min, total elution time= 13 min to deliver peak 1 from step 1. | dimethoxyphenyl)-5-(5-methyl-2-furanyl)-4H-1,2,4-triazol-3-yl)-1-methoxy-1-(5-methyl-2-pyrimidinyl)-2-propanesulfonamide.<br>$^1$H NMR (500 MHz, CD$_3$OD) δ 8.68 (s, 2 H) 7.62 (t, J = 8.41 Hz, 1 H) 6.86 (d, J = 8.80 Hz, 2 H) 6.03 (m, 1 H) 5.95 (d, J = 3.42 Hz, 1 H) 4.83 (m, 2 H) 4.58-4.68 (m, 1 H) 3.84 (s, 3 H) 3.81 (s, 3 H) 3.63 (dd, J = 8.19, 7.21 Hz, 1 H) 3.11 (s, 3 H) 2.37 (s, 3 H) 2.27 (s, 3 H) 1.03 (d, J = 7.34 Hz, 3 H). LCMS ESI (pos.) m/z: 529.0 (M + H)$^+$. |
| 227.0 | 3-bromo-4-(2,6-dimethoxyphenyl)-5-(5-methylfuran-2-yl)-4H-1,2,4-triazole (Example 364.1), (2R,3R)-3-(5-cyanopyridin-2-yl)-3-hydroxybutane-2-sulfonamide and (2R,3S)-3-(5-cyanopyridin-2-yl)-3-hydroxybutane-2-sulfonamide and (2S,3R)-3-(5-cyanopyridin-2-yl)-3-hydroxybutane-2-sulfonamide and (2S,3S)-3-(5-cyanopyridin-2-yl)-3-hydroxybutane-2-sulfonamide was prepared following the procedures described in Example 10.0, employing 1-(5-bromopyridin-2-yl)ethanone and Example 361.0. Preparative SFC method: Separation conditions Run on Thar 80 SFC with 250 x 30 mm OJ-H column with 9 g/min MeOH(neat)) + 61 g/min CO2, 13% co-solvent at 70 g/min. Outlet pressure = 101 bar; Temp. = 22 C.; Wavelength = 221 nm. Manually injected 0.5 mL of a solution from 29 mg sample dissolved in 2.5 mL of MeOH, c = 11.6 mg/mL; 5.8 mg per injection to deliver Peak 2, only the major set of diastereomers were purified. | 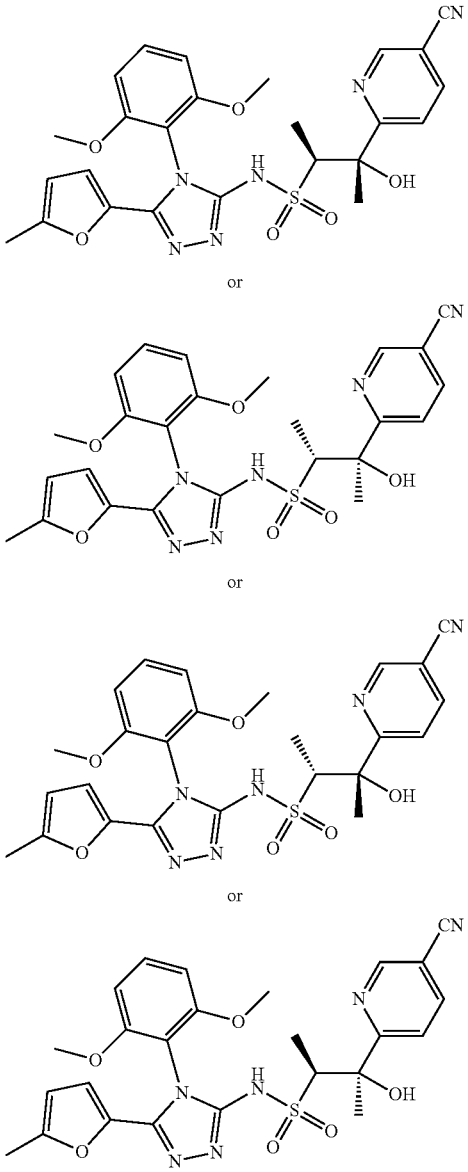<br>(2S,3S)-3-(5-cyano-2-pyridinyl)-N-(4-(2,6-dimethoxyphenyl)-5-(5-methyl-2-furanyl)-4H-1,2,4-triazol-3-yl)-3-hydroxy-2-butanesulfonamide.<br>$^1$H NMR (500 MHz, CD$_3$OD) δ 8.77 (s, 1 H) 8.04 (dd, J = 8.31, 1.96 Hz, 1 H) 7.58-7.67 (m, 2 H) 6.90 (t, J = 7.25 Hz, 2 H) 6.04 (s, 1 H) 5.98 |

TABLE 8-continued

| Example | Reagents | Structure, Name and Data |
|---|---|---|
| | | (d, J = 3.18 Hz, 1 H) 3.88 (m, 1 H) 3.84 (s, 3 H) 3.82 (s, 3 H) 2.27 (s, 3 H) 1.43-1.47 (s, 3 H) 1.46 (s, 3 H). LCMS ESI (pos.) m/z: 539.1 (M + H)+. |
| 228.0 | 3-bromo-4-(2,6-dimethoxyphenyl)-5-(5-methylfuran-2-yl)-4H-1,2,4-triazole (Example 364.1), (2R,3S)-3-(5-fluoropyrimidin-2-yl)-3-hydroxybutane-2-sulfonamide and (2R,3R)-3-(5-fluoropyrimidin-2-yl)-3-hydroxybutane-2-sulfonamide and (2S,3S)-3-(5-fluoropyrimidin-2-yl)-3-hydroxybutane-2-sulfonamide and (2S,3R)-3-(5-fluoropyrimidin-2-yl)-3-hydroxybutane-2-sulfonamide prepared employing 1-(5-fluoropyrimidin-2-yl)ethanone and Example 361.0 following procedures described in Example 10.0. Preparative SFC method: Run on 250x30 mm IC column with 55 mL/min EtOH (neat) + 55 g/min CO$_2$ on Thar 350 SFC. Outlet pressure = 100 bar; Temp. = 21° C.; Wavelength = 276 nm. Used 1.0 mL injections of 292 mg/35 mL (8.3 mg/mL) sample solution in MeOH:DCM (33:2), i.e. 8.3 mg/injection. Cycle time = 10.4 min, Runtime = 18 min to deliver a mixture of peak 3 and 4. | 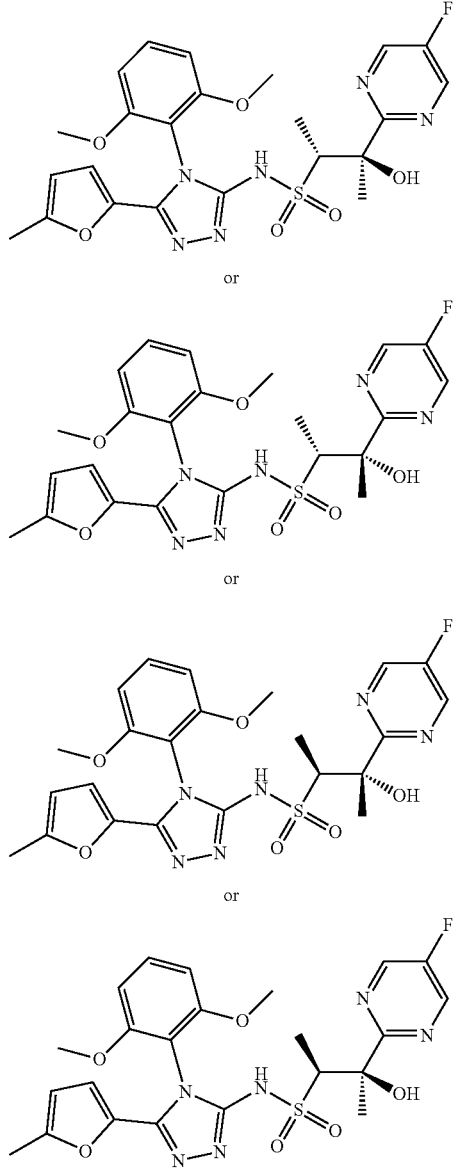<br>(2R,3S)-N-(4-(2,6-dimethoxyphenyl)-5-(5-methyl-2-furanyl)-4H-1,2,4-triazol-3-yl)-3-(5-fluoro-2-pyrimidinyl)-3-hydroxy-2-butanesulfonamide or (2R,3R)-N-(4-(2,6-dimethoxyphenyl)-5-(5-methyl-2-furanyl)-4H-1,2,4-triazol-3-yl)-3-(5-fluoro-2-pyrimidinyl)-3-hydroxy-2-butanesulfonamide or (2S,3S)-N-(4-(2,6-dimethoxyphenyl)-5-(5-methyl-2-furanyl)-4H-1,2,4-triazol-3-yl)-3-(5-fluoro-2-pyrimidinyl)-3-hydroxy-2-butanesulfonamide or (2S,3R)-N-(4-(2,6-d methyl-2-furanyl)-4H-1,2,4-triazol-3-yl)-3-(5-fluoro-2-pyrimidinyl)-3-hydroxy-2-butanesulfonamide. LCMS ESI (pos.) m/z: 540.1 (M + H)+. |

TABLE 8-continued

| Example | Reagents | Structure, Name and Data |
|---|---|---|
| 236.0 | 3-bromo-4-(2,6-dimethoxyphenyl)-5-(5-methylfuran-2-yl)-4H-1,2,4-triazole (Example 364.1), (2R,3S)-3-(5-fluoropyrimidin-2-yl)-3-hydroxybutane-2-sulfonamide and (2R,3R)-3-(5-fluoropyrimidin-2-yl)-3-hydroxybutane-2-sulfonamide and (2S,3S)-3-(5-fluoropyrimidin-2-yl)-3-hydroxybutane-2-sulfonamide and (2S,3R)-3-(5-fluoropyrimidin-2-yl)-3-hydroxybutane-2-sulfonamide prepared employing 1-(5-fluoropyrimidin-2-yl)ethanone and Example 361.0 following procedures described in Example 10.0. Preparative SFC method: Run on 250x30 mm IC column with 55 mL/min EtOH (neat) + 55 g/min $CO_2$ on Thar 350 SFC. Outlet pressure = 100 bar; Temp. = 21° C.; Wavelength = 276 nm. Used 1.0 mL injections of 292 mg/35 mL (8.3 mg/mL) sample solution in MeOH:DCM (33:2), i.e. 8.3 mg/injection. Cycle time =10.4 min, Runtime =18 min to deliver peak 1. | 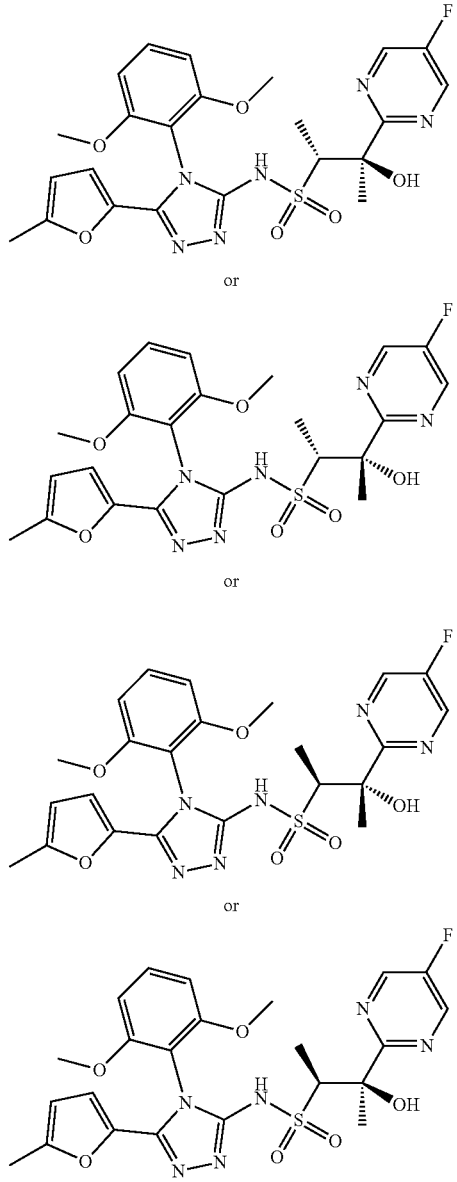<br>(2R,3S)-N-(4-(2,6-dimethoxyphenyl)-5-(5-methyl-2-furanyl)-4H-1,2,4-triazol-3-yl)-3-(5-fluoro-2-pyrimidinyl)-3-hydroxy-2-butanesulfonamide or (2R,3R)-N-(4-(2,6-dimethoxyphenyl)-5-(5-methyl-2-furanyl)-4H-1,2,4-triazol-3-yl)-3-(5-fluoro-2-pyrimidinyl)-3-hydroxy-2-butanesulfonamide or (2S,3S)-N-(4-(2,6-dimethoxyphenyl)-5-(5-methyl-2-furanyl)-4H-1,2,4-triazol-3-yl)-3-(5-fluoro-2-pyrimidinyl)-3-hydroxy-2-butanesulfonamide or (2S,3R)-N-(4-(2,6-dimethoxyphenyl)-5-(5-methyl-2-furanyl)-4H-1,2,4-triazol-3-yl)-3-(5-fluoro-2-pyrimidinyl)-3-hydroxy-2-butanesulfonamide.<br>LCMS ESI (pos.) m/z: 540.1 (M + H)$^+$. |

| Example | Reagents | Structure, Name and Data |
|---|---|---|
| 244.0 | 3-bromo-4-(2,6-dimethoxyphenyl)-5-(5-methylfuran-2-yl)-4H-1,2,4-triazole (Example 364.1), (1R,2R)-1-(5-fluoropyrimidin-2-yl)-1-hydroxypropane-2-sulfonamide and (1S,2S)-1-(5-fluoropyrimidin-2-yl)-1-hydroxypropane-2-sulfonamide (Example 355.0) and (1S,2R)-1-(5-fluoropyrimidin-2-yl)-1-hydroxypropane-2-sulfonamide and (1S,2R)-1-(5-fluoropyrimidin-2-yl)-1-hydroxypropane-2-sulfonamide (Example 355.1). Preparative SFC method: Run on Thar 200 with 250x30 mm AS-H column with 54 g/min MeOH (neat) and 66 g/min $CO_2$, 45% co-solvent at 120 g/min. Wavelength 276 nm. Injected 1.0 mL of 80 mg dissolved in 10.0 mL MeOH; c = 8.0 mg/mL, 8.0 mg/injection. Cycle time 7.0 min, run time 11 min to provide peak 2 of the minor set of diastereomers. | 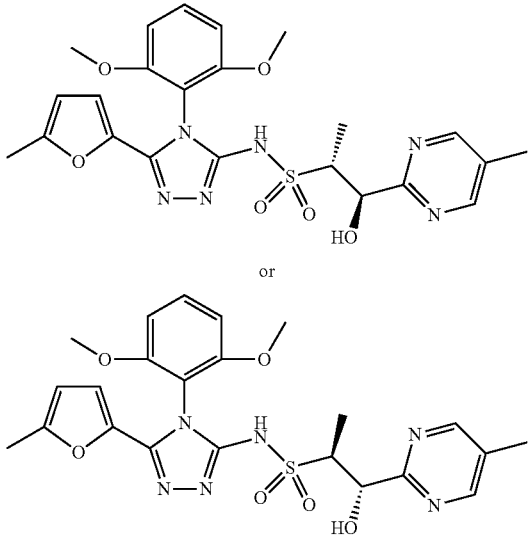<br>or<br>(1R,2R)-N-(4-(2,6-dimethoxyphenyl)-5-(5-methyl-2-furanyl)-4H-1,2,4-triazol-3-yl)-1-hydroxy-1-(5-methyl-2-pyrimidinyl)-2-propanesulfonamide or (1S,2S)-N-(4-(2,6-dimethoxyphenyl)-5-(5-methyl-2-furanyl)-4H-1,2,4-triazol-3-yl)-1-hydroxy-1-(5-methyl-2-pyrimidinyl)-2-propanesulfonamide.<br>$^1$H NMR (400 MHz, $CD_3OD$) δ 8.64 (s, 2 H) 7.55 (t, J = 8.41 Hz, 1 H) 6.84 (d, J = 8.61 Hz, 2 H) 6.02 (m, 1 H) 5.92 (m, 1 H) 4.99 (d, J = 7.43 Hz, 2 H) 4.59 (br. s., 2 H) 3.82 (s, 3 H) 3.79 (s, 3 H) 3.61-3.70 (m, 1 H) 2.35 (s, 3 H) 2.27 (s, 3 H) 1.13 (d, J = 7.04 Hz, 3 H). LCMS ESI (pos.) m/z: 515.0 (M + H)$^+$. |
| 247.0 | 3-bromo-4-(2,6-dimethoxyphenyl)-5-(5-methylfuran-2-yl)-4H-1,2,4-triazole (Example 364.1), (1R,2S)-1-hydroxy-1-(5-methylpyrazin-2-yl)propane-2-sulfonamide and (1S,2S)-1-hydroxy-1-(5-methylpyrazin-2-yl)propane-2-sulfonamide and (1R,2R)-1-hydroxy-1-(5-methylpyrazin-2-yl)propane-2-sulfonamide and (1S,2S)-1-hydroxy-1-(5-methylpyrazin-2-yl)propane-2-sulfonamide. This material was prepared in an analogous fashion to that described in Example 355.0 employing 5-methylpyrazine-2-carbaldehyde. Preparative SFC method: Dissolved 112 mg in 2.5 mL DCM + 2.5 mL meoh (22.4 mg/mL). Column: Chiralpak AS-H (250 x 21 mm, 5 μm), Mobile Phase: 80:20 (A:B), A: Liquid $CO_2$, B: MeOH, Flow Rate: 70 mL/min, 220 nm, 22.4 mg/injection to provide peak 2 of the major set of diastereomers. | 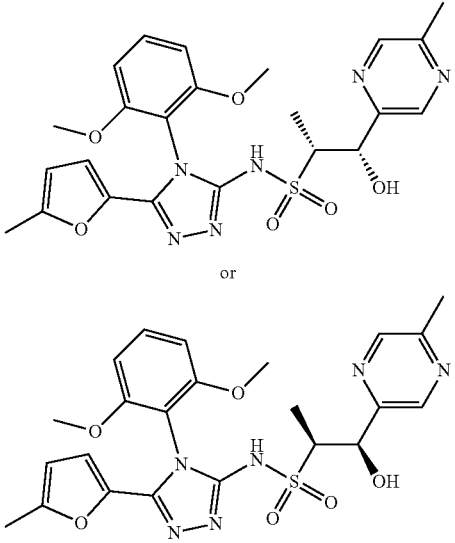<br>or<br>(1S,2R)-N-(4-(2,6-dimethoxyphenyl)-5-(5-methyl-2-furanyl)-4H-1,2,4-triazol-3-yl)-1-hydroxy-1-(5-methyl-2-pyrazinyl)-2-propanesulfonamide or (1R,2S)-N-(4-(2,6-dimethoxyphenyl)-5-(5-methyl-2-furanyl)-4H-1,2,4-triazol-3-yl)-1-hydroxy-1-(5-methyl-2-pyrazinyl)-2-propanesulfonamide.<br>$^1$H NMR (500 MHz, $CD_3OD$) δ 8.58 (s, 1H), 8.51 (s, 1H), 7.60 (d, J = 8.5, 8.5 Hz, 1H), 6.89 (dd, J = 8.4, 4.3 Hz, 2H), 6.07 (d, J = 3.5 Hz, |

TABLE 8-continued

| Example | Reagents | Structure, Name and Data |
|---|---|---|
| | | 1H), 6.01 (d, J = 3.5 Hz, 1H), 5.42 (br s, 1H), 3.82 (s, 3H), 3.80 (s, 3H), 3.63-3.69 (m, 1H), 2.58 (s, 3H), 2.29 (s, 3H), 1.18 (d, J = 7.0 Hz, 3H). LCMS ESI (pos.) m/z: 515.2 (M + H)+. |
| 250.0 | 3-bromo-4-(2,6-dimethoxyphenyl)-5-(5-methylfuran-2-yl)-4H-1,2,4-triazole (Example 364.1), (1S,2S)-1-methoxy-1-(5-methylpyrimidin-2-yl)propane-2-sulfonamide and (1R,2S)-1-methoxy-1-(5-methylpyrimidin-2-yl)propane-2-sulfonamide and (1S,2R)-1-methoxy-1-(5-methylpyriinidin-2-yl)propane-2-sulfonamide and (1R,2R)-1-methoxy-1-(5-methylpyrimidin-2-yl)propane-2-sulfonamide was prepared following procedures described in Example 356.0 employing 2,4-dimethoxy-benzylamine, 5-methylpyrimidine-2-carbaldehyde and MeI. Preparative SFC method: Chiral separation of the racemic mixture was conducted through a 2 step purification process. First purification step: Run on Thar 350 with 400x30 mm AD-H columns using 32 mL/min neat IPA and 58 g/min $CO_2$ on SFC, 35% co-solvent at 90 g/min. Outlet pressure = 100 bar; Temp. = 20° C.; Wavelength = 276 nm. Used 0.5 mL injections of 432 mg sample dissolved in 70 mL of solvent (55 mL IPA, 10 mL MeOH, 5 mL DCM); c = 6.5 mg/mL, 3.25 mg/injection. Cycle time = 11 min; Run time = 20 min. Separation conditions for step2: Run on Thar 80 SFC with 250 x 30 mm AS-H column with 28 g/min IPA(neat) + 52 g/min $CO_2$, 35% co-solvent at 80 g/min. Outlet pressure = 100 bar; Temp. = 21° C.; Wavelength = 276 nm. Injected 0.8 mL of a solution from 150 mg sample dissolved in 40 mL of IPA:MeOH 25:15 mL, c = 3.8 mg/mL; 3.0 mg per injection. Cycle time = 7.6 min, total elution time = 13 min to provide peak 3 from step 2. | 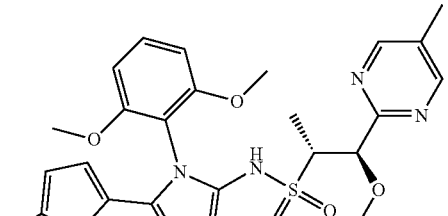<br>or<br>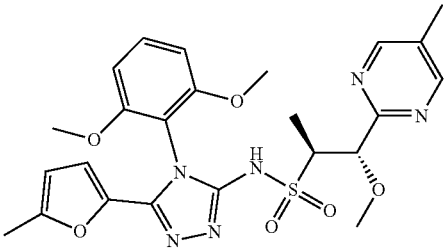<br>(1R,2R)-N-(4-(2,6-dimethoxyphenyl)-5-(5-methyl-2-furanyl)-4H-1,2,4-triazol-3-yl)-1-methoxy-1-(5-methyl-2-pyrimidinyl)-2-propanesulfonamide or (1S,2S)-N-(4-(2,6-dimethoxyphenyl)-5-(5-methyl-2-furanyl)-4H-1,2,4-triazol-3-yl)-1-methoxy-1-(5-methyl-2-pyrimidinyl)-2-propanesulfonamide.<br>$^1$H NMR (500 MHz, CD$_3$OD) δ 8.68 (s, 2 H) 7.56 (t, J = 8.41 Hz, 1 H) 6.86 (d, J = 8.80 Hz, 2 H) 6.03 (m, 1 H) 5.95 (d, J = 3.42 Hz, 1 H) 4.83 (m, 2 H) 4.58-4.68 (m, 1 H) 3.84 (s, 3 H) 3.81 (s, 3 H) 3.63 (dd, J = 8.19, 7.21 Hz, 1 H) 3.11 (s, 3 H) 2.37 (s, 3 H) 2.27 (s, 3 H) 1.03 (d, J = 7.34 Hz, 3 H). LCMS ESI (pos.) m/z: 529.0 (M + H)+. |
| 261.0 | 3-bromo-4-(2,6-dimethoxyphenyl)-5-(5-methylfuran-2-yl)-4H-1,2,4-triazole (Example 364.1), (1S,2S)-1-methoxy-1-(5-methylpyrimidin-2-yl)propane-2-sulfonamide and (1R,2S)-1-methoxy-1-(5-methylpyrimidin-2-yl)propane-2-sulfonamide and (1S,2R)-1-methoxy-1-(5-methylpyrimidin-2-yl)propane-2-sulfonamide and (1R,2R)-1-methoxy-1-(5-methylpyrimidin-2-yl)propane-2-sulfonamide was prepared following procedures described in Example 356.0 employing 2,4-dimethoxy-benzylamine, 5-methylpyrimidine-2-carbaldehyde and MeI. Preparative SFC method: Separation conditions for (step 1), chiral purification (1000 + 3700 mg): Run on Thar 350 SFC with 250x30 mm IC-H column at 50 g/min MeOH (neat) + 50 g/min $CO_2$, 50% co-solvent, at 100 g/min. Outlet pressure = 100 bar; Temp. = 20° C.; Wavelength = 276 nm. Material was dissolved in batches of 200-400 mg to avoid possible decomposition upon sitting in solution. Injected 2.0 mL of 400 mg sample in 17 mL, comprised of 10 mL DCM and 7 mL ACN. Solution | 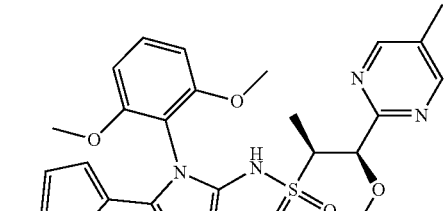<br>(1R,2S)-N-(4-(2,6-dimethoxyphenyl)-5-(5-methyl-2-furanyl)-4H-1,2,4-triazol-3-yl)-1-methoxy-1-(5-methyl-2-pyrimidinyl)-2-propanesulfonamide: $^1$H NMR (500 MHz, CD$_3$OD) δ 8.67 (d, J = 0.73 Hz, 2 H) 7.56 (t, J = 8.41 Hz, 1 H) 6.85 (d, J = 8.56 Hz, 2 H) 6.03 (s, 1 H) 5.95 (d, J = 3.42 Hz, 1 H) 5.00 (d, J = 3.67 Hz, 1 H) 3.80 (s, 3 H) 3.77 (s, 3 H) 3.54-3.59 (m, 1 H) 3.28 (s, 3 H) 2.36 (s, 3 H) 2.27 (s, 3 H) 1.25 (d, J = 6.85 Hz, 3 H). LCMS ESI (pos.) m/z: 529.0 (M + H)+. |

TABLE 8-continued

| Example | Reagents | Structure, Name and Data |
|---|---|---|
| | concentration = 23.5 mg/mL, resulting in 47 mg per injection. Cycle time 8.5 min; run time 16 min. Chiral separation of, step 2 (2500 mg) by preparative SFC. Run on Thar 200 with 2x(250x35) mm AS-H column with 19 g/min MeOH (neat) + 91 g/min $CO_2$, 17% co-solvent at 110 g/min. Temperature 21° C., Wavelength 297 nm. Injected 1.0 mL of a solution of e.g. 855 mg of sample (step 1, peak 1) dissolved in 35 mL (15 mL DCM = 20 mL ACN); c = 24.5 mg/mL; 24.5 mg/injection. Cycle time 7 min; runtime 16 min to provide step 2, peak 2. | |

The compound set forth in the following table were synthesized following the procedure in Example 1.0 using the starting material as described.

TABLE 9

| 251.0 | 1-(5-methylpyrimidin-2-yl)ethanone and Example 365.0. Preparative SFC method: chiral separation by prep. SFC: On Thar 200, conditions used were 30 g/min EtOH(neat) + 70 g/min $CO_2$ on 250 x 30 mm AS-H column. Outlet pressure = 100 bar, Temp. = 20° C., Wavelength = 270 nm. Used 1.0 mL injections of 173 mg sample in 10 mL MeOH/DCM (c = 17.3 mg/mL), resulting in 17 mg/injection. Run time 10.0 min., cycle time = 7.0 min to deliver peak 1. | 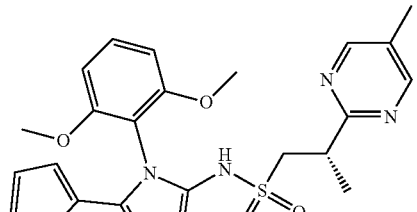<br>or<br>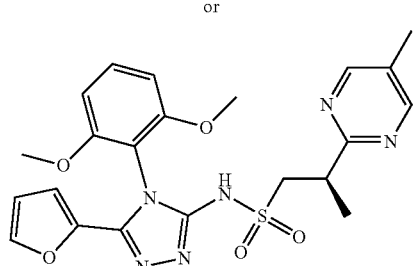<br><br>(2S)-N-(4-(2,6-dimethoxyphenyl)-5-(2-furanyl)-4H-1,2,4-triazol-3-yl)-2-(5-methyl-2-pyrimidinyl)-1-propanesulfonamide or (2R)-N-(4-(2,6-dimethoxy-phenyl)-5-(2-furanyl)-4H-1,2,4-triazol-3-yl)-2-(5-methyl-2-pyrimidinyl)-1-propanesulfonamide.<br>$^1$H NMR (400 MHz, $CD_3OD$) δ 8.56 (s, 2 H) 7.61 (s, 1 H) 7.56 (t, J = 8.61 Hz, 1 H) 6.86 (d, J = 8.61 Hz, 1 H) 6.84 (s, 1 H) 6.44 (dd, J = 3.52, 1.76 Hz, 1 H) 6.14 (dd, J = 3.52, 0.78 Hz, 1 H) 3.80 (app s, 6 H), 3.78 (m, 1 H) 3.29-3.34 (m, 2 H) 2.31 (s, 3 H) 1.39 (d, J = 7.04 Hz, 3 H). LCMS ESI (pos.) m/z: 485.1 (M + H)$^+$. |

Example 214.0. Preparation of 2-(5-chloro-1'-methyl-1',2',3',6'-tetrahydro-3,4'-bipyridin-2-yl)-N-(4-(2,6-dimethoxyphenyl)-5-(2-furanyl)-4H-1,2,4-triazol-3-yl)ethanesulfonamide

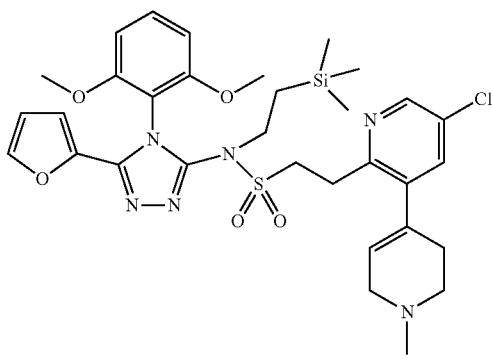

214.1

2-(5-Chloro-1'-methyl-1',2',3',6'-tetrahydro-[3,4'-bipyridin]-2-yl)-N-(4-(2,6-dimethoxyphenyl)-5-(furan-2-yl)-4H-1,2,4-triazol-3-yl)-N-(2-(trimethylsilyl)ethyl)ethanesulfonamide, Example 214.1. The title compound was prepared employing 1-methyl-1,2,3,6-tetrahydropyridine-4-boronic acid pinacol ester (commercially available from Sigma-Aldrich Corp., St. Louis, Mo., USA) and the procedure described for the synthesis of Example 220.1. LCMS-ESI (pos.) m/z: 685.2 (M+H)$^+$.

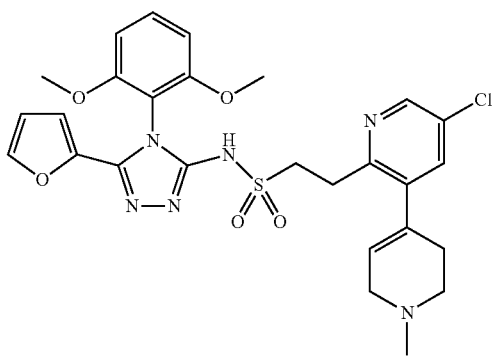

214.0

2-(5-Chloro-1'-methyl-1',2',3',6'-tetrahydro-3,4'-bipyridin-2-yl)-N-(4-(2,6-dimethoxyphenyl)-5-(2-furanyl)-4H-1,2,4-triazol-3-yl)ethanesulfonamide, Example 214.0. The title compound was prepared employing Example 214.1 following the procedures described in Example 264.0. $^1$H NMR (500 MHz, CD$_3$OD) δ 8.47 (s, 1H) 7.64 (d, J=2.45 Hz, 1H) 7.61 (dd, J=1.71, 0.73 Hz, 1H) 7.56 (t, J=8.38 Hz, 1H) 6.85 (d, J=8.56 Hz, 2H) 6.45 (dd, J=3.55, 1.83 Hz, 1H) 6.14 (d, J=3.61 Hz, 1H) 5.75-5.78 (m, 1H) 3.76 (app s, 6H) 3.39-3.49 (m, 2H) 3.20 (br. s., 2H) 3.03 (s, 3H). LCMS-ESI (pos.) m/z: 585.0 (M+H)$^+$.

Example 215.0. Preparation of 2-(5-chloro-3-(3,6-dihydro-2H-pyran-4-yl)-2-pyridinyl)-N-(4-(2,6-dimethoxyphenyl)-5-(2-furanyl)-4H-1,2,4-triazol-3-yl)ethanesulfonamide

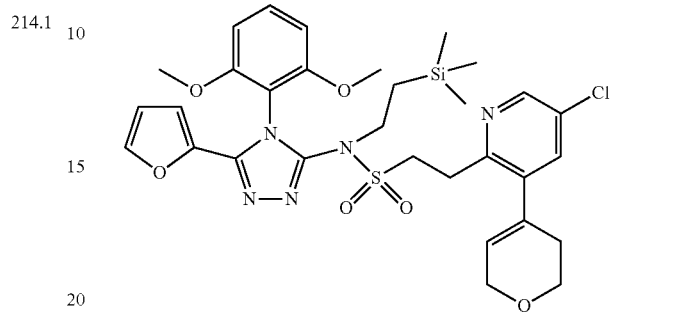

215.1

2-(5-Chloro-3-(3,6-dihydro-2H-pyran-4-yl)pyridin-2-yl)-N-(4-(2,6-dimethoxyphenyl)-5-(furan-2-yl)-4H-1,2,4-triazol-3-yl)-N-(2-(trimethylsilyl)ethyl)ethanesulfonamide, Example 215.1. The title compound was prepared employing 3,6-dihydro-2H-pyran-4-boronic acid pinacol ester (commercially available from Sigma-Aldrich Corp., St. Louis, Mo., USA) employing the procedures described in the synthesis of Example 220.1. LCMS-ESI (pos.) m/z: 672.2 (M+H)$^+$.

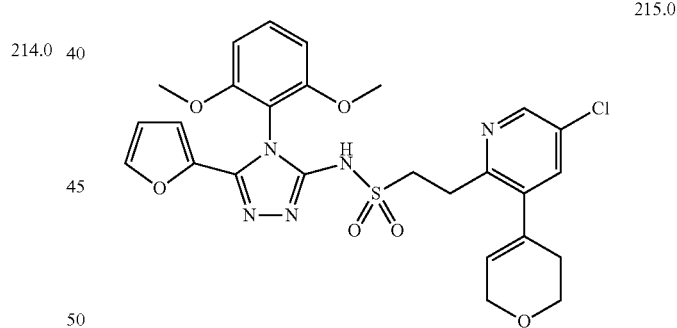

215.0

2-(5-Chloro-3-(3,6-dihydro-2H-pyran-4-yl)-2-pyridinyl)-N-(4-(2,6-dimethoxyphenyl)-5-(2-furanyl)-4H-1,2,4-triazol-3-yl)ethanesulfonamide, Example 215.0. The title compound was prepared employing Example 215.1 and the procedure described for the synthesis of Example 264.0. $^1$H NMR (400 MHz, CDCl$_3$) δ 8.42 (d, J=2.35 Hz, 1H) 7.54-7.67 (m, 2H) 6.85 (d, J=8.61 Hz, 2H) 6.45 (dd, J=3.52, 1.76 Hz, 1H) 6.15 (d, J=3.52 Hz, 1H) 5.79 (d, J=1.37 Hz, 1H) 4.25 (q, J=2.67 Hz, 2H) 3.88 (t, J=5.28 Hz, 2H) 3.76 (app s, 6H) 3.40-3.61 (m, 2H) 3.14-3.30 (m, 2H) 2.34 (dd, J=4.69, 2.93 Hz, 2H). LCMS-ESI (pos.) m/z: 572.0 (M+H)$^+$.

Example 218.0. Preparation of (2R,3R)—N-(4-(2,6-dimethoxyphenyl)-5-(2-furanyl)-4H-1,2,4-triazol-3-yl)-3-(5-fluoro-2-pyrimidinyl)-2-butanesulfonamide and (2S,3S)—N-(4-(2,6-dimethoxyphenyl)-5-(2-furanyl)-4H-1,2,4-triazol-3-yl)-3-(5-fluoro-2-pyrimidinyl)-2-butanesulfonamide

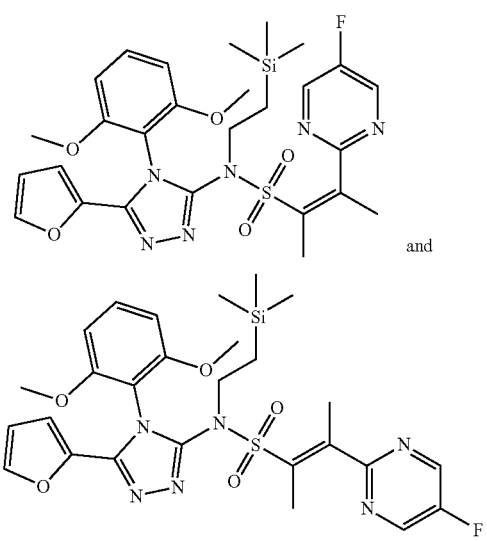

218.1

(Z)—N-(4-(2,6-Dimethoxyphenyl)-5-(furan-2-yl)-4H-1,2,4-triazol-3-yl)-3-(5-fluoropyrimidin-2-yl)-N-(2-(trimethylsilyl)ethyl)but-2-ene-2-sulfonamide and (E)-N-(4-(2,6-dimethoxyphenyl)-5-(furan-2-yl)-4H-1,2,4-triazol-3-yl)-3-(5-fluoropyrimidin-2-yl)-N-(2-(trimethylsilyl)ethyl)but-2-ene-2-sulfonamide, Example 218.1. Lithium bis(trimethylsilyl)amide (1.0 M, 2.4 mL, 2.4 mmol) was added to a THF (2.4 mL) solution containing Example 365.0 (0.74 g, 1.2 mmol) under argon and at RT. After 15 min, a dry THF solution containing 1-(5-fluoropyrimidin-2-yl)ethanone (0.336 g, 2.397 mmol) was added, and the resulting solution was heated at 60° C. overnight. The reaction was then partitioned with EtOAc and water, washed with brine, dried over sodium sulfate, and concentrated. The reaction was purified on silica eluting with a hexane/EtOAc gradient (0-100%). Desired fractions were then pooled and concentrated to give the title compound. LCMS-ESI (pos.) m/z: 601.0 (M+H)+.

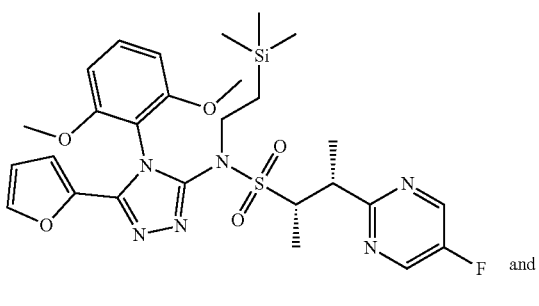

218.2

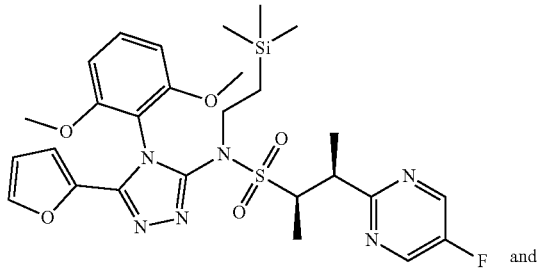

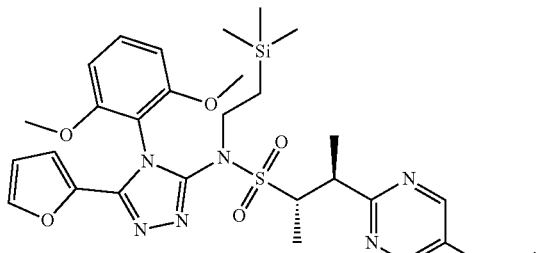

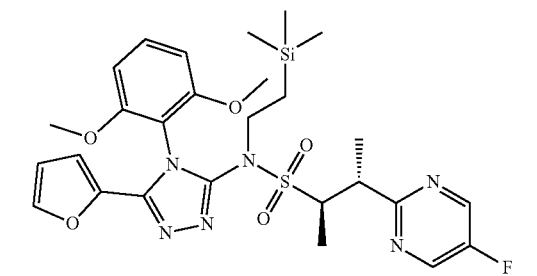

(2S,3S)—N-(4-(2,6-Dimethoxyphenyl)-5-(furan-2-yl)-4H-1,2,4-triazol-3-yl)-3-(5-fluoropyrimidin-2-yl)-N-(2-(trimethylsilyl)ethyl)butane-2-sulfonamide and (2S,3R)—N-(4-(2,6-dimethoxyphenyl)-5-(furan-2-yl)-4H-1,2,4-triazol-3-yl)-3-(5-fluoropyrimidin-2-yl)-N-(2-(trimethylsilyl)ethyl)butane-2-sulfonamide and (2R,3S)—N-(4-(2,6-dimethoxyphenyl)-5-(furan-2-yl)-4H-1,2,4-triazol-3-yl)-3-(5-fluoropyrimidin-2-yl)-N-(2-(trimethylsilyl)ethyl)butane-2-sulfonamide and (2R,3R)—N-(4-(2,6-dimethoxyphenyl)-5-(furan-2-yl)-4H-1,2,4-triazol-3-yl)-3-(5-fluoropyrimidin-2-yl)-N-(2-(trimethylsilyl)ethyl)butane-2-sulfonamide, Example 218.2. Raney nickel (catalytic) was suspended in an EtOH solution containing Example 218.1 (50.0 mg, 0.083 mmol). The mixture was then placed under an atmosphere of hydrogen and stirred for 3 h with constant LCMS monitoring. The reaction was filtered and concentrated. The reaction was used in the next step without further purification.

218.0

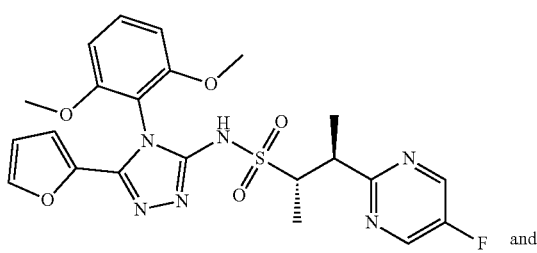

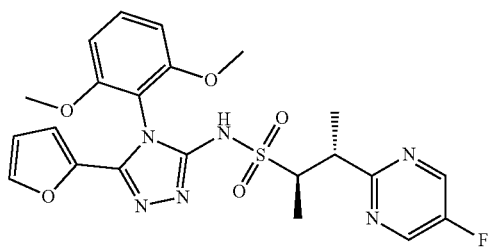

(2S,3S)—N-(4-(2,6-Dimethoxyphenyl)-5-(furan-2-yl)-4H-1,2,4-triazol-3-yl)-3-(5-fluoropyrimidin-2-yl)-N-(2-(trimethylsilyl)ethyl)butane-2-sulfonamide and (2R,3R)—N-(4-(2,6-dimethoxyphenyl)-5-(furan-2-yl)-4H-1,2,4-triazol-3-yl)-3-(5-fluoropyrimidin-2-yl)-N-(2-(trimethylsilyl)ethyl)butane-2-sulfonamide, Example 218.0. TASF (3 eq) was added to a DMF solution containing Example 218.2 (40 mg, 0.066 mmol). The reaction was heated at 80° C. for 4 h. The reaction was directly purified via reverse phase HPLC (Agilent SB-C8 column, 30×250 mm, 5 μm, 10-95% water/ACN gradient over 25 min., with 0.1% TFA, flow rate 50 mL/min). Separation of the mixture gave the desired compound as the initial mixture of diastereomers to elute from the column. The desired fractions were pooled and lyophilized to give pure product. LCMS-ESI (pos.) m/z: 503.0 (M+H)⁺.

Example 219.0. Preparation of 2-(5-chloro-3-(4-morpholinylmethyl)-2-pyridinyl)-N-(4-(2,6-dimethoxyphenyl)-5-(2-furanyl)-4H-1,2,4-triazol-3-yl)ethanesulfonamide

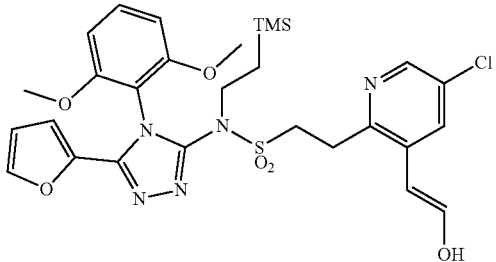

2-(5-Chloro-3-vinylpyridin-2-yl)-N-(4-(2,6-dimethoxyphenyl)-5-(furan-2-yl)-4H-1,2,4-triazol-3-yl)-N-(2-(trimethylsilyl)ethyl)ethanesulfonamide, Example 219.12. Example 27.2 (100.0 mg, 0.149 mmol) was added to a DMF (1495 μL) solution containing (Z)-tributyl(2-ethoxyvinyl)stannane (59.4 mg, 0.164 mmol) and 2-(3-bromo-5-chloropyridin-2-yl)-N-(4-(2,6-dimethoxyphenyl)-5-(furan-2-yl)-4H-1,2,4-triazol-3-yl)-N-(2-(trimethylsilyl)ethyl)ethanesulfonamide (100 mg, 0.149 mmol). The resulting mixture was stirred overnight at 100° C. The mixture was directly injected on the reverse phase HPLC (30-90% ACN Method). Desired fractions were pooled and concentrated to give the desired product. The residue was then treated with 3 N HCl (1.5 mL) and EtOH (1.5 mL). After stirring for 1 h, the solution was concentrated to dryness to give the title compound. This material was used in the next step without further purification. LCMS-ESI (pos.) m/z: 632.2 (M+H)⁺.

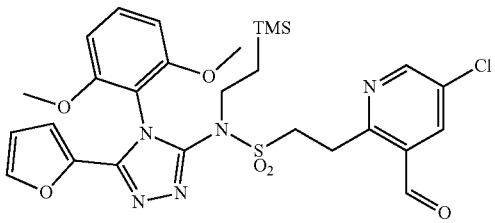

2-(5-Chloro-3-vinylpyridin-2-yl)-N-(4-(2,6-dimethoxyphenyl)-5-(furan-2-yl)-4H-1,2,4-triazol-3-yl)-N-(2-(trimethylsilyl)ethyl)ethanesulfonamide, Example 219.1. Tetrakis(triphenylphosphine)palladium(0) (31.1 mg, 0.027 mmol) was added to a DMF solution containing tributyl(vinyl)stannane (51.2 mg, 0.16 mmol) and Example 27.2 (90 mg, 0.135 mmol). The resulting mixture was heated in a microwave at 100° C. for 4 h. The mixture was directly injected on the reverse phase HPLC (10-90% ACN Method). Desired fractions were pooled and concentrated to give the desired product. LCMS-ESI (pos.) m/z: 616.2 (M+H)⁺.

2-(5-Chloro-3-formylpyridin-2-yl)-N-(4-(2,6-dimethoxyphenyl)-5-(furan-2-yl)-4H-1,2,4-triazol-3-yl)-N-(2-(trimethylsilyl)ethyl)ethanesulfonamide, Example 219.2. Osmium tetroxide (0.012 mL, 0.038 mmol) was added to a dioxane (6 mL)/water (2.0 mL) solution containing Example 219.1 (0.232 g, 0.38 mmol). After stirring for 10 min at RT, sodium periodate (0.042 mL, 0.754 mmol) was added to the dark solution. The reaction was then stirred at RT for an additional 3 h. The reaction was concentrated in vacuo. The residue was then partitioned with EtOAc/water and concentrated. The resulting residue was directly injected on the reverse phase HPLC (10-90% ACN Method). Desired fractions were pooled and lyopholized to give pure title compound. LCMS-ESI (pos.) m/z: 618.0 (M+H)⁺.

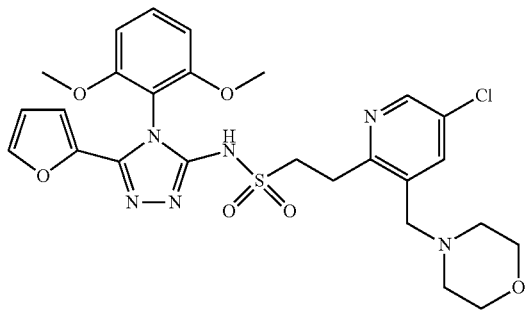

219.0

2-(5-Chloro-3-(4-morpholinylmethyl)-2-pyridinyl)-N-(4-(2,6-dimethoxyphenyl)-5-(2-furanyl)-4H-1,2,4-triazol-3-yl)ethanesulfonamide, Example 219.0. Sodium triacetoxyborohydride (5 eq.) was added to a DCM solution (0.5 M) containing Example 219.2 (1 eq.) and morpholine (5 eq.). The solution was stirred for 4 h at RT and then concentrated. The resulting residue was purified via preparative HPLC eluting with a 0.1% TFA water/ACN gradient. Desired fractions were pooled and lyophilized to give the desired product. Excess tris(dimethylamino)sulfonium difluorotrimethylsilicate (5 eq) was added to a DMF (286 μL) solution containing the silyl protected sulfonamide. The resulting mixture was stirred for 5 h at 80° C. The mixture was directly injected on the reverse phase HPLC (10-90% ACN Method). Desired fractions were pooled and lyophilized to give pure title compound. $^1$H NMR (500 MHz, CDCl$_3$) δ 8.53 (s, 1H) 7.88 (br. s., 1H) 7.55 (br. s., 1H) 7.45-7.51 (m, 1H) 6.75 (d, J=7.58 Hz, 2H) 6.37 (dd, J=3.67, 1.71 Hz, 1H) 6.04 (d, J=3.42 Hz, 1H) 4.27 (br. s., 2H) 3.90 (br. s., 4H) 3.78 (app s, 6H) 3.56-3.64 (m, 2H) 3.30 (t, J=5.99 Hz, 2H) 3.10 (br. s., 4H). LCMS-ESI (pos.) m/z: 589.2 (M+H)$^+$.

Example 220.0. Preparation of 2-(5-chloro-1',2',3',6'-tetrahydro-3,4'-bipyridin-2-yl)-N-(4-(2,6-dimethoxyphenyl)-5-(2-furanyl)-4H-1,2,4-triazol-3-yl)ethanesulfonamide 220.1

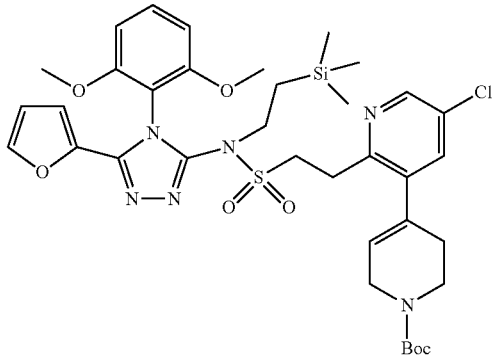

tert-Butyl 5-chloro-2-(2-(N-(4-(2,6-dimethoxyphenyl)-5-(furan-2-yl)-4H-1,2,4-triazol-3-yl)-N-(2-(trimethylsilyl)ethyl)sulfamoyl)ethyl)-5',6'-dihydro[3,4'-bipyridine]-1'(2'H)-carboxylate, Example 220.1. A mixture of Example 27.2 (100 mg, 0.15 mmol), N-Boc-1,2,3,6-tetrahydropyridine-4-boronic acid pinacol ester (commercially available from Sigma-Aldrich Corp., St. Louis, Mo., USA, 83 mg, 0.27 mmol), pd$_2$(dba)$_3$ (commercially available from Strem Chemicals, Inc., Newburyport, Mass., USA, 11 mg, 0.012 mmol), tricyclohexylphosphine (Strem, 7 mg, 0.024 mmol), potassium phosphate (1.3 M/water, 310 μL, 0.40 mmol) in dioxane (0.9 mL) was heated at 90° C. in a microwave until LCMS analysis indicated that the reaction was complete (2 h). Thereafter, the mixture was cooled to RT, diluted with DCM, filtered, and concentrated in vacuo. The residue was purified on a reverse-phase column, employing a gradient of 10-90% ACN in water (0.1% TFA in both eluents), to afford Example 220.1. LCMS-ESI (pos.) m/z: 771.2 (M+H)$^+$.

220.2

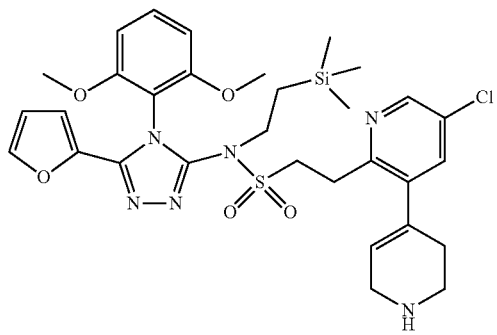

2-(5-Chloro-1',2',3',6'-tetrahydro-[3,4'-bipyridin]-2-yl)-N-(4-(2,6-dimethoxyphenyl)-5-(furan-2-yl)-4H-1,2,4-triazol-3-yl)-N-(2-(trimethylsilyl)ethyl)ethanesulfonamide, Example 220.2. Example 220.1 was stirred in 50% v/v TFA/DCM for 30 min at RT. Thereafter, the mixture was concentrated in vacuo to afford Example 220.2.

220.0

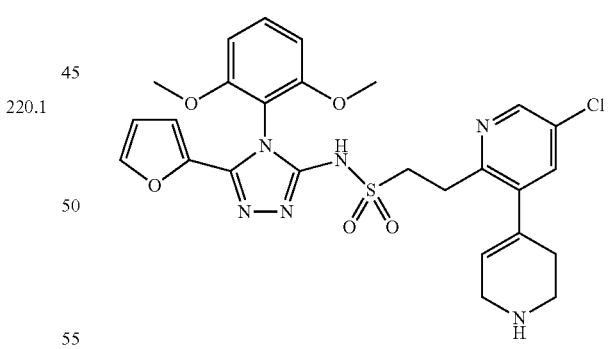

2-(5-Chloro-1',2',3',6'-tetrahydro-3,4'-bipyridin-2-yl)-N-(4-(2,6-dimethoxyphenyl)-5-(2-furanyl)-4H-1,2,4-triazol-3-yl)ethanesulfonamide, Example 220.0. The title compound was prepared employing Example 220.2 and the procedure described for the synthesis of Example 264.0. $^1$H NMR (400 MHz, CD$_3$OD) δ 8.47 (d, J=2.35 Hz, 1H) 7.53-7.65 (m, 3H) 6.85 (d, J=8.61 Hz, 2H) 6.45 (d, J=3.97 Hz, 1H) 6.15 (d, J=3.79 Hz, 1H) 5.75 (m, 1H) 3.83 (d, J=2.93 Hz, 2H) 3.77 (app s, 6H) 3.42-3.58 (m, 4H) 3.22 (d, J=8.02 Hz, 2H) 2.61 (d, J=1.96 Hz, 2H). LCMS-ESI (pos.) m/z: 571.0 (M+H)$^+$.

Example 221.0. Preparation of 2-(5-chloro-3,3'-bipyridin-2-yl)-N-(4-(2,6-dimethoxyphenyl)-5-(2-furanyl)-4H-1,2,4-triazol-3-yl)ethanesulfonamide

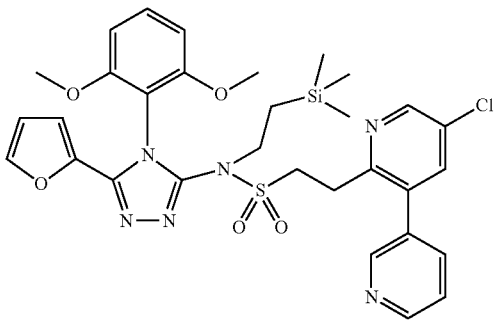

2-(5-Chloro-[3,3'-bipyridin]-2-yl)-N-(4-(2,6-dimethoxyphenyl)-5-(furan-2-yl)-4H-1,2,4-triazol-3-yl)-N-(2-(trimethylsilyl)ethyl)ethanesulfonamide, Example 221.1. The title compound was prepared employing 3-pyridinylboronic acid (commercially available from Sigma-Aldrich Corp., St. Louis, Mo., USA) and the procedure described for the synthesis of Example 220.1. LCMS-ESI (pos.) m/z: 667.2 (M+H)$^+$.

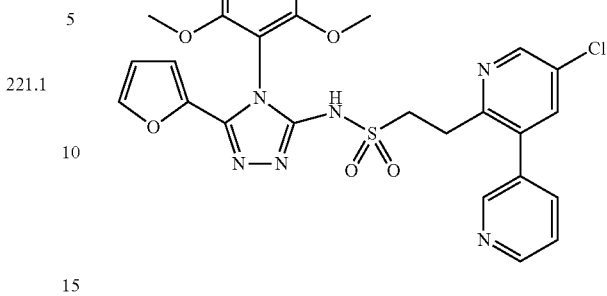

2-(5-Chloro-3,3'-bipyridin-2-yl)-N-(4-(2,6-dimethoxyphenyl)-5-(2-furanyl)-4H-1,2,4-triazol-3-yl)ethanesulfonamide, Example 221.0. The title compound was prepared employing Example 221.1 and the procedure described for the synthesis of Example 264.0. $^1$H NMR (400 MHz, CD$_3$OD) δ 8.67-8.78 (m, 2H) 8.62 (d, J=2.35 Hz, 1H) 8.22 (dt, J=7.97, 1.78 Hz, 1H) 7.79 (d, J=2.35 Hz, 1H) 7.75 (dd, J=7.92, 5.38 Hz, 1H) 7.61 (d, J=1.76 Hz, 1H) 7.55 (t, J=8.51 Hz, 1H) 6.80 (d, J=8.61 Hz, 2H) 6.44 (dd, J=3.52, 1.76 Hz, 1H) 6.12 (d, J=3.60 Hz, 1H) 3.72 (app s, 6H) 3.53 (t, J=7.34 Hz, 2H) 3.13 (t, J=7.34 Hz, 2H). LCMS-ESI (pos.) m/z: 567.0 (M+H)$^+$.

The compounds set forth in the following table were synthesized following the procedure in Example 221.0 using the starting materials as described.

TABLE 10

| Example | Reagents | Structure, Name and Data |
|---|---|---|
| 222.0 | 4-pyridinylboronic acid (commercially available from Sigma-Aldrich Corp., St. Louis, MO, USA). | 2-(5-chloro-3,4'-bipyridin-2-yl)-N-(4-(2,6-dimethoxyphenyl)-5-(2-furanyl)-4H-1,2,4-triazol-3-yl)ethanesulfonamide. $^1$H NMR (400 MHz, CD$_3$OD) δ 8.75 (d, J = 6.06 Hz, 2 H) 8.65 (d, J = 2.35 Hz, 1 H) 7.77-7.90 (m, 3 H) 7.61 (d, J = 1.76 Hz, 1 H) 7.55 (t, J = 8.51 Hz, 1 H) 6.81 (d, J = 8.41 Hz, 2 H) 6.45 (dd, J = 3.62, 1.86 Hz, 1 H) 6.13 (d, J = 3.66 Hz, 1 H) 3.72 (app s, 6 H) 3.55 (t, J = 7.24 Hz, 2 H) 3.16 (t, J = 7.34 Hz, 2 H). LCMS-ESI (pos.) m/z: 567.2 (M + H)$^+$. |

TABLE 10-continued

| Example | Reagents | Structure, Name and Data |
|---|---|---|
| 223.0 | 1H-pyrazole-5-boronic acid pinacol ester (commercially available from Sigma-Aldrich Corp., St. Louis, MO, USA). | 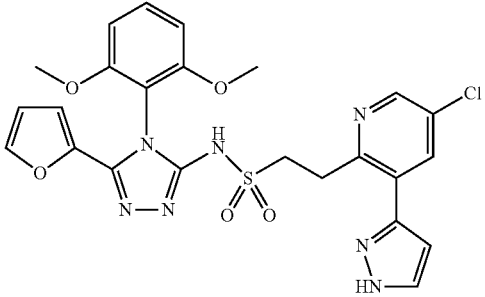 [SMILES: COc1cccc(OC)c1-n1c(NS(=O)(=O)CCc2ncc(Cl)cc2-c2cc[nH]n2)nnc1-c1ccco1]2-(5-chloro-3-(1H-pyrazol-3-yl)-2-pyridinyl)-N-(4-(2,6-dimethoxyphenyl)-5-(2-furanyl)-4H-1,2,4-triazol-3-yl)ethanesulfonamide.<br>$^1$H NMR (500 MHz, CD$_3$OD) δ 8.49 (d, J = 2.44 Hz, 1 H) 7.98 (d, J = 2.45 Hz, 1 H) 7.71 (d, J = 2.20 Hz, 1 H) 7.60 (d, J = 1.71 Hz, 1 H) 7.53 (t, J = 8.56 Hz, 1 H) 6.79 (d, J = 8.56 Hz, 2 H) 6.60 (d, J = 2.45 Hz, 1 H) 6.43 (dd, J = 3.55, 1.83 Hz, 1 H) 6.12 (d, J = 3.42 Hz, 1 H) 3.69 (app s, 6 H) 3.41-3.55 (m, 4 H). LCMS-ESI (pos.) m/z: 556.2 (M + H)$^+$. |

Example 224.0. Preparation of 2-(1'-acetyl-5-chloro-1',2',3',6'-tetrahydro-3,4'-bipyridin-2-yl)-N-(4-(2,6-dimethoxyphenyl)-5-(2-furanyl)-4H-1,2,4-triazol-3-yl)ethanesulfonamide

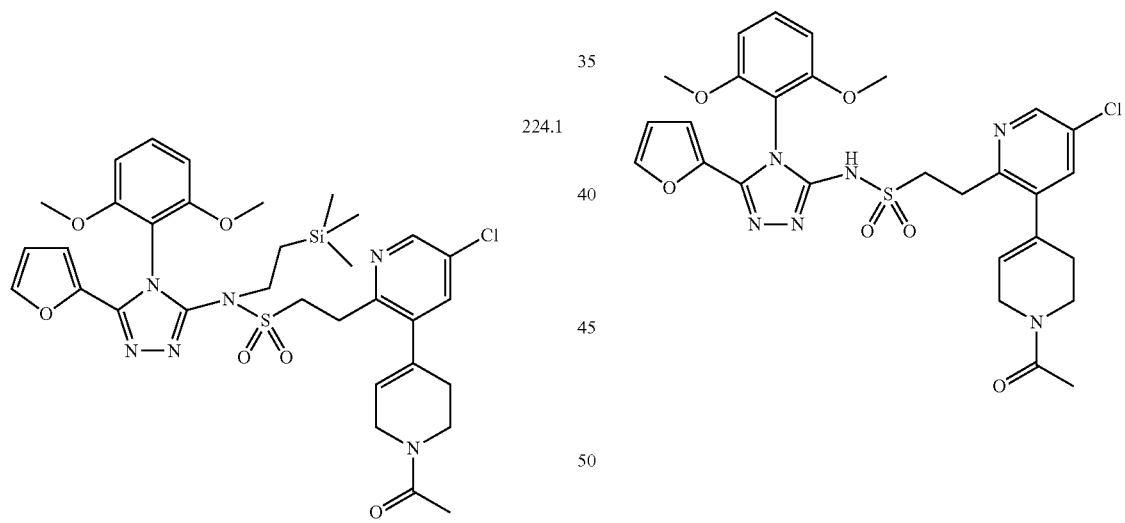

2-(1'-Acetyl-5-chloro-1',2',3',6'-tetrahydro-[3,4'-bipyridin]-2-yl)-N-(4-(2,6-dimethoxyphenyl)-5-(furan-2-yl)-4H-1,2,4-triazol-3-yl)-N-(2-(trimethylsilyl)ethyl)ethanesulfonamide, Example 224.1. Acetyl chloride (13 μL, 0.18 mmol) was added to a solution of Example 220.0 (30 mg, 0.045 mmol) and TEA (25 μL, 0.18 mmol) in DCM, and the mixture was stirred for 2 h at RT. Thereafter, the mixture was partitioned between water and DCM. The DCM layer was separated, dried over Na$_2$SO$_4$, filtered, and concentrated in vacuo to afford Example 224.1. LCMS-ESI (pos.) m/z: 713.2 (M+H)$^+$.

2-(1'-Acetyl-5-chloro-1',2',3',6'-tetrahydro-3,4'-bipyridin-2-yl)-N-(4-(2,6-dimethoxyphenyl)-5-(2-furanyl)-4H-1,2,4-triazol-3-yl)ethanesulfonamide, Example 224.0. The title compound was prepared employing Example 224.1 and the procedure described for the synthesis of Example 264.0. $^1$H NMR (400 MHz, CD$_3$OD) δ 8.42 (d, J=2.54 Hz, 1H) 7.60-7.63 (m, 2H) 7.56 (t, J=8.51 Hz, 1H) 6.85 (d, J=8.41 Hz, 2H) 6.45 (dd, J=3.52, 1.76 Hz, 1H) 6.15 (dd, J=3.52, 0.78 Hz, 1H) 5.72-5.79 (m, 1H) 4.16 (d, J=2.54 Hz, 2H) 3.76 (app s, 6H) 3.68 (t, J=5.58 Hz, 1H) 3.43-3.58 (m, 2H) 3.18-3.26 (m, 2H) 2.45 (d, J=1.57 Hz, 1H) 2.36 (d, J=1.57 Hz, 1H) 2.16 (d, J=4.70 Hz, 3H).

Example 229.0. Preparation of (2S)-2-(5-cyano-2-pyrimidinyl)-N-(4-(2,6-dimethoxyphenyl)-5-(5-methyl-2-furanyl)-4H-1,2,4-triazol-3-yl)-2-fluoro-1-propanesulfonamide and (2R)-2-(5-cyano-2-pyrimidinyl)-N-(4-(2,6-dimethoxyphenyl)-5-(5-methyl-2-furanyl)-4H-1,2,4-triazol-3-yl)-2-fluoro-1-propanesulfonamide 229.1

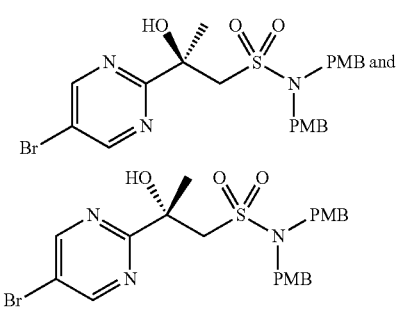

(S)-2-(5-Bromopyrimidin-2-yl)-2-hydroxy-N,N-bis(4-methoxybenzyl)propane-1-sulfonamide and (R)-2-(5-bromopyrimidin-2-yl)-2-hydroxy-N,N-bis(4-methoxybenzyl)propane-1-sulfonamide, Example 229.1. The title compound was prepared employing 1-(5-bromopyrimidin-2-yl)ethanone (commercially available from Bellen, Beijing, China) and the procedure described in Example 237.0. LCMS-ESI (pos.) m/z: 536.0 (M+H)$^+$.

229.2

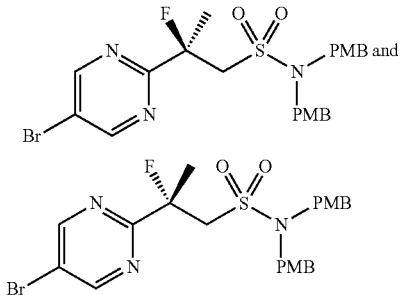

(S)-2-(5-Bromopyrimidin-2-yl)-2-fluoro-N,N-bis(4-methoxybenzyl)propane-1-sulfonamide and (R)-2-(5-bromopyrimidin-2-yl)-2-fluoro-N,N-bis(4-methoxybenzyl)propane-1-sulfonamide, Example 229.2. The title compound was prepared employing Example 229.1 and the procedure described for the synthesis of Example 237.0. LCMS-ESI (pos.) m/z: 539.9 (M+H)$^+$.

229.3

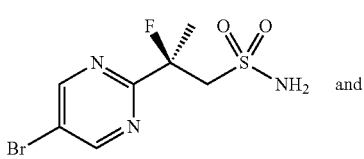

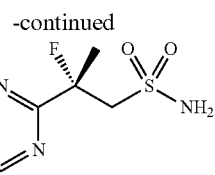

(S)-2-(5-Bromopyrimidin-2-yl)-2-fluoropropane-1-sulfonamide and (R)-2-(5-bromopyrimidin-2-yl)-2-fluoropropane-1-sulfonamide, Example 229.3. The title compound was prepared employing 229.2 and the procedure described for the synthesis of Example 237.0. LCMS-ESI (pos.) m/z: 297.9 (M+H)$^+$.

229.4

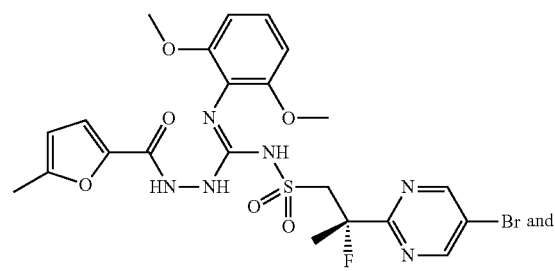

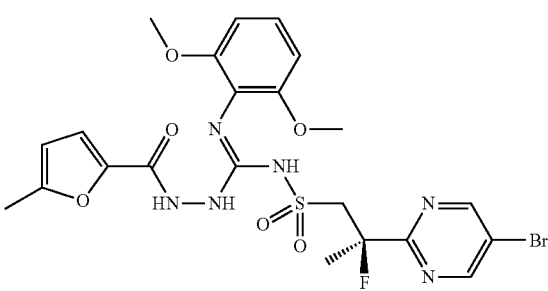

(R,Z)—N-((2-(5-Bromopyrimidin-2-yl)-2-fluoropropyl)sulfonyl)-N'-(2,6-dimethoxyphenyl)-2-(5-methylfuran-2-carbonyl)hydrazinecarboximidamide and (S,Z)—N-((2-(5-bromopyrimidin-2-yl)-2-fluoropropyl)sulfonyl)-N'-(2,6-dimethoxyphenyl)-2-(5-methylfuran-2-carbonyl)hydrazinecarboximidamide, Example 229.4. To a stirred solution of Example 229.3 (124 mg, 0.42 mmol) in ACN (21 mL) at RT was added 372.0 (81 mg, 0.42 mmol). Cesium carbonate (176 mg, 0.54 mmol) was then carefully added in portions and the mixture was stirred until LCMS analysis showed that formation of the intermediate was complete (20 h). 5-Methyl-2-furohydrazide (commercially available from Chembridge Corporation, San Diego, Calif., USA, 58 mg, 0.42 mmol) and silver nitrate (141 mg, 0.83 mmol) were then added, and the mixture was stirred for 15 min at RT. Thereafter, the mixture was filtered through a plug of Celite® brand filter aid rinsing with 10% IPA in DCM. The filtrate was then concentrated in vacuo to afford Example 229.4. LCMS-ESI (pos.) m/z: 598.9 (M+H)$^+$.

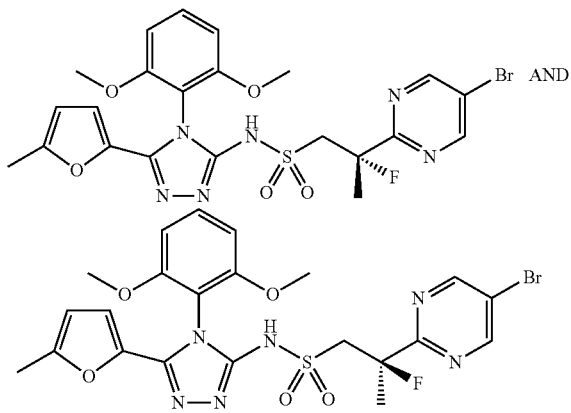

229.5

(R)-2-(5-Bromopyrimidin-2-yl)-N-(4-(2,6-dimethoxyphenyl)-5-(5-methylfuran-2-yl)-4H-1,2,4-triazol-3-yl)-2-fluoropropane-1-sulfonamide and (S)-2-(5-bromopyrimidin-2-yl)-N-(4-(2,6-dimethoxyphenyl)-5-(5-methylfuran-2-yl)-4H-1,2,4-triazol-3-yl)-2-fluoropropane-1-sulfonamide, Example 229.5. TFA (135 µL, 1.82 mmol) was added to a solution of Example 229.4 (273 mg, 0.46 mmol) in DMF (0.9 mL), and the mixture was stirred at 100° C. until LCMS analysis indicated that the reaction was complete (24 h). Thereafter, the mixture was cooled to RT and directly purified on a reverse-phase column employing a gradient of 10-95% ACN in water (0.1% TFA in both eluents) to afford Example 229.5 (55 mg, 0.094 mmol, 21%). LCMS-ESI (pos.) m/z: 580.8 (M+H)$^+$.

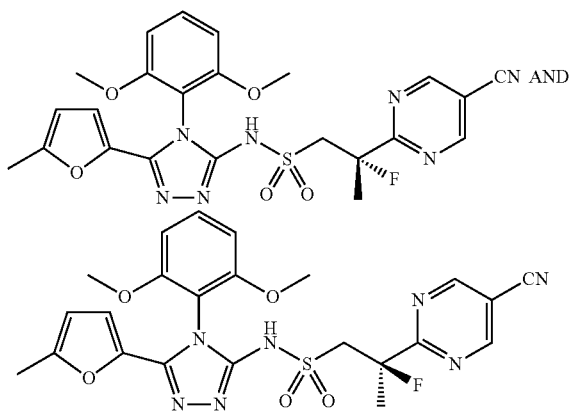

229.0

(2S)-2-(5-Cyano-2-pyrimidinyl)-N-(4-(2,6-dimethoxyphenyl)-5-(5-methyl-2-furanyl)-4H-1,2,4-triazol-3-yl)-2-fluoro-1-propanesulfonamide and (2R)-2-(5-cyano-2-pyrimidinyl)-N-(4-(2,6-dimethoxyphenyl)-5-(5-methyl-2-furanyl)-4H-1,2,4-triazol-3-yl)-2-fluoro-1-propanesulfonamide, Example 229.0. The title compound was prepared employing Example 229.5, and the procedure described for the synthesis of Example 50.0. $^1$H NMR (400 MHz, CDCl$_3$) δ 9.17 (s, 2H) 7.58 (t, J=8.61 Hz, 1H) 6.86 (dd, J=8.61, 1.76 Hz, 2H) 6.05 (dd, J=3.52, 0.98 Hz, 1H) 5.98 (d, J=3.52 Hz, 1H) 4.04 (s, 1H) 4.00 (d, J=6.26 Hz, 1H) 3.82 (s, 3H) 3.81 (s, 3H) 2.28 (s, 3H) 1.82-1.93 (m, 3H). LCMS-ESI (pos.) m/z: 528.0 (M+H)$^+$.

Example 230.0. Preparation of (2R,3S)-3-(5-cyanopyrimidin-2-yl)-N-(4-(2,6-dimethoxyphenyl)-5-(5-methylfuran-2-yl)-4H-1,2,4-triazol-3-yl)-3-fluorobutane-2-sulfonamide and (2S,3R)-3-(5-cyanopyrimidin-2-yl)-N-(4-(2,6-dimethoxyphenyl)-5-(5-methylfuran-2-yl)-4H-1,2,4-triazol-3-yl)-3-fluorobutane-2-sulfonamide or (2R,3R)-3-(5-cyanopyrimidin-2-yl)-N-(4-(2,6-dimethoxyphenyl)-5-(5-methylfuran-2-yl)-4H-1,2,4-triazol-3-yl)-3-fluorobutane-2-sulfonamide and (2S,3S)-3-(5-cyanopyrimidin-2-yl)-N-(4-(2,6-dimethoxyphenyl)-5-(5-methylfuran-2-yl)-4H-1,2,4-triazol-3-yl)-3-fluorobutane-2-sulfonamide

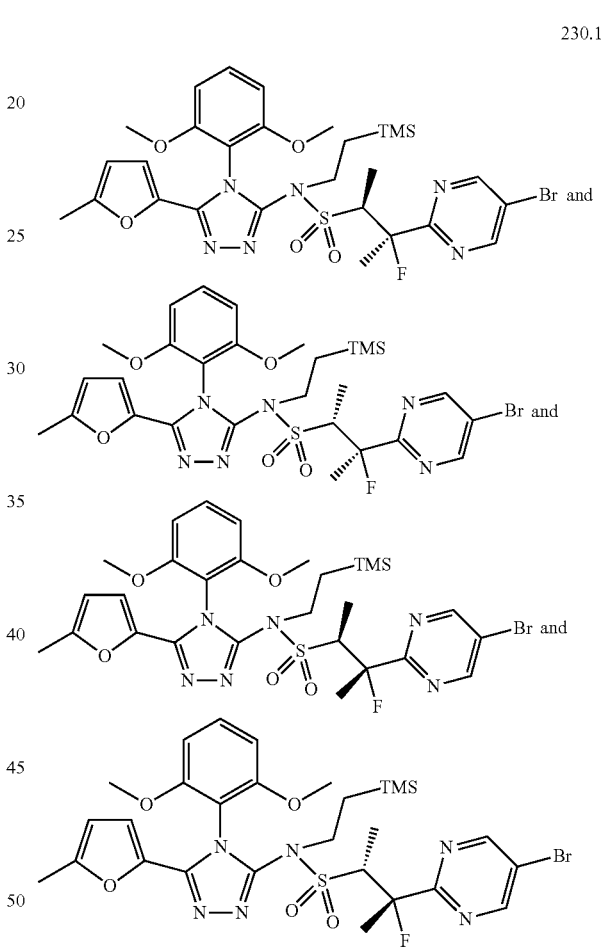

230.1

(2S,3R)-3-(5-Bromopyrimidin-2-yl)-N-(4-(2,6-dimethoxyphenyl)-5-(5-methylfuran-2-yl)-4H-1,2,4-triazol-3-yl)-3-fluoro-N-(2-(trimethylsilyl)ethyl)butane-2-sulfonamide and (2R,3R)-3-(5-bromopyrimidin-2-yl)-N-(4-(2,6-dimethoxyphenyl)-5-(5-methylfuran-2-yl)-4H-1,2,4-triazol-3-yl)-3-fluoro-N-(2-(trimethylsilyl)ethyl)butane-2-sulfonamide and (2S,3S)-3-(5-bromopyrimidin-2-yl)-N-(4-(2,6-dimethoxyphenyl)-5-(5-methylfuran-2-yl)-4H-1,2,4-triazol-3-yl)-3-fluoro-N-(2-(trimethylsilyl)ethyl)butane-2-sulfonamide and (2R,3S)-3-(5-bromopyrimidin-2-yl)-N-(4-(2,6-dimethoxyphenyl)-5-(5-methylfuran-2-yl)-4H-1,2,4-triazol-3-yl)-3-fluoro-N-(2-(trimethylsilyl)ethyl)butane-2-sulfonamide, Example 230.1. At −78° C., n-butyllithium (2.5 M, 0.294 mL, 0.735 mmol) was added to a THF (7.35 mL) solution containing Example 369.0. The resulting mixture was stirred 30 min at −78° C. Next, a THF solution of 1-(5-bromopyrimidin-2-yl)ethanone (0.208 g, 1.04 mmol) was added at −78° C. The reaction was continued at −78° C. and allowed to slowly warm to room temp and stirred overnight. The reaction was then quenched with a saturated solution of NH$_4$Cl and extracted with EtOAc (3×100 mL). After concentration by solvent removal from the combined organic layers, the reaction was purified on silica eluting with a hexane/EtOAc gradient (0-100%). Desired fractions were then pooled and concentrated in vacuo. The material was then subjected to the reaction conditions described in Example 229.2 to deliver the desired compound. LCMS-ESI (pos.) m/z: 695.0, 697.0 (M+H)$^+$.

mmol). This solution was heated at 60° C. for 5 h. After cooling to RT, the reaction was purified via reverse phase HPLC (Agilent SB-C8 column, 30×250 mm, 5 μm, 10-95% water/ACN gradient over 25 min., with 0.1% TFA, flow rate 50 mL/min). Desired fractions were pooled and lyophilized to give pure title compound. LCMS-ESI (pos.) m/z: 596.9 (M+H)$^+$.

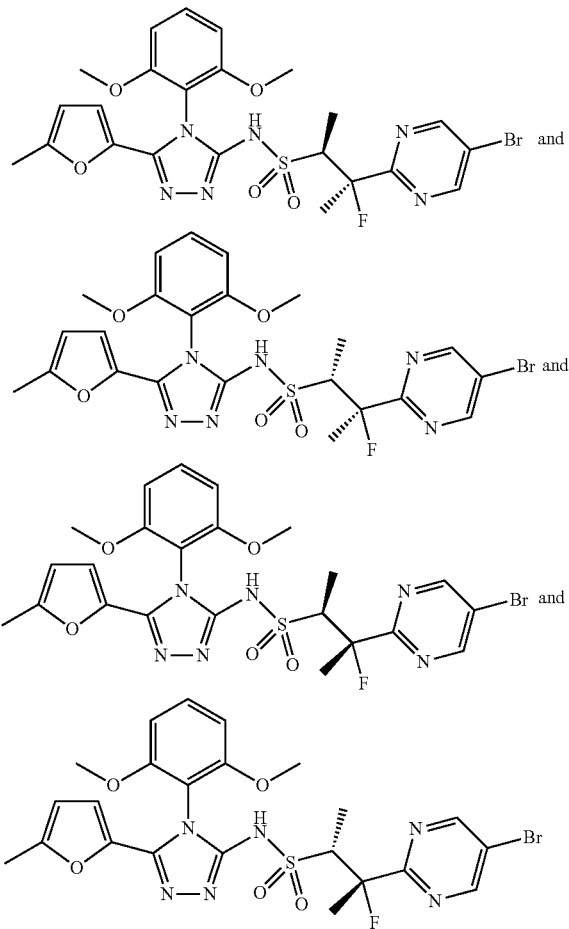

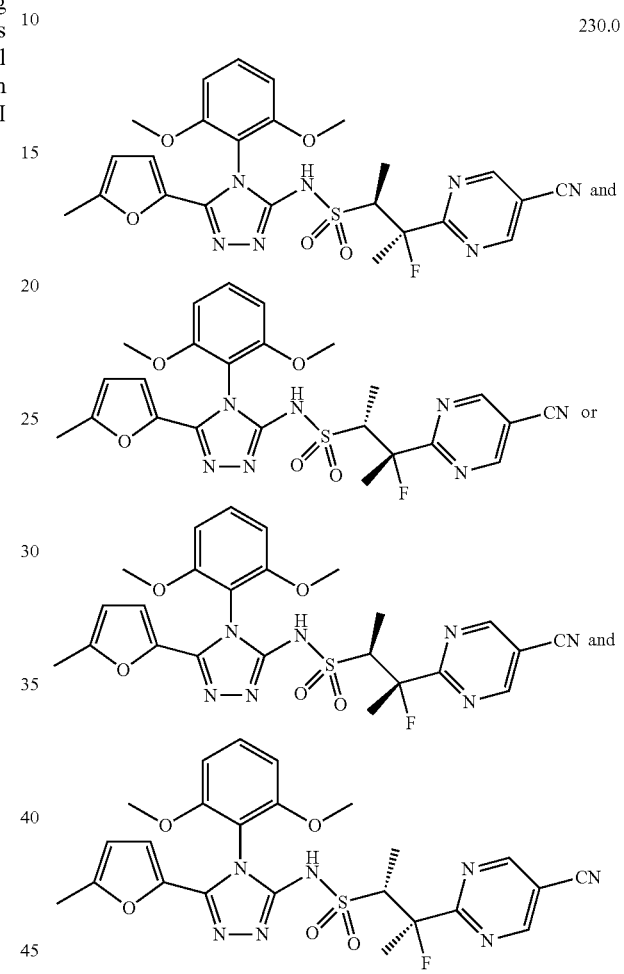

(2S,3S)-3-(5-Bromopyrimidin-2-yl)-N-(4-(2,6-dimethoxyphenyl)-5-(5-methylfuran-2-yl-4H-1,2,4-triazol-3-yl)-3-fluorobutane-2-sulfonamide and (2S,3S)-3-(5-bromopyrimidin-2-yl)-N-(4-(2,6-dimethoxyphenyl)-5-(5-methylfuran-2-yl)-4H-1,2,4-triazol-3-yl)-3-fluorobutane-2-sulfonamide and (2S,3S)-3-(5-bromopyrimidin-2-yl)-N-(4-(2,6-dimethoxyphenyl)-5-(5-methylfuran-2-yl)-4H-1,2,4-triazol-3-yl)-3-fluorobutane-2-sulfonamide and (2S,3S)-3-(5-bromopyrimidin-2-yl)-N-(4-(2,6-dimethoxyphenyl)-5-(5-methylfuran-2-yl)-4H-1,2,4-triazol-3-yl)-3-fluorobutane-2-sulfonamide, Example 230.2. TASF (5 eq) was added to a DMF solution containing Example 230.1 (120 mg, 0.172

(2R,3S)-3-(5-Cyanopyrimidin-2-yl)-N-(4-(2,6-dimethoxyphenyl)-5-(5-methylfuran-2-yl)-4H-1,2,4-triazol-3-yl)-3-fluorobutane-2-sulfonamide and (2S,3R)-3-(5-cyanopyrimidin-2-yl)-N-(4-(2,6-dimethoxyphenyl)-5-(5-methylfuran-2-yl)-4H-1,2,4-triazol-3-yl)-3-fluorobutane-2-sulfonamide or (2R,3R)-3-(5-cyanopyrimidin-2-yl)-N-(4-(2,6-dimethoxyphenyl)-5-(5-methylfuran-2-yl)-4H-1,2,4-triazol-3-yl)-3-fluorobutane-2-sulfonamide and (2S,3S)-3-(5-cyanopyrimidin-2-yl)-N-(4-(2,6-dimethoxyphenyl)-5-(5-methylfuran-2-yl)-4H-1,2,4-triazol-3-yl)-3-fluorobutane-2-sulfonamide, Example 230.0. A glass microwave reaction vessel was charged with Example 230.2 (30 mg, 0.050 mmol), zinc cyanide (0.013 mL, 0.202 mmol), and tetrakis(triphenylphosphine)palladium (5.82 mg, 5.04 μmol) in DMF (1 mL). The reaction mixture was stirred and heated in a Discover model microwave reactor (CEM, Matthews, N.C.) at 120° C. for 30 min. The reaction product was purified via reverse phase HPLC (Agilent SB-C8 column, 30×250 mm, 5 μm, 10-95% water/ACN gradient over 25 min., with 0.1% TFA, flow rate 50 mL/min). Desired fractions were pooled and lyophilized to give pure product. This material was purified via SFC chiral separation to deliver that the compound as a mixture of enantiomers. LCMS-ESI (pos.) m/z: 542.0 (M+H)+.

Example 231.0. Preparation of (2S)-2-(5-cyano-2-pyrimidinyl)-N-(4-(2,6-dimethoxyphenyl)-5-(5-methyl-2-furanyl)-4H-1,2,4-triazol-3-yl)-2-fluoro-1-propanesulfonamide or (2R)-2-(5-cyano-2-pyrimidinyl)-N-(4-(2,6-dimethoxyphenyl)-5-(5-methyl-2-furanyl)-4H-1,2,4-triazol-3-yl)-2-fluoro-1-propanesulfonamide

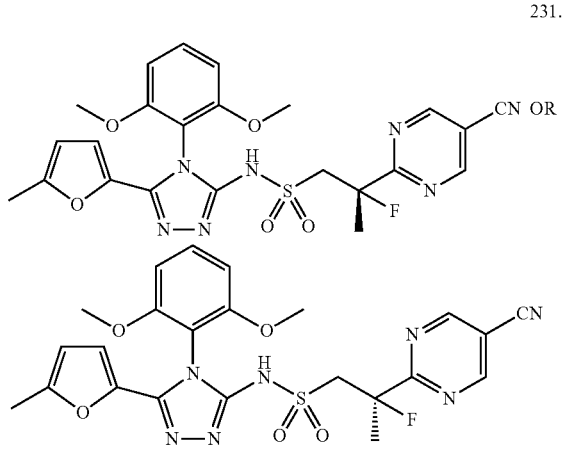

231.0

(2S)-2-(5-Cyano-2-pyrimidinyl)-N-(4-(2,6-dimethoxyphenyl)-5-(5-methyl-2-furanyl)-4H-1,2,4-triazol-3-yl)-2-fluoro-1-propanesulfonamide or (2R)-2-(5-cyano-2-pyrimidinyl)-N-(4-(2,6-dimethoxyphenyl)-5-(5-methyl-2-furanyl)-4H-1,2,4-triazol-3-yl)-2-fluoro-1-propanesulfonamide, Example 231.0. Purification of Example 229.0 by SFC [20×150 mm IC column with 35% MeOH (neat) in CO2 at 100 bar] afforded two enantiomers. The title compound was the first isomer to elute under these conditions. 1H NMR (500 MHz, CDCl3) δ 10.77 (br. s., 1H) 9.03 (s, 2H) 7.42-7.50 (m, 1H) 6.68 (dd, J=8.56, 3.91 Hz, 2H) 5.89-5.93 (m, 1H) 5.81 (d, J=3.42 Hz, 1H) 4.01 (d, J=6.60 Hz, 1H) 3.98 (s, 1H) 3.78 (s, 3H) 3.76 (s, 3H) 2.32 (s, 3H) 1.86-1.94 (m, 3H). LCMS-ESI (pos.) m/z: 528.0 (M+H)+.

Example 232.0. Preparation of 2-(5-chloro-3-(2-(1-pyrrolidinyl)ethyl)-2-pyridinyl)-N-(4-(2,6-dimethoxyphenyl)-5-(2-furanyl)-4H-1,2,4-triazol-3-yl)ethanesulfonamide

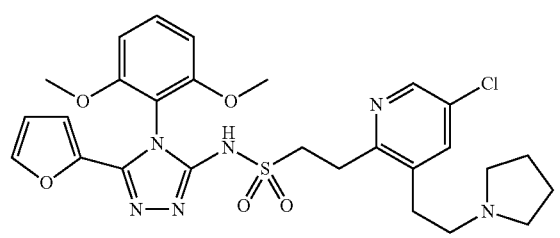

232.0

2-(5-Chloro-3-(2-(1-pyrrolidinyl)ethyl)-2-pyridinyl)-N-(4-(2,6-dimethoxyphenyl)-5-(2-furanyl)-4H-1,2,4-triazol-3-yl)ethanesulfonamide, Example 232.0. The title compound was prepared following the procedure described in Example 219.0 employing pyrrolidine (commercially available from Sigma-Aldrich Corp., St. Louis, Mo., USA) and Example 219.12. 1H NMR (400 MHz, CDCl3) δ 8.41 (s, 1H) 7.54 (br. s., 2H) 7.49 (d, J=1.17 Hz, 1H) 6.72 (d, J=8.02 Hz, 2H) 6.36 (dd, J=3.52, 1.76 Hz, 1H) 6.01 (d, J=3.33 Hz, 1H) 3.75 (s, 8H) 3.58 (t, J=6.46 Hz, 2H) 3.30 (br. s., 2H) 3.24 (t, J=6.55 Hz, 2H) 3.15 (br. s., 2H) 2.93 (br. s., 2H) 2.11 (br. s., 4H). LCMS-ESI (pos.) m/z: 587.0 (M+H)+.

Example 233.0. Preparation of (R)-2-(5-cyanopyrimidin-2-yl)-N-(4-(2,6-dimethoxyphenyl)-5-(5-methylfuran-2-yl)-4H-1,2,4-triazol-3-yl)-2-hydroxypropane-1-sulfonamide or (S)-2-(5-cyanopyrimidin-2-yl)-N-(4-(2,6-dimethoxyphenyl)-5-(5-methylfuran-2-yl)-4H-1,2,4-triazol-3-yl)-2-hydroxypropane-1-sulfonamide

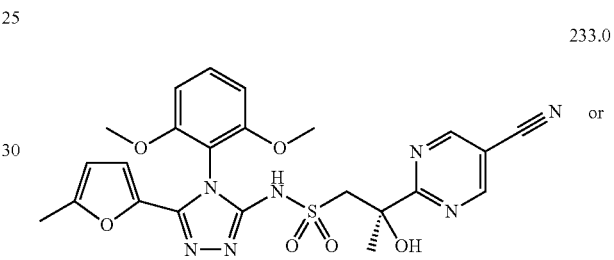

233.0

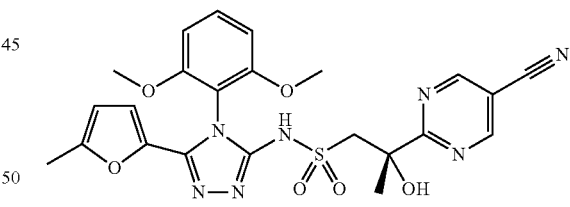

(R)-2-(5-Cyanopyrimidin-2-yl)-N-(4-(2,6-dimethoxyphenyl)-5-(5-methylfuran-2-yl)-4H-1,2,4-triazol-3-yl)-2-hydroxypropane-1-sulfonamide or (S)-2-(5-cyanopyrimidin-2-yl)-N-(4-(2,6-dimethoxyphenyl)-5-(5-methylfuran-2-yl)-4H-1,2,4-triazol-3-yl)-2-hydroxypropane-1-sulfonamide, Example 233.0. Example 233.0 is the enantiomer of Example 248.0. The title compound was the second isomer to elute on subjecting racemic Example 241.0 to the SFC conditions described in Example 248.0. 1H NMR (500 MHz, CDCl3) δ 9.07 (s, 2H) 7.57 (t, J=8.35 Hz, 1H) 6.86 (dd, J=8.56, 2.45 Hz, 2H) 6.03 (s, 1H) 5.96 (d, J=3.42 Hz, 1H) 3.84 (d, J=12.01 Hz, 1H) 3.82 (s, 3H) 3.81 (s, 3H) 3.72 (d, J=12.01 Hz, 1H) 2.26 (s, 3H) 1.65 (s, 3H). LCMS-ESI (pos.) m/z: 526.0 (M+H)+.

Example 234.0. Preparation of (2S)—N-(4-(2,6-dimethoxyphenyl)-5-(2-furanyl)-4H-1,2,4-triazol-3-yl)-1-(5-fluoro-4-methyl-2-pyrimidinyl)-2-propanesulfonamide and (2R)—N-(4-(2,6-dimethoxyphenyl)-5-(2-furanyl)-4H-1,2,4-triazol-3-yl)-1-(5-fluoro-4-methyl-2-pyrimidinyl)-2-propanesulfonamide

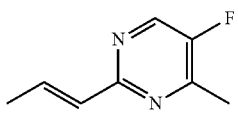

234.1

(E)-4-(5-Fluoro-2-(prop-1-en-1-yl)pyrimidin-4-yl)morpholine, Example 234.1. The title compound was prepared employing 2-chloro-5-fluoro-4-methylpyrimidine (commercially available from Bellen, Beijing, China) and potassium (E)-trifluoro(prop-1-en-1-yl)borate (commercially available from Frontier Scientific Services Inc.) and the procedure described for the synthesis of Example 4.3. LCMS-ESI (pos.) m/z: 153.2 (M+H)$^+$.

234.0

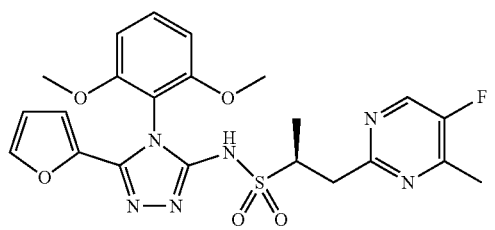

AND

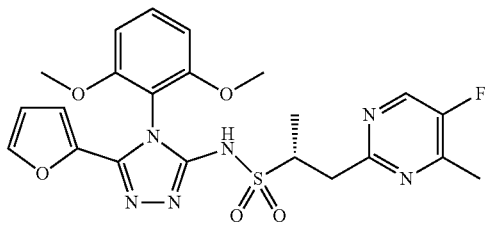

(2S)—N-(4-(2,6-Dimethoxyphenyl)-5-(2-furanyl)-4H-1,2,4-triazol-3-yl)-1-(5-fluoro-4-methyl-2-pyrimidinyl)-2-propanesulfonamide and (2R)—N-(4-(2,6-dimethoxyphenyl)-5-(2-furanyl)-4H-1,2,4-triazol-3-yl)-1-(5-fluoro-4-methyl-2-pyrimidinyl)-2-propanesulfonamide, Example 234.0. The title compound was prepared employing Example 234.1 and the procedure described for the syntheses of Example 34.0. $^1$H NMR (500 MHz, CDCl$_3$) δ 8.41 (d, J=1.47 Hz, 1H) 7.44-7.54 (m, 2H) 6.70 (dd, J=8.56, 1.96 Hz, 2H) 6.35 (dd, J=3.55, 1.83 Hz, 1H) 6.02 (d, J=3.67 Hz, 1H) 3.80-3.88 (m, 1H) 3.74-3.80 (m, 6H) 3.63 (dd, J=14.55, 5.01 Hz, 1H) 3.05 (dd, J=14.79, 9.41 Hz, 1H) 2.54 (d, J=2.45 Hz, 3H) 1.34 (d, J=6.85 Hz, 3H). LCMS-ESI (pos.) m/z: 503.2 (M+H)$^+$.

Example 235.0. Preparation of 2-(3-(2-(1-azetidinyl)ethyl)-5-chloro-2-pyridinyl)-N-(4-(2,6-dimethoxyphenyl)-5-(2-furanyl)-4H-1,2,4-triazol-3-yl)ethanesulfonamide

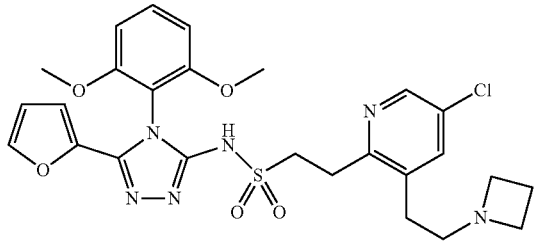

235.0

2-(3-(2-(1-Azetidinyl)ethyl)-5-chloro-2-pyridinyl)-N-(4-(2,6-dimethoxyphenyl)-5-(2-furanyl)-4H-1,2,4-triazol-3-yl)ethanesulfonamide, Example 235.0. The title compound was prepared following the procedure described in Example 219.0 employing azetidine (commercially available from Matrix Scientific, Columbia, S.C., USA) and Example 219.12. $^1$H NMR (500 MHz, CDCl$_3$) δ 11.46 (br. s., 1H) 8.48 (d, J=2.20 Hz, 1H) 7.63 (d, J=2.20 Hz, 1H) 7.52 (t, J=8.44 Hz, 1H) 7.48 (d, J=1.71 Hz, 1H) 6.71 (d, J=8.56 Hz, 2H) 6.35 (dd, J=3.55, 1.83 Hz, 1H) 6.02 (d, J=3.67 Hz, 1H) 4.25 (br. s., 2H) 3.97 (d, J=7.09 Hz, 2H) 3.74 (app s, 6H) 3.56-3.66 (m, 2H) 3.40 (br. s., 2H) 3.25-3.35 (m, 2H) 2.85-3.01 (m, 2H) 2.55-2.71 (m, 1H) 2.28-2.45 (m, 1H). LCMS-ESI (pos.) m/z: 573.3 (M+H)$^+$.

Example 237.0. Preparation of (2S)—N-(4-(2,6-dimethoxyphenyl)-5-(5-methyl-2-furanyl)-4H-1,2,4-triazol-3-yl)-2-fluoro-2-(5-fluoro-2-pyrimidinyl)-1-propanesulfonamide and (2R)—N-(4-(2,6-dimethoxyphenyl)-5-(5-methyl-2-furanyl)-4H-1,2,4-triazol-3-yl)-2-fluoro-2-(5-fluoro-2-pyrimidinyl)-1-propanesulfonamide

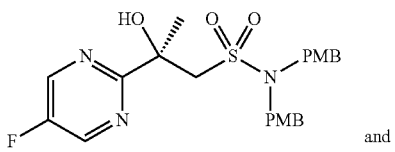

237.1 and

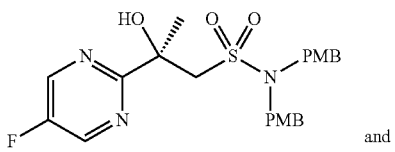

(S)-2-(5-Fluoropyrimidin-2-yl)-2-hydroxy-N,N-bis(4-methoxybenzyl)propane-1-sulfonamide and (R)-2-(5-fluoropyrimidin-2-yl)-2-hydroxy-N,N-bis(4-methoxybenzyl)propane-1-sulfonamide, Example 237.1. n-Butyllithium (commercially available from Sigma-Aldrich Corp., 2.5M in hexanes, 2.85 mL, 7.14 mmol) was added to a solution of N,N-bis(4-methoxybenzyl)methanesulfonamide (370.0, 2.4 g, 7.14 mmol) in THF (10 mL) at −78° C. After stirring for 30 min at −78° C., a solution of 1-(5-fluoropyrimidin-2-yl)ethanone (commercially available from Bellen, Beijing, China, 1.0 g, 7.14 mmol) in THF (4 mL) was added dropwise. After the addition was complete, the reaction vessel was removed from the cooling bath and the mixture was stirred at RT for 16 h. Thereafter, the reaction was quenched with a saturated aqueous solution of $NH_4Cl$ and extracted with EtOAc. The combined organic layers were dried over $Na_2SO_4$, filtered, and concentrated in vacuo. The residue was purified on a silica gel column employing a gradient of 0-100% EtOAc in hexanes to afford Example 237.1 (3.1 g, 6.55 mmol, 92%). LCMS-ESI (pos.) m/z: 476.0 $(M+H)^+$.

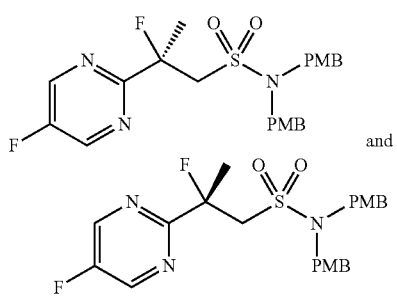

(S)-2-Fluoro-2-(5-fluoropyrimidin-2-yl)-N,N-bis(4-methoxybenzyl)propane-1-sulfonamide and (R)-2-fluoro-2-(5-fluoropyrimidin-2-yl)-N,N-bis(4-methoxybenzyl)propane-1-sulfonamide, Example 237.2. DAST (commercially available from Sigma-Aldrich Corp., St. Louis, Mo., USA, 235 mg, 1.46 mmol) was added to a solution of Example 237.1 (346 mg, 0.73 mmol) in DCM (25 mL) at 0° C., and the mixture was stirred until LCMS analysis indicated that the fluorination was complete (2 h). Thereafter, the mixture was quenched with MeOH (0.1 mL) and concentrated in vacuo. The residue was purified on a silica gel column employing a gradient of 0-100% EtOAc in hexanes to afford Example 237.2. LCMS-ESI (pos.) m/z: 478.1 $(M+H)^+$.

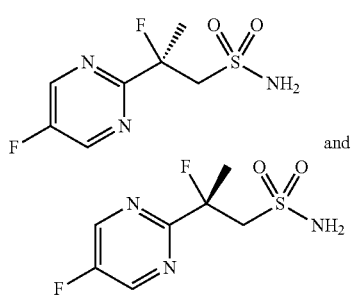

(S)-2-Fluoro-2-(5-fluoropyrimidin-2-yl)propane-1-sulfonamide and (R)-2-fluoro-2-(5-fluoropyrimidin-2-yl)propane-1-sulfonamide, Example 237.3. TFA (548 µL, 7.11 mmol) was added to Example 237.2 (338 mg, 0.71 mmol) and triethylsilane (827 mg, 7.11 mmol), and the mixture was stirred for 16 h at RT. Thereafter, the mixture was concentrated in vacuo and the residue was purified on a reverse-phase column employing a gradient of 10-95% ACN in water (0.1% TFA in both eluents) to afford Example 237.3 (61 mg, 0.26 mmol, 37%). LCMS-ESI (pos.) m/z: 238.0 $(M+H)^+$.

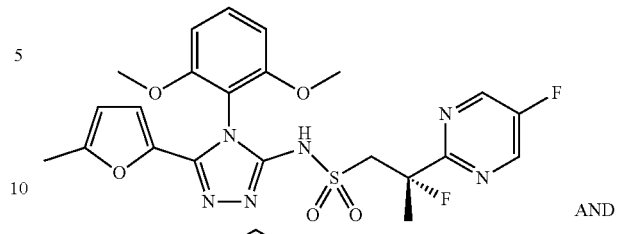

(2S)—N-(4-(2,6-Dimethoxyphenyl)-5-(5-methyl-2-furanyl)-4H-1,2,4-triazol-3-yl)-2-fluoro-2-(5-fluoro-2-pyrimidinyl)-1-propanesulfonamide and (2R)—N-(4-(2,6-dimethoxyphenyl)-5-(5-methyl-2-furanyl)-4H-1,2,4-triazol-3-yl)-2-fluoro-2-(5-fluoro-2-pyrimidinyl)-1-propanesulfonamide, Example 237.4. A suspension of Example 364.1 (122 mg, 0.33 mmol), Example 237.3 (61 mg, 0.26 mmol), rac-trans-N,N'-dimethylcyclohexane-1,2-diamine (73 mg, 0.51 mmol), and cesium carbonate (oven-dried, 209 mg, 0.64 mmol) in dioxane (1.0 mL) was sparged with argon for 3 min. Copper(I) iodide (25 mg, 0.13 mmol) was then added and the mixture was sparged with argon for 3 min. The reaction vessel was then heated at 80° C. for 16 h. Thereafter, the mixture was cooled to RT and filtered over Celite® brand filter aid rinsing with EtOAc. Water was then added and the mixture was extracted with EtOAc. The extracts were then combined, washed with brine, dried over $Na_2SO_4$, filtered, and concentrated in vacuo. The residue was purified on a reverse-phase column, employing a gradient of 10-95% ACN in water (0.1% TFA in both eluents) to afford Example 237.4. LCMS-ESI (pos.) m/z: 521.0 $(M+H)^+$.

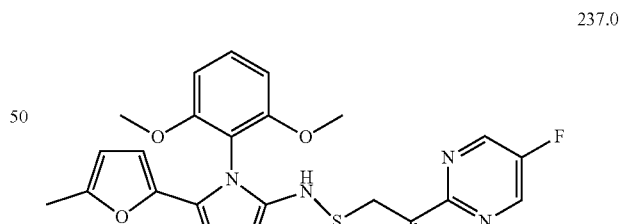

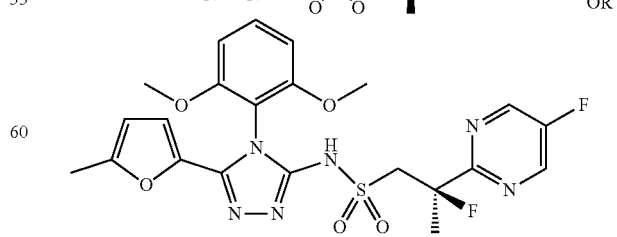

(2S)—N-(4-(2,6-Dimethoxyphenyl)-5-(5-methyl-2-furanyl)-4H-1,2,4-triazol-3-yl)-2-fluoro-2-(5-fluoro-2-pyrimidinyl)-1-propanesulfonamide or (2R)—N-(4-(2,6-dimethoxyphenyl)-5-(5-methyl-2-furanyl)-4H-1,2,4-triazol-3-yl)-2-fluoro-2-(5-fluoro-2-pyrimidinyl)-1-propanesulfonamide, Example 237.0. Purification of Example 237.4 by SFC [30×250 mm IC column with 36 g/min MeOH (neat) in 44 g/min CO$_2$ at 100 bar] afforded two enantiomers. The title compound was the second isomer to elute. $^1$H NMR (400 MHz, CD$_3$OD) δ 8.75 (s, 2H) 7.57 (t, J=8.35 Hz, 1H) 6.86 (dd, J=8.51, 2.05 Hz, 2H) 6.02-6.08 (m, 1H) 5.97 (d, J=3.52 Hz, 1H) 3.90-4.10 (m, 2H) 3.81 (s, 3H) 3.80 (s, 3H) 2.28 (s, 3H) 1.94-1.88 (d, J=20 Hz, 3H). LCMS-ESI (pos.) m/z: 521.0 (M+H)$^+$.

Example 238.0. Preparation of 2-(5-chloro-3-(2-((3S)-3-hydroxy-1-pyrrolidinyl)ethyl)-2-pyridinyl)-N-(4-(2,6-dimethoxyphenyl)-5-(2-furanyl)-4H-1,2,4-triazol-3-yl)ethanesulfonamide 238.0

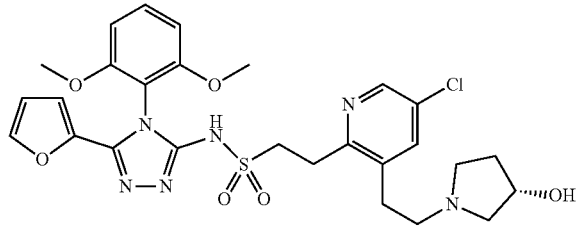

2-(5-Chloro-3-(2-((3S)-3-hydroxy-1-pyrrolidinyl)ethyl)-2-pyridinyl)-N-(4-(2,6-dimethoxyphenyl)-5-(2-furanyl)-4H-1,2,4-triazol-3-yl)ethanesulfonamide, Example 238.0. The title compound was prepared following the procedure described in Example 219.0 employing (S)-3-pyrrolidinol (commercially available from Sigma-Aldrich Corp., St. Louis, Mo., USA) and Example 219.12. $^1$H NMR (400 MHz, CDCl$_3$) δ 8.41 (br. s., 1H) 7.45-7.62 (m, 3H) 6.72 (d, J=8.41 Hz, 2H) 6.36 (dd, J=3.52, 1.76 Hz, 1H) 6.04 (d, J=3.52 Hz, 1H) 4.56 (br. s., 1H) 3.75 (app s, 6H) 3.67 (d, J=9.00 Hz, 1H) 3.59 (br. s., 2H) 3.21-3.50 (m, 5H) 3.12 (br. s., 3H) 2.15 (br. s., 2H). LCMS-ESI (pos.) m/z: 603.0 (M+H)$^+$.

Example 239.0. Preparation of 2-(5-chloro-3-(2-(4-morpholinyl)ethyl)-2-pyridinyl)-N-(4-(2,6-dimethoxyphenyl)-5-(2-furanyl)-4H-1,2,4-triazol-3-yl)ethanesulfonamide 239.0

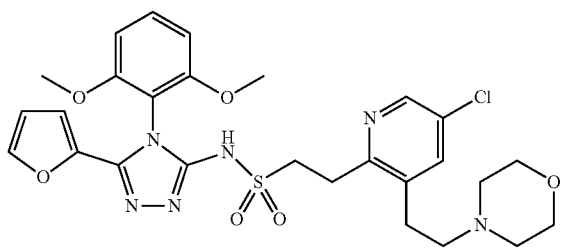

2-(5-Chloro-3-(2-(4-morpholinyl)ethyl)-2-pyridinyl)-N-(4-(2,6-dimethoxyphenyl)-5-(2-furanyl)-4H-1,2,4-triazol-3-yl)ethanesulfonamide, Example 239.0. The title compound was prepared following the procedure described in Example 219.0 employing morpholine (commercially available from Sigma-Aldrich Corp.) and Example 219.12. $^1$H NMR (400 MHz, CDCl$_3$) δ 8.58 (d, J=2.35 Hz, 1H) 7.83 (d, J=2.35 Hz, 1H) 7.49-7.54 (m, 1H) 7.48 (s, 1H) 6.70 (d, J=8.61 Hz, 2H) 6.36 (dd, J=3.52, 1.76 Hz, 1H) 6.04 (d, J=3.96 Hz, 1H) 4.04 (d, J=11.35 Hz, 2H) 3.91 (t, J=12.42 Hz, 2H) 3.74 (app s, 6H) 3.53-3.69 (m, 4H) 3.38-3.49 (m, 4H) 3.20-3.35 (m, 2H). LCMS-ESI (pos.) m/z: 603.1 (M+H)$^+$.

Example 240.0. Preparation of (2S)—N-(4-(2,6-dimethoxyphenyl)-5-(2-furanyl)-4H-1,2,4-triazol-3-yl)-1-(5-fluoro-3-((4R)-4-hydroxy-2-oxo-1-pyrrolidinyl)-2-pyridinyl)-2-propanesulfonamide or (2R)—N-(4-(2,6-dimethoxyphenyl)-5-(2-furanyl)-4H-1,2,4-triazol-3-yl)-1-(5-fluoro-3-((4R)-4-hydroxy-2-oxo-1-pyrrolidinyl)-2-pyridinyl)-2-propanesulfonamide 240.1

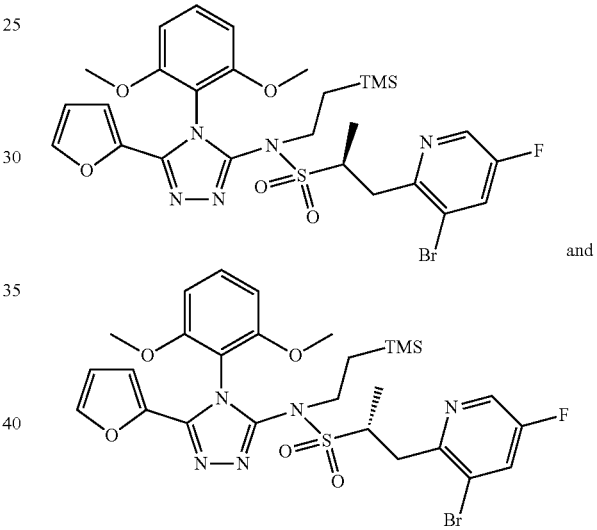

and (S)-1-(3-Bromo-5-fluoropyridin-2-yl)-N-(4-(2,6-dimethoxyphenyl)-5-(furan-2-yl)-4H-1,2,4-triazol-3-yl)-N-(2-(trimethylsilyl)ethyl)propane-2-sulfonamide and (R)-1-(3-bromo-5-fluoropyridin-2-yl)-N-(4-(2,6-dimethoxyphenyl)-5-(furan-2-yl)-4H-1,2,4-triazol-3-yl)-N-(2-(trimethylsilyl)ethyl)propane-2-sulfonamide, Example 240.1. To a solution of Example 366.0 (9.2 g, 14.96 mmol) in THF (46 mL) was added LiHMDS (1.0 M in THF, 17.9 mL, 17.96 mmol) dropwise at ambient temperature over 2 min. The reaction mixture was then stirred at ambient temperature for 15 min and a solution of 3-bromo-5-fluoropicolinaldehyde (4.57 g, 22.45 mmol) in THF (27.6 mL) was added dropwise. The reaction mixture was then stirred at ambient temperature for 2 h. After completion of the reaction (monitored by TLC), the reaction mixture was quenched with water (10 mL) and concentrated in vacuo. The material was purified by column chromatography (silica: 100-200 mesh; elution: 40% EtOAc in hexane) to give the desired olefin (7.0 g, 70.4%) as an off brown semi-solid. LCMS ESI (positive ion) m/z: 665.75 (M+H)$^+$. To a solution of the olefin (7.0 g, 10.53 mmol) in EtOH (300 mL) was added Raney-Ni (3.0 g, slurry in water 2 mL) under N$_2$ atmosphere at ambient temperature. The reaction mixture was stirred under H₂ atmosphere (1 atm.) for 3 h at ambient temperature. After completion of the reaction (monitored by LCMS), the reaction mixture was filtered over a Celite® brand filter aid pad and the pad was washed with EtOH (20 mL). The filtrate was concentrated in vacuo. The material was purified by Combiflash chromatography (column 120 g, elution: 40% EtOAc in hexane) and provided the title compound (5.0 g, 71.4%) as an off white solid. ¹H NMR (400 MHz, DMSO) δ 8.56 (s, 1H), 8.16 (d, J=8.3 Hz, 1H), 7.86 (s, 1H), 7.48 (t, J=8.5 Hz, 1H), 6.83 (d, J=8.6 Hz, 2H), 6.54 (d, J=3.2 Hz, 1H), 6.03 (d, J=3.6 Hz, 1H), 4.38 (dd, J=10.3, 6.4 Hz, 2H), 3.71 (s, 3H), 3.71 (s, 3H), 3.29-3.16 (m, 2H), 2.72-2.65 (m, 1H), 1.26 (t, J=8.5 Hz, 2H), 0.89 (d, J=6.6 Hz, 3H), 0.13-0.01 (m, 9H). LCMS ESI positive ion) m/z: 666.1 (M+H)⁺.

240.0

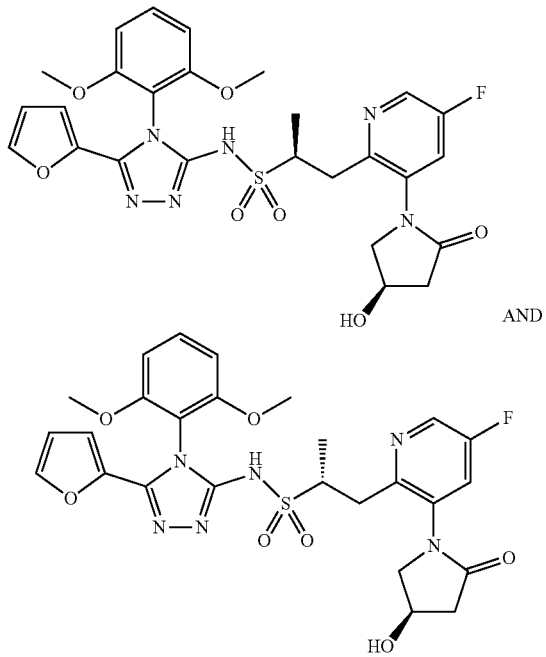

AND (2S)—N-(4-(2,6-Dimethoxyphenyl)-5-(2-furanyl)-4H-1,2,4-triazol-3-yl)-1-(5-fluoro-3-((4R)-4-hydroxy-2-oxo-1-pyrrolidinyl)-2-pyridinyl)-2-propanesulfonamide and (2R)—N-(4-(2,6-dimethoxyphenyl)-5-(2-furanyl)-4H-1,2,4-triazol-3-yl)-1-(5-fluoro-3-((4R)-4-hydroxy-2-oxo-1-pyrrolidinyl)-2-pyridinyl)-2-propanesulfonamide, Example 240.0. The title compound was prepared employing Example 240.1 and (R)-4-hydroxypyrrolidin-2-one (commercially available from Sigma-Aldrich Corp., St. Louis, Mo., USA) and the procedure described for the synthesis of Example 127.0. ¹H NMR (500 MHz, CDCl₃) δ 11.16 (br. s., 1H) 8.35 (d, J=2.45 Hz, 1H) 7.48-7.53 (m, 1H) 7.46 (d, J=1.22 Hz, 1H) 7.16 (dd, J=8.68, 2.57 Hz, 1H) 6.66-6.77 (m, 2H) 6.33 (dd, J=3.42, 1.71 Hz, 1H) 5.98 (d, J=3.42 Hz, 1H) 4.43 (t, J=5.38 Hz, 1H) 4.02 (dd, J=10.51, 4.89 Hz, 1H) 3.84 (d, J=10.51 Hz, 1H) 3.79 (s, 3H) 3.73-3.75 (m, 3H) 3.56-3.64 (m, 1H) 3.48-3.56 (m, 1H) 2.69-2.80 (m, 2H) 2.21 (d, J=17.61 Hz, 1H) 1.40-1.48 (m, 3H). LCMS-ESI (pos.) m/z: 587.1 (M+H)⁺.

Example 241.0. Preparation of (2S)-2-(5-cyano-2-pyrimidinyl)-N-(4-(2,6-dimethoxyphenyl)-5-(5-methyl-2-furanyl)-4H-1,2,4-triazol-3-yl)-2-hydroxy-1-propanesulfonamide and (2R)-2-(5-cyano-2-pyrimidinyl)-N-(4-(2,6-dimethoxyphenyl)-5-(5-methyl-2-furanyl)-4H-1,2,4-triazol-3-yl)-2-hydroxy-1-propanesulfonamide 241.1

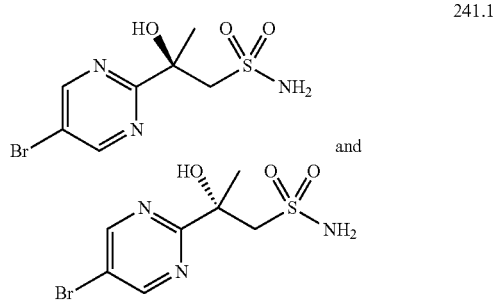

and (S)-2-(5-Bromopyrimidin-2-yl)-2-hydroxypropane-1-sulfonamide and (R)-2-(5-bromopyrimidin-2-yl)-2-hydroxypropane-1-sulfonamide, Example 241.1. The title compound was prepared employing Example 229.1 and the procedure described for the synthesis of Example 237.3.

241.2

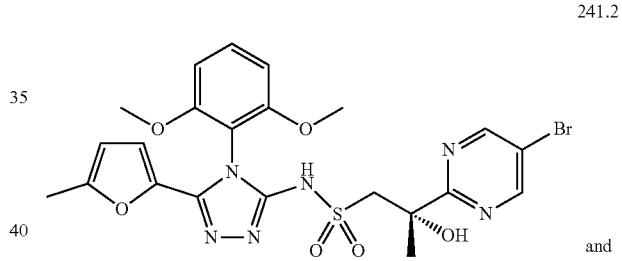

and

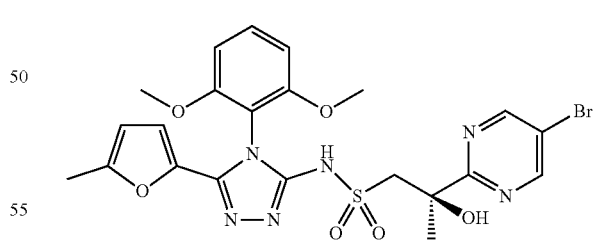

(S)-2-(5-Bromopyrimidin-2-yl)-N-(4-(2,6-dimethoxyphenyl)-5-(5-methylfuran-2-yl)-4H-1,2,4-triazol-3-yl)-2-hydroxypropane-1-sulfonamide and (R)-2-(5-bromopyrimidin-2-yl)-N-(4-(2,6-dimethoxyphenyl)-5-(5-methylfuran-2-yl)-4H-1,2,4-triazol-3-yl)-2-hydroxypropane-1-sulfonamide, Example 241.2. The title compound was prepared employing Example 241.1 and the procedure described in the synthesis of Example 229.0. LCMS-ESI (pos.) m/z: 578.8 (M+H)⁺.

241.0

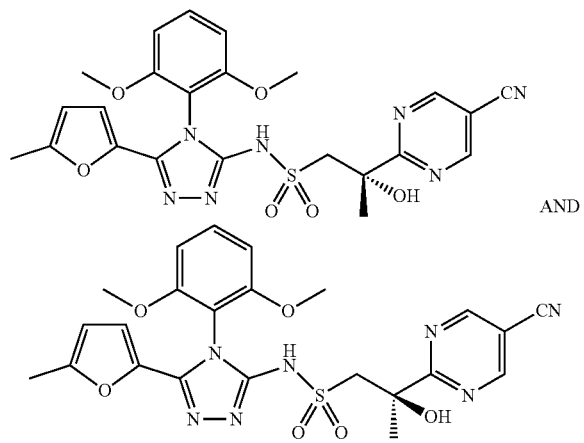

AND

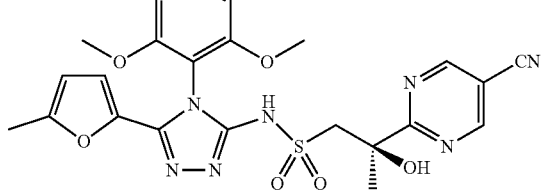

(2S)-2-(5-Cyano-2-pyrimidinyl)-N-(4-(2,6-dimethoxyphenyl)-5-(5-methyl-2-furanyl)-4H-1,2,4-triazol-3-yl)-2-hydroxy-1-propanesulfonamide and (2R)-2-(5-cyano-2-pyrimidinyl)-N-(4-(2,6-dimethoxyphenyl)-5-(5-methyl-2-furanyl)-4H-1,2,4-triazol-3-yl)-2-hydroxy-1-propanesulfonamide, Example 241.0. The title compound was prepared employing Example 241.2 and the procedure described in the synthesis of Example 50.0. $^1$H NMR (400 MHz, CD$_3$OD) δ 9.09 (s, 2H) 7.56-7.63 (m, 1H) 6.88 (dd, J=8.61, 1.76 Hz, 2H) 6.05 (dd, J=3.33, 0.98 Hz, 1H) 5.98 (d, J=3.33 Hz, 1H) 3.88-3.84 (m, 1H) 3.84 (s, 3H) 3.83 (s, 3H) 3.71-3.76 (m, 1H) 2.28 (s, 3H) 1.67 (s, 3H). LCMS-ESI (pos.) m/z: 526.0 (M+H)$^+$.

Example 248.0. Preparation of (2S)-2-(5-cyano-2-pyrimidinyl)-N-(4-(2,6-dimethoxyphenyl)-5-(5-methyl-2-furanyl)-4H-1,2,4-triazol-3-yl)-2-hydroxy-1-propanesulfonamide or (2R)-2-(5-cyano-2-pyrimidinyl)-N-(4-(2,6-dimethoxyphenyl)-5-(5-methyl-2-furanyl)-4H-1,2,4-triazol-3-yl)-2-hydroxy-1-propanesulfonamide 248.0

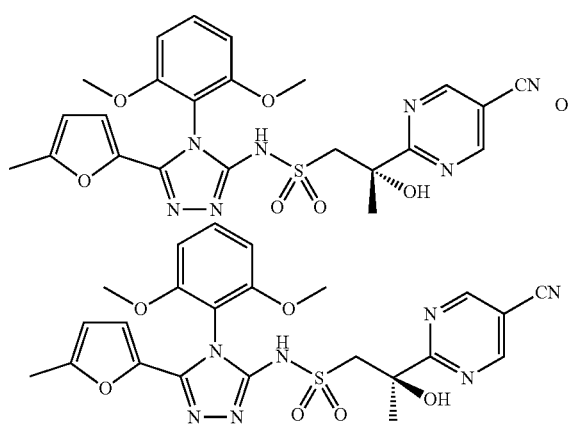

(2S)-2-(5-Cyano-2-pyrimidinyl)-N-(4-(2,6-dimethoxyphenyl)-5-(5-methyl-2-furanyl)-4H-1,2,4-triazol-3-yl)-2-hydroxy-1-propanesulfonamide or (2R)-2-(5-cyano-2-pyrimidinyl)-N-(4-(2,6-dimethoxyphenyl)-5-(5-methyl-2-furanyl)-4H-1,2,4-triazol-3-yl)-2-hydroxy-1-propanesulfonamide, Example 248.0. Purification of Example 241.0 by SFC [20×250 mm AS-H column with 15% MeOH (neat) in CO$_2$ at 100 bar] afforded two enantiomers. Example 248.0 was the first isomer to elute under these conditions. $^1$H NMR (500 MHz, CDCl$_3$) δ 9.09 (s, 2H) 7.579 (t, J=8.01 Hz, 1H) 6.87 (d, J=8.43 Hz, 1H) 6.89 (d, J=0.98 Hz, 1H) 6.05 (s, 1H) 5.97 (d, J=3.67 Hz, 1H) 3.87 (d, J=12.3 Hz, 1H) 3.84 (s, 3H) 3.83 (s, 3H) 3.74 (d, J=12.3 Hz, 1H) 2.28 (s, 3H) 1.67 (s, 3H). LCMS-ESI (pos.) m/z: 526.0 (M+H)$^+$.

Example 242.0. Preparation of (2S,3S)—N-(4-(2,6-dimethoxyphenyl)-5-(5-methyl-2-furanyl)-4H-1,2,4-triazol-3-yl)-3-(5-fluoro-2-pyrimidinyl)-3-hydroxy-2-butanesulfonamide or (2R,3R)—N-(4-(2,6-dimethoxyphenyl)-5-(5-methyl-2-furanyl)-4H-1,2,4-triazol-3-yl)-3-(5-fluoro-2-pyrimidinyl)-3-hydroxy-2-butanesulfonamide 242.0

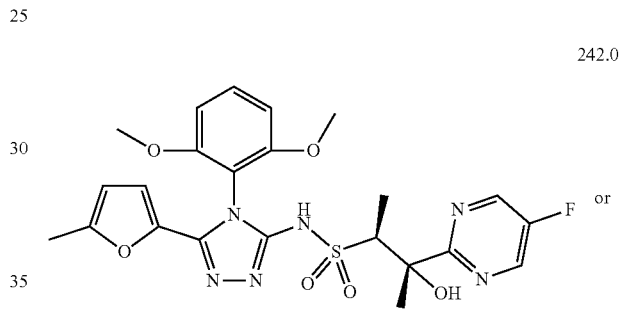

or

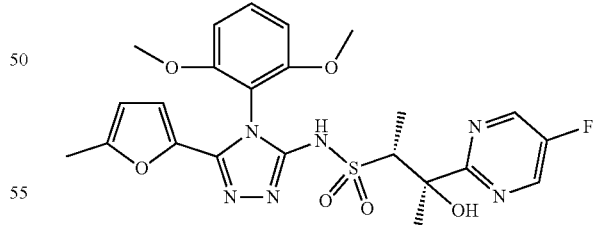

(2S,3S)—N-(4-(2,6-Dimethoxyphenyl)-5-(5-methyl-2-furanyl)-4H-1,2,4-triazol-3-yl)-3-(5-fluoro-2-pyrimidinyl)-3-hydroxy-2-butanesulfonamide, Example 242.0. Chiral separation of Example 236.0 delivered Example 242.0 as the first eluting peak. $^1$H NMR (400 MHz, CD$_3$OD) δ 8.66 (s, 2H) 7.53 (t, J=8.51 Hz, 1H) 6.80-6.91 (dd, J=8.51, 2.12 Hz, 2H) 5.99 (d, J=2.93 Hz, 1H) 5.86 (d, J=2.54 Hz, 1H) 4.01 (d, J=6.65 Hz, 1H) 3.82 (app s, 6H) 3.37 (s, 3H) 2.27 (s, 3H) 1.74 (s, 3H). LCMS ESI (pos.) m/z: 533.0 (M+H)$^+$.

Example 243.0. Preparation of (2S,3R)-3-amino-N-(4-(2,6-dimethoxyphenyl)-5-(5-methyl-2-furanyl)-4H-1,2,4-triazol-3-yl)-3-(5-fluoro-2-pyrimidinyl)-2-butanesulfonamide or (2R,3R)-3-amino-N-(4-(2,6-dimethoxyphenyl)-5-(5-methyl-2-furanyl)-4H-1,2,4-triazol-3-yl)-3-(5-fluoro-2-pyrimidinyl)-2-butanesulfonamide or (2S,3S)-3-amino-N-(4-(2,6-dimethoxyphenyl)-5-(5-methyl-2-furanyl)-4H-1,2,4-triazol-3-yl)-3-(5-fluoro-2-pyrimidinyl)-2-butanesulfonamide or (2R,3S)-3-amino-N-(4-(2,6-dimethoxyphenyl)-5-(5-methyl-2-furanyl)-4H-1,2,4-triazol-3-yl)-3-(5-fluoro-2-pyrimidinyl)-2-butanesulfonamide

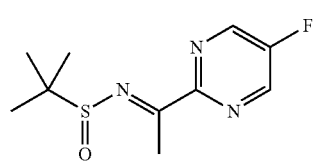

243.1

(E)-N-(1-(5-Fluoropyrimidin-2-yl)ethylidene)-2-methylpropane-2-sulfinamide, Example 243.1. Titanium (IV) ethoxide (11.82 mL, 57.1 mmol) was added to a 2-methyltetrahydrofuran (71.4 mL) solution containing 1-(5-fluoropyrimidin-2-yl)ethanone (2 g, 14.3 mmol) and 2-methylpropane-2-sulfinamide (3.46 g, 28.5 mmol). The resulting mixture was stirred overnight at 80° C. The reaction was then partitioned with EtOAc/water, washed with brine, dried over sodium sulfate, and concentrated in vacuo. The reaction was purified on silica eluting with a hexane/EtOAc gradient (0-70%). Desired fractions were pooled and concentrated in vacuo. LCMS ESI (pos.) m/z: 241.1 (M+H)$^+$.

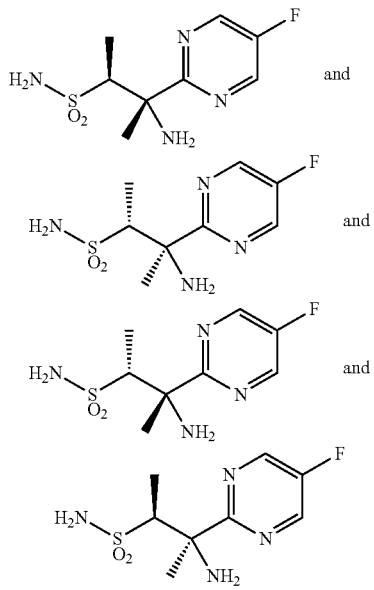

243.2

(2R,3S)-3-Amino-3-(5-fluoropyrimidin-2-yl)butane-2-sulfonamide and (2S,3S)-3-amino-3-(5-fluoropyrimidin-2-yl)butane-2-sulfonamide and (2R,3S)-3-amino-3-(5-fluoropyrimidin-2-yl)butane-2-sulfonamide and (2S,3R)-3-amino-3-(5-fluoropyrimidin-2-yl)butane-2-sulfonamide, Example 243.2. At −78° C., n-butyllithium (2.5 M in hexanes, 1.64 mL, 4.11 mmol) was added to a 2-methyltetrahydrofuran (8.22 mL) solution containing N,N-bis(4-methoxybenzyl) ethanesulfonamide, Example 361.0 (1.436 g, 4.11 mmol). The resulting mixture was stirred for 15 min and then a THF solution containing (E)-N-(1-(5-fluoropyrimidin-2-yl)ethylidene)-2-methylpropane-2-sulfinamide (1 g, 4.11 mmol) was added at −78° C. The resulting solution was allowed to slowly warm to RT and stirred overnight. The reaction was then partitioned with EtOAc/water, washed with brine, dried over sodium sulfate, and concentrated. The reaction was purified on silica eluting with a hexanes/EtOAc gradient (0-100%). Desired fractions were pooled and then concentrated in vacuo. The intermediate was then treated with neat TFA and triethylsilane and stirred overnight at room temp. After concentrating, the reaction was purified via reverse phase HPLC (Agilent SB-C8 column, 30×250 mm, 5 μm, 10-95% water/ACN gradient over 25 min., with 0.1% TFA, flow rate 50 mL/min). Desired fractions were pooled and lyophilized to give pure product. LCMS ESI (pos.) m/z: 249.1 (M+H)$^+$.

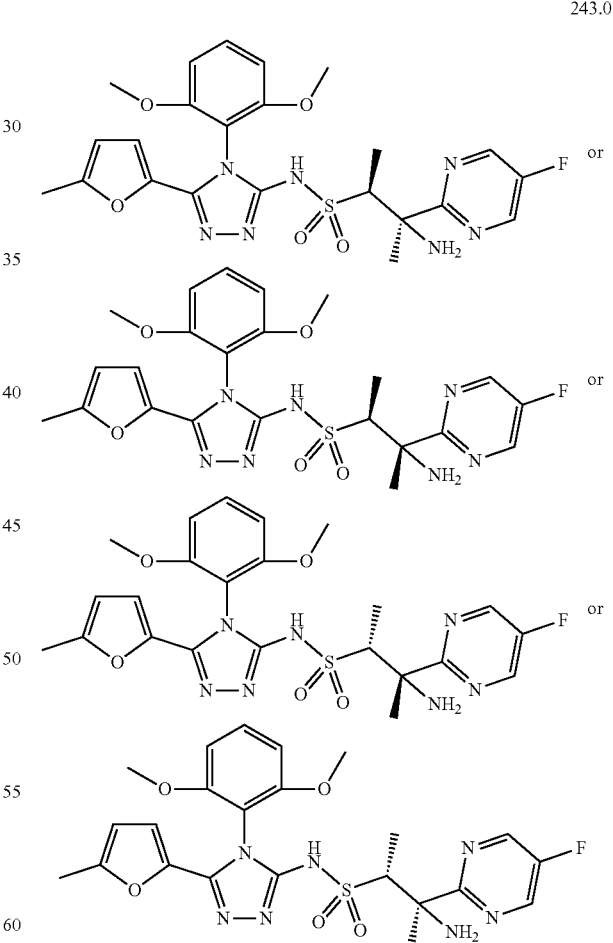

243.0

(2S,3R)-3-Amino-N-(4-(2,6-dimethoxyphenyl)-5-(5-methyl-2-furanyl)-4H-1,2,4-triazol-3-yl)-3-(5-fluoro-2-pyrimidinyl)-2-butanesulfonamide or (2R,3R)-3-amino-N-(4-(2,6-dimethoxyphenyl)-5-(5-methyl-2-furanyl)-4H-1,2,4-triazol-3-yl)-3-(5-fluoro-2-pyrimidinyl)-2- butanesulfonamide or (2S,3S)-3-amino-N-(4-(2,6-dimethoxyphenyl)-5-(5-methyl-2-furanyl)-4H-1,2,4-triazol-3-yl)-3-(5-fluoro-2-pyrimidinyl)-2-butanesulfonamide or (2R,3S)-3-amino-N-(4-(2,6-dimethoxyphenyl)-5-(5-methyl-2-furanyl)-4H-1,2,4-triazol-3-yl)-3-(5-fluoro-2-pyrimidinyl)-2-butanesulfonamide, Example 243.0. The title compound was prepared employing Example 243.2 and following the procedures described in Example 127.0. Chiral purification was conducted using the following conditions: Run on Thar 200 SFC with 250×21 mm AD-H column with 46 mL/min IPA+24 mL/min $CO_2$, 35% co-solvent at 70 mL/min. Outlet pressure=100 bar; Temp.=19° C.; Wavelength=277 nm. Manually injected 0.4 mL of a solution from 34.0 mg sample dissolved in 4.0 mL of MeOH and 1 mL DCM. This provided the title compound as the third eluting peak. $^1$H NMR (500 MHz, $CD_3OD$) δ 8.75 (s, 2H) 7.61 (t, J=8.44 Hz, 1H) 6.90 (t, J=8.28 Hz, 2H) 6.04 (m, 1H) 5.97 (d, J=3.42 Hz, 1H) 3.82 (s, 3H) 3.81 (s, 3H) 3.75 (q, J=7.09 Hz, 1H) 2.26 (s, 3H) 1.86 (s, 3H) 1.43 (d, J=7.09 Hz, 3H). LCMS ESI (pos.) m/z: 532.0 (M+H)$^+$.

Example 245.0. Preparation of (2R)-2-(5-cyano-2-pyrimidinyl)-N-(4-(2,6-dimethoxyphenyl)-5-(5-methyl-2-furanyl)-4H-1,2,4-triazol-3-yl)-2-fluoro-1-propanesulfonamide or (2S)-2-(5-cyano-2-pyrimidinyl)-N-(4-(2,6-dimethoxyphenyl)-5-(5-methyl-2-furanyl)-4H-1,2,4-triazol-3-yl)-2-fluoro-1-propanesulfonamide

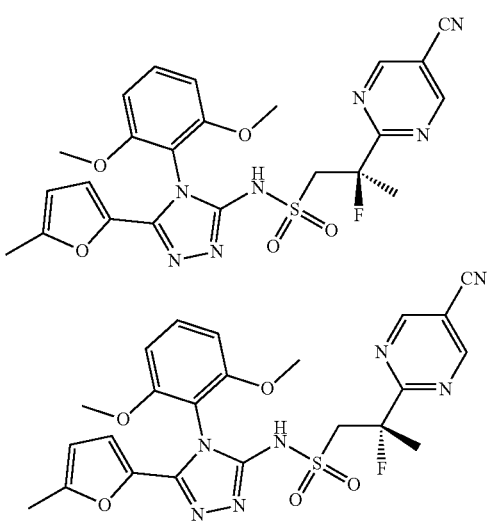

(2R)-2-(5-Cyano-2-pyrimidinyl)-N-(4-(2,6-dimethoxyphenyl)-5-(5-methyl-2-furanyl)-4H-1,2,4-triazol-3-yl)-2-fluoro-1-propanesulfonamide or (2S)-2-(5-cyano-2-pyrimidinyl)-N-(4-(2,6-dimethoxyphenyl)-5-(5-methyl-2-furanyl)-4H-1,2,4-triazol-3-yl)-2-fluoro-1-propanesulfonamide, Example 245.0. The title compound was isolated from chiral purification of Example 229.0. The title compound was purified by SFC on a IC column (2×15 cm), 35% MeOH/$CO_2$, 100 bar, 65 mL/min, 220 nm, inj vol.: 4 mL, 1 mg/mL 1:1 MeOH:DCM to provide the title compound as second eluting peak. $^1$H NMR (500 MHz, $CD_3OD$) δ 9.16 (s, 2H) 7.56 (t, J=8.41 Hz, 1H) 6.85 (d, J=8.19 Hz, 2H) 6.03 (s, 1H) 5.96 (d, J=3.42 Hz, 1H) 4.04 (s, 1H) 3.99 (d, J=7.34 Hz, 1H) 3.81 (s, 3H) 3.80 (s, 3H) 2.27 (s, 3H) 1.88 (d, J=12.01 Hz, 3H). LCMS ESI (pos.) m/z: 528.0 (M+H)$^+$.

Example 246.0. Preparation of (2S,3R)-3-amino-N-(4-(2,6-dimethoxyphenyl)-5-(5-methyl-2-furanyl)-4H-1,2,4-triazol-3-yl)-3-(5-fluoro-2-pyrimidinyl)-2-butanesulfonamide or (2R,3R)-3-amino-N-(4-(2,6-dimethoxyphenyl)-5-(5-methyl-2-furanyl)-4H-1,2,4-triazol-3-yl)-3-(5-fluoro-2-pyrimidinyl)-2-butanesulfonamide or (2S,3S)-3-amino-N-(4-(2,6-dimethoxyphenyl)-5-(5-methyl-2-furanyl)-4H-1,2,4-triazol-3-yl)-3-(5-fluoro-2-pyrimidinyl)-2-butanesulfonamide or (2R,3S)-3-amino-N-(4-(2,6-dimethoxyphenyl)-5-(5-methyl-2-furanyl)-4H-1,2,4-triazol-3-yl)-3-(5-fluoro-2-pyrimidinyl)-2-butanesulfonamide

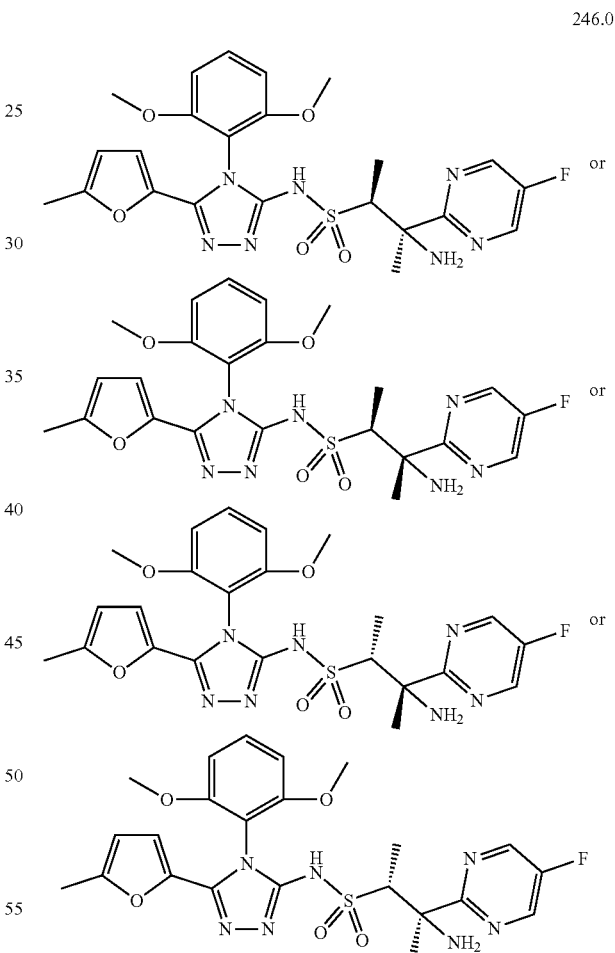

(2S,3R)-3-Amino-N-(4-(2,6-dimethoxyphenyl)-5-(5-methyl-2-furanyl)-4H-1,2,4-triazol-3-yl)-3-(5-fluoro-2-pyrimidinyl)-2-butanesulfonamide or (2R,3R)-3-amino-N-(4-(2,6-dimethoxyphenyl)-5-(5-methyl-2-furanyl)-4H-1,2,4-triazol-3-yl)-3-(5-fluoro-2-pyrimidinyl)-2-butanesulfonamide or (2S,3S)-3-amino-N-(4-(2,6-dimethoxyphenyl)-5-(5-methyl-2-furanyl)-4H-1,2,4-triazol-3-yl)-3-(5-fluoro-2-pyrimidinyl)-2-butanesulfonamide or (2R,3S)-3-amino-N-(4-(2,6-dimethoxyphenyl)-5-(5- methyl-2-furanyl)-4H-1,2,4-triazol-3-yl)-3-(5-fluoro-2-pyrimidinyl)-2-butanesulfonamide, Example 246.0. The title compound was isolated by chiral purification of Example 243.0. Chiral purification were as follows: Run on Thar 200 SFC with 250×21 mm AD-H column with 46 mL/min IPA+24 mL/min CO₂, 35% co-solvent at 70 mL/min. Outlet pressure=100 bar; Temp.=19° C.; Wavelength=277 nm. Manually injected 0.4 mL of a solution from 34.0 mg sample dissolved in 4.0 mL of MeOH and 1 mL DCM, followed by stage 2 separation. The further purified solution from peak 2 was evaporated to yield 8.0 mg. This was taken on to stage 2 using a 250×21 mm AD-H column with 16 mL/min EtOH+48 mL/min CO₂, 25% co-solvent at 64 mL/min. Outlet pressure=99 bar; Temp.=19° C.; Wavelength=277 nm. Injected 0.5 mL of a solution from 8.0 mg sample dissolved in 1.0 mL of MeOH, 2.0 mL and 1.5 mL DCM. Cycle time 7.5 min, run time 16 min. The title compound was the second eluting peak on stage 1 and the first eluting peak on stage 2. ¹H NMR (400 MHz, CD₃OD) δ 8.79 (s, 2H) 7.51 (t, J=8.51 Hz, 1H) 6.83 (d, J=10.17, 1H) 6.81 (d, J=8.61 Hz, 1H) 5.98 (dd, J=3.42, 0.88 Hz, 1H) 5.83 (d, J=3.13 Hz, 1H) 4.08 (q, J=8.01 Hz, 1H) 3.79 (s, 3H) 3.73 (s, 3H) 2.27 (s, 3H) 2.06 (s, 1H) 1.80 (s, 3H) 1.18 (d, J=8.01 Hz, 3H). LCMS ESI (pos.) m/z: 532.0 (M+H)⁺.

Example 249.0. Preparation of (2S)—N-(4-(2,6-dimethoxyphenyl)-5-(5-methyl-2-furanyl)-4H-1,2,4-triazol-3-yl)-2-(5-fluoro-2-pyrimidinyl)-2-hydroxy-1-propanesulfonamide and (2R)—N-(4-(2,6-dimethoxyphenyl)-5-(5-methyl-2-furanyl)-4H-1,2,4-triazol-3-yl)-2-(5-fluoro-2-pyrimidinyl)-2-hydroxy-1-propanesulfonamide 249.1

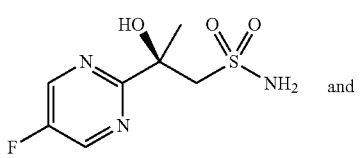

and

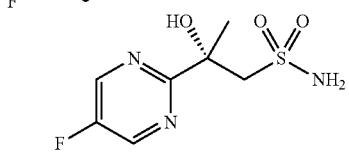

(S)-2-(5-Fluoropyrimidin-2-yl)-2-hydroxypropane-1-sulfonamide and (R)-2-(5-fluoropyrimidin-2-yl)-2-hydroxypropane-1-sulfonamide, Example 249.1. The title compound was prepared employing Example 237.1 and the procedure described for the synthesis of Example 237.3. LCMS-ESI (pos.) m/z: 236.0 (M+H)⁺.

249.2

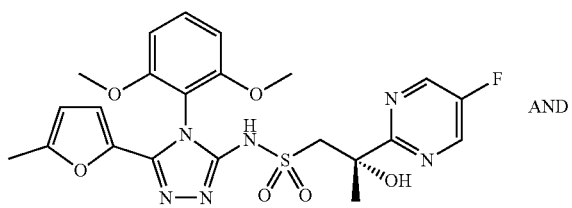

AND

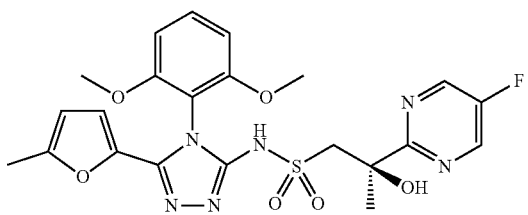

(2S)—N-(4-(2,6-Dimethoxyphenyl)-5-(5-methyl-2-furanyl)-4H-1,2,4-triazol-3-yl-2-(5-fluoro-2-pyrimidinyl)-2-hydroxy-1-propanesulfonamide and (2R)—N-(4-(2,6-dimethoxyphenyl)-5-(5-methyl-2-furanyl)-4H-1,2,4-triazol-3-yl)-2-(5-fluoro-2-pyrimidinyl)-2-hydroxy-1-propanesulfonamide, Example 249.2. The title compound was prepared employing Example 249.1 and the procedure described for the synthesis of Example 127.0. LCMS-ESI (pos.) m/z: 519.0 (M+H)⁺.

249.0

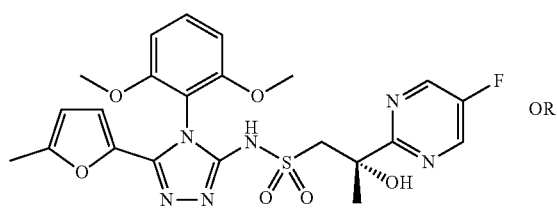

OR

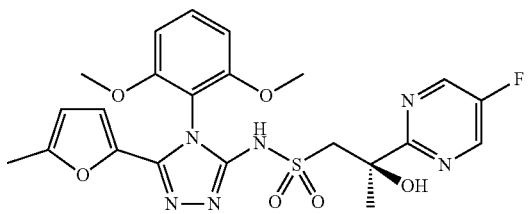

(2S)—N-(4-(2,6-Dimethoxyphenyl)-5-(5-methyl-2-furanyl)-4H-1,2,4-triazol-3-yl)-2-(5-fluoro-2-pyrimidinyl)-2-hydroxy-1-propanesulfonamide or (2R)—N-(4-(2,6-dimethoxyphenyl)-5-(5-methyl-2-furanyl)-4H-1,2,4-triazol-3-yl)-2-(5-fluoro-2-pyrimidinyl)-2-hydroxy-1-propanesulfonamide, Example 249.0. Purification of Example 249.2 by SFC [30×250 mm AS-H column with 30 g/min IPA (neat) in 50 g/min CO₂ at 100 bar] afforded two enantiomers. The title compound was the first isomer to elute under these conditions. ¹H NMR (400 MHz, CD₃OD) δ 8.67 (s, 2H) 7.58 (t, J=8.61 Hz, 1H) 6.88 (dd, J=3.52, 8.64 Hz, 2H) 6.05 (dd, J=3.52, 0.98 Hz, 1H) 5.97 (d, J=3.52 Hz, 1H) 3.78-3.88 (m, 6H) 3.64-3.76 (q, J=16.0, 2H) 2.28 (s, 3H) 1.67 (s, 3H). LCMS-ESI (pos.) m/z: 518.9 (M+H)⁺.

Example 252.0. Preparation of 2-(2-cyano-4-fluoro-phenyl)-N-(4-(4,6-dimethoxy-5-pyrimidinyl)-5-(2-furanyl)-4H-1,2,4-triazol-3-yl)ethanesulfonamide

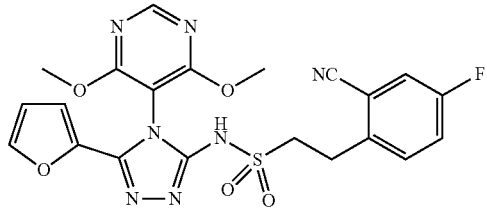

252.0

2-(2-Cyano-4-fluorophenyl)-N-(4-(4,6-dimethoxy-5-pyrimidinyl)-5-(2-furanyl)-4H-1,2,4-triazol-3-yl)ethanesulfonamide, Example 252.0. The title compound was prepared employing Example 253.3 and Example 352.6 following the procedure described in the synthesis of Example 111.0. $^1$H NMR (400 MHz, CDCl$_3$) δ 8.57 (s, 1H) 7.45 (dd, J=1.76, 0.78 Hz, 1H) 6.51-6.61 (m, 1H) 6.47 (d, J=1.76 Hz, 1H) 3.99 (app s, 6H) 3.26-3.45 (m, 4H).

Example 253.0. Preparation of 2-(4-chlorophenyl)-N-(4-(4,6-dimethoxy-5-pyrimidinyl)-5-(2-furanyl)-4H-1,2,4-triazol-3-yl)ethanesulfonamide

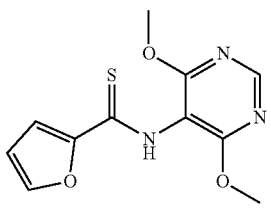

253.2

N-(4,6-Dimethoxypyrimidin-5-yl)furan-2-carbothioamide, Example 253.2. The title compound was prepared employing Example 372.1 following the procedures described in the syntheses of 362.0. The procedure afforded Example 253.2 (1.5 g (5.7 mmol). LCMS-ESI (pos.), m/z: 266.2 (M+H)$^+$.

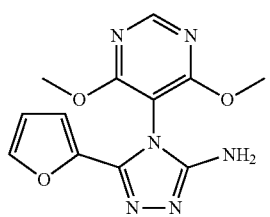

253.3

4-(4,6-Dimethoxypyrimidin-5-yl)-5-(furan-2-yl)-4H-1,2,4-triazol-3-amine, Example 253.3. The title compound was prepared employing Example 253.2 following the procedures described in the synthesis of 362.0.

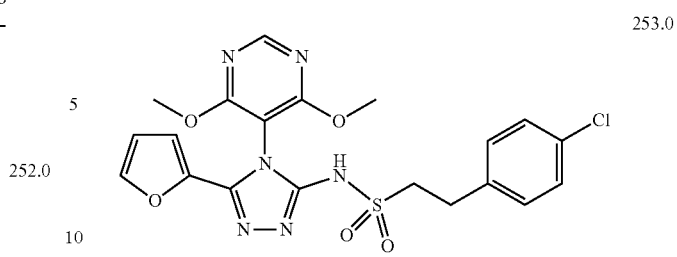

253.0

2-(4-Chlorophenyl)-N-(4-(4,6-dimethoxy-5-pyrimidinyl)-5-(2-furanyl)-4H-1,2,4-triazol-3-yl)ethanesulfonamide, Example 253.0. The title compound was prepared employing Example 253.3 (38 mg, 0.13 mmol) following the procedure described in the synthesis of Example 111.0. The procedure afforded Example 253.0 (17 mg (0.035 mmol, 27%). $^1$H NMR (500 MHz, CDCl$_3$) δ 10.96 (br. s., 1H) 8.47-8.68 (m, 1H) 7.39-7.55 (m, 1H) 7.29-7.30 (m, 1H) 7.27-7.28 (m, 1H) 7.03-7.22 (m, 2H) 6.57 (d, J=3.42 Hz, 1H) 6.47 (dd, J=3.55, 1.83 Hz, 1H) 3.86-4.05 (m, 6H) 3.21-3.37 (m, 2H) 2.99-3.21 (m, 2H). LCMS-ESI (pos.), m/z: 491.1 (M+H)$^+$.

Example 254.0. Preparation of (R)-2-(4-chlorophenyl)-N-(5-(furan-2-yl)-4-(2-(hydroxymethyl)-6-methoxyphenyl)-4H-1,2,4-triazol-3-yl)ethanesulfonamide and (S)-2-(4-chlorophenyl)-N-(5-(furan-2-yl)-4-(2-(hydroxymethyl)-6-methoxyphenyl)-4H-1,2,4-triazol-3-yl)ethanesulfonamide

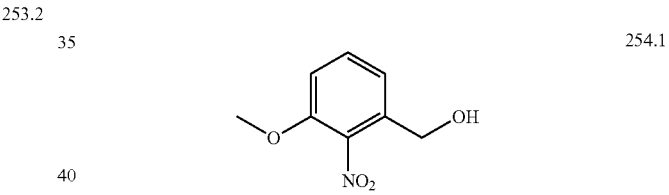

254.1

(3-Methoxy-2-nitrophenyl)methanol, Example 254.1. To a stirred solution of 3-methoxy-2-nitrobenzaldehyde (commercially available from Sigma-Aldrich Corp., St. Louis, Mo., USA, 9.8 g, 54.1 mmol) in EtOH (541 mL) was added NaBH$_4$ (10.2 g, 271 mmol) in small portions. The resulting mixture was then stirred at RT until LCMS analysis showed that the reaction was complete. Thereafter, the mixture was cooled in an ice bath and carefully quenched with 10% aqueous HCl. The mixture was then extracted with EtOAc (3×) and the combined organic layers were washed with aqueous NaHCO$_3$ and brine, and then dried over MgSO$_4$, filtered, and concentrated in vacuo to afford Example 254.1 (9.8 g, 53.6 mmol, 99%). $^1$H NMR (400 MHz, CDCl$_3$) δ 7.48 (t, J=8.12 Hz 1H) 7.11-7.20 (m, 1H) 6.96-7.07 (m, 1H) 4.69 (s, 2H) 3.94 (s, 3H).

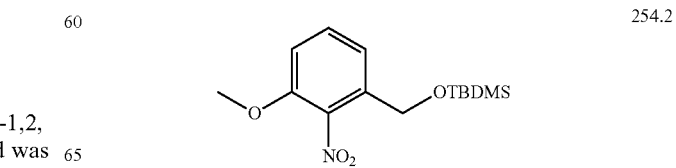

254.2 tert-Butyl((3-methoxy-2-nitrobenzyboxy)dimethylsilane, Example 254.2. Imidazole (4.4 g, 64.3 mmol) was added to a stirred solution of tert-butyldimethylsilyl chloride (50 wt % in toluene, commercially available from Alfa Aesar, 22.2 mL, 64.3 mmol) and Example 254.1 (9.8 g, 53.6 mmol) in DCM. The resulting mixture was then maintained at RT until LCMS analysis showed that the reaction was complete. Thereafter, the mixture was diluted with water and the DCM phase separated. The DCM phase was then washed with brine, dried over MgSO$_4$, filtered, and concentrated in vacuo to afford the initial TBS ether. The initial material was purified on a silica gel column, employing a gradient of 0-45% EtOAc in hexanes, to furnish Example 254.2. $^1$H NMR (400 MHz, CDCl$_3$) δ 7.42 (t, J=8.12 Hz, 1H) 7.16 (d, J=7.70 Hz, 1H) 6.96 (d, J=8.22 Hz, 1H) 4.73 (s, 2H) 3.90 (s, 3H) 0.90-0.95 (m, 9H) 0.07-0.11 (m, 6H).

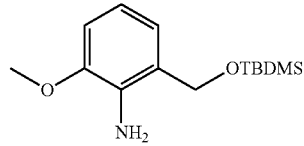

254.3

2-(((tert-Butyldimethylsilyl)oxy)methyl)-6-methoxyaniline, Example 254.3. Example 254.2, obtained from the previous step, was dissolved in EtOH, 10% Pd/C (10% Pd dry basis, 50% water, Degussa type, 500 mg, commercially available from Sigma-Aldrich Corp., St. Louis, Mo., USA) was added and the resulting mixture was stirred under 1 atm H$_2$ at RT until LCMS analysis showed that the reaction was complete. Thereafter, the reaction mixture was filtered and concentrated in vacuo to afford Example 254.3. $^1$H NMR (400 MHz, CDCl$_3$) δ 6.75-6.79 (m, 1H) 6.69-6.73 (m, 1H) 6.64-6.69 (m, 1H) 4.71 (s, 2H) 4.34 (br. s., 2H) 3.86 (s, 3H) 0.91 (s, 9H) 0.08 (s, 6H).

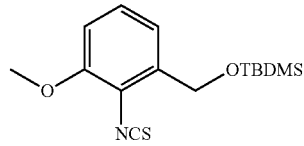

254.4 tert-Butyl((2-isothiocyanato-3-methoxybenzyl)oxy)dimethylsilane, Example 254.4. The title compound was prepared employing Example 254.3 instead of 2,6-dimethoxyaniline and following the procedure described in the syntheses of Example 161.1. Purification on silica gel using a gradient of 0-100% EtOAc in hexanes afforded Example 254.4 (6 g, 5.7 mmol, 90%).

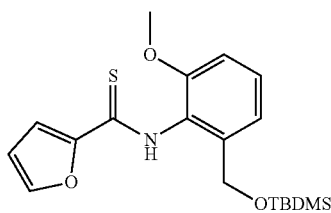

254.5

N-(2-(((tert-Butyldimethylsilyl)oxy)methyl)-6-methoxyphenyl)furan-2-carbothioamide, Example 254.5. The title compound was prepared employing Example 254.4 following the procedure described in the synthesis of 362.0 (except for the use of a gradient of 0-100% EtOAc in hexanes instead of a gradient of 0-30% EtOAc in DCM in the silica gel chromatography step). $^1$H NMR (500 MHz, CDCl$_3$) δ 9.31 (br. s., 1H) 7.49-7.55 (m, 1H) 7.46 (d, J=3.67 Hz, 1H) 7.35 (t, J=8.07 Hz, 1H) 7.09 (d, J=7.34 Hz, 1H) 6.95 (d, J=8.07 Hz, 1H) 6.55 (dd, J=3.42, 1.71 Hz, 1H) 4.70 (s, 2H) 3.86 (s, 3H) 0.92 (s, 9H) 0.06 (s, 6H).

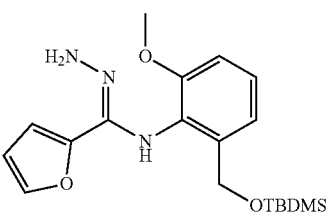

254.6

(E)-N-(2-(((tert-Butyldimethylsilyl)oxy)methyl)-6-methoxyphenyl)furan-2-carbohydrazonamide, Example 254.6. The title compound was prepared employing Example 254.5 (1.1 g, 3.0 mmol) following the procedure described for the synthesis of 362.0 (except for the use of anhydrous hydrazine instead of hydrazine hydrate). The procedure afforded Example 254.6 (0.5 g (3.0 mmol, 100%). LCMS-ESI (pos.), m/z: 376.4 (M+H)$^+$.

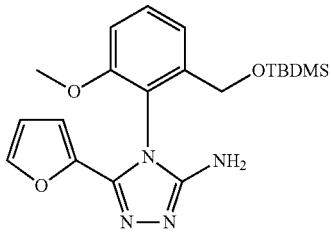

254.7

4-(2-(((tert-Butyldimethylsilyl)oxy)methyl)-6-methoxyphenyl)-5-(furan-2-yl)-4H-1,2,4-triazol-3-amine, Example 254.7. The title compound was prepared employing Example 254.6 (0.5 g, 3.0 mmol) following the procedure described for the synthesis of Example 362.0 (except for the use of silica gel chromatography employing a gradient of MeOH in DCM in the purification step). The procedure afforded Example 254.7 (206 mg, 0.52 mmol, 17%). LCMS-ESI (pos.), m/z: 401.2 (M+H)$^+$.

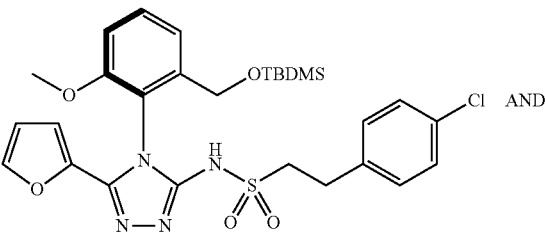

254.8

-continued

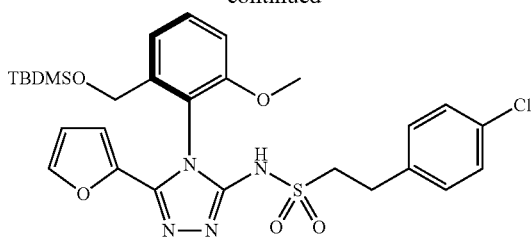

(P)—N-(4-(2-(((tert-Butyldimethylsilyl)oxy)methyl)-6-methoxyphenyl)-5-(furan-2-yl)-4H-1,2,4-triazol-3-yl)-2-(4-chlorophenyl)ethanesulfonamide and (M)-N-(4-(2-(((tert-butyldimethylsilyl)oxy)methyl)-6-methoxyphenyl)-5-(furan-2-yl)-4H-1,2,4-triazol-3-yl)-2-(4-chlorophenyl)ethanesulfonamide, Example 254.8. The title compound was prepared employing Example 254.7 (206 mg, 0.52 mmol) following the procedure described for the synthesis of Example 111.0. The procedure afforded Example 254.8 (68 mg, 0.11 mmol, 22%). LCMS-ESI (pos.), m/z: 603.2 (M+H)$^+$.

254.0

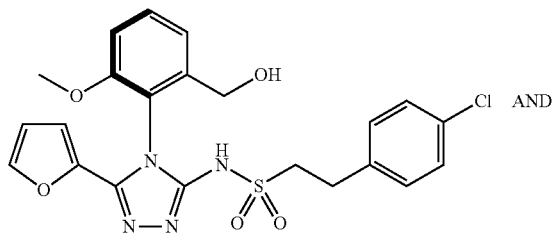

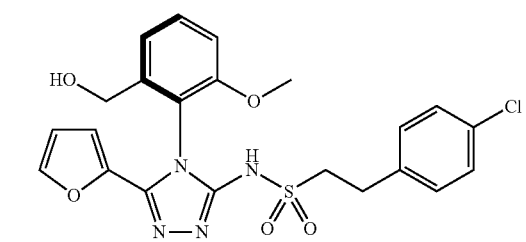

(R)-2-(4-Chlorophenyl)-N-(5-(furan-2-yl)-4-(2-(hydroxymethyl)-6-methoxyphenyl)-4H-1,2,4-triazol-3-yl)ethanesulfonamide and (S)-2-(4-chlorophenyl)-N-(5-(furan-2-yl)-4-(2-(hydroxymethyl)-6-methoxyphenyl)-4H-1,2,4-triazol-3-yl)ethanesulfonamide, Example 254.0. TBAF (1.0 M/THF, 0.34 mL, 0.34 mmol) was added to a solution of Example 254.8 (68 mg, 0.11 mmol) in THF (2 mL). The resulting mixture was then stirred at RT until LCMS analysis indicated that the reaction was complete (16 h). Thereafter, the mixture was directly purified on a reverse phase HPLC employing a gradient of 10-90% ACN in water as eluent to afford Example 254.0. $^1$H NMR (500 MHz, CDCl$_3$) δ 11.14 (br. s., 1H) 7.58 (t, J=8.12 Hz, 1H) 7.46 (dd, J=1.66, 0.68 Hz, 1H) 7.15-7.35 (m, 3H) 7.04-7.15 (m, 2H) 6.95-7.04 (m, 1H) 6.34 (dd, J=3.62, 1.86 Hz, 1H) 5.99 (dd, J=3.52, 0.59 Hz, 1H) 4.38-4.65 (m, 2H) 3.69 (s, 3H) 3.17-3.35 (m, 2H) 2.92-3.13 (m, 2H). LCMS-ESI (pos.), m/z: 489.2 (M+H)$^+$.

Example 255.0. Preparation of (R)-2-(4-chlorophenyl)-N-(5-(furan-2-yl)-4-(2-methoxy-6-(methoxymethyl)phenyl)-4H-1,2,4-triazol-3-yl)ethanesulfonamide and (S)-2-(4-chlorophenyl)-N-(5-(furan-2-yl)-4-(2-methoxy-6-(methoxymethyl)phenyl)-4H-1,2,4-triazol-3-yl)ethanesulfonamide 255.1

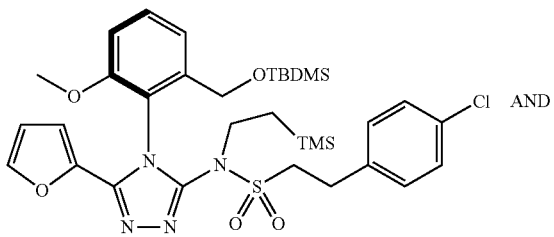

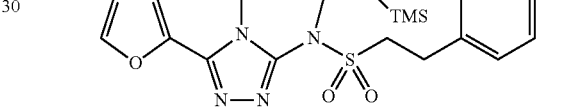

(R)—N-(4-(2-(((tert-Butyldimethylsilyl)oxy)methyl)-6-methoxyphenyl)-5-(furan-2-yl)-4H-1,2,4-triazol-3-yl)-2-(4-chlorophenyl)-N-(2-(trimethylsilyl)ethyl)ethanesulfonamide and (S)—N-(4-(2-(((tert-butyldimethylsilyl)oxy)methyl)-6-methoxyphenyl)-5-(furan-2-yl)-4H-1,2,4-triazol-3-yl)-2-(4-chlorophenyl)-N-(2-(trimethylsilyl)ethyl)ethanesulfonamide, Example 255.1. 2-(Trimethylsilyl)ethanol (0.13 mL, 0.90 mmol) was added to a solution of cyanomethylene tri-N-butylphosphorane (commercially available from VWR Scientific, Radnor, Pa., USA, 0.22 g, 0.90 mmol) and Example 254.8 (0.36 g, 0.60 mmol) in toluene. The resulting mixture was stirred at 90° C. until LCMS analysis indicated that the reaction was complete (3 h). Thereafter, the reaction was concentrated in vacuo and directly purified on a silica gel column employing a gradient of 0-100% EtOAc in hexanes to afford Example 255.1. LCMS-ESI (pos.), m/z: 703.2 (M+H)$^+$.

255.2

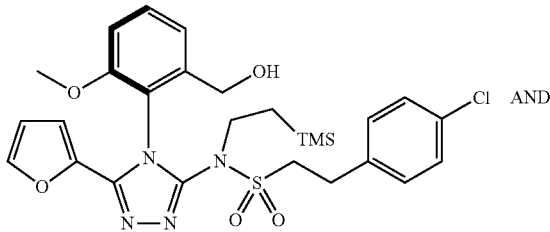

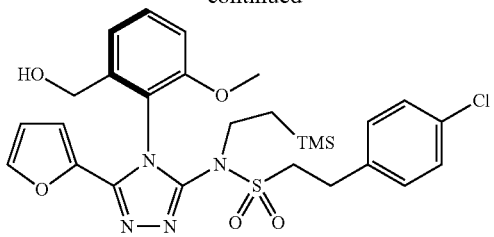

(R)-2-(4-Chlorophenyl)-N-(5-(furan-2-yl)-4-(2-(hydroxymethyl)-6-methoxyphenyl)-4H-1,2,4-triazol-3-yl)-N-(2-(trimethylsilyl)ethyl)ethanesulfonamide and (S)-2-(4-chlorophenyl)-N-(5-(furan-2-yl)-4-(2-(hydroxymethyl)-6-methoxyphenyl)-4H-1,2,4-triazol-3-yl)-N-(2-(trimethylsilyl)ethyl)ethanesulfonamide, Example 255.2. The title compound was prepared employing Example 255.1 following the procedure described in the synthesis of Example 254.0. The procedure afforded Example 255.1 (141 mg, 0.24 mmol, 84%). LCMS-ESI (pos.), m/z: 589.2 (M+H)$^+$.

255.3

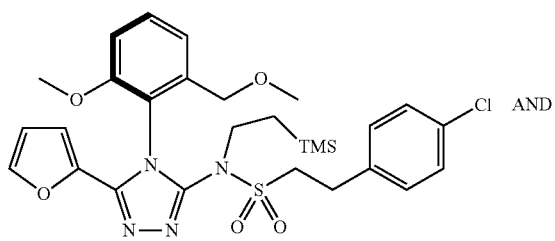

(R)-2-(4-Chlorophenyl)-N-(5-(furan-2-yl)-4-(2-methoxy-6-(methoxymethyl)phenyl)-4H-1,2,4-triazol-3-yl)-N-(2-(trimethylsilyl)ethyl)ethanesulfonamide and (S)-2-(4-chlorophenyl)-N-(5-(furan-2-yl)-4-(2-methoxy-6-(methoxymethyl)phenyl)-4H-1,2,4-triazol-3-yl)-N-(2-(trimethylsilyl)ethyl)ethanesulfonamide, Example 255.3. NaH (60%, 2.72 mg, 0.068 mmol) was added to a DMF solution containing Example 255.2 (40.0 mg, 0.068 mmol). The resulting mixture was stirred 10 min at RT. Next, methyl iodide (9.64 mg, 0.068 mmol) was added and the resulting solution was heated at 65° C. for 3 h. The mixture was directly injected on the reverse phase HPLC (10-90% ACN Method). Desired fractions were pooled and lyopholized to give pure product.

255.0

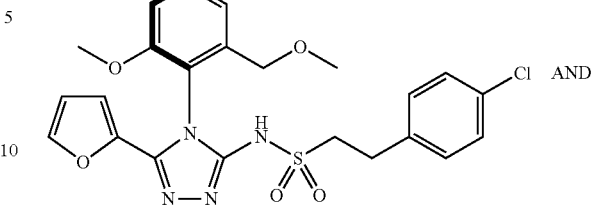

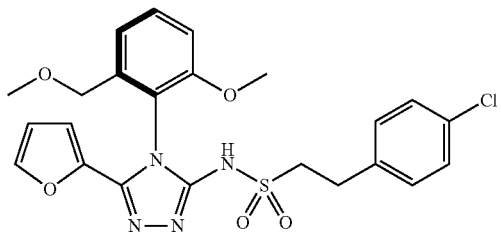

(R)-2-(4-Chlorophenyl)-N-(5-(furan-2-yl)-4-(2-methoxy-6-(methoxymethyl)phenyl)-4H-1,2,4-triazol-3-yl)ethanesulfonamide and (S)-2-(4-chlorophenyl)-N-(5-(furan-2-yl)-4-(2-methoxy-6-(methoxymethyl)phenyl)-4H-1,2,4-triazol-3-yl)ethanesulfonamide, Example 255.0. TASF (45.7 mg, 0.166 mmol) was added to a DMF solution containing Example 255.3 (20 mg, 0.033 mmol). The resulting mixture was stirred 2.5 h at 100° C. The mixture was directly injected on the reverse phase HPLC (10-90% ACN Method). Desired fractions were pooled and lyopholized to give the title compound. $^1$H NMR (400 MHz, CDCl$_3$) δ 7.57 (t, J=8.12 Hz, 1H) 7.48 (dd, J=1.76, 0.59 Hz, 1H) 7.23-7.31 (m, 3H) 7.18-7.23 (m, 1H) 7.06-7.14 (m, 2H) 6.99-7.06 (m, 1H) 6.35 (dd, J=3.52, 1.76 Hz, 1H) 6.00 (dd, J=3.52, 0.59 Hz, 1H) 4.24-4.40 (m, 2H) 3.72 (s, 3H) 3.25-3.31 (m, 2H) 3.23 (s, 3H) 3.02-3.10 (m, 2H). LCMS-ESI (pos.), m/z: 503.2 (M+H)$^+$.

Example 256.0. Preparation of (R)-2-(4-chlorophenyl)-N-(5-(furan-2-yl)-4-(2-methoxy-6-(pyrrolidin-1-ylmethyl)phenyl)-4H-1,2,4-triazol-3-yl)ethanesulfonamide and (S)-2-(4-chlorophenyl)-N-(5-(furan-2-yl)-4-(2-methoxy-6-(pyrrolidin-1-ylmethyl)phenyl)-4H-1,2,4-triazol-3-yl)ethanesulfonamide 256.1

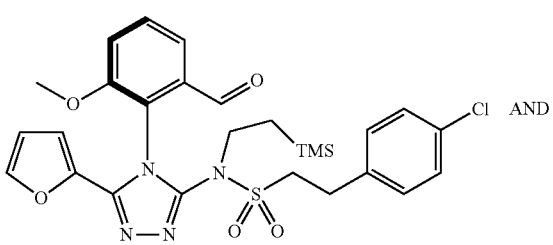

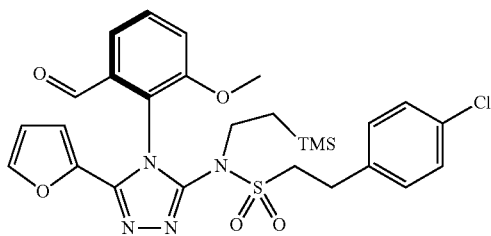

(R)-2-(4-Chlorophenyl)-N-(4-(2-formyl-6-methoxyphenyl)-5-(furan-2-yl)-4H-1,2,4-triazol-3-yl)-N-(2-(trimethylsilyl)ethyl)ethanesulfonamide and (S)-2-(4-chlorophenyl)-N-(4-(2-formyl-6-methoxyphenyl)-5-(furan-2-yl)-4H-1,2,4-triazol-3-yl)-N-(2-(trimethylsilyl)ethyl)ethanesulfonamide, Example 256.1. Sulfur trioxide pyridine complex (commercially available from Sigma-Aldrich Corp., St. Louis, Mo., USA, 46 mg, 0.29 mmol) was added to a solution of Example 255.2 (68 mg, 0.12 mmol) and TEA (40 µL, 0.29 mmol) in DMSO (1.2 mL). The resulting mixture was stirred at RT until LCMS analysis indicated that the reaction was complete (4 h). Thereafter, the reaction mixture was directly purified by reverse phase HPLC employing a gradient of 10-90% ACN in water to afford Example 256.1. LCMS-ESI (pos.), m/z: 587.2 (M+H)+.

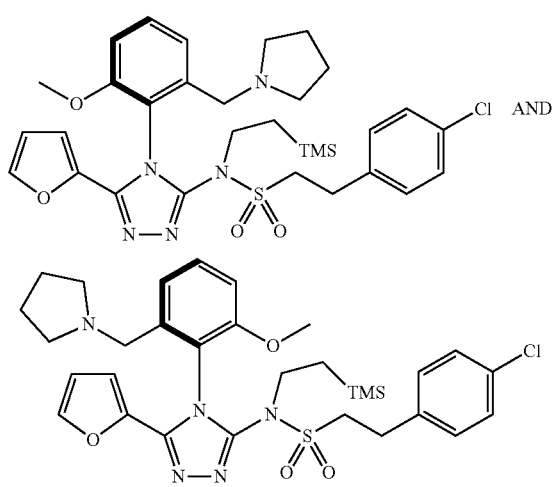

(R)-2-(4-Chlorophenyl)-N-(5-(furan-2-yl)-4-(2-methoxy-6-(pyrrolidin-1-ylmethyl)phenyl)-4H-1,2,4-triazol-3-yl)-N-(2-(trimethylsilyl)ethyl)ethanesulfonamide and (S)-2-(4-chlorophenyl)-N-(5-(furan-2-yl)-4-(2-methoxy-6-(pyrrolidin-1-ylmethyl) phenyl)-4H-1,2,4-triazol-3-yl)-N-(2-(trimethylsilyl)ethyl)ethanesulfonamide, Example 256.2. Sodium triacetoxyborohydride (36 mg, 0.17 mmol) was added to a solution of Example 256.1 (50 mg, 0.085 mmol) and pyrrolidine (12 mg, 0.17 mmol) in DCM. The resulting mixture was stirred at RT until LCMS analysis showed that the reaction was complete (16 h). Thereafter, the reaction mixture was concentrated in vacuo and purified by reverse phase HPLC employing a gradient of 10-90% ACN in water to afford Example 256.2. LCMS-ESI (pos.), m/z: 642.2 (M+H)+.

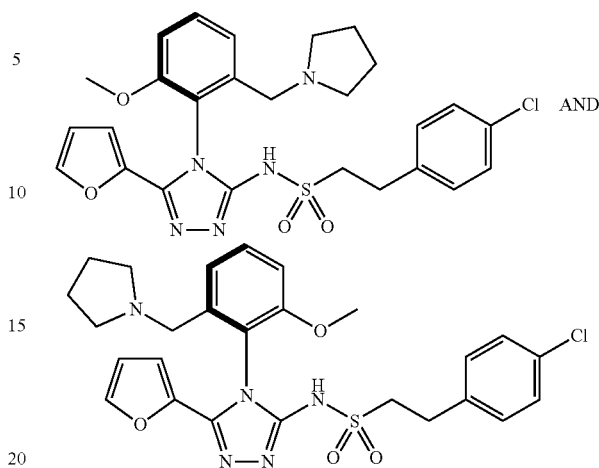

(R)-2-(4-Chlorophenyl)-N-(5-(furan-2-yl)-4-(2-methoxy-6-(pyrrolidin-1-ylmethyl)phenyl)-4H-1,2,4-triazol-3-yl)ethanesulfonamide and (S)-2-(4-chlorophenyl)-N-(5-(furan-2-yl)-4-(2-methoxy-6-(pyrrolidin-1-ylmethyl)phenyl)-4H-1,2,4-triazol-3-yl)ethanesulfonamide, Example 256.0. The title compound was prepared employing Example 256.2 following the procedure described in the synthesis of Example 255.0. $^{1}$H NMR (400 MHz, CDCl$_3$) δ 11.52 (br. s., 1H) 7.70 (t, J=8.12 Hz, 1H) 7.61 (d, J=7.82 Hz, 1H) 7.44 (d, J=1.17 Hz, 1H) 7.22-7.27 (m, 2H) 7.13 (d, J=8.22 Hz, 1H) 7.07 (m, J=8.41 Hz, 2H) 6.39 (dd, J=3.52, 1.76 Hz, 1H) 6.16 (d, J=3.52 Hz, 1H) 4.62 (d, J=13.69 Hz, 1H) 3.98 (d, J=13.69 Hz, 1H) 3.76 (br. s., 1H) 3.70 (s, 3H) 3.55-3.66 (m, 1H) 3.33 (br. s., 1H) 3.20-3.31 (m, 2H) 2.90-3.11 (m, 3H) 2.04-2.24 (m, 4H). LCMS-ESI (pos.), m/z: 542.2 (M+H)+.

Example 257.0. Preparation of N-(4-(2,6-dimethoxyphenyl)-5-(2-furanyl)-4H-1,2,4-triazol-3-yl)-2-(2,4-dimethyl-1,3-thiazol-5-yl)ethanesulfonamide

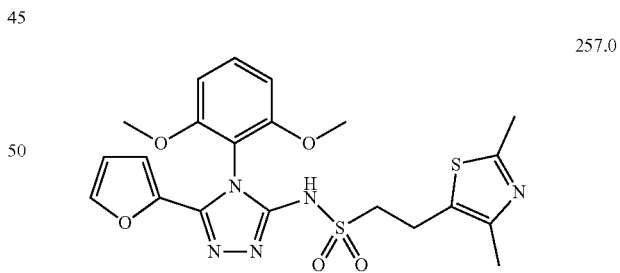

N-(4-(2,6-Dimethoxyphenyl)-5-(2-furanyl)-4H-1,2,4-triazol-3-yl)-2-(2,4-dimethyl-1,3-thiazol-5-yl)ethanesulfonamide, Example 257.0. The title compound was prepared employing 2,4-dimethylthiazole-5-carbaldehyde (commercially available from Sigma-Aldrich Corp., St. Louis, Mo., USA) following the procedures described in the synthesis of Example 34.0. $^{1}$H NMR (400 MHz, CDCl$_3$) δ 7.40-7.65 (m, 2H) 6.73 (d, J=8.61 Hz, 2H) 6.37 (dd, J=3.52, 1.76 Hz, 1H) 6.05 (dd, J=3.52, 0.59 Hz, 1H) 3.17-3.42 (m, 4H) 3.77 (s, 3H) 3.77 (s, 3H) 2.88 (s, 3H) 2.38 (s, 3H). LCMS-ESI (pos.) m/z: 490.2 (M+H)+.

Example 258.0. Preparation of N-(4-(2,6-dimethoxyphenyl)-5-(2-furanyl)-4H-1,2,4-triazol-3-yl)-2-(1-methyl-1H-imidazol-5-yl)ethanesulfonamide

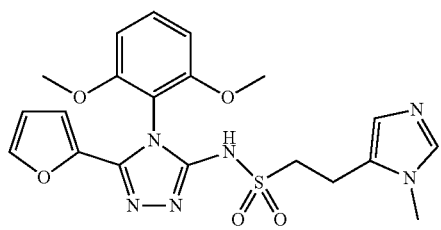

258.0

N-(4-(2,6-Dimethoxyphenyl)-5-(2-furanyl)-4H-1,2,4-triazol-3-yl)-2-(1-methyl-1H-imidazol-5-yl)ethanesulfonamide, Example 258.0. The title compound was prepared employing 1-methyl-1H-imidazole-5-carbaldehyde (commercially available from Sigma-Aldrich Corp., St. Louis, Mo., USA) following the procedures described in the synthesis of Example 34.0. $^1$H NMR (400 MHz, CDCl$_3$) δ 8.40 (s, 1H) 7.56 (t, J=8.51 Hz, 1H) 7.49 (dd, J=1.76, 0.59 Hz, 1H) 7.15 (s, 1H) 6.76 (d, J=8.41 Hz, 2H) 6.36 (dd, J=3.62, 1.86 Hz, 1H) 6.01 (dd, J=3.62, 0.68 Hz, 1H) 3.59-3.83 (m, 9H) 3.33 (t, J=6.94 Hz, 2H) 3.18 (t, J=6.94 Hz, 2H). LCMS-ESI (pos.) m/z: 459.2 (M+H)$^+$.

Example 259.0. Preparation of N-(4-(2,6-dimethoxyphenyl)-5-(2-furanyl)-4H-1,2,4-triazol-3-yl)-2-(2-ethyl-4-methyl-1H-imidazol-5-yl)ethanesulfonamide

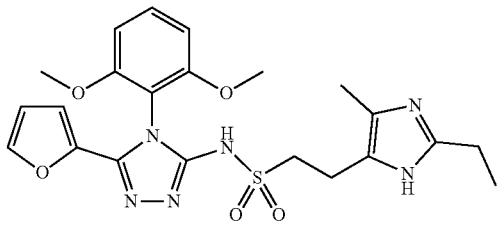

259.0

N-(4-(2,6-Dimethoxyphenyl)-5-(2-furanyl)-4H-1,2,4-triazol-3-yl)-2-(2-ethyl-4-methyl-1H-imidazol-5-yl)ethanesulfonamide, Example 259.0. The title compound was prepared employing 2-ethyl-4-methyl-1H-imidazole-5-carbaldehyde (commercially available from Sigma-Aldrich Corp., St. Louis, Mo., USA) following the procedures described in the synthesis of Example 34.0. $^1$H NMR (400 MHz, CD$_3$OD) δ 7.52-7.66 (m, 2H) 6.89 (d, J=8.61 Hz, 2H) 6.45 (dd, J=3.62, 1.86 Hz, 1H) 6.15 (dd, J=3.62, 0.68 Hz, 1H) 3.74-3.85 (m, 6H) 3.28 (t, J=7.14 Hz, 2H) 2.98-3.13 (m, 2H) 2.90 (q, J=7.63 Hz, 2H) 2.14 (s, 3H) 1.37 (t, J=7.63 Hz, 3H). LCMS-ESI (pos.) m/z: 487.2 (M+H)$^+$.

Example 260.0. Preparation of 2-(4-chloro-1-methyl-1H-pyrazol-3-yl)-N-(4-(2,6-dimethoxyphenyl)-5-(2-furanyl)-4H-1,2,4-triazol-3-yl)ethanesulfonamide

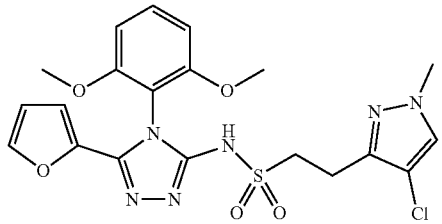

260.0

2-(4-Chloro-1-methyl-1H-pyrazol-3-yl)-N-(4-(2,6-dimethoxyphenyl)-5-(2-furanyl)-4H-1,2,4-triazol-3-yl)ethanesulfonamide, Example 260.0. The title compound was prepared employing 4-chloro-1-methyl-1H-pyrazole-3-carbaldehyde (commercially available from Sigma-Aldrich Corp., St. Louis, Mo., USA), following the procedures described in the synthesis of Example 34.0. $^1$H NMR (400 MHz, CDCl$_3$) δ 7.40-7.52 (m, 2H) 7.29 (s, 1H) 6.67 (d, J=8.61 Hz, 2H) 6.33 (dd, J=3.62, 1.86 Hz, 1H) 6.00 (dd, J=3.52, 0.59 Hz, 1H) 3.80 (s, 3H) 3.75 (s, 3H) 3.75 (s, 3H) 3.33-3.43 (m, 2H) 3.03-3.14 (m, 2H). LCMS-ESI (pos.) m/z: 493.2 (M+H)$^+$.

The compound set forth in the following table were synthesized following the procedure in Example 127.0 using the starting material as described.

TABLE 11

| Example | Reagents | Structure, Name and Data |
|---|---|---|
| 262.0 | (2S,3R)-3-(5-methylpyrimidin-2-yl)butane-2-sulfonamide (Example 371.0) and 3-bromo-4-(2,6-dimethoxyphenyl)-5-(5-methylfuran-2-yl)-4H-1,2,4-triazole (Example 364.1). | (2S,3R)-N-(4-(2,6-dimethoxyphenyl)-5-(5-methylfuran-2-yl)-4H-1,2,4-triazol-3-yl)-3-(5-methylpyrimidin-2-yl)butane-2-sulfonamide. |

$^1$H NMR (500 MHz, DMSO-d$_6$) δ = 13.17 (s, 1H), 8.58 (d, J = 0.7 Hz, 2H), 7.55 (t, J = 8.6 Hz, 1H), 6.87 (dd, J = 2.1, 8.7 Hz, 2H), 6.12 (dd, J = 1.0, 3.4 Hz, 1H), 5.79 (d, J = 3.4 Hz, 1H), 3.71-3.63 (m, 7H), 3.59 (dq, J = 3.4, 6.9 Hz, 1H), 2.25 (s, 3H), 2.23 (s, 3H), 1.23 (d, J = 7.1 Hz, 3H), 1.09 (d, J = 6.8 Hz, 3H). Mass Spectrum (pos.) m/z: 513.1 (M + H)$^+$.

Example 263.0. Preparation of (1R,2S)—N-(4-(2,6-dimethoxyphenyl)-5-(5-methyl-2-furanyl)-4H-1,2,4-triazol-3-yl)-1-imidazo[1,2-a]pyridin-2-yl-1-methoxy-2-propanesulfonamide or (1S,2R)—N-(4-(2,6-dimethoxyphenyl)-5-(5-methyl-2-furanyl)-4H-1,2,4-triazol-3-yl)-1-imidazo[1,2-a]pyridin-2-yl-1-methoxy-2-propanesulfonamide Example 264.0. Preparation of (1R,2S)—N-(4-(2,6-dimethoxyphenyl)-5-(5-methyl-2-furanyl)-4H-1,2,4-triazol-3-yl)-1-imidazo[1,2-a]pyridin-2-yl-1-methoxy-2-propanesulfonamide and (1S,2R)—N-(4-(2,6-dimethoxyphenyl)-5-(5-methyl-2-furanyl)-4H-1,2,4-triazol-3-yl)-1-imidazo[1,2-a]pyridin-2-yl-1-methoxy-2-propanesulfonamide

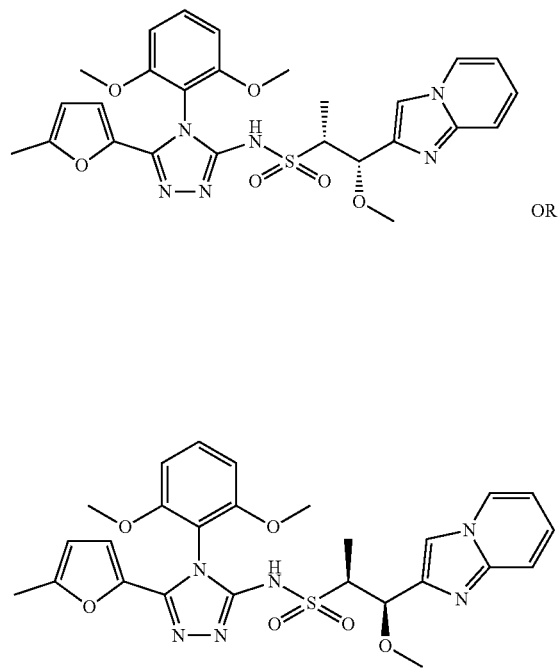

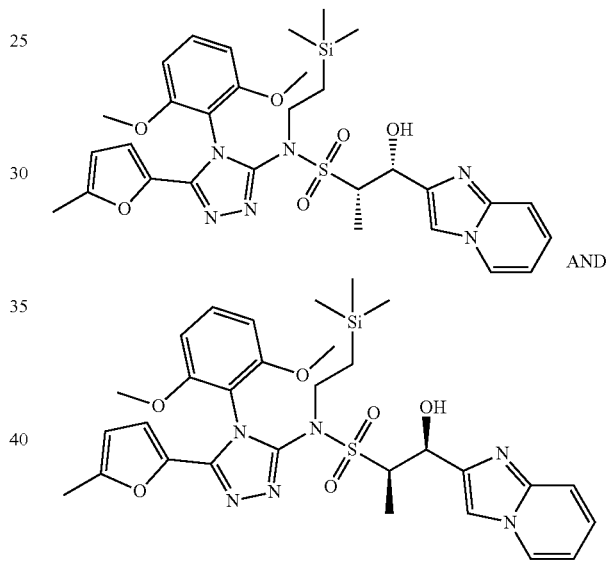

(1R,2S)—N-(4-(2,6-Dimethoxyphenyl)-5-(5-methyl-2-furanyl)-4H-1,2,4-triazol-3-yl)-1-imidazo[1,2-a]pyridin-2-yl-1-methoxy-2-propanesulfonamide or (1S,2R)—N-(4-(2,6-dimethoxyphenyl)-5-(5-methyl-2-furanyl)-4H-1,2,4-triazol-3-yl)-1-imidazo[1,2-a]pyridin-2-yl-1-methoxy-2-propanesulfonamide, Example 263.0. The racemic mixture (Example 264.0) was separated by SFC (250×30 mm CC4 column with 50 g/min MeOH (+20 mM NH$_3$)+60 g/min CO$_2$, 45% co-solvent at 100 g/min) on Thar 200 SFC. Two enantiomers were separated. The title compound (Example 263.0, 5 mg, 8.3 μmol, 33% yield) was the first isomer to elute under these conditions. $^1$H NMR (500 MHz, CD$_3$OD) δ 8.39 (d, J=6.8 Hz, 1H), 7.75 (s, 1H), 7.44-7.57 (m, 2H), 7.30 (t, J=7.7 Hz, 1H), 6.90 (t, J=6.7 Hz, 1H), 6.82 (d, J=8.6 Hz, 2H), 5.94-6.03 (m, 1H), 5.89 (br. s, 1H), 5.20 (s, 1H), 3.73 (s, 3H), 3.76 (s, 3H), 3.34 (s, 3H), 2.26 (s, 3H), 1.24 (d, J=6.8 Hz, 3H). LCMS-ESI (pos.) m/z: 553.1 (M+H)$^+$.

(1S,2R)—N-(4-(2,6-Dimethoxyphenyl)-5-(5-methylfuran-2-yl)-4H-1,2,4-triazol-3-yl)-1-hydroxy-1-(imidazo[1,2-a]pyridin-2-yl)-N-(2-(trimethylsilyl)ethyl)propane-2-sulfonamide and (1R,2S)—N-(4-(2,6-dimethoxyphenyl)-5-(5-methylfuran-2-yl)-4H-1,2,4-triazol-3-yl)-1-hydroxy-1-(imidazo[1,2-a]pyridin-2-yl)-N-(2-(trimethylsilyl)ethyl) propane-2-sulfonamide, Example 264.1. A vial containing Example 369.0 (384 mg, 0.78 mmol) was azeotroped with toluene. The residue was further dried under high vacuum. Anhydrous THF (1.8 mL) was added to the flask by syringe. Argon was bubbled through the solution for 15 min. The flask was then cooled in a dryice-acetone bath. After 20 min, n-butyllithium solution, (2.5 M in hexanes, 0.32 mL, 0.8 mmol) was carefully added dropwise to the cold solution. After 5 min, a solution of imidazo[1,2-a]pyridine-2-carbaldehyde (128 mg, 0.87 mmol) in anhydrous THF (1.8 mL) was added dropwise over 5 min. Upon complete addition, the reaction was maintained at −78° C. and monitored with LC-LCMS. After 2 h, the mixture was allowed to warm to RT. After 20 h, the reaction was transferred to an ice-water bath and then carefully quenched with saturated aqueous ammonium chloride solution. After extracting three times with CHCl₃, the organics were pooled and then dried over anhydrous MgSO₄. After filtration and concentration in vacuo, the dark brown residue was purified on silica gel eluting with 0-45% of (3:1 EtOAc: 2 M NH₃ in EtOH) in heptanes to afford the title compound (144 mg, 0.23 mmol, 29% yield) which was used without further purification. LCMS-ESI (pos.) m/z: 639.2 (M+H)⁺.

264.2

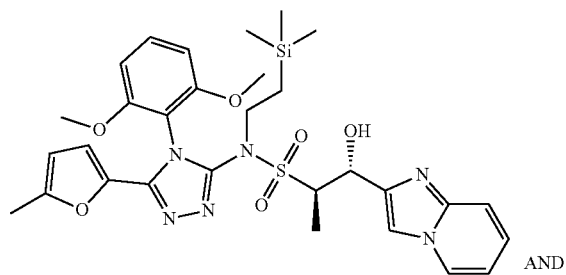

AND

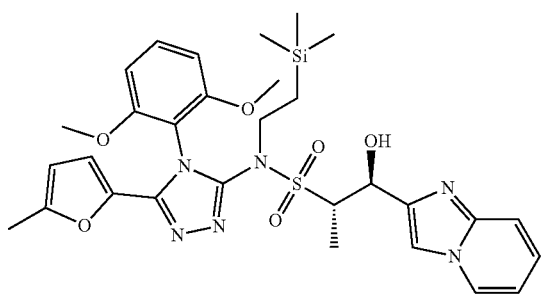

(1R,2R)—N-(4-(2,6-Dimethoxyphenyl)-5-(5-methyl-furan-2-yl)-4H-1,2,4-triazol-3-yl)-1-hydroxy-1-(imidazo[1,2-a]pyridin-2-yl)-N-(2-(trimethylsilyl)ethyl)propane-2-sulfonamide and (1S,2S)—N-(4-(2,6-dimethoxyphenyl)-5-(5-methylfuran-2-yl)-4H-1,2,4-triazol-3-yl)-1-hydroxy-1-(imidazo[1,2-a]pyridin-2-yl)-N-(2-(trimethylsilyl)ethyl)propane-2-sulfonamide, Example 264.2. Further elution under the conditions described in Example 264.1 gave the title compound (74 mg, 0.12 mmol, 15% yield) which was used without further purification. LCMS-ESI (pos.) m/z: 639.2 (M+H)⁺.

264.3

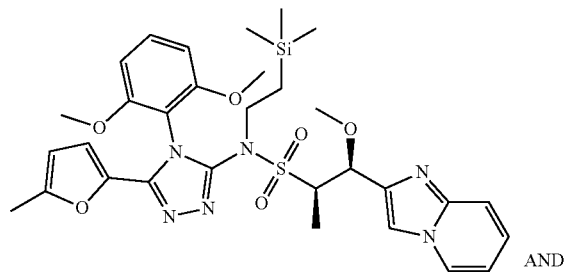

AND

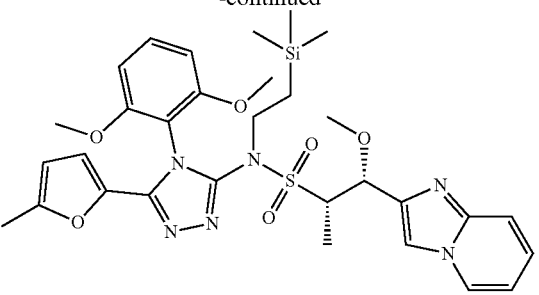

(1S,2R)—N-(4-(2,6-Dimethoxyphenyl)-5-(5-methyl-furan-2-yl)-4H-1,2,4-triazol-3-yl)-1-(imidazo[1,2-a]pyridin-2-yl)-1-methoxy-N-(2-(trimethylsilyl)ethyl)propane-2-sulfonamide and (1R,2S)—N-(4-(2,6-dimethoxyphenyl)-5-(5-methylfuran-2-yl)-4H-1,2,4-triazol-3-yl)-1-(imidazo[1,2-a]pyridin-2-yl)-1-methoxy-N-(2-(trimethylsilyl)ethyl)propane-2-sulfonamide, Example 264.3. To an ice-cold solution of Example 264.1 (134 mg, 0.21 mmol) in anhydrous DMF (2 mL) was added sodium hydride, (60% dispersion in mineral oil, 33 mg, 0.83 mmol) carefully in portions. After 10 min, methyl iodide (0.05 mL, 0.8 mmol) was added dropwise to the reaction mixture. Upon complete addition of methyl iodide, the mixture was allowed to warm to RT. After 2.5 h, the mixture was carefully quenched with water. After extracting three times with CHCl₃, the organic layers were combined and then dried over anhydrous MgSO₄. After filtration and concentration, the light yellow film was purified on silica gel eluting with 30-100% of (3:1 EtOAc: in EtOH) in heptanes to provide the title compound Example 264.3 (43 mg, 0.07 mmol, 32% yield) as a colorless film that was used without further purification. LCMS-ESI (pos.) m/z: 653.2 (M+H)⁺.

264.0

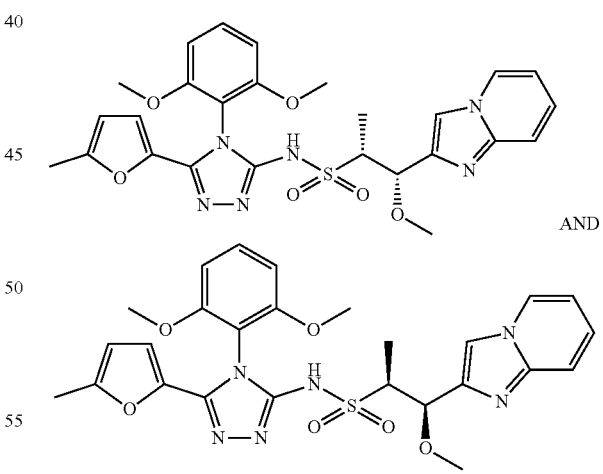

(1R,2S)—N-(4-(2,6-Dimethoxyphenyl)-5-(5-methyl-2-furanyl)-4H-1,2,4-triazol-3-yl)-1-imidazo[1,2-a]pyridin-2-yl-1-methoxy-2-propanesulfonamide and (1S,2R)—N-(4-(2,6-dimethoxyphenyl)-5-(5-methyl-2-furanyl)-4H-1,2,4-triazol-3-yl)-1-imidazo[1,2-a]pyridin-2-yl-1-methoxy-2-propanesulfonamide, Example 264.0. To a vial containing Example 264.3 (43 mg, 0.07 mmol) was added TASF (55 mg, 0.2 mmol) followed by dropwise addition of anhydrous DMF (1 mL). The mixture was carefully heated to 60° C.

and monitored with LC-LCMS. After 25 h, the mixture was cooled to RT and then purified with reverse-phase HPLC (10-90% of premixed 0.1% TFA in ACN in 0.1% TFA in water). Fractions containing desired product were combined and then concentrated in vacuo. The residue was treated with saturated aqueous NaHCO$_3$. After extracting three times with 10% IPA in CHCl$_3$, the organic layers were combined and then dried over anhydrous MgSO$_4$. After filtration and concentration, the off-white solid was identified as the title compound, Example 264.0 (16 mg, 0.03 mmol, 43% yield). $^1$H NMR (500 MHz, DMSO-d$_6$) δ 13.18 (br. s, 1H), 8.40-8.56 (m, 1H), 7.77 (br. s, 1H), 7.51 (d, J=9.0 Hz, 1H), 7.43 (br. s, 1H), 7.12-7.24 (m, 1H), 6.74-6.91 (m, 3H), 5.97 (br. s, 1H), 5.43 (br. s, 1H), 5.05 (d, J=1.2 Hz, 1H), 4.00 (br. s, 1H), 3.67 (s, 3H), 3.62 (br. s, 3H), 3.30 (br. s, 3H), 2.21 (s, 3H), 1.03-1.10 (m, 3H). LCMS-ESI (pos.) m/z: 553.2 (M+H)$^+$.

Example 265.0. Preparation of (1R,2S)—N-(4-(2,6-dimethoxyphenyl)-5-(5-methyl-2-furanyl)-4H-1,2,4-triazol-3-yl)-1-hydroxy-1-imidazo[1,2-a]pyridin-2-yl-2-propanesulfonamide or (1S,2R)—N-(4-(2,6-dimethoxyphenyl)-5-(5-methyl-2-furanyl)-4H-1,2,4-triazol-3-yl)-1-hydroxy-1-imidazo[1,2-a]pyridin-2-yl-2-propanesulfonamide 265.0

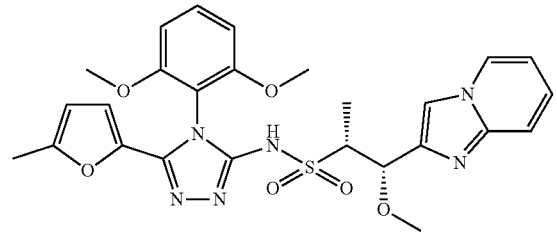

or

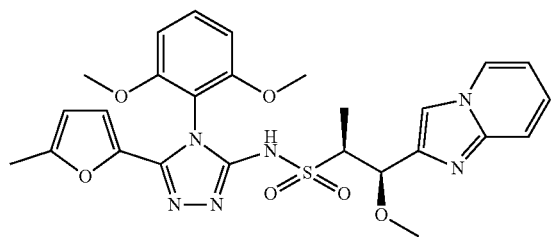

(1R,2S)—N-(4-(2,6-Dimethoxyphenyl)-5-(5-methyl-2-furanyl)-4H-1,2,4-triazol-3-yl)-1-hydroxy-1-imidazo[1,2-a]pyridin-2-yl-2-propanesulfonamide or (1S,2R)—N-(4-(2,6-dimethoxyphenyl)-5-(5-methyl-2-furanyl)-4H-1,2,4-triazol-3-yl)-1-hydroxy-1-imidazo[1,2-a]pyridin-2-yl-2-propanesulfonamide, Example 265.0. The racemic mixture (Example 269.0) was separated by SFC (150×20 mm IA column with 40% MeOH (0.1% NH$_4$OH)/CO$_2$ at 60 mL/min. Two enantiomers were separated. The title compound was the first isomer to elute under these conditions.

$^1$H NMR (500 MHz, DMSO-d$_6$) δ 13.30 (br. s, 1H), 8.51 (dt, J=6.8, 1.1 Hz, 1H), 7.78 (s, 1H), 7.57 (t, J=8.6 Hz, 1H), 7.44-7.51 (m, 1H), 7.20 (ddd, J=9.0, 6.7, 1.2 Hz, 1H), 6.82-6.96 (m, 3H), 6.14 (d, J=2.7 Hz, 1H), 5.83 (br. s, 1H), 5.42 (br. s, 1H), 4.86 (br. s, 1H), 3.69 (s, 3H), 3.72 (s, 3H), 3.48-3.56 (m, 1H), 2.26 (s, 3H), 1.04 (d, J=6.8 Hz, 3H). LCMS-ESI (pos.) m/z: 539.2 (M+H)$^+$.

Example 266.0. Preparation of (1R,2S)—N-(4-(2,6-dimethoxyphenyl)-5-(5-methyl-2-furanyl)-4H-1,2,4-triazol-3-yl)-1-hydroxy-1-pyrazolo[1,5-a]pyridin-2-yl-2-propanesulfonamide or (1S,2R)—N-(4-(2,6-dimethoxyphenyl)-5-(5-methyl-2-furanyl)-4H-1,2,4-triazol-3-yl-1-hydroxy-1-pyrazolo[1,5-a]pyridin-2-yl-2-propanesulfonamide 266.0

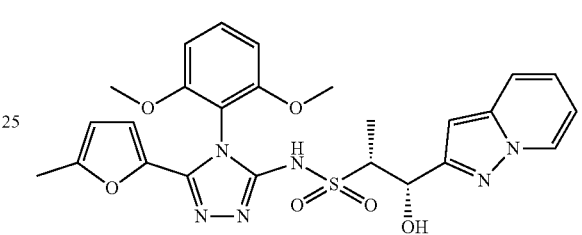

or (1R,2S)—N-(4-(2,6-Dimethoxyphenyl)-5-(5-methyl-2-furanyl)-4H-1,2,4-triazol-3-yl)-1-hydroxy-1-pyrazolo[1,5-a]pyridin-2-yl-2-propanesulfonamide or (1S,2R)—N-(4-(2,6-dimethoxyphenyl)-5-(5-methyl-2-furanyl)-4H-1,2,4-triazol-3-yl)-1-hydroxy-1-pyrazolo[1,5-a]pyridin-2-yl-2-propanesulfonamide, Example 266.0. The title compound was prepared from Example 369.0 and pyrazolo[1,5-a]pyridine-2-carbaldehyde using the procedure described in Example 281.0. The mixture was separated by SFC (150×30 mm AD-H column with 44 g/min MeOH (+20 mM ammonia)+36 g/min CO$_2$, 55% co-solvent at 80 g/min) on Thar 200 SFC. Two enantiomers were separated. The title compound was the second isomer to elute under these conditions (15 mg, 0.03 mmol, 42% yield). $^1$H NMR (400 MHz, CD$_3$OD) δ 8.44 (d, J=7.0 Hz, 1H), 7.57 (d, J=8.8 Hz, 1H), 7.50 (t, J=8.4 Hz, 1H), 7.17 (dd, J=8.5, 6.9 Hz, 1H), 6.81 (dd, J=8.5, 3.4 Hz, 3H), 6.57 (s, 1H), 5.96 (d, J=2.7 Hz, 1H), 5.83 (d, J=2.7 Hz, 1H), 5.72 (s, 1H), 3.71-3.80 (m, 6H), 3.66 (d, J=8.2 Hz, 1H), 2.20-2.23 (m, 3H), 1.26-1.31 (m, 3H). LCMS-ESI (pos.) m/z: 539.2 (M+H)$^+$.

Example 267.0. Preparation of (1R,2S)—N-(4-(2,6-dimethoxyphenyl)-5-(5-methyl-2-furanyl)-4H-1,2,4-triazol-3-yl-1-hydroxy-1-pyrazolo[1,5-a]pyridin-7-yl-2-propanesulfonamide or (1S,2R)—N-(4-(2,6-dimethoxyphenyl)-5-(5-methyl-2-furanyl)-4H-1,2,4-triazol-3-yl-1-hydroxy-1-pyrazolo[1,5-a]pyridin-7-yl-2-propanesulfonamide Example 268.0. Preparation of (1S,2S)—N-(4-(2,6-dimethoxyphenyl)-5-(5-methyl-2-furanyl)-4H-1,2,4-triazol-3-yl-1-imidazo[1,2-a]pyridin-2-yl-1-methoxy-2-propanesulfonamide or (1R,2R)—N-(4-(2,6-dimethoxyphenyl)-5-(5-methyl-2-furanyl)-4H-1,2,4-triazol-3-yl)-1-imidazo[1,2-a]pyridin-2-yl-1-methoxy-2-propanesulfonamide

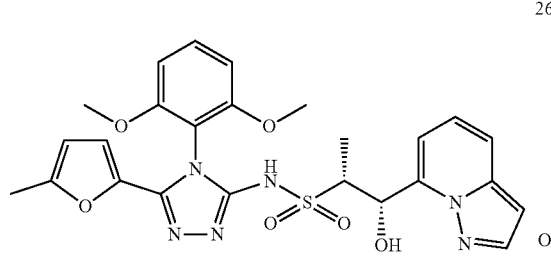

267.0

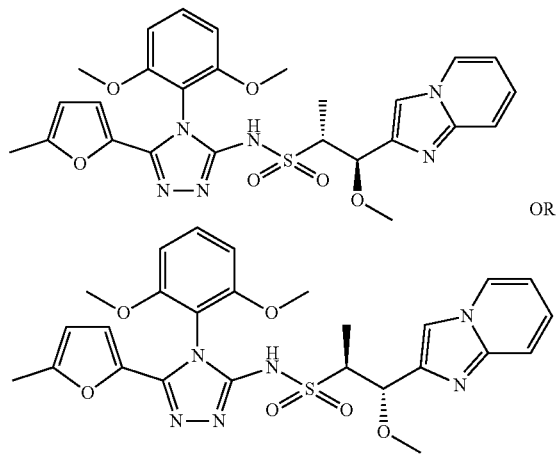

268.0

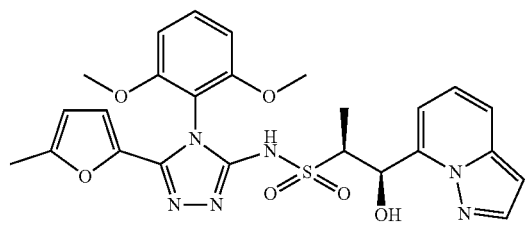

(1R,2S)—N-(4-(2,6-Dimethoxyphenyl)-5-(5-methyl-2-furanyl)-4H-1,2,4-triazol-3-yl)-1-hydroxy-1-pyrazolo[1,5-a]pyridin-7-yl-2-propanesulfonamide or (1S,2R)—N-(4-(2,6-dimethoxyphenyl)-5-(5-methyl-2-furanyl)-4H-1,2,4-triazol-3-yl)-1-hydroxy-1-pyrazolo[1,5-a]pyridin-7-yl-2-propanesulfonamide, Example 267.0. Following the procedure described in Example 274.0 employing N-(4-(2,6-dimethoxyphenyl)-5-(5-methylfuran-2-yl)-4H-1,2,4-triazol-3-yl)-N-(2-(trimethylsilyl)ethyl)ethanesulfonamide (Example 369.0) and pyrazolo[1,5-a]pyridine-7-carboxaldehyde delivered the syn isomers as the first eluting peak from the column employing the conditions described in Example 274.0. The product was separated by SFC (250×20 mm AS-H column with 20% MeOH/CO$_2$ at 65 mL/min). Two enantiomers were separated. The title compound was the second isomer to elute under these conditions (19 mg, 0.035 mmol, 40% yield). $^1$H NMR (400 MHz, CD$_3$OD) □ 7.89 (d, J=2.3 Hz, 1H), 7.51-7.63 (m, 2H), 7.22 (dd, J=8.8, 7.0 Hz, 1H), 7.00 (d, J=6.8 Hz, 1H), 6.83 (dd, J=8.6, 3.7 Hz, 2H), 6.59 (d, J=2.3 Hz, 1H), 6.07 (s, 1H), 6.02 (dd, J=3.4, 0.9 Hz, 1H), 5.96 (d, J=3.5 Hz, 1H), 4.10 (qd, J=7.1, 2.0 Hz, 1H), 3.72 (s, 3H), 3.66 (s, 3H), 2.27 (s, 3H), 1.15 (d, J=7.0 Hz, 3H). LCMS-ESI (pos.) m/z: 539.2 (M+H)$^+$.

(1S,2S)—N-(4-(2,6-Dimethoxyphenyl)-5-(5-methyl-2-furanyl)-4H-1,2,4-triazol-3-yl)-1-imidazo[1,2-a]pyridin-2-yl-1-methoxy-2-propanesulfonamide or (1R,2R)—N-(4-(2,6-dimethoxyphenyl)-5-(5-methyl-2-furanyl)-4H-1,2,4-triazol-3-yl)-1-imidazo[1,2-a]pyridin-2-yl-1-methoxy-2-propanesulfonamide, Example 268.0. The racemic mixture (Example 278.0) was separated by SFC (250×30 mm CC4 column with 50 g/min MeOH (+20 mM NH$_3$)+50 g/min CO$_2$, 50% co-solvent at 100 g/min) on Thar 200 SFC. Two enantiomers were separated. The title compound was the second isomer to elute under these conditions (7 mg, 0.014 mmol, 44% yield). $^1$H NMR (500 MHz, CD$_3$OD) δ 8.37 (d, J=6.6 Hz, 1H), 7.79 (1H, s, 1H), 7.46-7.59 (m, 2H), 7.31 (t, J=7.8 Hz, 1H), 6.91 (t, J=6.6 Hz, 1H), 6.75-6.87 (m, 2H), 5.94-6.04 (m, 1H), 5.88 (br. s, 1H), 4.66-4.79 (m, 1H), 3.76 (s, 3H), 3.78 (s, 3H), 3.14 (s, 3H), 2.25 (s, 3H), 1.13 (d, J=7.1 Hz, 3H). LCMS-ESI (pos.) m/z: 553.2 (M+H)$^+$.

Example 269.0. Preparation of (1R,2S)—N-(4-(2,6-dimethoxyphenyl)-5-(5-methyl-2-furanyl)-4H-1,2,4-triazol-3-yl)-1-hydroxy-1-imidazo[1,2-a]pyridin-2-yl-2-propanesulfonamide and (1S,2R)—N-(4-(2,6-dimethoxyphenyl)-5-(5-methyl-2-furanyl)-4H-1,2,4-triazol-3-yl)-1-hydroxy-1-imidazo[1,2-a]pyridin-2-yl-2-propanesulfonamide

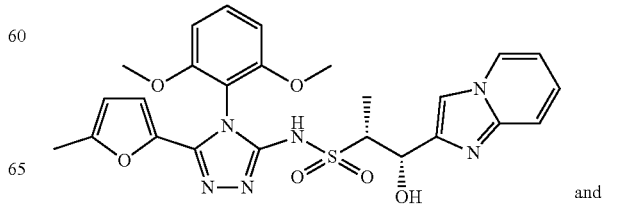

269.0 and

-continued

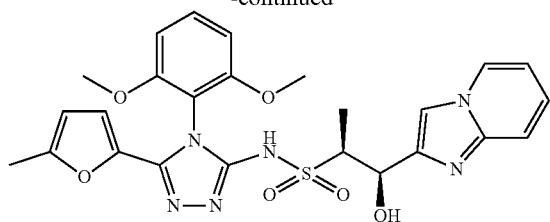

(1R,2S)—N-(4-(2,6-Dimethoxyphenyl)-5-(5-methyl-2-furanyl)-4H-1,2,4-triazol-3-yl)-1-hydroxy-1-imidazo[1,2-a]pyridin-2-yl-2-propanesulfonamide and (1S,2R)—N-(4-(2,6-dimethoxyphenyl)-5-(5-methyl-2-furanyl)-4H-1,2,4-triazol-3-yl)-1-hydroxy-1-imidazo[1,2-a]pyridin-2-yl-2-propanesulfonamide, Example 269.0. The title compound was prepared from Example 369.0 and imidazo[1,2-a]pyridine-2-carbaldehyde using the procedure described in Example 281.0. $^1$H NMR (500 MHz, DMSO-$d_6$) δ 13.29 (br. s, 1H), 8.50 (dt, J=6.7, 1.2 Hz, 1H), 7.77 (s, 1H), 7.56 (t, J=8.6 Hz, 1H), 7.42-7.50 (m, 1H), 7.19 (ddd, J=9.0, 6.7, 1.2 Hz, 1H), 6.81-6.92 (m, 3H), 6.13 (d, J=2.7 Hz, 1H), 5.82 (d, J=3.2 Hz, 1H), 5.41 (br. s, 1H), 4.85 (br. s, 1H), 3.68 (s, 3H), 3.71 (s, 3H), 3.46-3.54 (m, 1H), 2.25 (s, 3H), 1.03 (d, J=6.8 Hz, 3H). LCMS-ESI (pos.) m/z: 539.2 (M+H)$^+$.

Example 270.0. Preparation of (1R,2S)—N-(4-(2,6-dimethoxyphenyl)-5-(5-methyl-2-furanyl)-4H-1,2,4-triazol-3-yl)-1-hydroxy-1-imidazo[1,5-a]pyridin-1-yl-2-propanesulfonamide or (1S,2R)—N-(4-(2,6-dimethoxyphenyl)-5-(5-methyl-2-furanyl)-4H-1,2,4-triazol-3-yl)-1-hydroxy-1-imidazo[1,5-a]pyridin-1-yl-2-propanesulfonamide 270.0

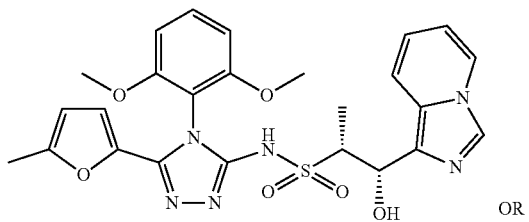

OR

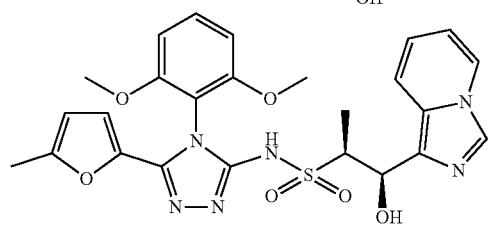

(1R,2S)—N-(4-(2,6-Dimethoxyphenyl)-5-(5-methyl-2-furanyl)-4H-1,2,4-triazol-3-yl)-1-hydroxy-1-imidazo[1,5-a]pyridin-1-yl-2-propanesulfonamide or (1S,2R)—N-(4-(2,6-dimethoxyphenyl)-5-(5-methyl-2-furanyl)-4H-1,2,4-triazol-3-yl)-1-hydroxy-1-imidazo[1,5-a]pyridin-1-yl-2-propanesulfonamide, Example 270.0. The title compound was prepared from Example 369.0 and imidazo[1,5-a]pyridine-1-carbaldehyde using the procedure described in Example 281.0. The mixture of diasteromers was separated by SFC (150×20 mm IA column with 25% MeOH (0.1% NH$_4$OH)/CO$_2$ at 60 mL/min. Three peaks were separated. The title compound was the second isomer to elute under these conditions. $^1$H NMR (500 MHz, DMSO-$d_6$) δ 13.30 (br. s, 1H), 8.22 (d, J=7.1 Hz, 1H), 7.47-7.61 (m, 2H), 7.30 (s, 1H), 6.87 (d, J=8.6 Hz, 1H), 6.76-6.83 (m, 2H), 6.62-6.68 (m, 1H), 6.11 (d, J=2.7 Hz, 1H), 5.75-5.84 (m, 1H), 5.54 (br. s, 2H), 3.79-3.87 (m, 1H), 3.70 (s, 3H), 3.46-3.53 (m, 3H), 2.24 (s, 3H), 1.42 (d, J=6.8 Hz, 3H). LCMS-ESI (pos.) m/z: 539.2 (M+H)$^+$.

Example 271.0. Preparation of (1S,2S)—N-(4-(2,6-dimethoxyphenyl)-5-(5-methyl-2-furanyl)-4H-1,2,4-triazol-3-yl)-1-hydroxy-1-pyrazolo[1,5-a]pyridin-2-yl-2-propanesulfonamide or (1R,2R)—N-(4-(2,6-dimethoxyphenyl)-5-(5-methyl-2-furanyl)-4H-1,2,4-triazol-3-yl-1-hydroxy-1-pyrazolo[1,5-a]pyridin-2-yl-2-propanesulfonamide 271.0

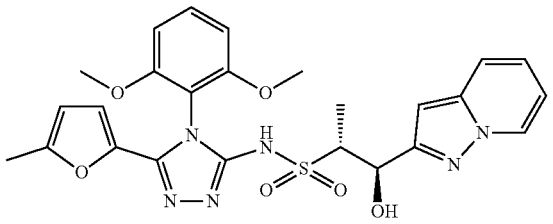

OR


(1S,2S)—N-(4-(2,6-Dimethoxyphenyl)-5-(5-methyl-2-furanyl)-4H-1,2,4-triazol-3-yl)-1-hydroxy-1-pyrazolo[1,5-a]pyridin-2-yl-2-propanesulfonamide or (1R,2R)—N-(4-(2,6-dimethoxyphenyl)-5-(5-methyl-2-furanyl)-4H-1,2,4-triazol-3-yl)-1-hydroxy-1-pyrazolo[1,5-a]pyridin-2-yl-2-propanesulfonamide, Example 271.0. The title compound was prepared from Example 369.0 and pyrazolo[1,5-a]pyridine-2-carbaldehyde using the procedure described in Example 281.0. The mixture was separated by SFC (250×30 mm AS column with 25 g/min MeOH (+20 mM NH$_3$)+75 g/min CO$_2$, 25% co-solvent at 100 g/min) on Thar 350 SFC. Two enantiomers were separated. The title compound (Example 271.0) was the first isomer to elute under these conditions. (9 mg, 0.02 mmol, 29% yield). $^1$H NMR (500 MHz, CD$_3$OD) δ 8.45 (d, J=7.1 Hz, 1H), 7.51-7.62 (m, 2H), 7.19 (dd, J=8.6, 7.1 Hz, 1H), 6.80-6.89 (m, 3H), 6.55 (s, 1H), 5.99-6.05 (m, 1H), 5.96 (d, J=3.2 Hz, 1H), 5.07 (d, J=8.6 Hz, 1H), 3.80 (s, 3H), 3.81 (s, 3H), 3.42-3.51 (m, 1H), 2.26 (s, 3H), 1.06 (d, J=7.1 Hz, 3H). LCMS-ESI (pos.) m/z: 539.2 (M+H)$^+$.

Example 272.0. Preparation of (1R,2S)—N-(4-(2,6-dimethoxyphenyl)-5-(5-methyl-2-furanyl)-4H-1,2,4-triazol-3-yl-1-hydroxy-1-pyrazolo[1,5-a]pyridin-2-yl-2-propanesulfonamide and (1S,2R)—N-(4-(2,6-dimethoxyphenyl)-5-(5-methyl-2-furanyl)-4H-1,2,4-triazol-3-yl-1-hydroxy-1-pyrazolo[1,5-a]pyridin-2-yl-2-propanesulfonamide 272.0

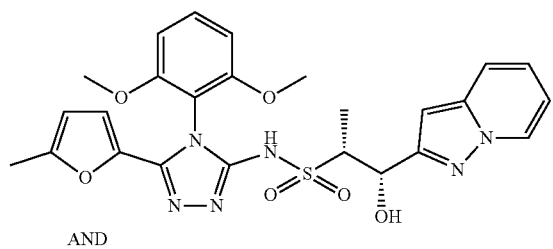

AND

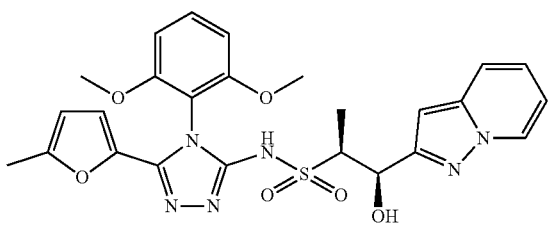

(1R,2S)—N-(4-(2,6-Dimethoxyphenyl)-5-(5-methyl-2-furanyl)-4H-1,2,4-triazol-3-yl)-1-hydroxy-1-pyrazolo[1,5-a]pyridin-2-yl-2-propanesulfonamide and (1S,2R)—N-(4-(2,6-dimethoxyphenyl)-5-(5-methyl-2-furanyl)-4H-1,2,4-triazol-3-yl)-1-hydroxy-1-pyrazolo[1,5-a]pyridin-2-yl-2-propanesulfonamide, Example 272.0. The title compound was prepared from Example 369.0 and pyrazolo[1,5-a]pyridine-2-carbaldehyde using the procedure described in Example 281.0. $^1$H NMR (500 MHz, DMSO-$d_6$) δ 8.61 (dd, J=6.8, 1.0 Hz, 1H), 7.57-7.64 (m, 1H), 7.41 (t, J=8.4 Hz, 1H), 7.15 (ddd, J=8.9, 6.7, 1.1 Hz, 1H), 6.75-6.84 (m, 3H), 6.50 (s, 1H), 5.91-5.98 (m, 2H), 5.54 (s, 1H), 5.49 (d, J=3.2 Hz, 1H), 3.61-3.69 (m, 7H), 2.21 (s, 3H), 0.98 (d, J=7.1 Hz, 3H). LCMS-ESI (pos.) m/z: 539.0 (M+H)$^+$.

Example 273.0. Preparation of (1R,2S)—N-(4-(2,6-dimethoxyphenyl)-5-(5-methyl-2-furanyl)-4H-1,2,4-triazol-3-yl)-1-hydroxy-1-(1-methyl-1H-imidazol-4-yl)-2-propanesulfonamide or (1S,2R)—N-(4-(2,6-dimethoxyphenyl)-5-(5-methyl-2-furanyl)-4H-1,2,4-triazol-3-yl)-1-hydroxy-1-(1-methyl-1H-imidazol-4-yl)-2-propanesulfonamide 273.0

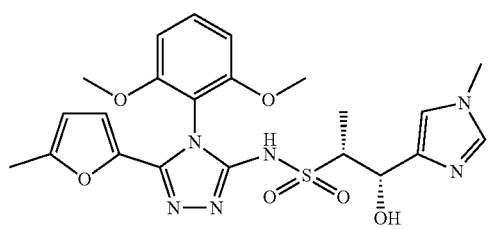

OR

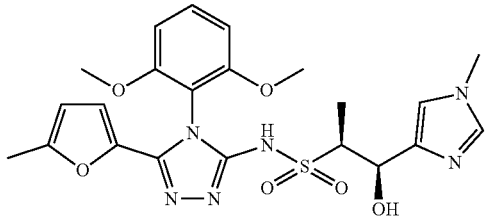

(1R,2S)—N-(4-(2,6-Dimethoxyphenyl)-5-(5-methyl-2-furanyl)-4H-1,2,4-triazol-3-yl)-1-hydroxy-1-(1-methyl-1H-imidazol-4-yl)-2-propanesulfonamide or (1S,2R)—N-(4-(2,6-dimethoxyphenyl)-5-(5-methyl-2-furanyl)-4H-1,2,4-triazol-3-yl)-1-hydroxy-1-(1-methyl-1H-imidazol-4-yl)-2-propanesulfonamide, Example 273.0. The title compound was prepared from Example 369.0 and 1-methyl-1H-imidazole-4-carbaldehyde using the procedure described in Example 281.0. The mixture was separated by SFC (250×30 mm IC column with 50 g/min MeOH (+20 mM NH$_3$)+50 g/min CO$_2$, 50% co-solvent at 100 g/min) on Thar 350 SFC. Two enantiomers were separated. The title compound (Example 273.0, 17 mg, 0.03 mmol, 38% yield) was the second isomer to elute under these conditions. $^1$H NMR (500 MHz, DMSO-$d_6$) δ 7.55 (t, J=8.4 Hz, 1H), 7.46 (s, 1H), 6.85-6.92 (3H, m, 3H), 6.12 (d, J=2.7 Hz, 1H), 5.81 (d, J=3.2 Hz, 1H), 5.16 (s, 1H), 4.42 (br. s, 1H), 3.70 (m, 6H), 3.59 (s, 3H), 3.30 (td, J=7.2, 6.2 Hz, 1H), 2.25 (3H, s), 1.03 (d, J=7.1 Hz, 3H). LCMS-ESI (pos.) m/z: 503.1 (M+H)$^+$.

Example 274.0. Preparation of (1S,2S)—N-(4-(2,6-dimethoxyphenyl)-5-(5-methyl-2-furanyl)-4H-1,2,4-triazol-3-yl)-1-hydroxy-1-pyrazolo[1,5-a]pyridin-7-yl-2-propanesulfonamide and (1R,2R)—N-(4-(2,6-dimethoxyphenyl)-5-(5-methyl-2-furanyl)-4H-1,2,4-triazol-3-yl)-1-hydroxy-1-pyrazolo[1,5-a]pyridin-7-yl-2-propanesulfonamide 274.1

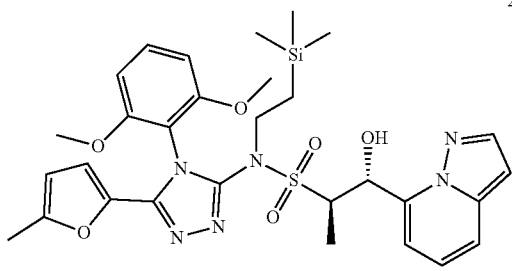

AND

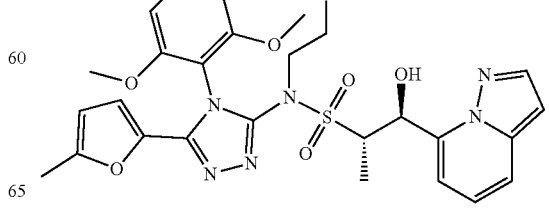

(1R,2R)—N-(4-(2,6-Dimethoxyphenyl)-5-(5-methyl-furan-2-yl)-4H-1,2,4-triazol-3-yl)-1-hydroxy-1-(pyrazolo[1,5-a]pyridin-7-yl)-N-(2-(trimethylsilyl)ethyl)propane-2-sulfonamide and (1S,2S)—N-(4-(2,6-dimethoxyphenyl)-5-(5-methylfuran-2-yl)-4H-1,2,4-triazol-3-yl-1-hydroxy-1-(pyrazolo[1,5-a]pyridin-7-yl)-N-(2-(trimethylsilyl)ethyl)propane-2-sulfonamide, Example 274.1. N-(4-(2,6-Dimethoxyphenyl)-5-(5-methylfuran-2-yl)-4H-1,2,4-triazol-3-yl)-N-(2-(trimethylsilyl)ethyl)ethanesulfonamide (Example 369.0, 340 mg, 0.69 mmol) in a vial was azeotroped three times with toluene. Anhydrous THF (2 mL) was added to the flask by syringe. Upon complete addition of THF, argon was bubbled through the solution for 15 min. The flask was cooled to −78° C. After 20 min, n-butyllithium (2.5 M solution in hexanes, 0.35 mL, 0.87 mmol) was carefully added dropwise to the cold solution. After 5 min, a solution of pyrazolo[1,5-a]pyridine-7-carboxaldehyde (commercially available from Matrix Scientific, 130 mg, 0.89 mmol) in anhydrous THF (2 mL) was added dropwise over 5 min. Upon complete addition, the reaction was maintained at −78° C. and monitored with LC-MS. After 2 h, the mixture was carefully quenched with saturated aqueous NH$_4$Cl solution. After extracting three times with CHCl$_3$, the organic layers were combined and then dried over anhydrous MgSO$_4$. After filtration and concentration in vacuo, the dark brown residue was purified on silica gel eluting with 0-50% EtOAc in heptanes to afford Example 274.1 (55 mg, 0.09 mmol, 13% yield) as the second eluting isomer. $^1$H NMR (500 MHz, DMSO-d$_6$) δ 7.98 (1H, d, J=2.2 Hz), 7.57-7.67 (2H, m), 7.21 (1H, dd, J=8.8, 6.8 Hz), 6.95 (1H, d, J=8.1 Hz), 6.86-6.92 (1H, m), 6.74 (1H, d, J=6.8 Hz), 6.63 (1H, d, J=2.4 Hz), 6.16 (1H, dd, J=3.4, 1.0 Hz), 5.84 (1H, d, J=3.4 Hz), 5.26 (1H, t, J=6.2 Hz), 5.20 (1H, d, J=6.6 Hz), 4.26-4.35 (2H, m), 3.70-3.83 (6H, m), 2.28 (3H, s), 1.19-1.26 (2H, m), 0.94 (3H, d, J=7.1 Hz), 0.00-0.08 (9H, m). Mass Spectrum (pos.) m/z: 639.2 (M+H)$^+$.

274.0

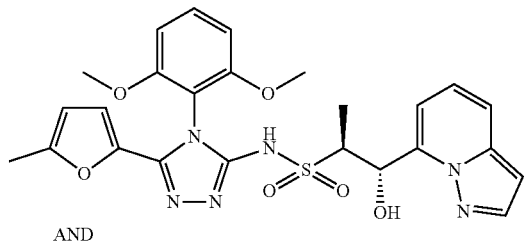

AND

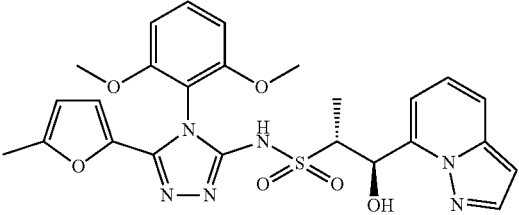

(1S,2S)—N-(4-(2,6-Dimethoxyphenyl)-5-(5-methyl-2-furanyl)-4H-1,2,4-triazol-3-yl)-1-hydroxy-1-pyrazolo[1,5-a]pyridin-7-yl-2-propanesulfonamide and (1R,2R)—N-(4-(2,6-dimethoxyphenyl)-5-(5-methyl-2-furanyl)-4H-1,2,4-triazol-3-yl)-1-hydroxy-1-pyrazolo[1,5-a]pyridin-7-yl-2-propanesulfonamide, Example 274.0. To a vial containing Example 274.1 (55 mg, 0.09 mmol) was added TASF (72 mg, 0.261 mmol) followed by dropwise addition of anhydrous DMF (1.5 mL). The mixture was carefully heated to 60° C. and monitored with LC-MS. After 3 h, the mixture was cooled to RT and then purified on silica gel eluting with 0-40% of (3:1 EtOAc:EtOH) in heptanes to afford Example 274.0 (29 mg, 0.05 mmol, 61% yield) as an off-white solid. $^1$H NMR (500 MHz, DMSO-d$_6$) δ 13.31 (1H, br. s.), 8.00 (1H, d, J=2.2 Hz), 7.64 (1H, dd, J=8.8, 1.2 Hz), 7.58 (1H, t, J=8.6 Hz), 7.22 (1H, dd, J=8.8, 7.1 Hz), 6.83-6.96 (3H, m), 6.65 (1H, d, J=2.4 Hz), 6.13 (1H, d, J=2.7 Hz), 5.83 (1H, d, J=3.2 Hz), 5.43 (1H, t, J=5.6 Hz), 5.37 (1H, br. s.), 3.90 (1H, quin, J=7.0 Hz), 3.76 (3H, s), 3.71 (3H, s), 2.25 (3H, s), 1.07 (3H, d, J=7.1 Hz). Mass Spectrum (pos.) m/z: 539.2 (M+H)$^+$.

Example 275.0. (1R,2S)—N-(4-(2,6-dimethoxyphenyl)-5-(5-methyl-2-furanyl)-4H-1,2,4-triazol-3-yl)-1-hydroxy-1-(2-methyl-1,3-oxazol-4-yl)-2-propanesulfonamide or (1S,2R)—N-(4-(2,6-dimethoxyphenyl)-5-(5-methyl-2-furanyl)-4H-1,2,4-triazol-3-yl)-1-hydroxy-1-(2-methyl-1,3-oxazol-4-yl)-2-propanesulfonamide 275.0

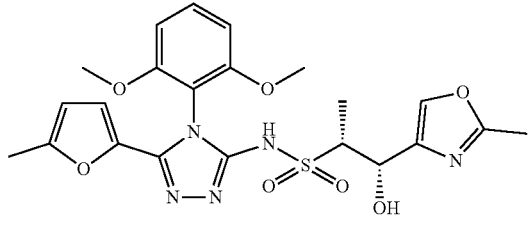

OR

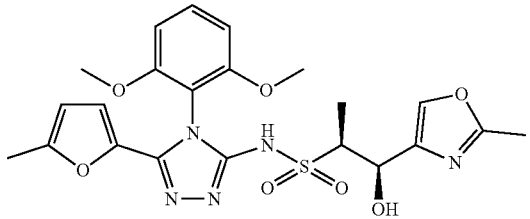

(1R,2S)—N-(4-(2,6-Dimethoxyphenyl)-5-(5-methyl-2-furanyl)-4H-1,2,4-triazol-3-yl)-1-hydroxy-1-(2-methyl-1,3-oxazol-4-yl)-2-propanesulfonamide or (1S,2R)—N-(4-(2,6-dimethoxyphenyl)-5-(5-methyl-2-furanyl)-4H-1,2,4-triazol-3-yl)-1-hydroxy-1-(2-methyl-1,3-oxazol-4-yl)-2-propanesulfonamide, Example 275.0. Example 284.0 was separated by SFC (150×20 mm IA column with 14% MeOH/CO$_2$ at 60 mL/min. Two enantiomers were separated. The title compound (Example 275.0) was the first isomer to elute under these conditions. $^1$H NMR (400 MHz, DMSO-d$_6$) δ 13.24 (br. s, 1H), 7.67 (d, J=1.4 Hz, 1H), 7.54 (t, J=8.5 Hz, 1H), 6.87 (d, J=8.4 Hz, 2H), 6.11 (d, J=2.7 Hz, 1H), 5.79 (br. s, 1H), 5.14 (s, 1H), 4.92 (br. s, 1H), 3.69 (s, 3H), 3.70 (s, 3H), 3.24 (q, J=6.3 Hz, 1H), 2.35 (s, 3H), 2.25 (s, 3H), 1.04 (d, J=6.8 Hz, 3H). LCMS-ESI (pos.) m/z: 504.0 (M+H)$^+$.

Example 276.0. Preparation of (1S,2S)—N-(4-(2,6-dimethoxyphenyl)-5-(5-methyl-2-furanyl)-4H-1,2,4-triazol-3-yl-1-hydroxy-1-pyrazolo[1,5-a]pyridin-7-yl-2-propanesulfonamide or (1R,2R)—N-(4-(2,6-dimethoxyphenyl)-5-(5-methyl-2-furanyl)-4H-1,2,4-triazol-3-yl-1-hydroxy-1-pyrazolo[1,5-a]pyridin-7-yl-2-propanesulfonamide Example 277.0. Preparation of (1S,2S)—N-(4-(2,6-dimethoxyphenyl)-5-(5-methyl-2-furanyl)-4H-1,2,4-triazol-3-yl-1-hydroxy-1-imidazo[1,2-a]pyridin-3-yl-2-propanesulfonamide or (1R,2R)—N-(4-(2,6-dimethoxyphenyl)-5-(5-methyl-2-furanyl)-4H-1,2,4-triazol-3-yl-1-hydroxy-1-imidazo[1,2-a]pyridin-3-yl-2-propanesulfonamide

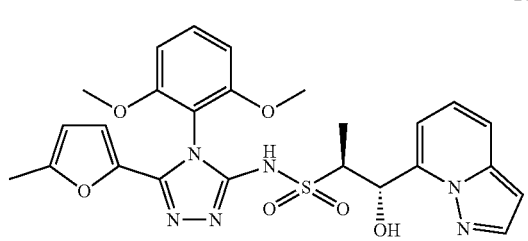

276.0

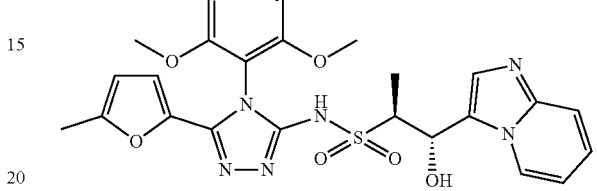

277.0

OR

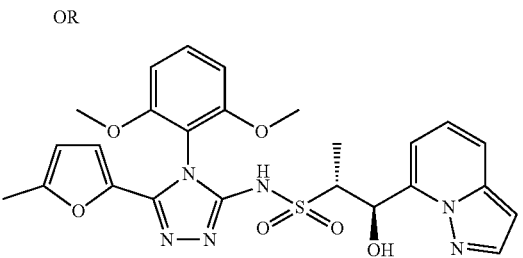

OR (1S,2S)—N-(4-(2,6-Dimethoxyphenyl)-5-(5-methyl-2-furanyl)-4H-1,2,4-triazol-3-yl)-1-hydroxy-1-pyrazolo[1,5-a]pyridin-7-yl-2-propanesulfonamide or (1R,2R)—N-(4-(2,6-dimethoxyphenyl)-5-(5-methyl-2-furanyl)-4H-1,2,4-triazol-3-yl)-1-hydroxy-1-pyrazolo[1,5-a]pyridin-7-yl-2-propanesulfonamide, Example 276.0. Example 274.0 was separated by SFC (250×30 mm AD column with 44 g/min MeOH (+20 mM $NH_3$)+66 g/min $CO_2$, 40% co-solvent at 110 g/min) on Thar 200 SFC. Two enantiomers were separated. The title compound was the first isomer to elute under these conditions. (7 mg, 0.013 mmol, 25% yield). $^1$H NMR (500 MHz, $CD_3OD$) δ 7.95 (d, J=2.4 Hz, 1H), 7.52-7.64 (m, 2H), 7.17 (dd, J=8.8, 6.8 Hz, 1H), 6.77-6.92 (m, 3H), 6.61 (d, J=2.2 Hz, 1H), 6.01 (d, J=2.7 Hz, 1H), 5.90-5.99 (m, 1H), 5.43 (d, J=7.1 Hz, 1H), 4.16 (quin, J=7.0 Hz, 1H), 3.81 (s, 3H), 3.77 (s, 3H), 2.26 (s, 3H), 1.17 (d, J=7.1 Hz, 3H). LCMS-ESI (pos.) m/z: 539.2 (M+H)$^+$.

(1S,2S)—N-(4-(2,6-Dimethoxyphenyl)-5-(5-methyl-2-furanyl)-4H-1,2,4-triazol-3-yl)-1-hydroxy-1-imidazo[1,2-a]pyridin-3-yl-2-propanesulfonamide or (1R,2R)—N-(4-(2,6-dimethoxyphenyl)-5-(5-methyl-2-furanyl)-4H-1,2,4-triazol-3-yl)-1-hydroxy-1-imidazo[1,2-a]pyridin-3-yl-2-propanesulfonamide, Example 277.0. The title compound was prepared from Example 369.0 and imidazo[1,2-a]pyridine-3-carbaldehyde using the procedure described in Example 281.0. The mixture of diasteromers was separated by SFC (150×20 mm AD-H column with 40% EtOH (0.1% $NH_4OH$)/$CO_2$ at 60 mL/min). Three peaks were separated. The title compound (Example 277.0, 12 mg, 0.022 mmol, 12% yield) was the second peak to elute under these conditions. $^1$H NMR (500 MHz, $CD_2Cl_2$) δ 8.39 (br. s, 1H), 7.51-7.65 (m, 2H), 7.46 (br. s, 1H), 7.20 (t, J=6.6 Hz, 1H), 6.72-6.83 (m, 3H), 5.95 (d, J=2.7 Hz, 1H), 5.90 (d, J=3.4 Hz, 1H), 5.26 (d, J=9.5 Hz, 1H), 3.77 (m, 6H), 3.60-3.70 (m, 1H), 2.29 (s, 3H), 0.96 (d, J=6.8 Hz, 3H). LCMS-ESI (pos.) m/z: 539.2 (M+H)$^+$.

Example 278.0. Preparation of (1R,2R)—N-(4-(2,6-dimethoxyphenyl)-5-(5-methyl-2-furanyl)-4H-1,2,4-triazol-3-yl)-1-imidazo[1,2-a]pyridin-2-yl-1-methoxy-2-propanesulfonamide and (1S,2S)—N-(4-(2,6-dimethoxyphenyl)-5-(5-methyl-2-furanyl)-4H-1,2,4-triazol-3-yl)-1-imidazo[1,2-a]pyridin-2-yl-1-methoxy-2-propanesulfonamide 278.0

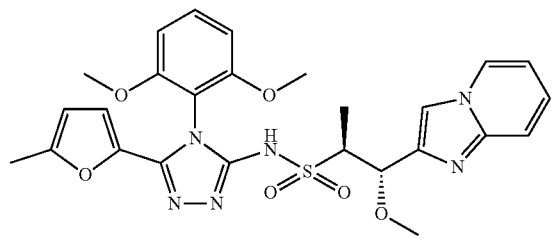

AND

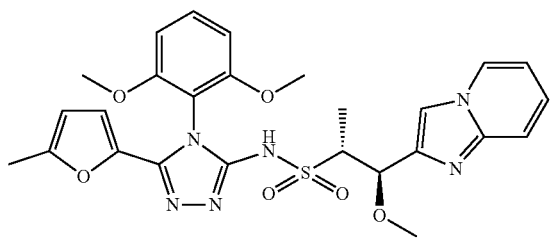

(1R,2R)—N-(4-(2,6-Dimethoxyphenyl)-5-(5-methyl-2-furanyl)-4H-1,2,4-triazol-3-yl)-1-imidazo[1,2-a]pyridin-2-yl-1-methoxy-2-propanesulfonamide and (1S,2S)—N-(4-(2,6-dimethoxyphenyl)-5-(5-methyl-2-furanyl)-4H-1,2,4-triazol-3-yl)-1-imidazo[1,2-a]pyridin-2-yl-1-methoxy-2-propanesulfonamide, Example 278.0. The title compound was prepared from Example 264.2 using the procedure described in Example 264.0. $^1$H NMR (500 MHz, DMSO-d$_6$) δ 13.16 (br. s, 1H), 8.50 (dt, J=6.8, 1.1 Hz, 1H), 7.86 (s, 1H), 7.48-7.61 (m, 2H), 7.22 (ddd, J=9.0, 6.6, 1.2 Hz, 1H), 6.83-6.95 (m, 3H), 6.12 (d, J=2.7 Hz, 1H), 5.78 (d, J=3.2 Hz, 1H), 4.54 (d, J=7.8 Hz, 1H), 3.72-3.79 (m, 6H), 3.45 (quin, J=6.7 Hz, 1H), 2.98 (s, 3H), 2.25 (s, 3H), 0.99 (d, J=7.1 Hz, 3H). LCMS-ESI (pos.) m/z: 553.2 (M+H)$^+$.

Example 279.0. Preparation of (1S,2S)—N-(4-(2,6-dimethoxyphenyl)-5-(5-methyl-2-furanyl)-4H-1,2,4-triazol-3-yl-1-hydroxy-1-imidazo[1,2-a]pyridin-2-yl-2-propanesulfonamide or (1R,2R)—N-(4-(2,6-dimethoxyphenyl)-5-(5-methyl-2-furanyl)-4H-1,2,4-triazol-3-yl)-1-hydroxy-1-imidazo[1,2-a]pyridin-2-yl-2-propanesulfonamide 279.0

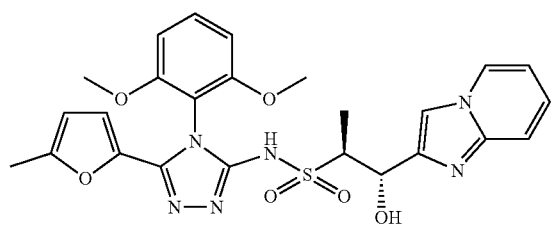

OR

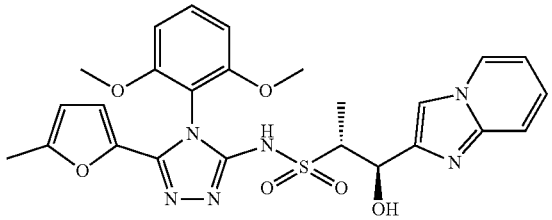

(1S,2S)—N-(4-(2,6-Dimethoxyphenyl)-5-(5-methyl-2-furanyl)-4H-1,2,4-triazol-3-yl)-1-hydroxy-1-imidazo[1,2-a]pyridin-2-yl-2-propanesulfonamide or (1R,2R)—N-(4-(2,6-dimethoxyphenyl)-5-(5-methyl-2-furanyl)-4H-1,2,4-triazol-3-yl)-1-hydroxy-1-imidazo[1,2-a]pyridin-2-yl-2-propanesulfonamide, Example 279.0. Example 285.0 was separated by SFC (250×21 mm AD-H column with 25 g/min MeOH (NH$_3$)+35 g/min CO$_2$, 42% co-solvent at 60 g/min on Thar 80 SFC. Two enantiomers were obtained. The title compound was the second isomer to elute under these conditions. $^1$H NMR (500 MHz, DMSO-d$_6$) δ 8.48 (d, J=6.8 Hz, 1H), 7.82 (s, 1H), 7.43-7.52 (m, 2H), 7.15-7.22 (m, 1H), 6.78-6.90 (m, 3H), 6.04 (br. s, 1H), 5.64 (br. s, 1H), 4.82 (d, J=8.3 Hz, 1H), 3.70 (s, 3H), 3.68 (s, 3H), 3.53-3.64 (m, 1H), 3.35-3.45 (m, 1H), 2.23 (s, 3H), 0.92 (d, J=6.6 Hz, 3H). LCMS-ESI (pos.) m/z: 539.2 (M+H)$^+$.

Example 280.0. Preparation of (1S,2R)-1-(6,7-dihydro-5H-pyrazolo[5,1-b][1,3]oxazin-2-yl)-N-(4-(2,6-dimethoxyphenyl)-5-(5-methyl-2-furanyl)-4H-1,2,4-triazol-3-yl)-1-hydroxy-2-propanesulfonamide or (1R,2S)-1-(6,7-dihydro-5H-pyrazolo[5,1-b][1,3]oxazin-2-yl)-N-(4-(2,6-dimethoxyphenyl)-5-(5-methyl-2-furanyl)-4H-1,2,4-triazol-3-yl)-1-hydroxy-2-propanesulfonamide 280.0

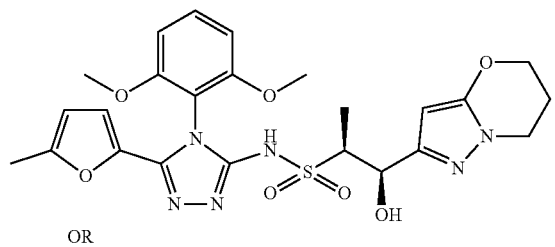

OR

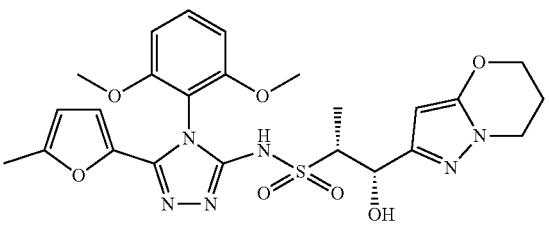

(1S,2R)-1-(6,7-Dihydro-5H-pyrazolo[5,1-b][1,3]oxazin-2-yl)-N-(4-(2,6-dimethoxyphenyl)-5-(5-methyl-2-furanyl)-4H-1,2,4-triazol-3-yl)-1-hydroxy-2-propanesulfonamide or (1R,2S)-1-(6,7-dihydro-5H-pyrazolo[5,1-b][1,3]oxazin-2-yl)-N-(4-(2,6-dimethoxyphenyl)-5-(5-methyl-2-furanyl)-4H-1,2,4-triazol-3-yl)-1-hydroxy-2-propanesulfonamide, Example 280.0. The title compound was prepared from Example 369.0 and 6,7-dihydro-5H-pyrazolo[5,1-b][1,3]oxazine-2-carbaldehyde using the procedure described in Example 281.0. The mixture of diasteromers was separated by SFC (150×20 mm IC column with 35% MeOH (0.1% NH$_4$OH)/CO$_2$ at 65 mL/min. Three peaks were separated. The second peak to elute under these conditions was a mixture of diastereomers that was repurified by SFC (250× 30 mm AD column with 40 mL/min MeOH (+20 mM NH$_3$)+60 g/min CO$_2$, 60% co-solvent at 100 g/min) on Thar 350 SFC. Two diastereomers were obtained. The title compound was the first isomer to elute under these conditions. $^1$H NMR (500 MHz, DMSO-d$_6$) δ 7.53 (t, J=8.6 Hz, 1H), 6.86 (d, J=8.6 Hz, 2H), 6.04-6.13 (m, 1H), 5.75 (br. s, 1H), 5.37 (s, 1H), 5.08-5.15 (m, 1H), 4.18-4.25 (m, 2H), 3.99 (t, J=6.2 Hz, 2H), 3.69 (s, 3H), 3.70 (s, 3H), 3.21-3.29 (m, 1H), 2.24 (s, 3H), 2.04-2.18 (m, 2H), 1.11 (d, J=7.1 Hz, 3H). LCMS-ESI (pos.) m/z: 545.2 (M+H)$^+$.

Example 281.0. Preparation of (1R,2S)—N-(4-(2,6-dimethoxyphenyl)-5-(5-methyl-2-furanyl)-4H-1,2,4-triazol-3-yl)-1-hydroxy-1-(1,3-thiazol-4-yl)-2-propanesulfonamide and (1S,2R)—N-(4-(2,6-dimethoxyphenyl)-5-(5-methyl-2-furanyl)-4H-1,2,4-triazol-3-yl)-1-hydroxy-1-(1,3-thiazol-4-yl)-2-propanesulfonamide

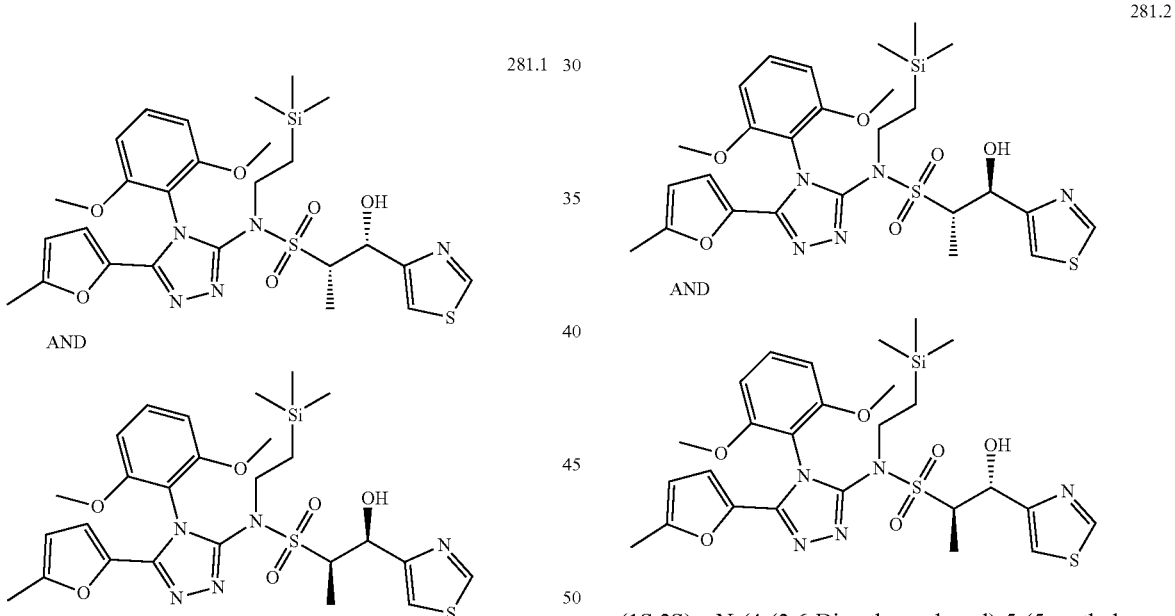

(1R,2S)—N-(4-(2,6-Dimethoxyphenyl)-5-(5-methyl-furan-2-yl)-4H-1,2,4-triazol-3-yl)-1-hydroxy-1-(thiazol-4-yl)-N-(2-(trimethylsilyl)ethyl)propane-2-sulfonamide and (1S,2R)—N-(4-(2,6-dimethoxyphenyl)-5-(5-methylfuran-2-yl)-4H-1,2,4-triazol-3-yl)-1-hydroxy-1-(thiazol-4-yl)-N-(2-(trimethylsilyl)ethyl)propane-2-sulfonamide, Example 281.1. Example 369.0 (350 mg, 0.71 mmol) in a flask was azeotroped with toluene and then anhydrous THF (2 mL) was added to the flask by syringe. Upon complete addition of THF, argon was bubbled through the solution for 15 min. The flask was then cooled in an acetone-dry ice bath. After 20 min, n-butyllithium, (2.5 M solution in hexanes, 0.28 mL, 0.7 mmol) was carefully added dropwise to the cold solution. After 5 min, a solution of thiazole-4-carboxaldehyde (91 mg, 0.81 mmol) in anhydrous THF (2 mL) was added dropwise over 5 min. Upon complete addition, the reaction was maintained at −78° C. and monitored with LC-LCMS. After 0.5 h, the mixture was transferred to an ice-water bath then carefully quenched with saturated aqueous NH$_4$Cl solution. After extracting three times with 20% IPA in DCM, the organic layers were combined and then dried over anhydrous MgSO$_4$. After filtration and concentration in vacuo, the dark brown residue was purified on silica gel eluting with (0-75% EtOAc in hexanes) to afford fractions that were concentrated in vacuo. The light yellow film was further purified on silica gel eluting with (10-35% EtOAc in DCM) to afford the following main compounds: The nonpolar eluting isomer off the column was a colorless film with arbitrarily assigned stereochemistry that was identified as the title compound (83 mg, 0.14 mmol, 19% yield) and was used without further purification. $^1$H NMR (500 MHz, DMSO-d$_6$) δ 9.02 (d, J=2.2 Hz, 1H), 7.52 (t, J=8.6 Hz, 1H), 7.34 (dd, J=2.0, 1.2 Hz, 1H), 6.82 (d, J=8.8 Hz, 1H), 6.86 (d, J=8.1 Hz, 1H), 6.15 (dd, J=3.4, 1.0 Hz, 1H), 5.80 (d, J=3.4 Hz, 1H), 5.32 (dt, J=3.7, 1.5 Hz, 1H), 4.82 (d, J=3.9 Hz, 1H), 4.31-4.44 (m, 2H), 3.73 (s, 3H), 3.69 (s, 3H), 3.20 (qd, J=6.9, 1.5 Hz, 1H), 2.28 (s, 3H), 1.22-1.30 (m, 2H), 0.79 (d, J=6.8 Hz, 3H), 0.06-0.10 (m, 9H). LCMS-ESI (pos.) m/z: 606.2 (M+H)$^+$.

(1S,2S)—N-(4-(2,6-Dimethoxyphenyl)-5-(5-methyl-furan-2-yl)-4H-1,2,4-triazol-3-yl)-1-hydroxy-1-(thiazol-4-yl)-N-(2-(trimethylsilyl)ethyl)propane-2-sulfonamide and (1R,2R)—N-(4-(2,6-dimethoxyphenyl)-5-(5-methylfuran-2-yl)-4H-1,2,4-triazol-3-yl)-1-hydroxy-1-(thiazol-4-yl)-N-(2-(trimethylsilyl)ethyl)propane-2-sulfonamide, Example 281.2. The more polar diastereomer to elute off the column described in Example 281.1 was a colorless film that was identified as 281.2 (37 mg, 0.07 mmol, 8.5% yield) and was used without further purification. $^1$H NMR (500 MHz, DMSO-d$_6$) δ 9.01 (d, J=2.0 Hz, 1H), 7.58 (t, J=8.6 Hz, 1H), 7.38 (d, J=2.0 Hz, 1H), 6.84-6.95 (m, 2H), 6.16 (dd, J=3.4, 1.0 Hz, 1H), 5.86 (d, J=3.4 Hz, 1H), 4.99 (d, J=2.7 Hz, 1H), 4.70 (dd, J=8.1, 2.7 Hz, 1H), 4.30-4.43 (m, 2H), 3.72 (s, 3H), 3.71 (s, 3H), 3.03-3.13 (m, 1H), 2.28 (s, 3H), 1.22-1.30 (m, 2H), 0.68 (d, J=6.8 Hz, 3H), 0.05-0.10 (m, 9H). LCMS-ESI (pos.) m/z: 606.2 (M+H)$^+$.

515

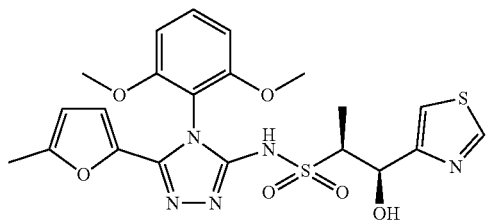

AND

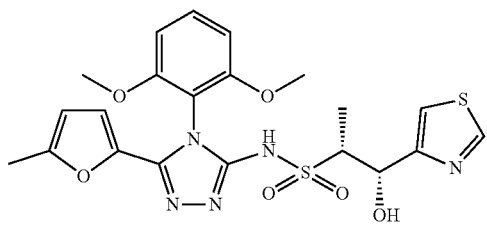

Example 281.0: (1S,2S)—N-(4-(2,6-Dimethoxyphenyl)-5-(5-methyl-2-furanyl)-4H-1,2,4-triazol-3-yl)-1-hydroxy-1-pyrazolo[1,5-a]pyridin-7-yl-2-propanesulfonamide and (1R,2R)—N-(4-(2,6-dimethoxyphenyl)-5-(5-methyl-2-furanyl)-4H-1,2,4-triazol-3-yl)-1-hydroxy-1-pyrazolo[1,5-a]pyridin-7-yl-2-propanesulfonamide, Example 281.0. Example 281.1 (79 mg, 0.13 mmol) in a vial was azeotroped with toluene and then dried under high vacuum. After 2 h, TASF (125 mg, 0.45 mmol) was added followed by dropwise addition of anhydrous DMF (1.3 mL). The mixture was carefully heated to 60° C. and monitored with LC-MS. After 1 h, the mixture was cooled to RT and then treated with water. The mixture was stirred at RT for 10 min and then the solid was filtered off. After rinsing the solid twice with water, it was dried overnight at 50° C. The white solid was identified as Example 281.0 (56.4 mg, 0.112 mmol, 86% yield). $^1$H NMR (500 MHz, DMSO-$d_6$) δ 13.27 (1H, br. s.), 9.04 (1H, d, J=2.0 Hz), 7.56 (1H, t, J=8.6 Hz), 7.44 (1H, dd, J=2.0, 1.2 Hz), 6.88 (2H, d, J=8.6 Hz), 6.13 (1H, dd, J=3.3, 0.9 Hz), 5.81 (1H, d, J=3.2 Hz), 5.40 (1H, s), 5.08 (1H, br. s.), 3.70 (3H, s), 3.67 (3H, s), 3.43 (1H, qd, J=7.0, 1.0 Hz), 2.25 (3H, s), 0.99 (3H, d, J=6.8 Hz). Mass Spectrum (pos.) m/z: 506.1 (M+H)$^+$.

Example 282.0. Preparation of (1S,2S)—N-(4-(2,6-dimethoxyphenyl)-5-(5-methyl-2-furanyl)-4H-1,2,4-triazol-3-yl)-1-hydroxy-1-imidazo[1,5-a]pyridin-1-yl-2-propanesulfonamide or (1R,2R)—N-(4-(2,6-dimethoxyphenyl)-5-(5-methyl-2-furanyl)-4H-1,2,4-triazol-3-yl)-1-hydroxy-1-imidazo[1,5-a]pyridin-1-yl-2-propanesulfonamide 282.0

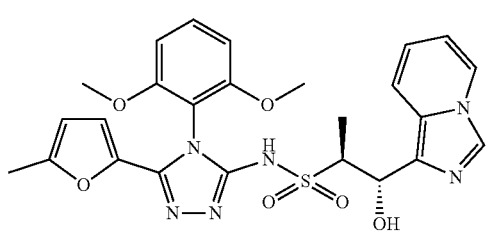

OR

516

-continued

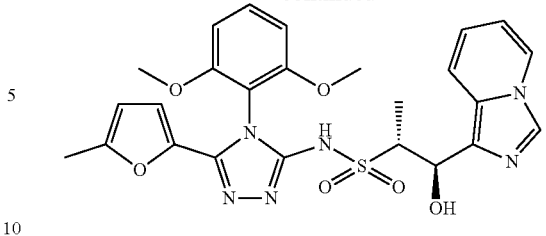

(1S,2S)—N-(4-(2,6-Dimethoxyphenyl)-5-(5-methyl-2-furanyl)-4H-1,2,4-triazol-3-yl)-1-hydroxy-1-imidazo[1,5-a]pyridin-1-yl-2-propanesulfonamide or (1R,2R)—N-(4-(2,6-dimethoxyphenyl)-5-(5-methyl-2-furanyl)-4H-1,2,4-triazol-3-yl)-1-hydroxy-1-imidazo[1,5-a]pyridin-1-yl-2-propanesulfonamide, Example 282.0. The title compound was prepared from Example 369.0 and imidazo[1,5-a]pyridine-1-carbaldehyde using the procedure described in Example 281.0. The mixture of diastereomers was separated by SFC (150×20 mm IA column with 25% MeOH (0.1% NH$_4$OH)/CO$_2$ at 60 mL/min. Three peaks were separated. The first peak to elute under these conditions was a mixture of anti isomers that was repurified by SFC (250×20 mm AD-H column with 25% EtOH/CO$_2$ at 65 mL/min. Two enantiomers were obtained. The title compound was the second isomer to elute under these conditions. $^1$H NMR (500 MHz, DMSO-$d_6$) δ 13.44 (br. s, 1H), 8.17 (d, J=7.1 Hz, 1H), 7.58 (t, J=8.6 Hz, 1H), 7.52 (d, J=9.3 Hz, 1H), 7.31 (s, 1H), 6.91 (dd, J=8.6, 3.9 Hz, 2H), 6.75 (dd, J=9.2, 6.2 Hz, 1H), 6.52-6.58 (m, 1H), 6.14 (d, J=2.7 Hz, 1H), 5.84 (br. s, 1H), 5.50 (br. s, 1H), 5.29 (d, J=7.3 Hz, 1H), 3.72-3.76 (m, 6H), 3.61-3.70 (m, 1H), 2.26 (s, 3H), 1.00 (d, J=6.8 Hz, 3H). LCMS-ESI (pos.) m/z: 539.2 (M+H)$^+$.

Example 283.0. Preparation of (1R,2S)—N-(4-(2,6-dimethoxyphenyl)-5-(5-methyl-2-furanyl)-4H-1,2,4-triazol-3-yl)-1-hydroxy-1-(1-methyl-1H-imidazol-4-yl)-2-propanesulfonamide and (1S,2R)—N-(4-(2,6-dimethoxyphenyl)-5-(5-methyl-2-furanyl)-4H-1,2,4-triazol-3-yl)-1-hydroxy-1-(1-methyl-1H-imidazol-4-yl)-2-propanesulfonamide 283.0

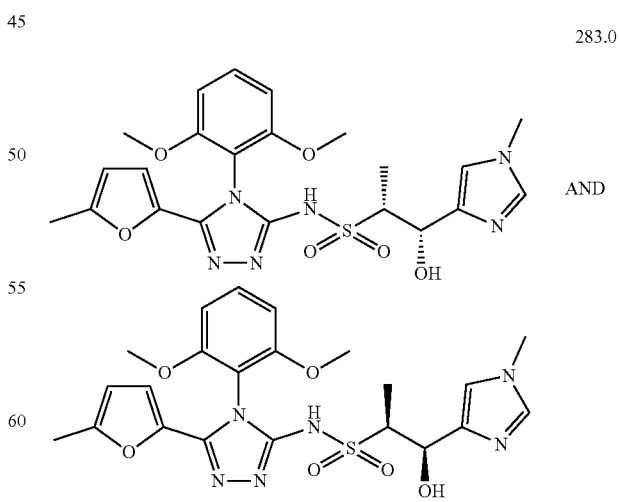

(1R,2S)—N-(4-(2,6-Dimethoxyphenyl)-5-(5-methyl-2-furanyl)-4H-1,2,4-triazol-3-yl)-1-hydroxy-1-(1-methyl-1H-imidazol-4-yl)-2-propanesulfonamide and (1S,2R)—N-(4-

(2,6-dimethoxyphenyl)-5-(5-methyl-2-furanyl)-4H-1,2,4-triazol-3-yl)-1-hydroxy-1-(1-methyl-1H-imidazol-4-yl)-2-propanesulfonamide, Example 283.0. The title compound was prepared from Example 369.0 and 1-methyl-1H-imidazole-4-carbaldehyde using the procedure described in Example 281.0. ¹H NMR (500 MHz, DMSO-d₆) δ 7.55 (t, J=8.6 Hz, 1H), 7.46 (d, J=1.0 Hz, 1H), 6.84-6.92 (m, 3H), 6.12 (dd, J=3.4, 0.7 Hz, 1H), 5.81 (d, J=3.2 Hz, 1H), 5.17 (s, 1H), 4.43 (br. s, 1H), 3.71 (s, 3H), 3.69 (s, 3H), 3.59 (s, 3H), 3.28-3.34 (m, 1H), 2.25 (s, 3H), 1.03 (d, J=7.1 Hz, 3H). LCMS-ESI (pos.) m/z: 503.0 (M+H)⁺.

Example 284.0. Preparation of (1R,2S)—N-(4-(2,6-dimethoxyphenyl)-5-(5-methyl-2-furanyl)-4H-1,2,4-triazol-3-yl)-1-hydroxy-1-(2-methyl-1,3-oxazol-4-yl)-2-propanesulfonamide and (1S,2R)—N-(4-(2,6-dimethoxyphenyl)-5-(5-methyl-2-furanyl)-4H-1,2,4-triazol-3-yl)-1-hydroxy-1-(2-methyl-1,3-oxazol-4-yl)-2-propanesulfonamide 284.0

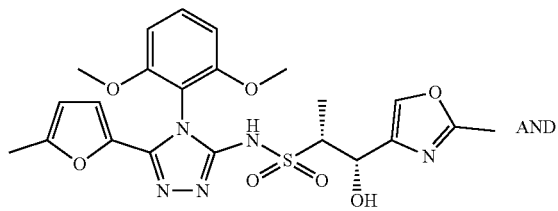

AND

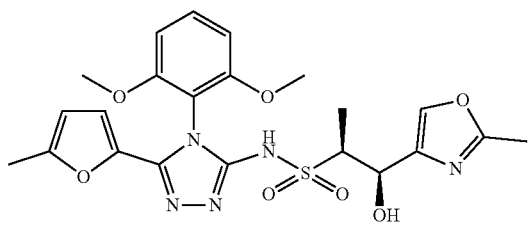

(1R,2S)—N-(4-(2,6-Dimethoxyphenyl)-5-(5-methyl-2-furanyl)-4H-1,2,4-triazol-3-yl)-1-hydroxy-1-(2-methyl-1,3-oxazol-4-yl)-2-propanesulfonamide and (1S,2R)—N-(4-(2, 6-dimethoxyphenyl)-5-(5-methyl-2-furanyl)-4H-1,2,4-triazol-3-yl)-1-hydroxy-1-(2-methyl-1,3-oxazol-4-yl)-2-propanesulfonamide, Example 284.0. The title compound was prepared from Example 369.0 and 2-methyloxazole-4-carbaldehyde using the procedure described in Example 281.0. ¹H NMR (400 MHz, DMSO-d₆) δ 13.24 (s, 1H), 7.68 (d, J=1.4 Hz, 1H), 7.56 (t, J=8.5 Hz, 1H), 6.83-6.92 (m, 2H), 6.13 (dd, J=3.5, 1.0 Hz, 1H), 5.82 (d, J=3.3 Hz, 1H), 5.09-5.19 (m, 1H), 4.86 (d, J=4.1 Hz, 1H), 3.70 (s, 3H), 3.71 (s, 3H), 3.22 (qd, J=7.0, 1.4 Hz, 1H), 2.35 (s, 3H), 2.25 (s, 3H), 1.06 (d, J=7.0 Hz, 3H). LCMS-ESI (pos.) m/z: 504.2 (M+H)⁺.

Example 285.0. Preparation of (1R,2R)—N-(4-(2,6-dimethoxyphenyl)-5-(5-methyl-2-furanyl)-4H-1,2,4-triazol-3-yl)-1-hydroxy-1-imidazo[1,2-a]pyridin-2-yl-2-propanesulfonamide and (1S,2S)—N-(4-(2,6-dimethoxyphenyl)-5-(5-methyl-2-furanyl)-4H-1,2,4-triazol-3-yl)-1-hydroxy-1-imidazo[1,2-a]pyridin-2-yl-2-propanesulfonamide 285.0

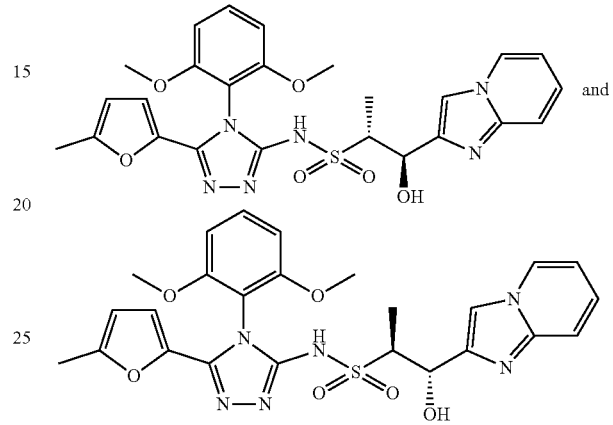

(1R,2R)—N-(4-(2,6-Dimethoxyphenyl)-5-(5-methyl-2-furanyl)-4H-1,2,4-triazol-3-yl)-1-hydroxy-1-imidazo[1,2-a]pyridin-2-yl-2-propanesulfonamide and (1S,2S)—N-(4-(2, 6-dimethoxyphenyl)-5-(5-methyl-2-furanyl)-4H-1,2,4-triazol-3-yl)-1-hydroxy-1-imidazo[1,2-a]pyridin-2-yl-2-propanesulfonamide, Example 285.0. The title compound was prepared from Example 369.0 and imidazo[1,2-a]pyridine-2-carbaldehyde using the procedure described in Example 281.0. ¹H NMR (500 MHz, DMSO-d₆) δ 13.57 (br. s, 1H), 8.45-8.52 (m, 1H), 7.81 (s, 1H), 7.56 (t, J=8.6 Hz, 1H), 7.47-7.53 (m, 1H), 7.21 (ddd, J=9.0, 6.7, 1.1 Hz, 1H), 6.84-6.92 (m, 3H), 6.13 (d, J=2.7 Hz, 1H), 5.76-5.90 (m, 1H), 5.12 (br. s, 1H), 4.89 (d, J=7.3 Hz, 1H), 3.74 (s, 3H), 3.75 (s, 3H), 3.37 (d, J=6.8 Hz, 1H), 2.26 (s, 3H), 1.01 (d, J=6.8 Hz, 3H). LCMS-ESI (pos.) m/z: 639.2 (M+H)⁺.

Example 286.0. Preparation of (1R,2S)—N-(4-(2,6-dimethoxyphenyl)-5-(5-methyl-2-furanyl)-4H-1,2,4-triazol-3-yl)-1-hydroxy-1-pyrazolo[1,5-a]pyridin-2-yl-2-propanesulfonamide or (1S,2R)—N-(4-(2,6-dimethoxyphenyl)-5-(5-methyl-2-furanyl)-4H-1,2,4-triazol-3-yl)-1-hydroxy-1-pyrazolo[1,5-a]pyridin-2-yl-2-propanesulfonamide 286.0

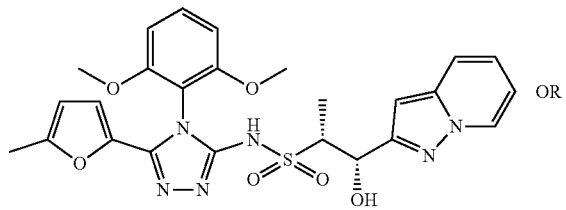

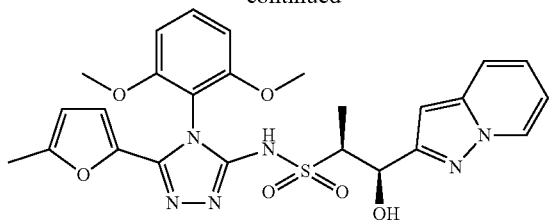

(1R,2S)—N-(4-(2,6-Dimethoxyphenyl)-5-(5-methyl-2-furanyl)-4H-1,2,4-triazol-3-yl)-1-hydroxy-1-pyrazolo[1,5-a]pyridin-2-yl-2-propanesulfonamide or (1S,2R)—N-(4-(2,6-dimethoxyphenyl)-5-(5-methyl-2-furanyl)-4H-1,2,4-triazol-3-yl)-1-hydroxy-1-pyrazolo[1,5-a]pyridin-2-yl-2-propanesulfonamide, Example 286.0. The title compound was prepared from Example 369.0 and pyrazolo[1,5-a]pyridine-2-carbaldehyde using the procedure described in Example 281.0. The mixture was separated by SFC (150×30 mm AD-H column with 44 g/min MeOH (+20 mM ammonia)+36 g/min CO₂, 55% co-solvent at 80 g/min) on Thar 200 SFC. Two enantiomers were separated. The title compound (14 mg, 0.03 mmol, 39% yield) was the first isomer to elute under these conditions. ¹H NMR (400 MHz, CD₃OD) δ 8.44 (dd, J=7.0, 0.8 Hz, 1H), 7.49-7.61 (m, 2H), 7.18 (ddd, J=8.9, 6.7, 0.8 Hz, 1H), 6.78-6.88 (m, 3H), 6.57 (s, 1H), 6.00 (d, J=2.5 Hz, 1H), 5.90 (d, J=2.9 Hz, 1H), 5.68 (s, 1H), 3.74 (s, 3H), 3.77 (s, 3H), 3.57-3.64 (m, 1H), 2.25 (s, 3H), 1.27 (d, J=7.0 Hz, 3H). LCMS-ESI (pos.) m/z: 539.2 (M+H)⁺.

Example 287.0. Preparation of (1R,2S)—N-(4-(2,6-dimethoxyphenyl)-5-(5-methyl-2-furanyl)-4H-1,2,4-triazol-3-yl-1-imidazo[1,2-a]pyridin-2-yl-1-methoxy-2-propanesulfonamide or (1S,2R)—N-(4-(2,6-dimethoxyphenyl)-5-(5-methyl-2-furanyl)-4H-1,2,4-triazol-3-yl-1-imidazo[1,2-a]pyridin-2-yl-1-methoxy-2-propanesulfonamide 287.0

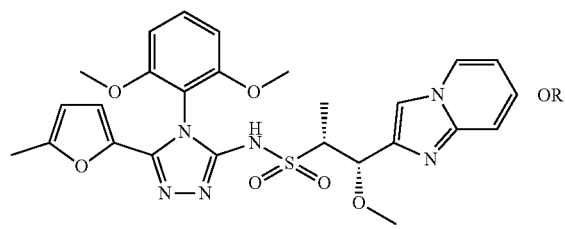

OR

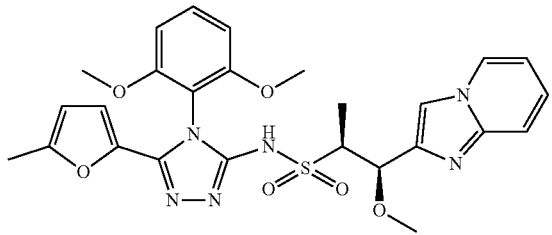

(1R,2S)—N-(4-(2,6-Dimethoxyphenyl)-5-(5-methyl-2-furanyl)-4H-1,2,4-triazol-3-yl)-1-imidazo[1,2-a]pyridin-2-yl-1-methoxy-2-propanesulfonamide or (1S,2R)—N-(4-(2,6-dimethoxyphenyl)-5-(5-methyl-2-furanyl)-4H-1,2,4-triazol-3-yl)-1-imidazo[1,2-a]pyridin-2-yl-1-methoxy-2-propanesulfonamide, Example 287.0. Example 264.0 was separated by SFC (250×30 mm CC4 column with 50 g/min MeOH (+20 mM NH₃)+60 g/min CO₂, 45% co-solvent at 100 g/min) on Thar 200 SFC. Two enantiomers were separated. The title compound (5 mg, 9.05 μmol, 36% yield) was the second isomer to elute under these conditions. ¹H NMR (500 MHz, CD₃OD) δ 8.39 (d, J=6.8 Hz, 1H), 7.75 (s, 1H), 7.46-7.55 (m, 2H), 7.30 (t, J=7.8 Hz, 1H), 6.90 (t, J=6.7 Hz, 1H), 6.78-6.84 (m, 2H), 5.99 (br. s, 1H), 5.87 (br. s, 1H), 5.21 (s, 1H), 3.71 (s, 3H), 3.75 (s, 3H), 3.34 (s, 3H), 2.26 (s, 3H), 1.24 (d, J=6.8 Hz, 3H). LCMS-ESI (pos.) m/z: 553.1 (M+H)⁺.

Example 288.0. Preparation of (1R,2S)—N-(4-(2,6-dimethoxyphenyl)-5-(5-methyl-2-furanyl)-4H-1,2,4-triazol-3-yl)-1-hydroxy-1-imidazo[1,5-a]pyridin-1-yl-2-propanesulfonamide or (1S,2R)—N-(4-(2,6-dimethoxyphenyl)-5-(5-methyl-2-furanyl)-4H-1,2,4-triazol-3-yl)-hydroxy-1-imidazo[1,5-a]pyridin-1-yl-2-propanesulfonamide 288.0

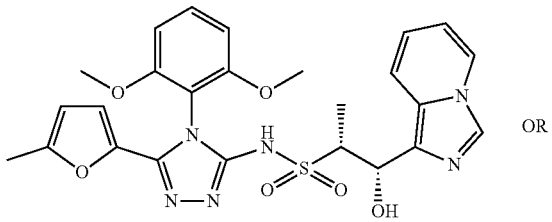

OR

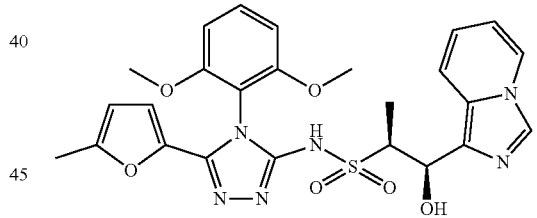

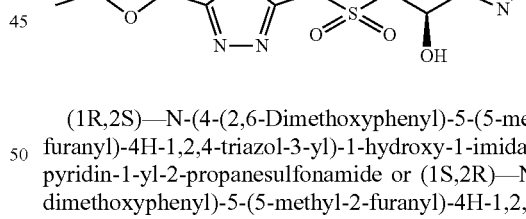

(1R,2S)—N-(4-(2,6-Dimethoxyphenyl)-5-(5-methyl-2-furanyl)-4H-1,2,4-triazol-3-yl)-1-hydroxy-1-imidazo[1,5-a]pyridin-1-yl-2-propanesulfonamide or (1S,2R)—N-(4-(2,6-dimethoxyphenyl)-5-(5-methyl-2-furanyl)-4H-1,2,4-triazol-3-yl)-1-hydroxy-1-imidazo[1,5-a]pyridin-1-yl-2-propanesulfonamide, Example 288.0. The title compound was prepared from Example 369.0 and imidazo[1,5-a]pyridine-1-carbaldehyde using the procedure described in Example 281.0. The mixture of diastereomers was separated by SFC (150×20 mm IA column with 25% MeOH (0.1% NH₄OH)/CO₂ at 60 mL/min. Three peaks were separated. The title compound was the third isomer to elute under these conditions. ¹H NMR (500 MHz, DMSO-d₆) δ 13.31 (br. s, 1H), 8.23 (d, J=7.1 Hz, 1H), 7.47-7.59 (m, 2H), 7.31 (s, 1H), 6.89 (d, J=8.3 Hz, 1H), 6.77-6.85 (m, 2H), 6.61-6.70 (m, 1H), 6.12 (d, J=2.7 Hz, 1H), 5.80 (d, J=2.9 Hz, 1H), 5.48-5.71 (m, 2H), 3.79-3.88 (m, 1H), 3.72 (s, 3H), 3.48-3.54 (m, 3H), 2.25 (s, 3H), 1.43 (d, J=6.8 Hz, 3H). LCMS-ESI (pos.) m/z: 539.2 (M+H)⁺.

521

Example 289.0. Preparation of (1R,2S)—N-(4-(2,6-dimethoxyphenyl)-5-(5-methyl-2-furanyl)-4H-1,2,4-triazol-3-yl)-1-hydroxy-1-imidazo[1,2-a]pyridin-2-yl-2-propanesulfonamide or (1S,2R)—N-(4-(2,6-dimethoxyphenyl)-5-(5-methyl-2-furanyl)-4H-1,2,4-triazol-3-yl)-1-hydroxy-1-imidazo[1,2-a]pyridin-2-yl-2-propanesulfonamide 289.0

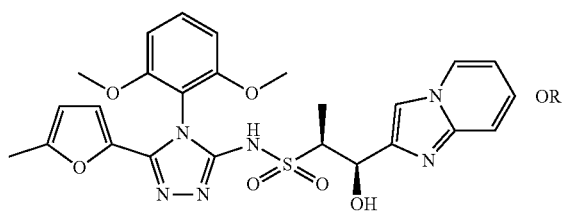

(1R,2S)—N-(4-(2,6-Dimethoxyphenyl)-5-(5-methyl-2-furanyl)-4H-1,2,4-triazol-3-yl)-1-hydroxy-1-imidazo[1,2-a]pyridin-2-yl-2-propanesulfonamide or (1S,2R)—N-(4-(2,6-dimethoxyphenyl)-5-(5-methyl-2-furanyl)-4H-1,2,4-triazol-3-yl)-1-hydroxy-1-imidazo[1,2-a]pyridin-2-yl-2-propanesulfonamide, Example 289.0. Example 269.0 was separated by SFC (150×20 mm IA column with 40% MeOH (0.1% NH$_4$OH)/CO$_2$ at 60 mL/min. Two enantiomers were separated. The title compound was the first isomer to elute under these conditions. $^1$H NMR (500 MHz, DMSO-d$_6$) δ 13.27 (br. s, 1H), 8.50 (dt, J=6.7, 1.2 Hz, 1H), 7.77 (s, 1H), 7.53 (t, J=8.1 Hz, 1H), 7.47 (dd, J=9.0, 0.7 Hz, 1H), 7.18 (ddd, J=9.0, 6.8, 1.2 Hz, 1H), 6.81-6.92 (m, 3H), 6.10 (br. s, 1H), 5.76 (br. s, 1H), 5.42 (s, 1H), 4.93 (br. s, 1H), 3.67 (s, 3H), 3.70 (s, 3H), 3.55 (br. s, 1H), 2.25 (s, 3H), 1.00 (d, J=6.8 Hz, 3H). LCMS-ESI (pos.) m/z: 539.2 (M+H)$^+$.

522

Example 290.0. Preparation of (1R,2R)-1-(6,7-dihydro-5H-pyrazolo[5,1-b][1,3]oxazin-2-yl)-N-(4-(2,6-dimethoxyphenyl)-5-(5-methyl-2-furanyl)-4H-1,2,4-triazol-3-yl)-1-hydroxy-2-propanesulfonamide and (1R,2S)-1-(6,7-dihydro-5H-pyrazolo[5,1-b][1,3]oxazin-2-yl)-N-(4-(2,6-dimethoxyphenyl)-5-(5-methyl-2-furanyl)-4H-1,2,4-triazol-3-yl-1-hydroxy-2-propanesulfonamide and (1S,2R)-1-(6,7-dihydro-5H-pyrazolo[5,1-b][1,3]oxazin-2-yl)-N-(4-(2,6-dimethoxyphenyl)-5-(5-methyl-2-furanyl)-4H-1,2,4-triazol-3-yl)-1-hydroxy-2-propanesulfonamide and (1S,2S)-1-(6,7-dihydro-5H-pyrazolo[5,1-b][1,3]oxazin-2-yl)-N-(4-(2,6-dimethoxyphenyl)-5-(5-methyl-2-furanyl)-4H-1,2,4-triazol-3-yl)-1-hydroxy-2-propanesulfonamide 290.0

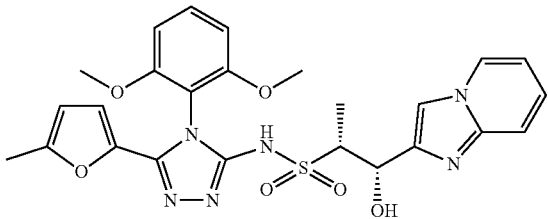

(1R,2R)-1-(6,7-Dihydro-5H-pyrazolo[5,1-b][1,3]oxazin-2-yl)-N-(4-(2,6-dimethoxyphenyl)-5-(5-methyl-2-furanyl)-4H-1,2,4-triazol-3-yl)-1-hydroxy-2-propanesulfonamide and (1R,2S)-1-(6,7-dihydro-5H-pyrazolo[5,1-b][1,3]oxazin-2-yl)-N-(4-(2,6-dimethoxyphenyl)-5-(5-methyl-2-furanyl)-4H-1,2,4-triazol-3-yl)-1-hydroxy-2-propanesulfonamide and (1S,2R)-1-(6,7-dihydro-5H-pyrazolo[5,1-b][1,3]oxazin-2-yl)-N-(4-(2,6-dimethoxyphenyl)-5-(5-methyl-2-furanyl)-4H-1,2,4-triazol-3-yl)-1-hydroxy-2-propanesulfonamide and (1S,2S)-1-(6,7-dihydro-5H-pyrazolo[5,1-b][1,3]oxazin-2-yl)-N-(4-(2,6-dimethoxyphenyl)-5-(5-methyl-2-furanyl)-4H-1,2,4-triazol-3-yl)-1-hydroxy-2-propanesulfonamide, Example 290.0. The title compound was prepared from Example 369.0 and 6,7-dihydro-5H-pyrazolo[5,1-b][1,3]oxazine-2-carbaldehyde using the procedure described in Example 281.0. LCMS-ESI (pos.) m/z: 545.2 (M+H)⁺.

Example 291.0. Preparation of (1R,2R)-1-(3,4-dihydro-2H-pyrano[3,2-b]pyridin-8-yl)-N-(4-(2,6-dimethoxyphenyl)-5-(5-methyl-2-furanyl)-4H-1,2,4-triazol-3-yl)-1-hydroxy-2-propanesulfonamide and (1S,2S)-1-(3,4-dihydro-2H-pyrano[3,2-b]pyridin-8-yl)-N-(4-(2,6-dimethoxyphenyl)-5-(5-methyl-2-furanyl)-4H-1,2,4-triazol-3-yl)-1-hydroxy-2-propanesulfonamide 291.0

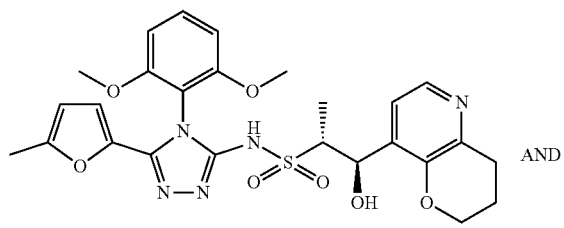

AND

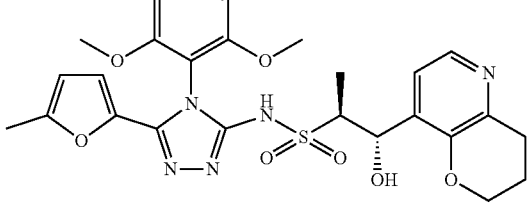

(1R,2R)-1-(3,4-Dihydro-2H-pyrano[3,2-b]pyridin-8-yl)-N-(4-(2,6-dimethoxyphenyl)-5-(5-methyl-2-furanyl)-4H-1,2,4-triazol-3-yl)-1-hydroxy-2-propanesulfonamide and (1S,2S)-1-(3,4-dihydro-2H-pyrano[3,2-b]pyridin-8-yl)-N-(4-(2,6-dimethoxyphenyl)-5-(5-methyl-2-furanyl)-4H-1,2,4-triazol-3-yl)-1-hydroxy-2-propanesulfonamide, Example 291.0. The title compound was prepared from Example 369.0 and 3,4-dihydro-2H-pyrano[3,2-b]pyridine-8-carbaldehyde using the procedure described in Example 281.0. $^1$H NMR (500 MHz, CD₃OD) δ 7.99 (d, J=5.1 Hz, 1H), 7.53-7.60 (m, 1H), 7.20 (d, J=5.1 Hz, 1H), 6.84-6.89 (m, 2H), 6.02 (dd, J=3.4, 1.0 Hz, 1H), 5.96 (d, J=3.4 Hz, 1H), 5.17 (d, J=7.6 Hz, 1H), 4.15-4.24 (m, 2H), 3.80 (s, 3H), 3.76-3.79 (m, 3H), 3.39 (quip, J=7.2 Hz, 1H), 2.92 (t, J=6.5 Hz, 2H), 2.25 (s, 3H), 2.06-2.12 (m, 2H), 1.11 (d, J=7.1 Hz, 3H). LCMS-ESI (pos.) m/z: 556.1 (M+H)⁺.

Example 292.0. Preparation of (1R,2S)-1-(6,7-dihydro-5H-pyrazolo[5,1-b][1,3]oxazin-2-yl)-N-(4-(2,6-dimethoxyphenyl)-5-(5-methyl-2-furanyl)-4H-1,2,4-triazol-3-yl)-1-hydroxy-2-propanesulfonamide or (1S,2R)-1-(6,7-dihydro-5H-pyrazolo[5,1-b][1,3]oxazin-2-yl)-N-(4-(2,6-dimethoxyphenyl)-5-(5-methyl-2-furanyl)-4H-1,2,4-triazol-3-yl)-1-hydroxy-2-propanesulfonamide 292.0

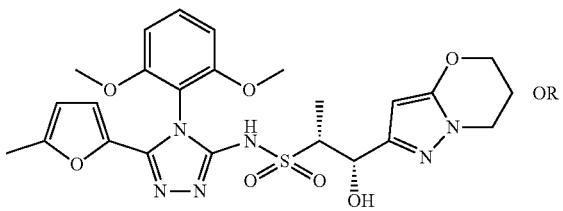

OR (1R,2S)-1-(6,7-Dihydro-5H-pyrazolo[5,1-b][1,3]oxazin-2-yl)-N-(4-(2,6-dimethoxyphenyl)-5-(5-methyl-2-furanyl)-4H-1,2,4-triazol-3-yl)-1-hydroxy-2-propanesulfonamide or (1S,2R)-1-(6,7-dihydro-5H-pyrazolo[5,1-b][1,3]oxazin-2-yl)-N-(4-(2,6-dimethoxyphenyl)-5-(5-methyl-2-furanyl)-4H-1,2,4-triazol-3-yl)-1-hydroxy-2-propanesulfonamide, Example 292.0. The title compound was prepared from Example 369.0 and 6,7-dihydro-5H-pyrazolo[5,1-b][1,3]oxazine-2-carbaldehyde using the procedure described in Example 281.0. The mixture of diastereomers was separated by SFC (150×20 mm IC column with 35% MeOH (0.1% NH₄OH)/CO₂ at 65 mL/min. Three peaks were separated. The title compound was the first isomer to elute under these conditions. $^1$H NMR (500 MHz, DMSO-d₆) δ 13.21 (br. s, 1H), 7.55 (t, J=8.6 Hz, 1H), 6.87 (d, J=8.6 Hz, 2H), 6.12 (d, J=2.7 Hz, 1H), 5.71-5.85 (m, 1H), 5.38 (s, 1H), 5.11 (s, 1H), 4.56 (d, J=4.9 Hz, 1H), 4.22 (dd, J=5.9, 4.9 Hz, 2H), 3.99 (t, J=6.1 Hz, 2H), 3.70 (s, 3H), 3.71 (s, 3H), 3.18-3.25 (m, 1H), 2.25 (s, 3H), 2.06-2.18 (m, 2H), 1.12 (d, J=7.1 Hz, 3H). LCMS-ESI (pos.) m/z: 545.2 (M+H)⁺.

Example 293.0. Preparation of (1R,2S)-1-(3,4-dihydro-2H-pyrano[3,2-b]pyridin-8-yl)-N-(4-(2,6-dimethoxyphenyl)-5-(5-methyl-2-furanyl)-4H-1,2,4-triazol-3-yl)-1-hydroxy-2-propanesulfonamide or (1S,2R)-1-(3,4-dihydro-2H-pyrano[3,2-b]pyridin-8-yl)-N-(4-(2,6-dimethoxyphenyl)-5-(5-methyl-2-furanyl)-4H-1,2,4-triazol-3-yl)-1-hydroxy-2-propanesulfonamide

Example 294.0. Preparation of (1R,2S)—N-(4-(2,6-dimethoxyphenyl)-5-(5-methyl-2-furanyl)-4H-1,2,4-triazol-3-yl)-1-hydroxy-1-imidazo[1,2-a]pyridin-3-yl-2-propanesulfonamide or (1S,2R)—N-(4-(2,6-dimethoxyphenyl)-5-(5-methyl-2-furanyl)-4H-1,2,4-triazol-3-yl)-1-hydroxy-1-imidazo[1,2-a]pyridin-3-yl-2-propanesulfonamide

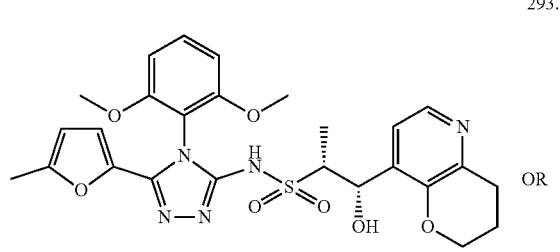

293.0

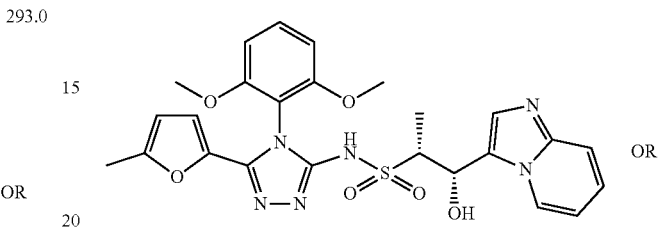

294.0

OR

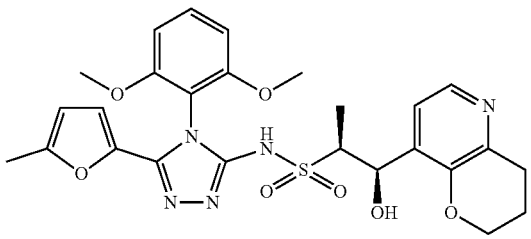

(1R,2S)-1-(3,4-Dihydro-2H-pyrano[3,2-b]pyridin-8-yl)-N-(4-(2,6-dimethoxyphenyl)-5-(5-methyl-2-furanyl)-4H-1,2,4-triazol-3-yl)-1-hydroxy-2-propanesulfonamide or (1S,2R)-1-(3,4-dihydro-2H-pyrano[3,2-b]pyridin-8-yl)-N-(4-(2,6-dimethoxyphenyl)-5-(5-methyl-2-furanyl)-4H-1,2,4-triazol-3-yl)-1-hydroxy-2-propanesulfonamide, Example 293.0. Example 302.0 was separated by SFC (250×30 mm IA column with 28 g/min MeOH (+20 mM NH$_3$)+72 g/min CO$_2$, 30% co-solvent at 100 g/min) on Thar 200 SFC. Two enantiomers were separated. The title compound (21 mg, 0.04 mmol, 42% yield) was the second isomer to elute under these conditions. $^1$H NMR (500 MHz, CD$_3$OD) δ 8.00 (d, J=4.9 Hz, 1H), 7.55 (t, J=8.6 Hz, 1H), 7.33 (d, J=4.9 Hz, 1H), 6.84 (t, J=8.2 Hz, 2H), 6.01 (d, J=2.7 Hz, 1H), 5.86-5.95 (m, 1H), 5.64 (s, 1H), 4.05-4.19 (m, 2H), 3.71-3.82 (m, 6H), 3.46-3.54 (m, 1H), 2.91 (t, J=6.6 Hz, 2H), 2.25 (s, 3H), 2.03-2.12 (m, 2H), 1.13 (d, J=7.1 Hz, 3H). LCMS-ESI (pos.) m/z: 556.1 (M+H)$^+$.

(1R,2S)—N-(4-(2,6-Dimethoxyphenyl)-5-(5-methyl-2-furanyl)-4H-1,2,4-triazol-3-yl)-1-hydroxy-1-imidazo[1,2-a]pyridin-3-yl-2-propanesulfonamide or (1S,2R)—N-(4-(2,6-dimethoxyphenyl)-5-(5-methyl-2-furanyl)-4H-1,2,4-triazol-3-yl)-1-hydroxy-1-imidazo[1,2-a]pyridin-3-yl-2-propanesulfonamide, Example 294.0. The title compound was prepared from Example 369.0 and imidazo[1,2-a]pyridine-3-carbaldehyde using the procedure described in Example 281.0. The mixture of diastereomers was separated by SFC (150×20 mm AD-H column with 40% EtOH (0.1% NR$_4$OH)/CO$_2$ at 60 mL/min). Three peaks were separated. The first peak to elute under these conditions was a mixture of diastereomers that was repurified by SFC (250×20 mm IC column with 40% EtOH (0.1% NH$_4$OH)/CO$_2$ 40 mL/min at 60 mL/min). Two diastereomers were obtained. The title compound (19 mg, 0.03 mmol, 9% yield) was the second isomer to elute under these conditions. $^1$H NMR (500 MHz, CD$_2$Cl$_2$) δ 8.15 (d, J=6.8 Hz, 1H), 7.52-7.58 (m, 2H), 7.46 (s, 1H), 7.14-7.22 (m, 1H), 6.81 (t, J=6.8 Hz, 1H), 6.70-6.77 (m, 2H), 5.95 (dd, J=3.4, 1.0 Hz, 1H), 5.90 (d, J=3.4 Hz, 1H), 5.79 (s, 1H), 3.77 (s, 3H), 3.72 (s, 3H), 3.37-3.44 (m, 1H), 2.30 (s, 3H), 1.45 (d, J=6.8 Hz, 3H). LCMS-ESI (pos.) m/z: 539.2 (M+H)$^+$.

Example 295.0. Preparation of (2S)-1-(5-fluoro-2-pyrimidinyl)-N-(4-(2-methoxyphenyl)-5-(5-methyl-2-furanyl)-4H-1,2,4-triazol-3-yl)-2-propanesulfonamide and (2R)-1-(5-fluoro-2-pyrimidinyl)-N-(4-(2-methoxyphenyl)-5-(5-methyl-2-furanyl)-4H-1,2,4-triazol-3-yl)-2-propanesulfonamide

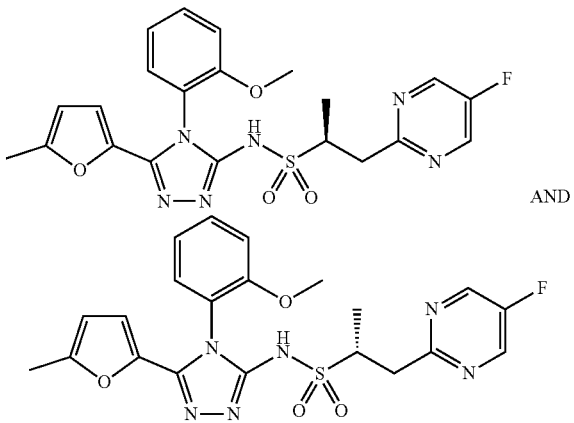

295.0

(2S)-1-(5-Fluoro-2-pyrimidinyl)-N-(4-(2-methoxyphenyl)-5-(5-methyl-2-furanyl)-4H-1,2,4-triazol-3-yl)-2-propanesulfonamide and (2R)-1-(5-fluoro-2-pyrimidinyl)-N-(4-(2-methoxyphenyl)-5-(5-methyl-2-furanyl)-4H-1,2,4-triazol-3-yl)-2-propanesulfonamide, Example 294.0. The title compound was prepared employing 5-methylfuran-2-carbohydrazide (commercially available from Chembridge Corporation, San Diego, Calif., USA), Example 353.0, and 2-methoxyphenyl isothiocyanate (commercially available from Sigma Aldrich) following the procedures described in the synthesis of Example 229.0. $^1$H NMR (500 MHz, DMSO-$d_6$) δ 13.25 (br. s, 1H), 8.79-8.84 (m, 2H), 7.51-7.62 (m, 1H), 7.40 (br. s, 1H), 7.24 (d, J=7.6 Hz, 1H), 7.12 (t, J=7.3 Hz, 1H), 6.07 (br. s, 1H), 5.67 (br. s, 1H), 3.67 (d, J=6.4 Hz, 4H), 3.44-3.52 (m, 1H), 2.82 (dd, J=14.4, 10.8 Hz, 1H), 2.23 (s, 3H), 1.07 (d, J=6.6 Hz, 3H). LCMS-ESI (pos.) m/z: 473.1 (M+H)$^+$.

Example 296.0. Preparation of (1R,2S)—N-(4-(2,6-dimethoxyphenyl)-5-(5-methyl-2-furanyl)-4H-1,2,4-triazol-3-yl)-1-hydroxy-1-pyrazolo[1,5-a]pyridin-7-yl-2-propanesulfonamide or (1S,2R)—N-(4-(2,6-dimethoxyphenyl)-5-(5-methyl-2-furanyl)-4H-1,2,4-triazol-3-yl)-1-hydroxy-1-pyrazolo[1,5-a]pyridin-7-yl-2-propanesulfonamide

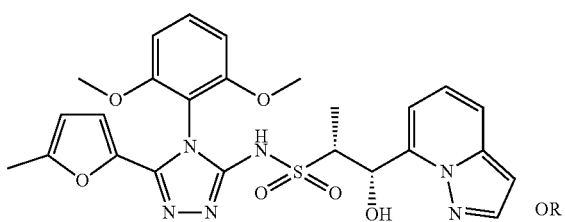

296.0

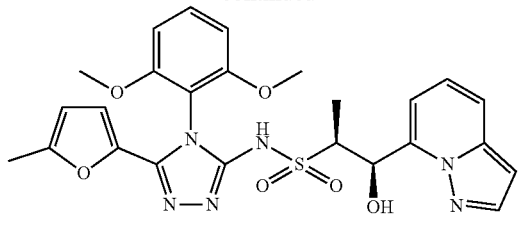

(1R,2S)—N-(4-(2,6-Dimethoxyphenyl)-5-(5-methyl-2-furanyl)-4H-1,2,4-triazol-3-yl)-1-hydroxy-1-pyrazolo[1,5-a]pyridin-7-yl-2-propanesulfonamide or (1S,2R)—N-(4-(2,6-dimethoxyphenyl)-5-(5-methyl-2-furanyl)-4H-1,2,4-triazol-3-yl)-1-hydroxy-1-pyrazolo[1,5-a]pyridin-7-yl-2-propanesulfonamide, Example 296.0. The title compound was prepared from Example 369.0 and pyrazolo[1,5-a]pyridine-7-carbaldehyde using the procedure described in Example 281.0. The mixture of diastereomers was separated by SFC (250×20 mm AS-H column with 20% MeOH/CO$_2$ at 65 mL/min). Two enantiomers were separated. The title compound (18 mg, 0.034 mmol, 39% yield) was the first isomer to elute under these conditions. $^1$H NMR (400 MHz, CD$_3$OD) δ 7.89 (d, J=2.3 Hz, 1H), 7.51-7.63 (m, 2H), 7.22 (dd, J=8.9, 6.9 Hz, 1H), 7.00 (d, J=6.8 Hz, 1H), 6.83 (dd, J=8.6, 3.7 Hz, 2H), 6.59 (d, J=2.3 Hz, 1H), 6.07 (s, 1H), 6.02 (dd, J=3.4, 0.9 Hz, 1H), 5.96 (d, J=3.5 Hz, 1H), 4.10 (qd, J=7.1, 1.9 Hz, 1H), 3.72 (s, 3H), 3.66 (s, 3H), 2.27 (s, 3H), 1.15 (d, J=7.0 Hz, 3H). LCMS-ESI (pos.) m/z: 539.2 (M+H)$^+$.

Example 297.0. Preparation of (1S,2R)—N-(4-(2,6-dimethoxyphenyl)-5-(5-methyl-2-furanyl)-4H-1,2,4-triazol-3-yl)-1-hydroxy-1-(1-methyl-1H-imidazol-2-yl)-2-propanesulfonamide or (1R,2S)—N-(4-(2,6-dimethoxyphenyl)-5-(5-methyl-2-furanyl)-4H-1,2,4-triazol-3-yl)-1-hydroxy-1-(1-methyl-1H-imidazol-2-yl)-2-propanesulfonamide 297.0

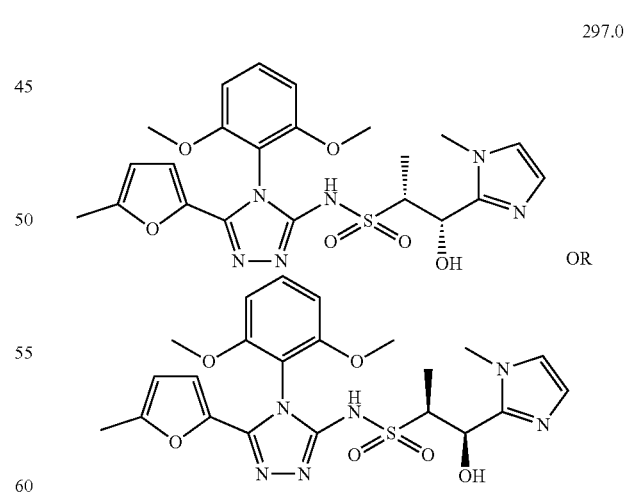

(1S,2R)—N-(4-(2,6-Dimethoxyphenyl)-5-(5-methyl-2-furanyl)-4H-1,2,4-triazol-3-yl)-1-hydroxy-1-(1-methyl-1H-imidazol-2-yl)-2-propanesulfonamide or (1R,2S)—N-(4-(2,6-dimethoxyphenyl)-5-(5-methyl-2-furanyl)-4H-1,2,4-triazol-3-yl)-1-hydroxy-1-(1-methyl-1H-imidazol-2-yl)-2-propanesulfonamide, Example 297.0. The title compound was prepared from Example 369.0 and 1-methyl-1H-imidazole-2-carbaldehyde using the procedure described in Example 281.0. The mixture of diastereomers was separated by SFC (250×21 mm AD-H column with 22 g/min MeOH (+20 mM NH₃)+38 g/min CO₂, 30% co-solvent at 60 g/min) on Thar 80 SFC. Three peaks were separated. The title compound was the third isomer to elute under these conditions. ¹H NMR (500 MHz, CD₃OD) δ 7.54 (t, J=8.6 Hz, 1H), 6.98-7.04 (m, 1H), 6.88-6.93 (m, 1H), 6.82 (d, J=8.6 Hz, 1H), 6.84 (d, J=8.1 Hz, 1H), 5.99-6.02 (m, 1H), 5.92 (d, J=3.4 Hz, 1H), 5.28 (d, J=4.2 Hz, 1H), 3.77 (s, 3H), 3.66-3.73 (m, 4H), 3.63 (s, 3H), 2.25 (s, 3H), 1.48 (d, J=6.8 Hz, 3H). LCMS-ESI (pos.) m/z: 503.0 (M+H)⁺.

Example 298.0. Preparation of (1R,2R)—N-(4-(2,6-dimethoxyphenyl)-5-(5-methyl-2-furanyl)-4H-1,2,4-triazol-3-yl)-1-hydroxy-1-(1,3-thiazol-4-yl)-2-propanesulfonamide or (1S,2S)—N-(4-(2,6-dimethoxyphenyl)-5-(5-methyl-2-furanyl)-4H-1,2,4-triazol-3-yl)-1-hydroxy-1-(1,3-thiazol-4-yl)-2-propanesulfonamide

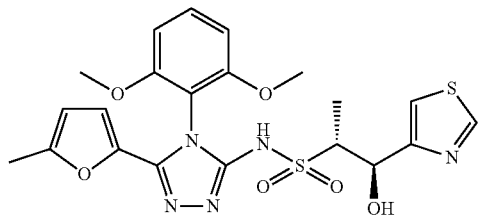

298.0

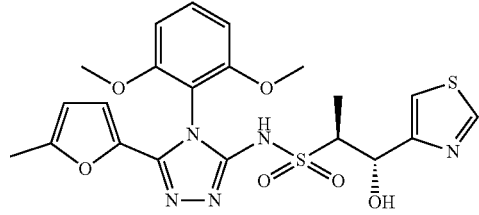

(1R,2R)—N-(4-(2,6-Dimethoxyphenyl)-5-(5-methyl-2-furanyl)-4H-1,2,4-triazol-3-yl)-1-hydroxy-1-(1,3-thiazol-4-yl)-2-propanesulfonamide or (1S,2S)—N-(4-(2,6-dimethoxyphenyl)-5-(5-methyl-2-furanyl)-4H-1,2,4-triazol-3-yl)-1-hydroxy-1-(1,3-thiazol-4-yl)-2-propanesulfonamide, Example 298.0. Example 305.0 was separated by SFC (250×30 mm IC column with 55 g/min MeOH+55 g/min CO₂, 50% co-solvent at 110 g/min on Thar 200 SFC. Two enantiomers were obtained. The title compound was the second isomer to elute under these conditions. ¹H NMR (500 MHz, CDCl₃) δ 8.77 (d, J=1.7 Hz, 1H), 7.43-7.50 (m, 1H), 7.29 (d, J=2.0 Hz, 1H), 6.68 (d, J=8.3 Hz, 2H), 5.93 (d, J=2.7 Hz, 1H), 5.85 (d, J=3.2 Hz, 1H), 5.10 (d, J=8.3 Hz, 1H), 3.76-3.83 (m, 6H), 3.59 (quip, J=7.3 Hz, 1H), 2.29-2.37 (m, 3H), 1.10 (d, J=7.1 Hz, 3H). LCMS-ESI (pos.) m/z: 506.1 (M+H)⁺.

Example 299.0. Preparation of (1R,2S)—N-(4-(2,6-dimethoxyphenyl)-5-(5-methyl-2-furanyl)-4H-1,2,4-triazol-3-yl)-1-hydroxy-1-imidazo[1,2-a]pyridin-5-yl-2-propanesulfonamide or (1S,2R)—N-(4-(2,6-dimethoxyphenyl)-5-(5-methyl-2-furanyl)-4H-1,2,4-triazol-3-yl)-1-hydroxy-1-imidazo[1,2-a]pyridin-5-yl-2-propanesulfonamide

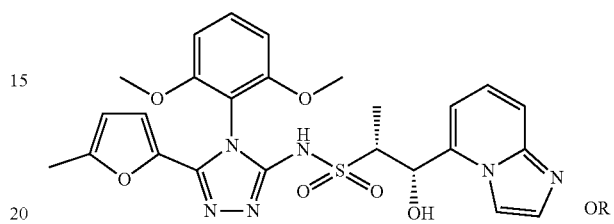

299.0

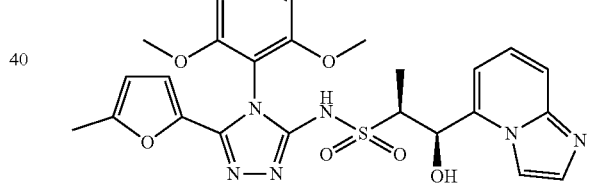

(1R,2S)—N-(4-(2,6-Dimethoxyphenyl)-5-(5-methyl-2-furanyl)-4H-1,2,4-triazol-3-yl)-1-hydroxy-1-imidazo[1,2-a]pyridin-5-yl-2-propanesulfonamide or (1S,2R)—N-(4-(2,6-dimethoxyphenyl)-5-(5-methyl-2-furanyl)-4H-1,2,4-triazol-3-yl)-1-hydroxy-1-imidazo[1,2-a]pyridin-5-yl-2-propanesulfonamide, Example 299.0. The title compound was prepared from Example 369.0 and pyrazolo[1,5-a]pyridine-7-carbaldehyde using the procedure described in Example 281.0. The mixture of diastereomers was separated by SFC (250×20 mm AS-H column with 15% EtOH (0.1% NH₄OH)/CO₂ at 60 mL/min). Two enantiomers were separated. The title compound (15 mg, 0.03 mmol, 33% yield) was the second isomer to elute under these conditions. ¹H NMR (400 MHz, CD₃OD) δ 7.50-7.64 (m, 4H), 7.39 (dd, J=9.0, 7.0 Hz, 1H), 7.09 (d, J=7.0 Hz, 1H), 6.89 (d, J=8.0 Hz, 1H), 6.83 (d, J=8.6 Hz, 1H), 6.02 (dd, J=3.4, 0.9 Hz, 1H), 5.95 (d, J=3.5 Hz, 1H), 5.68 (s, 1H), 3.78 (s, 3H), 3.68 (s, 3H), 3.26-3.36 (m, 1H), 2.26 (s, 3H), 1.27 (d, J=6.8 Hz, 3H). LCMS-ESI (pos.) m/z: 539.2 (M+H)⁺.

Example 300.0. Preparation of (1R,2R)—N-(4-(2,6-dimethoxyphenyl)-5-(5-methyl-2-furanyl)-4H-1,2,4-triazol-3-yl)-1-hydroxy-1-(2-methyl-1,3-oxazol-4-yl)-2-propanesulfonamide and (1S,2S)—N-(4-(2,6-dimethoxyphenyl)-5-(5-methyl-2-furanyl)-4H-1,2,4-triazol-3-yl)-1-hydroxy-1-(2-methyl-1,3-oxazol-4-yl)-2-propanesulfonamide

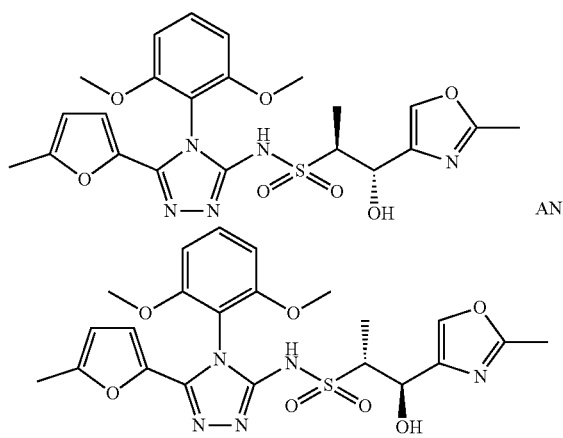

(1R,2R)—N-(4-(2,6-Dimethoxyphenyl)-5-(5-methyl-2-furanyl)-4H-1,2,4-triazol-3-yl)-1-hydroxy-1-(2-methyl-1,3-oxazol-4-yl)-2-propanesulfonamide and (1S,2S)—N-(4-(2,6-dimethoxyphenyl)-5-(5-methyl-2-furanyl)-4H-1,2,4-triazol-3-yl)-1-hydroxy-1-(2-methyl-1,3-oxazol-4-yl)-2-propanesulfonamide, Example 300.0. The title compound was prepared from Example 369.0 and 2-methyloxazole-4-carbaldehyde using the procedure described in Example 281.0. $^1$H NMR (400 MHz, DMSO-$d_6$) δ 13.31 (s, 1H), 7.74 (s, 1H), 7.57 (t, J=8.5 Hz, 1H), 6.89 (d, J=8.6 Hz, 2H), 6.13 (d, J=2.5 Hz, 1H), 5.82 (d, J=3.1 Hz, 1H), 4.96-5.08 (m, 1H), 4.68 (dd, J=7.2, 2.9 Hz, 1H), 3.73 (s, 3H), 3.74 (s, 3H), 3.19-3.29 (m, 1H), 2.36 (s, 3H), 2.25 (s, 3H), 1.02 (d, J=7.0 Hz, 3H). LCMS-ESI (pos.) m/z: 504.1 (M+H)$^+$.

Example 301.0. Preparation of (1R,2S)—N-(4-(2,6-dimethoxyphenyl)-5-(5-methyl-2-furanyl)-4H-1,2,4-triazol-3-yl)-1-hydroxy-1-(1-methyl-1H-imidazol-4-yl)-2-propanesulfonamide and (1S,2R)—N-(4-(2,6-dimethoxyphenyl)-5-(5-methyl-2-furanyl)-4H-1,2,4-triazol-3-yl)-1-hydroxy-1-(1-methyl-1H-imidazol-4-yl)-2-propanesulfonamide

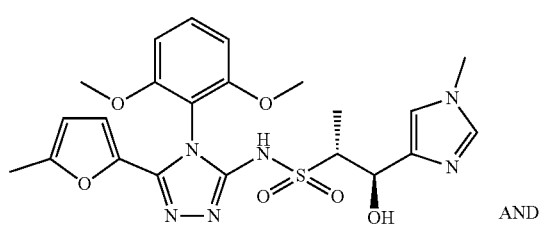

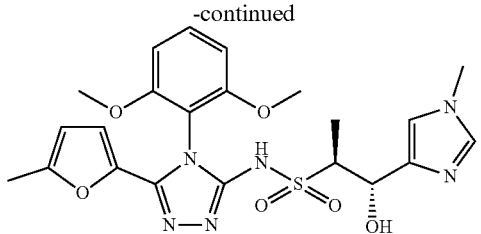

(1R,2S)—N-(4-(2,6-Dimethoxyphenyl)-5-(5-methyl-2-furanyl)-4H-1,2,4-triazol-3-yl)-1-hydroxy-1-(1-methyl-1H-imidazol-4-yl)-2-propanesulfonamide and (1S,2R)—N-(4-(2,6-dimethoxyphenyl)-5-(5-methyl-2-furanyl)-4H-1,2,4-triazol-3-yl)-1-hydroxy-1-(1-methyl-1H-imidazol-4-yl)-2-propanesulfonamide, Example 301.0. The title compound was prepared from Example 369.0 and 1-methyl-1H-imidazole-4-carbaldehyde using the procedure described in Example 281.0. $^1$H NMR (500 MHz, DMSO-$d_6$) δ 7.50-7.60 (m, 2H), 6.99 (d, J=1.2 Hz, 1H), 6.86-6.92 (m, 2H), 6.13 (dd, J=3.4, 1.0 Hz, 1H), 5.83 (d, J=3.4 Hz, 1H), 4.83 (br. s, 1H), 4.63 (d, J=7.6 Hz, 1H), 3.73 (s, 3H), 3.74 (s, 3H), 3.61 (s, 3H), 3.23 (quip, J=7.1 Hz, 1H), 2.25 (s, 3H), 0.95 (d, J=7.1 Hz, 3H). LCMS-ESI (pos.) m/z: 503.1 (M+H)$^+$.

Example 302.0. Preparation of (1R,2S)-1-(3,4-dihydro-2H-pyrano[3,2-b]pyridin-8-yl)-N-(4-(2,6-dimethoxyphenyl)-5-(5-methyl-2-furanyl)-4H-1,2,4-triazol-3-yl)-1-hydroxy-2-propanesulfonamide and (1S,2R)-1-(3,4-dihydro-2H-pyrano[3,2-b]pyridin-8-yl)-N-(4-(2,6-dimethoxyphenyl)-5-(5-methyl-2-furanyl)-4H-1,2,4-triazol-3-yl)-1-hydroxy-2-propanesulfonamide

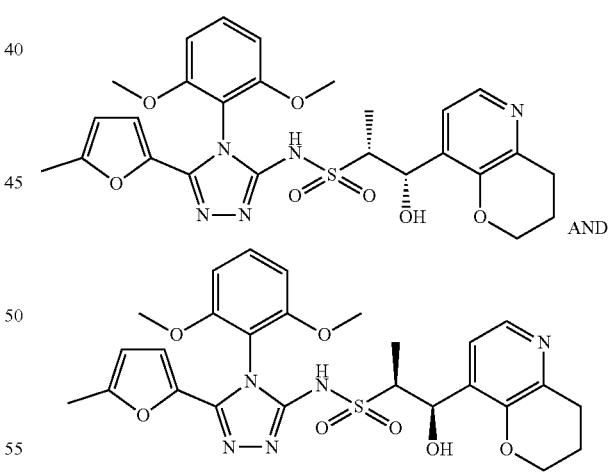

(1R,2S)-1-(3,4-Dihydro-2H-pyrano[3,2-b]pyridin-8-yl)-N-(4-(2,6-dimethoxyphenyl)-5-(5-methyl-2-furanyl)-4H-1,2,4-triazol-3-yl)-1-hydroxy-2-propanesulfonamide and (1S,2R)-1-(3,4-dihydro-2H-pyrano[3,2-b]pyridin-8-yl)-N-(4-(2,6-dimethoxyphenyl)-5-(5-methyl-2-furanyl)-4H-1,2,4-triazol-3-yl)-1-hydroxy-2-propanesulfonamide, Example 302.0. The title compound was prepared from Example 369.0 and 3,4-dihydro-2H-pyrano[3,2-b]pyridine-8-carbaldehyde using the procedure described in Example 281.0. $^1$H NMR (500 MHz, DMSO-$d_6$) δ 13.24 (br. s, 1H), 8.02 (d, J=4.9 Hz, 1H), 7.56 (t, J=8.1 Hz, 1H), 7.17 (d, J=4.6 Hz, 1H), 6.89 (t, J=7.3 Hz, 2H), 6.13 (br. s, 1H), 5.81 (br. s, 1H), 5.45 (s, 1H), 4.87 (br. s, 1H), 3.95-4.06 (m, 2H), 3.72 (s, 3H), 3.67 (s, 3H), 3.19-3.26 (m, 1H), 2.82 (t, J=6.5 Hz, 2H), 2.25 (s, 3H), 1.97 (quin, J=5.9 Hz, 2H), 0.98 (d, J=6.8 Hz, 3H). LCMS-ESI (pos.) m/z: 556.1 (M+H)$^+$.

Example 303.0. Preparation of (1R,2S)—N-(4-(2,6-dimethoxyphenyl)-5-(5-methyl-2-furanyl)-4H-1,2,4-triazol-3-yl)-1-hydroxy-1-(2-methyl-1,3-oxazol-4-yl)-2-propanesulfonamide or (1S,2R)—N-(4-(2,6-dimethoxyphenyl)-5-(5-methyl-2-furanyl)-4H-1,2,4-triazol-3-yl)-1-hydroxy-1-(2-methyl-1,3-oxazol-4-yl)-2-propanesulfonamide 303.0

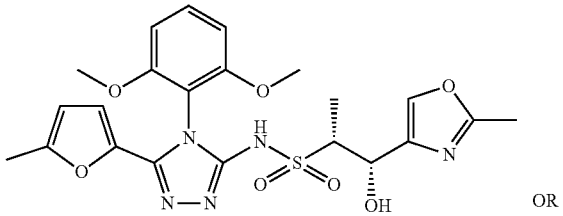

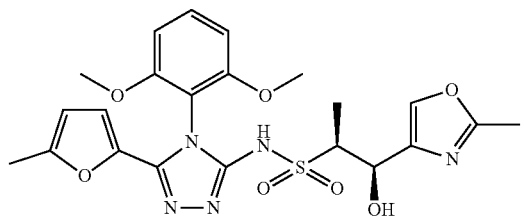

(1R,2S)—N-(4-(2,6-Dimethoxyphenyl)-5-(5-methyl-2-furanyl)-4H-1,2,4-triazol-3-yl)-1-hydroxy-1-(2-methyl-1,3-oxazol-4-yl)-2-propanesulfonamide or (1S,2R)—N-(4-(2,6-dimethoxyphenyl)-5-(5-methyl-2-furanyl)-4H-1,2,4-triazol-3-yl)-1-hydroxy-1-(2-methyl-1,3-oxazol-4-yl)-2-propanesulfonamide, Example 303.0. Example 284.0 was separated by SFC (150×20 mm IA column with 14% MeOH/CO$_2$ at 60 mL/min. Two enantiomers were separated. The title compound was the first isomer to elute under these conditions. $^1$H NMR (400 MHz, DMSO-d$_6$) δ 13.24 (br. s, 1H), 7.68 (d, J=1.4 Hz, 1H), 7.55 (t, J=8.5 Hz, 1H), 6.88 (d, J=8.6 Hz, 2H), 6.13 (dd, J=3.4, 0.9 Hz, 1H), 5.81 (d, J=3.3 Hz, 1H), 5.14 (s, 1H), 4.87 (br. s, 1H), 3.70 (s, 3H), 3.71 (s, 3H), 3.15-3.28 (m, 1H), 2.35 (s, 3H), 2.25 (s, 3H), 1.05 (d, J=7.0 Hz, 3H). LCMS-ESI (pos.) m/z: 504.0 (M+H)$^+$.

Example 304.0. Preparation of (1S,2S)—N-(4-(2,6-dimethoxyphenyl)-5-(5-methyl-2-furanyl)-4H-1,2,4-triazol-3-yl)-1-hydroxy-1-pyrazolo[1,5-a]pyridin-2-yl-2-propanesulfonamide or (1R,2R)—N-(4-(2,6-dimethoxyphenyl)-5-(5-methyl-2-furanyl)-4H-1,2,4-triazol-3-yl)-1-hydroxy-1-pyrazolo[1,5-a]pyridin-2-yl-2-propanesulfonamide 304.0

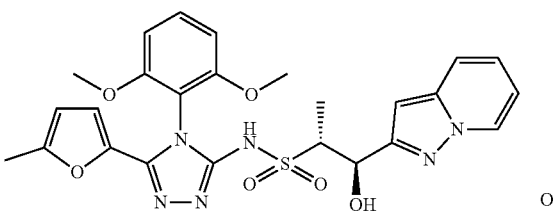

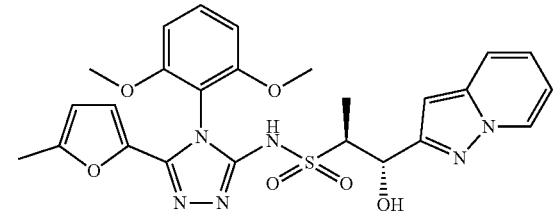

(1S,2S)—N-(4-(2,6-Dimethoxyphenyl)-5-(5-methyl-2-furanyl)-4H-1,2,4-triazol-3-yl)-1-hydroxy-1-pyrazolo[1,5-a]pyridin-2-yl-2-propanesulfonamide or (1R,2R)—N-(4-(2,6-dimethoxyphenyl)-5-(5-methyl-2-furanyl)-4H-1,2,4-triazol-3-yl)-1-hydroxy-1-pyrazolo[1,5-a]pyridin-2-yl-2-propanesulfonamide, Example 304.0. The title compound was prepared from Example 369.0 and pyrazolo[1,5-a]pyridine-2-carbaldehyde using the procedure described in Example 281.0. The mixture was separated by SFC (250×30 mm AS column with 25 g/min MeOH (+20 mM NH$_3$)+75 g/min CO$_2$, 25% co-solvent at 100 g/min) on Thar 350 SFC. Two enantiomers were separated. The title compound (7 mg, 0.01 mmol, 24% yield) was the second isomer to elute under these conditions. $^1$H NMR (500 MHz, CD$_3$OD) δ 8.45 (d, J=6.8 Hz, 1H), 7.52-7.61 (m, 2H), 7.19 (dd, J=8.4, 7.0 Hz, 1H), 6.79-6.88 (m, 3H), 6.55 (s, 1H), 6.02 (d, J=2.7 Hz, 1H), 5.96 (d, J=3.2 Hz, 1H), 5.07 (d, J=8.6 Hz, 1H), 3.80 (s, 3H), 3.81 (s, 3H), 3.43-3.52 (m, 1H), 2.26 (s, 3H), 1.06 (d, J=6.8 Hz, 3H). LCMS-ESI (pos.) m/z: 539.2 (M+H)$^+$.

Example 305.0. Preparation of (1R,2R)—N-(4-(2,6-dimethoxyphenyl)-5-(5-methyl-2-furanyl)-4H-1,2,4-triazol-3-yl)-1-hydroxy-1-(1,3-thiazol-4-yl)-2-propanesulfonamide, (1S,2S)—N-(4-(2,6-dimethoxyphenyl)-5-(5-methyl-2-furanyl)-4H-1,2,4-triazol-3-yl)-1-hydroxy-1-(1,3-thiazol-4-yl)-2-propanesulfonamide 305.0

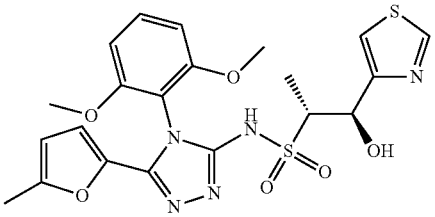

and

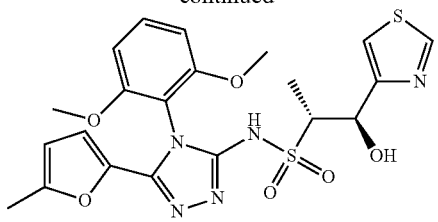

(1R,2R)—N-(4-(2,6-Dimethoxyphenyl)-5-(5-methyl-2-furanyl)-4H-1,2,4-triazol-3-yl)-1-hydroxy-1-(1,3-thiazol-4-yl)-2-propanesulfonamide and (1S,2S)—N-(4-(2,6-dimethoxyphenyl)-5-(5-methyl-2-furanyl)-4H-1,2,4-triazol-3-yl)-1-hydroxy-1-(1,3-thiazol-4-yl)-2-propanesulfonamide, Example 305.0. Example 281.2 (37 mg, 0.06 mmol) in a vial was azeotroped with toluene and then dried under high vacuum. After 2 h, TASF (89 mg, 0.32 mmol) was added followed by dropwise addition of anhydrous DMF (0.6 mL). The mixture was carefully heated to 60° C. and monitored with LC-LCMS. After 0.5 h, the mixture was cooled to RT and then water was carefully added to the mixture. The heterogeneous mixture was extracted twice with a 1:1 EtOAc:toluene solution. The organics were pooled and then dried over anhydrous sodium sulfate. After filtration and concentration, the light yellow film was purified on silica gel eluting with (0-60% 3:1 EtOAc:EtOH in heptanes) to afford the title compound (23 mg, 0.046 mmol, 76% yield) as a white solid. $^1$H NMR (500 MHz, DMSO-$d_6$) δ 13.34 (br. s, 1H), 9.03 (d, J=2.0 Hz, 1H), 7.57 (t, J=8.6 Hz, 1H), 7.53 (d, J=2.0 Hz, 1H), 6.89 (d, J=8.6 Hz, 2H), 6.13 (d, J=2.7 Hz, 1H), 5.82 (d, J=2.9 Hz, 1H), 5.15 (br. s, 1H), 4.94 (d, J=7.8 Hz, 1H), 3.73 (s, 3H), 3.74 (s, 3H), 3.32-3.41 (m, 1H), 2.25 (s, 3H), 0.92 (d, J=7.1 Hz, 3H). LCMS-ESI (pos.) m/z: 506.0 (M+H)$^+$.

Example 306.0. Preparation of (1R,2R)—N-(4-(2,6-dimethoxyphenyl)-5-(5-methyl-2-furanyl)-4H-1,2,4-triazol-3-yl)-1-hydroxy-1-imidazo[1,2-a]pyridin-5-yl-2-propanesulfonamide and (1S,2S)—N-(4-(2,6-dimethoxyphenyl)-5-(5-methyl-2-furanyl)-4H-1,2,4-triazol-3-yl)-1-hydroxy-1-imidazo[1,2-a]pyridin-5-yl-2-propanesulfonamide 306.0

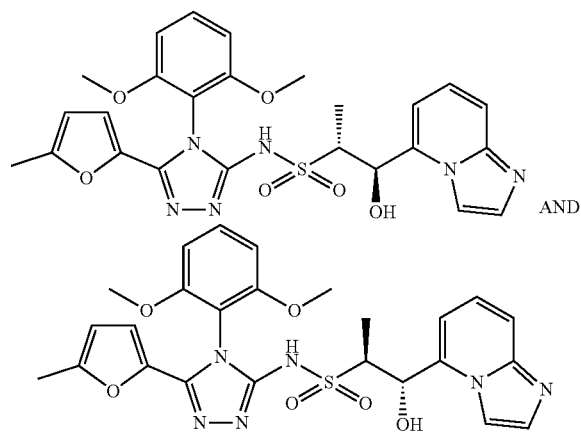

(1R,2R)—N-(4-(2,6-Dimethoxyphenyl)-5-(5-methyl-2-furanyl)-4H-1,2,4-triazol-3-yl)-1-hydroxy-1-imidazo[1,2-a]pyridin-5-yl-2-propanesulfonamide and (1S,2S)—N-(4-(2,6-dimethoxyphenyl)-5-(5-methyl-2-furanyl)-4H-1,2,4-triazol-3-yl)-1-hydroxy-1-imidazo[1,2-a]pyridin-5-yl-2-propanesulfonamide, Example 306.0. The title compound was prepared from Example 369.0 and imidazo[1,2-a]pyridine-5-carbaldehyde using the procedure described in Example 281.0. $^1$H NMR (500 MHz, DMSO-$d_6$) δ 13.40 (br. s, 1H), 7.97 (s, 1H), 7.50-7.62 (m, 3H), 7.21 (dd, J=9.0, 6.8 Hz, 1H), 6.92 (dd, J=8.6, 2.4 Hz, 2H), 6.77 (d, J=6.6 Hz, 1H), 6.13 (d, J=2.7 Hz, 1H), 5.82 (d, J=3.2 Hz, 2H), 5.14 (d, J=7.3 Hz, 1H), 3.73 (s, 3H), 3.69 (m, 4H), 2.25 (s, 3H), 0.88 (d, J=7.1 Hz, 3H). LCMS-ESI (pos.) m/z: 539.2 (M+H)$^+$.

Example 307.0. Preparation of (1S,2R)—N-(4-(2,6-dimethoxyphenyl)-5-(5-methyl-2-furanyl)-4H-1,2,4-triazol-3-yl)-1-hydroxy-1-(1,3-thiazol-4-yl)-2-propanesulfonamide or (1R,2S)—N-(4-(2,6-dimethoxyphenyl)-5-(5-methyl-2-furanyl)-4H-1,2,4-triazol-3-yl)-1-hydroxy-1-(1,3-thiazol-4-yl)-2-propanesulfonamide 307.0

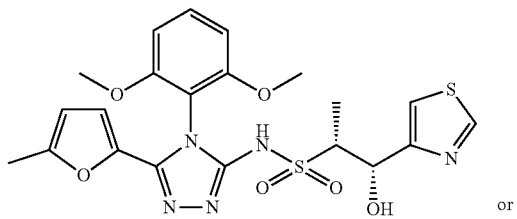

(1S,2R)—N-(4-(2,6-Dimethoxyphenyl)-5-(5-methyl-2-furanyl)-4H-1,2,4-triazol-3-yl)-1-hydroxy-1-(1,3-thiazol-4-yl)-2-propanesulfonamide or (1R,2S)—N-(4-(2,6-dimethoxyphenyl)-5-(5-methyl-2-furanyl)-4H-1,2,4-triazol-3-yl)-1-hydroxy-1-(1,3-thiazol-4-yl)-2-propanesulfonamide, Example 307.0. Example 281.0 was separated by SFC (250×30 mm IA-H column with 32 g/min MeOH+68 g/min CO$_2$, 32% co-solvent at 100 g/min on Thar 200 SFC. Two enantiomers were obtained. The title compound, Example 307.0, was the second isomer to elute under these conditions. $^1$H NMR (500 MHz, DMSO-$d_6$) δ 13.28 (br. s, 1H), 9.05 (d, J=2.0 Hz, 1H), 7.55 (t, J=8.4 Hz, 1H), 7.41-7.48 (m, 1H), 6.88 (d, J=8.6 Hz, 2H), 6.07-6.18 (m, 1H), 5.80 (br. s, 1H), 5.42 (s, 1H), 3.67 (s, 3H), 3.70 (s, 3H), 3.45 (m, 1H), 2.26 (s, 3H), 0.99 (d, J=7.1 Hz, 3H). LCMS-ESI (pos.) m/z: 506.1 (M+H)$^+$.

Example 308.0. Preparation of (1S,2S)—N-(4-(2,6-dimethoxyphenyl)-5-(5-methyl-2-furanyl)-4H-1,2,4-triazol-3-yl)-1-hydroxy-1-imidazo[1,2-a]pyridin-2-yl-2-propanesulfonamide or (1R,2R)—N-(4-(2,6-dimethoxyphenyl)-5-(5-methyl-2-furanyl)-4H-1,2,4-triazol-3-yl)-1-hydroxy-1-imidazo[1,2-a]pyridin-2-yl-2-propanesulfonamide 308.0

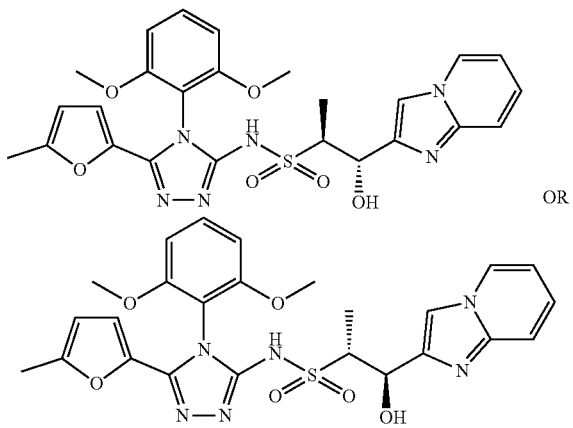

OR (1S,2S)—N-(4-(2,6-Dimethoxyphenyl)-5-(5-methyl-2-furanyl)-4H-1,2,4-triazol-3-yl)-1-hydroxy-1-imidazo[1,2-a]pyridin-2-yl-2-propanesulfonamide or (1R,2R)—N-(4-(2,6-dimethoxyphenyl)-5-(5-methyl-2-furanyl)-4H-1,2,4-triazol-3-yl)-1-hydroxy-1-imidazo[1,2-a]pyridin-2-yl-2-propanesulfonamide, Example 308.0. Example 285.0 was separated by SFC (250×21 mm AD-H column with 25 g/min MeOH (NH$_3$)+35 g/min CO$_2$, 42% co-solvent at 60 g/min on Thar 80 SFC). Two enantiomers were obtained. The title compound was the first isomer to elute under these conditions. $^1$H NMR (500 MHz, DMSO-d$_6$) δ 8.49 (d, J=6.6 Hz, 1H), 7.82 (s, 1H), 7.45-7.57 (m, 2H), 7.16-7.24 (m, 1H), 6.80-6.92 (m, 3H), 6.08 (br. s, 1H), 5.72 (br. s, 1H), 4.85 (d, J=7.8 Hz, 1H), 3.71 (s, 3H), 3.72 (s, 3H), 3.51 (m, 1H), 3.42, (m, 1H), 2.24 (s, 3H), 0.96 (d, J=6.1 Hz, 3H). LCMS-ESI (pos.) m/z: 539.2 (M+H)$^+$.

Example 309.0. Preparation of (1S,2S)—N-(4-(2,6-dimethoxyphenyl)-5-(5-methyl-2-furanyl)-4H-1,2,4-triazol-3-yl)-1-hydroxy-1-(1,3-thiazol-4-yl)-2-propanesulfonamide or (1R,2R)—N-(4-(2,6-dimethoxyphenyl)-5-(5-methyl-2-furanyl)-4H-1,2,4-triazol-3-yl)-1-hydroxy-1-(1,3-thiazol-4-yl)-2-propanesulfonamide 309.0

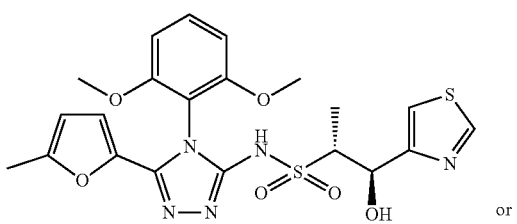

or

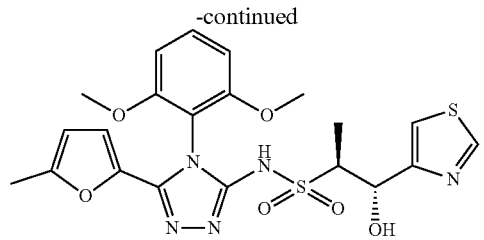

(1S,2S)—N-(4-(2,6-Dimethoxyphenyl)-5-(5-methyl-2-furanyl)-4H-1,2,4-triazol-3-yl)-1-hydroxy-1-(1,3-thiazol-4-yl)-2-propanesulfonamide or (1R,2R)—N-(4-(2,6-dimethoxyphenyl)-5-(5-methyl-2-furanyl)-4H-1,2,4-triazol-3-yl)-1-hydroxy-1-(1,3-thiazol-4-yl)-2-propanesulfonamide, Example 309.0. Example 305.0 was separated by SFC (250×30 mm IC column with 55 g/min MeOH+55 g/min CO$_2$, 50% co-solvent at 110 g/min on Thar 200 SFC). Two enantiomers were obtained. The title compound was the first isomer to elute under these conditions. $^1$H NMR (500 MHz, CDCl$_3$) δ 8.77 (d, J=2.0 Hz, 1H), 7.47 (t, J=8.6 Hz, 1H), 7.29 (d, J=1.7 Hz, 1H), 6.68 (d, J=8.1 Hz, 2H), 5.93 (d, J=2.7 Hz, 1H), 5.86 (d, J=3.4 Hz, 1H), 5.10 (d, J=8.3 Hz, 1H), 4.87 (br. s, 1H), 3.77-3.81 (m, 6H), 3.54-3.63 (m, 1H), 2.33 (s, 3H), 1.11 (d, J=7.1 Hz, 3H). LCMS-ESI (pos.) m/z: 506.1 (M+H)$^+$.

Example 310.0. Preparation of (2S)-1-(5-fluoro-2-pyrimidinyl)-N-(5-(2-furanyl)-4-(2-methoxyphenyl)-4H-1,2,4-triazol-3-yl)-2-propanesulfonamide and (2R)-1-(5-fluoro-2-pyrimidinyl)-N-(5-(2-furanyl)-4-(2-methoxyphenyl)-4H-1,2,4-triazol-3-yl)-2-propanesulfonamide 310.0

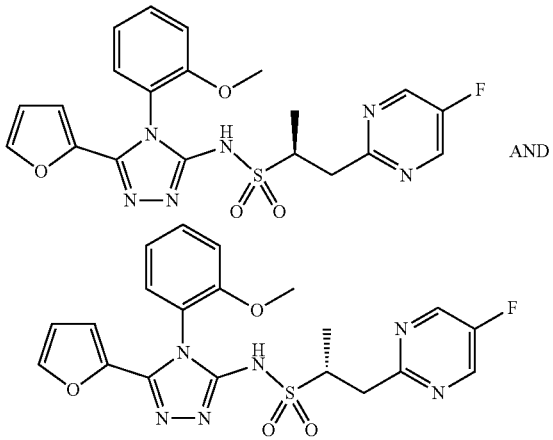

(2S)-1-(5-Fluoro-2-pyrimidinyl)-N-(5-(2-furanyl)-4-(2-methoxyphenyl)-4H-1,2,4-triazol-3-yl)-2-propanesulfonamide and (2R)-1-(5-fluoro-2-pyrimidinyl)-N-(5-(2-furanyl)-4-(2-methoxyphenyl)-4H-1,2,4-triazol-3-yl)-2-propanesulfonamide, Example 310.0. The title compound was prepared employing furan-2-carbohydrazide (commercially available from Alfa Aesar), Example 353.0, and 2-methoxyphenyl isothiocyanate (commercially available from Sigma Aldrich). The cyclisation step was conducted as follows. TFA (0.12 mL, 1.61 mmol) was added dropwise to the reaction mixture carried over from the previous step. The mixture was then heated to 110° C. and monitored with TLC and LCMS. After 21 h, additional aliquots of DMF (2 mL) and TFA (0.01 mL) were added and the mixture was maintained at 110° C. After 41 h, the mixture was cooled to RT, adjusted to pH 8-9 with saturated aqueous NaHCO$_3$ and extracted with DCM. The combined organic layers were then washed with brine, dried over MgSO$_4$, filtered, and concentrated in vacuo. The residue was purified in two stages. First on a silica gel column, employing a gradient of 0-25% EtOAc:EtOH (3:1) in heptanes, and second on a reverse-phase column employing a gradient of 10-75% ACN in water (0.1% TFA in both eluents). This afforded Example 310.0 (20 mg, 0.043 mmol, 7%). $^1$H NMR (500 MHz, DMSO-d$_6$) δ 13.31 (br. s, 1H), 8.79-8.86 (m, 2H), 7.77 (br. s, 1H), 7.56 (br. s, 1H), 7.43 (br. s, 1H), 7.24 (d, J=7.6 Hz, 1H), 7.12 (t, J=7.3 Hz, 1H), 6.48 (br. s, 1H), 5.91 (br. s, 1H), 3.66 (m, 4H), 3.45-3.51 (m, 1H), 2.79-2.86 (m, 1H), 1.08 (d, J=6.4 Hz, 3H). LCMS-ESI (pos.) m/z: 459.0 (M+H)$^+$.

Example 311.0. Preparation of (1S)—N-(4-(2,6-dimethoxyphenyl)-5-(5-methyl-2-furanyl)-4H-1,2,4-triazol-3-yl)-1-(3-hydroxy-3-oxetanyl)ethanesulfonamide and (1R)—N-(4-(2,6-dimethoxyphenyl)-5-(5-methyl-2-furanyl)-4H-1,2,4-triazol-3-yl)-1-(3-hydroxy-3-oxetanyl)ethanesulfonamide 311.1

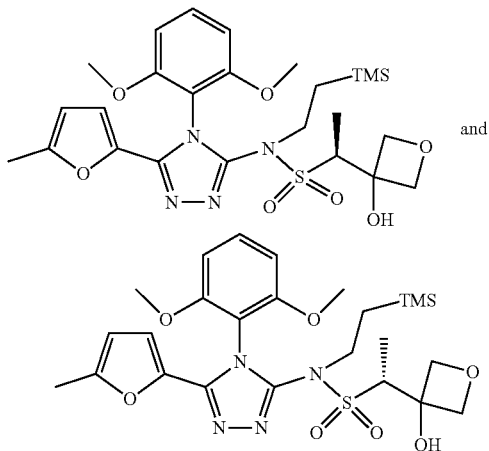

N-(4-(2,6-Dimethoxyphenyl)-5-(5-methylfuran-2-yl)-4H-1,2,4-triazol-3-yl)-1-(3-hydroxyoxetan-3-yl)-N-(2-(trimethylsilyl)ethyl)ethanesulfonamide, Example 311.1. Example 369.0 (327 mg, 0.66 mmol) in a flask was azeotroped with toluene before anhydrous THF (2 mL) was added by syringe. The resulting solution was sparged with argon for 15 min and the flask was subsequently cooled in an acetone-dry ice bath. After 20 min, n-butyllithium (2.5 M in hexanes, 0.3 mL, 0.75 mmol) was carefully added, dropwise to the stirred solution. After complete addition, the resulting mixture was stirred for 5 min before, 3-oxetanone (56 mg, 0.78 mmol) in anhydrous THF (2 mL) was added dropwise over 5 min. After complete addition, the reaction was maintained at −78° C. until LCMS analysis indicated that the reaction was complete (3 h). Thereafter, the mixture was transferred to an ice-water bath and carefully quenched with saturated aqueous NH$_4$Cl solution. After extracting with CHCl$_3$ (3×), the organic phases were combined, dried over MgSO$_4$, filtered, and concentrated in vacuo. The residue was purified on a silica gel column employing a gradient of 0-20% EtOAc in DCM to afford the title compound (296 mg, 0.52 mmol, 79%). LCMS-ESI (pos.) m/z: 565.2 (M+H)$^+$.

311.2

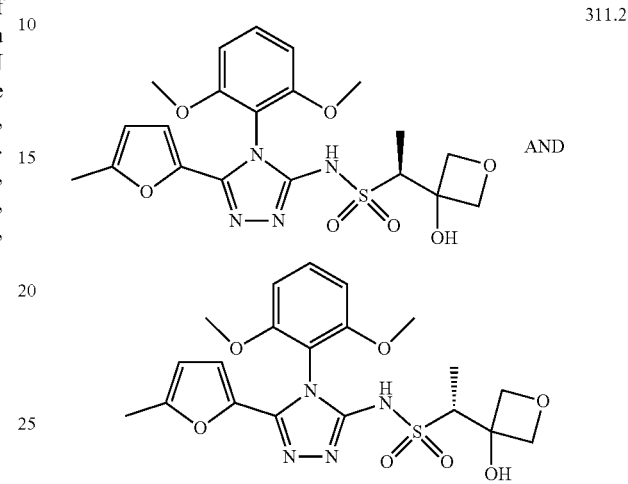

(1S)—N-(4-(2,6-Dimethoxyphenyl)-5-(5-methyl-2-furanyl)-4H-1,2,4-triazol-3-yl)-1-(3-hydroxy-3-oxetanyl)ethanesulfonamide and (1R)—N-(4-(2,6-dimethoxyphenyl)-5-(5-methyl-2-furanyl)-4H-1,2,4-triazol-3-yl)-1-(3-hydroxy-3-oxetanyl)ethanesulfonamide, Example 311.2. Example 311.1 (296 mg, 0.52 mmol) in a vial was azeotroped with toluene and then dried under high vacuum. After 2 h, tris(dimethylamino)sulfonium difluorotrimethylsilicate (444 mg, 1.61 mmol) was added followed by dropwise addition of anhydrous DMF (2.5 mL). The resulting mixture was then heated at 60° C. until LCMS analysis indicated that the reaction was complete (1 h). Thereafter, the mixture was cooled to RT and diluted with water. The cloudy mixture was extracted with 1:1 EtOAc/toluene (3×) and the combined organic layers were dried over Na$_2$SO$_4$, filtered, and concentrated in vacuo. The residue was purified on a silica gel column employing a gradient of 0-8% MeOH in DCM. This afforded Example 311.2 (150 mg, 0.32 mmol, 62%). $^1$H NMR (400 MHz, DMSO-d$_6$) δ 13.27 (s, 1H), 7.53-7.63 (m, 1H), 6.89 (dd, J=8.6, 1.6 Hz, 2H), 6.13 (dd, J=3.5, 1.0 Hz, 1H), 5.83 (d, J=3.3 Hz, 1H), 5.22 (s, 1H), 4.81 (d, J=7.0 Hz, 1H), 4.50 (d, J=6.7 Hz, 1H), 4.24 (dd, J=17.2, 6.8 Hz, 2H), 3.73 (m, 6H), 3.48 (q, J=6.8 Hz, 1H), 2.25 (s, 3H), 1.15 (d, J=7.0 Hz, 3H). LCMS-ESI (pos.) m/z: 465.0 (M+H)$^+$.

311.0

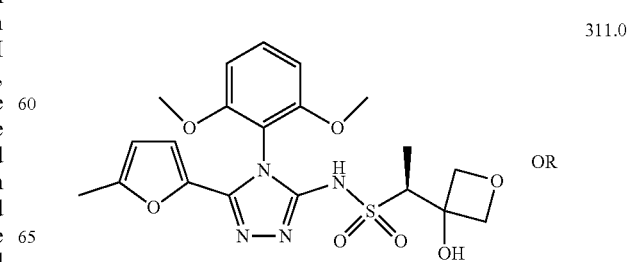

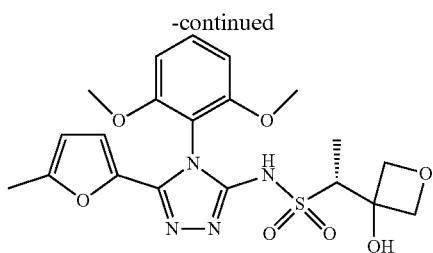

(1S)—N-(4-(2,6-Dimethoxyphenyl)-5-(5-methyl-2-furanyl)-4H-1,2,4-triazol-3-yl)-1-(3-hydroxy-3-oxetanyl)ethanesulfonamide or (1R)—N-(4-(2,6-dimethoxyphenyl)-5-(5-methyl-2-furanyl)-4H-1,2,4-triazol-3-yl)-1-(3-hydroxy-3-oxetanyl)ethanesulfonamide, Example 311.0. Purification of Example 311.2 by SFC [150×20 mm AD-H column with 10% MeOH (0.1% NH₄OH)/CO₂ at 70 mL/min on a Thar 80 SFC] afforded two enantiomers. The title compound was the first isomer to elute under these conditions. $^1$H NMR (400 MHz, DMSO-$d_6$) δ 13.27 (br. s, 1H), 7.56 (t, J=8.5 Hz, 1H), 6.82-6.95 (m, 2H), 6.12 (d, J=2.7 Hz, 1H), 5.80 (d, J=2.9 Hz, 1H), 5.26 (br. s, 1H), 4.80 (d, J=7.0 Hz, 1H), 4.50 (d, J=6.7 Hz, 1H), 4.24 (dd, J=16.1, 6.7 Hz, 2H), 3.73 (m, 6H), 3.51 (q, J=6.8 Hz, 1H), 2.25 (s, 3H), 1.15 (d, J=7.0 Hz, 3H). LCMS-ESI (pos.) m/z: 465.1 (M+H)⁺.

Example 312.0. Preparation of (2R)—N-(4-(2-fluorophenyl)-5-(2-furanyl)-4H-1,2,4-triazol-3-yl)-1-(5-fluoro-2-pyrimidinyl)-2-propanesulfonamide and (2S)—N-(4-(2-fluorophenyl)-5-(2-furanyl)-4H-1,2,4-triazol-3-yl)-1-(5-fluoro-2-pyrimidinyl)-2-propanesulfonamide

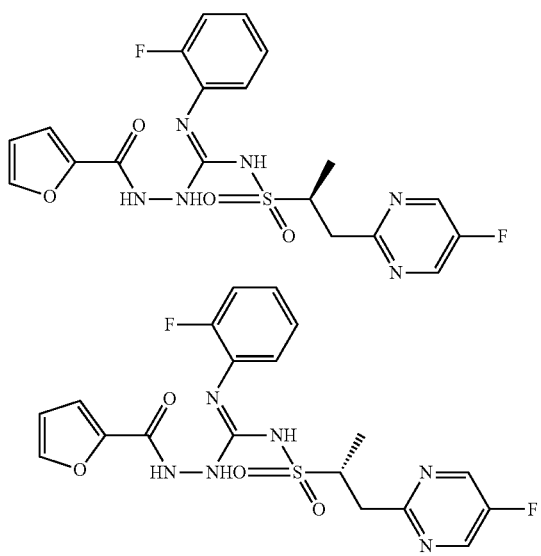

312.1

(R,Z)—N'-(2-Fluorophenyl)-N-((1-(5-fluoropyrimidin-2-yl)propan-2-yl)sulfonyl)-2-(furan-2-carbonyl)hydrazinecarboximidamide and (S,Z)—N'-(2-fluorophenyl)-N-((1-(5-fluoropyrimidin-2-yl)propan-2-yl)sulfonyl)-2-(furan-2-carbonyl)hydrazinecarboximidamide, Example 312.1. The title compound was prepared employing 1-fluoro-2-isothiocyanatobenzene (commercially available from Frontier Scientific Services Inc.) following the procedure described for the synthesis of Example 314.0. LCMS-ESI (pos.) m/z: 465.0 (M+H)⁺.

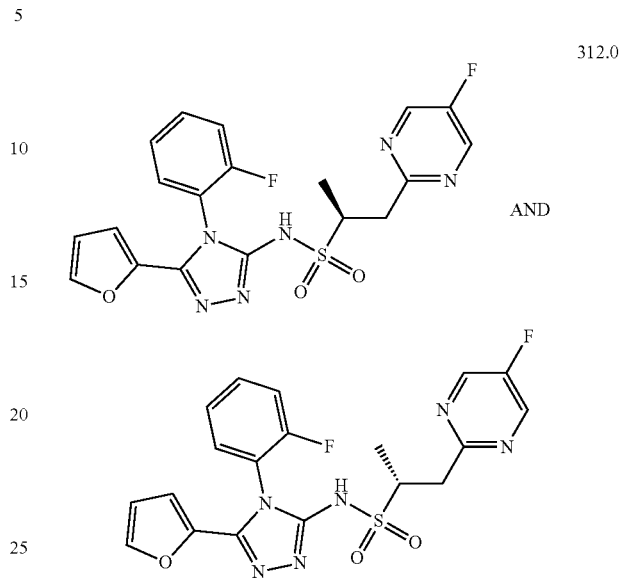

312.0

(2R)—N-(4-(2-Fluorophenyl)-5-(2-furanyl)-4H-1,2,4-triazol-3-yl)-1-(5-fluoro-2-pyrimidinyl)-2-propanesulfonamide and (2S)—N-(4-(2-fluorophenyl)-5-(2-furanyl)-4H-1,2,4-triazol-3-yl)-1-(5-fluoro-2-pyrimidinyl)-2-propanesulfonamide, Example 312.0. The title compound was prepared employing Example 312.1 following the procedure described in the synthesis of Example 314.0. $^1$H NMR (500 MHz, DMSO-$d_6$) δ 13.51 (d, J=8.8 Hz, 1H), 8.82 (s, 2H), 7.83 (d, J=1.2 Hz, 1H), 7.65-7.76 (m, 2H), 7.50-7.57 (m, 1H), 7.40-7.47 (m, 1H), 6.57 (dd, J=3.7, 1.7 Hz, 1H), 6.26 (dd, J=3.3, 1.6 Hz, 1H), 3.51-3.63 (m, 1H), 3.43-3.51 (m, 1H), 2.86 (ddd, J=14.7, 10.0, 7.6 Hz, 1H), 1.13 (t, J=6.2 Hz, 3H). LCMS-ESI (pos.) m/z: 447.0 (M+H)⁺.

Example 313.0. Preparation of (2R)—N-(4-cyclohexyl-5-(2-furanyl)-4H-1,2,4-triazol-3-yl)-1-(5-fluoro-2-pyrimidinyl)-2-propanesulfonamide and (2S)—N-(4-cyclohexyl-5-(2-furanyl)-4H-1,2,4-triazol-3-yl)-1-(5-fluoro-2-pyrimidinyl)-2-propanesulfonamide

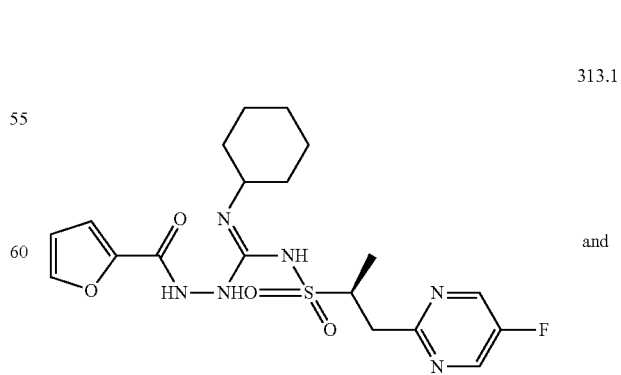

313.1

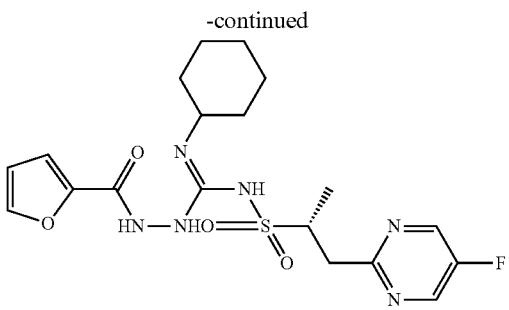

(R,Z)—N'-Cyclohexyl-N-((1-(5-fluoropyrimidin-2-yl)propan-2-yl)sulfonyl)-2-(furan-2-carbonyl)hydrazinecarboximidamide and (S,Z)—N'-cyclohexyl-N-((1-(5-fluoropyrimidin-2-yl)propan-2-yl)sulfonyl)-2-(furan-2-carbonyl)hydrazinecarboximidamide, Example 313.1. The title compound was prepared employing cyclohexyl isothiocyanate (commercially available from Sigma-Aldrich Corp., St. Louis, Mo., USA) following the procedure described in the synthesis of Example 314.1 (except the product was purified via silica gel chromatography employing a gradient of 0-20% 3:1 EtOAc:EtOH in heptanes). LCMS-ESI (pos.) m/z: 453.2 (M+H)$^+$.

313.0

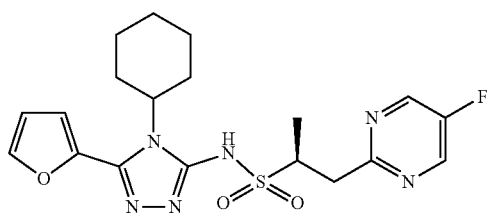

AND

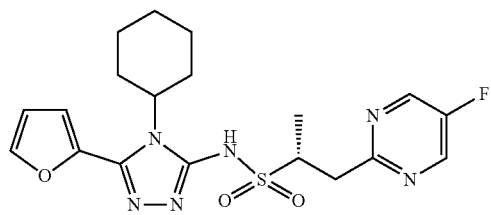

(2R)—N-(4-Cyclohexyl-5-(2-furanyl)-4H-1,2,4-triazol-3-yl)-1-(5-fluoro-2-pyrimidinyl)-2-propanesulfonamide and (2S)—N-(4-cyclohexyl-5-(2-furanyl)-4H-1,2,4-triazol-3-yl)-1-(5-fluoro-2-pyrimidinyl)-2-propanesulfonamide, Example 313.0. The title compound was prepared employing Example 313.1 following the procedures described in the synthesis of Example 314.0 (except for a further purification of the final product via reverse-phase HPLC, employing a gradient of 10-90% ACN in water (0.1% TFA in each eluent). $^1$H NMR (500 MHz, DMSO-d$_6$) δ 13.23 (br. s, 1H), 8.80 (s, 2H), 7.88 (br. s, 1H), 6.76 (br. s, 1H), 6.64 (br. s, 1H), 3.91-4.15 (m, 2H), 3.55 (dd, J=14.3, 3.3 Hz, 1H), 2.90 (dd, J=14.2, 11.2 Hz, 1H), 1.84-2.05 (m, 2H), 1.74 (d, J=13.0 Hz, 2H), 1.53-1.67 (m, 3H), 1.25 (q, J=13.0 Hz, 2H), 0.99-1.15 (m, 4H). LCMS-ESI (pos.) m/z: 435.2 (M+H)$^+$.

Example 314.0. Preparation of (2R)-1-(5-fluoro-2-pyrimidinyl)-N-(5-(2-furanyl)-4-(1-naphthalenyl)-4H-1,2,4-triazol-3-yl)-2-propanesulfonamide and (2S)-1-(5-fluoro-2-pyrimidinyl)-N-(5-(2-furanyl)-4-(1-naphthalenyl)-4H-1,2,4-triazol-3-yl)-2-propanesulfonamide 314.1

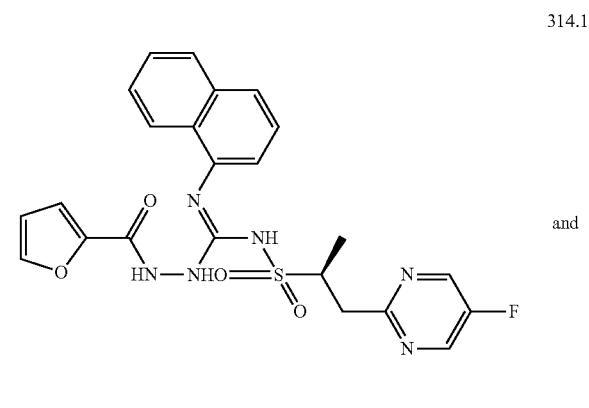

and

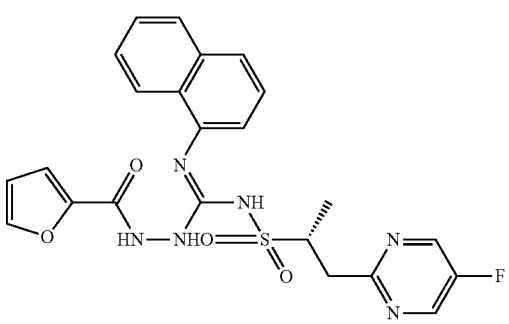

(R,Z)—N-((1-(5-Fluoropyrimidin-2-yl)propan-2-yl)sulfonyl)-2-(furan-2-carbonyl)-N'-(naphthalen-1-yl)hydrazinecarboximidamide and (S,Z)—N-((1-(5-fluoropyrimidin-2-yl)propan-2-yl)sulfonyl)-2-(furan-2-carbonyl)-N'-(naphthalen-1-yl)hydrazinecarboximidamide, Example 314.1. To a stirred solution of Example 353.0 (108 mg, 0.49 mmol) in DMF (1 mL) at RT was added 1-isothiocyanatonaphthalene (commercially available from Frontier Scientific Services Inc., 82 mg, 0.44 mmol). Cesium carbonate (201 mg, 0.62 mmol) was then carefully added in portions to the homogeneous solution, and the resulting mixture was stirred until LCMS analysis showed that the formation of the intermediate was complete (1 h). The mixture was then cooled in an ice-water bath and 2-furoic hydrazide (commercially available from Alfa Aesar, Ward Hill, Mass., USA) (67 mg, 0.53 mmol) and silver nitrate (155 mg, 0.91 mmol) were added followed immediately with dropwise addition of AcOH (0.11 mL, 1.9 mmol). The mixture was allowed to warm to RT and reaction progress was monitored by LCMS. After 15 min, the mixture was filtered through a plug of Celite® brand filter aid. The plug was rinsed with DCM and then with EtOAc. The filtrate was concentrated in vacuo. The dark residue was diluted with DCM and then carefully neutralized with aqueous saturated NaHCO$_3$. The organic layer was separated and then dried over anhydrous MgSO$_4$. Filtration and concentration yielded the title compound which was used without further purification. LCMS-ESI (pos.) m/z: 497.1 (M+H)$^+$.

314.0

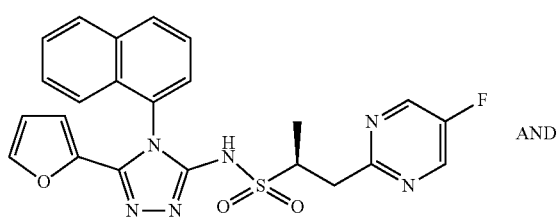

(2R)-1-(5-Fluoro-2-pyrimidinyl)-N-(5-(2-furanyl)-4-(1-naphthalenyl)-4H-1,2,4-triazol-3-yl)-2-propanesulfonamide and (2S)-1-(5-fluoro-2-pyrimidinyl)-N-(5-(2-furanyl)-4-(1-naphthalenyl)-4H-1,2,4-triazol-3-yl)-2-propanesulfonamide, Example 314.0. To a vial containing Example 314.1 (220 mg, 0.44 mmol) in anhydrous DMF (5 mL) was added TFA (0.1 mL, 1.35 mmol) dropwise. Upon complete addition of TFA, the mixture was heated on a preheated stir plate at 110° C. until LCMS analysis showed that the reaction was complete (4 d). Thereafter, the reaction was cooled to RT and then the pH was carefully adjusted with dropwise addition of a saturated aqueous NaHCO₃ solution to pH~8. The mixture was extracted three times with DCM. The organic layers were combined and washed once with brine. After drying over MgSO₄, filtration, and concentration in vacuo, the black residue was loaded onto a silica gel column (0-60% of 3:1 EtOAc:EtOH in heptanes) to afford a dark brown film that was triturated with IPA to provide Example 314.0 (51 mg, 0.11 mmol, 24% yield for two steps) as an off-white solid. ¹H NMR (500 MHz, DMSO-d₆) δ 13.53 (s, 1H), 8.74-8.85 (m, 2H), 8.22 (d, J=8.3 Hz, 1H), 8.12 (dd, J=8.3, 3.2 Hz, 1H), 7.76-7.86 (m, 1H), 7.67-7.75 (m, 2H), 7.43-7.65 (m, 3H), 6.37 (dd, J=3.7, 1.7 Hz, 1H), 5.68 (d, J=3.7 Hz, 1H), 3.46-3.59 (m, 1H), 3.33-3.43 (m, 1H), 2.75 (td, J=14.7, 10.3 Hz, 1H), 1.00-1.07 (m, 3H). LCMS-ESI (pos.) m/z: 479.1 (M+H)⁺.

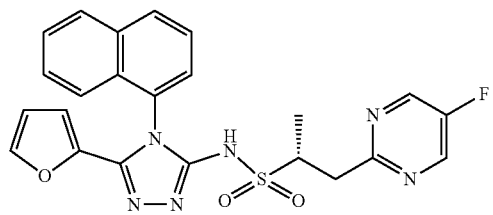

Example 315.0. Preparation of (2R)—N-(4-(2,4-dimethoxyphenyl)-5-(2-furanyl)-4H-1,2,4-triazol-3-yl)-1-(5-fluoro-2-pyrimidinyl)-2-propanesulfonamide and (2S)—N-(4-(2,4-dimethoxyphenyl)-5-(2-furanyl)-4H-1,2,4-triazol-3-yl)-1-(5-fluoro-2-pyrimidinyl)-2-propanesulfonamide 315.1

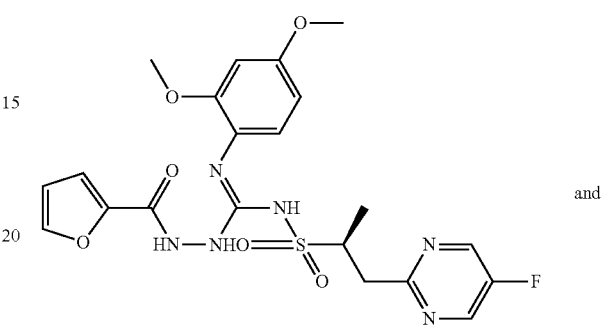

and

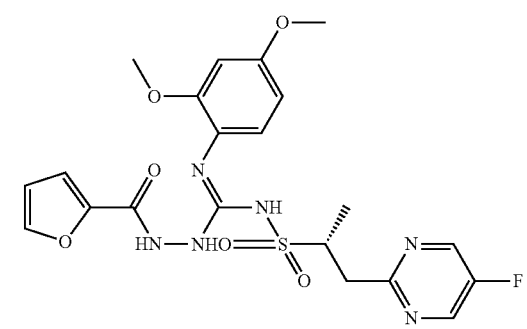

(R,Z)—N'-(2,4-Dimethoxyphenyl)-N-((1-(5-fluoropyrimidin-2-yl)propan-2-yl)sulfonyl)-2-(furan-2-carbonyl)hydrazinecarboximidamide and (S,Z)—N'-(2,4-dimethoxyphenyl)-N-((1-(5-fluoropyrimidin-2-yl)propan-2-yl)sulfonyl)-2-(furan-2-carbonyl)hydrazinecarboximidamide, Example 315.1. The title compound was prepared employing 1-isothiocyanato-2,4-dimethoxybenzene (commercially available from Frontier Scientific Services Inc.) following the procedures described in the synthesis of Example 314.0. LCMS-ESI (pos.) m/z: 507.0 (M+H)⁺.

315.0

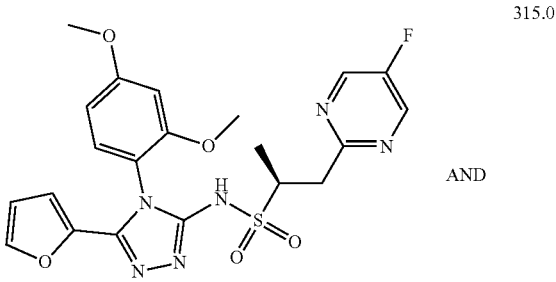

AND

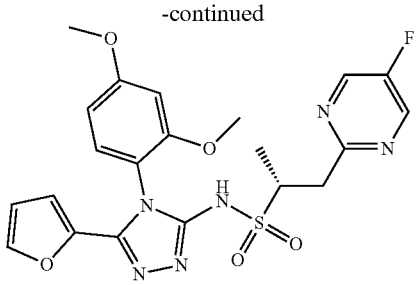

(2R)—N-(4-(2,4-Dimethoxyphenyl)-5-(2-furanyl)-4H-1,2,4-triazol-3-yl)-1-(5-fluoro-2-pyrimidinyl)-2-propanesulfonamide and (2S)—N-(4-(2,4-dimethoxyphenyl)-5-(2-furanyl)-4H-1,2,4-triazol-3-yl)-1-(5-fluoro-2-pyrimidinyl)-2-propanesulfonamide, Example 315.0. The title compound was prepared employing Example 315.1 following the procedures described in the synthesis of Example 314.0. $^1$H NMR (500 MHz, DMSO-$d_6$) δ 13.25 (d, J=6.1 Hz, 1H), 8.77-8.85 (m, 2H), 7.81-7.87 (m, 1H), 7.40 (dd, J=13.7, 8.6 Hz, 1H), 6.73-6.83 (m, 1H), 6.69 (dd, J=8.7, 2.6 Hz, 1H), 6.53 (dd, J=3.5, 1.8 Hz, 1H), 5.99 (d, J=3.4 Hz, 1H), 3.86 (d, J=1.5 Hz, 3H), 3.67 (d, J=4.2 Hz, 3H), 3.41-3.57 (m, 2H), 2.80-2.91 (m, 1H), 1.11 (t, J=7.0 Hz, 3H). LCMS-ESI (pos.) m/z: 489.0 (M+H)$^+$.

Example 316.0. Preparation of (2R)—N-(4-cyclopentyl-5-(5-methyl-2-furanyl)-4H-1,2,4-triazol-3-yl)-1-(5-fluoro-2-pyrimidinyl)-2-propanesulfonamide and (2S)—N-(4-cyclopentyl-5-(5-methyl-2-furanyl)-4H-1,2,4-triazol-3-yl)-1-(5-fluoro-2-pyrimidinyl)-2-propanesulfonamide 316.1

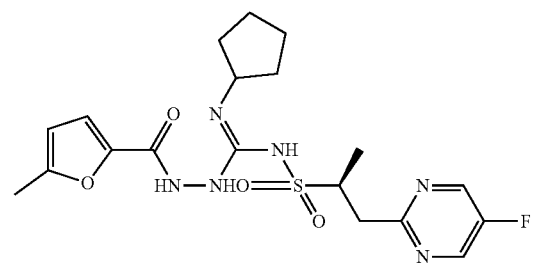

and

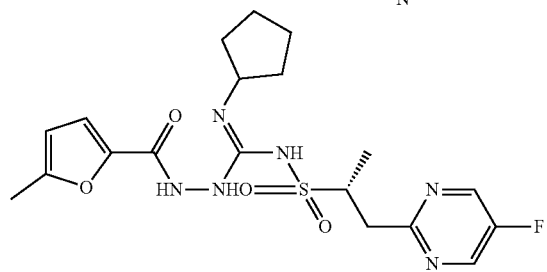

(R,Z)—N'-Cyclopentyl-N-((1-(5-fluoropyrimidin-2-yl)propan-2-yl)sulfonyl)-2-(5-methylfuran-2-carbonyl)hydrazinecarboximidamide and (S,Z)—N'-cyclopentyl-N-((1-(5-fluoropyrimidin-2-yl)propan-2-yl)sulfonyl)-2-(5-methylfuran-2-carbonyl)hydrazinecarboximidamide, Example 316.1. The title compound was prepared employing cyclopentyl isothiocyanate (commercially available from Ryan Scientific, Inc., Mount Pleasant, S.C., USA) and 5-methyl-2-furohydrazide (commercially available from Chembridge Corporation, San Diego, Calif., USA) following the procedures described in the synthesis of Example 314.1 (except for the use of anhydrous ACN as reaction solvent and the silica gel purification of the final product employing a gradient of 0-30% IPA in heptanes). LCMS-ESI (pos.) m/z: 453.2 (M+H)$^+$.

316.0

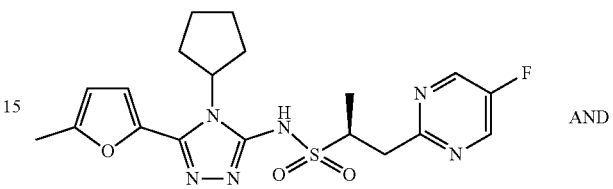

AND

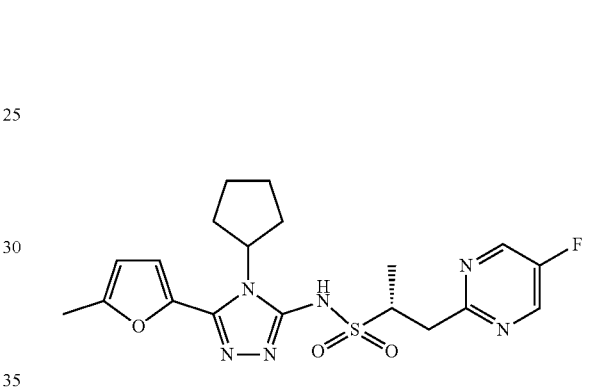

(2R)—N-(4-Cyclopentyl-5-(5-methyl-2-furanyl)-4H-1,2,4-triazol-3-yl)-1-(5-fluoro-2-pyrimidinyl)-2-propanesulfonamide and (2S)—N-(4-cyclopentyl-5-(5-methyl-2-furanyl)-4H-1,2,4-triazol-3-yl)-1-(5-fluoro-2-pyrimidinyl)-2-propanesulfonamide, Example 316.0. To a dry vial containing Example 316.1 (80 mg, 0.18 mmol) and Lawesson's reagent (186 mg, 0.46 mmol) was added anhydrous toluene (3 mL). The heterogeneous mixture was heated to 100° C. and monitored with LCMS. After 21 h, the reaction was quenched with aqueous saturated NaHCO$_3$ solution. After extracting three times with 20% IPA in CHCl$_3$, the organic layers were combined and then dried over anhydrous sodium sulfate. After filtration and concentration, the residue was loaded onto a silica gel column (0-40% of 3:1 EtOAc:EtOH in heptanes) to afford a colorless film that was dissolved in 3 mL of DMSO. The solution was purified with reverse-phase HPLC (10-90% of premixed 0.1% TFA in ACN in 0.1% TFA in water). Fractions containing desired product were combined and then concentrated in vacuo. The residue was treated with a saturated aqueous solution of sodium bicarbonate. After extracting three times with DCM, the organics were pooled then dried over anhydrous magnesium sulfate. After filtration and concentration, the light yellow solid was identified as the title compound (8 mg, 0.02 mmol, 10% yield). $^1$H NMR (400 MHz, DMSO-$d_6$) δ 13.15 (s, 1H), 8.82 (s, 2H), 6.99 (d, J=3.3 Hz, 1H), 6.33-6.40 (m, 1H), 4.69 (quin, J=8.7 Hz, 1H), 3.52-3.71 (m, 2H), 2.98 (dd, J=14.5, 9.4 Hz, 1H), 2.34-2.40 (m, 3H), 2.02-2.16 (m, 2H), 1.76-1.97 (m, 4H), 1.49-1.63 (m, 2H), 1.24 (d, J=6.8 Hz, 3H). LCMS-ESI (pos.) m/z: 435.2 (M+H)$^+$.

Example 317.0. Preparation of (2S)-1-(5-fluoro-2-pyrimidinyl)-N-(5-(5-methyl-2-furanyl)-4-(tetrahydro-2H-pyran-4-yl)-4H-1,2,4-triazol-3-yl)-2-propanesulfonamide and (2R)-1-(5-fluoro-2-pyrimidinyl)-N-(5-(5-methyl-2-furanyl)-4-(tetrahydro-2H-pyran-4-yl)-4H-1,2,4-triazol-3-yl)-2-propanesulfonamide

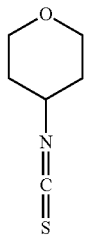

317.1

4-Isothiocyanatotetrahydro-2H-pyran, Example 317.1. The title compound was prepared employing 4-aminotetrahydropyran (commercially available from Peakdale Molecular, High Peak, UK) instead of 2,6-dimethoxyaniline following the procedure described in the synthesis of Example 372.0. $^1$H NMR (500 MHz, CD$_2$Cl$_2$) δ 3.92 (tt, J=8.2, 4.1 Hz, 1H) 3.84 (ddd, J=11.9, 6.1, 3.8 Hz, 2H) 3.50 (ddd, J=11.8, 8.4, 3.1 Hz, 2H) 1.93-2.01 (m, 2H), 1.74-1.82 (m, 2H).

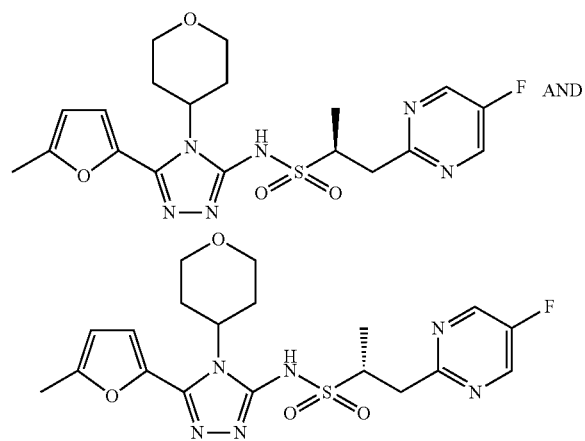

317.0

(2S)-1-(5-Fluoro-2-pyrimidinyl)-N-(5-(5-methyl-2-furanyl)-4-(tetrahydro-2H-pyran-4-yl)-4H-1,2,4-triazol-3-yl)-2-propanesulfonamide and (2R)-1-(5-fluoro-2-pyrimidinyl)-N-(5-(5-methyl-2-furanyl)-4-(tetrahydro-2H-pyran-4-yl)-4H-1,2,4-triazol-3-yl)-2-propanesulfonamide, Example 317.0. The title compound was prepared employing Example 317.1 following the procedures described in Example 316.0. $^1$H NMR (500 MHz, CDCl$_3$) δ 8.49 (s, 2H), 6.59 (d, J=2.7 Hz, 1H), 5.97-6.08 (m, 1H), 4.38 (t, J=11.9 Hz, 1H), 3.96 (d, J=8.1 Hz, 2H), 3.72-3.81 (m, 1H), 3.68 (dd, J=14.1, 3.3 Hz, 1H), 3.35 (t, J=12.0 Hz, 2H), 2.98-3.07 (m, 1H), 2.29-2.43 (m, 5H), 1.43-1.53 (m, 2H), 1.19-1.28 (m, 3H). LCMS-ESI (pos.) m/z: 451.1 (M+H)$^+$.

Example 318.0. Preparation of (2S)-1-(5-fluoro-2-pyrimidinyl)-N-(5-(2-furanyl)-4-(2-(trifluoromethyl)phenyl)-4H-1,2,4-triazol-3-yl)-2-propanesulfonamide and (2S)-1-(5-fluoro-2-pyrimidinyl)-N-(5-(2-furanyl)-4-(2-(trifluoromethyl)phenyl)-4H-1,2,4-triazol-3-yl)-2-propanesulfonamide

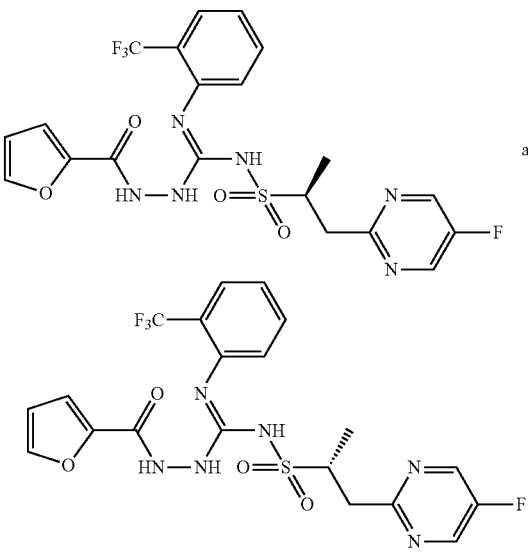

318.1 and (R,Z)—N-((1-(5-Fluoropyrimidin-2-yl)propan-2-yl)sulfonyl)-2-(furan-2-carbonyl)-N'-(2-(trifluoromethyl)phenyl) hydrazinecarboximidamide and (S,Z)—N-((1-(5-fluoropyrimidin-2-yl)propan-2-yl)sulfonyl)-2-(furan-2-carbonyl)-N'-(2-(trifluoromethyl)phenyl)hydrazinecarboximidamide, Example 318.1. The title compound was prepared employing 1-isothiocyanato-2-(trifluoromethyl)benzene (commercially available from Frontier Scientific Services Inc.), following the procedures described in Example 314.0. LCMS-ESI (pos.) m/z: 515.2 (M+H)$^+$.

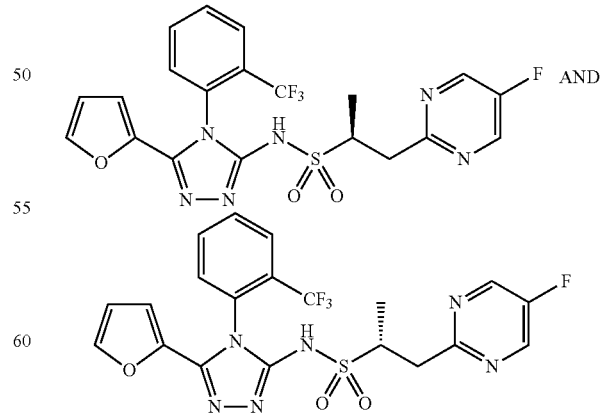

318.0

AND (2S)-1-(5-Fluoro-2-pyrimidinyl)-N-(5-(2-furanyl)-4-(2-(trifluoromethyl)phenyl)-4H-1,2,4-triazol-3-yl)-2-propanesulfonamide and (2S)-1-(5-fluoro-2-pyrimidinyl)-N-(5-(2- furanyl)-4-(2-(trifluoromethyl)phenyl)-4H-1,2,4-triazol-3-yl)-2-propanesulfonamide, Example 318.0. The title compound was prepared employing Example 318.1 following the procedures described in the synthesis of Example 314.0. $^1$H NMR (500 MHz, DMSO-d$_6$) δ 13.39-13.50 (m, 1H), 8.82 (s, 2H), 7.86-8.06 (m, 4H), 7.73-7.80 (m, 1H), 6.52 (dd, J=3.7, 1.7 Hz, 1H), 6.09 (d, J=3.4 Hz, 1H), 3.41-3.60 (m, 2H), 2.76-2.89 (m, 1H), 1.09 (d, J=6.8 Hz, 3H). LCMS-ESI (pos.) m/z: 497.0 (M+H)$^+$.

Example 319.0. Preparation of (2R)—N-(4-cyclopropyl-5-(5-methyl-2-furanyl)-4H-1,2,4-triazol-3-yl)-1-(5-fluoro-2-pyrimidinyl)-2-propanesulfonamide and (2S)—N-(4-cyclopropyl-5-(5-methyl-2-furanyl)-4H-1,2,4-triazol-3-yl)-1-(5-fluoro-2-pyrimidinyl)-2-propanesulfonamide 319.1

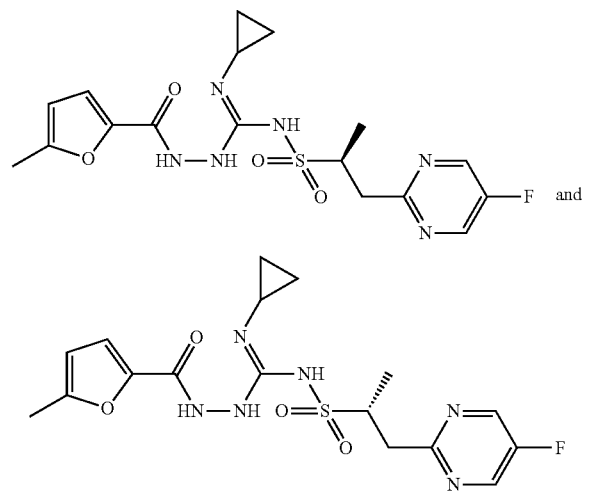

(R,Z)—N'-Cyclopropyl-N-((1-(5-fluoropyrimidin-2-yl)propan-2-yl)sulfonyl)-2-(5-methylfuran-2-carbonyl)hydrazinecarboximidamide and (S,Z)—N'-cyclopropyl-N-((1-(5-fluoropyrimidin-2-yl)propan-2-yl)sulfonyl)-2-(5-methylfuran-2-carbonyl)hydrazinecarboximidamide, Example 319.1. The title compound was prepared employing cyclopropyl isothiocyanate (commercially available from Ryan Scientific, Inc., Mount Pleasant, S.C., USA) and 5-methyl-2-furohydrazide (commercially available from Chembridge Corporation, San Diego, Calif., USA) instead of 1-isothiocyanatonaphthalene and 2-furoic hydrazide following the procedure described in the synthesis of Example 314.0. LCMS-ESI (pos.) m/z: 425.1 (M+H)$^+$.

319.0
AND

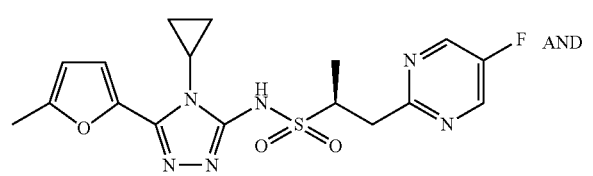

-continued

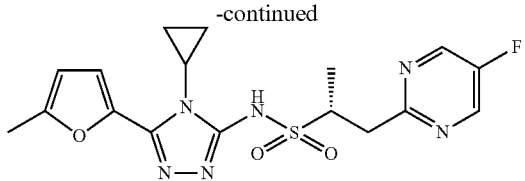

(2R)—N-(4-Cyclopropyl-5-(5-methyl-2-furanyl)-4H-1,2,4-triazol-3-yl)-1-(5-fluoro-2-pyrimidinyl)-2-propanesulfonamide and (2S)—N-(4-cyclopropyl-5-(5-methyl-2-furanyl)-4H-1,2,4-triazol-3-yl)-1-(5-fluoro-2-pyrimidinyl)-2-propanesulfonamide, Example 319.0. To a vial containing Example 319.1 (225 mg, 0.53 mmol) in anhydrous DMF (1 mL) was added polyphosphoric acid (commercially available from Sigma-Aldrich Corp., St. Louis, Mo., USA, 115% H$_3$PO$_4$ basis, 392 mg) dropwise. Upon complete addition, the mixture was stirred at 110° C. until LCMS analysis showed that the reaction was complete (19 h). Thereafter, the reaction was cooled to RT and diluted with water. The pH was carefully adjusted via dropwise addition of aqueous 2 N NaOH to give a pH~8. The mixture was then extracted three times with 20% IPA/CHCl$_3$ and the combined organic layers were dried over MgSO$_4$, filtered, and concentrated in vacuo. The resulting brown residue was loaded onto a silica gel column (0-50% of 3:1 EtOAc:EtOH in heptanes) to afford product. Subsequent purification by reverse-phase HPLC employing a gradient of 10-90% ACN in water [0.1% TFA in each eluent] afforded Example 319.0 (15 mg, 0.037 mmol, 7%). $^1$H NMR (400 MHz, CD$_2$Cl$_2$) δ 10.85 (br. s, 1H), 8.52-8.59 (m, 2H), 6.95 (d, J=3.5 Hz, 1H), 6.14-6.28 (m, 1H), 3.78 (m, 1H), 3.62-3.71 (m, 1H), 3.05-3.15 (m, 1H), 2.96-3.04 (m, 1H), 2.38-2.43 (m, 3H), 1.37 (d, J=6.8 Hz, 3H), 1.14-1.20 (m, 2H), 0.96-1.02 (m, 2H). LCMS-ESI (pos.) m/z: 407.1 (M+H)$^+$.

Example 320.0. Preparation of (3S,5R)-1-(4-cyanopyridin-2-yl)-N-(4-(2,6-dimethoxyphenyl)-5-(5-methylfuran-2-yl)-4H-1,2,4-triazol-3-yl)-5-hydroxypiperidine-3-sulfonamide or (3R,5S)-1-(4-cyanopyridin-2-yl)-N-(4-(2,6-dimethoxyphenyl)-5-(5-methylfuran-2-yl)-4H-1,2,4-triazol-3-yl)-5-hydroxypiperidine-3-sulfonamide 320.1

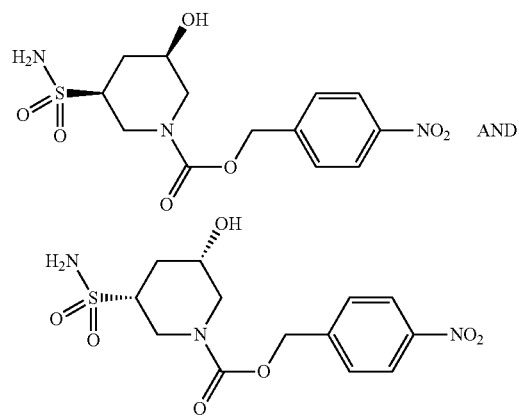

(3R,5S)-4-Nitrobenzyl 3-hydroxy-5-sulfamoylpiperidine-1-carboxylate and (3S,5R)-4-nitrobenzyl 3-hydroxy-5-sulfamoylpiperidine-1-carboxylate, Example 320.1. To a solution of Example 167.2 (2.97 g, 12.36 mmol) in water (30 mL) in a 250 mL RBF at RT, was added sodium bicarbonate (3.63 g, 43.3 mmol). To the mixture was added dropwise a solution of 4-nitrobenzyl chloroformate (3.46 g, 16.07 mmol) in dioxane (15 mL). The reaction mixture was stirred for 3 h. The reaction mixture was then extracted with DCM (3×100 mL). The combined organic layers were dried over Na$_2$SO$_4$. The solution was filtered and concentrated in vacuo to give an oil. The oil was dissolved in a minimum amount of EtOAc and then added to Et$_2$O (300 mL) while stirring. A white solid was collected by filtration and dried on high vacuum to provide the first crop of the desired product, Example 320.1 (1.31 g). The mother liquor was concentrated in vacuo. The residue thus obtained was absorbed onto a plug of silica gel and purified by chromatography through a Redi-Sep pre-packed silica gel column (80 g) eluting with a gradient of 0% to 50% EtOAc in DCM to provide a second crop of desired product, Example 320.1 (0.84 g), as a white solid. LCMS-ESI (pos.), m/z: 359.9 (M+H)$^+$.

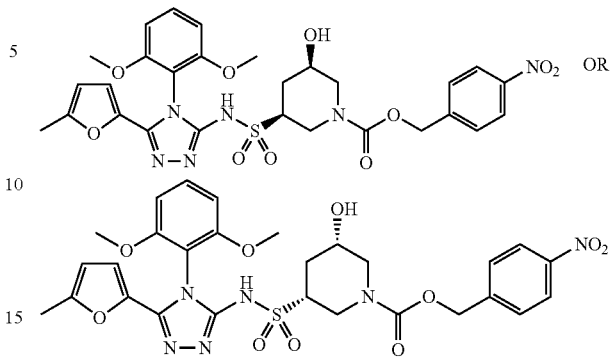

(3S,5R)-4-Nitrobenzyl 3-(N-(4-(2,6-dimethoxyphenyl)-5-(5-methylfuran-2-yl)-4H-1,2,4-triazol-3-yl)sulfamoyl)-5-

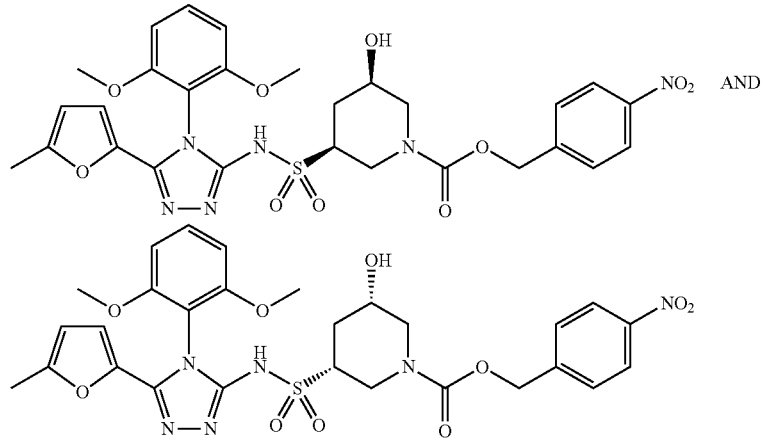

(3S,5R)-4-Nitrobenzyl 3-(N-(4-(2,6-dimethoxyphenyl)-5-(5-methylfuran-2-yl)-4H-1,2,4-triazol-3-yl)sulfamoyl)-5-hydroxypiperidine-1-carboxylate and (3R,5S)-4-nitrobenzyl 3-(N-(4-(2,6-dimethoxyphenyl)-5-(5-methylfuran-2-yl)-4H-1,2,4-triazol-3-yl)sulfamoyl)-5-hydroxypiperidine-1-carboxylate, Example 320.2. A mixture of Example 320.1 (1.28 g, 3.56 mmol), Example 364.1 (2.08 g, 5.70 mmol), cesium carbonate (0.713 mL, 8.90 mmol), and trans-N,N'-dimethyl-1,2-cyclohexanediamine (2.90 g, 7.12 mmol) in ACN (15 mL) was bubbled with argon gas for 5 min. Copper(I) iodide (0.814 g, 4.27 mmol) was added in one portion. The reaction mixture was heated at 83° C. for 16 h using an oil bath. The reaction mixture was cooled to RT. The solvent was evaporated on a rotary evaporator at 25° C. The residue was then diluted with water (150 mL) and extracted with DCM (1×150 mL, 2×20 mL). The combined organic layers were then washed with a saturated solution of NH$_4$Cl (200 mL), and then with 1 N NaOH (200 mL). The organic layer was dried over Na$_2$SO$_4$, filtered, and concentrated in vacuo. The residue was absorbed onto a plug of silica gel and purified by chromatography through a Redi-Sep pre-packed silica gel column (80 g) eluting with a gradient of 0% to 100% B/A (B=0.1% TFA in ACN, A=DCM) to provide the title compound, Example 320.2 (0.78 g, 1.2 mmol, 35%), as an off-white solid. LCMS-ESI (pos.), m/z: 643.1 (M+H)$^+$.

hydroxypiperidine-1-carboxylate or (3R,5S)-4-nitrobenzyl 3-(N-(4-(2,6-dimethoxyphenyl)-5-(5-methylfuran-2-yl)-4H-1,2,4-triazol-3-yl)sulfamoyl)-5-hydroxypiperidine-1-carboxylate, Example 320.3. Example 320.3 was prepared by the chiral SFC separation of Example 320.2 on an AS column under the following conditions: 250×30 mm AS-H column with 32 mL/min EtOH+(Neat)+68 g/min CO$_2$ on Thar 350 SFC. Outlet pressure=100 bar; Temp.=19° C.; Wavelength=272 nm. Used 1 mL injections of 1.4 g/60 mL (23 mg/mL) sample solution in MeOH:DCM (50:50), i.e. 23 mg/injection. Cycle time=8.5 min, Runtime=13 min. LCMS-ESI (pos.), m/z: 643.1 (M+H)$^+$.

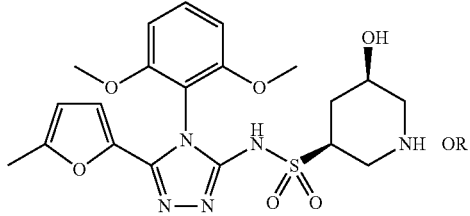

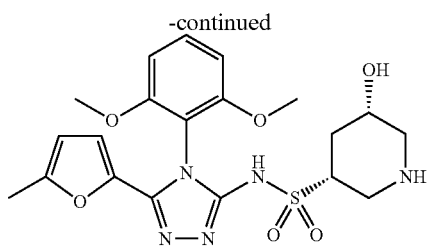

(3R,5S)—N-(4-(2,6-Dimethoxyphenyl)-5-(5-methyl-furan-2-yl)-4H-1,2,4-triazol-3-yl)-5-hydroxypiperidine-3-sulfonamide or (3S,5R)—N-(4-(2,6-dimethoxyphenyl)-5-(5-methylfuran-2-yl)-4H-1,2,4-triazol-3-yl)-5-hydroxypiperidine-3-sulfonamide, Example 320.4. To a mixture of Example 320.3 (932 mg, 1.45 mmol) in EtOH (30 mL) in a 100 mL RBF under $N_2$ atmosphere, was added palladium (10% wt. on activated carbon, 772 mg, 0.725 mmol). The reaction mixture was stirred under a $H_2$ balloon at RT for 2 h. More 10% Pd on activated carbon (386 mg) was added, and the reaction was further stirred for an additional 2 h. The catalyst was removed by filtering through a Celite® brand filter aid pad and the pad was then rinsed with MeOH (200 mL). The solution was concentrated in vacuo to provide the title compound Example 320.4 (775 mg, 1.67 mmol) as a light yellow powder. The material was used directly in the next step without further purification. LCMS-ESI (pos.), m/z: 464.1 (M+H)$^+$.

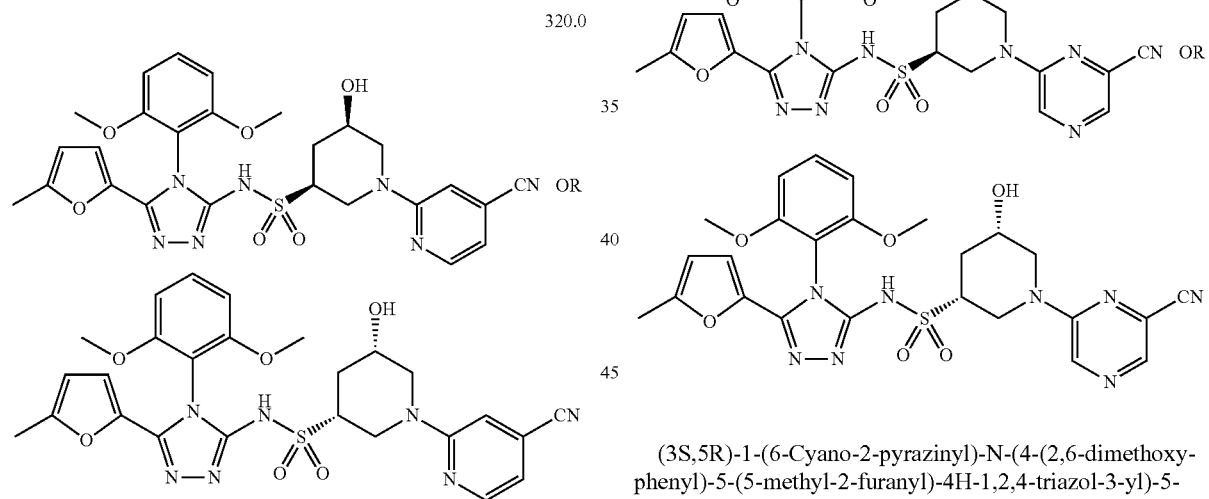

(3S,5R)-1-(4-Cyanopyridin-2-yl)-N-(4-(2,6-dimethoxyphenyl)-5-(5-methylfuran-2-yl)-4H-1,2,4-triazol-3-yl)-5-hydroxypiperidine-3-sulfonamide or (3R,5S)-1-(4-cyanopyridin-2-yl)-N-(4-(2,6-dimethoxyphenyl)-5-(5-methylfuran-2-yl)-4H-1,2,4-triazol-3-yl)-5-hydroxypiperidine-3-sulfonamide, Example 320.0. A mixture of Example 320.4 (76.8 mg, 0.166 mmol), 2-fluoroisonicotinonitrile (40.5 mg, 0.331 mmol) and DIEA (0.058 mL, 0.331 mmol) in DMSO (1 mL) was heated at 120° C. for 1 h using a microwave. The reaction mixture was then added dropwise into a stirred solution of 0.1 N HCl (10 mL) at RT and stirred for 1 h. A light brown solid (~93 mg) was collected by filtration, rinsed with water, and then rinsed with 5% EtOAc/hexanes. The solid obtained was absorbed onto a plug of silica gel and purified by chromatography through a Redi-Sep pre-packed silica gel column (12 g) eluting with a gradient of 0% to 20% B/A (B=23% EtOAc in EtOAc, A=DCM) to provide enriched product which was triturated with 5% EtOAc/1% MeOH/1% ACN/1% DCM in hexanes to give Example 320.0 (28 mg, 0.050 mmol, 30% yield) as a white solid. $^1$H NMR (400 MHz, CD$_3$OD) δ 8.25 (dd, J=5.09, 0.59 Hz, 1H) 7.57 (t, J=8.51 Hz, 1H) 7.06 (s, 1H) 6.84-6.88 (m, 3H) 6.02 (dd, J=3.67 Hz, 1H) 5.96 (d, J=3.33 Hz, 1H) 4.66-4.72 (m, 1H) 4.45 (dd, J=12.81, 4.60 Hz, 1H) 3.81 (s, 3H) 3.78 (s, 3H) 3.56-3.65 (m, 1H) 3.09-3.17 (m, 1H) 2.91 (dd, J=13.11, 11.35 Hz, 1H) 2.59 (dd, J=12.81, 10.66 Hz, 1H) 2.49 (d, J=11.74 Hz, 1H) 2.26 (s, 3H) 1.62-1.71 (m, 1H). LCMS-ESI (pos.) m/z: 566.2 (M+H)$^+$.

Example 321.0. Preparation of (3S,5R)-1-(6-cyano-2-pyrazinyl)-N-(4-(2,6-dimethoxyphenyl)-5-(5-methyl-2-furanyl)-4H-1,2,4-triazol-3-yl)-5-hydroxy-3-piperidinesulfonamide or (3R,5S)-1-(6-cyano-2-pyrazinyl)-N-(4-(2,6-dimethoxyphenyl)-5-(5-methyl-2-furanyl)-4H-1,2,4-triazol-3-yl)-5-hydroxy-3-piperidinesulfonamide (3S,5R)-1-(6-Cyano-2-pyrazinyl)-N-(4-(2,6-dimethoxyphenyl)-5-(5-methyl-2-furanyl)-4H-1,2,4-triazol-3-yl)-5-hydroxy-3-piperidinesulfonamide or (3R,5S)-1-(6-cyano-2-pyrazinyl)-N-(4-(2,6-dimethoxyphenyl)-5-(5-methyl-2-furanyl)-4H-1,2,4-triazol-3-yl)-5-hydroxy-3-piperidinesulfonamide, Example 321.0. The title compound was prepared from Example 320.4 (85.5 mg, 0.184 mmol) and 2-chloro-6-cyanopyrazine (51.5 mg, 0.369 mmol, commercially available from Frontier Scientific Services Inc.) following the procedures described in Example 320.0. This provided the title compound, Example 321.0 (10 mg, 0.015 mmol, 11% yield), as a white solid. $^1$H NMR (400 MHz, DMSO-d$_6$) δ 13.31 (s, 1H) 8.53 (s, 1H) 8.31 (s, 1H) 7.57 (t, J=8.51 Hz, 1H) 6.90 (d, J=8.23 Hz, 2H) 6.13 (dd, J=3.33, 0.98 Hz, 1H) 5.82 (d, J=3.33 Hz, 1H) 4.62 (dd, J=13.60, 2.45 Hz, 1H) 4.38 (dd, J=12.42, 3.81 Hz, 1H) 3.76 (s, 3H) 3.74 (s, 3H) 3.49-3.58 (m, 1H) 3.08-3.16 (m, 1H) 2.79 (t, J=12.32 Hz, 1H) 2.52-2.58 (m, 1H) 2.26-2.29 (m, 1H) 2.25 (s, 3H) 1.41-1.52 (m, 1H). LCMS-ESI (pos.) m/z: 567.0 (M+H)$^+$.

Example 322.0. Preparation of (3S,5R)-1-(6-chloro-5-cyano-3-pyridinyl)-N-(4-(2,6-dimethoxyphenyl)-5-(5-methyl-2-furanyl)-4H-1,2,4-triazol-3-yl)-5-hydroxy-3-piperidinesulfonamide and (3R,5S)-1-(6-chloro-5-cyano-3-pyridinyl)-N-(4-(2,6-dimethoxyphenyl)-5-(5-methyl-2-furanyl)-4H-1,2,4-triazol-3-yl)-5-hydroxy-3-piperidinesulfonamide

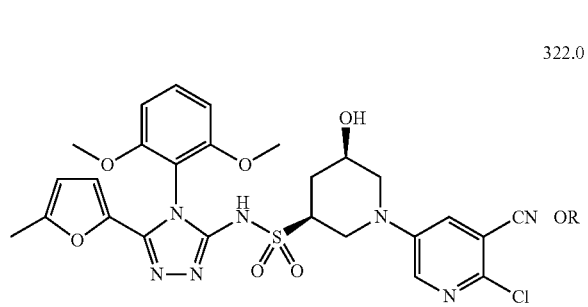

322.0

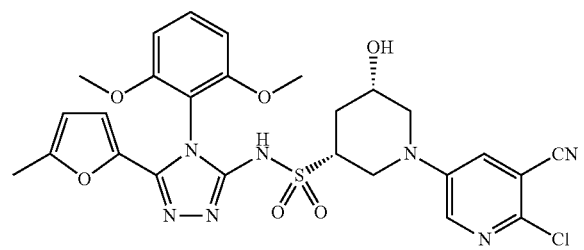

(3S,5R)-1-(6-Chloro-5-cyano-3-pyridinyl)-N-(4-(2,6-dimethoxyphenyl)-5-(5-methyl-2-furanyl)-4H-1,2,4-triazol-3-yl)-5-hydroxy-3-piperidinesulfonamide and (3R,5S)-1-(6-chloro-5-cyano-3-pyridinyl)-N-(4-(2,6-dimethoxyphenyl)-5-(5-methyl-2-furanyl)-4H-1,2,4-triazol-3-yl)-5-hydroxy-3-piperidinesulfonamide, Example 322.0. The title compound, Example 322.0 (3.0 mg, 0.0042 mmol, 3% yield), was obtained as a product during the synthesis of Example 331.0. $^1$H NMR (400 MHz, CD$_3$OD) δ 8.20 (d, J=3.33 Hz, 1H) 7.69 (d, J=3.33 Hz, 1H) 7.57 (t, J=8.51 Hz, 1H) 6.86 (t, J=8.10 Hz, 2H) 6.02 (dd, J=3.42, 0.88 Hz, 1H) 5.96 (d, J=3.33 Hz, 1H) 4.00-4.06 (m, 1H) 3.88 (dd, J=12.23, 4.60 Hz, 1H) 3.80 (s, 3H) 3.77 (s, 3H) 3.67-3.76 (m, 1H) 3.19-3.28 (m, 1H) 2.92 (dd, J=12.72, 11.35 Hz, 1H) 2.59 (dd, J=12.32, 10.56 Hz, 1H) 2.50 (d, J=11.74 Hz, 1H) 2.25 (s, 3H) 1.56-1.67 (m, 1H). LCMS-ESI (pos.) m/z: 600.0 (M+H)$^+$.

Example 323.0. Preparation of (3S,5R)—N-(4-(2,6-dimethoxyphenyl)-5-(5-methyl-2-furanyl)-4H-1,2,4-triazol-3-yl)-1-(5-fluoro-2-pyrimidinyl)-5-hydroxy-3-piperidinesulfonamide or (3R,5S)—N-(4-(2,6-dimethoxyphenyl)-5-(5-methyl-2-furanyl)-4H-1,2,4-triazol-3-yl)-1-(5-fluoro-2-pyrimidinyl)-5-hydroxy-3-piperidinesulfonamide

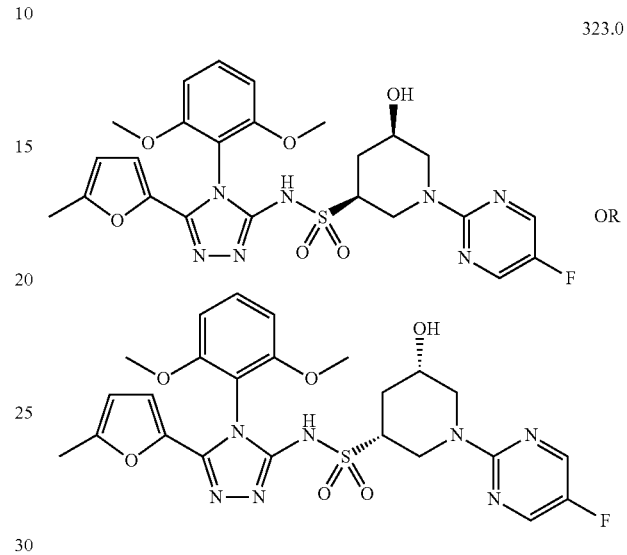

323.0

(3S,5R)—N-(4-(2,6-Dimethoxyphenyl)-5-(5-methyl-2-furanyl)-4H-1,2,4-triazol-3-yl)-1-(5-fluoro-2-pyrimidinyl)-5-hydroxy-3-piperidinesulfonamide or (3R,5S)—N-(4-(2,6-dimethoxyphenyl)-5-(5-methyl-2-furanyl)-4H-1,2,4-triazol-3-yl)-1-(5-fluoro-2-pyrimidinyl)-5-hydroxy-3-piperidinesulfonamide, Example 323.0. The title compound was prepared from Example 320.4 and 2-chloro-5-fluoro-pyrimidine (commercially available from Frontier Scientific Services Inc.) following the procedures described in Example 320.0. $^1$H NMR (400 MHz, CD$_3$OD) δ 8.27 (d, J=0.59 Hz, 2H) 7.56 (t, J=8.54 Hz, 1H) 6.85 (dd, J=8.41, 3.33 Hz, 2H) 6.02 (s, 1H) 5.95 (d, J=3.33 Hz, 1H) 5.03-5.11 (m, 1H) 4.78-4.90 (m, 1H) 3.81 (s, 3H) 3.79 (s, 3H) 3.52-3.62 (m, 1H) 3.08 (tt, J=11.86, 3.79 Hz, 1H) 2.84 (dd, J=12.81, 11.44 Hz, 1H) 2.44-2.55 (m, 2H) 2.26 (s, 3H) 1.58-1.70 (m, 1H). LCMS-ESI (pos.), m/z: 560.2 (M+H)$^+$.

Example 324.0. Preparation of (3S,5R)—N-(4-(2,6-dimethoxyphenyl)-5-(5-methyl-2-furanyl)-4H-1,2,4-triazol-3-yl)-5-hydroxy-1-(4-methoxy-2-pyrimidinyl)-3-piperidinesulfonamide and (3R,5S)—N-(4-(2,6-dimethoxyphenyl)-5-(5-methyl-2-furanyl)-4H-1,2,4-triazol-3-yl)-5-hydroxy-1-(4-methoxy-2-pyrimidinyl)-3-piperidinesulfonamide 324.1

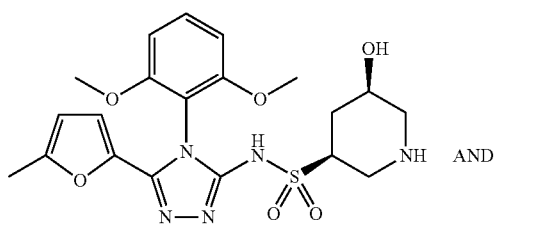

AND

-continued

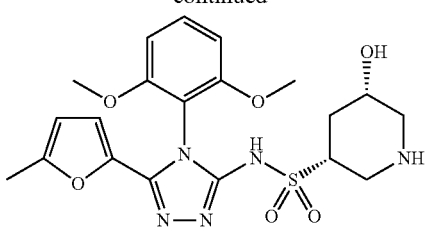

(3R,5S)—N-(4-(2,6-Dimethoxyphenyl)-5-(5-methyl-furan-2-yl)-4H-1,2,4-triazol-3-yl)-5-hydroxypiperidine-3-sulfonamide and (3S,5R)—N-(4-(2,6-dimethoxyphenyl)-5-(5-methylfuran-2-yl)-4H-1,2,4-triazol-3-yl-5-hydroxypiperidine-3-sulfonamide, Example 324.1. The title compound, Example 324.1, was isolated as a by-product in the preparation of Example 320.2. LCMS-ESI (pos.), m/z: 464.1 (M+H)⁺.

324.0

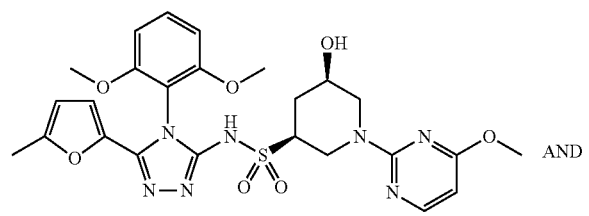
AND

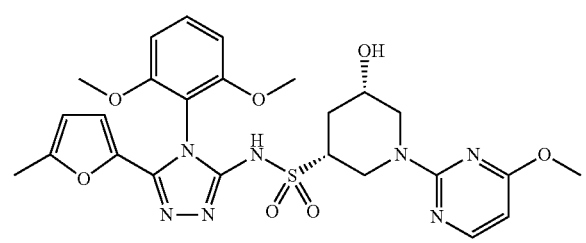

(3S,5R)—N-(4-(2,6-Dimethoxyphenyl)-5-(5-methyl-2-furanyl)-4H-1,2,4-triazol-3-yl)-5-hydroxy-1-(4-methoxy-2-pyrimidinyl)-3-piperidinesulfonamide and (3R,5S)—N-(4-(2,6-dimethoxyphenyl)-5-(5-methyl-2-furanyl)-4H-1,2,4-triazol-3-yl)-5-hydroxy-1-(4-methoxy-2-pyrimidinyl)-3-piperidinesulfonamide, Example 324.0. The title compound was prepared from Example 324.1 and 2-chloro-4-methoxy-pyrimidine (commercially available from Sigma Aldrich) following the procedures described in Example 320.0. This provided the title compound (4.8 mg, 0.007 mmol, 6% yield) as a white solid. LCMS-ESI (pos.) m/z: 572.2 (M+H)⁺.

Example 325.0. Preparation of (3S,5R)-1-(5-cyano-3-pyridinyl)-N-(4-(2,6-dimethoxyphenyl)-5-(5-methyl-2-furanyl)-4H-1,2,4-triazol-3-yl)-5-hydroxy-3-piperidinesulfonamide or (3R,5S)-1-(5-cyano-3-pyridinyl)-N-(4-(2,6-dimethoxyphenyl)-5-(5-methyl-2-furanyl)-4H-1,2,4-triazol-3-yl-5-hydroxy-3-piperidinesulfonamide 325.0

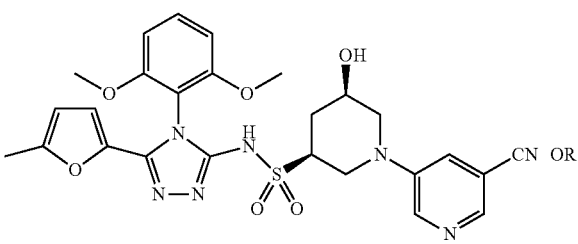

(3S,5R)-1-(5-Cyano-3-pyridinyl)-N-(4-(2,6-dimethoxyphenyl)-5-(5-methyl-2-furanyl)-4H-1,2,4-triazol-3-yl)-5-hydroxy-3-piperidinesulfonamide or (3R,5S)-1-(5-cyano-3-pyridinyl)-N-(4-(2,6-dimethoxyphenyl)-5-(5-methyl-2-furanyl)-4H-1,2,4-triazol-3-yl)-5-hydroxy-3-piperidinesulfonamide, Example 325.0. The title compound was prepared from Example 320.4 (53 mg, 0.114 mmol) and 3-cyano-5-fluoropyridine (69.8 mg, 0.57 mmol, commercially available Combi-Blocks Inc., San Diego, Calif., USA) following the procedures described in Example 320.0. This provided the title compound, Example 325.0 (21.8 mg, 33.7% yield), as an off-white solid. $^{1}$H NMR (400 MHz, DMSO-$d_6$) δ 13.31 (s, 1H) 8.42 (d, J=2.93 Hz, 1H) 8.32 (d, J=1.57 Hz, 1H) 7.66 (dd, J=2.84, 1.66 Hz, 1H) 7.57 (t, J=8.61 Hz, 1H) 6.90 (dd, J=8.51, 5.18 Hz, 2H) 6.13 (dd, J=3.52, 0.98 Hz, 1H) 5.82 (d, J=3.33 Hz, 1H) 4.02 (d, J=11.93 Hz, 1H) 3.93 (dd, J=11.93, 3.72 Hz, 1H) 3.74 (s, 3H) 3.72 (s, 3H) 3.51-3.62 (m, 1H) 3.14 (tt, J=11.86, 3.40 Hz, 1H) 2.79 (t, J=12.23 Hz, 1H) 2.26-2.36 (m, 2H) 2.25 (s, 3H) 1.43 (q, J=11.93 Hz, 1H). LCMS-ESI (pos.) m/z: 566.2 (M+H)⁺.

Example 326.0. Preparation of (3S,5R)—N-(4-(2,6-dimethoxyphenyl)-5-(5-methylfuran-2-yl)-4H-1,2,4-triazol-3-yl)-1-(4,6-dimethylpyrimidin-2-yl)-5-hydroxypiperidine-3-sulfonamide and (3R,5S)—N-(4-(2,6-dimethoxyphenyl)-5-(5-methylfuran-2-yl)-4H-1,2,4-triazol-3-yl)-1-(4,6-dimethylpyrimidin-2-yl)-5-hydroxypiperidine-3-sulfonamide Example 327.0. Preparation of (3S,5R)—N-(4-(2,6-dimethoxyphenyl)-5-(5-methyl-2-furanyl)-4H-1,2,4-triazol-3-yl)-5-hydroxy-1-(4-methoxy-2-pyrimidinyl)-3-piperidinesulfonamide or (3R,5S)—N-(4-(2,6-dimethoxyphenyl)-5-(5-methyl-2-furanyl)-4H-1,2,4-triazol-3-yl)-5-hydroxy-1-(4-methoxy-2-pyrimidinyl)-3-piperidinesulfonamide

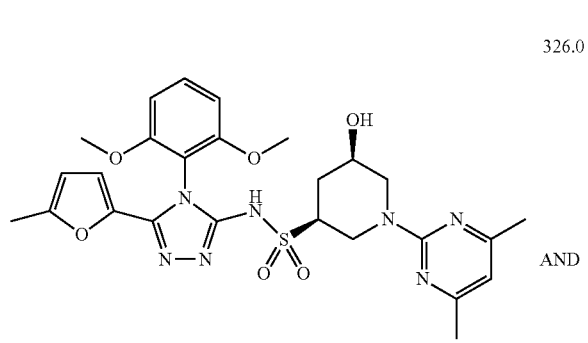

326.0

AND

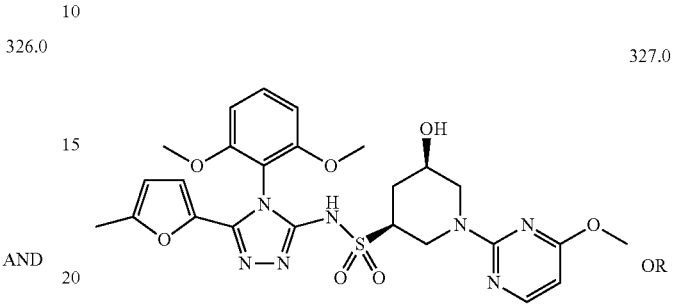

327.0

OR

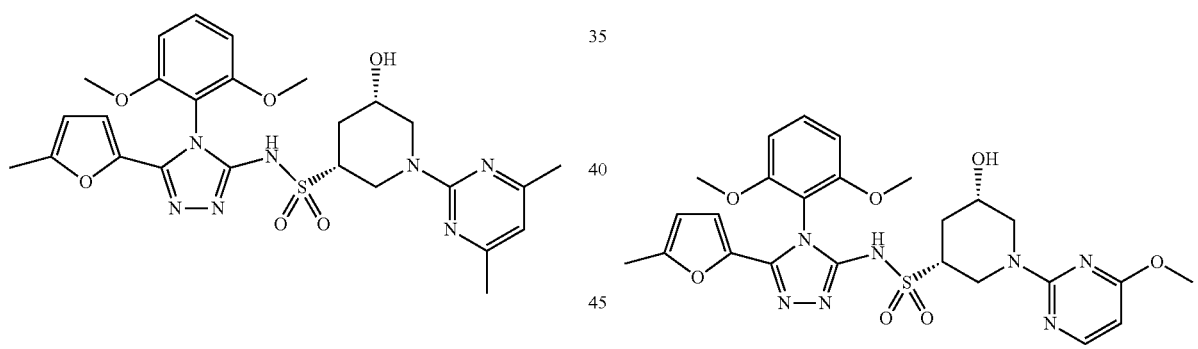

(3S,5R)—N-(4-(2,6-Dimethoxyphenyl)-5-(5-methylfuran-2-yl)-4H-1,2,4-triazol-3-yl)-1-(4,6-dimethylpyrimidin-2-yl)-5-hydroxypiperidine-3-sulfonamide and (3R,5S)—N-(4-(2,6-dimethoxyphenyl)-5-(5-methylfuran-2-yl)-4H-1,2,4-triazol-3-yl)-1-(4,6-dimethylpyrimidin-2-yl)-5-hydroxypiperidine-3-sulfonamide, Example 326.0. The title compound was prepared from Example 324.1 (58 mg, 0.13 mmol) and 2-chloro-4,6-dimethylpyrimidine (36 mg, 0.25 mmol, commercially available from Matrix Scientific, Columbia, S.C., USA) following the procedures described in Example 320.0. This provided the title compound, Example 326.0 (18 mg, 0.032 mmol, 26% yield), as an off-white solid. $^1$H NMR (400 MHz, DMSO-$d_6$) δ 13.26 (s, 1H) 7.56 (t, J=8.51 Hz, 1H) 6.89 (dd, J=8.61, 1.37 Hz, 2H) 6.41 (s, 1H) 6.13 (d, J=2.54 Hz, 1H) 5.82 (d, J=3.33 Hz, 1H) 5.18 (d, J=4.69 Hz, 1H) 5.04 (dd, J=12.42, 3.42 Hz, 1H) 4.81 (dd, J=12.52, 4.69 Hz, 1H) 3.74 (s, 3H) 3.72 (s, 3H) 3.36-3.47 (m, 1H) 2.90-3.01 (m, 1H) 2.59 (t, J=12.03 Hz, 1H) 2.26-2.34 (m, 2H) 2.25 (s, 3H) 2.20 (s, 3H) 2.20 (s, 3H) 1.41 (q, J=11.87 Hz, 1H). LCMS-ESI (pos.) m/z: 570.2 (M+H)$^+$.

(3S,5R)—N-(4-(2,6-Dimethoxyphenyl)-5-(5-methyl-2-furanyl)-4H-1,2,4-triazol-3-yl)-5-hydroxy-1-(4-methoxy-2-pyrimidinyl)-3-piperidinesulfonamide or (3R,5S)—N-(4-(2,6-dimethoxyphenyl)-5-(5-methyl-2-furanyl)-4H-1,2,4-triazol-3-yl)-5-hydroxy-1-(4-methoxy-2-pyrimidinyl)-3-piperidinesulfonamide, Example 327.0. The title compound was prepared from Example 320.4 (59 mg, 0.13 mmol) and 2-chloro-4-methoxypyrimidine (Aldrich, 37 mg, 0.26 mmol) following the procedures described in Example 320.0. To provided the title compound, Example 327.0 (4.8 mg, 0.0070 mmol, 6% yield), as a white solid. $^1$H NMR (400 MHz, DMSO-$d_6$) δ 13.29 (s, 1H) 8.10 (d, J=5.67 Hz, 1H) 7.58 (t, J=8.51 Hz, 1H) 6.91 (dd, J=8.51, 1.27 Hz, 2H) 6.08-6.22 (m, 2H) 5.84 (d, J=3.33 Hz, 1H) 4.92-5.09 (m, 1H) 4.73 (br dd, J=12.03, 4.40 Hz, 2H) 3.80 (s, 3H) 3.76 (s, 3H) 3.75 (s, 3H) 3.36-3.58 (m, 1H) 2.90-3.09 (m, 1H) 2.62-2.76 (m, 1H) 2.35-2.47 (m, 2H) 2.27 (s, 3H) 1.45 (q, J=12.06 Hz, 1H) LCMS-ESI (pos.) m/z: 572.2 (M+H)$^+$.

Example 328.0. Preparation of (3S,5R)-1-(5-chloro-2-pyrimidinyl)-N-(4-(2,6-dimethoxyphenyl)-5-(5-methyl-2-furanyl)-4H-1,2,4-triazol-3-yl)-5-hydroxy-3-piperidinesulfonamide and (3R,5S)-1-(5-chloro-2-pyrimidinyl)-N-(4-(2,6-dimethoxyphenyl)-5-(5-methyl-2-furanyl)-4H-1,2,4-triazol-3-yl)-5-hydroxy-3-piperidinesulfonamide Example 329.0. Preparation of (3S,5R)-1-(3-cyano-4-fluorophenyl)-N-(4-(2,6-dimethoxyphenyl)-5-(5-methyl-2-furanyl)-4H-1,2,4-triazol-3-yl)-5-hydroxy-3-piperidinesulfonamide and (3R,5S)-1-(3-cyano-4-fluorophenyl)-N-(4-(2,6-dimethoxyphenyl)-5-(5-methyl-2-furanyl)-4H-1,2,4-triazol-3-yl)-5-hydroxy-3-piperidinesulfonamide

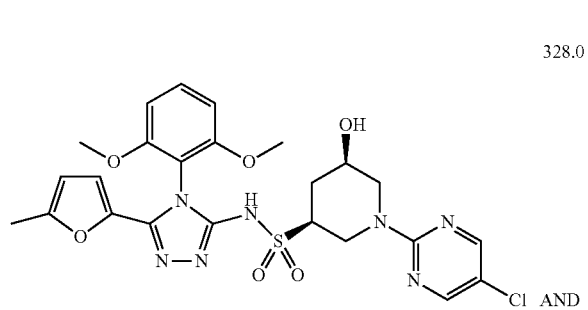

328.0

AND

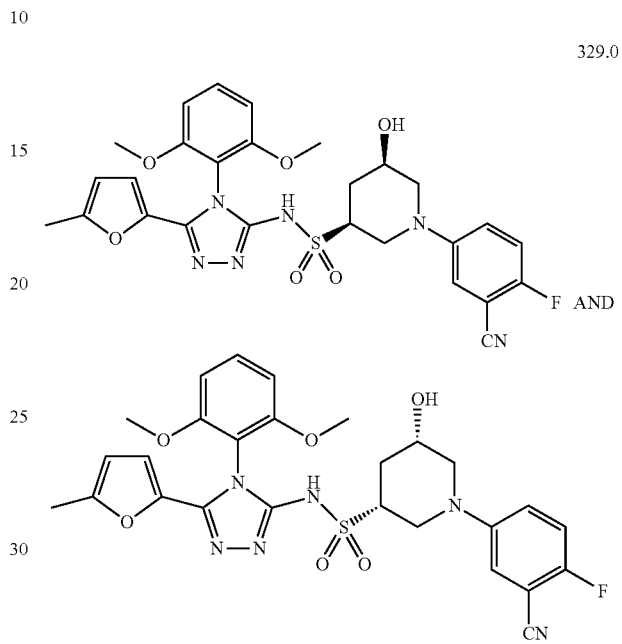

329.0

AND

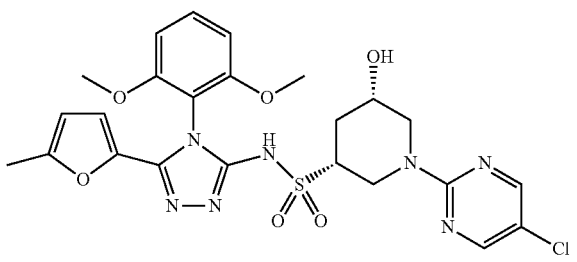

(3S,5R)-1-(5-Chloro-2-pyrimidinyl)-N-(4-(2,6-dimethoxyphenyl)-5-(5-methyl-2-furanyl)-4H-1,2,4-triazol-3-yl)-5-hydroxy-3-piperidinesulfonamide and (3R,5S)-1-(5-chloro-2-pyrimidinyl)-N-(4-(2,6-dimethoxyphenyl)-5-(5-methyl-2-furanyl)-4H-1,2,4-triazol-3-yl)-5-hydroxy-3-piperidinesulfonamide, Example 328.0. The title compound was prepared from Example 324.1 (79 mg, 0.17 mmol) 2,5-dichloropyrimidine (51 mg, 0.34 mmol, commercially available from Matrix Scientific, Columbia, S.C., USA) following the procedures described in Example 320.0. This provided the title compound, Example 328.0 (15 mg, 0.022 mmol, 13% yield), as a white solid. $^1$H NMR (400 MHz, CD$_3$OD) δ 8.29 (s, 2H) 7.56 (t, J=8.51 Hz, 1H) 6.86 (dd, J=8.61, 3.33 Hz, 2H) 6.02 (dd, J=3.74 Hz, 1H) 5.95 (d, J=3.33 Hz, 1H) 5.05-5.13 (m, 1H) 4.79-4.88 (m, 1H) 3.81 (s, 3H) 3.79 (s, 3H) 3.52-3.61 (m, 1H) 3.03-3.12 (m, 1H) 2.85 (dd, J=12.91, 11.54 Hz, 1H) 2.45-2.55 (m, 2H) 2.26 (s, 3H) 1.65 (q, J=12.13 Hz, 1H). LCMS-ESI (pos.) m/z: 576.0 (M+H)$^+$.

(3S,5R)-1-(3-Cyano-4-fluorophenyl)-N-(4-(2,6-dimethoxyphenyl)-5-(5-methyl-2-furanyl)-4H-1,2,4-triazol-3-yl)-5-hydroxy-3-piperidinesulfonamide and (3R,5S)-1-(3-cyano-4-fluorophenyl)-N-(4-(2,6-dimethoxyphenyl)-5-(5-methyl-2-furanyl)-4H-1,2,4-triazol-3-yl)-5-hydroxy-3-piperidinesulfonamide, Example 329.0. A mixture of Example 324.1 (53.6 mg, 0.116 mmol), chloro(2-dicyclohexylphosphino-2',6'-di-i-propoxy-1,1'-biphenyl)[2-(2-aminoethyl-phenyl)]Pd(II), methyl-t-butylether adduct (commercially available from Strem Chemicals, Inc., Newburyport, Mass., USA) (18 mg, 0.023 mmol), 5-bromo-2-fluorobenzonitrile (46.3 mg, 0.231 mmol) (Aldrich), and potassium carbonate (80 mg, 0.58 mmol) in t-BuOH (1 mL) was bubbled with nitrogen for a min. The reaction mixture was then heated at 100° C. for 4 h using a microwave. To the reaction mixture was added chloro(2-dicyclohexylphosphino-2',6'-di-i-propoxy-1,1'-biphenyl)[2-(2-aminoethyl-phenyl)]Pd(II), methyl-t-butylether adduct (18 mg, 0.023 mmol) and 5-bromo-2-fluorobenzonitrile (46.3 mg, 0.231 mmol). N$_2$ was then bubbled through the reaction for 1 min, and the reaction was then heated at 100° C. for an additional 16 h using the microwave. The reaction mixture was partitioned between DCM (5 mL) and 0.2 N HCl (5 mL). The layers were separated. The aqueous layer was extracted with DCM (2×5 mL). The combined organic layers were combined and dried over Na$_2$SO$_4$. The solution was filtered and concentrated in vacuo to give a brown oil. The material was diluted with MeOH (2 mL)/DMSO (2 mL), filtered through GHP Acrodisc 25 mm syringe filter, and then purified by preparative HPLC on a C-18 column (CAPCELL UG120 5 uM, 30 mm×250 mm) eluting with 20%-95% of B/A (B=0.1% TFA in ACN, A=0.1% TFA in water). The combined fractions was lyophilized to provide the title compound, Example 329.0 (3.8 mg, 0.0055 mmol, 5% yield), as an off-white solid. $^1$H NMR (400 MHz, DMSO-$d_6$) δ 13.30 (s, 1H) 7.57 (t, J=8.51 Hz, 1H) 7.31-7.37 (m, 1H) 7.26 (dd, J=5.09, 3.13 Hz, 1H) 7.16-7.22 (m, 1H) 6.89 (t, J=8.31 Hz, 2H) 6.13 (dd, J=3.52, 0.98 Hz, 1H) 5.82 (d, J=3.33 Hz, 1H) 3.84 (d, J=10.56 Hz, 1H) 3.74-3.79 (m, 1H) 3.73 (s, 3H) 3.70 (s, 3H) 3.57 (ddd, J=15.26, 10.76, 4.50 Hz, 1H) 3.08 (tt, J=11.66, 3.40 Hz, 1H) 2.67 (t, J=11.93 Hz, 1H) 2.38 (dd, J=12.03, 10.66 Hz, 1H) 2.26-2.32 (m, 1H) 2.25 (s, 3H) 1.38 (q, J=11.93 Hz, 1H). LCMS-ESI (pos.) m/z: 583.1 (M+H)$^+$.

Example 330.0. Preparation of (3S,5R)-1-(3-cyano-5-fluoro-2-pyridinyl)-N-(4-(2,6-dimethoxyphenyl)-5-(5-methyl-2-furanyl)-4H-1,2,4-triazol-3-yl)-5-hydroxy-3-piperidinesulfonamide and (3R,5S)-1-(3-cyano-5-fluoro-2-pyridinyl)-N-(4-(2,6-dimethoxyphenyl)-5-(5-methyl-2-furanyl)-4H-1,2,4-triazol-3-yl)-5-hydroxy-3-piperidinesulfonamide

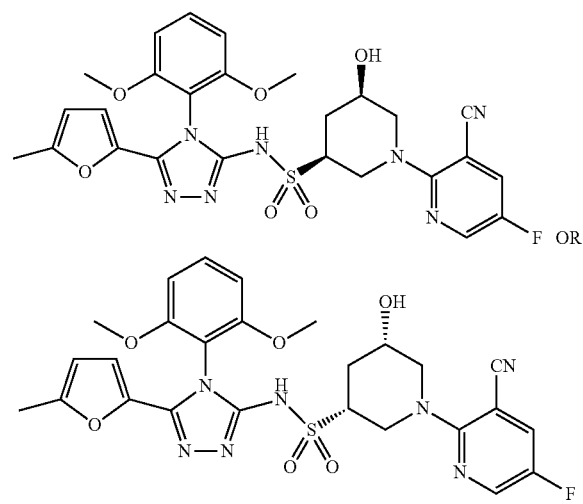

330.0

(3S,5R)-1-(3-Cyano-5-fluoro-2-pyridinyl)-N-(4-(2,6-dimethoxyphenyl)-5-(5-methyl-2-furanyl)-4H-1,2,4-triazol-3-yl)-5-hydroxy-3-piperidinesulfonamide and (3R,5S)-1-(3-cyano-5-fluoro-2-pyridinyl)-N-(4-(2,6-dimethoxyphenyl)-5-(5-methyl-2-furanyl)-4H-1,2,4-triazol-3-yl)-5-hydroxy-3-piperidinesulfonamide, Example 330.0. The title compound was prepared from Example 320.4 (140.2 mg, 0.302 mmol) and 2-chloro-5-fluoronicotinonitrile (95 mg, 0.605 mmol, commercially available from Insight chemical solutions, Liverpool, UK) following the procedures described in Example 320.0. This provided the title compound, Example 330.0 (52 mg, 0.075 mmol, 24.6% yield), as a pale yellow solid. $^1$H NMR (400 MHz, DMSO-$d_6$) δ 13.27 (s, 1H) 8.46 (d, J=3.13 Hz, 1H) 8.25 (dd, J=8.12, 3.03 Hz, 1H) 7.56 (t, J=8.51 Hz, 1H) 6.88 (dd, J=10.56, 8.61 Hz, 2H) 6.13 (dd, J=3.42, 0.88 Hz, 1H) 5.81 (d, J=3.33 Hz, 1H) 5.27 (br. s., 1H) 4.27 (d, J=11.15 Hz, 1H) 4.08 (dd, J=12.42, 4.40 Hz, 1H) 3.73 (s, 3H) 3.69 (s, 3H) 3.58-3.67 (m, 1H) 3.08-3.18 (m, 1H) 2.80 (t, J=12.03 Hz, 1H) 2.55 (dd, J=12.32, 10.76 Hz, 1H) 2.31 (d, J=11.54 Hz, 1H) 2.25 (s, 3H) 1.41 (q, J=12.00 Hz, 1H). LCMS-ESI (pos.) m/z: 584.2 (M+H)$^+$.

Example 331.0. Preparation of (3S,5R)-1-(3-cyano-5-fluoropyridin-2-yl)-N-(4-(2,6-dimethoxyphenyl)-5-(5-methylfuran-2-yl)-4H-1,2,4-triazol-3-yl)-5-hydroxypiperidine-3-sulfonamide and (3R,5S)-1-(3-cyano-5-fluoropyridin-2-yl)-N-(4-(2,6-dimethoxyphenyl)-5-(5-methylfuran-2-yl)-4H-1,2,4-triazol-3-yl)-5-hydroxypiperidine-3-sulfonamide

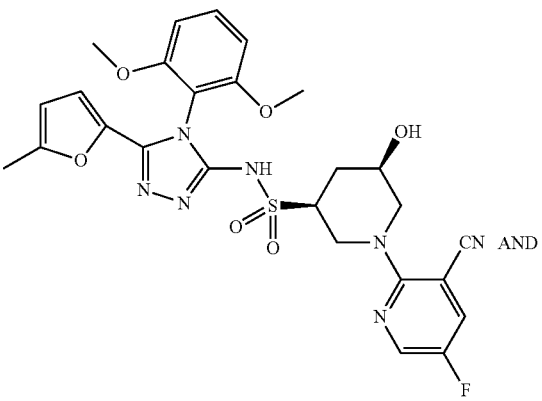

331.0

(3S,5R)-1-(3-Cyano-5-fluoropyridin-2-yl)-N-(4-(2,6-dimethoxyphenyl)-5-(5-methylfuran-2-yl)-4H-1,2,4-triazol-3-yl)-5-hydroxypiperidine-3-sulfonamide and (3R,5S)-1-(3-cyano-5-fluoropyridin-2-yl)-N-(4-(2,6-dimethoxyphenyl)-5-(5-methylfuran-2-yl)-4H-1,2,4-triazol-3-yl)-5-hydroxypiperidine-3-sulfonamide, Example 331.0. The title compound, Example 331.0, was prepared from Example 324.1 (63 mg, 0.14 mmol) and 2-chloro-5-fluoronicotinonitrile (43 mg, 0.27 mmol, commercially available from Insight chemical solutions, Liverpool, UK) following the procedures described in Example 320.0. This provided the title compound, Example 331.0 (11 mg, 0.016 mmol, 11% yield), as a white solid. $^1$H NMR (400 MHz, DMSO-$d_6$) δ 13.27 (s, 1H) 8.46 (d, J=3.13 Hz, 1H) 8.25 (dd, J=8.12, 3.03 Hz, 1H) 7.56 (t, J=8.51 Hz, 1H) 6.88 (dd, J=10.56, 8.61 Hz, 2H) 6.13 (dd, J=3.42, 0.88 Hz, 1H) 5.81 (d, J=3.33 Hz, 1H) 5.27 (br. s., 1H) 4.27 (d, J=11.15 Hz, 1H) 4.08 (dd, J=12.42, 4.40 Hz, 1H) 3.73 (s, 3H) 3.69 (s, 3H) 3.58-3.67 (m, 1H) 3.08-3.18 (m, 1H) 2.80 (t, J=12.03 Hz, 1H) 2.55 (dd, J=12.32, 10.76 Hz, 1H) 2.31 (d, J=11.54 Hz, 1H) 2.25 (s, 3H) 1.41 (q, J=12.00 Hz, 1H). LCMS-ESI (pos.) m/z: 584.2 (M+H)$^+$.

Example 332.0. Preparation of (3R,5R)—N-(4-(2,6-dimethoxyphenyl)-5-(5-methylfuran-2-yl)-4H-1,2,4-triazol-3-yl)-1-(5-fluoropyrimidin-2-yl)-5-hydroxypiperidine-3-sulfonamide and (3R,5S)—N-(4-(2,6-dimethoxyphenyl)-5-(5-methylfuran-2-yl)-4H-1,2,4-triazol-3-yl)-1-(5-fluoropyrimidin-2-yl)-5-hydroxypiperidine-3-sulfonamide and (3S,5R)—N-(4-(2,6-dimethoxyphenyl)-5-(5-methylfuran-2-yl)-4H-1,2,4-triazol-3-yl)-1-(5-fluoropyrimidin-2-yl)-5-hydroxypiperidine-3-sulfonamide and (3S,5S)—N-(4-(2,6-dimethoxyphenyl)-5-(5-methylfuran-2-yl)-4H-1,2,4-triazol-3-yl)-1-(5-fluoropyrimidin-2-yl)-5-hydroxypiperidine-3-sulfonamide 332.0

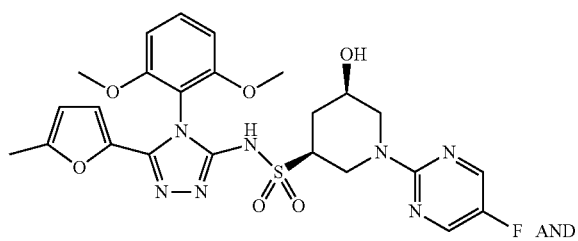
AND

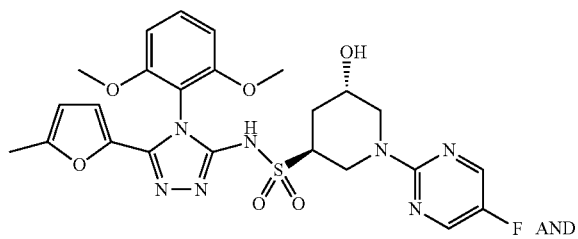
AND

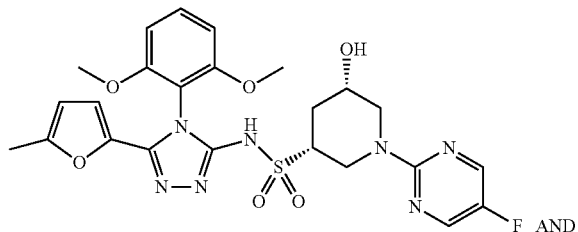
AND

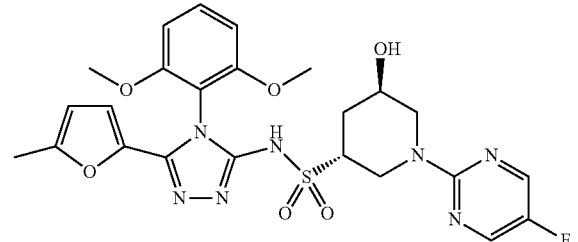

(3R,5R)—N-(4-(2,6-Dimethoxyphenyl)-5-(5-methylfuran-2-yl)-4H-1,2,4-triazol-3-yl)-1-(5-fluoropyrimidin-2-yl)-5-hydroxypiperidine-3-sulfonamide and (3R,5S)—N-(4-(2,6-dimethoxyphenyl)-5-(5-methylfuran-2-yl)-4H-1,2,4-triazol-3-yl)-1-(5-fluoropyrimidin-2-yl)-5-hydroxypiperidine-3-sulfonamide and (3S,5R)—N-(4-(2,6-dimethoxyphenyl)-5-(5-methylfuran-2-yl)-4H-1,2,4-triazol-3-yl)-1-(5-fluoropyrimidin-2-yl)-5-hydroxypiperidine-3-sulfonamide and (3S,5S)—N-(4-(2,6-dimethoxyphenyl)-5-(5-methylfuran-2-yl)-4H-1,2,4-triazol-3-yl)-1-(5-fluoropyrimidin-2-yl)-5-hydroxypiperidine-3-sulfonamide, Example 332.0. A stirred solution of Example 167.3 (218 mg, 0.789 mmol), Example 364.1 (460 mg, 1.26 mmol), cesium carbonate (643 mg, 1.97 mmol), and trans-N,N'-dimethyl-1,2-cyclohexanediamine (0.249 mL, 1.58 mmol) in ACN (2 mL) was bubbled with argon gas for 3 min. Copper(I) iodide (180 mg, 0.947 mmol) was added in one portion. The reaction mixture was heated at 83° C. for 20 h using an oil bath. The reaction mixture was cooled to RT. The reaction mixture was diluted with a saturated aqueous solution of NH$_4$Cl (50 mL), stirred for 1 h, and extracted with DCM (3×50 mL). The combined organic layers were dried over Na$_2$SO$_4$. The solution was filtered and concentrated in vacuo to provide a dark green oil. The initial material was absorbed onto a plug of silica gel and purified by chromatography through a Redi-Sep pre-packed silica gel column (24 g) eluting with a gradient of 0% to 100% EtOAc in DCM and then with 5% MeOH in DCM to provide enriched product. The enriched product was triturated with 5/5/90 EtOAc/MeOH/DCM in hexanes (3×3 mL) to provide the title compound, Example 332.0 (81 mg, 0.145 mmol, 18%), as a an off-white powder (a mixture of four diastereomers. The racemic cis isomers were the major products, and the racemic trans isomers were the minor products. LCMS-ESI (pos.), m/z: 560.2 (M+H)$^+$.

Example 333.0. Preparation of (3S,5R)-1-(4-cyanopyridin-2-yl)-N-(4-(2,6-dimethoxyphenyl)-5-(5-methylfuran-2-yl)-4H-1,2,4-triazol-3-yl)-5-hydroxypiperidine-3-sulfonamide and (3R,5S)-1-(4-cyanopyridin-2-yl)-N-(4-(2,6-dimethoxyphenyl)-5-(5-methylfuran-2-yl)-4H-1,2,4-triazol-3-yl)-5-hydroxypiperidine-3-sulfonamide 333.0

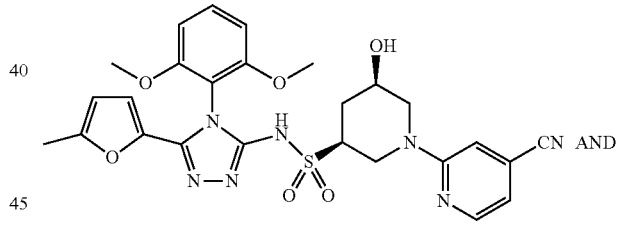
AND

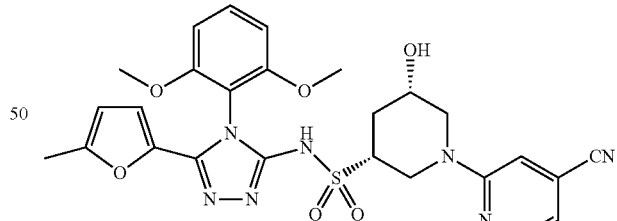

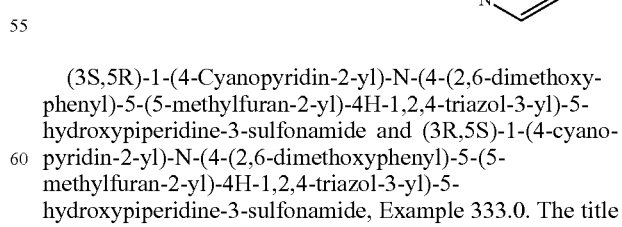

(3S,5R)-1-(4-Cyanopyridin-2-yl)-N-(4-(2,6-dimethoxyphenyl)-5-(5-methylfuran-2-yl)-4H-1,2,4-triazol-3-yl)-5-hydroxypiperidine-3-sulfonamide and (3R,5S)-1-(4-cyanopyridin-2-yl)-N-(4-(2,6-dimethoxyphenyl)-5-(5-methylfuran-2-yl)-4H-1,2,4-triazol-3-yl)-5-hydroxypiperidine-3-sulfonamide, Example 333.0. The title compound was prepared from Example 324.1 (80 mg, 0.17 mmol) and 2-fluoroisonicotinonitrile (42 mg, 0.35 mmol, commercially available from Combi-Blocks Inc., San Diego, Calif., USA) following the procedures described in Example 320.0. This provided the title compound, Example 333.0 (19 mg, 0.028 mmol, 16% yield), as an off-white solid. $^1$H NMR (400 MHz, CD$_3$OD) δ 8.25 (dd, J=5.09, 0.59 Hz, 1H) 7.57 (t, J=8.51 Hz, 1H) 7.06 (s, 1H) 6.84-6.88 (m, 3H) 6.02 (dd, J=3.67 Hz, 1H) 5.96 (d, J=3.33 Hz, 1H) 4.66-4.72 (m, 1H) 4.45 (dd, J=12.81, 4.60 Hz, 1H) 3.81 (s, 3H) 3.78 (s, 3H) 3.56-3.65 (m, 1H) 3.09-3.17 (m, 1H) 2.91 (dd, J=13.11, 11.35 Hz, 1H) 2.59 (dd, J=12.81, 10.66 Hz, 1H) 2.49 (d, J=11.74 Hz, 1H) 2.26 (s, 3H) 1.62-1.71 (m, 1H). LCMS-ESI (pos.) m/z: 566.2 (M+H)$^+$.

Example 334.0. Preparation of (3S,5R)-1-(5-cyanopyridin-3-yl)-N-(4-(2,6-dimethoxyphenyl)-5-(5-methylfuran-2-yl)-4H-1,2,4-triazol-3-yl)-5-hydroxypiperidine-3-sulfonamide and (3S,5R)-1-(5-cyanopyridin-3-yl)-N-(4-(2,6-dimethoxyphenyl)-5-(5-methylfuran-2-yl)-4H-1,2,4-triazol-3-3-yl)-5-hydroxypiperidine-3-sulfonamide 334.0

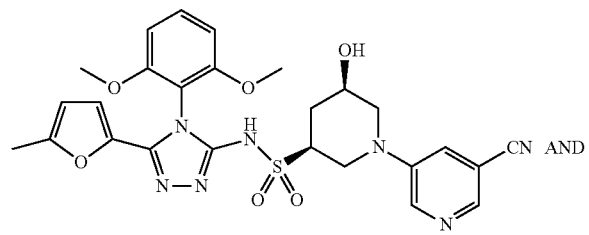

CN AND

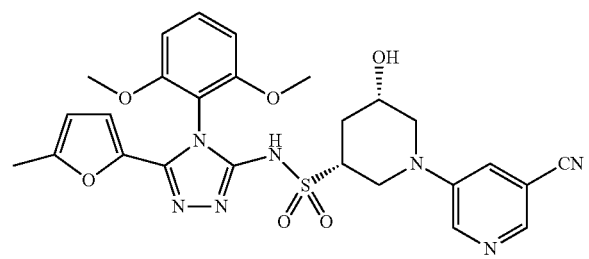

CN (3S,5R)-1-(5-Cyanopyridin-3-yl)-N-(4-(2,6-dimethoxyphenyl)-5-(5-methylfuran-2-yl)-4H-1,2,4-triazol-3-yl)-5-hydroxypiperidine-3-sulfonamide and (3S,5R)-1-(5-cyanopyridin-3-yl)-N-(4-(2,6-dimethoxyphenyl)-5-(5-methylfuran-2-yl)-4H-1,2,4-triazol-3-yl)-5-hydroxypiperidine-3-sulfonamide, Example 334.0. The title compound was prepared from Example 324.1 (58 mg, 0.13 mmol) and 3-cyano-5-fluoropyridine (31 mg, 0.25 mmol, commercially available Combi-Blocks Inc., San Diego, Calif., USA) following the procedures described in Example 320.0. This provided the title compound, Example 320.0 (15 mg, 0.022 mmol, 18% yield), as an off-white solid. $^1$H NMR (400 MHz, DMSO-d$_6$) δ 13.31 (s, 1H) 8.42 (d, J=2.93 Hz, 1H) 8.32 (d, J=1.57 Hz, 1H) 7.66 (dd, J=2.84, 1.66 Hz, 1H) 7.57 (t, J=8.61 Hz, 1H) 6.90 (dd, J=8.51, 5.18 Hz, 2H) 6.13 (dd, J=3.52, 0.98 Hz, 1H) 5.82 (d, J=3.33 Hz, 1H) 4.02 (d, J=11.93 Hz, 1H) 3.93 (dd, J=11.93, 3.72 Hz, 1H) 3.74 (s, 3H) 3.72 (s, 3H) 3.51-3.62 (m, 1H) 3.14 (tt, J=11.86, 3.40 Hz, 1H) 2.79 (t, J=12.23 Hz, 1H) 2.26-2.36 (m, 2H) 2.25 (s, 3H) 1.43 (q, J=11.93 Hz, 1H). LCMS-ESI (pos.) m/z: 566.2 (M+H)$^+$.

Example 335.0. Preparation of (3S,5R)—N-(4-(2,6-dimethoxyphenyl)-5-(5-methylfuran-2-yl)-4H-1,2,4-triazol-3-yl)-5-hydroxy-1-(5-methoxypyrimidin-2-yl)piperidine-3-sulfonamide and (3R,5S)—N-(4-(2,6-dimethoxyphenyl)-5-(5-methylfuran-2-yl)-4H-1,2,4-triazol-3-yl)-5-hydroxy-1-(5-methoxypyrimidin-2-yl)piperidine-3-sulfonamide 335.0

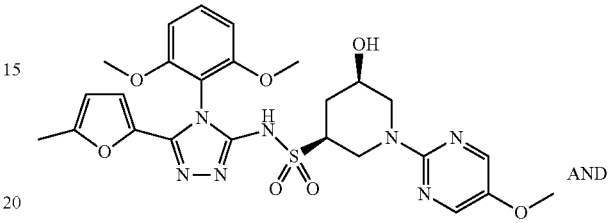

AND

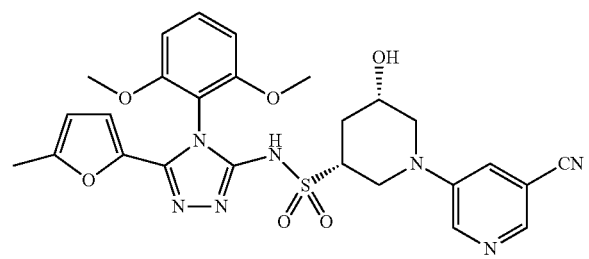

(3S,5R)—N-(4-(2,6-Dimethoxyphenyl)-5-(5-methylfuran-2-yl)-4H-1,2,4-triazol-3-yl)-5-hydroxy-1-(5-methoxypyrimidin-2-yl)piperidine-3-sulfonamide and (3R,5S)—N-(4-(2,6-dimethoxyphenyl)-5-(5-methylfuran-2-yl)-4H-1,2,4-triazol-3-yl)-5-hydroxy-1-(5-methoxypyrimidin-2-yl)piperidine-3-sulfonamide, Example 335.0. The title compound was prepared from Example 324.1 (57 mg, 0.12 mmol) and 2-chloro-5-methoxypyrimidine (Aldrich, 36 mg, 0.25 mmol) following the procedures described in Example 320.0. This provided the title compound, Example 335.0 (22 mg, 0.032 mmol, 26% yield), as a white solid. $^1$H NMR (400 MHz, DMSO-d$_6$) δ 13.24 (s, 1H) 8.19 (s, 2H) 7.57 (t, J=8.51 Hz, 1H) 6.90 (dd, J=8.61, 4.30 Hz, 2H) 6.13 (dd, J=3.52, 0.98 Hz, 1H) 5.82 (d, J=3.33 Hz, 1H) 4.87 (dd, J=12.52, 3.13 Hz, 1H) 4.63 (dd, J=12.42, 4.60 Hz, 1H) 3.77 (s, 3H) 3.75 (s, 3H) 3.73 (s, 3H) 3.38-3.47 (m, 1H) 2.92 (tt, J=11.91, 3.64 Hz, 1H) 2.60-2.68 (m, 1H) 2.31-2.38 (m, 1H) 2.26-2.29 (m, 1H) 2.25 (s, 3H) 1.41 (q, J=11.80 Hz, 1H). LCMS-ESI (pos.) m/z: 572.2 (M+H)$^+$.

Example 336.0. Preparation of (3S,5R)—N-(4-(2,6-dimethoxyphenyl)-5-(5-methylfuran-2-yl)-4H-1,2,4-triazol-3-yl)-1-(4,6-dimethylpyrimidin-2-yl)-5-hydroxypiperidine-3-sulfonamide or (3R,5S)—N-(4-(2,6-dimethoxyphenyl)-5-(5-methylfuran-2-yl)-4H-1,2,4-triazol-3-yl)-1-(4,6-dimethylpyrimidin-2-yl)-5-hydroxypiperidine-3-sulfonamide Example 337.0. Preparation of (3S,5R)-3-(N-(4-(2,6-dimethoxyphenyl)-5-(5-methylfuran-2-yl)-4H-1,2,4-triazol-3-yl)sulfamoyl)-5-hydroxy-N,N-dimethylpiperidine-1-carboxamide or (3R,5S)-3-(N-(4-(2,6-dimethoxyphenyl)-5-(5-methylfuran-2-yl)-4H-1,2,4-triazol-3-yl)sulfamoyl)-5-hydroxy-N,N-dimethylpiperidine-1-carboxamide

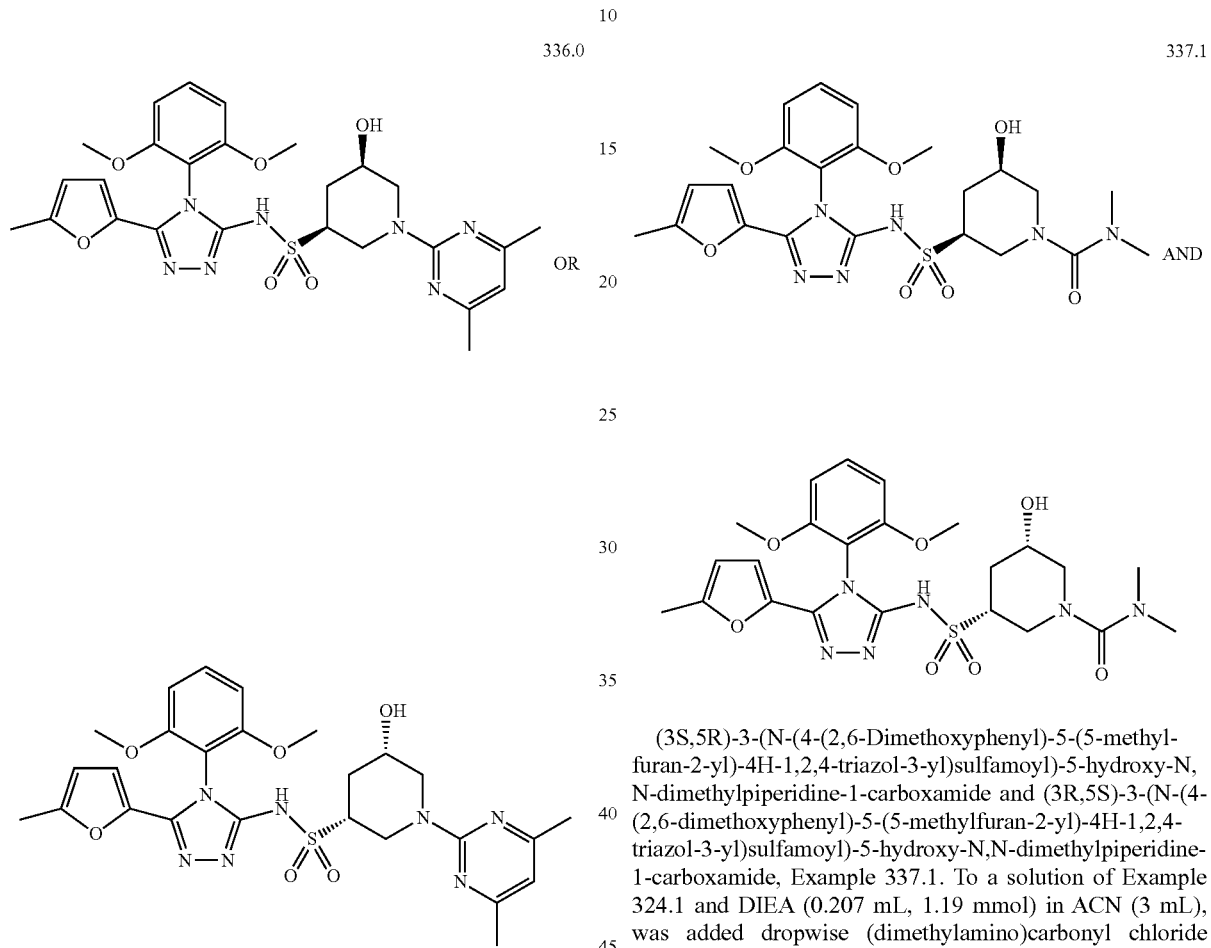

(3S,5R)—N-(4-(2,6-Dimethoxyphenyl)-5-(5-methylfuran-2-yl)-4H-1,2,4-triazol-3-yl)-1-(4,6-dimethylpyrimidin-2-yl)-5-hydroxypiperidine-3-sulfonamide or (3R,5S)—N-(4-(2,6-dimethoxyphenyl)-5-(5-methylfuran-2-yl)-4H-1,2,4-triazol-3-yl)-1-(4,6-dimethylpyrimidin-2-yl)-5-hydroxypiperidine-3-sulfonamide, Example 336.0. The title compound was prepared from Example 320.4 (83 mg, 0.18 mmol) and 2-chloro-4,6-dimethylpyrimidine (51 mg, 0.36 mmol, commercially available from Matrix Scientific, Columbia, S.C., USA) following the procedures described in Example 320.0. This provided the title compound, Example 336.0, as an off-white solid. $^1$H NMR (400 MHz, DMSO-d$_6$) δ 13.26 (s, 1H) 7.56 (t, J=8.51 Hz, 1H) 6.89 (dd, J=8.61, 1.37 Hz, 2H) 6.41 (s, 1H) 6.13 (d, J=2.54 Hz, 1H) 5.82 (d, J=3.33 Hz, 1H) 5.18 (d, J=4.69 Hz, 1H) 5.04 (dd, J=12.42, 3.42 Hz, 1H) 4.81 (dd, J=12.52, 4.69 Hz, 1H) 3.74 (s, 3H) 3.72 (s, 3H) 3.36-3.47 (m, 1H) 2.90-3.01 (m, 1H) 2.59 (t, J=12.03 Hz, 1H) 2.26-2.34 (m, 2H) 2.25 (s, 3H) 2.20 (s, 3H) 2.20 (s, 3H) 1.41 (q, J=11.87 Hz, 1H). LCMS-ESI (pos.) m/z: 570.2 (M+H)$^+$.

(3S,5R)-3-(N-(4-(2,6-Dimethoxyphenyl)-5-(5-methylfuran-2-yl)-4H-1,2,4-triazol-3-yl)sulfamoyl)-5-hydroxy-N,N-dimethylpiperidine-1-carboxamide and (3R,5S)-3-(N-(4-(2,6-dimethoxyphenyl)-5-(5-methylfuran-2-yl)-4H-1,2,4-triazol-3-yl)sulfamoyl)-5-hydroxy-N,N-dimethylpiperidine-1-carboxamide, Example 337.1. To a solution of Example 324.1 and DIEA (0.207 mL, 1.19 mmol) in ACN (3 mL), was added dropwise (dimethylamino)carbonyl chloride (0.066 mL, 0.715 mmol) in ACN (1.0 mL). The reaction mixture was stirred at RT overnight. The solvent was then evaporated on a rotary evaporator at 25° C. The material was dissolved in DCM (20 mL), washed with aqueous 0.2 N HCl (20 mL), and then washed with brine (20 mL). The organic solution was dried over Na$_2$SO$_4$, filtered, and concentrated in vacuo. The residue was diluted with 1:1 DMSO/MeOH (8 mL), filtered through a GHP Acrodisc 25 mm syringe filter (Lot 21740981), and then purified by preparative HPLC on a C-18 column (Phenomenex 00G-4436-V0, Gemini 10 u, C18, 110 A, 50 mm×250 mm, serial number 387099-1) eluting with 10%-95% of B/A (B=0.1% TFA in ACN, A=0.1% TFA in water) at 100 mL/min. The combined fractions were lyophilized to provide the title compound, Example 337.1 (93 mg, 0.21 mmol, 45%), as a white solid. $^1$H NMR (400 MHz, CD$_3$OD) δ 7.56 (t, J=8.51 Hz, 1H) 6.85 (d, J=8.41 Hz, 2H) 6.02 (dd, J=3.52, 0.98 Hz, 1H) 5.94 (d, J=3.52 Hz, 1H) 3.91-3.98 (m, 1H) 3.80 (s, 3H) 3.79 (s, 3H) 3.57-3.72 (m, 2H) 3.16 (ddt, J=12.37, 11.40, 3.67, 3.67 Hz, 1H) 2.82 (s, 3H) 2.82 (s, 3H) 2.73 (dd, J=12.81, 11.44 Hz, 1H) 2.38-2.49 (m, 2H) 2.25 (s, 3H) 1.47-1.57 (m, 1H). LCMS-ESI (pos.), m/z: 535.1 (M+H)$^+$.

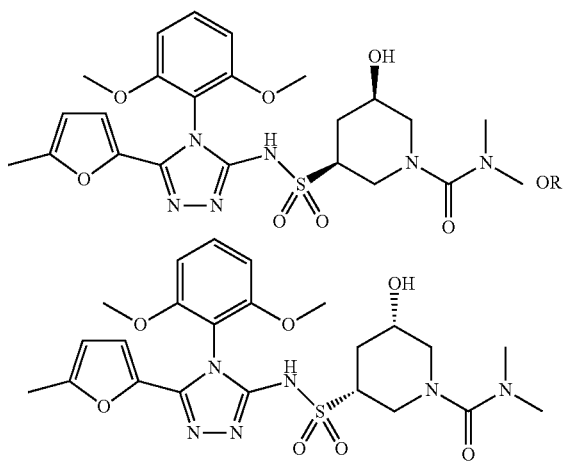

337.0

(3S,5R)-3-(N-(4-(2,6-Dimethoxyphenyl)-5-(5-methyl-furan-2-yl)-4H-1,2,4-triazol-3-yl)sulfamoyl)-5-hydroxy-N,N-dimethylpiperidine-1-carboxamide or (3R,5S)-3-(N-(4-(2,6-dimethoxyphenyl)-5-(5-methylfuran-2-yl)-4H-1,2,4-triazol-3-yl)sulfamoyl)-5-hydroxy-N,N-dimethylpiperidine-1-carboxamide, Example 337.0. The title compound, Example 337.0, was the first isomer to elute under the following SFC conditions: Thar 200, 54 g/min MeOH (Neat)+66 g/min CO$_2$ on 250×30 mm IC column Outlet pressure=100 bar, Temp.=25° C., Wavelength=277 nm. Used 0.5 mL injections solution of Example 337.1 (85 mg sample in 7 mL MeOH/DCM, c=12.1 mg/mL), resulting in 6 mg/injection. Run time 20.0 min., cycle time=8.8 min. $^1$H NMR (400 MHz, DMSO-d$_6$) δ 13.23 (br. s., 1H) 7.55 (t, J=8.51 Hz, 1H) 6.88 (d, J=8.61 Hz, 2H) 6.11 (d, J=1.57 Hz, 1H) 5.76 (br. s., 1H) 5.10 (d, J=4.50 Hz, 1H) 3.75-3.79 (m, 1H) 3.73 (s, 3H) 3.72 (s, 3H) 3.41-3.57 (m, 2H) 3.00-3.20 (m, 1H) 2.69 (s, 3H) 2.69 (s, 3H) 2.47-2.54 (m, 1H) 2.20-2.27 (m, 5H) 1.22-1.28 (m, 1H). LCMS-ESI (pos.), m/z: 535.1 (M+H)$^+$.

Example 338.0. Preparation of (3R)-3-((4-(2,6-dimethoxyphenyl)-5-(2-furanyl)-4H-1,2,4-triazol-3-yl)sulfamoyl)-N,N-dimethyl-1-piperidinecarboxamide and (S)-3-(N-(4-(2,6-dimethoxyphenyl)-5-(furan-2-yl)-4H-1,2,4-triazol-3-yl)sulfamoyl)-N,N-dimethyl-piperidine-1-carboxamide

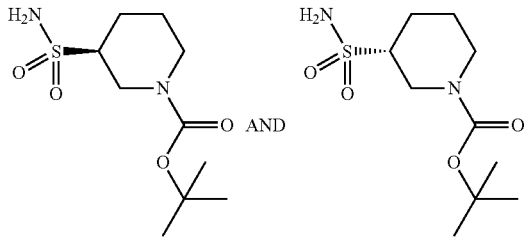

338.1

(S)-tert-Butyl 3-sulfamoylpiperidine-1-carboxylate and (R)-tert-butyl 3-sulfamoylpiperidine-1-carboxylate, Example 338.1. A solution of di-tert-butyl dicarbonate (8.22 g, 37.6 mmol) in DCM (50 mL) was added to a mixture of piperidine-3-sulfonamide acetate (Example 179.1, 9.02 g, 31.4 mmol) and TEA (21.9 mL, 157 mmol) in DCM (150 mL) in a 500 mL RBF. The reaction was then stirred at RT for 20 h. The reaction mixture was washed with 0.2N HCl (2×200 mL), washed with water (3×200 mL), and dried over Na$_2$SO$_4$. The solution was filtered and concentrated in vacuo. The initial material was absorbed onto a plug of silica gel and purified by chromatography through a Redi-Sep pre-packed silica gel column (220 g) eluting with a gradient of 0% to 100% EtOAc in DCM to provide the title compound, Example 338.1 (4.69 g, 17.7 mmol, 57% yield), as a white powder. $^1$H NMR (400 MHz, CD$_3$CN) δ 5.28 (br. s., 2H) 4.36 (d, J=11.15 Hz, 1H) 3.94 (d, J=12.91 Hz, 1H) 2.85-3.01 (m, 2H) 2.74 (br. s., 1H) 2.17-2.24 (m, 1H) 1.74-1.82 (m, 1H) 1.61-1.73 (m, 1H) 1.43 (s, 9H) 1.38-1.50 (m, 1H). LCMS-ESI (pos.) m/z: 265.0 (M+H)$^+$.

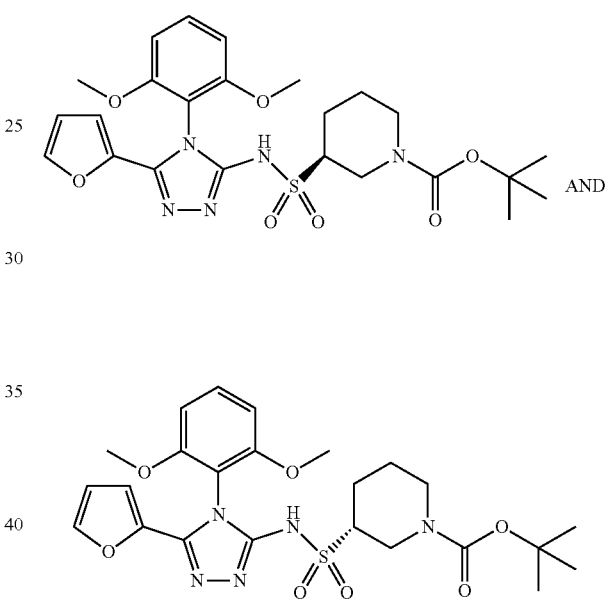

338.2

(S)-tert-Butyl 3-(N-(4-(2,6-dimethoxyphenyl)-5-(furan-2-yl)-4H-1,2,4-triazol-3-yl)sulfamoyl)piperidine-1-carboxylate and (S)-tert-butyl 3-(N-(4-(2,6-dimethoxyphenyl)-5-(furan-2-yl)-4H-1,2,4-triazol-3-yl)sulfamoyl)piperidine-1-carboxylate, Example 338.2. A mixture of Example 338.1 (2.21 g, 7.98 mmol), Example 364.3 (4.47 g, 12.8 mmol), cesium carbonate (6.50 g, 20.0 mmol), and N,N'-dimethylcyclohexane-1,2-diamine (2.27 g, 16.0 mmol) in ACN (10 mL) was bubbled with argon gas for 1 min. To the mixture was added copper(I) iodide (1.52 g, 7.98 mmol) in one portion. The reaction mixture was then heated at 83° C. using an oil bath for 21 h. The reaction mixture was diluted with a saturated aqueous solution of NH$_4$Cl (200 mL), stirred for 5 min, and extracted with DCM (3×200 mL). The combined organic layers were dried over Na$_2$SO$_4$. The solution was filtered and concentrated in vacuo to provide a dark green oil. The initial material was absorbed onto a plug of silica gel and purified by chromatography through a Redi-Sep pre-packed silica gel column (120 g) eluting with a gradient of 0% to 50% EtOAc in DCM to provide the title compound, Example 338.2 (2.25 g, 4.22 mmol, 53% yield), as a white solid. LCMS-ESI (pos.) m/z: 534.2 (M+H)$^+$.

338.3

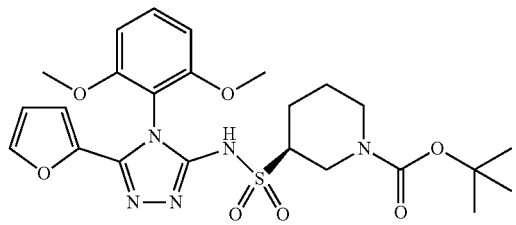

or

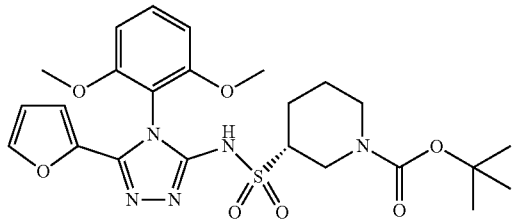

(R)-tert-Butyl 3-(N-(4-(2,6-dimethoxyphenyl)-5-(furan-2-yl)-4H-1,2,4-triazol-3-yl)sulfamoyl)piperidine-1-carboxylate and (S)-tert-butyl 3-(N-(4-(2,6-dimethoxyphenyl)-5-(furan-2-yl)-4H-1,2,4-triazol-3-yl)sulfamoyl)piperidine-1-carboxylate, Example 338.3. Example 338.3 was the second isomer to elute from an AD column on subjecting Example 338.2 under the following SFC conditions: 650×30 mm AD columns with 25 g/min EtOH+(neat)+75 g/min CO$_2$ on Thar 200 SFC. Outlet pressure=80 bar; Temp.=20° C.; Wavelength=220 nm. Used 2 mL injections of 2.5 g/210 mL (11.9 mg/mL) sample solution of Example 338.2 in MeOH, i.e. 23.8 mg/injection. Run time=23 min, cycle time=8 min. $^1$H NMR (400 MHz, DMSO-d$_6$) δ 13.33 (s, J=5.71 Hz, 1H) 7.83 (d, J=1.37 Hz, 1H) 7.56 (t, J=8.51 Hz, 1H) 6.90 (d, J=8.61 Hz, 2H) 6.52 (dd, J=3.52, 1.76 Hz, 1H) 6.03 (d, J=3.52 Hz, 1H) 4.24 (br. s., 1H) 3.86 (d, J=12.72 Hz, 1H) 3.74 (s, 3H) 3.74 (s, 3H) 2.79-2.90 (m, 1H) 2.53-2.75 (m, 2H) 2.01-2.10 (m, 1H) 1.70 (d, J=13.11 Hz, 1H) 1.41-1.53 (m, 1H) 1.36 (s, 9H) 1.25-1.33 (m, 1H). LCMS-ESI (pos.) m/z: 534.2 (M+H)$^+$.

338.4

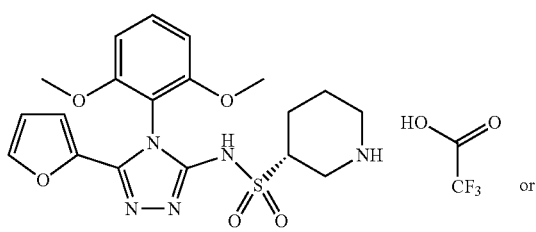

or

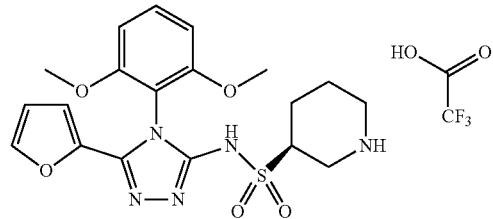

(R)—N-(4-(2,6-Dimethoxyphenyl)-5-(furan-2-yl)-4H-1,2,4-triazol-3-yl)piperidine-3-sulfonamide 2,2,2-trifluoroacetate and (S)—N-(4-(2,6-dimethoxyphenyl)-5-(furan-2-yl)-4H-1,2,4-triazol-3-yl)piperidine-3-sulfonamide 2,2,2-trifluoroacetate, Example 338.4. The title compound was prepared from Example 338.3 (729 mg, 1.37 mmol) and TFA using the procedure described in Example 339.2. This provided the title compound, Example 338.4 (848 mg, 1.55 mmol), as a white solid. LCMS-ESI (pos.) m/z 434.1 (M+H)$^+$.

338.0

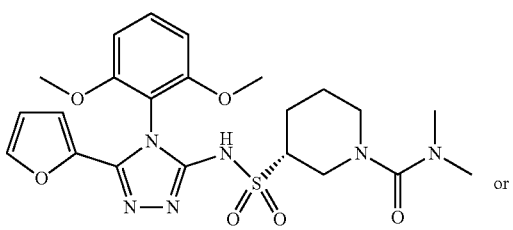

or

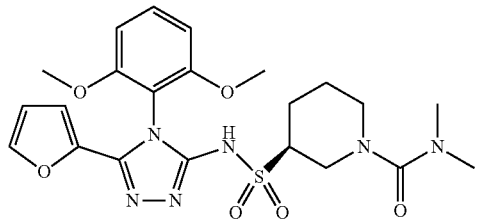

(R)-3-(N-(4-(2,6-Dimethoxyphenyl)-5-(furan-2-yl)-4H-1,2,4-triazol-3-yl)sulfamoyl)-N,N-dimethylpiperidine-1-carboxamide and (S)-3-(N-(4-(2,6-dimethoxyphenyl)-5-(furan-2-yl)-4H-1,2,4-triazol-3-yl)sulfamoyl)-N,N-dimethylpiperidine-1-carboxamide, Example 338.0. The title compound was prepared from Example 338.4 (84 mg, 0.15 mmol) using the procedure described in Example 337.1. This provided the title compound, Example 338.0 (41 mg, 0.081 mmol, 53% yield), as a white solid. $^1$H NMR (400 MHz, DMSO-d$_6$) δ 13.30 (s, 1H) 7.83 (dd, J=1.66, 0.68 Hz, 1H) 7.57 (t, J=8.61 Hz, 1H) 6.90 (dd, J=8.61, 0.78 Hz, 2H) 6.52 (dd, J=3.52, 1.76 Hz, 1H) 6.02 (d, J=3.52 Hz, 1H) 3.80 (dd, J=12.42, 3.23 Hz, 1H) 3.73 (s, 3H) 3.73 (s, 3H) 3.45 (d, J=12.52 Hz, 1H) 2.90-3.00 (m, 1H) 2.69 (s, 3H) 2.69 (s, 3H) 2.52-2.61 (m, 2H) 2.06 (d, J=8.02 Hz, 1H) 1.64-1.75 (m, 1H) 1.36-1.51 (m, 2H). LCMS-ESI (pos.) m/z: 505.1 (M+H)$^+$.

Example 339.0. (S)—N-(4-(2,6-dimethoxyphenyl)-5-(furan-2-yl)-4H-1,2,4-triazol-3-yl)-1-(isopropylsulfonyl)piperidine-3-sulfonamide or (R)—N-(4-(2,6-dimethoxyphenyl)-5-(furan-2-yl)-4H-1,2,4-triazol-3-yl)-1-(isopropylsulfonyl)piperidine-3-sulfonamide 339.1

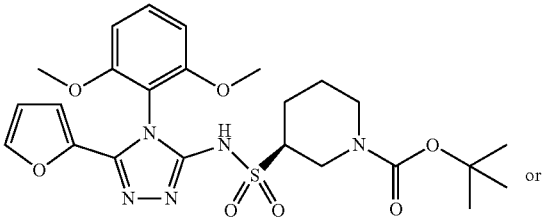

or

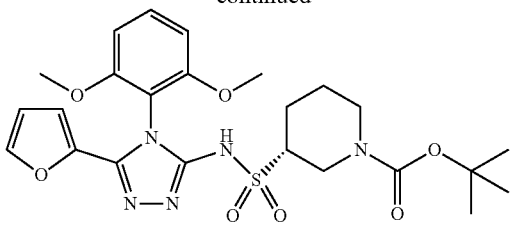

(S)-tert-butyl 3-(N-(4-(2,6-dimethoxyphenyl)-5-(furan-2-yl)-4H-1,2,4-triazol-3-yl)sulfamoyl)piperidine-1-carboxylate or (R)-tert-butyl 3-(N-(4-(2,6-dimethoxyphenyl)-5-(furan-2-yl)-4H-1,2,4-triazol-3-yl)sulfamoyl)piperidine-1-carboxylate, Example 339.1. The title compound, Example 339.1, was the first isomer to elute by chiral separation of Example 338.2 under the SFC conditions described in Example 338.3. $^1$H NMR (400 MHz, DMSO-$d_6$) δ 13.33 (s, 1H) 7.83 (d, J=0.98 Hz, 1H) 7.56 (t, J=8.51 Hz, 1H) 6.90 (d, J=8.61 Hz, 2H) 6.52 (dd, J=3.52, 1.76 Hz, 1H) 6.03 (d, J=3.52 Hz, 1H) 4.25 (br. s., 1H) 3.86 (d, J=12.91 Hz, 1H) 3.74 (s, 3H) 3.74 (s, 3H) 2.79-2.90 (m, 1H) 2.53-2.75 (m, 2H) 2.01-2.10 (m, 1H) 1.65-1.75 (m, 1H) 1.40-1.53 (m, 1H) 1.36 (s, 9H) 1.20-1.33 (m, 1H). LCMS-ESI (pos.) m/z: 534.2 (M+H)$^+$.

339.2

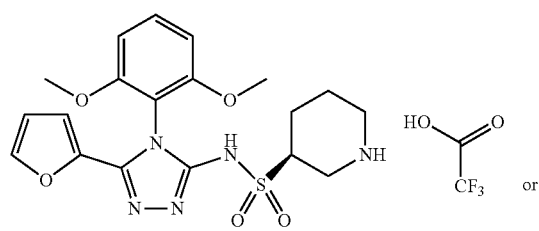

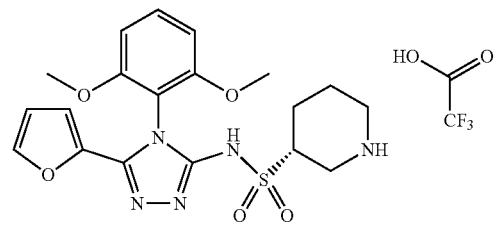

(S)—N-(4-(2,6-Dimethoxyphenyl)-5-(furan-2-yl)-4H-1,2,4-triazol-3-yl)piperidine-3-sulfonamide 2,2,2-trifluoroacetate and (R)—N-(4-(2,6-dimethoxyphenyl)-5-(furan-2-yl)-4H-1,2,4-triazol-3-yl)piperidine-3-sulfonamide 2,2,2-trifluoroacetate, Example 339.2. (S)-tert-Butyl 3-(N-(4-(2,6-dimethoxyphenyl)-5-(furan-2-yl)-4H-1,2,4-triazol-3-yl)sulfamoyl)piperidine-1-carboxylate Example 339.1 (2.55 g, 4.78 mmol) was treated with DCM (10 mL) and TFA (10 mL) at RT for 30 min. The solvents were then removed on a rotary evaporator. The residue was triturated with Et$_2$O (15 mL), decanted, and dried under high vacuum to provide the title compound (2.88 g, 5.26 mmol) as an off-white powder. The compound was used in the next step without further purification. LCMS-ESI (pos.) m/z: 434.0 (M+H)$^+$.

339.0

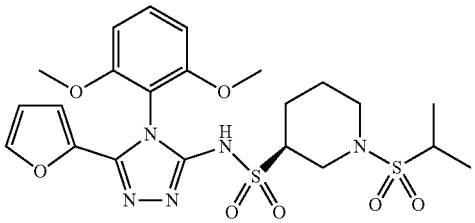

or

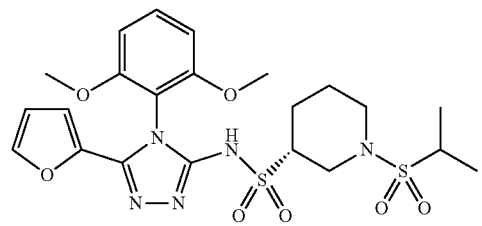

(S)—N-(4-(2,6-Dimethoxyphenyl)-5-(furan-2-yl)-4H-1,2,4-triazol-3-yl)-1-(isopropylsulfonyl)piperidine-3-sulfonamide or (R)—N-(4-(2,6-dimethoxyphenyl)-5-(furan-2-yl)-4H-1,2,4-triazol-3-yl)-1-(isopropylsulfonyl)piperidine-3-sulfonamide, Example 339.0. Isopropylsulfonyl chloride (9.30 μL, 0.083 mmol) was added to a solution of Example 339.2 (37.8 mg, 0.069 mmol) and TEA (0.029 mL, 0.207 mmol) in DCM (0.5 mL). The reaction was stirred at RT and monitored by LCMS. After 3 h, another batch of isopropylsulfonyl chloride (9.30 μL, 0.083 mmol) was added. The reaction mixture was then stirred for an additional 18 h. The solvent was then removed on a rotary evaporator. The residue was treated with 0.5 N aqueous HCl (2 mL), sonicated, and stirred for 30 min. A white precipitate was collected by filtration, rinsed with water, rinsed with 5% EtOAc/hexanes, and then dried in vacuo. The material thus obtained was absorbed onto a plug of silica gel and purified by chromatography through a Redi-Sep pre-packed silica gel column (4 g) eluting with a gradient of 0% to 100% EtOAc in hexanes. This provided the title compound, Example 339.0 (4.6 mg, 8.52 μmol, 12% yield), as a white powder. $^1$H NMR (400 MHz, DMSO-$d_6$) δ 13.39 (s, 1H) 7.83 (d, J=1.17 Hz, 1H) 7.57 (t, J=8.51 Hz, 1H) 6.90 (d, J=8.61 Hz, 2H) 6.53 (dd, J=3.52, 1.76 Hz, 1H) 6.03 (d, J=3.52 Hz, 1H) 3.93 (d, J=8.41 Hz, 1H) 3.75 (s, 3H) 3.75 (s, 3H) 3.59 (d, J=11.93 Hz, 1H) 2.88-2.98 (m, 1H) 2.75-2.83 (m, 1H) 2.65-2.74 (m, 1H) 2.09 (d, J=7.24 Hz, 1H) 1.78 (d, J=6.26 Hz, 1H) 1.37-1.51 (m, 2H) 1.18 (dd, J=6.65, 4.89 Hz, 6H). LCMS-ESI (pos.) m/z: 540.0 (M+H)$^+$.

Example 340.0. Preparation of (S)-3-(N-(4-(2,6-dimethoxyphenyl)-5-(furan-2-yl)-4H-1,2,4-triazol-3-yl)sulfamoyl)-N,N-dimethylpiperidine-1-carboxamide or (R)-3-(N-(4-(2,6-dimethoxyphenyl)-5-(furan-2-yl)-4H-1,2,4-triazol-3-yl)sulfamoyl)-N,N-dimethylpiperidine-1-carboxamide 340.0

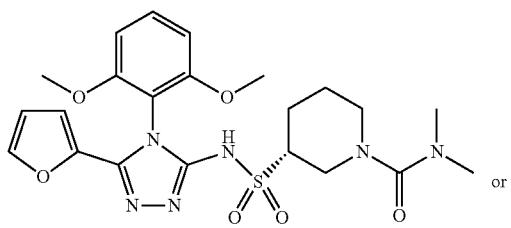

or

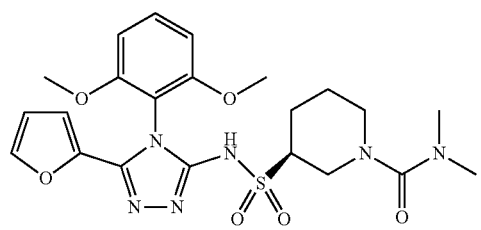

(S)-3-(N-(4-(2,6-Dimethoxyphenyl)-5-(furan-2-yl)-4H-1,2,4-triazol-3-yl)sulfamoyl)-N,N-dimethylpiperidine-1-carboxamide or (R)-3-(N-(4-(2,6-dimethoxyphenyl)-5-(furan-2-yl)-4H-1,2,4-triazol-3-yl)sulfamoyl)-N,N-dimethylpiperidine-1-carboxamide, Example 340.0. To a solution of Example 339.2 (38 mg, 0.069 mmol) and N-ethyl-N-isopropylpropan-2-amine (0.024 mL, 0.14 mmol) in DCM (0.5 mL) in a 2-dram vial, was added (dimethylamino)carbonyl chloride (7.6 μL, 0.083 mmol). The reaction mixture was then stirred at RT for 1 h. Next, a further aliquot of (dimethylamino)carbonyl chloride (7.6 μL, 0.083 mmol) was added, and the reaction was continued at RT for 2 days. The solvent was then removed using a rotary evaporator. The residue was diluted with 1:1 DMSO/MeOH (4 mL), filtered through a GHP Acrodisc 25 mm syringe filter (Lot 21734941), and then purified by preparative HPLC on a C-18 column (CAPCELL UG120 5 uM, 30 mm×250 mm) eluting with 5-95% of B/A (B=0.1% TFA in ACN, A=0.1% TFA in water). The combined fractions were lyophilized to provide the title compound, Example 340.0 (18 mg, 0.035 mmol, 51% yield), as a white powder. $^1$H NMR (400 MHz, DMSO-$d_6$) δ 13.30 (s, 1H) 7.83 (dd, J=1.76, 0.59 Hz, 1H) 7.57 (t, J=8.51 Hz, 1H) 6.90 (dd, J=8.71, 0.68 Hz, 2H) 6.52 (dd, J=3.52, 1.76 Hz, 1H) 6.02 (dd, J=3.52, 0.39 Hz, 1H) 3.79 (d, J=12.72 Hz, 1H) 3.73 (s, 3H) 3.73 (br. s., 1H) 3.47 (tt, J=11.05, 3.33 Hz, 1H) 2.69 (s, 3H) 2.69 (s, 3H) 2.52-2.61 (m, 2H) 2.06 (d, J=8.41 Hz, 1H) 1.66-1.75 (m, 1H) 1.37-1.50 (m, 2H). LCMS-ESI (pos.) m/z: 505.1 (M+H)$^+$.

Example 341.0. Preparation of (S)-1-((R)-2-cyano-2-methyl-6-oxopiperidin-1-yl)-N-(4-(2,6-dimethoxyphenyl)-5-(furan-2-yl)-4H-1,2,4-triazol-3-yl)propane-2-sulfonamide or (R)-1-((S)-2-cyano-2-methyl-6-oxopiperidin-1-yl)-N-(4-(2,6-dimethoxyphenyl)-5-(furan-2-yl)-4H-1,2,4-triazol-3-yl)propane-2-sulfonamide or (R)-1-((R)-2-cyano-2-methyl-6-oxopiperidin-1-yl)-N-(4-(2,6-dimethoxyphenyl)-5-(furan-2-yl)-4H-1,2,4-triazol-3-yl)propane-2-sulfonamide or (S)-1-((S)-2-cyano-2-methyl-6-oxopiperidin-1-yl)-N-(4-(2,6-dimethoxyphenyl)-5-(furan-2-yl)-4H-1,2,4-triazol-3-yl)propane-2-sulfonamide 341.1

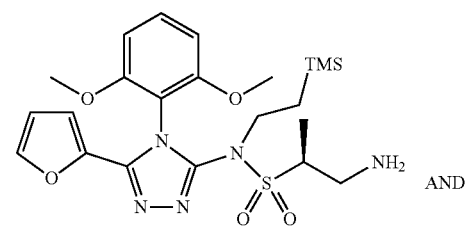

AND

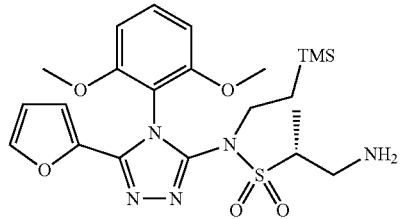

(R)-1-Amino-N-(4-(2,6-dimethoxyphenyl)-5-(furan-2-yl)-4H-1,2,4-triazol-3-yl)-N-(2-(trimethylsilyl)ethyl)propane-2-sulfonamide and (S)-1-amino-N-(4-(2,6-dimethoxyphenyl)-5-(furan-2-yl)-4H-1,2,4-triazol-3-yl)-N-(2-(trimethylsilyl)ethyl)propane-2-sulfonamide, Example 341.1. The title compound was prepared from Example 365.2 using the procedure described in Example 151.5. LCMS-ESI (pos.) m/z: 508.1 (M+H)$^+$.

341.2

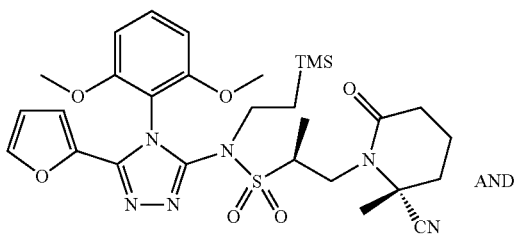

AND

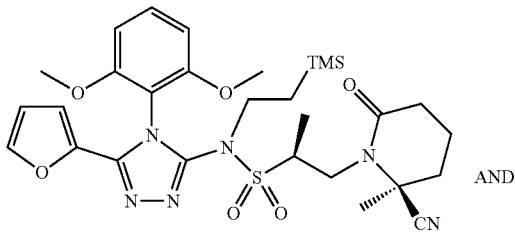

AND

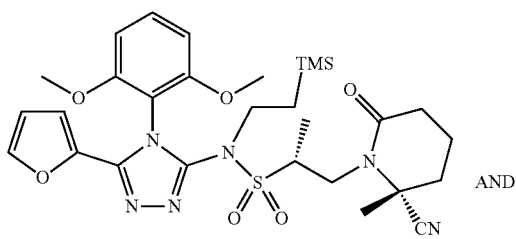

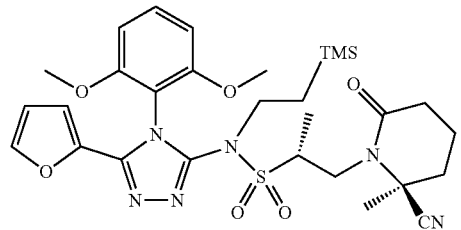

(R)-1-((R)-2-Cyano-2-methyl-6-oxopiperidin-1-yl)-N-(4-(2,6-dimethoxyphenyl)-5-(furan-2-yl)-4H-1,2,4-triazol-3-yl)-N-(2-(trimethylsilyl)ethyl)propane-2-sulfonamide and (R)-1-((S)-2-cyano-2-methyl-6-oxopiperidin-1-yl)-N-(4-(2,6-dimethoxyphenyl)-5-(furan-2-yl)-4H-1,2,4-triazol-3-yl)-N-(2-(trimethylsilyl)ethyl)propane-2-sulfonamide and (S)-1-((R)-2-cyano-2-methyl-6-oxopiperidin-1-yl)-N-(4-(2,6-dimethoxyphenyl)-5-(furan-2-yl)-4H-1,2,4-triazol-3-yl)-N-(2-(trimethylsilyl)ethyl)propane-2-sulfonamide and (S)-1-((S)-2-cyano-2-methyl-6-oxopiperidin-1-yl)-N-(4-(2,6-dimethoxyphenyl)-5-(furan-2-yl)-4H-1,2,4-triazol-3-yl)-N-(2-(trimethylsilyl)ethyl)propane-2-sulfonamide, Example 341.2. The title compound was prepared from Example 341.1 (110 mg, 0.217 mmol), 4-acetylbutyric acid (42.3 mg, 0.325 mmol, Aldrich), and trimethylsilyl cyanide (65 mg, 0.65 mmol, Aldrich) using the procedure described in Example 168.2. This provided the title compound, Example 341.2 (91 mg, 0.15 mmol, 67% yield), as a white solid. LCMS-ESI (pos.) m/z: 629.3 (M+H)$^+$.

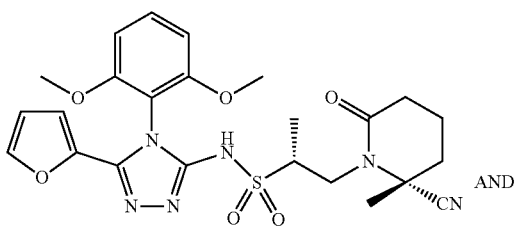

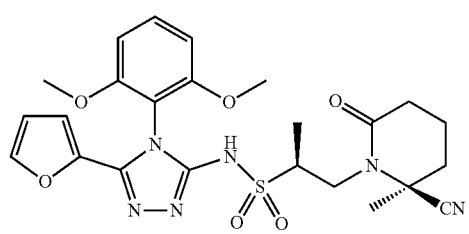

(R)-1-((R)-2-Cyano-2-methyl-6-oxopiperidin-1-yl)-N-(4-(2,6-dimethoxyphenyl)-5-(furan-2-yl)-4H-1,2,4-triazol-3-yl)propane-2-sulfonamide and (R)-1-((S)-2-cyano-2-methyl-6-oxopiperidin-1-yl)-N-(4-(2,6-dimethoxyphenyl)-5-(furan-2-yl)-4H-1,2,4-triazol-3-yl)propane-2-sulfonamide and (S)-1-((R)-2-cyano-2-methyl-6-oxopiperidin-1-yl)-N-(4-(2,6-dimethoxyphenyl)-5-(furan-2-yl)-4H-1,2,4-triazol-3-yl)propane-2-sulfonamide and (S)-1-((S)-2-cyano-2-methyl-6-oxopiperidin-1-yl)-N-(4-(2,6-dimethoxyphenyl)-5-(furan-2-yl)-4H-1,2,4-triazol-3-yl)propane-2-sulfonamide, Example 341.3. The title compound was prepared from Example 341.2 using the procedure described in Example 168.3. LCMS-ESI (pos.) m/z: 529.1 (M+H)$^+$.

341.3

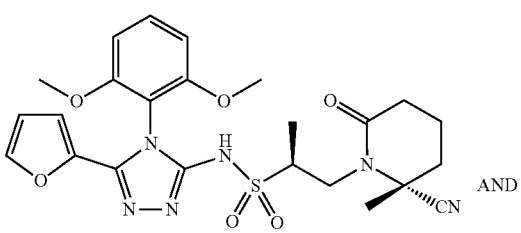

341.0

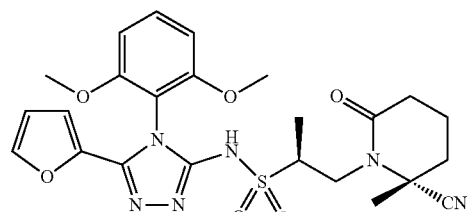

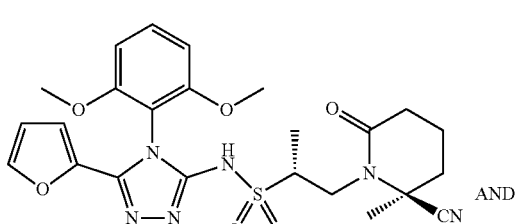

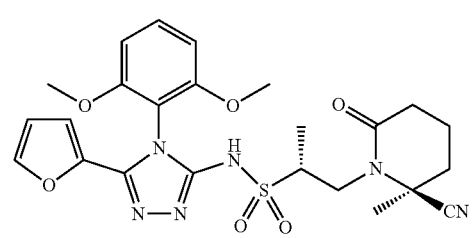

-continued

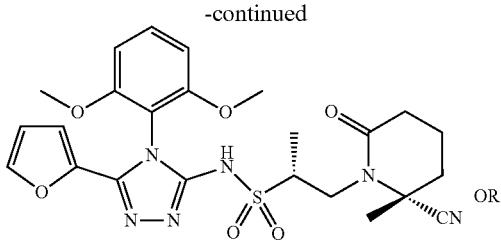

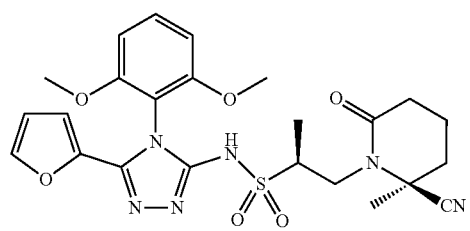

(R)-1-((R)-2-Cyano-2-methyl-6-oxopiperidin-1-yl)-N-(4-(2,6-dimethoxyphenyl)-5-(furan-2-yl)-4H-1,2,4-triazol-3-yl)propane-2-sulfonamide or (R)-1-((S)-2-cyano-2-methyl-6-oxopiperidin-1-yl)-N-(4-(2,6-dimethoxyphenyl)-5-(furan-2-yl)-4H-1,2,4-triazol-3-yl)propane-2-sulfonamide or (S)-1-((R)-2-cyano-2-methyl-6-oxopiperidin-1-yl)-N-(4-(2,6-dimethoxyphenyl)-5-(furan-2-yl)-4H-1,2,4-triazol-3-yl)propane-2-sulfonamide or (S)-1-((S)-2-cyano-2-methyl-6-oxopiperidin-1-yl)-N-(4-(2,6-dimethoxyphenyl)-5-(furan-2-yl)-4H-1,2,4-triazol-3-yl)propane-2-sulfonamide, Example 341.0. Example 341.0 was obtained from Example 341.3 using two stages of chiral SFC separation under the following conditions: Stage 1: 250×30 mm Lux2 column with 60 g/min MeOH+(20 mM NH$_3$)+60 g/min CO$_2$ on Thar 350 SFC. Outlet pressure=100 bar; Temp.=21° C.; Wavelength=271 nm. Used 1.0 mL injections of 59 mg/12 mL (4.9 mg/mL) solution of Example 341.3 in MeOH, i.e. 4.9 mg/injection. Run time=15 min, Cycle time=10 min. Stage 2: 250×30 mm OD column with 25 g/min MeOH+(20 mM NH$_3$)+114 g/min CO$_2$ on Thar 350 SFC. Outlet pressure=100 bar; Temp.=21° C.; Wavelength=271 nm. Used 0.6 mL injections of ~25 mg/10 mL (2.5 mg/mL) sample solution of the second peak from stage 1 in MeOH, i.e. 1.5 mg/injection. Run time=10 min, Cycle time=5 min. The title compound, Example 341.0, was the second peak to elute from the Lux2 column (stage 1) and then the first peak to elute from the OD column under the conditions of stage 2 as described above. $^1$H NMR (500 MHz, CD$_2$Cl$_2$) δ 7.53 (t, J=8.49 Hz, 1H) 7.49 (d, J=1.22 Hz, 1H) 6.75 (t, J=8.28 Hz, 2H) 6.35 (dd, J=3.55, 1.83 Hz, 1H) 6.05 (d, J=3.42 Hz, 1H) 3.81-3.87 (m, 1H) 3.81 (s, 3H) 3.77 (s, 3H) 3.55 (dd, J=14.31, 4.28 Hz, 1H) 3.37 (ddd, J=8.86, 6.79, 4.40 Hz, 1H) 2.41-2.51 (m, 1H) 2.30-2.40 (m, 1H) 2.18-2.29 (m, 1H) 1.87-2.04 (m, 3H) 1.67 (s, 3H) 1.29 (d, J=6.85 Hz, 3H). LCMS-ESI (pos.) m/z: 529.1 (M+H)$^+$.

Example 342.0. Preparation of (R)-1-((R)-2-cyano-2-methyl-6-oxopiperidin-1-yl)-N-(4-(2,6-dimethoxyphenyl)-5-(furan-2-yl)-4H-1,2,4-triazol-3-yl)propane-2-sulfonamide or (R)-1-((S)-2-cyano-2-methyl-6-oxopiperidin-1-yl)-N-(4-(2,6-dimethoxyphenyl)-5-(furan-2-yl)-4H-1,2,4-triazol-3-yl)propane-2-sulfonamide or (S)-1-((R)-2-cyano-2-methyl-6-oxopiperidin-1-yl)-N-(4-(2,6-dimethoxyphenyl)-5-(furan-2-yl)-4H-1,2,4-triazol-3-yl)propane-2-sulfonamide or (S)-1-((S)-2-cyano-2-methyl-6-oxopiperidin-1-yl)-N-(4-(2,6-dimethoxyphenyl)-5-(furan-2-yl)-4H-1,2,4-triazol-3-yl)propane-2-sulfonamide 342.0

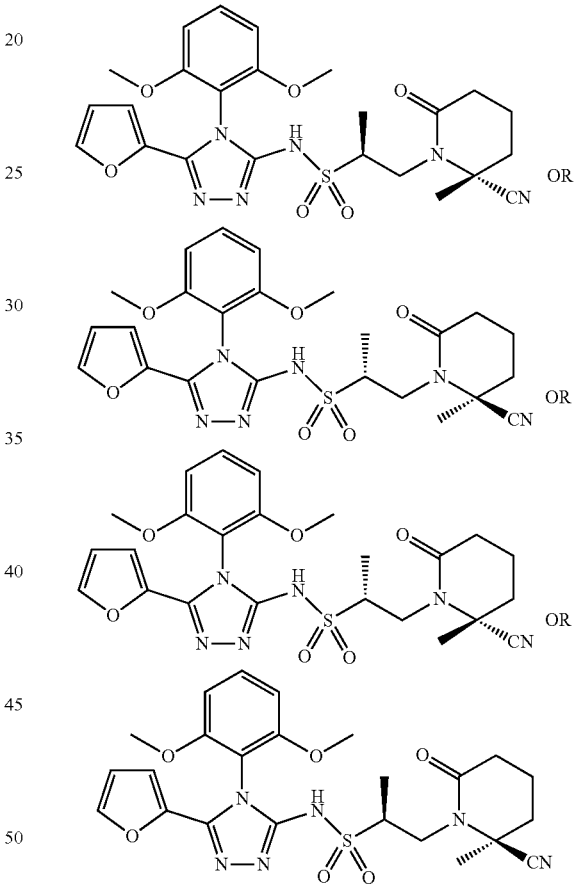

(R)-1-((R)-2-Cyano-2-methyl-6-oxopiperidin-1-yl)-N-(4-(2,6-dimethoxyphenyl)-5-(furan-2-yl)-4H-1,2,4-triazol-3-yl)propane-2-sulfonamide or (R)-1-((S)-2-cyano-2-methyl-6-oxopiperidin-1-yl)-N-(4-(2,6-dimethoxyphenyl)-5-(furan-2-yl)-4H-1,2,4-triazol-3-yl)propane-2-sulfonamide or (S)-1-((R)-2-cyano-2-methyl-6-oxopiperidin-1-yl)-N-(4-(2,6-dimethoxyphenyl)-5-(furan-2-yl)-4H-1,2,4-triazol-3-yl)propane-2-sulfonamide or (S)-1-((S)-2-cyano-2-methyl-6-oxopiperidin-1-yl)-N-(4-(2,6-dimethoxyphenyl)-5-(furan-2-yl)-4H-1,2,4-triazol-3-yl)propane-2-sulfonamide, Example 342.0. Example 342.0 is the diastereomer of Example 341.0. The title compound, Example 342.0, was obtained from Example 341.0 using two stages of chiral SFC separation under the following conditions. The title compound, Example 342.0, was the second peak to elute from the Lux2 column (stage 1, as described in Example 341.0), and then the second peak to elute from the OD column (stage 2, as described in Example 341.0). $^1$H NMR (500 MHz, CD$_2$Cl$_2$) δ 7.52 (t, J=8.56 Hz, 1H) 7.49 (d, J=1.22 Hz, 1H) 6.74 (dd, J=8.56, 3.67 Hz, 2H) 6.35 (dd, J=3.55, 1.83 Hz, 1H) 6.04 (d, J=3.42 Hz, 1H) 3.91-4.00 (m, 1H) 3.78 (s, 3H) 3.78 (s, 3H) 3.73 (d, J=3.67 Hz, 1H) 3.62-3.69 (m, 1H) 2.49-2.56 (m, 1H) 2.38 (ddd, J=17.85, 11.13, 6.97 Hz, 1H) 2.23-2.30 (m, 1H) 1.98-2.07 (m, 1H) 1.88-1.96 (m, 2H) 1.68 (s, 3H) 1.24 (d, J=6.85 Hz, 3H). LCMS-ESI (pos.) m/z: 529.1 (M+H)$^+$.

Example 343.0. Preparation of (3R,4R)—N-(4-(2,6-dimethoxyphenyl)-5-(furan-2-yl)-4H-1,2,4-triazol-3-yl)-3-(5-fluoropyrimidin-2-yl)-2-methylisoxazolidine-4-sulfonamide or (3S,4S)—N-(4-(2,6-dimethoxyphenyl)-5-(furan-2-yl)-4H-1,2,4-triazol-3-yl)-3-(5-fluoropyrimidin-2-yl)-2-methylisoxazolidine-4-sulfonamide

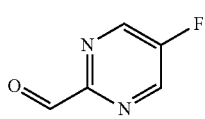

343.2

5-Fluoropyrimidine-2-carbaldehyde, Example 343.2. To a colorless solution of Example 351.1 (3.74 g, 30.1 mmol) in THF (60 mL) and water (20 mL) was added osmium(VIII) oxide (0.958 g, 0.151 mmol). The resulting dark purple-brown solution was stirred at RT. After 10 min, sodium meta-periodate (5.01 mL, 90.0 mmol) was added. The mixture was stirred for 4 h. The solid was removed by filtration and rinsed with DCM (3×50 mL). The solution was then extracted with water (25 mL). The two layers were separated. The organic layer was dried over MgSO$_4$, filtered, and rinsed with DCM (5×20 mL). The total volume of the solution was 275 mL, and this solution was used directly in the next step (a small fraction was concentrated on rotary evaporator and the residue was analyzed by $^1$H-NMR). NMR (400 MHz, CD$_2$Cl$_2$) δ 10.06 (s, 1H) 8.84 (s, 2H).

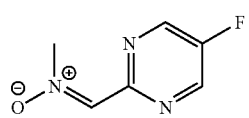

343.3

(E)-N-((5-Fluoropyrimidin-2-yl)methylene)methanamine oxide, Example 343.3. To a solution of Example 343.2 (100 mL, 11.00 mmol) in DCM/THF in a 500 mL RBF, was added anhydrous MgSO$_4$ (6.62 g, 55.0 mmol), hydroxylamine N-methyl-hydrochloride (0.919 g, 11.00 mmol) and NaHCO$_3$ (1.848 g, 22.00 mmol). The reaction mixture was then stirred overnight at RT. The solids were removed by filtration and rinsed with DCM. The filtrate was concentrated on a rotary evaporator. The material thus obtained was absorbed onto a plug of silica gel and purified by chromatography through a Redi-Sep pre-packed silica gel column (12 g) eluting with a gradient of 0% to 5% MeOH in DCM. This provided the title compound, Example 343.3 (0.419 g, 2.70 mmol, 25% yield), as an off-white crystalline solid. $^1$H NMR (400 MHz, CD$_2$Cl$_2$) δ 8.69 (s, 2H) 7.71 (s, 1H) 3.90 (s, 3H). LCMS-ESI (pos.) m/z: 155.9 (M+H)$^+$.

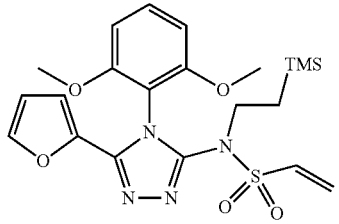

343.4

N-(4-(2,6-Dimethoxyphenyl)-5-(furan-2-yl)-4H-1,2,4-triazol-3-yl)-N-(2-(trimethylsilyl)ethyl)ethenesulfonamide, Example 343.4. To a solution of Example 365.0 (0.733 g, 1.22 mmol) in THF (10 mL) in a 40 mL vial at RT, was added dropwise lithium bis(trimethylsilyl)amide (1.0 M solution in THF, 0.475 mL, 2.44 mmol). After 15 min, polyoxymethylene (390 mg) was added in one portion to the reaction mixture which was then stirred for 19 h. Additional lithium bis(trimethylsilyl)amide (1.0 M solution in THF, 0.475 mL, 2.44 mmol) was then added to the reaction which was stirred for an additional 17 h. The reaction mixture was then absorbed onto a plug of silica gel and purified by chromatography through a Redi-Sep pre-packed silica gel column (4 g) eluting with a gradient of 0% to 100% EtOAc in hexane. This provided the title compound, Example 343.4 (0.492 g, 1.03 mmol, 85% yield), as off-white needles. LCMS-ESI (pos.) m/z: 477.0 (M+H)$^+$.

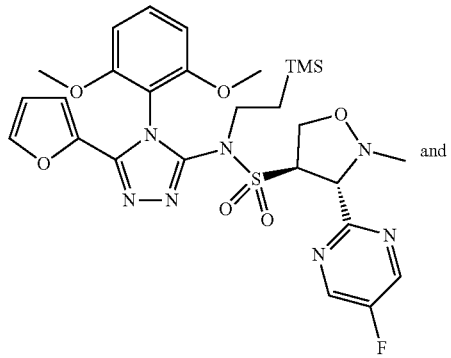

343.5

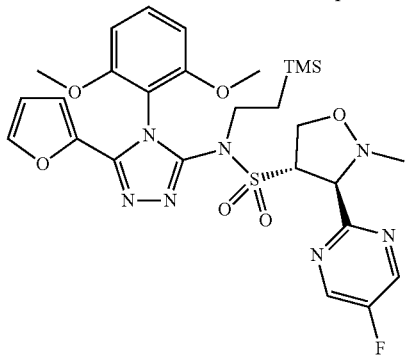

(3R,4R)—N-(4-(2,6-Dimethoxyphenyl)-5-(furan-2-yl)-4H-1,2,4-triazol-3-yl)-3-(5-fluoropyrimidin-2-yl)-2-methyl-N-(2-(trimethylsilyl)ethyl)isoxazolidine-4-sulfonamide and (3S,4S)—N-(4-(2,6-dimethoxyphenyl)-5-(furan-2-yl)-4H-

1,2,4-triazol-3-yl)-3-(5-fluoropyrimidin-2-yl)-2-methyl-N-(2-(trimethylsilyl)ethyl)isoxazolidine-4-sulfonamide, Example 343.5. A mixture of Example 343.4 (226 mg, 0.474 mmol) and Example 343.3 (88 mg, 0.569 mmol) in dioxane (4 mL) was heated at 110° C. for 30 min. Another batch of Example 343.3 (44 mg, 0.285 mmol) was then added, and the reaction mixture was heated at 110° C. for another 30 min. The solvent was removed on a rotary evaporator. The residue was absorbed onto a plug of silica gel and purified by chromatography through a Redi-Sep pre-packed silica gel column (12 g) eluting with a gradient of 0% to 50% acetone in hexanes to provide the title compound, Example 343.5 (91.7 mg, 0.145 mmol, 30% yield), as an off-white solid (faster eluent, trans-isomer). LCMS-ESI (pos.) m/z: 632.2 (M+H)⁺).

(m, 1H) 4.43 (d, J=1.76 Hz, 1H) 4.41 (s, 1H) 3.76 (s, 3H) 3.76 (s, 3H) 2.90 (br. s., 3H). LCMS-ESI (pos.) m/z: 532.1 (M+H)⁺.

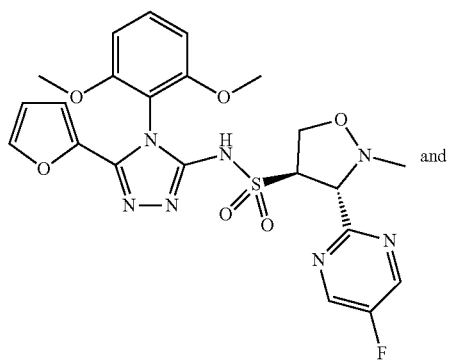

343.0

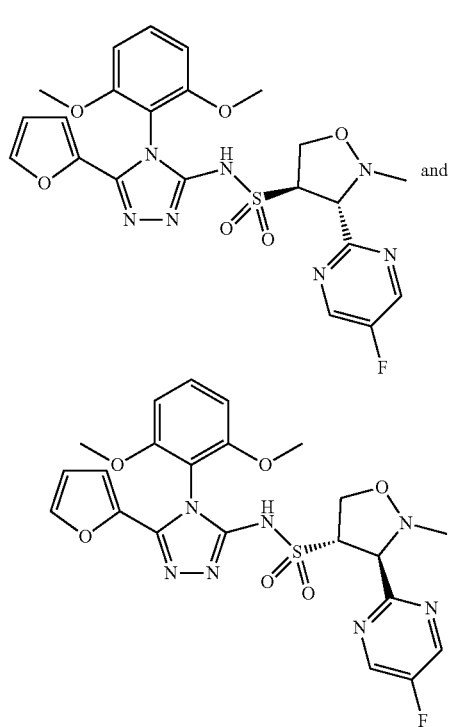

343.6

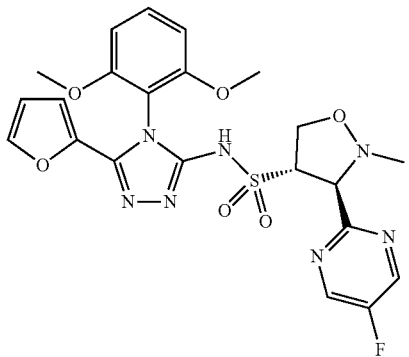

(3R,4R)—N-(4-(2,6-Dimethoxyphenyl)-5-(furan-2-yl)-4H-1,2,4-triazol-3-yl)-3-(5-fluoropyrimidin-2-yl)-2-methylisoxazolidine-4-sulfonamide and (3S,4S)—N-(4-(2,6-dimethoxyphenyl)-5-(furan-2-yl)-4H-1,2,4-triazol-3-yl)-3-(5-fluoropyrimidin-2-yl)-2-methylisoxazolidine-4-sulfonamide, Example 343.6. A mixture of Example 343.5 (81.7 mg, 0.129 mmol) and tris(dimethylamino)sulfur trimethylsilyl difluoride (107 mg, 0.388 mmol) in DMF (0.5 mL) was heated at 80° C. for 2 h. The reaction mixture was then diluted with MeOH (2 mL), filtered through a GHP Acrodisc 25 mm syringe filter (Lot 21734941), and then purified by preparative HPLC on a C-18 column (CAPCELL UG120 5 uM, 30 mm×250 mm) eluting with 5%-95% of B/A (B=0.1% TFA in ACN, A=0.1% TFA in water). The combined fractions were lyophilized to provide the title compound, Example 343.6 (54 mg, 0.083 mmol, 64% yield), as a white powder. ¹H NMR (400 MHz, CD₂Cl₂) δ 8.62 (s, 2H) 7.53 (t, J=8.27 Hz, 1H) 7.50 (dd, J=1.76, 0.59 Hz, 1H) 6.73 (dd, J=8.61, 2.15 Hz, 2H) 6.37 (dd, J=3.52, 1.76 Hz, 1H) 6.07 (dd, J=3.62, 0.68 Hz, 1H) 4.91-4.97 (m, 1H) 4.56-4.62

(3R,4R)—N-(4-(2,6-Dimethoxyphenyl)-5-(furan-2-yl)-4H-1,2,4-triazol-3-yl)-3-(5-fluoropyrimidin-2-yl)-2-methylisoxazolidine-4-sulfonamide or (3S,4S)—N-(4-(2,6-dimethoxyphenyl)-5-(furan-2-yl)-4H-1,2,4-triazol-3-yl)-3-(5-fluoropyrimidin-2-yl)-2-methylisoxazolidine-4-sulfonamide, Example 343.0. The title compound, Example 343.0, was prepared by chiral SFC separation of Example 343.6. Example 343.0 was the second enantiomer to elute from an AS-H column under the following conditions: 250 mm×30 mm AS-H column with 20 g/min MeOH (Neat)+60 g/min CO₂ on Thar 80 SFC. Outlet pressure=100 bar; Temp.=22° C.; Wavelength=270 nm. Used 0.9 mL injections of 50 mg/6 mL (8.3 mg/mL) solution of Example 343.6 in MeOH:DCM (10% DCM) i.e. 8.3 mg/injection. Run time=9 min, Cycle time=5.0 min. ¹H NMR (400 MHz, CD₂Cl₂) δ 8.60 (s, 2H) 7.52 (t, J=8.51 Hz, 1H) 7.49 (dd, J=1.76, 0.59 Hz, 1H) 6.73 (dd, J=8.61, 1.76 Hz, 2H) 6.36 (dd, J=4.12 Hz, 1H) 6.05 (dd, J=3.52, 0.59 Hz, 1H) 4.81 (td, J=7.38, 4.79 Hz, 1H) 4.16-4.31 (m, 3H) 3.76 (s, 3H) 3.76 (s, 3H) 2.69 (br. s., 3H). LCMS-ESI (pos.) m/z: 532.1 (M+H)⁺.

Example 344.0. Preparation of N-(4-(2,6-dimethoxyphenyl)-5-(furan-2-yl)-4H-1,2,4-triazol-3-yl)-2-(4-methylthiazol-2-yl)ethanesulfonamide

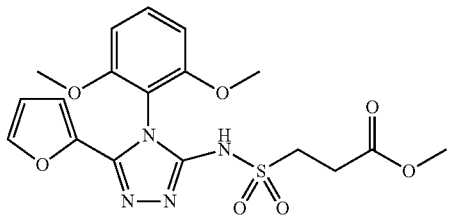

344.1

Methyl 3-(N-(4-(2,6-Dimethoxyphenyl)-5-(furan-2-yl)-4H-1,2,4-triazol-3-yl)sulfamoyl)propanoate, Example 344.1. To a 500 mL RBF was added Example 362.03 (8.44 g, 29.5 mmol) and TEA (20.50 mL, 147 mmol) in DCM (157 mL). At RT, 3-chlorosulfonyl-propionic acid methyl ester (6.60 mL, 35.4 mmol) in DCM (39.3 mL) was added dropwise with stirring. The reaction mixture was stirred at RT for 17 h. The reaction mixture was concentrated in vacuo and then diluted with 1 N HCl and extracted with DCM. The combined organic layers were washed with brine and dried over $Na_2SO_4$. The solution was filtered and concentrated in vacuo to give the initial product as a light-yellow solid. The material thus obtained was triturated with DCM/ether to provide the title compound, Example 344.1 (9.4 g, 21.5 mmol, 73% yield), as an off-white solid. The mother liquors were concentrated to afford another crop of Example 344.1 (2.0 g, 4.58 mmol, 16% yield) as a light-yellow solid. LCMS-ESI (pos.), m/z: 437.0 $(M+H)^+$.

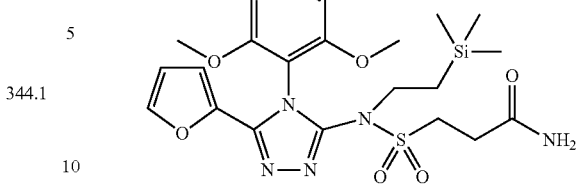

344.2

Methyl 3-(N-(4-(2,6-Dimethoxyphenyl)-5-(furan-2-yl)-4H-1,2,4-triazol-3-yl)-N-(2-(trimethylsilyl)ethyl)sulfamoyl)propanoate, Example 344.2. Example 344.1 (500 mg, 1.146 mmol), 2-(tributylphosphoranylidene)acetonitrile (304 mg, 1.260 mmol) and 2-(trimethylsilyl)ethanol (163 mg, 1.375 mmol) were mixed in toluene (5728 µL) under nitrogen gas. The reaction was heated at 90° C. for 2 h and then cooled to RT. The mixture was loaded onto a 40 g silica gel column eluting with 0-20% EtOAc/DCM to provide Example 344.2 (318 mg, 0.59 mmol, 52% yield) as a brown oil. LCMS-ESI (pos.), m/z: 537.2 $(M+H)^+$.

344.3

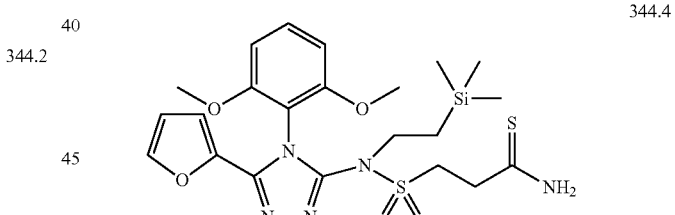

3-(N-(4-(2,6-Dimethoxyphenyl)-5-(furan-2-yl)-4H-1,2,4-triazol-3-yl)-N-(2-(trimethylsilyl)ethyl)sulfamoyl)propanamide, Example 344.3. Example 344.2 (303 mg, 0.565 mmol) was treated with ammonium hydroxide, (28% $NH_3$ in water, 5 mL, 128 mmol) and MeOH (5 mL) at RT. The reaction mixture was then stirred for 16 h. The reaction was then concentrated in vacuo. The residue thus obtained was partitioned between DCM (15 mL) and water (15 mL), and the layers were separated. The aqueous layer was extracted with DCM (15 mL) and then with 10% MeOH in DCM (15 mL). The organic layers were combined, dried over $Na_2SO_4$, filtered, and concentrated in vacuo. The material thus obtained was purified on a 24 g silica gel column gradient eluting with 0%-10% MeOH in DCM. This provided Example 344.3 (166 mg, 0.32 mmol, 56% yield) as an off-white powder. $^1$H NMR (400 MHz, $CD_2Cl_2$) δ 7.47-7.53 (m, 2H) 6.72 (d, J=8.61 Hz, 2H) 6.35 (dd, J=3.62, 1.86 Hz, 1H) 5.98 (dd, J=3.52, 0.78 Hz, 1H) 4.32-4.38 (m, 2H) 3.77 (s, 3H) 3.77 (s, 3H) 3.04 (t, J=7.43 Hz, 2H) 2.43 (t, J=7.43 Hz, 2H) 1.55 (s, 3H) 1.26-1.39 (m, 2H) 0.09-0.12 (m, 9H). LCMS-ESI (pos.), m/z: 522.2 $(M+H)^+$.

344.4

3-(N-(4-(2,6-Dimethoxyphenyl)-5-(furan-2-yl)-4H-1,2,4-triazol-3-yl)-N-(2-(trimethylsilyl)ethyl)sulfamoyl)propanethioamide, Example 344.4. Lawesson's reagent (64.4 mg, 0.159 mmol) and Example 344.3 (166 mg, 0.318 mmol) were mixed in THF (3 mL) in a 40 mL vial and nitrogen gas was bubbled through the mixture for 2 min. The reaction mixture was then heated at 70° C. for 3 h. The solvent was removed on a rotary evaporator with a trap containing bleach. The residue was purified with a 24 g silica gel column eluting with a 0-100% EtOAc in hexanes gradient to provide Example 344.4 (142 mg, 0.264 mmol, 83% yield) as a white powder. $^1$H NMR (400 MHz, $CD_2Cl_2$) δ 7.53 (t, J=8.77 Hz, 1H) 7.49 (s, 1H) 6.74 (d, J=8.46 Hz, 2H) 6.35 (dd, J=4.18 Hz, 1H) 5.99 (d, J=3.52 Hz, 1H) 4.33-4.40 (m, 2H) 3.78 (s, 3H) 3.78 (s, 3H) 3.14 (t, J=6.65 Hz, 2H) 2.91 (t, J=6.65 Hz, 2H) 1.59 (br. s., 2H) 1.30-1.37 (m, 2H) 0.09-0.12 (m, 9H). LCMS-ESI (pos.), m/z: 538.1 $(M+H)^+$.

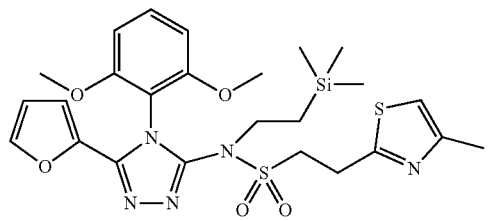

344.5

N-(4-(2,6-Dimethoxyphenyl)-5-(furan-2-yl)-4H-1,2,4-triazol-3-yl)-2-(4-methylthiazol-2-yl)-N-(2-(trimethylsilyl)ethyl)ethanesulfonamide, Example 344.5. Example 344.4 (32 mg, 0.059 mmol) and 1-chloropropan-2-one (6.5 mg, 0.070 mmol) were mixed in EtOH (0.5 mL) in a 2-dram vial and heated at 80° C. for 6 h. The solvent was removed in vacuo. The initial residue was purified on a 4 g silica gel column eluting with a 0%-100% EtOAc in hexanes gradient to provide the title compound, Example 344.5 (17 mg, 0.029 mmol, 50% yield), which was used in the next step without further purification. $^1$H NMR (400 MHz, DMSO-$d_6$) δ 7.86 (dd, J=1.76, 0.59 Hz, 1H) 7.53 (t, J=8.51 Hz, 1H) 7.09 (d, J=0.98 Hz, 1H) 6.85 (d, J=8.61 Hz, 2H) 6.54 (dd, J=3.99 Hz, 1H) 6.04 (dd, J=3.62, 0.68 Hz, 1H) 4.29-4.38 (m, 2H) 3.71-3.74 (m, 6H) 3.04-3.13 (m, 2H) 2.94-3.03 (m, 2H) 2.30 (d, J=0.98 Hz, 3H) 1.22-1.28 (m, 2H) 0.05-0.08 (m, 9H). LCMS-ESI (pos.), m/z: 576.2 (M+H)$^+$.

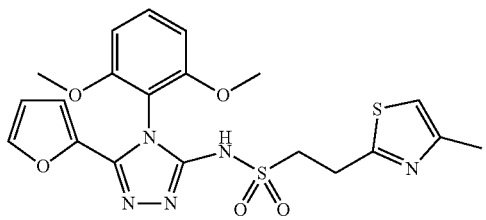

344.0

N-(4-(2,6-Dimethoxyphenyl)-5-(furan-2-yl)-4H-1,2,4-triazol-3-yl)-2-(4-methylthiazol-2-yl)ethanesulfonamide, Example 344.0. To a solution of Example 344.5 (14.9 mg, 0.026 mmol) in DMF (0.50 mL) in a 2-dram vial was added tris(dimethylamino)sulfonium difluorotrimethylsilicate(IV) (18 mg, 0.065 mmol). The mixture was heated at 80° C. for 2 h. The reaction mixture was then diluted with MeOH (1.0 mL), filtered through a GHP Acrodisc 13 mm Syringe Filter with 0.45 μm GHP membrane (Lot 21756741), and then purified by preparative HPLC on a C-18 column (CAPCELL type UG120, 5 μm, 30 mm×250 mm) gradient eluting with a 5%-95% ACN with 0.1% TFA in water with 0.1% TFA to provide Example 344.0 (6.1 mg, 0.013 mmol, 50% yield) as a white powder. $^1$H NMR (400 MHz, DMSO-$d_6$) δ 13.43 (br. s., 1H) 7.83 (dd, J=1.66, 0.68 Hz, 1H) 7.57 (t, J=8.51 Hz, 1H) 7.12 (d, J=1.17 Hz, 1H) 6.90 (d, J=8.41 Hz, 2H) 6.53 (dd, J=3.52, 1.76 Hz, 1H) 6.04 (dd, J=3.52, 0.59 Hz, 1H) 3.72 (s, 3H) 3.72 (s, 3H) 3.30-3.34 (m, 2H) 3.18-3.24 (m, 2H) 2.31 (d, J=0.98 Hz, 3H). LCMS-ESI (pos.), m/z: 476.1 (M+H)$^+$.

Example 345.0. Preparation of N-(4-(2,6-dimethoxyphenyl)-5-(furan-2-yl)-4H-1,2,4-triazol-3-yl)-2-(4,5-dimethylthiazol-2-yl)ethanesulfonamide

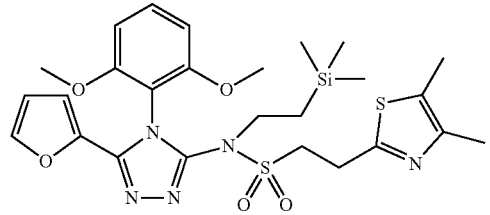

345.1

N-(4-(2,6-Dimethoxyphenyl)-5-(furan-2-yl)-4H-1,2,4-triazol-3-yl)-2-(4,5-dimethylthiazol-2-yl)-N-(2-(trimethylsilyl)ethyl)ethanesulfonamide, Example 345.1. Example 344.4 (32 mg, 0.059 mmol) and 3-chlorobutan-2-one (7.6 mg, 0.071 mmol) were mixed in EtOH (0.5 mL) in a 2-dram vial and heated at 80° C. for 16 h. The reaction mixture was then loaded on a 4 g silica gel column, gradient eluting with 0%-100% EtOAc in hexane to provide the enriched title compound, 345.1 (15 mg, 0.025 mmol, 43% yield), which was used in the next step without further purification. LCMS-ESI (pos.), m/z: 590.2 (M+H)$^+$.

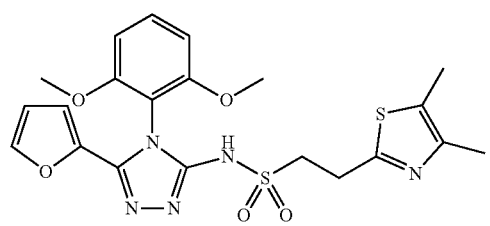

345.0

N-(4-(2,6-Dimethoxyphenyl)-5-(furan-2-yl)-4H-1,2,4-triazol-3-yl)-2-(4,5-dimethylthiazol-2-yl)ethanesulfonamide, Example 345.0. The title compound was prepared from Example 345.1 (13 mg, 0.023 mmol) using the procedure described in Example 344.0. This provided Example 345.0 (1.8 mg, 0.0037 mmol, 16% yield) as a white solid. $^1$H NMR (400 MHz, CD$_2$Cl$_2$) δ 7.53 (t, J=8.51 Hz, 1H) 7.49 (d, J=1.76 Hz, 1H) 6.72-6.76 (m, 2H) 6.36 (dd, J=3.72, 1.76 Hz, 1H) 6.06 (d, J=3.52 Hz, 1H) 3.77 (s, 3H) 3.77 (s, 3H) 3.38-3.44 (m, 2H) 3.29-3.36 (m, 2H) 2.30 (s, 3H) 2.28 (s, 3H). LCMS-ESI (pos.), m/z: 490.1 (M+H)$^+$.

Example 346.0. Preparation of N-(4-(2,6-dimethoxyphenyl)-5-(furan-2-yl)-4H-1,2,4-triazol-3-yl)-2-(2-methyloxazol-4-yl)ethanesulfonamide 346.1

(E)-N-(4-(2,6-Dimethoxyphenyl)-5-(furan-2-yl)-4H-1,2,4-triazol-3-yl)-2-(2-methyloxazol-4-yl)-N-(2-(trimethylsilyl)ethyl)ethenesulfonamide, Example 346.1. To a solution of Example 365.0 (110 mg, 0.18 mmol) in THF (1.0 mL) at RT, was added lithium bis(trimethylsilyl)amide (1.0 M solution in THF, 0.37 mL, 0.37 mmol). The reaction mixture was stirred for 15 min. To the reaction mixture was added a solution of 2-methyloxazole-4-carbaldehyde (31 mg, 0.28 mmol) in THF (1.0 mL) dropwise. The mixture was then stirred for 2 h. The reaction was quenched with MeOH (0.5 mL) and then concentrated in vacuo. The material thus obtained was purified on a 4 g silica gel column gradient eluting with 0-100% EtOAc in hexanes to provide the title compound Example 346.1 (82 mg, 0.15 mmol, 80% yield) as a colorless film. $^1$H NMR (400 MHz, CD$_2$Cl$_2$) δ 7.52 (s, 1H) 7.45-7.50 (m, 2H) 6.83 (d, J=15.06 Hz, 1H) 6.78 (d, J=15.26 Hz, 1H) 6.67 (d, J=8.61 Hz, 2H) 6.34 (dd, J=3.52, 1.76 Hz, 1H) 5.97 (dd, J=3.52, 0.78 Hz, 1H) 4.31-4.38 (m, 2H) 3.74 (s, 3H) 3.74 (s, 3H) 2.43 (s, 3H) 1.26-1.37 (m, 2H) 0.09-0.12 (m, 9H). LCMS-ESI (pos.), m/z: 558.1 (M+H)$^+$.

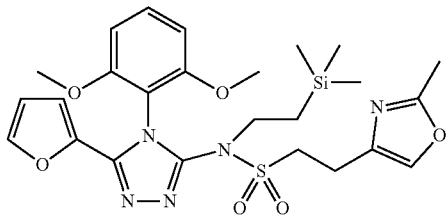

346.2

N-(4-(2,6-Dimethoxyphenyl)-5-(furan-2-yl)-4H-1,2,4-triazol-3-yl)-2-(2-methyloxazol-4-yl)-N-(2-(trimethylsilyl)ethyl)ethanesulfonamide, Example 346.2. A solution of Example 346.1 (72 mg, 0.129 mmol) in EtOH (2.0 mL) in a 50 mL RBF was purged with nitrogen. To the reaction mixture was added palladium (10% wt. on activated carbon, 69 mg, 0.065 mmol). The reaction mixture was stirred under a hydrogen balloon overnight at RT. The catalyst was removed by filtration through a GHP Acrodisc 25 mm syringe filter, and the solvent was then removed on a rotary evaporator to provide Example 346.2 (56 mg) as a white foam which was used without further purification. $^1$H NMR (400 MHz, CD$_2$Cl$_2$) δ 7.35-7.41 (m, 2H) 7.09 (t, J=1.08 Hz, 1H) 6.59 (d, J=8.41 Hz, 2H) 6.23 (dd, J=3.52, 1.76 Hz, 1H) 5.87 (dd, J=3.52, 0.59 Hz, 1H) 4.21-4.28 (m, 2H) 3.66 (s, 3H) 3.66 (s, 3H) 2.88-2.94 (m, 2H) 2.55-2.61 (m, 2H) 2.25 (s, 3H) 1.19-1.26 (m, 2H) −0.01-0.01 (m, 9H). LCMS-ESI (pos.), m/z: 560.2 (M+H)$^+$.

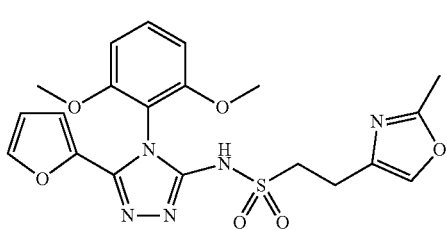

346.0

N-(4-(2,6-Dimethoxyphenyl)-5-(furan-2-yl)-4H-1,2,4-triazol-3-yl)-2-(2-methyloxazol-4-yl)ethanesulfonamide, Example 346.0. The title compound was prepared from Example 346.2 (50 mg) using the procedure described in Example 344.0. This provided the title compound, Example 346.0 (7.2 mg, 0.016 mmol, 12% yield for two steps), as a white solid. $^1$H NMR (400 MHz, CD$_2$Cl$_2$) δ 7.50-7.56 (m, 1H) 7.49 (dd, J=1.76, 0.78 Hz, 1H) 7.34 (s, 1H) 6.74 (d, J=8.41 Hz, 2H) 6.36 (dd, J=3.52, 1.76 Hz, 1H) 6.06 (dd, J=3.62, 0.68 Hz, 1H) 3.76 (s, 3H) 3.76 (s, 3H) 3.21-3.29 (m, 2H) 2.90-2.95 (m, 2H) 2.42 (s, 3H). LCMS-ESI (pos.), m/z: 460.1 (M+H)$^+$.

Example 347.0. Preparation of N-(4-(2,6-dimethoxyphenyl)-5-(furan-2-yl)-4H-1,2,4-triazol-3-yl)-2-(2,5-dimethyloxazol-4-yl)ethanesulfonamide

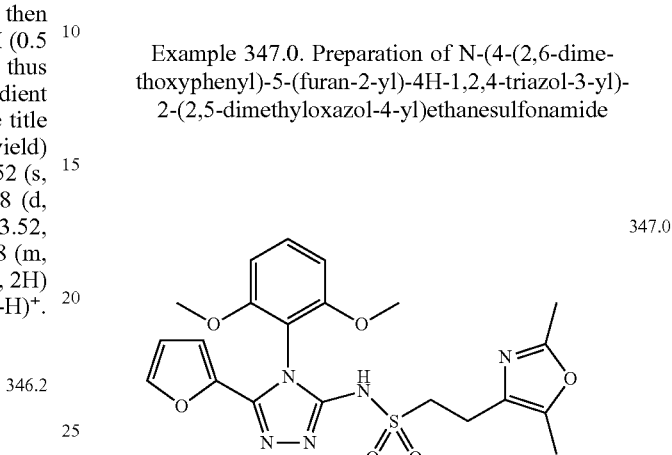

347.0

N-(4-(2,6-Dimethoxyphenyl)-5-(furan-2-yl)-4H-1,2,4-triazol-3-yl)-2-(2,5-dimethyloxazol-4-yl)ethanesulfonamide, Example 347.0. The title compound was prepared from Example 365.0 (177 mg, 0.295 mmol) and 2,5-dimethyl-1,3-oxazole-4-carbaldehyde (commercially available from Maybridge, Cornwall, UK, 40.6 mg, 0.324 mmol) using the procedure described in Example 346.0. This provided the title compound, Example 347.0 (45 mg, 0.096 mmol, 33% yield for three steps), as a white solid. $^1$H NMR (400 MHz, CD$_2$Cl$_2$) δ 11.19 (br. s., 1H) 7.52 (t, J=8.51 Hz, 1H) 7.49 (dd, J=1.76, 0.78 Hz, 1H) 6.74 (d, J=8.61 Hz, 2H) 6.36 (dd, J=3.52, 1.76 Hz, 1H) 6.05 (dd, J=3.62, 0.68 Hz, 1H) 3.77 (s, 3H) 3.77 (s, 3H) 3.18-3.24 (m, 2H) 2.75-2.82 (m, 2H) 2.32 (s, 3H) 2.16 (s, 3H). LCMS-ESI (pos.), m/z: 474.0 (M+H)$^+$.

Example 348.0. Preparation of (R)-3-cyclohexyl-N-(4-(2,6-dimethoxyphenyl)-5-(furan-2-yl)-4H-1,2,4-triazol-3-yl)-3-hydroxypropane-1-sulfonamide or (S)-3-cyclohexyl-N-(4-(2,6-dimethoxyphenyl)-5-(furan-2-yl)-4H-1,2,4-triazol-3-yl)-3-hydroxypropane-1-sulfonamide 348.1

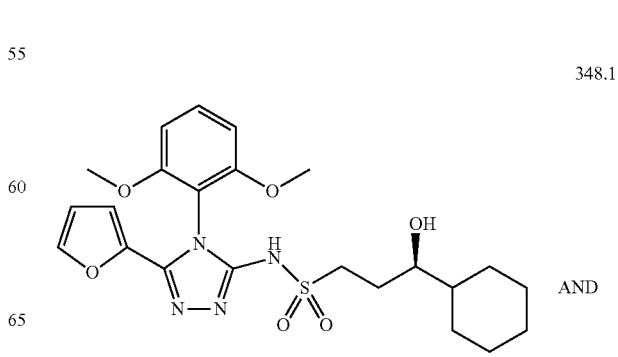

AND

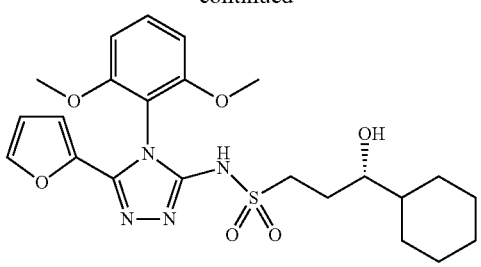

(R)-3-Cyclohexyl-N-(4-(2,6-dimethoxyphenyl)-5-(furan-2-yl)-4H-1,2,4-triazol-3-yl)-3-hydroxypropane-1-sulfonamide and (S)-3-cyclohexyl-N-(4-(2,6-dimethoxyphenyl)-5-(furan-2-yl)-4H-1,2,4-triazol-3-yl)-3-hydroxypropane-1-sulfonamide, Example 348.1. The title compound was prepared from Example 199.2 (236 mg, 0.581 mmol) and cyclohexylmagnesium chloride in diethyl ether (2.0 M, 0.871 mL, 1.74 mmol) using the procedure described in Example 199.3. This provided Example 348.1 (118 mg, 0.240 mmol, 41% yield) as a white solid. LCMS-ESI (pos.), m/z: 491.1 (M+H)+.

348.0

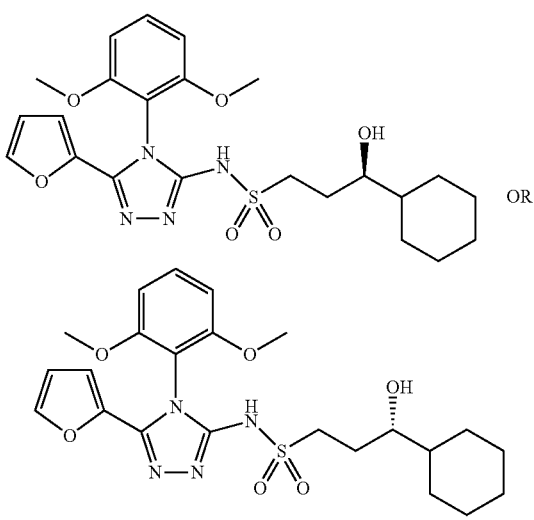

(R)-3-Cyclohexyl-N-(4-(2,6-dimethoxyphenyl)-5-(furan-2-yl)-4H-1,2,4-triazol-3-yl)-3-hydroxypropane-1-sulfonamide or (R)-3-cyclohexyl-N-(4-(2,6-dimethoxyphenyl)-5-(furan-2-yl)-4H-1,2,4-triazol-3-yl)-3-hydroxypropane-1-sulfonamide, Example 348.0. The title compound was the first isomer to elute under the following SFC conditions: AD-H (2×25 cm), 40% IPA/CO2, 100 bar, 70 mL/min, 220 nm. Injection vol.: 0.5-1 mL, 4.5 mg/mL 1:1 MeOH/DCM solution of Example 348.1. 1H NMR (400 MHz, DMSO-d6) δ 13.22 (s, 1H) 7.82 (dd, J=1.66, 0.68 Hz, 1H) 7.55 (t, J=8.51 Hz, 1H) 6.89 (d, J=8.61 Hz, 2H) 6.52 (dd, J=3.52, 1.76 Hz, 1H) 6.01 (dd, J=3.62, 0.68 Hz, 1H) 4.46 (d, J=5.67 Hz, 1H) 3.73 (s, 3H) 33.73 (s, 3H) 3.15-3.24 (m, 1H) 2.97-3.07 (m, 1H) 2.84 (ddd, J=13.84, 11.30, 4.79 Hz, 1H) 1.48-1.74 (m, 7H) 1.03-1.21 (m, 4H) 0.84-1.02 (m, 2H). LCMS-ESI (pos.), m/z: 491.1 (M+H)+.

Example 349.0. Preparation of (R)-3-cyclopentyl-N-(4-(2,6-dimethoxyphenyl)-5-(furan-2-yl)-4H-1,2,4-triazol-3-yl)-3-hydroxybutane-1-sulfonamide and (S)-3-cyclopentyl-N-(4-(2,6-dimethoxyphenyl)-5-(furan-2-yl)-4H-1,2,4-triazol-3-yl)-3-hydroxybutane-1-sulfonamide 349.1

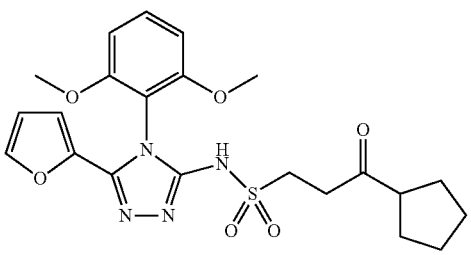

3-Cyclopentyl-N-(4-(2,6-dimethoxyphenyl)-5-(furan-2-yl)-4H-1,2,4-triazol-3-yl)-3-oxopropane-1-sulfonamide, Example 349.1. To a solution of Example 199.3 (388 mg, 0.814 mmol) in DCM (15 mL) and water (0.015 mL) in a 50 mL RBF, was added Dess-Martin periodinane (380 mg, 0.896 mmol). The reaction was then stirred at RT for 16 h. A further portion of Dess-Martin periodinane (115 mg, 0.271 mmol) was added and stirring was continued for 2 h. Additional Dess-Martin periodinane (115 mg, 0.271) was added, and the reaction was further stirred for an additional 1 h. The reaction mixture was then loaded onto a 24 g silica gel column gradient eluting with 0-100% EtOAc in hexanes to provide the title compound, Example 349.1 (265 mg, 0.558 mmol, 69% yield), as a white powder. 1H NMR (400 MHz, DMSO-d6) δ 13.34 (s, 1H) 7.83 (dd, J=1.76, 0.59 Hz, 1H) 7.56 (t, J=8.51 Hz, 1H) 6.90 (d, J=8.61 Hz, 2H) 6.52 (dd, J=3.72, 1.76 Hz, 1H) 6.03 (dd, J=3.62, 0.68 Hz, 1H) 3.73 (s, 3H) 3.73 (s, 3H) 3.09 (t, J=7.53 Hz, 2H) 2.86-2.96 (m, 1H) 2.73-2.80 (m, 2H) 1.67-1.77 (m, 2H) 1.47-1.65 (m, 6H). LCMS-ESI (pos.), m/z: 475.1 (M+H)+.

349.0

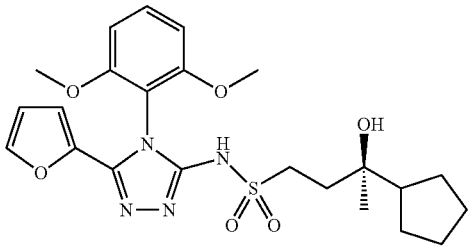

AND

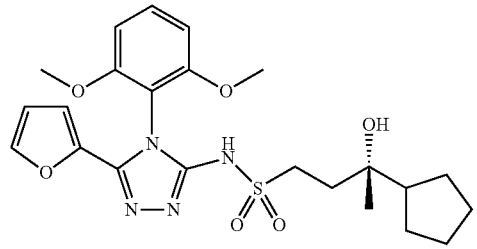

(R)-3-Cyclopentyl-N-(4-(2,6-dimethoxyphenyl)-5-(furan-2-yl)-4H-1,2,4-triazol-3-yl)-3-hydroxybutane-1-sulfonamide and (S)-3-cyclopentyl-N-(4-(2,6-dimethoxyphenyl)-5-(furan-2-yl)-4H-1,2,4-triazol-3-yl)-3-hydroxybutane-1-sulfonamide, Example 349.0. To a suspension of Example 349.1 (57.8 mg, 0.122 mmol) in THF at −78° C., was added dropwise methylmagnesium bromide (0.261 mL, 0.365 mmol). The reaction mixture was stirred at −78° C. for 40 min and then was warmed to 0° C. for 30 min. The reaction was quenched with a saturated aqueous solution of NH$_4$Cl (2.0 mL) at 0° C. It was then acidified to a pH of 2 by adding aqueous 2 N HCl. The mixture was then extracted with DCM (5×DCM). The organic layers were combined, dried over Na$_2$SO$_4$, filtered, and concentrated in vacuo. The residue was dissolved in 1/1 DMSO/MeOH (4.5 mL), filtered through a GHP Acrodisc 13 mm Syrigen filter with 0.45 um GHP membrane (Life Sciences, Lot 21756741), and then purified by preparative HPLC on a C-18 column (CAPCELL TYPE UG120, 5 µm, size 30 mm×250 mm) gradient eluting with 0%-95% CAN with 0.1% TFA in water with 0.1% TFA. The pure fractions were combined and lyophilized to provide the title compound, Example 349.0 (8.5 mg, 0.017 mmol, 14% yield), as a white powder. $^1$H NMR (400 MHz, CD$_2$Cl$_2$) δ 7.53 (t, J=8.61 Hz, 1H) 7.49 (dd, J=1.66, 0.68 Hz, 1H) 6.74 (d, J=8.61 Hz, 2H) 6.36 (dd, J=3.62, 1.86 Hz, 1H) 6.04 (dd, J=3.52, 0.59 Hz, 1H) 3.77 (s, 3H) 3.77 (s, 3H) 3.03-3.20 (m, 2H) 1.80-1.96 (m, 3H) 1.47-1.67 (m, 6H) 1.22-1.43 (m, 2H) 1.09 (s, 3H). LCMS-ESI (pos.), m/z: 491.1 (M+H)$^+$.

Example 350. Preparation of 1-(4-chlorophenyl)-N-(5-(2-furanyl)-4-(2-methoxyphenyl)-4H-1,2,4-triazol-3-yl)methanesulfonamide

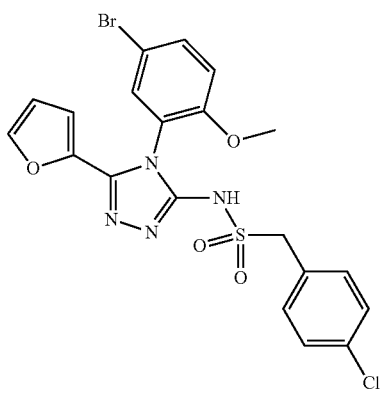

N-(4-(5-Bromo-2-methoxyphenyl)-5-(furan-2-yl)-4H-1,2,4-triazol-3-yl)-1-(4-chlorophenyl)methanesulfonamide, Example 350.1. Example 209.4 (200 mg, 0.597 mmol) was dissolved in pyridine (2984 µL). (4-Chlorophenyl)methanesulfonyl chloride (403 mg, 1.79 mmol) was then added slowly. The reaction mixture was stirred at 80° C. for 18 h. The reaction mixture was then diluted with water and extracted with EtOAc. The combined organic layers were concentrated and the product purified on silica gel eluting with 0-30% (5% MeOH, 1% NH$_3$ in DCM) in DCM. This afforded the title compound. $^1$H NMR (400 MHz, CD$_3$OD) δ 7.74 (1H, dd, J=9.0, 2.5 Hz), 7.58 (2H, dd, J=9.3, 2.1 Hz), 7.33 (4H, s), 7.19 (1H, d, J=9.0 Hz), 6.49 (1H, dd, J=3.5, 1.8 Hz), 6.32 (1H, d, J=3.5 Hz), 4.29 (2H, d, J=2.3 Hz), 3.76 (3H, s). MS (ESI) m/z: 524 (M+H)$^+$.

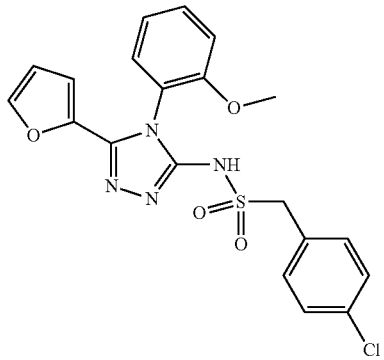

1-(4-Chlorophenyl)-N-(5-(2-furanyl)-4-(2-methoxyphenyl)-4H-1,2,4-triazol-3-yl)methanesulfonamide, Example 350.0. Example 350.1 (50 mg, 0.095 mmol) was dissolved in EtOH. Nitrogen was then bubbled through the mixture for 2 min before palladium on carbon (10.16 mg, 0.095 mmol) was added. The reaction was then placed under an atmosphere of H$_2$ The reaction was complete after 12 h. The reaction mixture was then filtered through a pad of Celite® brand filter aid (Celpure P300, USP-NF, Pharmaceutical Grade) and concentrated in vacuo. The sample was preloaded on silica gel and purified with flash chromatography on a CombiFlash column (40 g silica gel column, Teledyne Isco, gradient 0%-5% MeOH in DCM). This afforded the title compound. $^1$H NMR (400 MHz, CD$_3$OD) δ 7.60-7.67 (1H, m), 7.58-7.60 (1H, m), 7.34-7.40 (1H, m), 7.32 (3H, d, J=6.1 Hz), 7.24-7.30 (2H, m), 7.18 (1H, td, J=7.7, 1.1 Hz), 6.44 (1H, dd, J=3.6, 1.9 Hz), 6.11 (1H, dd, J=3.6, 0.7 Hz), 4.25 (2H, s), 3.76-3.81 (3H, m). MS (ESI) m/z=445 (M+H)$^+$.

Example 351.0. Preparation of 2-(5-fluoropyrimidin-2-yl)ethanesulfonamide

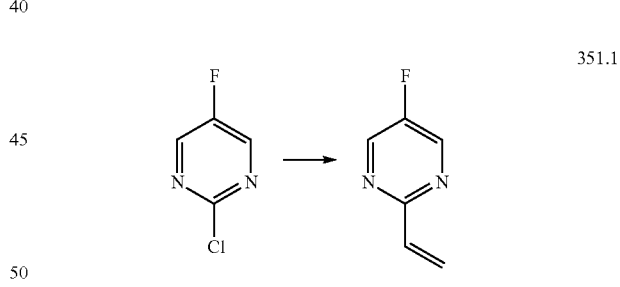

5-Fluoro-2-vinylpyrimidine, Example 351.1. To a solution of 2-chloro-5-fluoropyrimidine (10.0 g, 75.46 mmol, Sigma Aldrich) in DMF (100 mL) was added tributyl(vinyl)tin (31.1 g, 98.09 mmol) at ambient temperature. The reaction mixture was purged with N$_2$ for 5 min and then Pd(PPh$_3$)$_4$ (2.62 g, 2.26 mmol) was added. The reaction mixture was further degassed with N$_2$ for 5 min and then stirred at 100° C. for 24 h. After completion of the reaction (monitored by TLC), the reaction mixture was cooled to ambient temperature and quenched with water (100 mL). The aqueous layer was extracted with Et$_2$O (2×100 mL) and the combined organic layers were washed with brine (100 mL), dried over anhydrous Na$_2$SO$_4$, and then concentrated in vacuo providing initial product which was purified by silica gel column chromatography (Redisep column 120 g; elution: 6% EtOAc in hexanes). This provided Example 351.1 (8.0 g, 85% yield) as an oil. ¹H NMR (400 MHz, CDCl₃) δ 8.58-8.49 (m, 2H), 6.86 (dd, J=17.4, 10.6 Hz, 1H), 6.53 (d, J=17.3 Hz, 1H), 5.70 (d, J=10.6 Hz, 1H).

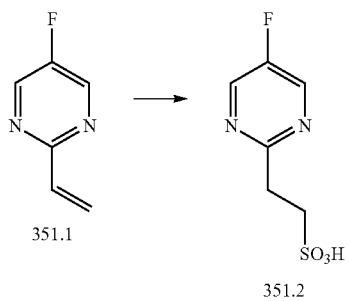

2-(5-Fluoropyrimidin-2-yl) ethanesulfonic acid, Example 351.2. A solution of Example 351.1 (20.0 g, 16.12 mmol) in saturated aqueous NaHSO₃ (80 mL) was stirred at RT for 12 h. After completion of the reaction (monitored by TLC), the reaction mixture was concentrated in vacuo, and the residue was purified by flash column chromatography (120 g Redisep elution: 4-10% H₂O in ACN). This provided Example 351.2 (16.0 g, 48% yield) as a white solid. ¹H NMR (400 MHz, DMSO-d₆) δ 8.89-8.73 (m, 2H), 3.17 (t, J=8.2 Hz, 2H), 2.85 (t, J=8.2 Hz, 2H).

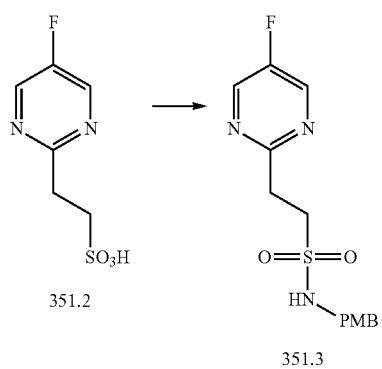

2-(5-Fluoropyrimidin-2-yl)-N-(4-methoxybenzyl)ethanesulfonamide, Example 351.3. To a suspension of 351.2 (16.0 g, 77.30 mmol) in DCM (385 mL) was added oxalyl chloride (29.4 g, 231.8 mmol) followed by DMF (1 mL) at 0° C. The reaction mixture was then stirred at ambient temperature for 1 h and concentrated in vacuo. The reaction mixture was then azeotroped with cyclopentylmethylether. Next, the reaction mixture was diluted with DCM (385 mL), cooled to 0° C., and 4-methoxybenzylamine (31.8 g, 231.88 mmol) and then TEA (39.1 g, 386.4 mmol) were added. The reaction mixture was stirred at ambient temperature for 12 h. After completion of the reaction (monitored by TLC), the reaction mixture was quenched with water (500 mL). The aqueous layer was extracted with DCM (2×400 mL). The organic layers were combined and washed with brine (1.0 L), dried over anhydrous Na₂SO₄, and concentrated in vacuo to obtain the initial product which was purified by column chromatography (silica gel, 100-200 mesh; elution 55% EtOAc in hexanes) and provided Example 351.3 (13.5 g, 54% yield) as an off yellow solid. LCMS-ESI (pos.) m/z:= 326.1.

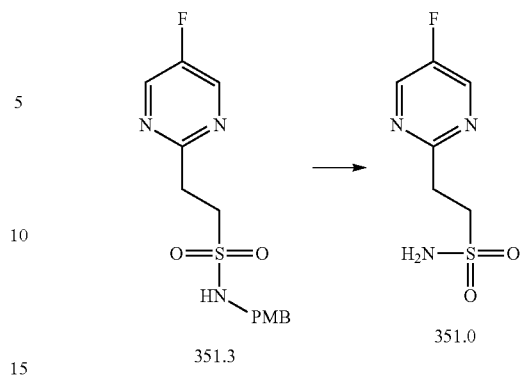

2-(5-Fluoropyrimidin-2-yl)ethanesulfonamide, Example 351.0. To a suspension of 351.3 (13.5 g, 41.41 mmol) in DCM (46 mL) was added TFA (207 mL) at 0° C. The reaction mixture was stirred at ambient temperature for 12 h. After completion of the reaction (monitored by TLC), the reaction mixture was concentrated in vacuo. The residue was purified by flash chromatography (elution: 65% EtOAc in hexanes) and provided Exampl;e 351.0 (5.3 g, 63% yield) as an off yellow solid. ¹H NMR (400 MHz, DMSO-d₆) δ 8.77 (s, 2H), 6.92 (s, 2H), 3.54-3.48 (m, 2H), 3.24-3.20 (s, 2H).

Example 352.0. Preparation of 2-(2-cyano-4-fluorophenyl)ethanesulfonamide

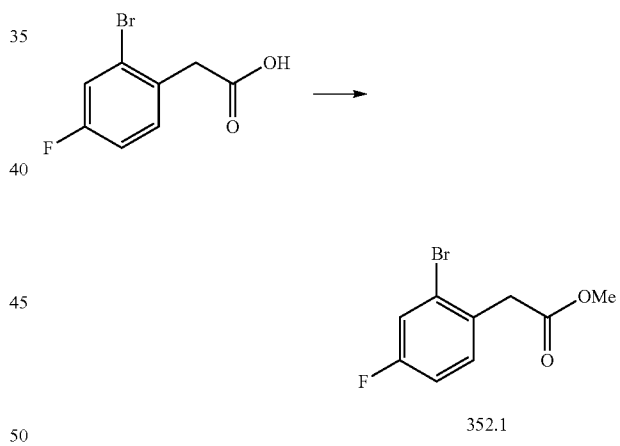

Methyl 2-(2-bromo-4-fluorophenyl) acetate, Example 352.1. To a solution of 2-bromo-4-fluorophenylacetic acid (commercially available from Combi-Blocks Inc., San Diego, Calif., USA) (25.0 g, 0.11 mol) in MeOH (100 mL) was added thionyl chloride (23.5 mL, 0.32 mol) dropwise at 0° C. The resulting mixture was then heated at 80° C. for 16 h. The mixture was cooled to RT, and the volatiles were removed under vacuum. The material thus obtained was diluted with DCM and washed with an aqueous solution of NaHCO₃ and water. The organic layers were dried over sodium sulfate, filtered, and the solvent was removed. This afforded Example 352.1 (26 g, 100% yield) which was used in the next step as prepared. ¹H NMR (400 MHz, DMSO-d₆) δ 7.59 (dd, J=8.6, 2.6 Hz, 1H), 7.47 (dd, J=8.5, 6.2 Hz, 1H), 7.25 (td, J=8.5, 2.7 Hz, 1H), 3.82 (s, 2H), 3.63 (s, 3H).

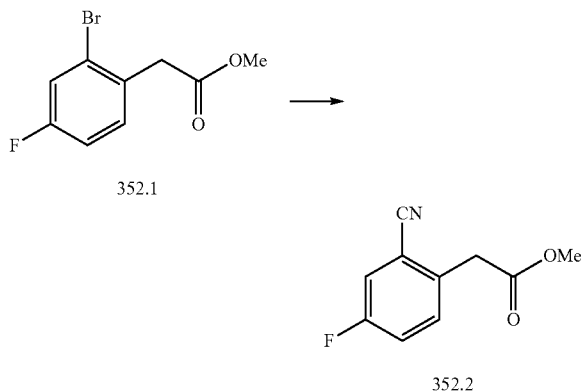

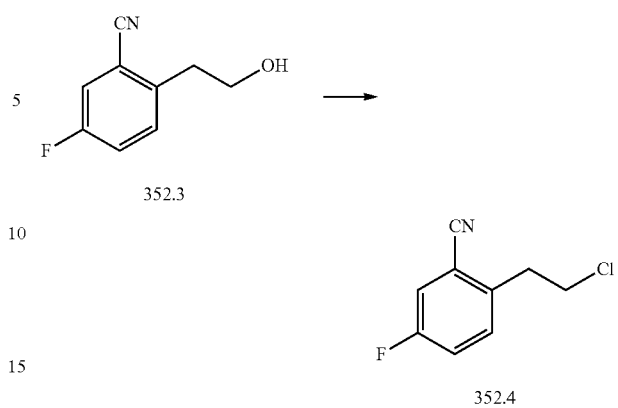

Methyl 2-(2-cyano-4-fluorophenyl) acetate, Example 352.2. To a solution of 352.1 (8.0 g, 0.032 mol) in DMAc (60 mL) was added zinc cyanide (5.7 g, 0.049 mol). The flask was then degassed with argon and bis-(tri-tert-butylphosphine)palladium (1.7 g, 0.003 mol) was added. The resulting mixture was then heated at 110° C. for 18 h in a sealed tube. Thereafter, the reaction mixture was cooled to RT, diluted with water, and extracted with EtOAc. The combined organic layers were dried over sodium sulfate, filtered, and the solvent was removed. The product thus obtained was purified by column chromatography using silica gel and 20-25% EtOAc and hexanes as eluent to obtain Example 352.2 (5.4 g, 86% yield) as a light brown liquid. $^1$H NMR (400 MHz, DMSO-$d_6$) δ 7.91-7.81 (m, 1H), 7.68-7.51 (m, 2H), 3.95 (s, 2H), 3.65 (s, 3H). LCMS-ESI (neg.) m/z: 192.2 (M−H)$^−$.

2-(2-Chloroethyl)-5-fluorobenzonitrile, Example 352.4. To a solution of Example 352.3 (3.0 g, 0.018 mol) in DCM (50 mL) was added thionyl chloride (6.6 mL, 0.091 mol) dropwise followed by DMF (4 drops) at 0° C. The resulting mixture was then heated at 55° C. for 7 h. After completion of the reaction (monitored by TLC), the reaction mixture was concentrated in vacuo to obtain the initial product which was diluted with water and extracted with EtOAc. The combined organic layers were dried over $Na_2SO_4$, filtered, and the solvents were removed in vacuo. This provided Example 352.4 (3.0 g, 90% yield) as a brown liquid which was used in the next step without further purification. $^1$H NMR (400 MHz, DMSO-$d_6$) δ 7.81-7.84 (dd, J=2.4 Hz, 8.8 Hz, 1H), 7.56-7.66 (m, 2H), 3.90-3.94 (t, J=6.8 Hz, 13.6 Hz, 2H), 3.22-3.25 (t, J=6.8 Hz, 13.2 Hz, 2H). LCMS-ESI (neg.) m/z: 182.0 (M−H)$^−$.

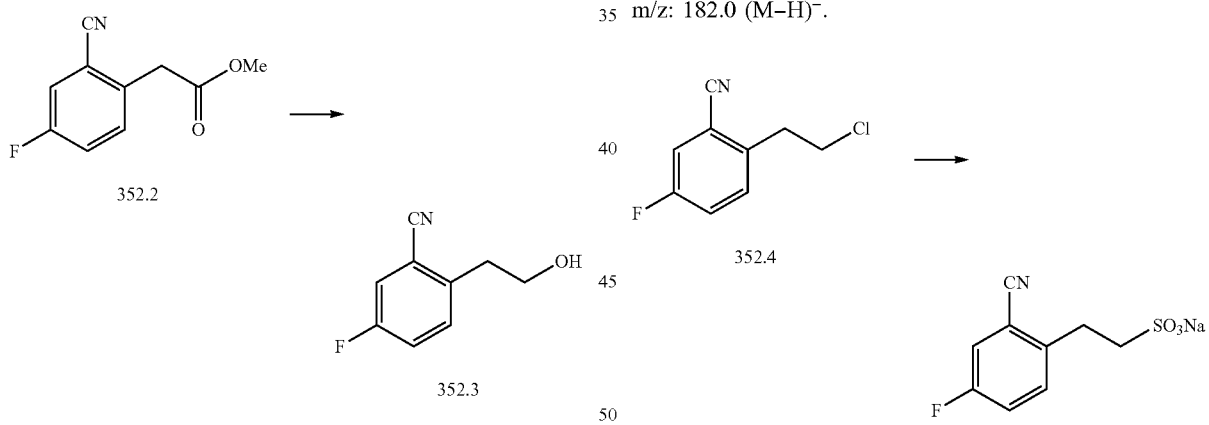

5-Fluoro-2-(2-hydroxyethyl)benzonitrile, Example 352.3. To a solution of Example 352.2 (5.3 g, 0.027 mol) in THF (60 mL) at 0° C. was added $LiBH_4$ (1.20 g, 0.055 mol) portion-wise. The resulting mixture was stirred at 25° C. for 5 h. After completion of the reaction (monitored by TLC), the reaction mixture was cooled to 0° C. and quenched with water. The solvent was removed to obtain the initial material which was further diluted with water and extracted with EtOAc. The combined organic layers were dried over $Na_2SO_4$, filtered, and the solvent was removed in vacuo to obtain the product, which was further purified by column chromatography using silica gel and 15-20% EtOAc in hexanes as eluent to obtain Example 352.3 (3.1 g, 67% yield) as a light brown liquid. $^1$H NMR (400 MHz, DMSO-$d_6$) δ 7.81-7.73 (m, 1H), 7.52 (dd, J=10.6, 8.0 Hz, 2H), 4.82 (t, J=5.2 Hz, 1H), 3.64 (dd, J=11.9, 6.5 Hz, 2H), 2.91 (t, J=6.6 Hz, 2H).

Sodium 2-(2-cyano-4-fluorophenyl)ethanesulfonate, Example 352.5. To a solution of Example 352.4 (3.0 g, 0.016 mol) in $H_2O$ (50 mL) at RT was added sodium sulfite (3.1 g, 0.024 mol). The reaction mixture was heated at reflux for 18 h. After completion of the reaction (monitored by TLC), the reaction mixture was concentrated in vacuo to obtain the initial material which was further stirred with EtOAc and filtered to obtain Example 352.5 (5.8 g) as an off-white solid which was used in the next reaction without further purification. $^1$H NMR (400 MHz, DMSO-$d_6$) δ 7.74-7.76 (dd, J=2 Hz, 8.4 Hz, 1H), 7.47-7.55 (m, 2H), 3.05-3.09 (t, J=8 Hz, 16.4 Hz, 2H), 2.69-2.74 (t, J=8.4 Hz, 16.4 Hz, 2H). LCMS-ESI (neg.) m/z: 228.0 (M−H)$^−$.

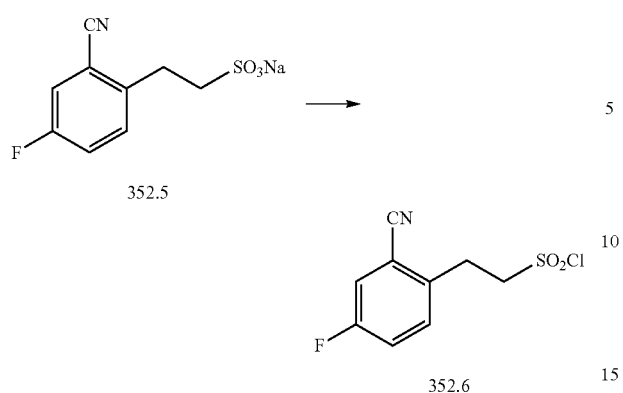

352.5

352.6

2-(2-Cyano-4-fluorophenyl)ethanesulfonyl chloride, Example 352.6. To a solution of Example 352.5 (5.8 g) in benzene (50 mL) was added thionyl chloride (2.5 mL, 0.035 mol) dropwise followed by DMF (3 drops) at 0° C. The resulting mixture was heated to reflux for 16 h. After completion of the reaction (monitored by TLC), the mixture was cooled to 25° C., poured into ice water, and extracted with EtOAc. The EtOAc layer was dried over $Na_2SO_4$, filtered, and the solvents were removed in vacuo. This provided Example 352.6 (3.4 g, 84% yield over two steps) as a brown solid. $^1$H NMR (400 MHz, CDCl$_3$) δ 7.47-7.38 (m, 2H), 7.33 (td, J=8.2, 2.7 Hz, 1H), 3.98 (dd, J=8.7, 6.7 Hz, 2H), 3.56-3.53 (m, 2H). LCMS-ESI (neg.) m/z: 245.9 (M−H)$^−$.

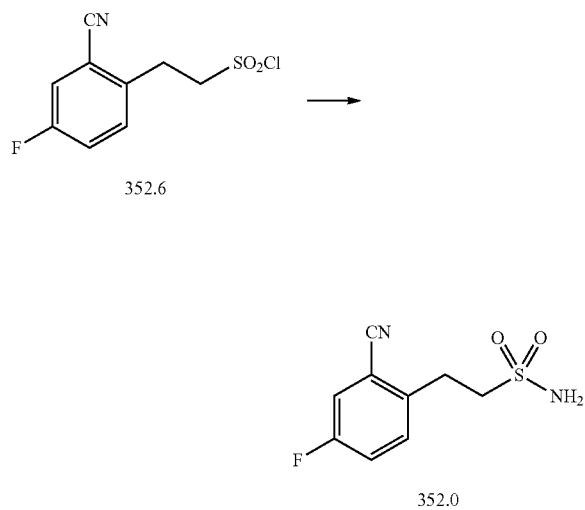

352.6

352.0

2-(2-Cyano-4-fluorophenyl)ethanesulfonamide, Example 352.0. To a mixture of aqueous ammonia (10 mL, 77 mmol) and DCM (30 mL, 468 mmol) was added Example 352.6 (1.42 g, 5.73 mmol) in portions at RT. The reaction mixture was stirred at RT for 2 h. LCMS analysis indicated the reaction was complete. The mixture was neutralized by adding concentrated HCl solution and then was extracted with DCM. The extract was washed with water and saturated aqueous NaHCO$_3$ solution twice. It was then dried over Na$_2$SO$_4$ and concentrated in vacuo. The residue was dried to provide Example 352.0 (1.1 g, 84% yield) as a white solid. LCMS-ESI (pos.), m/z: 229.1 (M+H)$^+$.

Example 353.0. Preparation of (S)-1-(5-fluoropyrimidin-2-yl)propane-2-sulfonamide and (R)-1-(5-fluoropyrimidin-2-yl)propane-2-sulfonamide

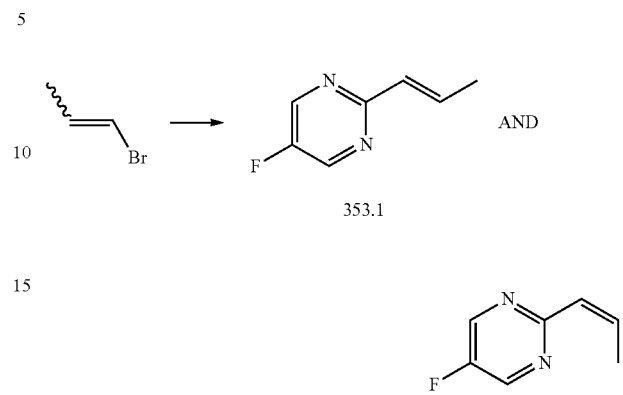

353.1

(E)-5-Fluoro-2-(prop-1-en-1-yl)pyrimidine and (Z)-5-fluoro-2-(prop-1-en-1-yl)pyrimidine, Example 353.1. To magnesium turnings (9.0 g, 371.9 mmol) was added 1-2 crystals of iodine under anhydrous conditions. The mixture was heated at 60° C. for 5 min in vacuo to activate the magnesium. The flask was then cooled to RT and THF (370 mL) was added. The resulting mixture was heated to 65° C. and then (Z/E)-1-bromo-1-propene (45 g, 371.9 mmol) was added dropwise. The resulting mixture was then stirred at 65° C. for 2 h under a nitrogen atmosphere. Thereafter, the mixture was cooled to RT and transferred to an ice bath. Zinc chloride (1 M in diethyl ether, 283 mL, 283 mmol) was then added dropwise over 10 min. The internal temperature of the reaction was kept at about 10-15° C. during the addition, and the resulting organozinc reagent was stirred at RT for 45 min. In a separate RBF, a solution of 2-chloro-5-fluoropyrimidine (commercially available from Novochemy, Jupiter, Fla., USA, 25 g, 189 mmol), S-phos (7.7 g, 18.8 mmol) and palladium (II) acetate (2.1 g, 9.4 mmol) in THF (38 mL) were degassed with nitrogen gas for 5 min. The organozinc reagent was then added dropwise to the above mixture. The resulting mixture was heated at 60° C. for 12 h. After completion of reaction (monitored by TLC), the reaction mixture was quenched with water (50 mL) and acidified with 1.0 N HCl (700 mL, pH 2). The mixture was then extracted with Et$_2$O (2×500 mL). The combined organic layers were washed with brine (200 mL), dried over sodium sulfate, and concentrated in vacuo at 20° C. to a volume of approximately 50 mL containing Example 353.1 which was used as such in the next step.

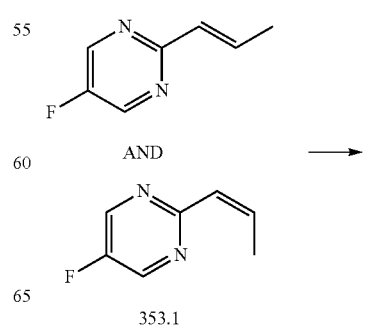

353.1

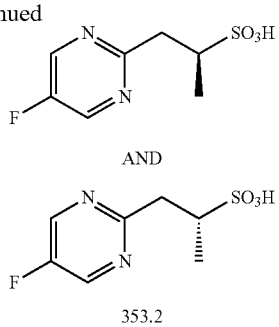

353.2

(S)-1-(5-Fluoropyrimidin-2-yl)propane-2-sulfonic acid and (R)-1-(5-fluoropyrimidin-2-yl)propane-2-sulfonic acid, Example 353.2. To a solution of 353.1 (188.6 mmol) in THF (50 mL) was added an aqueous solution of sodium bisulfite (19.6 g, 188.6 mmol in 100 mL of H$_2$O). The reaction mixture was stirred at ambient temperature for 20 h. Once the reaction was complete (monitored by TLC), the mixture was acidified to approximately pH 1 with concentrated HCl (10 mL). The aqueous layer was then concentrated in vacuo to furnish the initial product which was suspended in EtOH (250 mL). The product thus obtained was heated to reflux, filtered hot, and rinsed with hot EtOH (100 mL). The filtrate was concentrated in vacuo to give a brown solid which was recrystallized from IPA (50 mL) to afford Example 353.2 (20 g, 48% yield) as a brown solid. $^1$H NMR (400 MHz, D$_2$O) δ 8.69 (s, 2H), 3.47 (td, J=9.8, 8.2, 4.0 Hz, 2H), 3.06 (dd, J=16.1, 10.2 Hz, 1H), 1.24 (d, J=6.5 Hz, 3H). LCMS-ESI (neg.) m/z: 118.9 (M−H)$^−$.

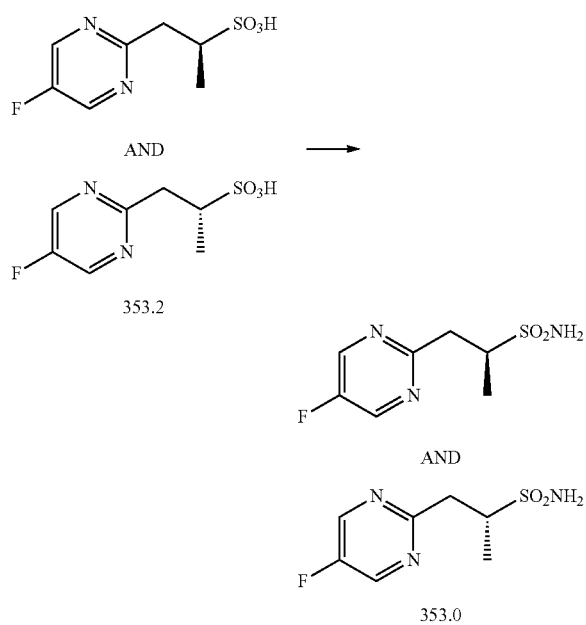

353.2

(S)-1-(5-Fluoropyrimidin-2-yl)propane-2-sulfonamide and (R)-1-(5-fluoropyrimidin-2-yl)propane-2-sulfonamide, Example 353.0. A solution of Example 353.2 (80 g, 360 mmol) in thionyl chloride (268 mL, 3600 mmol) was heated at 60° C. for 3 h. The reaction was concentrated in vacuo to afford the sulfonyl chloride compound which was azeotroped with toluene (3×300 mL). The residue was diluted with DCM (1.0 L) and ammonia gas was bubbled through the solution for 15 min at −78° C. The mixture was then stirred at RT for 1 h. Thereafter, the reaction mixture was filtered through a pad of Celite® brand filter agent and the pad was washed with DCM (100 mL) and EtOAc (100 mL). The combined filtrate was then concentrated in vacuo to obtain a residue which was purified by column chromatography (silica gel, elution 0-60% EtOAc in hexanes). This provided Example 353.0 (43 g, 54% yield) as a white solid. $^1$H NMR (400 MHz, DMSO-d$_6$) δ 8.86 (d, J=1.1 Hz, 2H), 6.90 (s, 2H), 3.57-3.51 (m, 2H), 2.93 (dd, J=15.4, 11.1 Hz, 1H), 1.19 (d, J=6.5 Hz, 3H). LCMS-ESI (pos.) m/z: 220.0 (M+H)$^+$.

Example 354.0. Preparation of (2S,3R)-3-(5-fluoropyrimidin-2-yl)butane-2-sulfonamide and (2R,3S)-3-(5-fluoropyrimidin-2-yl)butane-2-sulfonamide and (2R,3R)-3-(5-fluoropyrimidin-2-yl)butane-2-sulfonamide and (2S,3S)-3-(5-fluoropyrimidin-2-yl)butane-2-sulfonamide

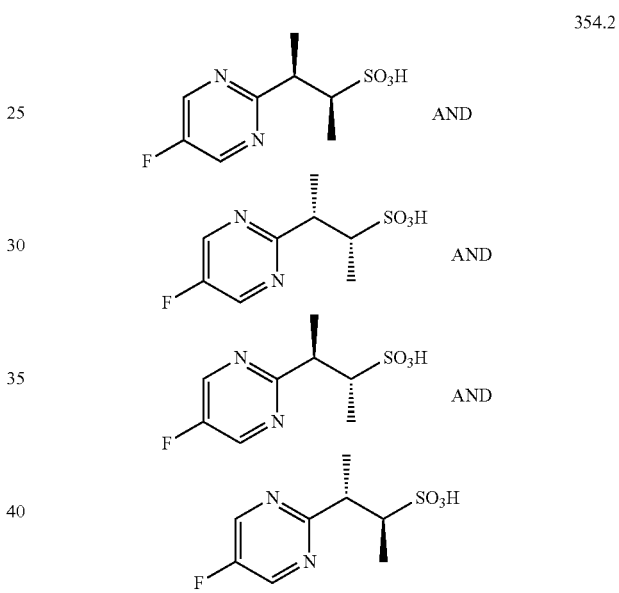

354.2

(2S,3R)-3-(5-Fluoropyrimidin-2-yl)butane-2-sulfonic acid and (2R,3S)-3-(5-fluoropyrimidin-2-yl)butane-2-sulfonic acid (2R,3R)-3-(5-fluoropyrimidin-2-yl)butane-2-sulfonic acid and (2S,3S)-3-(5-fluoropyrimidin-2-yl)butane-2-sulfonic acid, Example 354.2. To a solution of Example 56.1 (1.10 g, 7.2 mmol) in THF (12 mL) was added a solution of sodium bisulfite (2.26 g, 21.7 mmol) in water (4 mL). The mixture was heated at 60° C. for 3 d and then concentrated in vacuo. The residue was purified in batches by reverse phase preparatory HPLC (Sunfire 5 μM C18 column, eluent: 0-40% ACN in water where both solvents contain 0.1% TFA) and provided Example 354.2 (1.03 g, 61% yield) as a white solid. LCMS-ESI (pos.) m/z: 235.1 (M+H)$^+$.

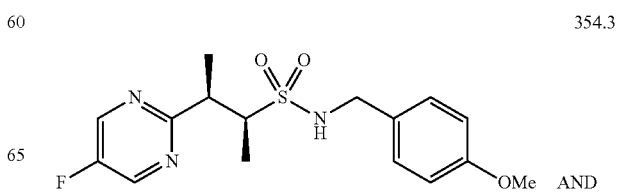

354.3

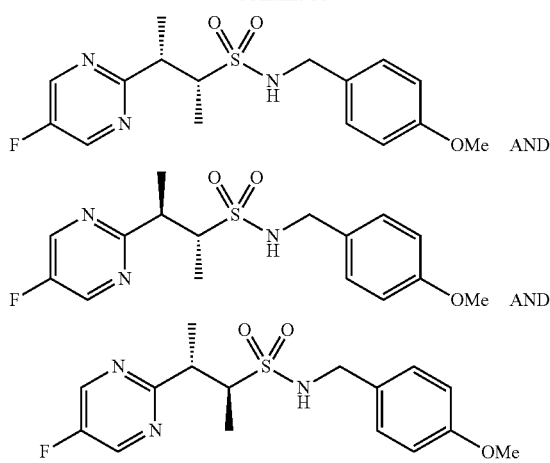

(2S,3R)-3-(5-Fluoropyrimidin-2-yl)-N-(4-methoxybenzyl)butane-2-sulfonamide and (2R,3S)-3-(5-fluoropyrimidin-2-yl)-N-(4-methoxybenzyl)butane-2-sulfonamide and (2R,3R)-3-(5-fluoropyrimidin-2-yl)-N-(4-methoxybenzyl)butane-2-sulfonamide and (2S,3S)-3-(5-fluoropyrimidin-2-yl)-N-(4-methoxybenzyl)butane-2-sulfonamide, Example 354.3. To a suspension of Example 354.2 (49.2 mg, 0.21 mmol) in DCM (2.5 mL) was added oxalyl chloride (37 μL, 0.42 mmol) via syringe followed by a catalytic amount of DMF via syringe. Vigorous bubbling was observed. The resulting white slurry was stirred at RT for 2.5 h and then was concentrated. The residue was azeotroped to dryness with benzene and then was suspended in DCM (2.5 mL). 4-Methoxybenzylamine (60 μL, 0.46 mmol) and TEA (102 μL, 0.74 mmol) were then added sequentially via syringe. The resulting light yellow slurry was stirred at RT overnight. The reaction mixture was partitioned between water and DCM (3×). The combined organic layers were dried over anhydrous MgSO₄, filtered, and concentrated. The residue was purified by reverse phase preparatory HPLC (Sunfire 5 μM C18 column, eluent: 30%-70% ACN in water where both solvents contain 0.1% TFA) and provided Example 354.3 (16.2 mg, 22% yield) as a light yellow oil. LCMS-ESI (pos.) m/z: 376.1 (M+Na)⁺.

354.0

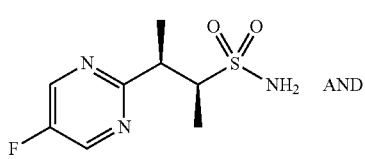

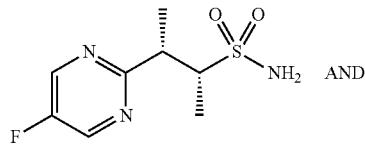

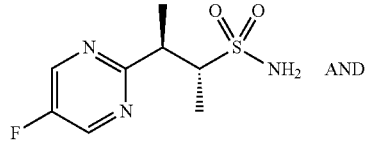

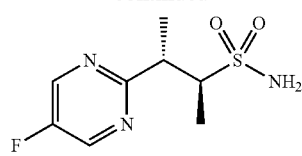

(2S,3R)-3-(5-Fluoropyrimidin-2-yl)butane-2-sulfonamide and (2R,3S)-3-(5-fluoropyrimidin-2-yl)butane-2-sulfonamide and (2R,3R)-3-(5-fluoropyrimidin-2-yl)butane-2-sulfonamide and (2S,3S)-3-(5-fluoropyrimidin-2-yl)butane-2-sulfonamide, Example 354.0. A flask was charged with 354.3 (84 mg, 0.21 mmol) and treated with TFA (4.0 mL, 54 mmol) via syringe. The resulting red solution was stirred for 20 h and then was directly concentrated. The residue was purified by silica gel chromatography (eluent: 0-3% MeOH in DCM over 60 min) to provide Example 354.0 (112 mg, 65% yield) as a yellow solid. LCMS-ESI (pos.) m/z: 234.1 (M+H)⁺.

Example 355.0. Preparation of (1R,2R)-1-(5-fluoropyrimidin-2-yl)-1-hydroxypropane-2-sulfonamide and (1S,2S)-1-(5-fluoropyrimidin-2-yl)-1-hydroxypropane-2-sulfonamide 355.01

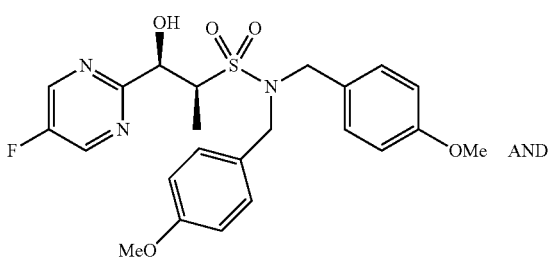

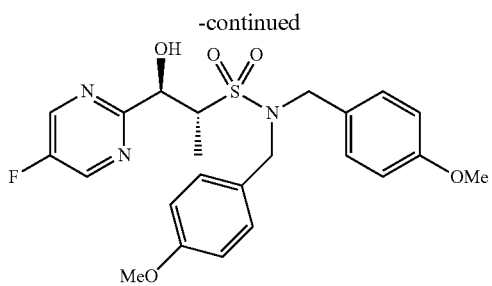

(1R,2S)-1-(5-Fluoropyrimidin-2-yl)-1-hydroxy-N,N-bis (4-methoxybenzyl)propane-2-sulfonamide and (1S,2R)-1-(5-fluoropyrimidin-2-yl)-1-hydroxy-N,N-bis(4-methoxybenzyl)propane-2-sulfonamide and (1R,2R)-1-(5-fluoropyrimidin-2-yl)-1-hydroxy-N,N-bis(4-methoxybenzyl)propane-2-sulfonamide and (1S,2S)-1-(5-fluoropyrimidin-2-yl)-1-hydroxy-N,N-bis(4-methoxybenzyl)propane-2-sulfonamide, Example 355.01. To a −60° C. solution of Example 361.0 (2.20 g, 6.3 mmol) in THF (13 mL) was added n-butyllithium (2.5 M solution in hexanes, 2.72 mL, 6.8 mmol) slowly via syringe. After 10 min, a solution of Example 343.2 (660 mg, 5.2 mmol) in THF (5 mL) was added dropwise via cannula at −60° C. The resulting mixture was stirred at −60° C. for 15 min and was then allowed to warm to RT and stirred overnight. The reaction was quenched with saturated aqueous NH$_4$Cl and extracted with EtOAc (3×). The combined organic layers were dried over anhydrous sodium sulfate, filtered, and concentrated. The residue was purified by silica gel chromatography (eluent was 20-70% EtOAc in hexanes over 30 min) to provide Example 355.01 (547 mg, 22% yield) as a red solid. LCMS-ESI (pos.) m/z: 498.0 (M+Na)$^+$.

355.0

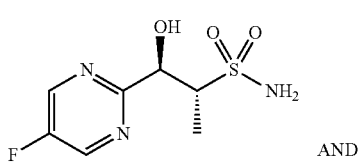

AND

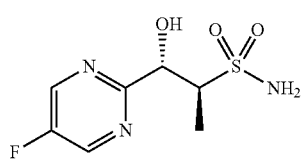

(1R,2R)-1-(5-Fluoropyrimidin-2-yl)-1-hydroxypropane-2-sulfonamide and (1S,2S)-1-(5-fluoropyrimidin-2-yl)-1-hydroxypropane-2-sulfonamide, Example 355.0. A flask was charged with Example 355.01 (545 mg, 1.15 mmol) and was then treated with TFA (11.5 mL, 155 mmol) via syringe and anisole (501 μL, 4.6 mmol) via syringe. The resulting red solution was stirred overnight and then was directly concentrated. The residue was purified twice by silica gel chromatography (eluent was 1-6% MeOH in DCM over 50 min). This provided Example 355.0 (trans diastereomer, 69 mg, 51% yield) as a pink solid and as the first-eluting peak. LCMS-ESI (pos.) m/z: 236.2 (M+H)$^+$.

Example 355.1. Preparation of (1R,2S)-1-(5-fluoropyrimidin-2-yl)-1-hydroxypropane-2-sulfonamide and (1S,2R)-1-(5-fluoropyrimidin-2-yl)-1-hydroxypropane-2-sulfonamide 355.1

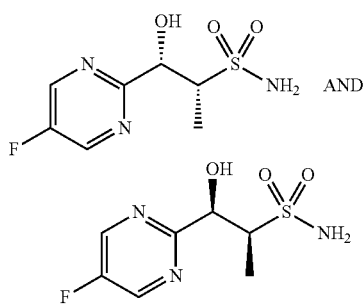

(1R,2S)-1-(5-Fluoropyrimidin-2-yl)-1-hydroxypropane-2-sulfonamide and (1S,2R)-1-(5-fluoropyrimidin-2-yl)-1-hydroxypropane-2-sulfonamide, Example 355.1. Further elution under the conditions described in Example 355.0 provided Example 355.1 (cis diastereomer, 66 mg, 49% yield) as the second-eluting peak. The product was a pink solid. LCMS-ESI (pos.) m/z: 236.2 (M+H)$^+$.

Example 356.0. Preparation of (1S,2R)-1-ethoxy-1-(5-methylpyrimidin-2-yl)propane-2-sulfonamide and (1R,2S)-1-ethoxy-1-(5-methylpyrimidin-2-yl)propane-2-sulfonamide Sulfonamide 356.01

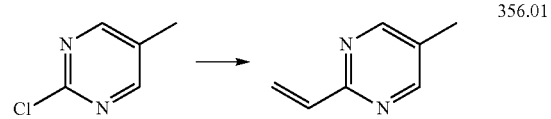

5-Methyl-2-vinylpyrimidine, Example 356.01. A 3-necked 3 L RBF was fitted with a reflux condenser, a temperature controller and a septum and was charged with 2-chloro-5-methylpyrimidine (100 g, 778 mmol), potassium vinyltrifluoroborate (156 g, 1167 mmol), triphenylphosphine (20.5 g, 78 mmol), cesium carbonate (633.7 g, 1945 mmol), and a large stir bar. Water (1565 mL) was added, and the mixture was stirred for several min and then THF (244 mL) was added. Argon was bubbled through the mixture for 5 min and then palladium (II) chloride (1.72 g, 38.9 mmol) was added. The reaction was then further sparged with argon for 5 min. The temperature was raised to 62° C., and the mixture was stirred until completion. The reaction was ten cooled to RT and filtered through two Whatman GF/F filter cups rinsing with ether. The mixture was transferred to a separatory funnel and the layers were separated. The aqueous layer was further extracted with Et$_2$O (4×). The combined organic layers were dried over anhydrous MgSO$_4$ and partially concentrated in vacuo at 20° C. and 115 torr for an extended period of time to give an orange liquid. The initial product was purified by Kugelrohr distillation to provide Example 356.01 (65.4 g, 70% yield) as a light yellow oil. LCMS-ESI (pos.) m/z: 121.1 (M+H)$^+$.

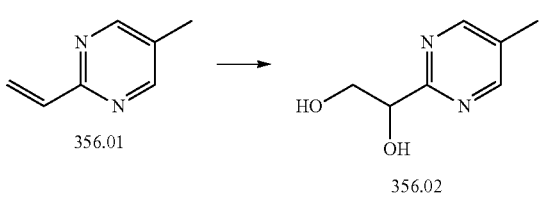

1-(5-Methylpyrimidin-2-yl)ethane-1,2-diol, Example 356.02. To a 2 L RBF was added Example 356.01 (64.5 g, 537 mmol), osmium tetroxide (0.204 mL, 3.93 mmol), 1,4-dioxane (537 mL, 537 mmol), 4-methylmorpholine-N-oxide (50% wt. in water, 40 mL, 341 mmol), and 4-methylmorpholine-4-oxide (94 g, 805 mmol). The resulting mixture was stirred for 2 d and the solvent was then removed in vacuo. The residue was purified by silica gel chromatography (eluent: 0-100% EtOAc/EtOH mixture (3:1) in hexanes). The desired product was isolated and was triturated with 40% EtOAc in hexanes. The solid was filtered, washed with 20% EtOAc in hexanes and dried affording Example 56.02 (67.3 g, 81% yield). $^1$H NMR (400 MHz, CDCl$_3$) δ 8.59 (s, 2H), 4.81-4.98 (m, 1H), 3.88-4.19 (m, 2H), 2.36 (s, 3H).

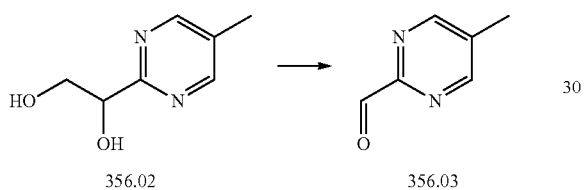

5-Methylpyrimidine-2-carbaldehyde, Example 356.03. A 5 L RBF was equipped with a mechanical stirrer and charged with Example 356.02 (64.3 g, 417 mmol), 1,4-dioxane (1.04 L) and water (261 mL). The reaction mixture was cooled to 0° C. Sodium periodate (223 g, 1043 mmol) was then added and the reaction was allowed to gradually warm to RT. After an additional 2.3 h at RT, DCM (2 L) was added. The resulting solution was filtered through a plug of anhydrous MgSO$_4$ (700 g), and the plug was washed with additional DCM (7 L). The solvent was concentrated in vacuo and the residue was azeotroped with toluene to provide Example 356.03 (44 g, 86% yield) as a white solid. LCMS-ESI (pos.) m/z: 122.8 (M+H)$^+$.

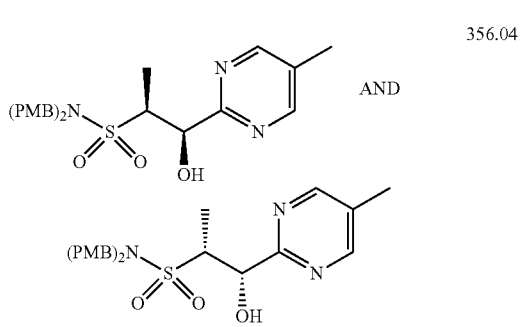

(1R,2S)-1-Hydroxy-N,N-bis(4-methoxybenzyl)-1-(5-methylpyrimidin-2-yl)propane-2-sulfonamide and (1S,2S)-1-hydroxy-N,N-bis(4-methoxybenzyl)-1-(5-methylpyrimidin-2-yl)propane-2-sulfonamide, Example 356.04. A 3 L 3-necked RBF was charged with Example 361.0 (151 g, 432 mmol) and THF (1.2 L) under nitrogen. A pre-dried addition funnel was attached and the flask was cooled to −78° C. n-Butyllithium (1.6 M solution in hexanes, 270 mL, 432 mmol) was added via the addition funnel, and the reaction was stirred for 10 min. A solution of Example 356.03 (44 g, 360 mmol) in THF (300 mL) was then added via cannula. The resulting mixture was stirred at −78° C. for 45 min and then warmed to RT and stirred for an additional 2.2 h. The reaction was quenched with saturated aqueous NH$_4$Cl and extracted with EtOAc. The combined organic layers were dried over anhydrous sodium sulfate and concentrated. The residue was purified by silica gel chromatography (eluent: 0-50% EtOAc in DCM) and provided the cis diastereomer, Example 356.04 (cis diastereomer, 56.4 g, 33% yield), as the first-eluting peak. LCMS-ESI (pos.) m/z: 472.1 (M+H)$^+$.

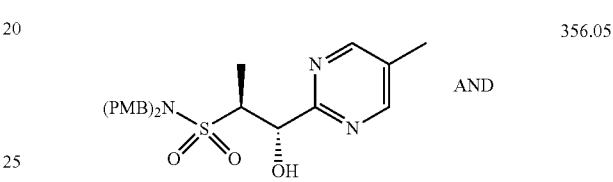

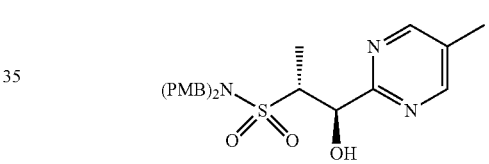

(1R,2R)-1-Hydroxy-N,N-bis(4-methoxybenzyl)-1-(5-methylpyrimidin-2-yl)propane-2-sulfonamide and (1S,2R)-1-hydroxy-N,N-bis(4-methoxybenzyl)-1-(5-methylpyrimidin-2-yl)propane-2-sulfonamide, Example 356.05. Further elution under the conditions described in Example 356.04 delivered Example 356.05 (trans diastereomer) as the second-eluting peak. LCMS-ESI (pos.) m/z: 472.1 (M+H)$^+$.

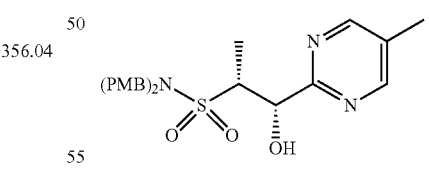

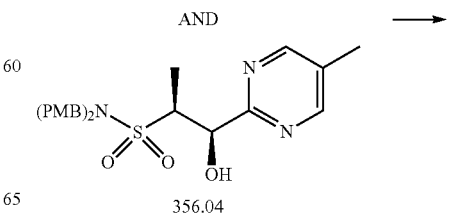

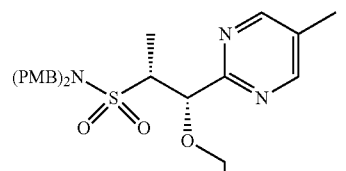

AND

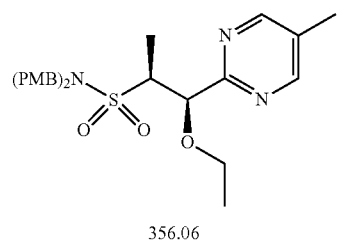

356.06

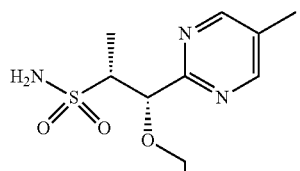

AND

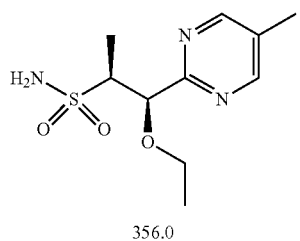

356.0

(1R,2S)-1-Ethoxy-N,N-bis(4-methoxybenzyl)-1-(5-methylpyrimidin-2-yl)propane-2-sulfonamide and (1S,2R)-1-ethoxy-N,N-bis(4-methoxybenzyl)-1-(5-methylpyrimidin-2-yl)propane-2-sulfonamide, Example 356.06. To a −78° C. solution of Example 356.04 (1.62 g, 3.4 mmol) in THF (70 mL) was added potassium bis(trimethylsilyl)amide (1.0 M solution in THF, 10.6 mL, 10.6 mmol) slowly via syringe. After 1.25 h, ethyl trifluoromethanesulfonate (1.4 mL, 10.6 mmol) was added slowly via syringe. The resulting orange solution was stirred at −78° C. for 45 min and then was quenched with a 2:1 mixture of saturated aqueous NH$_4$Cl and water (75 mL). The resulting mixture was extracted with EtOAc (4×). The combined organic layers were dried over anhydrous sodium sulfate, filtered, and concentrated. The residue was purified by silica gel chromatography (eluent: 10-65% EtOAc in hexanes) and provided Example 356.06 (1.02 g, 60% yield) as a light yellow oil. LCMS-ESI (pos.) m/z: 500.1 (M+H)$^+$.

(1S,2R)-1-Ethoxy-1-(5-methylpyrimidin-2-yl)propane-2-sulfonamide and (1R,2S)-1-ethoxy-1-(5-methylpyrimidin-2-yl)propane-2-sulfonamide, Example 356.0. Example 356.06 (1.02 g, 2.0 mmol) was dissolved in TFA (14 mL). Anisole (466 μL, 4.3 mmol) was then added via syringe. The resulting orange solution was stirred at RT for 16.5 h and concentrated in vacuo. The residue was purified by silica gel chromatography (eluent: 0-4.5% MeOH in DCM) to provide 356.0 (495 mg, 93% yield) as a white solid. LCMS-ESI (pos.) m/z: 260.0 (M+H)$^+$.

The compounds set forth in the following table were synthesized following the procedure in Example 356.0 as described above.

TABLE 12

| Example | Reagents | Structure, Name and Data |
|---|---|---|
| 356.1 | (1R,2R)-1-hydroxy-N,N-bis(4-methoxybenzyl)-1-(5-methylpyrimidin-2-yl)propane-2-sulfonamide and (1S,2R)-1-hydroxy-N,N-bis(4-methoxybenzyl)-1-(5-methylpyrimidin-2-yl)propane-2-sulfonamide, Example 356.05. Material prepared in an analagous mariner to that of Example 356.0 employing sulfonamide 356.05 | (1S,2S)-1-ethoxy-1-(5-methylpyrimidin-2-yl)propane-2-sulfonamide and(1R,2R)-1-ethoxy-1-(5-methylpyrimidin-2-yl)propane-2-sulfonamide. LCMS-ESI (pos.) m/z: 260.0 (M + H)$^+$. |

Example 357.0. Preparation of (1S,2S)-1-((tert-butyldimethylsilyl)oxy)-1-(5-fluoropyrimidin-2-yl)propane-2-sulfonamide and (1R,2R)-1-((tert-butyldimethylsilyl)oxy)-1-(5-fluoropyrimidin-2-yl)propane-2-sulfonamide

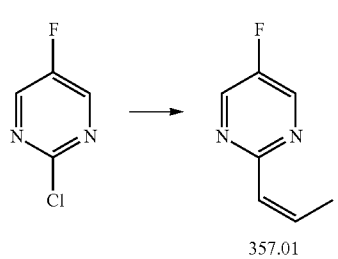

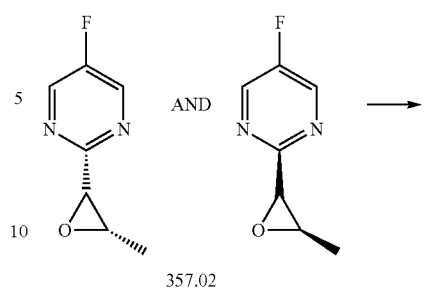

357.02

(Z)-5-Fluoro-2-(prop-1-en-1-yl)pyrimidine, Example 357.01. Tetrakis(triphenylphosphine)palladium (4.62 g, 4.00 mmol) was added to a degassed solution of 2-chloro-5-fluoropyrimidine (21.2 g, 160 mmol, Matrix Scientific), cis-1-propen-1-ylboronic acid (16.5 g, 192 mmol, Sigma-Aldrich) and sodium carbonate (33.9 g, 320 mmol) in a mixture of THF (213 mL) and water (107 mL). The reaction was heated at 100° C. for 2.5 d. The white precipitate was then filtered off and rinsed with ether. The filtrate was extracted with DCM (2×). The combined organic layers were then dried over anhydrous magnesium sulfate and partially concentrated (note that the product is volatile). The residue was purified by silica gel chromatography (eluent: 0-50% DCM in hexanes) to provide 357.01 (19.4 g, 88% yield). $^1$H NMR (500 MHz, CDCl$_3$) δ: 8.58 (s, 2H), 6.51-6.60 (m, 1H), 6.25 (dq, J=11.8, 7.3 Hz, 1H), 2.24 (dd, J=7.2, 1.8 Hz, 3H). LCMS-ESI (pos.) m/z: 139.4 (M+H)$^+$.

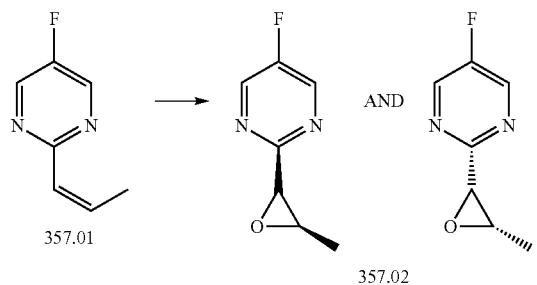

(5-Fluoro-2-((2S,3R)-3-methyloxiran-2-yl)pyrimidine and 5-fluoro-2-((2R,3S)-3-methyloxiran-2-yl)pyrimidine, Example 357.02. To an ice-cooled solution of 357.01 (12.65 g, 92 mmol) in a mixture of tert-butanol and water (1/1, v/v, 183 mL) was added N-bromosuccinimide (32.6 g, 183 mmol). The reaction was allowed to warm to RT overnight and a solution of NaOH (10 M, 27.5 mL, 275 mmol) was slowly added being careful to not allow the internal temperature to exceed 32° C. The mixture was extracted with EtOAc (3×) and the combined organic layers were dried over anhydrous magnesium sulfate and concentrated. The residue was purified by silica gel chromatography (eluent: pure hexanes grading to pure DCM) to provide the title compound 357.02 (10.2 g, 72% yield). LCMS-ESI (pos.) m/z: 155.2 (M+H)$^+$.

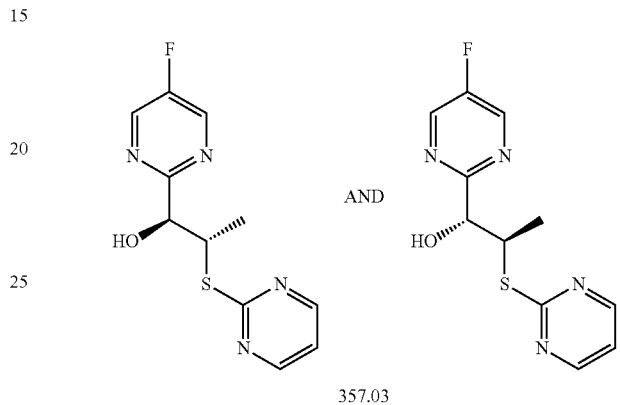

357.03

(1S,2S)-1-(5-Fluoropyrimidin-2-yl)-2-(pyrimidin-2-ylthio)propan-1-ol and (1R,2R)-1-(5-fluoropyrimidin-2-yl)-2-(pyrimidin-2-ylthio)propan-1-ol, Example 357.03. To a solution of 357.02 (2.14 g, 13.9 mmol) in DCM (46 mL) was added pyrimidine-2-thiol (3.11 g, 27.8 mmol, Sigma-Aldrich) followed by ytterbium(III)trifluoromethanesulfonate (431 mg, 0.69 mmol, Sigma-Aldrich). The resulting yellow slurry was stirred overnight and then additional ytterbium(III)trifluoromethanesulfonate (431 mg, 0.69 mmol) was added. After another 3 h, the reaction was filtered through Celite® brand filter agent and the filtrate was neutralized with saturated aqueous sodium bicarbonate solution. The mixture was extracted with DCM (3×), and the combined organic layers were dried over anhydrous magnesium sulfate and concentrated. The residue was purified by silica gel chromatography (eluent: 30-60% EtOAc in hexanes) to provide the title compound 357.03 (2.53 g, 68% yield). LCMS-ESI (pos.) m/z: 267.0 (M+H)$^+$.

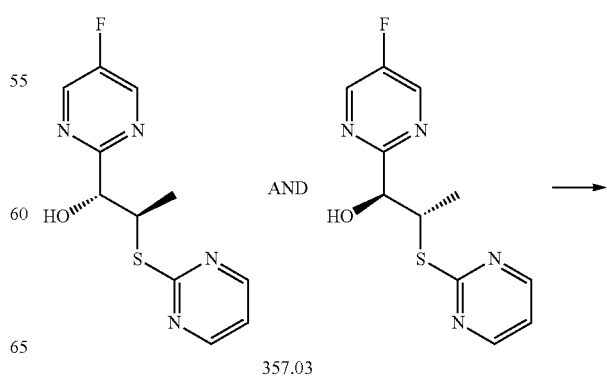

357.03

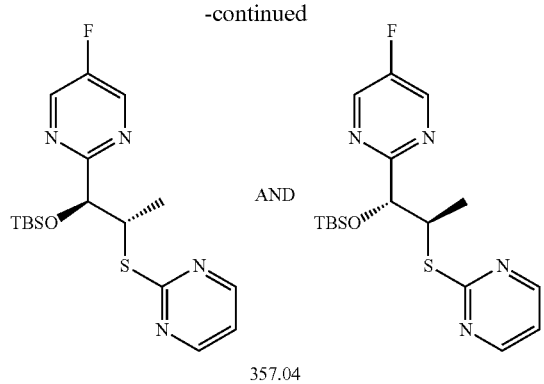

357.04

2-((1S,2S)-1-((tert-Butyldimethylsilyl)oxy)-2-(pyrimidin-2-ylthio)propyl)-5-fluoropyrimidine and 2-((1R,2R)-1-((tert-butyldimethylsilyl)oxy)-2-(pyrimidin-2-ylthio)propyl)-5-fluoropyrimidine, Example 7.04. To a solution of 357.03 (2.44 g, 9.16 mmol) in DCM (92 mL) was added TBSOTf (2.32 mL, 10.08 mmol, Sigma-Aldrich) followed by 2,6-lutidine (1.17 mL, 10.08 mmol). After 20 min, the reaction was concentrated. The residue was purified by silica gel chromatography (eluent: 10-50% EtOAc in hexanes) to provide 357.04 (3.28 g, 94% yield) as a colorless oil. LCMS-ESI (pos.) m/z: 381.0 (M+H)$^+$.

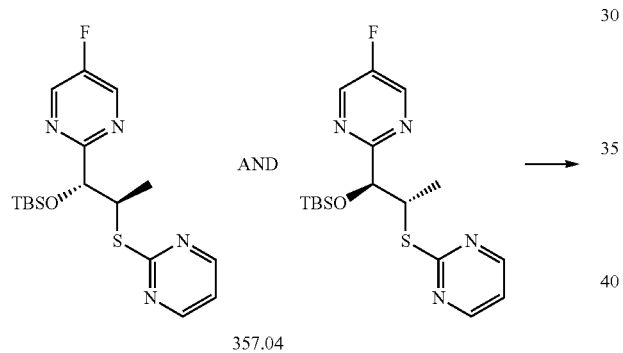

357.04

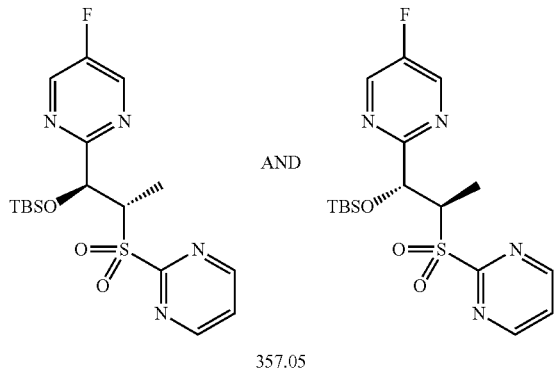

357.05

2-((1S,2S)-1-((tert-Butyldimethylsilyl)oxy)-2-(pyrimidin-2-ylsulfonyl)propyl)-5-fluoropyrimidine and 2-((1R,2R)-1-((tert-butyldimethylsilyl)oxy)-2-(pyrimidin-2-ylsulfonyl)propyl)-5-fluoropyrimidine, Example 357.05. To a solution of 357.04 (3.27 g, 8.59 mmol) in DCM (43 mL) was added 3-chloroperoxybenzoic acid, (77% max., 3.85 g, 17.2 mmol). After 4 h at RT, the reaction was heated at 40° C. for an additional 2 h. After this time period, the heating bath was removed and stirring was continued at RT overnight. The reaction was concentrated and the residue was purified by silica gel chromatography (eluent: 10-100% EtOAc in hexanes) to provide 357.05 (3.54 g, 100%). LCMS-ESI (pos.) m/z: 413.0 (M+H)$^+$.

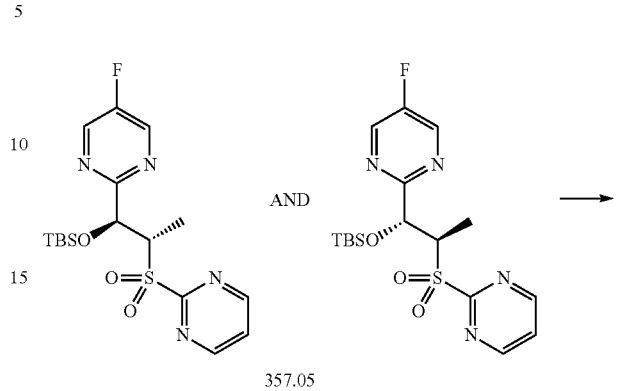

357.05

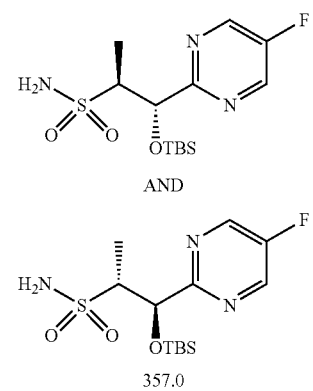

357.0

(1S,2S)-1-((tert-Butyldimethylsilyl)oxy)-1-(5-fluoropyrimidin-2-yl)propane-2-sulfonamide and (1R,2R)-1-((tert-butyldimethylsilyl)oxy)-1-(5-fluoropyrimidin-2-yl)propane-2-sulfonamide, Example 357.0. To a solution of 357.05 (3.40 g, 8.2 mmol) in MeOH (41 mL) was added potassium carbonate (1.14 g, 8.2 mmol). After stirring at RT overnight, additional potassium carbonate (342 mg, 2.8 mmol) was added. After another 6 h at RT, the reaction was concentrated in vacuo. The residue was dissolved in water (80 mL) and then potassium acetate (1.29 g, 13.2 mmol) and hydroxylamine-O-sulfonic acid (1.21 g, 10.7 mmol) were added sequentially. The reaction mixture was stirred at RT for 2 h and then was extracted with EtOAc (3×). The combined organic layers were dried over anhydrous magnesium sulfate and concentrated. The residue was purified by silica gel chromatography (eluent: 10-40% EtOAc in hexanes) to provide the title compound 357.0 (1.51 g, 54% yield) as a white solid. LCMS-ESI (pos.) m/z: 350.1 (M+H)$^+$.

The compounds set forth in the following table were synthesized following the procedure in Example 357.0 using the known starting material as described.

TABLE 13

| Example | Reagents | Structure, Name and Data |
|---|---|---|
| 357.1 | trans-1-propen-1-ylboronic acid (Sigma-Aldrich) | 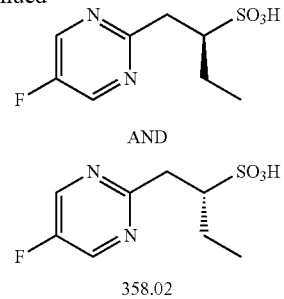<br>AND<br><br>(1S,2R)-1-((tert-Butyldimethylsilyl)oxy)-1-(5-fluoropyrimidin-2-yl)propane-2-sulfonamide and (1S,1R)-1-((tert-butyldimethylsilyl)oxy)-1-(5-fluoropyrimidin-2-yl)propane-2-sulfonamide.<br>LCMS-ESI (pos.) mz: 350.1 (M + H)⁺. |

Example 358.0. Preparation of (S)-1-(5-fluoropyrimidin-2-yl)butane-2-sulfonamide and (R)-1-(5-fluoropyrimidin-2-yl)butane-2-sulfonamide

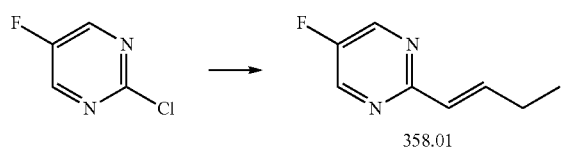

(E)-2-(But-1-en-1-yl)-5-fluoropyrimidine, Example 358.01. A slurry of (E)-but-1-en-1-ylboronic acid (Matrix Scientific, 488 mg, 4.9 mmol), potassium carbonate (1.35 g, 9.8 mmol) and 2-chloro-5-fluoro-pyrimidine (603 µL, 4.9 mmol) in ACN (5 mL) and water (2.5 mL) in a microwave vial was deoxygenated with an Ar stream. Tetrakis(triphenylphosphine)palladium (564 mg, 0.49 mmol) was added and the yellow slurry was again deoxygenated with an Ar strem. The reaction was sealed and heated in a microwave at 100° C. for 10 h. The reaction mixture was then diluted with water (75 mL) and extracted with ethyl ether (2×). The combined organic layers were washed with water (1×) and brine (1×) and dried over anhydrous sodium sulfate and partially concentrated on a rotary evaporator at 200 torr. The remaining solution was purified by silica gel chromatography (eluent: pure DCM) to provide 358.01 (656 mg, 88% yield) as a light yellow oil. LCMS-ESI (pos.) m/z: 153.2 (M+H)⁺.

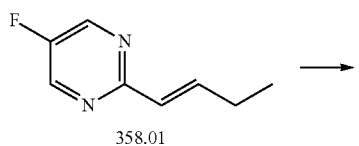

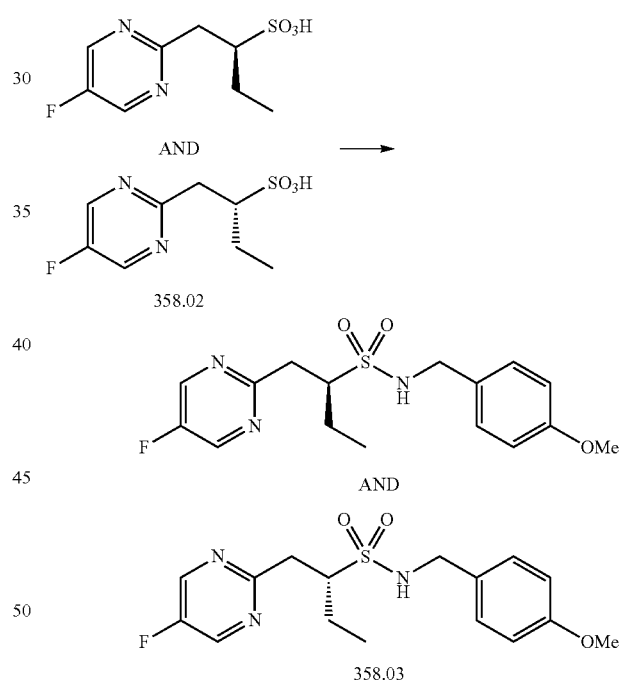

(S)-1-(5-Fluoropyrimidin-2-yl)butane-2-sulfonic acid and (R)-1-(5-fluoropyrimidin-2-yl)butane-2-sulfonic acid, Example 358.02. To a solution of 358.01 (650 mg, 4.3 mmol) in THF (6 mL) was added an aqueous solution of sodium bisulfite (1.33 g, 12.8 mmol in 2 mL of H₂O). The yellow slurry was then heated at 60° C. for 19 h and then concentrated. The residue was purified by reverse phase preparatory HPLC (Sunfire 5 µM C18 column, eluent: 0-40% ACN in water where both solvents contain 0.1% TFA) to provide 358.02 (426 mg, 43% yield) as a white solid. LCMS-ESI (pos.) m/z: 235.1 (M+H)⁺.

(S)-1-(5-Fluoropyrimidin-2-yl)-N-(4-methoxybenzyl)butane-2-sulfonamide and (R)-1-(5-fluoropyrimidin-2-yl)-N-(4-methoxybenzyl)butane-2-sulfonamide, Example 358.03. To an ice-cooled suspension of 358.02 (426 mg, 1.8 mmol) in DCM (18 mL) was added oxalyl chloride (323 µL, 3.6 mmol) via syringe followed by a catalytic amount of DMF via syringe. Vigorous bubbling was observed. The resulting white slurry was warmed to RT and stirred for 2.25 h. The reaction was then concentrated. The residue was azeotroped to dryness with benzene (2×) and then was suspended in DCM (18 mL) and cooled to 0° C. 4-Methoxybenzylamine (519 µL, 4.0 mmol) and TEA (885 µL, 6.4 mmol) were added sequentially via syringe. The resulting yellow slurry was stirred at 0° C. for 15 min and then warmed to RT and stirred for an additional 20 h. The reaction mixture was partitioned between water (30 mL) and DCM (3×). The combined organic layers were dried over anhydrous sodium sulfate and concentrated. The residue was purified by reverse phase preparatory HPLC (Sunfire 5 μM C18 column, eluent: 30-75% ACN in water where both solvents contain 0.1% TFA) to provide 358.03 (490 mg, 76% yield) as a light yellow oil. LCMS-ESI (pos.) m/z: 376.1 (M+Na)$^+$.

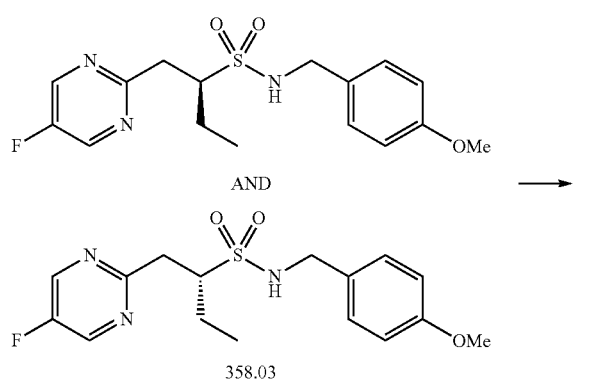

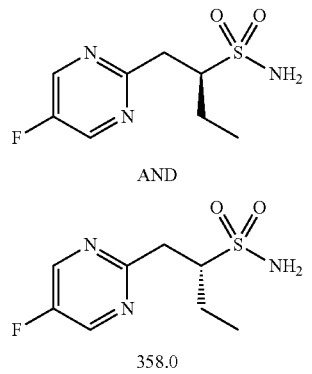

(S)-1-(5-Fluoropyrimidin-2-yl)butane-2-sulfonamide and (R)-1-(5-fluoropyrimidin-2-yl)butane-2-sulfonamide, Example 358.0. An ice-cooled flask containing 358.03 (489 mg, 1.4 mmol) was treated with TFA (5 mL, 67.3 mmol) via syringe. The resulting yellow solution was warmed to RT and stirred for 16 h and then was directly concentrated. The residue was purified by reverse phase preparatory HPLC (Sunfire 5 μM C18 column, eluent: 5-45% ACN in water where both solvents contain 0.1% TFA) to provide 358.0 (264 mg, 82% yield) as a white solid. LCMS-ESI (pos.) m/z: 234.1 (M+H)$^+$.

Example 359.0. Preparation of (1R,2S)-1-(5-fluoropyrimidin-2-yl)-1-methoxypropane-2-sulfonamide and (1S,2R)-1-(5-fluoropyrimidin-2-yl)-1-methoxypropane-2-sulfonamide

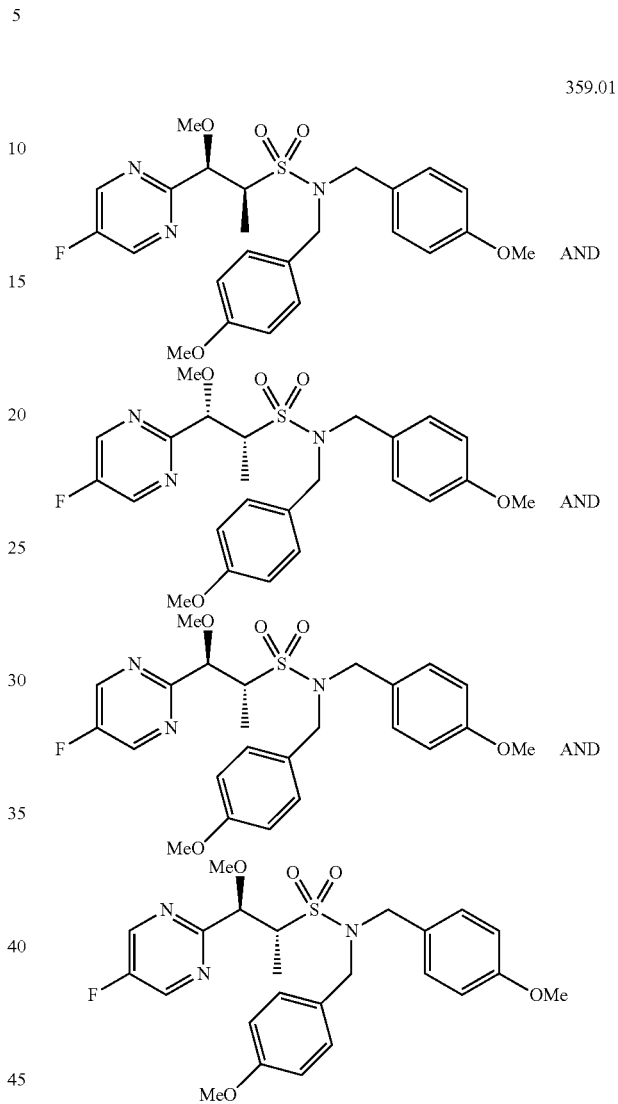

((1R,2S)-1-(5-Fluoropyrimidin-2-yl)-1-methoxy-N,N-bis(4-methoxybenzyl)propane-2-sulfonamide and ((1S,2R)-1-(5-fluoropyrimidin-2-yl)-1-methoxy-N,N-bis(4-methoxybenzyl)propane-2-sulfonamide and (1R,2R)-1-(5-fluoropyrimidin-2-yl)-1-methoxy-N,N-bis(4-methoxybenzyl)propane-2-sulfonamide and (1S,2S)-1-(5-fluoropyrimidin-2-yl)-1-methoxy-N,N-bis(4-methoxybenzyl)propane-2-sulfonamide, Example 359.01. To an ice-cooled solution of 355.01 (274 mg, 0.58 mmol) in DMF (8 mL) was added sodium hydride (60% dispersion in mineral oil, 81 mg, 2.0 mmol). The ice bath was removed and the resulting orange slurry was stirred at RT for 15 min. Next, iodomethane (179 μL, 2.9 mmol) was added slowly via syringe. After an additional 25 min at RT, the reaction was quenched with water (90 mL) and extracted with EtOAc (2×). The combined organic layers were dried over anhydrous sodium sulfate and concentrated. The residue was purified by silica gel chromatography (eluent: 10-65% EtOAc in hexanes) to provide 359.01 (183 mg, 65% yield) as a white solid. LCMS-ESI (pos.) m/z: 512.2 (M+Na)$^+$.

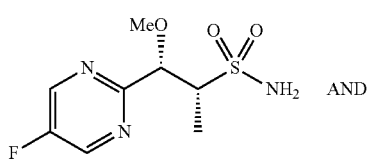

359.0

AND

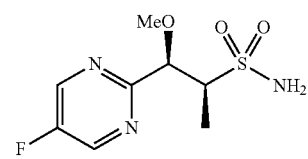

(1R,2S)-1-(5-Fluoropyrimidin-2-yl)-1-methoxypropane-2-sulfonamide and (1S,2R)-1-(5-fluoropyrimidin-2-yl)-1-methoxypropane-2-sulfonamide, Example 359.0. A flask was charged with 359.01 (175 mg, 0.36 mmol) and was then treated with TFA (5.5 mL, 74 mmol) and anisole (194 μL, 1.8 mmol). The resulting yellow solution was stirred for 20 h and then was directly concentrated. The residue was purified by silica gel chromatography (eluent: 0.8-6% MeOH in DCM) to provide 359.0 (cis diastereomer, 31 mg, 35% yield, white solid) as the first-eluting peak. LCMS-ESI (pos.) m/z: 250.1 (M+H)+.

Example 359.1: Preparation of (1R,2R)-1-(5-fluoropyrimidin-2-yl)-1-methoxypropane-2-sulfonamide and (1S,2S)-1-(5-fluoropyrimidin-2-yl)-1-methoxypropane-2-sulfonamide

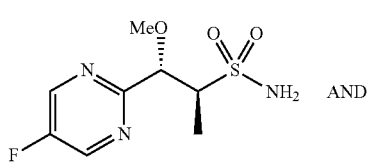

359.1

AND (1R,2R)-1-(5-Fluoropyrimidin-2-yl)-1-methoxypropane-2-sulfonamide and (1S,2S)-1-(5-fluoropyrimidin-2-yl)-1-methoxypropane-2-sulfonamide, Example 359.1. Further elution under the conditions described in Example 359.0, provided Example 359.1 (trans diastereomer, 56 mg, 63% yield, white solid) as the second-eluting peak. LCMS-ESI (pos.) m/z: 250.1 (M+H)+.

Example 360.0. Preparation of (1R,2S)-1-hydroxy-N,N-bis(4-methoxybenzyl)-1-(5-methylpyrimidin-2-yl)propane-2-sulfonamide

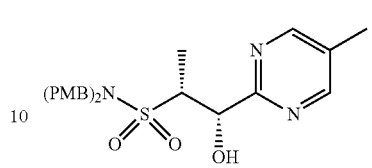

AND

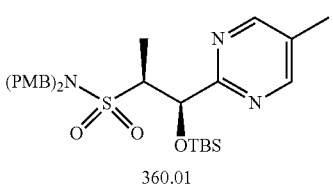

356.04

(1R,2S)-1-((tert-Butyldimethylsilyl)oxy)-N,N-bis(4-methoxybenzyl)-1-(5-methylpyrimidin-2-yl)propane-2-sulfonamide, Example 360.01. To an ice-cooled solution of 356.04 (160 g, 339 mmol) in DCM (1 L) was added TBSOTf (86 mL, 373 mmol) via syringe followed by TEA (52 mL, 373 mmol) via syringe. The reaction was warmed to RT and stirred for 60 min and then was transferred to a separatory funnel and washed with brine (2×250 mL). The organic layer was dried over anhydrous sodium sulfate and concentrated in vacuo. The racemic material was separated by chiral SFC (2×15 cm Chiralpak AD-H column, 20% EtOH/CO2, outlet pressure=100 bar; wavelength=220 nM) to provide 360.01 (70.6 g, 36% yield) as the second-eluting peak. LCMS-ESI (pos.) m/z: 586.4 (M+H)+.

360.01

360.0

(1R,2S)-1-Hydroxy-N,N-bis(4-methoxybenzyl)-1-(5-methylpyrimidin-2-yl)propane-2-sulfonamide, Example 360.0. To a solution of 360.01 (4.14 g, 7.1 mmol) in THF (90 mL) was added TBAF (1.0 M solution in THF, 7.8 mL, 7.8 mmol) via syringe. The resulting light yellow solution was stirred for 3 h and then more TBAF (1.0 M solution in THF, 3.5 mL, 3.5 mmol) was added. After an additional 2 h at RT, the reaction was partitioned between 1.0 N HCl (50 mL) and EtOAc (2×). The combined organic layers were washed with water (8×), dried over anhydrous sodium sulfate and concentrated. The residue was purified by silica gel chromatography (eluent: 30-100% EtOAc in hexanes) to provide 360.0 (1.76 g, 53% yield) as a white solid. LCMS-ESI (pos.) m/z: 472.1 (M+H)⁺.

Example 361.0. Preparation of N,N-bis(4-methoxybenzyl)ethanesulfonamide

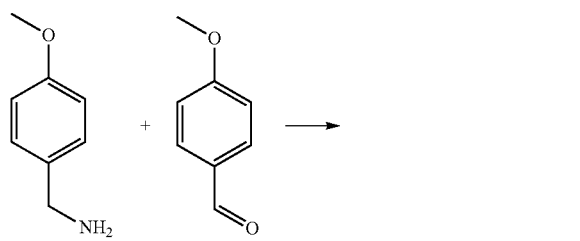

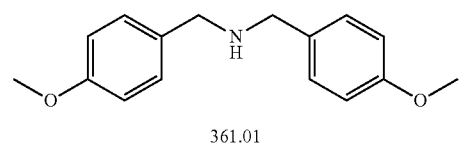

361.01

Bis(4-methoxybenzyl)amine, Example 361.01. 4-Methoxybenzylamine (600 g, 4.37 mol) and 4-methoxybenzaldehyde (532 mL, 4.37 mol) were added to a 10 L RBF at ambient temperature. An exotherm was observed and a white precipitate formed. The mixture was stirred for 1 h and then anhydrous EtOH (4.8 L) was added. After an additional 15-30 min at RT, sodium borohydride granules (99 g, 2.62 mol) were added portionwise over ~2 h (during the addition of the NaBH₄, the internal temperature of the reaction rose to 42° C.), and the mixture was further stirred at RT overnight. The reaction was then quenched slowly with water (600 mL) and then was concentrated in vacuo. The residue was partitioned between water (4 L) and DCM (4 L), and the aqueous layer was extracted with more DCM (2×2 L). The combined organic layers were dried over anhydrous sodium sulfate, filtered, and concentrated in vacuo to provide 361.01 (1112 g, 99% yield) as a semi-solid. The material was used directly in the next step without further purification. ¹H-NMR (400 MHz, CDCl₃) δ 7.28 (t, J=7.1 Hz, 4H), 6.89 (d, J=8.6 Hz, 4H), 3.83 (m, 6H), 3.76 (s, 4H). LCMS-ESI (pos.) m/z: 258.4 (M+H)⁺.

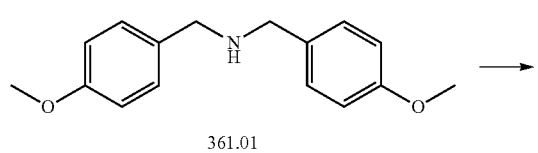

361.01

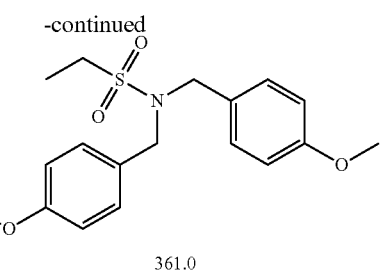

361.0

N,N-Bis(4-methoxybenzyl)ethanesulfonamide, Example 361.0. To an ice-cooled solution of 361.01 (900 g, 3.49 mol) in DCM (9 L) was added TEA (634 mL, 4.55 mol) followed by ethanesulfonyl chloride (399 mL, 4.19 mol, 1.2 eq) dropwise. (Note: The internal temperature was kept between 5-10° C. during the addition of the ethane sulfonyl chloride). Once the addition was complete, the cooling bath was removed. After 1.5 h, TLC showed complete loss of starting material. The reaction was quenched with water (4 L), and the layers were separated. The aqueous layer was then extracted with more DCM (2×2 L). The combined organic layers were washed with brine (2×1 L), dried over anhydrous sodium sulfate, filtered, and concentrated. The residue was absorbed onto a plug of silica gel purified by silica gel chromatography (eluent: 10-80% EtOAc in hexanes) to provide 361.0 (1125 g, 92% yield) as a white solid. ¹H-NMR (400 MHz, CDCl₃) δ 7.23 (dd, J=2.1, 6.6 Hz, 4H), 6.90 (dd, J=2.1, 6.6 Hz, 4H), 4.29 (s, 4H), 3.83 (s, 3H) 3.83 (s, 3H), 2.92 (q, J=7.4 Hz, 2H), 1.33 (t, J=7.4 Hz, 3H). LCMS-ESI (pos.) m/z: 372.2 (M+Na)⁺.

Example 362.0. Preparation of 4-(2,6-dimethoxyphenyl)-5-(5-methylfuran-2-yl)-4H-1,2,4-triazol-3-amine

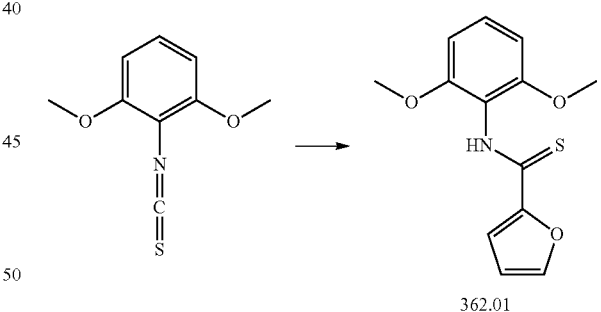

362.01

N-(2,6-Dimethoxyphenyl)furan-2-carbothioamide, Example 362.01. To an ice-cooled solution of furan (11.6 mL, 160 mmol) in THF (133 mL) was added a solution of n-butyllithium in hexanes (1.6 M solution in hexanes, 90 mL, 144 mmol) via syringe. The reaction was then stirred at 0° C. for 1.5 h. A solution of 2-isothiocyanato-1,3-dimethoxybenzene, Example 372.0, 15.6 g, 80 mmol) in THF (133 mL) was then added quickly via syringe. The reaction was allowed to warm to RT over a 2 h period. The reaction was then quenched with a saturated aqueous ammonium chloride solution. The mixture was extracted with EtOAc, and the organic layer was washed with brine (1×), dried over anhydrous sodium sulfate, and concentrated. The residue was purified by silica gel chromatography (eluent: 0-30%

EtOAc in DCM) to provide 362.01 (16.2 g, 77% yield) as a white solid. LCMS-ESI (pos.) m/z: 264.0 (M+H)+.

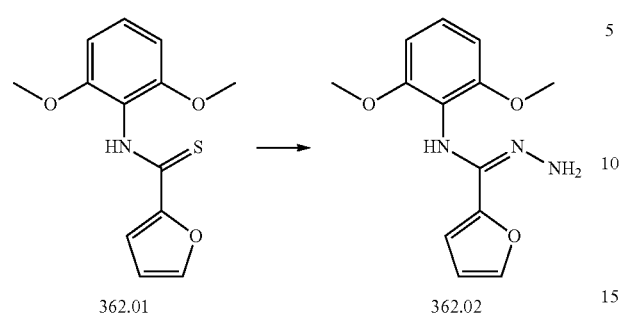

(E)-N-(2,6-Dimethoxyphenyl)furan-2-carbohydrazonamide, Example 362.02. To a solution of 362.01 (8.7 g, 33 mmol) in THF (219 mL) was added hydrazine hydrate (16.5 mL, 329 mmol) at RT. The reaction was warmed to 50° C. and stirred for 3 h and then quenched with a saturated aqueous sodium bicarbonate solutions and extracted with EtOAc. The organic layer was washed with brine (1×), dried over anhydrous sodium sulfate, and concentrated. The residue was triturated with ethyl ether to provide 362.02 (5.9 g, 69% yield) as a white solid. The filtrate was concentrated and rinsed with ether/hexanes to afford another portion of 362.02 (1.8 g, 21% yield) as a light yellow solid. LCMS-ESI (pos.) m/z: 262.1 (M+H)+.

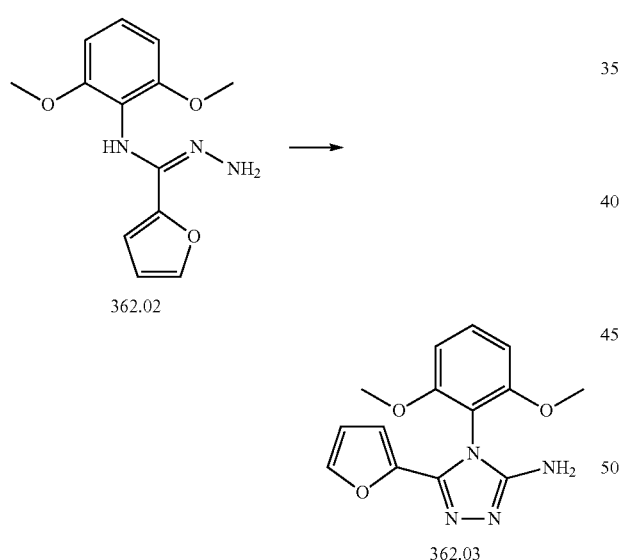

4-(2,6-Dimethoxyphenyl)-5-(furan-2-yl)-4H-1,2,4-triazol-3-amine, Example 362.03. To a solution of 362.02 (600 mg, 2.4 mmol) in dioxane (16 mL) was added cyanogen bromide (5.0 M solution in ACN, 0.5 mL, 2.5 mmol) at RT. The reaction was warmed to 90° C. and stirred for 16 h and then was cooled to RT and partitioned between a saturated aqueous sodium bicarbonate solution and DCM. The organic layer was washed with brine (1×), dried over anhydrous sodium sulfate, and concentrated. The residue was purified by silica gel chromatography (eluent: 0-30% MeOH in DCM) to provide 362.03 (450 mg, 66% yield) as a light yellow solid. LCMS-ESI (pos.) m/z: 287.1 (M+H)+.

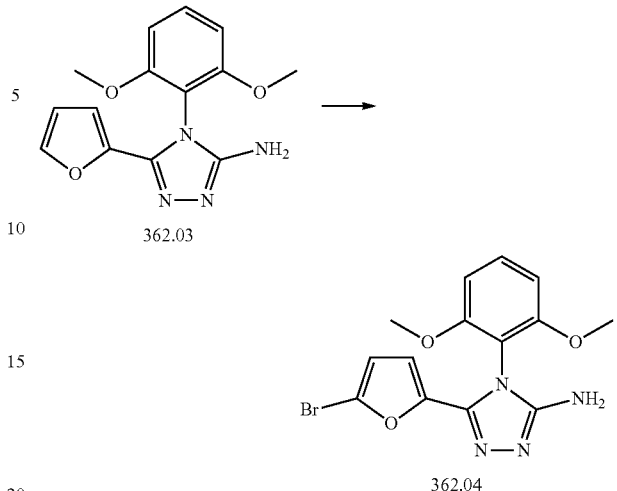

5-(5-Bromofuran-2-yl)-4-(2,6-dimethoxyphenyl)-4H-1,2,4-triazol-3-amine, Example 362.04. To a slurry of 362.03 (1.0 g, 3.5 mmol) and sodium acetate (1.15 g, 14.0 mmol) in AcOH (17.5 mL) was added bromine (197 µL, 3.8 mmol) dropwise via syringe. The resulting brown solution was stirred at RT for 3.5 h and then the reaction was quenched with 10% aqueous sodium hydroxide solution (30 mL). The mixture was extracted with EtOAc, and the organic layer was washed with more 10% aqueous sodium hydroxide (1×) and brine (1×). The organic layer was dried over anhydrous sodium sulfate and concentrated. The residue was purified in three batches by reverse phase preparatory HPLC (Sunfire 5 µM C18 column, eluent: 15-40% ACN in water where both solvents contain 0.1% TFA) to provide 362.04 (626 mg, 49% yield) as a light yellow solid. LCMS-ESI (pos.) m/z: 365.1 (M+H)+.

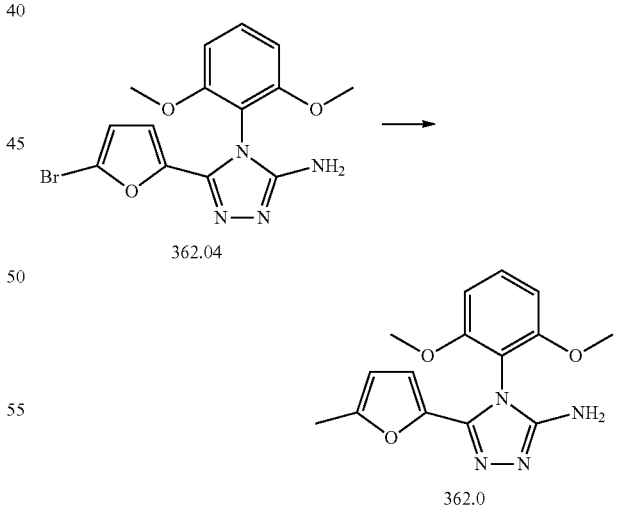

4-(2,6-Dimethoxyphenyl)-5-(5-methylfuran-2-yl)-4H-1,2,4-triazol-3-amine, Example 362.0. A microwave vial was charged with a slurry of 362.04 (411 mg, 1.1 mmol), potassium carbonate (778 mg, 5.6 mmol) and trimethylboroxine (283 mg, 2.3 mmol) in dioxane (9.5 mL). The suspension was deoxygenated with a stream of argon for 1 min and then tetrakis(triphenylphosphine)palladium (130 mg, 0.11 mmol) was added. The suspension was again deoxygenated with a stream of argon for 2 min and then was capped and heated in a microwave at 120° C. for a 2 h period. After cooling to RT, the reaction mixture was partitioned between water (45 mL) and EtOAc (3×). The combined organic layers were dried over anhydrous sodium sulfate and concentrated. The residue was purified in two batches by reverse phase preparatory HPLC (Sunfire 5 µM C18 column, eluent: 20-40% ACN in water where both solvents contain 0.1% TFA) to provide 362.0 (208 mg, 62% yield) as a white solid. LCMS-ESI (pos.) m/z: 301.1 (M+H)$^+$.

Example 363.0. Preparation of 4-(2,6-dimethoxyphenyl)-5-(5-(trifluoromethyl)furan-2-yl)-4H-1,2,4-triazol-3-amine

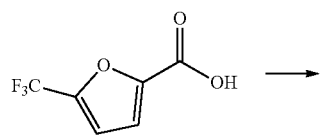

N-(2,6-Dimethoxyphenyl)-5-(trifluoromethyl)furan-2-carboxamide, Example 363.01. An ice-cooled solution of 5-(trifluoromethyl)-2-furoic acid (Oakwood Products, 1.65 g, 9.1 mmol) in DMF (31 mL) was treated with TEA (3.56 mL, 25.6 mmol) via syringe followed directly by HATU (4.17 g, 11.0 mmol). After 5 min, 2,6-dimethoxyaniline (Amfinecom Inc., 1.4 g, 9.1 mmol) was added. The resulting orange solution was warmed to RT and stirred for 60 min. The mixture was then partitioned between water (130 mL) and EtOAc (2×). The combined organic layers were washed with water (1×) and brine (1×) and then were dried over anhydrous sodium sulfate and concentrated. The residue was purified by silica gel chromatography (eluent: 10-100% EtOAc in hexanes) to provide 363.01 (2.52 g, 87% yield) as a white solid. LCMS-ESI (pos.) m/z: 316.0 (M+H)$^+$.

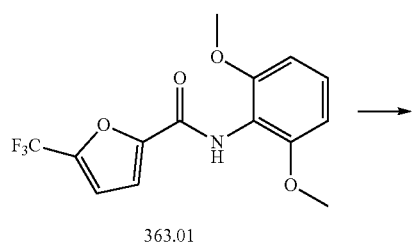

363.01

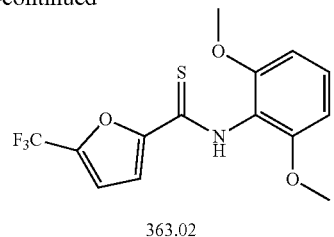

363.02

N-(2,6-Dimethoxyphenyl)-5-(trifluoromethyl)furan-2-carbothioamide, Example 363.02. To a suspension of 363.01 (2.52 g, 8.0 mmol) in toluene (85 mL) was added Lawesson's reagent (1.94 g, 4.8 mmol). The resulting light yellow slurry was heated at reflux for 3.25 h and then was allowed to cool to RT. The reaction was quenched with water (100 mL) and extracted with EtOAc (2×). The combined organic layers were washed with brine (1×), dried over anhydrous sodium sulfate, and concentrated. The residue was purified by silica gel chromatography (eluent: 5-95% EtOAc in hexanes) to provide 363.02 (2.58 g, 97% yield) as a bright yellow solid. LCMS-ESI (pos.) m/z: 332.0 (M+H)$^+$.

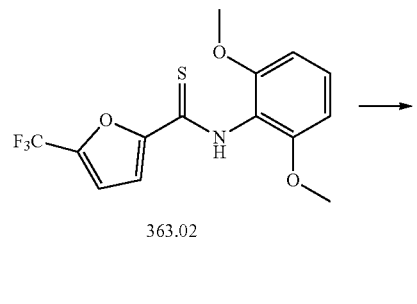

363.02

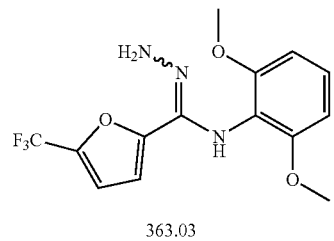

363.03

N-(2,6-Dimethoxyphenyl)-5-(trifluoromethyl)furan-2-carbohydrazonamide, Example 363.03. To a slurry of 363.02 (796 mg, 2.4 mmol) in THF (24 mL) was added hydrazine hydrate (80%, 1.46 mL, 24.0 mmol) via syringe. The resulting light yellow slurry was heated at 50° C. for 3 h and then was allowed to cool to RT. The reaction was quenched with saturated aqueous sodium bicarbonate (75 mL) and extracted with EtOAc (1×). The organic layer was washed with brine (1×), dried over anhydrous sodium sulfate, and concentrated. The residue was triturated with ethyl ether to provide 363.03 (553 mg, 70% yield) as a yellow solid. LCMS-ESI (pos.) m/z: 330.2 (M+H)$^+$.

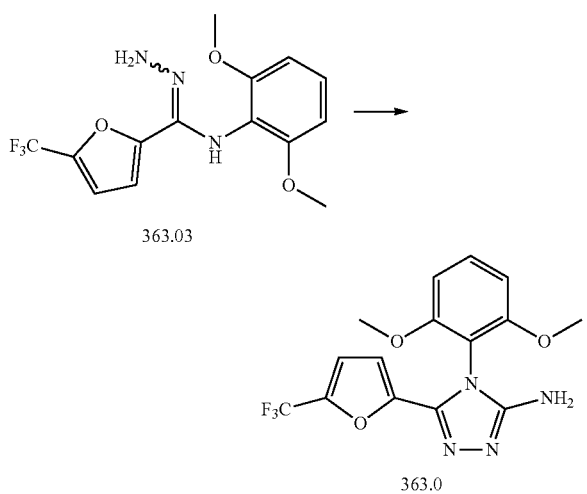

363.03

363.0

4-(2,6-Dimethoxyphenyl)-5-(5-(trifluoromethyl)furan-2-yl)-4H-1,2,4-triazol-3-amine, Example 363.0. To a slurry of 363.03 (553 mg, 1.7 mmol) in EtOH (21 mL) was added cyanogen bromide (5.0 M solution in ACN, 2.0 mL, 10.0 mmol) slowly via syringe over 7 min. The resulting yellow slurry was heated at 60° C. for 17 h and then was allowed to cool to RT. The reaction was quenched with water (2.5 mL) and concentrated. The residue was purified in two batches by reverse phase preparatory HPLC (Sunfire 5 µM C18 column, eluent: 40-65% ACN in water where both solvents contain 0.1% TFA) to provide 363.0 (369 mg, 62% yield) as an orange solid. LCMS-ESI (pos.) m/z: 355.2 $(M+H)^+$.

The compounds set forth in the following table were synthesized following the procedure in Example 363.0 using the known starting materials as described.

TABLE 14

| Example | Reagents | Structure, Name and Data |
|---|---|---|
| 363.1 | 5-ethylfuran-2-carboxylic acid (Matrix Scientific). | 4-(2,6-dimethoxyphenyl)-5-(5-ethylfuran-2-yl)-4H-1,2,4-triazol-3-amine<br>LCMS-ESI (pos.) m/z: 315.0 $(M + H)^+$. |
| 363.2 | 5-(tert-butylfuran)-2-carboxylic acid (Chembridge). | 5-(5-(tert-butyl)furan-2-yl)-4-(2,6-dimethoxyphenyl)-4H-1,2,4-triazol-3-amine.<br>LCMS-ESI (pos.) m/z: 343.2 $(M + H)^+$. |
| 363.3 | 5-(methoxymethyl)-2-furoic acid (Sigma-Aldrich). | 4-(2,6-dimethoxyphenyl)-5-(5-(methoxymethyl)furan-2-yl)-4H-1,2,4-triazol-3-amine<br>LCMS-ESI (pos.) m/z: 331.2 $(M + H)^+$. |

TABLE 14-continued

| Example | Reagents | Structure, Name and Data |
|---|---|---|
| 363.4 | 3-methyl-2-furoic acid (Sigma-Aldrich). | 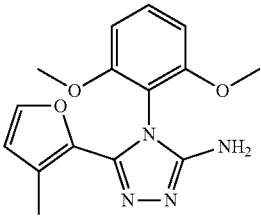 [SMILES: COc1cccc(OC)c1-n1c(N)nnc1-c1occc1C]<br>4-(2,6-dimethoxyphenyl)-5-(3-methylfuran-2-yl)-4H-1,2,4-triazol-3-amine.<br>LCMS-ESI (pos.) m/z: 301.1 (M + H)+. |

Example 364.0. Preparation of 3-bromo-4-(2,6-dimethoxyphenyl)-5-(5-(trifluoromethyl)furan-2-yl)-4H-1,2,4-triazole

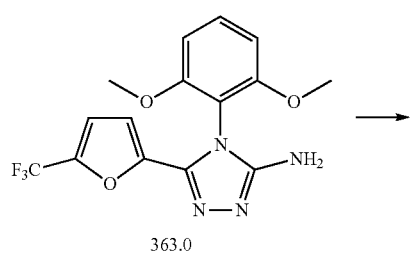

363.0

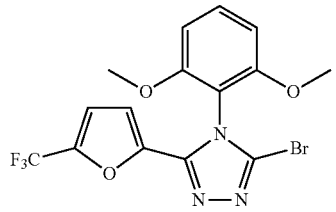

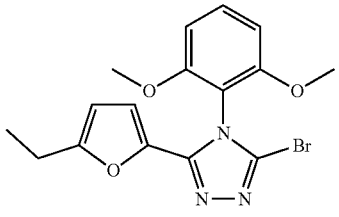 [SMILES: CCc1ccc(-c2nnc(Br)n2-c2c(OC)cccc2OC)o1]

364.0

3-Bromo-4-(2,6-dimethoxyphenyl)-5-(5-(trifluoromethyl)furan-2-yl)-4H-1,2,4-triazole, Example 364.0. To a slurry of 363.0 (214 mg, 0.60 mmol) in dibromomethane (3.1 mL) was added benzyltriethylammonium bromide (493 mg, 1.8 mmol) and sodium nitrite (834 mg, 12.1 mmol) directly followed by 2,2-dichloroacetic acid (100 µL, 1.21 mmol) slowly via syringe. The resulting dark orange slurry was stirred at RT for 3 h and then was loaded directly onto a silica gel column and purified by silica gel chromatography (eluent: 0-4% MeOH in DCM) to provide 364.0 (111 mg, 44% yield) as an orange solid. LCMS-ESI (pos.) m/z: 418.0 (M+H)+.

The compounds set forth in the following table were synthesized following the procedure in Example 364.0 using the starting material as described.

TABLE 15

| Example | Reagents | Structure, Name and Data |
|---|---|---|
| 364.1 | 4-(2,6-dimethoxyphenyl)-5-(5-methylfuran-2-yl)-4H-1,2,4-triazol-3-amine, Example 362.0. | 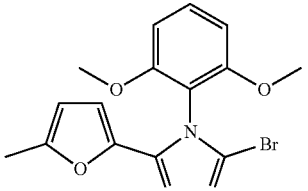<br>3-bromo-4-(2,6-dimethoxyphenyl)-5-(5-methylfuran-2-yl)-4H-1,2,4-triazole.<br>LCMS-ESI (pos.) m/z: 364.0 (M + H)+. |
| 364.2 | 4-(2,6-dimethoxyphenyl)-5-(5-ethylfuran-2-yl)-4H-1,2,4-triazol-3-amine, Example 363.1. | 3-bromo-4-(2,6-dimethoxyphenyl)-5-(5-ethylfuran-2-yl)-4H-1,2,4-triazole.<br>LCMS-ESI (pos.) m/z: 378.0 (M + H)+. |
| 364.3 | 4-(2,6-dimethoxyphenyl)-5-(furan-2-yl)-4H-1,2,4-triazol-3-amine, Example 362.03. | 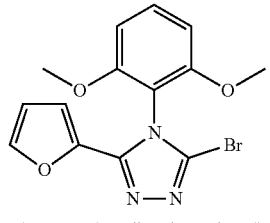 [SMILES: COc1cccc(OC)c1-n1c(Br)nnc1-c1ccco1]<br>3-bromo-4-(2,6-dimethoxyphenyl)-5-(furan-2-yl)-4H-1,2,4-triazole.<br>LCMS-ESI (pos.) m/z: 350.0 (M + H)+. |

Example 365.0. Preparation of diethyl ((N-(4-(2,6-dimethoxyphenyl)-5-(furan-2-yl)-4H-1,2,4-triazol-3-yl)-N-(2-(trimethylsilyl)ethyl)sulfamoyl)methyl)phosphonate

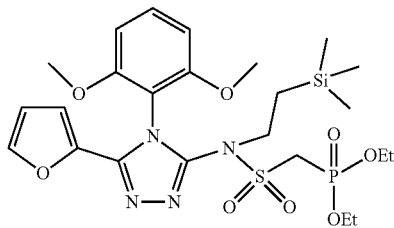

365.0

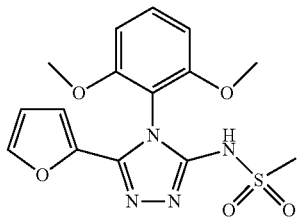

365.1

N-(4-(2,6-Dimethoxyphenyl)-5-(furan-2-yl)-4H-1,2,4-triazol-3-yl)methanesulfonamide, Example 365.1. A mixture of Example 362.03 (50.0 g, 174.6 mmol) in pyridine (705 mL, 8732 mmol) was heated to 90° C. until the solution become clear (15 min). The solution was allowed to cool to 30° C. In a separate RBF methanesulfonic anhydride (63.3 g, 363 mmol) was dissolved in DCM (145 mL) and heated to 50° C. to obtain a clear solution which was then cooled to 30° C. The methanesulfonic anhydride solution was added to the solution of Example 362.03 dropwise over 10 min. The temperature of the reaction mixture rose from 30° C. to 40° C. during the addition. The reaction was then heated at 90° C. for 60 min. The reaction was cooled to RT and concentrated in vacuo. The initial material thus obtained was added to water (200 mL) and cooled to 0° C. 2 N aqueous HCl was slowly added to adjust the pH to around 2. The precipitate thus formed was collected by filtration and washed with water (2×200 mL). Water was removed azeotropically using toluene, and the product was dried in vacuo to obtain 365.1 (35.0 g, 56%). LCMS-ESI (pos.) m/z: 365.0 (M+H)+.

Diethyl ((N-(4-(2,6-dimethoxyphenyl)-5-(furan-2-yl)-4H-1,2,4-triazol-3-yl)-N-(2-(trimethylsilyl)ethyl)sulfamoyl)methyl)phosphonate, Example 365.0. LiHMDS (1.0 M in toluene, 142 mL, 142 mmol) was added dropwise over 5 min to a solution of Example 365.2 (30.0 g, 64.5 mmol) in THF (194 mL) at −30° C. The reaction mixture was then warmed to 10° C. for 30 min. The mixture was then cooled to −25° C. Diethyl chlorophosphate (10.3 mL, 71 mmol) was then added dropwise over 2 min and the reaction mixture was stirred at 0° C. for 4 h. Thereafter, the reaction was quenched with water (200 mL) and extracted with EtOAc (3×200 mL). The combined organic layers were dried over $Na_2SO_4$, filtered, and concentrated under reduced pressure. The initial product was purified on a silica gel column employing a gradient of 0-100% EtOAc in hexanes to recover the unreacted starting material, and then the eluent was changed to 0-10% MeOH in DCM; to provide Example 365.0 (15 g, 39%). $^1$H NMR (400 MHz, DMSO-$d_6$) δ 7.86 (d, J=1.8 Hz, 1H) 7.56 (t, J=8.5 Hz, 1H) 6.88 (d, J=8.5 Hz, 2H) 6.54 (dd, J=3.5, 1.8 Hz, 1H) 6.01 (d, J=3.6 Hz, 1H) 4.40-4.16 (m, 2H) 4.07-3.87 (m, 4H) 3.72 (s, 3H) 3.72 (s, 3H) 3.44 (d, J=16.8 Hz, 2H) 1.28-1.09 (m, 8H) 0.13-0.00 (m, 9H). LCMS-ESI (pos.) m/z: 600.9 (M+H)+.

Example 366.0. Preparation of Diethyl (1-(N-(4-(2,6-dimethoxyphenyl)-5-(furan-2-yl)-4H-1,2,4-triazol-3-yl)-N-(2-(trimethylsilyl)ethyl)sulfamoyl)ethyl)phosphonate

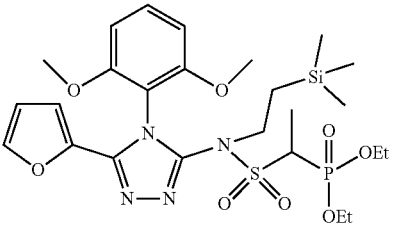

366.0

365.2

N-(4-(2,6-Dimethoxyphenyl)-5-(furan-2-yl)-4H-1,2,4-triazol-3-yl)-N-(2-(trimethylsilyl)ethyl)methanesulfonamide, Example 365.2. To a mixture of 365.1 (57.0 g, 96 mmol) in toluene (384 mL) at 30° C. was added 2-(trimethylsilyl)ethanol (commercially available from Fluorochem, Derbyshire, UK) (16.5 mL, 115.2 mmol). Cyanomethylenetributylphosphorane (commercially available from TCI America, Portland, or, USA) (33.0 mL, 124.8 mmol) was then added to the mixture in one portion. The reaction mixture was heated at 90° C. for 3 h. The reaction mixture was then cooled to RT and concentrated in vacuo. The dark red residue thus obtained was purified on a silica gel column, employing a gradient of 0-50% EtOAc in hexanes, to afford 365.2 (30 g, 67%). LCMS-ESI (pos.) m/z: 465.1 (M+H)+.

Diethyl (1-(N-(4-(2,6-dimethoxyphenyl)-5-(furan-2-yl)-4H-1,2,4-triazol-3-yl)-N-(2-(trimethylsilyl)ethyl)sulfamoyl)ethyl)phosphonate, Example 366.0. A solution of Example 365.0 (10 g, 16.6 mmol) in THF (100 mL) was cooled to 0° C. and potassium tert-butoxide (2.2 g, 19.9 mmol) was added portion-wise. The mixture was stirred for 30 min and then methyl iodide (1.5 mL, 24.9 mmol) was added dropwise over 2 min. The mixture was warmed to RT and stirred for 16 h. Thereafter, the mixture was quenched with water (100 mL) and extracted with EtOAc (2×100 mL). The organic layers were combined, dried over $Na_2SO_4$, filtered, and concentrated in vacuo. The residue was purified on a silica gel column employing a gradient of 0-65% EtOAc in hexanes to provide Example 366.0 (4.0 g, 39%). ¹H NMR (400 MHz, DMSO-d₆) δ 7.85 (d, J=1.9 Hz, 1H) 7.56 (t, J=8.5 Hz, 1H) 6.87 (d, J=8.5 Hz, 2H) 6.54 (dd, J=3.5, 1.7 Hz, 1H) 6.02 (d, J=3.6 Hz, 1H) 4.32 (td, J=7.5, 2.9 Hz, 2H) 4.11-3.83 (m, 4H) 3.71 (app s, 6H) 3.19 (dq, J=18.6, 7.0 Hz, 1H) 1.32-1.09 (m, 11H) 0.14-0.02 (m, 9H). LCMS-ESI (pos.) m/z: 615.1 (M+H)⁺.

Example 367.0. Preparation of 4-(2,6-dimethoxyphenyl)-5-(5-methylfuran-2-yl)-4H-1,2,4-triazol-3-amine

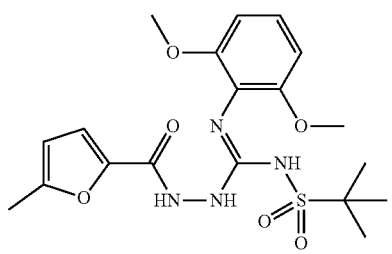

367.1

(Z)—N-(tert-Butylsulfonyl)-N'-(2,6-dimethoxyphenyl)-2-(5-methylfuran-2-carbonyl)hydrazinecarboximidamide, Example 367.1. To a solution of Example 372.0 (1400 g, 2.05 mol) and t-butylsulfonamide (295 g, 2.15 mol) in ACN (8.0 L), was added cesium carbonate (868 g, 2.67 mol) in 10 portions. The mixture was stirred at RT for 16 h during which the formation of intermediate isothiourea was monitored by LCMS and NMR. To the intermediate, was added successively 5-methyl-2-furohydrazide (commercially available from Chembridge Corporation, San Diego, Calif., USA, 301.5 g, 2.15 mol) and silver nitrate (696.5 g, 4.1 mol) in 10 portions. The progress of the reaction was monitored by LCMS which showed it was complete after 1 h. Thereafter, Celite® brand filter aid was added, and the resulting mixture was stirred for 15 min. The mixture was then filtered through a separate pad of Celite® brand filter aid. After rinsing the pad with DCM and 5% MeOH in DCM, the filtrate was concentrated in vacuo to afford a black residue which was purified on a silica gel column employing a gradient of 0-5% MeOH in DCM to afford Example 367.1 (900 g, 2.05 mol, 100%) as a white solid. LCMS-ESI (pos.) m/z: 438.8 (M+H)⁺.

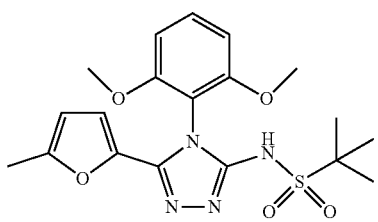

367.2

N-(4-(2,6-Dimethoxyphenyl)-5-(5-methylfuran-2-yl)-4H-1,2,4-triazol-3-yl)-2-methylpropane-2-sulfonamide, Example 367.2. To a solution of 367.1 (3500 g, 1.14 mol) in dioxane (2.5 L) was added TFA (434 mL, 5.7 mol). The resulting mixture was then heated at reflux (100° C.) until LCMS analysis indicated that the reaction was complete (36 h). Thereafter, the mixture was cooled to RT and concentrated in vacuo to afford Example 367.2 which was used without further purification. LCMS-ESI (pos.) m/z: 420.8 (M+H)⁺.

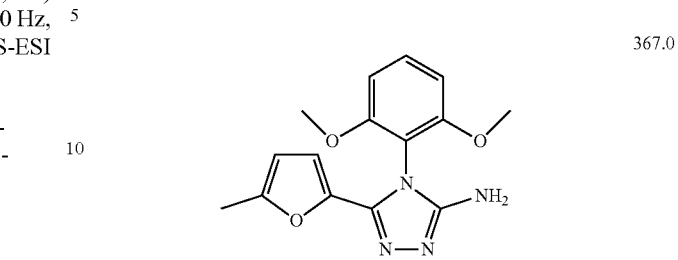

367.0

4-(2,6-Dimethoxyphenyl)-5-(5-methylfuran-2-yl)-4H-1,2,4-triazol-3-amine, Example 367.0. To a solution of 479 g of 367.2 (479 g, 1.14 mol) in TFA (2.5 L) was added anisole (374 mL, 3.42 mol). The resulting mixture was heated at 100° C. for 36 h. Thereafter, the TFA was removed in vacuo, a small amount of ice was added, and the pH was adjusted to 8-9 using 10% aqueous NaHCO₃. The solids formed were filtered off and washed with water, petroleum ether and diethyl ether, and then dried to obtain Example 367.0 (330 g, 96% for two steps) as a beige solid. ¹H NMR (400 MHz, DMSO-d₆) δ 7.49 (t, J=8.5 Hz, 1H) 6.84 (d, J=8.5 Hz, 2H) 6.02-5.95 (m, 1H) 5.60-5.52 (m, 3H) 3.69 (s, 3H) 3.69 (s, 3H) 2.20 (s, 3H). LCMS-ESI (pos.) m/z: 301.2 (M+H)⁺.

Example 368.0. Preparation of N-(4-(2,6-dimethoxyphenyl)-5-(5-methylfuran-2-yl)-4H-1,2,4-triazol-3-yl)-N-(2-(trimethylsilyl)ethyl)methanesulfonamide

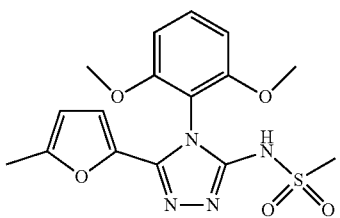

368.1

N-(4-(2,6-Dimethoxyphenyl)-5-(5-methylfuran-2-yl)-4H-1,2,4-triazol-3-yl)methanesulfonamide, Example 368.1. To a slurry of Example 367.0 (18 g, 0.059 mol) in THF (180 mL), was added potassium tert-butoxide (1.0 M/THF, 150 mL, 0.15 mol) dropwise over 15 min. Methanesulfonyl chloride (12 mL, 0.149 mol, 2.5 eq) was then added dropwise at 0° C. over 15 min. The resulting mixture was removed from the cooling bath and stirred until TLC analysis indicated that the reaction was complete. Thereafter, the reaction was quenched with saturated aqueous NH₄Cl (200 mL) and then extracted with EtOAc (300 mL). The aqueous layer was extracted with EtOAc (2×100 mL) and the combined organic layers were washed with brine (2×100 mL), dried over Na₂SO₄, and concentrated in vacuo. The material thus obtained was absorbed onto a plug of silica gel and purified on a silica gel column employing 70% EtOAc in petroleum ether as eluent to afford Example 368.1 (10 g, 0.026 mol, 44%). ¹H NMR (400 MHz, CDCl₃) δ 7.46 (t, J=8.5 Hz, 1H) 6.68 (d, J=8.5 Hz, 2H) 5.92 (dd, J=3.0, 0.9

Hz, 1H) 5.81 (d, J=3.5 Hz, 1H) 3.76 (app s, 6H) 2.96 (s, 3H) 2.31 (s, 3H). LCMS-ESI (pos.) m/z: 379.0 (M+H)$^+$.

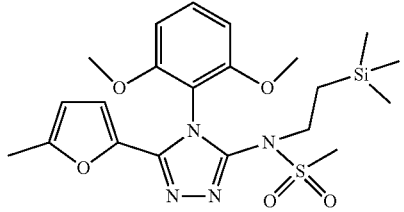

368.0

N-(4-(2,6-Dimethoxyphenyl)-5-(5-methylfuran-2-yl)-4H-1,2,4-triazol-3-yl)-N-(2-(trimethylsilyl)ethyl)methanesulfonamide, Example 368.0. To a suspension of Example 368.1 (10.0 g, 0.027 mol) in toluene (70 mL) at RT, was added 2-(trimethylsilyl)ethanol (4.6 mL, 0.032 mol). Cyanomethylenetributylphosphorane (9.2 mL, 0.035 mol) was then added in one portion. The resulting mixture was then heated at 90° C. for 2 h. Thereafter, the mixture was cooled to RT and concentrated in vacuo. The residue was purified on a silica gel column employing 0-30% EtOAc in petroleum ether as eluent to afford Example 368.0 (7.2 g, 0.015 mol, 57%). $^1$H NMR (400 MHz, CDCl$_3$) δ 7.50 (t, J=8.5 Hz, 1H) 6.69 (d, J=8.5 Hz, 2H) 5.91 (dd, J=3.4, 1.2 Hz, 1H) 5.76 (d, J=3.4 Hz, 1H) 4.47-4.08 (m, 2H) 3.80 (app s, 6H) 2.84 (s, 3H) 2.35 (s, 3H) 1.49-1.19 (m, 2H) 0.12 (s, 9H). LCMS-ESI (pos.) m/z: 479.2 (M+H)$^+$.

Example 369.0. Preparation of N-(4-(2,6-dimethoxyphenyl)-5-(5-methylfuran-2-yl)-4H-1,2,4-triazol-3-yl)-N-(2-(trimethylsilyl)ethyl)ethanesulfonamide

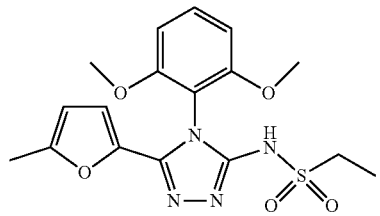

369.1

N-(4-(2,6-Dimethoxyphenyl)-5-(5-methylfuran-2-yl)-4H-1,2,4-triazol-3-yl)ethanesulfonamide, Example 369.1. The title compound was prepared employing ethanesulfonyl chloride, instead of methanesulfonyl chloride following the procedure described in the synthesis of Example 369.1. $^1$H NMR (400 MHz, CDCl$_3$) δ 7.46 (t, J=8.5 Hz, 1H) 6.68 (d, J=8.5 Hz, 2H) 5.91 (dd, J=3.5, 1.0 Hz, 1H) 5.78 (dd, J=3.4, 0.6 Hz, 1H) 3.76 (app s, 6H) 3.04 (q, J=7.4 Hz, 2H) 2.32 (s, 3H) 1.32 (t, J=7.4 Hz, 3H). LCMS-ESI (pos.) m/z: 393.2 (M+H)$^+$.

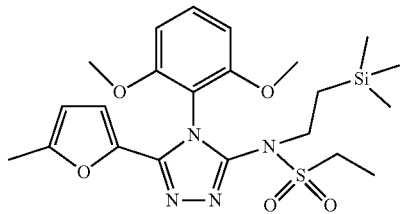

369.0

N-(4-(2,6-Dimethoxyphenyl)-5-(5-methylfuran-2-yl)-4H-1,2,4-triazol-3-yl)-N-(2-(trimethylsilyl)ethyl)ethanesulfonamide, Example 369.0. The title compound was prepared employing 369.1 following the procedures described in the synthesis of Example 368.0. $^1$H NMR (400 MHz, CDCl$_3$) δ 7.49 (t, J=8.5, 1.0 Hz, 1H) 6.69 (dd, J=8.6, 1.0 Hz, 2H) 5.91 (dd, J=3.5, 1.1 Hz, 1H) 5.77 (d, J=3.4 Hz, 1H) 4.45-4.24 (m, 2H) 3.79 (s, 3H) 3.79 (s, 3H) 3.01-2.79 (m, 2H) 2.35 (s, J=1.0 Hz, 3H) 1.46-1.30 (m, 2H) 1.25-1.11 (m, 3H) 0.12 (d, J=1.0 Hz, 9H). LCMS-ESI (pos.) m/z: 493.4 (M+H)$^+$.

Example 370.0. Preparation of N,N-bis(4-methoxybenzyl)methanesulfonamide

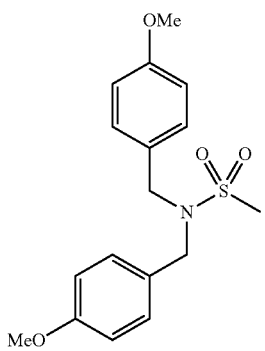

370.0

N,N-Bis(4-methoxybenzyl)methanesulfonamide, Example 370.0. To a stirred solution of Example 361.01 (100 g, 0.39 mol) in DCM (1 L) was added TEA (71 mL, 0.51 mol), followed by dropwise addition of methanesulfonyl chloride (36 mL, 0.47 mol). The internal temperature was kept between 5-10° C. during the addition of the methane sulfonyl chloride. Once the addition was complete, the cooling bath was removed, and the mixture was stirred at RT until TLC analysis indicated that the reaction was complete. Thereafter, water (1 L) was added, the layers were separated, and the aqueous layer was extracted with DCM (2×500 mL). The combined organic layers were washed with brine (2×1 L), dried over Na$_2$SO$_4$, and concentrated in vacuo. The residue was purified on a silica gel column employing a gradient of 10-80% EtOAc in hexanes to afford Example 370.0 (120 g, 0.36 mol, 92%) as a white solid. $^1$H-NMR (400 MHz, CDCl$_3$) δ 7.26 (dd, J=2.12, 6.60 Hz, 4H) 6.91 (dd, J=2.12, 6.62 Hz, 4H) 4.28 (s, 4H) 3.83 (app s, 6H) 2.75 (s, 3H).

Example 371.0. Preparation of (2S,3R)-3-(5-methylpyrimidin-2-yl)butane-2-sulfonamide

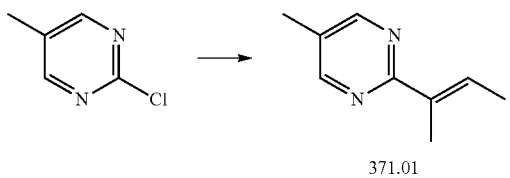

371.01

(E)-2-(But-2-en-2-yl)-5-methylpyrimidine, Example 371.01. 2-Chloro-5-methyl-pyrimidine (18 mL, 151 mmol), potassium (Z)-but-2-en-2-yltrifluoroborate (Sigma Aldrich, 31 g, 191 mmol), tricyclohexylphosphine (8.5 g, 30.2 mmol), and $Pd_2(dba)_3$ (13.82 g, 15.09 mmol) were added to a flask which was then degassed and backfilled with nitrogen. To the flask was added 1,4-dioxane (252 mL) and aqueous potassium phosphate tribasic (37.5 mL, 453 mmol). The resulting reaction was heated at 100° C. for 16 h. The reaction was then cooled to RT. The residue was filtered through a plug of silica gel and then loaded onto silica gel (0-20% EtOAc in heptanes) to afford (E)-2-(but-2-en-2-yl)-5-methylpyrimidine, Example 371.01 (19 g, 125 mmol), in 83% yield.

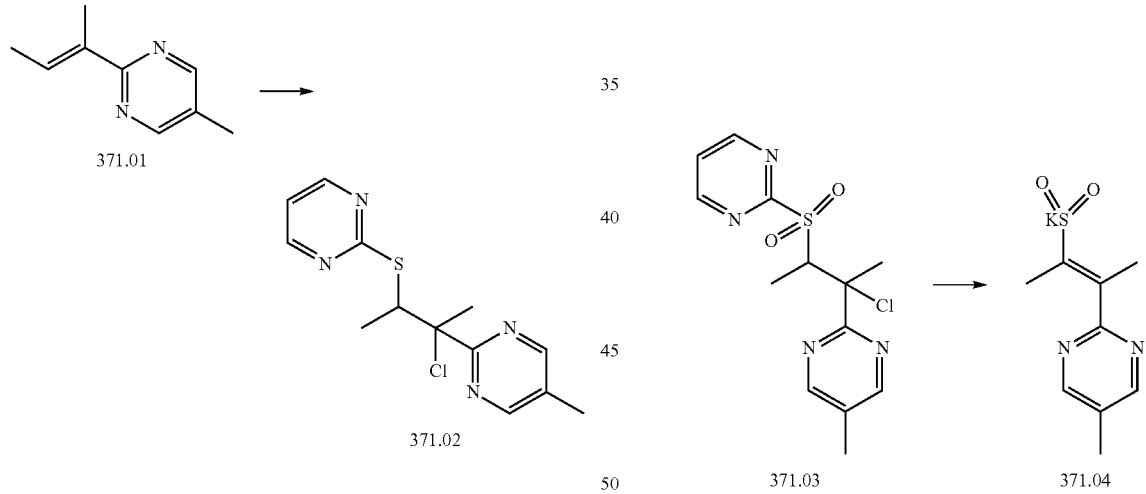

2-(2-Chloro-3-(pyrimidin-2-ylthio)butan-2-yl)-5-methylpyrimidine, Example 371.02. To a solution of pyrimidine-2-thiol (14.8 g, 132 mmol) in DCM (440 mL) was added sulfuryl chloride (10.73 mL, 132 mmol). The reaction was stirred at 0° C. for 1 h and a further 1 h at RT. To the cloudy reaction mixture was added (E)-2-(but-2-en-2-yl)-5-methylpyrimidine (Example 371.01, 20 g, 132 mmol) dropwise, and the mixture was further stirred for 2 h. The reaction mixture was then concentrated in vacuo. Aqueous sodium bicarbonate was added to the mixture to neutralize the reaction mixture. The reaction was then extracted with EtOAc and concentrated in vacuo. The residue was purified on silica gel with 0-25% EtOAc in hexanes to give the desired product 2-(2-chloro-3-(pyrimidin-2-ylthio)butan-2-yl)-5-methylpyrimidine, Example 371.02 (30 g in 76% yield.

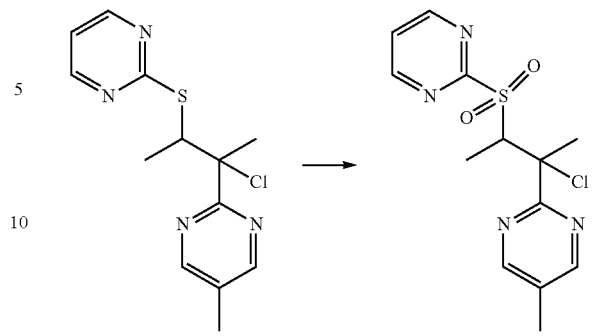

2-(2-Chloro-3-(pyrimidin-2-ylsulfonyl)butan-2-yl)-5-methylpyrimidine, Example 371.03. To a solution of 2-(2-chloro-3-(pyrimidin-2-ylthio)butan-2-yl)-5-methylpyrimidine Example 371.02 (30 g, 100 mmol) in DCM (201 mL) was added meta-chloroperoxybenzoic acid (45.0 g, 201 mmol). The reaction was stirred at RT for 1 d. The reaction was then concentrated in vacuo and aqueous sodium bicarbonate and sodium thiosulfate were added. The mixture was extracted with EtOAc and concentrated in vacuo to give the desired product 2-(2-chloro-3-(pyrimidin-2-ylsulfonyl)butan-2-yl)-5-methylpyrimidine, Example 371.03 (33.2 g, 100 mmol) in 100% yield.

Potassium (E)-3-(5-methylpyrimidin-2-yl)but-2-ene-2-sulfinate, Example 371.04. To a solution of 2-(2-chloro-3-(pyrimidin-2-ylsulfonyl)butan-2-yl)-5-methylpyrimidine (Example 371.03, 33 g, 100 mmol) in MeOH (249 mL) was added potassium carbonate (27.6 g, 200 mmol). The reaction was stirred at RT for 16 h. The reaction was then concentrated in vacuo to give the desired product potassium (E)-3-(5-methylpyrimidin-2-yl)but-2-ene-2-sulfinate, Example 371.04 (21.57 g) in 100% yield that was used without further purification.

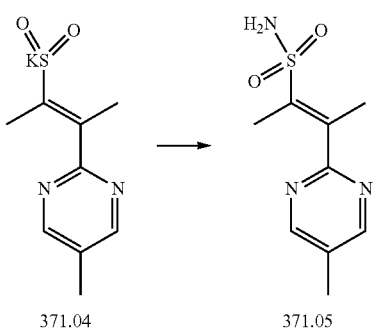

371.04     371.05

(E)-3-(5-Methylpyrimidin-2-yl)but-2-ene-2-sulfonamide, Example 371.05. To a solution of potassium (E)-3-(5-methylpyrimidin-2-yl)but-2-ene-2-sulfinate (Example 371.04, 21.57 g, 85 mmol) in water (424 mL, 85 mmol) was added potassium acetate (5.30 mL, 85 mmol) followed by amidoperoxymonosulfuric acid (19.18 g, 170 mmol). The reaction was stirred at 23° C. for 24 h. The reaction was then extracted with EtOAc and concentrated in vacuo. The product thus obtained was purified on silica gel eluting with 0-50% EtOAc in hexanes to give the desired product (E)-3-(5-methylpyrimidin-2-yl)but-2-ene-2-sulfonamide, 371.05 (12 g), in 61% yield.

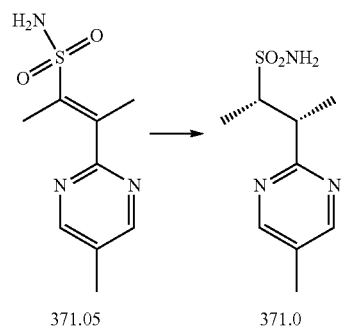

371.05     371.0

(2S,3R)-3-(5-Methylpyrimidin-2-yl)butane-2-sulfonamide, Example 371.0. A 900 mL pressure reactor was charged under $N_2$ flow with (E)-3-(5-methylpyrimidin-2-yl)but-2-ene-2-sulfonamide (Example 371.05, 40.00 g, 0.1760 mol, 1 equiv), zinc trifluoromethane sulfonate (12.79 g, 0.0352 mol, 0.2 equiv, Aldrich), bis(1,5-cyclooctadiene)rhodium(I) tetrafluoroborate (1.43 g, 0.00352 mol, 0.02 equiv, Strem Chemicals, Inc.), (S)-1-[(R)-2-(di-1-naphthylphosphino)ferrocenyl]-ethyl-di-tert.-butylphosphine (2.60 g, 0.00405 mol, 0.023 equiv, Solvias), and MeOH (520 mL). The mixture was purged with nitrogen and then with hydrogen and the reaction mixture was then stirred under 3-4 bars of hydrogen for 20 h. The reaction was monitored by HPLC and showed a complete conversion to product. The reactor was purged with nitrogen, and the resulting suspension was concentrated at 35° C. under industrial vacuum to give the initial material as an orange solid. The orange solid was mixed with EtOH (742 mL) and the resulting suspension was stirred at 20-25° C. for 40 min. The solid was filtered, washed with EtOH (2×97 mL), and dried at 40° C. under vacuum to give the title compound as a white powder (85.2% yield, 99% ee). $^1$H NMR (400 MHz, DMSO-$d_6$): δ 8.61 (s, 2H), 6.84 (s, 2H), 3.69 (tt, J=12.4, 4.5 Hz, 2H), 2.25 (s, 3H), 1.32 (d, J=6.9 Hz, 3H), 1.20 (d, J=7.0 Hz, 3H). LCMS (ESI, positive ion) m/z; 230.1 (M+H)$^+$.

The compounds in the following table were synthesized following the procedure in Example 371.0 using the known starting material as described.

TABLE 16

| Example | Reagents | Structure, Name and Data |
|---|---|---|
| 371.1 | 2-chloro-5-fluoro-pyrimidine. | (2S,3R)-3-(5-fluoropyrimidin-2-yl)butane-2-sulfonamide. LCMS ESI (pos.) m/z: 234.4 (M + H)$^+$. |

TABLE 16-continued

| Example | Reagents | Structure, Name and Data |
|---|---|---|
| 371.2 | 2-bromo-5-methylpyrazine. The title compound was the first isomer to elute under the following SFC conditions: Run on Thar 200 SFC with 250 × 30 mm AD-H column with 20 mL/min MeOH (+ 20 mM NH₃) + 80 g/min CO₂, 20% co-solvent at 100 g/min. Temperature. = 29° C., Outlet pressure = 100 bar, Wavelength = 271 nm. Injected 1.0 mL of 550 mg of the enantiomerically enriched product dissolved in 20 mL MeOH:DCM, 15:5; c = 27.5 mg/mL and 27.5 mg per injection. Cycle time 5.0 min, run time 13 min. \ | 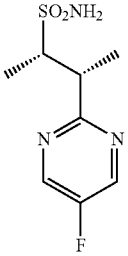<br>(2S,3R)-3-(5-methylpyrazin-2-yl)butane-2-sulfonamide.<br>$^1$H NMR (400 MHz, DMSO-$d_6$) δ 8.46 (d, J = 6.5 Hz, 2H), 6.84 (s, 2H), 3.63 (qd, J = 7.0, 4.3 Hz, 1H), 3.44 (qd, J = 7.0, 4.3 Hz, 1H), 2.47 (s, 3H), 1.31 (d, J = 7.0 Hz, 3H), 1.23 (d, J = 7.0 Hz, 3H). LCMS (ESI, pos.) m/z; 230.0 (M + H)⁺. |
| 371.3 | 2-bromo-5-methylpyrazine. The title compound is the enantioiner of Example 371.2. Example 371.3 is the second isomer to elute from the AD-H column on subjecting the cnantiomerically enriched product to the SFC conditions described in Example 371.2. | 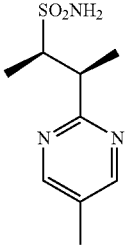<br>(2R,3S)-3-(5-methylpyrazin-2-yl)butane-2-sulfonamide.<br>LCMS-ESI (pos.) m/z: 230.0 (M + H)⁺. |
| 371.4 | 2-chloro-5-chloro-pyrimidine. Recrystallization: Example 371.4 (38 g, 90% ce) was dissolved in IPA (400 mL) at 70° C.. | 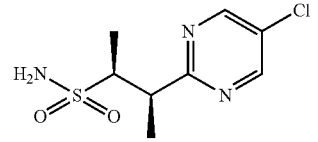<br>(2S,3R)-3-(5-chloropyrimidin-2-yl)butane-2-sulfonamide.<br>$^1$H NMR (400 MHz, DMSO-$d_6$) δ 8.93-8.85 (m, 2H), 6.86 (d, J = 4.0 Hz, 2H), 3.73-3.59 (m, 2H), 1.31 (dt, J = 7.3, 2.4 Hz, 3H), 1.25-1.19 (m, 3H). LCMS (ESI pos.) m/z: 250.2 (M + H)⁺. |
| 371.5 | 2-bromo-5-methoxypyrazine. | 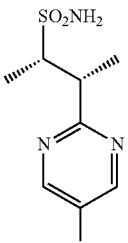<br>(2S,3R)-3-(5-methoxypyrazin-2-yl)butane-2-sulfonamide.<br>$^1$H NMR (400 MHz, DMSO-$d_6$) δ 8.26 (d, J = 1.4 Hz, 1H), 8.12 (d, J = 1.4 Hz, 1H), 6.84 (s, 2H), 3.90 (d, J = 1.5 Hz, 3H), 3.62 (dd, J = 7.1, 4.3 Hz, 1H), 3.42-3.38 (m, 1H), 1.32 (d, J = 1.5 Hz, 3H), 1.23-1.21 (m, 3H). LCMS (ESI pos.) m/z: 246.2 (M + H)⁺. |

Example 372.0. Preparation of 2-isothiocyanato-1,3-dimethoxybenzene

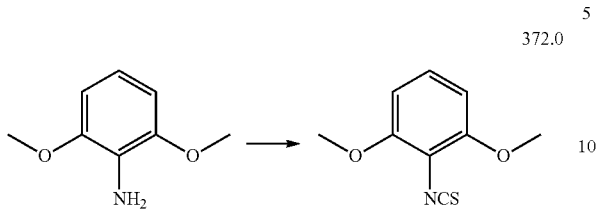

2-Isothiocyanato-1,3-dimethoxybenzene, Example 372.0. To a solution of 2,6-dimethoxyaniline (500 g, 3.25 mol, 1 eq) in DCM (5.0 L) was added 2,6-lutidine (1.5 L, 13.0 mol, 4 eq). The reaction mixture was cooled to 0° C. (internal temperature) and $CSCl_2$ (374 mL, 4.88 mol, 1.5 eq) was added dropwise. The reaction mixture was then stirred for 2 h. The solvent was evaporated in vacuo and the initial mass was purified by $SiO_2$ column to provide the title compound, Example 372.0, as a white solid (1.06 g, 2.80 mol, 86%). LCMS (ESI pos. ion) m/z: (M+1)+=196. $^1$H NMR (400 MHz, $CDCl_3$) δ 7.16 (t, J=8.48 Hz, 1H), 6.55 (d, J=8.48 Hz, 2H), 3.90 (m, 6H).

The compounds set forth in the following table were synthesized following the procedure in Example 82.0 using the known starting material as described.

Example 373.0. Preparation of (1R,2S)-1-methoxy-1-(5-methylpyrimidin-2-yl)propane-2-sulfonamide

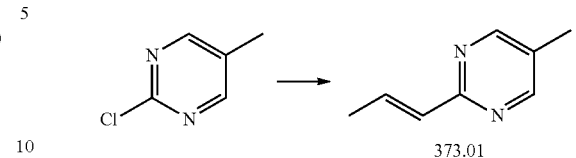

(E)-5-Methyl-2-(prop-1-en-1-yl)pyrimidine, Example 373.01. To a 500 mL RBF was added 2-chloro-5-methylpyrimidine (12 g, 93 mmol), potassium (E)-trifluoro(prop-1-en-1-yl)borate (17.27 g, 117 mmol), and potassium phosphate (59.4 g, 280 mmol). The flask was purged with $N_2$ (5×) and then 1,4-dioxane (200 mL) and water (20 mL) were added. The resulting yellow suspension was bubbled with Ar for 15 min and then 1,1-bis[(di-t-butyl-p-methylaminophenyl]palladium(II) chloride (Amphos, commercially available from Strem, 2.64 g, 3.73 mmol) was added, a reflux condenser was attached, and the reaction warmed to 90° C. in an oil bath and stirred under $N_2$ for 16.5 h. The reaction was then cooled to RT. The reaction was diluted with water (250 mL) and extracted with EtOAc (2×250 mL). The organic layers were combined, dried ($MgSO_4$), and concentrated. The residue was purified by flash chromatography on

TABLE 17

| Example | Reagents | Structure, Name and Data |
|---------|----------|--------------------------|
| 372.1 | 4,6-dimethoxypyrimidin-5-amine (D-L Chiral chemicals). | 5-isothiocyanato-4,6-dimethoxypyrimidine. LCMS-ESI (pos.) m/z: 198.1 (M + H)+. |
| 372.2 | 2-methoxyaniline (Aldrich). | 1-isothiocyanato-2-methoxybenzene. $^1$H NMR (400 MHz, DMSO-d) δ 3.89 (s, 3H), 6.96 (td, J = 7.68, 1.27 Hz, 1H), 7.16 (dd, J = 8.31, 1.27 Hz, 1H), 7.30 (dd, J = 7.92, 1.66 Hz, 1H), 7.31-7.37 (m, 1H). |
| 372.3 | 3,5-difluoropyridin-4-amine (commercially available from Ark Pharm Inc, Libertyville, IL). | 3,5-difluoro-4-isothiocyanatopyridine. LCMS-ESI (pos.) m/z: 173.0 (M + H)+. | silica gel eluting with 0-20% EtOAc/hexanes) to afford (E)-5-methyl-2-(prop-1-en-1-yl)pyrimidine 373.01 (12.96 g, 97 mmol, 100% yield) as a yellow/orange oily solid. $^1$H NMR (300 MHz, CDCl$_3$) δ 8.49 (s, 2H), 7.01-7.20 (m, 1H), 6.57 (dd, J=15.6, 1.7 Hz, 1H), 2.29 (s, 3H), 1.97 (dd, J=6.8, 1.6 Hz, 3H). LCMS (ESI pos.) m/z: 135.2 (M+H)$^+$.

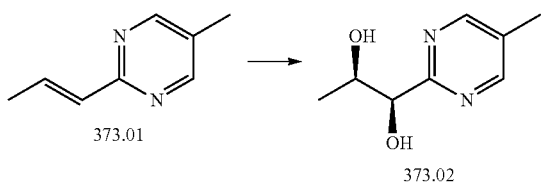

(1R,2R)-1-(5-Methylpyrimidin-2-yl)propane-1,2-diol, Example 373.02. Racemic conditions. To a solution of (E)-5-methyl-2-(prop-1-en-1-yl)pyrimidine, 373.01 (5.75 g, 42.9 mmol) and 4-methylmorpholine-4-oxide (7.53 g, 64.3 mmol) in acetone (60 mL) and water (6 mL), was added osmium tetroxide (4 wt. %, in water (0.681 mL, 0.111 mmol)). The resulting reaction mixture was stirred at RT under N$_2$ for 21.5 h. LCMS showed complete conversion to a product corresponding to the mass of the desired product (M+H)$^+$=169). The reaction was passed through a Varian Chem-Elut cartridge to remove water and concentrated in vacuo. Water was still present, and the residue was dissolved in DCM, dried (MgSO$_4$), and concentrated in vacuo. The residue was purified by flash chromatography (120 g SiO$_2$, 0-10% MeOH/DCM) to give the racemic syn-diol (1S,2S)-1-(5-methylpyrimidin-2-yl)propane-1,2-diol and (2R,2R)-1-(5-methylpyrimidin-2-yl)propane-1,2-diol (5.85 g, 34.8 mmol, 81% yield) as a light yellow solid. $^1$H NMR (300 MHz, CDCl$_3$) δ 8.59 (s, 2H), 4.67 (br. s., 1H), 4.33 (br. s., 1H), 4.09-4.25 (m, 1H), 2.86 (d, J=7.2 Hz, 1H), 2.36 (s, 3H), 1.30 (d, J=6.6 Hz, 3H). LCMS (ESI pos.) m/z: 169.2 (M+H). Chiral conditions. A batch of AD-mix-beta was prepared from: (26 mg, 0.07 mmol) K$_2$OsO$_2$(OH)$_4$; (16.4 g, 49.9 mmol) K$_3$Fe(CN)$_6$; (6.89 g, 49.9 mmol) K$_2$CO$_3$; (125 mg, 0.16 mmol), and (DHQD)$_2$PHAL. In a 50 mL RBF was added t-BuOH (5 mL), water (5.00 mL), and 1.4 g of AD-mix-beta (prepared above) and methanesulfonamide (95 mg, 1.00 mmol). The mixture was stirred at RT until clear, and then cooled to 0° C. (E)-5-Methyl-2-(prop-1-en-1-yl)pyrimidine (Example 373.01, 168 mg, 1 mmol) in t-BuOH (1 mL) was added, and the slurry was stirred at 0° C. for 2 h. LCMS (1.5 h) showed ~10% conversion. The reaction was allowed to warm slowly to RT as the ice bath melted, and the mixture was stirred an additional 22 h. LCMS showed ~90% conversion to product. The reaction was then quenched with saturated aqueous sodium sulfite (10 mL) and extracted with EtOAc (2×20 mL). The combined organic layers were washed with 2 N NaOH (10 mL), dried (MgSO$_4$), and concentrated. The aqueous layer was extracted with DCM (2×50 mL), EtOAc (2×50 mL), and 10% IPA in CHCl$_3$ (2×50 mL). The combined organic layers were concentrated and the residue purified by flash column chromatography (12 g SiO$_2$, 5-100% 3:1 EtOAc:EtOH/heptanes) to give (1R,2R)-1-(5-methylpyrimidin-2-yl)propane-1,2-diol (Example 373.02, 89 mg, 0.53 mmol, 53% yield) as a clear, colorless oil. Chiral Analysis: SFC Chiral Analysis showed the % ee to be 94.8% using an AS-H (100×2.1 mm, 3 um), 10% organic modifier (IPA with 20 mM ammonia), 90% carbon dioxide. F=1.0 mL/min, column temperature=RT, BRP=105 bar.

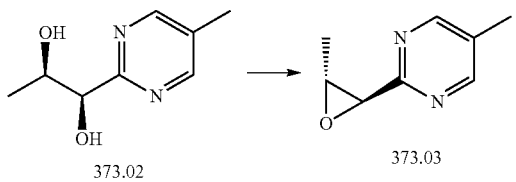

5-Methyl-2-((2R,3R)-3-methyloxiran-2-yl)pyrimidine, Example 373.03. To a solution of Example 373.02 (1.46 g, 8.68 mmol) in DCM (25 mL) (cooled with a RT water bath) was added 1,1,1-trimethoxyethane (2.50 mL, 2.29 mmol). Chlorotrimethylsilane (2.50 mL, 19.7 mmol) was then added in 2 portions 5 min apart. The reaction had a small exotherm on the first portion of addition of the TMSCl (23-28° C.). The reaction was stirred at RT under N$_2$ for 23 h. LCMS indicated incomplete conversion. Thus, an additional 1.25 equiv. of 1,1,1-trimethoxyethane (1.25 mL, 9.95 mmol) and chlorotrimethylsilane (1.25 mL, 9.85 mmol) were added, and the reaction was stirred for an additional 24 h. LCMS gave a peak at ((M+H)$^+$=229. The reaction was then concentrated in vacuo. The residue was dissolved in MeOH (20 mL) and potassium carbonate (1.50 g, 10.85 mmol) was added. The reaction was then stirred at RT for 4 h. LCMS (4 h) showed complete conversion to the product corresponding to desired epoxide (M+H)$^+$=151) formation. The reaction was filtered, and the filter cake was washed with DCM (5 mL). The combined filtrates were concentrated in vacuo. The residue was purified by flash column chromatography on silica gel eluting with 0-100% EtOAc/hexanes) to afford 5-methyl-2-((2R,3R)-3-methyloxiran-2-yl)pyrimidine, 373.03 (1.00 g, 6.6 mmol, 77%), as a clear, light yellow oil. $^1$H NMR (300 MHz, CDCl$_3$) δ 8.54 (s, 2H), 3.81 (d, J=1.9 Hz, 1H), 3.32-3.53 (m, 1H), 2.31 (s, 3H), 1.50 (d, J=5.1 Hz, 3H). LCMS (ESI pos.) m/z: 151.2 (M+H)$^+$.

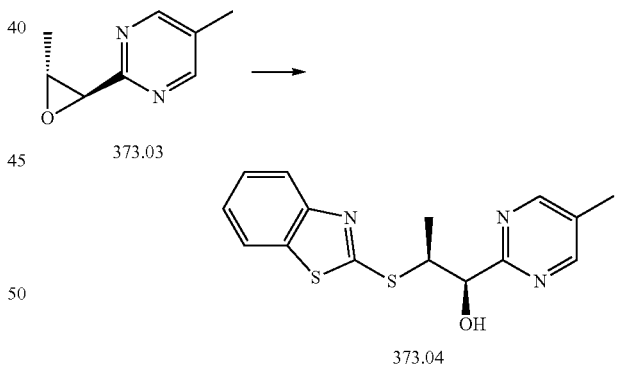

(1R,2S)-2-(Benzo[d]thiazol-2-ylthio)-1-(5-methylpyrimidin-2-yl)propan-1-ol, Example 373.04. To a solution of 5-methyl-2-((2R,3R)-3-methyloxiran-2-yl)pyrimidine 373.03 (250 mg, 1.33 mmol) in DCM (5 mL) was added benzo[d]thiazole-2-thiol (245 mg, 1.465 mmol) followed by tris(((trifluoromethyl)sulfonyl)oxy)ytterbium (83 mg, 0.133 mmol). The suspension was heated in a 35° C. heating block for 17 h and showed 100% conversion to the desired product. The reaction was cooled to RT, loaded on a plug of silica, and purified by flash chromatography (12 g SiO$_2$, 5-100% 3:1 EtOAc:EtOH/heptanes) to afford (1R,2S)-2-(benzo[d]thiazol-2-ylthio)-1-(5-methylpyrimidin-2-yl)propan-1-ol, 373.04 (428 mg, 1.35 mmol, 100% yield), as a clear colorless oil. ¹H NMR (300 MHz, CDCl₃) δ 8.60 (s, 2H), 7.88 (d, J=7.6 Hz, 1H), 7.71-7.81 (m, 1H), 7.42 (td, J=7.7, 1.3 Hz, 1H), 7.27-7.35 (m, 1H), 5.31 (s, 1H), 4.70 (qd, J=7.1, 3.1 Hz, 1H), 2.32 (s, 3H), 1.33 (d, J=7.0 Hz, 3H). LCMS (ESI pos.) m/z: 318.2 (M+H)⁺.

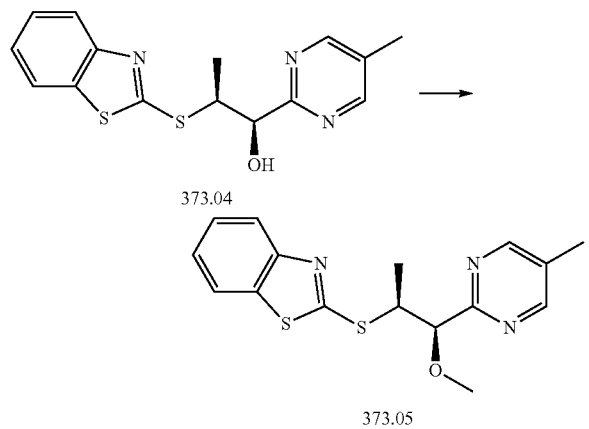

2-(((1R,2S)-1-Methoxy-1-(5-methylpyrimidin-2-yl)propan-2-yl)thio)benzo[d]thiazole, Example 373.05. To a 50 mL flask equipped with a magnetic stirrer was charged Example 373.04 (350 mg, 1.103 mmol) in 2-methyltetrahydrofuran (1.1 mL). The reaction mixture was cooled to −78° C. and potassium bis(trimethylsilyl)amide (1.0 M solution in THF, 1.32 μL, 1.32 mmol) was added dropwise (total addition time: 2 min., turned to yellow solution). The resulting mixture was stirred for 1 h and then MeOTf (374 μL, 3.31 mmol) was added dropwise (the reaction turned to a lighter yellow solution). The reaction mixture was then stirred at −78° C. for 15 min. LCMS showed complete conversion to the product. The reaction mixture was quenched by adding a saturated aqueous solution of NH₄Cl solution (30 mL) at −78° C. The reaction was then allowed to warm to RT and the aqueous layer was back extracted with EtOAc (3×75 mL). The combined organic layers were washed with brine, dried (Na₂SO₄), and concentrated in vacuo. The material thus obtained was purified by chromatography through a Biotage 50 g ultra silica gel column, eluting with a gradient of 0-25% EtOAc in hexanes to provide Example 373.05 (0.32 g, 75% for two runs) as a light-yellow oil.

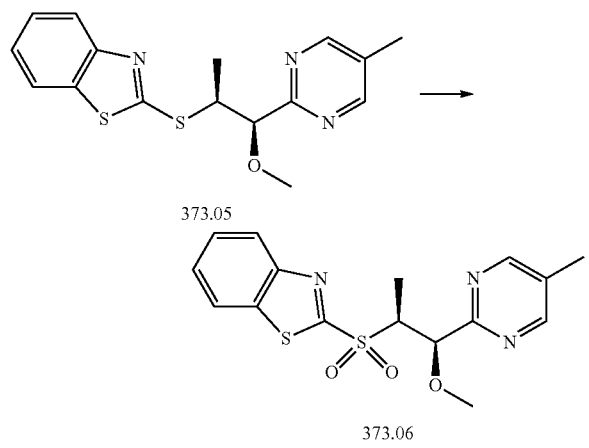

2-(((1R,2S)-1-Methoxy-1-(5-methylpyrimidin-2-yl)propan-2-yl)sulfonyl)benzo[d]thiazole, Example, Example 373.06. A solution of Example 373.05 (313 mg, 0.94 mmol) in DCM (2.8 mL) at 0° C. was treated with 3-chloroperoxybenzoic acid, (77% max, 476 mg, 2.13 mmol). The reaction was stirred at 0° C. for 1 h before the ice bath was removed. LCMS showed desired product, sulfoxide, and the presumed sulfoxide/sulfone. The mixture was allowed to warm to ambient temperature and stirred for an additional 40 h. The reaction was then quenched with saturated aqueous sodium bisulfite (6 mL), saturated aqueous sodium bicarbonate (5 mL), and was then stirred for 10 min. The reaction was extracted with EtOAc (2×20 mL) and the organic layers were combined, washed with a saturated aqueous solution of NaHCO₃ (10 mL), brine (10 mL), dried (MgSO₄), and filtered. Iodide/starch strip indicator showed no peroxide present. The filtrates were concentrated to give a clear colorless oil (360 mg). Purification of the residue by flash chromatography (40 g SiO₂, 0-100% 3:1 EtOAc:EtOH/heptanes) gave Example 373.06 (285 mg, 0.78 mmol, 83% yield, 77% purity) as a white foam. ¹H NMR (300 MHz, CDCl₃) δ 8.57 (s, 2H), 8.18-8.28 (m, 1H) 7.97-8.05 (m, 1H), 7.54-7.67 (m, 2H), 5.25-5.34 (m, 1H), 4.23 (qd, J=7.2, 3.1 Hz, 1H), 3.41 (s, 3H), 2.31 (s, 3H), 1.49 (d, J=7.2 Hz, 3H). LCMS (ESI pos.) m/z: 364.0 (M+H).

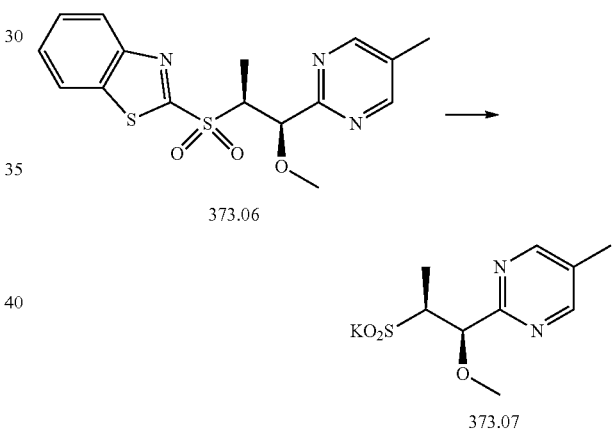

Potassium (1R,2S)-1-methoxy-1-(5-methylpyrimidin-2-yl)propane-2-sulfinate, Example 373.07. To a solution of Example 373.06 (268 mg, 0.74 mmol) in MeOH (1843 μL) was added potassium carbonate (204 mg, 1.48 mmol). The reaction was stirred at RT for 17 h. LCMS showed desired product formation as the sulfinic acid Example 373.07 (LCMS ((M+H)⁺=231.1)). The reaction was concentrated in vacuo (yellow solid) and used directly in the following step. Note: Epimerization occurred in this reaction (~15%).

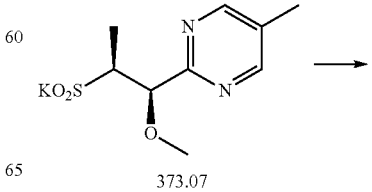

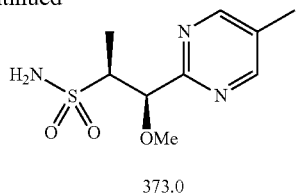

373.0

(1R,2S)-1-Methoxy-1-(5-methylpyrimidin-2-yl)propane-2-sulfonamide, Example 373.0. To a suspension of Example 373.07 (198 mg, 0.74 mmol) in water (3.7 mL) was added potassium acetate (72.4 mg, 0.74 mmol), followed by hydroxylamine-o-sulfonic acid, 97% (167 mg, 1.476 mmol). The reaction mixture was stirred at RT for 4.5 h. LCMS showed desired product formation plus a small peak that corresponded to the stereoisomer. The reaction mixture was extracted with EtOAc (2×) and the organic layers were combined, dried (Na$_2$SO$_4$), and concentrated in vacuo. The residue was loaded onto a silica gel column eluting with 0-30% (3:1 EtOAc:EtOH)/DCM to afford Example 373.0 (114 mg, 0.465 mmol, 63.0% yield) as a white solid. (contained ~15% other diastereomer). $^1$H NMR (300 MHz, CDCl$_3$) δ 8.63 (s, 2H), 5.10 (d, J=3.3 Hz, 1H), 4.78 (br. s., 2H), 3.74 (qd, J=7.1, 3.3 Hz, 1H), 3.51 (s, 3H), 2.36 (s, 3H), 1.33 (d, J=7.1 Hz, 3H). LCMS (ESI pos.) m/z: 246.1 (M+H)$^+$.

The compounds set forth in the following table were synthesized following the procedure in Example 373.0 using the known starting material as described.

TABLE 18

| Example | Reagents | Structure, Name and Data |
| --- | --- | --- |
| 373.1 | 2-bromo-5-methyl pyrazine (NOWA pharmaceuticals). | (1R,2S)-1-methoxy-1-(5-methylpyrazin-2-yl)propane-2-sulfonamide. LCMS-ESI (pos.) m/z: 246.2 (M + H)$^+$. |
| 373.2 | 2-chloro-5-fluoropyrimidine (Oakwood). | (1R,2S)-1-(5-fluoropyrimidin-2-yl)-1-methoxypropane-2-sulfonamide. LCMS-ESI (pos.) m/z: 250.1 (M + H)$^+$. |
| 373.3 | 2,5-dichloropyrimidine (Oakwood). | (1R,2S)-1-(5-chloropyrimidin-2-yl)-1-methoxypropane-2-sulfonamide. LCMS-ESI (pos.) m/z: 265.9 (M + H)$^+$. |
| 373.4 | 2-chloropyrimidine (Acros Organics). | (1R,2S)-1-methoxy-1-(pyrimidin-2-yl)propane-2-sulfonamide. LCMS-ESI (pos.) m/z: 232.0 (M + H)$^+$. |
| 373.5 | 2-chloro-5-fluoropyrimidine (Oakwood) EtOTf used in place of MeOTf in Example 83.5. | (1R,2S)-1-ethoxy-1-(5-fluoropyrimidin-2-yl)propane-2-sulfonamide. LCMS-ESI (pos.) m/z: 264.0 (M + H)$^+$. |

TABLE 18-continued

| Example | Reagents | Structure, Name and Data |
|---|---|---|
| 373.6 | 2-chloro-5-fluoropyrimidine (Oakwood) TBSOTf used in place of MeOTf in Example 83.5. | 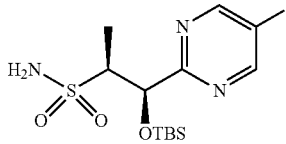<br>(1R,2S)-1-((tert-butyldimethylsilyl)oxy)-1-(5-fluoropyrimidin-2-yl)propane-2-sulfonamide.<br>LCMS-ESI (pos.) m/z: 350.1 (M + H)+. |
| 373.7 | 2,5-dichloropyrimidine (Oakwood), EtOTf used in place of MeOTf in Example 83.05. | 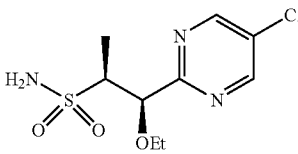<br>(1R,2S)-1-(5-chloropyrimidin-2-yl)-1-ethoxypropane-2-sulfonamide.<br>LCMS-ESI (pos.) m/z: 279.9. |

Example 373.8: Preparation of (1R,2S)-1-methoxy-1-(5-methoxypyrimidin-2-yl)propane-2-sulfonamide

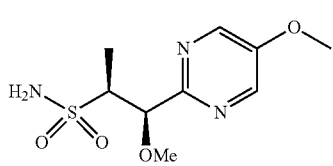

373.8

(1R,2S)-1-Methoxy-1-(5-methoxypyrimidin-2-yl)propane-2-sulfonamide, Example 373.8. The title compound was obtained as a by-product of the synthesis of (1R,2S)-1-methoxy-1-(5-fluoropyrimidin-2-yl)propane-2-sulfonamide (Example 373.2) during the step to prepare 373.07 and was isolated in the final step of the synthesis of Example 373.2 to give the title compound Example 373.8 (240 mg, 10.2% yield) as a white solid. $^1$H NMR (CDCl$_3$) δ: 8.46 (s, 2H), 5.11 (d, J=3.4 Hz, 1H), 4.77 (br. s, 2H), 3.97 (s, 3H), 3.67-3.77 (m, 1H), 3.50 (s, 3H), 1.35 (d, J=7.0 Hz, 3H). LCMS-ESI (pos.) m/z: 284.1 (M+Na)+.

Example 374.0. Preparation of (1S,2S)-1-isopropoxy-1-(5-methylpyrimidin-2-yl)propane-2-sulfonamide

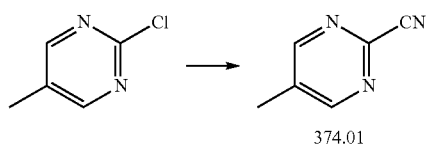

374.01

5-Methylpyrimidine-2-carbonitrile, Example 374.01. A solution of 2-chloro-5-methylpyrimidine (500 g, 3889 mmol, 1.0 equiv) in DMF (5000 mL) was degassed with N$_2$ for 20 min and then dppf (108 g, 194 mmol, 0.05 equiv) and Pd$_2$(dba)$_3$ (178 g, 194 mmol, 0.05 equiv) were added to the reaction mixture. Zn(CN)$_2$ (685 g, 5834 mmol, 1.5 equiv) was added, and the reaction mixture was heated at 100° C. for 16 h. The reaction was quenched with water (5 L) and stirred for 10 min. The reaction mixture was filtered through Celite® brand filter aid pad. The filtrate was diluted with water (4 L) and extracted with EtOAc (2×4 L). The combined organic layers were washed with brine (4 L), dried over Na$_2$SO$_4$, filtered, and concentrated in vacuo to give the initial product which was further purified by column chromatography using silica gel (60-120 mesh) and 0-10% EtOAc in hexane to obtain Example 374.01 (330 g, 71%) as an off white solid. $^1$H NMR (400 MHz, DMSO-d$_6$) δ 8.89 (s, 2H), 2.39 (s, 3H).

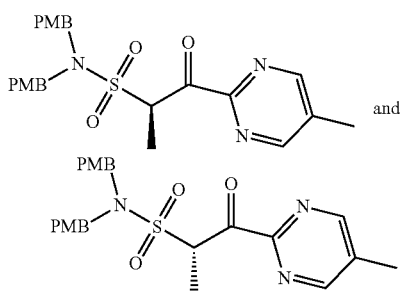

374.2

(R)—N,N-Bis(4-methoxybenzyl)-1-(5-methylpyrimidin-2-yl)-1-oxopropane-2-sulfonamide and (S)—N,N-bis(4-methoxybenzyl)-1-(5-methylpyrimidin-2-yl)-1-oxopropane-2-sulfonamide, Example 374.2. To a solution of Example 361.0 (293 g, 839 mmol, 2.0 equiv) in THF (2 L) was added isopropylmagnesium chloride (420 mL, 839 mmol, 2.0 equiv, 2.0 M in diethyl ether) at 0° C. The reaction mixture was stirred at 25° C. for 3 h. To that reaction mixture was added 5-methylpyrimidine-2-carbonitrile (374.01, 50 g, 420 mmol, 1.0 equiv) in THF (100 mL) at 0° C., and the resulting mixture was stirred at RT for 2 h. The reaction was then quenched 1.5 N HCl (500 mL) and water (2 L) and stirred for 10 min. The mixture was extracted with EtOAc (2×1 L), and the combined organic layers were washed with brine (500 mL), dried over Na$_2$SO$_4$ and filtered. The organic layer was concentrated in vacuo to give the initial compound which was purified by column chromatography using silica gel (100-200 mesh) and 0-50% EtOAc in hexane as eluent to obtain Example 374.2 (60 g, 30% yield) as a brown liquid. ¹H NMR (400 MHz, DMSO-d₆) δ 8.90 (s, 2H), 7.15-7.09 (m, 4H), 6.85-6.80 (m, 4H), 4.34-4.18 (m, 5H), 3.71 (m, 6H), 2.39 (s, 3H), 1.50 (d, J=6.9 Hz, 3H). LCMS (ESI pos.) m/z: (M+H)⁺: 470.0.

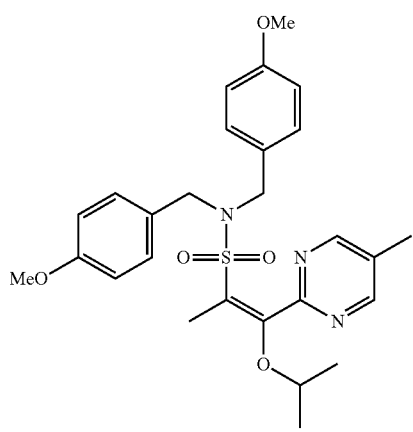

374.3

(E)-1-Isopropoxy-N,N-bis(4-methoxybenzyl)-1-(5-methylpyrimidin-2-yl)prop-1-ene-2-sulfonamide, Example 374.3. A solution of Example 374.2 (120 g, 256 mmol, 1.0 equiv) in DMF (1.2 L) was added 2-iodopropane (129 mL, 1278 mmol, 5.0 equiv) and potassium carbonate (70.6 g, 511 mmol, 2.0 equiv). The reaction mixture was stirred at 60° C. for 14 h. The reaction was then quenched with water (1 L), stirred for 10 min, and then extracted with EtOAc (2×1 L). The combined organic layers were washed with brine (1000 mL), dried over Na₂SO₄, filtered, and concentrated in vacuo to give the initial material. The initial product was purified by column chromatography using silica gel (100-200 mesh) and 0-50% EtOAc in hexanes as eluent to obtain Example 374.3 (75 g, 57.4% yield) as an off white solid. ¹H NMR (400 MHz, DMSO-d₆) δ 8.72 (s, 2H), 7.09 (d, J=8.3 Hz, 4H), 6.86 (d, J=8.3 Hz, 4H), 4.16 (s, 4H), 3.73 (s 3H), 3.73 (s 3H), 3.71-3.67 (m, 1H), 2.31 (s, 3H), 1.87 (s, 3H), 1.19-1.16 (m, 6H). LCMS (ESI pos.) m/z: (M+H)⁺: 512.1.

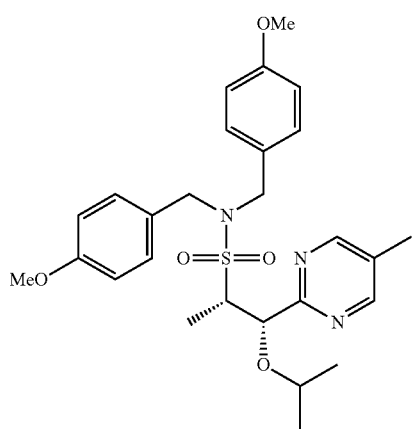

374.4

(1S,2R)-1-Isopropoxy-N,N-bis(4-methoxybenzyl)-1-(5-methylpyrimidin-2-yl)propane-2-sulfonamide, Example 374.4. To a solution of Example 374.3 (180 g, 352 mmol, 1.0 equiv) in MeOH (1.8 L) were added zinc triflate (256 g, 704 mmol, 2.0 equiv) and (S)—RuCl[(p-cymene(BINAP)]Cl (6.54 g, 7.04 mmol, 0.02 equiv). The resulting mixture was heated at 60° C. under H₂ pressure (60 psi) for 16 h. The reaction mixture was then concentrated in vacuo to obtain the initial which was further purified by column chromatography using silica gel (60-120 mesh) and 0-50% EtOAc in DCM as eluent to obtain Example 374.4 (140 g, 77%, 92% ee) as an off white solid. ¹H NMR (400 MHz, DMSO-d₆) δ 8.71 (s, 2H), 7.25-7.15 (m, 4H), 6.95-6.75 (m, 4H), 4.82 (dd, J=7.8, 1.8 Hz, 1H), 4.39 (d, J=15.6 Hz, 2H), 4.13 (d, J=15.7 Hz, 2H), 3.82 (qd, J=8.5, 7.9, 6.0 Hz, 1H), 3.65 (app s, 6H), 3.41-3.35 (m, 1H), 2.27 (s, 3H), 1.12 (dd, J=6.2, 1.8 Hz, 3H), 1.02 (dd, J=7.1, 2.0 Hz, 3H), 0.96 (dd, J=6.3, 1.8 Hz, 3H). LCMS (ESI pos.) m/z: (M+H)⁺: 514.2.

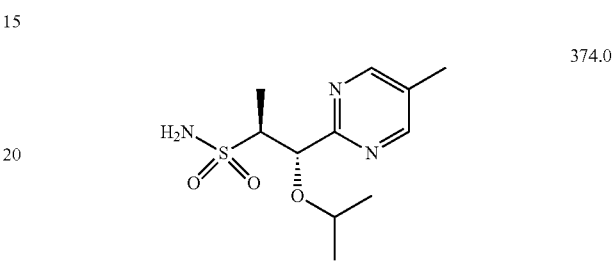

374.0

(1S,2S)-1-Isopropoxy-1-(5-methylpyrimidin-2-yl)propane-2-sulfonamide, Example 374.0. To a solution of Example 374.4 (140.0 g, 273 mmol, 1.0 equiv) in DCM (500 mL) was added TFA (250 mL) at 0° C., and the reaction mixture was allowed to stir at RT for 16 h. The reaction mixture was concentrated in vacuo to obtain the initial material which was dissolved in DCM (1 L) and washed with saturated aqueous NaHCO₃ solution (1 L). The organic layer was dried over Na₂SO₄, filtered, and concentrated in vacuo to obtain the initial material which was further purified by column chromatography using silica gel (60-120 mesh) and 0-2% MeOH in DCM to obtain Example 374.0 (72 g, 97% yield, 90% ee) as an off white solid. Example 374.0 (72 g, 90% ee) was suspended in IPA (500 mL) and heated at 70° C. until the mixture become homogeneous. Once the solution became homogeneous, the mixture was cooled to RT overnight. The white solid thus obtained was filtered and dried under vacuum to obtain compound-6 (30 g, >99%). The mother liquor was concentrated, and the solid obtained was recrystallized again following the same procedure. ¹H NMR (400 MHz, DMSO-d₆) δ 8.70 (d, J=2.3 Hz, 2H), 6.45 (d, J=2.4 Hz, 2H), 4.68 (dd, J=8.8, 2.5 Hz, 1H), 3.59-3.52 (m, 1H), 3.48 (ddd, J=9.7, 7.4, 4.9 Hz, 1H), 2.29 (d, J=2.6 Hz, 3H), 1.13 (dd, J=6.1, 2.5 Hz, 3H), 0.93 (dd, J=7.1, 2.5 Hz, 3H), 0.88 (dd, J=6.3, 2.5 Hz, 3H). LCMS (ESI pos.) m/z: (M+H)⁺: 274.1.

The compounds in the following table were synthesized following the procedure in Example 374.0 using the known starting material as described.

TABLE 19

| Example | Reagents | Structure, Name and Data |
|---|---|---|
| 374.1 | 2-chloro-5-chloropyrimidine. | |

TABLE 19-continued

| Example | Reagents | Structure, Name and Data |
|---|---|---|
| | | (1S,2S)-1-(5-chloropyrimidin-2-yl)-1-isopropoxypropane-2-sulfonamide. LCMS ESI (pos.) m/z: 294.2 (M + H)+. |

Example 375.0. Preparation of (2S,3R)-3-(5-chloropyridin-2-yl)butane-2-sulfonamide

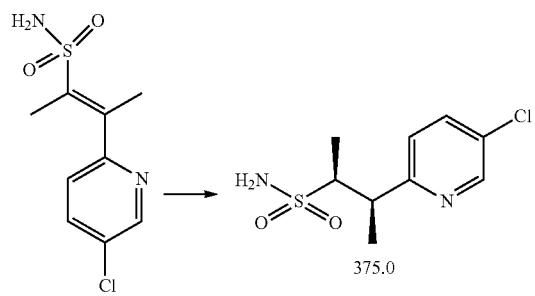

(2S,3R)-3-(5-Chloropyridin-2-yl)butane-2-sulfonamide, Example 375.0. To a solution of (E)-2-(5-chloropyridin-2-yl)ethenesulfonamide (10 g, 40.5 mmol) in MeOH (100 mL) was added zinc trifluoromethanesulfonate (2.95 g, 8.11 mmol), bis(1,5-cyclooctadiene)rhodium(I) tetrafluoroborate (0.329 g, 0.811 mmol), and (S)-1-[(R)-2-(di-1-naphthylphosphino)ferrocenyl]-ethyl-di-tert-butylphosphine (0.651 g, 1.013 mmol). The reaction mixture was then degassed with argon and hydrogen three times. Hydrogen (50 PSI) was then charged into the vessel and the mixture was reacted in a 200 mL Mini-clave at RT for 16 h followed by heating at 65° C. for 16 h. TLC indicated completion of reaction with starting material completely absent. The reaction was concentrated in vacuo to get the initial product which was purified by column chromatography (silica gel 60-120 mesh) using 40-45% of EtOAc in petroleum ether as an eluent to obtain the desired product, (2S,3R)-3-(5-chloropyridin-2-yl)butane-2-sulfonamide (Example 375.0, 9 g, 36.2 mmol, 89%), as a brownish solid in 82% ee. Recrystallization from i-PrOH yielded>97% ee material. $^1$H NMR (400 MHz, DMSO-$d_6$) δ 1.19 (d, J=7.05 Hz, 3H) 1.29 (d, J=7.05 Hz, 3H) 3.46 (qd, J=7.08, 3.84 Hz, 1H) 3.63 (qd, J=7.08, 3.84 Hz, 1H) 6.82 (s, 2H) 7.36 (d, J=8.50 Hz, 1H) 7.88 (dd, J=8.50, 2.70 Hz, 1H) 8.56 (d, J=2.28 Hz, 1H). LCMS-ESI (pos.) m/z: 249.0 (M+H)+.

Example 376.0. Preparation of (1R,2R)-1-isopropoxy-1-(5-methylpyrazin-2-yl)propane-2-sulfonamide or (1S,2S)-1-isopropoxy-1-(5-methylpyrazin-2-yl)propane-2-sulfonamide

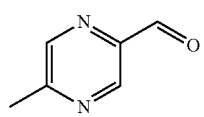

376.1

5-Methylpyrazine-2-carbaldehyde, Example 376.1. A solution of lithium aluminium hydride (164.0 mL, 0.164 mol, 1.0 M in THF, 0.5 equiv.) was added to a suspension of methyl 5-methylpyrazine-2-carboxylate (50 g, 0.328 mol, 1.0 equiv.) in anhydrous THF (750 mL) at −78° C. (the internal temperature was kept below −72° C. during addition of the lithium aluminium hydride). Upon completion of addition, the reaction mixture was stirred at −78° C. for a further 20 min and then quenched with glacial AcOH (50.0 mL) at the same temperature. The resulting mixture was warmed to RT and the volatiles were removed by evaporation under pressure. The residue was dissolved in 1.5 N HCl (500 mL) and extracted with DCM (2×2 L). The organic layers were combined, washed with saturated aqueous NaHCO$_3$ solution (2×500 mL), dried over anhydrous Na$_2$SO$_4$, filtered, and concentrated in vacuo to yield the initial product as a brown oil. The residue was purified by column chromatography (silica gel 60-120 mesh) eluting with a gradient of 10% EtOAc in petroleum ether to provide the title compound as a pale yellow liquid (21.3 g, 53%). $^1$H NMR (400 MHz, CDCl$_3$) δ 10.14 (s, 1H), 9.07 (d, J=1.5 Hz, 1H), 8.63 (d, J=1.4 Hz, 1H), 2.70 (s, 3H). LCMS (ESI positive ion) m/z: 123 (M+H)+.

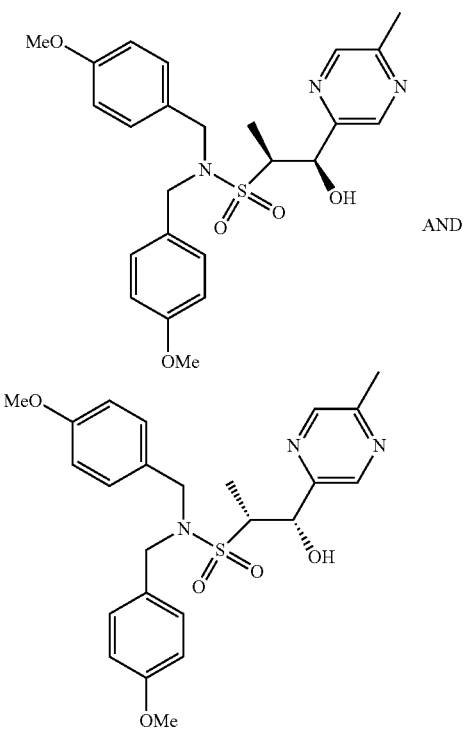

(1R,2S)-1-Hydroxy-N,N-bis(4-methoxybenzyl)-1-(5-methylpyrazin-2-yl)propane-2-sulfonamide and (1S,2R)-1-hydroxy-N,N-bis(4-methoxybenzyl)-1-(5-methylpyrazin-2-yl)propane-2-sulfonamide, Example 376.2. To a solution of N,N-bis(4-methoxybenzyl)ethanesulfonamide (Example 361.0, 73.13 g, 0.209 mol, 1.2 equiv.) in anhydrous THF (600 mL) at −78° C. was added n-butyllithium (83.71 mL, 0.21 mol, 2.5 M solution in hexanes, 1.2 equiv.) via additional funnel slowly, and the resulting mixture was stirred for 10 min. A solution of 5-methylpyrazine-2-carbaldehyde (Example 376.1, 21.3 g, 0.17 mol, 1.0 equiv.) in anhydrous THF (150 mL) was then added, and the mixture was stirred at the same temperature for 45 min and then allowed to warm to RT for 2 h. The reaction mixture was quenched by addition of aqueous ammonium chloride (200 mL) and extracted with EtOAc (2×2 L). The combined organic layers were washed with brine (2×500 mL). After drying over anhydrous $Na_2SO_4$, the filtrate was concentrated in vacuo to afford the initial product as an oil. The oil was purified by flash column chromatography (silica gel, 230-400 mesh) to afford the two isomers. The faster moving isomer (32 g as white solid) was obtained from the column with a gradient of 10% to 30% EtOAc in petroleum ether. $^1$H NMR (400 MHz, DMSO-$d_6$) δ 8.61 (d, J=1.5 Hz, 1H), 8.51 (d, J=1.5 Hz, 1H), 7.22-7.11 (m, 4H), 6.90-6.80 (m, 4H), 6.10 (d, J=5.9 Hz, 1H), 5.29 (dd, J=5.9, 2.2 Hz, 1H), 4.36-4.16 (m, 4H), 3.73 (app s, 6H), 3.70-3.66 (m, 1H) 2.50 (merged with solvent peak, 3H) and 1.10 (d, J=7.0 Hz, 3H). LCMS (ESI positive ion) m/z: 472.4 (M+H)$^+$.

376.3

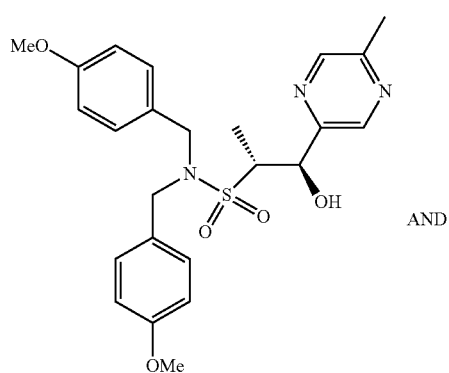

AND

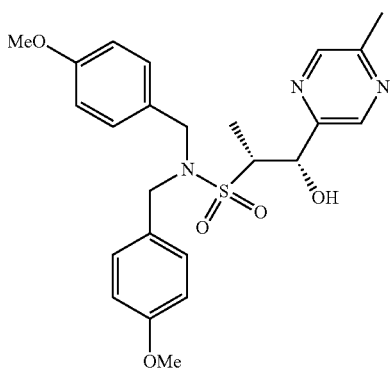

(1S,2S)-1-Hydroxy-N,N-bis(4-methoxybenzyl)-1-(5-methyl-pyrazin-2-yl)propane-2-sulfonamide and (1R,2R)-1-hydroxy-N,N-bis(4-methoxybenzyl)-1-(5-methyl-pyrazin-2-yl)propane-2-sulfonamide, Example 28.3. Further elution of the mixture with a gradient of 30% to 35% EtOAc in petroleum ether yielded Example 376.3 (16 g) as a pale yellow gummy liquid). $^1$H NMR (400 MHz, CDCl$_3$) δ 8.62 (d, J=1.6 Hz, 1H), 8.44 (d, J=1.5 Hz, 1H), 7.25-7.12 (m, 4H), 6.93-6.82 (m, 4H), 5.17 (d, J=7.1 Hz, 1H), 4.47 (d, J=15.2 Hz, 3H), 4.14 (d, J=15.4 Hz, 2H), 3.82 (s, 3H), 3.82 (s, 3H), 3.66-3.61 (m, 1H), 2.60 (d, J=2.0 Hz, 3H), and 1.08 (dd, J=7.2, 2.1 Hz, 3H). LCMS (ESI pos.) m/z: 472.4 (M+H)$^+$.

376.4

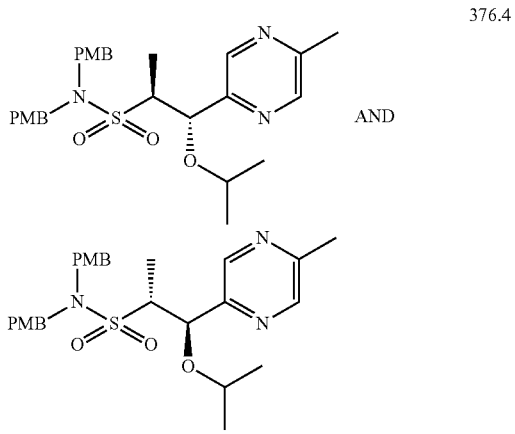

AND (1S,2S)-1-Isopropoxy-N,N-bis(4-methoxybenzyl)-1-(5-methylpyrazin-2-yl)propane-2-sulfonamide and (1R,2R)-1-isopropoxy-N,N-bis(4-methoxybenzyl)-1-(5-methyl-pyrazin-2-yl)propane-2-sulfonamide, Example 376.4. To a flask containing Example 376.3 (4.16 g, 8.81 mmol) and isopropyl iodide (12.3 mL, 123 mmol) in anhydrous toluene (35 mL) was carefully added silver(I) oxide (4.17 g, 18.0 mmol) in portions. Upon complete addition of silver oxide, the reaction was protected from light and heated to an internal temperature of 72° C. After 60 h, the mixture was cooled to RT and then filtered through a Chemglass disposable filter that was rinsed with EtOAc. The filtrate was concentrated in vacuo. The dark brown residue was loaded onto a silica gel column (10-55% EtOAc in heptanes). Fractions containing the product were combined and then concentrated in vacuo to afford a dark brown oil as the title compound (Example 376.4, 1.52 g, 2.97 mmol, 34% yield) that was used without further purification. $^1$H NMR (400 MHz, DMSO-$d_6$) δ 8.58 (d, J=1.5 Hz, 1H), 8.54 (d, J=0.8 Hz, 1H), 7.20-7.15 (m, 4H), 6.89-6.85 (m, 4H), 4.81 (d, J=7.0 Hz, 1H), 4.35-4.29 (m, 2H), 4.20-4.13 (m, 2H), 3.76-3.71 (m, 7H), 3.39 (quin, J=6.1 Hz, 1H), 2.51 (s, 3H), 1.13 (d, J=6.0 Hz, 3H), 1.05 (d, J=7.3 Hz, 3H), 0.99 (d, J=6.2 Hz, 3H). LCMS (ESI pos.) m/z: 514.0 (M+H)$^+$.

376.5

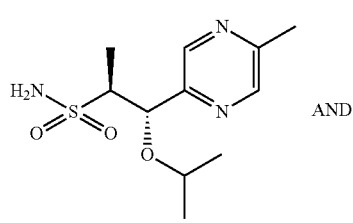

AND

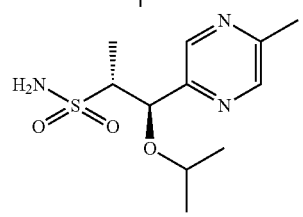

(1R,2R)-1-Isopropoxy-1-(5-methylpyrazin-2-yl)propane-2-sulfonamide and (1S,2S)-1-isopropoxy-1-(5-methyl-pyrazin-2-yl)propane-2-sulfonamide, Example 376.5. Anisole (1.3 mL, 11.9 mmol) was added to a flask containing Example 376.4 (1.5 g, 3 mmol) and DCM (7.5 mL). The homogeneous solution was cooled in an ice-water bath. After 15 min, TFA (7.6 mL, 99 mmol) was added dropwise to the reaction solution. Upon complete addition of TFA, the reaction was allowed to warm to RT. After 20 h, the brownish reaction solution was concentrated in vacuo. The residue was loaded onto a silica gel column (15-85% EtOAc in heptanes). Fractions containing the product were concentrated in vacuo to afford Example 376.5 (714 mg, 2.6 mmol, 88% yield) as an off white solid. LCMS (ESI pos.) m/z: 274.0 (M+H)+.

376.5 delivered the second eluting peak as Example 376.0 (303 mg, 1.11 mmol, 37% yield). $^1$H NMR (400 MHz, DMSO-$d_6$) δ 8.60 (d, J=1.5 Hz, 1H), 8.53 (d, J=1.0 Hz, 1H), 6.52 (s, 2H), 4.77 (d, J=7.0 Hz, 1H), 3.58-3.44 (m, 2H), 1.27-1.14 (m, 3H), 1.05 (d, J=7.0 Hz, 3H), 1.00-0.91 (m, 3H). (Obscured $CH_3$ in DMSO peak). LCMS (ESI pos.) m/z: 274.2 (M+H)+.

Example 360.01: Preparation of (1R,2S)-1-((tert-butyldimethylsilyl)oxy)-N,N-bis(4-methoxybenzyl)-1-(5-methylpyrimidin-2-yl)propane-2-sulfonamide

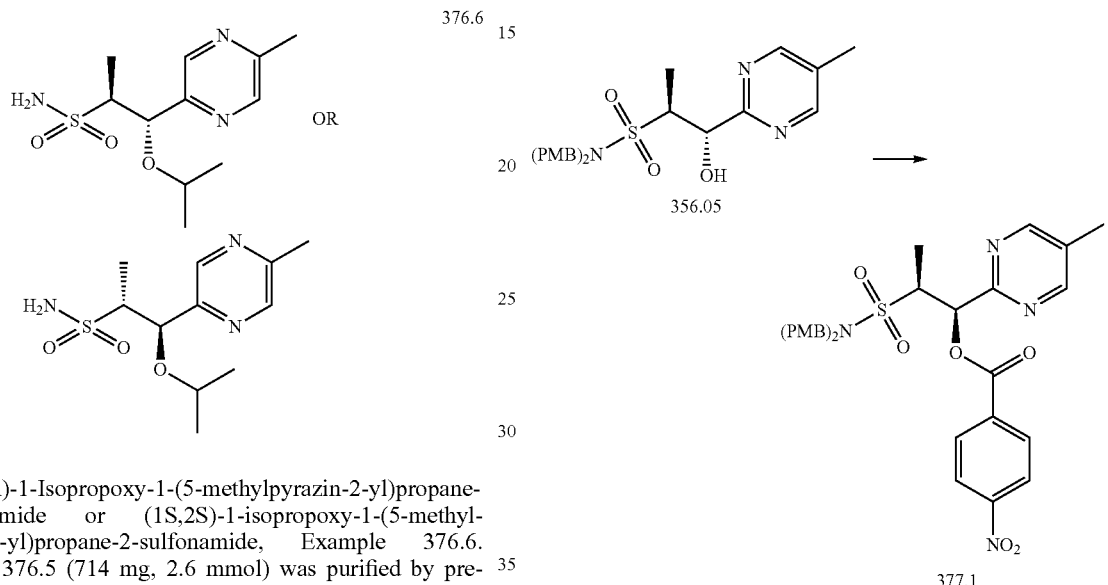

376.6

(1R,2R)-1-Isopropoxy-1-(5-methylpyrazin-2-yl)propane-2-sulfonamide or (1S,2S)-1-isopropoxy-1-(5-methyl-pyrazin-2-yl)propane-2-sulfonamide, Example 376.6. Example 376.5 (714 mg, 2.6 mmol) was purified by preparative SFC using the following methodology: Column: IC (2×25 cm) Mobile Phase: 70:30 (A:B) A: Liquid $CO_2$, B: IPA to afford peak 1 as Example 376.6, (293 mg, 1.07 mmol, 36% yield). $^1$H NMR (400 MHz, DMSO-$d_6$) δ 8.60 (d, J=1.5 Hz, 1H), 8.53 (d, J=0.8 Hz, 1H), 6.52 (s, 2H), 4.77 (d, J=7.0 Hz, 1H), 3.56-3.45 (m, 2H), 1.15 (d, J=6.0 Hz, 3H), 1.05 (d, J=7.0 Hz, 3H), 0.96 (d, J=6.2 Hz, 3H). (Obscured $CH_3$ in DMSO peak). LCMS (ESI pos.) m/z: 274.2 (M+H)+.

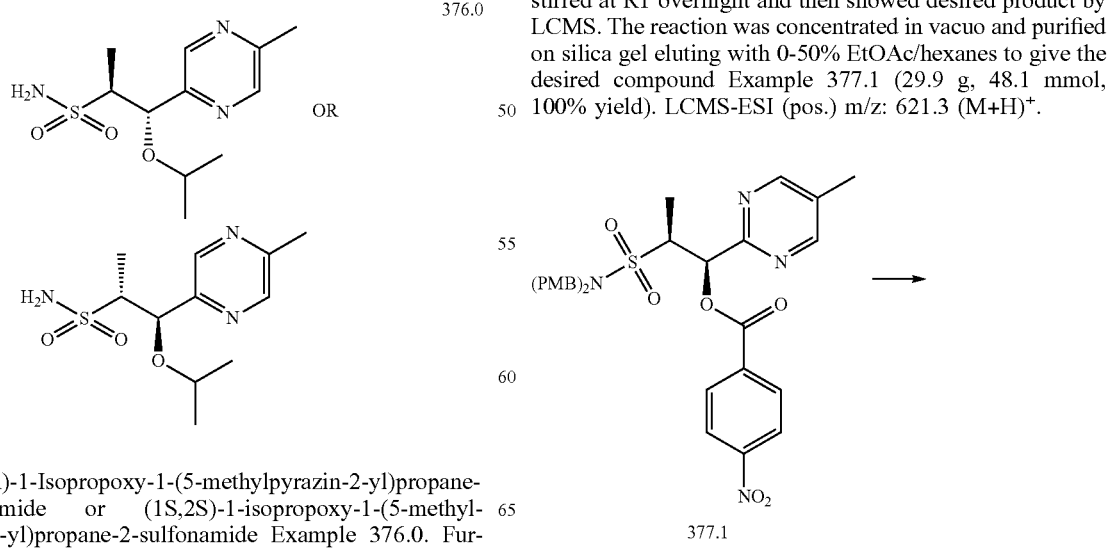

377.1

(1R,2S)-2-(N,N-Bis(4-methoxybenzyl)sulfamoyl)-1-(5-methylpyrimidin-2-yl)propyl 4-nitrobenzoate, Example 377.1. To a stirred solution of 356.05 (22.7 g, 48.1 mmol) in toluene (241 mL) was added 4-nitrobenzoic acid (12.07 g, 72.2 mmol), and triphenylphosphine (18.94 g, 72.2 mmol) followed by dropwise addition of (E)-diisopropyl diazene-1,2-dicarboxylate (14.22 mL, 72.2 mmol). The mixture was stirred at RT overnight and then showed desired product by LCMS. The reaction was concentrated in vacuo and purified on silica gel eluting with 0-50% EtOAc/hexanes to give the desired compound Example 377.1 (29.9 g, 48.1 mmol, 100% yield). LCMS-ESI (pos.) m/z: 621.3 (M+H)+.

(1R,2R)-1-Isopropoxy-1-(5-methylpyrazin-2-yl)propane-2-sulfonamide or (1S,2S)-1-isopropoxy-1-(5-methyl-pyrazin-2-yl)propane-2-sulfonamide Example 376.0. Further elution under the conditions described in Example -continued

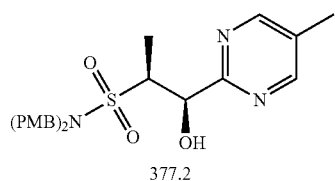

377.2

(1R,2S)-2-(N,N-Bis(4-methoxybenzyl)sulfamoyl)-1-(5-methylpyrimidin-2-yl)propyl 4-nitrobenzoate, Example 377.2. To a stirred solution of Example 377.1 (76 g, 122 mmol) in MeOH (612 mL) at 0° C. was added potassium carbonate (16.92 g, 122 mmol). The mixture was allowed to warm to RT over 1 h and showed the desired product by LCMS. The reaction was concentrated in vacuo and purified on silica gel eluting with 0-40% EtOAc in hexanes to give Example 377.2. LCMS-ESI (pos.) m/z: 472.0 (M+H)$^+$.

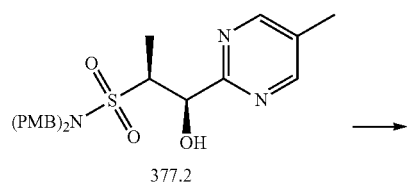

377.2

→

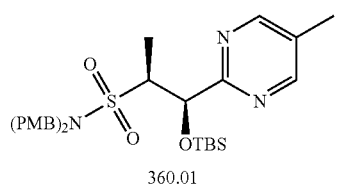

360.01

(1R,2S)-1-((tert-Butyldimethylsilyl)oxy)-N,N-bis(4-methoxybenzyl)-1-(5-methylpyrimidin-2-yl)propane-2-sulfonamide, Example 360.01. To a stirred solution of Example 377.2 (28 g, 59.4 mmol) in DCM (297 mL, 59.4 mmol) at 0° C. was added TBSOTf (15.00 mL, 65.3 mmol) followed by TEA (9.12 mL, 65.3 mmol). The mixture was allowed to warm to RT over 1 h and then showed the desired product by LCMS. The reaction was concentrated in vacuo and purified on silica gel eluting with 0-30% EtOAc in hexane to give the desired compound, Example 360.01 (15 g, 25.6 mmol, 43.1% yield). LCMS-ESI (pos.) m/z: 586.0 (M+H)$^+$.

Example 378.0. Preparation of (2R,3R)—N-(4-(2,6-dimethoxyphenyl)-5-(3-pyridinyl)-4H-1,2,4-triazol-3-yl)-3-(5-methoxy-2-pyrazinyl)-2-butanesulfonamide and (2R,3S)—N-(4-(2,6-dimethoxyphenyl)-5-(3-pyridinyl)-4H-1,2,4-triazol-3-yl)-3-(5-methoxy-2-pyrazinyl)-2-butanesulfonamide and (2S,3R)—N-(4-(2,6-dimethoxyphenyl)-5-(3-pyridinyl)-4H-1,2,4-triazol-3-yl)-3-(5-methoxy-2-pyrazinyl)-2-butanesulfonamide and (2S,3S)—N-(4-(2,6-dimethoxyphenyl)-5-(3-pyridinyl)-4H-1,2,4-triazol-3-yl)-3-(5-methoxy-2-pyrazinyl)-2-butanesulfonamide

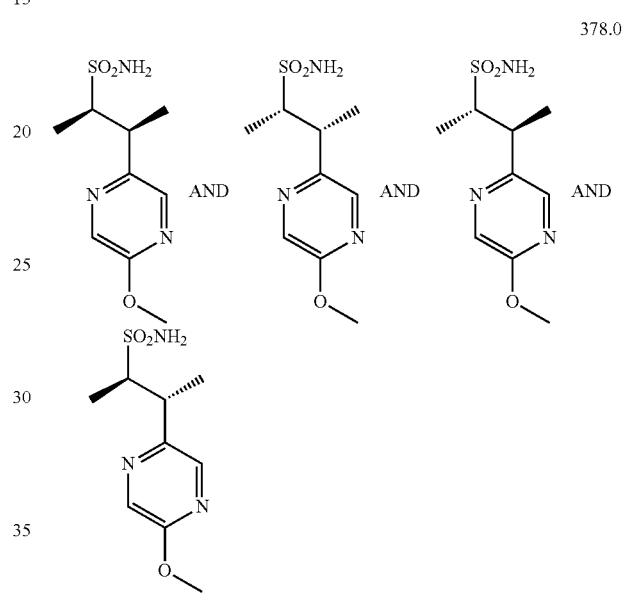

(2R,3R)-3-(5-Methoxypyrazin-2-yl)butane-2-sulfonamide and (2R,3S)-3-(5-methoxypyrazin-2-yl)butane-2-sulfonamide and (2S,3R)-3-(5-methoxypyrazin-2-yl)butane-2-sulfonamide and (2S,3S)-3-(5-methoxypyrazin-2-yl)butane-2-sulfonamide, Example 378.0. Example 378.0 was synthesized following the procedure in Example 375.0 using 2-bromo-5-methoxypyrazine (commercially available from Ark Pharm, Inc.). LCMS-ESI (pos.) m/z: 246.2 (M+H)$^+$.

Example 379.0. Preparation of (2S,3R)—N-(4-(2,6-dimethoxyphenyl)-5-((2R)-1,4-dioxan-2-yl)-4H-1,2,4-triazol-3-yl)-3-(5-methoxy-2-pyrimidinyl)-2-butanesulfonamide or (2S,3R)—N-(4-(2,6-dimethoxyphenyl)-5-((2R)-1,4-dioxan-2-yl)-4H-1,2,4-triazol-3-yl)-3-(5-methoxy-2-pyrimidinyl)-2-butanesulfonamide

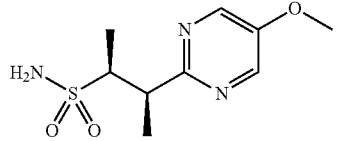

(2S,3R)-3-(5-Methoxypyrimidin-2-yl)butane-2-sulfonamide, Example 379.1. A RBF was charged with (2S,3R)-3-

(5-fluoropyrimidin-2-yl)butane-2-sulfonamide (575 mg, 2.47 mmol, Example 56.5), MeOH (7 mL), and potassium carbonate (679 mg, 4.91 mmol). The reaction was stirred at RT. After 48 h, the reaction was heated to 50° C. and stirred for 24 h. The temperature was then raised to 65° C. and the reaction mixture was stirred for 48 h. LCMS-ESI showed the reaction was 75% complete. The reaction was then allowed to cool to RT and filtered. The solids were rinsed with MeOH (2×5 mL). The filtrate was concentrated in vacuo and adsorbed onto a plug of silica gel and chromatographed through a RediSep® pre-packed silica gel column, eluting with 0-40% EtOAc:EtOH (3:1) in heptanes. The organic layer from several fractions were concentrated in vacuo to give a mixture of starting material and the title compound (56 mg, 0.23 mmol, 9% yield) as an off-white solid. The fractions with a water layer were combined and the aqueous layer was saturated with NaCl and extracted with CHCl$_3$:IPA (9:1, 3×15 mL). The combined organic layers were dried over MgSO$_4$ and concentrated in vacuo to give more title compound (114 mg). The material was carried forward without further purification. LCMS-ESI (pos.) m/z: 246.1 (M+H)$^+$.

Example 380.0. Preparation of (3R,5S)—N-(4-(4,6-dimethoxy-5-pyrimidinyl)-5-((2R)-1,4-dioxan-2-yl)-4H-1,2,4-triazol-3-yl)-1-(5-fluoro-2-pyrimidinyl)-5-(1-methylethoxy)-3-piperidinesulfonamide or (3R,5S)—N-(4-(4,6-dimethoxy-5-pyrimidinyl)-5-((2S)-1,4-dioxan-2-yl)-4H-1,2,4-triazol-3-yl)-1-(5-fluoro-2-pyrimidinyl)-5-(1-methylethoxy)-3-piperidinesulfonamide or (3S,5R)—N-(4-(4,6-dimethoxy-5-pyrimidinyl)-5-((2R)-1,4-dioxan-2-yl)-4H-1,2,4-triazol-3-yl)-1-(5-fluoro-2-pyrimidinyl)-5-(1-methylethoxy)-3-piperidinesulfonamide or (3S,5R)—N-(4-(4,6-dimethoxy-5-pyrimidinyl)-5-((2S)-1,4-dioxan-2-yl)-4H-1,2,4-triazol-3-yl)-1-(5-fluoro-2-pyrimidinyl)-5-(1-methylethoxy)-3-piperidinesulfonamide

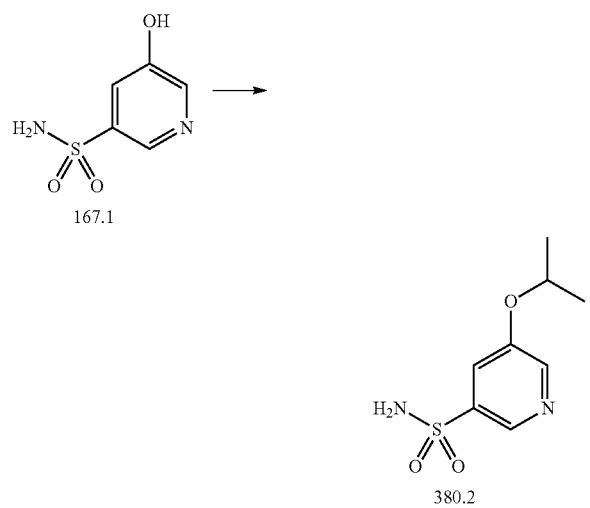

167.1

380.2

5-Isopropoxypyridine-3-sulfonamide, Example 380.2. To a suspension of 5-hydroxypyridine-3-sulfonamide, Example 167.1 (1.1 g, 6.32 mmol) in THF (16 mL) and IPA (16 mL), was added triphenylphosphine (1.99 g, 7.58 mmol). The mixture was bubbled with argon for 3 min before diisopropyl azodicarboxylate (1.49 mL, 7.58 mmol) was added dropwise at 0° C. under a stream of N$_2$. The reaction was then stirred at 0° C. to RT for 15 h and then concentrated in vacuo. The material thus obtained was absorbed onto a plug of silica gel and purified by chromatography through a RediSep pre-packed silica gel column (40 g), eluting with a gradient of 0% to 100% EtOAc in heptanes to provide the enriched product fractions, which were combined, and extracted with 1 N HCl. The desired product was enriched in the acidic aqueous solution which was then brought to a pH of greater than 8 by addition of a saturated aqueous solution of NaHCO$_3$. The basic aqueous solution was then extracted with DCM. The combined organic layers were washed with brine and dried over Na$_2$SO$_4$. The solution was then filtered and concentrated in vacuo to give Example 380.2, 5-isopropoxypyridine-3-sulfonamide (0.95 g, 70% yield), as a white solid. LCMS-ESI (pos.) m/z: 217.2 (M+H)$^+$.

380.3

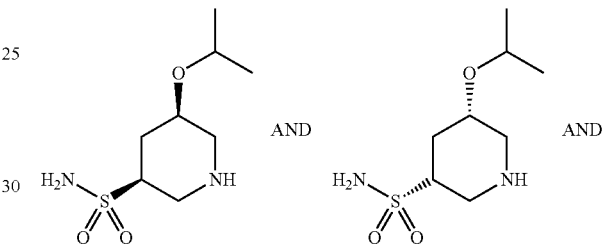

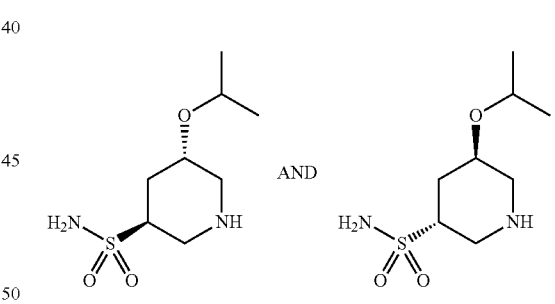

(3S,5R)-5-Isopropoxypiperidine-3-sulfonamide and (3R,5R)-5-isopropoxypiperidine-3-sulfonamide and (3S,5S)-5-isopropoxypiperidine-3-sulfonamide and (3R,5S)-5-isopropoxypiperidine-3-sulfonamide, Example 380.3. A solution of Example 380.2, 5-isopropoxypyridine-3-sulfonamide (1.8 g, 8.32 mmol), in AcOH (41.6 mL) was bubbled with argon gas for 2 min before platinum (IV) oxide (1.89 g, 8.32 mmol) was added under a stream of argon. The reaction mixture was then stirred at RT under 45 psi of hydrogen gas for 2 days. Celite® brand filter aid (5 g) was then added to the reaction mixture. The mixture was stirred at RT for 10 min. The mixture was filtered, and the solution was concentrated in vacuo to give the initial product mixture as a light yellow oil, which was used in the next step without further purification. LCMS-ESI (pos.), m/z: 223.3 (M+H)$^+$.

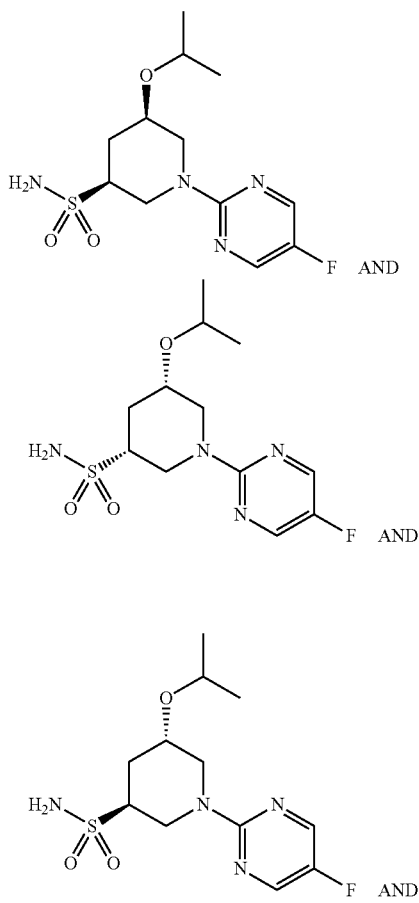

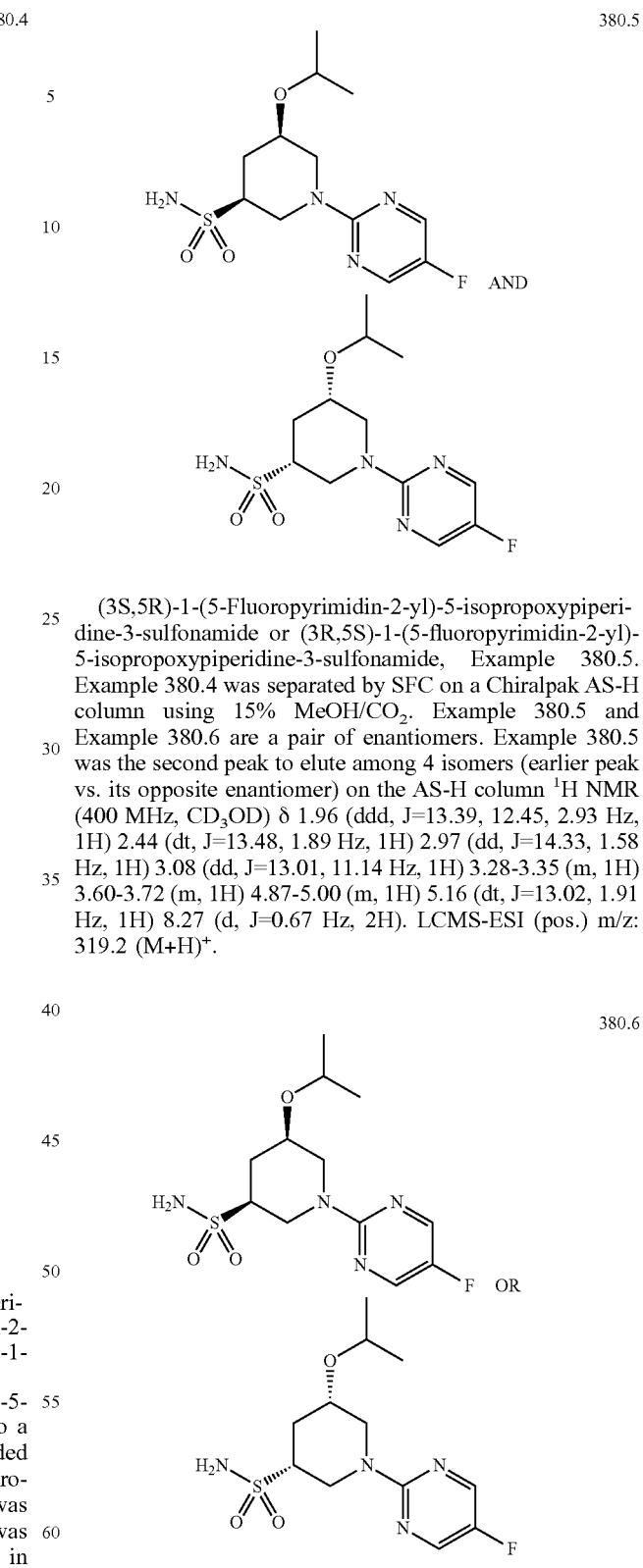

(3R,5R)-1-(5-Fluoropyrimidin-2-yl)-5-isopropoxypiperidine-3-sulfonamide and (3S,5R)-1-(5-fluoropyrimidin-2-yl)-5-isopropoxypiperidine-3-sulfonamide and (3S,5S)-1-(5-fluoropyrimidin-2-yl)-5-isopropoxypiperidine-3-sulfonamide and (3R,5S)-1-(5-fluoropyrimidin-2-yl)-5-isopropoxypiperidine-3-sulfonamide, Example 380.4. To a 40 mL vial with a pressure release septum was added Example 380.3 (2.0 g, 4.96 mmol) and 2-chloro-5-fluoropyrimidine (3.29 g, 24.79 mmol). The reaction mixture was stirred at 90° C. for 21 h. LCMS indicated the reaction was complete. The reaction mixture was then concentrated in vacuo. The initial material was absorbed onto a plug of silica gel and purified by chromatography through a RediSep pre-packed silica gel column (40 g) eluting with a gradient of 0% to 100% EtOAc in heptanes to provide Example 380.4 (0.5 g, 1.6 mmol, 32% yield) as an off-white solid. LCMS-ESI (pos.), m/z: 319.2 (M+H)$^+$.

(3S,5R)-1-(5-Fluoropyrimidin-2-yl)-5-isopropoxypiperidine-3-sulfonamide or (3R,5S)-1-(5-fluoropyrimidin-2-yl)-5-isopropoxypiperidine-3-sulfonamide, Example 380.5. Example 380.4 was separated by SFC on a Chiralpak AS-H column using 15% MeOH/CO$_2$. Example 380.5 and Example 380.6 are a pair of enantiomers. Example 380.5 was the second peak to elute among 4 isomers (earlier peak vs. its opposite enantiomer) on the AS-H column $^1$H NMR (400 MHz, CD$_3$OD) δ 1.96 (ddd, J=13.39, 12.45, 2.93 Hz, 1H) 2.44 (dt, J=13.48, 1.89 Hz, 1H) 2.97 (dd, J=14.33, 1.58 Hz, 1H) 3.08 (dd, J=13.01, 11.14 Hz, 1H) 3.28-3.35 (m, 1H) 3.60-3.72 (m, 1H) 4.87-5.00 (m, 1H) 5.16 (dt, J=13.02, 1.91 Hz, 1H) 8.27 (d, J=0.67 Hz, 2H). LCMS-ESI (pos.) m/z: 319.2 (M+H)$^+$.

(3S,5R)-1-(5-Fluoropyrimidin-2-yl)-5-isopropoxypiperidine-3-sulfonamide or (3R,5S)-1-(5-fluoropyrimidin-2-yl)-5-isopropoxypiperidine-3-sulfonamide, Example 380.6. Further elution under the conditions described in Example 380.5 gave Example 380.6 as the third peak. $^1$H NMR (400

MHz, CD₃OD) δ 1.96 (ddd, J=13.39, 12.45, 2.93 Hz, 1H) 2.44 (dt, J=13.48, 1.89 Hz, 1H) 2.97 (dd, J=14.33, 1.58 Hz, 1H) 3.08 (dd, J=13.01, 11.14 Hz, 1H) 3.28-3.35 (m, 1H) 3.60-3.72 (m, 1H) 4.87-5.00 (m, 1H) 5.16 (dt, J=13.02, 1.91 Hz, 1H) 8.27 (d, J=0.67 Hz, 2H). LCMS-ESI (pos.) m/z: 319.2 (M+H)⁺.

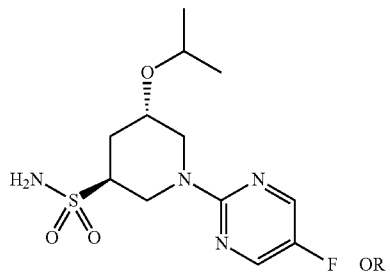

91.7

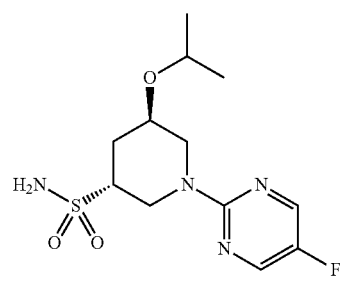

380.8

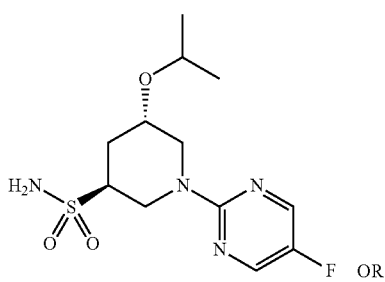

(3R,5R)-1-(5-Fluoropyrimidin-2-yl)-5-isopropoxypiperidine-3-sulfonamide or (3S,5S)-1-(5-fluoropyrimidin-2-yl)-5-isopropoxypiperidine-3-sulfonamide, Example 380.7. Examples 380.7 and 380.8 are a pair of enantiomers, Example 380.7 was the first peak to elute among 4 isomers (earlier peak vs. its opposite enantiomer) on the AS-H column under the conditions described in Example 380.5. ¹H NMR (400 MHz, CD₃OD) δ 0.92 (d, J=6.12 Hz, 3H) 1.08 (d, J=6.01 Hz, 3H) 1.98 (ddd, J=13.19, 12.15, 2.95 Hz, 1H) 2.33 (dtdd, J=13.26, 3.68, 3.68, 1.97, 1.87 Hz, 1H) 3.01 (dd, J=14.10, 1.66 Hz, 1H) 3.13 (dd, J=13.06, 10.99 Hz, 1H) 3.33-3.45 (m, 1H) 3.74 (dt, J=12.13, 6.06 Hz, 1H) 3.86-3.93 (m, 1H) 4.77-4.83 (m, 1H) 5.11 (ddt, J=13.05, 3.69, 1.79, 1.79 Hz, 1H) 8.27 (d, J=0.62 Hz, 2H). LCMS-ESI (pos.) m/z: 319.2 (M+H)⁺.

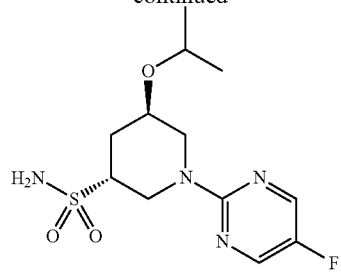

(3R,5R)-1-(5-Fluoropyrimidin-2-yl)-5-isopropoxypiperidine-3-sulfonamide or (3S,5S)-1-(5-fluoropyrimidin-2-yl)-5-isopropoxypiperidine-3-sulfonamide, Example 380.8. Further elution under the conditions described in Example 380.5 gave Example 380.8 as the fourth peak. ¹H NMR (400 MHz, CD₃OD) δ 0.92 (d, J=6.12 Hz, 3H) 1.08 (d, J=6.01 Hz, 3H) 1.98 (ddd, J=13.19, 12.15, 2.95 Hz, 1H) 2.33 (dtdd, J=13.26, 3.68, 3.68, 1.97, 1.87 Hz, 1H) 3.01 (dd, J=14.10, 1.66 Hz, 1H) 3.13 (dd, J=13.06, 10.99 Hz, 1H) 3.33-3.45 (m, 1H) 3.74 (dt, J=12.13, 6.06 Hz, 1H) 3.86-3.93 (m, 1H) 4.77-4.83 (m, 1H) 5.11 (ddt, J=13.05, 3.69, 1.79, 1.79 Hz, 1H) 8.27 (d, J=0.62 Hz, 2H). LCMS-ESI (pos.) m/z: 319.2 (M+H)⁺.

Example 381.3. Preparation of (3S,5R)-1-(5-fluoropyrimidin-2-yl)-5-methoxypiperidine-3-sulfonamide and (3R,5S)-1-(5-fluoropyrimidin-2-yl)-5-methoxypiperidine-3-sulfonamide

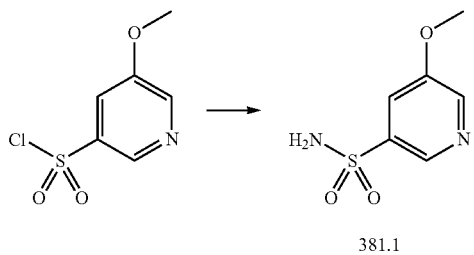

381.1

5-Methoxypyridine-3-sulfonamide, Example 381.1. A reaction mixture of 5-methoxypyridine-3-sulfonyl chloride (commercially available from Enamine, KIEV, Ukraine) (1.0 g, 4.82 mmol) and ammonia, (0.5 M solution in 1,4-dioxane, 96 mL, 48.2 mmol) was stirred at 0° C. to RT for 30 min. LCMS indicated the reaction was complete. The reaction was then filtered and the cake was rinsed with dioxane. The combined solution was concentrated in vacuo to give the title compound (0.91 g, 100% yield) as a light yellow foam which was used in the next step without further purification. LCMS-ESI (pos.) m/z: 189.2 (M+H)⁺.

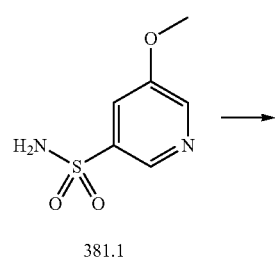

381.1

-continued

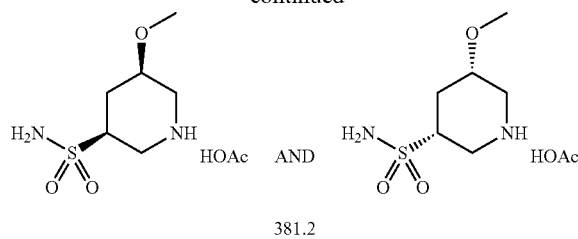

381.2

(3S,5R)-5-Methoxypiperidine-3-sulfonamide acetate and (3R,5S)-5-methoxypiperidine-3-sulfonamide acetate, Example 381.2. A solution of 5-methoxypyridine-3-sulfonamide (0.9 g, 4.78 mmol) in AcOH (31.9 mL) was bubbled with argon gas for 2 min before platinum (IV) oxide (1.09 g, 4.78 mmol) was added under an argon stream. The reaction mixture was then stirred at RT under 45 psi of hydrogen gas for 38 h. The mixture was filtered and the filtrate was concentrated in vacuo to give the title compound (1.22 g, 100% yield) as a light yellow foam, which was used as such in the next step. LCMS-ESI (pos.) m/z: 195.2 (M+H)$^+$.

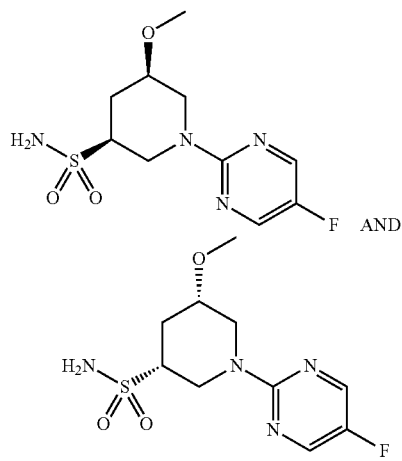

381.3

(3S,5R)-1-(5-Fluoropyrimidin-2-yl)-5-methoxypiperidine-3-sulfonamide and (3R,5S)-1-(5-fluoropyrimidin-2-yl)-5-methoxypiperidine-3-sulfonamide, Example 381.3. To a 40 mL vial with a pressure release septum was added 5-methoxypiperidine-3-sulfonamide acetate, (381.2, 2.45 g, 9.62 mmol), N-ethyl-N-isopropylpropan-2-amine (16.75 mL, 96 mmol), and 2-chloro-5-fluoropyrimidine (6.37 g, 48.1 mmol) in DMSO (48 mL). The reaction mixture was stirred at 100° C. for 23 h. LCMS indicated formation of the desired product. The reaction mixture was then diluted with water and extracted with DCM. The combined organic layers were washed with saturated aqueous NaCl, brine, and dried over Na$_2$SO$_4$. The solution was filtered and concentrated in vacuo to give the initial material as an orange oil. The initial material was absorbed onto a plug of silica gel and purified by chromatography through RediSeppre-packed silica gel column (40 g), eluting with a gradient of 0% to 100% 1/3 EtOH/EtOAc in heptanes to provide the title compound, 381.3 (0.51 g, 18% yield) as white solid. LCMS-ESI (pos.) m/z: 291.0 (M+H)$^+$.

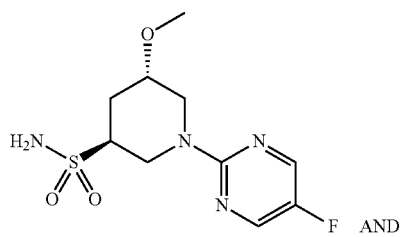

381.4

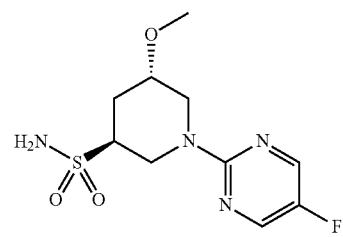

(3S,5S)-1-(5-Fluoropyrimidin-2-yl)-5-methoxypiperidine-3-sulfonamide and (3R,5R)-1-(5-fluoropyrimidin-2-yl)-5-methoxypiperidine-3-sulfonamide, Example 381.4. Further elution under the conditions described in Example 381.3 delivered 381.4 (0.24 g, 0.832 mmol, 8.65% yield) as a light yellow solid. LCMS-ESI (pos.) m/z: 291.0 (M+H)$^+$.

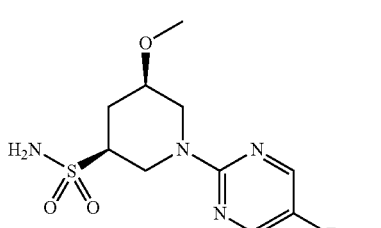

381.5

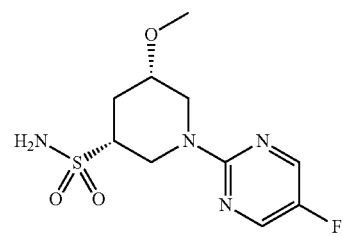

(3S,5R)-1-(5-Fluoropyrimidin-2-yl)-5-methoxypiperidine-3-sulfonamide or (3R,5S)-1-(5-fluoropyrimidin-2-yl)-5-methoxypiperidine-3-sulfonamide, Example 381.5. Example 381.5 was obtained by chiral separation of 381.3 using SFC: Chiralpak AD-H, 30% MeOH/CO$_2$, with 0.2% DEA. Example 381.5 was the earlier peak to elute on the Chiralpak AD-H column. $^1$H NMR (400 MHz, CD$_3$OD) δ 1.65 (td, J=12.28, 10.88 Hz, 1H) 2.57-2.72 (m, 2H) 2.98 (dd, J=13.06, 11.40 Hz, 1H) 3.14 (ddt, 1H) 3.27-3.36 (m, 1H) 3.45 (s, 3H) 4.97 (ddt, 1H) 5.17 (ddt, 1H) 8.32 (d, J=0.62 Hz, 2H). LCMS-ESI (pos.) m/z: 291.0 (M+H)$^+$.

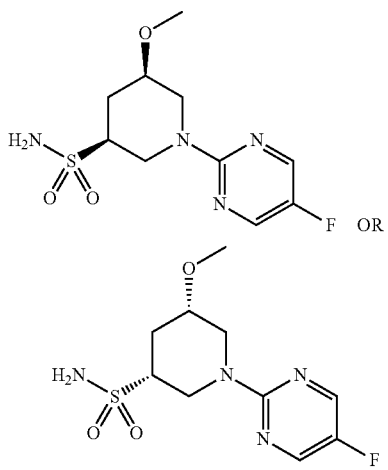

381.6

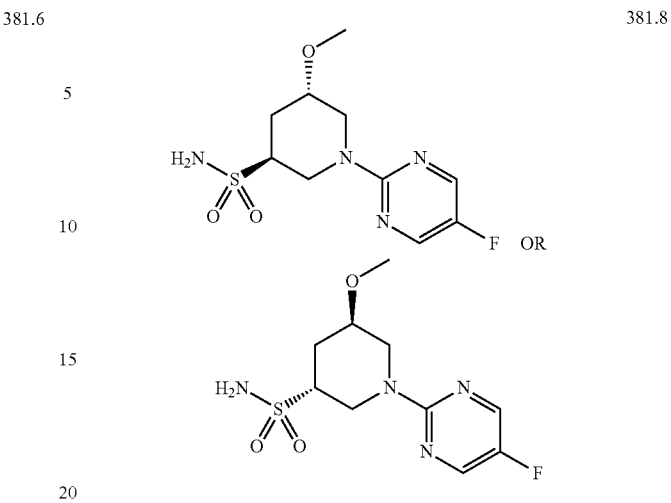

381.8

(3S,5R)-1-(5-Fluoropyrimidin-2-yl)-5-methoxypiperi-dine-3-sulfonamide or (3R,5S)-1-(5-fluoropyrimidin-2-yl)-5-methoxypiperidine-3-sulfonamide, Example 381.6. Further elution under the conditions described in Example 381.5 delivered Example 381.6. $^1$H NMR (400 MHz, CD$_3$OD) δ 1.65 (td, J=12.28, 10.88 Hz, 1H) 2.57-2.71 (m, 2H) 2.94-3.04 (m, 1H) 3.14 (ddt, 1H) 3.31-3.36 (m, 1H) 3.45 (s, 3H) 4.97 (ddt, 1H) 5.17 (ddt, 1H) 8.32 (s, 2H). LCMS-ESI (pos.) m/z: 291.0 (M+H)$^+$.

(3R,5R)-1-(5-Fluoropyrimidin-2-yl)-5-methoxypiperi-dine-3-sulfonamide or (3S,5S)-1-(5-fluoropyrimidin-2-yl)-5-methoxypiperidine-3-sulfonamide, Example 381.8. Further elution under the conditions described in Example 381.6 delivered Example 381.8. $^1$H NMR (400 MHz, CD$_3$OD) δ 1.96 (ddd, J=13.39, 12.45, 2.93 Hz, 1H) 2.44 (dt, J=13.48, 1.89 Hz, 1H) 2.97 (dd, J=14.33, 1.58 Hz, 1H) 3.08 (dd, J=13.01, 11.14 Hz, 1H) 3.28-3.35 (m, 1H) 3.32 (s, 3H) 3.60-3.72 (m, 1H) 4.87-5.00 (m, 1H) 5.16 (dt, J=13.02, 1.91 Hz, 1H) 8.27 (d, J=0.67 Hz, 2H). LCMS-ESI (pos.) m/z: 291.0 (M+H)$^+$.

Example 88.8. Preparation of (1R,2R)-1-hydroxy-N,N-bis(4-methoxybenzyl)-1-(5-methylpyrimidin-2-yl)propane-2-sulfonamide

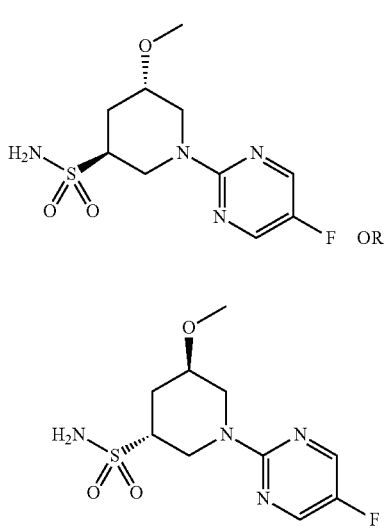

381.7

382.1

(3S,5S)-1-(5-Fluoropyrimidin-2-yl)-5-methoxypiperi-dine-3-sulfonamide or (3R,5R)-1-(5-fluoropyrimidin-2-yl)-5-methoxypiperidine-3-sulfonamide, Example 381.7. Example 381.7 was obtained by chiral separation of 381.3 using SFC: Chiralpak AD-H, 25% MeOH/CO$_2$, with 0.2% DEA. Example 381.7 was the earlier peak to elute on the Chiralpak AD-H column. $^1$H NMR (400 MHz, CD$_3$OD) δ 1.98 (ddd, J=13.42, 12.39, 3.01 Hz, 1H) 2.41-2.51 (m, 1H) 2.98 (dd, J=14.31, 1.66 Hz, 1H) 3.10 (dd, J=13.06, 11.20 Hz, 1H) 3.29-3.36 (m, 1H) 3.32 (s, 3H) 3.66-3.71 (m, 1H) 4.98 (dq, J=14.38, 2.19 Hz, 1H) 5.18 (ddt, 1H) 8.29 (d, J=0.83 Hz, 2H). LCMS-ESI (pos.) m/z: 291.0 (M+H)$^+$.

N-Methoxy-N,5-dimethylpyrimidine-2-carboxamide, Example 382.1. To a solution of 5-methylpyrimidine-2-carboxylic acid (1 g, 7.24 mmol) in DMF (72.4 mL) was added N,O-dimethylhydroxylamine hydrochloride (0.777 g, 7.96 mmol). The mixture was cooled to 0° C. and 1-propa-nephosphonic acid cyclic anhydride (50 wt. % solution in EtOAc, 9.21 mL, 14.48 mmol) was added dropwise. The mixture was then allowed to warm to RT overnight. LCMS indicated complete conversion to product. The mixture was then diluted with water, extracted with CHCl$_3$:IPA (3:1) and washed with brine, and a saturated aqueous NaHCO$_3$ solution. The mixture was then dried over Na$_2$SO$_4$, concentrated in vacuo, and purified by silica gelchromatograph (0-100% Heptanes:EtOAc) providing N-methoxy-N,5-dimethylpy-rimidine-2-carboxamide (0.7 g, 3.86 mmol, 53.4% yield). $^1$H NMR (500 MHz, CDCl$_3$) δ 8.61-8.69 (m, 2H) 3.61-3.79 (m, 3H) 3.27-3.47 (m, 3H) 2.34-2.45 (m, 3H). LCMS-ESI (pos.) m/z: 182.2 (M+H)$^+$.

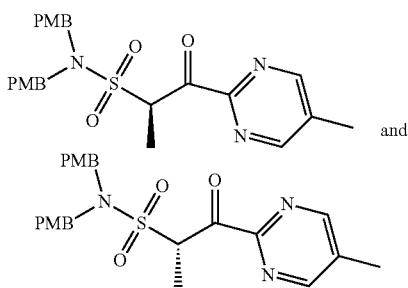

374.2

(R)—N,N-Bis(4-methoxybenzyl)-1-(5-methylpyrimidin-2-yl)-1-oxopropane-2-sulfonamide and (S)—N,N-bis(4-methoxybenzyl)-1-(5-methylpyrimidin-2-yl)-1-oxopropane-2-sulfonamide, Example 374.2. A solution of N,N-bis(4-methoxybenzyl)ethanesulfonamide (azeotroped three times with toluene before use) (Example 361.0, 0.771 g, 2.208 mmol) dissolved in THF (3.68 mL) was cooled to −78° C. using a dry ice acetone bath (internal reaction temperature/bath temperature not monitored). To this was added a solution of n-butyllithium (0.883 mL, 2.21 mmol, 2.5M in hexanes). The reaction turned pink immediately and then slowly faded to yellow upon stirring at −78° C. for 30 mins. This solution was then added quickly to a solution of N-methoxy-N,5-dimethylpyrimidine-2-carboxamide (Example 382.1, 0.2 g, 1.104 mmol) in THF (0.5 mL) at RT. The reaction was stirred at RT for 20 mins after which LCMS indicated complete consumption of Weinreb amide and conversion to product. The reaction was quenched by addition to a separatory funnel that contained 1.0 M HCl (~15 mL). The mixture was extracted with DCM, dried over $Na_2SO_4$ and concentrated in vacuo. The mixture was then purified by silica gel chromatography 0-100% EtOAc:heptanes to yield Example 374.2 (0.36 g, 0.767 mmol, 69.5% yield). $^1$H NMR (500 MHz, DMSO-$d_6$) δ 8.86-8.93 (m, 2H) 7.06-7.15 (m, 4H) 6.79-6.87 (m, 4H) 5.87-5.95 (m, 1H) 4.20-4.34 (m, 4H) 3.67-3.73 (m, 6H) 2.38-2.42 (m, 3H) 1.46-1.55 (m, 3H). LCMS-ESI (pos.) m/z: 470.0 (M+H)$^+$.

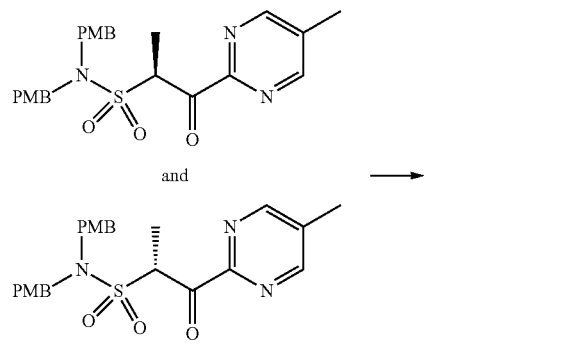

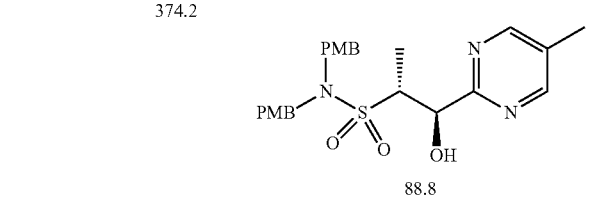

(1R,2R)-1-Hydroxy-N,N-bis(4-methoxybenzyl)-1-(5-methylpyrimidin-2-yl)propane-2-sulfonamide, Example 88.8. To a solution of Example 374.2 (1.0 g, 2.130 mmol) in DMF (22.18 mL) was added (N-((1S,2S)-1,2-diphenyl-2-((3-phenylpropyl)amino)ethyl)-4-methylphenylsulfonamido)ruthenium(II) chloride (9.91 mg, 0.016 mmol). The mixture was then degassed by placing under vacuum and backfilling with $N_2$ three times. To this was added a solution of HCOOH:Et$_3$N (5:2 v/v) (0.55 mL) and the reaction stirred at RT for 12 h after which LCMS indicated complete conversion to product and 7:1 d.r. (syn:anti). The mixture was then washed with 5% LiCl (aq), extracted with DCM then CHCl$_3$:IPA (3:1). The aqueous layer was checked for product by LCMS. The organic layers were combined, dried over $Na_2SO_4$ and concentrated in vacuo. The mixture was loaded directly onto a silica gel column and purified using a gradient of 0-100% heptanes:EtOAc. DMF caused both syn and anti to co-elute. The factions were combined and concentrated. The mixture was repurified using the same gradient to yield (1R,2R)-1-hydroxy-N,N-bis(4-methoxybenzyl)-1-(5-methylpyrimidin-2-yl)propane-2-sulfonamide (0.77 g, 1.63 mmol, 77% yield) as an off white solid. $^1$H NMR (500 MHz, DMSO-$d_6$) δ 8.85-8.93 (m, 2H) 7.08-7.15 (m, 4H) 6.78-6.86 (m, 4H) 5.86-5.96 (m, 1H) 4.20-4.35 (m, 4H) 3.68-3.75 (m, 6H) 3.28-3.34 (m, 2H) 2.37-2.42 (m, 3H) 1.47-1.54 (m, 3H). LCMS-ESI (pos.) m/z: 572.2 (M+H)$^+$.

Example 383.0. Preparation of (2S,3R)-3-(5-chloropyrimidin-2-yl)-N-(4-(4,6-dimethoxypyrimidin-5-yl)-5-(5-methylfuran-2-yl)-4H-1,2,4-triazol-3-yl)butane-2-sulfonamide

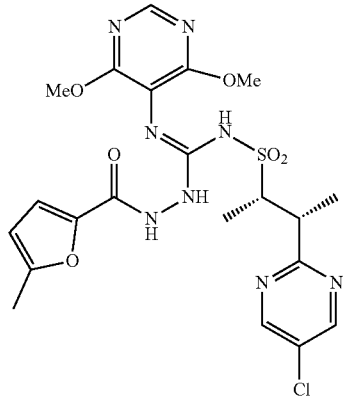

383.1

(Z)—N-(((2S,3R)-3-(5-Chloropyrimidin-2-yl)butan-2-yl)sulfonyl)-N'-(4,6-dimethoxypyrimidin-5-yl)-2-(5-methylfuran-2-carbonyphydrazinecarboximidamide, Example 383.1. To a solution of Example 371.4 (347 mg, 1.39 mmol) and 5-isothiocyanato-4,6-dimethoxypyrimidine (Example 372.1 (274 mg, 1.39 mmol) in ACN (6.9 mL) was added cesium carbonate (589 mg, 1.81 mmol). The reaction was stirred at RT for 64 h (over the weekend). The reaction mixture was then cooled to 0° C. To the stirred reaction mixture was added 5-methylfuran-2-carbohydrazide (195 mg, 1.39 mmol) followed by silver(I) nitrate (472 mg, 2.78 mmol). Stirring was continued for 30 mins at RT. The initial material was absorbed onto a plug of silica gel and purified by chromatography through a Redi-Sep pre-packed silica gel column (12 g), eluting with a gradient of 10% to 100% 1/3 EtOH/EtOAc in heptanes, to provide the title compound Example 383.1 (730 mg, 95% yield) as a white solid. LCMS ESI (pos.) m/z: 553.1 (M+H)+.

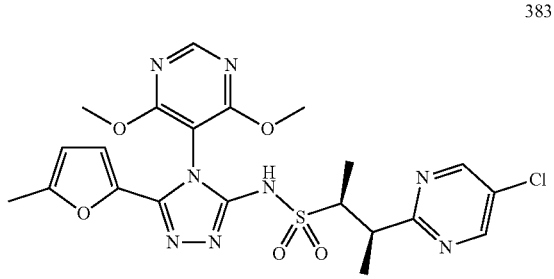

383.0

(2S,3R)-3-(5-Chloropyrimidin-2-yl)-N-(4-(4,6-dimethoxypyrimidin-5-yl)-5-(5-methylfuran-2-yl)-4H-1,2,4-triazol-3-yl)butane-2-sulfonamide, Example 383.0. To a solution of Example 383.1 (730 mg, 1.32 mmol) in water (2.2 mL) and IPA (4.4 mL) was added sodium hydroxide, 1.0 N (1.6 mL). The reaction was stirred at 80° C. for two days. The reaction mixture was cooled to RT and diluted with a saturated solution of $NH_4Cl$ and extracted with DCM. The combined organic layers were concentrated in vacuo to give the initial material which was absorbed onto a plug of silica gel and purified by chromatography through a Redi-Sep pre-packed silica gel column (12 g), eluting with a gradient of 10% to 100% EtOAc in heptane (33% EtOH in EtOAc), to provide pure title compound Example 383.0 (450 mg, 74% yield) as a white solid. $^1$H NMR (400 MHz, DMSO-$d_6$) δ 1.13 (d, J=6.89 Hz, 3H) 1.25 (d, J=7.00 Hz, 3H) 2.21 (s, 3H) 3.55-3.67 (m, 2H) 3.91 (s, 3H) 3.91 (s, 3H) 6.22 (dd, J=3.45, 0.96 Hz, 1H) 6.43 (d, J=3.42 Hz, 1H) 8.73 (s, 1H) 8.86 (s, 2H) 13.37 (s, 1H). LCMS ESI (pos.) m/z: 535.0 (M+H)+.

The compounds set forth in the following table were synthesized following the procedure in Example 383.0 using the starting material as described.

TABLE 20

| Example | Reagents | Structure, Name and Data |
|---|---|---|
| 384.0 | 2-5-isothiocyanato-4,6-dimethoxypyrimidine (Example 372.1), 5-methylfuran-2-carbohydrazide, and (1R,2S)-1-(5-chloropyrimidin-2-yl)-1-methoxypropane-2-sulfonamide Example 373.3. | (1R,2S)-1-(5-chloro-2-pyrimidinyl)-N-(4-(4,6-dimethoxy-5-pyrimidinyl)-5-(5-methyl-2-furanyl)-4H-1,2,4-triazol-3-yl)-1-methoxy-2-propanesulfonamide. $^1$H NMR (500 MHz, DMSO-$d_6$) δ 13.35 (br s, 1 H) 8.93 (s, 2 H) 8.73 (s, 1 H) 6.43 (br d, J = 3.37 Hz, 1 H) 6.22 (br d, J = 2.60 Hz, 1 H) 4.80 (br d, J = 3.89 Hz, 1 H) 3.94 (br s, 3 H) 3.92 (br s, 3 H) 3.43 (br dd, J = 6.75, 4.15 Hz, 1 H) 3.14 (s, 3 H) 2.21 (s, 3 H) 1.16 (br d, J = 7.01 Hz, 3 H). LCMS-ESI (pos.) m/z: 551.1 (M + H)+. |
| 385.0 | 2-isothiocyanato-1,3-dimethoxypropane, Example 385.1, 5-methylfuran-2-carbohydrazide, and (1R,2S)-1-(5-chloropyrimidin-2-yl)-1-methoxypropane-2-sulfonamide Example 373.3. | (1R,2S)-1-(5-chloro-2-pyrimidinyl)-1-methoxy-N-(4-(1-(methoxymethyl)cyclopropyl)-5-(5-methyl-2-furanyl)-4H-1,2,4-triazol-3-yl)-2-propanesulfonamide. $^1$H NMR (500 MHz, DMSO-$d_6$) δ 12.94 (br s, 1 H) 8.94 (s, 2 H) 6.34 (br d, J = 2.59 Hz, 1 H) 4.98 (br d, J = 3.63 Hz, 1 H) 4.07 (br d, J = 3.89 Hz, 1 H) 2.85-3.68 (m, 11 H) 2.35 (s, 3 H) 0.74-1.58 (m, 5 H). LCMS-ESI (pos.) m/z: 495.1 (M + H)+. |

TABLE 20-continued

| Example | Reagents | Structure, Name and Data |
|---|---|---|
| 386.0 | (1R,2S)-1-(5-chloropyrimidin-2-yl)-1-methoxypropane-2-sulfonamide, Example 373.3, 2-methoxyethyl isothiocyanate (commercially available from Sigma Aldrich), and 5-methylfuran-2-carbohydrazide (commercially available from Bellen). | 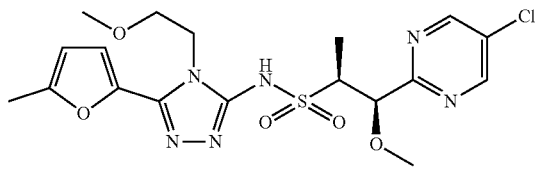 [SMILES: COCCn1c(NS(=O)(=O)[C@@H](C)[C@H](OC)c2ncc(Cl)cn2)nnc1-c1ccc(C)o1]<br>(1R,2S)-1-(5-chloropyrimidin-2-yl)-1-methoxy-N-(4-(2-methoxyethyl)-5-(5-methylfuran-2-yl)-4H-1,2,4-triazol-3-yl)propane-2-sulfonamide.<br>$^1$H NMR (400 MHz, DMSO-d$_6$) δ 13.10 (s, 1H), 8.91 (s, 2H), 7.06 (s, 1H), 6.35 (s, 1H), 4.87 (d, J = 3.5 Hz, 1H), 4.03 (s, 2H), 3.64-3.52 (m, 3H), 3.18 (s, 3H), 3.15-3.08 (m, 3H), 2.37 (s, 3H), 1.29 (d, J = 6.6 Hz, 3H). LCMS-ESI (pos.) m/z: 471.0 (M + H)$^+$. |
| 387.0 | 5-methylfuran-2-carbohydrazide (commercially available from Bellen), (1R,2S)-1-(5-chloropyrimidin-2-yl)-1-methoxypropane-2-sulfonamide, Example 373.3, and 2-isothiocyanato-1,3-dimethoxypropane, Example 385.1. | 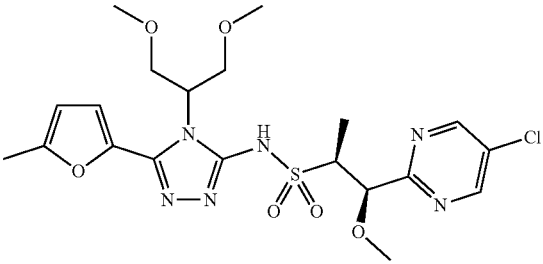 [SMILES: COCC(COC)n1c(NS(=O)(=O)[C@@H](C)[C@H](OC)c2ncc(Cl)cn2)nnc1-c1ccc(C)o1]<br>(1R,2S)-1-(5-chloro-2-pyrimidinyl)-N-(4-(1,3-dimethoxy-2-propanyl)-5-(5-methyl-2-furanyl)-4H-1,2,4-triazol-3-yl)-1-methoxy-2-propanesulfonamide.<br>$^1$H NMR (600 MHz, DMSO-d$_6$) δ 8.96 (s, 2 H) 6.90 (br d, J = 2.02 Hz, 1 H) 6.34 (d, J = 2.80 Hz, 1 H) 4.94 (d, J = 3.89 Hz, 1 H) 4.71-4.80 (m, 1 H) 3.95-4.10 (m, 2 H) 3.54-3.66 (m, 3 H) 3.22 (s, 3 H) 3.20 (s, 3 H) 3.18 (s, 3 H) 2.37 (s, 3 H) 1.26 (d, J = 7.01 Hz, 3 H). LCMS-ESI (pos.) m/z: 515.2 (M + H)$^+$. |
| 388.0 | 5-methylfuran-2-carbohydrazide (commericially available from Chembridge, CA, USA), 2-isothiocyanatopropane (comercially avilable from Sigma-Aldrich Inc.), and (1R,2S)-1-(5-chloropyrimidin-2-yl)-1-methoxypropane-2-sulfonamide (Example 373.3). | 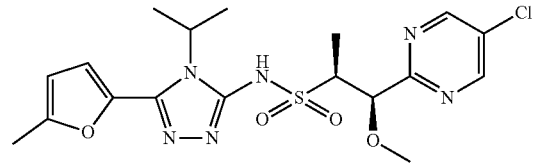 [SMILES: CO[C@H](c1ncc(Cl)cn1)[C@H](C)S(=O)(=O)Nc1nnc(-c2ccc(C)o2)n1C(C)C]<br>(1R,2S)-1-(5-chloropyrimidin-2-yl)-N-(4-isopropyl-5-(5-methylfuran-2-yl)-4H-1,2,4-triazol-3-yl)-1-methoxypropane-2-sulfonamide.<br>$^1$H NMR (600 MHz, DMSO-d6) δ 8.88-8.98 (m, 2 H) 6.86-6.94 (m, 1 H) 6.30-6.39 (m, 1 H) 4.88-4.94 (m, 1 H) 4.53-4.63 (m, 1 H) 3.56-3.62 (m, 1 H) 3.12-3.14 (m, 3 H) 2.36-2.40 (m, 3 H) 1.35-1.44 (m, 6 H) 1.24-1.31 (m, 3 H). LCMS-ESI (pos.) m/z: 455.2 (M + H)$^+$. |

Example 385.1. Preparation of 2-isothiocyanato-1,3-dimethoxypropane

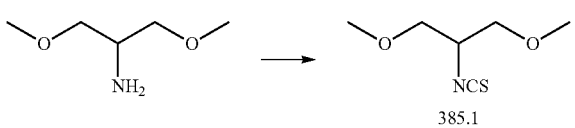

385.1

2-Isothiocyanato-1,3-dimethoxypropane, Example 385.1. To a dry 200 mL RBF was added di(2-pyridyl) thionocarbonate (5.34 g, 23.00 mmol) in DCM (73.0 mL). 2-Amino-1,3-dimethoxypropane in DCM (15 mL) was then added dropwise via an addition funnel over 5 min. The reaction mixture was stirred at RT for 3.5 h. The reaction mixture was concentrated in vacuo. The material was absorbed onto a plug of silica gel and purified by chromatography through a Redi-Sep pre-packed silica gel column (40 g), eluting with a gradient of 0% to 50% EtOAc in heptanes, to provide 2-isothiocyanato-1,3-dimethoxypropane (3.28 g, 20.34 mmol, 93% yield) as a colorless oil. LCMS-ESI (pos.) m/z: 162.2 (M+H)$^+$.

The compounds set forth in the following table were synthesized following the procedure in Example 385.1 using the known starting material as described.

TABLE 21

| Example | Reagents | Structure, Name and Data |
|---|---|---|
| 385.2 | 1-(methoxymethyl)cyclopropanamine hydrochloride (J&W Pharm Lab), DIEA (Sigma Aldrich). | 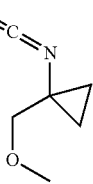<br>1-isothiocyanato-1-(methoxymethyl)cyclopropane.<br>$^1$H NMR (400 MHz, CDCl$_3$) δ 3.47 (s, 2H), 3.43 (s, 3H), 1.06-1.16 (m, 2H), 0.81-0.94 (m, 2H). |

Example 389.1. Preparation of (S)-3-isothiocyanatotetrahydro-2H-pyran

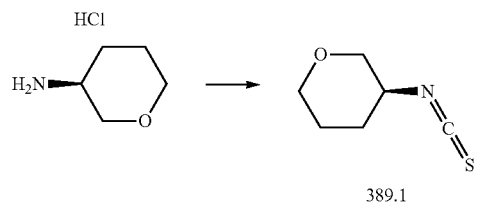 [SMILES: Cl ; N[C@H]1CCCOC1 ; S=C=N[C@H]1CCCOC1]

389.1

(S)-3-Isothiocyanatotetrahydro-2H-pyran, Example 389.1. To a dry 200 mL RBF was added di(2-pyridyl)thionocarbonate (1.69 g, 7.27 mmol, commerically available from Sigma Aldrich) and (3S)-oxan-3-amine hydrochloride (1.00 g, 7.27 mmol, commerically available from Accela ChemBio Inc) in DCM (24 mL). N-Ethyl-N-isopropylpropan-2-amine (1.33 mL, 7.63 mmol, commerically available from Sigma Aldrich) in DCM (20 mL) was then added dropwise via a addition funnel over 20 min at RT with stirring. The reaction mixture was stirred at RT for 15 h. The reaction mixture was concentrated in vacuo. The material thus obtained was absorbed onto a plug of silica gel and purified by chromatography through a Redi-Sep pre-packed silica gel column (24 g), eluting with a gradient of 0% to 50% EtOAc in heptane, to provide (S)-3-isothiocyanatotetrahydro-2H-pyran (0.99 g, 6.91 mmol, 95% yield) as a colorless oil. $^1$H NMR (400 MHz, CDCl$_3$) δ 3.81-3.85 (m, 1H), 3.55-3.72 (m, 4H), 2.04-2.11 (m, 1H), 1.81-1.89 (m, 2H), 1.56-1.64 (m, 1H).

The compound set forth in the following table was synthesized following the procedure in Example 389.1 using the known starting material as described.

TABLE 22

| Example | Reagents | Structure, Name and Data |
|---|---|---|
| 389.2 | (3R)-oxan-3-amine hydrochloride (commerically available from Accela ChemBio Inc). | 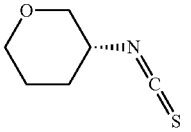<br>(R)-3-isothiocyanatotetrahydro-2H-pyran.<br>LCMS-ESI (pos.) m/z: 143.8 (M + H)$^+$. |

The compounds set forth in the following table were synthesized following the procedure in Example 383.0 using the known starting material as described.

TABLE 23

| Example | Reagents | Structure, Name and Data |
|---|---|---|
| 390.0 | 5-methylfuran-2-carbohydrazide (commericially available from Enamine), (S)-3-isothiocyanatotetrahydro-2H-pyran (Example 389.1), and (1R,2S)-1-(5-chloropyrimidin-2-yl)-1-methoxypropane-2-sulfonamide (Example 373.3). | 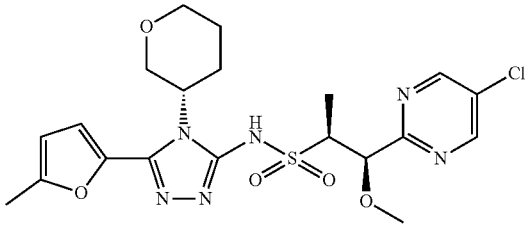 [SMILES: CO[C@H](c1ncc(Cl)cn1)[C@H](C)S(=O)(=O)Nc1nnc(-c2ccc(C)o2)n1[C@H]1CCCOC1]<br>(1R,2S)-1-(5-chloropyrimidin-2-yl)-1-methoxy-N-(5-(5-methylfuran-2-yl)-4-((S)-tetrahydro-2H-pyran-3-yl)-4H-1,2,4-triazol-3-yl)propane-2-sulfonamide.<br>$^1$H NMR (600 MHz, DMSO-d$_6$) δ 13.20 (s, 1H), 8.95 (s, 1H), 6.97 (d, J = 3.27 Hz, 1H), 6.38 (d, J = 2.80 Hz, 1H), 4.94 (d, J = 3.74 Hz, 1H), 4.28-4.35 (m, 1H), 3.98 (t, J = 10.67 Hz, 1H), 3.80-3.91 (m, 2H), 3.63 (s, 1H), 3.45-3.52 (m, 1H), 3.20-3.27 (m, 1H), 3.11 (s, 3H), 2.40 (s, 3H), 2.30 (br dd, J = 4.13, 12.53 Hz, 1H), 1.88 (br d, J = 11.37 Hz, 1H), 1.71-1.77 (m, 1H), 1.59-1.70 (m, 1H), 1.28 (d, J = 7.01 Hz, 3H). LCMS-ESI (pos.) m/z: 497.2 (M + H)$^+$ |

TABLE 23-continued

| Example | Reagents | Structure, Name and Data |
|---|---|---|
| 391.0 | 5-methylfuran-2-carbohydrazide (commericially available from Enamine), (R)-3-isothiocyanatotetrahydro-2H-pyran (Example 389.2), and (1R,2S)-1-(5-chloropyrimidin-2-yl)-1-methoxypropane-2-sulfonamide (Example 373.3). | 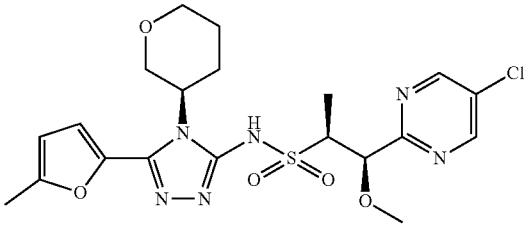 [SMILES: CO[C@H](c1ncc(Cl)cn1)[C@H](C)S(=O)(=O)Nc1nnc(-c2ccc(C)o2)n1[C@@H]1CCCOC1]<br>(1R,2S)-1-(5-chloropyrimidin-2-yl)-1-methoxy-N-(5-(5-methylfuran-2-yl)-4-((R)-tetrahydro-2H-pyran-3-yl)-4H-1,2,4-triazol-3-yl)propane-2-sulfonamide.<br>$^1$H NMR (600 MHz, DMSO-d6) δ 8.93 (s, 2H), 6.88 (br s, 1H), 6.35 (d, J = 2.65 Hz, 1H), 4.90 (d, J = 4.20 Hz, 1H), 4.22-4.29 (m, 1H), 3.93 (t, J = 10.59 Hz, 1H), 3.70-3.85 (m, 2H), 3.63 (s, 1H), 3.15-3.25 (m, 2H), 3.13 (s, 3H), 2.38 (s, 3H), 2.24-2.36 (m, 1H), 1.78-1.86 (m, 1H), 1.68-1.75 (m, 1H), 1.51-1.67 (m, 1H), 1.27 (d, J = 7.01 Hz, 3H). LCMS-ESI (pos.) m/z: 497.2 (M + H)$^+$ |

Example 395.0. Preparation of (2S,3R)—N-(4-(4,6-dimethoxy-5-pyrimidinyl)-5-(5-trideuteromethyl-2-furanyl)-4H-1,2,4-triazol-3-yl)-3-(5-fluoro-2-pyrimidinyl)-2-butanesulfonamide

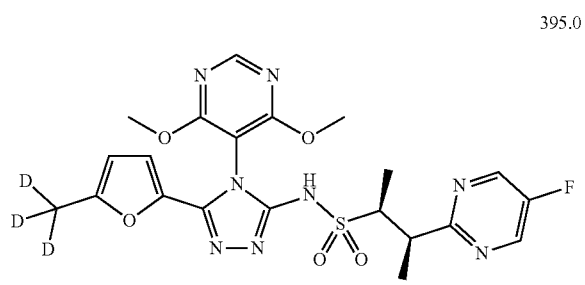 [SMILES: [2H]C([2H])([2H])c1ccc(-c2nnc(NS(=O)(=O)[C@@H](C)[C@H](C)c3ncc(F)cn3)n2-c2c(OC)ncnc2OC)o1]

395.0

(2S,3R)—N-(4-(4,6-Dimethoxy-5-pyrimidinyl)-5-(5-trideuteromethyl-2-furanyl)-4H-1,2,4-triazol-3-yl)-3-(5-fluoro-2-pyrimidinyl)-2-butanesulfonamide, Example 395.0. Example 394.0 (181 mg, 0.31 mmol), methyl-d3-boronic acid (51 mg, 0.81 mmol, commercially available from CombiPhos Catalysts, Inc.), tricyclohexylphosphine (27 mg, 0.1 mmol), tris (dibenzylideneacetone) dipalladium (0) (43 mg, 0.05 mmol) and potassium phosphate tribasic (232 mg, 1.1 mmol) were added to a vial. The vial was evacuated and then backfilled with nitrogen three times. After evacuation and backfilling, 1,4-dioxane (1.4 mL) and water (0.15 mL) were added separately by syringe and the reaction was heated to 90° C. and monitored with LCMS. After 19 h, the reaction was cooled to RT and then loaded onto a silica gel column (20-30% 3:1 EtOAc:EtOH in heptane). Fractions containing product were combined and then concentrated in vacuo to afford a yellow film that was diluted with DMSO and water and then filtered through a 0.45μ syringe tip filter. The homogeneous solution was purified by preparative HPLC: 50 u Silica Gel 19×100 mm+XSelect CSH Prep C18 10 μm ODB 19×100 mm, A: Water 0.1% formic acid B: ACN 0.1% formic acid, Gradient: 5% (2 min), 25-70% (12 min), Flow Rate: 40 mL/min, monitored @ 215 nm. Fractions containing product were collected and concentrated in vacuo to afford Example 395.0 as a white solid. $^1$H NMR (400 MHz, CD$_2$Cl$_2$) δ 8.56 (s, 1H), 8.54 (s, 2H), 6.33 (d, J=3.3 Hz, 1H), 6.04 (d, J=3.3 Hz, 1H), 3.96 (s, 3H), 3.95 (s, 3H), 3.78-3.69 (m, 2H), 1.34 (d, J=6.8 Hz, 3H), 1.30 (d, J=6.8 Hz, 3H). LCMS-ESI (pos.) m/z: 522.0 (M+H)$^+$.

The compounds set forth in the following Table were synthesized following the procedure in Example 383.0 using the starting material as described.

TABLE 24

| Example | Reagents | Structure, Name and Data |
|---|---|---|
| 392.0 | 5-methylfuran-2-carbohydrazide (commercially available from Bellen), (1S,2S)-1-(5-chloropyrimidin-2-yl)-1-isopropoxypropane-2-sulfonamide (Example 374.1) and 2-isothiocyanato-1,3-dimethoxypropane (Example 385.1). | 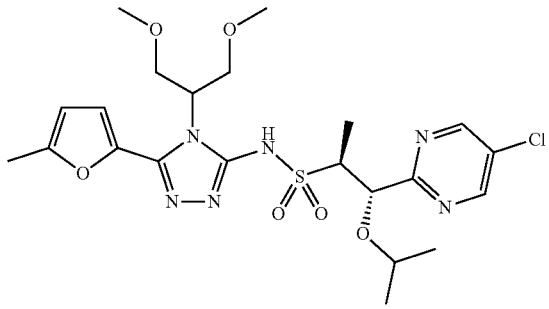 [SMILES: COCC(COC)n1c(NS(=O)(=O)[C@@H](C)[C@@H](OC(C)C)c2ncc(Cl)cn2)nnc1-c1ccc(C)o1] |

| Example | Reagents | Structure, Name and Data |
|---|---|---|
| | | (1S,2S)-1-(5-chloro-2-pyrimidinyl)-N-(4-(1,3-dimethoxy-2-propanyl)-5-(5-methyl-2-furanyl)-4H-1,2,4-triazol-3-yl)-1-(2-propanyloxy)-2-propanesulfonamide.<br>$^1$H NMR (400 MHz, CDCl$_3$) δ 12.02 (br s, 1 H) 8.74 (s, 2 H) 6.93 (d, J = 3.32 Hz, 1 H) 6.16 (dd, J = 3.32, 0.93 Hz, 1 H) 4.91 (d, J = 3.84 Hz, 1 H) 4.79 (tt, J = 8.40, 5.29 Hz, 1 H) 4.18 (t, J = 9.28 Hz, 1 H) 4.10 (dd, J = 9.90, 8.24 Hz, 1 H) 3.82 (qd, J = 7.03, 3.89 Hz, 1 H) 3.72 (ddd, J = 13.86, 9.98, 5.29 Hz, 2 H) 3.56 (m, 1 H) 3.35 (s, 3 H) 3.31 (s, 3 H) 2.41 (s, 3 H) 1.57 (d, J = 7.05 Hz, 3 H) 1.10 (d, J = 6.01 Hz, 3 H) 0.95 (d, J = 6.12 Hz, 3 H). LCMS-ESI (pos.) m/z: 543.0 (M + H)$^+$. |
| 393.0 | (2S,3R)-3-(5-fluoropyrimidin-2-yl)butane-2-sulfonamide (Example 371.1), 2-5-isothiocyanato-4,6-dimethoxypyrimidine (Example 372.1), and 5-methylfuran-2-carbohydrazide (commercially available from Bellen). | 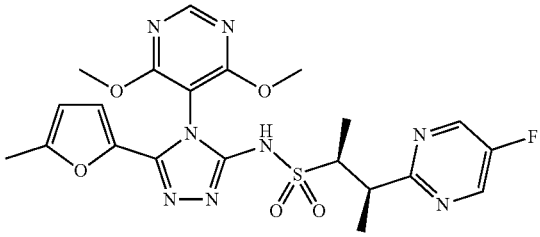 [SMILES: COc1ncnc(OC)c1-n1c(NS(=O)(=O)[C@@H](C)[C@H](C)c2ncc(F)cn2)nnc1-c1ccc(C)o1]<br>(2S,3R)-N-(4-(4,6-dimethoxy-5-pyrimidinyl)-5-(5-methyl-2-furanyl)-4H-1,2,4-triazol-3-yl)-3-(5-fluoro-2-pyrimidinyl)-2-butanesulfonamide.<br>$^1$H NMR (400 MHz, DMSO-d$_6$) δ 13.38 (br s, 1H), 8.82 (d, J = 0.8 Hz, 2H), 8.72 (s, 1H), 6.41 (d, J = 3.1 Hz, 1H), 6.21 (dd, J = 0.8, 3.3 Hz, 1H), 3.93-3.88 (m, 6H), 3.73-3.66 (m, 1H), 3.65-3.57 (m, 1H), 2.21 (s, 3H), 1.26 (d, J = 7.0 Hz, 3H), 1.12 (d, J = 7.0 Hz, 3H). LCMS-ESI (pos.) m/z: 519.0 (M + H)$^+$. |
| 394.0 | (2S,3R)-3-(5-fluoropyrimidin-2-yl)butane-2-sulfonamide (Example 371.1), 2-5-isothiocyanato-4,6-dimethoxypyrimidine (Example 372.1), and 5-bromofuran-2-carbohydrazide (commercially available from ChemBridge). | 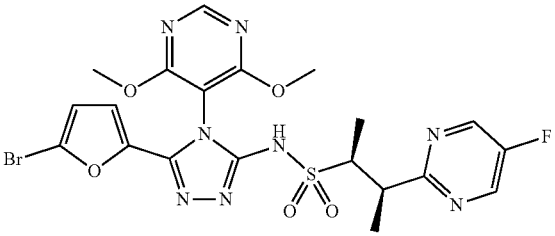 [SMILES: COc1ncnc(OC)c1-n1c(NS(=O)(=O)[C@@H](C)[C@H](C)c2ncc(F)cn2)nnc1-c1ccc(Br)o1]<br>(2S,3R)-N-(5-(5-bromo-2-furanyl)-4-(4,6-dimethoxy-5-pyrimidinyl)-4H-1,2,4-triazol-3-yl)-3-(5-fluoro-2-pyrimidinyl)-2-butanesulfonamide.<br>$^1$H NMR (400 MHz, DMSO-d$_6$) δ 13.55 (s, 1H), 8.82 (d, J = 0.6 Hz, 2H), 8.74 (s, 1H), 6.76-6.71 (m, 2H), 3.93-3.90 (m, 6H), 3.71-3.64 (m, 1H), 3.62-3.55 (m, 1H), 1.25 (d, J = 7.0 Hz, 3H), 1.13 (d, J = 6.8 Hz, 3H). LCMS-ESI (pos.) m/z: 582.8 (M + H)$^+$. |
| 396.0 | 5-methylfuran-2-carbohydrazide (commercially available from Bellen), (1S,2S)-1-(5-chloropyrimidin-2-yl)-1-isopropoxypropane-2-sulfonamide (Example 374.1), and isothiocyanatocyclopropane (commercially available from Sigma Aldrich). | 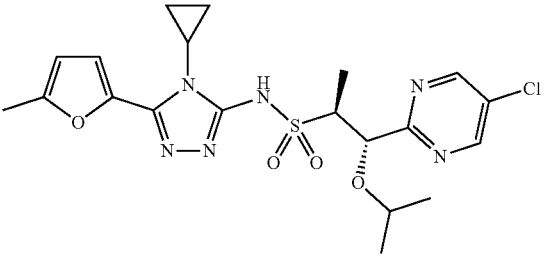 [SMILES: Cc1ccc(-c2nnc(NS(=O)(=O)[C@@H](C)[C@@H](OC(C)C)c3ncc(Cl)cn3)n2C2CC2)o1]<br>(1S,2S)-1-(5-chloro-2-pyrimidinyl)-N-(4-cyclopropyl-5-(5-methyl-2-furanyl)-4H-1,2,4-triazol-3-yl)-1-(2-propanyloxy)-2-propanesulfonamide.<br>$^1$H NMR (600 MHz, DMSO-d$_6$) δ 12.74 (s, 1 H) 8.96 (s, 2 H) 7.10 (d, J = 3.27 Hz, 1 H) 6.37 (dd, J = 3.35, 1.01 Hz, 1 H) 4.86 (d, J = 7.40 Hz, 1 H) 3.57 (quin, J = 7.18 Hz, 1 H) 3.30 (dt, J = 12.20, 6.08 Hz, 1 H) 3.01-3.11 (m, 1 H) 2.37 (s, 3 H) 1.02-1.15 (m, 6 H) 0.97 (d, J = 6.07 Hz, 3 H) 0.71-0.80 (m, 1 H) 0.66 (d, J = 6.15 Hz, 3 H). LCMS-ESI (pos.) m/z: 481.0 (M + H)$^+$. |

TABLE 24-continued

| Example | Reagents | Structure, Name and Data |
|---|---|---|
| 398.0 | (2S,3R)-3-(5-chloropyrimidin-2-yl)butane-2-sulfonamide (Example 371.4), (S)-2-isothiocyanato-1-methoxypropane (Example 398.1), and 5-methylfuran-2-carbohydrazide (commercially available from Bellen). | 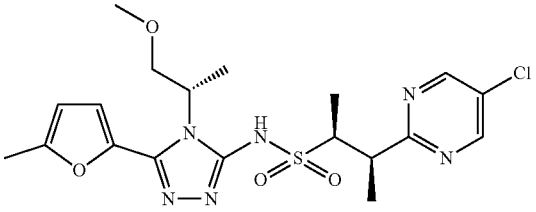 [SMILES: COC[C@H](C)n1c(NS(=O)(=O)[C@@H](C)[C@H](C)c2ncc(Cl)cn2)nnc1-c1ccc(C)o1]<br>(2S,3R)-3-(5-chloro-2-pyrimidinyl)-N-(4-((2S)-1-methoxy-2-propanyl)-5-(5-methyl-2-furanyl)-4H-1,2,4-triazol-3-yl)-2-butanesulfonamide.<br>$^1$H NMR (600 MHz, DMSO-d$_6$) δ 13.09 (br s, 1 H) 8.87 (s, 2 H) 6.94 (br s, 1 H) 6.35 (d, J = 2.41 Hz, 1 H) 4.58-4.69 (m, 1 H) 3.94 (br t, J = 9.54 Hz, 1 H) 3.67-3.78 (m, 2 H) 3.43 (dd, J = 10.08, 4.87 Hz, 1 H) 3.14 (s, 3 H) 2.37 (s, 3 H) 1.39 (d, J = 7.01 Hz, 3 H) 1.35 (d, J = 7.01 Hz, 3 H) 1.24 (d, J = 6.85 Hz, 3 H). LCMS-ESI (pos.) m/z: 469.0 (M + H)$^+$. |
| 400.0 | 2-5-isothiocyanato-4,6-dimethoxypyrimidine (Example 372.1), 5-methylfuran-2-carbohydrazide (commercially available from Bellen), and (2S,3R)-3-(5-chloropyridin-2-yl)butane-2-sulfonamide (Example 375.0). | 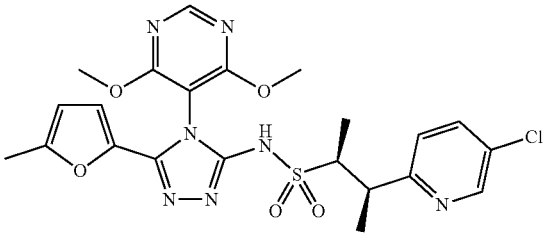 [SMILES: COc1ncnc(OC)c1-n1c(NS(=O)(=O)[C@@H](C)[C@H](C)c2ccc(Cl)cn2)nnc1-c1ccc(C)o1]<br>(2S,3R)-3-(5-chloro-2-pyridinyl)-N-(4-(4,6-dimethoxy-5-pyrimidinyl)-5-(5-methyl-2-furanyl)-4H-1,2,4-triazol-3-yl)-2-butanesulfonamide.<br>$^1$H NMR (600 MHz, DMSO-d$_6$) δ13.45 (s, 1 H) 8.74 (s, 1 H) 8.54 (d, J = 2.34 Hz, 1 H) 7.86 (dd, J = 8.41, 2.57 Hz, 1 H) 7.30 (d, J = 8.41 Hz, 1 H) 6.43 (d, J = 3.43 Hz, 1 H) 6.23 (dd, J = 3.43, 0.93 Hz, 1 H) 3.90 (s, 3 H) 3.90 (s, 3 H) 3.58 (qd, J = 7.03, 3.43 Hz, 1 H) 3.41 (qd, J = 6.92, 3.46 Hz, 1 H) 2.21 (s, 3 H) 1.22 (d, J = 7.08 Hz, 3 H) 1.08 (d, J = 7.01 Hz, 3 H). LCMS-ESI (pos.) m/z: 534.0 (M + H)$^+$. |
| 401.0 | 2-5-isothiocyanato-4,6-dimethoxypyrimidine (Example 372.1), 5-methylfuran-2-carbohydrazide (commercially available from Bellen), and (1S,2S)-1-(5-chloropyrimidin-2-yl)-1-isopropoxypropane-2-sulfonamide (Example 374.1) | 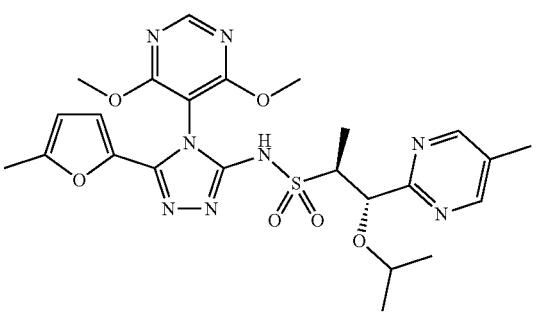<br>(1S,2S)-N-(4-(4,6-dimethoxypyrimidin-5-yl)-5-(5-methylfuran-2-yl)-4H-1,2,4-triazol-3-yl)-1-isopropoxy-1-(5-methylpyrimidin-2-yl)propane-2-sulfonamide.<br>$^1$H NMR (400 MHz, CDCl$_3$) δ 1.00 (d, J = 6.22 Hz, 3 H) 1.12 (d, J = 6.01 Hz, 3 H) 1.52 (d, J = 7.05 Hz, 3 H) 2.30 (s, 3 H) 2.36 (s, 3H) 3.59 (s, 1 H) 3.68-3.78 (m, 1 H) 3.93 (s, 3 H) 4.02 (s, 3 H) 4.88 (d, J = 3.52 Hz, 1 H) 5.97-6.04 (m, 1 H) 6.16 (s, 1 H) 8.54 (s, 1 H) 8.65 (s, 2 H), 13.10 (br. s., 1 H). LCMS-ESI (pos.) m/z: 559.2 (M + H)$^+$. |

Example 398.1. Preparation of (S)-2-isothiocyanato-1-methoxypropane

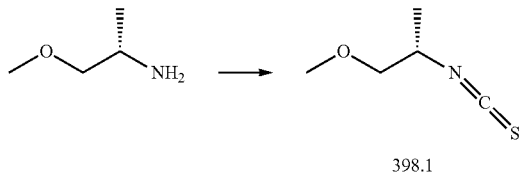

398.1

(S)-2-Isothiocyanato-1-methoxypropane, Example 398.1. Example 398.1 was prepared from (2S)-1-methoxy-2-propanamine (commercially available from Sigma Aldrich) using the procedure described in Example 385.1. $^1$H NMR (400 MHz, CDCl$_3$) δ 3.93 (m, 1H) 3.36-3.46 (m, 5H) 1.33 (d, J=6.74 Hz, 3H).

Example 397.0. Preparation of (2S,3R)-3-(5-cyano-2-pyrimidinyl)-N-(4-(4,6-dimethoxy-5-pyrimidinyl)-5-(5-methyl-2-furanyl)-4H-1,2,4-triazol-3-yl)-2-butanesulfonamide

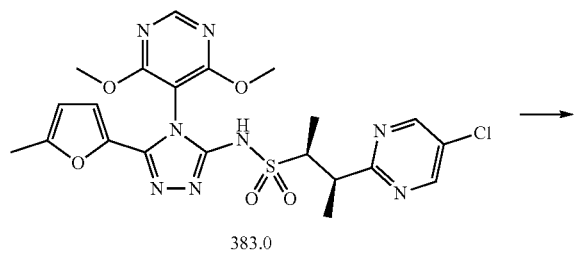

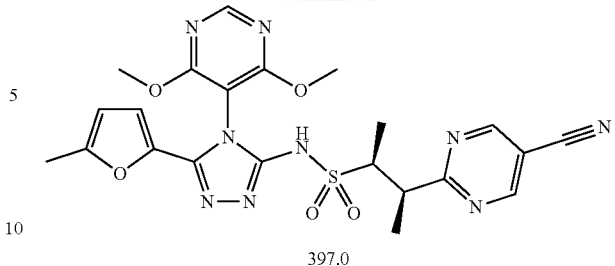

397.0

(2S,3R)-3-(5-Cyano-2-pyrimidinyl)-N-(4-(4,6-dimethoxy-5-pyrimidinyl)-5-(5-methyl-2-furanyl)-4H-1,2,4-triazol-3-yl)-2-butanesulfonamide, Example 397.0. To a 50-mL round-bottomed flask was added Example 383.0 (166 mg, 0.310 mmol), [(2-di-tert-butylphosphino-3,6-dimethoxy-2',4',6'-triisopropyl-1,1'-biphenyl)-2-(2'-amino-1,1'-biphenyl)]palladium(II) methanesulfonate (commercially available from Sigma Aldrich, 106 mg, 0.124 mmol) and zinc cyanide (72.9 mg, 0.621 mmol) in DMAc (3103 µl) under a stream of argon. The mixture was then bubbled with argon for 3 min. The reaction mixture was then stirred at 100° C. for 1.6 h. LCMS indicated formation of the desired product. The reaction mixture was next allowed to cool to room temperature. The material thus obtained was absorbed onto a plug of silica gel and purified by chromatography through a Redi-Sep pre-packed silica gel column (12 g), eluting with a gradient of 0% to 100% 1/3 EtOH/EtOAc in heptane, to provide the enriched material, which was further purified on reverse phase prep HPLC. Purification was performed with 0.1% formic acid in ACN and water as mobile phase to afford the title compound, Example 397.0, as a white solid. $^1$H NMR (600 MHz, DMSO-d$_6$) δ 13.39 (br s, 1H) 9.24 (s, 2H) 8.74 (s, 1H) 6.43 (br d, J=2.88 Hz, 1H) 6.23 (d, J=2.57 Hz, 1H) 3.91 (s, 3H) 3.91 (s, 3H) 3.58-3.67 (m, 2H) 2.21 (s, 3H) 1.26 (d, J=6.85 Hz, 3H) 1.15 (d, J=6.70 Hz, 3H). LCMS-ESI (pos.) m/z: 526.2 (M+H)$^+$.

The compounds set forth in the following Table were synthesized following the procedure in Example 94.0 using the known starting material as described.

TABLE 25

| | | |
|---|---|---|
| 402.0 | 3-bromo-4-(2,6-dimethoxyphenyl)-5-(5-methylfuran-2-yl)-4H-1,2,4-triazole (Example 364.1) and 4-hydroxytetrahydro-2H-pyran-3-sulfonamide (Example 402.1). The compound was purified by SFC chromatography: Chiralcel OZ-H, 2 × 25 cm, 40% MeOH Flow rate: 80 mL/min, UV Detector Wavelength: 277 nm. This was the first isomer to elute under these conditions. | 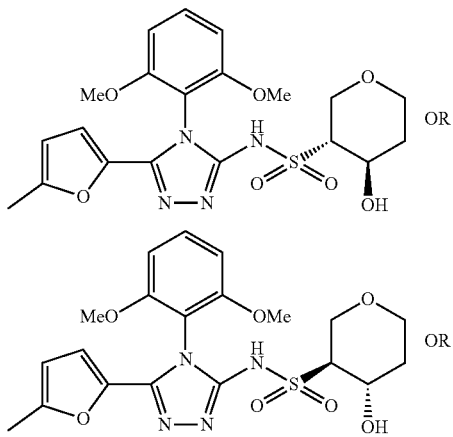 |

TABLE 25-continued

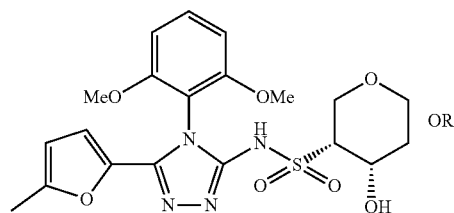 [SMILES: COc1cccc(OC)c1-n1c(NS(=O)(=O)[C@@H]2COCC[C@@H]2O)nnc1-c1ccc(C)o1]

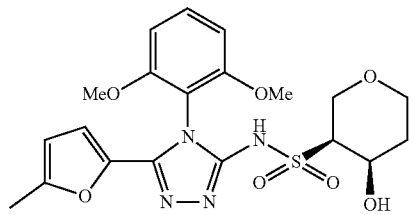 [SMILES: COc1cccc(OC)c1-n1c(NS(=O)(=O)[C@H]2COCC[C@H]2O)nnc1-c1ccc(C)o1]

(3R,4S)-N-(4-(2,6-dimethoxyphenyl)-5-(5-methyl-2-furanyl)-4H-1,2,4-triazol-3-yl)-4-hydroxytetrahydro-2H-pyran-3-sulfonamide or (3S,4R)-N-(4-(2,6-dimethoxyphenyl)-5-(5-methyl-2-furanyl)-4H-1,2,4-triazol-3-yl)-4-hydroxytetrahydro-2H-pyran-3-sulfonamide or (3R,4R)-N-(4-(2,6-dimethoxyphenyl)-5-(5-methyl-2-furanyl)-4H-1,2,4-triazol-3-yl)-4-hydroxytetrahydro-2H-pyran-3-sulfonamide or (3S,4S)-N-(4-(2,6-dimethoxyphenyl)-5-(5-methyl-2-furanyl)-4H-1,2,4-triazol-3-yl)-4-hydroxytetrahydro-2H-pyran-3-sulfonamide.

$^1$H NMR (500 MHz, CDCl$_3$) δ 10.59-10.98 (m, 1 H) 7.45-7.54 (m, 1 H) 6.65-6.75 (m, 2 H) 5.92-5.97 (m, 1 H) 5.86-5.92 (m, 1 H) 4.22-4.32 (m, 1 H) 4.06-4.16 (m, 1 H) 3.93-4.01 (m, 1 H) 3.78-3.82 (m, 6 H) 3.37-3.49 (m, 2 H) 3.07-3.15 (m, 1 H) 2.31-2.36 (m, 3 H) 1.98-2.04 (m, 1 H) 1.57-1.71 (m, 2 H) LCMS-ESI (pos.) m/z: 465.2 (M + H)$^+$.

403.0 3-bromo-4-(2,6-dimethoxyphenyl)-5-(5-methylfuran-2-yl)-4H-1,2,4-triazole (Example 364.1) and 4-hydroxytetrahydro-2H-pyran-3-sulfonamide (Example 402.1). The compound was purified by SFC chromatography: Chiralcel OZ-H, 2 × 25 cm, 40% MeOH, Flow rate: 80 mL/min, UV Detector Wavelength: 277 nm. This was the second isomer to elute under these conditions.

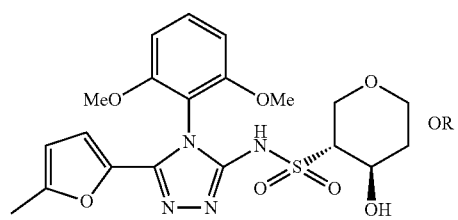 [SMILES: COc1cccc(OC)c1-n1c(NS(=O)(=O)[C@@H]2COCC[C@@H]2O)nnc1-c1ccc(C)o1]

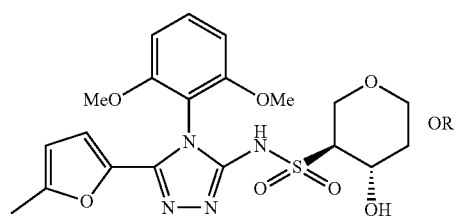

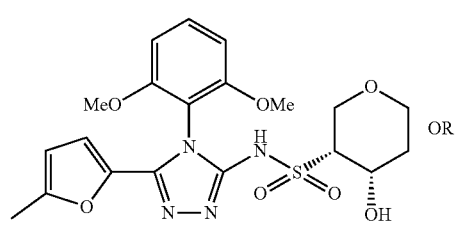 [SMILES: COc1cccc(OC)c1-n1c(NS(=O)(=O)[C@@H]2COCC[C@@H]2O)nnc1-c1ccc(C)o1]

TABLE 25-continued

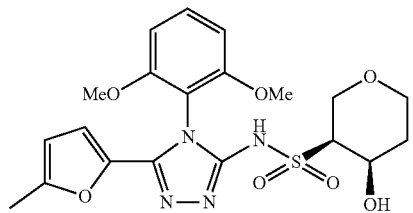 [SMILES: COc1cccc(OC)c1-n1c(NS(=O)(=O)[C@H]2COCC[C@H]2O)nnc1-c1ccc(C)o1]

(3R,4S)-N-(4-(2,6-dimethoxyphenyl)-5-(5-methyl-2-
furanyl)-4H-1,2,4-triazol-3-yl)-4-hydroxytetrahydro-
2H-pyran-3-sulfonamide or (3S,4R)-N-(4-(2,6-
dimethoxyphenyl)-5-(5-methyl-2-furanyl)-4H-1,2,4-
triazol-3-yl)-4-hydroxytetrahydro-2H-pyran-3-
sulfonamide or (3R,4R)-N-(4-(2,6-dimethoxyphenyl)-
5-(5-methyl-2-furanyl)-4H-1,2,4-triazol-3-yl)-4-
hydroxytetrahydro-2H-pyran-3-sulfonamide or
(3S,4S)-N-(4-(2,6-dimethoxyphenyl)-5-(5-methyl-2-
furanyl)-4H-1,2,4-triazol-3-yl)-4-hydroxytetrahydro-
2H-pyran-3-sulfonamide.
$^1$H NMR (500 MHz, CDCl$_3$) δ 10.57-10.96 (m, 1 H)
7.44-7.55 (m, 1 H) 6.65-6.76 (m, 2 H) 5.93-6.00
(m, 1 H) 5.86-5.91 (m, 1 H) 4.23-4.33 (m, 1 H) 4.06-
4.20 (m, 1 H) 3.97-4.04 (m, 1 H) 3.79-3.82 (m, 3
H) 3.77-3.79 (m, 3 H) 3.36-3.50 (m, 2 H) 3.06-3.14
(m, 1 H) 2.31-2.35 (m, 3 H) 1.98-2.05 (m, 1 H) 1.60-
1.70 (m, 1 H) 1.23-1.36 (m, 1 H). LCMS-ESI (pos.)
m/z: 465.2 (M + H)$^+$.

404.0 3-bromo-4-(2,6-dimethoxyphenyl)-
5-(5-methylfuran-2-yl)-4H-1,2,4-
triazole (Example 364.1) and 4-
hydroxytetrahydro-2H-pyran-3-
sulfonamide (Example 402.1).
The compound was purified by
SFC chromatography: Chiralcel
OZ-H, 2 × 25 cm, 40% MeOH,
Flow rate: 80 mL/min, UV Detector
Wavelength: 277 nm. This was the
third isomer to elute under these
conditions.

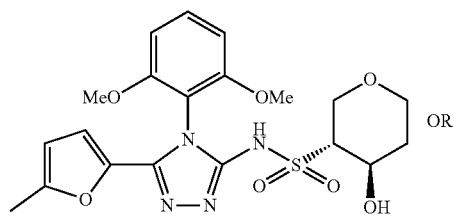

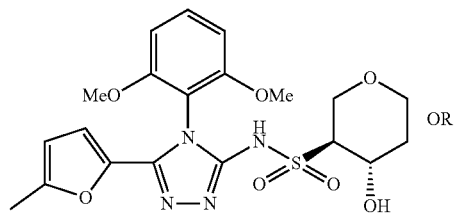

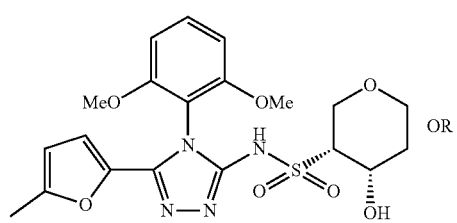 [SMILES: COc1cccc(OC)c1-n1c(NS(=O)(=O)[C@@H]2COCC[C@@H]2O)nnc1-c1ccc(C)o1]

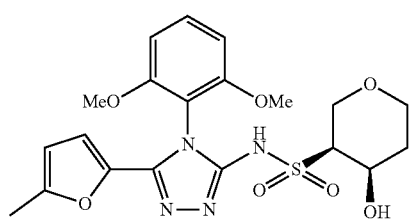 [SMILES: COc1cccc(OC)c1-n1c(NS(=O)(=O)[C@H]2COCC[C@H]2O)nnc1-c1ccc(C)o1]

(3R,4S)-N-(4-(2,6-dimethoxyphenyl)-5-(5-methyl-2-
furanyl)-4H-1,2,4-triazol-3-yl)-4-hydroxytetrahydro-
2H-pyran-3-sulfonamide or (3S,4R)-N-(4-(2,6-
dimethoxyphenyl)-5-(5-methyl-2-furanyl)-4H-1,2,4-
triazol-3-yl)-4-hydroxytetrahydro-2H-pyran-3-
sulfonamide or (3R,4R)-N-(4-(2,6-dimethoxyphenyl)-

| | | |
|---|---|---|
| | | 5-(5-methyl-2-furanyl)-4H-1,2,4-triazol-3-yl)-4-hydroxytetrahydro-2H-pyran-3-sulfonamide or (3S,4S)-N-(4-(2,6-dimethoxyphenyl)-5-(5-methyl-2-furanyl)-4H-1,2,4-triazol-3-yl)-4-hydroxytetrahydro-2H-pyran-3-sulfonamide.<br>¹H NMR (500 MHz, CDCl₃) δ 10.57-10.96 (m, 1 H) 7.44-7.55 (m, 1 H) 6.65-6.76 (m, 2 H) 5.93-6.00 (m, 1 H) 5.86-5.91 (m, 1 H) 4.23-4.33 (m, 1 H) 4.06-4.20 (m, 1 H) 3.97-4.04 (m, 1 H) 3.79-3.82 (m, 3 H) 3.77-3.79 (m, 3 H) 3.36-3.50 (m, 2 H) 3.06-3.14 (m, 1 H) 2.31-2.35 (m, 3 H) 1.98-2.05 (m, 1 H) 1.60-1.70 (m, 1 H) 1.23-1.36 (m, 1 H). LCMS-ESI (pos.) m/z: 465.2 (M + H)⁺. |
| 405.0 | 3-bromo-4-(2,6-dimethoxyphenyl)-5-(5-methylfuran-2-yl)-4H-1,2,4-triazole (Example 364.1) and 4-hydroxytetrahydro-2H-pyran-3-sulfonamide (Example 402.1). The compound was purified by SFC chromatography: Chiralcel OZ-H, 2 × 25 cm, 40% MeOH, Flow rate: 80 mL/min, UV Detector Wavelength: 277 nm. This was the fourth isomer to elute under these conditions. | 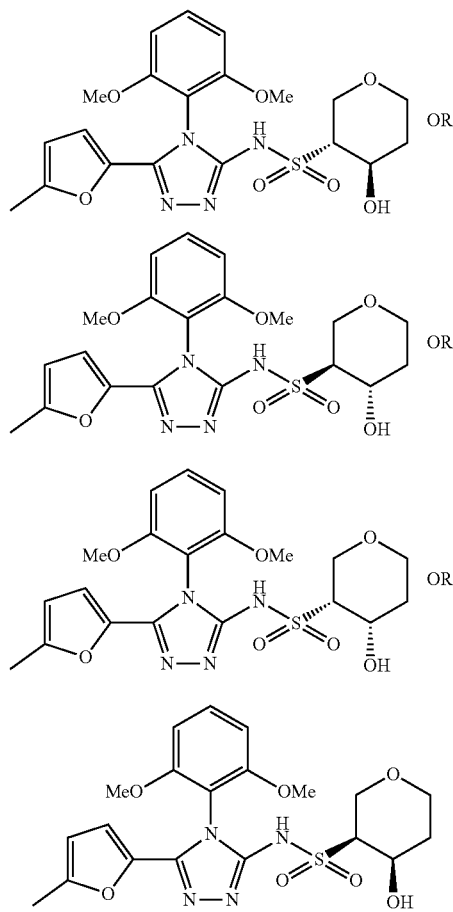<br>(3R,4S)-N-(4-(2,6-dimethoxyphenyl)-5-(5-methyl-2-furanyl)-4H-1,2,4-triazol-3-yl)-4-hydroxytetrahydro-2H-pyran-3-sulfonamide or (3S,4R)-N-(4-(2,6-dimethoxyphenyl)-5-(5-methyl-2-furanyl)-4H-1,2,4-triazol-3-yl)-4-hydroxytetrahydro-2H-pyran-3-sulfonamide or (3R,4R)-N-(4-(2,6-dimethoxyphenyl)-5-(5-methyl-2-furanyl)-4H-1,2,4-triazol-3-yl)-4-hydroxytetrahydro-2H-pyran-3-sulfonamide or (3S,4S)-N-(4-(2,6-dimethoxyphenyl)-5-(5-methyl-2-furanyl)-4H-1,2,4-triazol-3-yl)-4-hydroxytetrahydro-2H-pyran-3-sulfonamide.<br>¹H NMR (500 MHz, CDCl₃) δ 10.71-11.00 (m, 1 H) 7.43-7.57 (m, 1 H) 6.63-6.82 (m, 2 H) 5.85-6.00 (m, 2 H) 4.50-4.61 (m, 1 H) 4.09 (dd, J = 10.8, 4.1 Hz, 1 H) 3.66-3.93 (m, 8 H) 3.25 (dd, J = 11.2, 4.0 Hz, 1 H) 2.31-2.35 (m, 3 H) 1.71-1.85 (m, 2 H). LCMS-ESI (pos.) m/z: 465.2 (M + H)⁺. |

TABLE 25-continued

| | | |
|---|---|---|
| 406.0 | 3-bromo-4-(2,6-dimethoxyphenyl)-5-(5-methylfuran-2-yl)-4H-1,2,4-triazole (Example 364.1) and (1S,3R,4R)-3,4-dihydroxycyclohexane-1-sulfonamide and (1R,3R,4R)-3,4-dihydroxycyclohexane-1-sulfonamide (Example 406.1). The final material was purified by SFC. Column: Chiralpak AD-H, 2 × 25 cm. Mobile Phase: 40% IPA. Flow rate: 80 mL/min. UV Detector Wavelength: 277 nm This was the first isomer to elute under these conditions. | 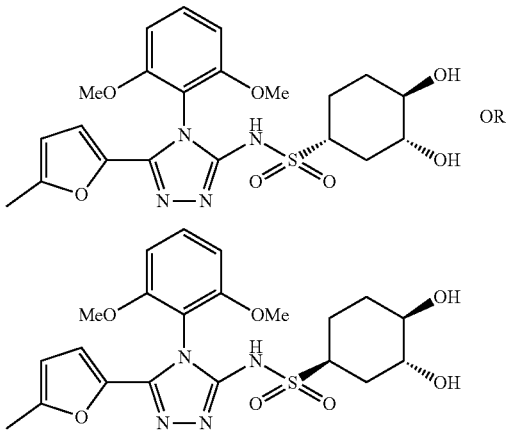<br><br>(1R,3R,4R)-N-(4-(2,6-dimethoxyphenyl)-5-(5-methylfuran-2-yl)-4H-1,2,4-triazol-3-yl)-3,4-dihydroxycyclohexane-1-sulfonamide OR (1S,3R,4R)-N-(4-(2,6-dimethoxyphenyl)-5-(5-methylfuran-2-yl)-4H-1,2,4-triazol-3-yl)-3,4-dihydroxycyclohexane-1-sulfonamide.<br>$^1$H NMR (500 MHz, DMSO-$d_6$) δ 12.92-13.07 (m, 1 H) 7.47-7.65 (m, 1 H) 6.84-6.99 (m, 2 H) 6.06-6.18 (m, 1 H) 5.71-5.94 (m, 1 H) 4.69-4.81 (m, 1 H) 4.52-4.63 (m, 1 H) 3.71-3.77 (m, 6 H) 3.64-3.70 (m, 1 H) 3.46-3.53 (m, 1 H) 2.91-3.02 (m, 1 H) 2.23-2.27 (m, 3 H) 1.73-1.80 (m, 2 H) 1.59-1.70 (m, 3 H) 1.48-1.57 (m, 1 H). LCMS-ESI (pos.) m/z: 479.2 (M + H)$^+$. |
| 407.0 | 3-bromo-4-(2,6-dimethoxyphenyl)-5-(5-methylfuran-2-yl)-4H-1,2,4-triazole (Example 364.1) and (1S,3R,4R)-3,4-dihydroxycyclohexane-1-sulfonamide and (1R,3R,4R)-3,4-dihydroxycyclohexane-1-sulfonamide (Example 406.1). The final material was purified by SFC. Column: Chiralpak AD-H, 2 × 25 cm. Mobile Phase: 40% IPA Flow rate: 80 mL/min. UV Detector Wavelength: 277 nm. This was the second isomer to elute under these conditions. | 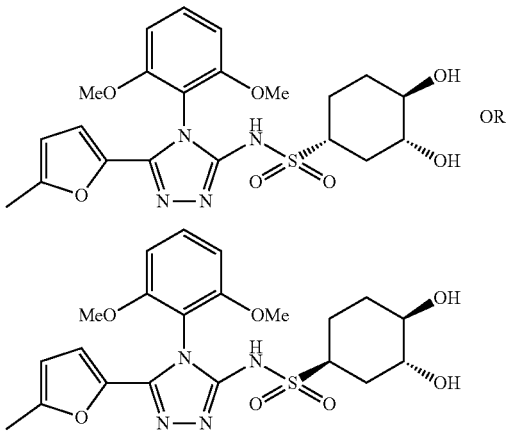<br><br>(1R,3R,4R)-N-(4-(2,6-dimethoxyphenyl)-5-(5-methylfuran-2-yl)-4H-1,2,4-triazol-3-yl)-3,4-dihydroxycyclohexane-1-sulfonamide OR (1S,3R,4R)-N-(4-(2,6-dimethoxyphenyl)-5-(5-methylfuran-2-yl)-4H-1,2,4-triazol-3-yl)-3,4-dihydroxycyclohexane-1-sulfonamide.<br>$^1$H NMR (500 MHz, DMSO-$d_6$) δ 12.99 (s, 1 H) 9.72-9.75 (m, 1 H) 7.50-7.63 (m, 1 H) 6.78-6.97 (m, 2 H) 6.07-6.18 (m, 1 H) 5.79 (d, J = 3.4 Hz, 1 H) 4.74 (d, J = 3.9 Hz, 1 H) 4.58 (d, J = 3.0 Hz, 1 H) 3.73 (m, 6 H) 3.63-3.69 (m, 1 H) 3.44-3.51 (m, 1 H) 2.91-3.01 (m, 1 H) 2.24 (s, 3 H) 1.73-1.81 (m, 2 H) 1.60-1.69 (m, 3 H) 1.48-1.56 (m, 1 H). LCMS-ESI (pos.) m/z: 479.2 (M + H)$^+$. |

TABLE 25-continued

| 409.0 | 3-bromo-4-(2,6-dimethoxyphenyl)-5-(5-methylfuran-2-yl)-4H-1,2,4-triazole (Example 364.1) and 3-(hydroxymethyl)benzenesulfonamide (commercially available from Enamine). | 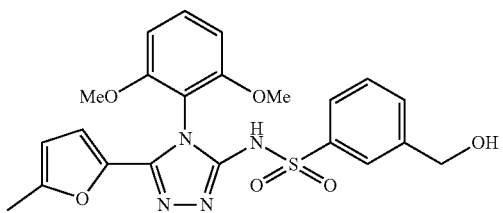 [SMILES: COc1cccc(OC)c1-n1c(NS(=O)(=O)c2cccc(CO)c2)nnc1-c1ccc(C)o1]<br>N-(4-(2,6-dimethoxyphenyl)-5-(5-methyl-2-furanyl)-4H-1,2,4-triazol-3-yl)-3-(hydroxymethyl)benzenesulfonamide<br>$^1$H NMR (600 MHz, DMSO-$d_6$) δ 13.17-13.41 (m, 1 H) 7.74 (s, 1 H) 7.58-7.67 (m, 1 H) 7.52-7.58 (m, 1 H) 7.41-7.49 (m, 2 H) 6.83-6.89 (m, 2 H) 6.07-6.17 (m, 1 H) 5.76-5.85 (m, 1 H) 5.29-5.40 (m, 1 H) 4.49-4.56 (m, 2 H) 3.59-3.66 (m, 6 H) 2.18-2.25 (m, 3 H). LCMS-ESI (pos.) m/z: 471.2 (M + H)$^+$. |
|---|---|---|
| 410.0 | 3-bromo-4-(2,6-dimethoxyphenyl)-5-(5-methylfuran-2-yl)-4H-1,2,4-triazole (Example 364.1) and 3-(1-hydroxyethyl)benzenesulfonamide (commercially available from Enamine). The final material was was separated by SFC: Column: Chiralpak AD-H, 2 × 25 cm Mobile Phase: 25% MeOH Flow rate: 80 mL/min UV Detector Wavelength: 215 nm. This was the first isomer to elute under these conditions. | 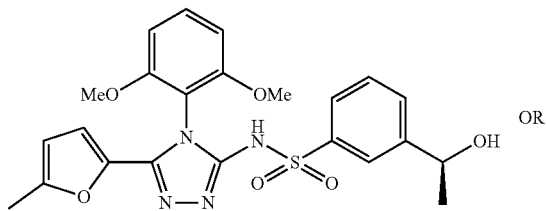 OR<br>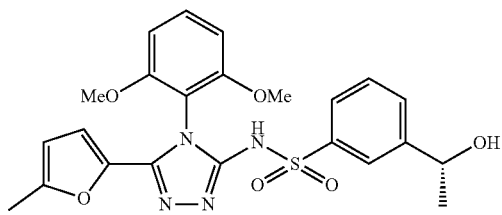<br>(R)-N-(4-(2,6-dimethoxyphenyl)-5-(5-methylfuran-2-yl)-4H-1,2,4-triazol-3-yl)-3-(1-hydroxyethyl)benzenesulfonamide or (S)-N-(4-(2,6-dimethoxyphenyl)-5-(5-methylfuran-2-yl)-4H-1,2,4-triazol-3-yl)-3-(1-hydroxyethyl)benzenesulfonamide.<br>$^1$H NMR (500 MHz, CDCl$_3$) δ 10.52-11.29 (m, 1 H) 7.83-7.99 (m, 1 H) 7.75-7.81 (m, 1 H) 7.50-7.55 (m, 1 H) 7.36-7.47 (m, 2 H) 6.60-6.67 (m, 2 H) 5.89-5.92 (m, 1 H) 5.79-5.83 (m, 1 H) 4.94 (q, J = 6.5 Hz, 1 H) 3.58-3.65 (m, 6 H) 2.27-2.36 (m, 3 H) 1.72-1.83 (m, 1 H) 1.48-1.52 (m, 3 H). LCMS-ESI (pos.) m/z: 485.0 (M + H)$^+$. |
| 411.0 | 3-bromo-4-(2,6-dimethoxyphenyl)-5-(5-methylfuran-2-yl)-4H-1,2,4-triazole (Example 364.1) and 3-(1-hydroxyethyl)benzenesulfonamide (commercially available from Enamine). The final material was was separated by SFC: Column: Chiralpak AD-H, 2 × 25 cm Mobile Phase: 25% MeOH. Flow rate: 80 mL/min UV Detector Wavelength: 215 nm. This was the second isomer to elute under these conditions. | 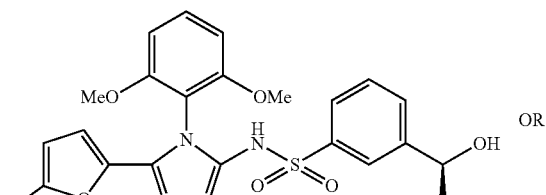 OR<br>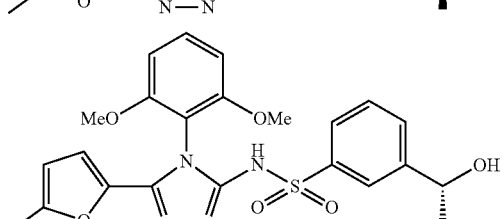<br>(R)-N-(4-(2,6-dimethoxyphenyl)-5-(5-methylfuran-2-yl)-4H-1,2,4-triazol-3-yl)-3-(1-hydroxyethyl)benzenesulfonamide or (S)-N-(4-(2,6-dimethoxyphenyl)-5-(5-methylfuran-2-yl)-4H-1,2,4- | triazol-3-yl)-3-(1-hydroxyethyl)benzenesulfonamide. $^1$H NMR (500 MHz, CDCl$_3$) δ 10.52-11.29 (m, 1 H) 7.83-7.99 (m, 1 H) 7.75-7.81 (m, 1 H) 7.50-7.55 (m, 1 H) 7.36-7.47 (m, 2 H) 6.60-6.67 (m, 2 H) 5.89-5.92 (m, 1 H) 5.79-5.83 (m, 1 H) 4.94 (q, J = 6.5 Hz, 1 H) 3.58-3.65 (m, 6 H) 2.27-2.36 (m, 3 H) 1.72-1.83 (m, 1 H) 1.48-1.52 (m, 3 H). LCMS-ESI (pos.) m/z: 485.0 (M + H)$^+$.

Example 406.1. Preparation of (1R,3R,4R)-3,4-dihydroxycyclohexane-1-sulfonamide and (1S,3R,4R)-3,4-dihydroxycyclohexane-1-sulfonamide

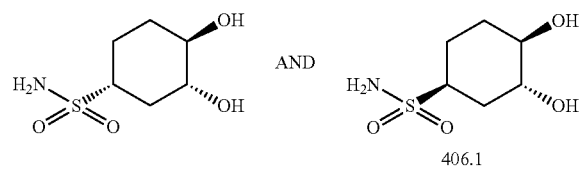 [SMILES: NS(=O)(=O)[C@@H]1CC[C@@H](O)[C@H](O)C1 ; NS(=O)(=O)[C@H]1CC[C@@H](O)[C@H](O)C1]

406.1

(1R,3R,4R)-3,4-Dihydroxycyclohexane-1-sulfonamide and (1S,3R,4R)-3,4-dihydroxycyclohexane-1-sulfonamide, Example 406.1. To a solution of cyclohex-3-ene-1-sulfonamide (1.00 ml, 6.20 mmol) in anhydrous chloroform (24 mL) was added 3-chloroperoxybenzoic acid (2.68 g, 9.30 mmol) in portions. The mixture was then stirred at RT for 12 h after which a white solid precipitated. The mixture was concentrated in vacuo and loaded directly onto silica gel and and purified with column chromatography with a gradient of 0-100 EtOAc:EtOH (3:1) in heptanes. The title product was isolated (1.0 g, 5.12 mmol, 83% yield). $^1$H NMR (500 MHz, DMSO-d$_6$) δ 1.22-1.33 (m, 2H) 1.51-1.58 (m, 1H) 1.65-1.74 (m, 3H) 1.80-1.88 (m, 2H) 1.97-2.01 (m, 1H) 2.94-3.05 (m, 1H) 3.48-3.56 (m, 1H) 3.66-3.74 (m, 1H) 4.65 (br s, 1H) 4.81 (br s, 1H) 6.50-6.66 (m, 2H).

Example 402.1. Preparation of 4-hydroxytetrahydro-2H-pyran-3-sulfonamide

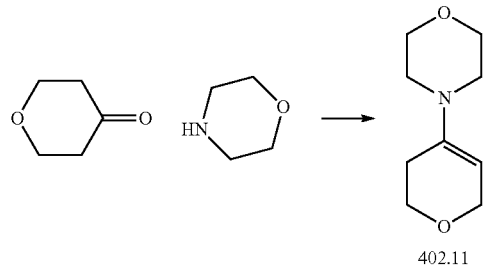

402.11

4-(3,6-dihydro-2H-pyran-4-yl)morpholine, Example 402.11. A solution of 4-tetrahydropyranone (10.19 mL, 110 mmol), morpholine (16.34 mL, 187 mmol) in toluene (110 mL) was heated to 115° C. under Dean Stark conditions for 5 hrs after which full conversion to the product was obtained. The mixture was cooled to RT and concentrated under vacuum to yield the desired product. The material thus obtained was carried forward without further purification.

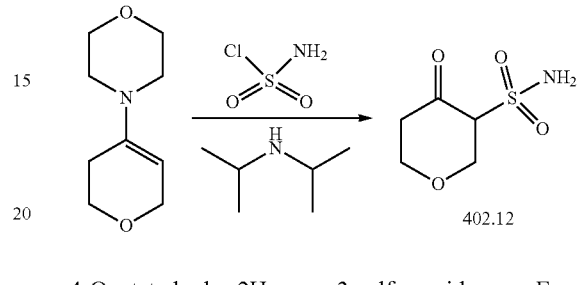

402.12

4-Oxotetrahydro-2H-pyran-3-sulfonamide, Example 402.12. A solution of 4-(3,6-dihydro-2H-pyran-4-yl)morpholine (10 g, 59.1 mmol) in THF (100 mL) was cooled to −40° C. and sulfamoyl chloride (10.24 g, 89 mmol) followed by DIPA (41.4 mL, 295 mmol) were added. The mixture was then warmed to RT and stirred at RT for 20 h after which a precipitate was observed. The mixture was filtered and washed with MeOH. The material thus obtained was used directly in the next step.

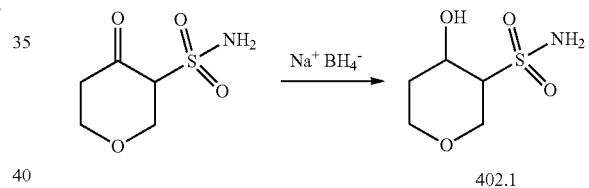

402.1

4-Hydroxytetrahydro-2H-pyran-3-sulfonamide, Example 402.1. A solution of 4-oxotetrahydro-2H-pyran-3-sulfonamide (10 g, 55.8 mmol) in THF (100 mL) was cooled to 0° C. To this was added sodium borohydride (2.170 mL, 61.4 mmol) and the reaction was then allowed to warm to RT. The mixture was stirred at RT for 20 h after which it was quenched with water and the pH adjusted to pH=2 with 6N HCl. The mixture was then concentrated to dryness and purified by column chromatography (DCM/MeOH=10:0 to 9:1) to afford Example 402.1 as a solid (10.8 g, 41 wt %, with 2.2 equiv DIPA). $^1$H NMR (500 MHz, DMSO-d$_6$) δ 1.55-1.84 (m, 2H) 3.51-3.77 (m, 2H) 3.77-3.94 (m, 2H) 4.30-4.52 (m, 1H) 5.04-5.27 (m, 1H) 6.40-6.87 (m, 2H).

Biological Activity

[$^{35}$S]GTPγS Binding

The human APJ receptor was cloned by polymerase chain reaction and the gene encoding the receptor was subcloned in pFLAG-CMV™-3 expression vector (Sigma, Saint Louis, Mo. USA) in-house at Amgen. A GTPγS binding assay was performed on membranes prepared from CHO cells stably expressing human APJ receptor. The optimum experimental conditions for the concentrations of GDP, MgCl$_2$, and NaCl in the assay buffer were initially determined. The assay was performed in assay buffer [20 mM HEPES, pH 7.5, 5 mM MgCl$_2$, and 0.1% (w/v) BSA with 200 mM NaCl, 3 µM GDP] and membranes expressing human APJ receptor/well along with WGA PS beads. The reaction was initiated by addition of 0.2 nM [$^{35}$S]GTPγS (Perkin Elmer Life and Analytical Sciences, Waltham USA) in the absence or presence of various ligands and incubated at RT for 90 min. Nonspecific binding was determined in the presence of 100 µM GTPγS and was always less than 0.2% of total binding. All the results presented are means of several independent experiments and analyzed by non-linear regression methods using commercially available program Prism (GraphPad, San Diego, Calif.) to obtain EC$_{50}$ detailed in Table 26.

Evidence for Load Independent Inotropic Effects with APJ Agonists Using Ex Vivo Assay (Isolated Perfused Rat Hearts)

Naive Sprague Dawley® SD rats (Harlan laboratories (Livermore, Calif. USA)) were anaesthetized and hearts were excised followed by cannulation in the Langendorff apparatus (Harvard apparatus, Holliston, Mass. USA) via aorta. The heart was perfused retrograde with modified oxygenated Krebs-Henseleit buffer (Skrzypiec-Spring M et al., (2007) J. Pharmacol Toxicol Methods 55: 113-126). The pressure of the solution causes the aortic valve to shut and the perfusate is then forced into the ostium and the coronary vessels. This allows the heart to beat for several hours. A balloon was inserted into the left ventricle (LV) to measure dP/dt$_{max}$ (derivative of left ventricular pressure) as an index of cardiac contractility. The APJ agonist was perfused constantly in a dose dependent manner into the heart to examine cardiac contractility. Administration of APJ agonist showed a dose-dependent increase in inotropic and lusitropic effects at varying degrees (Table 27). APJ agonists of the present invention showed improvement in cardiac contractility and relaxation when perfused into the heart as described above.

Figure 1B:
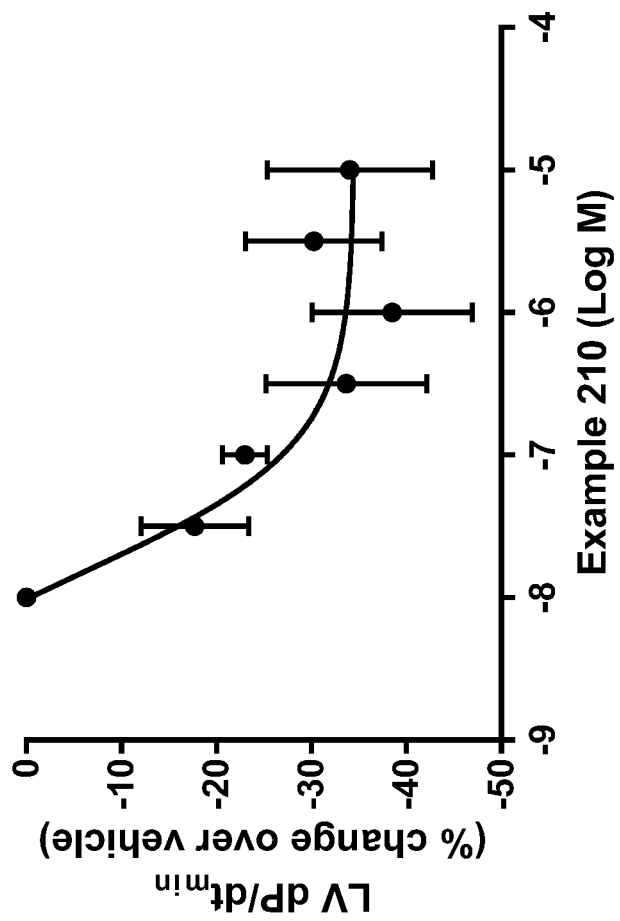
FIG. 1B is a graph of left ventricular $dP/dt_{min}$ as a function of concentration of Example 210.0 compared with vehicle in ex vivo naive Sprague Dawley rat hearts obtained using the Langendorff apparatus. This shows Example 210.0 increases load independent cardiac relaxation in isolated perfused rat hearts.
Figure 2A:
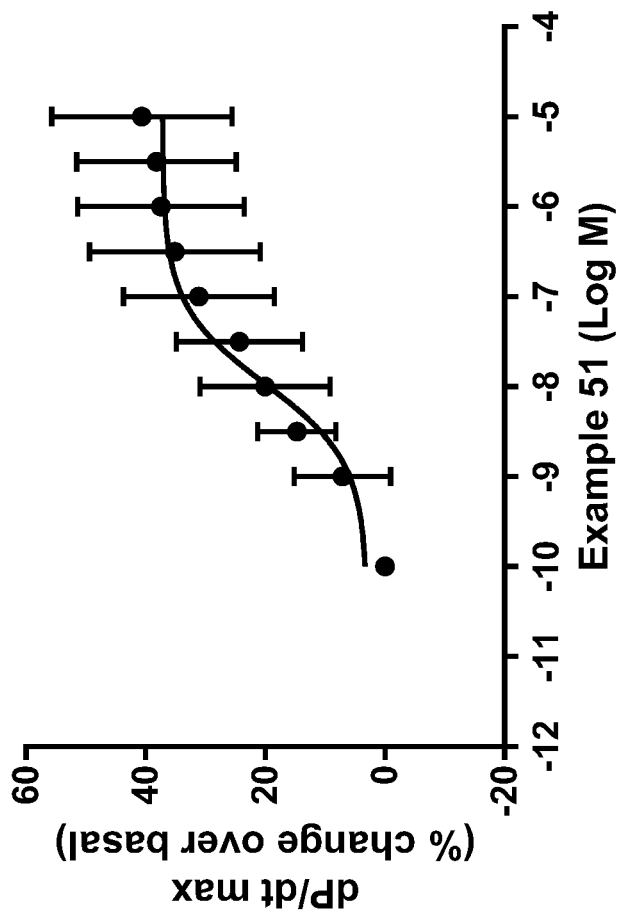
FIG. 2A is a graph of left ventricular $dP/dt_{max}$ as a function of concentration of Example 51.0 compared with vehicle in ex vivo naive Sprague Dawley rat hearts obtained using the Langendorff apparatus. This shows Example 51.0 increases load independent cardiac contractility in isolated perfused rat hearts.
Figure 2B:
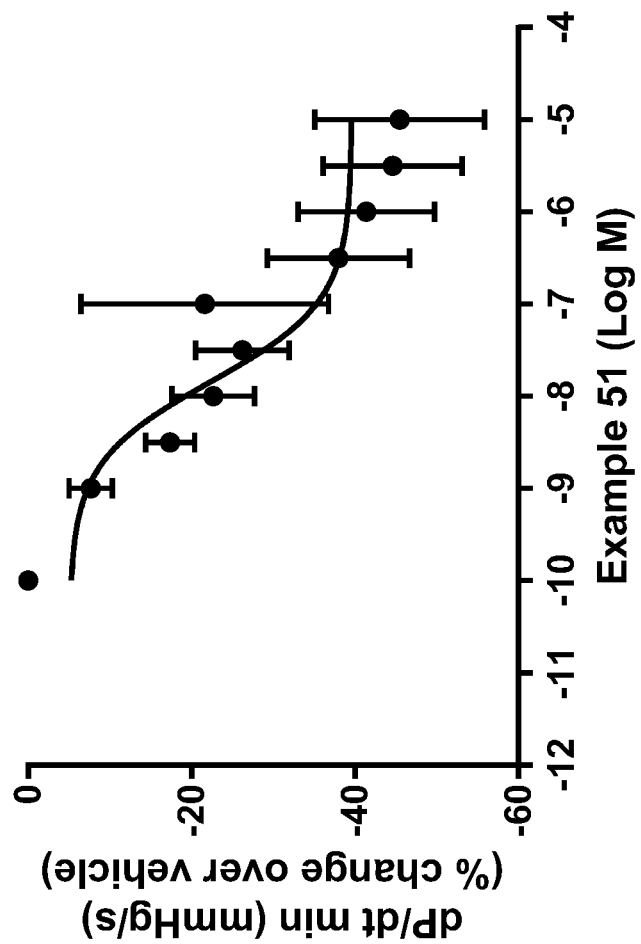
FIG. 2B is a graph of left ventricular $dP/dt_{min}$ as a function of concentration of Example 51.0 compared with vehicle in ex vivo naive Sprague Dawley rat hearts obtained using the Langendorff apparatus. This shows Example 51.0 increases load independent cardiac relaxation in isolated perfused rat hearts.

FIG. 1A shows the effect of Example 210.0 on load independent contractility in isolated perfused rat hearts. Example 210.0 was infused at different concentrations and load independent contractility was measured by index of LV dP/dt$_{max}$ and the results are expressed as a percent change over vehicle. FIG. 1B shows the effect of Example 210.0 on left ventricular relaxation in isolated perfused rat hearts. Example 210.0 was infused at different concentrations and load independent lusitropic effect (relaxation) was measured by index of LV dP/dt$_{min}$ where results are expressed as percent change over vehicle. FIG. 2A shows the effect of Example 51.0 on load independent contractility in isolated perfused rat hearts. Example 51.0 was infused at different concentrations and load independent contractility was measured by index of LV dP/dt$_{max}$ and the results are expressed as a percent change over vehicle. FIG. 2B shows the effect of Example 51.0 on left ventricular relaxation in isolated perfused rat hearts. Example 51.0 was infused at different concentrations and load independent lusitropic effect (relaxation) was measured by index of LV dP/dt$_{min}$ where results are expressed as percent change over vehicle.

Evidence for Improvement in Cardiac Contractility In Vivo in Heart Failure Rat Model Based on the ex vivo findings in isolated heart assay, APJ agonists were dosed in vivo to investigate the translation of cardiac contractility in in vivo settings. Male Lewis rats (Charles River, USA) at 2-3 months of age were used for the study. Heart failure was induced by permanent ligation of the left descending coronary artery which results in injury to the heart with an ejection fraction of <35%. APJ agonists were administered dose dependently acutely for a period of 30 min. Administration of example compounds lead to an increase in cardiac contractility as measured by dP/dt$_{max}$ (derivative of left ventricular pressure) (Table 27).

The following table includes biological activity data obtained using the procedures and assays set forth above for the example compounds described herein.

TABLE 26

Biological Activity Information for Example Compounds.

| Example | Activity hAPJ SPA EC$_{50}$ IP (µM) |
|---|---|
| 1.0 | — |
| 2.0 | 13 |
| 3.0 | 0.00031 |
| 4.0 | 0.00077 |
| 5.0 | 0.00095 |
| 6.0 | 0.00098 |
| 7.0 | 0.0030 |
| 8.0 | 0.028 |
| 9.0 | 0.000091 |
| 10.0 | 0.00011 |
| 11.0 | 0.00014 |
| 12.0 | 0.00015 |
| 13.0 | 0.00019 |
| 14.0 | 0.00020 |
| 15.0 | 0.00021 |
| 16.0 | 0.00022 |
| 17.0 | 0.00026 |
| 18.0 | 0.00028 |
| 19.0 | 0.00029 |
| 20.0 | 0.00030 |
| 21.0 | 0.00031 |
| 22.0 | 0.00031 |
| 23.0 | 0.00036 |
| 24.0 | 0.00036 |
| 25.0 | 0.00037 |
| 26.0 | 0.00042 |
| 27.0 | 0.00046 |
| 28.0 | 0.00048 |
| 29.0 | 0.00082 |
| 30.0 | 0.0012 |
| 31.0 | 0.0019 |
| 32.0 | 0.0023 |
| 33.0 | 0.0024 |
| 34.0 | 0.0032 |
| 35.0 | 0.0035 |
| 36.0 | 0.0035 |
| 37.0 | 0.0036 |
| 38.0 | 0.0038 |
| 39.0 | 0.0066 |
| 40.0 | 0.011 |
| 41.0 | 0.012 |
| 42.0 | 0.012 |
| 43.0 | 0.025 |
| 44.0 | 0.044 |
| 45.0 | 0.072 |
| 46.0 | 0.30 |
| 47.0 | — |
| 48.0 | — |
| 49.0 | — |
| 50.0 | — |
| 51.0 | 0.0010 |
| 52.0 | 0.00029 |
| 53.0 | 0.0034 |
| 54.0 | 0.0083 |
| 55.0 | 0.028 |
| 56.0 | 0.000071 |
| 57.0 | 0.00011 |
| 58.0 | 0.00013 |
| 59.0 | 0.00016 |
| 60.0 | 0.00017 |
| 61.0 | 0.00020 |
| 62.0 | 0.00022 |
| 63.0 | 0.00024 |
| 64.0 | 0.00029 |
| 65.0 | 0.00031 |
| 66.0 | 0.00032 |
| 67.0 | 0.00036 |
| 68.0 | 0.00037 |

TABLE 26-continued

Biological Activity Information for Example Compounds.

| Example | Activity hAPJ SPA EC$_{50}$ IP (μM) |
|---|---|
| 69.0 | 0.00039 |
| 70.0 | 0.00040 |
| 71.0 | 0.00047 |
| 72.0 | 0.00048 |
| 73.0 | 0.00049 |
| 74.0 | 0.00054 |
| 75.0 | 0.00055 |
| 76.0 | 0.00060 |
| 77.0 | 0.00077 |
| 78.0 | 0.00077 |
| 79.0 | 0.00098 |
| 80.0 | 0.0011 |
| 81.0 | 0.0011 |
| 82.0 | 0.018 |
| 83.0 | — |
| 84.0 | — |
| 85.0 | 0.00017 |
| 86.0 | 0.00023 |
| 87.0 | 0.00041 |
| 88.0 | 0.00051 |
| 89.0 | 0.0019 |
| 90.0 | 0.0039 |
| 91.0 | 0.0042 |
| 92.0 | 0.00013 |
| 93.0 | 0.00014 |
| 94.0 | 0.00017 |
| 95.0 | 0.00032 |
| 96.0 | 0.00034 |
| 97.0 | 0.00040 |
| 98.0 | 0.00045 |
| 99.0 | 0.0010 |
| 100.0 | 0.0020 |
| 101.0 | 0.0020 |
| 102.0 | 0.0028 |
| 103.0 | 0.0045 |
| 104.0 | 0.022 |
| 105.0 | 0.030 |
| 106.0 | — |
| 107.0 | — |
| 108.0 | 0.00025 |
| 109.0 | 0.00087 |
| 110.0 | 0.00097 |
| 111.0 | 0.0078 |
| 112.0 | — |
| 113.0 | — |
| 114.0 | — |
| 115.0 | 0.00020 |
| 116.0 | 0.000056 |
| 117.0 | 0.000061 |
| 118.0 | 0.000084 |
| 119.0 | 0.00015 |
| 120.0 | 0.00015 |
| 121.0 | 0.00015 |
| 122.0 | 0.00022 |
| 123.0 | 0.00024 |
| 125.0 | 0.00034 |
| 126.0 | 0.00045 |
| 127.0 | 0.00065 |
| 128.0 | 0.0011 |
| 129.0 | 0.0033 |
| 130.0 | 0.0035 |
| 131.0 | 0.0039 |
| 132.0 | 0.0068 |
| 134.0 | 0.010 |
| 135.0 | 0.016 |
| 136.0 | .019 |
| 137.0 | — |
| 138.0 | — |
| 139.0 | — |
| 140.0 | — |
| 141.0 | — |
| 142.0 | — |
| 143.0 | 0.000072 |
| 144.0 | 0.000073 |
| 145.0 | 0.000090 |
| 146.0 | 0.00013 |
| 147.0 | 0.00014 |
| 148.0 | 0.00019 |
| 149.0 | 0.00021 |
| 150.0 | 0.00022 |
| 151.0 | 0.00024 |
| 152.0 | 0.00025 |
| 153.0 | 0.00026 |
| 154.0 | 0.00032 |
| 155.0 | 0.00035 |
| 156.0 | 0.00036 |
| 157.0 | 0.00039 |
| 158.0 | 0.00040 |
| 159.0 | 0.00048 |
| 160.0 | 0.00050 |
| 161.0 | 0.00067 |
| 162.0 | 0.00068 |
| 163.0 | 0.00070 |
| 164.0 | 0.00074 |
| 165.0 | 0.00075 |
| 166.0 | 0.00075 |
| 167.0 | 0.00094 |
| 168.0 | 0.00097 |
| 169.0 | 0.0010 |
| 170.0 | 0.0011 |
| 171.0 | 0.0012 |
| 172.0 | 0.0012 |
| 173.0 | 0.0016 |
| 174.0 | 0.0019 |
| 175.0 | 0.0019 |
| 176.0 | 0.0021 |
| 177.0 | 0.0028 |
| 178.0 | 0.0030 |
| 179.0 | 0.0032 |
| 180.0 | 0.0036 |
| 181.0 | 0.0059 |
| 182.0 | 0.026 |
| 183.0 | 0.028 |
| 184.0 | 0.028 |
| 185.0 | 0.033 |
| 186.0 | 0.037 |
| 187.0 | 0.051 |
| 188.0 | 0.075 |
| 189.0 | 0.11 |
| 190.0 | — |
| 191.0 | 0.015 |
| 192.0 | 0.0028 |
| 193.0 | — |
| 194.0 | — |
| 195.0 | — |
| 196.0 | — |
| 197.0 | — |
| 198.0 | — |
| 199.0 | — |
| 200.0 | — |
| 201.0 | — |
| 202.0 | — |
| 203.0 | — |
| 204.0 | 0.00026 |
| 205.0 | 0.0023 |
| 206.0 | 0.0048 |
| 207.0 | — |
| 208.0 | — |
| 209.0 | — |
| 210.0 | 0.0032 |
| 211.0 | 0.0041 |
| 212.0 | 0.000074 |
| 213.0 | 0.00012 |
| 214.0 | 0.00021 |
| 215.0 | 0.00022 |
| 216.0 | 0.00023 |
| 217.0 | 0.00024 |
| 218.0 | 0.00025 |
| 219.0 | 0.00026 |
| 220.0 | 0.00027 |

TABLE 26-continued

Biological Activity Information for Example Compounds.

| Example | Activity hAPJ SPA EC$_{50}$ IP (µM) |
|---|---|
| 221.0 | 0.00030 |
| 222.0 | 0.00031 |
| 223.0 | 0.00032 |
| 224.0 | 0.00032 |
| 225.0 | 0.00033 |
| 226.0 | 0.00035 |
| 227.0 | 0.00035 |
| 228.0 | 0.00039 |
| 229.0 | 0.00039 |
| 230.0 | 0.00041 |
| 231.0 | 0.00044 |
| 232.0 | 0.00045 |
| 233.0 | 0.0005 |
| 234.0 | 0.00054 |
| 235.0 | 0.00056 |
| 236.0 | 0.00057 |
| 237.0 | 0.00058 |
| 238.0 | 0.00059 |
| 239.0 | 0.00060 |
| 240.0 | 0.00061 |
| 241.0 | 0.00065 |
| 242.0 | 0.00081 |
| 243.0 | 0.00087 |
| 244.0 | 0.00094 |
| 245.0 | 0.00095 |
| 246.0 | 0.0014 |
| 247.0 | 0.0015 |
| 248.0 | 0.0016 |
| 249.0 | 0.0025 |
| 250.0 | 0.0033 |
| 251.0 | 0.0067 |
| 252.0 | 0.0097 |
| 253.0 | 0.015 |
| 254.0 | — |
| 255.0 | — |
| 256.0 | — |
| 257.0 | — |
| 258.0 | — |
| 259.0 | — |
| 260.0 | — |
| 261.0 | 0.00013 |
| 262.0 | 0.000070 |
| 263.0 | 0.000086 |
| 264.0 | 0.000167 |
| 265.0 | 0.00018 |
| 266.0 | 0.00021 |
| 267.0 | 0.00043 |
| 268.0 | 0.00047 |
| 269.0 | 0.00049 |
| 270.0 | 0.00056 |
| 271.0 | 0.00062 |
| 272.0 | 0.00065 |
| 273.0 | 0.00072 |
| 274.0 | 0.00079 |
| 275.0 | 0.00085 |
| 276.0 | 0.00087 |
| 277.0 | 0.00096 |
| 278.0 | 0.00096 |
| 279.0 | 0.0010 |
| 280.0 | 0.0012 |
| 281.0 | 0.0012 |
| 282.0 | 0.0014 |
| 283.0 | 0.0014 |
| 284.0 | 0.0016 |
| 285.0 | 0.0025 |
| 286.0 | 0.0037 |
| 287.0 | 0.0041 |
| 288.0 | 0.0042 |
| 289.0 | 0.0049 |
| 290.0 | 0.0050 |
| 291.0 | 0.0050 |
| 292.0 | 0.0051 |
| 293.0 | 0.0055 |
| 294.0 | 0.0058 |
| 295.0 | 0.0061 |
| 296.0 | 0.0068 |
| 297.0 | 0.0088 |
| 298.0 | 0.011 |
| 299.0 | 0.011 |
| 300.0 | 0.012 |
| 301.0 | 0.013 |
| 302.0 | 0.013 |
| 303.0 | 0.013 |
| 304.0 | 0.016 |
| 305.0 | 0.016 |
| 306.0 | 0.018 |
| 307.0 | 0.028 |
| 308.0 | 0.033 |
| 309.0 | 0.061 |
| 310.0 | 0.083 |
| 311.0 | 0.19 |
| 312.0 | 0.21 |
| 313.0 | 0.23 |
| 314.0 | 0.23 |
| 315.0 | 0.27 |
| 316.0 | 0.27 |
| 317.0 | 0.31 |
| 318.0 | 0.42 |
| 319.0 | 0.61 |
| 320.0 | 0.00017 |
| 321.0 | 0.00018 |
| 322.0 | 0.00020 |
| 323.0 | 0.00020 |
| 324.0 | 0.00021 |
| 325.0 | 0.00023 |
| 326.0 | 0.00024 |
| 327.0 | 0.00025 |
| 328.0 | 0.00030 |
| 329.0 | 0.00038 |
| 330.0 | 0.00043 |
| 331.0 | 0.00045 |
| 332.0 | 0.00045 |
| 333.0 | 0.00045 |
| 334.0 | 0.00047 |
| 335.0 | 0.00052 |
| 336.0 | 0.00055 |
| 337.0 | 0.0013 |
| 338.0 | 0.019 |
| 339.0 | 0.062 |
| 340.0 | 0.075 |
| 341.0 | 0.081 |
| 342.0 | 0.121 |
| 343.0 | 0.20 |
| 344.0 | — |
| 345.0 | — |
| 346.0 | — |
| 347.0 | — |
| 348.0 | — |
| 349.0 | — |
| 350.0 | — |
| 383.0 | 0.000060 |
| 384.0 | 0.00015 |
| 385.0 | 0.00038 |
| 386.0 | 0.037 |
| 387.0 | 0.0021 |
| 388.0 | 0.037 |
| 390.0 | 0.013 |
| 391.0 | 0.0084 |
| 392.0 | 0.00055 |
| 393.0 | 0.00028 |
| 394.0 | 0.00031 |
| 395.0 | 0.00026 |
| 396.0 | — |
| 397.0 | 0.00051 |
| 398.0 | 0.010 |
| 400.0 | 0.00010 |
| 401.0 | 0.00053 |
| 402.0 | 0.065 |
| 403.0 | 0.057 |
| 404.0 | 0.036 |

TABLE 26-continued

Biological Activity Information for Example Compounds.

| Example | Activity hAPJ SPA EC$_{50}$ IP (µM) |
|---|---|
| 405.0 | 0.064 |
| 406.0 | 0.067 |
| 407.0 | 0.18 |
| 409.0 | 0.043 |
| 410.0 | 0.011 |
| 411.0 | 0.032 |

The following table includes data obtained using the procedures and assays set forth above for the example compounds described herein.

TABLE 27

Contractile Effects of Examples Observed in ex vivo (Isolated Heart Assay) and in vivo (MI Rat Model).

| Example(s) | Isolated Heart Assay | | MI Rat Model |
|---|---|---|---|
| | dP/dt$_{max}$ (%) | dP/dt$_{min}$ (%) | dP/dt$_{max}$ (%) |
| 26 | 10.20 | 11.1 | 58 |
| 41 | 22.1 | 22.7 | nd* |
| 51 | 40.6 | 33.8 | 38 |
| 56 | 23.0 | 24.9 | 30 |
| 108 | 38.8 | 30.1 | nd* |
| 111 | 19.5 | 24.9 | 97 |
| 115 | 32.6 | 34.7 | 30 |
| 204 | 24.6 | 29.0 | No effect |
| 205 | 18.8 | 20.5 | nd* |
| 210 | 25.9 | 34.0 | 95.6 |
| 261 | 34.5 | 53.8 | 30 |

*nd is not determined

APJ is a G-protein coupled receptor that is closely related to the Angiotensin II Type 1 receptor (AT1R) with 50% homology in the transmembrane domain. Apelin is a known endogenous ligand for APJ and recently another ligand named ELABELA has been identified as another potential ligand for the APJ receptor (Tatemoto, K. et al., Biochem. Biophys. Res. Commun, 251, pp. 471-476 (1998); Pauli, A. et al., Science, 343, pp. 1248636 (2014)). Since its discovery, there is accumulating evidence indicating the role of the apelin-APJ receptor in the pathophysiology of cardiovascular diseases. Pre-clinical and clinical studies have shown that acute infusion of apelin or APJ agonists improve cardiac function under heart failure settings (Berry, M. F., et al., Circulation, 110(11) pp. 11187-11193 (2004); Japp, A. G. et al., Circulation, 121, pp. 1818-1827 (2010)).

A key emerging aspect of the apelin-APJ system is its interaction with the renin-angiotensin system. Apelin is also known to counter-regulate the vasoconstriction actions of AngII. Apelin knockout mice show a strong increased vasopressor response to AngII indicating that the apelin/APJ system exerts the hypotensive effect in vivo against the pressor action of AngII. In addition, the apelin activated APJ pathway inhibited angiotensin-mediated formation of atherosclerosis through interaction with the AT1R (Chun, H. J., et al., J. Clin. Invest., 118, pp. 3343-3354 (2008), Siddiquee, K. et al., J. Hypertens., 29, pp. 724-731 (2011), Sun, X. et al., Hypertens. Res., 34, pp. 701-706 (2011)). This could be mediated by convergence of two independent intracellular signaling pathways or via direct physical interaction of APJ with AT1R to form a heterodimer. Siddiquee et al. showed that the AngII signaling is antagonized through apelin-dependent heterodimerization and APJ mediated negative allosteric modulation of AT1R function (Siddiquee, K. et al., Br. J. Pharmacol., 168, pp. 1104-1117 (2013).

We were interested to understand if the heterodimerization of APJ-AT1R upon activation by APJ agonists would have any beneficial outcome clinically in heart failure patients considering most of these patients are on standard of care drugs such as angiotensin blockers (angiotensin II receptor antagonists or angiotensin receptor blockers (ARBs)) and angiotensin converting enzyme (ACE) inhibitors. In order to explore the cross-talk between APJ and the AT1R receptor, we examined IP1 signaling mediated by AT1R upon activation with APJ agonists. Surprisingly and contrary to the findings by Siddique et al., activation of the APJ pathway resulted in positive cooperativity of AngII by shifting its potency to the left and also increasing the efficacy of the IP response (see methods and results section below). Conversely, blocking the AT1R receptor by an ARB such as losartan relieved the inhibition of the APJ receptor and up regulates its signaling which is observed as synergistic effects in both ex-vivo and in vivo studies. This work establishes a new paradigm for cross-talk interaction/heterodimerization between APJ & AT1R which might have implications for approaches to pharmacological interventions in heart failure populations.

The interaction between acetyl cholinesterase (ACE2) and Apelin biology is complicated. To investigate the interaction between the Apelin-APJ and ACE signalling pathways, we examined the improvement in cardiac function with APJ small molecule agonists in the presence of ACE inhibitor captopril in heart failure rats in vivo. Captopril alone, under acute settings, does not show a marked improvement in contractility or ejection fraction acutely. However, in the presence of an APJ agonist, there was a shift in potency to the left with marked improvement in contractility and ejection fraction without changes in heart rate. These findings provide a new reference for the understanding of the regulation of ACE2 for the renin angiotensin aldosterone system (RAAS), independent of AT1R signaling and offer new potential drug targets for the treatment of diseases such as hypertension and heart failure. This work clearly establishes that combination of an agonist of the APJ receptor with an ARB such as losartan and/or with an ACE inhibitor such as captopril which may play an important role in providing greater efficacy in treating heart failure patients, for example in improving contractility and ejection fraction without changing the heart rate.

Evidence for Allosteric Interaction between APJ and AT1R Using IP Assay

Methods

Single and double stable recombinant cell lines were generated for human APJ and the AT1R receptor in CHO K1 cells tagged either with FLAG or hemagglutinin (HA) tag. Briefly, the CHO-K1 APJ/AT1R cells were seeded in culture medium of DMEM-F12 and 10% FBS at a density of 15 k/well in a 96 well plate overnight. The next day, the culture medium was replaced with medium containing no serum for 4 hours. The compound AngII at a range of concentrations (1 pM-10 µM) with or without different concentrations of APJ agonists were diluted in stimulation buffer and added to the cell plate. The plate was sealed and incubated for 1 hour. This was followed by addition of IP-d2 conjugate followed by europium cryptate antibody conjugate into the wells. The plate was sealed, followed with incubation for 2 hours at RT. Time-resolved fluorescence resonance energy (TR-FRET) at 620 nm and 665 nm was measured after 2 hours with an Envision reader. The signal ratios and delta F were calculated and the amount of IP1 produced was inversely proportional to the TR-FRET ratio, 665/620 nm.

Results

Figure 3:
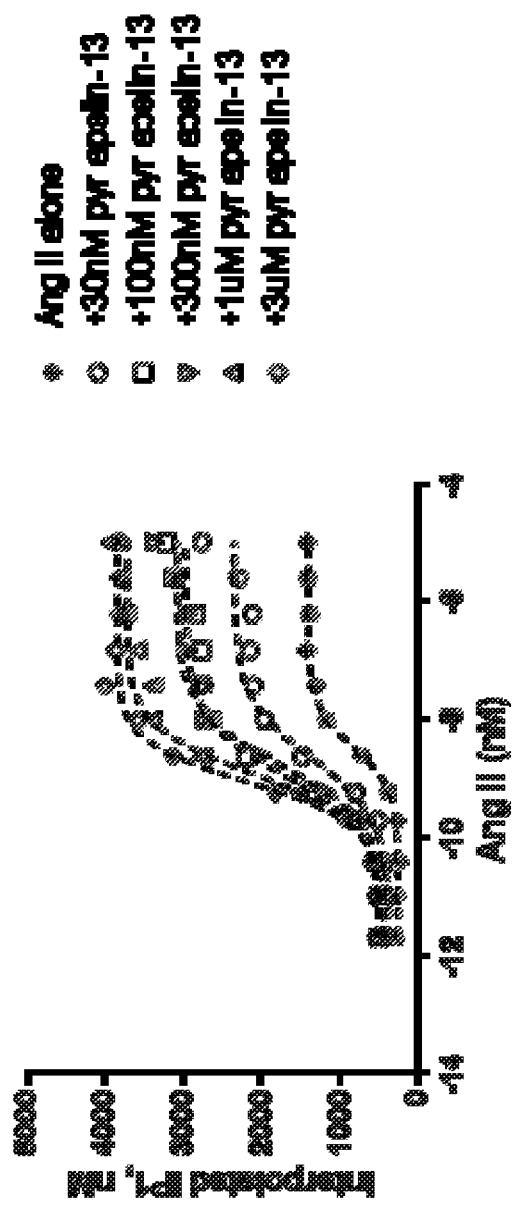
FIG. 3 is a graph plotting different concentrations of angiotensin (AngII) with fixed concentration of pyrapelin-13 added to the human APJ-AT1R (angiotensin Type 1) double stable CHO cell line. The function of the inositol phosphate accumulation (IP1) was measured by Time-resolved fluorescence resonance energy (TR-FRET) at 620 nm and 665 nm respectively. Addition of pyrapelin-13 induces the positive cooperativity on the AT1R upon activation by APJ receptor.
Figure 4:
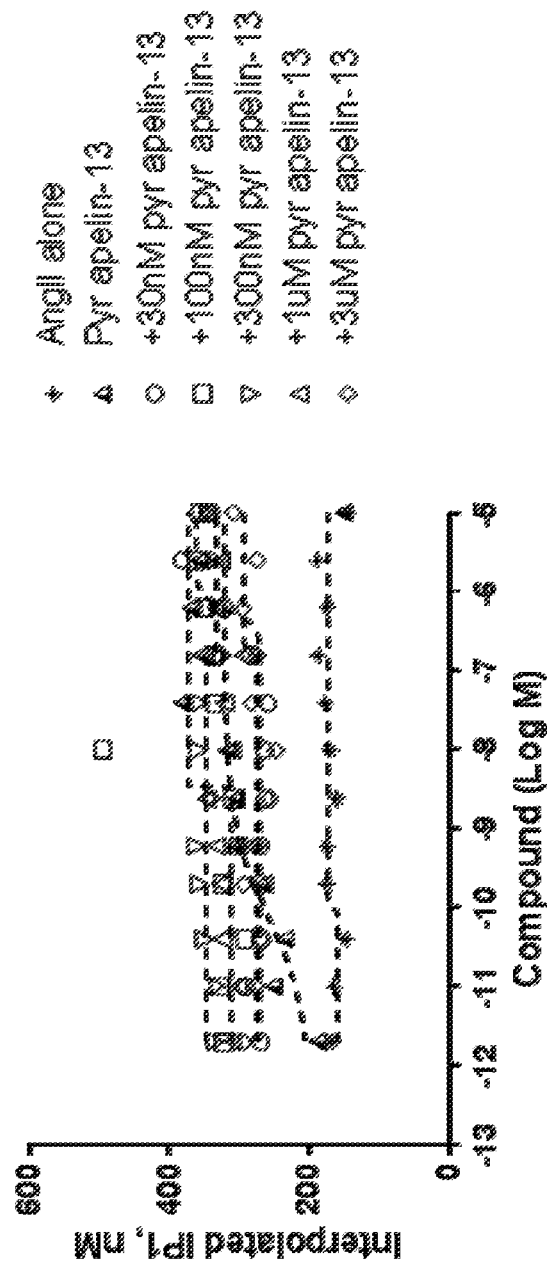
FIG. 4 is a graph plotting different concentrations of angiotensin (AngII) with fixed concentration of pyrapelin-13 added to the human APJ receptor expressed in the CHO cell line. The function of the inositol phosphate accumulation (IP1) was measured by Time-resolved fluorescence resonance energy (TR-FRET) at 620 nm and 665 nm respectively. There was no positive cooperativity observed upon treatment with pyrapelin-13 when the human APJ receptor is expressed alone.
Figure 5:
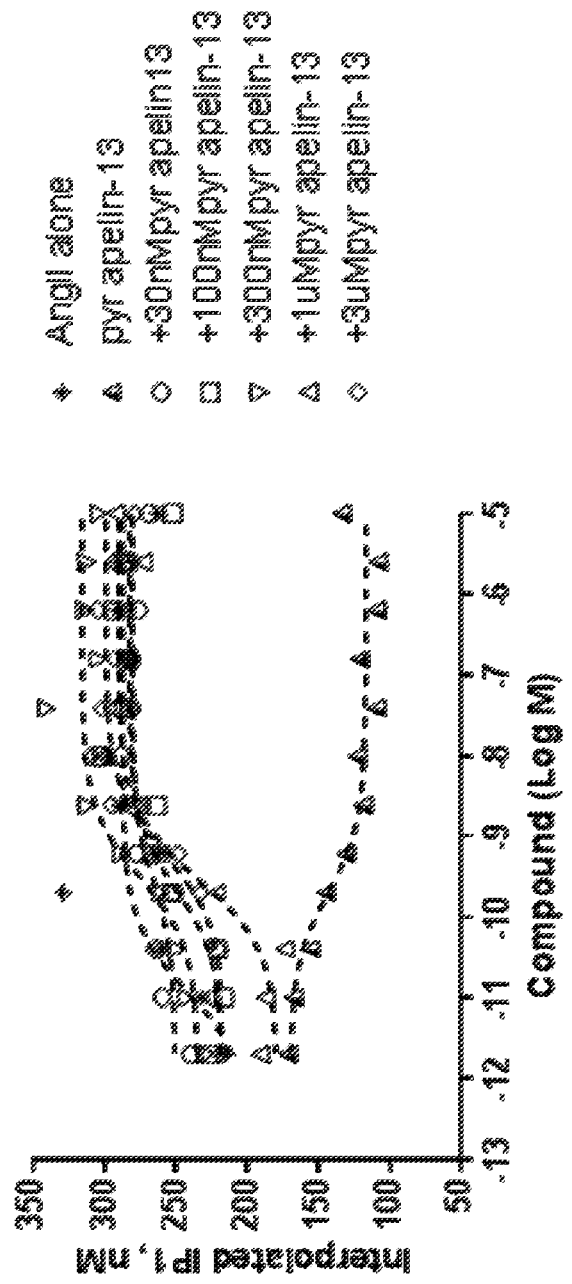
FIG. 5 is a graph plotting different concentrations of angiotensin (AngII) with fixed concentration of pyrapelin-13 added to the human AT1R receptor expressed in the CHO cell line. The function of the inositol phosphate accumulation (IP1) was measured by Time-resolved fluorescence resonance energy (TR-FRET) at 620 nm and 665 nm respectively. There was no positive cooperativity observed when the human AT1R receptor is expressed alone by pyrapelin-13 in the absence of APJ expression.
Figure 6A:
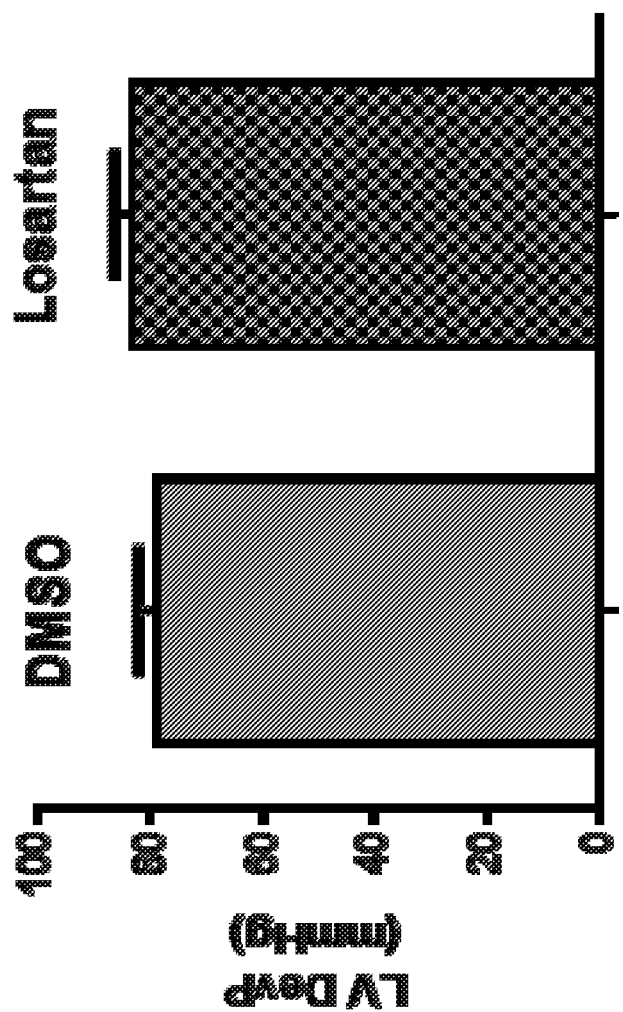
FIG. 6A is a graph of left ventricular (LV) developed pressure (DevP) as a function of administration of losartan or control (DMSO) in ex vivo naive Sprague Dawley rat hearts obtained using the Langendorff apparatus showing there is no impact on developed pressure with losartan as compared to the control (DMSO).
Figure 6B:
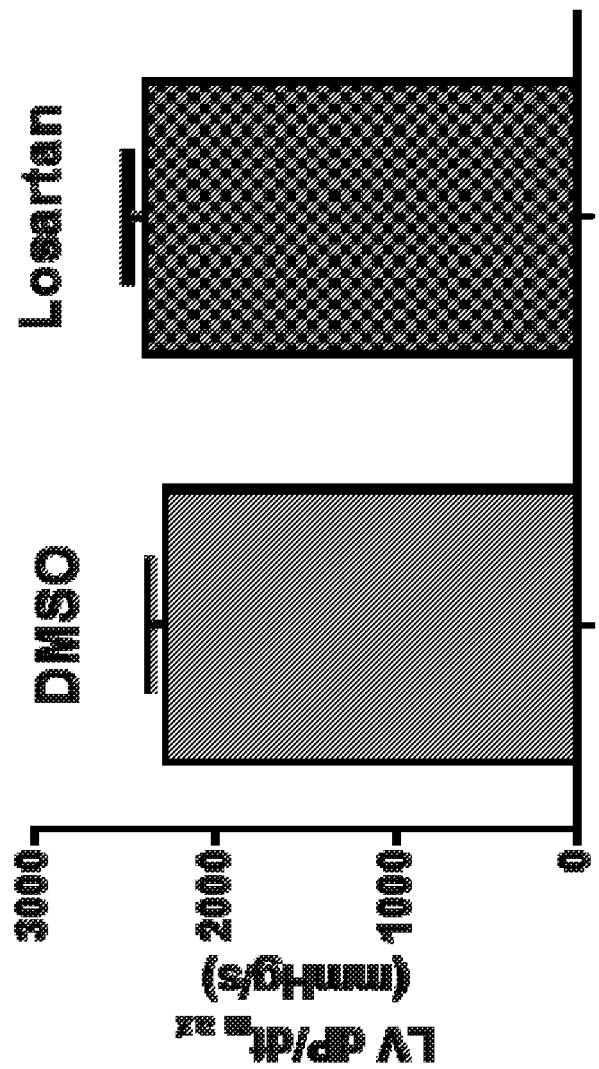
FIG. 6B is a graph of left ventricular (LV) $dP/dt_{max}$ as a function of administration of losartan or control (DMSO) in ex vivo naive Sprague Dawley rat hearts obtained using the Langendorff apparatus showing there is no impact on cardiac contraction with losartan as compared to the control (DMSO).
Figure 6C:
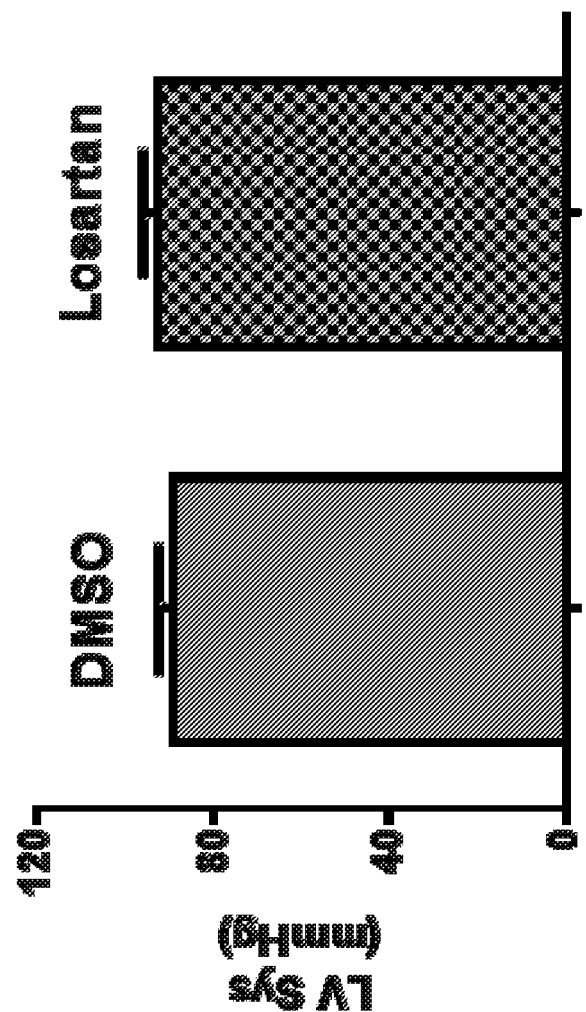
FIG. 6C is a graph of left ventricular (LV) systolic pressure (Sys) as a function of administration of losartan or control (DMSO) in ex vivo naive Sprague Dawley rat hearts obtained using the Langendorff apparatus showing there is no impact on systolic pressure with losartan as compared to the control (DMSO).
Figure 6D:
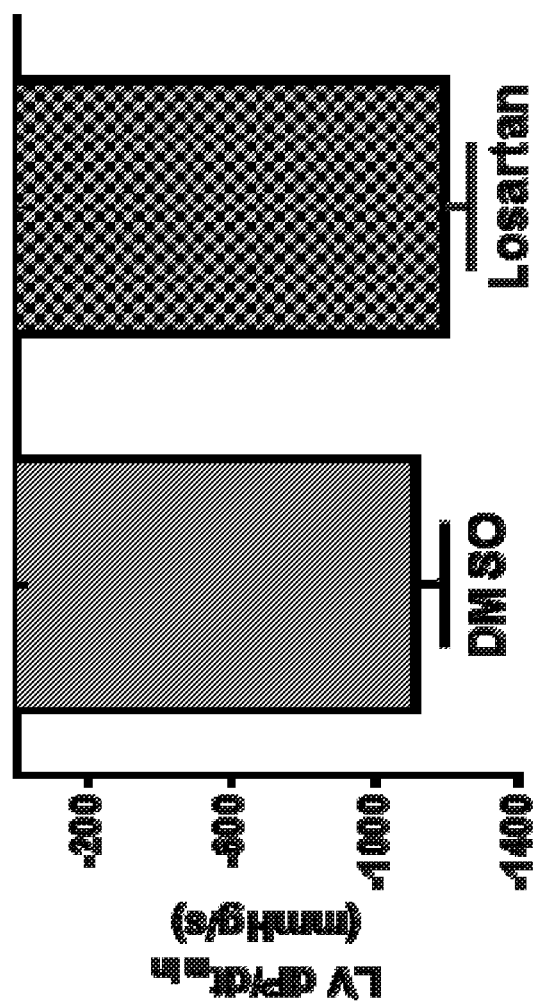
FIG. 6D is a graph of left ventricular (LV) $dP/dt_{min}$ as a function of administration of losartan or control (DMSO) in ex vivo naive Sprague Dawley rat hearts obtained using the Langendorff apparatus showing there is no impact on cardiac relaxation with losartan as compared to the control (DMSO).

In cells expressing both APJ and the AT1R receptor, addition of APJ agonists at different concentrations increased the maximal response of AngII and also shifted the potency to the left. The increase in IP1 response reached a maximal effect both in potency and E max indicating a ceiling effect which is a hallmark for allosteric cooperativity between the AT1R and APJ receptor (FIG. 3). However, this effect of cooperativity was not observed in either APJ or AT1R recombinant stable cell lines indicating that there is functional cross-talk between the two receptors through physical interaction or with downstream effectors (FIG. 4 and FIG. 5). Based on the above findings of cooperativity, we rationalized that if an APJ agonist can induce heterodimerization of APJ with AT1R, blocking the AT1R with losartan would enhance the activation of APJ upon addition of small molecule agonists. We observed that APJ small molecule agonists induced positive cooperativity in the presence of AngII and addition of losartan relieved this cooperativity and resulted in synergistic effects of enhancing the efficacy of the APJ receptor. This work clearly establishes that combination of an agonist of the APJ receptor with an ARB such as losartan or an ACE inhibitor such as captopril may play an important role in providing greater efficacy in treatment of heart failure patients.

Evidence for Blockade of AT1R Signaling Enhances the APJ Receptor Signaling Using Ex-Vivo (Isolated Rat Heart Assay) and In Vivo (Myocardial Infraction (MI)-Induced Heart Failure Model)

Methods

Naive Sprague Dawley® SD rats were anaesthetized and hearts were excised followed by cannulation in the Langendorff apparatus via aorta. The heart was perfused retrograde with modified oxygenated Krebs-Henseleit buffer. The pressure of the solution causes the aortic valve to shut and the perfusate was then forced into the ostium and the coronary vessels. This allowed the heart to beat for several hours. A balloon was inserted into the left ventricle to measure $dp/dt_{max}$ as an index of cardiac contractility. The APJ agonist (Example 56.0) was perfused in the presence or absence of AT1R blocker losartan.

Results

Figure 7:
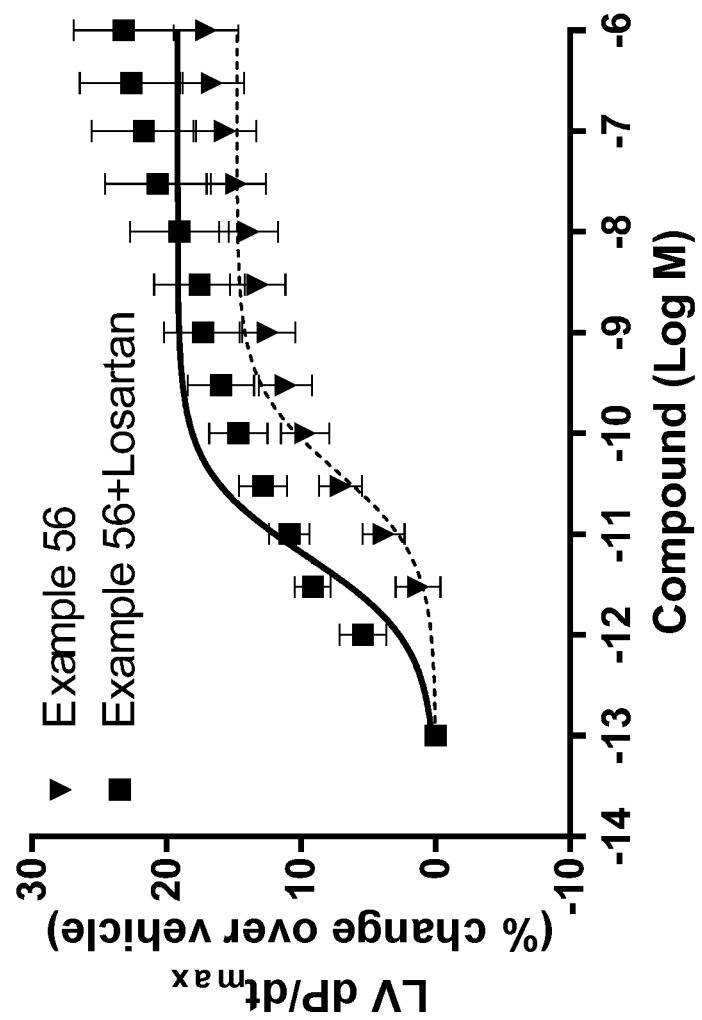
FIG. 7 is a graph showing the effect of different concentrations of APJ agonist Example 56.0 alone or in combination with losartan on the left ventricular (LV) $dP/dt_{max}$ in ex vivo naive Sprague Dawley rat hearts obtained using the Langendorff apparatus.
Figure 8A:
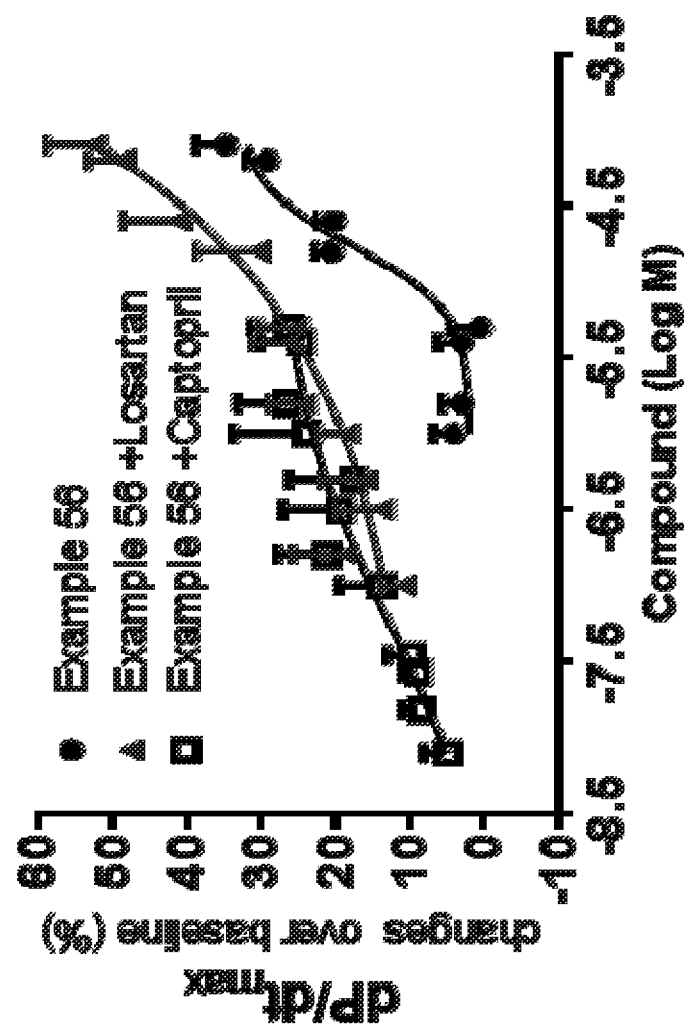
FIG. 8A is a graph showing the in vivo efficacy in a MI induced heart failure model of different concentrations of APJ agonist Example 56.0 alone or in combination with losartan or with captopril on the left ventricular (LV) $dP/dt_{max}$.
Figure 8B:
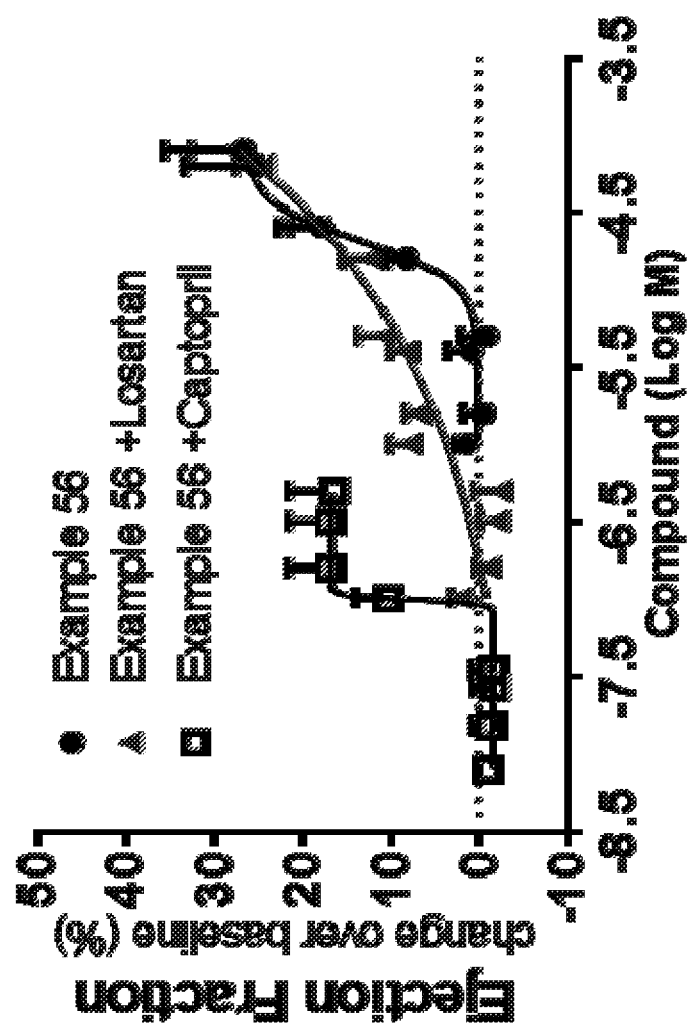
FIG. 8B is a graph showing the in vivo efficacy in a MI induced heart failure model of different concentrations of APJ agonist Example 56.0 alone or in combination with losartan or with captopril on the ejection fraction.
Figure 8C:
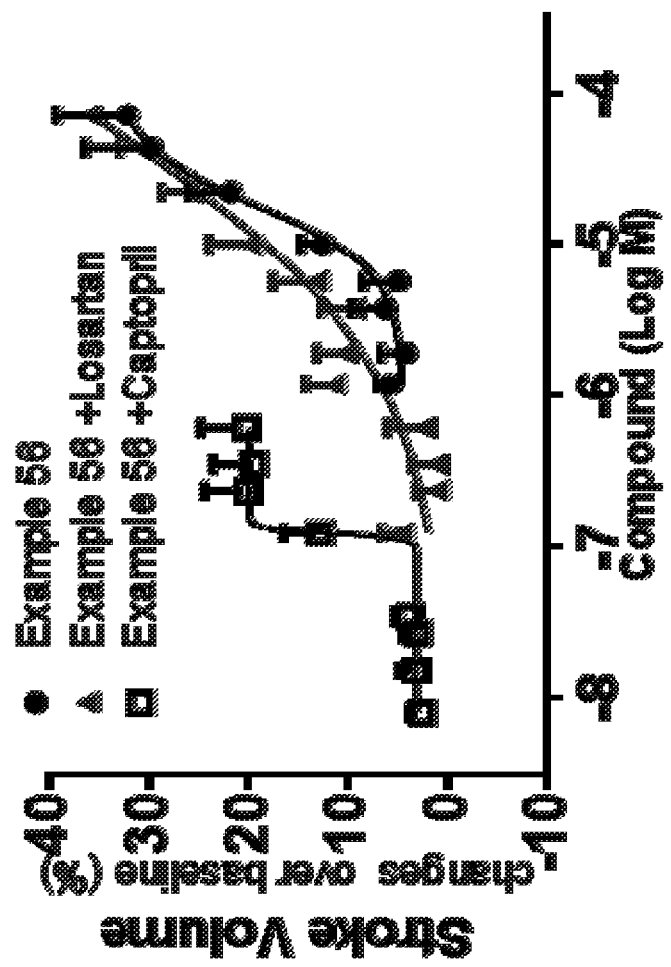
FIG. 8C is a graph showing the in vivo efficacy in a MI induced heart failure model of different concentrations of APJ agonist Example 56.0 alone or in combination with losartan or with captopril on the stroke volume.
Figure 8D:
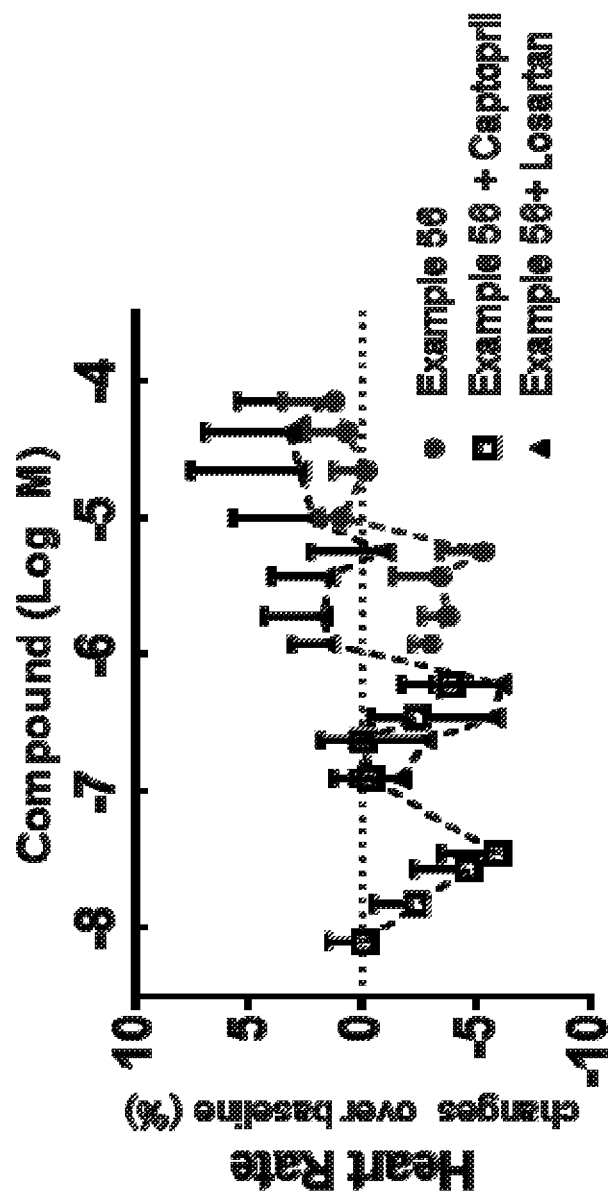
FIG. 8D is a graph showing the in vivo efficacy in a MI induced heart failure model of different concentrations of APJ agonist Example 56.0 alone or in combination with losartan or with captopril on the heart rate.

Losartan alone did not have any impact on cardiac contraction ($dp/dt_{max}$), cardiac relaxation ($dp/dt_{min}$), systolic pressure (Sys) and developed pressure (DevP) when compared to the control (DMSO) as shown in FIG. 6A, FIG. 6B, FIG. 6C, and FIG. 6D. Administration of APJ agonist (Example 56.0) showed a dose-dependent increase in inotropic effects and co-infusion of AT1R blocker losartan increased the potency by 5 fold along with $E_{max}$ (FIG. 7). Based on these ex-vivo findings, it can be inferred that inhibiting the AT1R pathway with losartan unmasks the APJ pathway which could be either from cross-regulation with downstream effectors or by shifting the equilibrium from the heterodimer of APJ-AT1R to monomer of APJ receptors.

Cardiovascular Effects of Example 56.0 and Captopril/Losartan on MI-Induced Heart Failure Rats Methods Male Lewis rats at 2-3 months of age were used for the study. MI was induced by ligation of the LAD. Echocardiography (Echo) was performed at one-week post-MI on rats for verification of infarct size and animal enrollment Animals with ejection fractions more than 40% or no visible infarct in myocardium were excluded from the study. All eligible MI rats were randomly divided into 3 groups: 1) those treated with vehicle; 2) those treated with losartan (0.5 g/L in drink water); and 3) those treated with captopril (0.5 g/L in drink water). Treatments were initiated approximately five weeks post-MI and animals were continuously treated with losartan and captopril in drinking water up to 15 days prior to being assigned into each subgroup. These subgroup groups included the following: 1) cohort treated with vehicle; 2) cohort treated with Example 56.0 at various doses; 3) cohort treated only with losartan; 4) cohort treated with losartan and Example 56.0 at various doses; 5) cohort treated only with captopril; and 6) cohort treated with captopril and Example 56.0 at various doses. A Millar PV catheter was inserted into the right common carotid artery and then advanced to the left ventricle (LV) for cardiac hemodynamic assessment and the peripheral arterial pressure was also monitored by a pressure transducer via a femoral artery access in all rats. Following hemodynamic stabilization, baseline steady-state data was acquired Animals in any Example 56 treated group received intravenous infusion of Example 56.0 in a dose-escalated fashion during cardiac hemodynamic assessment. Blood was drawn for actual PK exposure to derive a PK/PD profile.

Results

Example 56.0 alone improved cardiovascular hemodynamics manifested by an increase in ejection fraction, $dp/dt_{max}$, over vehicle. Example 56.0 plus losartan or captopril further augmented contractile function over Example 56.0 therapy alone. Potency shift to the left and $E_{max}$ increase was observed in most contractile parameters including $dp/dt_{max}$, ejection fraction, and stroke volume, indicating that reducing AngII/AT1R may enhance the APJ-mediated cardiovascular effect (see FIG. 8A, FIG. 8B, FIG. 8C, and FIG. 8D). Heart rate did not significantly change either in groups treated with APJ agonist Example 56.0 alone or in groups treated with an APJ agonist (Example 56.0) in combination with either an ARB or ACE inhibitor. This observation supports the important clinical benefits that could be achieved using a small molecule APJ agonist such as Example 56.0 in combination with standard therapeutic agents such as an ARB such as losartan or an ACE inhibitor such as captopril in heart failure patients.

All publications and patent applications cited in this specification are hereby incorporated by reference herein in their entireties and for all purposes as if each individual publication or patent application were specifically and individually indicated as being incorporated by reference and as if each reference was fully set forth in its entirety. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:

1. A compound of Formula I or Formula II:

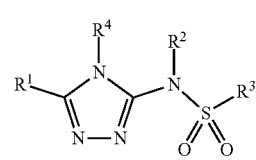

-continued

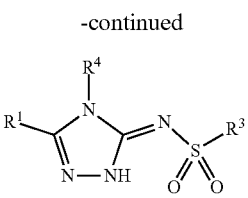

II or a pharmaceutically acceptable salt thereof, a tautomer thereof, a pharmaceutically acceptable salt of the tautomer, a stereoisomer of any of the foregoing, or a mixture thereof,
wherein:
$R^1$ is an unsubstituted furanyl, or is a furanyl substituted with 1, 2, or 3 $R^{1a}$ substituents;
$R^{1a}$ in each instance is independently selected from —F, —Cl, —Br, —I, —$C_1$-$C_6$ alkyl, —$C_1$-$C_6$ haloalkyl, —$C_1$-$C_6$ perhaloalkyl, —($C_1$-$C_6$ alkyl)-O—($C_1$-$C_6$ alkyl), —CN, —OH, —O—($C_1$-$C_6$ alkyl), —O—($C_1$-$C_6$ haloalkyl), —O—($C_1$-$C_6$ perhaloalkyl), —$C_2$-$C_6$ alkenyl, —O—($C_1$-$C_6$ alkyl)-OH, —O—($C_1$-$C_6$ alkyl)-O—($C_1$-$C_6$ alkyl), —O—($C_1$-$C_6$ haloalkyl)-OH, —O—($C_1$-$C_6$ haloalkyl)-O—($C_1$-$C_6$ alkyl), —O—($C_1$-$C_6$ perhaloalkyl)-OH, —O—($C_1$-$C_6$ perhaloalkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), or —C(=O)N($C_1$-$C_6$ alkyl)$_2$;
$R^2$ is selected from —H, or $C_1$-$C_4$ alkyl in the compounds of Formula I, or is absent in the compounds of Formula II;
$R^3$ is selected from an unsubstituted $C_1$-$C_{10}$ alkyl, a $C_1$-$C_{10}$ alkyl substituted with 1, 2, or 3 $R^{3a}$ substituents, a group of formula —($CR^{3b}R^{3c}$)-Q, a group of formula —($CR^{3b}R^{3c}$)—C(=O)-Q, a group of formula —($CR^{3d}R^{3e}$)—($CR^{3f}R^{3g}$)-Q, a group of formula —($CR^{3d}R^{3e}$)—($CR^{3f}R^{3g}$)—C(=O)-Q, a group of formula —($CR^{3d}R^{3e}$)—($CR^{3f}R^{3g}$)—CH(OH)-Q, a group of formula —($CR^{3d}R^{3e}$)—($CR^{3f}R^{3g}$)—($CR^{3f}R^{3g}$)-Q, a group of formula —($CR^{3b}$=$CR^{3c}$)-Q, a group of formula —($C_3$-$C_8$ cycloalkyl)-Q, a group of formula -(heterocyclyl)-Q, or -Q, wherein the heterocyclyl of the -(heterocyclyl)-Q group has 5 to 7 ring members of which 1, 2, or 3 are heteroatoms independently selected from N, O, or S and is unsubstituted or is substituted with 1, 2, or 3 $R^{3h}$ substituents, and further wherein the $C_3$-$C_8$ cycloalkyl of the —($C_3$-$C_8$ cycloalkyl)-Q group is unsubstituted or is substituted with 1 or 2 $R^{3h}$ substituents;
$R^{3a}$ in each instance is independently selected from —F, —Cl, —CN, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$C_2$-$C_6$ alkenyl, —$C_2$-$C_6$ alkynyl, —$NH_2$, —NH($C_1$-$C_6$ alkyl), or —N($C_1$-$C_6$ alkyl)$_2$;
$R^{3b}$ and $R^{3c}$ are independently selected from —H, —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;
$R^{3d}$ and $R^{3e}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;
$R^{3f}$ and $R^{3g}$ are independently selected from —H, —F, —Cl, —CN, —$C_1$-$C_6$ alkyl, —$C_1$-$C_6$ haloalkyl, —$C_1$-$C_6$ perhaloalkyl, —OH, —($C_1$-$C_6$ alkyl)-OH, —($C_1$-$C_6$ alkyl)-O—($C_1$-$C_6$ alkyl), —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), or —N($C_1$-$C_6$ alkyl)$_2$;
$R^{3h}$ in each instance is independently selected from —F, —Cl, —CN, —$C_1$-$C_6$ alkyl, —$C_1$-$C_6$ haloalkyl, —$C_1$-$C_6$ perhaloalkyl, —OH, —O—($C_1$-$C_6$ alkyl), —O—($C_1$-$C_6$ haloalkyl), —O—($C_1$-$C_6$ perhaloalkyl), —O—($C_1$-$C_6$ alkyl)-OH, —O—($C_1$-$C_6$ alkyl)-O—($C_1$-$C_6$ alkyl), —$NH_2$, —NH($C_1$-$C_6$ alkyl), —N($C_1$-$C_6$ alkyl)$_2$, —C(=O)—($C_1$-$C_6$ alkyl), —C(=O)—($C_3$-$C_6$ cycloalkyl), —C(=O)—O—($C_1$-$C_6$ alkyl), oxo, or —C(=O)-(heterocyclyl), wherein the heterocyclyl group of the $R^h$ —C(=O)-(heterocyclyl) has 5 or 6 ring members of which 1 or 2 are heteroatoms independently selected from N, or S or has 3 or 4 ring members of which 1 is a heteroatom selected from N, O, or S;
Q is a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a $C_3$-$C_8$ cycloalkyl group, a 3 to 10 membered heterocyclyl group containing 1, 2, or 3 heteroatoms independently selected from N, O, or S, —C(=O)NH(—$C_1$-$C_6$ alkyl), —C(=O)N(—$C_1$-$C_6$ alkyl)$_2$, or —S(=O)$_2$—$C_1$-$C_6$alkyl, wherein the $C_6$-$C_{10}$ aryl, the heteroaryl, the cycloalkyl, and the heterocyclyl Q groups are unsubstituted or are substituted with 1, 2, 3, or 4 $R^Q$ substituent;
$R^Q$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —$C_2$-$C_6$ alkenyl, —$C_2$-$C_6$ alkynyl, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, —NHC(=O)($C_1$-$C_6$ alkyl), —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, —S(=O)$_2$—($C_1$-$C_6$ alkyl), —($C_1$-$C_6$ alkyl)-OH, —($C_1$-$C_6$ alkyl)-O—($C_1$-$C_6$ alkyl), phenyl, a heterocyclyl group, a —($C_1$-$C_6$ alkyl)heterocyclyl group, or a heteroaryl group with 5 or 6 ring members and 1, 2, or 3 heteroatoms independently selected from N, O, or S, wherein the heterocyclyl groups of the $R^Q$ heterocyclyl and —($C_1$-$C_6$ alkyl)heterocyclyl groups have 3 to 6 ring members of which 1 or 2 are heteroatoms independently selected from N, O, or S, wherein the Q heterocyclyl group may additionally be substituted with 1 or 2 oxo substituents, and the Q heteroaryl group may include an N-oxide if the heteroaryl includes a N heteroatom, and further wherein the heterocyclyl and the heterocyclyl of the —($C_1$-$C_6$ alkyl)heterocyclyl $R^Q$ groups may be further substituted with one or two oxo substituents and a substituent selected from —F, —Cl, —Br, —I, —CN, —OH, —$C_1$-$C_6$ alkyl, or —C(=O)—($C_1$-$C_6$ alkyl);
$R^4$ is selected from a monocyclic or bicyclic $C_6$-$C_{10}$ aryl group, a monocyclic or bicyclic heteroaryl group with 5 to 10 ring members containing 1, 2, or 3 heteroatoms independently selected from N, O, or S, a monocyclic or bicyclic heterocyclyl group with 5 to 10 ring members containing 1, 2, 3, or 4 heteroatoms independently selected from N, O, or S, a monocyclic 3-6 membered cycloalkyl group, or a straight or branched chain $C_1$-$C_6$ alkyl group, wherein the $C_6$-$C_{10}$ aryl, the heteroaryl, the heterocyclyl, and the cycloalkyl $R^4$ group are unsubstituted or are substituted with 1, 2, 3, or 4 $R^{4a}$ substituents, and further wherein the straight or branched chain $C_1$-$C_6$ alkyl group is unsubstituted or is substituted with 1, 2, or 3 $R^{4b}$ substituents;

$R^{4a}$ in each instance is independently selected from —F, —Cl, —Br, —I, —CN, —$C_1$-$C_6$ alkyl, —$C_1$-$C_6$ haloalkyl, —$C_1$-$C_6$ perhaloalkyl, —($C_1$-$C_6$ alkyl)-OH, —($C_1$-$C_6$ alkyl)-O—($C_1$-$C_6$ alkyl), —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, phenyl, —S(=O)$_2$—($C_1$-$C_6$ alkyl), —($C_1$-$C_6$ alkyl)-heterocyclyl, or heterocyclyl, wherein the heterocyclyl of the —($C_1$-$C_6$ alkyl)-heterocyclyl and heterocyclyl $R^{4a}$ groups is a 3-6 membered ring comprising 1 or 2 heteroatoms independently selected from N, O, or S, and is unsaturated or partially unsaturated and is optionally substituted with 1 or 2 oxo substituents and may include an S=O or $SO_2$ moiety, and further wherein the heterocyclyl of the $R^4$ group may be further substituted with 1 oxo substituent; and $R^{4b}$ in each instance is selected from —F, —Cl, —Br, —I, —CN, —OH, —O—($C_1$-$C_6$ alkyl), —O—($C_1$-$C_6$ haloalkyl), —O—($C_1$-$C_6$ perhaloalkyl), —$NH_2$, —NH($C_1$-$C_6$ alkyl), —N($C_1$-$C_6$ alkyl)$_2$, NH($C_1$-$C_6$ alkyl-OH), —N($C_1$-$C_6$ alkyl-OH)$_2$, —C(=O)—($C_1$-$C_6$ alkyl), —C(=O)OH, —C(=O)—O—($C_1$-$C_6$ alkyl), —C(=O)$NH_2$, —C(=O)NH($C_1$-$C_6$ alkyl), —C(=O)N($C_1$-$C_6$ alkyl)$_2$, or —S(=O)$_2$—($C_1$-$C_6$ alkyl).

2. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^1$ is a an unsubstituted furan-2-yl or a furan-2-yl substituted with 1 or 2 $R^{1a}$ substituents independently selected from —F, —Cl, —Br, —I, —$C_1$-$C_6$ alkyl, —$C_1$-$C_6$ haloalkyl, —$C_1$-$C_6$ perhaloalkyl, or —($C_1$-$C_6$ alkyl)-O—($C_1$-$C_6$ alkyl).

3. The compound of claim 2 or the pharmaceutically acceptable salt thereof, the tautomer thereof, the pharmaceutically acceptable salt of the tautomer, the stereoisomer of any of the foregoing, or the mixture thereof, wherein $R^1$ is an unsubstituted or substituted furan-2-yl having the formula

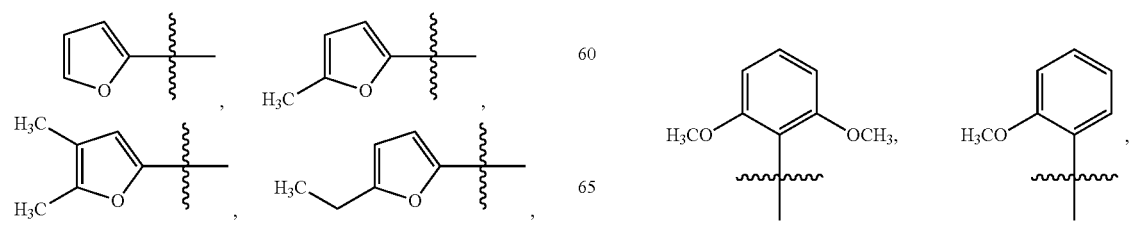

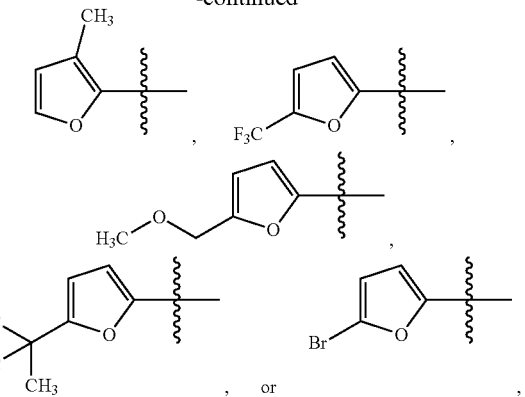

wherein the symbol ∼∼, when drawn across a bond, indicates the point of attachment to the rest of the molecule.

4. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^1$ is an unsubstituted furan-2-yl or a substituted furan-2-yl and $R^{1a}$ is independently selected from —$CH_3$, —$CH_2CH_3$, —C($CH_3$)$_3$, —$CF_3$, —$CH_2OCH_3$, or —Br.

5. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^2$ is —H in the compounds of Formula I, or is absent in the compounds of Formula II.

6. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^4$ is a phenyl, pyridinyl, pyrimidinyl, naphthyl, tetrahydropyranyl, cyclohexyl, cyclopentyl, or cyclopropyl, any of which may be unsubstituted or substituted with 1, 2, 3, or 4 $R^{4a}$ substituents.

7. The compound of claim 6 or the pharmaceutically acceptable salt thereof, the tautomer thereof, the pharmaceutically acceptable salt of the tautomer, the stereoisomer of any of the foregoing, or the mixture thereof, wherein $R^{4a}$ is in each instance independently selected from —F, —Br, —CN, —$C_1$-$C_6$ alkyl, —$C_1$-$C_6$ haloalkyl, —$C_1$-$C_6$ perhaloalkyl, —($C_1$-$C_6$ alkyl)-OH, —O—($C_1$-$C_6$ alkyl), —O—($C_1$-$C_6$ haloalkyl), —O—($C_1$-$C_6$ perhaloalkyl), or —($C_1$-$C_6$ alkyl)-heterocyclyl, wherein the heterocyclyl of the —($C_1$-$C_6$ alkyl)-heterocyclyl $R^{4a}$ group is a 3-6 membered ring comprising 1 or 2 heteroatoms independently selected from N, O, or S.

8. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^4$ is selected from -continued

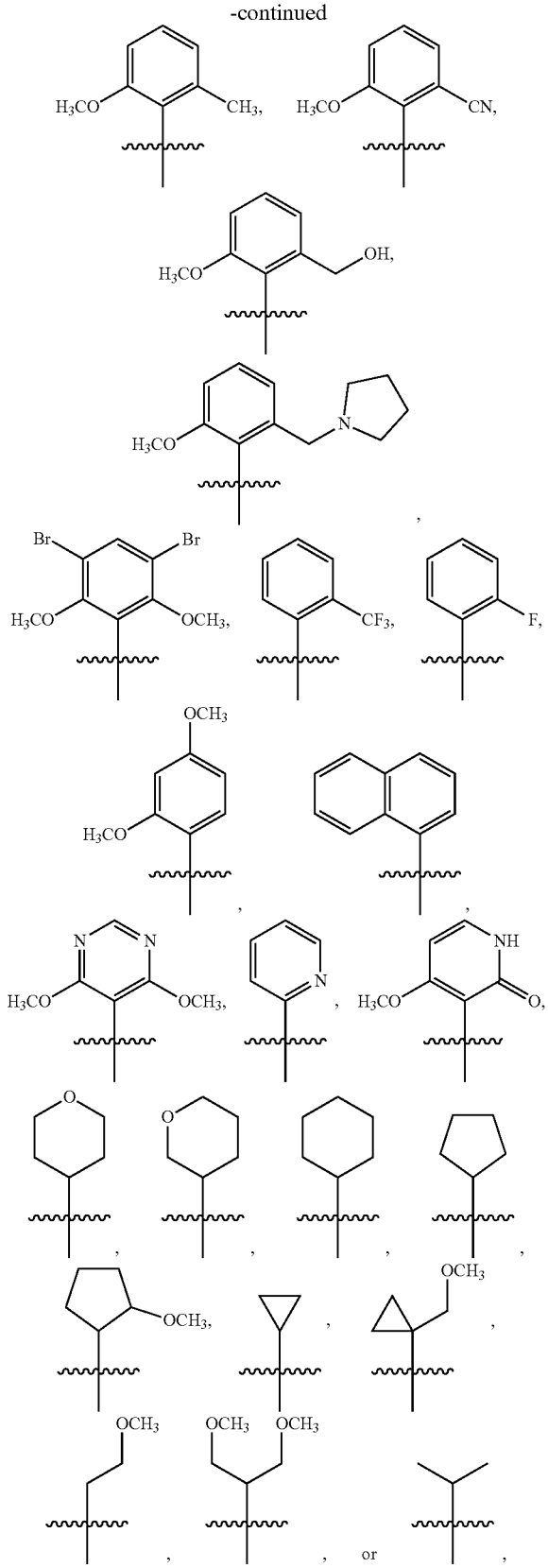

wherein the symbol ∿, when drawn across a bond, indicates the point of attachment to the rest of the molecule.

9. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^4$ is a phenyl substituted with 1 or 2 $R^{4a}$ substituents, wherein the $R^{4a}$ substituents are —O—($C_1$-$C_2$ alkyl) groups.

10. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^4$ is

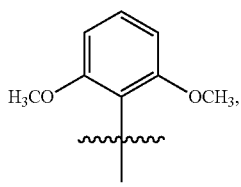

wherein the symbol ∿, when drawn across a bond, indicates the point of attachment to the rest of the molecule.

11. The compound of claim 1 or the pharmaceutically acceptable salt thereof, the tautomer thereof, the pharmaceutically acceptable salt of the tautomer, the stereoisomer of any of the foregoing, or the mixture thereof, wherein Q is selected from pyrimidinyl, pyrazinyl, pyradizinyl, pyridinyl, phenyl, oxazolyl, thiazolyl, imidazolyl, pyrazolyl, piperidin-2-onyl, tetrahydropyrimidin-2(1H)-onyl, 1,3-oxazinan-2-onyl, pyrrolidin-2-onyl, pyrrolidinyl, cyclohexyl, benzimidazolyl, isoindolinonyl, 1H-imidazo[4,5-c]pyridinyl, pyrazolo[1,5-a]pyridinyl, imidazo[1,2-a]pyridinyl, imidazo[1,5-a]pyridinyl, 6,7-dihydro-5H-pyrazolo[5,1-b][1,3]oxazinyl, or 3,4-dihydro-2H-pyrano[3,2-b]pyridinyl, any of which may be unsubstituted or substituted with 1 or 2 $R^Q$ substituents.

12. The compound of claim 1 or the pharmaceutically acceptable salt thereof, the tautomer thereof, the pharmaceutically acceptable salt of the tautomer, the stereoisomer of any of the foregoing, or the mixture thereof, wherein Q is a monocyclic heteroaryl group with 5 or 6 ring members containing 1 or 2 heteroatoms selected from N, O, or S and Q is unsubstituted or is substituted with 1 or 2 $R^Q$ substituents.

13. The compound of claim 1 or the pharmaceutically acceptable salt thereof, the tautomer thereof, the pharmaceutically acceptable salt of the tautomer, the stereoisomer of any of the foregoing, or the mixture thereof, wherein Q is selected from

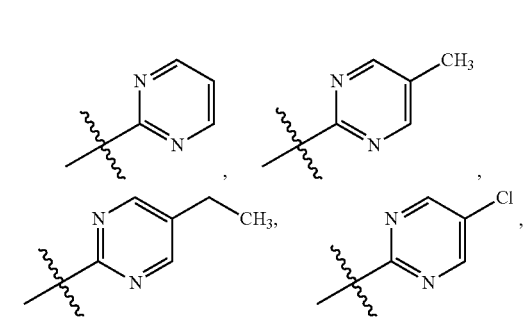

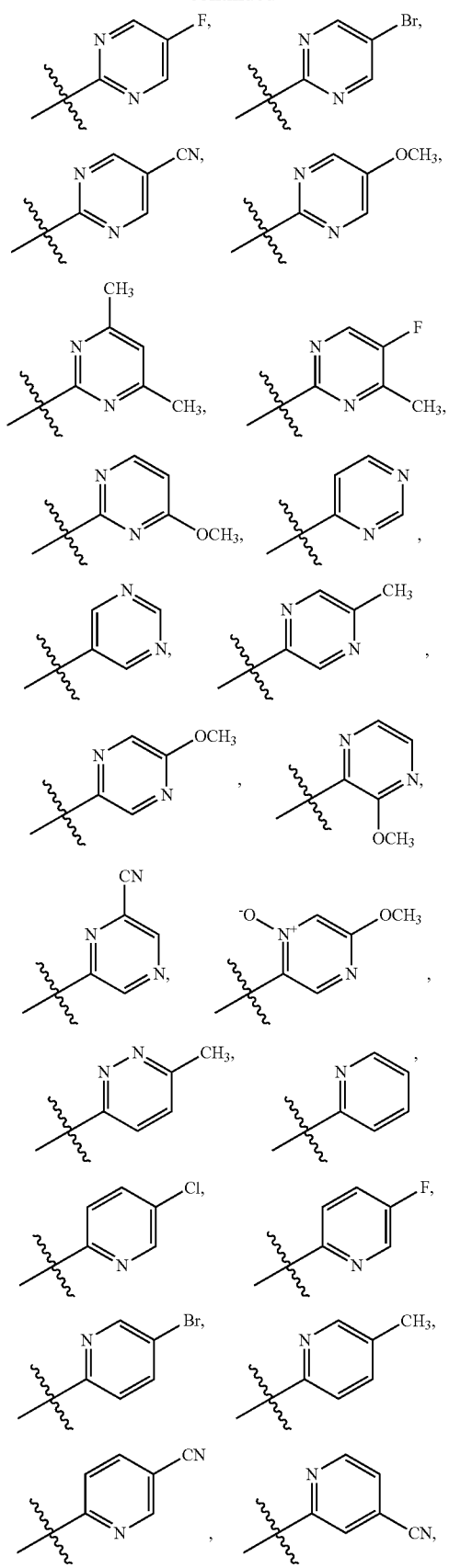
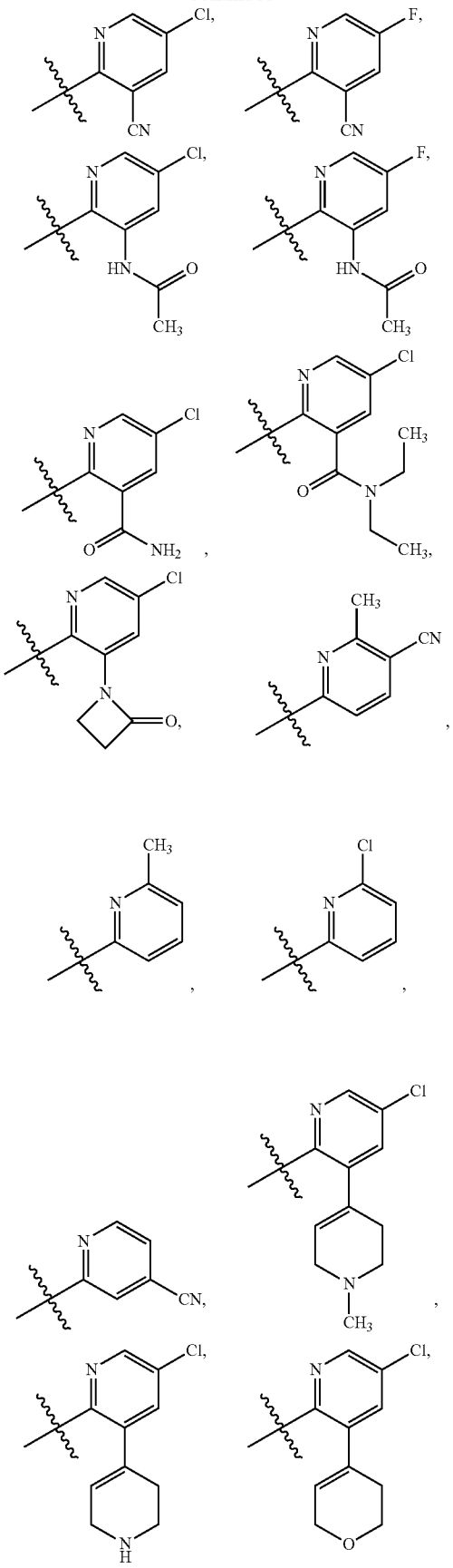

-continued
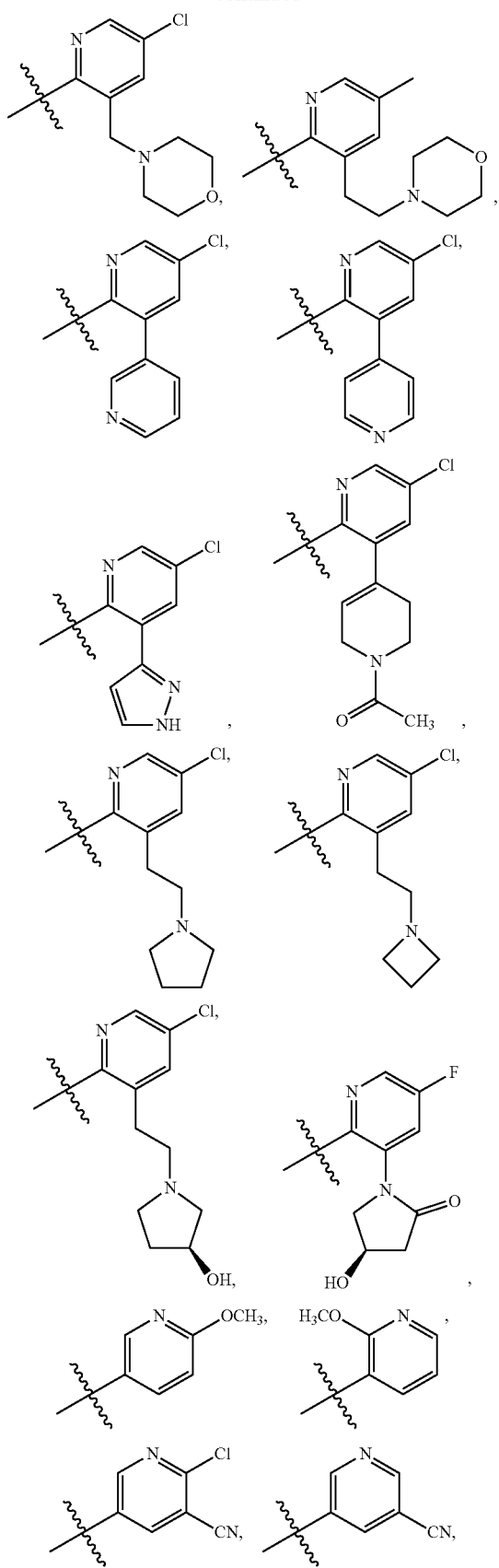
-continued
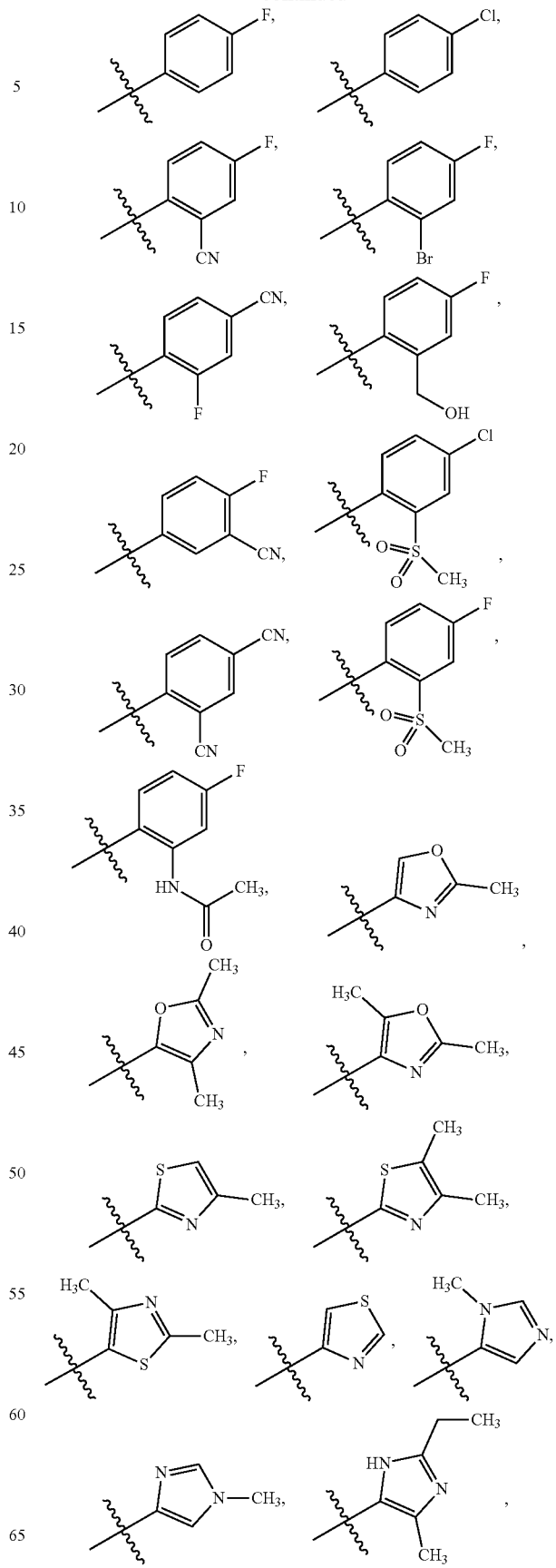

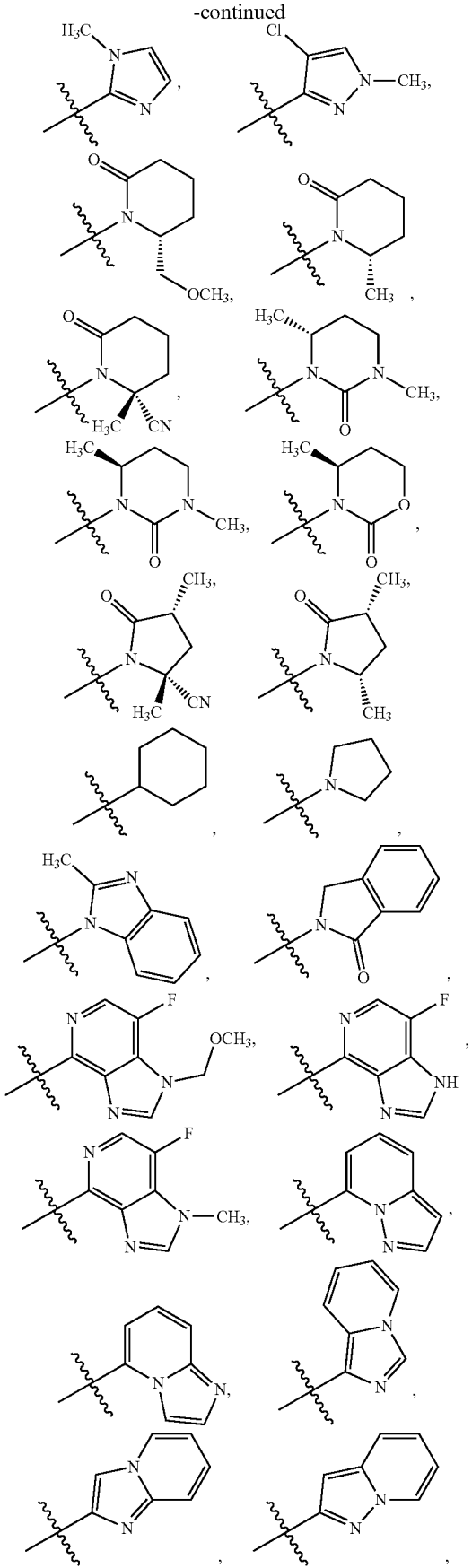
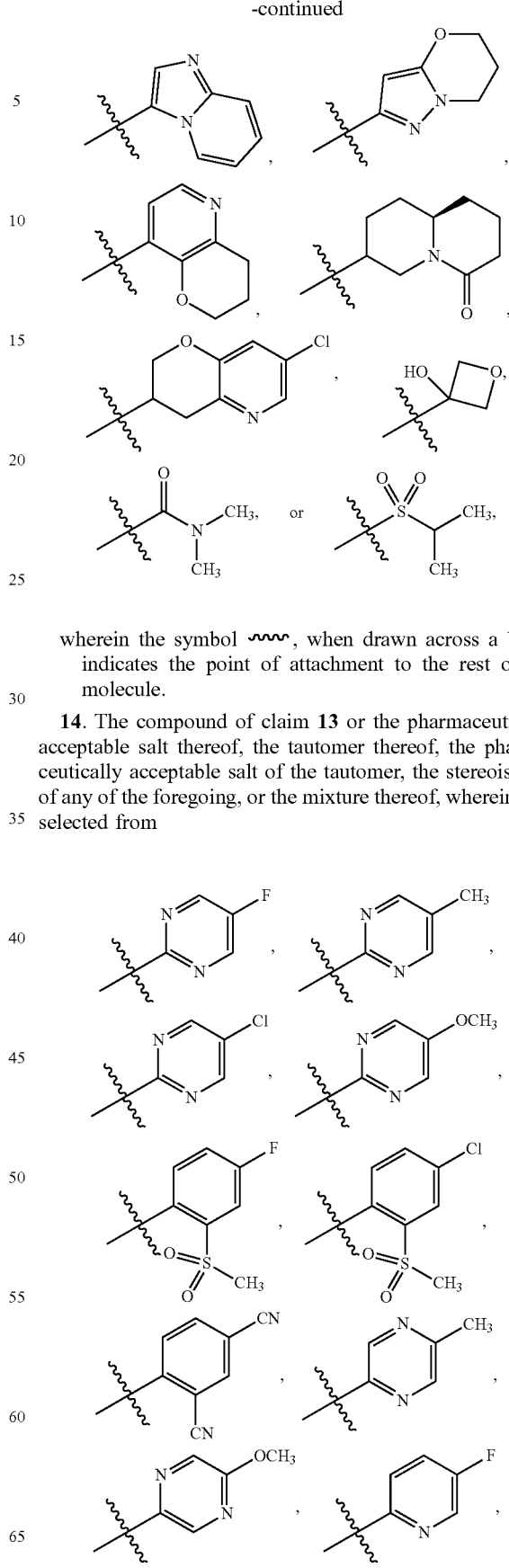
wherein the symbol ᨈ, when drawn across a bond, indicates the point of attachment to the rest of the molecule.
14. The compound of claim 13 or the pharmaceutically acceptable salt thereof, the tautomer thereof, the pharmaceutically acceptable salt of the tautomer, the stereoisomer of any of the foregoing, or the mixture thereof, wherein Q is selected from

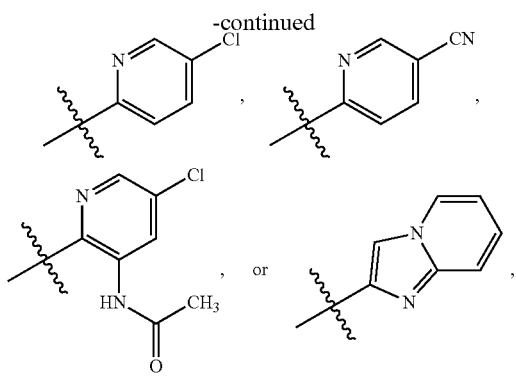

wherein the symbol ~~~, when drawn across a bond, indicates the point of attachment to the rest of the molecule.

15. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^3$ is selected from a group of formula —$(CR^{3b}R^{3c})$-Q, a group of formula —$(CR^{3d}R^{3e})$—$(CR^{3f}R^{3g})$-Q, a group of formula —$(CR^{3d}R^{3e})$—$(CR^{3f}R^{3g})$—C(=O)-Q, a group of formula —$(CR^{3d}R^{3e})$—$(CR^{3f}R^{3g})$—CH(OH)-Q, a group of formula —$(CR^{3d}R^{3e})$—$(CR^{3f}R^{3g})$—$(CR^{3f}R^{3g})$-Q, a group of formula —$(C_3$-$C_8$ cycloalkyl)-Q, a group of formula -(heterocyclyl)-Q, or -Q.

16. The compound of claim 15 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula —$(CR^{3d}R^{3e})$—$(CR^{3f}R^{3g})$-Q.

17. The compound of claim 16 or the pharmaceutically acceptable salt thereof, the tautomer thereof, the pharmaceutically acceptable salt of the tautomer, the stereoisomer of any of the foregoing, or the mixture thereof, wherein $R^3$ is a group of formula —$(CR^{3d}R^{3e})$—$(CR^{3f}R^{3g})$-Q and further wherein, $R^{3d}$ and $R^{3e}$ are independently selected from —H, —$C_1$-$C_6$ alkyl, —($C_1$-$C_6$ alkyl)-OH, or —($C_1$-$C_6$ alkyl)-O—($C_1$-$C_6$ alkyl); and $R^{3f}$ and $R^{3g}$ are independently selected from —H, —F, —$C_1$-$C_6$ alkyl, —OH, —O—($C_1$-$C_6$ alkyl), —O—($C_1$-$C_6$ alkyl)-OH, —O—($C_1$-$C_6$ alkyl)-O—($C_1$-$C_6$ alkyl), or —NH$_2$.

18. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^3$ is selected from

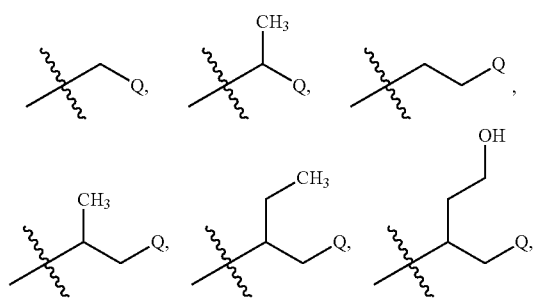

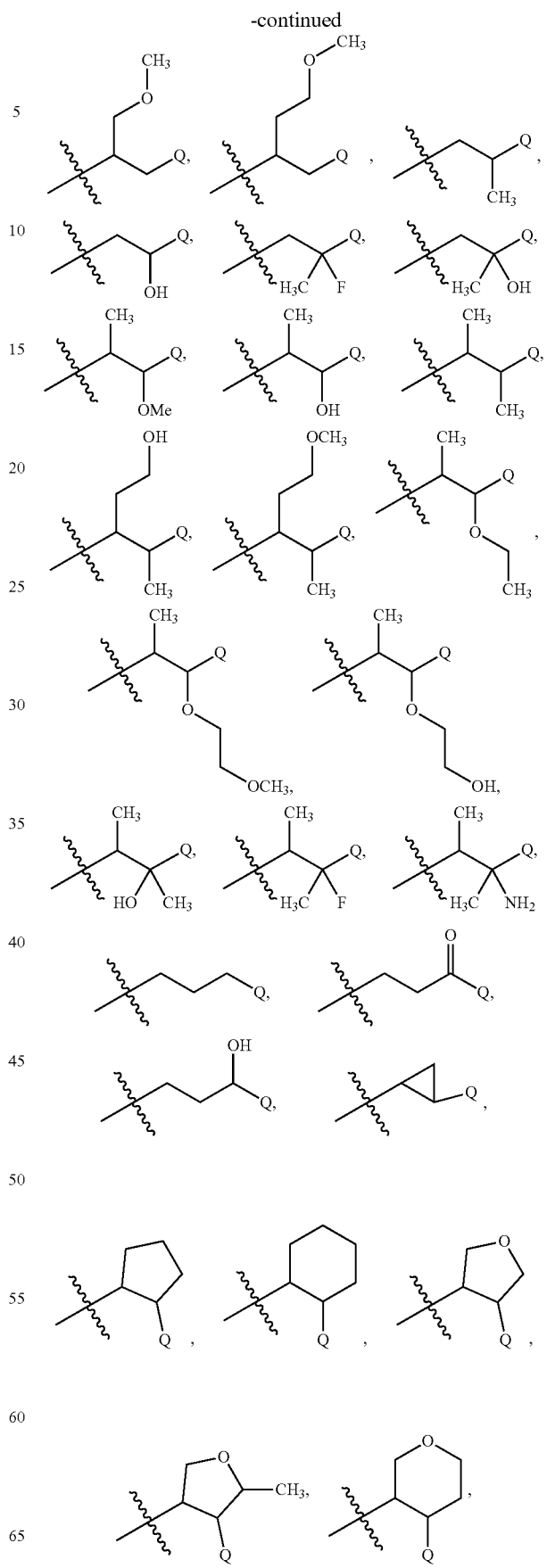

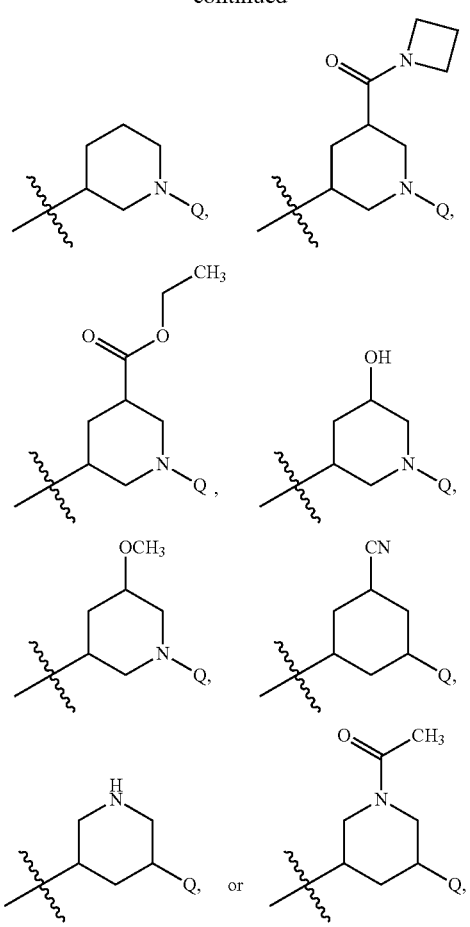
wherein the symbol ∿, when drawn across a bond, indicates the point of attachment to the rest of the molecule.
19. The compound of claim 1 or the pharmaceutically acceptable salt thereof, the tautomer thereof, the pharmaceutically acceptable salt of the tautomer, the stereoisomer of any of the foregoing, or the mixture thereof, wherein $R^3$ is selected from
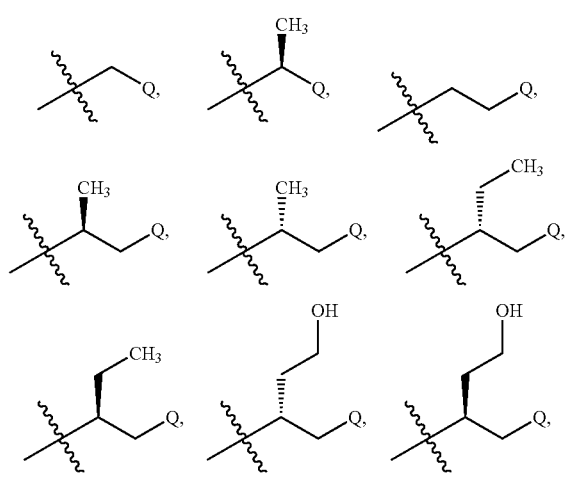
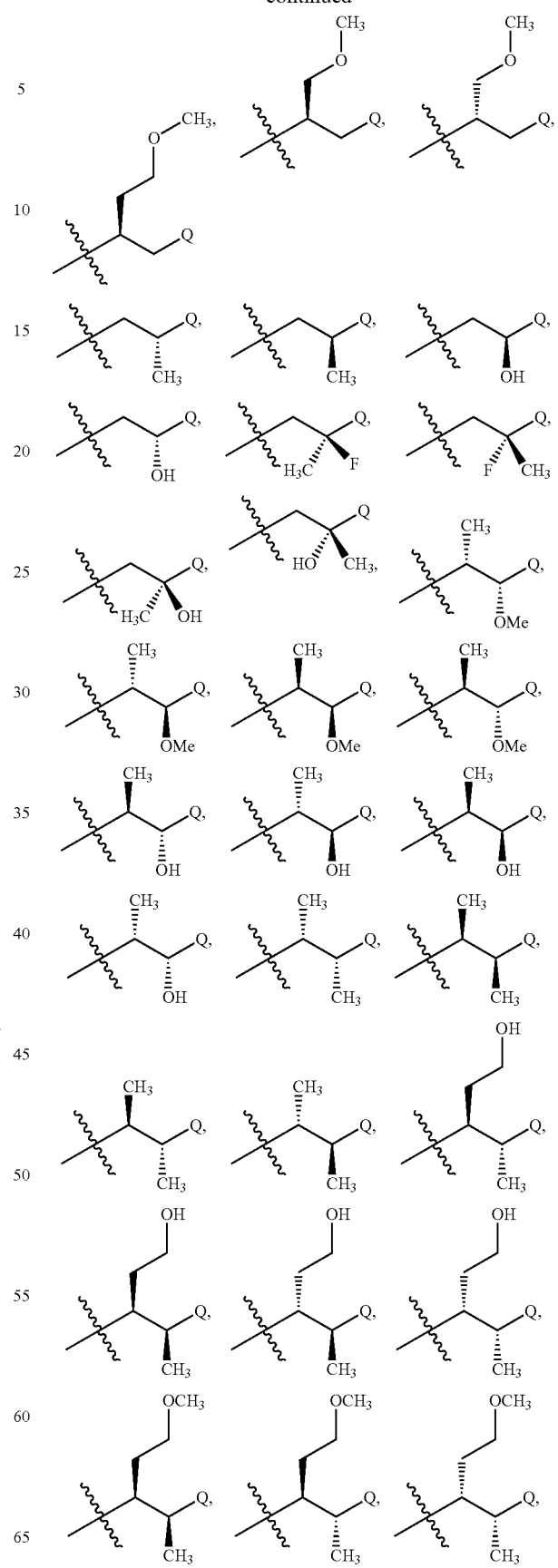

wherein the symbol ~~~, when drawn across a bond, indicates the point of attachment to the rest of the molecule.

20. The compound of claim 1, wherein the compound is selected from

733
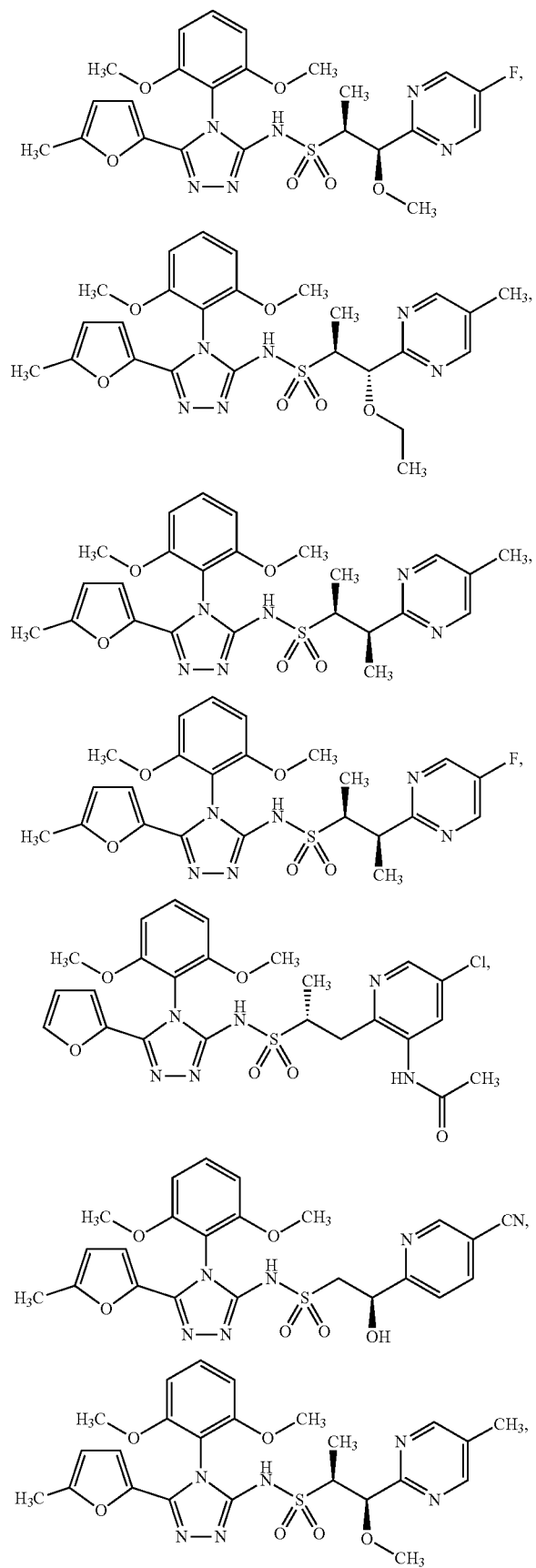
734
-continued
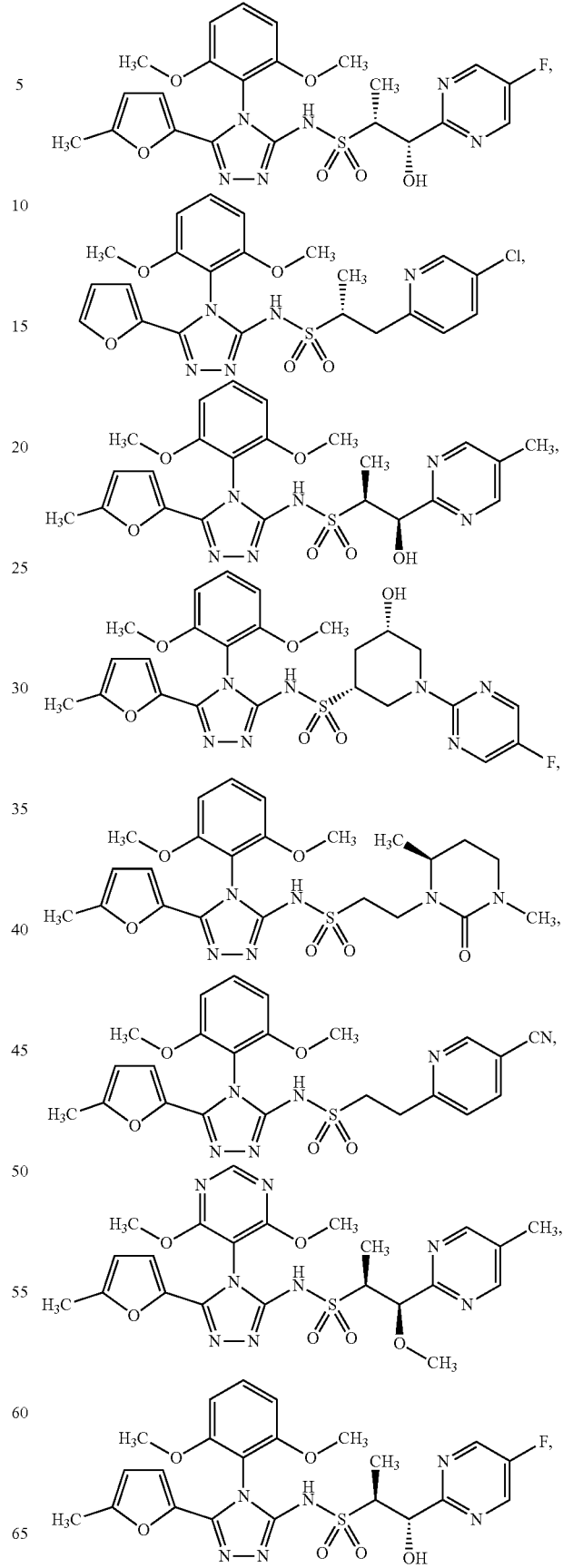

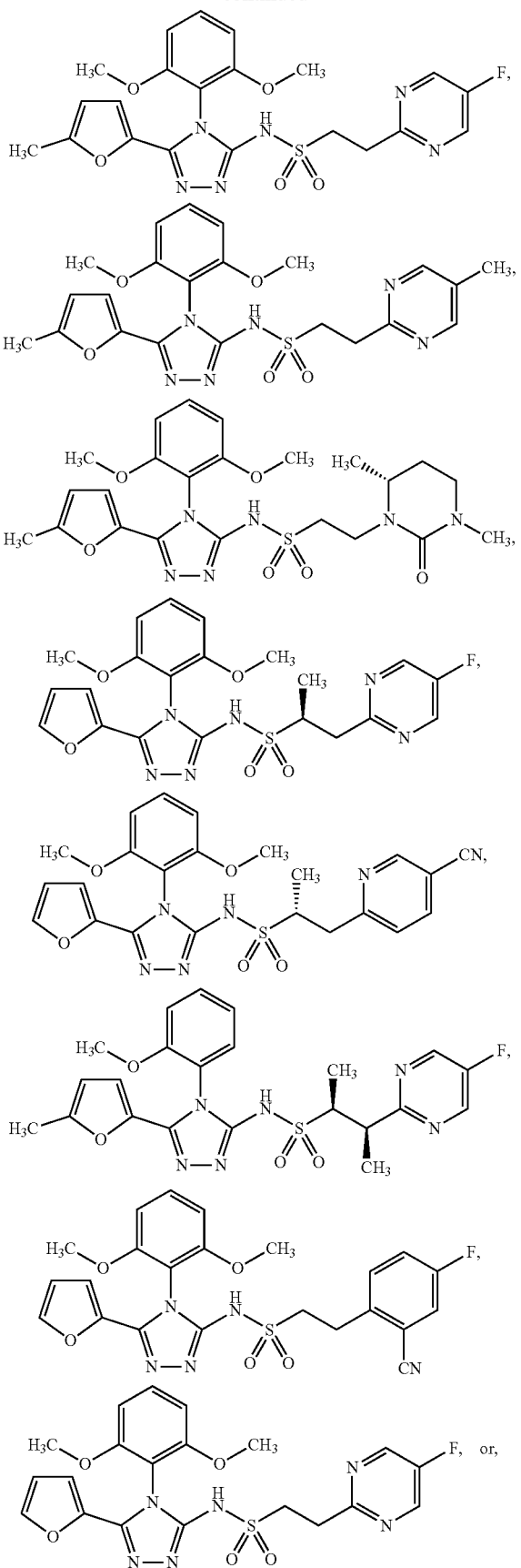

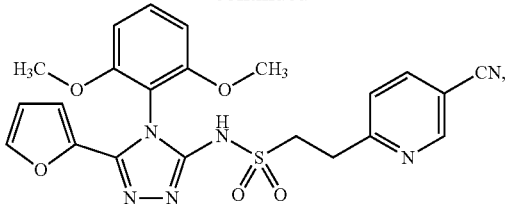

or the pharmaceutically acceptable salt thereof, or the mixture thereof.

21. The compound of claim 1, wherein the compound has the formula IA

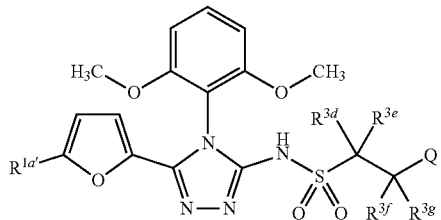

or the pharmaceutically acceptable salt thereof, the tautomer thereof, the pharmaceutically acceptable salt of the tautomer, the stereoisomer of any of the foregoing, or the mixture thereof, wherein:
  $R^{1a'}$ is selected from —H or —$C_1$-$C_4$ alkyl;
  $R^{3d}$ and $R^{3e}$ are independently selected from —H, or —$C_1$-$C_3$ alkyl;
  $R^{3f}$ and $R^{3g}$ are independently selected from —H, —$C_1$-$C_3$ alkyl, —OH, or —O—($C_1$-$C_3$ alkyl);
  Q is a phenyl group, a monocyclic heteroaryl group with 6 ring members containing 1 or 2 N heteroatoms, or a bicyclic heteroaryl group with 9 or 10 ring members containing 1 or 2 N heteroatoms, wherein the phenyl, the monocyclic heteroaryl, and the bicyclic heteroaryl aryl Q groups are unsubstituted or are substituted with 1 or 2 $R^Q$ substituent; and
  $R^Q$ is independently selected from —F, —Cl, —CN, —$C_1$-$C_6$ alkyl, —O—($C_1$-$C_6$ alkyl), —NHC(=O) ($C_1$-$C_6$ alkyl), or —S(=O)$_2$—($C_1$-$C_6$ alkyl).

22. The compound of claim 21 or is the pharmaceutically acceptable salt thereof, the tautomer thereof, the pharmaceutically acceptable salt of the tautomer, the stereoisomer of any of the foregoing, or the mixture thereof, wherein:
  $R^{1a'}$ is selected from —H, —$CH_3$, or —$CH_2CH_3$;
  $R^{3d}$ and $R^{3e}$ are independently selected from —H, or —$CH_3$;
  $R^{3f}$ and $R^{3g}$ are independently selected from —H, —$CH_3$, —OH, —$OCH_3$, or —$OCH_2CH_3$;
  Q is a phenyl, a pyrimidinyl, a pyridinyl, a pyrazinyl, or an imidazo[1,2a]pyridinyl group any of which are unsubstituted or are substituted with 1 or 2 $R^Q$ substituent; and
  $R^Q$ is independently selected from —F, —Cl, —CN, —$CH_3$, —$OCH_3$, —NHC(=O)—$CH_3$, or —S(=O)$_2$—$CH_3$.

23. A pharmaceutical composition, comprising the compound of claim 1 or the pharmaceutically acceptable salt thereof, the tautomer thereof, the pharmaceutically acceptable salt of the tautomer, the stereoisomer of any of the foregoing, or the mixture thereof, and at least one pharmaceutically acceptable excipient.

24. A pharmaceutical composition, comprising the compound of claim 1 or the pharmaceutically acceptable salt thereof, and at least one pharmaceutically acceptable excipient.

25. The pharmaceutical composition of claim 24, further comprising a therapeutic agent selected from an α-blocker, a β-blocker, an angiotensin converting enzyme (ACE) inhibitor, an angiotensin-receptor blocker (ARB), a calcium channel blocker, a diuretic, an inhibitor of the funny current, a myosin activator, or a neutral endopeptidase (NEP) inhibitor.

* * * * *